(12) United States Patent
Hatada et al.

(10) Patent No.: US 6,251,620 B1
(45) Date of Patent: Jun. 26, 2001

(54) THREE DIMENSIONAL STRUCTURE OF A ZAP TYROSINE PROTEIN KINASE FRAGMENT AND MODELING METHODS

(75) Inventors: Marcos H. Hatada, Charlestown; Xiaode Lu, Revere; Ellen R. Laird, Newton; Jennifer L. Karas, Lexington; Mark J. Zoller, Weston; Dennis A. Holt, Stow, all of MA (US)

(73) Assignee: Ariad Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/975,040

(22) Filed: Nov. 18, 1997

Related U.S. Application Data

(62) Division of application No. 08/605,578, filed on Feb. 22, 1996.
(60) Provisional application No. 60/003,312, filed on Sep. 6, 1995, and provisional application No. 60/002,312, filed on Aug. 30, 1995.

(51) Int. Cl.[7] ............................... C12Q 1/48; G06F 19/00
(52) U.S. Cl. ............................... 435/15; 435/194; 436/86; 436/350; 702/19
(58) Field of Search ................................... 702/19; 435/15, 435/194; 436/86; 530/350

(56) References Cited

PUBLICATIONS

Hatada et al. "Molecular bases for the interaction of the protein tyrosine kinase ZAP–70 with the T–cell receptor" Nature 377, 32–338, Sep. 7, 1995.*

\* cited by examiner

*Primary Examiner*—Nashaat T. Nashed
(74) *Attorney, Agent, or Firm*—Matthew P. Vincent; Isabelle M. Clauss; Foley, Hoag & Eliot

(57) ABSTRACT

The invention relates to human ZAP-70, and in particular, to the region of ZAP-70 containing the tandem Src homology-2 ("SH2") domains, to crystalline forms thereof, liganded or unliganded, which are particularly useful for the determination of the three-dimensional structure of the protein. The three dimensional structure of the tandem SH2 region of ZAP provides information useful for the design of pharmaceutical compositions which inhibit the biological function of ZAP and other members of the ZAP family of SH2 domain-containing proteins, particularly those biological functions mediated by molecular interactions involving one or both SH2 domains.

7 Claims, 14 Drawing Sheets

```
                           SEQUENCE LISTING (1) GENERAL INFORMATION:

(iii) NUMBER OF SEQUENCES: 39

(2) INFORMATION FOR SEQ ID NO: 1:

(i) SEQUENCE CHARACTERISTICS:
         (A) LENGTH: 15 amino acids
         (B) TYPE: amino acid
         (C) STRANDEDNESS: <Unknown>
         (D) TOPOLOGY: linear (ii) MOLECULE TYPE: peptide (xi) SEQUENCE DESCRIPTION: SEQ ID NO: 1:

Tyr Xaa Xaa Leu Xaa Xaa Xaa Xaa Xaa Xaa Xaa Tyr Xaa Xaa Leu
```

(2) INFORMATION FOR SEQ ID NO: 2:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated"

(ix) FEATURE:
        (A) NAME/KEY: Modified-site
        (B) LOCATION: 4
        (D) OTHER INFORMATION: /product= "phosphotyrosine"

(ix) FEATURE:
        (A) NAME/KEY: Modified-site
        (B) LOCATION: 15
        (D) OTHER INFORMATION: /product= "phosphotyrosine"

(ix) FEATURE:
        (A) NAME/KEY: Modified-site
        (B) LOCATION: 19
        (D) OTHER INFORMATION: /product= "amidated"

(xi) SEQUENCE DESCRIPTION: SEQ ID NO: 2:

```
Asp Gly Val Tyr Thr Gly Leu Ser Thr Arg Asn Gln Glu Thr Tyr Glu
1               5                   10                  15

Thr Leu Lys
```

(2) INFORMATION FOR SEQ ID NO: 3:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated phosphotyrosine"

(ix) FEATURE:
        (A) NAME/KEY: Modified-site
        (B) LOCATION: 12
        (D) OTHER INFORMATION: /product= "phosphotyrosine"

(ix) FEATURE:
        (A) NAME/KEY: Modified-site
        (B) LOCATION: 15
        (D) OTHER INFORMATION: /product= "amidated"

(xi) SEQUENCE DESCRIPTION: SEQ ID NO: 3:

```
Tyr Thr Gly Leu Ser Thr Arg Asn Gln Glu Thr Tyr Glu Thr Leu
1               5                   10                  15
```

(2) INFORMATION FOR SEQ ID NO: 4:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear

```
        (ii) MOLECULE TYPE: peptide (ix) FEATURE:
              (A) NAME/KEY: Modified-site
              (B) LOCATION: 1
              (D) OTHER INFORMATION: /product= "Acetylated"

(ix) FEATURE:
              (A) NAME/KEY: Modified-site
              (B) LOCATION: 4
              (D) OTHER INFORMATION: /product= "phosphotyrosine"

(ix) FEATURE:
              (A) NAME/KEY: Modified-site
              (B) LOCATION: 15
              (D) OTHER INFORMATION: /product= "phosphotyrosine"

(xi) SEQUENCE DESCRIPTION: SEQ ID NO: 4:

Asp Gly Val Tyr Thr Gly Leu Ser Thr Arg Asn Gln Glu Thr Tyr Glu
1               5                   10                  15

Thr Leu Lys His Glu Lys Pro Pro Gln
            20                  25

(2) INFORMATION FOR SEQ ID NO: 5:

(i) SEQUENCE CHARACTERISTICS:
              (A) LENGTH: 27 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "Acetylated"

(ix) FEATURE:
              (A) NAME/KEY: Modified-site
              (B) LOCATION: 6
              (D) OTHER INFORMATION: /product= "phosphotyrosine"

(ix) FEATURE:
              (A) NAME/KEY: Modified-site
              (B) LOCATION: 17
              (D) OTHER INFORMATION: /product= "phosphotyrosine"

(xi) SEQUENCE DESCRIPTION: SEQ ID NO: 5:

Lys Ser Asp Gly Val Tyr Thr Gly Leu Ser Thr Arg Asn Gln Glu Thr
1               5                   10                  15

Tyr Glu Thr Leu Lys His Glu Lys Pro Pro Gln
            20                  25

(2) INFORMATION FOR SEQ ID NO: 6:

(i) SEQUENCE CHARACTERISTICS:
              (A) LENGTH: 19 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "Acetylated"

(ix) FEATURE:
              (A) NAME/KEY: Modified-site
              (B) LOCATION: 4
```

```
          (D) OTHER INFORMATION: /product= "phosphotyrosine"

(ix) FEATURE:
          (A) NAME/KEY: Modified-site
          (B) LOCATION: 15
          (D) OTHER INFORMATION: /product= "phosphotyrosine"

(ix) FEATURE:
          (A) NAME/KEY: Modified-site
          (B) LOCATION: 19
          (D) OTHER INFORMATION: /product= "amidated"

(xi) SEQUENCE DESCRIPTION: SEQ ID NO: 6:

Asn Gln Leu Tyr Asn Glu Leu Asn Leu Gly Arg Arg Glu Glu Tyr Asp
 1               5                  10                  15

Val Leu Asp (2) INFORMATION FOR SEQ ID NO: 7:

(i) SEQUENCE CHARACTERISTICS:
          (A) LENGTH: 19 amino acids
          (B) TYPE: amino acid
          (C) STRANDEDNESS: <Unknown>
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "Acetylated"

(ix) FEATURE:
          (A) NAME/KEY: Modified-site
          (B) LOCATION: 3
          (D) OTHER INFORMATION: /product= "phosphotyrosine"

(ix) FEATURE:
          (A) NAME/KEY: Modified-site
          (B) LOCATION: 11
          (D) OTHER INFORMATION: /product= "Norleucine"

(ix) FEATURE:
          (A) NAME/KEY: Modified-site
          (B) LOCATION: 19
          (D) OTHER INFORMATION: /product= "amidated"

(xi) SEQUENCE DESCRIPTION: SEQ ID NO: 7:

Gly Leu Tyr Asn Glu Leu Gln Lys Asp Lys Xaa Ala Glu Ala Tyr Ser
 1               5                  10                  15

Glu Ile Gly (2) INFORMATION FOR SEQ ID NO: 8:

(i) SEQUENCE CHARACTERISTICS:
          (A) LENGTH: 19 amino acids
          (B) TYPE: amino acid
          (C) STRANDEDNESS: <Unknown>
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "Acetylated"

(ix) FEATURE:
          (A) NAME/KEY: Modified-site
          (B) LOCATION: 4
          (D) OTHER INFORMATION: /product= "phosphotyrosine"

(ix) FEATURE:
```

(A) NAME/KEY: Modified-site
        (B) LOCATION: 15
        (D) OTHER INFORMATION: /product= "phosphotyrosine"

(ix) FEATURE:
        (A) NAME/KEY: Modified-site
        (B) LOCATION: 19
        (D) OTHER INFORMATION: /product= "amidated"

(xi) SEQUENCE DESCRIPTION: SEQ ID NO: 8:

Asp Gly Leu Tyr Gln Gly Leu Ser Thr Ala Thr Lys Asp Thr Tyr Asp
1               5                   10                  15

Ala Leu His (2) INFORMATION FOR SEQ ID NO: 9:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated phosphotyrosine"

(ix) FEATURE:
        (A) NAME/KEY: Modified-site
        (B) LOCATION: 12
        (D) OTHER INFORMATION: /product= "phosphotyrosine"

(ix) FEATURE:
        (A) NAME/KEY: Modified-site
        (B) LOCATION: 16
        (D) OTHER INFORMATION: /product= "amidated"

(xi) SEQUENCE DESCRIPTION: SEQ ID NO: 9:

Tyr Asn Glu Leu Asn Leu Gly Arg Arg Glu Glu Tyr Asp Val Leu Asp
1               5                   10                  15

(2) INFORMATION FOR SEQ ID NO: 10:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated"

(ix) FEATURE:
        (A) NAME/KEY: Modified-site
        (B) LOCATION: 4
        (D) OTHER INFORMATION: /product= "difluorophosphonomethyl
            phenylalanine"

(ix) FEATURE:
        (A) NAME/KEY: Modified-site
        (B) LOCATION: 15
        (D) OTHER INFORMATION: /product= "difluorophosphonomethyl
            phenylalanine"

(ix) FEATURE:
        (A) NAME/KEY: Modified-site
        (B) LOCATION: 19
        (D) OTHER INFORMATION: /product= "amidated"

(xi) SEQUENCE DESCRIPTION: SEQ ID NO: 10:

Asn Gln Leu Phe Asn Glu Leu Asn Leu Gly Arg Arg Glu Glu Phe Asp
1               5                   10                  15

Val Leu Asp (2) INFORMATION FOR SEQ ID NO: 11:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated"

(ix) FEATURE:
        (A) NAME/KEY: Modified-site
        (B) LOCATION: 4
        (D) OTHER INFORMATION: /product= "phosphotyrosine"

(ix) FEATURE:
        (A) NAME/KEY: Modified-site
        (B) LOCATION: 12
        (D) OTHER INFORMATION: /product= "phosphotyrosine"

(ix) FEATURE:
        (A) NAME/KEY: Modified-site
        (B) LOCATION: 16
        (D) OTHER INFORMATION: /product= "amidated"

(xi) SEQUENCE DESCRIPTION: SEQ ID NO: 11:

Asp Gly Val Tyr Thr Gly Leu Ala Ala Ala Ala Tyr Glu Thr Leu Lys
1               5                   10                  15

(2) INFORMATION FOR SEQ ID NO: 12:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated"

(ix) FEATURE:
        (A) NAME/KEY: Modified-site
        (B) LOCATION: 11
        (D) OTHER INFORMATION: /product= "phosphotyrosine"

(ix) FEATURE:
        (A) NAME/KEY: Modified-site
        (B) LOCATION: 14
        (D) OTHER INFORMATION: /product= "amidated"

(xi) SEQUENCE DESCRIPTION: SEQ ID NO: 12:

Asn Glu Leu Asn Leu Gly Arg Arg Glu Glu Tyr Asp Val Leu
1               5                   10

(2) INFORMATION FOR SEQ ID NO: 13:

(i) SEQUENCE CHARACTERISTICS:

```
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated phosphotyrosine"

(ix) FEATURE:
        (A) NAME/KEY: Modified-site
        (B) LOCATION: 3
        (D) OTHER INFORMATION: /product= "N-methyl glycine"

(ix) FEATURE:
        (A) NAME/KEY: Modified-site
        (B) LOCATION: 4
        (D) OTHER INFORMATION: /product= "amidated N-methyl leucine"

(xi) SEQUENCE DESCRIPTION: SEQ ID NO: 13:

Tyr Thr Gly Leu
1

(2) INFORMATION FOR SEQ ID NO: 14:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "phosphotyrosine"

(ix) FEATURE:
        (A) NAME/KEY: Modified-site
        (B) LOCATION: 15
        (D) OTHER INFORMATION: /product= "phosphotyrosine"

(xi) SEQUENCE DESCRIPTION: SEQ ID NO: 14:

Asn Gln Leu Tyr Asn Glu Leu Asn Leu Gly Arg Arg Glu Glu Tyr Asp
1               5                   10                  15

Val Leu Asp (2) INFORMATION FOR SEQ ID NO: 15:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "phosphotyrosine"

(ix) FEATURE:
        (A) NAME/KEY: Modified-site
        (B) LOCATION: 15
        (D) OTHER INFORMATION: /product= "phosphotyrosine"

(xi) SEQUENCE DESCRIPTION: SEQ ID NO: 15:

Asn Gln Leu Tyr Asn Glu Leu Asn Leu Gly Arg Arg Glu Glu Tyr Asp
```

```
1               5                  10                  15

Val Leu Asp (2) INFORMATION FOR SEQ ID NO: 16:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated"

(ix) FEATURE:
        (A) NAME/KEY: Modified-site
        (B) LOCATION: 7
        (D) OTHER INFORMATION: /product= "phosphotyrosine"

(ix) FEATURE:
        (A) NAME/KEY: Modified-site
        (B) LOCATION: 18
        (D) OTHER INFORMATION: /product= "phosphotyrosine"

(ix) FEATURE:
        (A) NAME/KEY: Modified-site
        (B) LOCATION: 22
        (D) OTHER INFORMATION: /product= "amidated"

(xi) SEQUENCE DESCRIPTION: SEQ ID NO: 16:

Lys Gly Gly Asn Gln Leu Tyr Asn Glu Leu Asn Leu Gly Arg Arg Glu
1               5                  10                  15

Glu Tyr Asp Val Leu Asp
            20

(2) INFORMATION FOR SEQ ID NO: 17:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 15
        (D) OTHER INFORMATION: /product= "phosphotyrosine"

(xi) SEQUENCE DESCRIPTION: SEQ ID NO: 17:

Asn Gln Leu Tyr Asn Glu Leu Asn Leu Gly Arg Arg Glu Glu Tyr Asp
1               5                  10                  15

Val Leu Asp (2) INFORMATION FOR SEQ ID NO: 18:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
```

(B) LOCATION: 1
        (D) OTHER INFORMATION: /product= "Acetylated"

(ix) FEATURE:
        (A) NAME/KEY: Modified-site
        (B) LOCATION: 18
        (D) OTHER INFORMATION: /product= "phosphotyrosine"

(ix) FEATURE:
        (A) NAME/KEY: Modified-site
        (B) LOCATION: 22
        (D) OTHER INFORMATION: /product= "amidated"

(xi) SEQUENCE DESCRIPTION: SEQ ID NO: 18:

Lys Gly Gly Asn Gln Leu Tyr Asn Glu Leu Asn Leu Gly Arg Arg Glu
1               5                   10                  15

Glu Tyr Asp Val Leu Asp
            20

(2) INFORMATION FOR SEQ ID NO: 19:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "phosphotyrosine"

(ix) FEATURE:
        (A) NAME/KEY: Modified-site
        (B) LOCATION: 15
        (D) OTHER INFORMATION: /product= "phosphotyrosine"

(xi) SEQUENCE DESCRIPTION: SEQ ID NO: 19:

Asp Gly Val Tyr Thr Gly Leu Ser Thr Arg Asn Gln Glu Thr Tyr Glu
1               5                   10                  15

Thr Leu Lys (2) INFORMATION FOR SEQ ID NO: 20:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated"

(ix) FEATURE:
        (A) NAME/KEY: Modified-site
        (B) LOCATION: 7
        (D) OTHER INFORMATION: /product= "phosphotyrosine"

(ix) FEATURE:
        (A) NAME/KEY: Modified-site
        (B) LOCATION: 18
        (D) OTHER INFORMATION: /product= "phosphotyrosine"

(ix) FEATURE:
        (A) NAME/KEY: Modified-site
        (B) LOCATION: 22
        (D) OTHER INFORMATION: /product= "amidated"

(xi) SEQUENCE DESCRIPTION: SEQ ID NO: 20:

Cys Gly Gly Asp Gly Val Tyr Thr Gly Leu Ser Thr Arg Asn Gln Glu
1               5                   10                  15

Thr Tyr Glu Thr Leu Lys
            20

(2) INFORMATION FOR SEQ ID NO: 21:

(i) SEQUENCE CHARACTERISTICS:
        (A) LENGTH: 98 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 21:

Trp Tyr Phe Gly Lys Ile Thr Arg Arg Glu Ser Glu Arg Leu Leu Leu
1               5                   10                  15

Asn Pro Glu Asn Pro Arg Gly Thr Phe Leu Val Arg Glu Ser Glu Thr
                20                  25                  30

Thr Lys Gly Ala Tyr Cys Leu Ser Val Ser Asp Phe Asp Asn Ala Lys
            35                  40                  45

Gly Leu Asn Val Lys His Tyr Lys Ile Arg Lys Leu Asp Ser Gly Gly
    50                  55                  60

Phe Tyr Ile Thr Ser Arg Thr Gln Phe Asn Ser Leu Gln Gln Leu Val
65                  70                  75                  80

Ala Tyr Tyr Ser Lys His Ala Asp Gly Leu Cys His Arg Leu Thr Thr
                85                  90                  95

Val Cys (2) INFORMATION FOR SEQ ID NO: 22:

(i) SEQUENCE CHARACTERISTICS:
        (A) LENGTH: 98 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 22:

Trp Phe Phe Lys Asn Leu Ser Arg Lys Asp Ala Glu Arg Gln Leu Leu
1               5                   10                  15

Ala Pro Gly Asn Thr His Gly Ser Phe Leu Ile Arg Glu Ser Glu Ser
                20                  25                  30

Thr Ala Gly Ser Phe Ser Leu Ser Val Arg Asp Phe Asp Gln Asn Gln
            35                  40                  45

Gly Glu Val Val Lys His Tyr Lys Ile Arg Asn Leu Asp Asn Gly Gly
    50                  55                  60

Phe Tyr Ile Ser Pro Arg Ile Thr Phe Pro Gly Leu His Glu Leu Val
65                  70                  75                  80

Arg His Tyr Thr Asn Ala Ser Asp Gly Leu Cys Thr Arg Leu Ser Arg
                85                  90                  95

Pro Cys (2) INFORMATION FOR SEQ ID NO: 23:

(i) SEQUENCE CHARACTERISTICS:
        (A) LENGTH: 97 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 23:

```
Trp Phe His Pro Asn Ile Thr Gly Val Glu Ala Glu Asn Leu Leu Leu
 1               5                  10                  15

Thr Arg Gly Val Asp Gly Ser Phe Leu Ala Arg Pro Ser Lys Ser Asn
            20                  25                  30

Pro Gly Asp Phe Thr Leu Ser Val Arg Arg Asn Gly Ala Val Thr His
            35                  40                  45

Ile Lys Ile Gln Asn Thr Gly Asp Tyr Tyr Asp Leu Tyr Gly Gly Glu
 50                  55                  60

Lys Phe Ala Thr Leu Ala Glu Leu Val Gln Tyr Tyr Met Glu His His
 65                  70                  75                  80

Gly Gln Leu Lys Glu Lys Asn Gly Asp Val Ile Glu Leu Lys Tyr Pro
                85                  90                  95

Leu
```

(2) INFORMATION FOR SEQ ID NO: 24:

(i) SEQUENCE CHARACTERISTICS:
        (A) LENGTH: 93 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 24:

```
Phe Phe Tyr Gly Ser Ile Ser Arg Ala Glu Ala Glu His Leu Lys
 1               5                  10                  15

Leu Ala Gly Met Ala Asp Gly Leu Phe Leu Leu Arg Gln Cys Leu Arg
            20                  25                  30

Ser Leu Gly Gly Tyr Val Leu Ser Leu Val His Asp Val Arg Phe His
            35                  40                  45

His Phe Pro Ile Glu Arg Gln Leu Asn Gly Thr Tyr Ala Ile Ala Gly
 50                  55                  60

Gly Lys Ala His Cys Gly Pro Ala Gly Leu Cys Glu Phe Tyr Ser Arg
 65                  70                  75                  80

Asp Pro Asp Gly Leu Pro Cys Asn Leu Arg Lys Pro Cys
                85                  90
```

(2) INFORMATION FOR SEQ ID NO: 25:

(i) SEQUENCE CHARACTERISTICS:
        (A) LENGTH: 92 amino acids
        (B) TYPE: amino acid
        (C) STRANDEDNESS: <Unknown>
        (D) TOPOLOGY: linear (ii) MOLECULE TYPE: protein (v) FRAGMENT TYPE: internal (xi) SEQUENCE DESCRIPTION: SEQ ID NO: 25:

Trp Tyr His Ser Ser Leu Thr Arg Glu Glu Ala Glu Arg Lys Leu Tyr
1               5                   10                  15

Ser Gly Ala Gln Thr Asp Gly Lys Phe Leu Leu Arg Pro Arg Lys Glu
                20                  25                  30

Gln Gly Thr Tyr Ala Leu Ser Leu Ile Tyr Gly Lys Thr Val Tyr His
            35                  40                  45

Tyr Leu Ile Ser Gln Asp Lys Ala Gly Lys Tyr Cys Ile Pro Glu Gly
        50                  55                  60

Thr Lys Phe Asp Thr Leu Trp Gln Leu Val Glu Tyr Leu Lys Leu Lys
65                  70                  75                  80

Ala Asp Gly Leu Ile Tyr Cys Leu Lys Glu Ala Cys
                85                  90

(2) INFORMATION FOR SEQ ID NO: 26:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "phosphotyrosine"

(xi) SEQUENCE DESCRIPTION: SEQ ID NO: 26:

Thr Tyr Glu Thr Leu
1               5

(2) INFORMATION FOR SEQ ID NO: 27:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "phosphotyrosine"

(xi) SEQUENCE DESCRIPTION: SEQ ID NO: 27:

Tyr Xaa Xaa Leu
1

(2) INFORMATION FOR SEQ ID NO: 28:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5..12
        (D) OTHER INFORMATION: /product= "variable amino acids may
            encompass a region of 7-8"

(xi) SEQUENCE DESCRIPTION: SEQ ID NO: 28:

Tyr Xaa Xaa Xaa Xaa Xaa Xaa Xaa Xaa Xaa Xaa Xaa Tyr Xaa Xaa Xaa
1               5                   10                  15

(2) INFORMATION FOR SEQ ID NO: 29:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

Leu Val Pro Arg Gly Ser
1               5

(2) INFORMATION FOR SEQ ID NO: 30:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "phosphotyrosine"

(xi) SEQUENCE DESCRIPTION: SEQ ID NO: 30:

Tyr Asn Glu Leu
1

(2) INFORMATION FOR SEQ ID NO: 31:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "phosphotyrosine"

(xi) SEQUENCE DESCRIPTION: SEQ ID NO: 31:

Tyr Glu Glu Ile
1

(2) INFORMATION FOR SEQ ID NO: 32:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 32:

Asn Leu Gly Arg Arg Glu Glu
1               5

(2) INFORMATION FOR SEQ ID NO: 33:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "phosphotyrosine"

(xi) SEQUENCE DESCRIPTION: SEQ ID NO: 33:

Tyr Asp Val Leu
1

(2) INFORMATION FOR SEQ ID NO: 34:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "phosphotyrosine"

(xi) SEQUENCE DESCRIPTION: SEQ ID NO: 34:

Asp Gly Val Tyr Thr Gly Leu Ser Thr Arg Asn Gln Glu Thr Tyr Glu
1             5                   10                15

Thr Leu Lys (2) INFORMATION FOR SEQ ID NO: 35:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Acetylated"

(ix) FEATURE:
        (A) NAME/KEY: Modified-site
        (B) LOCATION: 7
        (D) OTHER INFORMATION: /product= "phosphotyrosine"

(ix) FEATURE:
        (A) NAME/KEY: Modified-site
        (B) LOCATION: 22
        (D) OTHER INFORMATION: /product= "amidated"

(xi) SEQUENCE DESCRIPTION: SEQ ID NO: 35:

Cys Gly Gly Asp Gly Val Tyr Thr Gly Leu Ser Thr Arg Asn Gln Glu
1             5                   10                15

Thr Tyr Glu Thr Leu Lys
          20

(2) INFORMATION FOR SEQ ID NO: 36:

(i) SEQUENCE CHARACTERISTICS:
        (A) LENGTH: 261 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 36:

```
Gly Ser Met Pro Asp Pro Ala Ala His Leu Pro Phe Phe Tyr Gly Ser
1               5                   10                  15
Ile Ser Arg Ala Glu Ala Glu His Leu Lys Leu Ala Gly Met Ala
            20                  25                  30
Asp Gly Leu Phe Leu Leu Arg Gln Cys Leu Arg Ser Leu Gly Gly Tyr
            35                  40                  45
Val Leu Ser Leu Val His Asp Val Arg Phe His His Phe Pro Ile Glu
    50                  55                  60
Arg Gln Leu Asn Gly Thr Tyr Ala Ile Ala Gly Gly Lys Ala His Cys
65                  70                  75                  80
Gly Pro Ala Glu Leu Cys Glu Phe Tyr Ser Arg Asp Pro Asp Gly Leu
                85                  90                  95
Pro Cys Asn Leu Arg Lys Pro Cys Asn Arg Pro Ser Gly Leu Glu Pro
                100                 105                 110
Gln Pro Gly Val Phe Asp Cys Leu Arg Asp Ala Met Val Arg Asp Tyr
            115                 120                 125
Val Arg Gln Thr Trp Lys Leu Glu Gly Glu Ala Leu Glu Gln Ala Ile
    130                 135                 140
Ile Ser Gln Ala Pro Gln Val Glu Lys Leu Ile Ala Thr Thr Ala His
145                 150                 155                 160
Glu Arg Met Pro Trp Tyr His Ser Ser Leu Thr Arg Glu Glu Ala Glu
                165                 170                 175
Arg Lys Leu Tyr Ser Gly Ala Gln Thr Asp Gly Lys Phe Leu Leu Arg
            180                 185                 190
Pro Arg Lys Glu Gln Gly Thr Tyr Ala Leu Ser Leu Ile Tyr Gly Lys
        195                 200                 205
Thr Val Tyr His Tyr Leu Ile Ser Gln Asp Lys Ala Gly Lys Tyr Cys
    210                 215                 220
Ile Pro Glu Gly Thr Lys Phe Asp Thr Leu Trp Gln Leu Val Glu Tyr
225                 230                 235                 240
Leu Lys Leu Lys Ala Asp Gly Leu Ile Tyr Cys Leu Lys Glu Ala Cys
                245                 250                 255
Pro Asn Ser Ser Ala
            260
```

(2) INFORMATION FOR SEQ ID NO: 37:

(i) SEQUENCE CHARACTERISTICS:
        (A) LENGTH: 260 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 37:

```
Met Ala Asp Ser Ala Asn His Leu Pro Phe Phe Gly Asn Ile Thr
1               5                   10                  15
```

```
Arg Glu Ala Glu Asp Tyr Leu Val Gln Gly Gly Met Ser Asp Gly
         20                  25                  30

Leu Tyr Leu Leu Arg Gln Ser Arg Asn Tyr Leu Gly Gly Phe Ala Leu
             35                  40                  45

Ser Val Ala His Gly Arg Lys Ala His His Tyr Thr Ile Glu Arg Glu
 50                  55                  60

Leu Asn Gly Thr Tyr Ala Ile Ala Gly Gly Arg Thr His Ala Ser Pro
 65                  70                  75                  80

Ala Asp Leu Cys His Tyr His Ser Gln Glu Ser Asp Gly Leu Val Cys
             85                  90                  95

Leu Leu Lys Lys Pro Phe Asn Arg Pro Gln Gly Val Gln Pro Lys Thr
             100                 105                 110

Gly Pro Phe Glu Asp Leu Lys Glu Asn Leu Ile Arg Glu Tyr Val Lys
             115                 120                 125

Gln Thr Trp Asn Leu Gln Gly Gln Ala Leu Glu Gln Ala Ile Ile Ser
             130                 135                 140

Gln Lys Pro Gln Leu Glu Lys Leu Ile Ala Thr Thr Ala His Glu Lys
145                 150                 155                 160

Met Pro Trp Phe His Gly Lys Ile Ser Arg Glu Glu Ser Glu Gln Ile
                 165                 170                 175

Val Leu Ile Gly Ser Lys Thr Asn Gly Lys Phe Leu Ile Arg Ala Arg
             180                 185                 190

Asp Asn Asn Gly Ser Tyr Ala Leu Cys Leu Leu His Glu Gly Lys Val
             195                 200                 205

Leu His Tyr Arg Ile Asp Lys Asp Lys Thr Gly Lys Leu Ser Ile Pro
 210                 215                 220

Glu Gly Lys Lys Phe Asp Thr Leu Trp Gln Leu Val Glu His Tyr Ser
225                 230                 235                 240

Tyr Lys Ala Asp Gly Leu Leu Arg Val Leu Thr Val Pro Cys Gln Lys
                 245                 250                 255

Ile Gly Thr Gln
             260

(2) INFORMATION FOR SEQ ID NO: 38:

(i) SEQUENCE CHARACTERISTICS:
        (A) LENGTH: 259 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 38:

Met Pro Asp Pro Ala Ala His Leu Pro Phe Phe Tyr Gly Ser Ile Ser
 1               5                  10                  15

Arg Ala Glu Ala Glu Glu His Leu Lys Leu Ala Gly Met Ala Asp Gly
             20                  25                  30

Leu Phe Leu Leu Arg Gln Cys Leu Arg Ser Leu Gly Gly Tyr Val Leu
             35                  40                  45

Ser Leu Val His Asp Val Arg Phe His His Phe Pro Ile Glu Arg Gln
 50                  55                  60

Leu Asn Gly Thr Tyr Ala Ile Ala Gly Gly Lys Ala His Cys Gly Pro
 65                  70                  75                  80

Ala Glu Leu Cys Glu Phe Tyr Ser Arg Asp Pro Asp Gly Leu Pro Cys
             85                  90                  95
```

```
Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
        210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala (2) INFORMATION FOR SEQ ID NO: 39:

(i) SEQUENCE CHARACTERISTICS:
        (A) LENGTH: 112 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 39:

Gly Ser Arg Arg Ala Ser Val Gly Ser His Glu Lys Met Pro Trp Phe
1               5                   10                  15

His Gly Lys Ile Ser Arg Glu Glu Ser Glu Gln Ile Val Leu Ile Gly
            20                  25                  30

Ser Lys Thr Asn Gly Lys Phe Leu Ile Arg Ala Arg Asp Asn Asn Gly
        35                  40                  45

Ser Tyr Ala Leu Cys Leu Leu His Glu Gly Lys Val Leu His Tyr Arg
    50                  55                  60

Ile Asp Lys Asp Lys Thr Gly Lys Leu Ser Ile Pro Glu Gly Lys Lys
65                  70                  75                  80

Phe Asp Thr Leu Trp Gln Leu Val Glu His Tyr Ser Tyr Lys Ala Asp
                85                  90                  95

Gly Leu Leu Arg Val Leu Thr Val Pro Cys Gln Lys Ile Gly Thr Gln
            100                 105                 110
```

THREE DIMENSIONAL STRUCTURE OF A ZAP TYROSINE PROTEIN KINASE FRAGMENT AND MODELING METHODS

This application is a divisional of application Ser. No. 08/605,578, filed on Feb. 22, 1996, which claim priority from of, co-owned Provisional U.S. patent applications Ser. Nos. 601002,972 filed Aug. 30, 1995 and 60/003,312 filed Sep. 6, 1995.

COPYRIGHT NOTICE

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention relates to human ZAP-70, and in particular, to the region of ZAP-70 containing the tandem Src homology-2 ("SH2") domains, to crystalline forms thereof, liganded or unliganded, which are particularly useful for the determination of the three-dimensional structure of the protein. The three dimensional structure of the tandem SH2 region of ZAP provides information useful for the design of pharmaceutical compositions which inhibit the biological function of ZAP and other proteins of the ZAP family, particularly those biological functions mediated by molecular interactions involving one or both SH2 domains.

BACKGROUND

Safe and effective immunosuppressive agents are required for the treatment of patients suffering from autoimmune disorders and for recipients of transplanted organs or tissues. For instance, in the absence of an effective immunosuppressive agent, patients often reject a transplanted organ, sometimes with fatal consequences. The immunosuppressive agent must block the immune response, but must also be sufficiently well tolerated by the body to permit chronic application. For instance, one compound with immunosuppressive activity, FK506, has been used to prevent rejection of transplanted livers. However, severe kidney toxicity has been observed in patients receiving FK506, in some cases requiring kidney transplant following the liver transplant.

Research aimed at discovering new immunosuppressive agents has been hampered by the lack of information about precise molecular mechanisms of the immune response. As a result, random screening of compounds has accounted for a substantial share of research efforts aimed at identifying new immunosuppressive drugs. More recently, "structure-based" approaches to drug design have been attempted. For example, compounds designed to bind to the protein FKBP, one of the cellular targets of FK506, were synthesized as candidate immunosuppressive agents. Those efforts were unfortunately doomed by the lack of understanding of the actual molecular mechanism of immunosuppression mediated by FK506. It is now known that FKS506 binds in a complex with two proteins, FKBP and calcineurin. FK506's immunosuppressive effects are due to the inhibition of calcineurin in T cells. However, since calcineurin is present and important in other cells, FK506 affects other cells and tissues leading to undesired effects.

Meanwhile, independent efforts have led to the identification of a protein tyrosine kinase, ZAP-70, as a critical mediator of the immune response. Blocking the biological function of ZAP-70 will lead to immunosuppression. Unfortunately, until now, three-dimensional structural details of ZAP-70 have been completely unknown. In the absence of three-dimensional structural details for that protein, designing inhibitors based on that structure would have been impossible. We have now obtained crystals of a critical region of ZAP-70 containing its tandem SH2 domains, with and without bound ligands of various types, and have determined its three dimensional structure. With this information, it is now possible for the first time to rationally design inhibitors of ZAP-70 which can function as immunosuppressive agents, e.g. compounds which inhibit molecular interactions involving one or both of the ZAP-70 SH2 domains. Although the three-dimensional structures for several individual SH2 domains of other proteins are known, no one has heretofore reported determining the three-dimensional structure of a tandem SH2 region. And, as we discuss below, the three-dimensional coordinates of previously known SH2 domains would have been insufficient to solve the structure of the ZAP-70 tandem SH2 region.

SUMMARY OF THE INVENTION

This invention concerns the region of human ZAP-70 spanning its two SH2 domains. We refer to that region as the "ZAP tandem SH2 region" or simply "ZAP-NC" (SEQ ID NO: 38), since the region contains both the more N-terminal SH2 domain and the more C-terminal SH2 domain of human ZAP-70 (see FIG. 4). The invention begins with obtaining crystals of human ZAP-NC (SEQ ID NO: 36), complexed or uncomplexed with various ligands, of sufficient quality to determine the three dimensional (tertiary) structure of the protein by X-ray diffraction methods.

In considering our work, it should be appreciated that obtaining protein crystals in any case is a somewhat unpredictable art, especially in cases in which the practitioner lacks the guidance of prior successes in preparing and/or crystallizing any closely related proteins. Obtaining our first crystals of ZAP-NC (SEQ ID NO: 36) was therefore itself an unexpected result. In addition, our determination of the three-dimensional structure of ZAP-NC (SEQ ID NO: 36) represents the first solution of a three-dimensional structure for a tandem SH2 region from any protein and revealed an unpredicted array of surface features which contained truly surprising structural aspects. Our results are useful in a number of applications.

For example, the knowledge obtained concerning ZAP-NC (SEQ ID NO: 36) can be used to model the tertiary structure of related proteins. For instance, the structure of renin has been modeled using the tertiary structure of endothiapepsin as a starting point for the derivation. Model building of cercarial elastase and tophozoite cysteine protease were each built from known serine and cysteine proteases that have less than 35% sequence identity. The resultant models were used to design inhibitors in the low micromolar range. (*Proc. Natl. Acad. Sci.* 1993, 90, 3583). Furthermore, alternative methods of tertiary structure determination that do not rely on X-ray diffraction techniques and thus do not require crystallization of the protein, such as NMR techniques, are simplified if a model of the structure is available for refinement using the additional data gathered by the alternative technique. Thus, knowledge of the tertiary structure of the ZAP tandem SH2 region provides a significant window to the structure of the other ZAP family members, including for example SYK.

Knowledge of the three-dimensional structure of a tandem SH2 region such as ZAP-NC (SEQ ID NO: 36) provides a means for investigating the mechanism of action of the protein and tools for identifying inhibitors of its function. For example, SH2 domains are known to be involved in intramolecular and intermolecular interactions, usually protein-protein interactions, which are critical for biological activity of the SH2-bearing protein. Knowledge of the three-dimensional structure of the tandem SH2 region allows one to design molecules capable of binding thereto, including molecules which are thereby capable of inhibiting the interaction of the tandem SH2 region with its natural ligand(s).

Accordingly, one object of this invention is to provide a composition comprising a protein in crystalline form having a peptide sequence derived or selected from that of a protein of the ZAP family. The protein will comprise at least one, and preferably two SH2 domains, e.g., a protein containing the tandem SH2 region of ZAP-70, SYK or other related tandem SH2 containing protein. In the case of ZAP-70, the protein may comprise a peptide sequence spanning at least amino acid residues 3-279. Such a crystalline composition may contain one or more heavy atoms, e.g., one or more lead, mercury, gold and/or selenium atoms, for instance. Such a heavy atom derivative may be obtained, for example, by expressing a gene encoding the protein under conditions permitting the incorporation of one or more heavy atom labels (e.g. as in the incorporation of selenomethionine), reacting the protein with a reagent capable of linking a heavy atom to the protein (e.g. trimethyl lead acetate) or soaking a substance containing a heavy atom into the crystals.

The protein may be in the form of a complex with one or more ligand molecules, "ligand" being used in the broadest sense, referring to any substance capable of observable binding to the protein. The peptide sequence of naturally occuring ligands ("ITAMs", see below) for a number of SH2 domains is known and consensus sequence information on peptide ligands for SH2 domains has been discussed in the scientific literature. In the case of ZAP-70, peptide ligands of 15–19 residues derived in sequence from naturally occurring ligands for ZAP-70 or other SH2 domains may be used. Those ligands typically contain one or two phosphorylated tyrosine residues. Alternatively, one or both of such phosphorylated tyrosine moieties may be replaced by phosphotyrosine mimetic reagents, numerous examples of which are known in the art.

Illustrative crystalline compositions of this invention having various physicochemical characteristics are disclosed infra. Preferred crystalline compositions of this invention are capable of diffracting x-rays to a resolution of better than about 3.5 Å, and more preferably to a resolution of 2.6 Å or better, and even more preferably to a resolution of 2.2 Å or better, and are useful for determining the three-dimensional structure of the material. (The smaller the number of angstroms, the better the resolution.)

Crystalline compositions of this invention specifically include those in which the crystals comprise ZAP-family proteins characterized by the structural coordinates set forth in any of the accompanying Tables 17–20 or characterized by coordinates having a root mean square deviation therefrom, with respect to backbone atoms of amino acids listed in Tables 17–20, of 1.5 Å or less.

Structural coordinates of a crystalline composition of this invention may be stored in a machine-readable form on a machine-readable storage medium, e.g. a computer hard drive, diskette, DAT tape, etc., for display as a three-dimensional shape or for other uses involving computer-assisted manipulation of, or computation based on, the structural coordinates or the three-dimensional structures they define. For example, data defining the three dimensional structure of a protein of the ZAP family, or portions or structurally similar homologues of such proteins, may be stored in a machine-readable storage medium, and may be displayed as a graphical three-dimensional representation of the protein structure, typically using a computer capable of reading the data from said storage medium and programmed with instructions for creating the representation from such data. This invention thus encompasses a machine, such as a computer, having a memory which contains data representing the structural coordinates of a crystalline composition of this invention, e.g. the coordinates set forth in Tables 17–20, together with additional optional data and instructions for manipulating such data. Such data may be used for a variety of purposes, such as the elucidation of other related structures and drug discovery.

For example, a first set of such machine readable data may be combined with a second set of machine-readable data using a machine programmed with instructions for using the first data set and the second data set to determine at least a portion of the coordinates corresponding to the second set of machine-readable data. For instance, the first set of data may comprise a Fourier transform of at least a portion of the coordinates for ZAP or SYK proteins set forth in Tables 17–20, while the second data set may comprise X-ray diffraction data of a molecule or molecular complex.

More specifically, one of the objects of this invention is to provide three-dimensional structural information on new complexes of ZAP family members with various ligands, as well as structural information on other tandem SH2 regions, previously unsolved individual SH2 domains, new ZAP family members and muteins or other variants of any of the foregoing. To that end, we provide for the use of the structural coordinates of a crystalline composition of this invention, or portions thereof, to solve, e.g., by molecular replacement, the three dimensional structure of a crystalline form of such a protein or protein:ligand complex, typically involving a protein containing at least one SH2 domain. Doing so involves obtaining x-ray diffraction data for crystals of the protein or protein:ligand co-complex for which one wishes to determine the three dimensional structure. Then, one determines the three-dimensional structure of that protein or complex by analyzing the x-ray diffraction data using molecular replacement techniques with reference to the previous structural coordinates. As described in U.S. Pat. No. 5,353,236, for instance, molecular replacement uses a molecule having a known structure as a starting point to model the structure of an unknown crystalline sample. This technique is based on the principle that two molecules which have similar structures, orientations and positions in the unit cell diffract similarly. Molecular replacement involves positioning the known structure in the unit cell in the same location and orientation as the unknown structure. Once positioned, the atoms of the known structure in the unit cell are used to calculate the structure factors that would result from a hypothetical diffraction experiment. This involves rotating the known structure in the six dimensions (three angular and three spatial dimensions) until alignment of the known structure with the experimental data is achieved. This approximate structure can be fine-tuned to yield a more accurate and often higher resolution structure using various refinement techniques. For instance, the resultant model for the structure defined by the experimental data may be subjected to rigid body refinement in which the model is subjected to limited additional rotation in the six dimensions yielding positioning shifts of under about 5%. The refined model may then be further refined using other known refinement methods.

For example, one may use molecular replacement to exploit a set of coordinates such as set forth in Table 17, 18, or 19 to determine the structure of a crystalline co-complex of ZAP-NC (SEQ ID NO: 36), or a portion thereof, with a ligand other than the ζ1 peptide (SEQ ID No. 6). Likewise one may use that same approach to determine the three dimensional structure of a co-complex of SYK-NC (SEQ ID NO: 37), or a portion thereof, with a ligand therefor.

Another object of the invention is to provide a method for determining the three-dimensional structure of a protein containing at least one SH2 domain, or a co-complex of the protein with a ligand therefor, using homology modeling techniques and structural coordinates for a composition of this invention. Homology modeling involves constructing a model of an unknown structure using structural coordinates of one or more related proteins, protein domains and/or subdomains. Homology modeling may be conducted by fitting common or homologous portions of the protein or peptide whose three dimensional structure is to be solved to the three dimensional structure of homologous structural elements. Homology modeling can include rebuilding part or all of a three dimensional structure with replacement of amino acids (or other components) by those of the related structure to be solved. For example, using the structural coordinates of ZAP-NC (SEQ ID NO: 36) complexed with the ζ1 peptide (SEQ ID NO: 6), one may determine the three dimensional structure of SYK-NC (SEQ ID NO: 37) or a portion thereof, using homology modeling. A set of coordinates defining the three dimensional structure of SYK-C (SEQ ID No. 39) complexed with the peptide Thr-pTyr-Glu-Thr-Leu (SEQ ID NO: 26) which were obtained from evaluation of NMR data are set forth in Table 20. Those coordinates may be stored, displayed, manipulated and otherwise used in like fashion as the ZAP-NC (SEQ ID NO: 36) coordinates of Tables 17–19.

Thus, crystalline compositions of this invention provide a starting material for use in solving the three-dimensional structure of other members of the ZAP-70 family of proteins, notably SYK, as well as newly discovered proteins containing at least one SH2 domain and linking polypeptide (i.e., non-SH2 polypeptide) where the linking polypeptide has at least about 25% peptide sequence similarity, or preferably identity, to a portion (preferably at least six amino acids) of the ZAP-NC (SEQ ID NO: 36) or SYK-NC inter-SH2 linking domain. Sequence similarity may be determined using any conventional similarity matrix. See e.g. Dayhoff, M. O.; Schwartz, R. M.; Orcutt, B. C., *Atlas of Protein Sequence and Structure* 1979, 5, Suppl. 3,345; Greer, J., *J. Mol. Biol.* 1981, 153, 1027; and Gonnet, G. H., Cohen, M. A., Benner, S. A. *Science* 1992, 256, 1443. Proteins containing at least one SH2 domain together with non-SH2 domain peptide sequence homologous to the inter-domain linker of ZAP or SYK, i.e. containing at least 25% peptide sequence identity or similarity as described above, are considered ZAP family members for the purpose of this disclosure.

By way of further example, the structure defined by the machine readable data may be computationally evaluated for its ability to associate with various chemical entities. The term "chemical entity", as used herein, refers to chemical compounds, complexes of at least two chemical compounds, and fragments of such compounds or complexes.

For instance, a first set of machine-readable data defining the 3-D structure of a ZAP-family protein, or a portion or co-complex thereof, is combined with a second set of machine-readable data defining the structure of a chemical entity or moiety of interest using a machine programmed with instructions for evaluating the ability of the chemical entity or moiety to associate with the ZAP-family protein or portion or complex thereof and/or the location and/or orientation of such association. Such methods provide insight into the location, orientation and energetics of association of the ZAP family protein with such chemical entities.

Chemical entities that are capable of associating with the ZAP family member may inhibit its interaction with naturally occurring ligands for the protein and may inhibit biological functions mediated by such interaction. In the case of ZAP-70, such biological functions include activation of T cells during an immune response. Such chemical entities are potential drug candidates.

The protein structure encoded by the data may be displayed in a graphical format permitting visual inspection of the structure, as well as visual inspection of the structure's association with chemical entities. Alternatively, more quantitative or computational methods may be used. For example, one method of this invention for evaluating the ability of a chemical entity to associate with any of the molecules or molecular complexes set forth herein comprises the steps of: a) employing computational means to perform a fitting operation between the chemical entity and a binding pocket or other surface feature of the molecule or molecular complex; and b) analyzing the results of said fitting operation to quantify the association between the chemical entity and the binding pocket.

This invention further provides for the use of the structural coordinates of a crystalline composition of this invention, or portions thereof, to identify reactive amino acids, such as cysteine residues, within the three-dimensional structure, preferably within or adjacent to a ligand binding site; to generate and visualize a molecular surface, such as a water-accessible surface or a surface comprising the space-filling van der Waals surface of all atoms; to calculate and visualize the size and shape of surface features of the protein or complex, e.g., ligand binding pockets; to locate potential H-bond donors and acceptors within the three-dimensional structure, preferably within or adjacent to a ligand binding site; to calculate regions of hydrophobicity and hydrophilicity within the three-dimensional structure, preferably within or adjacent to a ligand binding site; and to calculate and visualize regions on or adjacent to the protein surface of favorable interaction energies with respect to selected functional groups of interest (e.g. amino, hydroxyl, carboxyl, methylene, alkyl, alkenyl, aromatic carbon, aromatic rings, heteroaromatic rings, substituted and unsubstituted phosphates, substituted and unsubstituted phosphonates, substituted and unsubstituted fluoro and difluorophosphonates; etc.). One may use the foregoing approaches for characterizing the protein and its interactions with moieties of potential ligands to design or select compounds capable of specific covalent attachment to reactive amino acids (e.g., cysteine) and to design or select compounds of complementary characteristics (e.g., size, shape, charge, hydrophobicity/hydrophilicity, ability to participate in hydrogen bonding, etc.) to surface features of the protein, a set of which may be preselected. Using the structural coordinates, one may also predict or calculate the orientation, binding constant or relative affinity of a given ligand to the protein in the complexed state, and use that information to design or select compounds of improved affinity.

In such cases, the structural coordinates of the ZAP family protein, or portion or complex thereof, are entered in machine readable form into a machine programmed with instructions for carrying out the desired operation and containing any necessary additional data, e.g. data defining structural and/or functional characteristics of a potential ligand or moiety thereof, defining molecular characteristics of the various amino acids, etc.

One method of this invention provides for selecting from a database of chemical structures a compound capable of binding to a ZAP family protein. The method starts with structural coordinates of a crystalline composition of the invention, e.g., coordinates defining the three dimensional structure of a ZAP family protein or a portion thereof. Points associated with that three dimensional structure are characterized with respect to the favorability of interactions with one or more functional groups. A database of chemical structures is then searched for candidate compounds containing one or more functional groups disposed for favorable interaction with the protein based on the prior characterization. Compounds having structures which best fit the points of favorable interaction with the three dimensional structure are thus identified.

It is often preferred, although not required, that such searching be conducted with the aid of a computer. In that case a first set of machine-readable data defining the 3D structure of a ZAP-family protein, or a portion or protein-ligand complex thereof, is combined with a second set of machine readable data defining one or more moieties or functional groups of interest, using a machine programmed with instructions for identifying preferred locations for favorable interaction between the functional group(s) and atoms of the protein. A third set of data, i.e. data defining the location(s) of favorable interaction between protein and functional group(s) is so generated. That third set of data is then combined with a fourth set of data defining the 3D structures of one or more chemical entities using a machine programmed with instructions for identifying chemical entities containing functional groups so disposed as to best fit the locations of their respective favorable interaction with the protein.

Compounds of the structures selected or designed by any of the foregoing means may be tested for their ability to bind to a ZAP family protein, inhibit the binding of a ZAP family protein to a natural or non-natural ligand therefor, and/or inhibit a biological function mediated by a ZAP family member.

This invention also provides peptidomimetic methods for designing a compound capable of binding to a ZAP family protein. One such method involves graphically displaying a three-dimensional representation based on coordinates defining the three-dimensional structure of a ZAP family protein or a portion thereof complexed with a ligand. interactions between portions of a ligand and the protein are characterized in order to identify candidate moieties for replacement. One or more portions of the ligand which interact with the protein may be replaced with substitute moieties selected from a knowledge base of one or more candidate substitute moieties, and/or moieties may be added to the ligand to permit additional interactions with the protein.

The computational approaches and structural insights disclosed herein also permit the design or identification of molecules with reduced capability, or substantial inability, to bind to a ZAP family protein. To such end, one may apply the same modeling and computational methods to the data described herein, but with the opposite goal, i.e., to design or identify compounds which lack substantial binding affinity to one or more ZAP family members. That can be useful in research efforts aimed at discovery of inhibitors of SH2-mediated interactions other than those mediated by a ZAP family member. The goal of such efforts are inhibitors of those other SH2-mediated interactions which lack ZAP-family mediated activities, such as immunosuppression, which in that context, would be undesired side effects.

Compounds first identified by any of the methods described herein are also encompassed by this invention.

unboxed areas are excluded from the calculation due to the presence of gaps for one or more of the sequences. Notation below the alignments indicate structurally conserved regions, and use the previously reported nomenclature;[20] these regions were used for the "core" r.m.s. deviation calculation. Shaded regions indicate the secondary structural elements in ZAP-NC. Src=avian Src; Lck=human p56-Lck; Syp-N=N-terminal SH2 of murine Syp phosphatase (PTP1D); ZAP-N(C)=N- or C-terminal SH2 of human ZAP-70.

Figure 1A:
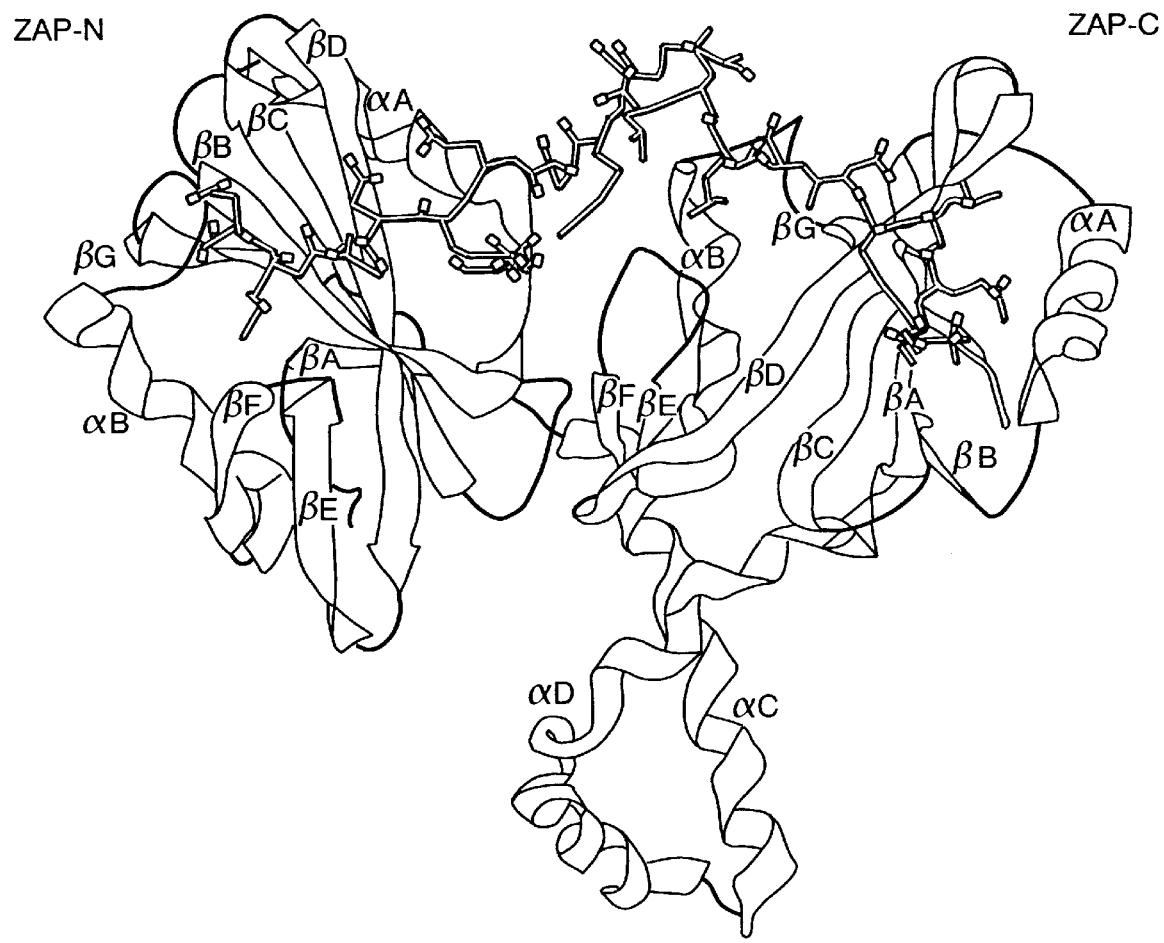
FIG. 1A Backbone ribbon representation of the overall fold of the complex of ZAP-NC (SEQ ID NO: 36) and the ζ1 peptide (SEQ ID NO: 6) oriented such that the N-terminal SH2 domain is on the left-hand side of the figure, the C-terminal SH2 domain is on the right-hand side of the figure and the inter-SH2 domain region is in the middle, dropping toward the bottom of the figure. Secondary structural elements are labeled according to the convention for SH2 domains. [20] An α-carbon trace of the peptide is included. All elements are labeled in ZAP-N; in ZAP-C, only the central sheet and helices are labeled. Termini of the protein and peptide are denoted by N and C. Loop regions are named for the secondary elements which they connect, i.e., the BC loop connects strands B and C. The N terminus of the peptide is at the right-hand side of the figure. The peptide consists of 19 residues, starting at residue 48 of the mature ζ subunit of the T cell receptor (TCR). Phosphotyrosines are at relative positions 4 and 15 (SEQ ID NO: 6). Definition of least squares planes fitted to the main chain atoms of each pYXXL motif (SEQ ID NO: 27) generates a pair of planes at an angle of 120°. Due to the staggered orientation of the SH2 domains, the pYXXL motifs (SEQ ID NO: 27) are separated by an "S"-shaped segment of peptide. This sequence contains nearly one full turn of an α-helix between residues ζ Asn 8 and ζ Arg 12 (SEQ ID NO: 6). Pockets for each pY and pY+3 residue are visible. It is notable that the N-terminal $ζ_1$ residues contribute to the enclosure of ζpTyr 4 (SEQ ID NO: 6). The figure was generated with Sybyl (Tripos). An electron density map of the region near the interface between the two SH2 domains may be calculated with $2|F_o|-|F_c|$ coefficients for data between 15.0 and 1.9 Å, contoured at 1.0 s.
Figure 1B:
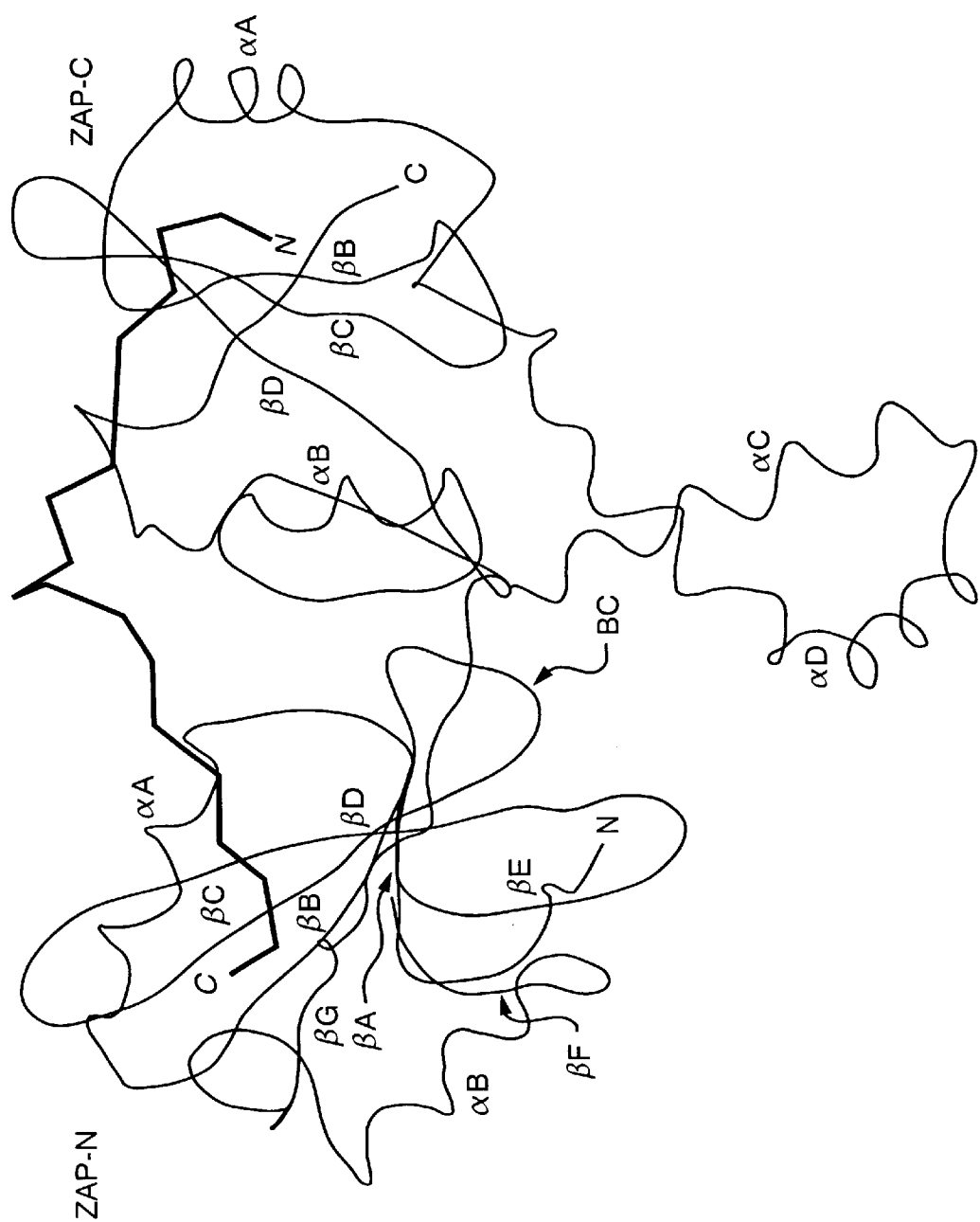
FIG. 1B The BC loop, from β B5 to β C3, of ZAP-N may be superimposed with the corresponding residues of the Lck SH2:middle T complex[20] and the relative position of the BC loops examined when the structures are fitted according to secondary structural elements. Superimposition of the backbone atoms of the loops results in an r.m.s. deviation of 0.65 Å. Similar results are observed with the BC loop of ZAP-C. In complexes of phosphopeptides with isolated SH2 domains, the BC loop contributes nearly half of the direct hydrogen bonds to the phosphate group. For both SH2 domains of ZAP-NC (SEQ ID NO: 36), the BC loop is extended such that several waters are mediating contact between the loop and the phosphate group. An extended conformation is also observed for uncomplexed SH2 domains, and has been reported in complexes with peptides in which the phosphate group is replaced by a phosphonate.[14] The loop is repositioned via a hinged motion about the residues at β B5 and β C3. The BC loop of ZAP-C is more extended; ZAP-N experiences hindered motion about BC due to its interactions with ZAP-C.
Figure 2:
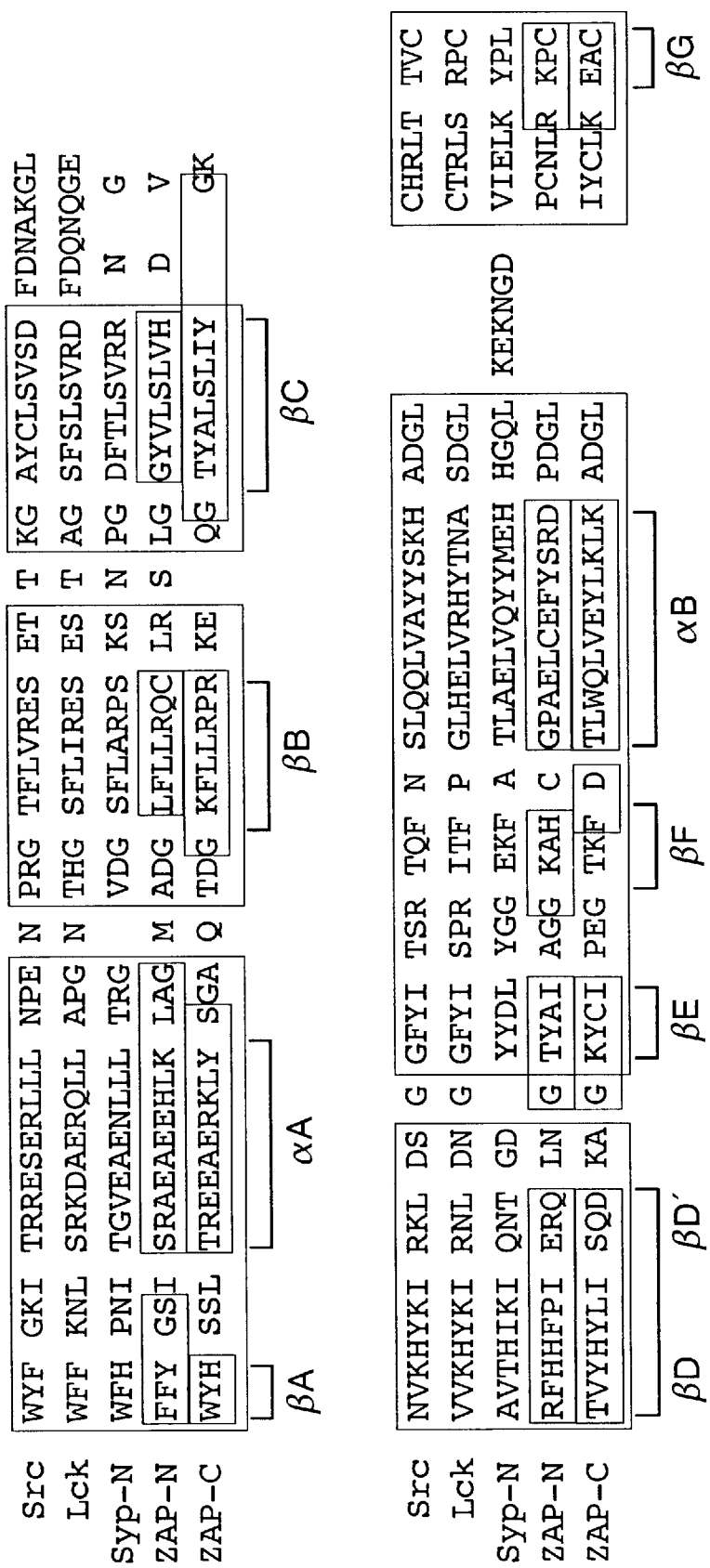
FIG. 2 [SEQ ID NOS. 21–25] Sequence alignments for selected SH2 domains.[33] Boxed areas indicate segments used for measuring "full" backbone r.m.s. deviation.
Figure 3A:
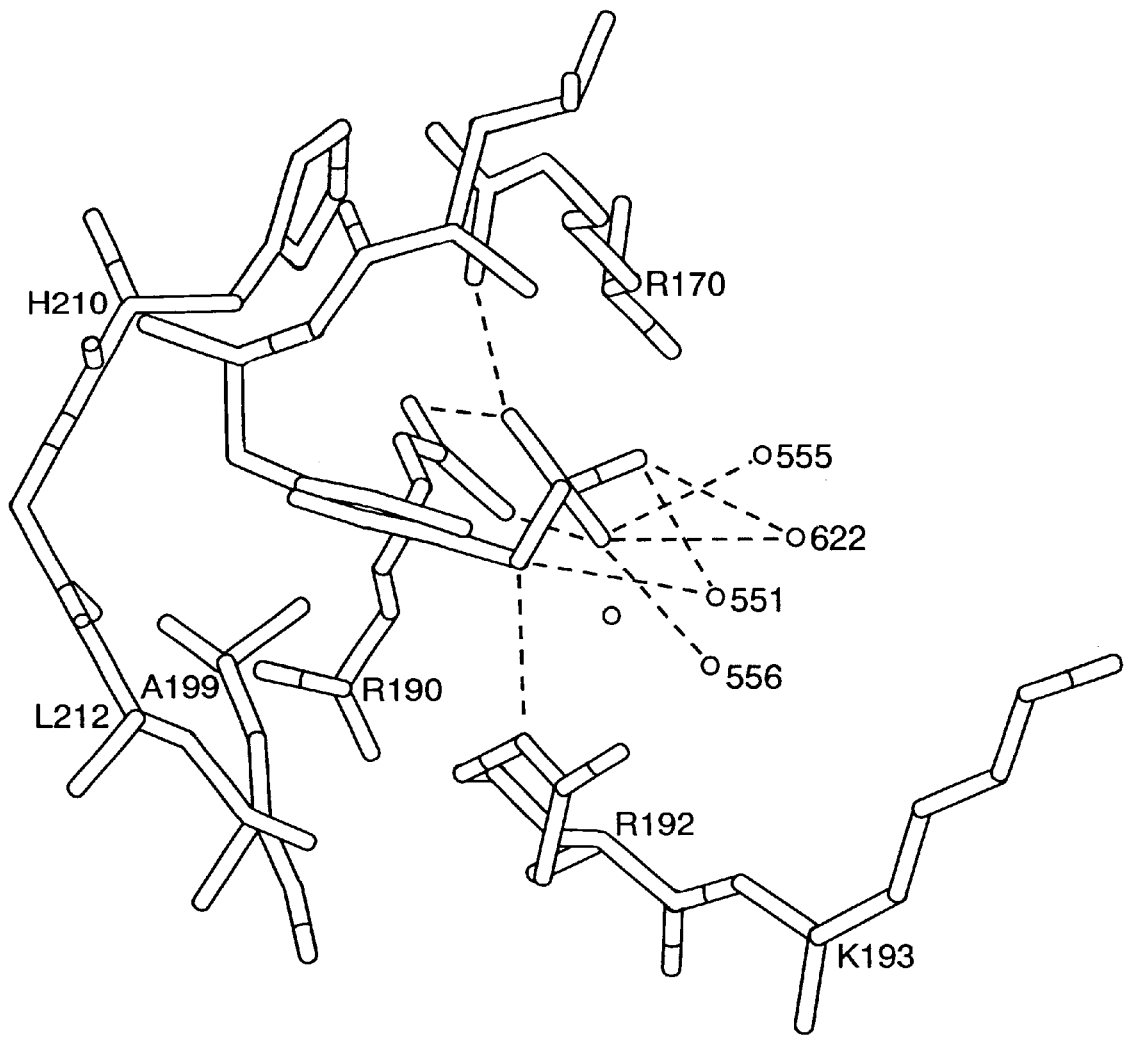
Figure 3B:
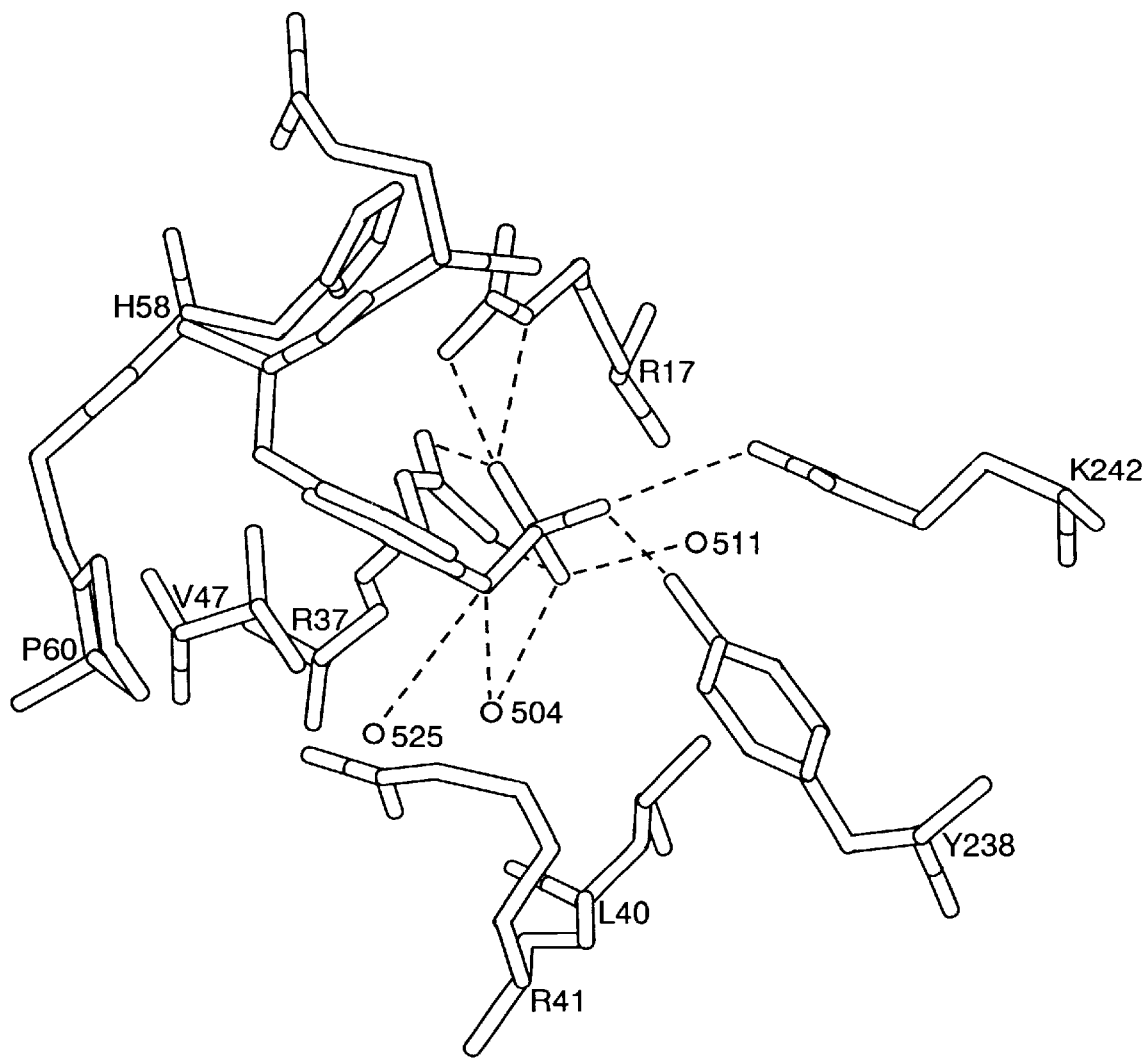
Figure 3C:
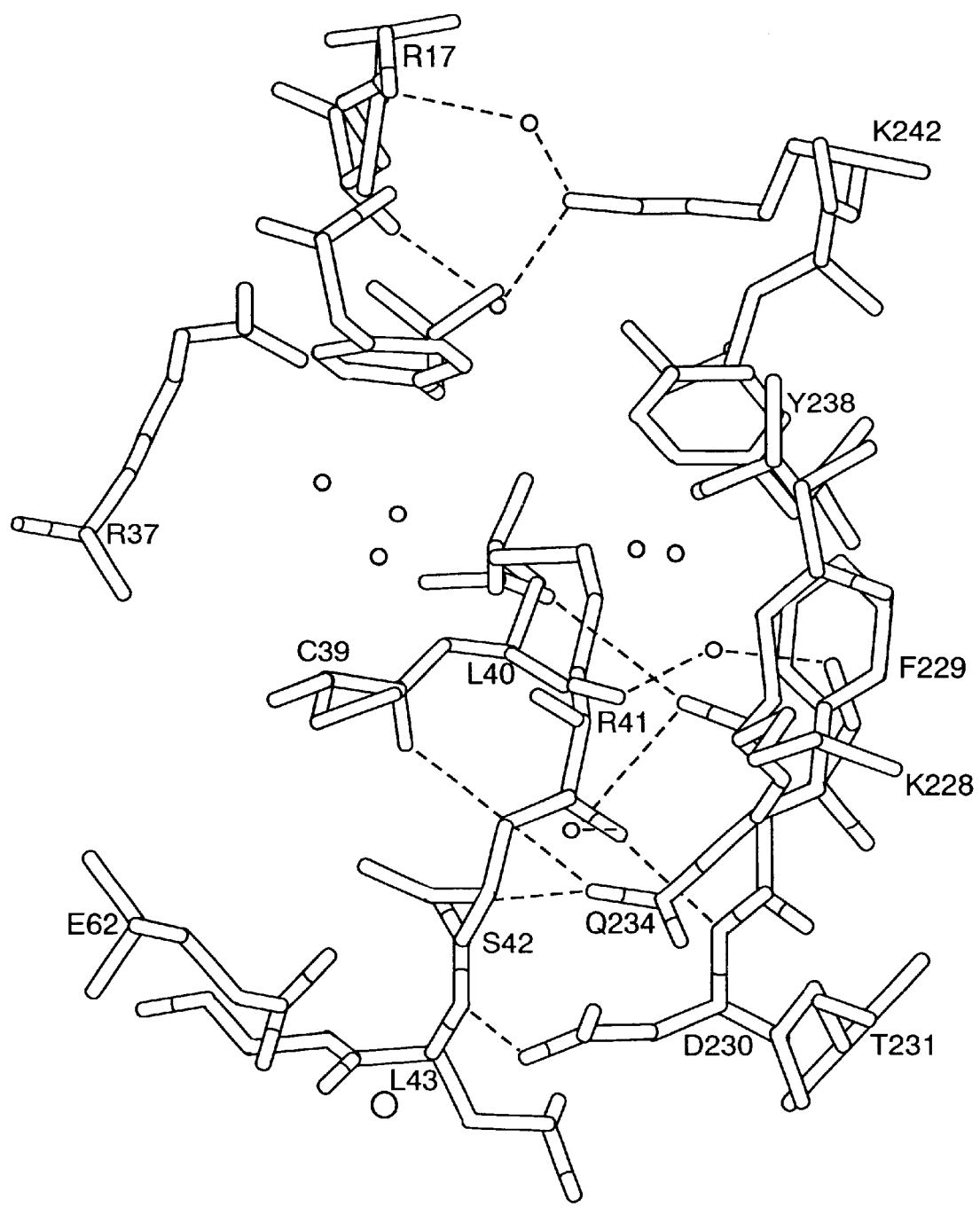

FIG. 3 Phosphotyrosine binding sites. The phosphotyrosine residues are oriented in a similar fashion in each figure to facilitate direct comparison. (a) Selected residues for the ζ pTyr 4 (SEQ ID NO: 6) association with ZAP-C. Direct hydrogen bonds to the phosphate group of ζ pTyr 4 (SEQ ID NO: 6) are indicated by dashed lines. Crystallographic waters are indicated as spheres; waters labeled 551, 555, and 556 make bridging contacts between the phosphate and the SH2 domain, water 622 forms a bridge to $\zeta_1$ (SEQ ID NO: 6). (b) Selected residues in close association with ζ pTyr 15 (SEQ ID NO: 6). As in a, dashed lines indicate direct hydrogen bonds to the phosphate group. Tyr 238 and Lys 242 from ZAP-C complete the hydrogen-bonding network of the phosphate. Waters are represented as spheres; all of them are involved in salt-bridging the phosphotyrosine to the SH2 domains. Several residues that form the pocket have been omitted for clarity. (c) The interface between the SH2 domains involves an extensive network of hydrogen bonds. Interactions involving ζ pTyr 15 have been described elsewhere herein. Several hydrophobic contacts also exist, the most provocative of these is the protrusion of Arg 41 (ZAP-N BC loop) into a small hydrophobic depression formed by Phe 229 (ZAP-C βF), Tyr 238 (ZAP-C αB), and the side chain of Thr 227 (ZAP-C EF loop) (SEQ ID NO: 36). Arg 41 (SEQ ID NO: 6) also has three hydrogen-bonding contacts to ZAP-C. This is the first of three residues in the BC loop of ZAP-N that form an artificial parallel sheet with strand F in ZAP-C. Only one of the three hydrogen-bonding contacts involves main chain atoms exclusively.

Figure 4:
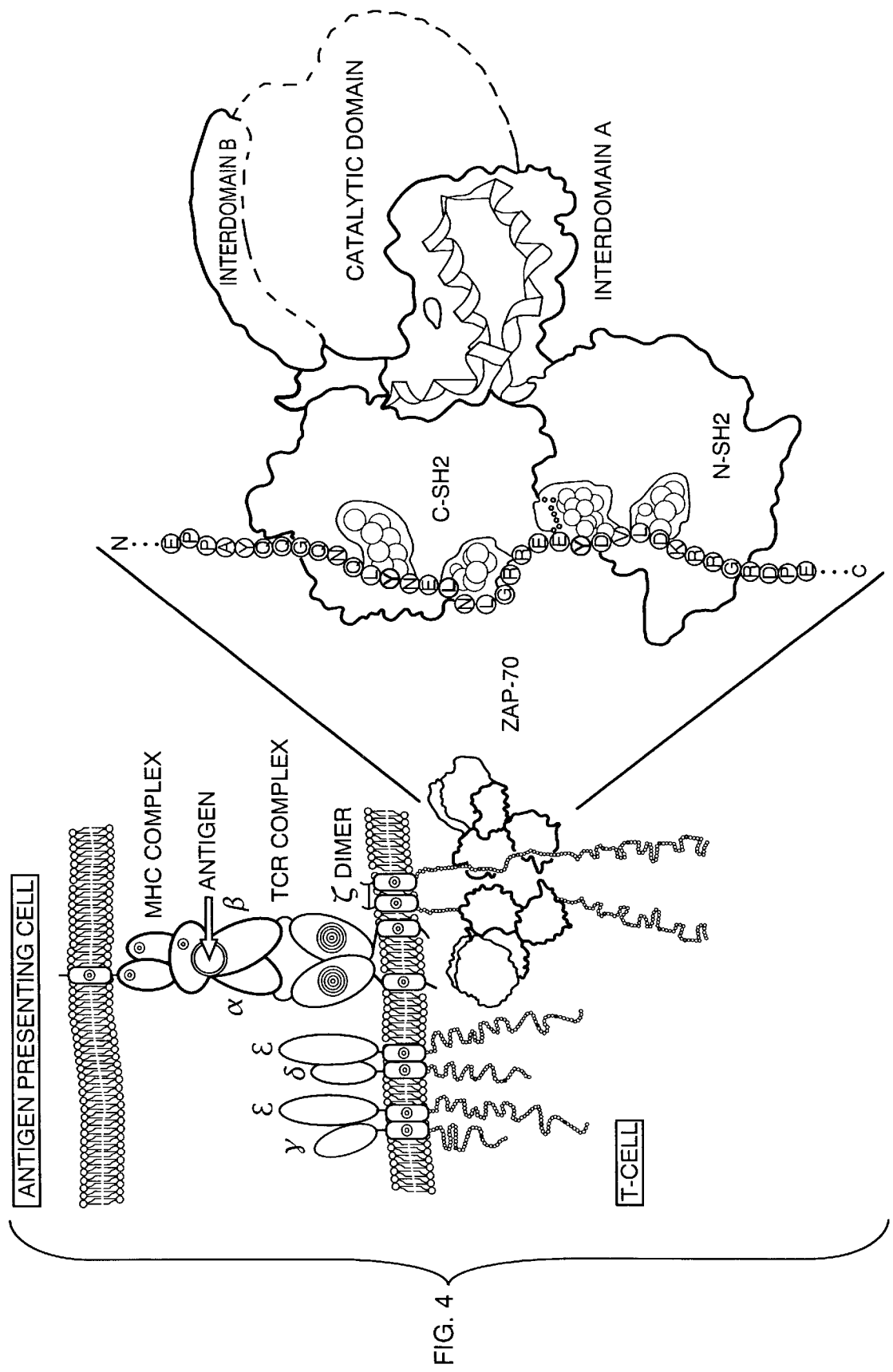

FIG. 4 Schematic view of ZAP-70 bound to the $\zeta_1$ (SEQ ID NO: 6) subunit of the activated T cell receptor. Left: Activation of T cells is initiated by association of the T cell receptor (TCR) with a peptide antigen bound to the major histocompatibility complex (MHC) on an antigen-presenting cell. TCR-MHC association stimulates phosphorylation of T cell receptor subunits on tyrosines within the ITAMs (most likely by the Src family PTKs, Lck or Fyn). ZAP-70 binds to the phosphorylated ITAM via its tandem SH2 domains (amino acids 1–259) in an orientation such that the N-SH2 domain binds to the C-proximal pYXXL (SEQ ID NO: 27) motif and the C-SH2 domain binds the N-proximal pYXXL motif. Proposed positions of the other domains of ZAP-70, referred to as interdomain B (amino acids 260–310) and catalytic domain (amino acids 311–620) are illustrated. Two ZAP-70 molecules could bind to the activated TCR complex since the ζ subunit is present as a disulfide-linked dimer. Right: Schematic representation of the complex between the SH2 domains of ZAP-70 in complex with the doubly-phosphorylated $\zeta_1$ ITAM (SEQ ID NO: 6). The SH2 domains of ZAP-70 make extensive contacts with the $\zeta_1$ peptide (SEQ ID NO: 6). The primary determinants of binding are the phosphotyrosine and leucine residues of two pYXXL sequences (SEQ ID NO: 27) within an ITAM. The structure reveals a unique binding pocket for the pY of the C-proximal pYXXL motif (SEQ ID NO: 27) in the interface between the two SH2 domains. In addition, the crystal structure reveals that interdomain A forms a coiled-coil helical structure. This domain may participate in positioning the two SH2 domains for association with ITAMs, and in communicating structural changes to interdomain B and/or the kinase domain upon receptor engagement.

Figure 5A:
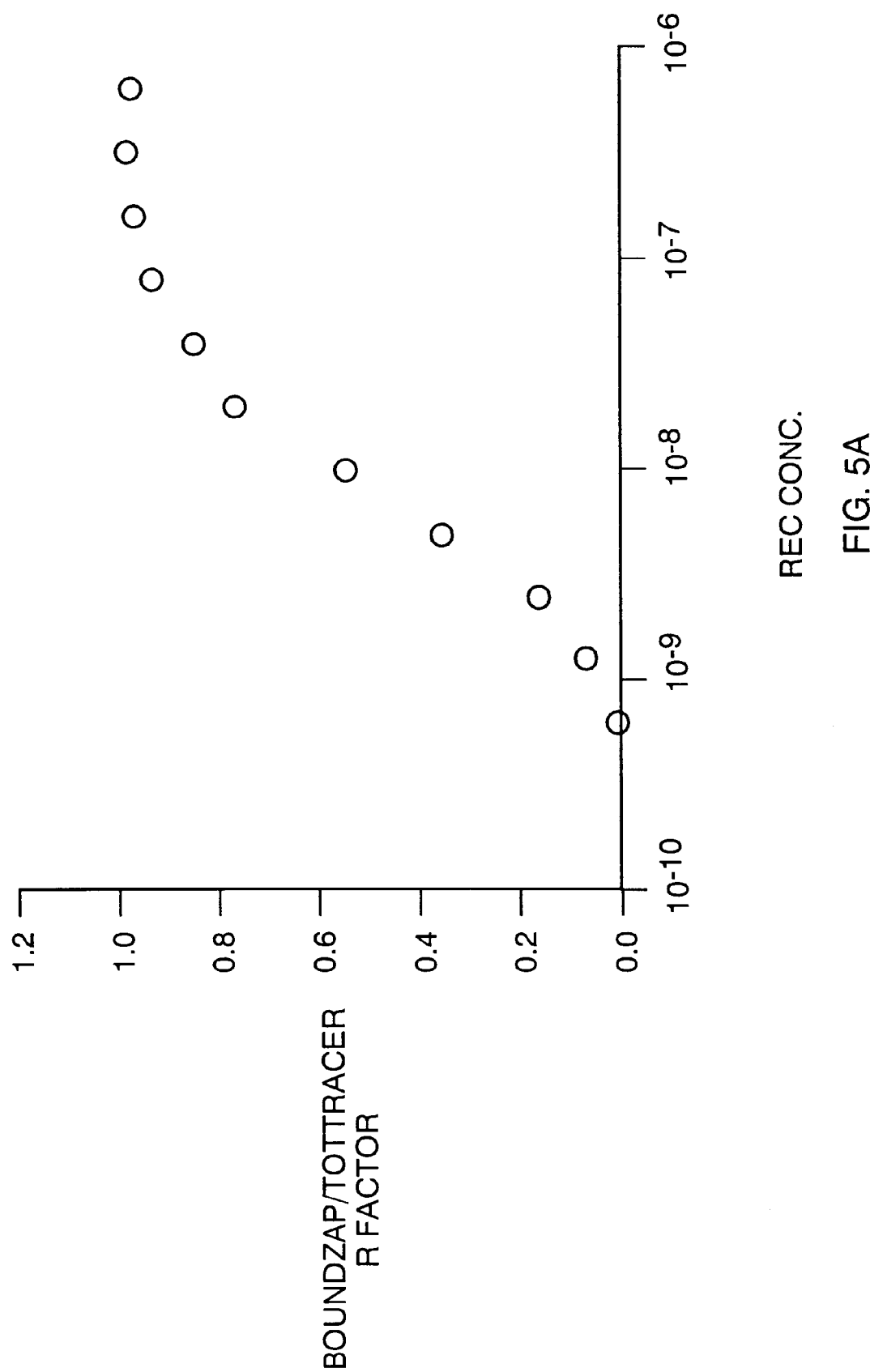
Figure 5B:
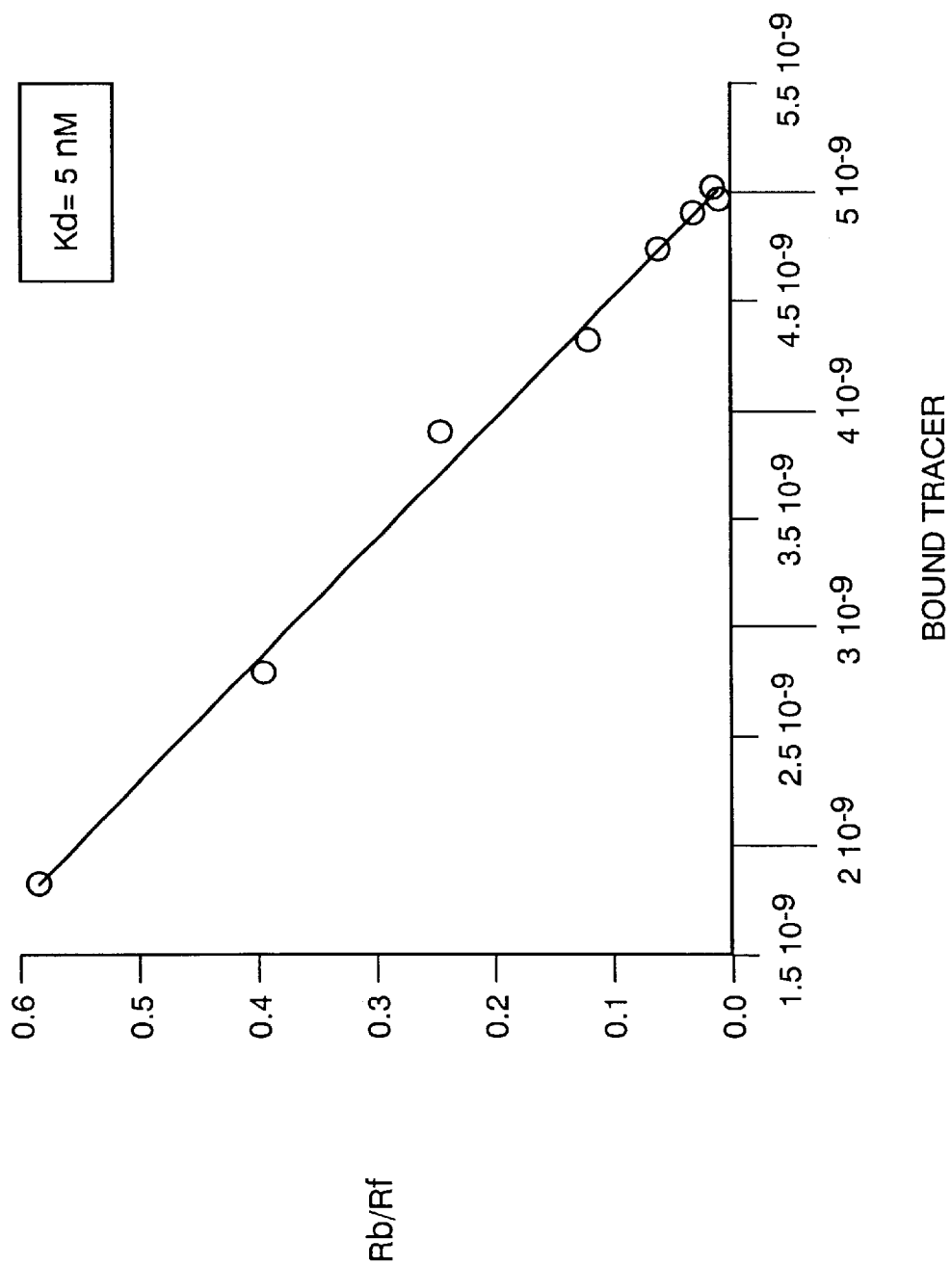

FIG. 5 depicts a binding curve of a doubly-phosphorylated ζ-1:ZAP-NC complex, with associated Scatchard plot of the data, as determined by fluorescence polarization.

Figure 6:
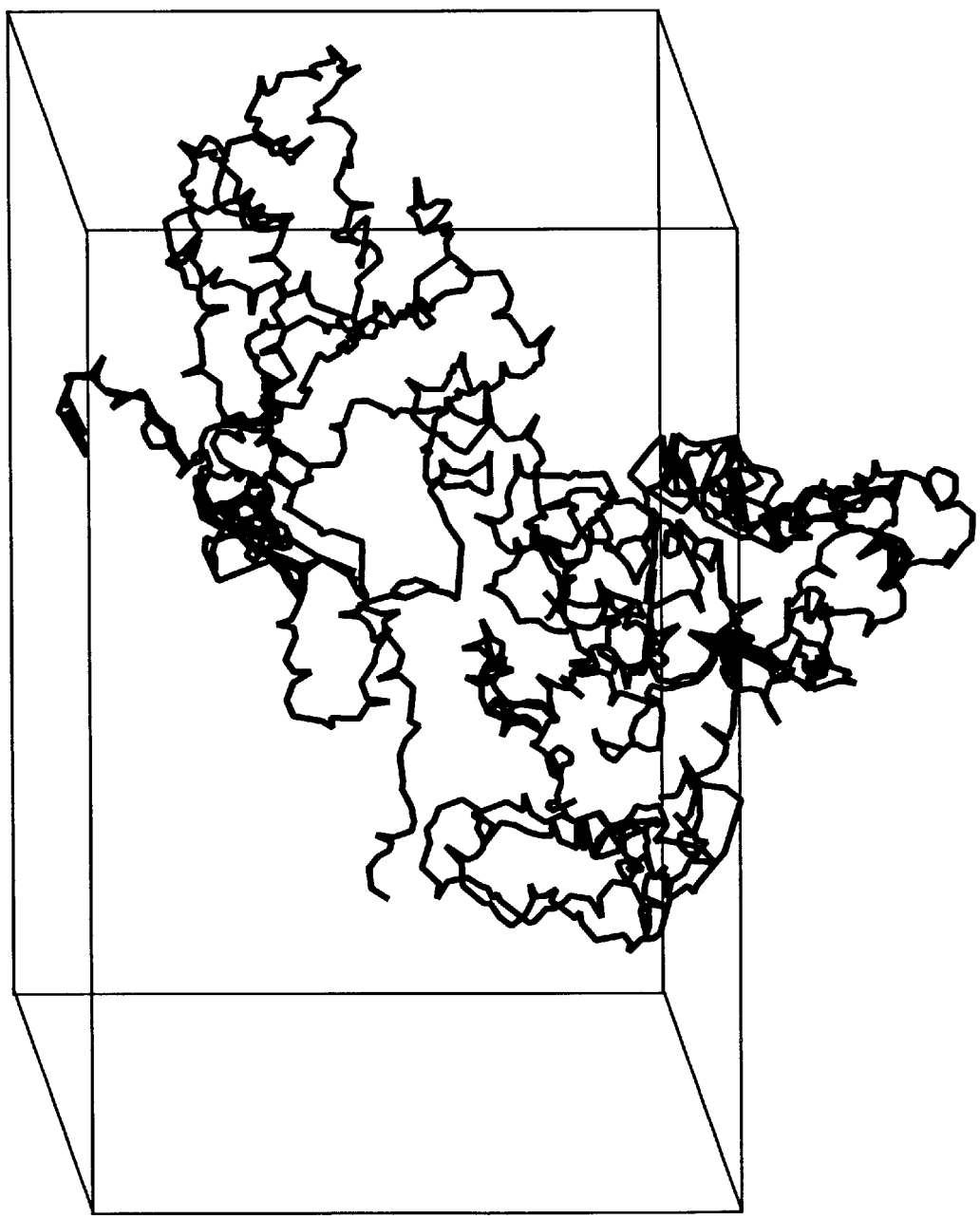

FIG. 6 depicts the ZAP-NC: ζ1 complex encased in a gridded box for receptor site mapping.

Figure 7A:
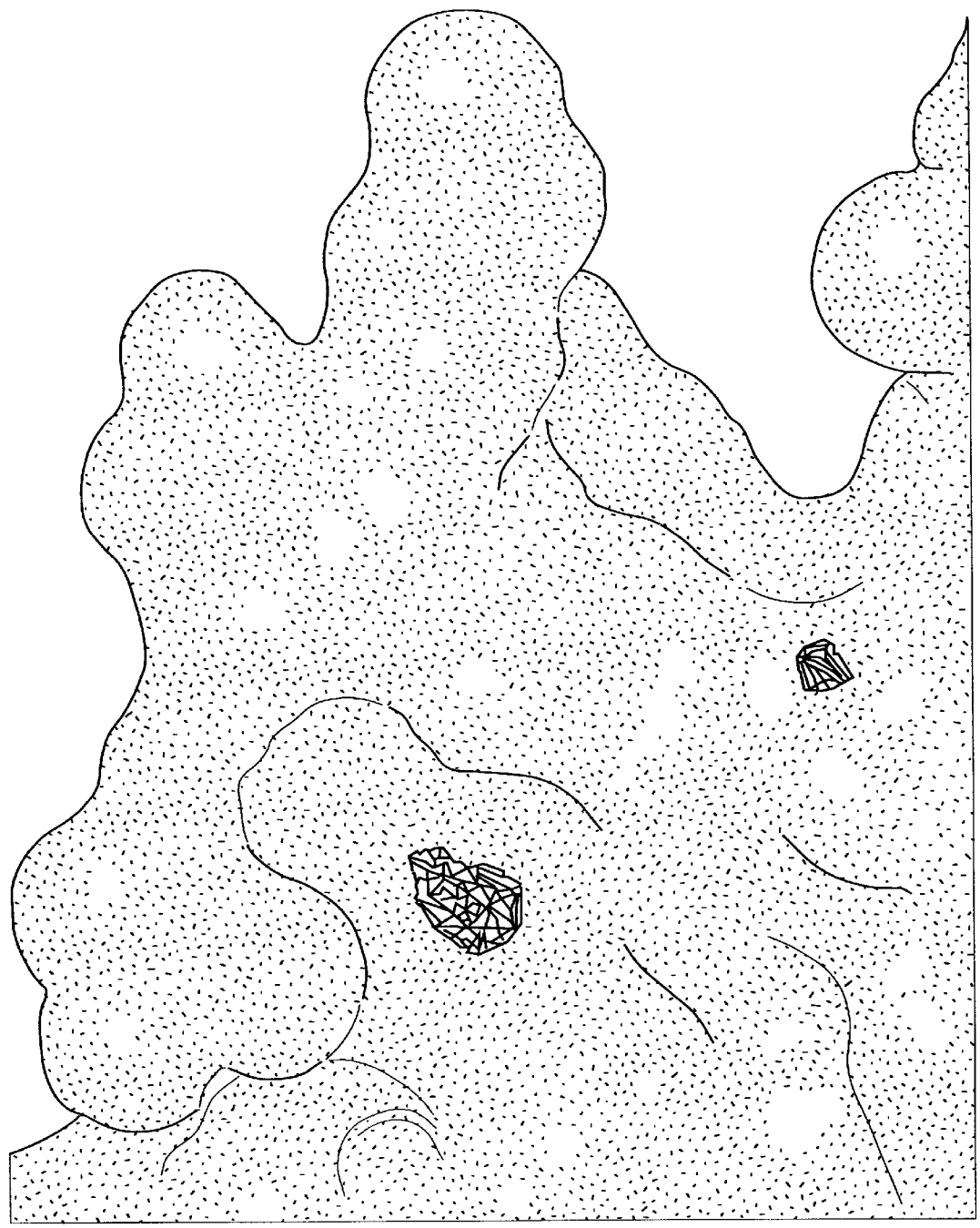
Figure 7B:
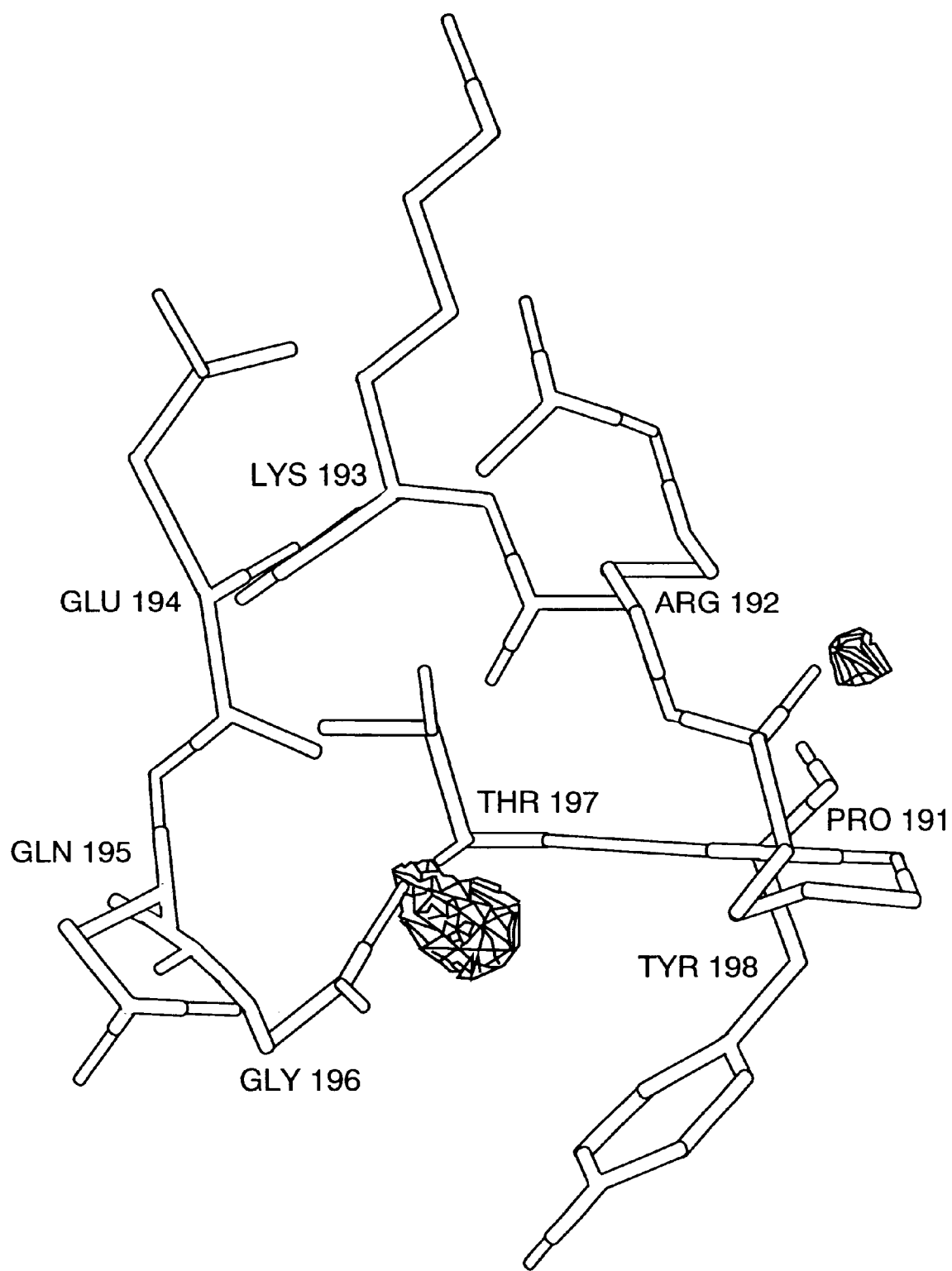

FIGS. 7A and 7B depict two representations of a representative site contour map of ZAP-NC (SEQ ID NO: 36).

Figure 8:
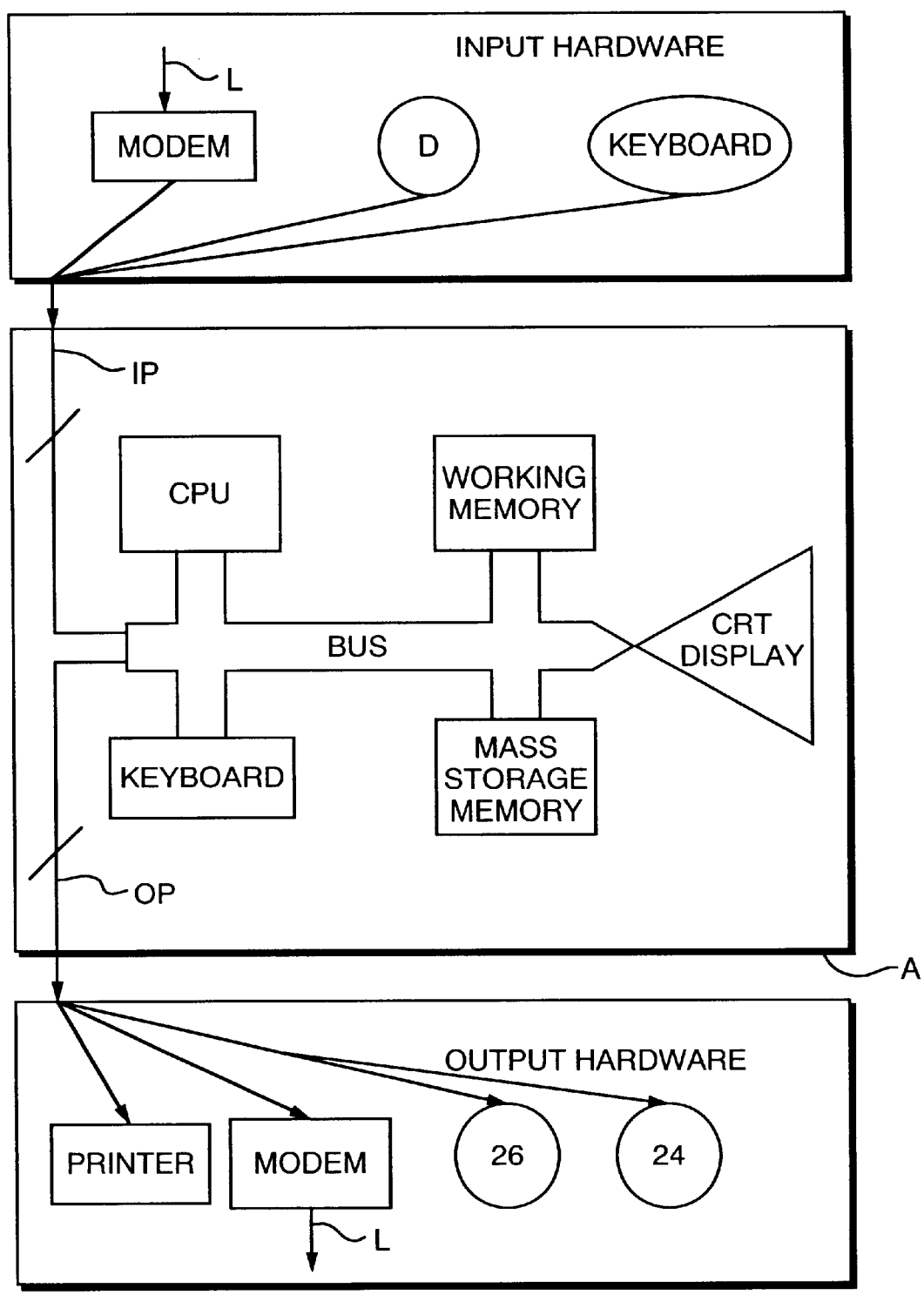

FIG. 8 depicts a computer system.

Figure 9A:
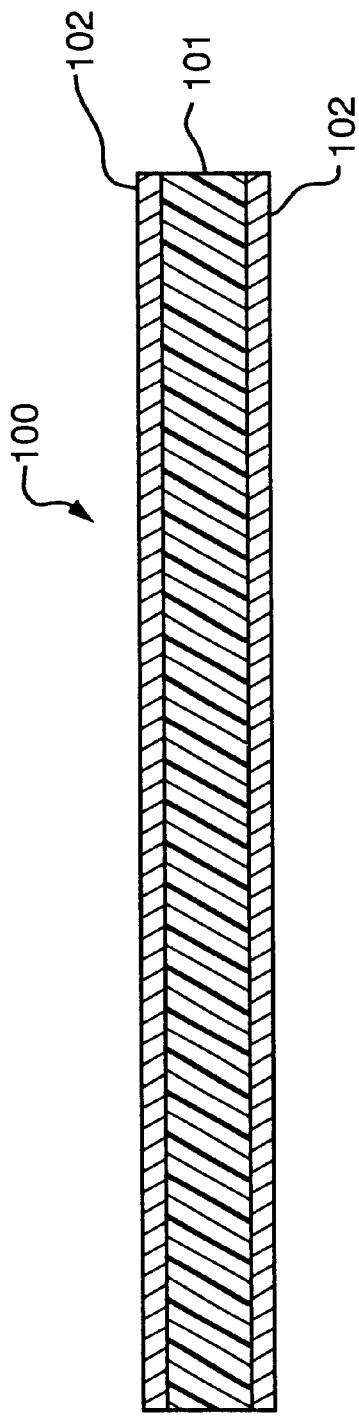

FIG. 9A shows a cross section of a magnetic data storage medium.

Figure 9B:
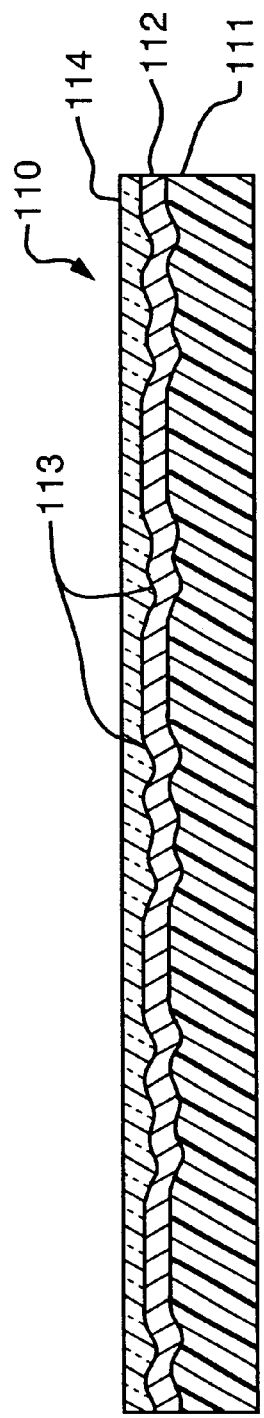

FIG. 9B shows a cross section of an optically-readable data storage medium. These media can be used to store coordinates, as described below

DETAILED DESCRIPTION OF THE INVENTION

A. Introduction: The Immune Response is Mediated by Signalling Through the T Cell Receptor Complex with Which ZAP-70 is Associated T cell recognition of antigen-presenting cells initiates a cascade of intracellular processes that ultimately result in changes in gene expression, the production of secreted mediators, and cellular proliferation.[1,2] This recognition is mediated by the T cell receptor (TCR), which consists of the antigen binding subunits α and β, the CD3 complex of δ-ε and γ-ε heterodimers, and the ζ homodimer. With the exception of α and β, the intracellular portion of each subunit includes one to three peptide sequences that contain the motif YXX(L/I)X$_{(7-8)}$YXX(L/I) (SEQ ID NO: 28), where X is variable.[3] Following receptor stimulation, these immunoreceptor tyrosine activation motifs, or ITAMs, become phosphorylated on tyrosine residues and in this modified form, provide binding sites for downstream signaling proteins.

The TCR has no intrinsic protein tyrosine kinase (PTK) activity, however members of both the Src family and the SYK/ZAP-70 family of PTKs are implicated in the functioning of antigen receptors.[4] Current evidence indicates that Src family kinases phosphorylate the ITAMs of the TCR.[4] ZAP-70 then associates with the doubly-phosphorylated ITAMs of the ζ and CD3 ε chains through its SH2 domains[5] and is itself phosphorylated during early T cell activation.[6] ZAP-70 (ζ associated protein) is a 70 KDa protein tyrosine kinase that is expressed exclusively in T cells and NK cells.[7] ZAP-70 is known to play a critical role in T cell activation. Genetic alterations in the ZAP-70 gene that cause loss of expression of ZAP-70 in humans prevent antigen activation of CD4⁺ T cells, inhibit maturation of CD8⁺ T cells, and lead to severe combined immunodeficiencies.[8,9] ZAP-70 binding to the TCR is believed to be essential for signal transduction since peptides that block the association of ZAP-70 with the ζ chain also inhibit T cell signaling events.[10] For these reasons, ZAP-70 is an ideal target for the development of novel immunosuppressive therapies.

The first 259 residues of ZAP-70 consist of two SH2 domains that are connected by a 65 residue segment and are followed by a second connecting region and a catalytic domain.[7] SH2 domains consist of approximately 100 amino acids. Their role in the specific recognition of tyrosine-phosphorylated proteins is integral to a variety of intracellular signaling events (recently reviewed in [11, 12]). Several SH2 domains have been demonstrated to retain the ability to bind with high affinity to short peptides that contain phosphotyrosine (pY) when expressed as isolated proteins. Selectivity for isolated SH2 domains is dependent upon recognition of residues immediately C-terminal to the phosphorylated tyrosine (pY+n). The three-dimensional structures of several isolated SH2 domains (both liganded and unliganded), [13, 14] as well as one SH3-SH2 complex[15] and one SH3-SH2-SH3 protein,[16] have been determined by X-ray crystallography or NMR. In order to bind to the TCR, ZAP requires that both of its SH2 domains are present and functional and that both tyrosines within the ITAM are phosphoryiated. [17 - 19]

B. Structure Determination

Despite the pivotal role of ZAP-70 in the immune response, nothing was known of the three-dimensional architecture by which the tandem SH2 region of ZAP-70 engages the ITAMs in the interactions required for its biological activity. X-ray crystallographic techniques could in principle address such issues. However, notwithstanding the key biological functions mediated by ZAP-70 and other ZAP family members such as SYK, there have been no reports disclosing that suitable crystals had been or could be obtained, let alone reports disclosing any x-ray crystallographic data or other information concerning the three-dimensional structure of any tandem SH2 domain. Even in the event that crystals had been obtained, then-available three-dimensional structural data relating to individual SH2 domains would not have been useful in solving the tandem structure, at least in part, because it wouldn't have permitted least squares minimization techniques necessary for structure refinement.

Nonetheless, we have succeeded in producing a protein containing the peptide sequence of the region of human ZAP-70 spanning both the more N-terminal SH2 domain, the more C-terminal SH2 domain and the linking region ("ZAP-NC" (SEQ ID NO: 38)), and have obtained crystals of that protein, crystallized in unliganded form and in complexes with various ligands. Using such materials, we have solved the three-dimensional structure of ZAP-NC (SEQ ID NO: 36) using x-ray diffraction techniques. In view of our successes as disclosed herein, it can now be said that proteins comprising tandem SH2 domains, especially those of ZAP family members such as ZAP and SYK, can be produced in stable form, purified, and crystallized whether in complexes with a ligand or not, and that their three-dimensional structures can be determined, all using materials and methods such as disclosed herein.

Materials

As mentioned elsewhere, ZAP-NC (SEQ ID NO: 38) is one of a number of proteins that contain two src-homology 2 (SH2) domains. The presence and boundaries of an SH2 domain in a protein sequence can be identified by using a computer alignment program that identifies amino acid sequence homology to a known SH2 domain. Generally, the SH2 domain (amino acids between 140–255) of Src are used for such analyses, but SH2 domains from other proteins can be used as well. The alignment method typically used by such programs is the Needleman-Wunch alignment. See e.g., "A General Method Applicable to the Search for Similarities in the Amino Acid Sequence of Two Proteins." Neediman, S. B.; Wunch, C. D. *J. Mol. Biol.* 1970, 48, 443–453. SH2 domains have been identified in a large and growing number of proteins, some of which contain multiple SH2 domains. For example, tandem SH2 regions are present in human ZAP-70 (spanning amino acids 1–259), human SYK (spanning amino acids 6–265), $PLC_\gamma$, PI3K, rasGAP, SH-PTP1, and SH-PTP2.

We expressed ZAP-NC (SEQ ID NO: 36) as a glutathione-Stransferase (GST) fusion protein. The cDNA encoding residues 1–259 from human ZAP-70 [10] was cloned into the pGEX2T expression vector[41] and transformed into *E. coli* BL21 or *E. coli* B834. The resulting construct produced a fusion protein of GST-ZAP-NC linked by a polypeptide segment containing the sequence —LVPRGS— (SEQ ID NO: 29) which comprises a thrombin cleavage site. The selenomethionyl (SeMet) ZAP-NC was produced using the auxotrophic strain of *E. coli* 834 [42] with the selenomethionine replacing methionine in a defined media. The GST-ZAP-NC fusion protein was isolated using glutathione agarose and then cleaved with thrombin. Cleavage yields two polypeptides, the GST and ZAP-NC (SEQ ID NO: 36). The ZAP-NC (SEQ ID NO: 36) polypeptide contains two extra amino acids (Gly-Ser) at the amino terminus from the linker segment of the pGEX2T expression vector. These two extra amino acids were shown to have no functional effect on ZAP-NC (SEQ ID NO: 36) binding to peptide ligands. ZAP-NC (SEQ ID NO: 36) was separated from GST by binding ZAP-NC (SEQ ID NO: 36) to a phosphotyrosine agarose column and eluting with a salt gradient. Subsequently, ZAP-NC (SEQ ID NO: 36) was further purified on a phenyl sepharose column. ZAP-NC:peptide ligand complexes were formed by mixing two-fold excess of peptide and purified ZAP-NC (SEQ ID NO: 36), then subjecting the mixture to chromatography using a superdex 75 gel filtration column. Fractions containing the purified ZAP-NC:peptide complex were combined and used for subsequent crystallization experiments.

Other ZAP-NC proteins may also be used, including ZAP-NC proteins truncated at the N-terminus and/or C-terminus to contain just the SH2 homology boundaries. Likewise, the protein may be extended at the C-terminus to include additional amino acids extending to include additional domains (spacer B) up to the entire ZAP-70 protein (amino acids 1–620). Additionally, other tandem SH2 regions, especially from human and non-human ZAP family members, including proteins such as human SYK, may be prepared and used in analogous fashion to that described herein. It should further be appreciated that other expression systems may be readily employed. For instance, the tandem SH2 protein may be produced in *E coli* using T7, maltose-binding protein fusion (MBP), with epitope tags (His6, HA, myc, Flag) included or cleaved off. Baculoviral expression may be used, e.g. using pVL1393 or derivatives, for tandem SH2 protein, fused (or not) to epitope tag or fusion partner such as GST. Conventional materials and methods for expression in mammalian, yeast or other cells may also be used.

Peptide ligands for co-crystallization with ZAP-NC (SEQ ID NO: 36) or other tandem SH2 proteins may be prepared using conventional methods, containing peptide sequences based on naturally occurring ITAM sequences such as ITAM sequences derived from the T cell receptor $\zeta 1$, $\zeta 2$, $\zeta 3$, $\epsilon$, $\gamma$ or $\delta$ subunits or from the $\beta$ or $\gamma$ subunits of the IgE receptor, for example. In most cases such ligands will contain the 15 amino acid minimal ITAM sequence YXXLXXXXXXX-YXXL [SEQ ID NO. 1] and may contain additional amino acids at either or both the N- and C-termini. The N-terminus may comprise a free amino group or may be modified, e.g.

amidated. Likewise, the C-terminus may be a free carboxylate or may be amidated or otherwise modified. Tyrosines may (each) be phosphorylated (pTyr). Alternatively, difluourophosphono Tyr, phosphonomethyl phenylalanine, hemiphosphorylated Tyr, or other pTyr mimetics may be used in place of pTyr. The ligand may contain amino acid replacements, insertions or deletions with respect to a naturally occurring ITAM sequence. Furthermore, hybrid peptide-nonpeptide ligands and non-peptide ligands may also be used. Examples of such ligands are depicted in Table 1.

Crystallization

Crystallization experiments were conducted using a sparse matrix screening approach, in the case of ZAP-NC (SEQ ID NO: 36) crystals, beginning with a Crystal Screen 1 kit (Hampton Research, Riverside, Calif.). Crystals containing SYK-NC (SEQ ID NO: 37) were obtained as described below. In the case of ZAP-NC (SEQ ID NO: 36), best results were obtained using protein stabilized in 0.5 M NaCl, followed by removal of salt by dialysis prior to the crystallization experiments. Special handling of that sort was not necessary for SYK-NC (SEQ ID NO: 37), but may be useful for other tandem SH2 containing proteins.

For example, crystals of ZAP-NC (SEQ ID NO: 36) complexed with the doubly-phosphorylated 19meric $\zeta_1$ ITAM peptide (Ligand 5, Table 1, SEQ ID NO: 6) were grown from polyethylene glycol (PEG) 4000. The structure was elucidated by multiple isomorphous replacement at 1.9 Å resolution. It was not possible to solve the structure by molecular replacement alone using coordinates for previously determined SH2 domains. This was due to the low sequence identity with other SH2 domains and between the two ZAP domains, as well as to the presence of the 65 residue interdomain region. The details of crystallization, data collection, multiple isomorphous replacement (MIR), and refinement are described below.

Specifically, ZAP-NC (SEQ ID NO: 36) complexed with doubly-phosphorylated $\zeta_1$ peptide (SEQ ID NO: 6) was concentrated to 30 mg/ml in 20 mM Tris, pH 8.5, 200 mM sodium chloride and 20 mM dithiothreitol. The complex was treated with 4 mM trimethyllead acetate (TML). Crystals were obtained by vapor diffusion in hanging drops containing 13.5 mg/ml complex and 10% PEG 4000, 50 mM sodium citrate, 100 mM ammonium acetate, 0.005% sodium azide and 20 mM dithiothreitol, pH 6.2, over reservoirs of 20% PEG 4000 and 20 mM dithiothreitol. The crystals are monoclinic (P2$_1$, a=50.11, b=63.37, c=54.00 Å, β=114.44°) with one molecule per asymmetric unit.

In other experiments, using similar conditions, we were also able to obtain crystals of ZAP-NC (SEQ ID NO: 36) complexed with doubly-phosphorylated $\zeta_1$ peptide (SEQ ID NO: 6) which were found to contain two molecules per asymmetric unit. Those crystals are also monoclinic (P2$_1$, a=65.17, b=62.00, c=78.67 Å, β=111.32°).

As described in detail in Experimental Example III (A) and (B), crystals were also obtained under similar conditions of liganded and unliganded ZAP-NC (SEQ ID NO: 36) and SYK-NC (SEQ ID NO: 37) proteins, including complexes with non-phosphopeptide ligands.

TABLE 1

Various Tandem SH2 Ligands (1) IgEγTAM 19mer [SEQ ID NO. 2]
Ac.Asp.Gly.Val.pTyr.Thr.Gly.Leu.Ser.Thr.Arg.Asn.Gln.-Glu.Thr.pTyr.Glu.Thr.Leu.Lys.NH$_2$
(2) IgEγTAM 15mer [SEQ ID NO. 3]
Ac.pTyr.Thr.Gly.Leu.Ser.Thr.Arg.Asn.Gln.Glu.Thr.pTyr.Glu.Thr.Leu.NH$_2$
(3) Ac-[pY$^{4,15}$]IgEγTAM 25mer [SEQ ID NO. 4]
Ac.Asp.Gly.Val.pTyr.Thr.Gly.Leu.Ser.Thr.Arg.Asn.Gln.-
Glu.Thr.pTyr.Glu.Thr.Leu.Lys.His.Glu.Lys.Pro.Pro.Gln.OH
(4) Ac-[pY$^{6,17}$]IgEγTAM 27mer [SEQ ID NO. 5]
Ac.Lys.Ser.Asp.Gly.Val.pTyr.Thr.Gly.Leu.Ser.Thr.Arg.Asn.Gln.-
Glu.Thr.pTyr.Glu.Thr.Leu.Lys.His.Glu.Lys.Pro.Pro.Gln.OH
(5) [pY$^{4,15}$]TCRζTAM 1(19merζ$_1$) [SEQ ID NO. 6]
Ac.Asn.Gln.Leu.pTyr.Asn.Glu.Leu.Asn.Leu.Gly.Arg.Arg.Glu.Glu.pTyr.Asp.Val.Leu.Asp.NH$_2$
(6) Ac-pY$^{[3,15]}$-Nle$^{[11]}$-NH$_2$ (19merζ$_2$) [SEQ ID NO. 7]
Ac.Gly.Leu.pTyr.Asn.Glu.Leu.Gln.Lys.Asp.Lys.Nle.Ala.Glu.Ala.pTyr.Ser.Glu.Ile.Gly.NH$_2$
(7) Ac-pY$^{[4,15]}$-TCRζ3 [SEQ ID NO. 8]
Ac.Asp.Gly.Leu.pTyr.Gln.Gly.Leu.Ser.Thr.Ala.Thr.Lys.Asp.Thr.pTyr.Asp.Ala.Leu.His.NH$_2$
(8) Ac-[Phe(p-I)$^3$]-TCRζTAM(1)-NH$_2$ [SEQ ID NO. 9]

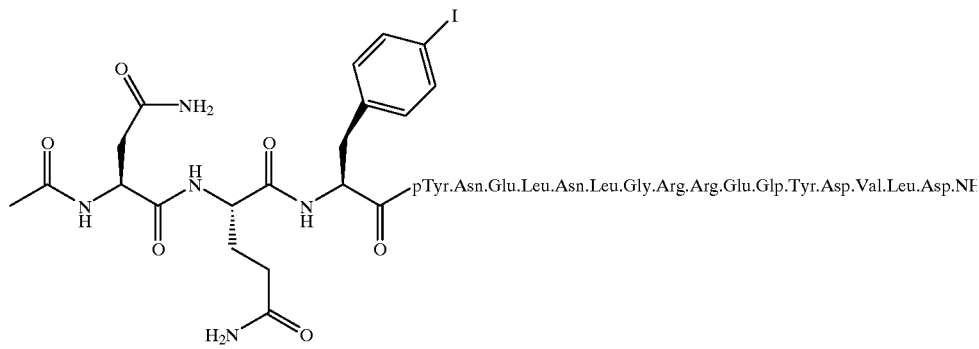

(9) Ac-F2Pmp$^{[4,15]}$-ζ$_1$ NH$_2$ [SEQ ID NO. 10]
Ac.Asn.Gln.Leu.F2Pmp.Asn.Glu.Leu.Asn.Leu.Gly.Arg.Arg.Glu.-
Glu.F2Pmp.Asp.Val.Leu.Asp.NH$_2$ [SEQ ID NO. 10]

TABLE 1-continued

Various Tandem SH2 Ligands

(10) IgEγanalog [SEQ ID NO. 11]
Ac.Asp.Gly.Val.pTyr.Thr.Gly.Leu.Ala.Ala.Ala.Ala.pTyr.Glu.Thr.Leu.Lys.NH₂ [SEQ ID NO. 11]
(11) Fmoc.dnY.Asn.Glu.Leu.Asn.Leu.Gly.Arg.Arg.Glu.Glu.pTyr.Asp.Val.Leu.NH₂ [SEQ ID NO. 12]

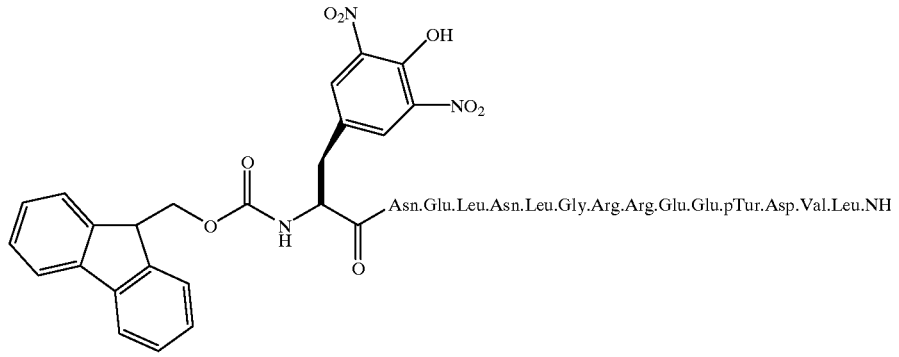

(12) Ac-pY-Thr-nmGly-nmLeu-NH₂ [SEQ ID NO. 13]

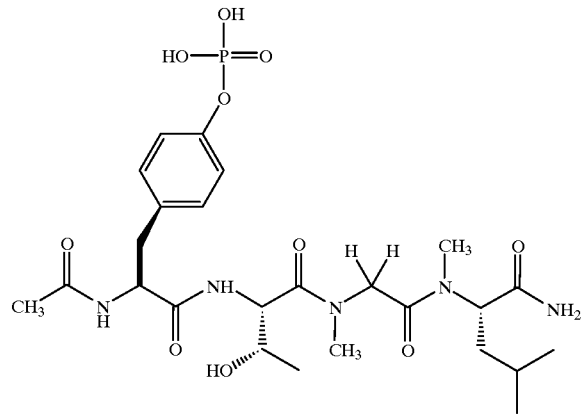

Notes:
(a) Ligands (1), (5)–(10) and (12) co-crystallized with ZAP-NC (SEQ ID NO: 36). Of those, (5), (7), (8) and (9) formed dimeric crystals, i.e., containing two ligand: ZAP-NC complexes per asymmetric unit. (1), (5), (6) and (10) formed crystals containing one ligand: ZAP-NC (containing lead) per asymmetric unit. (1)–(5) and (11) co-crystallized with SKC-NC, with several molecules of complex per asymmetric unit.
(b) The standard triple and single letter codes for abbreviating the names of amino acids are used, i.e, Alanine (Ala, A); Arginine (Arg, R); Asparagine (Asn, N); Aspartic Acid (Asp, D); Cysteine (Cys, C); Glutamine (Gln, Q); Glutamic Acid (Glu, E); Glycine (Gly, G); Histidine (His, H); Isoleucine (Ile, I); Leucine (Leu, L); Lysine (Lys, K); Methionine (Met, M); Phenylalanine (Phe, F); Proline (Pro, P); Serine (Ser, S); Threonine (Thr, T); Tryptophan (Trp, W); Tyrosine (Tyr); and Valine (Val, V). The following terms are also abbreviated: phosphotyrosine (pTyr, pY), difluorophosphonophenylalanine (F2Pmp) and acetyl (Ac).

Data Collection

Diffraction data were collected with an Rigaku R-AXIS II area detector with graphite monochromated Cu $K_\alpha$ X-rays. Diffraction data were collected as 2° oscillation images and reduced to integrated intensities with DENZO.[43] Scaling parameters for each image were calculated with ROTA-VATA[44] and applied with AGROVATA.[44] Data sets were collected for all SYK and ZAP crystals (with and without bound ligands) at −160° C. except for those collected at room temperature for crystals containing ZAP-NC (SEQ ID NO: 36) protein containing lead.

MIR Analysis and Refinement

SeMet ZAP-NC was crystallized with TML under the same conditions and data collected. Positions of the lead and selenium atoms were determined from the difference Patterson function. Anomalous dispersion measurements were included for both datasets. Heavy atom parameters were refined, and phases were obtained at 2.8 Å with the program MLPHARE.[44] The MIR phases were improved with the program DM[44] with a combination of solvent flattening/histogram mapping and phase extension to 2.0 Å. Electron density maps with MLPHARE and DM phases were calculated, and the polypeptide chain model was built with the program O[45]. SIGMMAA[44] was used to perform several cycles of phase combination using partial model and experimental phases. Least squares refinement with simulated annealing was done using X-PLOR.[46] The current model has all residues from Asp 3 to Asn 256 of the protein (SEQ ID NO: 36), all 19 peptide residues of zeta-1 (SEQ ID NO: 6), and 113 water molecules, plus one lead and three selenium atoms. TML is bound to Cys 117. See Table 2.

Structural Coordinates, Their Storage and Use

The structural coordinates of crystalline compositions of this invention may be obtained as described in detail herein. By way of example, Table 17, 18, or 19 set forth the structural coordinates, in PDB format, for crystalline compositions comprising ZAP-NC: ζ1 "monomer" (one molecule of complex per unit cell), ZAP-NC: ζ2, and ZAP-NC: ζ1 "dimer" (two molecules of complex per unit cell).

This invention encompasses crystalline compositions containing a ZAP family protein having a region characterized by structural coordinates set forth in Table 17, 18, or 19, or by coordinates having a root mean square deviation therefrom of less than about 1.5 Å, preferably less than about 1 Å, and even more preferably less than about 0.5 Å, with respect to backbone atoms of amino acid residues listed there.

fitting algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any set of structural coordinates of a ZAP family protein, portion of a ZAP family protein or molecular complex thereof that has a root mean square deviation of conserved residue backbone atoms (N, Cα, C, O) of less than 1.5 Å when superimposed—using backbone atoms—on the relevant structural coordinates of a

TABLE 2

Statistics for data collection, phase determination, and refinement for ZAP-NC: ζ1 "monomer"

Data Collection

|  | Resolution (Å) | Reflections (N) | Completeness (%) | Rsym (%) | Rc | FOM | Phasing Power (20–2.8 Å) |
|---|---|---|---|---|---|---|---|
| TML | 25–2.5 | 15,506 | 98.3 | 6.3 | | | |
| SeMet TML | 25–2.9 | 23,978 | 98.9 | 4.9 | 0.71 | 0.50 | 1.38 |

Refinement
Model 272 residues, 113 water molecules, 1 lead, 3 selenium atoms

| Resolution | Reflections (F > 2σ) (%) | R-value | Free R-value* (%) | Rms deviations Bonds (Å) | Angles (°) |
|---|---|---|---|---|---|
| 10–1.9 | 23,697 | 20.9 | 25.5 | 0.006 | 1.58 |

Notes:
$R_{sym} = ? \mid l_i - <l> \mid / ? \, l_i \times 100$.
$R_c = ? \, \|F_{ph} \pm F_p\| - F_{hcalc}|/F_{ph} \pm F_p|$ for centric reflections.
Phasing power, $F_h/E$ where E = rms lack of closure error.
FOM = Figure of merit
$R_{value} = ? \, \|F_{obs}\| - |F_{calc}\|/ ? \, |F_{obs}| \times 100$.
subset of data (10%) was excluded from refinement and used for free R-value calculation. All data with F >2σ were used for refinement.

As practitioners in this art will appreciate, various computational analyses may be used to determine the degree of similarity between the three dimensional structure of a given protein (or a portion or complex thereof and ZAP-NC (SEQ ID NO: 36) or another ZAP family protein or portion or complex thereof such as are described herein. Such analyses may be carried out with commercially available software applications, such as the Molecular Similarity application of QUANTA (Molecular Simulations Inc., Waltham, Mass.) version 3.3, and as described in the accompanying User's Guide, Volume 3 pgs. 134–135.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we define equivalent atoms as protein backbone atoms (N, Cα, C and O) for all conserved residues between the two structures being compared and consider only rigid fitting operations.

When a rigid fitting method is used, the working structure is translated and rotated to obtain an optimum fit with the target structure. The fitting operation uses a least squares protein or complex of this invention, e.g. the coordinates listed in Table 17, 18, or 19, are considered identical. More preferably, the root mean square deviation is less than 1.0 Å. Most preferably, the root mean square deviation is less than 0.5 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of a protein of this invention, such as ZAP-NC (SEQ ID NO: 36), as defined by the structural coordinates of Table 17, 18, or 19 and described herein.

The term "least squares" refers to a method based on the principle that the best estimate of a value is that in which the sum of the squares of the deviations of observed values is a minimum.

In order to use the structural coordinates generated for a crystalline substance of this invention, e.g. the structural coordinates of ZAP-NC (SEQ ID NO: 36), ζ1 (SEQ ID NO: 6), ζ2 (SEQ ID NO: 7), or the various complexes as depicted in Table 17, Table 18 or Table 19, it is often necessary or desirable to display them as, or convert them to, a three-dimensional shape, or to otherwise manipulate them. This is typically accomplished by the use of commercially available software such as a program which is capable of generating three-dimensional graphical representations of molecules or portions thereof from a set of structural coordinates.

By way of illustration, a non-exclusive list of computer programs for viewing or otherwise manipulating protein structures include the following:

Midas (University of California, San Francisco)
MidasPlus (University of California, San Francisco)
MOIL (Univeristy of Illinois)
Yummie (Yale University)
Sybyl (Tripos, Inc.)
Insight/Discover (Biosym Technologies)
MacroModel (Columbia University)
Quanta (Molecular Simulations, Inc.)
Cerius (Molucular Simulations, Inc.)
Alchemy (Tripos, Inc.)
LabVision (Tripos, Inc.)
Rasmol (Glaxo Research and Development)
Ribbon (University of Alabama)
NAOMI (Oxford University)
Explorer Eyechem (Silicon Graphics, Inc.)
Univision (Cray Research)
Molscript (Uppsala University)
Chem-3D (Cambridge Scientific)
Chain (Baylor College of Medicine)
O (Uppsala University)
GRASP (Columbia University)
X-Plor (Molecular Simulations, Inc.; Yale University)
Spartan (Wavefunction, Inc.)
Catalyst (Molecular Simulations, Inc.)
Molcadd (Tripos, Inc.)
VMD (University of Illinois/Beckman Institute)
Sculpt (Interactive Simulations, Inc.)
Procheck (Brookhaven National Laboratory)
DGEOM (QCPE)
RE_VIEW (Brunel University)
Modeller (Birbeck College, University of London)
Xmol (Minnesota Supercomputing Center)
Protein Expert (Cambridge Scientific)
HyperChem (Hypercube)
MD Display (University of Washington)
PKB (National Center for Biotechnology Information, NIH)
ChemX (Chemical Design, Ltd.)
Cameleon (Oxford Molecular, Inc.)
Iditis (Oxford Molecular, Inc.)

For storage, transfer and use with such programs of structural coordinates for a crystalline substance of this invention, a machine-readable storage medium is provided comprising a data storage material encoded with machine readable data which, when using a machine programmed with instructions for using said data, e.g. a computer loaded with one or more programs of the sort identified above, is capable of displaying a graphical three-dimensional representation of any of the molecules or molecular complexes described herein. Machine-readable storage media comprising a data storage material include conventional computer hard drives, floppy disks, DAT tape, CD-ROM, and other magnetic, magneto-optical, optical, floptical and other media which may be adapted for use with a computer.

Even more preferred is a machine-readable data storage medium that is capable of displaying a graphical three-dimensional representation of a molecule or molecular complex that is defined by the structural coordinates of a protein of the ZAP family, e.g. ZAP-NC (SEQ ID NO: 36) or SYK-NC (SEQ ID NO: 37), or portion thereof, and in particular, structural coordinates of ZAP-NC:ζ1 or ZAP-NC:ζ2 set forth in Table 17, 18, or 19 (or derivatives thereof such as zapNC-z1.pdb, discussed elsewhere herein) ± a root mean square deviation from the backbone atoms of the amino acids of such protein of not more than 1.5 Å. An illustrative embodiment of this aspect of the invention is a conventional 3.5" diskette, DAT tape or hard drive encoded with a data set, preferably in PDB format, comprising the coordinates of Table 17, Table 18 or Table 19.

In another embodiment, the machine-readable data storage medium comprises a data storage material encoded with a first set of machine readable data which comprises the Fourier transform of the structural coordinates set forth in Table 17, 18, or 19 (or again, a derivative thereof), and which, when using a machine programmed with instructions for using said data, can be combined with a second set of machine readable data comprising the X-ray diffraction pattern of a molecule or molecular complex to determine at least a portion of the structural coordinates corresponding to the second set of machine readable data.

FIG. 8 illustrates one version of these embodiments. The depicted system includes a computer A comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines (IP), and one or more output lines (OP), all of which are interconnected by a conventional bidirectional system bus.

Input hardware B, coupled to computer A by input lines, may be implemented in a variety of ways. Machine-readable data of this invention may be inputted via the use of a modem or modems connected by a telephone line or dedicated data line L. Alternatively or additionally, the input hardware may comprise CD-ROM drives or disk drives D. In conjunction with the CRT display terminal, a keyboard may also be used as an input device.

Output hardware, coupled to computer A by output lines, may similarly be implemented by conventional devices. By way of example, output hardware may include a CRT display terminal for displaying a graphical representation of a protein of this invention (or portion thereof) using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage and accesses to and from working memory, and determines the sequence of data processing steps. A number of programs may be used to process the machine-readable data of this invention. Examples of such programs are discussed in reference to the computational methods of drug discovery as described herein. Specific references to components of the hardware system of FIG. 8 are included as appropriate throughout the following description of the data storage medium.

FIG. 9A shows a cross section of a magnetic data storage medium 100 which can be encoded with a machine-readable data that can be carried out by a system such as a system of FIG. 8. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in a manner which may be conventional, machine readable data such as that described herein, for execution by a system such as a system of FIG. 8.

FIG. 9B shows a cross section of an optically-readable data storage medium 110 which also can be encoded with such machine-readable data, or set of instructions, which can be carried out by a system such as a system of FIG. 8. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

C. Description of the Tertiary Structure of ZAP-NC:$\zeta_1$

Solving the X-ray crystal structure of the tandem SH2 region of human ZAP-70 (ZAP-NC (SEQ ID NO: 36)) in complex with a 19meric peptide derived from the sequence of the first ITAM of the $\zeta$ subunit ($\zeta_1$) (SEQ ID NO: 6) of the TCR allowed us to conduct the first three dimensional characterizaiton of the protein:ligand complex. The complex involves an elaborate array of contacts between the peptide and both SH2 domains. The 65 residue inter-SH2 region exists as a coiled-coil of $\alpha$-helices and assists in the formation of an interface between the two SH2 domains. The structure reveals the startling fact that both SH2 domains contribute to the recognition of phosphotyrosine in the second pYXXL (SEQ ID NO: 27) motif. This work reveals the first structural insights into the SYK/ZAP family of protein tyrosine kinases and provides the first view of an intracellular component of the TCR.

General Topology

The first 259 residue segment of ZAP-70 consists of two SH2 domains that are connected by a helical region. The overall fold is Y-shaped where the SH2 domains constitute each upper branch and the intervening 65 amino acid domain forms the stem. The fragment of ZAP-70 used in the crystal structure determination terminates before the kinase domain; therefore, we refer to the two SH2 regions as ZAP-N and ZAP-C, for ZAP N-terminal SH2 and ZAP C-terminal SH2, respectively. There is high structural similarity between each of the SH2 domains and those previously reported, e.g., v-Src[13] and p56-Lck[20]. Each of the individual ZAP SH2 domains possesses a central antiparallel $\beta$-sheet that is flanked by two $\alpha$-helices. The inter-SH2 region begins as a $\beta$-strand that is a continuation of the central sheet of ZAP-N. This is followed by two antiparallel $\alpha$-helices that intertwine to form a coiled-coil motif. The two SH2 domains are in a partially staggered orientation; the central $\beta$-sheets are separated by about 29 Å at an angle of ca. 52°. This arrangement allows direct contact between the two SH2 domains, which is a requisite for peptide binding. The central $\beta$-sheet in ZAP-C is extended by distinct hydrogen bonds with several residues in ZAP-N, including some side chain contacts.

The $\zeta_1$ peptide (SEQ ID NO: 6) is extended over both faces of the SH2 domains, straddles both central $\beta$-sheets, and makes extensive contacts with the protein surface. The binding orientation is head to tail, that is, the N-terminus of the peptide is in contact with the C-terminal SH2 domain. The N-terminal pYXXL (SEQ ID NO: 27) segment of the peptide is bound to ZAP-C in a conformation similar to that seen for singly-phosphorylated peptides bound to isolated SH2 domains.[20, 21] The peptide segment that separates the two pYXXL motifs (SEQ ID NO: 27) is largely in contact with ZAP-C. The C-terminal phosphotyrosine is bound in a pocket that is formed by contributions from both SH2 domains. The remainder of the second pYXXL motif (SEQ ID NO: 27) is bound in a fashion similar to the first motif and in other complexes.[20, 21]

The ZAP SH2 Domains

All residues between Asp 3- Asn 256 (SEQ ID NO: 36) are in good electron density, with no breaks. Residues Gln 2 to Leu 18 of the $\zeta_1$ peptide (SEQ ID NO: 6) reside in good density, and the two terminal residues are in weak, but observable density. The nomenclature defined previously[20] for structural features of SH2 domains is used here for clarity. For the N-terminal SH2 domain (ZAP-N), the secondary structural elements are conserved but are slightly longer for strands A, E, F, and G. Due to the elongation of these strands, the sequence corresponding to a minor $\beta$-sheet (observed in previously reported SH2 domains) is an integral part of the central $\beta$-sheet in ZAP-N. More notably, helix A is longer by three residues, which extends the helix nearly a full turn. The C-terminal SH2 domain of ZAP (ZAP-C) also possesses minor extensions to several secondary structural elements. Strands B, C, and E are longer by one or two residues. Helix A is also extended by a single residue. Strand F consists of only two residues and replaces the FB loop. The BC loop of ZAP-C is extended. There is very strong electron density for a number of structural waters, both within each SH2 domain and in all domain interfaces. The existence of a large number of observed waters in the phosphotyrosine binding pockets is unique to ZAP-NC (SEQ ID NO: 36).

The Helical Interdomain A

The inter-SH2 spacer begins in a type II reverse turn followed by a long $\beta$-strand that makes significant contact to strand A of ZAP-N, thus forming an extension to the central $\beta$ sheet. Hydrogen bonds exist between main chain atoms of Gln 111 and Tyr 12 and between Gln 111 and Ser 14 (SEQ ID NO: 36). A water-mediated contact exists between the main chain atoms of Glu 109 and Tyr 12 (SEQ ID NO: 36). In addition to the hydrogen bonds, hydrophobic packing exists between Leu 108 and Tyr 12 and between Pro 110 and Phe 11 (SEQ ID NO: 36).

This segment is followed by a five-turn $\alpha$-helix (designated helix C) that extends away from both SH2 domains, forming the stem of the overall Y shape of ZAP-NC (SEQ ID NO: 36). This helix is followed by a turn consisting of Leu 133 and Glu 134 (SEQ ID NO: 36). A second $\alpha$-helix (helix D) curves around the axis formed by helix C. Helix D is distorted, with a break at Pro 147 (SEQ ID NO: 36); a second break occurs at Ala 154 which precedes a short $3_{10}$-helix that spans residues Thr 155- Met 161 (SEQ ID NO: 36). Helices C and D both make several hydrophobic contacts to ZAP-C, most notably a p-stacked arrangement of Phe 115 ($\alpha$C) to Trp 233 (SEQ ID NO: 36). Several water-mediated hydrogen bonds exist between helix D and ZAP-C. These antiparallel helices form a coiled-coil structure, with direct contact between several hydrophobic residues forming its core.

For proteins that contain multiple SH2 domains, the region separating the two domains is highly variable in length. This region may be as short as 10–15 residues (e.g., PLC-γ1, SHPTP-1 and -2), which would force the two SH2 domains into a back-to-back orientation. SYK has an inter-SH2 domain region which is of comparable length to that of ZAP, exhibits 68% sequence identity to the helical spacer described here. It should maintain the same overall conformation observed in ZAP-NC (SEQ ID NO: 36). The tandem SH2 domains of the p85 subunit of phosphtidylinositol 3' kinase (PI 3-K) are connected by a significantly larger domain of 163 residues which has been predicted to also form a coiled coil of two antiparallel α-helices.[22]

Binding Interactions for the Complexed $\zeta_1$ Peptide

The ZAP-NC:$\zeta_1$ complex includes a 19 amino acid peptide (SEQ ID NO: 6) that is phosphorylated on both tyrosine residues and is based on the first ITAM-containing segment of the human TCR ζ chain ($\zeta_1$) which has the sequence NQLpYNELNLGRREEpYDVLD [SEQ ID NO. 14]. For clarity, numbering for peptide residues begins at ζ Asn 1. The bound conformation of the $\zeta_1$ peptide (SEQ ID NO: 6) is largely extended, although nearly one full α-helical turn exists between residues ζ Asn 8 and ζ Arg 12. The backbone conformation for each pYXXL motif (SEQ ID NO: 27) is similar to conformations observed for high affinity complexes of SH2 domains with singly-phosphorylated peptides.[20, 21, 23]

All residues of the $\zeta_1$ peptide (SEQ ID NO: 6), except for ζ Gly 10, are in contact with ZAP-NC (SEQ ID NO: 36). The area of the peptide-protein interface is over 1300 Å$^2$. Although this interface area is typical for protein-protein interactions, the nature of the contacts is quite different from those generally observed.[24] For example, interfaces in antibody-antigen complexes and protease:protein-inhibitor complexes usually contain few bridging waters. The interaction of ZAP-NC (SEQ ID NO: 36) with $\zeta_1$ (SEQ ID NO: 6) includes 21 bridging waters. The majority of contacts in protein-protein interfaces are usually classified as hydrophobic. In contrast, half of the contacts between ZAP-NC (SEQ ID NO: 36) and $\zeta_1$ (SEQ ID NO: 6) are due to direct hydrogen bonds. The total number of contacts observed is considerably larger than is observed for protein-protein structures of similar interfacial areas. Binding of phosphorylated peptides to individual SH2 domains has been described as reminiscent of a "socket and plug";[21] this general arrangement is also present in ZAP-C and ZAP-N. Each socket consists of a highly charged pocket that recognizes phosphotyrosine residues and a second pocket that prefers hydrophobic residues at the pY+3 position.

Binding of Motif-1 (-pYNEL-) (SEQ ID NO: 30) is Exclusive to ZAP-C

The amino terminal pYXXL motif (SEQ ID NO: 27) of ζ1 (SEQ ID NO: 6) is associated exclusively with ZAP-C. The first two residues of $\zeta_1$ (SEQ ID NO: 6), ζ Asn 1 and ζ Gln 2, are largely involved in intrapeptide interactions. The single contact between ζ Leu 3 (SEQ ID NO: 6) and ZAP-NC (SEQ ID NO: 36), a hydrogen bond between the main chain carbonyl of ζ Leu 3 (SEQ ID NO: 6) and NH1 of Arg 170 (SEQ ID NO: 36), is typical for the pY-1 residue.

The pocket for ζ pTyr 4 (SEQ ID NO: 6) is formed by residues from helix A, strands B, C, and D, and the BC loop. Hydrophobic contacts involve residues from β D, from which His 210, Tyr 211, and Leu 212 (SEQ ID NO: 36) form one edge of the pTyr cavity. In addition, ζ Asn 1 and ζ Gln 2 of the peptide (SEQ ID NO: 6) itself form hydrophobic contacts on the opposing side. The side chain of Leu 212 (SEQ ID NO: 36) is twisted away from the pTyr ring and is packed against Trp 131 (SEQ ID NO: 36) from a symmetry-related molecule. This neighboring Trp, which constitutes the only intermolecular crystal contact with any $\zeta_1$ (SEQ ID NO: 6) residue, is also in hydrophobic contact to ζ pTyr 4 (SEQ ID NO: 6). Direct hydrogen-bonding contacts to the phosphate are made by only three residues. Arg 170 (αA) and Arg 190 (βB) (SEQ ID NO: 36) interact through their terminal nitrogens. Arg 192 (SEQ ID NO: 36) is the only residue in the BC loop of sufficient length for direct hydrogen bonding to the phosphate group and interacts via its Nε. The BC loop is extended; thus, the pTyr binding region resembles a deep groove that continues toward the AA loop. The inclusion of the pY-2 and pY-3 residues as an integral part of the binding site results in the formation of a channel into which the pTyr protrudes. Five waters with very strong density and low temperature factors exist in this region and are part of a large hydrogen-bonding network.

As is typical for complexes with SH2 domains,[20, 21, 23] the pY+1 and pY+2 residues are extended along the surface of the protein. The pY+1 residue (ζ Asn 5) (SEQ ID NO: 6) makes contacts that are similar to those observed in the hamster middle T peptide ( . . . pYEEI . . . ) (SEQ ID NO: 31) in complex with the SH2 domains of Lck[20] and v-Src.[21] The pY+2 residue (ζ Glu 6) (SEQ ID NO: 6) is direct away from the surface of the protein.

The pocket that surrounds ζ Leu 7 (pY+3) (SEQ ID NO: 6) is very deep and is formed by residues from β D, the EF loop, helix B and the BG loop. Due to the size of this pocket, ζ Leu 7 (SEQ ID NO: 6) is directly contacted by only 5 residues—Tyr 211, lle 223, Gly 226, Gly 245, and Leu 246 (SEQ ID NO: 36). The depth of this pocket is partially due to the presence of a leucine in helix B in ZAP-C that is occupied by a tyrosine in many other SH2 domains.[23] Even in the absence of tyrosine, very strong density is observed for two waters near this site. The main chain of ζ Leu 7 (SEQ ID NO: 6) is involved in a water-mediated hydrogen bond to the carbonyl oxygen of Pro 224 (SEQ ID NO: 36). A second contribution to the overall shape of the pY+3 pocket is provided by a repositioning of the β turn in the EF loop. In complexes of isolated SH2 domains, this loop is involved in forming the steep solvent-exposed wall of the pocket. In ZAP-C, the EF loop slides toward strand D to allow the remainder of the peptide to continue on its path toward ZAP-N.

Binding of Intermotif(-NLGRREE-) (SEQ ID No: 32)

The peptide segment that separates the pYXXL motifs (SEQ ID NO: 27) in $\zeta_1$ (SEQ ID NO: 6) consists of seven amino acids which make the bulk of their contacts to ZAP-C. Since nearly a full turn of an α-helix begins at ζ Asn 8 and continues to ζ Arg 12 (SEQ ID NO: 6), many contacts for this sequence are intrapeptide. ζ Asn 8 (SEQ ID NO: 6) makes a main chain hydrogen bond to the carbonyl oxygen of Gly 245 (BG), and ζ Arg 12 (SEQ ID NO: 6) is involved in both direct and water-mediated hydrogen bonds to the backbone carbonyl of Glu 225 (EF loop); two other water-mediated hydrogen bonds connect ζ Arg 12 (SEQ ID NO: 6) to Gly 226 and Lys 228 (SEQ ID NO: 36). The side chains of ζ Leu 9 and ζ Arg 12 (SEQ ID NO: 6) close off the pY+3 pocket of ZAP-C.

Two glutamate residues complete this segment of the $\zeta_1$ peptide (SEQ ID NO: 6), and because they are the pY-1 and pY-2 residues of the second pYXXL motif (SEQ ID NO: 27), they constitute the first contacts to ZAP-N. ζ Glu 13 (SEQ ID NO: 6) makes a main chain hydrogen bond to the backbone carbonyl of Asp 244 (SEQ ID NO: 36). More interestingly, ζ Glu 13 (SEQ ID NO: 6) is involved in a direct hydrogen bond through its side chain carboxyl to the side chain amino group of Lys 242 (ZAP-C αB) which is an integral part of the phosphotyrosine pocket of the N-terminal SH2 domain. ζ Glu 13 (SEQ ID NO: 6) also maintains van der Waals contact to Lys 242 (SEQ ID NO: 36), as well as to Tyr 238 (ZAP-C αB) (SEQ ID NO: 36) and the guanidinium group of Arg 17 (ZAP-N αA) (SEQ ID NO: 36), which also contribute to the N-terminal pY pocket. ζ Glu 14 (SEQ ID NO: 6) maintains the characteristic pY-1 main chain carbonyl hydrogen bond to both terminal nitrogens of Arg 17 (SEQ ID NO: 36) which, in turn, contacts the aromatic ring and phosphate group of ζ pTyr 15 (SEQ ID NO: 6).

Binding of Motif-2 (-pYDVL-) (SEQ ID NO: 33) Requires Both Domains

Perhaps the most remarkable feature of the complex between ZAP-NC (SEQ ID NO: 36) and $\zeta_1$ (SEQ ID NO: 36) is the observation that the recognition pocket of ζ pTyr 15 (SEQ ID NO: 6) is composed of residues from both SH2 domains. This is the first report of a phosphotyrosine binding site of this nature. The impinging of ZAP-C on ZAP-N sequesters ζ pTyr 15 (SEQ ID NO: 6) in a deep tunnel. The side chain of ζ pTyr 15 (SEQ ID NO: 6) makes van der Waals contacts to Arg 41 (BC loop), Val 47 (βC), His 58 (βD), and Pro 60 (βD) (SEQ ID NO: 36). The side chain of Arg 17 (SEQ ID NO: 36) is positioned over the aromatic ring of ζ pTyr 15 (SEQ ID NO: 6), forming an amino-aromatic contact in addition to bridging the carbonyl of the pY-1 residue to the phosphate oxygens of ζ pTyr 15 (SEQ ID NO: 6). The phosphate group is closely associated with the side chains of Tyr 238 (ZAP-C αB), Lys 242 (ZAP-C αB), Arg 17 (αA), and Arg 37 (βB) (SEQ ID NO: 36), forming a total of six direct hydrogen bonds. Six water-mediated hydrogen bonds exist between the phosphate group and Arg 17 (αA), Cys 39 (βC), Leu 40 (BC loop), Arg 41(BC loop), and Lys 242 (ZAP-C αB) (SEQ ID NO: 36). The relative importance of each residue in this interface may be determined through mutagenesis experiments. Four waters with strong electron density contribute to this extensive network; the presence of these waters may be a consequence of the intrusion of ZAP-C onto residues of the BC loop (vide infra). In this arrangement, each oxygen of the phosphate group possesses its full complement of hydrogen-bonding partners.

As described for the first pYXXL motif (SEQ ID NO: 27), the pY+1 and pY+2 residues (ζ Asp 16 and ζ Val 17 (SEQ ID NO: 6)) make contacts that are characteristic for these positions in other SH2 complexes.[20,21, 23] ζ Leu 18 (SEQ ID NO: 6) resides in a hydrophobic pocket that is of similar dimension to the pY+3 pockets observed in high affinity peptide complexes with Src family SH2 domains. A single water-mediated hydrogen bond connects the main chain NH of ζ Leu 18 (SEQ ID NO: 6) to the carbonyl of Ala 72 (SEQ ID NO: 36) on the EF loop. Contact to several hydrophobic residues is evident: β D contributes Phe 59; interaction with the EF loop involves lle 71, Ala 72, Gly 73, and Gly 74; helix B presents Tyr 87; and the BG loop makes contact via Gly 93 and Leu 94 (SEQ ID NO: 36). Asp 19 of $\zeta_1$ (SEQ ID NO: 6) resides in weaker density and appears to form only one hydrogen bond from its main chain nitrogen to the carbonyl of Gly 93 (BG loop) (SEQ ID NO: 36).

Interdomain Contacts

Unlike the extensive contact area of $\zeta_1$ (SEQ ID NO: 6) to ZAP-NC (SEQ ID NO: 36), the total interaction area between the ZAP-N and ZAP-C SH2 domains is small, measuring only ca. 200 Å$^2$. The surface area of ZAP-N that is buried by ZAP-C and the inter-SH2 spacer is only about 400 Å$^2$; the corresponding buried area in ZAP-C is not significantly larger. Total burial of ZAP-N in the full complex is 620 Å$^2$ which accounts for approximately 13% of the total surface area of the domain. Conversely, burial of ZAP-C is computed to be ca. 1000 Å$^2$ which constitutes 20% of its total surface area. This difference is due to the presence of a large solvent accessible channel formed by the convergence of the convex side of the BC loop of ZAP-N, the FB loop and helix B of ZAP-C, and both helices of the inter-SH2 spacer. This irregularly shaped funnel has an approximate diameter of 5–7 Å, and extends fully enclosed for ca. 12 Å before flaring open for an additional 8 Å. For the interface that is exclusively between the ZAP-N and ZAP-C domains, each SH2 domain contributes nine residues. Most of the contacts are through hydrogen bonds, and most of these are water-mediated. However, some van der Waals contacts do exist.

Given that the total interface that is exclusive to the two SH2 domains may not exist in the absence of the peptide, the inter-SH2 spacer is likely to stabilize the appropriate orientation for tandem binding by permitting only minor displacements through scissoring or wagging motions. In isoelectric focusing gels, uncomplexed ZAP-NC (SEQ ID NO: 36) exists as multiple bands which collapse into a single band when the $\zeta_1$ peptide (SEQ ID NO: 6) is added. This microheterogeneity observed with uncomplexed ZAP-NC (SEQ ID NO: 36) is consistent with conformational variability.

Comparison to other SH2:Phosphopeptide Complexes

Despite the low sequence identity (33%) between ZAP-N and ZAP-C, the similarity in overall fold is notable. Side chain positions are remarkably well-conserved between the two domains. The overall backbone root-mean-square (r.m.s.) deviation is 1.07 Å; the same measurement for ZAP-N or ZAP-C to Src family SH2 domains (individually) is typically 1.50 Å, although the percentage of sequence identity is similar. As reported for previous structures of individual SH2 domains,[14, 20, 21] the loop regions display the largest positional variance, most notably loops AA, BC, CD, and EF. The CD loops of both ZAP-N and ZAP-C have a large truncation relative to the SH2 domains of the Src family; this truncation is also evident from the sequences of a large number SH2 domains.[23]

Although each pYXXL motif (SEQ ID NO: 27) of $\zeta_1$ (SEQ ID NO: 6) resides in a similar backbone conformation in the complex, the orientation of the phosphotyrosines varies between ZAP-N and ZAP-C. The aromatic ring of ζ pTyr 4 (SEQ ID NO: 6) superimposes remarkably well with the pTyr in both p56-Lck[20] and v-Src.[21] For ζ pTyr 15 (SEQ ID NO: 6), however, the ring is repositioned 0.7 Å toward the guanidinium of Arg 17 (SEQ ID NO: 36) and slips 0.8 Å away from strand D. This is likely to be due to the direction $\zeta_1$ takes as it moves into the ZAP-C domain, as well as the strong hydrogen-bonding interactions between the phosphate group and Tyr 238 and Lys 242 (SEQ ID NO: 36) on ZAP-C. Both pTyr pockets of ZAP-NC (SEQ ID NO: 36) are large enough to permit the inclusion of several waters; this enlargement relative to other SH2 domains is due to the repositioning of the BC loop. The extended position for the BC (phosphotyrosine binding) loop observed for both SH2 domains of ZAP has been observed previously for uncomplexed SH2 domains and has been described as a hinge in the binding of tyrosine phosphorylated and phosphonated pepfides.[14, 21] Although the loop is reoriented, the internal conformation for the BC loop is strongly maintained.

The pY+3 pocket of ZAP-C is strikingly large compared to this site in other SH2 domains. This is due, in part, to repositioning of ZAP-C EF residues Pro 224 and Glu 225 (SEQ ID NO: 36), as described earlier. Aside from the absence of a Tyr in αB, the location of other side chains that form this pocket are notably similar to the corresponding sites in Lck and Src.

Also, in comparison with all other crystal structures of complexes of SH2 domains, a significant number of waters are present in ZAP-NC (SEQ ID NO: 36). Several are involved in bridging phosphotyrosine to the protein. These intervening water molecules may contribute to the weak affinity of individual ZAP SH2 domains for phosphorylated ITAM ligands.[17-19, 25] Additionally, a large number of buried or trapped waters exist in all of the various interfaces.

Biological Significance

The structure of the tandem SH2 domains of ZAP-70 in complex with a component of the ζ chain of the T cell receptor provides the first molecular glimpse into the intracellular machinery of the TCR (summarized in FIG. 4). Several unique features of this structure suggest that each SH2 domain does not function as an independent module, and that interactions between the domains play a critical role in the recognition of phosphorylated ITAM sequences of the TCR by ZAP-70. In addition, the structural information is key to the interpretation of genetic and biochemical data and provides a framework for exploring the mechanism of action of ZAP-70.

The tandem SH2 domains of ZAP-70 exhibit strong selectivity for the phosphorylated ζ and ε subunits of the TCR, while isolated SH2 domains from other proteins bind more promiscuously to many tyrosine phosphorylated proteins in total cell extracts.[5] Ligand binding and selectivity for isolated SH2 domains is mediated by recognition of a phosphotyrosine and several residues C-terminal to phosphotyrosine, particularly the hydrophobic residue at the pY+3 position[12]. The high degree of selectivity of ZAP-70 for doubly-phosphorylated ITAM sequences appears to be a consequence of multiple structural features. The distance between the two pYXXL motifs (SEQ ID NO: 6) of the ζ or ε chain provides properly spaced partners for a pair of SH2 domains that are tethered in close association by an inter-SH2 coiled coil. Association of the pair of SH2 domains with the phosphotyrosines and other ITAM residues stabilizes a conformation that permits direct interaction between the domains and hence the formation of a deep pocket for sequestering one phosphotyrosine at the domain interface.

While ZAP-NC (SEQ ID NO: 38) exhibits high affinity for doubly-phosphorylated ITAMS and selectivity for the ζ and ε chains, the individual SH2 domains of ZAP-70 have not been found to bind appreciably to phosphorylated peptides[5]. In addition, ZAP-NC (SEQ ID NO: 38) binds to monophosphorylated ITAM-based peptides with affinities that are 100–1000 times lower than for the corresponding doubly-phosphorylated ones.[17-19, 25] Consequently, for high-affinity binding, both SH2 domains must cooperate, and two phosphotyrosine residues must be present and arranged appropriately. The structural manifestation of this cooperativity and selectivity is also the most remarkable feature of the complex between ZAP-NC (SEQ ID NO: 36) and $\zeta_1$ (SEQ ID NO: 6), that is, the convergence of residues from both SH2 domains to enmesh pTyr 15 (SEQ ID NO: 6).

To this point, it has been assumed that SH2 domains adopt their native fold when extracted from their natural molecular context and possess their full ability to recognize and bind to phosphorylated proteins.[12, 14] We present structural evidence that the N-terminal SH2 domain of ZAP-70, if expressed in isolation, is incomplete. The groove-like nature of the pY pocket of ZAP-C suggests that this domain may also require contributions from neighboring domains or proteins.

From the crystal structure, we ascertain that the orientation adopted by ZAP-70 upon association with the TCR aligns ZAP-C with the N-proximal pYXXL motif (SEQ ID NO: 27) of $\zeta_1$ (SEQ ID NO: 6), and ZAP-N with the C-proximal motif, as depicted in FIG. 4. We believe that this orientation may be important for positioning the catalytic domain of ZAP-70 for its activation and subsequent phosphorylation of downstream substrates in the signal transduction cascade.

All of the ITAMs of the TCR have a spacing of seven residues between the pYXXL motifs (SEQ ID NO: 27), except $\zeta_2$ (SEQ ID NO: 7) which has a spacing of eight. In vitro binding experiments of ZAP-NC (SEQ ID NO: 38) with synthetic phosphopeptides indicate that the binding hierarchy is $\zeta_1=\zeta_2>\epsilon=\zeta_3$.[25] These results suggest that one additional residue between the pYXXL motifs (SEQ ID NO: 27) is tolerated. Conversely, a two amino-acid deletion in the corresponding region of ε drastically reduces ZAP-70 binding and eliminates IL-2 production.[17] Therefore, the distance between the two pYXXL motifs (SEQ ID NO: 27) is important for association and signaling. In order to determine the relative contribution of each residue in the ITAM, experiments utilizing CD8-$\zeta_1$ chimeras were conducted, in which each residue was systematically replaced with alanine. The results demonstrate that only the replacement of each pY and pY+3 residue eliminates signaling completely, as measured by IL-2 production.[26] With the exception of these residues, the specific sequence of the ITAM is less important for selectivity than the distance between pYXXL motifs (SEQ ID NO: 27). More radical changes, such as the simultaneous replacement of multiple residues, are necessary to assess the contribution of ITAM sequences to selectivity.

As described earlier, the inter-SH2 region constrains the SH2 domains within a distance that permits association. However, because a significant portion of the antiparallel helices are directed away from the SH2 domains, this region may also be involved in inter- or intramolecular contacts, regulation of kinase activity, and/or receptor clustering. The evidence that this domain forms a coiled coil of α-helices is of great interest, since these structural units are commonly involved in protein-protein interactions.[27] The inter-SH2 region of the p85 subunit of PI 3-K, which has been predicted to form a coiled coil, is necessary and sufficient for interaction of p85 with the p110 catalytic subunit of PI 3-K.[22] One intriguing possibility evident from our structure is that the ZAP interdomain is involved in regulation of its kinase activity. The interdomain may inhibit catalytic activity directly or indirectly, and this inhibition might be relieved upon binding of the SH2 domains to the ITAM. Experiments with PI 3-K[25] and SYK[28], the PTK homologous to ZAP-70, support such a model. Addition of a phosphotyrosine-containing peptide that corresponds to Tyr 751 region of a known PI-3K SH2 binding site from the PDGFβ receptor causes activation of PI 3-K in vitro.[29] Likewise, phosphorylated ITAM peptides derived from the γ subunit of the IgE receptor increase SYK kinase activity by 5–10 fold.[30, 31] Another function for the inter-SH2 region may be to bind to proteins that either regulate ZAP-70 activity, such as Lck and/or Fyn, or that are substrates for ZAP-70. Tyrosine 126 in the inter-SH2 region is phosphorylated by Lck in vitro[32] and could be involved in interactions with other SH2 domain-containing proteins. Finally, the inter-SH2 domain may be important for the intermolecular association between ZAP-70 molecules which might occur in the activated TCR complex.

SYK should also exhibit these structural features in view of its functional similarities and sequence identity of 57% with respect to ZAP. SYK is expressed in several types of hematopoietic cells and functions in mast cells and B cells by binding to ITAM sequences in the cytoplasmic domains of IgE and B cell receptors, respectively.[28] By comparing the ZAP-70 and SYK sequences,[33] most of the residues in ZAP-NC (SEQ ID NO: 38) that contact pTyr 15 (SEQ ID NO: 6) are conserved in the corresponding positions in SYK. The N-terminal SH2 domain of SYK does not bind to phosphotyrosine ligands or to phosphotyrosine affinity columns,[34] which suggests that, as in ZAP-NC (SEQ ID NO: 38), this phosphotyrosine site also requires the C-terminal SH2 domain in order to form a complete pocket. Doubly-phosphorylated peptides derived from the γ ITAM of the IgE receptor induce SYK activation.[30] Our complex of ZAP-NC (SEQ ID NO: 36) with $\zeta_1$ may therefore represent the conformation of the SH2 domains adopted in the activated kinase.

ZAP-70 has emerged as an attractive target for the development of safe and potent immunosuppressive drugs. ZAP-70 has been shown to be required for T cell-mediated immune responses in humans, and loss of ZAP-70 does not affect other tissues.[8] Thus, ZAP antagonists would specifically inhibit T cells and avoid the toxicity of the currently used immunosuppressive drugs, FK506 and cyclosporin[35, 36], which target the more ubiquitously expressed protein calcineurin.[37, 38] This protein phosphatase is required for T cell immune responses, as well as functions in several other tissues, and as a consequence, cydosporin and FK506 cause serious side effects in the kidney and central nervous system which limit their application largely to pateients with organ transplant rejection.[36] New immunosuppressive drugs with less toxicity are needed to expand the routine use of such therapies to autoimmune diseases.

One approach to inhibition of T cell activation is to develop small (i.e., preferably having a molecular weight below about 1200, more preferably below about 750 and even more preferably below about 500), preferably non-peptidic, membrane permeant, molecules that bind to ZAP and prevent its association with the TCR. Such a compound may bind, preferably with high affinity, to either SH2 domain of ZAP-70 or to the inter-SH2 domain interaction. Our crystal structure reveals the molecular details of the three dimensional structure of ZAP and provides insights into its interactions with the TCR. The unique structural features of each SH2 ligand binding site and the unanticipated inter-SH2 association now can be exploited for structure-based design of highly specific small molecule ZAP ligands and structurally biased compound libraries.

D. Use of Three-dimensional Structure of ZAP-NC (SEQ ID NO: 36) in Solving the Structures of Other Tandem SH2 Proteins Having solved the ZAP-NC (SEQ ID NO: 36) structure we contemplate that other proteins containing two SH2 domains, especially ZAP family members, will have this unique binding pocket formed by interdomain association and that it can be exploited for the design of interfering compounds. The protein currently considered to be most closely related to ZAP is SYK. (see figure of sequence alignment). Using the structure of ZAP-NC (SEQ ID NO: 36), a three-dimensional model of SYK-NC (SEQ ID NO: 37) can be obtained through homology modeling. Prior to solving the ZAP-NC (SEQ ID NO: 36) structure, this would have been difficult if not impossible since the sequence identity between the SH2 domains of Syk and SH2 domains of known structure is low and none of the previously solved SH2 domains contain two SH2 domains. Other currently known proteins with tandem SH2 domains are PLCγ, PI3K, rasGAP, SH-PTP1, and SH-PTP2. Additional proteins with two SH2 domains are expected to be discovered through genome sequencing or other cloning methods.

E. Use of Structure in Drug Discovery
Utilization of the Structure of the Tandem SH2 Domains of ZAP-70 in Computer-aided Drug Design (CADD)

The availability of the three-dimensional structure of the tandem SH2 domains of the protein tyrosine kinase ZAP-70 (ZAP-NC (SEQ ID NO: 36)) makes structure-based drug discovery approaches possible. Structure-based approaches include de Novo molecular design, computer-aided optimization of lead molecules, and computer-based selection of candidate drug structures based on structural criteria. New peptidomimetic modules may be developed directly from the structure of the peptide ligand by design or database searches for conformationally-restricted peptide replacements. Alternatively, structure-based lead discovery may be accomplished using the target protein structure stripped of its ligand. Multiple uncomplexed states of ZAP-NC (SEQ ID NO: 36) can be generated by several methods to provide additional target conformations. The experimental coordinates and the resulting uncomplexed models can be subjected to techniques such as receptor site mapping to identify sites of favorable interaction energies between the structure of the target protein and potential ligands or chemical moieties ("fragments" or "seeds"). Such evaluation may be followed by procedures such as fragment seed linking and growth. Fragment seed linking refers to methods for designing structures that contain "linked" "seeds", i.e. chemical structures comprising two or more of the mapped moieties appropriately spaced to reach the respective sites of favorable interactions. Growth refers to the design of structures which extend, based on receptor site mappping or to fill available space, a given molecule or moiety. Based on the receptor site mapping data, one may also select potential ligands from databases of chemical structures. Potential ligands, or suboptimal ligands, of whatever source, can be refined by using the receptor site maps to filter multiple ligand conformations and orientations according to energetic preferences. Finally, in view of the high degree of sequence similarity to the tandem SH2 domains of p72$^{Syk}$, the structure of ZAP-NC (SEQ ID NO: 36) permits one to generate a high-quality model of SYK-NC (SEQ ID NO: 37) by either knowledge-based homology template methods or iterative site-mutations followed by minimizations. The generated structure of SYK-NC (SEQ ID NO: 37) may then be treated as an additional protein target by the methods outlined above. These methods and their application to ZAP-NC (SEQ ID NO: 36) are described in the sections that follow.

Peptidomimetics of the $\zeta_1$ peptide (SEQ ID NO: 6) may be developed from the bound conformation of a peptide ligand by design, by searching databases for replacements of one or more peptide segments, or by enhancement of existing ligand-protein interactions (i.e., by replacing a component moiety of a ligand with a substitute moiety capable of greater interaction with the target protein, whether through accessible protein contact points or by extrusion of otherwise sequestered waters). Knowledge of the bound conformation of a peptide can suggest avenues for conformational restriction and peptide bond replacement. A less biased approach involves computer algorithms for searching databases of three dimensional structures to identify replacements for one or more portions of the peptide ligand, preferably non-peptidic replacement moieties. By this method, one can generate compounds for which the bioactive conformation is heavily populated, i.e., compounds which are based on particularly biologically relevant conformations of the peptide ligand. Algorithms for this purpose are implemented in programs such as Cast-3D (Chemical Abstracts Service), 3DB Unity (Tripos, Inc.), Quest-3D (Cambridge Crystallographic Data Center), and MACCS/ISIS-3D (Molecular Design Limited). These geometric searches can be augmented by steric searching, in which the size and shape requirements of the binding site are used to weed out hits that have prohibitive dimensions. Programs that may be used to synchronize the geometric and steric requirements in a search applied to ZAP-NC (SEQ ID NO: 36) include CAVEAT (University of California, Berkeley), HOOK (MSI), and ALADDIN (Daylight Software). All of these searching protocols may be used in conjunction with existing corporate databases, the Cambridge Structural Database, or available chemical databases from chemical suppliers.

In addition to the retention of potential pharmacophoric elements that are present in the peptide explicitly, the incorporation into a ligand structure of hydrogen-bond donating or accepting groups that can displace ordered water molecules usually provides a significant entropic gain that leads to a favorable free energy of binding. Such ordered waters are identifiable from the structure, and other ordered waters may be located during computer simulations of a fully solvated structure, as described more thoroughly in a subsequent section.

Generation of alternate binding site conformations of the target protein may be desired in view of the flexibility of the phosphotyrosine binding region, the nature of the interface between the two SH2 domains, and overall, in view of the possibility of an induced fit, i.e., conformational changes in both ligand and protein upon binding. For example, the loop that connects β-strands B and C (the BC or phosphotyrosine binding loop) has been reported to act as a functional hinge in Src-family SH2 domains. In addition, charged residues in the phosphotyrosine binding pocket are capable of side chain reorientations. A variety of theoretical methods, such as Metropolis Monte Carlo or molecular dynamics simulations (implemented in programs such as MCPro [Yale Univeristy], AMBER [UCSF], CHARMm [Harvard University], and GROMOS [ETH/Groningen]) may be used locally to generate Boltzmann distributions of uncomplexed states, and hence provide a set of additional conformations that are valid for molecular design. Alternate side chain reorientations can also be examined by Dead End Elimination and A* algorithms (University of Southhampton), by iterative systematic conformational searches of each side chain, or by comparison of each residue type to members of the Protein Data Bank that have the same backbone torsions. Valid conformations of the BC loop (or loops EF and BG) may be created by searching the Brookhaven Protein Data Bank for loops that have similar anchoring geometries or by imposing random backbone conformations within the selected loops and filtering the results to fit the anchor residues. Both of these knowledge-based methods generate initial structures which can be subjected to force-field minimizations to produce feasible geometries.

In addition to the flexibility inherent to the peptide binding site, the interface between the two SH2 domains provides opportunities for exploring additional conformational states. The interface that is exclusive to the two SH2 domains provides a total buried surface area of only about 200 Å$^2$, and consists largely of hydrogen bonding contacts, many of which are mediated by water. Experiments with isoelectric focusing gels suggest that uncomplexed ZAP-NC (SEQ ID NO: 38) exhibits conformational mobility between the two SH2 domains that is subdued upon binding to the $\zeta_1$ peptide (SEQ ID NO: 6). Since ZAP function requires that both SH2 domains associate simultaneously with a doubly-phosphorylated ITAM of the TCR, gross displacements between the two SH2 domains may play a regulatory role. Thus, conformations in which the SH2 domains are separated may represent an inactivated state, and inhibitors that stabilize this orientation become attractive. Molecular dynamics simulations of a fully solvated ZAP-NC (SEQ ID NO: 38) may provide insight into the structural manifestation of a possible dissociation between the SH2 domains, and an additional target conformation of the uncomplexed protein.

Receptor site mapping encompasses a variety of computational procedures that identify energetically favorable binding sites on macromolecules. The most straighforward procedures involve "painting" a solvent-accessible surface (or an otherwise generated cast) of the macromolecular target according to empirically determined physical properties, such as electrostatic or lipophilic potential, degree of curvature, and hydrogen-bonding character. Such methods for thus characterizing the surface of a macromolecule are incorporated in programs such as Grasp (Columbia University), DelPhi (Biosym Technologies), MOLCAD (Tripos, Inc.), and Hint (Virginia Commonwealth University). Subsequent molecule design involves identification or design of ligands that possess features complimentary to the identified surface characteristics. More advanced algorithms involve the actual calculation of interaction enthalpies between the target and potential ligands or fragments. In practice, the coordinates of the protein or protein fragment of interest (which may be rotated or otherwise transformed) are stripped of any undesired ligand (or portion thereof) and/or of any undesired solvent molecules. The coordinates are then processed to attach molecular mechanics parameters to the atomic positions to provide a processed target for mapping. The target may be partitioned into discrete binding sites. The target or partitioned sites thereof are flooded with given functional group fragments that are subsequently allowed to relax into desired locations, as in the program MCSS (Molecular Simulations, Inc.), or are encased within a regular lattice of site points on which single fragment probes are positioned sequentially; examples of programs that exploit the site-lattice algorithm include Grin/Grid (Molecular Discovery, Ltd.), Ludi (Biosym Technologies), Leapfrog (Tripos, Inc.), and Legend (University of Tokyo). In both techniques, the enthalpic contribution to binding affinity is estimated with a molecular mechanics force-field, and appropriate positions of selected functional groups are determined systematically.

In the site-lattice approach, a box is defined enclosing a desired portion of the target within a defined lattice. The lattice resolution, i.e., the distance between lattice points, may be defined by the practitioner or may be set by the computer program. Likewise, other parameters of points within the lattice, such as hydrophobicity or other characteristics, may be similarly defined. Probes (i.e. computer models) of one or more selected moieties, functional groups, molecules or molecular fragments are positioned at lattice points and the interaction energy of the probe-target pair is determined for each such lattice point. The data for each selected moiety, functional group, etc. is collected and may be recovered as a data set, visualized on a computer monitor or printed out in various text or graphic formats.

As an alternative to positioning a moiety at each of a set of lattice points, one may, as previously mentioned, flood the target (defined by the coordinates as described above) with multiple copies of a selected fragment, moiety, molecule, etc. by superimposing the multiple copies into the vicinity of the protein target. The model is then subjected to group minimization (i.e., molecular mechanics minimization) calculations to identify points or areas of favorable interaction. Data may be handled as in the lattice approach.

One application of this method to the structure of ZAP-NC (SEQ ID NO: 36) involves the crystal structure coordinates stripped of both the peptide ligand ($\zeta_1$) (SEQ ID NO: 6) and experimentally observed water molecules. The binding site so revealed comprises all protein residues that reside within van der Waals distance of any position previously occupied by the peptide. This "conventional" binding site is enlarged to include the bulk of the proximal protein surface, hence additional crevices and depressions not occupied by known ligands for any SH2 domains are considered as potential "auxiliary" binding regions, and their occupation could contribute significantly to the inhibition of ZAP association with the T cell receptor. Similar definition of the binding face of ZAP-NC (SEQ ID NO: 36) applies to any alternate coordinates derived experimentally or via the modeling procedures described above. Receptor site mapping, as well as other methods described herein, may be applied to the 3-D structure of a ZAP family member to design or select ligands capable of binding to an SH2 domain or other site within the ZAP-NC (SEQ ID NO: 36) (or ZAP family-NC) structure.

Receptor site maps provide the seeds for ligand evolution via Database searches, which are described above, and for Grow/link methods for de Novo design of new chemical entities. Programs for ligand growth first access extensible fragment dictionaries in order to place appropriate functional groups at site points. A genetic algorithm or a subgraph isomorphism protocol is then invoked to connect the fragments with small aliphatic chains or rings. Stochastic enhancements may be introduced by modification of internal degrees of freedom as well as translation and rotation of the candidate model within the binding cavity. The resulting sets of molecules are scored and filtered by functions that consider the steric constraints of the binding site, the complimentarity of electrostatic and hydrophobic interactions, and a solvation estimate. Programs of this type that could be applied for the design of new ligands for ZAP-NC (SEQ ID NO: 38) indude Ludi (Biosym Technologies), Leapfrog (Tripos, Inc.), Legend (University of Tokyo), Grow (Upjohn), Builder/Delegate (University of California, San Francisco), and Sprout (University of Leeds). Clique detection methods provide an alternative strategy to site mapping and ligand growth. DOCK (University of California, San Francisco) and similar programs fill a given binding site with the smallest set of atom-sized spheres possible; a database search then attempts to orient ligands such that the atoms superimpose onto the centers (or "nuclei") of the site-filling spheres. The shape complimentarity is augmented by scoring functions that include the steric requirements of the cavity and a potential energy function.

Optimization of ligands (from any source) may be enhanced using the three dimensional structural of ZAP-NC (SEQ ID NO: 36). Use of receptor site maps or hydropathic profiles of ZAP-NC (SEQ ID NO: 36) may be used to identify preferred positions for functional group components of ligands, and can be used to filter or constrain conformational searches of ligand structures which would otherwise typically be controlled by minimal steric considerations of the ligand structures themselves. The availability of an explicit binding site also permits one to determine the mode of ligand binding to the target protein via methods that utilize force-fields directly in simulated annealing, distance geometry, Metropolis Monte Carlo, or stochastic searches for binding modes. Examples of programs that can be applied to rationalize ligand binding to ZAP-NC (SEQ ID NO: 36) include Autodock (Scripps Clinic), DGEOM (QCPE #590), Sculpt (interactive Simulations, Inc.), or any of the molecular dynamics programs described above. Once a tractable set of possible binding orientations is obtained, one can readily identify the appropriate mode of binding through modifications in test ligands designed to alter in a predictable fashion the binding affinity of each model under consideration. For instance, a ligand may be modified to contain a functional group at a position which is inconsistent with one binding model, yet consistent with another model. Binding data can then be used to weed out "disproven" models. Once iterative weeding of unlikely binding modes generates an appropriate model, possibilities for improvement of the lead become readily apparent from the local protein environment.

An alternative protocol for ligand optimization involves 3D database searching in conjunction with knowledge of the binding site. Modeling can reveal multiple candidates for the bioactive conformation of a given ligand. A probe for the correct conformation can include a 3D search to identify several constrained mimics of each possible conformer. Structure-activity relationships of the unconstrained ligand would suggest which functional groups should be retained in the constrained mimics. Finally, the steric and electrostatic requirements of the binding site could constitute a filter for prioritizing the resultant possibilities.

The structure of ZAP-NC (SEQ ID NO: 36) permits accurate model-building of homologous proteins, and their subsequent use in drug design. The SH2 domains and inter-domain coiled coil regions of the protein tyrosine kinase $p72^{Syk}$ share a high degree of sequence similarity with ZAP-70. The ZAP-NC (SEQ ID NO: 36) structure may be readily used in the development of a reliable model of SYK-NC (SEQ ID NO: 37) by either knowlege-based template building methods, or by iterations of directed point mutations followed by local molecular mechanics minimizations. Examples of programs that can be applied in the development of a model of SYK-NC (SEQ ID NO: 37) include Composer (Birbeck College), Modeler (MSI), and Homology (Biosym Technologies). The resultant model can then be subjected to any of the CADD techniques described above.

F. Characterization of Compounds

Compounds designed, selected and/or optimized by methods described above may be evaluated for binding activity with respect to proteins containing one or more SH2 domains of interest using various approaches, a number of which are well known in the art. For instance, compounds may be evaluated for activity as competitive inhibitors of the binding of an SH2 domain with a phosphorylated ligand thereto. See e.g. Pawson, U.S. Pat. No. 5,352,660 (Oct. 4, 1994). Surface plasmon resonance (SPR) technology may be used for evaluating the binding properties of compounds with respect to one or more SH2 domains of interest (see e.g., Panayotou et al, 1993, Molecular and Cellular Biology 13: 3567–3576), as can fluorescence proximity methods, and other methods known in the art.

SPR methodologies measure the interaction between two or more macromolecules in real-time through the generation of a quantum-mechanical surface plasmon. The SPR methodology as exploited by the BIAcore Biosensor ® (Pharmacia Biosensor, Piscatawy, N.J.) focuses a beam of polychromatic light at the interface between a gold film (provided as a disposable biosensor "chip") and a buffer compartment that can be regulated by the user. Attached to the gold film is a 100 nm thick "hydrogel" composed of carboxylated dextran which provides a matrix for the covalent immobilization of analytes of interest. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies which are depleted, the BIAcore establishes an optical interface which accurately reports the behavior of the generated surface plasmon resonance. When designed as above, the plasmon resonance—and thus the depletion spectrum—is exquisitely sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and exremely sensitive real-time measurement of the molecular interactions without the need to label either component.

Fluorescence polarization (FP) is a measurement technique that can readily be applied to protein-protein and protein-ligand interactions in order to derive IC50s and $K_d$s of the association reaction between two molecules. In this technique one of the molecules of interest must be conjugated with a fluorophore: this is generally the smaller molecule in the system (in the case of a SH2 system, a phospho-tyrosine-containing peptide). The sample mixture, containing both the ligand-probe conjugate and the protein receptor, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore.

With proper controls, changes in the degree of polarization of the emitted light depends only on changes in the apparent molecular weight of the fluorophore, which in-turn depends on whether the probe-ligand conjugate is free in solution, or is bound to a protein receptor. Binding assays based on FP have a number of important advantages. Key among these are the measurement of IC50s and Kds under true homogenous equilibrium conditions, speed of analysis and amenity to automation, and ability to screen in cloudy suspensions and colored solutions.

Automation of such an FP-based assay is achieved using a 96-well fluorescence polarization plate reader. This reader can read polarization values at a sensitivity level of 1 mM for fluorescein-labeled molecules, and can read an individual plate in 3 minutes.

Fluorescence polarization equilibrium binding assays have been adapted for ZAP, Syk, and Src domains. A binding curve of a doubly-phosphorylated ζ-1 sequence (SEQ ID NO: 6) to N,C-ZAP, with associated Scatchard plot of the data is shown in FIG. 5.

It will often be preferred that a compound preferentially inhibits the interaction of a particular SH2-containing protein with its natural ligand (or a portion thereof or analog based thereon), e.g. at least an order of magnitude, and even more preferably, at least two orders of magnitude better (by any measure) than it inhibits some other SH2-ligand interaction.

Such compounds may be further evaluated for activity in inhibiting cellular or other biological events mediated by a pathway involving the interaction of interest using a suitable cell-based assay or an animal model. Cell-based assays and animal models suitable for evaluating inhibitory actvity of a compound with respect to a wide variety of cellular and other biological events are known in the art. New assays and models are regularly developed and reported in the scientific literature.

For example, compounds which bind to ZAP-70 may be evaluated for biological activity in inhibiting T cell activation using any conventional assay methods and materials. Thus, compounds which bind to ZAP may be assayed for inhibition of CD4+ and CD8+ T-lymphocytes in vitro and for lack of in vitro toxicity on cytotoxic T cells within the dose range used to demonstrate in vitro activity. A battery of in vivo models may be used to profile the breadth of the compound's immunosuppressive activity and compare the profile to those of positive controls such as cyclosporin and FK506. Comparisons may also be made to other currently accepted immunosuppressive compounds, i.e. rapamycin, cyclophosphamide, and leflunomide. Initial in vivo screening models include: Delayed type hypersensitivity testing, Allogeneic skin transplantation, and Popliteal lymph node hyperplasia. Compounds demonstrating optimal profiles in the above models are advanced into more sophisticated models designed to confirm immunosuppressive activity in specific therapeutic areas including: Rheumatoid arthritis, Transplantation, Graft vs. host disease, and Asthma.

Compounds which bind to SYK may be evaluated for inhibitory activity in a mast cell or basophil degranulation assay. The inhibitory activity of a compound of this invention with respect to cellular release of specific mediators such as histamine, leukotrienes, hormonal mediators and/or cytokines as well as its biological activity with respect to the levels of phosphatidylinositol hydrolysis or tyrosine phosphorylation can be characterized with conventional in vitro assays as an indication of biological activity. (See e.g."IgE-induced histamine release from rat basophilic leukemia cell lines: isolation of releasing and nonreleasing clones". Edward L. Barsumian, Chaviva Isersky, Marianne G. Petrino and Reuben P. Siraganian. Eur. J. Immunol. 1981. 11:317–323; Forrest, M J, 1991, Biochemical Pharmacology 42:1221–1228 (measuring N-acetyl-β glucosaminadase from activated netrophils); and Stephan, V. M., et al., *J. Biol. Chem.* 267:5434–5441 (1992)). For example, histamine release can be measured by a radioimmunoassay using a kit available from AMAC Inc. (Westbrook, Me.). One can thus evaluate the biological activity of compounds which bind to SYK and compare them to one another and to known active compounds such as leflunomide (and its active metabolite, A771726), vanadate, staurosporine, genistein, or other compounds, including clinically relevant compounds, which can be used as positive controls.

Generally speaking, in such assays $IC_{50}$ scores of 150–300 μM are considered of interest, scores of 50–150 μM are considered good, and scores below about 50 μM are of high interest.

Compounds which bind to SYK may also be tested in an ex vivo assay for their ability to block antigen-stimulated contraction of sensitized guinea pig tracheal strip tissue. Activity in this assay has been shown to be useful in predicting the efficacy of potential anti-asthma drugs. Numerous animal models of asthma have been developed and can be used (for reviews, see Larson, "Experimental Models of Reversible Airway Obstruction", in THE LUNG, Scientific Foundations, Crystal, West et al. (eds.), Raven Press, New York, pp. 953–965 (1991); Warner et al., 1990, *Am. Rev. Respir. Dis.* 141:253–257). Species used in animal models of asthma include mice, rats, guinea pigs, rabbits, dogs, sheep and primates. Other in vivo models available are described in Cross et al., *Lab Invest.* 63:162–170 (1990)); and Koh, et al., *Science,* 256:1210–1213 (1992)).

By way of further illustration, compounds which bind to an SH2-bearing protein involved in the transduction of a signal involved in the initiation, maintenance or spread of cancerous growth may be evaluated in relevant conventional in vitro and in vivo assays. See e.g., Ishii et al., J. Antibiot. XLII:1877–1878 (1989) (in vitro evaluation of cytotoxic/ antitumor activity); Sun et al, U.S. Pat. No. 5,206,249 (issued Apr. 27, 1993)(in vitro evaluation of growth inhibitory activity on cultured leukemia cells); and Sun et al, supra (xenograft models using various human tumor cell lines xenografted into mice, as well as various transgenic animal models).

Single and multiple (e.g., 5 to 7 days) dose investigative toxicology studies are typically performed in the efficacy test species using the intended route of administration for the efficacy study. These investigative toxicology studies are performed to identify maximum tolerated dose, subjective bioavailability from the intraperitoneal or oral routes of administration, and estimation of an initial safety margin. Initial bioavailability and pharmacokinetics (blood clearance) of the compounds may be determined, with standard cold or radioactive assay methods, to assist in defining appropriate dosing regimens for the compounds in the animal models.

Illustration of Drug Design

To illustrate one approach to using the structure of a ZAP family member in drug design, we used the structural coordinates of the ZAP-NC: ζ1 complex (see e.g. Table 17) to characterize amino acid residues of interest with respect to their capability for interaction with ligand molecules. For instance, using the program Sybyl we identified amino acid residues from the N-terminal SH2 domain and C-terminal SH2 domains which are within 10 angstroms of the ζ-1 peptide ligand (SEQ ID NO: 6) and which reside on the protein surface. Residues from that region which are capable of entering hydrophobic interactions with moieties on ligand molecules are listed in Table 3. The residue numbers correspond with the residue numbers of ZAP-70, as set forth in Table 17, and the residues of SEQ ID NO: 36. Acidic residues from that region which are capable of entering hydrogen-bonding interactions or ionic (salt-bridge) interactions with moieties on ligand molecules are listed in Table 4. Basic residues from that region which are capable of entering hydrogen-bonding interactions or ionic (salt-bridge) interactions with moieties on ligand molecules are listed in Table 5. Neutral residues from that region which are capable of entering hydrogen-bonding interactions with moieties on ligand molecules are listed in Table 6. Residues from that region having appropriately disposed backbone amide carbonyls which are capable of entering hydrogen-bond accepting interactions with moieties on ligand molecules are listed in Table 7. Residues from that region having appropriately disposed backbone amide nitrogens which are capable of entering hydrogen-bond donating interactions with moieties on ligand molecules are listed in Table 8.

| Table 3 | Table 4 | Table 5 | Table 6 | Table 7 | Table 8 |
|---|---|---|---|---|---|
| ALA18 | GLU19 | ARG17 | SER14 | PHE56 | ARG17 |
| LEU40 | GLU21 | ARG37 | SER16 | HIS58 | LEU40 |
| VAL47 | GLU62 | ARG41 | GLN38 | ALA72 | HIS58 |
| LEU48 | ASP90 | HIS52 | CYS39 | GLY73 | CYS96 |
| LEU50 | ASP92 | ARG55 | SER42 | ASP92 | ARG170 |
| PHE56 | GLU171 | HIS57 | TYR87 | GLY93 | LYS193 |
| PHE59 | GLU172 | HIS58 | THR169 | LEU168 | GLU194 |
| PRO60 | GLU174 | LYS75 | TYR178 | PRO191 | HIS210 |
| ILE61 | GLU194 | ARG170 | SER201 | TYR198 | LEU212 |
| ILE71 | GLU225 | ARG190 | TYR204 | VAL208 | GLU225 |
| ALA72 | GLU237 | ARG192 | THR207 | HIS210 | LYS228 |
| PHE86 | ASP244 | LYS193 | TYR209 | PRO224 | LEU241 |
| TYR87 | | HIS210 | TYR211 | GLU225 | ALA243 |
| PRO91 | | LYS228 | SER214 | GLY226 | GLY245 |
| LEU94 | | LYS242 | CYS222 | LYS228 | ILE247 |
| PRO95 | | LYS251 | THR227 | ASP244 | CYS249 |
| TYR178 | | | TYR238 | GLY245 | |
| LYS193 | | | CYS249 | LEU246 | |
| ALA199 | | | | | |
| LEU200 | | | | | |
| TYR204 | | | | | |
| VAL208 | | | | | |
| TYR209 | | | | | |
| TYR211 | | | | | |
| LEU212 | | | | | |
| LEU223 | | | | | |
| PRO224 | | | | | |
| LYS228 | | | | | |
| PHE229 | | | | | |
| LEU235 | | | | | |
| TYR238 | | | | | |
| LEU239 | | | | | |
| LEU241 | | | | | |
| LYS242 | | | | | |
| ALA243 | | | | | |
| LEU246 | | | | | |
| ILE247 | | | | | |
| TYR248 | | | | | |
| LEU250 | | | | | |

Similarly, we have identified amino acid residues from the C-terminal domain and the N-terminal domain which reside at the interface between these two domains which would be capable of interacting with ligand molecules in such a manner as to disrupt the juxtapositioning of domains necessary for binding ZAP-70 to the phosphorylated T-cell receptor. Residues from that region which are capable of entering hydrophobic interactions with moieties on ligand molecules are listed in Table 9. Acidic residues from that region which are capable of entering hydrogen-bonding interactions or ionic (salt-bridge) interactions with moieties on ligand molecules are listed in Table 10. Basic residues from that region which are capable of entering hydrogen-bonding interactions or ionic (salt-bridge) interactions with moieties on ligand molecules are listed in Table 11. Neutral residues from that region which are capable of entering hydrogen-bonding interactions with moieties on ligand molecules are listed in Table 12.

| Table 9 | Table 10 | Table 11 | Table 12 |
|---|---|---|---|
| ILE15 | GLU62 | LYS220 | SER14 |
| LEU40 | ASP230 | LYS242 | SER15 |
| LEU43 | GLU237 | | GLN38 |
| MET161 | GLU244 | | SER42 |
| LYS220 | | | THR231 |
| PHE229 | | | GLN234 |
| TRP233 | | | TYR238 |
| TYR238 | | | |

| -continued | | | |
|---|---|---|---|
| Table 9 | Table 10 | Table 11 | Table 12 |
| LEU241 | | | |
| LYS242 | | | |

Similarly, we have identified amino acid residues from the interdomain (also called spacer A) region which reside at the interface between the two a-helical coils of this region and which would be capable of interacting with ligand molecules in such a manner as to disrupt the observed folding of the NC-ZAP domain. Residues from that region which are capable of entering hydrophobic interactions with moieties on ligand molecules are listed in Table 17. Acidic residues from that region which are capable of entering hydrogen-bonding interactions or ionic (salt-bridge) interactions with moieties on ligand molecules are listed in Table 18. Basic residues from that region which are capable of entering hydrogen-bonding interactions or ionic (salt-bridge) interactions with moieties on ligand molecules are listed in Table 19. Neutral residues from that region which are capable of entering hydrogen-bonding interactions with moieties on ligand molecules are listed in Table 20.

| Table 17 | Table 18 | Table 19 | Table 20 |
|---|---|---|---|
| ILE142 | GLU134 | ARG119 | GLN145 |
| ILE153 | GLU150 | ARG124 | THR156 |
| LEU133 | | ARG160 | TYR126 |
| LEU138 | | | |
| LEU152 | | | |
| MET122 | | | |
| PHE115 | | | |
| TRP131 | | | |
| TYR126 | | | |
| VAL114 | | | |
| VAL123 | | | |
| VAL127 | | | |
| VAL149 | | | |

The amino acid residues listed in Tables 3–16 can be used to define binding sites on the ZAP-70 protein for moieties on ligand molecules. A binding site comprises any subset of the foregoing residues which are within about 10 angstroms of one another. For example, the residues CYS39, ARG41, SER42, PRO60, GLU62, LYS220, and ASP230 comprise such a binding site.

We contemplate a new class of ligands for ZAP family members based on the foregoing type of evaluation. Specifically, this class comprises compounds containing one or more moieties which are each capable of interacting with one or more of the foregoing residues, preferably with one or more binding sites defined by the foregoing residues. A subset of such compounds are those which contain at least two moieties, of which at least one is a substituted or unsubstituted phosphate or phosphate mimic (e.g., a substituted or unsubstituted phosphonate moiety). In embodiments in which those moieties are substituted, the substituent may be alkyl, aryl, or arylalkyl.

The term alkyl is intended to include both saturated and unsaturated straight chain, branched, cyclic, or polycyclic aliphatic hydrocarbons which may contain oxygen, sulfur, or nitrogen in place of one or more carbon atoms, and which are optionally substituted with one or more functional groups selected from the group consisting of hydroxy, $C_1$–$C_8$ alkoxy, acyloxy, carbamoyl, amino, N-acylamino, ketone, halogen, cyano, carboxyl, and aryl. Alkyl groups are preferably lower alkyl, i.e. containing 1 to 8 carbon atoms.

The term aryl is intended to include stable cyclic, heterocyclic, polycyclic, and polyheterocyclic unsaturated $C_3$–$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$–$C_8$ alkoxy, $C_1$–$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry).

The ligands may contain one or more amide bonds, but are preferably non-peptidic. Preferably the molecular weight of the ligands is under 1200, more preferably under 750, more preferably under 500. Peptides and peptidic molecules comprise two or more naturally occurring α-amino acids linked by peptide bonds (primary amide bonds, except where the amino acid is proline).

The ability of a ligand or a moiety on a ligand to interact with a particular residue or set of residues in a binding site may be determined by noting the proximity of a ligand moiety to a residue of interest. Proximity may be determined by physical methods such as x-ray crystallography or NMR evaluation of a co-complex of the protein and ligand, or may be determined through modeling studies in which the structure of the ligand is docked with the structure of the protein using programs such as described above. A number of commercially available programs are capable of conveniently evaluating a modeled or experimentally determined structure and identifying atoms involved in hydrogen-bonding or hydrophobic interactions. Generally, hydrogen bonding (which includes salt bridge and other ionic interactions) occurs across distances of about 2.8–3.5 angstroms, more usually up to about 3.2 angstroms, and through donor-H-acceptor angles of about 180°±60°. Hydrophobic interactions occur accross distances of up to about 5 angstroms, more preferably up to about 4.5 angstroms and more frequently up to about 4 angstroms, depending on the nature of the atoms involved. Again, any of a number of commercially available computer programs may be used to identify hydrogen bonding and hydrophobic interactions between ligand moieties and protein atoms.

G. Pharmaceutical Compositions and Uses of Inhibitors of ZAP Family Members

Compounds which bind to one or more ZAP family members may be used as biological reagents in binding assays as described herein for functional classification of an SH2-bearing protein, particularly a newly discovered protein, based on ligand specificity.

Moreover, compounds identified as described above can be used to inhibit the occurrence of biological events resulting from molecular interactions mediated by a ZAP family protein containing one or more SH2 domains. This invention thus provides a method and materials for inhibiting (totally or partially) the interaction between such a protein and a natural ligand thereto (i.e., a naturally occurring protein (typically), or a portion or analog thereof, which binds in a cell to the ZAP family protein) or a biological activity mediated by such interaction. In this method, a compound identified or obtained as described herein is combined or contacted with the ZAP family protein, such as by introducing the compound into a cell in which the molecular interaction is to be inhibited. Following introduction of the compound, the interaction of the ZAP family protein and its natural ligand is inhibited as may be readily detected. Inhibiting such interactions can be useful in research aimed at better understanding the biology of SH2-mediated events.

In general, inhibitors of SH2-mediated interactions would be useful, for example, in the diagnosis, prevention or treatment of conditions or diseases resulting from a cellular processes mediated by the interaction of SH2 bearing protein with a natural ligand therefor. For example, a patient can be treated to prevent the occurence or progression of osteoporosis or to reverse its course by administering to the patient in need thereof an SH2 binding or blocking agent which selectively binds Src SH2. There are many other conditions for which SH2 binding or blocking agents may be useful therapeutically, including breast cancer where the SH2 domain-containing proteins Src, PLCg and Grb7 have been implicated. Other relevant conditions include prostate cancer, in which case targeting Grb2, PLCg, and PI3K, all of which contain SH2 domains, may be useful in treatment or prevention of the disease. Inhibition of the interaction of Grb2 or Abl SH2 domains with Bcr-abl may be useful to treat chronic mylogenous leukemia (CML) or acute myelogenous leukemia (AML). Still other relevant applications of an SH2 inhibitor would be to prevent interferon-, growth factor-, or cytokine-mediated diseases (e.g. inflammatory diseases) by targeting the SH2 domains of STAT proteins.

Of particular interest are agents that block the interaction of ZAP family members with their natural ligands. For instance, inhibitors of interactions involving ZAP-70, which is believed to be involved in activation of T-cells, would be useful as an immunosuppressant in the treatment and prevention of autoimmune diseases and to prevent rejection of skin and organ transplants. Inhibitors of interactions of SYK with natural ligands would be useful in the treatment and prevention of asthma and untoward allergic reactions.

An inhibitor selected or identified in accordance with this invention can be formulated into a pharmaceutical composition containing a pharmaceutically acceptable carrier and/or other excipient(s) using conventional materials and means. Such a composition can be administered to an animal, either human or non-human, for therapy of a disease or condition resulting from cellular events involving a molecular interaction mediated by a ZAP family protein. Administration of such composition may be by any conventional route (parenteral, oral, inhalation, and the like) using appropriate formulations as are well known in this art. The inhibitor of this invention can be employed in admixture with conventional excipients, ie, pharmaceutically acceptable organic or inorganic carrier substances suitable for parenteral administration.

Pharmaceutical Applications

By virtue of its capacity to inhibit protein-protein interactions required for cellular events of pharmacologic importance, a compound identified as described herein may be used in pharmaceutical compositions and methods for treatment or prevention of various diseases and disorders in a mammal in need thereof.

Mammals include rodents such as mice, rats and guinea pigs as well as dogs, cats, horses, cattle, sheep, non-human primates and humans.

The preferred method of such treatment or prevention is by administering to a mammal an effective amount of the compound to prevent, alleviate or cure said disease or disorder. Such effective amounts can be readily determined by evaluating the compounds of this invention in conventional assays well-known in the art, including assays described herein.

Therapeutic/Prophylactic Administration & Pharmaceutical Compositions

The invention provides methods of treating, preventing and/or alleviating the symptoms and/or severity of a disease or disorder referred to above by administration to a subject of a in an amount effective therefor. The subject will be an animal, including but not limited to animals such as cows, pigs, chickens, etc., and is preferably a mammal, and most preferably human.

Various delivery systems are known and can be used to administer the inhibitor, e.g., encapsulation in liposomes, microparticles, microcapsules, etc. One mode of delivery of interest is via pulmonary administration, as detailed more fully infra. Other methods of introduction include but are not limited to intradermal, intramuscular, intraperitoneal, intravenous, subcutaneous, intranasal, epidural and oral routes. The inhibitor may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In specific embodiments, it may thus be desirable to administer the inhibitor locally to the area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

This invention also provides pharmaceutical compositions. Such compositions comprise a therapeutically (or prophylactically) effective amount of the inhibitor, and a pharmaceut-ically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachefte indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the inhibitor can also be accomplished topically by administering the compound(s) directly to the affected area of the skin of the individual.

For this purpose, the inhibitor is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary.

In addition, in certain instances, it is expected that the inhibitor may be disposed within devices placed upon, in, or under the skin. Such devices include patches, implants, and injections which release the compound into the skin, by either passive or active release mechanisms.

Materials and methods for producing the various formulations are well known in the art [see e.g. U.S. Pat. Nos. 5,182,293 and 4,837,311 (tablets, capsules and other oral formulations as well as intravenous formulations)].

The effective dose of the inhibitor will typically be in the range of about 0.01 to about 50 mg/kgs, preferably about 0.1 to about 10 mg/kg of mammalian body weight, administered in single or multiple doses. Generally, the inhibitor may be administered to patients in need of such treatment in a daily dose range of about 1 to about 2000 mg per patient.

The amount of the inhibitor which will be effective in the treatment or prevention of a particular disorder or condition will depend on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level of the inhibitor, as the active component (s), should be determined as in the case of all pharmaceutical treatments, by the attending physician or other health care provider and will depend upon well known factors, including route of administration, and the age, body weight, sex and general health of the individual; the nature, severity and clinical stage of the disease; and the use (or not) of concomitant therapies.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

Pulmonary Administration

In one embodiment of this invention, the inhibitor is administered by pulmonary administration, e.g. via aerosolization. This route of administration may be particularly useful for treatment or prophylaxis of bronchial or pulmonary infection or tumors.

Pulmonary administration can be accomplished, for example, using any of various delivery devices known in the art (see e.g., Newman, S. P., 1984, in Aerosols and the Lung, Clarke and Davia (eds.), Butterworths, London, England, pp. 197–224; PCT Publication No. WO 92/16192 dated Oct. 1, 1992; PCT Publication No. WO 91/08760 dated Jun. 27, 1991; NTIS Pat. Application 7-504-047 filed Apr. 3, 1990 by Roosdorp and Crystal), including but not limited to nebulizers, metered dose inhalers, and powder inhalers. Various delivery devices are commercially available and can be employed, e.g., Ultravent nebulizer (Mallinckrodt, Inc., St. Louis, Mo.); Acom II nebulizer (Marquest Medical Products, Englewood, Colo.); Ventolin metered dose inhaler (Glaxo Inc., Research Triangle Park, N.C.); Spinhaler powder inhaler (Fisons Corp., Bedford, Mass.) or Turbohaler (Astra). Such devices typically entail the use of formulations suitable for dispensing from such a device, in which a propellant material may be present.

Ultrasonic nebulizers tend to be more efficient than jet nebulizers in producing an aerosol of respirable size from a liquid (Smith and Spino, "Pharmacokinetics of Drugs in Cystic Fibrosis," Consensus Conference, Clinical Outcomes for Evaluation of New CF Therapies, Rockville, Md., Dec. 10–11, 1992, Cystic Fibrosis Foundation).

A nebulizer may be used to produce aerosol particles, or any of various physiologically acceptable inert gases may be used as an aerosolizing agent. Other components such as physiologically acceptable surfactants (e.g., glycerides), excipients (e.g., lactose), carriers, and diluents may also be included.

This invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various patents, patent applications and publications are cited herein, the disclosures of which are incorporated by reference in their entireties.

EXPERIMENTAL EXAMPLES

I. Protein Preparation

A. ZAP-NC (SEQ ID NO: 36): Expression, Purification and Complex Formation

Cloning

The ZAP-NC (SEQ ID NO: 36) was expressed as a glutathione-S-transferase (GST) fusion protein. The DNA sequence encoding residues 1–259 from human ZAP 70 (A. C. Chan, M. Iwashima, C. W.Turck, A. Weiss Cell 71 649–662 (1992)) was cloned into the pGex expression vector (D. B. Smith, K. S. Johnson Gene 67, 31–40 (1988)) and transformed into *E. coli* BL21 or *E Coli* B834. The resulting construct coded for a thrombin cleavage site and two extra residues (G and S) at the N-terminus of the ZAP-NC (SEQ ID NO: 36).

Expression

In a typical preparation the ZAP-NC (SEQ ID NO: 36) was produced by the growth and induction of two liters of culture (BL21) in BHI medium. The culture was grown at 25° C. to an OD 595 nm of 0.8 and induced with 1 mM IPTG for 5 hours.

The selenomethionyl (SeMet) ZAP-NC was produced using the auxotrophic strain of *E coli* 834 (D. J. Leahy, H. P. Erickson, I. Aukhil, P. Joshi, W. Hendrickson Proteins 19 48–54 (1994)) with the selenomethionine replacing the methionine in a defined media. The SeMet ZAP-NC was grown in 10 liters of defined media (J. O. Boles, W. H. Tolleson, J. C. Schmidt, R. B. Dunlap, J. D. Odom, *J. Biol. Chem.* 267, 22217–22223 (1992)) supplemented with 0.5% thiamine using 50 mg/L of D,L selenomethionine. The culture was grown at 30° C. to an OD 595 nm of 0.8 and induced for 10–15 hours.

Purification

The GST fusion proteins were isolated using glutathione agarose and then cleaved with thrombin. ZAP-NC (SEQ ID NO: 36) was separated from the GST by binding the tandem SH2 domain to a phosphotyrosine agarose column and eluting with a salt gradient. Subsequently the ZAP-NC (SEQ ID NO: 36) was further purified by hydrophobic interaction chromatography on a phenyl sepharose column. The protein was stored under argon with 500 mM NaCl and 10 mM dithiothreitol at 4° C. A typical purification is listed below. Both the ZAP-NC (SEQ ID NO: 36) and the SeMet ZAP-NC were judged to be >95% pure by N-terminal analysis and SDS gel electrophoresis. Mass spectrometric analysis of the ZAP-NC (SEQ ID NO: 36) and SeMet ZAP-NC indicated >95% incorporation of the selenomethione.

Complex Preparation

Complexes of the ZAP-NC (SEQ ID NO: 36) plus the ζ1 peptide (NQLpYNELNLGRREEpYDVLD) (SEQ ID NO: 15) were prepared by adding a 2-fold excess of peptide to the protein and then running the sample on a gel filtration column. The peptide was dissolved in 200 ul of 100 mM Tris, pH 8.0. and added to 6 mg of protein. The sample was incubated at room temperature for ~30 min, then filtered through a 0.2 micron filter. A Superdex 75 16/60 column was equilibrated in 20 mM Tris containing 100 mM NaCl and 5 mM DTT, pH 8.0 and the sample was loaded and 3 mL fractions were collected. The complex eluted at 65.6 mL and peak fractions were pooled based on protein A(280). Analysis of complexation was done on a homogenous 20% native gel.

A typical ZAP-NC (SEQ ID NO: 36) Purification

Cell Lysis

1) Lysed ~20 g cells using French pressure cell in 40 mL of Buffer A:
2) Diluted 1:1 with Buffer B
3) Centrifuged at ~30,000×g for 30 min & removed the supernatant.

Glutathione Column 2.6×10

1) Loaded the supernatant onto a glutathione column equilibrated into Buffer B.
2) Washed with ~100 mL Buffer B then Buffer C to baseline.
3) Eluted in Buffer D; 5 mL fractions were collected and pooled.

Thrombin Cleavage

1) Added 200 mM NaCl to the pool, then added human thrombin at 1 ug/mg protein
2) Incubated on nutator at room temp. Samples were taken & run on an SDS gel while continuing to incubate. Reaction was complete at 40 min. (PMSF can be added to stop the reaction.)
3) Diluted the pool x5 when cleavage was complete with 20 mM Tris pH 8/5 mM DTT.

Phosphotyrosine Column: 26×7.5 cm

1) Loaded the pool onto the column equilibrated in Buffer E:
2) Washed & eluted using a 5 CV gradient to buffer F. 5 mL fractions were collected.
3) Pooled peak.

Phenyl Sepharose Column 26×17.5 cm

1) Diluted the pool 1:1 with 3 M (NH$_4$)$_2$SO$_4$
2) Equilibrated the column with Buffer G:
3) Loaded the protein, washed to baseline, then eluted in a 3 CV gradient to Buffer H: Pooled peak fractions.
4) Added 500 mM NaCl to peak pool and 5 mM DTT. Stored at 4° C. under argon.

Buffers Used

| Glutathione | Phosphotyrosine | Phenyl Separose |
|---|---|---|
| Buffer A | Buffer E: | Buffer G: |
| PBS/0.5% Triton | 20 mM Tris pH 7.6 | 20 mM Tris pH 8 |
| 400 mM NaCl | 50 mM NaCl | 1.5 M (NH4)2SO4 |
| 5 mM DTT | 5 mM DTT | 5 mM DTT |
| 1 mM Pefabloc | Buffer F: | Buffer H: |
| Buffer B | 20 mM Tris pH 7.6 | 20 mM Tris pH 8 |
| PBS/0.5% Triton | 2 M NaCl | 5 mM DTT |
| 5 mM DTT | 5 mM DTT | |
| Buffer C | | |
| PBS/ | | |
| 5 mM DTT | | |
| Buffer D: | | |
| 100 mM Tris pH 8 | | |
| 100 mM NaCl | | |
| 20 mM reduced glutathione | | |
| 2 mM DTT | | |

B. SYK-NC (SEQ ID NO: 37)

Cloning and Expression

The DNA sequence encoding residues 6–265 of human Syk was cloned into the pET expression vector and transformed into *E. coli* BL21 (DE3) (Shiue, L., et al. *Molecular and Cellular Biology* 15, 272–281 (1995)) In a typical preparation SYK-NC (SEQ ID NO: 37) was produced from the growth and induction of two liters of culture in BHI medium supplemented with 200 ug/mL ampicillin. The culture was grown at 25° C. to an OD at 595 nm of 1–2, induced with 1 mM IPTG, and harvested 4 hours later.

Purification

All operations were performed in a cold room at 4° C. The cells were lysed using a French pressure cell and 2x volumes of lysis buffer, 20 mM Tris pH 8, 500 mM NaCl, 5 mM DTT, and 1 mM pefabloc. The supernatant was collected by high speed centrifugation, diluted 2-fold with buffer A (20 mM Tris pH 8, 5 mM DTT) and applied to a 1.6×10 cm polyethylenimine anion exchange column equilibrated with the same buffer. The flow through was dialyzed overnight vs. buffer B (20 mM Tris pH 7.4, 5 mM DTT, 50 mM NaCl) and then loaded onto a 50 mL phosphotyrosine agarose column. The SYK-NC (SEQ ID NO: 37) protein bound to the column and was eluted with a salt gradient, 50 mM to 2M NaCl in 4 CV. The SYK-NC (SEQ ID NO: 37) protein was collected and dialyzed into buffer C: 50 mM Mes pH 6.2, 5 mM CaC$_2$, 5 mM DTT. After dialysis the protein sample was centrifuged at high speed and then applied to a Source 15S column (16×10 cm) equilibrated in buffer C. The column was then washed with buffer C and eluted using a salt gradient, 0 to 750 mM NaCl in 5 CVs. The peak fraction was pooled. SDS gel electrophoresis indicated that the protein was >95% pure. N-terminal sequencing and mass spec analysis confirmed the expected sequence. The protein concentration was determined by measuring the absorption at 280 nm. The purified protein was stored at 4° with 10 mM DTT.

SYK-NC (SEQ ID NO: 37) and Peptide Complexes

Complexes have been made with a number of different γ and ζ peptides of different lengths. In a typical experiment, a two fold excess of peptide was dissolved in 100 mM Tris buffer and added to 10 mg of SYK-NC (SEQ ID NO: 37). The sample was incubated at RT for 30 minutes, and then run on a Superdex 75 column (16×60 cm) equilibrated in 20 mM Tris pH 8, 100 mM NaCl, 10 mM DTT. Three mL fractions were collected and the peak was pooled.

C. Syk-C Experimental

Cloning and Expression

The C-terminal SH2 domain of human Syk encoding residues 163–265 was cloned into the pGEX2TK expression vector and transformed into *E. coli* BL21 (DE3) (Shiue, L., et al. Molecular and *Cellular Biology* 15, 272–281 (1995); Law, C. L., et al. *J. Biol. Chem.* 269, 12310–12319 (1994)). Isotopically labeled glutathione-S-transferase (GST)-Syk-C was produced from the growth and induction of two liters of culture in M9 medium supplemented with 1 g/L of $^{15}NH_4Cl$ and/or 3 g/L of $^{13}C$ glucose to obtain uniformly labeled Syk-C SH2. The fractionally labeled (~10%) $^{13}C$ Syk-C sample was prepared by supplementing the M9 medium with 4.15 g/L of a mixture containing a 9:1 ratio of unlabeled glucose:$^{13}C$ glucose just prior to induction. In a typical preparation the culture was grown at 25° C. to an optical density (OD) at 595 nm of 1.0, induced with 1 mM isopropyl-b-D-thiogalactopyranoside (IPTG), and harvested 5 hours later. Cells were stored at −80° C. until use.

Purification

The cells were lysed and the protein was affinity purified over glutathione agarose. The GST fusion protein was cleaved with thrombin, and further purified over phosphotyrosine agarose and ion exchange resin to yield an SH2 domain that was >98% pure by SDS gel electrophoresis. A typical purification is outlined below. N-terminal sequencing and mass spectroscopic analysis have confirmed the expected sequence. The purified protein was stored under argon with an excess of dithiothreitol (DTT).

Complex Preparation

Syk-C SH2 protein: pTyr76 peptide complex samples were prepared by adding a two fold molar excess of the pTyr76 peptide dissolved in 0.5 mL NMR buffer (50mM Tris-$d_{11}$, 0.15N NaCl, 10 mM DTT-$d_8$, 0.025% $NaN_3$, pH=7.0) to the Syk-C protein dissolved in the same buffer. This mixture was incubated overnight at 8° C. then concentrated and further equilibrated using Centricon10 microconcentrators at 14° C. Five exchanges of buffer, 2 mL to 200 mL, ensured complete equilibration. Aliquots of the filtrate and the final complex solution were taken and analyzed by HPLC. All NMR samples contained 2–4 mM protein.

A Typical Syk-C Purification

Cell Lysis

1) About 7 g frozen pelleted cells were thawed in two volumes of PBS, 0.5% Triton X-100, 500 mM NaCl, 5 mM DTT, 2 mM EDTA, 1 mM PMSF. 2) The resulting homogenate was lysed using a 20K Manual-Fill FRENCH Pressure Cell at 16,000 psi for two passes.

3) Lysed cells were again diluted with two volumes fresh lysis buffer, stirred for 10 minutes, then centrifuged for 40 minutes at 30,600×g to sediment cell debris.

4) Supernatant was filtered through 0.8 μm Supor membrane filters prior to column loading. All actions carried out at 4° C.

Glutathione Agarose Chromatography 1) 26×100 mm Glutathione Agarose column was equilibrated with PBS, 2 mM DTT.

2) Filtered bacterial lysate was loaded at 2 ml/minute, then column was washed with PBS, 0.5% Triton X-100, 500 mM NaCl, 2 mM DTT, followed by PBS, 2 mM DTT.

3) GST fusion protein was eluted with 100 mM Tris, 100 mM NaCl, 20 mM Reduced Glutathione, 2 mM DTT, pH 8.0.

Enzymatic Cleavage of GST Fusion Protein 1) 1 unit of human thrombin was added per mg of total protein in the Glutathione Agarose eluate.

2) The thrombin was allowed to react for ~16 hours at 4° C. with slow magnetic stirring.

3) Completion of cleavage was verified by 20% SDS gel, then the reaction was stopped with 1 mM PMSF.

4) Cleaved fusion protein was filtered through 0.2 μm Supor membrane prior to loading on Phosphotyrosine Agarose column.

Phosphotyrosine Agarose Chromatography 1) 26×100 mm Phosphotyrosine Agarose column was equilibrated with Buffer A (20 mM Tris, 100 mM NaCl, 5 mM DTT, pH 7.4.)

2) Cleaved fusion protein was loaded at 2 ml/minute then washed back to baseline with Buffer A.

3) Syk-C was eluted with a 0–100% B gradient in 4 column volumes. Buffer B=A+1.9 M additional NaCl.

PEI Chromatography 1) 16×53 mm polyethyleneimine column was equilibrated with Phosphotyrosine Buffer A.

2) Pooled Phosphotyrosine peak was loaded over PEI at 5 ml/minute then washed with Buffer A. Syk-C was in the flowthrough.

D. ZAP-C Experimental

Cloning and Expression

The C-terminal SH2 domain of human ZAP 70 was produced as a glutathione-S-transferase (GST) fusion protein. Residues 155–258 of ZAP 70 were cloned into a pGEX expression vector and transformed into *E. coli* BL21. In a typical fermentation ZAP-C was produced from the growth and induction of four liters of culture in LB media supplemented with 200 mg/mL ampicillin. The culture was grown at 37° C. to an OD at 595 nm of 1, induced with 1 mM IPTG and harvested four hours later. Just prior to induction the temperature was dropped to 25° C. $^{15}N$-labeled ZAP-C was produced from the growth and induction of culture in M9 medium supplemented with 1 g/L of $^{15}NH_4Cl$. Cells were stored at −80° C.

Purification

The ZAP-C cells were lysed and the protein was affinity purified over glutathione agarose. The GST fusion protein was cleaved with thrombin, and further purified over phosphotyrosine agarose to yield an SH2 domain that was >95% pure by sodium dodecyl sulfate (SDS) gel electrophoresis. N-terminal sequencing confirmed the expected sequence. The purified protein was stored under argon with an excess of dithiothreitol (DTT).

A Typical ZAP-C Purification

Cell Lysis 1) 50 g of frozen ZAP-C cells were thawed in two volumes of PBS, 0.5% Triton, 500 mM NaCl, 5 mM DTT, 2 mM EDTA, 1 mM PMSF.

2) The resulting homogenate was lysed using a Minnie Rannie cell disruptor at 16,000 psi for three passes.

3) The cell lysate was centrifuged for 40 minutes at 30,000×g.

4) The supernatant was collected and filtered through a 0.8 mm membrane prior to column loading. All actions were carried out at 4° C.

Glutathione Agarose Chromatography

1) A 26×100 mm glutathione agarose column was equilibrated with PBS, 2 mM DTT.

2) Filtered bacterial lysate was loaded at 2 mL/minute, then column was washed with PBS,0.5% Triton, 500 mM NaCl, 2 mM DTT followed by PBS, 2 mM DTT.

3) GST fusion protein was eluted with 100 mM Tris, 100 mM NaCl, 2 mM DTT 20 mM reduced glutathione pH 8.

Enzymatic Cleavage of GST Fusion Protein 1) 1 unit of human thrombin was added per mg of protein in the glutathione agarose eluate.

2) The thrombin was allowed to react overnight at 4° C. with slow stirring.

3) Additional thrombin (1 unit/mg protein) was added to the protein solution in the morning and the cleavage reaction was monitored by SDS gel. Upon completion the reaction was stopped with 1 mM PMSF.

Phosphotyrosine Agarose Chromatography

1) A 26×80 mm phosphotyrosine agarose column was equilibrated with Buffer A (20 mM Tris, 100 mM NaCl, 2 mM DTT, 2 mM EDTA, pH 7.4.)

2) One-half of the cleaved fusion protein was loaded on the column at 2 mL/minute and then washed to baseline with Buffer A. The ZAP-C was eluted with a 0–100% B gradient in 4 column volumes. (Buffer B=A+1.9M NaCl.)

3) The phosphotyrosine chromatography was then applied to the second half of the cleaved fusion protein. The ZAP-C fractions were collected and analyzed by UV/visible spectroscopy.

Preparation Of Ligands

All peptides were synthesized by automated solid-phase synthesis on Applied Biosystems 431A or 433A synthesizers using N-fluorenylmethoxycarbonyl (Fmoc) amino acids bearing TFA-labile side chain protection. Syntheses were performed on a 0.25 to 0.5 mmol scale on Rink resin (Rink, H. *Tetrahedron Lett.* 1987, 28, 3787–3790). Amino acids (1.0 mmol) were coupled using HBTU/HOBt/DIEA (1:1:2) as activating agents. Coupling reactions are 30–50 min. Assembled peptides are acetylated (Ac$_2$O/pyridine in DMA) either prior to phosphorylation (single 5 min reaction) or after phosphorylation (2×10 min reaction).

Phosphorylation[39, 40]

Resin-bound peptide (0.25 mmol) and tetrazole (25–40 equiv/OH) are combined and dried under vacuum in the presence of NaOH pellets in a desiccator overnight. The flask is then flushed with N$_2$ and DMA (6 mL) added. ($^t$BuO)$_2$PNEt$_2$ (10 equiv/OH) is added and the mixture sonicated for 60–90 min. The resin is filtered, washed with DMA (3×5 mL) and CH$_2$Cl$_2$ (4×5 mL). CH2Cl2 (5 m mCPBA (2–5 equiv per OH) are added and the mixture sonicated for a further 20–50 min. The resin is filtered, washed with CH$_2$Cl$_2$ (6×5 mL), and dried under suction.

Cleavage and Deprotection

Phosphorylated peptide-resin is treated with either TFA: phenol: water (90:5:5), or TFA: water: ethanedithiol: anisole: phenol (95:5:5:5:2) for 90–120 min. The resin is filtered, washed with TFA and the filtrate concentrated by rotary evaporation. Diethyl ether is added to precipitate the crude peptide, which is filtered, washed with Et$_2$O and dried.

Peptides are purified by a combination of gel filtration, preparative HPLC, and gel desalting. Gel filtration. Crude peptide is dissolve in 0.1 M NH$_4$HCO$_3$ (10–20 mL) and applied to a Sephadex G-25 column (2.6×100 cm) eluted at ca. 0.5 mL/min. Eluent is monitored at 254 or 278 nm and product-containing fractions are identifed by analytical HPLC, pooled, and lyophilised.

Preparative HPLC. Peptides were purified on a reversed phase Kromasil C8 column (10 micron particle size, 100 Å pore size, 20×250 mm) with UV monitoring at 220 nm. Product was eluted with a gradient of either 60/40 MeCN/ H$_2$O (0.1% TFA) in 0.1% aq. TFA, or 60/40 MeCN/25 mM Et$_3$N phosphate pH7 in 25 mM Et$_3$N phosphate. The latter buffer required that the isolated pure peptide be desalted, which was achieved by applying the lyophilised product to a Sephadex G-10 or G-15 column (2.6×30 cm) eluted with 0.1 M NH$_4$HCO$_3$ at 1–2 mL/min.

Ligand (9)

The solid phase synthesis of ligand (9) was performed according to the procedures described above, using Nα-Fmoc-(O,O-diethyl-α,α-difluorophosphonomethyl) phenylalanine (Fmoc-F$_2$Pmp(OEt)$_2$OH) (Burke, T. R.; Smyth, M. S.; Otaka, A.; Nomizu, M.; Roller, P. P.; Wolf, G.; Case R.; Shoelson, S. E. Nonhydrolyzable Phosphotyrosyl Mimetics for the Preparation of Phosphatase-Resistant SH2 Domain Inhibitors. *Biochem.* 1994, 33, 6490–6494) The peptide was cleaved from the resin using TFA:phenol:H$_2$O:ethanedithiol:anisole (18:1:1:1:1) to afford the crude bis-O,O-diethyl difluorophosphonate-containing product. Final deprotection was achieved by treatment of the crude product with TMS-I:MeCN (1:1) for 20 min at RT. The solvent was evaporated and the residue dissolved in 0.2 M sodium phosphate (pH 7.0:50 mL). The solution was washed with diethyl ether (6×15 mL) and lyophilised. The product was purified as described above.

N-Fmoc-3,5-dinitro-L-tyrosine

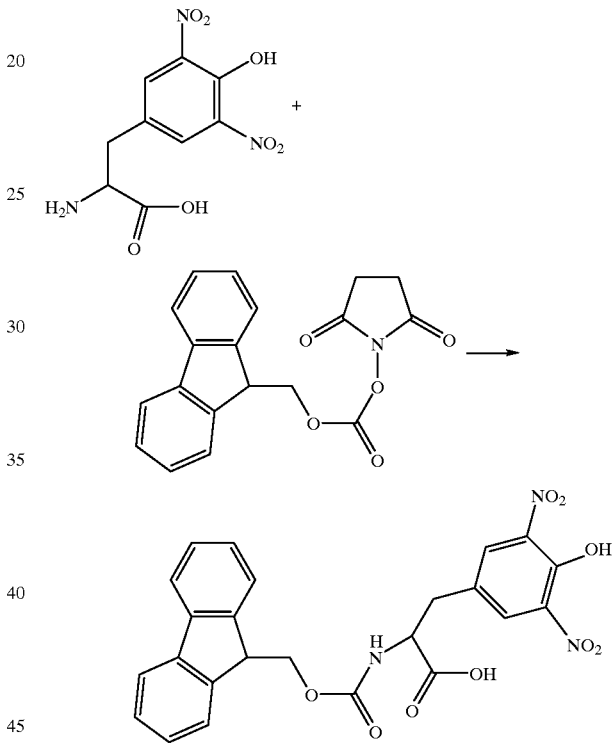

Synthesis of N-Fmoc-3,5dinitro-L-Tyr (Fmoc-dnY) which may be used in the preparation of ligand (11) was carried out as follows (descriptions of using Fmoc-OSu to protect the α-amino group of amino acids with Fmoc can be found in A. Paquet (1982) Can. J. Chem. 60, 976). 1.5 g of 3,5-Dinitr-L-tyrosine monohydrate (Aldrich) was added to 200 mls deionized H$_2$O, with 6.6 mis of 10% Na$_2$CO$_3$. Solution was stirred until a clear yellow solution was obtained. pH was adjusted to approximately 7 using small portions of 10% Na$_2$CO$_3$. 200 mls of dimethoxy ethane (DME) was added to above with stirring. 1.1 eq. (1.9 g) of Fmoc-OSu was dissolved in a minimum amount of DME. This Fmoc-OSu solution was added dropwise to the solution of dinitro-L-tyrosine with stirring. The reaction was carried out overnight with stirring at room temperature.

The next morning, the completion of the reaction was judged to be greater than 95% by TLC, and DME was removed by rotory evaporation under reduced pressure at 40 deg. The reaction mixture was extracted 3× with dietheyl ether, and excess ether is removed by rotory evaporation under reduced pressure (at room temp.) The reaction mixture was acidified to pH 2–3 using 10% KHSO$_4$. A whitish-yellow precipitate formed. The reaction mixture left overnight in a 4 deg. refrigerator.

The next morning the precipitate was vacuum filtered using a buchner funnel (number 1 Whatman filter paper). The filtrate was resuspended and washed 3× with small portions of ice-cold 0.1N HCl, and then 2× with ice-cold deionized water. The filtrate was dried overnight under vacuum with P$_2$O$_5$ as a dessicant. Yield was 2.55 g, 96% by weight. FAB MS measured [M−H]=492; calc C$_{24}$H$_{18}$N$_3$O$_9$= 492.

Crystallization & Structure Determination

A ZAP-NC (SEQ ID NO: 36) was Crystallized in Complexes with Various Ligands (see Table 1) as follows 1. Zap/ζ1: The binary complex of ZAP-NC (SEQ ID NO: 36) and the ζ1 19mer (Ligand 5, Table 1) (SEQ ID NO: 6) was concentrated to 30 mg/ml in a buffer containing 20 mM Tris at pH 8.5, 200 mM sodium chloride, and 20 mM dithiothreitol. The complex of ZAP-NC (SEQ ID NO: 36) with ζ1 peptide (SEQ ID NO: 6) was further treated with 4 mM trimethyllead acetate. Crystals spontaneously grew within 3 weeks in hanging drops containing 13.5 mg/ml protein complex and 10% polyethyleneglycol 4000, 50 mM sodium citrate at pH 6.2, 100 mM ammonium acetate, 0.005% sodium azide and 20 mM dithiothreitol over reservoirs of 20% polyethyleneglycol 4000 and 20 mM dithiothreitol. Large crystals were obtained overnight through microseeding. The crystals are monoclinic (P2$_1$, a=50.11, b=63.37, c=54.00 Å, and β=114.44°), with one molecule per asymmetric unit. Crystals of ZAP-NC (SEQ ID NO: 36) complexed with Ligand 8 (Table 1) (SEQ ID NO: 9) were obtained under the same conditions.

2. Zap/ζ2: Crystals of the binary complex of ZAP-NC (SEQ ID NO: 36) and the ζ2 19mer (Ligand 6, Table 1) (SEQ ID NO: 7) were obtained under conditions similar to those used for Zap/ζ1, with the few modifications noted below. Protein was concentrated in 10 mM Tris at pH 8.5, 0.5 M sodium chloride, 20 mM DTT. 20 to 26 mg/ml protein was treated with 2 mM trimenthyllead accetate for one hour before crystallization set-up. The drops contained 20 mM sodium accetate and 0.2 M sodium chloride in addition to the conditions described for Zap/ζ1 complex. The final pH in the drops is 6.4 to 6.5. The crystallization was with Zap/ζ1 microseeding. (no spontanoues crystallization was obtained). The crystals are monoclinic (P2$_1$, a=50.00, b=63.19, c=54.22 Å, and β=114.6°), with one molecule per asymmetric unit, and diffracted x-rays to a resolution of 2.2 Å.

3. Zap/ζ3: Crystals of the binary complex of ZAP-NC (SEQ ID NO: 36) and the ζ3 19mer (Ligand 7, Table 1) (SEQ ID NO: 8) were obtained as described for ZAP-NC/ζ2 except for the inclusion of sodium acetate in the drops. Crystallization was obtained following microseeding with Zap/ζ1 crystals. The crystals are monoclinic (P2$_1$, a=49.85, b=63.38, c=54.01 Å, and β=114.43°), with one molecule per asymmetric unit, and diffracted x-rays to a resolution of 2.6 Å.

4. Zap/difluorophosphonoζ1: Crystals of the binary complex of ZAP-NC and the difluorophosphono analog of ζ1 19mer (Ligand 9, Table 1) (SEQ ID NO: 10) were obtained as described for ZAP-NC/ζ1 following microseeding with Zap/ζ1 crystals. The crystals are monoclinic (P2$_1$, a=49.77, b=60.87, c=53.58 Å, and β=117.09°), with one molecule per asymmetric unit, and diffracted x-rays to a resolution of 2.2 Å.

5. Zap/IgE γTAM 19mer: Crystals of the binary complex of ZAP-NC (SEQ ID NO: 36) and the IgE γTAM 19mer (Ligand 1, Table 1) (SEQ ID NO: 2) were obtained as described for ZAP-NC/ζ1, but at pH 6.6, following microseeding with Zap/ζ3 crystals.

6. Zap/IgE γTAM 16mer analog: Crystals of the binary complex of ZAP-NC (SEQ ID NO: 36) and the IgE γTAM 16mer analog (Ligand 10, Table 1) (SEQ ID NO: 11) were obtained as described for ZAP-NC/ζ1, but at pH 7.0 with microseeding of Zap/gama crystals in the present of 2% glycerol.

7. Zap/Ligand 12: ZAP-NC (SEQ ID NO: 36) was mixed with 3 mM Ligand 12 (Table 1) (SEQ ID NO: 13) and treated with trimethyllead acetate. Crystals were obtained from a mixture of 12.5 mg/mi ZAP-NC (SEQ ID NO: 36) protein, 1.5 mM Ligand 12 and 1.5 mM trimethyllead acetate in a solution of 10% PEG 4K, 50 mM Tris at pH 8.23 and 10 mM DTT.

B. SYK-NC (SEQ ID NO: 37) was crystallized with and without ligand (see Table 1), as follows 1. SYK-NC (SEQ ID NO: 37) (without ligand) was concentrated in 20 mM Tris at pH 8.0, 0.2 M sodium chloride, 40 mM DTT. Crystals were obtained with 12.5 mg/ml protein in 10% PEG 4k, 0.2 M sodium chloride, 50 mM phosphate buffer, pH 7.3, 30 mM DTT.

2. syk/ζ1: Crystals of the binary complex of SYK-NC (SEQ ID NO: 37) and the ζ1 19mer (Ligand 5, Table 1) (SEQ ID NO: 6) were obtained with 11 mg/ml syk/ζ1 complex in 50 mM Hepes at pH 7.2, 9% PEG4k, 4% 2-propanol, 0.25 M sodium chloride, 30 mM DTT.

3. syk/γ19: Crystals of the binary complex of SYK-NC (SEQ ID NO: 37) and the IgE γ 19mer (Ligand 1, Table 1) (SEQ ID NO: 2) were obtained with 11 mg/ml syk/ζ1 complex in 50 mM Tris at pH 7.68 or 50 mM Imidazole at pH 7.36, 11% PEG4k, 3.5% 2-propanol, 0.3 M sodium chloride, 30 mM DTT.

4. syk/γ15: Crystals of the binary complex of SYK-NC (SEQ ID NO: 37) and the IgE γ 15mer (Ligand 2, Table 1) (SEQ ID NO: 3) were obtained under several different sets of conditions:

a. 18 mg/ml complex in 10% PEG 4K, 50 mM citrate/phosphate buffer at pH 5.6, 0.1 M ammonium chloride, 0.01% sodium azide, 30 mm DTT.

b. 18 mg/ml complex in 10% PEG 4K, 50 mM sodium citrate buffer at pH 5.6, 0.1 M ammonium acetate, 0.5% methylpentanediol, 0.01% sodium azide, 30 mM DTT.

c. 18 mg/ml complex in 10% PEG 6K, 50 mM phosphate buffer at pH 6.2, 0.2 M sodium chloride, 50 mM ammonium accetate, 0.01% sodium azide, 30 mM DTT.

5. syk/γ25: Crystals of the binary complex of SYK-NC (SEQ ID NO: 37) and the IgE γ 25mer (Ligand 3, Table 1) (SEQ ID NO: 4) were obtained under several different sets of conditions:

a. 12.5 mg/ml SYK-NC/ligand complex in 16% PEG 2K, 50 mM sodium citrate, 5% glycerol, 20 mM DTT, pH6.46.

b. 12.5 mg/ml SYK-NC/ligand complex in 10% PEG 4K, 50 mM sodium citrate, 0.1 M ammonium acetate, 20 mM DTT, pH6.3.

6. syk/γTam 27mer: Crystals of SYK-NC (SEQ ID NO: 37) with the IgE γ 27mer (Ligand 4, Table 1) (SEQ ID NO: 5) were obtained as described immediately above in the case of the IgE γ 25mer (Ligand 3, Table 1) (SEQ ID NO: 4).

7. syk/Fmoc dinitrotyrosyl ζ1 analog: Crystals of the binary complex of SYK-NC (SEQ ID NO: 37) and Ligand 11, Table 1 (SEQ ID NO: 12) were obtained with 10 mg/ml syk/ligand complex in 10% PEG 4k, 0.2 M sodium chloride, 50 mM phosphate buffer, pH 6.9, 30 mM DTT.

C. ZAP-NC:ζ1 Three Dimensional Structure

X-ray diffraction data obtained using crystals of the ZAP-NC:ζ-1 complex (one complex per unit cell) were analyzed as described elsewhere (see also Table 2), yielding coordinates defining the three dimensional structure of the crystalline complex. The structure of the ZAP-NC:ζ2 complex was determined by molecular replacement using the X-ray diffraction data for the ZAP-NC:ζ2 complex and the structure of the ZAP-NC:ζ-1 complex as represented by the coordinates of Table 17. Rigid body refinement was conducted using the ZAP-NC:ζ1 model. The resultant model was rebuilt by replacement of the ζ1 peptide with ζ2, followed by conventional refinement. The X-ray data of the ZAP-NC:ζ-1 "dimeric" complex (two complexes per unit cell) was also solved by molecular replacement using the ZAP-NC:ζ-1 ("monomer") structure. Rigid body refinement was conducted using the complete ZAP-NC:ζ-1 "monomeric" model, followed by rigid body refinement using individual SH2 domains and rebuilding of the helical domain region. Those structural coordinates are set forth in Protein Databank format in Table 17 (ZAP-NC:ζ-1 complex, "monmeric"), Table 18 ( ZAP-NC:ζ2 complex) and Table 19 (ZAP-NC:ζ-1 complex, "dimeric"), below. Such data may be transferred to any desired medium, and formatted as desired, for the practitioner's computer.

This invention encompasses those coordinates as well as any translation or rotation or the like thereof which maintains the internal coordinates, i.e., which maintains their intrinsic, internal relationship. Those skilled in the art will appreciate that the coordinates may be subjected to other transformations including, e.g. molecular mechanics calculations such as dynamic simulation, minimization, etc. This invention further encompasses the use of coordinates of ZAP-NC (SEQ ID NO: 36) or the corresponding region of other ZAP family members, and in particular, the coordinates set forth in Table 17, Table 18 or Table 19, in conducting such transformations (or more extensive transformations such as the generation of alternative conformations), as well as the products of such transformations (i.e., derivatives of the coordinates).

IV. Modeling

To illustrate the receptor site mapping approach, we used the Molecular Discovery suite of programs (Molecular Discovery Ltd; Goodford, P. J. "A Computational Procedure for Determining Energetically Favorable Binding Sites on Biologically Important Macromolecules" *J. Med. Chem.* 1985, 28, 849–857) on a Silicon Graphics Onyx workstation running Irix 5.2 to evaluate ZAP-NC (SEQ ID NO: 36) as follows:

(1) The Protein Data Bank (PDB) coordinate file of ZAP-NC (SEQ ID NO: 36) +ζ1 (SEQ ID NO: 6) was stripped of the ζ1 peptide (SEQ ID NO: 6) and all crystallographically observed water molecules (using the Remove Atom feature of Sybil).

(2) The resultant PDB file was merged with a set of molecular mechanics parameters that are suitable for the study of proteins. (Suitable such parameter sets include the user extensible data files which typically accompany the computer program.)

(3) A three-dimensional box that encapsulated the entire peptide binding face of each SH2 domain and the interfacial regions between the two domains was generated. The box dimensions were 60 Å×40 Å×37 Å, and a regular lattice of points positioned at 0.5 Å intervals was designated to fill the box. The box position is illustrated in FIG. 6.

(4) At each lattice point, 46 atomic and polyatomic probes were positioned sequentially. These probes encompass parameters that are representative of a large variety of chemical moieties. The energy of interaction between each probe with the protein was computed at each point of the lattice according to an empirical potential energy function that includes explicit terms for Lennard-Jones, electrostatic, and hydrogen-bonding potentials. The degree of burial for each probe was computed by the method of images.

(5) A binary contour map was generated, which can be used to visualize the sites of favorable interaction of a given probe at a given potential energy. An example is provided in FIG. 7.

Data from this receptor site mapping experiment were transferred to a DAT tape written in tar format on a Silicon Graphics Onyx workstation running Irix 5.2. The map data uses the file extensions .cnt and .Iont for the binary contour maps and the ASCII output, respectively. The orientation of the maps corresponds to our file zapNC-z1.pdb, which is in the Brookhaven Protein Databank format. The contour files are readable by Sybyl 6.1 (Tripos, Inc., St. Louis, Mo.). Filenames correspond to the probe nomenclature in the Molecular Discover Programmes, Version 12.

Information provided by site mapping via these or other programs as described in the Computational Methods section can be used to determine the spatial arrangement of potential pharmacophores, and thus provide the seed points for searches of 3-D databases or de Novo programs that attempt to grow from or link together the selected points. For an illustration of a pharmacophoric substructure for use in computational approaches, see e.g. Fesik (1993) cited elsewhere herein.

For example, the data defining binary contour maps may be displayed as 3D structures identifying preferred locations for selected functional groups using a software program such as Sybyl. By visual inspection of those displayed representations, one can select corresponding compounds containing moieties appropriately disposed with respect to each other such that they coincide with preferred locations shown by the maps (i.e., locations identified for each selected functional group characterized by favorable interaction energies with the target protein). Using computer programs such as LeapFrog one may "grow" a compound stochastically from one or more selected moieties located within appropriately mapped locations. Alternatively, starting with mapped favorable locations for two or more moieties, one may define"vectors" defining the spatial relationship between those moieties, and then use those vectors to select or design compounds embodying the selected moieties in the appropriate spatial relationship. Databases containing 3D structures of potential ligands contain experimentally determined or computationally generated structures. The selection or design process may be conducted with the aid of computer using a programs such as ALADDIN (Van Drie et al, 1989, J Comput-Aided Mol Des 3, 225–251), MACCS-3D (Moock et al, 1990, Chemical Information Systems, (Eds, Bawden & Mitchell, Chichester, pp 42–49), 3D SEARCH, ChemDBS-3D, SYBYL/3DB and CAVEAT. See e.g., Fesik, 1993, J Biomolecular NMR 3, 261–269.

V. Assays

(1) Binding Assays (a) Competitive Binding Assays

Binding may be measured by competition using surface plasmon resonance and allied technologies (Malmqvist, M.

*Current Opinions in Immunology* 5, 282–286; (1993); Malmqvist, M., *Nature* 361:186–187 (1993); Jonsson, U. and Malmqvist, M.,*Advances in Biosensors,* JAI Press Ltd., London, 1992, pp. 291–336; Jonsson, U. et al., *Bio Techniques* 11(5):620–627 (1991). SH2 domains are typically pre-incubated with various concentrations of test compound and the ability of the test compound to competitively inhibit SH2 binding to an immobilized phosphopeptide ligand measured. Results are compared to binding measured in the absence of competitor and expressed as percent inhibition. IC50 values reflect the concentration of inhibitor required to reduce binding by 50%. Specifics of individual assays are described below. All assays are run in HEPES Buffered Saline (HBS) composed of 10 mM HEPES (pH 7.4)/150 mM NaCl/3.4 mM EDTA/0.05% Tween 20±10 mM DTT at 25° C.

Primary Screen

Test compound (e.g. 50 uM) is preincubated with the target SH2 in HBS±10 mM DTT for a minimum of 1 hr at 4° C. The ability of the compound to inhibit binding of the SH2 domain to a target phosphopeptide is measured using SPR. Compounds that inhibit SH2 phosphopetide association by a predetermined increment (e.g. $\geq$50%) are subjected to a secondary screen.

Secondary Screen

Log dilutions of test compound ($10^{-4}, 10^{-5}, 10^{-6}, \ldots$) are preincubated with the target SH2 in HBS±10 mM DTT. The ability of the compound to inhibit binding of the SH2 domain to the target phosphopeptide is measured using SPR. IC50s are determined from the plot of per cent inhibition (compared to SH2 domain in the absence of inhibitor) vs. compound concentration.

Specifics of Tandem ZAP Assay

A peptide corresponding to the ζ-chain ITAM-1 of the human T-cell receptor [NQLY(PO$_4$)NELNLGRREEY(PO$_4$)DVLD] [SEQ ID NO. 15] was synthesized as a part of a larger peptide [Ac-KGGNQLY(PO$_4$)NELNLGRREEY-(PO$_4$)DVLD-NH$_2$] [SEQ ID NO. 16] and used to generate a ZAP-sensitive biosensor surface. Specifically, a Biosensor Chip CM5 was activated with 200 mM EDC 50 mM NHS to generate a surface reactive to primary amines and the ITAM peptide immobilized through the N-terminal lysine. Unreacted sites were blocked with ethanolamine (1 M in water) and the chip cleaned of non-covalently bound peptide using 6 M guanidine hydrochloride. Assays were run in HBS+10 NM DTT using 10 nM pp70$^{ZAP}$(1–259) +/– test inhibitor.

Specifics of N-ZAP Assay

A peptide corresponding to the ζ-chain ITAM-1 of the human T-cell receptor [NQLYNELNLGRREEY(PO$_4$)DVLD] [SEQ ID NO. 17] was synthesized as a part of a larger peptide [Ac-KGGNQLYNELNLGRREEY-(PO$_4$)DVLD-NH$_2$] [SEQ ID NO. 18] and used to generate a ZAP-sensitive biosensor surface as described above. Assays were run in HBS +10 mM DTT using pp70$^{ZAP}$(1–259) R195K (a mutant where Arginine-195 is replaced by Lysine to inactivate the C-terminal SH2 domain) +/– test inhibitor.

Specifics of C-ZAP Assay

A peptide corresponding to the ζ-chain ITAM-1 of the human T-cell receptor [NQLYNELNLGRREEY(PO$_4$)DVLD] [SEQ ID NO. 17] was synthesized as a part of a larger peptide [Ac-KGGNQLYNELNLGRREEY-(PO$_4$)DVLD-NH$_2$] [SEQ ID NO. 18] and used to generate a ZAP-sensitive biosensor surface as described above. Assays were run in HBS+10 mM DTT using pp70$^{ZAP}$(1–259)R37K (a mutant where Arginine-37 is replaced by Lysine to inactivate the N-terminal SH2 domain) or pp70$^{ZAP}$(161–259)+/– test inhibitor.

Specifics of Tandem Syk Assay

A pp72$^{syk}$ peptide ligand corresponding to the γ-chain ITAM of human Fc$_\epsilon$RI [DGV(PO$_4$)TGLSTRNQETY(PO$_4$)ETLK] [SEQ ID NO. 19] was synthesized as part of a larger peptide [Ac-CGGDGVY(PO$_4$)TGLSTRNQETY-(PO$_4$)ETLK-NH$_2$] [SEQ ID NO. 20] and used to generate a Syk-sensitive biosensor surface. Specifically, a Biosensor Chip CM5 was activated with 200 mM ethyl-3-(3-dimethylaminopropyl)-carbodiimide hydrochloride (EDC)/50 mM N-hydroxysuccinimide (NHS) to generate a surface reactive to primary amines; treated with ethylenediamine to generate a surface rich in primary amines; activated with m-maleimidobenzoyl-N-hydroxysuccinimide ester (sulfo-MBS; 50 mM in 25 mM NaHCO$_3$) to generate a surface reactive to free thiols; and the ITAM peptide immobilized through the N-terminal cysteine. Unreacted sites were blocked with β-mercaptoethanol and the chip cleaned of non-covalently bound peptide using 6 M guanidine hydrochloride. Assays were run in HBS using 20 nM pp72$^{syk}$ (1–265) +/– test inhibitor.

Specifics of C-Syk Assay

A pp72$^{syk}$ peptide ligand corresponding to a hemiphosphorylated γ-chain ITAM of human Fc$_\epsilon$RI [DGVY(PO$_4$)TGLSTRNQETYETLK] (SEQ ID NO: 34) was synthesized as part of a larger peptide [Ac-CGGDGVY(PO$_4$)TGLSTRNQETYETLK-NH$_2$] (SEQ ID NO: 35) and used to generate a C-Syk-sensitive biosensor surface as described above for tandem syk. Assays were run in HBS using 270 nM pp72$^{syk}$(163–265) +/– test inhibitor.

(2) Cell-based Assays (a) T Cell Assay (T Cell Receptor-dependent Transcription)

Purpose and description of assay

This assay measures the ability of a compound to inhibit TCR activation of the IL-2 transcription pathway in the human Jurkat T cell line. These Jurkat cells have been transfected with a construct containing the β-galactosidase gene under the control of an upstream promoter element, the NF-AT binding site, which normally regulates IL-2 production.[18] When cells are activated, β-galactosidase is produced.

Drug Treatment of Cells and Stimulation

The compounds to be assayed are serially diluted into assay buffer and each dilution is added to the Jurkat cells for a 1 hour pre-incubation. After the pre-incubation, the cells are transferred to plates coated with antibody to the CD3 component of the TCR. This antibody crosslinks the TCR, leading to activation of receptor signaling pathways. The cells are incubated for 4 hours, then the amount of β-gal produced is measured.

Measurement of β-galactosidase

The assay is used to quantitate the amounts of β-galactosidase produced is the MUG assay. MUG, 4-methylumbelliferone galactose, is cleaved by β-galactosidase to form a fluorescent derivative, 7-hydroxy-4-methylcoumarin. The observed fluorescence correlates with the amount of cleavage product, and thus with the amount of β-galactosidase. Production of β-gal without the addition of compound determines the 100% value for each well. The raw data is converted into "percent of control", triplicate wells are averaged, and then the data is plotted as % of control release vs. concentration of test compound.

(b) Cytotoxic T Lymphocyte Killing

Purpose and Description of Assay

This assay measures the ability of a compound to inhibit the cytolytic function of human cytotoxic lymphocyte lines.

Human CD8+ CTL were generated from mitogen-stimulated peripheral blood lymphocytes. Mitogen activated cells were grown in IL2 and re-stimulated every 3 weeks with antibodies directed against the T cell receptor complex and CD4+ cells were sorted and cloned. Clone T9 vias selected for use in the CTL assay. Since the T cells were selected nonspecifically, i.e. no specific antigen was used for induction, the target chosen for the assay was the B cell hybridoma OKT3. This cell line expresses anti-CD3 on its surface(an antibody against one of the subunits of the T cell receptor). The recognition of the T cell receptor by the antibody induces the cytolytic process of the target Drug Treatment of Cells and Stimulation The compounds to be assayed are serially diluted into assay buffer and each dilution is added to the CTL's for a 1 hour pre-incubation. After the pre-incubation, the cells are mixed with $^{51}Cr$ labelled OKT3 cells at a ratio of 3:1 (effector:target) and incubated for 3 hours. This ratio of effector to targets results in approximately 30% specific release.

Measurement of $^{51}Cr$ release

The cell mixture is centrifuged and the supernatant is removed. The amount of $^{51}Cr$ released into the media is measured on a γ counter and the specific release is determined using detergent lysed target cells as the 100% value. The data is plotted as % specific release vs. concentration of test compound.

(3) Animal Models (a) Delayed Type Hypersensitivity

An initial screening model is delayed type hypersensitivity. Mouse abdomens are painted with sensitizing chemicals (sensitization) such as dinitroflourobenzene or oxazalone. Seven days later the ears of sensitized mice are painted (challenge) with a lower concentration of the compound. Antigen processing and presentation, T lymphocyte activation, leukocyte infiltration, humoral mediator release, increased microvascular permeability, and plasma exudation all result from challenge of sensitized mice and lead to edema formation. Edema presents as a two- to three- fold increase in ear thickness within twenty-four hours.

The test compounds or standards can be applied (topical or parenteral) at various times before or after the sensitization or challenge phases. Increased ear thickness is prevented by several compounds including immunosuppressive agents and steroids. This model is a primary model for contact dermatitis.

(b) Allogeneic Skin Transplantation

An allogeneic skin transplant model is used to identify immunosuppressive activity of test compounds. In this model, donor mouse thoracic skin (Balb/c) is surgically grafted onto the thorax of recipient mice (C57bl/6). Host rejection of the graft is evidenced by erythema, drying out, and retraction of donor skin. The mean graft survival time is 10 to 11 days, with 80% of the grafts being rejected by 12 days. Active novel immunosuppressive compounds, like existing immunosuppressive compounds, will prolong graft survival.

(c) Popliteal Lymph Node Hyperplasia

This model directly assesses T lymphocyte proliferation in vivo. Spleen cells, obtained from Balb/c mice, are isolated and administered into the foot pads of C3H mice. Within four days, the popliteal lymph nodes can be removed from the recipient mice and weighed. Other hematological assessments including FACS scanning for T lymphocyte subpopulations may also be performed. Active compounds, like existing immunosuppressive compounds, will inhibit the increase in node mass.

(d) Rheumatoid Arthritis

Several models are available for assessment of anti-arthritic activity, including adjuvant-induced, carageenan-induced, and collagen-induced arthritis in rats and/or mice. Paw pads are injected with one of these agents Paws increase in volume, and measurements are made between 20 and 30 days later. The ability of test compounds to prevent the induction of paw swelling is tested with daily treatment for 12 consecutive days following the injection of inducing agent. The ability for the test compounds to reverse the progression of the paw swelling is tested by administration of the compound for 12 consecutive days beginning on the twelfth clay following the injection of inducing agent. Paw swelling measurements are made by water displacement plethysmography. Histology is also an appropriate endpoint for these studies. The MRL/Ipr-mouse model, described above, is required for the rheumatoid arthritis indication. This model is a spontaneous autoimmune model that develops rheumatoid arthritis resembling the human condition, including the presence of circulating rheumatoid factor, pannus formation, and bone and cartilage erosion.

(e) Systemic Lupus Erythematosus

Systemic lupus erythematosus is another autoimmune disease with several animal models. Several murine strains develop spontaneous SLE. One such strain is MRL/Ipr-mice. These mice, over time (20 to 30 weeks) develop auto-antibodies against dsDNA, nuclear antigens, and renal basement membrane. This leads to complement fixation and immune complex formation. Damage to the kidney becomes apparent with the on set of proteinuria. Many of the other physiologic, hematologic, and immunologic aberrations described below for the CGVHD model are present. Immunosuppressive compounds such as cyclosporin, cyclophosphamide, and leflunomide can prevent and reverse the course of disease in this model. Interestingly, these mice also develop pathologies akin to rheumatoid arthritis.

The murine chronic graft versus host disease model (CGVHD, described below) is a model of SLE that contains many of the clinical features of SLE. Activity in this model has been shown to be predictive of activity in the more clinically relevant SLE models.

(f) Transplantation

Allograft transplantation (skin graft) assay is often used as an initial test of immunosuppressive activity. While this model is useful as a screen, it may be supplemented with assays based on animal transplant models involving transplantation of internal organ (heart, liver, kidney, bone marrow) with use of "clinically acceptable" physiologic endpoints to assess graft survival. Efficacy of test compounds in only a very limited number of these rodent models is required. Following observation of activity in a rodent model, the test compounds are typically tested in further animal models (e.g., canine, porcine or non-human primate). Active compounds decrease acute and chronic rejection and prolong transplant survival.

(a) Graft vs. Host Disease

Chronic GVHD (CGVHD) can be used to model CD4+-dependent humoral immunity. It is induced in $BDF_1$ mice (which are progeny of DBA/2 male ×C57BU6 female matings) by administering to them isolated spleen:lymph node cells from DBA/2 mice. This results in: a) disregulation and stimulation of CD4+ T lymphocyte ($Ly1^+$; murine marker) activity due to incompatibilities at MHC II molecules, and b) abnormal T-B lymphocyte cooperation. The resulting pathological state, in many ways, mimics systemic lupus erythematosus (SLE). Several measurable endpoints develop within 14 days; including, circulating anti-host IgG and IgE antibodies, altered T and B lymphocyte proliferation activity measured in vitro, complement utilization, hemagglutination, slow progressive wasting, dermal aberrations, splenomegaly, lymphoid hyperplasia, and proteinuria. Only a few of these endpoints need to be measured. Active compounds are those which limit T lymphocyte disregulation and abrogate changes in these variables. Many steroids (e.g., prednisolone), cyclosporine, FK-506, cyclophosphamide, and leflunomide are all active in this model and can be used as positive controls The acute GVHD model (AGVHD) is also produced in $BDF_1$ mice. In this case, isolated spleen:lymph node cells from C57BL/6 mice are administered. This results in disregulation and stimulation of $CD8^+$ T lymphocytes due to incompatibilities in the MHC I molecules. Elevated cytokine levels and donor clonal expansion occurs. Ultimately, donor cytotoxic T lymphocytes and NK cells rapidly reject host tissue and cause relatively rapid death of the recipient. The progression of AGVHD in this model is assessed by measurement of hematologic abnormalities (including T cell number and type), cytokine elevations (TNF, IL-1, IL-2, and/or IL4), low body weight, hypoγglobulinemia, circulating hematologic characteristics indicative of aplastic aneniia (granulocytopenia, thrombocytopenia), ex vivo NK or CTL activity, and host survival. Active compounds are those which abrogate changes in the variables, and prolong survival over 4 to 6 weeks.

(h) Asthma

Asthma offers another opportunity for safe immunosuppressive therapy. Atopic asthmatics have antibody mediated hypersensitivity and the often occurring late phase reaction is likened to a DTH response. Asthma has only recently been defined as an inflammatory disease (1992). Since then, several publications from prominent asthmatologists demonstrate the presence of activated $CD4^+$ and $CD8^+$ T lymphocytes in bronchoalveolar lavage fluid and blood of atopic asthmatics. The ratios of these cells changes in asthmatic conditions. Furthermore, several of the T cell associated cytokines (IL-1, IL-2, IL4, IL-5, and TNF) are all implicated in clinical and experimental asthma. Inflammatory events in asthma are now considered to be T lymphocyte driven. Initial clinical trials with inhaled cyclosporin suggest that local immunosuppression can ameliorate airway hyperreactivity—the underlying defect in asthma.

The guinea pig model of antigen-induced pulmonary aberrations is used as a model for asthma. These animals are actively sensitized to ovalbumin to generate high circulating titers of anti-ovalbumin antibody with seroconversion to the IgE class, as is the case with atopic asthmatics. Aerosol challenge of sensitized guinia pigs results in measurable eosinophil rich pulmonary infiltrates (approximately a 16-fold increase in eosinophils), pulmonary edema, and mucous plugging of the small airways; all culminating in the expression of the underlying defect in asthma—airway hyperreactivity (approximately a 3 to 4-fold increase in reactivity) Acute bronchoconstriction is obviously present and points the aforementioned presence of the pathophysiologic sequelae. Active compounds are those which lessen or abrogate such symptoms.

The above description is meant to illustrate, rather than limit the scope of the invention. Given the foregoing description, numerous variations in the materials or methods employed in performing the invention will be obvious to one skilled in the art. Any such obvious variation is to be considered within the scope of the invention.

References

1. Weiss, A. & Littman, D. R. *Cell* 76,263–274 (1994).
2. Isakov, N., Wange, R. L. & Samelson, L. E. *J. Leuk. Biol.* 55, 265–271 (1994).
3. Reth, M. *Nature* 338, 383–384 (1989).
4. Weiss, A. *Cell* 73, 209–212 (1993).
5. Wange, R. L., Malek, S. N., Desiderio, S. & Samelson, L. E. *J. Biol. Chem.* 268, 19797–19801 (1993).
6. Chan, A., Irving, B. A., Fraser, J. D. & Weiss, A. *Proc. Natl. Acad. Sci.* 88, 9166–9170 (1991).
7. Chan, A. C., Iwashima, M., Turck, C. W. & Weiss, A. *Cell* 71, 649–662 (1992).
8. Elder, M. E., et al. *Science* 264, 1596–1599 (1994).
9. Arpaia, E., Shahar, M., Dadi, H., Cohen, A. & Roifman, C. M. *Cell* 76, 947–958 (1994).
10. Wange, R. L., et al. *J. Biol. Chem.* 270,944–948 (1995).
11. Cohen, G. B., Ren, R. & Baltimore, D. *Cell* 80,237–248 (1995).
12. Pawson, T. *Nature* 373, 573–580 (1995).
13. Waksman, G., et al. *Nature* 358, 646–653 (1992).
14. Mikol, V., Baumann, G., Keller, T. H., Manning, U. & Zurini, M. G. *J. Mol. Biol.* 246, 344–355 (1995).
15. Eck, M. J., Atwell, S. K., Shoelson, S. E. & Harrison, S. C. *Nature* 368, 764–769 (1994).
16. Maigan, S., et al. *Science* 268, 291–293 (1995).
17. Letoumeur, F. & Klausner, R. D. *Proc. Natl. Acad. Sci. USA* 88, 8905–8909 (1991).
18. Gauen, L. K. T., et al. *Mol. Cell. Biol.* 14, 3729–3741 (1994).
19. Iwashima, M., Irving, B. A., van Oers, N. S. C., Chan, A. C. & Weiss, A. *Science* 263, 1136–1139 (1994).
20. Eck, M. J., Shoelson, S. E. & Harrison, S. C. *Nature* 362, 87–91 (1993).
21. Waksman, G., Shoelson, S. E., Pant, N., Cowburn, D. & Kuriyan, J. *Cell* 72, 779–790 (1993).
22. Dhand, R., et al. *The EMBO Journal* 13, 511–521 (1994).
23. Lee, C., et al. *Structure* 2, 423–438 (1994).
24. Janin, J. & Chothia, C. *J. Biol. Chem.* 265, 16027–16030 (1990).
25. Isakov, N., et al. *J. Exp. Med.* 181, 375–380 (1995).
26. Koyasu, S., et al. *Proc. Natl. Acad. Sci. USA* 91, 6693–6697 (1994).
27. Cohen, C. & Parry, D. A. D. *Science* 263,488–489 (1994).
28. Taniguchi, T., et al. *J. Biol. Chem.* 266, 15790–15796 (1991).
29. Carpenter, C. L., et al. *J. Biol. Chem.* 268, 9478–9483 (1993).
30. Shiue, L., Zoller, M. J. & Brugge, J. S. *J. Biol. Chem.* 270,10498–10502 (1995).
31. Rowley, R. B., Burkhardt, A. L., Chao, H. G., Matsueda, G. R. & Bolen, J. B. *J. Biol. Chem.* 270, 11590–11594 (1995).
32. Watts, J. D., et al. *J. Biol. Chem.* 269, 29520–29529 (1994).
33. Koch, C. A., Anderson, D., Moran, M. F., Ellis, C. & Pawson, T. *Science* 252, 668–674 (1991).
34. Shiue, L., et al. *Mol. Cell. Biol.* 15, 272–281 (1995).
35. Sigal, N. H., et al. *J. Exp. Med.* 173, 619–628 (1991).
36. Dumont, F. J., et al. *J. Exp. Med.* 176, 751–760 (1992).
37. Liu, J., et al. *Cell* 66, 807–815 (1991).
38. Liu, J., et al. *Biochem.* 31, 3896–3901 (1992).
39. Andrews, D. M., Kitchin, J. & Seale, P. W. *Int. J. Pep. Pro. Res.* 38, 469–475 (1991).
40. Perich, J. W. *Int. J. Pep. Pro. Res.* 40, 134–140 (1992).
41. Smith, D. B. & Johnson, K. S. *Gene* 67, 31–40 (1988).

42. Leahy, D. J., Erickson, H. P., Aukhil, I., Joshi, P. & Henrickson, W. *Proteins* 19, 48–54 (1994).
43. Otwinowski, Z. Data Collection and Processing (SERC Daresbury Laboratory, Warrington, UK, 1993).
44. CCP4. CCP4: A suite of Programs for Protein Crystallography (SERC Collaborative Computing Project no. 4, Warrington, UK, 1979).
45. Jones, T. A., Zou, J. Y., Cowan, S. W. & Kjeldgaard, M. Acta Crystallogr. 47, 110–119 (1991).
46. Brunger, A. T. X-PLOR, Versiona 1, A Systen for X-Ray Crystallography and NMR (Yale University Press, New Haven, Conn., 1992).
47. Ferrin, T. E. *J. Mol. Graph.* 6,13–27 (1988).

TABLE 21

Coordinates for the 3D structure of ZAP-NC:ζ1*

REMARK FILENAME="test-slow.pdb"
REMARK TOPH19.pep -MACRO for protein sequence
created by user: marcos

| | Atom Number | Atom type | amino acid residue | | x | y | z | occ | temp factor |
|---|---|---|---|---|---|---|---|---|---|
| ATOM | 1 | CB | ASP | 3 | −1.489 | −4.706 | 36.906 | 1.00 | 37.30 |
| ATOM | 2 | CG | ASP | 3 | −2.232 | −3.399 | 37.163 | 1.00 | 38.04 |
| ATOM | 3 | OD1 | ASP | 3 | −2.949 | −3.304 | 38.181 | 1.00 | 39.49 |
| ATOM | 4 | OD2 | ASP | 3 | −2.094 | −2.461 | 36.353 | 1.00 | 34.64 |
| ATOM | 5 | C | ASP | 3 | −1.755 | −4.886 | 34.408 | 1.00 | 34.63 |
| ATOM | 6 | O | ASP | 3 | −0.595 | −4.867 | 34.003 | 1.00 | 34.56 |
| ATOM | 7 | HT1 | ASP | 3 | −0.506 | −6.812 | 35.572 | 1.00 | 0.00 |
| ATOM | 8 | HT2 | ASP | 3 | −1.947 | −7.433 | 34.967 | 1.00 | 0.00 |
| ATOM | 9 | N | ASP | 3 | −1.527 | −6.899 | 35.753 | 1.00 | 40.12 |
| ATOM | 10 | HT3 | ASP | 3 | −1.707 | −7.382 | 36.652 | 1.00 | 0.00 |
| ATOM | 11 | CA | ASP | 3 | −2.095 | −5.522 | 35.754 | 1.00 | 36.56 |
| ATOM | 12 | N | PRO | 4 | −2.771 | −4.385 | 33.690 | 1.00 | 31.82 |
| ATOM | 13 | CD | PRO | 4 | −4.186 | −4.460 | 34.087 | 1.00 | 32.51 |
| ATOM | 14 | CA | PRO | 4 | −2.640 | −3.739 | 32.379 | 1.00 | 29.95 |
| ATOM | 15 | CB | PRO | 4 | −4.058 | −3.243 | 32.113 | 1.00 | 30.71 |
| ATOM | 16 | CG | PRO | 4 | −4.895 | −4.275 | 32.774 | 1.00 | 31.34 |
| ATOM | 17 | C | PRO | 4 | −1.652 | −2.579 | 32.341 | 1.00 | 28.61 |
| ATOM | 18 | O | PRO | 4 | −1.211 | −2.170 | 31.265 | 1.00 | 30.48 |
| ATOM | 19 | N | ALA | 5 | −1.333 | −2.029 | 33.509 | 1.00 | 25.13 |
| ATOM | 20 | H | ALA | 5 | −1.777 | −2.325 | 34.322 | 1.00 | 0.00 |
| ATOM | 21 | CA | ALA | 5 | −0.411 | −0.905 | 33.592 | 1.00 | 21.95 |
| ATOM | 22 | CB | ALA | 5 | −1.029 | 0.206 | 34.437 | 1.00 | 20.80 |
| ATOM | 23 | C | ALA | 5 | 0.973 | −1.261 | 34.121 | 1.00 | 20.21 |
| ATOM | 24 | O | ALA | 5 | 1.884 | −0.442 | 34.064 | 1.00 | 19.51 |
| ATOM | 25 | N | ALA | 6 | 1.151 | −2.504 | 34.553 | 1.00 | 19.03 |
| ATOM | 26 | H | ALA | 6 | 0.413 | −3.137 | 34.469 | 1.00 | 0.00 |
| ATOM | 27 | CA | ALA | 6 | 2.422 | −2.958 | 35.124 | 1.00 | 18.99 |
| ATOM | 28 | CB | ALA | 6 | 2.339 | −4.443 | 35.462 | 1.00 | 22.76 |
| ATOM | 29 | C | ALA | 6 | 3.674 | −2.679 | 34.296 | 1.00 | 16.60 |
| ATOM | 30 | O | ALA | 6 | 4.755 | −2.485 | 34.847 | 1.00 | 14.22 |
| ATOM | 31 | N | HIS | 7 | 3.527 | −2.665 | 32.977 | 1.00 | 15.98 |
| ATOM | 32 | H | HIS | 7 | 2.628 | −2.813 | 32.643 | 1.00 | 0.00 |
| ATOM | 33 | CA | HIS | 7 | 4.660 | −2.422 | 32.091 | 1.00 | 16.26 |
| ATOM | 34 | CB | HIS | 7 | 4.424 | −3.096 | 30.736 | 1.00 | 16.78 |
| ATOM | 35 | CG | HIS | 7 | 3.194 | −2.622 | 30.027 | 1.00 | 16.42 |
| ATOM | 36 | CD2 | HIS | 7 | 3.033 | −1.729 | 29.021 | 1.00 | 16.56 |
| ATOM | 37 | ND1 | HIS | 7 | 1.933 | −3.092 | 30.324 | 1.00 | 15.90 |
| ATOM | 38 | HD1 | HIS | 7 | 1.674 | −3.788 | 30.967 | 1.00 | 0.00 |
| ATOM | 39 | CE1 | HIS | 7 | 1.049 | −2.511 | 29.534 | 1.00 | 16.52 |
| ATOM | 40 | NE2 | HIS | 7 | 1.692 | −1.681 | 28.734 | 1.00 | 17.76 |
| ATOM | 41 | HE2 | HIS | 7 | 1.276 | −1.120 | 28.048 | 1.00 | 0.00 |
| ATOM | 42 | C | HIS | 7 | 5.014 | −0.943 | 31.891 | 1.00 | 17.19 |
| ATOM | 43 | O | HIS | 7 | 6.082 | −0.629 | 31.357 | 1.00 | 18.03 |
| ATOM | 44 | N | LEU | 8 | 4.125 | −0.038 | 32.300 | 1.00 | 14.61 |
| ATOM | 45 | H | LEU | 8 | 3.316 | −0.310 | 32.782 | 1.00 | 0.00 |
| ATOM | 46 | CA | LEU | 8 | 4.382 | 1.393 | 32.143 | 1.00 | 14.75 |
| ATOM | 47 | CB | LEU | 8 | 3.106 | 2.216 | 32.371 | 1.00 | 15.09 |
| ATOM | 48 | CG | LEU | 8 | 2.051 | 2.374 | 31.267 | 1.00 | 19.47 |
| ATOM | 49 | CD1 | LEU | 8 | 2.669 | 2.167 | 29.891 | 1.00 | 21.37 |
| ATOM | 50 | CD2 | LEU | 8 | 0.911 | 1.417 | 31.472 | 1.00 | 23.01 |
| ATOM | 51 | C | LEU | 8 | 5.481 | 1.879 | 33.085 | 1.00 | 13.31 |
| ATOM | 52 | O | LEU | 8 | 5.432 | 1.628 | 34.288 | 1.00 | 13.01 |
| ATOM | 53 | N | PRO | 9 | 6.478 | 2.609 | 32.551 | 1.00 | 13.43 |
| ATOM | 54 | CD | PRO | 9 | 6.691 | 2.982 | 31.141 | 1.00 | 13.38 |
| ATOM | 55 | CA | PRO | 9 | 7.571 | 3.113 | 33.385 | 1.00 | 12.50 |
| ATOM | 56 | CB | PRO | 9 | 8.523 | 3.736 | 32.363 | 1.00 | 12.42 |
| ATOM | 57 | CG | PRO | 9 | 7.617 | 4.159 | 31.267 | 1.00 | 14.81 |
| ATOM | 58 | C | PRO | 9 | 7.117 | 4.122 | 34.440 | 1.00 | 10.81 |
| ATOM | 59 | O | PRO | 9 | 7.783 | 4.297 | 35.459 | 1.00 | 12.13 |
| ATOM | 60 | N | PHE | 10 | 5.985 | 4.776 | 34.200 | 1.00 | 11.91 |
| ATOM | 61 | H | PHE | 10 | 5.502 | 4.601 | 33.371 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 62 | CA | PHE | 10 | 5.451 | 5.761 | 35.140 | 1.00 | 11.80 |
| ATOM | 63 | CB | PHE | 10 | 4.981 | 7.029 | 34.406 | 1.00 | 10.49 |
| ATOM | 64 | CG | PHE | 10 | 4.009 | 6.769 | 33.289 | 1.00 | 12.16 |
| ATOM | 65 | CD1 | PHE | 10 | 2.642 | 6.722 | 33.536 | 1.00 | 11.91 |
| ATOM | 66 | CD2 | PHE | 10 | 4.460 | 6.579 | 31.985 | 1.00 | 12.16 |
| ATOM | 67 | CE1 | PHE | 10 | 1.738 | 6.492 | 32.505 | 1.00 | 14.05 |
| ATOM | 68 | CE2 | PHE | 10 | 3.561 | 6.348 | 30.949 | 1.00 | 11.03 |
| ATOM | 69 | CZ | PHE | 10 | 2.198 | 6.305 | 31.210 | 1.00 | 10.40 |
| ATOM | 70 | C | PHE | 10 | 4.348 | 5.220 | 36.063 | 1.00 | 10.35 |
| ATOM | 71 | O | PHE | 10 | 3.648 | 5.994 | 36.714 | 1.00 | 9.59 |
| ATOM | 72 | N | PHE | 11 | 4.172 | 3.901 | 36.085 | 1.00 | 10.23 |
| ATOM | 73 | H | PHE | 11 | 4.752 | 3.312 | 35.559 | 1.00 | 0.00 |
| ATOM | 74 | CA | PHE | 11 | 3.179 | 3.263 | 36.944 | 1.00 | 9.09 |
| ATOM | 75 | CB | PHE | 11 | 2.539 | 2.060 | 36.241 | 1.00 | 8.78 |
| ATOM | 76 | CG | PHE | 11 | 1.602 | 1.266 | 37.119 | 1.00 | 8.82 |
| ATOM | 77 | CD1 | PHE | 11 | 0.374 | 1.787 | 37.504 | 1.00 | 9.98 |
| ATOM | 78 | CD2 | PHE | 11 | 1.949 | −0.011 | 37.548 | 1.00 | 12.08 |
| ATOM | 79 | CE1 | PHE | 11 | −0.497 | 1.046 | 38.301 | 1.00 | 10.58 |
| ATOM | 80 | CE2 | PHE | 11 | 1.083 | −0.759 | 38.345 | 1.00 | 11.57 |
| ATOM | 81 | CZ | PHE | 11 | −0.141 | −0.230 | 38.722 | 1.00 | 10.29 |
| ATOM | 82 | C | PHE | 11 | 3.904 | 2.819 | 38.214 | 1.00 | 10.01 |
| ATOM | 83 | O | PHE | 11 | 4.890 | 2.084 | 38.157 | 1.00 | 10.38 |
| ATOM | 84 | N | TYR | 12 | 3.421 | 3.279 | 39.360 | 1.00 | 8.54 |
| ATOM | 85 | H | TYR | 12 | 2.645 | 3.868 | 39.342 | 1.00 | 0.00 |
| ATOM | 86 | CA | TYR | 12 | 4.050 | 2.962 | 40.628 | 1.00 | 7.85 |
| ATOM | 87 | CB | TYR | 12 | 4.154 | 4.229 | 41.471 | 1.00 | 9.01 |
| ATOM | 88 | CG | TYR | 12 | 5.234 | 5.165 | 40.994 | 1.00 | 9.41 |
| ATOM | 89 | CD1 | TYR | 12 | 5.079 | 5.911 | 39.829 | 1.00 | 11.88 |
| ATOM | 90 | CE1 | TYR | 12 | 6.098 | 6.737 | 39.371 | 1.00 | 10.68 |
| ATOM | 91 | CD2 | TYR | 12 | 6.432 | 5.275 | 41.688 | 1.00 | 10.27 |
| ATOM | 92 | CE2 | TYR | 12 | 7.444 | 6.094 | 41.242 | 1.00 | 10.04 |
| ATOM | 93 | CZ | TYR | 12 | 7.275 | 6.821 | 40.086 | 1.00 | 10.17 |
| ATOM | 94 | OH | TYR | 12 | 8.296 | 7.629 | 39.659 | 1.00 | 14.36 |
| ATOM | 95 | HH | TYR | 12 | 8.048 | 7.993 | 38.798 | 1.00 | 0.00 |
| ATOM | 96 | C | TYR | 12 | 3.398 | 1.856 | 41.436 | 1.00 | 8.85 |
| ATOM | 97 | O | TYR | 12 | 3.909 | 1.466 | 42.483 | 1.00 | 9.35 |
| ATOM | 98 | N | GLY | 13 | 2.278 | 1.340 | 40.950 | 1.00 | 11.20 |
| ATOM | 99 | H | GLY | 13 | 1.920 | 1.683 | 40.111 | 1.00 | 0.00 |
| ATOM | 100 | CA | GLY | 13 | 1.597 | 0.284 | 41.669 | 1.00 | 12.09 |
| ATOM | 101 | C | GLY | 13 | 0.762 | 0.814 | 42.818 | 1.00 | 12.99 |
| ATOM | 102 | O | GLY | 13 | 0.266 | 1.940 | 42.769 | 1.00 | 12.85 |
| ATOM | 103 | N | SER | 14 | 0.635 | 0.010 | 43.865 | 1.00 | 12.55 |
| ATOM | 104 | H | SER | 14 | 1.068 | −0.867 | 43.854 | 1.00 | 0.00 |
| ATOM | 105 | CA | SER | 14 | −0.167 | 0.356 | 45.027 | 1.00 | 14.38 |
| ATOM | 106 | CB | SER | 14 | −0.680 | −0.931 | 45.685 | 1.00 | 13.42 |
| ATOM | 107 | OG | SER | 14 | −1.532 | −0.657 | 46.784 | 1.00 | 21.30 |
| ATOM | 108 | HG | SER | 14 | −1.068 | −0.007 | 47.331 | 1.00 | 0.00 |
| ATOM | 109 | C | SER | 14 | 0.542 | 1.232 | 46.060 | 1.00 | 15.49 |
| ATOM | 110 | O | SER | 14 | 0.894 | 0.760 | 47.144 | 1.00 | 18.54 |
| ATOM | 111 | N | ILE | 15 | 0.748 | 2.506 | 45.737 | 1.00 | 14.76 |
| ATOM | 112 | H | ILE | 15 | 0.428 | 2.829 | 44.869 | 1.00 | 0.00 |
| ATOM | 113 | CA | ILE | 15 | 1.390 | 3.423 | 46.676 | 1.00 | 12.31 |
| ATOM | 114 | CB | ILE | 15 | 2.571 | 4.210 | 46.040 | 1.00 | 12.37 |
| ATOM | 115 | CG2 | ILE | 15 | 3.712 | 3.256 | 45.687 | 1.00 | 13.51 |
| ATOM | 116 | CG1 | ILE | 15 | 2.101 | 5.014 | 44.827 | 1.00 | 11.08 |
| ATOM | 117 | CD | ILE | 15 | 3.131 | 6.016 | 44.347 | 1.00 | 12.11 |
| ATOM | 118 | C | ILE | 15 | 0.354 | 4.398 | 47.226 | 1.00 | 10.69 |
| ATOM | 119 | O | ILE | 15 | −0.750 | 4.488 | 46.701 | 1.00 | 11.71 |
| ATOM | 120 | N | SER | 16 | 0.700 | 5.099 | 48.299 | 1.00 | 8.45 |
| ATOM | 121 | H | SER | 16 | 1.588 | 5.018 | 48.689 | 1.00 | 0.00 |
| ATOM | 122 | CA | SER | 16 | −0.219 | 6.053 | 48.899 | 1.00 | 12.16 |
| ATOM | 123 | CB | SER | 16 | 0.073 | 6.199 | 50.393 | 1.00 | 8.73 |
| ATOM | 124 | OG | SER | 16 | 1.380 | 6.711 | 50.597 | 1.00 | 11.59 |
| ATOM | 125 | HG | SER | 16 | 1.483 | 6.783 | 51.560 | 1.00 | 0.00 |
| ATOM | 126 | C | SER | 16 | −0.073 | 7.411 | 48.225 | 1.00 | 11.37 |
| ATOM | 127 | O | SER | 16 | 0.883 | 7.640 | 47.474 | 1.00 | 10.80 |
| ATOM | 128 | N | ARG | 17 | −1.006 | 8.315 | 48.509 | 1.00 | 10.26 |
| ATOM | 129 | H | ARG | 17 | −1.743 | 8.056 | 49.105 | 1.00 | 0.00 |
| ATOM | 130 | CA | ARG | 17 | −0.944 | 9.657 | 47.947 | 1.00 | 8.92 |
| ATOM | 131 | CB | ARG | 17 | −2.148 | 10.492 | 48.385 | 1.00 | 9.48 |
| ATOM | 132 | CG | ARG | 17 | −2.033 | 11.962 | 47.998 | 1.00 | 8.28 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 133 | CD | ARG | 17 | −3.228 | 12.766 | 48.448 | 1.00 | 8.69 |
| ATOM | 134 | NE | ARG | 17 | −4.417 | 12.388 | 47.701 | 1.00 | 8.47 |
| ATOM | 135 | HE | ARG | 17 | −4.400 | 11.503 | 47.308 | 1.00 | 0.00 |
| ATOM | 136 | CZ | ARG | 17 | −5.470 | 13.173 | 47.505 | 1.00 | 10.19 |
| ATOM | 137 | NH1 | ARG | 17 | −5.499 | 14.402 | 48.002 | 1.00 | 10.59 |
| ATOM | 138 | HH11 | ARG | 17 | −4.717 | 14.750 | 48.520 | 1.00 | 0.00 |
| ATOM | 139 | HH12 | ARG | 17 | −6.295 | 14.988 | 47.859 | 1.00 | 0.00 |
| ATOM | 140 | NH2 | ARG | 17 | −6.490 | 12.734 | 46.789 | 1.00 | 8.14 |
| ATOM | 141 | HH21 | ARG | 17 | −6.457 | 11.804 | 46.413 | 1.00 | 0.00 |
| ATOM | 142 | HH22 | ARG | 17 | −7.292 | 13.305 | 46.629 | 1.00 | 0.00 |
| ATOM | 143 | C | ARG | 17 | 0.342 | 10.321 | 48.426 | 1.00 | 11.05 |
| ATOM | 144 | O | ARG | 17 | 1.039 | 10.974 | 47.649 | 1.00 | 12.01 |
| ATOM | 145 | N | ALA | 18 | 0.666 | 10.131 | 49.704 | 1.00 | 9.21 |
| ATOM | 146 | H | ALA | 18 | 0.067 | 9.605 | 50.279 | 1.00 | 0.00 |
| ATOM | 147 | CA | ALA | 18 | 1.872 | 10.708 | 50.286 | 1.00 | 11.20 |
| ATOM | 148 | CB | ALA | 18 | 2.001 | 10.301 | 51.745 | 1.00 | 15.06 |
| ATOM | 149 | C | ALA | 18 | 3.123 | 10.303 | 49.521 | 1.00 | 12.57 |
| ATOM | 150 | O | ALA | 18 | 3.959 | 11.152 | 49.193 | 1.00 | 12.90 |
| ATOM | 151 | N | GLU | 19 | 3.250 | 9.008 | 49.240 | 1.00 | 11.57 |
| ATOM | 152 | H | GLU | 19 | 2.542 | 8.381 | 49.517 | 1.00 | 0.00 |
| ATOM | 153 | CA | GLU | 19 | 4.403 | 8.488 | 48.514 | 1.00 | 11.99 |
| ATOM | 154 | CB | GLU | 19 | 4.364 | 6.960 | 48.465 | 1.00 | 13.36 |
| ATOM | 155 | CG | GLU | 19 | 4.482 | 6.297 | 49.820 | 1.00 | 20.61 |
| ATOM | 156 | CD | GLU | 19 | 4.358 | 4.790 | 49.742 | 1.00 | 21.71 |
| ATOM | 157 | OE1 | GLU | 19 | 5.400 | 4.108 | 49.647 | 1.00 | 29.81 |
| ATOM | 158 | OE2 | GLU | 19 | 3.216 | 4.285 | 49.774 | 1.00 | 19.69 |
| ATOM | 159 | C | GLU | 19 | 4.449 | 9.043 | 47.099 | 1.00 | 11.13 |
| ATOM | 160 | O | GLU | 19 | 5.524 | 9.357 | 46.584 | 1.00 | 12.79 |
| ATOM | 161 | N | ALA | 20 | 3.280 | 9.155 | 46.472 | 1.00 | 12.51 |
| ATOM | 162 | H | ALA | 20 | 2.463 | 8.875 | 46.939 | 1.00 | 0.00 |
| ATOM | 163 | CA | ALA | 20 | 3.177 | 9.681 | 45.109 | 1.00 | 13.22 |
| ATOM | 164 | CB | ALA | 20 | 1.730 | 9.596 | 44.616 | 1.00 | 10.29 |
| ATOM | 165 | C | ALA | 20 | 3.679 | 11.127 | 45.052 | 1.00 | 11.20 |
| ATOM | 166 | O | ALA | 20 | 4.466 | 11.494 | 44.175 | 1.00 | 11.31 |
| ATOM | 167 | N | GLU | 21 | 3.243 | 11.933 | 46.009 | 1.00 | 10.24 |
| ATOM | 168 | H | GLU | 21 | 2.638 | 11.588 | 46.693 | 1.00 | 0.00 |
| ATOM | 169 | CA | GLU | 21 | 3.652 | 13.328 | 46.071 | 1.00 | 10.86 |
| ATOM | 170 | CB | GLU | 21 | 2.804 | 14.091 | 47.082 | 1.00 | 7.73 |
| ATOM | 171 | CG | GLU | 21 | 1.349 | 14.202 | 46.656 | 1.00 | 8.58 |
| ATOM | 172 | CD | GLU | 21 | 0.488 | 15.002 | 47.625 | 1.00 | 10.14 |
| ATOM | 173 | OE1 | GLU | 21 | −0.692 | 15.230 | 47.308 | 1.00 | 9.72 |
| ATOM | 174 | OE2 | GLU | 21 | 0.985 | 15.414 | 48.693 | 1.00 | 13.94 |
| ATOM | 175 | C | GLU | 21 | 5.142 | 13.468 | 46.374 | 1.00 | 12.31 |
| ATOM | 176 | O | GLU | 21 | 5.780 | 14.425 | 45.942 | 1.00 | 13.09 |
| ATOM | 177 | N | GLU | 22 | 5.706 | 12.487 | 47.073 | 1.00 | 13.22 |
| ATOM | 178 | H | GLU | 22 | 5.162 | 11.739 | 47.388 | 1.00 | 0.00 |
| ATOM | 179 | CA | GLU | 22 | 7.124 | 12.508 | 47.394 | 1.00 | 11.25 |
| ATOM | 180 | CB | GLU | 22 | 7.454 | 11.396 | 48.389 | 1.00 | 16.27 |
| ATOM | 181 | CG | GLU | 22 | 8.811 | 11.551 | 49.035 | 1.00 | 25.51 |
| ATOM | 182 | CD | GLU | 22 | 9.194 | 10.364 | 49.891 | 1.00 | 32.11 |
| ATOM | 183 | OE1 | GLU | 22 | 8.324 | 9.852 | 50.631 | 1.00 | 36.02 |
| ATOM | 184 | OE2 | GLU | 22 | 10.371 | 9.948 | 49.818 | 1.00 | 34.67 |
| ATOM | 185 | C | GLU | 22 | 7.942 | 12.345 | 46.107 | 1.00 | 11.86 |
| ATOM | 186 | O | GLU | 22 | 8.902 | 13.080 | 45.873 | 1.00 | 10.75 |
| ATOM | 187 | N | HIS | 23 | 7.537 | 11.406 | 45.255 | 1.00 | 9.76 |
| ATOM | 188 | H | HIS | 23 | 6.741 | 10.889 | 45.512 | 1.00 | 0.00 |
| ATOM | 189 | CA | HIS | 23 | 8.226 | 11.162 | 43.987 | 1.00 | 9.26 |
| ATOM | 190 | CB | HIS | 23 | 7.651 | 9.927 | 43.286 | 1.00 | 7.86 |
| ATOM | 191 | CG | HIS | 23 | 8.087 | 8.634 | 43.903 | 1.00 | 10.39 |
| ATOM | 192 | CD2 | HIS | 23 | 9.315 | 8.090 | 44.050 | 1.00 | 8.91 |
| ATOM | 193 | ND1 | HIS | 23 | 7.205 | 7.746 | 44.482 | 1.00 | 14.23 |
| ATOM | 194 | HD1 | HIS | 23 | 6.236 | 7.854 | 44.576 | 1.00 | 0.00 |
| ATOM | 195 | CE1 | HIS | 23 | 7.873 | 6.713 | 44.960 | 1.00 | 10.97 |
| ATOM | 196 | NE2 | HIS | 23 | 9.156 | 6.898 | 44.711 | 1.00 | 13.67 |
| ATOM | 197 | HE2 | HIS | 23 | 9.898 | 6.306 | 44.998 | 1.00 | 0.00 |
| ATOM | 198 | C | HIS | 23 | 8.156 | 12.361 | 43.045 | 1.00 | 10.69 |
| ATOM | 199 | O | HIS | 23 | 9.148 | 12.708 | 42.394 | 1.00 | 10.64 |
| ATOM | 200 | N | LEU | 24 | 6.986 | 12.992 | 42.978 | 1.00 | 10.63 |
| ATOM | 201 | H | LEU | 24 | 6.232 | 12.680 | 43.521 | 1.00 | 0.00 |
| ATOM | 202 | CA | LEU | 24 | 6.792 | 14.159 | 42.117 | 1.00 | 10.53 |
| ATOM | 203 | CB | LEU | 24 | 5.309 | 14.532 | 42.046 | 1.00 | 10.68 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 204 | CG | LEU | 24 | 4.393 | 13.515 | 41.350 | 1.00 | 11.63 |
| ATOM | 205 | CD1 | LEU | 24 | 2.935 | 13.881 | 41.539 | 1.00 | 9.03 |
| ATOM | 206 | CD2 | LEU | 24 | 4.724 | 13.449 | 39.874 | 1.00 | 7.43 |
| ATOM | 207 | C | LEU | 24 | 7.636 | 15.343 | 42.599 | 1.00 | 11.35 |
| ATOM | 208 | O | LEU | 24 | 8.165 | 16.110 | 41.790 | 1.00 | 11.67 |
| ATOM | 209 | N | LYS | 25 | 7.790 | 15.472 | 43.914 | 1.00 | 11.16 |
| ATOM | 210 | H | LYS | 25 | 7.347 | 14.841 | 44.523 | 1.00 | 0.00 |
| ATOM | 211 | CA | LYS | 25 | 8.595 | 16.548 | 44.480 | 1.00 | 10.68 |
| ATOM | 212 | CB | LYS | 25 | 8.465 | 16.587 | 46.001 | 1.00 | 9.16 |
| ATOM | 213 | CG | LYS | 25 | 7.135 | 17.068 | 46.517 | 1.00 | 6.98 |
| ATOM | 214 | CD | LYS | 25 | 7.109 | 16.971 | 48.018 | 1.00 | 8.43 |
| ATOM | 215 | CE | LYS | 25 | 5.794 | 17.436 | 48.586 | 1.00 | 9.56 |
| ATOM | 216 | NZ | LYS | 25 | 5.858 | 17.440 | 50.075 | 1.00 | 9.88 |
| ATOM | 217 | HZ1 | LYS | 25 | 6.621 | 18.081 | 50.375 | 1.00 | 0.00 |
| ATOM | 218 | HZ2 | LYS | 25 | 6.068 | 16.480 | 50.403 | 1.00 | 0.00 |
| ATOM | 219 | HZ3 | LYS | 25 | 4.953 | 17.769 | 50.472 | 1.00 | 0.00 |
| ATOM | 220 | C | LYS | 25 | 10.051 | 16.323 | 44.125 | 1.00 | 12.70 |
| ATOM | 221 | O | LYS | 25 | 10.728 | 17.226 | 43.634 | 1.00 | 15.29 |
| ATOM | 222 | N | LEU | 26 | 10.518 | 15.096 | 44.334 | 1.00 | 14.74 |
| ATOM | 223 | H | LEU | 26 | 9.913 | 14.405 | 44.690 | 1.00 | 0.00 |
| ATOM | 224 | CA | LEU | 26 | 11.906 | 14.746 | 44.057 | 1.00 | 16.13 |
| ATOM | 225 | CB | LEU | 26 | 12.231 | 13.357 | 44.618 | 1.00 | 13.92 |
| ATOM | 226 | CG | LEU | 26 | 12.231 | 13.216 | 46.145 | 1.00 | 13.80 |
| ATOM | 227 | CD1 | LEU | 26 | 12.430 | 11.772 | 46.521 | 1.00 | 16.36 |
| ATOM | 228 | CD2 | LEU | 26 | 13.320 | 14.072 | 46.761 | 1.00 | 17.12 |
| ATOM | 229 | C | LEU | 26 | 12.252 | 14.818 | 42.574 | 1.00 | 18.06 |
| ATOM | 230 | O | LEU | 26 | 13.427 | 14.852 | 42.207 | 1.00 | 19.38 |
| ATOM | 231 | N | ALA | 27 | 11.226 | 14.853 | 41.730 | 1.00 | 19.46 |
| ATOM | 232 | H | ALA | 27 | 10.312 | 14.818 | 42.076 | 1.00 | 0.00 |
| ATOM | 233 | CA | ALA | 27 | 11.414 | 14.926 | 40.285 | 1.00 | 20.96 |
| ATOM | 234 | CB | ALA | 27 | 10.309 | 14.154 | 39.576 | 1.00 | 19.82 |
| ATOM | 235 | C | ALA | 27 | 11.495 | 16.356 | 39.741 | 1.00 | 20.81 |
| ATOM | 236 | O | ALA | 27 | 11.713 | 16.551 | 38.544 | 1.00 | 24.10 |
| ATOM | 237 | N | GLY | 28 | 11.285 | 17.352 | 40.596 | 1.00 | 20.02 |
| ATOM | 238 | H | GLY | 28 | 11.099 | 17.182 | 41.546 | 1.00 | 0.00 |
| ATOM | 239 | CA | GLY | 28 | 11.369 | 18.723 | 40.132 | 1.00 | 19.49 |
| ATOM | 240 | C | GLY | 28 | 10.100 | 19.554 | 40.161 | 1.00 | 21.05 |
| ATOM | 241 | O | GLY | 28 | 10.164 | 20.764 | 39.955 | 1.00 | 22.70 |
| ATOM | 242 | N | SEM | 29 | 8.946 | 18.926 | 40.374 | 1.00 | 20.23 |
| ATOM | 243 | H | SEM | 29 | 8.927 | 17.952 | 40.496 | 1.00 | 0.00 |
| ATOM | 244 | CA | SEM | 29 | 7.669 | 19.650 | 40.438 | 1.00 | 21.17 |
| ATOM | 245 | CB | SEM | 29 | 7.641 | 20.595 | 41.645 | 1.00 | 24.34 |
| ATOM | 246 | CG | SEM | 29 | 7.505 | 19.914 | 42.994 | 1.00 | 28.45 |
| ATOM | 247 | A | SEM | 29 | 5.834 | 18.935 | 43.183 | 1.00 | 33.82 |
| ATOM | 248 | CE | SEM | 29 | 4.660 | 20.332 | 43.772 | 1.00 | 30.42 |
| ATOM | 249 | C | SEM | 29 | 7.311 | 20.438 | 39.177 | 1.00 | 19.69 |
| ATOM | 250 | O | SEM | 29 | 6.640 | 21.471 | 39.250 | 1.00 | 18.65 |
| ATOM | 251 | N | ALA | 30 | 7.749 | 19.948 | 38.025 | 1.00 | 19.92 |
| ATOM | 252 | H | ALA | 30 | 8.251 | 19.114 | 38.032 | 1.00 | 0.00 |
| ATOM | 253 | CA | ALA | 30 | 7.459 | 20.612 | 36.760 | 1.00 | 20.38 |
| ATOM | 254 | CB | ALA | 30 | 8.314 | 20.023 | 35.641 | 1.00 | 20.76 |
| ATOM | 255 | C | ALA | 30 | 5.985 | 20.454 | 36.428 | 1.00 | 21.88 |
| ATOM | 256 | O | ALA | 30 | 5.346 | 19.494 | 36.857 | 1.00 | 22.02 |
| ATOM | 257 | N | ASP | 31 | 5.434 | 21.423 | 35.705 | 1.00 | 21.51 |
| ATOM | 258 | H | ASP | 31 | 5.990 | 22.173 | 35.411 | 1.00 | 0.00 |
| ATOM | 259 | CA | ASP | 31 | 4.034 | 21.367 | 35.304 | 1.00 | 22.50 |
| ATOM | 260 | CB | ASP | 31 | 3.582 | 22.700 | 34.704 | 1.00 | 26.22 |
| ATOM | 261 | CG | ASP | 31 | 3.559 | 23.818 | 35.723 | 1.00 | 32.04 |
| ATOM | 262 | OD1 | ASP | 31 | 2.465 | 24.354 | 35.985 | 1.00 | 38.46 |
| ATOM | 263 | OD2 | ASP | 31 | 4.632 | 24.163 | 36.265 | 1.00 | 39.17 |
| ATOM | 264 | C | ASP | 31 | 3.897 | 20.263 | 34.271 | 1.00 | 18.87 |
| ATOM | 265 | O | ASP | 31 | 4.762 | 20.106 | 33.407 | 1.00 | 18.52 |
| ATOM | 266 | N | GLY | 32 | 2.826 | 19.488 | 34.376 | 1.00 | 17.28 |
| ATOM | 267 | H | GLY | 32 | 2.174 | 19.611 | 35.099 | 1.00 | 0.00 |
| ATOM | 268 | CA | GLY | 32 | 2.609 | 18.403 | 33.445 | 1.00 | 15.03 |
| ATOM | 269 | C | GLY | 32 | 3.263 | 17.108 | 33.890 | 1.00 | 15.03 |
| ATOM | 270 | O | GLY | 32 | 3.047 | 16.073 | 33.263 | 1.00 | 18.44 |
| ATOM | 271 | N | LEU | 33 | 4.079 | 17.159 | 34.942 | 1.00 | 15.47 |
| ATOM | 272 | H | LEU | 33 | 4.234 | 18.007 | 35.398 | 1.00 | 0.00 |
| ATOM | 273 | CA | LEU | 33 | 4.746 | 15.965 | 35.470 | 1.00 | 14.99 |
| ATOM | 274 | CB | LEU | 33 | 5.765 | 16.359 | 36.545 | 1.00 | 14.41 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 275 | CG | LEU | 33 | 6.585 | 15.272 | 37.248 | 1.00 | 15.28 |
| ATOM | 276 | CD1 | LEU | 33 | 7.603 | 14.664 | 36.297 | 1.00 | 14.45 |
| ATOM | 277 | CD2 | LEU | 33 | 7.278 | 15.869 | 38.461 | 1.00 | 12.37 |
| ATOM | 278 | C | LEU | 33 | 3.648 | 15.093 | 36.078 | 1.00 | 13.99 |
| ATOM | 279 | O | LEU | 33 | 2.833 | 15.582 | 36.868 | 1.00 | 12.54 |
| ATOM | 280 | N | PHE | 34 | 3.625 | 13.810 | 35.726 | 1.00 | 13.31 |
| ATOM | 281 | H | PHE | 34 | 4.305 | 13.484 | 35.098 | 1.00 | 0.00 |
| ATOM | 282 | CA | PHE | 34 | 2.581 | 12.918 | 36.224 | 1.00 | 13.12 |
| ATOM | 283 | CB | PHE | 34 | 1.410 | 12.877 | 35.225 | 1.00 | 10.40 |
| ATOM | 284 | CG | PHE | 34 | 1.713 | 12.111 | 33.955 | 1.00 | 13.52 |
| ATOM | 285 | CD1 | PHE | 34 | 1.269 | 10.798 | 33.796 | 1.00 | 13.58 |
| ATOM | 286 | CD2 | PHE | 34 | 2.460 | 12.694 | 32.934 | 1.00 | 10.22 |
| ATOM | 287 | CE1 | PHE | 34 | 1.567 | 10.078 | 32.640 | 1.00 | 14.14 |
| ATOM | 288 | CE2 | PHE | 34 | 2.762 | 11.985 | 31.776 | 1.00 | 12.23 |
| ATOM | 289 | CZ | PHE | 34 | 2.314 | 10.671 | 31.628 | 1.00 | 13.01 |
| ATOM | 290 | C | PHE | 34 | 3.050 | 11.494 | 36.462 | 1.00 | 11.75 |
| ATOM | 291 | O | PHE | 34 | 4.097 | 11.083 | 35.967 | 1.00 | 12.17 |
| ATOM | 292 | N | LEU | 35 | 2.240 | 10.738 | 37.197 | 1.00 | 11.21 |
| ATOM | 293 | H | LEU | 35 | 1.413 | 11.119 | 37.565 | 1.00 | 0.00 |
| ATOM | 294 | CA | LEU | 35 | 2.522 | 9.336 | 37.470 | 1.00 | 8.87 |
| ATOM | 295 | CB | LEU | 35 | 3.428 | 9.168 | 38.701 | 1.00 | 8.10 |
| ATOM | 296 | CG | LEU | 35 | 2.980 | 9.520 | 40.123 | 1.00 | 8.50 |
| ATOM | 297 | CD1 | LEU | 35 | 2.063 | 8.438 | 40.681 | 1.00 | 9.19 |
| ATOM | 298 | CD2 | LEU | 35 | 4.209 | 9.637 | 41.002 | 1.00 | 6.81 |
| ATOM | 299 | C | LEU | 35 | 1.190 | 8.615 | 37.637 | 1.00 | 7.92 |
| ATOM | 300 | O | LEU | 35 | 0.153 | 9.251 | 37.855 | 1.00 | 8.48 |
| ATOM | 301 | N | LEU | 36 | 1.209 | 7.297 | 37.498 | 1.00 | 8.12 |
| ATOM | 302 | H | LEU | 36 | 2.057 | 6.836 | 37.350 | 1.00 | 0.00 |
| ATOM | 303 | CA | LEU | 36 | 0.000 | 6.502 | 37.626 | 1.00 | 8.05 |
| ATOM | 304 | CB | LEU | 36 | −0.258 | 5.734 | 36.327 | 1.00 | 9.30 |
| ATOM | 305 | CG | LEU | 36 | −1.676 | 5.210 | 36.089 | 1.00 | 15.30 |
| ATOM | 306 | CD1 | LEU | 36 | −2.635 | 6.386 | 35.956 | 1.00 | 15.10 |
| ATOM | 307 | CD2 | LEU | 36 | −1.716 | 4.348 | 34.832 | 1.00 | 17.89 |
| ATOM | 308 | C | LEU | 36 | 0.164 | 5.532 | 38.789 | 1.00 | 8.05 |
| ATOM | 309 | O | LEU | 36 | 1.238 | 4.961 | 38.991 | 1.00 | 8.20 |
| ATOM | 310 | N | ARG | 37 | −0.887 | 5.380 | 39.581 | 1.00 | 8.30 |
| ATOM | 311 | H | ARG | 37 | −1.714 | 5.882 | 39.404 | 1.00 | 0.00 |
| ATOM | 312 | CA | ARG | 37 | −0.853 | 4.468 | 40.716 | 1.00 | 8.39 |
| ATOM | 313 | CB | ARG | 37 | −0.583 | 5.229 | 42.015 | 1.00 | 6.96 |
| ATOM | 314 | CG | ARG | 37 | −1.508 | 6.396 | 42.282 | 1.00 | 6.89 |
| ATOM | 315 | CD | ARG | 37 | −0.974 | 7.196 | 43.451 | 1.00 | 10.99 |
| ATOM | 316 | NE | ARG | 37 | −1.722 | 8.428 | 43.678 | 1.00 | 8.74 |
| ATOM | 317 | HE | ARG | 37 | −1.529 | 9.196 | 43.101 | 1.00 | 0.00 |
| ATOM | 318 | CZ | ARG | 37 | −2.647 | 8.577 | 44.617 | 1.00 | 10.85 |
| ATOM | 319 | NH1 | ARG | 37 | −2.956 | 7.567 | 45.423 | 1.00 | 9.35 |
| ATOM | 320 | HH11 | ARG | 37 | −2.500 | 6.681 | 45.337 | 1.00 | 0.00 |
| ATOM | 321 | HH12 | ARG | 37 | −3.658 | 7.697 | 46.120 | 1.00 | 0.00 |
| ATOM | 322 | NH2 | ARG | 37 | −3.236 | 9.751 | 44.775 | 1.00 | 8.78 |
| ATOM | 323 | HH21 | ARG | 37 | −2.988 | 10.517 | 44.184 | 1.00 | 0.00 |
| ATOM | 324 | HH22 | ARG | 37 | −3.915 | 9.870 | 45.480 | 1.00 | 0.00 |
| ATOM | 325 | C | ARG | 37 | −2.166 | 3.706 | 40.783 | 1.00 | 6.82 |
| ATOM | 326 | O | ARG | 37 | −3.161 | 4.125 | 40.193 | 1.00 | 8.12 |
| ATOM | 327 | N | GLN | 38 | −2.150 | 2.547 | 41.432 | 1.00 | 8.06 |
| ATOM | 328 | H | GLN | 38 | −1.324 | 2.268 | 41.866 | 1.00 | 0.00 |
| ATOM | 329 | CA | GLN | 38 | −3.353 | 1.735 | 41.549 | 1.00 | 9.21 |
| ATOM | 330 | CB | GLN | 38 | −2.996 | 0.311 | 41.974 | 1.00 | 13.08 |
| ATOM | 331 | CG | GLN | 38 | −4.203 | −0.585 | 42.170 | 1.00 | 18.32 |
| ATOM | 332 | CD | GLN | 38 | −3.832 | −1.990 | 42.590 | 1.00 | 18.70 |
| ATOM | 333 | OE1 | GLN | 38 | −2.998 | −2.195 | 43.472 | 1.00 | 19.47 |
| ATOM | 334 | NE2 | GLN | 38 | −4.463 | −2.968 | 41.967 | 1.00 | 22.25 |
| ATOM | 335 | HE21 | GLN | 38 | −5.116 | −2.694 | 41.275 | 1.00 | 0.00 |
| ATOM | 336 | HE22 | GLN | 38 | −4.267 | −3.889 | 42.210 | 1.00 | 0.00 |
| ATOM | 337 | C | GLN | 38 | −4.293 | 2.359 | 42.565 | 1.00 | 10.19 |
| ATOM | 338 | O | GLN | 38 | −3.848 | 2.856 | 43.594 | 1.00 | 12.74 |
| ATOM | 339 | N | CYS | 39 | −5.589 | 2.339 | 42.278 | 1.00 | 11.02 |
| ATOM | 340 | H | CYS | 39 | −5.895 | 1.887 | 41.464 | 1.00 | 0.00 |
| ATOM | 341 | CA | CYS | 39 | −6.569 | 2.909 | 43.194 | 1.00 | 12.42 |
| ATOM | 342 | CB | CYS | 39 | −7.918 | 3.079 | 42.496 | 1.00 | 9.94 |
| ATOM | 343 | SG | CYS | 39 | −9.205 | 3.852 | 43.504 | 1.00 | 12.92 |
| ATOM | 344 | C | CYS | 39 | −6.720 | 2.008 | 44.414 | 1.00 | 12.91 |
| ATOM | 345 | O | CYS | 39 | −6.736 | 0.782 | 44.291 | 1.00 | 13.19 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 346 | N | LEU | 40 | −6.776 | 2.620 | 45.592 | 1.00 | 10.63 |
| ATOM | 347 | H | LEU | 40 | −6.680 | 3.598 | 45.633 | 1.00 | 0.00 |
| ATOM | 348 | CA | LEU | 40 | −6.934 | 1.875 | 46.833 | 1.00 | 12.90 |
| ATOM | 349 | CB | LEU | 40 | −6.139 | 2.543 | 47.965 | 1.00 | 11.53 |
| ATOM | 350 | CG | LEU | 40 | −4.629 | 2.680 | 47.747 | 1.00 | 13.24 |
| ATOM | 351 | CD1 | LEU | 40 | −4.020 | 3.500 | 48.863 | 1.00 | 12.45 |
| ATOM | 352 | CD2 | LEU | 40 | −3.969 | 1.317 | 47.657 | 1.00 | 12.54 |
| ATOM | 353 | C | LEU | 40 | −8.401 | 1.789 | 47.226 | 1.00 | 11.01 |
| ATOM | 354 | O | LEU | 40 | −8.748 | 1.127 | 48.201 | 1.00 | 12.23 |
| ATOM | 355 | N | ARG | 41 | −9.269 | 2.412 | 46.439 | 1.00 | 10.95 |
| ATOM | 356 | H | ARG | 41 | −8.957 | 2.869 | 45.631 | 1.00 | 0.00 |
| ATOM | 357 | CA | ARG | 41 | −10.690 | 2.431 | 46.758 | 1.00 | 12.13 |
| ATOM | 358 | CB | ARG | 41 | −11.185 | 3.872 | 46.820 | 1.00 | 10.86 |
| ATOM | 359 | CG | ARG | 41 | −10.390 | 4.754 | 47.756 | 1.00 | 10.97 |
| ATOM | 360 | CD | ARG | 41 | −10.855 | 6.190 | 47.675 | 1.00 | 14.51 |
| ATOM | 361 | NE | ARG | 41 | −10.749 | 6.723 | 46.321 | 1.00 | 13.81 |
| ATOM | 362 | HE | ARG | 41 | −9.859 | 6.768 | 45.924 | 1.00 | 0.00 |
| ATOM | 363 | CZ | ARG | 41 | −11.774 | 7.178 | 45.612 | 1.00 | 16.54 |
| ATOM | 364 | NH1 | ARG | 41 | −12.996 | 7.177 | 46.121 | 1.00 | 18.89 |
| ATOM | 365 | HH11 | ARG | 41 | −13.161 | 6.844 | 47.050 | 1.00 | 0.00 |
| ATOM | 366 | HH12 | ARG | 41 | −13.760 | 7.526 | 45.579 | 1.00 | 0.00 |
| ATOM | 367 | NH2 | ARG | 41 | −11.582 | 7.602 | 44.373 | 1.00 | 21.20 |
| ATOM | 368 | HH21 | ARG | 41 | −10.666 | 7.569 | 43.973 | 1.00 | 0.00 |
| ATOM | 369 | HH22 | ARG | 41 | −12.355 | 7.948 | 43.842 | 1.00 | 0.00 |
| ATOM | 370 | C | ARG | 41 | −11.603 | 1.636 | 45.846 | 1.00 | 13.35 |
| ATOM | 371 | O | ARG | 41 | −12.672 | 1.203 | 46.274 | 1.00 | 14.24 |
| ATOM | 372 | N | SER | 42 | −11.210 | 1.472 | 44.589 | 1.00 | 14.81 |
| ATOM | 373 | H | SER | 42 | −10.362 | 1.815 | 44.255 | 1.00 | 0.00 |
| ATOM | 374 | CA | SER | 42 | −12.032 | 0.738 | 43.637 | 1.00 | 15.10 |
| ATOM | 375 | CB | SER | 42 | −12.471 | 1.660 | 42.496 | 1.00 | 16.52 |
| ATOM | 376 | OG | SER | 42 | −11.357 | 2.145 | 41.768 | 1.00 | 17.93 |
| ATOM | 377 | HG | SER | 42 | −11.715 | 2.592 | 40.982 | 1.00 | 0.00 |
| ATOM | 378 | C | SER | 42 | −11.298 | −0.476 | 43.080 | 1.00 | 15.55 |
| ATOM | 379 | O | SER | 42 | −10.080 | −0.598 | 43.220 | 1.00 | 16.20 |
| ATOM | 380 | N | LEU | 43 | −12.054 | −1.394 | 42.490 | 1.00 | 15.52 |
| ATOM | 381 | H | LEU | 43 | −13.012 | −1.234 | 42.420 | 1.00 | 0.00 |
| ATOM | 382 | CA | LEU | 43 | −11.484 | −2.600 | 41.904 | 1.00 | 16.45 |
| ATOM | 383 | CB | LEU | 43 | −12.504 | −3.741 | 41.923 | 1.00 | 19.56 |
| ATOM | 384 | CG | LEU | 43 | −12.877 | −4.324 | 43.285 | 1.00 | 21.50 |
| ATOM | 385 | CD1 | LEU | 43 | −13.998 | −5.333 | 43.111 | 1.00 | 22.99 |
| ATOM | 386 | CD2 | LEU | 43 | −11.661 | −4.976 | 43.916 | 1.00 | 21.68 |
| ATOM | 387 | C | LEU | 43 | −11.064 | −2.319 | 40.470 | 1.00 | 15.54 |
| ATOM | 388 | O | LEU | 43 | −11.874 | −1.871 | 39.657 | 1.00 | 16.36 |
| ATOM | 389 | N | GLY | 44 | −9.786 | −2.542 | 40.184 | 1.00 | 15.64 |
| ATOM | 390 | H | GLY | 44 | −9.170 | −2.822 | 40.896 | 1.00 | 0.00 |
| ATOM | 391 | CA | GLY | 44 | −9.267 | −2.324 | 38.846 | 1.00 | 16.00 |
| ATOM | 392 | C | GLY | 44 | −9.138 | −0.875 | 38.411 | 1.00 | 15.01 |
| ATOM | 393 | O | GLY | 44 | −8.965 | −0.602 | 37.222 | 1.00 | 16.12 |
| ATOM | 394 | N | GLY | 45 | −9.188 | 0.048 | 39.368 | 1.00 | 12.81 |
| ATOM | 395 | H | GLY | 45 | −9.242 | −0.234 | 40.305 | 1.00 | 0.00 |
| ATOM | 396 | CA | GLY | 45 | −9.075 | 1.459 | 39.044 | 1.00 | 10.47 |
| ATOM | 397 | C | GLY | 45 | −7.666 | 1.983 | 39.226 | 1.00 | 9.12 |
| ATOM | 398 | O | GLY | 45 | −6.795 | 1.292 | 39.766 | 1.00 | 9.20 |
| ATOM | 399 | N | TYR | 46 | −7.443 | 3.220 | 38.800 | 1.00 | 9.58 |
| ATOM | 400 | H | TYR | 46 | −8.185 | 3.734 | 38.409 | 1.00 | 0.00 |
| ATOM | 401 | CA | TYR | 46 | −6.137 | 3.859 | 38.914 | 1.00 | 10.00 |
| ATOM | 402 | CB | TYR | 46 | −5.426 | 3.889 | 37.548 | 1.00 | 10.79 |
| ATOM | 403 | CG | TYR | 46 | −5.110 | 2.528 | 36.977 | 1.00 | 12.05 |
| ATOM | 404 | CD1 | TYR | 46 | −4.019 | 1.793 | 37.440 | 1.00 | 11.46 |
| ATOM | 405 | CE1 | TYR | 46 | −3.758 | 0.514 | 36.960 | 1.00 | 10.52 |
| ATOM | 406 | CD2 | TYR | 46 | −5.931 | 1.952 | 36.010 | 1.00 | 13.57 |
| ATOM | 407 | CE2 | TYR | 46 | −5.678 | 0.674 | 35.525 | 1.00 | 13.97 |
| ATOM | 408 | CZ | TYR | 46 | −4.592 | −0.037 | 36.007 | 1.00 | 14.16 |
| ATOM | 409 | OH | TYR | 46 | −4.362 | −1.311 | 35.554 | 1.00 | 15.79 |
| ATOM | 410 | HH | TYR | 46 | −5.246 | −1.670 | 35.351 | 1.00 | 0.00 |
| ATOM | 411 | C | TYR | 46 | −6.340 | 5.290 | 39.376 | 1.00 | 9.80 |
| ATOM | 412 | O | TYR | 46 | −7.472 | 5.747 | 39.525 | 1.00 | 9.96 |
| ATOM | 413 | N | VAL | 47 | −5.243 | 5.967 | 39.679 | 1.00 | 9.60 |
| ATOM | 414 | H | VAL | 47 | −4.355 | 5.549 | 39.641 | 1.00 | 0.00 |
| ATOM | 415 | CA | VAL | 47 | −5.298 | 7.365 | 40.057 | 1.00 | 9.96 |
| ATOM | 416 | CB | VAL | 47 | −5.092 | 7.619 | 41.573 | 1.00 | 9.82 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 417 | CG1 | VAL | 47 | −5.205 | 9.113 | 41.861 | 1.00 | 7.41 |
| ATOM | 418 | CG2 | VAL | 47 | −6.117 | 6.867 | 42.390 | 1.00 | 10.33 |
| ATOM | 419 | C | VAL | 47 | −4.180 | 8.045 | 39.286 | 1.00 | 8.75 |
| ATOM | 420 | O | VAL | 47 | −3.044 | 7.561 | 39.261 | 1.00 | 6.17 |
| ATOM | 421 | N | LEU | 48 | −4.536 | 9.117 | 38.590 | 1.00 | 9.67 |
| ATOM | 422 | H | LEU | 48 | −5.470 | 9.398 | 38.591 | 1.00 | 0.00 |
| ATOM | 423 | CA | LEU | 48 | −3.585 | 9.907 | 37.827 | 1.00 | 10.81 |
| ATOM | 424 | CB | LEU | 48 | −4.275 | 10.520 | 36.604 | 1.00 | 14.82 |
| ATOM | 425 | CG | LEU | 48 | −3.499 | 10.808 | 35.312 | 1.00 | 18.26 |
| ATOM | 426 | CD1 | LEU | 48 | −4.357 | 11.691 | 34.420 | 1.00 | 19.66 |
| ATOM | 427 | CD2 | LEU | 48 | −2.178 | 11.482 | 35.582 | 1.00 | 16.76 |
| ATOM | 428 | C | LEU | 48 | −3.174 | 11.022 | 38.786 | 1.00 | 9.47 |
| ATOM | 429 | O | LEU | 48 | −4.020 | 11.754 | 39.302 | 1.00 | 9.86 |
| ATOM | 430 | N | SER | 49 | −1.888 | 11.119 | 39.064 | 1.00 | 8.65 |
| ATOM | 431 | H | SER | 49 | −1.257 | 10.496 | 38.640 | 1.00 | 0.00 |
| ATOM | 432 | CA | SER | 49 | −1.386 | 12.145 | 39.956 | 1.00 | 12.04 |
| ATOM | 433 | CB | SER | 49 | −0.590 | 11.479 | 41.084 | 1.00 | 13.48 |
| ATOM | 434 | OG | SER | 49 | −0.103 | 12.428 | 42.009 | 1.00 | 30.10 |
| ATOM | 435 | HG | SER | 49 | 0.614 | 12.893 | 41.557 | 1.00 | 0.00 |
| ATOM | 436 | C | SER | 49 | −0.510 | 13.088 | 39.125 | 1.00 | 10.25 |
| ATOM | 437 | O | SER | 49 | 0.481 | 12.655 | 38.537 | 1.00 | 11.37 |
| ATOM | 438 | N | LEU | 50 | −0.868 | 14.361 | 39.040 | 1.00 | 12.50 |
| ATOM | 439 | H | LEU | 50 | −1.689 | 14.672 | 39.504 | 1.00 | 0.00 |
| ATOM | 440 | CA | LEU | 50 | −0.114 | 15.319 | 38.252 | 1.00 | 13.14 |
| ATOM | 441 | CB | LEU | 50 | −0.803 | 15.591 | 36.906 | 1.00 | 14.83 |
| ATOM | 442 | CG | LEU | 50 | −2.188 | 16.241 | 36.861 | 1.00 | 18.60 |
| ATOM | 443 | CD1 | LEU | 50 | −2.066 | 17.749 | 36.713 | 1.00 | 18.66 |
| ATOM | 444 | CD2 | LEU | 50 | −2.959 | 15.691 | 35.681 | 1.00 | 22.06 |
| ATOM | 445 | C | LEU | 50 | 0.181 | 16.629 | 38.973 | 1.00 | 14.34 |
| ATOM | 446 | O | LEU | 50 | −0.481 | 16.982 | 39.951 | 1.00 | 14.49 |
| ATOM | 447 | N | VAL | 51 | 1.190 | 17.339 | 38.481 | 1.00 | 13.90 |
| ATOM | 448 | H | VAL | 51 | 1.680 | 17.006 | 37.698 | 1.00 | 0.00 |
| ATOM | 449 | CA | VAL | 51 | 1.591 | 18.615 | 39.052 | 1.00 | 14.39 |
| ATOM | 450 | CB | VAL | 51 | 3.124 | 18.688 | 39.277 | 1.00 | 13.58 |
| ATOM | 451 | CG1 | VAL | 51 | 3.512 | 20.051 | 39.833 | 1.00 | 12.21 |
| ATOM | 452 | CG2 | VAL | 51 | 3.581 | 17.592 | 40.218 | 1.00 | 12.91 |
| ATOM | 453 | C | VAL | 51 | 1.218 | 19.757 | 38.111 | 1.00 | 16.09 |
| ATOM | 454 | O | VAL | 51 | 1.329 | 19.637 | 36.890 | 1.00 | 17.31 |
| ATOM | 455 | N | HIS | 52 | 0.755 | 20.857 | 38.688 | 1.00 | 17.95 |
| ATOM | 456 | H | HIS | 52 | 0.631 | 20.876 | 39.664 | 1.00 | 0.00 |
| ATOM | 457 | CA | HIS | 52 | 0.417 | 22.050 | 37.930 | 1.00 | 19.66 |
| ATOM | 458 | CB | HIS | 52 | −0.950 | 21.947 | 37.264 | 1.00 | 21.46 |
| ATOM | 459 | CG | HIS | 52 | −1.278 | 23.126 | 36.400 | 1.00 | 25.94 |
| ATOM | 460 | CD2 | HIS | 52 | −2.324 | 23.985 | 36.417 | 1.00 | 26.46 |
| ATOM | 461 | ND1 | HIS | 52 | −0.447 | 23.555 | 35.385 | 1.00 | 27.09 |
| ATOM | 462 | HD1 | HIS | 52 | 0.379 | 23.112 | 35.092 | 1.00 | 0.00 |
| ATOM | 463 | CE1 | HIS | 52 | −0.965 | 24.630 | 34.818 | 1.00 | 24.62 |
| ATOM | 464 | NE2 | HIS | 52 | −2.105 | 24.911 | 35.426 | 1.00 | 27.73 |
| ATOM | 465 | HE2 | HIS | 52 | −2.713 | 25.644 | 35.178 | 1.00 | 0.00 |
| ATOM | 466 | C | HIS | 52 | 0.429 | 23.217 | 38.899 | 1.00 | 21.92 |
| ATOM | 467 | O | HIS | 52 | −0.241 | 23.176 | 39.926 | 1.00 | 20.84 |
| ATOM | 468 | N | ASP | 53 | 1.245 | 24.221 | 38.592 | 1.00 | 26.19 |
| ATOM | 469 | H | ASP | 53 | 1.857 | 24.140 | 37.845 | 1.00 | 0.00 |
| ATOM | 470 | CA | ASP | 53 | 1.374 | 25.421 | 39.415 | 1.00 | 26.69 |
| ATOM | 471 | CB | ASP | 53 | 0.043 | 26.185 | 39.499 | 1.00 | 30.60 |
| ATOM | 472 | CG | ASP | 53 | −0.369 | 26.803 | 38.176 | 1.00 | 37.06 |
| ATOM | 473 | OD1 | ASP | 53 | 0.465 | 26.855 | 37.246 | 1.00 | 41.34 |
| ATOM | 474 | OD2 | ASP | 53 | −1.537 | 27.243 | 38.070 | 1.00 | 39.93 |
| ATOM | 475 | C | ASP | 53 | 1.859 | 25.075 | 40.811 | 1.00 | 25.96 |
| ATOM | 476 | O | ASP | 53 | 1.337 | 25.589 | 41.802 | 1.00 | 27.13 |
| ATOM | 477 | N | VAL | 54 | 2.844 | 24.181 | 40.876 | 1.00 | 24.42 |
| ATOM | 478 | H | VAL | 54 | 3.192 | 23.818 | 40.037 | 1.00 | 0.00 |
| ATOM | 479 | CA | VAL | 54 | 3.441 | 23.735 | 42.136 | 1.00 | 25.36 |
| ATOM | 480 | CB | VAL | 54 | 4.218 | 24.896 | 42.834 | 1.00 | 25.58 |
| ATOM | 481 | CG1 | VAL | 54 | 5.100 | 24.360 | 43.949 | 1.00 | 27.09 |
| ATOM | 482 | CG2 | VAL | 54 | 5.077 | 25.639 | 41.816 | 1.00 | 30.24 |
| ATOM | 483 | C | VAL | 54 | 2.395 | 23.130 | 43.083 | 1.00 | 24.41 |
| ATOM | 484 | O | VAL | 54 | 2.551 | 23.140 | 44.310 | 1.00 | 24.03 |
| ATOM | 485 | N | ARG | 55 | 1.338 | 22.576 | 42.500 | 1.00 | 22.42 |
| ATOM | 486 | H | ARG | 55 | 1.250 | 22.563 | 41.527 | 1.00 | 0.00 |
| ATOM | 487 | CA | ARG | 55 | 0.273 | 21.957 | 43.272 | 1.00 | 23.20 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 488 | CB | ARG | 55 | -0.956 | 22.865 | 43.334 | 1.00 | 28.27 |
| ATOM | 489 | CG | ARG | 55 | -0.807 | 23.981 | 44.356 | 1.00 | 39.63 |
| ATOM | 490 | CD | ARG | 55 | -2.051 | 24.848 | 44.467 | 1.00 | 48.23 |
| ATOM | 491 | NE | ARG | 55 | -1.954 | 25.777 | 45.595 | 1.00 | 56.45 |
| ATOM | 492 | HE | ARG | 55 | -2.462 | 25.560 | 46.404 | 1.00 | 0.00 |
| ATOM | 493 | CZ | ARG | 55 | -1.222 | 26.891 | 45.602 | 1.00 | 60.28 |
| ATOM | 494 | NH1 | ARG | 55 | -0.509 | 27.240 | 44.535 | 1.00 | 63.46 |
| ATOM | 495 | HH11 | ARG | 55 | -0.514 | 26.661 | 43.716 | 1.00 | 0.00 |
| ATOM | 496 | HH12 | ARG | 55 | 0.028 | 28.083 | 44.550 | 1.00 | 0.00 |
| ATOM | 497 | NH2 | ARG | 55 | -1.192 | 27.657 | 46.686 | 1.00 | 60.77 |
| ATOM | 498 | HH21 | ARG | 55 | -1.725 | 27.400 | 47.491 | 1.00 | 0.00 |
| ATOM | 499 | HH22 | ARG | 55 | -0.647 | 28.494 | 46.685 | 1.00 | 0.00 |
| ATOM | 500 | C | ARG | 55 | -0.084 | 20.600 | 42.694 | 1.00 | 18.98 |
| ATOM | 501 | O | ARG | 55 | 0.024 | 20.377 | 41.488 | 1.00 | 18.12 |
| ATOM | 502 | N | PHE | 56 | -0.499 | 19.692 | 43.567 | 1.00 | 17.36 |
| ATOM | 503 | H | PHE | 56 | -0.588 | 19.942 | 44.514 | 1.00 | 0.00 |
| ATOM | 504 | CA | PHE | 56 | -0.854 | 18.341 | 43.164 | 1.00 | 15.57 |
| ATOM | 505 | CB | PHE | 56 | -0.498 | 17.347 | 44.270 | 1.00 | 14.98 |
| ATOM | 506 | CG | PHE | 56 | 0.950 | 17.344 | 44.634 | 1.00 | 12.04 |
| ATOM | 507 | CD1 | PHE | 56 | 1.371 | 17.844 | 45.862 | 1.00 | 11.96 |
| ATOM | 508 | CD2 | PHE | 56 | 1.897 | 16.847 | 43.749 | 1.00 | 13.48 |
| ATOM | 509 | CE1 | PHE | 56 | 2.714 | 17.852 | 46.203 | 1.00 | 13.52 |
| ATOM | 510 | CE2 | PHE | 56 | 3.245 | 16.850 | 44.079 | 1.00 | 12.78 |
| ATOM | 511 | CZ | PHE | 56 | 3.654 | 17.353 | 45.310 | 1.00 | 14.92 |
| ATOM | 512 | C | PHE | 56 | -2.320 | 18.183 | 42.824 | 1.00 | 14.57 |
| ATOM | 513 | O | PHE | 56 | -3.192 | 18.802 | 43.439 | 1.00 | 16.84 |
| ATOM | 514 | N | HIS | 57 | -2.586 | 17.340 | 41.838 | 1.00 | 12.74 |
| ATOM | 515 | H | HIS | 57 | -1.838 | 16.904 | 41.364 | 1.00 | 0.00 |
| ATOM | 516 | CA | HIS | 57 | -3.942 | 17.049 | 41.412 | 1.00 | 13.90 |
| ATOM | 517 | CB | HIS | 57 | -4.248 | 17.741 | 40.080 | 1.00 | 17.35 |
| ATOM | 518 | CG | HIS | 57 | -4.144 | 19.235 | 40.145 | 1.00 | 22.06 |
| ATOM | 519 | CD2 | HIS | 57 | -3.097 | 20.066 | 39.924 | 1.00 | 21.97 |
| ATOM | 520 | ND1 | HIS | 57 | -5.198 | 20.041 | 40.523 | 1.00 | 23.17 |
| ATOM | 521 | HD1 | HIS | 57 | -6.107 | 19.754 | 40.750 | 1.00 | 0.00 |
| ATOM | 522 | CE1 | HIS | 57 | -4.802 | 21.303 | 40.536 | 1.00 | 23.20 |
| ATOM | 523 | NE2 | HIS | 57 | -3.532 | 21.344 | 40.178 | 1.00 | 22.64 |
| ATOM | 524 | HE2 | HIS | 57 | -2.966 | 22.151 | 40.144 | 1.00 | 0.00 |
| ATOM | 525 | C | HIS | 57 | -4.014 | 15.533 | 41.294 | 1.00 | 11.98 |
| ATOM | 526 | O | HIS | 57 | -3.099 | 14.901 | 40.765 | 1.00 | 11.55 |
| ATOM | 527 | N | HIS | 58 | -5.058 | 14.944 | 41.867 | 1.00 | 10.33 |
| ATOM | 528 | H | HIS | 58 | -5.780 | 15.455 | 42.288 | 1.00 | 0.00 |
| ATOM | 529 | CA | HIS | 58 | -5.217 | 13.499 | 41.848 | 1.00 | 8.93 |
| ATOM | 530 | CB | HIS | 58 | -5.063 | 12.945 | 43.266 | 1.00 | 5.64 |
| ATOM | 531 | CG | HIS | 58 | -3.765 | 13.316 | 43.913 | 1.00 | 8.00 |
| ATOM | 532 | CD2 | HIS | 58 | -3.449 | 14.312 | 44.772 | 1.00 | 5.61 |
| ATOM | 533 | ND1 | HIS | 58 | -2.591 | 12.636 | 43.667 | 1.00 | 6.85 |
| ATOM | 534 | HD1 | HIS | 58 | -2.468 | 11.854 | 43.085 | 1.00 | 0.00 |
| ATOM | 535 | CE1 | HIS | 58 | -1.609 | 13.197 | 44.349 | 1.00 | 6.57 |
| ATOM | 536 | NE2 | HIS | 58 | -2.102 | 14.217 | 45.024 | 1.00 | 6.83 |
| ATOM | 537 | HE2 | HIS | 58 | -1.588 | 14.836 | 45.576 | 1.00 | 0.00 |
| ATOM | 538 | C | HIS | 58 | -6.570 | 13.158 | 41.267 | 1.00 | 9.13 |
| ATOM | 539 | O | HIS | 58 | -7.603 | 13.507 | 41.831 | 1.00 | 12.23 |
| ATOM | 540 | N | PHE | 59 | -6.551 | 12.519 | 40.107 | 1.00 | 9.57 |
| ATOM | 541 | H | PHE | 59 | -5.709 | 12.287 | 39.679 | 1.00 | 0.00 |
| ATOM | 542 | CA | PHE | 59 | -7.769 | 12.150 | 39.408 | 1.00 | 12.32 |
| ATOM | 543 | CB | PHE | 59 | -7.703 | 12.621 | 37.948 | 1.00 | 11.96 |
| ATOM | 544 | CG | PHE | 59 | -7.623 | 14.109 | 37.789 | 1.00 | 13.50 |
| ATOM | 545 | CD1 | PHE | 59 | -6.397 | 14.762 | 37.851 | 1.00 | 12.51 |
| ATOM | 546 | CD2 | PHE | 59 | -8.777 | 14.861 | 37.599 | 1.00 | 13.89 |
| ATOM | 547 | CE1 | PHE | 59 | -6.318 | 16.146 | 37.731 | 1.00 | 17.22 |
| ATOM | 548 | CE2 | PHE | 59 | -8.713 | 16.248 | 37.478 | 1.00 | 17.22 |
| ATOM | 549 | CZ | PHE | 59 | -7.481 | 16.893 | 37.544 | 1.00 | 17.16 |
| ATOM | 550 | C | PHE | 59 | -8.021 | 10.650 | 39.427 | 1.00 | 13.06 |
| ATOM | 551 | O | PHE | 59 | -7.232 | 9.868 | 38.893 | 1.00 | 12.71 |
| ATOM | 552 | N | PRO | 60 | -9.108 | 10.220 | 40.075 | 1.00 | 14.37 |
| ATOM | 553 | CD | PRO | 60 | -10.034 | 10.958 | 40.953 | 1.00 | 13.14 |
| ATOM | 554 | CA | PRO | 60 | -9.374 | 8.782 | 40.094 | 1.00 | 15.39 |
| ATOM | 555 | CB | PRO | 60 | -10.420 | 8.640 | 41.206 | 1.00 | 15.06 |
| ATOM | 556 | CG | PRO | 60 | -11.125 | 9.952 | 41.195 | 1.00 | 16.60 |
| ATOM | 557 | C | PRO | 60 | -9.881 | 8.310 | 38.719 | 1.00 | 15.44 |
| ATOM | 558 | O | PRO | 60 | -10.659 | 9.000 | 38.051 | 1.00 | 16.09 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 559 | N | ILE | 61 | −9.355 | 7.180 | 38.267 | 1.00 | 15.98 |
| ATOM | 560 | H | ILE | 61 | −8.723 | 6.742 | 38.838 | 1.00 | 0.00 |
| ATOM | 561 | CA | ILE | 61 | −9.724 | 6.582 | 36.986 | 1.00 | 15.23 |
| ATOM | 562 | CB | ILE | 61 | −8.472 | 6.222 | 36.164 | 1.00 | 14.68 |
| ATOM | 563 | CG2 | ILE | 61 | −8.868 | 5.536 | 34.856 | 1.00 | 15.39 |
| ATOM | 564 | CG1 | ILE | 61 | −7.655 | 7.482 | 35.886 | 1.00 | 13.45 |
| ATOM | 565 | CD | ILE | 61 | −6.296 | 7.211 | 35.307 | 1.00 | 12.44 |
| ATOM | 566 | C | ILE | 61 | −10.497 | 5.309 | 37.308 | 1.00 | 17.07 |
| ATOM | 567 | O | ILE | 61 | −9.978 | 4.413 | 37.984 | 1.00 | 16.51 |
| ATOM | 568 | N | GLU | 62 | −11.739 | 5.240 | 36.845 | 1.00 | 19.22 |
| ATOM | 569 | H | GLU | 62 | −12.099 | 5.968 | 36.290 | 1.00 | 0.00 |
| ATOM | 570 | CA | GLU | 62 | −12.582 | 4.084 | 37.112 | 1.00 | 23.18 |
| ATOM | 571 | CB | GLU | 62 | −13.981 | 4.541 | 37.538 | 1.00 | 30.15 |
| ATOM | 572 | CG | GLU | 62 | −14.906 | 3.407 | 37.975 | 1.00 | 39.45 |
| ATOM | 573 | CD | GLU | 62 | −16.305 | 3.882 | 38.332 | 1.00 | 44.10 |
| ATOM | 574 | OE1 | GLU | 62 | −16.458 | 4.548 | 39.381 | 1.00 | 48.25 |
| ATOM | 575 | OE2 | GLU | 62 | −17.251 | 3.579 | 37.569 | 1.00 | 44.87 |
| ATOM | 576 | C | GLU | 62 | −12.688 | 3.162 | 35.910 | 1.00 | 23.10 |
| ATOM | 577 | O | GLU | 62 | −12.709 | 3.619 | 34.766 | 1.00 | 21.60 |
| ATOM | 578 | N | ARG | 63 | −12.721 | 1.862 | 36.180 | 1.00 | 24.50 |
| ATOM | 579 | H | ARG | 63 | −12.684 | 1.558 | 37.114 | 1.00 | 0.00 |
| ATOM | 580 | CA | ARG | 63 | −12.848 | 0.861 | 35.135 | 1.00 | 28.70 |
| ATOM | 581 | CB | ARG | 63 | −12.152 | −0.437 | 35.547 | 1.00 | 31.42 |
| ATOM | 582 | CG | ARG | 63 | −12.177 | −1.521 | 34.477 | 1.00 | 36.91 |
| ATOM | 583 | CD | ARG | 63 | −11.909 | −2.885 | 35.079 | 1.00 | 40.57 |
| ATOM | 584 | NE | ARG | 63 | −12.927 | −3.223 | 36.072 | 1.00 | 46.47 |
| ATOM | 585 | HE | ARG | 63 | −13.820 | −2.825 | 35.972 | 1.00 | 0.00 |
| ATOM | 586 | CZ | ARG | 63 | −12.730 | −4.030 | 37.111 | 1.00 | 47.98 |
| ATOM | 587 | NH1 | ARG | 63 | −11.546 | −4.600 | 37.306 | 1.00 | 48.36 |
| ATOM | 588 | HH11 | ARG | 63 | −10.792 | −4.431 | 36.671 | 1.00 | 0.00 |
| ATOM | 589 | HH12 | ARG | 63 | −11.407 | −5.204 | 38.089 | 1.00 | 0.00 |
| ATOM | 590 | NH2 | ARG | 63 | −13.714 | −4.247 | 37.975 | 1.00 | 47.23 |
| ATOM | 591 | HH21 | ARG | 63 | −14.605 | −3.810 | 37.847 | 1.00 | 0.00 |
| ATOM | 592 | HH22 | ARG | 63 | −13.559 | −4.855 | 38.754 | 1.00 | 0.00 |
| ATOM | 593 | C | ARG | 63 | −14.332 | 0.590 | 34.944 | 1.00 | 28.52 |
| ATOM | 594 | O | ARG | 63 | −15.002 | 0.123 | 35.867 | 1.00 | 29.96 |
| ATOM | 595 | N | GLN | 64 | −14.851 | 0.931 | 33.771 | 1.00 | 29.71 |
| ATOM | 596 | H | GLN | 64 | −14.266 | 1.330 | 33.103 | 1.00 | 0.00 |
| ATOM | 597 | CA | GLN | 64 | −16.257 | 0.706 | 33.464 | 1.00 | 33.43 |
| ATOM | 598 | CB | GLN | 64 | −16.672 | 1.454 | 32.196 | 1.00 | 36.64 |
| ATOM | 599 | CG | GLN | 64 | −17.287 | 2.819 | 32.432 | 1.00 | 39.67 |
| ATOM | 600 | CD | GLN | 64 | −16.263 | 3.870 | 32.775 | 1.00 | 40.97 |
| ATOM | 601 | OE1 | GLN | 64 | −16.145 | 4.290 | 33.929 | 1.00 | 42.60 |
| ATOM | 602 | NE2 | GLN | 64 | −15.511 | 4.307 | 31.774 | 1.00 | 41.46 |
| ATOM | 603 | HE21 | GLN | 64 | −15.640 | 3.928 | 30.878 | 1.00 | 0.00 |
| ATOM | 604 | HE22 | GLN | 64 | −14.861 | 4.992 | 32.008 | 1.00 | 0.00 |
| ATOM | 605 | C | GLN | 64 | −16.545 | −0.778 | 33.279 | 1.00 | 35.62 |
| ATOM | 606 | O | GLN | 64 | −15.648 | −1.570 | 32.982 | 1.00 | 35.48 |
| ATOM | 607 | N | LEU | 65 | −17.816 | −1.133 | 33.412 | 1.00 | 38.38 |
| ATOM | 608 | H | LEU | 65 | −18.450 | −0.436 | 33.661 | 1.00 | 0.00 |
| ATOM | 609 | CA | LEU | 65 | −18.268 | −2.510 | 33.264 | 1.00 | 42.81 |
| ATOM | 610 | CB | LEU | 65 | −19.792 | −2.583 | 33.418 | 1.00 | 47.54 |
| ATOM | 611 | CG | LEU | 65 | −20.691 | −1.926 | 32.359 | 1.00 | 51.72 |
| ATOM | 612 | CD1 | LEU | 65 | −22.145 | −2.279 | 32.653 | 1.00 | 54.58 |
| ATOM | 613 | CD2 | LEU | 65 | −20.501 | −0.410 | 32.318 | 1.00 | 51.28 |
| ATOM | 614 | C | LEU | 65 | −17.849 | −3.137 | 31.934 | 1.00 | 43.23 |
| ATOM | 615 | O | LEU | 65 | −17.547 | −4.327 | 31.873 | 1.00 | 44.38 |
| ATOM | 616 | N | ASN | 66 | −17.801 | −2.329 | 30.879 | 1.00 | 42.92 |
| ATOM | 617 | H | ASN | 66 | −18.004 | −1.382 | 30.987 | 1.00 | 0.00 |
| ATOM | 618 | CA | ASN | 66 | −17.421 | −2.825 | 29.559 | 1.00 | 42.31 |
| ATOM | 619 | CB | ASN | 66 | −18.052 | −1.973 | 28.456 | 1.00 | 45.73 |
| ATOM | 620 | CG | ASN | 66 | −17.404 | −0.612 | 28.327 | 1.00 | 48.82 |
| ATOM | 621 | OD1 | ASN | 66 | −16.998 | −0.009 | 29.321 | 1.00 | 52.33 |
| ATOM | 622 | ND2 | ASN | 66 | −17.292 | −0.124 | 27.100 | 1.00 | 52.00 |
| ATOM | 623 | HD21 | ASN | 66 | −17.611 | −0.677 | 26.357 | 1.00 | 0.00 |
| ATOM | 624 | HD22 | ASN | 66 | −16.904 | 0.765 | 26.986 | 1.00 | 0.00 |
| ATOM | 625 | C | ASN | 66 | −15.909 | −2.916 | 29.346 | 1.00 | 41.37 |
| ATOM | 626 | O | ASN | 66 | −15.444 | −3.072 | 28.215 | 1.00 | 42.54 |
| ATOM | 627 | N | GLY | 67 | −15.144 | −2.788 | 30.425 | 1.00 | 39.06 |
| ATOM | 628 | H | GLY | 67 | −15.525 | −2.652 | 31.316 | 1.00 | 0.00 |
| ATOM | 629 | CA | GLY | 67 | −13.700 | −2.884 | 30.321 | 1.00 | 35.20 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 630 | C | GLY | 67 | −12.924 | −1.642 | 29.927 | 1.00 | 31.27 |
| ATOM | 631 | O | GLY | 67 | −11.718 | −1.728 | 29.706 | 1.00 | 32.16 |
| ATOM | 632 | N | THR | 68 | −13.594 | −0.501 | 29.801 | 1.00 | 28.74 |
| ATOM | 633 | H | THR | 68 | −14.552 | −0.492 | 29.964 | 1.00 | 0.00 |
| ATOM | 634 | CA | THR | 68 | −12.897 | 0.732 | 29.450 | 1.00 | 26.00 |
| ATOM | 635 | CB | THR | 68 | −13.738 | 1.639 | 28.531 | 1.00 | 26.73 |
| ATOM | 636 | OG1 | THR | 68 | −14.997 | 1.940 | 29.149 | 1.00 | 28.49 |
| ATOM | 637 | HG1 | THR | 68 | −15.528 | 1.140 | 29.220 | 1.00 | 0.00 |
| ATOM | 638 | CG2 | THR | 68 | −13.962 | 0.970 | 27.186 | 1.00 | 27.12 |
| ATOM | 639 | C | THR | 68 | −12.536 | 1.480 | 30.731 | 1.00 | 24.27 |
| ATOM | 640 | O | THR | 68 | −12.941 | 1.075 | 31.821 | 1.00 | 23.18 |
| ATOM | 641 | N | TYR | 69 | −11.769 | 2.558 | 30.600 | 1.00 | 22.13 |
| ATOM | 642 | H | TYR | 69 | −11.499 | 2.867 | 29.726 | 1.00 | 0.00 |
| ATOM | 643 | CA | TYR | 69 | −11.345 | 3.355 | 31.744 | 1.00 | 20.20 |
| ATOM | 644 | CB | TYR | 69 | −9.845 | 3.184 | 31.984 | 1.00 | 17.55 |
| ATOM | 645 | CG | TYR | 69 | −9.452 | 1.783 | 32.360 | 1.00 | 15.74 |
| ATOM | 646 | CD1 | TYR | 69 | −9.286 | 0.801 | 31.386 | 1.00 | 16.67 |
| ATOM | 647 | CE1 | TYR | 69 | −8.936 | −0.501 | 31.731 | 1.00 | 18.61 |
| ATOM | 648 | CD2 | TYR | 69 | −9.256 | 1.433 | 33.693 | 1.00 | 15.77 |
| ATOM | 649 | CE2 | TYR | 69 | −8.905 | 0.138 | 34.050 | 1.00 | 17.24 |
| ATOM | 650 | CZ | TYR | 69 | −8.745 | −0.824 | 33.065 | 1.00 | 18.54 |
| ATOM | 651 | OH | TYR | 69 | −8.389 | −2.102 | 33.417 | 1.00 | 19.33 |
| ATOM | 652 | HH | TYR | 69 | −8.332 | −2.618 | 32.605 | 1.00 | 0.00 |
| ATOM | 653 | C | TYR | 69 | −11.646 | 4.818 | 31.489 | 1.00 | 20.07 |
| ATOM | 654 | O | TYR | 69 | −11.509 | 5.296 | 30.360 | 1.00 | 19.19 |
| ATOM | 655 | N | ALA | 70 | −12.038 | 5.538 | 32.534 | 1.00 | 20.74 |
| ATOM | 656 | H | ALA | 70 | −12.144 | 5.122 | 33.421 | 1.00 | 0.00 |
| ATOM | 657 | CA | ALA | 70 | −12.346 | 6.951 | 32.380 | 1.00 | 22.43 |
| ATOM | 658 | CB | ALA | 70 | −13.703 | 7.123 | 31.701 | 1.00 | 20.46 |
| ATOM | 659 | C | ALA | 70 | −12.333 | 7.727 | 33.683 | 1.00 | 23.77 |
| ATOM | 660 | O | ALA | 70 | −12.569 | 7.169 | 34.760 | 1.00 | 23.69 |
| ATOM | 661 | N | ILE | 71 | −11.975 | 9.001 | 33.573 | 1.00 | 24.06 |
| ATOM | 662 | H | ILE | 71 | −11.708 | 9.364 | 32.704 | 1.00 | 0.00 |
| ATOM | 663 | CA | ILE | 71 | −11.982 | 9.909 | 34.704 | 1.00 | 24.49 |
| ATOM | 664 | CB | ILE | 71 | −11.079 | 11.134 | 34.450 | 1.00 | 23.76 |
| ATOM | 665 | CG2 | ILE | 71 | −11.206 | 12.132 | 35.593 | 1.00 | 23.11 |
| ATOM | 666 | CG1 | ILE | 71 | −9.623 | 10.691 | 34.285 | 1.00 | 22.21 |
| ATOM | 667 | CD | ILE | 71 | −8.669 | 11.832 | 34.009 | 1.00 | 18.51 |
| ATOM | 668 | C | ILE | 71 | −13.445 | 10.346 | 34.719 | 1.00 | 26.14 |
| ATOM | 669 | O | ILE | 71 | −14.057 | 10.481 | 33.659 | 1.00 | 23.83 |
| ATOM | 670 | N | ALA | 72 | −14.016 | 10.525 | 35.904 | 1.00 | 29.31 |
| ATOM | 671 | H | ALA | 72 | −13.481 | 10.391 | 36.712 | 1.00 | 0.00 |
| ATOM | 672 | CA | ALA | 72 | −15.417 | 10.922 | 36.026 | 1.00 | 33.39 |
| ATOM | 673 | CB | ALA | 72 | −15.759 | 11.228 | 37.480 | 1.00 | 33.93 |
| ATOM | 674 | C | ALA | 72 | −15.764 | 12.113 | 35.138 | 1.00 | 34.98 |
| ATOM | 675 | O | ALA | 72 | −15.242 | 13.212 | 35.324 | 1.00 | 34.89 |
| ATOM | 676 | N | GLY | 73 | −16.628 | 11.874 | 34.158 | 1.00 | 36.34 |
| ATOM | 677 | H | GLY | 73 | −16.960 | 10.963 | 34.030 | 1.00 | 0.00 |
| ATOM | 678 | CA | GLY | 73 | −17.044 | 12.932 | 33.254 | 1.00 | 36.52 |
| ATOM | 679 | C | GLY | 73 | −16.171 | 13.105 | 32.025 | 1.00 | 35.63 |
| ATOM | 680 | O | GLY | 73 | −16.375 | 14.032 | 31.239 | 1.00 | 37.15 |
| ATOM | 681 | N | GLY | 74 | −15.201 | 12.215 | 31.852 | 1.00 | 33.13 |
| ATOM | 682 | H | GLY | 74 | −15.099 | 11.459 | 32.459 | 1.00 | 0.00 |
| ATOM | 683 | CA | GLY | 74 | −14.320 | 12.301 | 30.706 | 1.00 | 32.37 |
| ATOM | 684 | C | GLY | 74 | −14.561 | 11.132 | 29.782 | 1.00 | 34.04 |
| ATOM | 685 | O | GLY | 74 | −15.276 | 10.191 | 30.131 | 1.00 | 34.17 |
| ATOM | 686 | N | LYS | 75 | −13.954 | 11.178 | 28.604 | 1.00 | 34.83 |
| ATOM | 687 | H | LYS | 75 | −13.391 | 11.953 | 28.407 | 1.00 | 0.00 |
| ATOM | 688 | CA | LYS | 75 | −14.112 | 10.109 | 27.630 | 1.00 | 35.85 |
| ATOM | 689 | CB | LYS | 75 | −13.575 | 10.550 | 26.266 | 1.00 | 40.25 |
| ATOM | 690 | CG | LYS | 75 | −14.604 | 11.333 | 25.454 | 1.00 | 48.14 |
| ATOM | 691 | CD | LYS | 75 | −13.992 | 12.101 | 24.290 | 1.00 | 53.33 |
| ATOM | 692 | CE | LYS | 75 | −13.261 | 13.349 | 24.773 | 1.00 | 57.38 |
| ATOM | 693 | NZ | LYS | 75 | −12.808 | 14.218 | 23.647 | 1.00 | 59.74 |
| ATOM | 694 | HZ1 | LYS | 75 | −13.632 | 14.560 | 23.114 | 1.00 | 0.00 |
| ATOM | 695 | HZ2 | LYS | 75 | −12.192 | 13.677 | 23.006 | 1.00 | 0.00 |
| ATOM | 696 | HZ3 | LYS | 75 | −12.282 | 15.027 | 24.027 | 1.00 | 0.00 |
| ATOM | 697 | C | LYS | 75 | −13.461 | 8.807 | 28.082 | 1.00 | 34.24 |
| ATOM | 698 | O | LYS | 75 | −12.416 | 8.812 | 28.741 | 1.00 | 33.16 |
| ATOM | 699 | N | ALA | 76 | −14.114 | 7.695 | 27.767 | 1.00 | 31.87 |
| ATOM | 700 | H | ALA | 76 | −14.954 | 7.758 | 27.270 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 701 | CA | ALA | 76 | −13.606 | 6.380 | 28.126 | 1.00 | 31.22 |
| ATOM | 702 | CB | ALA | 76 | −14.719 | 5.342 | 28.061 | 1.00 | 30.23 |
| ATOM | 703 | C | ALA | 76 | −12.479 | 6.005 | 27.179 | 1.00 | 28.77 |
| ATOM | 704 | O | ALA | 76 | −12.464 | 6.419 | 26.022 | 1.00 | 30.26 |
| ATOM | 705 | N | HIS | 77 | −11.525 | 5.237 | 27.683 | 1.00 | 27.21 |
| ATOM | 706 | H | HIS | 77 | −11.587 | 4.898 | 28.592 | 1.00 | 0.00 |
| ATOM | 707 | CA | HIS | 77 | −10.389 | 4.800 | 26.893 | 1.00 | 27.71 |
| ATOM | 708 | CB | HIS | 77 | −9.130 | 5.559 | 27.313 | 1.00 | 27.15 |
| ATOM | 709 | CG | HIS | 77 | −9.230 | 7.040 | 27.123 | 1.00 | 28.63 |
| ATOM | 710 | CD2 | HIS | 77 | −8.946 | 7.826 | 26.057 | 1.00 | 27.68 |
| ATOM | 711 | ND1 | HIS | 77 | −9.699 | 7.888 | 28.105 | 1.00 | 29.85 |
| ATOM | 712 | HD1 | HIS | 77 | −10.027 | 7.624 | 28.994 | 1.00 | 0.00 |
| ATOM | 713 | CE1 | HIS | 77 | −9.699 | 9.130 | 27.652 | 1.00 | 28.48 |
| ATOM | 714 | NE2 | HIS | 77 | −9.248 | 9.118 | 26.412 | 1.00 | 29.23 |
| ATOM | 715 | HE2 | HIS | 77 | −9.158 | 9.891 | 25.818 | 1.00 | 0.00 |
| ATOM | 716 | C | HIS | 77 | −10.236 | 3.302 | 27.118 | 1.00 | 28.88 |
| ATOM | 717 | O | HIS | 77 | −10.611 | 2.786 | 28.169 | 1.00 | 27.46 |
| ATOM | 718 | N | CYS | 78 | −9.703 | 2.599 | 26.128 | 1.00 | 29.61 |
| ATOM | 719 | H | CYS | 78 | −9.406 | 3.050 | 25.306 | 1.00 | 0.00 |
| ATOM | 720 | CA | CYS | 78 | −9.542 | 1.153 | 26.224 | 1.00 | 30.03 |
| ATOM | 721 | CB | CYS | 78 | −9.278 | 0.566 | 24.841 | 1.00 | 34.14 |
| ATOM | 722 | SG | CYS | 78 | −8.119 | 1.534 | 23.883 | 1.00 | 44.93 |
| ATOM | 723 | C | CYS | 78 | −8.489 | 0.668 | 27.211 | 1.00 | 25.84 |
| ATOM | 724 | O | CYS | 78 | −8.370 | −0.530 | 27.443 | 1.00 | 26.98 |
| ATOM | 725 | N | GLY | 79 | −7.733 | 1.590 | 27.797 | 1.00 | 23.67 |
| ATOM | 726 | H | GLY | 79 | −7.837 | 2.542 | 27.613 | 1.00 | 0.00 |
| ATOM | 727 | CA | GLY | 79 | −6.714 | 1.202 | 28.754 | 1.00 | 18.52 |
| ATOM | 728 | C | GLY | 79 | −6.019 | 2.397 | 29.371 | 1.00 | 18.97 |
| ATOM | 729 | O | GLY | 79 | −6.128 | 3.513 | 28.854 | 1.00 | 18.14 |
| ATOM | 730 | N | PRO | 80 | −5.281 | 2.194 | 30.473 | 1.00 | 18.06 |
| ATOM | 731 | CD | PRO | 80 | −5.090 | 0.904 | 31.157 | 1.00 | 18.29 |
| ATOM | 732 | CA | PRO | 80 | −4.559 | 3.264 | 31.165 | 1.00 | 17.93 |
| ATOM | 733 | CB | PRO | 80 | −3.931 | 2.536 | 32.357 | 1.00 | 20.63 |
| ATOM | 734 | CG | PRO | 80 | −3.791 | 1.121 | 31.873 | 1.00 | 19.63 |
| ATOM | 735 | C | PRO | 80 | −3.510 | 3.963 | 30.289 | 1.00 | 17.24 |
| ATOM | 736 | O | PRO | 80 | −3.408 | 5.190 | 30.300 | 1.00 | 14.92 |
| ATOM | 737 | N | ALA | 81 | −2.757 | 3.192 | 29.510 | 1.00 | 15.32 |
| ATOM | 738 | H | ALA | 81 | −2.864 | 2.214 | 29.533 | 1.00 | 0.00 |
| ATOM | 739 | CA | ALA | 81 | −1.742 | 3.776 | 28.635 | 1.00 | 15.99 |
| ATOM | 740 | CB | ALA | 81 | −0.945 | 2.682 | 27.941 | 1.00 | 15.92 |
| ATOM | 741 | C | ALA | 81 | −2.367 | 4.713 | 27.600 | 1.00 | 16.17 |
| ATOM | 742 | O | ALA | 81 | −1.862 | 5.810 | 27.363 | 1.00 | 15.48 |
| ATOM | 743 | N | GLU | 82 | −3.481 | 4.284 | 27.009 | 1.00 | 18.46 |
| ATOM | 744 | H | GLU | 82 | −3.847 | 3.436 | 27.305 | 1.00 | 0.00 |
| ATOM | 745 | CA | GLU | 82 | −4.188 | 5.066 | 25.994 | 1.00 | 18.23 |
| ATOM | 746 | CB | GLU | 82 | −5.298 | 4.238 | 25.334 | 1.00 | 20.10 |
| ATOM | 747 | CG | GLU | 82 | −4.808 | 3.159 | 24.372 | 1.00 | 25.98 |
| ATOM | 748 | CD | GLU | 82 | −4.489 | 1.824 | 25.043 | 1.00 | 30.34 |
| ATOM | 749 | OE1 | GLU | 82 | −4.351 | 0.817 | 24.317 | 1.00 | 35.16 |
| ATOM | 750 | OE2 | GLU | 82 | −4.382 | 1.763 | 26.284 | 1.00 | 30.98 |
| ATOM | 751 | C | GLU | 82 | −4.780 | 6.333 | 26.591 | 1.00 | 17.53 |
| ATOM | 752 | O | GLU | 82 | −4.855 | 7.368 | 25.928 | 1.00 | 15.66 |
| ATOM | 753 | N | LEU | 83 | −5.199 | 6.244 | 27.846 | 1.00 | 16.88 |
| ATOM | 754 | H | LEU | 83 | −5.136 | 5.386 | 28.316 | 1.00 | 0.00 |
| ATOM | 755 | CA | LEU | 83 | −5.769 | 7.383 | 28.548 | 1.00 | 17.11 |
| ATOM | 756 | CB | LEU | 83 | −6.359 | 6.929 | 29.888 | 1.00 | 17.19 |
| ATOM | 757 | CG | LEU | 83 | −6.973 | 7.966 | 30.825 | 1.00 | 16.72 |
| ATOM | 758 | CD1 | LEU | 83 | −8.124 | 7.338 | 31.597 | 1.00 | 16.47 |
| ATOM | 759 | CD2 | LEU | 83 | −5.907 | 8.526 | 31.766 | 1.00 | 15.85 |
| ATOM | 760 | C | LEU | 83 | −4.694 | 8.454 | 28.742 | 1.00 | 17.05 |
| ATOM | 761 | O | LEU | 83 | −4.927 | 9.632 | 28.462 | 1.00 | 17.29 |
| ATOM | 762 | N | CYS | 84 | −3.506 | 8.039 | 29.167 | 1.00 | 16.35 |
| ATOM | 763 | H | CYS | 84 | −3.372 | 7.082 | 29.354 | 1.00 | 0.00 |
| ATOM | 764 | CA | CYS | 84 | −2.412 | 8.979 | 29.377 | 1.00 | 17.56 |
| ATOM | 765 | CB | CYS | 84 | −1.265 | 8.308 | 30.129 | 1.00 | 16.45 |
| ATOM | 766 | SG | CYS | 84 | −1.663 | 7.902 | 31.846 | 1.00 | 14.67 |
| ATOM | 767 | C | CYS | 84 | −1.925 | 9.578 | 28.060 | 1.00 | 20.60 |
| ATOM | 768 | O | CYS | 84 | −1.586 | 10.761 | 27.999 | 1.00 | 20.51 |
| ATOM | 769 | N | GLU | 85 | −1.911 | 8.766 | 27.005 | 1.00 | 22.93 |
| ATOM | 770 | H | GLU | 85 | −2.190 | 7.833 | 27.119 | 1.00 | 0.00 |
| ATOM | 771 | CA | GLU | 85 | −1.486 | 9.218 | 25.680 | 1.00 | 23.75 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 772 | CB | GLU | 85 | −1.420 | 8.034 | 24.703 | 1.00 | 27.58 |
| ATOM | 773 | CG | GLU | 85 | −0.364 | 6.990 | 25.079 | 1.00 | 36.56 |
| ATOM | 774 | CD | GLU | 85 | −0.285 | 5.806 | 24.115 | 1.00 | 40.46 |
| ATOM | 775 | OE1 | GLU | 85 | −1.165 | 4.919 | 24.169 | 1.00 | 38.44 |
| ATOM | 776 | OE2 | GLU | 85 | 0.681 | 5.751 | 23.319 | 1.00 | 46.15 |
| ATOM | 777 | C | GLU | 85 | −2.439 | 10.298 | 25.164 | 1.00 | 23.52 |
| ATOM | 778 | O | GLU | 85 | −2.002 | 11.304 | 24.602 | 1.00 | 23.99 |
| ATOM | 779 | N | PHE | 86 | −3.735 | 10.109 | 25.404 | 1.00 | 23.07 |
| ATOM | 780 | H | PHE | 86 | −4.026 | 9.296 | 25.868 | 1.00 | 0.00 |
| ATOM | 781 | CA | PHE | 86 | −4.758 | 11.063 | 24.981 | 1.00 | 22.06 |
| ATOM | 782 | CB | PHE | 86 | −6.158 | 10.499 | 25.245 | 1.00 | 23.30 |
| ATOM | 783 | CG | PHE | 86 | −7.265 | 11.504 | 25.064 | 1.00 | 25.88 |
| ATOM | 784 | CD1 | PHE | 86 | −7.693 | 11.867 | 23.795 | 1.00 | 28.15 |
| ATOM | 785 | CD2 | PHE | 86 | −7.874 | 12.093 | 26.169 | 1.00 | 27.77 |
| ATOM | 786 | CE1 | PHE | 86 | −8.713 | 12.803 | 23.628 | 1.00 | 30.93 |
| ATOM | 787 | CE2 | PHE | 86 | −8.892 | 13.029 | 26.015 | 1.00 | 27.23 |
| ATOM | 788 | CZ | PHE | 86 | −9.314 | 13.385 | 24.742 | 1.00 | 30.08 |
| ATOM | 789 | C | PHE | 86 | −4.609 | 12.408 | 25.679 | 1.00 | 22.18 |
| ATOM | 790 | O | PHE | 86 | −4.657 | 13.457 | 25.032 | 1.00 | 22.09 |
| ATOM | 791 | N | TYR | 87 | −4.438 | 12.378 | 26.998 | 1.00 | 20.74 |
| ATOM | 792 | H | TYR | 87 | −4.421 | 11.516 | 27.464 | 1.00 | 0.00 |
| ATOM | 793 | CA | TYR | 87 | −4.291 | 13.604 | 27.776 | 1.00 | 20.26 |
| ATOM | 794 | CB | TYR | 87 | −4.562 | 13.340 | 29.250 | 1.00 | 17.65 |
| ATOM | 795 | CG | TYR | 87 | −6.021 | 13.088 | 29.531 | 1.00 | 19.72 |
| ATOM | 796 | CD1 | TYR | 87 | −6.455 | 11.844 | 29.967 | 1.00 | 20.21 |
| ATOM | 797 | CE1 | TYR | 87 | −7.798 | 11.603 | 30.242 | 1.00 | 25.37 |
| ATOM | 798 | CD2 | TYR | 87 | −6.970 | 14.099 | 29.371 | 1.00 | 19.83 |
| ATOM | 799 | CE2 | TYR | 87 | −8.320 | 13.873 | 29.644 | 1.00 | 21.99 |
| ATOM | 800 | CZ | TYR | 87 | −8.727 | 12.618 | 30.081 | 1.00 | 25.65 |
| ATOM | 801 | OH | TYR | 87 | −10.052 | 12.356 | 30.364 | 1.00 | 25.64 |
| ATOM | 802 | HH | TYR | 87 | −10.057 | 11.542 | 30.886 | 1.00 | 0.00 |
| ATOM | 803 | C | TYR | 87 | −2.967 | 14.337 | 27.578 | 1.00 | 20.79 |
| ATOM | 804 | O | TYR | 87 | −2.795 | 15.458 | 28.061 | 1.00 | 20.79 |
| ATOM | 805 | N | SER | 88 | −2.026 | 13.691 | 26.895 | 1.00 | 24.94 |
| ATOM | 806 | H | SER | 88 | −2.190 | 12.769 | 26.608 | 1.00 | 0.00 |
| ATOM | 807 | CA | SER | 88 | −0.737 | 14.305 | 26.584 | 1.00 | 28.11 |
| ATOM | 808 | CB | SER | 88 | 0.268 | 13.249 | 26.112 | 1.00 | 27.90 |
| ATOM | 809 | OG | SER | 88 | 0.565 | 12.303 | 27.124 | 1.00 | 35.96 |
| ATOM | 810 | HG | SER | 88 | −0.251 | 11.986 | 27.522 | 1.00 | 0.00 |
| ATOM | 811 | C | SER | 88 | −0.989 | 15.288 | 25.443 | 1.00 | 29.72 |
| ATOM | 812 | O | SER | 88 | −0.360 | 16.344 | 25.361 | 1.00 | 30.51 |
| ATOM | 813 | N | ARG | 89 | −1.917 | 14.924 | 24.563 | 1.00 | 31.17 |
| ATOM | 814 | H | ARG | 89 | −2.399 | 14.082 | 24.692 | 1.00 | 0.00 |
| ATOM | 815 | CA | ARG | 89 | −2.265 | 15.750 | 23.418 | 1.00 | 35.74 |
| ATOM | 816 | CB | ARG | 89 | −2.712 | 14.874 | 22.243 | 1.00 | 40.10 |
| ATOM | 817 | CG | ARG | 89 | −1.582 | 14.360 | 21.356 | 1.00 | 47.31 |
| ATOM | 818 | CD | ARG | 89 | −0.637 | 13.443 | 22.108 | 1.00 | 51.57 |
| ATOM | 819 | NE | ARG | 89 | 0.489 | 13.018 | 21.281 | 1.00 | 54.95 |
| ATOM | 820 | HE | ARG | 89 | 0.313 | 12.782 | 20.44 | 1.00 | 0.00 |
| ATOM | 821 | CZ | ARG | 89 | 1.742 | 12.918 | 21.719 | 1.00 | 56.98 |
| ATOM | 822 | NH1 | ARG | 89 | 2.039 | 13.215 | 22.980 | 1.00 | 56.68 |
| ATOM | 823 | HH11 | ARG | 89 | 1.325 | 13.519 | 23.611 | 1.00 | 0.00 |
| ATOM | 824 | HH12 | ARG | 89 | 2.982 | 13.141 | 23.303 | 1.00 | 0.00 |
| ATOM | 825 | NH2 | ARG | 89 | 2.700 | 12.511 | 20.897 | 1.00 | 57.57 |
| ATOM | 826 | HH21 | ARG | 89 | 2.477 | 12.279 | 19.950 | 1.00 | 0.00 |
| ATOM | 827 | HH22 | ARG | 89 | 3.642 | 12.430 | 21.228 | 1.00 | 0.00 |
| ATOM | 828 | C | ARG | 89 | −3.352 | 16.762 | 23.734 | 1.00 | 35.85 |
| ATOM | 829 | O | ARG | 89 | −3.263 | 17.924 | 23.334 | 1.00 | 36.15 |
| ATOM | 830 | N | ASP | 90 | −4.375 | 16.327 | 24.457 | 1.00 | 37.16 |
| ATOM | 831 | H | ASP | 90 | −4.418 | 15.403 | 24.786 | 1.00 | 0.00 |
| ATOM | 832 | CA | ASP | 90 | −5.484 | 17.206 | 24.793 | 1.00 | 38.14 |
| ATOM | 833 | CB | ASP | 90 | −6.696 | 16.820 | 23.935 | 1.00 | 41.72 |
| ATOM | 834 | CG | ASP | 90 | −7.849 | 17.796 | 24.064 | 1.00 | 45.64 |
| ATOM | 835 | OD1 | ASP | 90 | −9.005 | 17.364 | 23.872 | 1.00 | 49.81 |
| ATOM | 836 | OD2 | ASP | 90 | −7.608 | 18.992 | 24.342 | 1.00 | 47.83 |
| ATOM | 837 | C | ASP | 90 | −5.841 | 17.147 | 26.278 | 1.00 | 35.95 |
| ATOM | 838 | O | ASP | 90 | −6.216 | 16.094 | 26.786 | 1.00 | 35.57 |
| ATOM | 839 | N | PRO | 91 | −5.724 | 18.285 | 26.992 | 1.00 | 35.06 |
| ATOM | 840 | CD | PRO | 91 | −5.220 | 19.578 | 26.497 | 1.00 | 34.31 |
| ATOM | 841 | CA | PRO | 91 | −6.040 | 18.368 | 28.424 | 1.00 | 34.83 |
| ATOM | 842 | CB | PRO | 91 | −5.934 | 19.865 | 28.705 | 1.00 | 33.84 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 843 | CG | PRO | 91 | −4.858 | 20.296 | 27.778 | 1.00 | 35.60 |
| ATOM | 844 | C | PRO | 91 | −7.453 | 17.855 | 28.705 | 1.00 | 34.95 |
| ATOM | 845 | O | PRO | 91 | −7.685 | 17.165 | 29.695 | 1.00 | 34.91 |
| ATOM | 846 | N | ASP | 92 | −8.393 | 18.245 | 27.844 | 1.00 | 34.68 |
| ATOM | 847 | H | ASP | 92 | −8.121 | 18.822 | 27.107 | 1.00 | 0.00 |
| ATOM | 848 | CA | ASP | 92 | −9.796 | 17.837 | 27.934 | 1.00 | 34.83 |
| ATOM | 849 | CB | ASP | 92 | −9.980 | 16.465 | 27.261 | 1.00 | 38.56 |
| ATOM | 850 | CG | ASP | 92 | −11.441 | 16.132 | 26.973 | 1.00 | 43.08 |
| ATOM | 851 | OD1 | ASP | 92 | −11.864 | 14.990 | 27.264 | 1.00 | 46.42 |
| ATOM | 852 | OD2 | ASP | 92 | −12.165 | 17.008 | 26.452 | 1.00 | 46.09 |
| ATOM | 853 | C | ASP | 92 | −10.380 | 17.841 | 29.358 | 1.00 | 33.28 |
| ATOM | 854 | O | ASP | 92 | −11.021 | 16.879 | 29.789 | 1.00 | 32.13 |
| ATOM | 855 | N | GLY | 93 | −10.165 | 18.939 | 30.078 | 1.00 | 32.19 |
| ATOM | 856 | H | GLY | 93 | −9.648 | 19.684 | 29.719 | 1.00 | 0.00 |
| ATOM | 857 | CA | GLY | 93 | −10.691 | 19.042 | 31.428 | 1.00 | 30.80 |
| ATOM | 858 | C | GLY | 93 | −9.647 | 19.125 | 32.523 | 1.00 | 28.16 |
| ATOM | 859 | O | GLY | 93 | −9.932 | 19.620 | 33.614 | 1.00 | 29.26 |
| ATOM | 860 | N | LEU | 94 | −8.456 | 18.600 | 32.262 | 1.00 | 25.58 |
| ATOM | 861 | H | LEU | 94 | −8.292 | 18.164 | 31.399 | 1.00 | 0.00 |
| ATOM | 862 | CA | LEU | 94 | −7.380 | 18.642 | 33.244 | 1.00 | 25.19 |
| ATOM | 863 | CB | LEU | 94 | −6.266 | 17.654 | 32.867 | 1.00 | 23.59 |
| ATOM | 864 | CG | LEU | 94 | −6.578 | 16.165 | 32.692 | 1.00 | 21.25 |
| ATOM | 865 | CD1 | LEU | 94 | −5.314 | 15.463 | 32.246 | 1.00 | 20.19 |
| ATOM | 866 | CD2 | LEU | 94 | −7.097 | 15.552 | 33.978 | 1.00 | 20.15 |
| ATOM | 867 | C | LEU | 94 | −6.813 | 20.064 | 33.290 | 1.00 | 27.14 |
| ATOM | 868 | O | LEU | 94 | −6.956 | 20.826 | 32.329 | 1.00 | 26.74 |
| ATOM | 869 | N | PRO | 95 | −6.160 | 20.439 | 34.407 | 1.00 | 27.36 |
| ATOM | 870 | CD | PRO | 95 | −5.991 | 19.647 | 35.637 | 1.00 | 27.79 |
| ATOM | 871 | CA | PRO | 95 | −5.571 | 21.774 | 34.568 | 1.00 | 27.68 |
| ATOM | 872 | CB | PRO | 95 | −5.025 | 21.736 | 35.999 | 1.00 | 28.71 |
| ATOM | 873 | CG | PRO | 95 | −4.772 | 20.274 | 36.244 | 1.00 | 28.16 |
| ATOM | 874 | C | PRO | 95 | −4.475 | 22.088 | 33.544 | 1.00 | 27.92 |
| ATOM | 875 | O | PRO | 95 | −4.074 | 23.245 | 33.386 | 1.00 | 28.39 |
| ATOM | 876 | N | CYS | 96 | −3.953 | 21.041 | 32.912 | 1.00 | 28.28 |
| ATOM | 877 | H | CYS | 96 | −4.241 | 20.128 | 33.129 | 1.00 | 0.00 |
| ATOM | 878 | CA | CYS | 96 | −2.917 | 21.145 | 31.884 | 1.00 | 27.50 |
| ATOM | 879 | CB | CYS | 96 | −1.596 | 21.666 | 32.467 | 1.00 | 27.76 |
| ATOM | 880 | SG | CYS | 96 | −0.775 | 20.589 | 33.668 | 1.00 | 30.21 |
| ATOM | 881 | C | CYS | 96 | −2.721 | 19.754 | 31.295 | 1.00 | 27.05 |
| ATOM | 882 | O | CYS | 96 | −3.133 | 18.762 | 31.899 | 1.00 | 28.24 |
| ATOM | 883 | N | ASN | 97 | −2.137 | 19.678 | 30.106 | 1.00 | 24.88 |
| ATOM | 884 | H | ASN | 97 | −1.807 | 20.482 | 29.650 | 1.00 | 0.00 |
| ATOM | 885 | CA | ASN | 97 | −1.903 | 1B.386 | 29.473 | 1.00 | 24.53 |
| ATOM | 886 | CB | ASN | 97 | −1.602 | 1B.556 | 27.980 | 1.00 | 26.26 |
| ATOM | 887 | CG | ASN | 97 | −0.321 | 19.321 | 27.727 | 1.00 | 27.29 |
| ATOM | 888 | OD1 | ASN | 97 | −0.142 | 20.430 | 28.230 | 1.00 | 33.19 |
| ATOM | 889 | ND2 | ASN | 97 | 0.577 | 18.737 | 26.950 | 1.00 | 29.41 |
| ATOM | 890 | HD21 | ASN | 97 | 0.365 | 17.861 | 26.558 | 1.00 | 0.00 |
| ATOM | 891 | HD22 | ASN | 97 | 1.409 | 19.221 | 26.806 | 1.00 | 0.00 |
| ATOM | 892 | C | ASN | 97 | −0.746 | 17.667 | 30.165 | 1.00 | 23.01 |
| ATOM | 893 | O | ASN | 97 | 0.075 | 18.291 | 30.847 | 1.00 | 21.65 |
| ATOM | 894 | N | LEU | 98 | −0.691 | 16.353 | 29.992 | 1.00 | 21.64 |
| ATOM | 895 | H | LEU | 98 | −1.373 | 15.929 | 29.433 | 1.00 | 0.00 |
| ATOM | 896 | CA | LEU | 98 | 0.359 | 15.546 | 30.594 | 1.00 | 21.20 |
| ATOM | 897 | CB | LEU | 98 | −0.034 | 14.069 | 30.570 | 1.00 | 17.06 |
| ATOM | 898 | CG | LEU | 98 | −1.357 | 13.699 | 31.251 | 1.00 | 16.71 |
| ATOM | 899 | CD1 | LEU | 98 | −1.549 | 12.185 | 31.223 | 1.00 | 12.58 |
| ATOM | 900 | CD2 | LEU | 98 | −1.370 | 14.216 | 32.684 | 1.00 | 14.60 |
| ATOM | 901 | C | LEU | 98 | 1.684 | 15.754 | 29.867 | 1.00 | 23.86 |
| ATOM | 902 | O | LEU | 98 | 1.835 | 15.360 | 28.708 | 1.00 | 26.15 |
| ATOM | 903 | N | ARG | 99 | 2.630 | 16.392 | 30.549 | 1.00 | 26.16 |
| ATOM | 904 | H | ARG | 99 | 2.455 | 16.653 | 31.475 | 1.00 | 0.00 |
| ATOM | 905 | CA | ARG | 99 | 3.951 | 16.674 | 29.994 | 1.00 | 28.30 |
| ATOM | 906 | CB | ARG | 99 | 4.241 | 18.177 | 30.025 | 1.00 | 26.96 |
| ATOM | 907 | CG | ARG | 99 | 3.171 | 19.070 | 29.447 | 1.00 | 30.41 |
| ATOM | 908 | CD | ARG | 99 | 3.508 | 20.526 | 29.734 | 1.00 | 34.41 |
| ATOM | 909 | NE | ARG | 99 | 2.427 | 21.433 | 29.355 | 1.00 | 38.66 |
| ATOM | 910 | HE | ARG | 99 | 1.995 | 21.299 | 28.487 | 1.00 | 0.00 |
| ATOM | 911 | CZ | ARG | 99 | 1.982 | 22.430 | 30.116 | 1.00 | 41.42 |
| ATOM | 912 | NH1 | ARG | 99 | 2.521 | 22.659 | 31.307 | 1.00 | 44.31 |
| ATOM | 913 | HH11 | ARG | 99 | 3.261 | 22.076 | 31.642 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 914 | HH12 | ARG 99 | 2.176 | 23.402 | 31.880 | 1.00 | 0.00 |
| ATOM | 915 | NH2 | ARG 99 | 0.991 | 23.199 | 29.685 | 1.00 | 42.74 |
| ATOM | 916 | HH21 | ARG 99 | 0.582 | 23.034 | 28.788 | 1.00 | 0.00 |
| ATOM | 917 | HH22 | ARG 99 | 0.656 | 23.950 | 30.253 | 1.00 | 0.00 |
| ATOM | 918 | C | ARG 99 | 5.022 | 15.981 | 30.827 | 1.00 | 30.19 |
| ATOM | 919 | O | ARG 99 | 5.260 | 16.353 | 31.973 | 1.00 | 35.13 |
| ATOM | 920 | N | LYS 100 | 5.682 | 14.992 | 30.245 | 1.00 | 29.39 |
| ATOM | 921 | H | LYS 100 | 5.435 | 14.728 | 29.337 | 1.00 | 0.00 |
| ATOM | 922 | CA | LYS 100 | 6.746 | 14.275 | 30.935 | 1.00 | 27.27 |
| ATOM | 923 | CB | LYS 100 | 7.818 | 15.244 | 31.451 | 1.00 | 28.94 |
| ATOM | 924 | CG | LYS 100 | 9.056 | 14.548 | 31.998 | 1.00 | 38.33 |
| ATOM | 925 | CD | LYS 100 | 10.106 | 15.539 | 32.483 | 1.00 | 43.68 |
| ATOM | 926 | CE | LYS 100 | 11.359 | 14.824 | 32.989 | 1.00 | 45.64 |
| ATOM | 927 | NZ | LYS 100 | 11.077 | 13.949 | 34.166 | 1.00 | 47.84 |
| ATOM | 928 | HZ1 | LYS 100 | 10.401 | 13.212 | 33.886 | 1.00 | 0.00 |
| ATOM | 929 | HZ2 | LYS 100 | 10.658 | 14.516 | 34.932 | 1.00 | 0.00 |
| ATOM | 930 | HZ3 | LYS 100 | 11.961 | 13.513 | 34.494 | 1.00 | 0.00 |
| ATOM | 931 | C | LYS 100 | 6.306 | 13.355 | 32.070 | 1.00 | 23.90 |
| ATOM | 932 | O | LYS 100 | 5.879 | 13.802 | 33.136 | 1.00 | 21.73 |
| ATOM | 933 | N | PRO 101 | 6.365 | 12.043 | 31.827 | 1.00 | 20.62 |
| ATOM | 934 | CD | PRO 101 | 6.598 | 11.395 | 30.525 | 1.00 | 19.79 |
| ATOM | 935 | CA | PRO 101 | 5.985 | 11.063 | 32.840 | 1.00 | 18.73 |
| ATOM | 936 | CB | PRO 101 | 5.909 | 9.762 | 32.040 | 1.00 | 20.97 |
| ATOM | 937 | CG | PRO 101 | 6.897 | 9.978 | 30.934 | 1.00 | 22.39 |
| ATOM | 938 | C | PRO 101 | 7.058 | 10.992 | 33.923 | 1.00 | 17.30 |
| ATOM | 939 | O | PRO 101 | 8.252 | 11.122 | 33.644 | 1.00 | 16.81 |
| ATOM | 940 | N | CYS 102 | 6.633 | 10.823 | 35.165 | 1.00 | 15.53 |
| ATOM | 941 | H | CYS 102 | 5.688 | 10.683 | 35.322 | 1.00 | 0.00 |
| ATOM | 942 | CA | CYS 102 | 7.563 | 10.720 | 36.268 | 1.00 | 13.89 |
| ATOM | 943 | CB | CYS 102 | 6.898 | 11.178 | 37.557 | 1.00 | 13.31 |
| ATOM | 944 | SG | CYS 102 | 7.994 | 11.195 | 38.960 | 1.00 | 16.63 |
| ATOM | 945 | C | CYS 102 | 7.929 | 9.245 | 36.344 | 1.00 | 14.55 |
| ATOM | 946 | O | CYS 102 | 7.358 | 8.488 | 37.130 | 1.00 | 15.10 |
| ATOM | 947 | N | ASN 103 | 8.853 | 8.834 | 35.485 | 1.00 | 14.85 |
| ATOM | 948 | H | ASN 103 | 9.232 | 9.505 | 34.875 | 1.00 | 0.00 |
| ATOM | 949 | CA | ASN 103 | 9.283 | 7.440 | 35.421 | 1.00 | 15.80 |
| ATOM | 950 | CB | ASN 103 | 10.196 | 7.218 | 34.212 | 1.00 | 16.28 |
| ATOM | 951 | CG | ASN 103 | 9.503 | 7.509 | 32.896 | 1.00 | 15.02 |
| ATOM | 952 | OD1 | ASN 103 | 8.353 | 7.121 | 32.679 | 1.00 | 16.41 |
| ATOM | 953 | ND2 | ASN 103 | 10.196 | 8.205 | 32.013 | 1.00 | 20.99 |
| ATOM | 954 | HD21 | ASN 103 | 11.100 | 8.507 | 32.225 | 1.00 | 0.00 |
| ATOM | 955 | HD22 | ASN 103 | 9.759 | 8.409 | 31.149 | 1.00 | 0.00 |
| ATOM | 956 | C | ASN 103 | 9.966 | 6.941 | 36.688 | 1.00 | 17.75 |
| ATOM | 957 | O | ASN 103 | 10.709 | 7.676 | 37.341 | 1.00 | 17.16 |
| ATOM | 958 | N | ARG 104 | 9.699 | 5.684 | 37.027 | 1.00 | 16.96 |
| ATOM | 959 | H | ARG 104 | 9.110 | 5.152 | 36.460 | 1.00 | 0.00 |
| ATOM | 960 | CA | ARG 104 | 10.274 | 5.054 | 38.207 | 1.00 | 19.38 |
| ATOM | 961 | CB | ARG 104 | 9.781 | 3.610 | 38.330 | 1.00 | 19.40 |
| ATOM | 962 | CG | ARG 104 | 8.431 | 3.450 | 38.999 | 1.00 | 17.82 |
| ATOM | 963 | CD | ARG 104 | 8.002 | 1.999 | 39.007 | 1.00 | 17.65 |
| ATOM | 964 | NE | ARG 104 | 7.520 | 1.576 | 37.696 | 1.00 | 26.48 |
| ATOM | 965 | HE | ARG 104 | 6.667 | 1.930 | 37.380 | 1.00 | 0.00 |
| ATOM | 966 | CZ | ARG 104 | 8.170 | 0.759 | 36.874 | 1.00 | 25.18 |
| ATOM | 967 | NH1 | ARG 104 | 9.350 | 0.260 | 37.213 | 1.00 | 29.12 |
| ATOM | 968 | HH11 | ARG 104 | 9.760 | 0.484 | 38.095 | 1.00 | 0.00 |
| ATOM | 969 | HH12 | ARG 104 | 9.829 | −0.357 | 36.586 | 1.00 | 0.00 |
| ATOM | 970 | NH2 | ARG 104 | 7.628 | 0.429 | 35.712 | 1.00 | 30.66 |
| ATOM | 971 | HH21 | ARG 104 | 6.735 | 0.803 | 35.464 | 1.00 | 0.00 |
| ATOM | 972 | HH22 | ARG 104 | 8.101 | −0.194 | 35.088 | 1.00 | 0.00 |
| ATOM | 973 | C | ARG 104 | 11.796 | 5.059 | 38.163 | 1.00 | 23.50 |
| ATOM | 974 | O | ARG 104 | 12.395 | 4.746 | 37.133 | 1.00 | 23.54 |
| ATOM | 975 | N | PRO 105 | 12.440 | 5.453 | 39.273 | 1.00 | 27.13 |
| ATOM | 976 | CD | PRO 105 | 11.847 | 5.983 | 40.512 | 1.00 | 29.49 |
| ATOM | 977 | CA | PRO 105 | 13.902 | 5.487 | 39.341 | 1.00 | 29.70 |
| ATOM | 978 | CB | PRO 105 | 14.160 | 5.980 | 40.760 | 1.00 | 30.41 |
| ATOM | 979 | CG | PRO 105 | 12.960 | 6.824 | 41.053 | 1.00 | 31.24 |
| ATOM | 980 | C | PRO 105 | 14.429 | 4.070 | 39.163 | 1.00 | 32.78 |
| ATOM | 981 | O | PRO 105 | 13.750 | 3.103 | 39.517 | 1.00 | 33.65 |
| ATOM | 982 | N | SER 106 | 15.631 | 3.946 | 38.613 | 1.00 | 36.54 |
| ATOM | 983 | H | SER 106 | 16.143 | 4.736 | 38.342 | 1.00 | 0.00 |
| ATOM | 984 | CA | SER 106 | 16.241 | 2.638 | 38.393 | 1.00 | 37.78 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 985 | CB | SER | 106 | 17.652 | 2.810 | 37.829 | 1.00 | 40.86 |
| ATOM | 986 | OG | SER | 106 | 17.637 | 3.643 | 36.680 | 1.00 | 45.12 |
| ATOM | 987 | HG | SER | 106 | 17.148 | 3.214 | 35.971 | 1.00 | 0.00 |
| ATOM | 988 | C | SER | 106 | 16.282 | 1.840 | 39.697 | 1.00 | 37.20 |
| ATOM | 989 | O | SER | 106 | 16.701 | 2.350 | 40.741 | 1.00 | 37.55 |
| ATOM | 990 | N | GLY | 107 | 15.808 | 0.601 | 39.636 | 1.00 | 36.08 |
| ATOM | 991 | H | GLY | 107 | 15.421 | 0.264 | 38.806 | 1.00 | 0.00 |
| ATOM | 992 | CA | GLY | 107 | 15.794 | −0.239 | 40.817 | 1.00 | 35.61 |
| ATOM | 993 | C | GLY | 107 | 14.462 | −0.209 | 41.544 | 1.00 | 34.68 |
| ATOM | 994 | O | GLY | 107 | 14.281 | −0.921 | 42.532 | 1.00 | 37.59 |
| ATOM | 995 | N | LEU | 108 | 13.536 | 0.621 | 41.071 | 1.00 | 31.21 |
| ATOM | 996 | H | LEU | 108 | 13.708 | 1.194 | 40.292 | 1.00 | 0.00 |
| ATOM | 997 | CA | LEU | 108 | 12.219 | 0.719 | 41.683 | 1.00 | 29.48 |
| ATOM | 998 | CB | LEU | 108 | 11.828 | 2.184 | 41.901 | 1.00 | 31.06 |
| ATOM | 999 | CG | LEU | 108 | 10.439 | 2.415 | 42.506 | 1.00 | 33.10 |
| ATOM | 1000 | CD1 | LEU | 108 | 10.341 | 1.718 | 43.849 | 1.00 | 35.40 |
| ATOM | 1001 | CD2 | LEU | 108 | 10.173 | 3.897 | 42.660 | 1.00 | 34.68 |
| ATOM | 1002 | C | LEU | 108 | 11.201 | 0.036 | 40.786 | 1.00 | 28.12 |
| ATOM | 1003 | O | LEU | 108 | 11.107 | 0.337 | 39.600 | 1.00 | 27.81 |
| ATOM | 1004 | N | GLU | 109 | 10.463 | −0.908 | 41.353 | 1.00 | 27.83 |
| ATOM | 1005 | H | GLU | 109 | 10.572 | −1.085 | 42.309 | 1.00 | 0.00 |
| ATOM | 1006 | CA | GLU | 109 | 9.448 | −1.644 | 40.612 | 1.00 | 26.64 |
| ATOM | 1007 | CB | GLU | 109 | 9.663 | −3.1s1 | 40.801 | 1.00 | 33.21 |
| ATOM | 1008 | CG | GLU | 109 | 11.066 | −3.653 | 40.433 | 1.00 | 42.25 |
| ATOM | 1009 | CD | GLU | 109 | 11.373 | −3.558 | 38.940 | 1.00 | 48.40 |
| ATOM | 1010 | OE1 | GLU | 109 | 11.182 | −4.568 | 38.228 | 1.00 | 52.92 |
| ATOM | 1011 | OE2 | GLU | 109 | 11.821 | −2.485 | 38.479 | 1.00 | 51.82 |
| ATOM | 1012 | C | GLU | 109 | 8.080 | −1.236 | 41.156 | 1.00 | 23.58 |
| ATOM | 1013 | O | GLU | 109 | 7.989 | −0.648 | 42.241 | 1.00 | 23.49 |
| ATOM | 1014 | N | PRO | 110 | 7.002 | −1.480 | 40.389 | 1.00 | 19.24 |
| ATOM | 1015 | CD | PRO | 110 | 6.918 | −1.981 | 39.007 | 1.00 | 16.22 |
| ATOM | 1016 | CA | PRO | 110 | 5.678 | −1.103 | 40.896 | 1.00 | 16.34 |
| ATOM | 1017 | CB | PRO | 110 | 4.753 | −1.406 | 39.715 | 1.00 | 14.78 |
| ATOM | 1018 | CG | PRO | 110 | 5.496 | −2.439 | 38.930 | 1.00 | 18.83 |
| ATOM | 1019 | C | PRO | 110 | 5.337 | −1.920 | 42.144 | 1.00 | 16.63 |
| ATOM | 1020 | O | PRO | 110 | 5.600 | −3.119 | 42.202 | 1.00 | 16.68 |
| ATOM | 1021 | N | GLN | 111 | 4.803 | −1.245 | 43.155 | 1.00 | 16.60 |
| ATOM | 1022 | H | GLN | 111 | 4.634 | −0.287 | 43.041 | 1.00 | 0.00 |
| ATOM | 1023 | CA | GLN | 111 | 4.447 | −1.869 | 44.425 | 1.00 | 16.91 |
| ATOM | 1024 | CB | GLN | 111 | 4.206 | −0.774 | 45.469 | 1.00 | 21.09 |
| ATOM | 1025 | CG | GLN | 111 | 3.892 | −1.263 | 46.873 | 1.00 | 29.38 |
| ATOM | 1026 | CD | GLN | 111 | 5.096 | −1.852 | 47.581 | 1.00 | 35.11 |
| ATOM | 1027 | OE1 | GLN | 111 | 6.224 | −1.390 | 47.404 | 1.00 | 39.80 |
| ATOM | 1028 | NE2 | GLN | 111 | 4.863 | −2.881 | 48.389 | 1.00 | 39.14 |
| ATOM | 1029 | HE21 | GLN | 111 | 3.934 | −3.187 | 48.464 | 1.00 | 0.00 |
| ATOM | 1030 | HE22 | GLN | 111 | 5.625 | −3.267 | 48.862 | 1.00 | 0.00 |
| ATOM | 1031 | C | GLN | 111 | 3.220 | −2.778 | 44.329 | 1.00 | 15.31 |
| ATOM | 1032 | O | GLN | 111 | 2.161 | −2.358 | 43.856 | 1.00 | 12.08 |
| ATOM | 1033 | N | PRO | 112 | 3.356 | −4.052 | 44.738 | 1.00 | 16.34 |
| ATOM | 1034 | CD | PRO | 112 | 4.563 | −4.760 | 45.201 | 1.00 | 15.65 |
| ATOM | 1035 | CA | PRO | 112 | 2.207 | −4.961 | 44.676 | 1.00 | 16.29 |
| ATOM | 1036 | CB | PRO | 112 | 2.831 | −6.322 | 44.999 | 1.00 | 17.56 |
| ATOM | 1037 | CG | PRO | 112 | 3.981 | −5.966 | 45.896 | 1.00 | 18.96 |
| ATOM | 1038 | C | PRO | 112 | 1.162 | −4.553 | 45.716 | 1.00 | 13.47 |
| ATOM | 1039 | O | PRO | 112 | 1.510 | −4.094 | 46.810 | 1.00 | 12.01 |
| ATOM | 1040 | N | GLY | 113 | −0.110 | −4.671 | 45.348 | 1.00 | 14.46 |
| ATOM | 1041 | H | GLY | 113 | −0.338 | −5.036 | 44.467 | 1.00 | 0.00 |
| ATOM | 1042 | CA | GLY | 113 | −1.184 | −4.317 | 46.256 | 1.00 | 14.99 |
| ATOM | 1043 | C | GLY | 113 | −1.504 | −5.450 | 47.212 | 1.00 | 15.75 |
| ATOM | 1044 | O | GLY | 113 | −1.523 | −6.625 | 46.827 | 1.00 | 15.37 |
| ATOM | 1045 | N | VAL | 114 | −1.735 | −5.107 | 48.471 | 1.00 | 13.61 |
| ATOM | 1046 | H | VAL | 114 | −1.698 | −4.160 | 48.725 | 1.00 | 0.00 |
| ATOM | 1047 | CA | VAL | 114 | −2.060 | −6.104 | 49.472 | 1.00 | 12.01 |
| ATOM | 1048 | CB | VAL | 114 | −2.103 | −5.481 | 50.884 | 1.00 | 11.85 |
| ATOM | 1049 | CG1 | VAL | 114 | −2.511 | −6.519 | 51.915 | 1.00 | 11.29 |
| ATOM | 1050 | CG2 | VAL | 114 | −0.738 | −4.914 | 51.236 | 1.00 | 11.92 |
| ATOM | 1051 | C | VAL | 114 | −3.386 | −6.787 | 49.134 | 1.00 | 11.03 |
| ATOM | 1052 | O | VAL | 114 | −3.474 | −8.014 | 49.197 | 1.00 | 11.50 |
| ATOM | 1053 | N | PHE | 115 | −4.389 | −6.012 | 48.721 | 1.00 | 10.78 |
| ATOM | 1054 | H | PHE | 115 | −4.259 | −5.036 | 48.674 | 1.00 | 0.00 |
| ATOM | 1055 | CA | PHE | 115 | −5.698 | −6.580 | 48.382 | 1.00 | 11.16 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1056 CB | PHE | 115 | −6.701 | −5.485 | 48.003 | 1.00 | 9.84 |
| ATOM | 1057 CG | PHE | 115 | −8.145 | −5.914 | 48.109 | 1.00 | 10.03 |
| ATOM | 1058 CD1 | PHE | 115 | −8.517 | −6.981 | 48.927 | 1.00 | 7.64 |
| ATOM | 1059 CD2 | PHE | 115 | −9.136 | −5.237 | 47.409 | 1.00 | 11.26 |
| ATOM | 1060 CE1 | PHE | 115 | −9.852 | −7.364 | 49.044 | 1.00 | 9.24 |
| ATOM | 1061 CE2 | PHE | 115 | −10.475 | −5.615 | 47.520 | 1.00 | 10.69 |
| ATOM | 1062 CZ | PHE | 115 | −10.830 | −6.676 | 48.338 | 1.00 | 9.26 |
| ATOM | 1063 C | PHE | 115 | −5.598 | −7.604 | 47.255 | 1.00 | 11.82 |
| ATOM | 1064 O | PHE | 115 | −6.187 | −8.678 | 47.338 | 1.00 | 12.23 |
| ATOM | 1065 N | ASP | 116 | −4.853 | −7.262 | 46.207 | 1.00 | 12.76 |
| ATOM | 1066 H | ASP | 116 | −4.437 | −6.379 | 46.194 | 1.00 | 0.00 |
| ATOM | 1067 CA | ASP | 116 | −4.649 | −8.154 | 45.062 | 1.00 | 13.21 |
| ATOM | 1068 CB | ASP | 116 | −3.735 | −7.493 | 44.019 | 1.00 | 15.79 |
| ATOM | 1069 CG | ASP | 116 | −4.448 | −6.435 | 43.187 | 1.00 | 18.80 |
| ATOM | 1070 OD1 | ASP | 116 | −5.617 | −6.109 | 43.476 | 1.00 | 22.22 |
| ATOM | 1071 OD2 | ASP | 116 | −3.831 | −5.933 | 42.227 | 1.00 | 23.70 |
| ATOM | 1072 C | ASP | 116 | −4.001 | −9.448 | 45.534 | 1.00 | 12.02 |
| ATOM | 1073 O | ASP | 116 | −4.399 | −10.547 | 45.137 | 1.00 | 12.26 |
| ATOM | 1074 N | CLE | 117 | −3.004 | −9.295 | 46.395 | 1.00 | 12.55 |
| ATOM | 1075 H | CLE | 117 | −2.749 | −8.387 | 46.652 | 1.00 | 0.00 |
| ATOM | 1076 CA | CLE | 117 | −2.267 | −10.413 | 46.952 | 1.00 | 15.65 |
| ATOM | 1077 CB | CLE | 117 | −1.156 | −9.892 | 47.847 | 1.00 | 16.88 |
| ATOM | 1078 SG | CLE | 117 | 0.032 | −11.145 | 48.309 | 1.00 | 24.55 |
| ATOM | 1079 B | CLE | 117 | 1.502 | −9.640 | 49.805 | 1.20 | 27.84 |
| ATOM | 1080 C | CLE | 117 | −3.171 | −11.348 | 47.746 | 1.00 | 17.48 |
| ATOM | 1081 O | CLE | 117 | −3.040 | −12.573 | 47.655 | 1.00 | 18.50 |
| ATOM | 1082 N | LEU | 118 | −4.077 | −10.772 | 48.533 | 1.00 | 16.22 |
| ATOM | 1083 H | LEU | 118 | −4.145 | −9.793 | 48.594 | 1.00 | 0.00 |
| ATOM | 1084 CA | LEU | 118 | −5.004 | −11.564 | 49.333 | 1.00 | 15.66 |
| ATOM | 1085 CB | LEU | 118 | −5.621 | −10.727 | 50.458 | 1.00 | 15.67 |
| ATOM | 1086 CG | LEU | 118 | −4.653 | −10.113 | 51.472 | 1.00 | 20.69 |
| ATOM | 1087 CD1 | LEU | 118 | −5.420 | −9.697 | 52.717 | 1.00 | 25.46 |
| ATOM | 1088 CD2 | LEU | 118 | −3.561 | −11.107 | 51.840 | 1.00 | 26.35 |
| ATOM | 1089 C | LEU | 118 | −6.107 | −12.191 | 48.484 | 1.00 | 15.77 |
| ATOM | 1090 O | LEU | 118 | −6.496 | −13.339 | 48.718 | 1.00 | 15.49 |
| ATOM | 1091 N | ARG | 119 | −6.603 | −11.452 | 47.495 | 1.00 | 14.72 |
| ATOM | 1092 H | ARG | 119 | −6.276 | −10.543 | 47.372 | 1.00 | 0.00 |
| ATOM | 1093 CA | ARG | 119 | −7.654 | −11.971 | 46.624 | 1.00 | 16.75 |
| ATOM | 1094 CB | ARG | 119 | −8.187 | −10.900 | 45.672 | 1.00 | 14.68 |
| ATOM | 1095 CG | ARG | 119 | −8.923 | −9.767 | 46.355 | 1.00 | 17.93 |
| ATOM | 1096 CD | ARG | 119 | −9.927 | −9.104 | 45.426 | 1.00 | 20.84 |
| ATOM | 1097 NE | ARG | 119 | −9.383 | −8.767 | 44.110 | 1.00 | 26.76 |
| ATOM | 1098 HE | ARG | 119 | −9.540 | −9.392 | 43.371 | 1.00 | 0.00 |
| ATOM | 1099 CZ | ARG | 119 | −8.678 | −7.672 | 43.837 | 1.00 | 29.78 |
| ATOM | 1100 NH1 | ARG | 119 | −8.412 | −6.790 | 44.789 | 1.00 | 31.04 |
| ATOM | 1101 HH11 | ARG | 119 | −8.728 | −6.943 | 45.724 | 1.00 | 0.00 |
| ATOM | 1102 HH12 | ARG | 119 | −7.872 | −5.976 | 44.576 | 1.00 | 0.00 |
| ATOM | 1103 NH2 | ARG | 119 | −8.256 | −7.447 | 42.600 | 1.00 | 32.50 |
| ATOM | 1104 HH21 | ARG | 119 | −8.466 | −8.097 | 41.867 | 1.00 | 0.00 |
| ATOM | 1105 HH22 | ARG | 119 | −7.723 | −6.624 | 42.397 | 1.00 | 0.00 |
| ATOM | 1106 C | ARG | 119 | −7.161 | −13.164 | 45.823 | 1.00 | 18.07 |
| ATOM | 1107 O | ARG | 119 | −7.940 | −14.053 | 45.491 | 1.00 | 21.21 |
| ATOM | 1108 N | ASP | 120 | −5.870 | −13.188 | 45.514 | 1.00 | 17.45 |
| ATOM | 1109 H | ASP | 120 | −5.289 | −12.442 | 45.768 | 1.00 | 0.00 |
| ATOM | 1110 CA | ASP | 120 | −5.294 | −14.298 | 44.766 | 1.00 | 17.83 |
| ATOM | 1111 CB | ASP | 120 | −3.790 | −14.087 | 44.576 | 1.00 | 22.04 |
| ATOM | 1112 CG | ASP | 120 | −3.118 | −15.265 | 43.903 | 1.00 | 23.22 |
| ATOM | 1113 OD1 | ASP | 120 | −3.371 | −15.490 | 42.702 | 1.00 | 26.00 |
| ATOM | 1114 OD2 | ASP | 120 | −2.341 | −15.969 | 44.581 | 1.00 | 27.30 |
| ATOM | 1115 C | ASP | 120 | −5.544 | −15.602 | 45.515 | 1.00 | 16.21 |
| ATOM | 1116 O | ASP | 120 | −6.080 | −16.554 | 44.953 | 1.00 | 14.21 |
| ATOM | 1117 N | ALA | 121 | −5.192 | −15.614 | 46.798 | 1.00 | 13.03 |
| ATOM | 1118 H | ALA | 121 | −4.782 | −14.809 | 47.181 | 1.00 | 0.00 |
| ATOM | 1119 CA | ALA | 121 | −5.366 | −16.787 | 47.647 | 1.00 | 13.21 |
| ATOM | 1120 CB | ALA | 121 | −4.778 | −16.523 | 49.029 | 1.00 | 11.07 |
| ATOM | 1121 C | ALA | 121 | −6.825 | −17.220 | 47.773 | 1.00 | 11.40 |
| ATOM | 1122 O | ALA | 121 | −7.132 | −18.415 | 47.772 | 1.00 | 11.87 |
| ATOM | 1123 N | SEM | 122 | −7.721 | −16.248 | 47.885 | 1.00 | 9.79 |
| ATOM | 1124 H | SEM | 122 | −7.400 | −15.319 | 47.872 | 1.00 | 0.00 |
| ATOM | 1125 CA | SEM | 122 | −9.141 | −16.521 | 48.025 | 1.00 | 9.76 |
| ATOM | 1126 CB | SEM | 122 | −9.884 | −15.251 | 48.433 | 1.00 | 12.08 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1127 | CG | SEM | 122 | −9.471 | −14.699 | 49.790 | 1.00 | 17.34 |
| ATOM | 1128 | A | SEM | 122 | −10.315 | −12.991 | 50.177 | 1.00 | 20.79 |
| ATOM | 1129 | CE | SEM | 122 | −9.148 | −12.427 | 51.564 | 1.00 | 22.20 |
| ATOM | 1130 | C | SEM | 122 | −9.752 | −17.115 | 46.762 | 1.00 | 10.01 |
| ATOM | 1131 | O | SEM | 122 | −10.609 | −17.995 | 46.844 | 1.00 | 11.95 |
| ATOM | 1132 | N | VAL | 123 | −9.329 | −16.627 | 45.600 | 1.00 | 10.94 |
| ATOM | 1133 | H | VAL | 123 | −8.673 | −15.894 | 45.592 | 1.00 | 0.00 |
| ATOM | 1134 | CA | VAL | 123 | −9.836 | −17.140 | 44.333 | 1.00 | 12.22 |
| ATOM | 1135 | CB | VAL | 123 | −9.371 | −16.272 | 43.134 | 1.00 | 13.58 |
| ATOM | 1136 | CG1 | VAL | 123 | −9.759 | −16.926 | 41.810 | 1.00 | 15.25 |
| ATOM | 1137 | CG2 | VAL | 123 | −10.003 | −14.894 | 43.220 | 1.00 | 13.81 |
| ATOM | 1138 | C | VAL | 123 | −9.367 | −18.583 | 44.165 | 1.00 | 11.57 |
| ATOM | 1139 | O | VAL | 123 | −10.145 | −19.454 | 43.786 | 1.00 | 15.13 |
| ATOM | 1140 | N | ARG | 124 | −8.105 | −18.843 | 44.489 | 1.00 | 13.03 |
| ATOM | 1141 | H | ARG | 124 | −7.519 | −18.104 | 44.781 | 1.00 | 0.00 |
| ATOM | 1142 | CA | ARG | 124 | −7.559 | −20.192 | 44.384 | 1.00 | 15.09 |
| ATOM | 1143 | CB | ARG | 124 | −6.089 | −20.219 | 44.804 | 1.00 | 19.47 |
| ATOM | 1144 | CG | ARG | 124 | −5.177 | −19.326 | 43.978 | 1.00 | 29.40 |
| ATOM | 1145 | CD | ARG | 124 | −3.720 | −19.503 | 44.389 | 1.00 | 34.85 |
| ATOM | 1146 | NE | ARG | 124 | −3.238 | −20.849 | 44.085 | 1.00 | 39.82 |
| ATOM | 1147 | HE | ARG | 124 | −3.340 | −21.538 | 44.777 | 1.00 | 0.00 |
| ATOM | 1148 | CZ | ARG | 124 | −2.669 | −21.201 | 42.934 | 1.00 | 40.38 |
| ATOM | 1149 | NH1 | ARG | 124 | −2.497 | −20.304 | 41.967 | 1.00 | 40.47 |
| ATOM | 1150 | HH11 | ARG | 124 | −2.791 | −19.357 | 42.092 | 1.00 | 0.00 |
| ATOM | 1151 | HH12 | ARG | 124 | −2.060 | −20.584 | 41.111 | 1.00 | 0.00 |
| ATOM | 1152 | NH2 | ARG | 124 | −2.295 | −22.461 | 42.740 | 1.00 | 39.07 |
| ATOM | 1153 | HH21 | ARG | 124 | −2.439 | −23.141 | 43.460 | 1.00 | 0.00 |
| ATOM | 1154 | HH22 | ARG | 124 | −1.862 | −22.734 | 41.883 | 1.00 | 0.00 |
| ATOM | 1155 | C | ARG | 124 | −8.356 | −21.143 | 45.271 | 1.00 | 13.87 |
| ATOM | 1156 | O | ARG | 124 | −8.776 | −22.210 | 44.829 | 1.00 | 11.56 |
| ATOM | 1157 | N | ASP | 125 | −8.581 | −20.738 | 46.517 | 1.00 | 13.96 |
| ATOM | 1158 | H | ASP | 125 | −8.214 | −19.874 | 46.802 | 1.00 | 0.00 |
| ATOM | 1159 | CA | ASP | 125 | −9.333 | −21.554 | 47.464 | 1.00 | 14.81 |
| ATOM | 1160 | CB | ASP | 125 | −9.308 | −20.925 | 48.861 | 1.00 | 18.19 |
| ATOM | 1161 | CG | ASP | 125 | −9.967 | −21.807 | 49.908 | 1.00 | 20.88 |
| ATOM | 1162 | OD1 | ASP | 12S | −10.978 | −21.373 | 50.496 | 1.00 | 26.61 |
| ATOM | 1163 | OD2 | ASP | 125 | −9.482 | −22.937 | 50.135 | 1.00 | 20.43 |
| ATOM | 1164 | C | ASP | 125 | −10.770 | −21.783 | 46.996 | 1.00 | 13.18 |
| ATOM | 1165 | O | ASP | 125 | −11.287 | −22.894 | 47.097 | 1.00 | 14.12 |
| ATOM | 1166 | N | TYR | 126 | −11.407 | −20.747 | 46.463 | 1.00 | 12.51 |
| ATOM | 1167 | H | TYR | 126 | −10.954 | −19.881 | 46.429 | 1.00 | 0.00 |
| ATOM | 1168 | CA | TYR | 126 | −12.773 | −20.879 | 45.958 | 1.00 | 14.80 |
| ATOM | 1169 | CB | TYR | 126 | −13.310 | −19.525 | 45.483 | 1.00 | 16.19 |
| ATOM | 1170 | CG | TYR | 126 | −14.764 | −19.552 | 45.050 | 1.00 | 19.94 |
| ATOM | 1171 | CD1 | TYR | 126 | −15.789 | −19.431 | 45.984 | 1.00 | 22.56 |
| ATOM | 1172 | CE1 | TYR | 126 | −17.129 | −19.440 | 45.595 | 1.00 | 25.33 |
| ATOM | 1173 | CD2 | TYR | 126 | −15.115 | −19.687 | 43.705 | 1.00 | 21.52 |
| ATOM | 1174 | CE2 | TYR | 126 | −16.453 | −19.699 | 43.304 | 1.00 | 22.94 |
| ATOM | 1175 | CZ | TYR | 126 | −17.456 | −19.573 | 44.256 | 1.00 | 24.54 |
| ATOM | 1176 | OH | TYR | 126 | −18.781 | −19.560 | 43.871 | 1.00 | 25.75 |
| ATOM | 1177 | HH | TYR | 126 | −19.331 | −19.523 | 44.667 | 1.00 | 0.00 |
| ATOM | 1178 | C | TYR | 126 | −12.825 | −21.880 | 44.799 | 1.00 | 14.74 |
| ATOM | 1179 | O | TYR | 126 | −13.666 | −22.779 | 44.776 | 1.00 | 12.46 |
| ATOM | 1180 | N | VAL | 127 | −11.917 | −21.723 | 43.838 | 1.00 | 14.94 |
| ATOM | 1181 | H | VAL | 127 | −11.265 | −21.000 | 43.917 | 1.00 | 0.00 |
| ATOM | 1182 | CA | VAL | 127 | −11.865 | −22.608 | 42.679 | 1.00 | 15.31 |
| ATOM | 1183 | CB | VAL | 127 | −10.846 | −22.100 | 41.628 | 1.00 | 16.12 |
| ATOM | 1184 | CG1 | VAL | 127 | −10.675 | −23.120 | 40.506 | 1.00 | 14.89 |
| ATOM | 1185 | CG2 | VAL | 127 | −11.320 | −20.766 | 41.050 | 1.00 | 14.29 |
| ATOM | 1186 | C | VAL | 127 | −11.554 | −24.049 | 43.086 | 1.00 | 15.31 |
| ATOM | 1187 | O | VAL | 127 | −12.166 | −24.991 | 42.577 | 1.00 | 14.57 |
| ATOM | 1188 | N | ARG | 128 | −10.640 | −24.213 | 44.036 | 1.00 | 15.60 |
| ATOM | 1189 | H | ARG | 128 | −10.202 | −23.424 | 44.413 | 1.00 | 0.00 |
| ATOM | 1190 | CA | ARG | 128 | −10.265 | −25.536 | 44.519 | 1.00 | 18.18 |
| ATOM | 1191 | CB | ARG | 128 | −9.071 | −25.435 | 45.464 | 1.00 | 20.53 |
| ATOM | 1192 | CG | ARG | 128 | −8.535 | −26.774 | 45.921 | 1.00 | 26.43 |
| ATOM | 1193 | CD | ARG | 128 | −7.466 | −26.610 | 46.986 | 1.00 | 31.14 |
| ATOM | 1194 | NE | ARG | 128 | −6.274 | −25.919 | 46.494 | 1.00 | 32.88 |
| ATOM | 1195 | HE | ARG | 128 | −5.736 | −26.363 | 45.803 | 1.00 | 0.00 |
| ATOM | 1196 | CZ | ARG | 128 | −5.882 | −24.719 | 46.911 | 1.00 | 33.15 |
| ATOM | 1197 | NH1 | ARG | 128 | −6.592 | −24.062 | 47.822 | 1.00 | 33.64 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1198 | HH11 | ARG | 128 | −7.423 | −24.475 | 48.195 | 1.00 | 0.00 |
| ATOM | 1199 | HH12 | ARG | 128 | −6.310 | −23.161 | 48.136 | 1.00 | 0.00 |
| ATOM | 1200 | NH2 | ARG | 128 | −4.754 | −24.197 | 46.451 | 1.00 | 31.81 |
| ATOM | 1201 | HH21 | ARG | 128 | −4.207 | −24.708 | 45.789 | 1.00 | 0.00 |
| ATOM | 1202 | HH22 | ARG | 128 | −4.451 | −23.298 | 46.770 | 1.00 | 0.00 |
| ATOM | 1203 | C | ARG | 128 | −11.439 | −26.220 | 45.228 | 1.00 | 19.96 |
| ATOM | 1204 | O | ARG | 128 | −11.724 | −27.386 | 44.980 | 1.00 | 20.08 |
| ATOM | 1205 | N | GLN | 129 | −12.136 | −25.485 | 46.087 | 1.00 | 21.86 |
| ATOM | 1206 | H | GLN | 129 | −11.861 | −24.558 | 46.234 | 1.00 | 0.00 |
| ATOM | 1207 | CA | GLN | 129 | −13.278 | −26.040 | 46.812 | 1.00 | 24.92 |
| ATOM | 1208 | CB | GLN | 129 | −13.783 | −25.056 | 47.875 | 1.00 | 27.32 |
| ATOM | 1209 | CG | GLN | 129 | −12.763 | −24.641 | 48.919 | 1.00 | 3.13 |
| ATOM | 1210 | CD | GLN | 129 | −12.195 | −25.806 | 49.700 | 1.00 | 43.53 |
| ATOM | 1211 | OE1 | GLN | 129 | −10.983 | −25.900 | 49.895 | 1.00 | 49.52 |
| ATOM | 1212 | NE2 | GLN | 129 | −13.066 | −26.693 | 50.167 | 1.00 | 46.67 |
| ATOM | 1213 | HE21 | GLN | 129 | −14.022 | −26.565 | 50.000 | 1.00 | 0.00 |
| ATOM | 1214 | HE22 | GLN | 129 | −12.673 | −27.439 | 50.665 | 1.00 | 0.00 |
| ATOM | 1215 | C | GLN | 129 | −14.444 | −26.388 | 45.887 | 1.00 | 22.91 |
| ATOM | 1216 | O | GLN | 129 | −15.075 | −27.427 | 46.040 | 1.00 | 25.98 |
| ATOM | 1217 | N | THR | 130 | −14.745 | −25.500 | 44.950 | 1.00 | 21.09 |
| ATOM | 1218 | H | THR | 130 | −14.243 | −24.663 | 44.875 | 1.00 | 0.00 |
| ATOM | 1219 | CA | THR | 130 | −15.858 | −25.700 | 44.036 | 1.00 | 20.03 |
| ATOM | 1220 | CB | THR | 130 | −16.267 | −24.365 | 43.386 | 1.00 | 21.01 |
| ATOM | 1221 | OG1 | THR | 130 | −16.598 | −23.426 | 44.415 | 1.00 | 24.86 |
| ATOM | 1222 | HG1 | THR | 130 | −17.447 | −23.676 | 44.803 | 1.00 | 0.00 |
| ATOM | 1223 | CG2 | THR | 130 | −17.471 | −24.545 | 42.470 | 1.00 | 18.89 |
| ATOM | 1224 | C | THR | 130 | −15.639 | −26.749 | 42.951 | 1.00 | 20.64 |
| ATOM | 1225 | O | THR | 130 | −16.476 | −27.634 | 42.771 | 1.00 | 21.45 |
| ATOM | 1226 | N | TRP | 131 | −14.524 | −26.660 | 42.234 | 1.00 | 18.24 |
| ATOM | 1227 | H | TRP | 131 | −13.871 | −25.958 | 42.438 | 1.00 | 0.00 |
| ATOM | 1228 | CA | TRP | 131 | −14.248 | −27.599 | 41.147 | 1.00 | 18.29 |
| ATOM | 1229 | CB | TRP | 131 | −13.573 | −26.873 | 39.976 | 1.00 | 17.75 |
| ATOM | 1230 | CG | TRP | 131 | −14.368 | −25.715 | 39.462 | 1.00 | 18.23 |
| ATOM | 1231 | CD2 | TRP | 131 | −15.316 | −25.731 | 38.385 | 1.00 | 20.51 |
| ATOM | 1232 | CE2 | TRP | 131 | −15.833 | −24.419 | 38.265 | 1.00 | 19.78 |
| ATOM | 1233 | CE3 | TRP | 131 | −15.781 | −26.722 | 37.510 | 1.00 | 20.37 |
| ATOM | 1234 | CD1 | TRP | 131 | −14.349 | −24.433 | 39.935 | 1.00 | 18.07 |
| ATOM | 1235 | NE1 | TRP | 131 | −15.225 | −23.651 | 39.223 | 1.00 | 19.62 |
| ATOM | 1236 | HE1 | TRP | 131 | −15.376 | −22.692 | 39.377 | 1.00 | 0.00 |
| ATOM | 1237 | CZ2 | TRP | 131 | −16.793 | −24.073 | 37.305 | 1.00 | 18.47 |
| ATOM | 1238 | CZ3 | TRP | 131 | −16.737 | −26.376 | 36.553 | 1.00 | 19.44 |
| ATOM | 1239 | CH2 | TRP | 131 | −17.230 | −25.062 | 36.460 | 1.00 | 19.54 |
| ATOM | 1240 | C | TRP | 131 | −13.434 | −28.831 | 41.539 | 1.00 | 17.51 |
| ATOM | 1241 | O | TRP | 131 | −13.250 | −29.734 | 40.718 | 1.00 | 17.01 |
| ATOM | 1242 | N | LYS | 132 | −12.956 | −28.863 | 42.783 | 1.00 | 17.08 |
| ATOM | 1243 | H | LYS | 132 | −13.131 | −28.128 | 43.405 | 1.00 | 0.00 |
| ATOM | 1244 | CA | LYS | 132 | −12.155 | −29.977 | 43.300 | 1.00 | 21.35 |
| ATOM | 1245 | CB | LYS | 132 | −13.010 | −31.246 | 43.476 | 1.00 | 22.55 |
| ATOM | 1246 | CG | LYS | 132 | −13.864 | −31.290 | 44.741 | 1.00 | 27.05 |
| ATOM | 1247 | CD | LYS | 132 | −15.049 | −30.351 | 44.661 | 1.00 | 28.94 |
| ATOM | 1248 | CE | LYS | 132 | −15.917 | −30.429 | 45.909 | 1.00 | 27.71 |
| ATOM | 1249 | NZ | LYS | 132 | −15.176 | −30.035 | 47.141 | 1.00 | 28.94 |
| ATOM | 1250 | HZ1 | LYS | 132 | −14.777 | −29.086 | 47.010 | 1.00 | 0.00 |
| ATOM | 1251 | HZ2 | LYS | 132 | −14.398 | −30.705 | 47.312 | 1.00 | 0.00 |
| ATOM | 1252 | HZ3 | LYS | 132 | −15.821 | −30.030 | 47.956 | 1.00 | 0.00 |
| ATOM | 1253 | C | LYS | 132 | −10.952 | −30.279 | 42.410 | 1.00 | 21.09 |
| ATOM | 1254 | O | LYS | 132 | −10.616 | −31.441 | 42.177 | 1.00 | 22.12 |
| ATOM | 1255 | N | LEU | 133 | −10.311 | −29.227 | 41.915 | 1.00 | 22.01 |
| ATOM | 1256 | H | LEU | 133 | −10.601 | −28.334 | 42.179 | 1.00 | 0.00 |
| ATOM | 1257 | CA | LEU | 133 | −9.152 | −29.376 | 41.044 | 1.00 | 24.78 |
| ATOM | 1258 | CB | LEU | 133 | −9.266 | −28.439 | 39.841 | 1.00 | 24.76 |
| ATOM | 1259 | CG | LEU | 133 | −10.384 | −28.729 | 38.840 | 1.00 | 23.74 |
| ATOM | 1260 | CD1 | LEU | 133 | −10.423 | −27.640 | 37.792 | 1.00 | 18.82 |
| ATOM | 1261 | CD2 | LEU | 133 | −10.168 | −30.093 | 38.197 | 1.00 | 20.87 |
| ATOM | 1262 | C | LEU | 133 | −7.851 | −29.107 | 41.782 | 1.00 | 26.48 |
| ATOM | 1263 | O | LEU | 133 | −7.844 | −28.489 | 42.843 | 1.00 | 26.77 |
| ATOM | 1264 | N | GLU | 134 | −6.745 | −29.561 | 41.204 | 1.00 | 31.08 |
| ATOM | 1265 | H | GLU | 134 | −6.783 | −30.056 | 40.359 | 1.00 | 0.00 |
| ATOM | 1266 | CA | GLU | 134 | −5.436 | −29.365 | 41.810 | 1.00 | 36.68 |
| ATOM | 1267 | CB | GLU | 134 | −5.146 | −30.478 | 42.821 | 1.00 | 42.39 |
| ATOM | 1268 | CG | GLU | 134 | −4.135 | −30.097 | 43.901 | 1.00 | 50.47 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1269 | CD | GLU | 134 | −4.605 | −28.933 | 44.762 | 1.00 | 54.00 |
| ATOM | 1270 | OE1 | GLU | 134 | −3.922 | −27.885 | 44.772 | 1.00 | 56.35 |
| ATOM | 1271 | OE2 | GLU | 134 | −5.658 | −29.065 | 45.426 | 1.00 | 55.94 |
| ATOM | 1272 | C | GLU | 134 | −4.369 | −29.349 | 40.720 | 1.00 | 36.98 |
| ATOM | 1273 | O | GLU | 134 | −4.655 | −29.660 | 39.559 | 1.00 | 37.05 |
| ATOM | 1274 | N | GLY | 135 | −3.156 | −28.946 | 41.087 | 1.00 | 37.39 |
| ATOM | 1275 | H | GLY | 135 | −3.008 | −28.662 | 42.009 | 1.00 | 0.00 |
| ATOM | 1276 | CA | GLY | 135 | −2.062 | −28.894 | 40.133 | 1.00 | 38.80 |
| ATOM | 1277 | C | GLY | 135 | −2.340 | −27.998 | 38.941 | 1.00 | 39.61 |
| ATOM | 1278 | O | GLY | 135 | −3.038 | −26.986 | 39.062 | 1.00 | 40.95 |
| ATOM | 1279 | N | GLU | 136 | −1.816 | −28.385 | 37.781 | 1.00 | 38.99 |
| ATOM | 1280 | H | GLU | 136 | −1.290 | −29.209 | 37.748 | 1.00 | 0.00 |
| ATOM | 1281 | CA | GLU | 136 | −1.999 | −27.616 | 36.553 | 1.00 | 38.69 |
| ATOM | 1282 | CB | GLU | 136 | −1.244 | −28.259 | 35.386 | 1.00 | 43.51 |
| ATOM | 1283 | CG | GLU | 136 | 0.134 | −27.652 | 35.129 | 1.00 | 51.02 |
| ATOM | 1284 | CD | GLU | 136 | 0.073 | −26.157 | 34.827 | 1.00 | 54.54 |
| ATOM | 1285 | OE1 | GLU | 136 | 0.533 | −25.357 | 35.672 | 1.00 | 54.76 |
| ATOM | 1286 | OE2 | GLU | 136 | −0.437 | −25.783 | 33.746 | 1.00 | 57.49 |
| ATOM | 1287 | C | GLU | 136 | −3.454 | −27.403 | 36.172 | 1.00 | 35.47 |
| ATOM | 1288 | O | GLU | 136 | −3.795 | −26.386 | 35.564 | 1.00 | 33.83 |
| ATOM | 1289 | N | ALA | 137 | −4.304 | −28.367 | 36.514 | 1.00 | 32.94 |
| ATOM | 1290 | H | ALA | 137 | −3.975 | −29.157 | 36.985 | 1.00 | 0.00 |
| ATOM | 1291 | CA | ALA | 137 | −5.729 | −28.268 | 36.215 | 1.00 | 31.07 |
| ATOM | 1292 | CB | ALA | 137 | −6.440 | −29.556 | 36.605 | 1.00 | 31.83 |
| ATOM | 1293 | C | ALA | 137 | −6.314 | −27.079 | 36.976 | 1.00 | 27.50 |
| ATOM | 1294 | O | ALA | 137 | −7.031 | −26.257 | 36.405 | 1.00 | 29.33 |
| ATOM | 1295 | N | LEU | 138 | −5.963 | −26.973 | 38.254 | 1.00 | 24.80 |
| ATOM | 1296 | H | LEU | 138 | −5.350 | −27.643 | 38.627 | 1.00 | 0.00 |
| ATOM | 1297 | CA | LEU | 138 | −6.435 | −25.884 | 39.097 | 1.00 | 23.90 |
| ATOM | 1298 | CB | LEU | 138 | −5.909 | −26.053 | 40.520 | 1.00 | 21.92 |
| ATOM | 1299 | CG | LEU | 138 | −6.161 | −24.920 | 41.514 | 1.00 | 21.33 |
| ATOM | 1300 | CD1 | LEU | 138 | −7.648 | −24.709 | 41.716 | 1.00 | 22.45 |
| ATOM | 1301 | CD2 | LEU | 138 | −5.493 | −25.252 | 42.830 | 1.00 | 21.62 |
| ATOM | 1302 | C | LEU | 138 | −5.932 | −24.573 | 38.527 | 1.00 | 26.43 |
| ATOM | 1303 | O | LEU | 138 | −6.686 | −23.611 | 38.401 | 1.00 | 25.96 |
| ATOM | 1304 | N | GLU | 139 | −4.649 | −24.550 | 38.179 | 1.00 | 30.25 |
| ATOM | 1305 | H | GLU | 139 | −4.110 | −25.355 | 38.336 | 1.00 | 0.00 |
| ATOM | 1306 | CA | GLU | 139 | −4.003 | −23.373 | 37.610 | 1.00 | 32.41 |
| ATOM | 1307 | CB | GLU | 139 | −2.546 | −23.690 | 37.274 | 1.00 | 34.88 |
| ATOM | 1308 | CG | GLU | 139 | −1.524 | −22.848 | 38.024 | 1.00 | 40.02 |
| ATOM | 1309 | CD | GLU | 139 | −1.489 | −23.111 | 39.524 | 1.00 | 42.46 |
| ATOM | 1310 | OE1 | GLU | 139 | −2.188 | −24.025 | 40.014 | 1.00 | 46.36 |
| ATOM | 1311 | OE2 | GLU | 139 | −0.743 | −22.394 | 40.220 | 1.00 | 44.75 |
| ATOM | 1312 | C | GLU | 139 | −4.726 | −22.880 | 36.363 | 1.00 | 33.95 |
| ATOM | 1313 | O | GLU | 139 | −4.906 | −21.679 | 36.181 | 1.00 | 33.01 |
| ATOM | 1314 | N | GLN | 140 | −5.130 | −23.808 | 35.500 | 1.00 | 36.05 |
| ATOM | 1315 | H | GLN | 140 | −4.957 | −24.758 | 35.685 | 1.00 | 0.00 |
| ATOM | 1316 | CA | GLN | 140 | −5.845 | −23.446 | 34.280 | 1.00 | 38.93 |
| ATOM | 1317 | CB | GLN | 140 | −6.008 | −24.660 | 33.356 | 1.00 | 43.55 |
| ATOM | 1318 | CG | GLN | 140 | −4.703 | −25.295 | 32.911 | 1.00 | 50.09 |
| ATOM | 1319 | CD | GLN | 140 | −3.702 | −24.272 | 32.420 | 1.00 | 54.44 |
| ATOM | 1320 | OE1 | GLN | 140 | −3.865 | −23.688 | 31.347 | 1.00 | 57.43 |
| ATOM | 1321 | NE2 | GLN | 140 | −2.662 | −24.039 | 33.212 | 1.00 | 54.84 |
| ATOM | 1322 | HE21 | GLN | 140 | −2.611 | −24.543 | 34.051 | 1.00 | 0.00 |
| ATOM | 1323 | HE22 | GLN | 140 | −2.010 | −23.377 | 32.911 | 1.00 | 0.00 |
| ATOM | 1324 | C | GLN | 140 | −7.220 | −22.895 | 34.633 | 1.00 | 37.85 |
| ATOM | 1325 | O | GLN | 140 | −7.643 | −21.865 | 34.106 | 1.00 | 38.61 |
| ATOM | 1326 | N | ALA | 141 | −7.904 | −23.581 | 35.543 | 1.00 | 35.28 |
| ATOM | 1327 | H | ALA | 141 | −7.494 | −24.378 | 35.939 | 1.00 | 0.00 |
| ATOM | 1328 | CA | ALA | 141 | −9.238 | −23.188 | 35.974 | 1.00 | 33.81 |
| ATOM | 1329 | CB | ALA | 141 | −9.806 | −24.218 | 36.930 | 1.00 | 33.21 |
| ATOM | 1330 | C | ALA | 141 | −9.297 | −21.796 | 36.598 | 1.00 | 33.71 |
| ATOM | 1331 | O | ALA | 141 | −10.220 | −21.034 | 36.308 | 1.00 | 33.79 |
| ATOM | 1332 | N | ILE | 142 | −8.321 | −21.452 | 37.436 | 1.00 | 34.36 |
| ATOM | 1333 | H | ILE | 142 | −7.602 | −22.089 | 37.625 | 1.00 | 0.00 |
| ATOM | 1334 | CA | ILE | 142 | −8.324 | −20.137 | 38.069 | 1.00 | 35.58 |
| ATOM | 1335 | CB | ILE | 142 | −7.237 | −19.979 | 39.178 | 1.00 | 37.48 |
| ATOM | 1336 | CG2 | ILE | 142 | −7.376 | −21.080 | 40.221 | 1.00 | 36.69 |
| ATOM | 1337 | CG1 | ILE | 142 | −5.833 | −19.991 | 38.580 | 1.00 | 40.54 |
| ATOM | 1338 | CD | ILE | 142 | −4.736 | −19.774 | 39.600 | 1.00 | 41.71 |
| ATOM | 1339 | C | ILE | 142 | −8.189 | −19.035 | 37.027 | 1.00 | 35.75 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1340 | O | ILE | 142 | −8.807 | −17.985 | 37.156 | 1.00 | 36.45 |
| ATOM | 1341 | N | ILE | 143 | −7.421 | −19.288 | 35.974 | 1.00 | 36.98 |
| ATOM | 1342 | H | ILE | 143 | −6.962 | −20.154 | 35.905 | 1.00 | 0.00 |
| ATOM | 1343 | CA | ILE | 143 | −7.244 | −18.299 | 34.917 | 1.00 | 39.87 |
| ATOM | 1344 | CB | ILE | 143 | −6.211 | −18.782 | 33.846 | 1.00 | 40.93 |
| ATOM | 1345 | CG2 | ILE | 143 | −6.582 | −18.283 | 32.451 | 1.00 | 39.88 |
| ATOM | 1346 | CG1 | ILE | 143 | −4.804 | −18.288 | 34.195 | 1.00 | 41.89 |
| ATOM | 1347 | CD | ILE | 143 | −4.260 | −18.790 | 35.509 | 1.00 | 44.53 |
| ATOM | 1348 | C | ILE | 143 | −8.592 | −17.996 | 34.266 | 1.00 | 41.03 |
| ATOM | 1349 | O | ILE | 143 | −8.953 | −16.835 | 34.073 | 1.00 | 43.88 |
| ATOM | 1350 | N | SER | 144 | −9.349 | −19.046 | 33.977 | 1.00 | 41.09 |
| ATOM | 1351 | H | SER | 144 | −9.002 | −19.948 | 34.145 | 1.00 | 0.00 |
| ATOM | 1352 | CA | 9ER | 144 | −10.652 | −18.908 | 33.345 | 1.00 | 42.72 |
| ATOM | 1353 | CB | SER | 144 | −11.084 | −20.261 | 32.786 | 1.00 | 43.70 |
| ATOM | 1354 | OG | SER | 144 | −10.009 | −20.876 | 32.098 | 1.00 | 48.58 |
| ATOM | 1355 | HG | SER | 144 | −10.277 | −21.685 | 31.660 | 1.00 | 0.00 |
| ATOM | 1356 | C | SER | 144 | −11.740 | −18.364 | 34.274 | 1.00 | 42.64 |
| ATOM | 1357 | O | SER | 144 | −12.612 | −17.606 | 33.845 | 1.00 | 43.71 |
| ATOM | 1358 | N | GLN | 145 | −11.692 | −18.756 | 35.543 | 1.00 | 42.82 |
| ATOM | 1359 | H | GLN | 145 | −10.944 | −19.324 | 35.823 | 1.00 | 0.00 |
| ATOM | 1360 | CA | GLN | 145 | −12.691 | −18.335 | 36.520 | 1.00 | 42.48 |
| ATOM | 1361 | CB | GLN | 145 | −12.879 | −19.419 | 37.585 | 1.00 | 43.50 |
| ATOM | 1362 | CG | GLN | 145 | −13.600 | −20.664 | 37.092 | 1.00 | 46.68 |
| ATOM | 1363 | CD | GLN | 145 | −15.042 | −20.391 | 36.708 | 1.00 | 49.02 |
| ATOM | 1364 | OE1 | GLN | 145 | −15.882 | −20.086 | 37.562 | 1.00 | 49.76 |
| ATOM | 1365 | NE2 | GLN | 145 | −15.341 | −20.506 | 35.419 | 1.00 | 48.88 |
| ATOM | 1366 | HE21 | GLN | 145 | −14.639 | −20.764 | 34.792 | 1.00 | 0.00 |
| ATOM | 1367 | HE22 | GLN | 145 | −16.274 | −20.325 | 35.164 | 1.00 | 0.00 |
| ATOM | 1368 | C | GLN | 145 | −12.442 | −16.996 | 37.204 | 1.00 | 41.52 |
| ATOM | 1369 | O | GLN | 145 | −13.393 | −16.275 | 37.503 | 1.00 | 42.42 |
| ATOM | 1370 | N | ALA | 146 | −11.175 | −16.657 | 37.423 | 1.00 | 41.08 |
| ATOM | 1371 | H | ALA | 146 | −10.480 | −17.248 | 37.094 | 1.00 | 0.00 |
| ATOM | 1372 | CA | ALA | 146 | −10.786 | −15.418 | 38.102 | 1.00 | 42.09 |
| ATOM | 1373 | CB | ALA | 146 | −9.305 | −15.113 | 37.861 | 1.00 | 43.64 |
| ATOM | 1374 | C | ALA | 146 | −11.638 | −14.178 | 37.818 | 1.00 | 42.22 |
| ATOM | 1375 | O | ALA | 146 | −12.169 | −13.570 | 38.748 | 1.00 | 40.36 |
| ATOM | 1376 | N | PRO | 147 | −11.807 | −13.801 | 36.535 | 1.00 | 42.75 |
| ATOM | 1377 | CD | PRO | 147 | −11.279 | −14.419 | 35.303 | 1.00 | 42.03 |
| ATOM | 1378 | CA | PRO | 147 | −12.614 | −12.617 | 36.213 | 1.00 | 42.24 |
| ATOM | 1379 | CB | PRO | 147 | −12.433 | −12.486 | 34.699 | 1.00 | 42.92 |
| ATOM | 1380 | CG | PRO | 147 | −12.233 | −13.908 | 34.258 | 1.00 | 42.35 |
| ATOM | 1381 | C | PRO | 147 | −14.092 | −12.720 | 36.595 | 1.00 | 41.91 |
| ATOM | 1382 | O | PRO | 147 | −14.694 | −11.741 | 37.039 | 1.00 | 43.04 |
| ATOM | 1383 | N | GLN | 148 | −14.656 | −13.915 | 36.452 | 1.00 | 42.14 |
| ATOM | 1384 | H | GLN | 148 | −14.092 | −14.663 | 36.166 | 1.00 | 0.00 |
| ATOM | 1385 | CA | GLN | 148 | −16.065 | −14.164 | 36.753 | 1.00 | 41.99 |
| ATOM | 1386 | CB | GLN | 148 | −16.476 | −15.527 | 36.191 | 1.00 | 46.02 |
| ATOM | 1387 | CG | GLN | 148 | −16.113 | −15.735 | 34.728 | 1.00 | 52.36 |
| ATOM | 1388 | CD | GLN | 148 | −16.424 | −17.140 | 34.245 | 1.00 | 56.58 |
| ATOM | 1389 | OE1 | GLN | 148 | −17.548 | −17.624 | 34.391 | 1.00 | 60.22 |
| ATOM | 1390 | NE2 | GLN | 148 | −15.426 | −17.805 | 33.673 | 1.00 | 57.78 |
| ATOM | 1391 | HE21 | GLN | 148 | −14.538 | −17.383 | 33.597 | 1.00 | 0.00 |
| ATOM | 1392 | HE22 | GLN | 148 | −15.637 | −18.697 | 33.339 | 1.00 | 0.00 |
| ATOM | 1393 | C | GLN | 148 | −16.403 | −14.109 | 38.246 | 1.00 | 40.35 |
| ATOM | 1394 | O | GLN | 148 | −17.445 | −13.576 | 38.643 | 1.00 | 42.32 |
| ATOM | 1395 | N | VAL | 149 | −15.530 | −14.677 | 39.070 | 1.00 | 35.77 |
| ATOM | 1396 | H | VAL | 149 | −14.725 | −15.083 | 38.684 | 1.00 | 0.00 |
| ATOM | 1397 | CA | VAL | 149 | −15.747 | −14.705 | 40.512 | 1.00 | 30.92 |
| ATOM | 1398 | CB | VAL | 149 | −15.297 | −16.056 | 41.116 | 1.00 | 29.67 |
| ATOM | 1399 | CG1 | VAL | 149 | −16.047 | −17.195 | 40.452 | 1.00 | 31.16 |
| ATOM | 1400 | CG2 | VAL | 149 | −13.798 | −16.245 | 40.942 | 1.00 | 27.34 |
| ATOM | 1401 | C | VAL | 149 | −15.034 | −13.569 | 41.242 | 1.00 | 29.41 |
| ATOM | 1402 | O | VAL | 149 | −15.112 | −13.469 | 42.466 | 1.00 | 25.93 |
| ATOM | 1403 | N | GLU | 150 | −14.375 | −12.697 | 40.485 | 1.00 | 29.98 |
| ATOM | 1404 | H | GLU | 150 | −14.357 | −12.827 | 39.513 | 1.00 | 0.00 |
| ATOM | 1405 | CA | GLU | 150 | −13.627 | −11.574 | 41.049 | 1.00 | 32.17 |
| ATOM | 1406 | CB | GLU | 150 | −13.075 | −10.693 | 39.922 | 1.00 | 38.43 |
| ATOM | 1407 | CG | GLU | 150 | −11.690 | −10.097 | 40.191 | 1.00 | 47.19 |
| ATOM | 1408 | CD | GLU | 150 | −10.566 | −11.124 | 40.092 | 1.00 | 51.56 |
| ATOM | 1409 | OE1 | GLU | 150 | −9.728 | −10.999 | 39.171 | 1.00 | 53.66 |
| ATOM | 1410 | OE2 | GLU | 150 | −10.512 | −12.052 | 40.930 | 1.00 | 54.50 |

TABLE 21-continued

Coordinates for the 3D structure of ZAP-NCζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1411 | C | GLU | 150 | −14.431 | −10.720 | 42.038 | 1.00 | 29.05 |
| ATOM | 1412 | O | GLU | 150 | −14.033 | −10.555 | 43.192 | 1.00 | 25.94 |
| ATOM | 1413 | N | LYS | 151 | −15.565 | −10.195 | 41.582 | 1.00 | 27.58 |
| ATOM | 1414 | H | LYS | 151 | −15.817 | −10.387 | 40.655 | 1.00 | 0.00 |
| ATOM | 1415 | CA | LYS | 151 | −16.432 | −9.358 | 42.406 | 1.00 | 25.61 |
| ATOM | 1416 | CB | LYS | 151 | −17.655 | −8.926 | 41.590 | 1.00 | 29.92 |
| ATOM | 1417 | CG | LYS | 151 | −18.689 | −8.102 | 42.352 | 1.00 | 36.35 |
| ATOM | 1418 | CD | LYS | 151 | −18.247 | −6.660 | 42.574 | 1.00 | 42.81 |
| ATOM | 1419 | CE | LYS | 151 | −18.173 | −5.880 | 41.266 | 1.00 | 47.01 |
| ATOM | 1420 | NZ | LYS | 151 | −17.791 | −4.452 | 41.481 | 1.00 | 51.50 |
| ATOM | 1421 | HZ1 | LYS | 151 | −16.880 | −4.410 | 41.984 | 1.00 | 0.00 |
| ATOM | 1422 | HZ2 | LYS | 151 | −18.521 | −3.974 | 42.046 | 1.00 | 0.00 |
| ATOM | 1423 | HZ3 | LYS | 151 | −17.696 | −3.973 | 40.563 | 1.00 | 0.00 |
| ATOM | 1424 | C | LYS | 151 | −16.886 | −10.100 | 43.656 | 1.00 | 23.86 |
| ATOM | 1425 | O | LYS | 151 | −16.864 | −9.553 | 44.761 | 1.00 | 21.86 |
| ATOM | 1426 | N | LEU | 152 | −17.288 | −11.352 | 43.468 | 1.00 | 22.21 |
| ATOM | 1427 | H | LEU | 152 | −17.238 | −11.726 | 42.566 | 1.00 | 0.00 |
| ATOM | 1428 | CA | LEU | 152 | −17.768 | −12.195 | 44.556 | 1.00 | 20.16 |
| ATOM | 1429 | CB | LEU | 152 | −18.151 | −13.579 | 44.008 | 1.00 | 24.21 |
| ATOM | 1430 | CG | LEU | 152 | −18.970 | −14.587 | 44.830 | 1.00 | 28.31 |
| ATOM | 1431 | CD1 | LEU | 152 | −18.079 | −15.648 | 45.449 | 1.00 | 30.35 |
| ATOM | 1432 | CD2 | LEU | 152 | −19.813 | −13.875 | 45.883 | 1.00 | 31.40 |
| ATOM | 1433 | C | LEU | 152 | −16.736 | −12.305 | 45.681 | 1.00 | 18.41 |
| ATOM | 1434 | O | LEU | 152 | −17.049 | −12.034 | 46.839 | 1.00 | 17.53 |
| ATOM | 1435 | N | ILE | 153 | −15.501 | −12.650 | 45.333 | 1.00 | 15.66 |
| ATOM | 1436 | H | ILE | 153 | −15.300 | −12.822 | 44.388 | 1.00 | 0.00 |
| ATOM | 1437 | CA | ILE | 153 | −14.445 | −12.782 | 46.327 | 1.00 | 14.50 |
| ATOM | 1438 | CB | ILE | 153 | −13.169 | −13.439 | 45.728 | 1.00 | 14.50 |
| ATOM | 1439 | CG2 | ILE | 153 | −11.944 | −13.093 | 46.556 | 1.00 | 13.04 |
| ATOM | 1440 | CG1 | ILE | 153 | −13.311 | −14.966 | 45.702 | 1.00 | 18.16 |
| ATOM | 1441 | CD | ILE | 153 | −14.378 | −15.489 | 44.791 | 1.00 | 18.78 |
| ATOM | 1442 | C | ILE | 153 | −14.102 | −11.446 | 46.986 | 1.00 | 14.37 |
| ATOM | 1443 | O | ILE | 153 | −13.967 | −11.377 | 48.209 | 1.00 | 13.54 |
| ATOM | 1444 | N | ALA | 154 | −14.018 | −10.386 | 46.187 | 1.00 | 13.14 |
| ATOM | 1445 | H | ALA | 154 | −14.184 | −10.504 | 45.232 | 1.00 | 0.00 |
| ATOM | 1446 | CA | ALA | 154 | −13.681 | −9.052 | 46.693 | 1.00 | 15.23 |
| ATOM | 1447 | CB | ALA | 154 | −13.464 | −8.088 | 45.530 | 1.00 | 12.01 |
| ATOM | 1448 | C | ALA | 154 | −14.690 | −8.462 | 47.685 | 1.00 | 14.41 |
| ATOM | 1449 | O | ALA | 154 | −14.309 | −7.939 | 48.740 | 1.00 | 12.98 |
| ATOM | 1450 | N | THR | 155 | −15.973 | −8.553 | 47.366 | 1.00 | 14.48 |
| ATOM | 1451 | H | THR | 155 | −16.254 | −8.987 | 46.535 | 1.00 | 0.00 |
| ATOM | 1452 | CA | THR | 155 | −16.989 | −7.997 | 48.250 | 1.00 | 16.73 |
| ATOM | 1453 | CB | THR | 155 | −18.355 | −7.861 | 47.542 | 1.00 | 18.64 |
| ATOM | 1454 | OG1 | THR | 155 | −18.794 | −9.139 | 47.073 | 1.00 | 18.35 |
| ATOM | 1455 | HG1 | THR | 155 | −18.242 | −9.431 | 46.333 | 1.00 | 0.00 |
| ATOM | 1456 | CG2 | THR | 155 | −18.239 | −6.912 | 46.361 | 1.00 | 21.11 |
| ATOM | 1457 | C | THR | 155 | −17.152 | −8.754 | 49.567 | 1.00 | 18.25 |
| ATOM | 1458 | O | THR | 155 | −17.628 | −8.191 | 50.556 | 1.00 | 19.74 |
| ATOM | 1459 | N | THR | 156 | −16.690 | −10.000 | 49.608 | 1.00 | 16.51 |
| ATOM | 1460 | H | THR | 156 | −16.290 | −10.405 | 48.811 | 1.00 | 0.00 |
| ATOM | 1461 | CA | THR | 156 | −16.816 | −10.803 | 50.816 | 1.00 | 16.53 |
| ATOM | 1462 | CB | THR | 156 | −17.514 | −12.151 | 50.491 | 1.00 | 18.06 |
| ATOM | 1463 | OG1 | THR | 156 | −17.884 | −12.806 | 51.710 | 1.00 | 29.31 |
| ATOM | 1464 | HG1 | THR | 156 | −17.083 | −13.066 | 52.183 | 1.00 | 0.00 |
| ATOM | 1465 | CG2 | THR | 156 | −16.601 | −13.057 | 49.683 | 1.00 | 11.43 |
| ATOM | 1466 | C | THR | 156 | −15.502 | −11.024 | 51.584 | 1.00 | 15.34 |
| ATOM | 1467 | O | THR | 156 | −15.498 | −11.642 | 52.653 | 1.00 | 13.11 |
| ATOM | 1468 | N | ALA | 157 | −14.406 | −10.461 | 51.076 | 1.00 | 13.94 |
| ATOM | 1469 | H | ALA | 157 | −14.471 | −9.981 | 50.225 | 1.00 | 0.00 |
| ATOM | 1470 | CA | ALA | 157 | −13.086 | −10.594 | 51.696 | 1.00 | 13.07 |
| ATOM | 1471 | CB | ALA | 157 | −12.043 | −9.841 | 50.878 | 1.00 | 9.00 |
| ATOM | 1472 | C | ALA | 157 | −13.006 | −10.169 | 53.163 | 1.00 | 13.45 |
| ATOM | 1473 | O | ALA | 157 | −12.221 | −10.725 | 53.930 | 1.00 | 13.99 |
| ATOM | 1474 | N | HIS | 158 | −13.805 | −9.180 | 53.549 | 1.00 | 12.36 |
| ATOM | 1475 | H | HIS | 158 | −14.354 | −8.762 | 52.857 | 1.00 | 0.00 |
| ATOM | 1476 | CA | HIS | 158 | −13.809 | −8.685 | 54.925 | 1.00 | 13.60 |
| ATOM | 1477 | CB | HIS | 158 | −14.763 | −7.495 | 55.061 | 1.00 | 13.48 |
| ATOM | 1478 | CG | HIS | 158 | −16.195 | −7.824 | 54.759 | 1.00 | 12.57 |
| ATOM | 1479 | CD2 | HIS | 158 | −17.222 | −8.159 | 55.574 | 1.00 | 7.29 |
| ATOM | 1480 | ND1 | HIS | 158 | −16.705 | −7.830 | 53.479 | 1.00 | 12.96 |
| ATOM | 1481 | HD1 | HIS | 158 | −16.243 | −7.591 | 52.643 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1482 | CE1 | HIS | 158 | −17.984 | −8.158 | 53.516 | 1.00 | 9.68 |
| ATOM | 1483 | NE2 | HIS | 158 | −18.321 | −8.364 | 54.776 | 1.00 | 10.23 |
| ATOM | 1484 | HE2 | HIS | 158 | −19.222 | −8.640 | 55.059 | 1.00 | 0.00 |
| ATOM | 1485 | C | HIS | 158 | −14.173 | −9.752 | 55.957 | 1.00 | 13.56 |
| ATOM | 1486 | O | HIS | 158 | −13.696 | −9.718 | 57.085 | 1.00 | 12.70 |
| ATOM | 1487 | N | GLU | 159 | −14.999 | −10.709 | 55.551 | 1.00 | 16.31 |
| ATOM | 1488 | H | GLU | 159 | −15.284 | −10.757 | 54.616 | 1.00 | 0.00 |
| ATOM | 1489 | CA | GLU | 159 | −15.451 | −11.779 | 56.434 | 1.00 | 21.01 |
| ATOM | 1490 | CB | GLU | 159 | −16.550 | −12.589 | 55.749 | 1.00 | 21.32 |
| ATOM | 1491 | CG | GLU | 159 | −17.756 | −11.749 | 55.365 | 1.00 | 26.36 |
| ATOM | 1492 | CD | GLU | 159 | −18.864 | −12.541 | 54.710 | 1.00 | 30.62 |
| ATOM | 1493 | OE1 | GLU | 159 | −18.718 | −13.769 | 54.541 | 1.00 | 36.67 |
| ATOM | 1494 | OE2 | GLU | 159 | −19.892 | −11.925 | 54.360 | 1.00 | 36.45 |
| ATOM | 1495 | C | GLU | 159 | −14.354 | −12.715 | 56.930 | 1.00 | 23.45 |
| ATOM | 1496 | O | GLU | 159 | −14.571 | −13.489 | 57.868 | 1.00 | 26.52 |
| ATOM | 1497 | N | ARG | 160 | −13.178 | −12.631 | 56.316 | 1.00 | 23.94 |
| ATOM | 1498 | H | ARG | 160 | −13.026 | −11.977 | 55.608 | 1.00 | 0.00 |
| ATOM | 1499 | CA | ARG | 160 | −12.052 | −13.481 | 56.682 | 1.00 | 24.21 |
| ATOM | 1500 | CB | ARG | 160 | −11.340 | −13.972 | 55.419 | 1.00 | 26.28 |
| ATOM | 1501 | CG | ARG | 160 | −12.276 | −14.488 | 54.342 | 1.00 | 29.92 |
| ATOM | 1502 | CD | ARG | 160 | −11.522 | −15.319 | 53.331 | 1.00 | 35.32 |
| ATOM | 1503 | NE | ARG | 160 | −10.957 | −16.502 | 53.971 | 1.00 | 38.70 |
| ATOM | 1504 | HE | ARG | 160 | −10.355 | −16.364 | 54.730 | 1.00 | 0.00 |
| ATOM | 1505 | CZ | ARG | 160 | −11.186 | −17.749 | 53.578 | 1.00 | 41.35 |
| ATOM | 1506 | NH1 | ARG | 160 | −11.965 | −17.989 | 52.530 | 1.00 | 41.68 |
| ATOM | 1507 | HH11 | ARG | 160 | −12.388 | −17.232 | 52.035 | 1.00 | 0.00 |
| ATOM | 1508 | HH12 | ARG | 160 | −12.144 | −18.927 | 52.235 | 1.00 | 0.00 |
| ATOM | 1509 | NH2 | ARG | 160 | −10.669 | −18.759 | 54.266 | 1.00 | 43.07 |
| ATOM | 1510 | HH21 | ARG | 160 | −10.108 | −18.586 | 55.074 | 1.00 | 0.00 |
| ATOM | 1511 | HH22 | ARG | 160 | −10.839 | −19.698 | 53.968 | 1.00 | 0.00 |
| ATOM | 1512 | C | ARG | 160 | −11.046 | −12.749 | 57.562 | 1.00 | 23.53 |
| ATOM | 1513 | O | ARG | 160 | −10.110 | −13.355 | 58.090 | 1.00 | 23.47 |
| ATOM | 1514 | N | SEM | 161 | −11.239 | −11.444 | 57.716 | 1.00 | 21.32 |
| ATOM | 1515 | H | SEM | 161 | −12.039 | −11.020 | 57.353 | 1.00 | 0.00 |
| ATOM | 1516 | CA | SEM | 161 | −10.329 | −10.623 | 58.501 | 1.00 | 18.41 |
| ATOM | 1517 | CB | SEM | 161 | −10.334 | −9.192 | 57.963 | 1.00 | 18.20 |
| ATOM | 1518 | CG | SEM | 161 | −10.002 | −9.089 | 56.474 | 1.00 | 17.50 |
| ATOM | 1519 | A | SEM | 161 | −8.302 | −9.909 | 56.033 | 1.00 | 19.57 |
| ATOM | 1520 | CE | SEM | 161 | −7.032 | −8.759 | 56.813 | 1.00 | 18.11 |
| ATOM | 1521 | C | SEM | 161 | −10.665 | −10.643 | 59.990 | 1.00 | 16.60 |
| ATOM | 1522 | O | SEM | 161 | −11.834 | −10.647 | 60.370 | 1.00 | 17.62 |
| ATOM | 1523 | N | PRO | 162 | −9.635 | −10.613 | 60.850 | 1.00 | 16.11 |
| ATOM | 1524 | CD | PRO | 162 | −8.216 | −10.576 | 60.459 | 1.00 | 17.97 |
| ATOM | 1525 | CA | PRO | 162 | −9.766 | −10.629 | 62.314 | 1.00 | 17.72 |
| ATOM | 1526 | CB | PRO | 162 | −8.326 | −10.423 | 62.779 | 1.00 | 17.28 |
| ATOM | 1527 | CG | PRO | 162 | −7.530 | −11.077 | 61.704 | 1.00 | 19.86 |
| ATOM | 1528 | C | PRO | 162 | −10.669 | −9.526 | 62.867 | 1.00 | 18.66 |
| ATOM | 1529 | O | PRO | 162 | −11.363 | −9.716 | 63.869 | 1.00 | 17.42 |
| ATOM | 1530 | N | TRP | 163 | −10.633 | −8.368 | 62.215 | 1.00 | 18.22 |
| ATOM | 1531 | H | TRP | 163 | −10.058 | −8.304 | 61.429 | 1.00 | 0.00 |
| ATOM | 1532 | CA | TRP | 163 | −11.419 | −7.214 | 62.634 | 1.00 | 14.35 |
| ATOM | 1533 | CB | TRP | 163 | −10.816 | −5.914 | 62.076 | 1.00 | 12.07 |
| ATOM | 1534 | CG | TRP | 163 | −10.401 | −5.950 | 60.614 | 1.00 | 11.68 |
| ATOM | 1535 | CD2 | TRP | 163 | −11.256 | −5.810 | 59.471 | 1.00 | 10.99 |
| ATOM | 1536 | CE2 | TRP | 163 | −10.426 | −5.805 | 58.326 | 1.00 | 11.80 |
| ATOM | 1537 | CE3 | TRP | 163 | −12.641 | −5.682 | 59.303 | 1.00 | 12.54 |
| ATOM | 1538 | CD1 | TRP | 163 | −9.124 | −6.034 | 60.126 | 1.00 | 10.94 |
| ATOM | 1539 | NE1 | TRP | 163 | −9.133 | −5.941 | 58.754 | 1.00 | 12.98 |
| ATOM | 1540 | HE1 | TRP | 163 | −8.326 | −5.895 | 58.178 | 1.00 | 0.00 |
| ATOM | 1541 | CZ2 | TRP | 163 | −10.938 | −5.674 | 57.030 | 1.00 | 11.75 |
| ATOM | 1542 | CZ3 | TRP | 163 | −13.151 | −5.550 | 58.012 | 1.00 | 15.49 |
| ATOM | 1543 | CH2 | TRP | 163 | −12.299 | −5.548 | 56.894 | 1.00 | 11.88 |
| ATOM | 1544 | C | TRP | 163 | −12.915 | −7.278 | 62.354 | 1.00 | 13.04 |
| ATOM | 1545 | O | TRP | 163 | −13.662 | −6.417 | 62.816 | 1.00 | 14.42 |
| ATOM | 1546 | N | TYR | 164 | −13.363 | −8.280 | 61.607 | 1.00 | 13.04 |
| ATOM | 1547 | H | TYR | 164 | −12.770 | −8.981 | 61.266 | 1.00 | 0.00 |
| ATOM | 1548 | CA | TYR | 164 | −14.783 | −8.400 | 61.317 | 1.00 | 14.03 |
| ATOM | 1549 | CB | TYR | 164 | −15.034 | −8.901 | 59.893 | 1.00 | 11.45 |
| ATOM | 1550 | CG | TYR | 164 | −16.502 | −8.909 | 59.522 | 1.00 | 10.45 |
| ATOM | 1551 | CD1 | TYR | 164 | −17.209 | −7.717 | 59.384 | 1.00 | 11.63 |
| ATOM | 1552 | CE1 | TYR | 164 | −18.568 | −7.714 | 59.062 | 1.00 | 11.94 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1553 | CD2 | TYR | 164 | −17.189 | −10.107 | 59.326 | 1.00 | 11.28 |
| ATOM | 1554 | CE2 | TYR | 164 | −18.543 | −10.114 | 59.002 | 1.00 | 12.61 |
| ATOM | 1555 | CZ | TYR | 164 | −19.225 | −8.917 | 58.873 | 1.00 | 13.23 |
| ATOM | 1556 | OH | TYR | 164 | −20.563 | −8.923 | 58.556 | 1.00 | 18.84 |
| ATOM | 1557 | HH | TYR | 164 | −20.907 | −8.037 | 58.691 | 1.00 | 0.00 |
| ATOM | 1558 | C | TYR | 164 | −15.466 | −9.327 | 62.311 | 1.00 | 14.87 |
| ATOM | 1559 | O | TYR | 164 | −15.013 | −10.447 | 62.538 | 1.00 | 15.57 |
| ATOM | 1560 | N | HIS | 165 | −16.552 | −8.846 | 62.908 | 1.00 | 15.89 |
| ATOM | 1561 | H | HIS | 165 | −16.875 | −7.950 | 62.663 | 1.00 | 0.00 |
| ATOM | 1562 | CA | HIS | 165 | −17.315 | −9.622 | 63.878 | 1.00 | 17.82 |
| ATOM | 1563 | CB | HIS | 165 | −17.376 | −8.902 | 65.231 | 1.00 | 18.47 |
| ATOM | 1564 | CG | HIS | 165 | −16.045 | −8.762 | 65.910 | 1.00 | 16.54 |
| ATOM | 1565 | CD2 | HIS | 165 | −14.915 | −8.114 | 65.538 | 1.00 | 14.16 |
| ATOM | 1566 | ND1 | HIS | 165 | −15.776 | −9.320 | 67.142 | 1.00 | 14.58 |
| ATOM | 1567 | HD1 | HIS | 165 | −16.276 | −9.959 | 67.702 | 1.00 | 0.00 |
| ATOM | 1568 | CE1 | HIS | 165 | −14.541 | −9.018 | 67.500 | 1.00 | 15.81 |
| ATOM | 1569 | NE2 | HIS | 165 | −13.997 | −8.289 | 66.543 | 1.00 | 15.66 |
| ATOM | 1570 | HE2 | HIS | 165 | −13.064 | −8.031 | 66.556 | 1.00 | 0.00 |
| ATOM | 1571 | C | HIS | 165 | −18.713 | −9.820 | 63.321 | 1.00 | 18.44 |
| ATOM | 1572 | O | HIS | 165 | −19.497 | −8.876 | 63.238 | 1.00 | 19.84 |
| ATOM | 1573 | N | SER | 166 | −19.007 | −11.056 | 62.925 | 1.00 | 21.85 |
| ATOM | 1574 | H | SER | 166 | −18.316 | −11.751 | 62.997 | 1.00 | 0.00 |
| ATOM | 1575 | CA | SER | 166 | −20.296 | −11.434 | 62.345 | 1.00 | 24.63 |
| ATOM | 1576 | CB | SER | 166 | −20.289 | −12.922 | 61.981 | 1.00 | 25.45 |
| ATOM | 1577 | OG | SER | 166 | −19.253 | −13.209 | 61.056 | 1.00 | 36.62 |
| ATOM | 1578 | HG | SER | 166 | −18.382 | −13.082 | 61.448 | 1.00 | 0.00 |
| ATOM | 1579 | C | SER | 166 | −21.521 | −11.138 | 63.203 | 1.00 | 24.57 |
| ATOM | 1580 | O | SER | 166 | −22.593 | −10.850 | 62.672 | 1.00 | 24.97 |
| ATOM | 1581 | N | SER | 167 | −21.382 | −11.261 | 64.518 | 1.00 | 25.49 |
| ATOM | 1582 | H | SER | 167 | −20.541 | −11.538 | 64.921 | 1.00 | 0.00 |
| ATOM | 1583 | CA | SER | 167 | −22.504 | −11.000 | 65.408 | 1.00 | 30.48 |
| ATOM | 1584 | CB | SER | 167 | −23.222 | −12.301 | 65.777 | 1.00 | 31.09 |
| ATOM | 1585 | OG | SER | 167 | −23.709 | −12.957 | 64.618 | 1.00 | 36.91 |
| ATOM | 1586 | HG | SER | 167 | −24.177 | −12.308 | 64.074 | 1.00 | 0.00 |
| ATOM | 1587 | C | SER | 167 | −22.069 | −10.265 | 66.662 | 1.00 | 30.67 |
| ATOM | 1588 | O | SER | 167 | −21.564 | −10.863 | 67.617 | 1.00 | 34.44 |
| ATOM | 1589 | N | LEU | 168 | −22.237 | −8.952 | 66.629 | 1.00 | 27.52 |
| ATOM | 1590 | H | LEU | 168 | −22.633 | −8.515 | 65.836 | 1.00 | 0.00 |
| ATOM | 1591 | CA | LEU | 168 | −21.894 | −8.096 | 67.747 | 1.00 | 23.85 |
| ATOM | 1592 | CB | LEU | 168 | −20.504 | −7.487 | 67.587 | 1.00 | 23.06 |
| ATOM | 1593 | CG | LEU | 168 | −19.283 | −8.162 | 68.190 | 1.00 | 22.81 |
| ATOM | 1594 | CD1 | LEU | 168 | −18.189 | −7.116 | 68.286 | 1.00 | 20.60 |
| ATOM | 1595 | CD2 | LEU | 168 | −19.596 | −8.715 | 69.558 | 1.00 | 22.00 |
| ATOM | 1596 | C | LEU | 168 | −22.886 | −6.969 | 67.769 | 1.00 | 22.39 |
| ATOM | 1597 | O | LEU | 168 | −23.127 | −6.325 | 66.747 | 1.00 | 23.43 |
| ATOM | 1598 | N | THR | 169 | −23.498 | −6.751 | 68.920 | 1.00 | 20.11 |
| ATOM | 1599 | H | THR | 169 | −23.297 | −7.292 | 69.704 | 1.00 | 0.00 |
| ATOM | 1600 | CA | THR | 169 | −24.431 | −5.655 | 69.047 | 1.00 | 18.64 |
| ATOM | 1601 | CB | THR | 169 | −25.503 | −5.944 | 70.120 | 1.00 | 20.52 |
| ATOM | 1602 | OG1 | THR | 169 | −24.876 | −6.164 | 71.390 | 1.00 | 21.40 |
| ATOM | 1603 | HG1 | THR | 169 | −25.601 | −6.350 | 72.002 | 1.00 | 0.00 |
| ATOM | 1604 | CG2 | THR | 169 | −26.313 | −7.180 | 69.738 | 1.00 | 22.55 |
| ATOM | 1605 | C | THR | 169 | −23.547 | −4.494 | 69.485 | 1.00 | 16.14 |
| ATOM | 1606 | O | THR | 169 | −22.355 | −4.682 | 69.759 | 1.00 | 14.33 |
| ATOM | 1607 | N | ARG | 170 | −24.125 | −3.304 | 69.557 | 1.00 | 17.90 |
| ATOM | 1608 | H | ARG | 170 | −25.076 | −3.202 | 69.314 | 1.00 | 0.00 |
| ATOM | 1609 | CA | ARG | 170 | −23.383 | −2.125 | 69.975 | 1.00 | 16.65 |
| ATOM | 1610 | CB | ARG | 170 | −24.302 | −0.907 | 69.956 | 1.00 | 15.78 |
| ATOM | 1611 | CG | ARG | 170 | −23.645 | 0.392 | 70.358 | 1.00 | 16.09 |
| ATOM | 1612 | CD | ARG | 170 | −24.672 | 1.495 | 70.345 | 1.00 | 17.74 |
| ATOM | 1613 | NE | ARG | 170 | −24.099 | 2.796 | 70.649 | 1.00 | 17.11 |
| ATOM | 1614 | HE | ARG | 170 | −23.788 | 2.980 | 71.549 | 1.00 | 0.00 |
| ATOM | 1615 | CZ | ARG | 170 | −23.966 | 3.775 | 69.762 | 1.00 | 16.57 |
| ATOM | 1616 | NH1 | ARG | 170 | −23.442 | 4.933 | 70.132 | 1.00 | 15.48 |
| ATOM | 1617 | HH11 | ARG | 170 | −23.176 | 5.091 | 71.081 | 1.00 | 0.00 |
| ATOM | 1618 | HH12 | ARG | 170 | −23.372 | 5.687 | 69.486 | 1.00 | 0.00 |
| ATOM | 1619 | NH2 | ARG | 170 | −24.327 | 3.589 | 68.501 | 1.00 | 15.05 |
| ATOM | 1620 | HH21 | ARG | 170 | −24.701 | 2.709 | 68.207 | 1.00 | 0.00 |
| ATOM | 1621 | HH22 | ARG | 170 | −24.185 | 4.334 | 67.852 | 1.00 | 0.00 |
| ATOM | 1622 | C | ARG | 170 | −22.799 | −2.329 | 71.375 | 1.00 | 16.82 |
| ATOM | 1623 | O | ARG | 170 | −21.631 | −2.013 | 71.616 | 1.00 | 16.43 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1624 N | GLU | 171 | −23.603 | −2.877 | 72.284 | 1.00 | 16.19 |
| ATOM | 1625 H | GLU | 171 | −24.524 | −3.101 | 72.035 | 1.00 | 0.00 |
| ATOM | 1626 CA | GLU | 171 | −23.157 | −3.114 | 73.654 | 1.00 | 17.65 |
| ATOM | 1627 CB | GLU | 171 | −24.296 | −3.656 | 74.521 | 1.00 | 20.42 |
| ATOM | 1628 CG | GLU | 171 | −23.890 | −3.861 | 75.985 | 1.00 | 28.15 |
| ATOM | 1629 CD | GLU | 171 | −24.931 | −4.598 | 76.818 | 1.00 | 33.50 |
| ATOM | 1630 OE1 | GLU | 171 | −24.529 | −5.400 | 77.688 | 1.00 | 35.78 |
| ATOM | 1631 OE2 | GLU | 171 | −26.144 | −4.371 | 76.619 | 1.00 | 38.13 |
| ATOM | 1632 C | GLU | 171 | −21.980 | −4.075 | 73.721 | 1.00 | 15.35 |
| ATOM | 1633 O | GLU | 171 | −20.990 | −3.816 | 74.418 | 1.00 | 13.06 |
| ATOM | 1634 N | GLU | 172 | −22.095 | −5.187 | 73.001 | 1.00 | 16.60 |
| ATOM | 1635 H | GLU | 172 | −22.905 | −5.331 | 72.465 | 1.00 | 0.00 |
| ATOM | 1636 CA | GLU | 172 | −21.041 | −6.193 | 72.977 | 1.00 | 16.42 |
| ATOM | 1637 CB | GLU | 172 | −21.497 | −7.427 | 72.206 | 1.00 | 18.60 |
| ATOM | 1638 CG | GLU | 172 | −22.697 | −8.119 | 72.818 | 1.00 | 24.77 |
| ATOM | 1639 CD | GLU | 172 | −23.255 | −9.223 | 71.940 | 1.00 | 30.30 |
| ATOM | 1640 OE1 | GLU | 172 | −23.063 | −9.176 | 70.706 | 1.00 | 30.79 |
| ATOM | 1641 OE2 | GLU | 172 | −23.901 | −10.141 | 72.486 | 1.00 | 35.30 |
| ATOM | 1642 C | GLU | 172 | −19.780 | −5.617 | 72.357 | 1.00 | 15.63 |
| ATOM | 1643 O | GLU | 172 | −18.674 | −5.933 | 72.790 | 1.00 | 18.34 |
| ATOM | 1644 N | ALA | 173 | −19.946 | −4.763 | 71.351 | 1.00 | 16.15 |
| ATOM | 1645 H | ALA | 173 | −20.848 | −4.556 | 71.029 | 1.00 | 0.00 |
| ATOM | 1646 CA | ALA | 173 | −18.805 | −4.132 | 70.695 | 1.00 | 13.89 |
| ATOM | 1647 CB | ALA | 173 | −19.273 | −3.292 | 69.520 | 1.00 | 14.91 |
| ATOM | 1648 C | ALA | 173 | −18.053 | −3.266 | 71.703 | 1.00 | 11.93 |
| ATOM | 1649 O | ALA | 173 | −16.831 | −3.338 | 71.806 | 1.00 | 12.06 |
| ATOM | 1650 N | GLU | 174 | −18.791 | −2.471 | 72.471 | 1.00 | 13.97 |
| ATOM | 1651 H | GLU | 174 | −19.767 | −2.481 | 72.349 | 1.00 | 0.00 |
| ATOM | 1652 CA | GLU | 174 | −18.178 | −1.603 | 73.471 | 1.00 | 13.42 |
| ATOM | 1653 CB | GLU | 174 | −19.204 | −0.636 | 74.064 | 1.00 | 12.52 |
| ATOM | 1654 CG | GLU | 174 | −19.696 | 0.413 | 73.072 | 1.00 | 13.96 |
| ATOM | 1655 CD | GLU | 174 | −20.406 | 1.582 | 73.734 | 1.00 | 16.34 |
| ATOM | 1656 OE1 | GLU | 174 | −20.943 | 2.438 | 73.004 | 1.00 | 17.65 |
| ATOM | 1657 OE2 | GLU | 174 | −20.423 | 1.658 | 74.979 | 1.00 | 20.00 |
| ATOM | 1658 C | GLU | 174 | −17.517 | −2.418 | 74.574 | 1.00 | 14.72 |
| ATOM | 1659 O | GLU | 174 | −16.446 | −2.059 | 75.062 | 1.00 | 16.13 |
| ATOM | 1660 N | ARG | 175 | −18.144 | −3.525 | 74.953 | 1.00 | 16.98 |
| ATOM | 1661 H | ARG | 175 | −18.996 | −3.758 | 74.523 | 1.00 | 0.00 |
| ATOM | 1662 CA | ARG | 175 | −17.592 | −4.387 | 75.987 | 1.00 | 17.73 |
| ATOM | 1663 CB | ARG | 175 | −18.566 | −5.516 | 76.317 | 1.00 | 20.45 |
| ATOM | 1664 CG | ARG | 175 | −18.072 | −6.491 | 77.373 | 1.00 | 27.83 |
| ATOM | 1665 CD | ARG | 175 | −19.238 | −7.101 | 78.146 | 1.00 | 32.77 |
| ATOM | 1666 NE | ARG | 175 | −20.332 | −7.531 | 77.274 | 1.00 | 38.89 |
| ATOM | 1667 HE | ARG | 175 | −20.118 | −8.137 | 76.537 | 1.00 | 0.00 |
| ATOM | 1668 CZ | ARG | 175 | −21.602 | −7.152 | 77.416 | 1.00 | 41.12 |
| ATOM | 1669 NH1 | ARG | 175 | −21.955 | −6.333 | 78.400 | 1.00 | 40.50 |
| ATOM | 1670 HH11 | ARG | 175 | −21.266 | −5.992 | 79.041 | 1.00 | 0.00 |
| ATOM | 1671 HH12 | ARG | 175 | −22.906 | −6.052 | 78.508 | 1.00 | 0.00 |
| ATOM | 1672 NH2 | ARG | 175 | −22.522 | −7.585 | 76.563 | 1.00 | 42.19 |
| ATOM | 1673 HH21 | ARG | 175 | −22.264 | −8.200 | 75.819 | 1.00 | 0.00 |
| ATOM | 1674 HH22 | ARG | 175 | −23.475 | −7.301 | 76.675 | 1.00 | 0.00 |
| ATOM | 1675 C | ARG | 175 | −16.245 | −4.944 | 75.542 | 1.00 | 18.13 |
| ATOM | 1676 O | ARG | 175 | −15.305 | −4.989 | 76.330 | 1.00 | 17.99 |
| ATOM | 1677 N | LYS | 176 | −16.133 | −5.319 | 74.270 | 1.00 | 19.22 |
| ATOM | 1678 H | LYS | 176 | −16.906 | −5.249 | 73.671 | 1.00 | 0.00 |
| ATOM | 1679 CA | LYS | 176 | −14.872 | −5.853 | 73.757 | 1.00 | 19.25 |
| ATOM | 1680 CB | LYS | 176 | −15.070 | −6.569 | 72.420 | 1.00 | 20.57 |
| ATOM | 1681 CG | LYS | 176 | −15.907 | −7.827 | 72.531 | 1.00 | 24.61 |
| ATOM | 1682 CD | LYS | 176 | −15.949 | −8.609 | 71.230 | 1.00 | 31.16 |
| ATOM | 1683 CE | LYS | 176 | −14.759 | −9.547 | 71.088 | 1.00 | 36.55 |
| ATOM | 1684 NZ | LYS | 176 | −13.455 | −8.837 | 70.995 | 1.00 | 41.60 |
| ATOM | 1685 HZ1 | LYS | 176 | −13.289 | −8.308 | 71.876 | 1.00 | 0.00 |
| ATOM | 1686 HZ2 | LYS | 176 | −13.483 | −8.179 | 70.192 | 1.00 | 0.00 |
| ATOM | 1687 HZ3 | LYS | 176 | −12.687 | −9.525 | 70.849 | 1.00 | 0.00 |
| ATOM | 1688 C | LYS | 176 | −13.806 | −4.776 | 73.622 | 1.00 | 19.16 |
| ATOM | 1689 O | LYS | 176 | −12.645 | −5.006 | 73.952 | 1.00 | 20.81 |
| ATOM | 1690 N | LEU | 177 | −14.199 | −3.597 | 73.150 | 1.00 | 18.33 |
| ATOM | 1691 H | LEU | 177 | −15.133 | −3.466 | 72.878 | 1.00 | 0.00 |
| ATOM | 1692 CA | LEU | 177 | −13.251 | −2.499 | 72.994 | 1.00 | 18.62 |
| ATOM | 1693 CB | LEU | 177 | −13.857 | −1.375 | 72.153 | 1.00 | 14.79 |
| ATOM | 1694 CG | LEU | 177 | −14.119 | −1.701 | 70.681 | 1.00 | 14.52 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1695 CD1 | LEU | 177 | −14.746 | −0.502 | 70.016 | 1.00 | 14.81 |
| ATOM | 1696 CD2 | LEU | 177 | −12.833 | −2.073 | 69.972 | 1.00 | 12.01 |
| ATOM | 1697 C | LEU | 177 | −12.742 | −1.950 | 74.328 | 1.00 | 19.76 |
| ATOM | 1698 O | LEU | 177 | −11.562 | −1.628 | 74.456 | 1.00 | 20.72 |
| ATOM | 1699 N | TYR | 178 | −13.632 | −1.839 | 75.312 | 1.00 | 20.07 |
| ATOM | 1700 H | TYR | 178 | −14.555 | −2.105 | 75.139 | 1.00 | 0.00 |
| ATOM | 1701 CA | TYR | 178 | −13.263 | −1.334 | 76.634 | 1.00 | 21.20 |
| ATOM | 1702 CB | TYR | 178 | −14.507 | −0.935 | 77.425 | 1.00 | 18.72 |
| ATOM | 1703 CG | TYR | 178 | −15.063 | 0.420 | 77.073 | 1.00 | 16.53 |
| ATOM | 1704 CD1 | TYR | 178 | −14.238 | 1.543 | 77.029 | 1.00 | 17.03 |
| ATOM | 1705 CE1 | TYR | 178 | −14.752 | 2.796 | 76.738 | 1.00 | 14.85 |
| ATOM | 1706 CD2 | TYR | 178 | −16.418 | 0.587 | 76.813 | 1.00 | 15.41 |
| ATOM | 1707 CE2 | TYR | 178 | −16.942 | 1.833 | 76.520 | 1.00 | 14.24 |
| ATOM | 1708 CZ | TYR | 178 | −16.105 | 2.935 | 76.485 | 1.00 | 15.80 |
| ATOM | 1709 OH | TYR | 178 | −16.624 | 4.177 | 76.198 | 1.00 | 17.17 |
| ATOM | 1710 HH | TYR | 178 | −17.593 | 4.110 | 76.183 | 1.00 | 0.00 |
| ATOM | 1711 C | TYR | 178 | −12.471 | −2.349 | 77.446 | 1.00 | 24.65 |
| ATOM | 1712 O | TYR | 178 | −11.596 | −1.986 | 78.233 | 1.00 | 26.95 |
| ATOM | 1713 N | SER | 179 | −12.791 | −3.622 | 77.266 | 1.00 | 31.05 |
| ATOM | 1714 H | SER | 179 | −13.473 | −3.885 | 76.617 | 1.00 | 0.00 |
| ATOM | 1715 CA | SER | 179 | −12.116 | −4.680 | 77.998 | 1.00 | 35.86 |
| ATOM | 1716 CB | SER | 179 | −13.067 | −5.861 | 78.220 | 1.00 | 37.01 |
| ATOM | 1717 OG | SER | 179 | −14.265 | −5.444 | 78.868 | 1.00 | 38.69 |
| ATOM | 1718 HG | SER | 179 | −14.778 | −5.012 | 78.177 | 1.00 | 0.00 |
| ATOM | 1719 C | SER | 179 | −10.869 | −5.126 | 77.251 | 1.00 | 39.08 |
| ATOM | 1720 O | SER | 179 | −10.909 | −6.065 | 76.456 | 1.00 | 42.60 |
| ATOM | 1721 N | GLY | 180 | −9.765 | −4.432 | 77.498 | 1.00 | 42.38 |
| ATOM | 1722 H | GLY | 180 | −9.787 | −3.665 | 78.115 | 1.00 | 0.00 |
| ATOM | 1723 CA | GLY | 180 | −8.516 | −4.773 | 76.846 | 1.00 | 45.79 |
| ATOM | 1724 C | GLY | 180 | −7.445 | −3.734 | 77.103 | 1.00 | 47.21 |
| ATOM | 1725 O | GLY | 180 | −7.400 | −3.126 | 78.171 | 1.00 | 47.24 |
| ATOM | 1726 N | ALA | 181 | −6.590 | −3.519 | 76.109 | 1.00 | 48.92 |
| ATOM | 1727 H | ALA | 181 | −6.697 | −4.028 | 75.282 | 1.00 | 0.00 |
| ATOM | 1728 CA | ALA | 181 | −5.508 | −2.549 | 76.222 | 1.00 | 50.24 |
| ATOM | 1729 CB | ALA | 181 | −4.423 | −2.857 | 75.197 | 1.00 | 49.84 |
| ATOM | 1730 C | ALA | 181 | −6.006 | −1.111 | 76.055 | 1.00 | 51.23 |
| ATOM | 1731 O | ALA | 181 | −5.331 | −0.165 | 76.465 | 1.00 | 54.12 |
| ATOM | 1732 N | GLN | 182 | −7.179 | −0.953 | 75.446 | 1.00 | 50.07 |
| ATOM | 1733 H | GLN | 182 | −7.676 | −1.742 | 75.154 | 1.00 | 0.00 |
| ATOM | 1734 CA | GLN | 182 | −7.772 | 0.365 | 75.214 | 1.00 | 47.88 |
| ATOM | 1735 CB | GLN | 182 | −8.274 | 0.993 | 76.521 | 1.00 | 49.86 |
| ATOM | 1736 CG | GLN | 182 | −9.511 | 0.332 | 77.103 | 1.00 | 53.43 |
| ATOM | 1737 CD | GLN | 182 | −10.189 | 1.192 | 78.152 | 1.00 | 57.83 |
| ATOM | 1738 OE1 | GLN | 182 | −10.327 | 0.796 | 79.308 | 1.00 | 60.70 |
| ATOM | 1739 NE2 | GLN | 182 | −10.616 | 2.383 | 77.752 | 1.00 | 58.70 |
| ATOM | 1740 HE21 | GLN | 182 | −10.461 | 2.650 | 76.828 | 1.00 | 0.00 |
| ATOM | 1741 HE22 | GLN | 182 | −11.079 | 2.922 | 78.427 | 1.00 | 0.00 |
| ATOM | 1742 C | GLN | 182 | −6.832 | 1.332 | 74.497 | 1.00 | 43.44 |
| ATOM | 1743 O | GLN | 182 | −6.892 | 2.548 | 74.703 | 1.00 | 41.92 |
| ATOM | 1744 N | THR | 183 | −5.972 | 0.789 | 73.643 | 1.00 | 39.92 |
| ATOM | 1745 H | THR | 183 | −5.956 | −0.170 | 73.460 | 1.00 | 0.00 |
| ATOM | 1746 CA | THR | 183 | −5.036 | 1.606 | 72.891 | 1.00 | 36.35 |
| ATOM | 1747 CB | THR | 183 | −3.864 | 0.758 | 72.357 | 1.00 | 38.51 |
| ATOM | 1748 OG1 | THR | 183 | −4.351 | −0.519 | 71.923 | 1.00 | 42.00 |
| ATOM | 1749 HG1 | THR | 183 | −3.917 | −0.732 | 71.092 | 1.00 | 0.00 |
| ATOM | 1750 CG2 | THR | 183 | −2.830 | 0.542 | 73.457 | 1.00 | 39.77 |
| ATOM | 1751 C | THR | 183 | −5.758 | 2.321 | 71.749 | 1.00 | 32.35 |
| ATOM | 1752 O | THR | 183 | −6.676 | 1.772 | 71.132 | 1.00 | 29.04 |
| ATOM | 1753 N | ASP | 184 | −5.367 | 3.567 | 71.508 | 1.00 | 27.99 |
| ATOM | 1754 H | ASP | 184 | −4.644 | 3.943 | 72.040 | 1.00 | 0.00 |
| ATOM | 1755 CA | ASP | 184 | −5.975 | 4.376 | 70.460 | 1.00 | 27.05 |
| ATOM | 1756 CB | ASP | 184 | −5.285 | 5.742 | 70.374 | 1.00 | 27.76 |
| ATOM | 1757 CG | ASP | 184 | −5.617 | 6.647 | 71.553 | 1.00 | 29.09 |
| ATOM | 1758 OD1 | ASP | 184 | −4.767 | 7.483 | 71.914 | 1.00 | 30.44 |
| ATOM | 1759 OD2 | ASP | 184 | −6.729 | 6.539 | 72.109 | 1.00 | 30.19 |
| ATOM | 1760 C | ASP | 184 | −5.973 | 3.701 | 69.092 | 1.00 | 23.21 |
| ATOM | 1761 O | ASP | 184 | −5.000 | 3.054 | 68.704 | 1.00 | 22.81 |
| ATOM | 1762 N | GLY | 185 | −7.088 | 3.826 | 68.385 | 1.00 | 22.28 |
| ATOM | 1763 H | GLY | 185 | −7.863 | 4.278 | 68.784 | 1.00 | 0.00 |
| ATOM | 1764 CA | GLY | 185 | −7.200 | 3.235 | 67.068 | 1.00 | 20.98 |
| ATOM | 1765 C | GLY | 185 | −7.690 | 1.800 | 67.065 | 1.00 | 20.58 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1766 | O | GLY | 185 | −7.879 | 1.223 | 65.994 | 1.00 | 21.98 |
| ATOM | 1767 | N | LYS | 186 | −7.847 | 1.198 | 68.241 | 1.00 | 19.39 |
| ATOM | 1768 | H | LYS | 186 | −7.620 | 1.668 | 69.072 | 1.00 | 0.00 |
| ATOM | 1769 | CA | LYS | 186 | −8.343 | −0.173 | 68.330 | 1.00 | 19.96 |
| ATOM | 1770 | CB | LYS | 186 | −8.385 | −0.628 | 69.790 | 1.00 | 24.49 |
| ATOM | 1771 | CG | LYS | 186 | −8.935 | −2.022 | 69.996 | 1.00 | 30.49 |
| ATOM | 1772 | CD | LYS | 186 | −8.020 | −3.081 | 69.408 | 1.00 | 39.02 |
| ATOM | 1773 | CE | LYS | 186 | −6.799 | −3.343 | 70.288 | 1.00 | 47.08 |
| ATOM | 1774 | NZ | LYS | 186 | −5.832 | −2.209 | 70.348 | 1.00 | 51.52 |
| ATOM | 1775 | HZ1 | LYS | 186 | −6.284 | −1.364 | 70.753 | 1.00 | 0.00 |
| ATOM | 1776 | HZ2 | LYS | 186 | −5.492 | −1.990 | 69.391 | 1.00 | 0.00 |
| ATOM | 1777 | HZ3 | LYS | 186 | −5.026 | −2.478 | 70.946 | 1.00 | 0.00 |
| ATOM | 1778 | C | LYS | 186 | −9.753 | −0.153 | 67.742 | 1.00 | 17.33 |
| ATOM | 1779 | O | LYS | 186 | −10.603 | 0.617 | 68.198 | 1.00 | 17.32 |
| ATOM | 1780 | N | PHE | 187 | −10.008 | −1.010 | 66.756 | 1.00 | 14.12 |
| ATOM | 1781 | H | PHE | 187 | −9.312 | −1.637 | 66.467 | 1.00 | 0.00 |
| ATOM | 1782 | CA | PHE | 187 | −11.305 | −1.032 | 66.092 | 1.00 | 10.45 |
| ATOM | 1783 | C | PHE | 187 | −11.202 | 0.237 | 64.786 | 1.00 | 11.01 |
| ATOM | 1784 | CG | PHE | 187 | −10.455 | −0.967 | 63.697 | 1.00 | 12.30 |
| ATOM | 1785 | CD1 | PHE | 187 | −11.142 | −1.525 | 62.618 | 1.00 | 11.77 |
| ATOM | 1786 | CD2 | PHE | 187 | −9.073 | 1.137 | 63.770 | 1.00 | 10.05 |
| ATOM | 1787 | CE1 | PHE | 187 | −10.461 | −2.246 | 61.635 | 1.00 | 10.76 |
| ATOM | 1788 | CE2 | PHE | 187 | −8.385 | −1.857 | 62.788 | 1.00 | 10.66 |
| ATOM | 1789 | CZ | PHE | 187 | −9.081 | −2.411 | 61.723 | 1.00 | 8.89 |
| ATOM | 1790 | C | PHE | 187 | −11.844 | −2.421 | 65.754 | 1.00 | 11.49 |
| ATOM | 1791 | O | PHE | 187 | −11.157 | −3.432 | 65.903 | 1.00 | 12.56 |
| ATOM | 1792 | N | LEU | 188 | −13.071 | −2.437 | 65.243 | 1.00 | 11.03 |
| ATOM | 1793 | H | LEU | 188 | −13.567 | −1.591 | 65.168 | 1.00 | 0.00 |
| ATOM | 1794 | CA | LEU | 188 | −13.752 | −3.644 | 64.802 | 1.00 | 10.57 |
| ATOM | 1795 | CB | LEU | 188 | −14.276 | −4.474 | 65.988 | 1.00 | 13.68 |
| ATOM | 1796 | CG | LEU | 188 | −15.280 | −3.955 | 67.030 | 1.00 | 12.79 |
| ATOM | 1797 | CD1 | LEU | 188 | −16.689 | −3.832 | 66.447 | 1.00 | 12.29 |
| ATOM | 1798 | CD2 | LEU | 188 | −15.290 | −4.941 | 68.190 | 1.00 | 10.52 |
| ATOM | 1799 | C | LEU | 188 | −14.888 | −3.218 | 63.881 | 1.00 | 10.06 |
| ATOM | 1800 | O | LEU | 188 | −15.359 | −2.082 | 63.956 | 1.00 | 11.34 |
| ATOM | 1801 | N | LEU | 189 | −15.286 | −4.107 | 62.980 | 1.00 | 11.08 |
| ATOM | 1802 | H | LEU | 189 | −14.863 | −4.989 | 62.944 | 1.00 | 0.00 |
| ATOM | 1803 | CA | LEU | 189 | −16.363 | −3.830 | 62.039 | 1.00 | 11.26 |
| ATOM | 1804 | CB | LEU | 189 | −15.845 | −3.967 | 60.597 | 1.00 | 14.05 |
| ATOM | 1805 | CG | LEU | 189 | −16.568 | −3.364 | 59.379 | 1.00 | 18.08 |
| ATOM | 1806 | CD1 | LEU | 189 | −17.908 | −4.020 | 59.126 | 1.00 | 20.55 |
| ATOM | 1807 | CD2 | LEU | 189 | −16.725 | −1.869 | 59.551 | 1.00 | 21.24 |
| ATOM | 1808 | C | LEU | 189 | −17.449 | −4.858 | 62.332 | 1.00 | 10.17 |
| ATOM | 1809 | O | LEU | 189 | −17.160 | −6.037 | 62.539 | 1.00 | 9.97 |
| ATOM | 1810 | N | ARG | 190 | −18.696 | −4.416 | 62.364 | 1.00 | 8.42 |
| ATOM | 1811 | H | ARG | 190 | −18.893 | −3.469 | 62.193 | 1.00 | 0.00 |
| ATOM | 1812 | CA | ARG | 190 | −19.803 | −5.313 | 62.658 | 1.00 | 10.21 |
| ATOM | 1813 | CB | ARG | 190 | −20.199 | −5.183 | 64.137 | 1.00 | 12.50 |
| ATOM | 1814 | CG | ARG | 190 | −20.586 | −3.758 | 64.560 | 1.00 | 11.39 |
| ATOM | 1815 | CD | ARG | 190 | −20.747 | −3.613 | 66.072 | 1.00 | 10.81 |
| ATOM | 1816 | NE | ARG | 190 | −20.865 | −2.210 | 66.479 | 1.00 | 10.25 |
| ATOM | 1817 | HE | ARG | 190 | −20.054 | −1.759 | 66.795 | 1.00 | 0.00 |
| ATOM | 1818 | CZ | ARG | 190 | −21.993 | −1.501 | 66.454 | 1.00 | 8.67 |
| ATOM | 1819 | NH1 | ARG | 190 | −23.133 | −2.044 | 66.050 | 1.00 | 8.01 |
| ATOM | 1820 | HH11 | ARG | 190 | −23.143 | −3.001 | 65.758 | 1.00 | 0.00 |
| ATOM | 1821 | HH12 | ARG | 190 | −23.970 | −1.501 | 66.030 | 1.00 | 0.00 |
| ATOM | 1822 | NH2 | ARG | 190 | −21.975 | −0.220 | 66.799 | 1.00 | 11.12 |
| ATOM | 1823 | HH21 | ARG | 190 | −21.118 | 0.212 | 67.080 | 1.00 | 0.00 |
| ATOM | 1824 | HH22 | ARG | 190 | −22.814 | 0.312 | 66.777 | 1.00 | 0.00 |
| ATOM | 1825 | C | ARG | 190 | −20.996 | −4.977 | 61.789 | 1.00 | 12.50 |
| ATOM | 1826 | O | ARG | 190 | −21.172 | −3.826 | 61.380 | 1.00 | 14.16 |
| ATOM | 1827 | N | PRO | 191 | −21.785 | −5.991 | 61.416 | 1.00 | 14.16 |
| ATOM | 1828 | CD | PRO | 191 | −21.581 | −7.440 | 61.603 | 1.00 | 14.81 |
| ATOM | 1829 | CA | PRO | 191 | −22.960 | −5.721 | 60.587 | 1.00 | 14.23 |
| ATOM | 1830 | CB | PRO | 191 | −23.281 | −7.094 | 60.004 | 1.00 | 15.24 |
| ATOM | 1831 | CG | PRO | 191 | −22.890 | −8.023 | 61.119 | 1.00 | 16.17 |
| ATOM | 1832 | C | PRO | 191 | −24.081 | −5.222 | 61.500 | 1.00 | 14.24 |
| ATOM | 1833 | O | PRO | 191 | −24.039 | −5.444 | 62.712 | 1.00 | 15.68 |
| ATOM | 1834 | N | ARG | 192 | −25.036 | −4.492 | 60.937 | 1.00 | 15.51 |
| ATOM | 1835 | H | ARG | 192 | −25.006 | −4.277 | 59.982 | 1.00 | 0.00 |
| ATOM | 1836 | CA | ARG | 192 | −26.164 | −3.988 | 61.712 | 1.00 | 18.28 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1837 | CB | ARG 192 | −26.369 | −2.489 | 61.458 | 1.00 | 13.36 |
| ATOM | 1838 | CG | ARG 192 | −25.210 | −1.623 | 61.914 | 1.00 | 11.77 |
| ATOM | 1839 | CD | ARG 192 | −25.445 | −0.158 | 61.606 | 1.00 | 12.79 |
| ATOM | 1840 | NE | ARG 192 | −26.554 | 0.404 | 62.374 | 1.00 | 13.77 |
| ATOM | 1841 | HE | ARG 192 | −26.455 | 0.472 | 63.346 | 1.00 | 0.00 |
| ATOM | 1842 | CZ | ARG 192 | −27.707 | 0.809 | 61.849 | 1.00 | 15.28 |
| ATOM | 1843 | NH1 | ARG 192 | −27.925 | 0.718 | 60.544 | 1.00 | 14.55 |
| ATOM | 1844 | HH11 | ARG 192 | −27.221 | 0.344 | 59.941 | 1.00 | 0.00 |
| ATOM | 1845 | HH12 | ARG 192 | −28.799 | 1.103 | 60.162 | 1.00 | 0.00 |
| ATOM | 1846 | NH2 | ARG 192 | −28.643 | 1.322 | 62.631 | 1.00 | 16.15 |
| ATOM | 1847 | HH21 | ARG 192 | −28.468 | 1.402 | 63.611 | 1.00 | 0.00 |
| ATOM | 1848 | HH22 | ARG 192 | −29.515 | 1.625 | 62.246 | 1.00 | 0.00 |
| ATOM | 1849 | C | ARG 192 | −27.406 | −4.779 | 61.311 | 1.00 | 20.44 |
| ATOM | 1850 | O | ARG 192 | −27.345 | −5.612 | 60.404 | 1.00 | 21.80 |
| ATOM | 1851 | N | LYS 193 | −28.523 | −4.532 | 61.988 | 1.00 | 26.86 |
| ATOM | 1852 | H | LYS 193 | −28.484 | −3.869 | 62.709 | 1.00 | 0.00 |
| ATOM | 1853 | CA | LYS 193 | −29.773 | −5.232 | 61.690 | 1.00 | 30.35 |
| ATOM | 1854 | CB | LYS 193 | −30.876 | −4.793 | 62.654 | 1.00 | 34.92 |
| ATOM | 1855 | CG | LYS 193 | −30.577 | −5.067 | 64.117 | 1.00 | 42.06 |
| ATOM | 1856 | CD | LYS 193 | −31.765 | −4.694 | 64.990 | 1.00 | 48.13 |
| ATOM | 1857 | CE | LYS 193 | −31.490 | −4.992 | 66.457 | 1.00 | 52.32 |
| ATOM | 1858 | NZ | LYS 193 | −32.702 | −4.794 | 67.307 | 1.00 | 53.88 |
| ATOM | 1859 | HZ1 | LYS 193 | −33.436 | −5.457 | 66.987 | 1.00 | 0.00 |
| ATOM | 1860 | HZ2 | LYS 193 | −33.047 | −3.819 | 67.206 | 1.00 | 0.00 |
| ATOM | 1861 | HZ3 | LYS 193 | −32.473 | −4.984 | 68.304 | 1.00 | 0.00 |
| ATOM | 1862 | C | LYS 193 | −30.226 | −5.004 | 60.246 | 1.00 | 32.33 |
| ATOM | 1863 | O | LYS 193 | −30.611 | −5.950 | 59.557 | 1.00 | 33.07 |
| ATOM | 1864 | N | GLU 194 | −30.176 | −3.751 | 59.795 | 1.00 | 31.89 |
| ATOM | 1865 | H | GLU 194 | −29.824 | −3.055 | 60.377 | 1.00 | 0.00 |
| ATOM | 1866 | CA | GLU 194 | −30.575 | −3.401 | 58.430 | 1.00 | 31.91 |
| ATOM | 1867 | CB | GLU 194 | −30.744 | −1.884 | 58.274 | 1.00 | 32.74 |
| ATOM | 1868 | CG | GLU 194 | −32.021 | −1.301 | 58.861 | 1.00 | 35.26 |
| ATOM | 1869 | CD | GLU 194 | −32.036 | −1.294 | 60.376 | 1.00 | 36.36 |
| ATOM | 1870 | OE1 | GLU 194 | −32.968 | −1.885 | 60.956 | 1.00 | 40.45 |
| ATOM | 1871 | OE2 | GLU 194 | −31.128 | −0.694 | 60.989 | 1.00 | 38.26 |
| ATOM | 1872 | C | GLU 194 | −29.541 | −3.882 | 57.424 | 1.00 | 30.11 |
| ATOM | 1873 | O | GLU 194 | −28.362 | −3.556 | 57.536 | 1.00 | 31.42 |
| ATOM | 1874 | N | GLN 195 | −29.986 | −4.651 | 56.438 | 1.00 | 30.67 |
| ATOM | 1875 | H | GLN 195 | −30.939 | −4.860 | 56.409 | 1.00 | 0.00 |
| ATOM | 1876 | CA | GLN 195 | −29.097 | −5.168 | 55.405 | 1.00 | 30.73 |
| ATOM | 1877 | CB | GLN 195 | −29.866 | −6.090 | 54.460 | 1.00 | 37.53 |
| ATOM | 1878 | CG | GLN 195 | −30.238 | −7.431 | 55.070 | 1.00 | 48.32 |
| ATOM | 1879 | CD | GLN 195 | −29.120 | −8.457 | 54.969 | 1.00 | 54.80 |
| ATOM | 1880 | OE1 | GLN 195 | −29.252 | −9.457 | 54.264 | 1.00 | 59.01 |
| ATOM | 1881 | NE2 | GLN 195 | −28.016 | −8.216 | 55.669 | 1.00 | 57.50 |
| ATOM | 1882 | HE21 | GLN 195 | −27.917 | −7.416 | 56.226 | 1.00 | 0.00 |
| ATOM | 1883 | HE22 | GLN 195 | −27.317 | −8.894 | 55.589 | 1.00 | 0.00 |
| ATOM | 1884 | C | GLN 195 | −28.477 | −4.024 | 54.617 | 1.00 | 27.43 |
| ATOM | 1885 | O | GLN 195 | −29.171 | −3.094 | 54.209 | 1.00 | 26.89 |
| ATOM | 1886 | N | GLY 196 | −27.170 | −4.095 | 54.410 | 1.00 | 24.53 |
| ATOM | 1887 | H | GLY 196 | −26.647 | −4.854 | 54.751 | 1.00 | 0.00 |
| ATOM | 1888 | CA | GLY 196 | −26.491 | −3.050 | 53.672 | 1.00 | 23.48 |
| ATOM | 1889 | C | GLY 196 | −25.943 | −1.969 | 54.579 | 1.00 | 22.43 |
| ATOM | 1890 | O | GLY 196 | −25.454 | −0.946 | 54.094 | 1.00 | 21.55 |
| ATOM | 1891 | N | THR 197 | −26.067 | −2.166 | 55.891 | 1.00 | 19.48 |
| ATOM | 1892 | H | THR 197 | −26.503 | −2.975 | 56.238 | 1.00 | 0.00 |
| ATOM | 1893 | CA | THR 197 | −25.548 | −1.203 | 56.852 | 1.00 | 17.30 |
| ATOM | 1894 | CB | THR 197 | −26.665 | −0.454 | 57.610 | 1.00 | 18.42 |
| ATOM | 1895 | OG1 | THR 197 | −27.334 | −1.352 | 58.501 | 1.00 | 18.98 |
| ATOM | 1896 | HG1 | THR 197 | −27.449 | −2.142 | 57.983 | 1.00 | 0.00 |
| ATOM | 1897 | CG2 | THR 197 | −27.667 | 0.147 | 56.635 | 1.00 | 17.56 |
| ATOM | 1898 | C | THR 197 | −24.652 | −1.933 | 57.841 | 1.00 | 16.36 |
| ATOM | 1899 | O | THR 197 | −24.952 | −3.057 | 58.261 | 1.00 | 16.10 |
| ATOM | 1900 | N | TYR 198 | −23.539 | −1.294 | 58.178 | 1.00 | 13.90 |
| ATOM | 1901 | H | TYR 198 | −23.392 | −0.390 | 57.840 | 1.00 | 0.00 |
| ATOM | 1902 | CA | TYR 198 | −22.542 | −1.834 | 59.092 | 1.00 | 13.70 |
| ATOM | 1903 | CB | TYR 198 | −21.324 | −2.317 | 58.302 | 1.00 | 15.79 |
| ATOM | 1904 | CG | TYR 198 | −21.644 | −3.336 | 57.239 | 1.00 | 16.67 |
| ATOM | 1905 | CD1 | TYR 198 | −22.117 | −2.941 | 55.988 | 1.00 | 16.60 |
| ATOM | 1906 | CE1 | TYR 198 | −22.441 | −3.876 | 55.016 | 1.00 | 18.00 |
| ATOM | 1907 | CD2 | TYR 198 | −21.498 | −4.699 | 57.490 | 1.00 | 17.21 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1908 | CE2 | TYR | 198 | −21.817 | −5.643 | 56.525 | 1.00 | 20.80 |
| ATOM | 1909 | CZ | TYR | 198 | −22.289 | −5.226 | 55.290 | 1.00 | 20.28 |
| ATOM | 1910 | OH | TYR | 198 | −22.612 | −6.159 | 54.330 | 1.00 | 23.06 |
| ATOM | 1911 | HH | TYR | 198 | −22.386 | −7.044 | 54.647 | 1.00 | 0.00 |
| ATOM | 1912 | C | TYR | 198 | −22.101 | −0.708 | 60.006 | 1.00 | 12.46 |
| ATOM | 1913 | O | TYR | 198 | −22.450 | 0.448 | 59.783 | 1.00 | 15.43 |
| ATOM | 1914 | N | ALA | 199 | −21.317 | −1.033 | 61.019 | 1.00 | 12.73 |
| ATOM | 1915 | H | ALA | 199 | −21.033 | −1.954 | 61.164 | 1.00 | 0.00 |
| ATOM | 1916 | CA | ALA | 199 | −20.833 | −0.12 | 61.927 | 1.00 | 10.15 |
| ATOM | 1917 | CB | ALA | 199 | −21.628 | −0.023 | 63.221 | 1.00 | 11.67 |
| ATOM | 1918 | C | ALA | 199 | −19.363 | −0.225 | 62.210 | 1.00 | 11.06 |
| ATOM | 1919 | O | ALA | 199 | −18.900 | −1.361 | 62.357 | 1.00 | 11.49 |
| ATOM | 1920 | N | LEU | 200 | −18.624 | 0.876 | 62.204 | 1.00 | 10.36 |
| ATOM | 1921 | H | LEU | 200 | −19.053 | 1.732 | 62.000 | 1.00 | 0.00 |
| ATOM | 1922 | CA | LEU | 200 | −17.206 | 0.870 | 62.492 | 1.00 | 9.26 |
| ATOM | 1923 | CB | LEU | 200 | −16.483 | 1.830 | 61.550 | 1.00 | 12.13 |
| ATOM | 1924 | CG | LEU | 200 | −15.092 | 1.470 | 61.028 | 1.00 | 17.52 |
| ATOM | 1925 | CD1 | LEU | 200 | −14.463 | 2.731 | 60.451 | 1.00 | 19.60 |
| ATOM | 1926 | CD2 | LEU | 200 | −14.204 | 0.905 | 62.129 | 1.00 | 20.00 |
| ATOM | 1927 | C | LEU | 200 | −17.122 | 1.389 | 63.927 | 1.00 | 10.58 |
| ATOM | 1928 | O | LEU | 200 | −17.605 | 2.483 | 64.225 | 1.00 | 11.51 |
| ATOM | 1929 | N | SER | 201 | −16.590 | 0.577 | 64.829 | 1.00 | 10.65 |
| ATOM | 1930 | H | SER | 201 | −16.248 | −0.304 | 64.561 | 1.00 | 0.00 |
| ATOM | 1931 | CA | SER | 201 | −16.465 | 0.972 | 66.223 | 1.00 | 11.10 |
| ATOM | 1932 | CB | SER | 201 | −17.216 | −0.016 | 67.121 | 1.00 | 11.49 |
| ATOM | 1933 | OG | SER | 201 | −18.576 | −0.156 | 66.728 | 1.00 | 13.41 |
| ATOM | 1934 | HG | SER | 201 | −18.554 | −0.583 | 65.856 | 1.00 | 0.00 |
| ATOM | 1935 | C | SER | 201 | −14.998 | 1.007 | 66.610 | 1.00 | 13.09 |
| ATOM | 1936 | O | SER | 201 | −14.274 | 0.031 | 66.405 | 1.00 | 15.42 |
| ATOM | 1937 | N | LEU | 202 | −14.538 | 2.145 | 67.112 | 1.00 | 13.25 |
| ATOM | 1938 | H | LEU | 202 | −15.116 | 2.931 | 67.224 | 1.00 | 0.00 |
| ATOM | 1939 | CA | LEU | 202 | −13.155 | 2.258 | 67.535 | 1.00 | 14.15 |
| ATOM | 1940 | CB | LEU | 202 | −12.259 | 2.865 | 66.439 | 1.00 | 16.72 |
| ATOM | 1941 | CG | LEU | 202 | −12.277 | 4.272 | 65.816 | 1.00 | 18.51 |
| ATOM | 1942 | CD1 | LEU | 202 | −13.589 | 4.533 | 65.121 | 1.00 | 18.26 |
| ATOM | 1943 | CD2 | LEU | 202 | −11.956 | 5.347 | 66.840 | 1.00 | 21.05 |
| ATOM | 1944 | C | LEU | 202 | −13.054 | 3.024 | 68.843 | 1.00 | 15.33 |
| ATOM | 1945 | O | LEU | 202 | −13.968 | 3.753 | 69.224 | 1.00 | 14.20 |
| ATOM | 1946 | N | ILE | 203 | −11.973 | 2.796 | 69.567 | 1.00 | 18.07 |
| ATOM | 1947 | H | ILE | 203 | −11.290 | 2.170 | 69.241 | 1.00 | 0.00 |
| ATOM | 1948 | CA | ILE | 203 | −11.777 | 3.470 | 70.835 | 1.00 | 19.49 |
| ATOM | 1949 | CB | ILE | 203 | −11.514 | 2.444 | 71.974 | 1.00 | 18.21 |
| ATOM | 1950 | CG2 | ILE | 203 | −10.279 | 1.623 | 71.687 | 1.00 | 21.96 |
| ATOM | 1951 | CG1 | ILE | 203 | −11.419 | 3.146 | 73.326 | 1.00 | 21.52 |
| ATOM | 1952 | CD | ILE | 203 | −11.469 | 2.190 | 74.496 | 1.00 | 21.43 |
| ATOM | 1953 | C | ILE | 203 | −10.669 | 4.517 | 70.703 | 1.00 | 20.13 |
| ATOM | 1954 | O | ILE | 203 | −9.645 | 4.288 | 70.048 | 1.00 | 20.26 |
| ATOM | 1955 | N | TYR | 204 | −10.940 | 5.707 | 71.226 | 1.00 | 20.23 |
| ATOM | 1956 | H | TYR | 204 | −11.801 | 5.874 | 71.657 | 1.00 | 0.00 |
| ATOM | 1957 | CA | TYR | 204 | −9.997 | 6.809 | 71.186 | 1.00 | 21.84 |
| ATOM | 1958 | CB | TYR | 204 | −10.257 | 7.691 | 69.960 | 1.00 | 23.09 |
| ATOM | 1959 | CG | TYR | 204 | −9.371 | 8.909 | 69.903 | 1.00 | 28.63 |
| ATOM | 1960 | CD1 | TYR | 204 | −7.983 | 8.783 | 69.891 | 1.00 | 31.65 |
| ATOM | 1961 | CE1 | TYR | 204 | −7.160 | 9.905 | 69.885 | 1.00 | 35.44 |
| ATOM | 1962 | CD2 | TYR | 204 | −9.917 | 10.189 | 69.901 | 1.00 | 31.96 |
| ATOM | 1963 | CE2 | TYR | 204 | −9.102 | 11.320 | 69.894 | 1.00 | 36.73 |
| ATOM | 1964 | CZ | TYR | 204 | −7.726 | 11.171 | 69.887 | 1.00 | 37.11 |
| ATOM | 1965 | OH | TYR | 204 | −6.915 | 12.283 | 69.889 | 1.00 | 43.01 |
| ATOM | 1966 | HH | TYR | 204 | −7.453 | 13.075 | 69.817 | 1.00 | 0.00 |
| ATOM | 1967 | C | TYR | 204 | −10.164 | 7.618 | 72.465 | 1.00 | 21.93 |
| ATOM | 1968 | O | TYR | 204 | −11.271 | 8.048 | 72.792 | 1.00 | 20.87 |
| ATOM | 1969 | N | GLY | 205 | −9.069 | 7.796 | 73.199 | 1.00 | 22.69 |
| ATOM | 1970 | H | GLY | 205 | −8.223 | 7.424 | 72.920 | 1.00 | 0.00 |
| ATOM | 1971 | CA | GLY | 205 | −9.117 | 8.540 | 74.446 | 1.00 | 23.60 |
| ATOM | 1972 | C | GLY | 205 | −10.061 | 7.891 | 75.442 | 1.00 | 23.74 |
| ATOM | 1973 | O | GLY | 205 | −10.865 | 8.572 | 76.075 | 1.00 | 26.62 |
| ATOM | 1974 | N | LYS | 206 | −9.993 | 6.565 | 75.533 | 1.00 | 22.74 |
| ATOM | 1975 | H | LYS | 206 | −9.361 | 6.092 | 74.946 | 1.00 | 0.00 |
| ATOM | 1976 | CA | LYS | 206 | −10.834 | 5.784 | 76.437 | 1.00 | 22.71 |
| ATOM | 1977 | CB | LYS | 206 | −10.498 | 6.085 | 77.900 | 1.00 | 26.75 |
| ATOM | 1978 | CG | LYS | 206 | −9.177 | 5.500 | 78.359 | 1.00 | 34.97 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 1979 CD | LYS | 206 | −9.136 | 5.336 | 79.874 | 1.00 | 40.88 |
| ATOM | 1980 CE | LYS | 206 | −7.962 | 4.464 | 80.300 | 1.00 | 45.58 |
| ATOM | 1981 NZ | LYS | 206 | −7.989 | 4.126 | 81.753 | 1.00 | 48.73 |
| ATOM | 1982 HZ1 | LYS | 206 | −8.863 | 3.613 | 81.978 | 1.00 | 0.00 |
| ATOM | 1983 HZ2 | LYS | 206 | −7.937 | 4.997 | 82.313 | 1.00 | 0.00 |
| ATOM | 1984 HZ3 | LYS | 206 | −7.170 | 3.524 | 81.979 | 1.00 | 0.00 |
| ATOM | 1985 C | LYS | 206 | −12.326 | 5.963 | 76.175 | 1.00 | 21.73 |
| ATOM | 1986 O | LYS | 206 | −13.132 | 5.757 | 77.093 | 1.00 | 21.98 |
| ATOM | 1987 N | THR | 207 | −12.685 | 6.330 | 74.972 | 1.00 | 20.32 |
| ATOM | 1988 H | THR | 207 | −12.028 | 6.508 | 74.270 | 1.00 | 0.00 |
| ATOM | 1989 CA | THR | 207 | −14.079 | 6.524 | 74.604 | 1.00 | 21.18 |
| ATOM | 1990 CB | THR | 207 | −14.401 | 8.020 | 74.393 | 1.00 | 23.74 |
| ATOM | 1991 OG1 | THR | 207 | −13.997 | 8.769 | 75.547 | 1.00 | 30.73 |
| ATOM | 1992 HG1 | THR | 207 | −13.029 | 8.728 | 75.573 | 1.00 | 0.00 |
| ATOM | 1993 CG2 | THR | 207 | −15.888 | 8.214 | 74.174 | 1.00 | 26.96 |
| ATOM | 1994 C | THR | 207 | −14.309 | 5.776 | 73.296 | 1.00 | 17.81 |
| ATOM | 1995 O | THR | 207 | −13.429 | 5.741 | 72.443 | 1.00 | 17.93 |
| ATOM | 1996 N | VAL | 208 | −15.469 | 5.151 | 73.150 | 1.00 | 18.45 |
| ATOM | 1997 H | VAL | 208 | −16.138 | 5.204 | 73.866 | 1.00 | 0.00 |
| ATOM | 1998 CA | VAL | 208 | −15.776 | 4.406 | 71.935 | 1.00 | 17.67 |
| ATOM | 1999 CB | VAL | 208 | −16.454 | 3.040 | 72.245 | 1.00 | 17.07 |
| ATOM | 2000 CG1 | VAL | 208 | −16.790 | 2.305 | 70.950 | 1.00 | 16.77 |
| ATOM | 2001 CG2 | VAL | 208 | −15.539 | 2.182 | 73.095 | 1.00 | 11.55 |
| ATOM | 2002 C | VAL | 208 | −16.656 | 5.205 | 70.893 | 1.00 | 18.54 |
| ATOM | 2003 O | VAL | 208 | −17.696 | 5.741 | 71.377 | 1.00 | 17.58 |
| ATOM | 2004 N | TYR | 209 | −16.216 | 5.276 | 69.730 | 1.00 | 18.01 |
| ATOM | 2005 H | TYR | 209 | −15.380 | 4.834 | 69.510 | 1.00 | 0.00 |
| ATOM | 2006 CA | TYR | 209 | −16.923 | 5.978 | 68.666 | 1.00 | 16.80 |
| ATOM | 2007 CB | TYR | 209 | −15.953 | 6.871 | 67.888 | 1.00 | 15.72 |
| ATOM | 2008 CG | TYR | 209 | −15.356 | 7.983 | 68.715 | 1.00 | 19.87 |
| ATOM | 2009 CD1 | TYR | 209 | −15.781 | 9.298 | 68.551 | 1.00 | 22.52 |
| ATOM | 2010 CE1 | TYR | 209 | −15.260 | 10.324 | 69.329 | 1.00 | 24.59 |
| ATOM | 2011 CD2 | TYR | 209 | −14.387 | 7.721 | 69.679 | 1.00 | 18.42 |
| ATOM | 2012 CE2 | TYR | 209 | −13.860 | 8.741 | 70.462 | 1.00 | 21.29 |
| ATOM | 2013 CZ | TYR | 209 | −14.302 | 10.037 | 70.282 | 1.00 | 23.10 |
| ATOM | 2014 OH | TYR | 209 | −13.798 | 11.052 | 71.058 | 1.00 | 27.37 |
| ATOM | 2015 HH | TYR | 209 | −14.236 | 11.878 | 70.826 | 1.00 | 0.00 |
| ATOM | 2016 C | TYR | 209 | −17.522 | 4.945 | 67.719 | 1.00 | 14.63 |
| ATOM | 2017 O | TYR | 209 | −16.941 | 3.882 | 67.505 | 1.00 | 14.50 |
| ATOM | 2018 N | HIS | 210 | −18.706 | 5.238 | 67.195 | 1.00 | 13.02 |
| ATOM | 2019 H | HIS | 210 | −19.145 | 6.068 | 67.452 | 1.00 | 0.00 |
| ATOM | 2020 CA | HIS | 210 | −19.378 | 4.345 | 66.359 | 1.00 | 12.53 |
| ATOM | 2021 CB | HIS | 210 | −20.662 | 3.786 | 66.864 | 1.00 | 12.65 |
| ATOM | 2022 CG | HIS | 210 | −20.459 | 3.040 | 68.144 | 1.00 | 16.12 |
| ATOM | 2023 CD2 | HIS | 210 | −20.531 | 3.447 | 69.432 | 1.00 | 14.44 |
| ATOM | 2024 ND1 | HIS | 210 | −20.151 | 1.697 | 68.182 | 1.00 | 14.83 |
| ATOM | 2025 HD1 | HIS | 210 | −19.968 | 1.099 | 67.418 | 1.00 | 0.00 |
| ATOM | 2026 CE1 | HIS | 210 | −20.047 | 1.309 | 69.440 | 1.00 | 15.80 |
| ATOM | 2027 NE2 | HIS | 210 | −20.271 | 2.352 | 70.217 | 1.00 | 14.45 |
| ATOM | 2028 HE2 | HIS | 210 | −20.186 | 2.357 | 71.186 | 1.00 | 0.00 |
| ATOM | 2029 C | HIS | 210 | −19.734 | 5.160 | 65.031 | 1.00 | 13.68 |
| ATOM | 2030 O | HIS | 210 | −20.289 | 6.249 | 65.161 | 1.00 | 15.52 |
| ATOM | 2031 N | TYR | 211 | −19.363 | 4.664 | 63.853 | 1.00 | 13.00 |
| ATOM | 2032 H | TYR | 211 | −18.867 | 3.819 | 63.799 | 1.00 | 0.00 |
| ATOM | 2033 CA | TYR | 211 | −19.658 | 5.333 | 62.590 | 1.00 | 10.84 |
| ATOM | 2034 CB | TYR | 211 | −18.379 | 5.684 | 61.835 | 1.00 | 10.80 |
| ATOM | 2035 CG | TYR | 211 | −17.516 | 6.669 | 62.535 | 1.00 | 12.06 |
| ATOM | 2036 CD1 | TYR | 211 | −16.582 | 6.304 | 63.492 | 1.00 | 13.54 |
| ATOM | 2037 CE1 | TYR | 211 | −15.788 | 7.231 | 64.144 | 1.00 | 15.10 |
| ATOM | 2038 CD2 | TYR | 211 | −17.631 | 8.056 | 62.247 | 1.00 | 13.72 |
| ATOM | 2039 CE2 | TYR | 211 | −16.835 | 8.997 | 62.896 | 1.00 | 13.35 |
| ATOM | 2040 CZ | TYR | 211 | −15.919 | 8.575 | 63.843 | 1.00 | 15.06 |
| ATOM | 2041 OH | TYR | 211 | −15.127 | 9.487 | 64.494 | 1.00 | 16.21 |
| ATOM | 2042 HH | TYR | 211 | −14.660 | 9.055 | 65.212 | 1.00 | 0.00 |
| ATOM | 2043 C | TYR | 211 | −20.486 | 4.397 | 61.743 | 1.00 | 11.32 |
| ATOM | 2044 O | TYR | 211 | −20.200 | 3.199 | 61.667 | 1.00 | 11.69 |
| ATOM | 2045 N | LEU | 212 | −21.511 | 4.950 | 61.114 | 1.00 | 9.85 |
| ATOM | 2046 H | LEU | 212 | −21.636 | 5.919 | 61.180 | 1.00 | 0.00 |
| ATOM | 2047 CA | LEU | 212 | −22.415 | 4.194 | 60.266 | 1.00 | 11.52 |
| ATOM | 2048 CB | LEU | 212 | −23.775 | 4.912 | 60.217 | 1.00 | 11.56 |
| ATOM | 2049 CG | LEU | 212 | −25.035 | 4.391 | 59.503 | 1.00 | 15.30 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2050 | CD1 | LEU | 212 | −25.117 | 4.895 | 58.086 | 1.00 | 16.57 |
| ATOM | 2051 | CD2 | LEU | 212 | −25.126 | 2.883 | 59.563 | 1.00 | 13.66 |
| ATOM | 2052 | C | LEU | 212 | −21.830 | 4.050 | 58.863 | 1.00 | 12.35 |
| ATOM | 2053 | O | LEU | 212 | −21.269 | 4.996 | 58.319 | 1.00 | 11.11 |
| ATOM | 2054 | N | ILE | 213 | −21.906 | 2.842 | 58.317 | 1.00 | 11.83 |
| ATOM | 2055 | H | ILE | 213 | −22.310 | 2.108 | 58.828 | 1.00 | 0.00 |
| ATOM | 2056 | CA | ILE | 213 | −21.431 | 2.564 | 56.968 | 1.00 | 11.63 |
| ATOM | 2057 | CB | ILE | 213 | −20.299 | 1.504 | 56.954 | 1.00 | 12.05 |
| ATOM | 2058 | CG2 | ILE | 213 | −19.934 | 1.142 | 55.505 | 1.00 | 9.05 |
| ATOM | 2059 | CG1 | ILE | 213 | −19.070 | 2.022 | 57.704 | 1.00 | 10.26 |
| ATOM | 2060 | CD | ILE | 213 | −17.985 | 0.988 | 57.897 | 1.00 | 9.92 |
| ATOM | 2061 | C | ILE | 213 | −22.626 | 1.997 | 56.209 | 1.00 | 12.13 |
| ATOM | 2062 | O | ILE | 213 | −23.269 | 1.063 | 56.685 | 1.00 | 13.61 |
| ATOM | 2063 | N | SER | 214 | −22.970 | 2.592 | 55.073 | 1.00 | 12.35 |
| ATOM | 2064 | H | SER | 214 | −22.502 | 3.387 | 54.736 | 1.00 | 0.00 |
| ATOM | 2065 | CA | SER | 214 | −24.084 | 2.091 | 54.279 | 1.00 | 16.58 |
| ATOM | 2066 | CB | SER | 214 | −25.328 | 2.965 | 54.462 | 1.00 | 20.18 |
| ATOM | 2067 | OG | SER | 214 | −25.052 | 4.321 | 54.167 | 1.00 | 28.58 |
| ATOM | 2068 | HG | SER | 214 | −25.884 | 4.781 | 54.279 | 1.00 | 0.00 |
| ATOM | 2069 | C | SER | 214 | −23.683 | 2.063 | 52.817 | 1.00 | 17.82 |
| ATOM | 2070 | O | SER | 214 | −22.747 | 2.753 | 52.413 | 1.00 | 17.93 |
| ATOM | 2071 | N | GLN | 215 | −24.331 | 1.218 | 52.028 | 1.00 | 20.77 |
| ATOM | 2072 | H | GLN | 215 | −25.045 | 0.650 | 52.395 | 1.00 | 0.00 |
| ATOM | 2073 | CA | GLN | 215 | −23.995 | 1.175 | 50.620 | 1.00 | 25.66 |
| ATOM | 2074 | CB | GLN | 215 | −23.692 | −0.247 | 50.140 | 1.00 | 28.54 |
| ATOM | 2075 | CG | GLN | 215 | −24.821 | −1.247 | 50.204 | 1.00 | 32.61 |
| ATOM | 2076 | CD | GLN | 215 | −24.390 | −2.603 | 49.665 | 1.00 | 34.57 |
| ATOM | 2077 | OE1 | GLN | 215 | −24.663 | −3.638 | 50.270 | 1.00 | 38.97 |
| ATOM | 2078 | NE2 | GLN | 215 | −23.684 | −2.599 | 48.539 | 1.00 | 32.79 |
| ATOM | 2079 | HE21 | GLN | 215 | −23.457 | −1.751 | 48.109 | 1.00 | 0.00 |
| ATOM | 2080 | HE22 | GLN | 215 | −23.416 | −3.468 | 48.179 | 1.00 | 0.00 |
| ATOM | 2081 | C | GLN | 215 | −25.063 | 1.853 | 49.784 | 1.00 | 26.76 |
| ATOM | 2082 | O | GLN | 215 | −26.257 | 1.704 | 50.042 | 1.00 | 27.55 |
| ATOM | 2083 | N | ASP | 216 | −24.621 | 2.676 | 48.840 | 1.00 | 27.69 |
| ATOM | 2084 | H | ASP | 216 | −23.650 | 2.786 | 48.753 | 1.00 | 0.00 |
| ATOM | 2085 | CA | ASP | 216 | −25.536 | 3.407 | 47.977 | 1.00 | 28.52 |
| ATOM | 2086 | CB | ASP | 216 | −24.862 | 4.672 | 47.417 | 1.00 | 27.76 |
| ATOM | 2087 | CG | ASP | 216 | −23.572 | 4.381 | 46.642 | 1.00 | 26.36 |
| ATOM | 2088 | OD1 | ASP | 216 | −23.455 | 3.317 | 46.003 | 1.00 | 26.80 |
| ATOM | 2089 | OD2 | ASP | 216 | −22.670 | 5.242 | 46.654 | 1.00 | 26.55 |
| ATOM | 2090 | C | ASP | 216 | −26.111 | 2.558 | 46.851 | 1.00 | 30.65 |
| ATOM | 2091 | O | ASP | 216 | −25.818 | 1.367 | 46.745 | 1.00 | 29.83 |
| ATOM | 2092 | N | LYS | 217 | −26.910 | 3.196 | 46.001 | 1.00 | 35.42 |
| ATOM | 2093 | H | LYS | 217 | −27.102 | 4.124 | 46.214 | 1.00 | 0.00 |
| ATOM | 2094 | CA | LYS | 217 | −27.538 | 2.543 | 44.857 | 1.00 | 38.73 |
| ATOM | 2095 | CB | LYS | 217 | −28.406 | 3.540 | 44.074 | 1.00 | 42.89 |
| ATOM | 2096 | CG | LYS | 217 | −27.645 | 4.721 | 43.478 | 1.00 | 48.87 |
| ATOM | 2097 | CD | LYS | 217 | −27.269 | 5.752 | 44.537 | 1.00 | 53.40 |
| ATOM | 2098 | CE | LYS | 217 | −26.291 | 6.785 | 43.996 | 1.00 | 58.31 |
| ATOM | 2099 | NZ | LYS | 217 | −24.979 | 6.187 | 43.601 | 1.00 | 59.73 |
| ATOM | 2100 | HZ1 | LYS | 217 | −25.131 | 5.461 | 42.871 | 1.00 | 0.00 |
| ATOM | 2101 | HZ2 | LYS | 217 | −24.529 | 5.743 | 44.426 | 1.00 | 0.00 |
| ATOM | 2102 | HZ3 | LYS | 217 | −24.352 | 6.930 | 43.224 | 1.00 | 0.00 |
| ATOM | 2103 | C | LYS | 217 | −26.502 | 1.913 | 43.925 | 1.00 | 38.15 |
| ATOM | 2104 | O | LYS | 217 | −26.749 | 0.865 | 43.328 | 1.00 | 40.41 |
| ATOM | 2105 | N | ALA | 218 | −25.340 | 2.552 | 43.814 | 1.00 | 35.55 |
| ATOM | 2106 | H | ALA | 218 | −25.215 | 3.381 | 44.311 | 1.00 | 0.00 |
| ATOM | 2107 | CA | ALA | 218 | −24.265 | 2.052 | 42.959 | 1.00 | 33.42 |
| ATOM | 2108 | CB | ALA | 218 | −23.274 | 3.168 | 42.659 | 1.00 | 33.11 |
| ATOM | 2109 | C | ALA | 218 | −23.535 | 0.850 | 43.563 | 1.00 | 31.29 |
| ATOM | 2110 | O | ALA | 218 | −22.651 | 0.274 | 42.928 | 1.00 | 32.67 |
| ATOM | 2111 | N | GLY | 219 | −23.891 | 0.490 | 44.794 | 1.00 | 28.81 |
| ATOM | 2112 | H | GLY | 219 | −24.622 | 0.946 | 45.252 | 1.00 | 0.00 |
| ATOM | 2113 | CA | GLY | 219 | −23.253 | −0.633 | 45.461 | 1.00 | 25.16 |
| ATOM | 2114 | C | GLY | 219 | −21.997 | −0.266 | 46.235 | 1.00 | 21.96 |
| ATOM | 2115 | O | GLY | 219 | −21.363 | −1.132 | 46.841 | 1.00 | 21.31 |
| ATOM | 2116 | N | LYS | 220 | −21.642 | 1.015 | 46.223 | 1.00 | 18.93 |
| ATOM | 2117 | H | LYS | 220 | −22.183 | 1.645 | 45.717 | 1.00 | 0.00 |
| ATOM | 2118 | CA | LYS | 220 | −20.465 | 1.499 | 46.929 | 1.00 | 17.78 |
| ATOM | 2119 | CB | LYS | 220 | −19.940 | 2.767 | 46.266 | 1.00 | 20.25 |
| ATOM | 2120 | CG | LYS | 220 | −19.307 | 2.495 | 44.913 | 1.00 | 24.18 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2121 CD | LYS | 220 | −18.898 | 3.771 | 44.211 | 1.00 | 31.09 |
| ATOM | 2122 CE | LYS | 220 | −18.088 | 3.470 | 42.960 | 1.00 | 34.60 |
| ATOM | 2123 NZ | LYS | 220 | −18.821 | 2.569 | 42.026 | 1.00 | 37.47 |
| ATOM | 2124 HZ1 | LYS | 220 | −19.718 | 3.013 | 41.752 | 1.00 | 0.00 |
| ATOM | 2125 HZ2 | LYS | 220 | −19.017 | 1.663 | 42.495 | 1.00 | 0.00 |
| ATOM | 2126 HZ3 | LYS | 220 | −18.261 | 2.395 | 41.170 | 1.00 | 0.00 |
| ATOM | 2127 C | LYS | 220 | −20.746 | 1.743 | 48.407 | 1.00 | 16.48 |
| ATOM | 2128 O | LYS | 220 | −21.865 | 2.094 | 48.780 | 1.00 | 17.93 |
| ATOM | 2129 N | TYR | 221 | −19.728 | 1.535 | 49.236 | 1.00 | 12.90 |
| ATOM | 2130 H | TYR | 221 | −18.873 | 1.259 | 48.858 | 1.00 | 0.00 |
| ATOM | 2131 CA | TYR | 221 | −19.837 | 1.709 | 50.680 | 1.00 | 13.00 |
| ATOM | 2132 CB | TYR | 221 | −19.086 | 0.593 | 51.414 | 1.00 | 14.73 |
| ATOM | 2133 CG | TYR | 221 | −19.541 | −0.805 | 51.080 | 1.00 | 14.94 |
| ATOM | 2134 CD1 | TYR | 221 | −19.019 | −1.481 | 49.982 | 1.00 | 14.31 |
| ATOM | 2135 CE1 | TYR | 221 | −19.413 | −2.779 | 49.682 | 1.00 | 17.85 |
| ATOM | 2136 CD2 | TYR | 221 | −20.479 | −1.464 | 51.876 | 1.00 | 18.01 |
| ATOM | 2137 CE2 | TYR | 221 | −20.881 | −2.769 | 51.583 | 1.00 | 19.06 |
| ATOM | 2138 CZ | TYR | 221 | −20.339 | −3.418 | 50.483 | 1.00 | 18.46 |
| ATOM | 2139 OH | TYR | 221 | −20.710 | −4.712 | 50.187 | 1.00 | 21.74 |
| ATOM | 2140 HH | TYR | 221 | −21.440 | −4.960 | 50.769 | 1.00 | 0.00 |
| ATOM | 2141 C | TYR | 221 | −19.239 | 3.026 | 51.127 | 1.00 | 13.74 |
| ATOM | 2142 O | TYR | 221 | −18.268 | 3.505 | 50.537 | 1.00 | 13.39 |
| ATOM | 2143 N | CYS | 222 | −19.792 | 3.588 | 52.196 | 1.00 | 12.18 |
| ATOM | 2144 H | CYS | 222 | −20.597 | 3.211 | 52.622 | 1.00 | 0.00 |
| ATOM | 2145 CA | CYS | 222 | −19.270 | 4.832 | 52.738 | 1.00 | 12.71 |
| ATOM | 2146 CB | CYS | 222 | −19.460 | 5.988 | 51.746 | 1.00 | 12.80 |
| ATOM | 2147 SG | CYS | 222 | −21.164 | 6.569 | 51.564 | 1.00 | 18.19 |
| ATOM | 2148 C | CYS | 222 | −19.924 | 5.225 | 54.042 | 1.00 | 11.87 |
| ATOM | 2149 O | CYS | 222 | −21.011 | 4.751 | 54.382 | 1.00 | 13.51 |
| ATOM | 2150 N | ILE | 223 | −19.194 | 6.019 | 54.814 | 1.00 | 11.88 |
| ATOM | 2151 H | ILE | 223 | −18.278 | 6.244 | 54.525 | 1.00 | 0.00 |
| ATOM | 2152 CA | ILE | 223 | −19.709 | 6.588 | 56.049 | 1.00 | 11.29 |
| ATOM | 2153 CB | ILE | 223 | −18.542 | 7.030 | 56.971 | 1.00 | 10.12 |
| ATOM | 2154 CG2 | ILE | 223 | −19.073 | 7.735 | 58.217 | 1.00 | 9.33 |
| ATOM | 2155 CG1 | ILE | 223 | −17.712 | 5.801 | 57.366 | 1.00 | 10.22 |
| ATOM | 2156 CD | ILE | 223 | −16.409 | 6.116 | 58.065 | 1.00 | 12.74 |
| ATOM | 2157 C | ILE | 223 | −20.409 | 7.805 | 55.418 | 1.00 | 13.19 |
| ATOM | 2158 O | ILE | 223 | −19.883 | 8.380 | 54.461 | 1.00 | 14.19 |
| ATOM | 2159 N | PRO | 224 | −21.627 | 8.158 | 55.864 | 1.00 | 13.86 |
| ATOM | 2160 CD | PRO | 224 | −22.436 | 7.580 | 56.951 | 1.00 | 15.81 |
| ATOM | 2161 CA | PRO | 224 | −22.313 | 9.314 | 55.269 | 1.00 | 14.75 |
| ATOM | 2162 CB | PRO | 224 | −23.430 | 9.593 | 56.271 | 1.00 | 15.29 |
| ATOM | 2163 CG | PRO | 224 | −23.798 | 8.225 | 56.718 | 1.00 | 16.55 |
| ATOM | 2164 C | PRO | 224 | −21.418 | 10.538 | 55.052 | 1.00 | 13.87 |
| ATOM | 2165 O | PRO | 224 | −20.737 | 10.999 | 55.972 | 1.00 | 14.06 |
| ATOM | 2166 N | GLU | 225 | −21.406 | 11.024 | 53.812 | 1.00 | 16.66 |
| ATOM | 2167 H | GLU | 225 | −21.973 | 10.588 | 53.143 | 1.00 | 0.00 |
| ATOM | 2168 CA | GLU | 225 | −20.611 | 12.184 | 53.399 | 1.00 | 18.98 |
| ATOM | 2169 CB | GLU | 225 | −20.880 | 13.377 | 54.321 | 1.00 | 23.00 |
| ATOM | 2170 CG | GLU | 225 | −22.332 | 13.822 | 54.340 | 1.00 | 31.63 |
| ATOM | 2171 CD | GLU | 225 | −22.586 | 14.925 | 55.345 | 1.00 | 38.26 |
| ATOM | 2172 OE1 | GLU | 225 | −22.900 | 14.610 | 56.514 | 1.00 | 44.60 |
| ATOM | 2173 OE2 | GLU | 225 | −22.472 | 16.111 | 54.965 | 1.00 | 44.04 |
| ATOM | 2174 C | GLU | 225 | −19.109 | 11.901 | 53.325 | 1.00 | 17.01 |
| ATOM | 2175 O | GLU | 225 | −18.297 | 12.827 | 53.247 | 1.00 | 17.14 |
| ATOM | 2176 N | GLY | 226 | −18.745 | 10.623 | 53.308 | 1.00 | 14.45 |
| ATOM | 2177 H | GLY | 226 | −19.411 | 9.908 | 53.330 | 1.00 | 0.00 |
| ATOM | 2178 CA | GLY | 226 | −17.347 | 10.255 | 53.244 | 1.00 | 11.18 |
| ATOM | 2179 C | GLY | 226 | −16.950 | 9.659 | 51.910 | 1.00 | 10.31 |
| ATOM | 2180 O | GLY | 226 | −17.741 | 9.618 | 50.969 | 1.00 | 9.78 |
| ATOM | 2181 N | THR | 227 | −15.713 | 9.189 | 51.843 | 1.00 | 12.43 |
| ATOM | 2182 H | THR | 227 | −15.132 | 9.231 | 52.635 | 1.00 | 0.00 |
| ATOM | 2183 CA | THR | 227 | −15.161 | 8.580 | 50.642 | 1.00 | 13.92 |
| ATOM | 2184 CB | THR | 227 | −13.660 | 8.259 | 50.845 | 1.00 | 13.92 |
| ATOM | 2185 OG1 | THR | 227 | −12.995 | 9.405 | 51.387 | 1.00 | 14.17 |
| ATOM | 2186 HG1 | THR | 227 | −12.972 | 10.110 | 50.731 | 1.00 | 0.00 |
| ATOM | 2187 CG2 | THR | 227 | −13.004 | 7.903 | 49.531 | 1.00 | 13.18 |
| ATOM | 2188 C | THR | 227 | −15.907 | 7.288 | 50.339 | 1.00 | 13.19 |
| ATOM | 2189 O | THR | 227 | −16.348 | 6.600 | 51.256 | 1.00 | 15.61 |
| ATOM | 2190 N | LYS | 228 | −16.064 | 6.968 | 49.061 | 1.00 | 12.19 |
| ATOM | 2191 H | LYS | 228 | −15.734 | 7.560 | 48.345 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2192 | CA | LYS | 228 | −16.751 | 5.746 | 48.676 | 1.00 | 14.24 |
| ATOM | 2193 | CB | LYS | 228 | −17.773 | 6.035 | 47.582 | 1.00 | 17.80 |
| ATOM | 2194 | CG | LYS | 228 | −18.879 | 6.939 | 48.084 | 1.00 | 18.53 |
| ATOM | 2195 | CD | LYS | 228 | −19.925 | 7.208 | 47.046 | 1.00 | 24.24 |
| ATOM | 2196 | CE | LYS | 228 | −21.091 | 7.919 | 47.693 | 1.00 | 25.57 |
| ATOM | 2197 | NZ | LYS | 228 | −21.680 | 7.085 | 48.782 | 1.00 | 26.31 |
| ATOM | 2198 | HZ1 | LYS | 228 | −20.949 | 6.908 | 49.499 | 1.00 | 0.00 |
| ATOM | 2199 | HZ2 | LYS | 228 | −22.012 | 6.178 | 48.395 | 1.00 | 0.00 |
| ATOM | 2200 | HZ3 | LYS | 228 | −22.481 | 7.585 | 49.217 | 1.00 | 0.00 |
| ATOM | 2201 | C | LYS | 228 | −15.765 | 4.663 | 48.258 | 1.00 | 14.50 |
| ATOM | 2202 | O | LYS | 228 | −14.730 | 4.948 | 47.650 | 1.00 | 13.50 |
| ATOM | 2203 | N | PHE | 229 | −16.093 | 3.424 | 48.612 | 1.00 | 11.73 |
| ATOM | 2204 | H | PHE | 229 | −16.935 | 3.271 | 49.091 | 1.00 | 0.00 |
| ATOM | 2205 | CA | PHE | 229 | −15.256 | 2.266 | 48.331 | 1.00 | 11.12 |
| ATOM | 2206 | CB | PHE | 229 | −14.666 | 1.726 | 49.633 | 1.00 | 10.16 |
| ATOM | 2207 | CG | PHE | 229 | −13.962 | 2.761 | 50.453 | 1.00 | 10.70 |
| ATOM | 2208 | CD1 | PHE | 229 | −14.669 | 3.545 | 51.364 | 1.00 | 10.54 |
| ATOM | 2209 | CD2 | PHE | 229 | −12.596 | 2.969 | 50.309 | 1.00 | 9.61 |
| ATOM | 2210 | CE1 | PHE | 229 | −14.026 | 4.516 | 52.112 | 1.00 | 9.20 |
| ATOM | 2211 | CE2 | PHE | 229 | −11.944 | 3.940 | 51.057 | 1.00 | 9.06 |
| ATOM | 2212 | CZ | PHE | 229 | −12.657 | 4.715 | 51.959 | 1.00 | 9.11 |
| ATOM | 2213 | C | PHE | 229 | −16.083 | 1.168 | 47.688 | 1.00 | 12.28 |
| ATOM | 2214 | O | PHE | 229 | −17.298 | 1.086 | 47.980 | 1.00 | 10.19 |
| ATOM | 2215 | N | ASP | 230 | −15.426 | 0.325 | 46.898 | 1.00 | 10.90 |
| ATOM | 2216 | H | ASP | 230 | −14.463 | 0.469 | 46.747 | 1.00 | 0.00 |
| ATOM | 2217 | CA | ASP | 230 | −16.105 | −0.786 | 46.233 | 1.00 | 12.50 |
| ATOM | 2218 | CB | ASP | 230 | −15.298 | −1.275 | 45.027 | 1.00 | 11.22 |
| ATOM | 2219 | CG | ASP | 230 | −15.537 | −0.441 | 43.784 | 1.00 | 14.98 |
| ATOM | 2220 | OD1 | ASP | 230 | −14.994 | −0.805 | 42.725 | 1.00 | 16.87 |
| ATOM | 2221 | OD2 | ASP | 230 | −16.267 | 0.569 | 43.852 | 1.00 | 18.88 |
| ATOM | 2222 | C | ASP | 230 | −16.353 | −1.947 | 47.185 | 1.00 | 10.65 |
| ATOM | 2223 | O | ASP | 230 | −17.276 | −2.736 | 46.984 | 1.00 | 11.11 |
| ATOM | 2224 | N | THR | 231 | −15.529 | −2.047 | 48.224 | 1.00 | 11.48 |
| ATOM | 2225 | H | THR | 231 | −14.831 | −1.374 | 48.373 | 1.00 | 0.00 |
| ATOM | 2226 | CA | THR | 231 | −15.664 | −3.120 | 49.197 | 1.00 | 7.69 |
| ATOM | 2227 | CB | THR | 231 | −14.672 | −4.283 | 48.916 | 1.00 | 7.51 |
| ATOM | 2228 | OG1 | THR | 231 | −13.326 | −3.812 | 49.047 | 1.00 | 6.84 |
| ATOM | 2229 | HG1 | THR | 231 | −13.152 | −3.283 | 48.249 | 1.00 | 0.00 |
| ATOM | 2230 | CG2 | THR | 231 | −13.152 | −3.283 | 48.249 | 1.00 | 0.00 |
| ATOM | 2231 | C | THR | 231 | −14.867 | −4.851 | 47.514 | 1.00 | 9.18 |
| ATOM | 2232 | O | THR | 231 | −14.786 | −1.549 | 50.787 | 1.00 | 6.01 |
| ATOM | 2233 | N | LEU | 232 | −15.803 | −3.394 | 51.587 | 1.00 | 11.12 |
| ATOM | 2234 | H | LEU | 232 | −16.301 | −4.202 | 51.349 | 1.00 | 0.00 |
| ATOM | 2235 | CA | LEU | 232 | −15.576 | −3.069 | 52.991 | 1.00 | 11.15 |
| ATOM | 2236 | CB | LEU | 232 | −16.452 | −3.943 | 53.890 | 1.00 | 10.62 |
| ATOM | 2237 | CG | LEU | 232 | −17.944 | −3.612 | 53.890 | 1.00 | 10.59 |
| ATOM | 2238 | CD1 | LEU | 232 | −18.702 | −4.656 | 54.692 | 1.00 | 9.60 |
| ATOM | 2239 | CD2 | LEU | 232 | −18.163 | −2.225 | 54.474 | 1.00 | 9.95 |
| ATOM | 2240 | C | LEU | 232 | −14.106 | −3.254 | 53.355 | 1.00 | 10.18 |
| ATOM | 2241 | O | LEU | 232 | −13.591 | −2.556 | 54.224 | 1.00 | 10.71 |
| ATOM | 2242 | N | TRP | 233 | −13.433 | −4.188 | 52.682 | 1.00 | 7.94 |
| ATOM | 2243 | H | TRP | 233 | −13.899 | −4.714 | 52.004 | 1.00 | 0.00 |
| ATOM | 2244 | CA | TRP | 233 | −12.019 | −4.454 | 52.930 | 1.00 | 7.29 |
| ATOM | 2245 | CB | TRP | 233 | −11.547 | −5.644 | 52.082 | 1.00 | 6.24 |
| ATOM | 2246 | CG | TRP | 233 | −10.206 | −6.191 | 52.486 | 1.00 | 8.76 |
| ATOM | 2247 | CD2 | TRP | 233 | −8.918 | −5.653 | 52.152 | 1.00 | 10.99 |
| ATOM | 2248 | CE2 | TRP | 233 | −7.949 | −6.473 | 52.772 | 1.00 | 8.57 |
| ATOM | 2249 | CE3 | TRP | 233 | −8.487 | −4.551 | 51.394 | 1.00 | 10.97 |
| ATOM | 2250 | CD1 | TRP | 233 | −9.971 | −7.291 | 53.265 | 1.00 | 9.24 |
| ATOM | 2251 | NE1 | TRP | 233 | −8.619 | −7.463 | 53.441 | 1.00 | 9.83 |
| ATOM | 2252 | HE1 | TRP | 233 | −8.218 | −8.194 | 53.968 | 1.00 | 0.00 |
| ATOM | 2253 | CZ2 | TRP | 233 | −6.577 | −6.229 | 52.658 | 1.00 | 9.97 |
| ATOM | 2254 | CZ3 | TRP | 233 | −7.120 | −4.307 | 51.281 | 1.00 | 9.13 |
| ATOM | 2255 | CH2 | TRP | 233 | −6.183 | −5.144 | 51.913 | 1.00 | 11.33 |
| ATOM | 2256 | C | TRP | 233 | −11.197 | −3.207 | 52.599 | 1.00 | 7.04 |
| ATOM | 2257 | O | TRP | 233 | −10.319 | −2.799 | 53.370 | 1.00 | 7.78 |
| ATOM | 2258 | N | GLN | 234 | −11.503 | −2.593 | 51.461 | 1.00 | 8.41 |
| ATOM | 2259 | H | GLN | 234 | −12.219 | −2.958 | 50.896 | 1.00 | 0.00 |
| ATOM | 2260 | CA | GLN | 234 | −10.803 | −1.388 | 51.014 | 1.00 | 9.39 |
| ATOM | 2261 | CB | GLN | 234 | −11.165 | −1.071 | 49.652 | 1.00 | 8.16 |
| ATOM | 2262 | CG | GLN | 234 | −10.565 | −2.062 | 48.559 | 1.00 | 10.01 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2263 CD | GLN | 234 | −11.154 | −1.939 | 47.158 | 1.00 | 12.43 |
| ATOM | 2264 OE1 | GLN | 234 | −12.366 | −2.054 | 46.969 | 1.00 | 11.45 |
| ATOM | 2265 NE2 | GLN | 234 | −10.292 | −1.740 | 46.168 | 1.00 | 12.16 |
| ATOM | 2266 HE21 | GLN | 234 | −9.333 | −1.691 | 46.378 | 1.00 | 0.00 |
| ATOM | 2267 HE22 | GLN | 234 | −10.642 | −1.644 | 45.264 | 1.00 | 0.00 |
| ATOM | 2268 C | GLN | 234 | −11.057 | −0.179 | 51.916 | 1.00 | 8.34 |
| ATOM | 2269 O | GLN | 234 | −10.160 | 0.632 | 51.240 | 1.00 | 11.19 |
| ATOM | 2270 N | LEU | 235 | −12.275 | −0.065 | 52.434 | 1.00 | 9.44 |
| ATOM | 2271 H | LEU | 235 | −12.961 | −0.717 | 52.193 | 1.00 | 0.00 |
| ATOM | 2272 CA | LEU | 235 | −12.644 | 1.025 | 53.336 | 1.00 | 9.31 |
| ATOM | 2273 CB | LEU | 235 | −14.137 | 0.914 | 53.705 | 1.00 | 10.64 |
| ATOM | 2274 CG | LEU | 235 | −14.799 | 1.893 | 54.690 | 1.00 | 8.65 |
| ATOM | 2275 CD1 | LEU | 235 | −16.276 | 2.014 | 54.359 | 1.00 | 12.30 |
| ATOM | 2276 CD2 | LEU | 235 | −14.606 | 1.444 | 56.139 | 1.00 | 8.88 |
| ATOM | 2277 C | LEU | 235 | −11.768 | 0.979 | 54.592 | 1.00 | 10.98 |
| ATOM | 2278 O | LEU | 235 | −11.118 | 1.964 | 54.949 | 1.00 | 10.19 |
| ATOM | 2279 N | VAL | 236 | −11.726 | −0.185 | 55.232 | 1.00 | 11.09 |
| ATOM | 2280 H | VAL | 236 | −12.243 | −0.941 | 54.873 | 1.00 | 0.00 |
| ATOM | 2281 CA | VAL | 236 | −10.941 | −0.372 | 56.446 | 1.00 | 13.11 |
| ATOM | 2282 CB | VAL | 236 | −11.160 | −1.792 | 57.035 | 1.00 | 13.64 |
| ATOM | 2283 CG1 | VAL | 236 | −10.210 | −2.052 | 58.198 | 1.00 | 9.34 |
| ATOM | 2284 CG2 | VAL | 236 | −12.606 | −1.937 | 57.497 | 1.00 | 9.82 |
| ATOM | 2285 C | VAL | 236 | −9.460 | −0.122 | 56.202 | 1.00 | 12.74 |
| ATOM | 2286 O | VAL | 236 | −8.814 | 0.617 | 56.947 | 1.00 | 12.87 |
| ATOM | 2287 N | GLU | 237 | −8.936 | −0.692 | 55.124 | 1.00 | 11.87 |
| ATOM | 2288 H | GLU | 237 | −9.506 | −1.255 | 54.555 | 1.00 | 0.00 |
| ATOM | 2289 CA | GLU | 237 | −7.526 | −0.530 | 54.810 | 1.00 | 14.06 |
| ATOM | 2290 CB | GLU | 237 | −7.131 | −1.443 | 53.654 | 1.00 | 18.30 |
| ATOM | 2291 CG | GLU | 237 | −6.010 | −2.409 | 54.009 | 1.00 | 27.57 |
| ATOM | 2292 CD | GLU | 237 | −6.418 | −3.258 | 55.236 | 1.00 | 33.91 |
| ATOM | 2293 OE1 | GLU | 237 | −5.411 | −3.405 | 56.082 | 1.00 | 36.05 |
| ATOM | 2294 OE2 | GLU | 237 | −7.452 | −3.781 | 55.356 | 1.00 | 36.98 |
| ATOM | 2295 C | GLU | 237 | −7.140 | 0.911 | 54.513 | 1.00 | 11.41 |
| ATOM | 2296 O | GLU | 237 | −6.046 | 1.347 | 54.862 | 1.00 | 13.53 |
| ATOM | 2297 N | TYR | 238 | −8.048 | 1.651 | 53.887 | 1.00 | 10.99 |
| ATOM | 2298 H | TYR | 238 | −8.918 | 1.250 | 53.660 | 1.00 | 0.00 |
| ATOM | 2299 CA | TYR | 238 | −7.811 | 3.051 | 53.547 | 1.00 | 10.24 |
| ATOM | 2300 CB | TYR | 238 | −8.917 | 3.539 | 52.616 | 1.00 | 8.37 |
| ATOM | 2301 CG | TYR | 238 | −8.736 | 4.938 | 52.070 | 1.00 | 9.95 |
| ATOM | 2302 CD1 | TYR | 238 | −7.791 | 5.165 | 50.923 | 1.00 | 11.03 |
| ATOM | 2303 CE1 | TYR | 238 | −7.866 | 6.436 | 50.731 | 1.00 | 11.61 |
| ATOM | 2304 CD2 | TYR | 238 | −9.385 | 6.023 | 52.655 | 1.00 | 9.61 |
| ATOM | 2305 CE2 | TYR | 238 | −9.286 | 7.295 | 52.109 | 1.00 | 13.06 |
| ATOM | 2306 CZ | TYR | 238 | −8.530 | 7.494 | 50.969 | 1.00 | 12.38 |
| ATOM | 2307 OH | TYR | 238 | −8.461 | 8.750 | 50.423 | 1.00 | 15.47 |
| ATOM | 2308 HH | TYR | 238 | −7.934 | 8.739 | 49.623 | 1.00 | 0.00 |
| ATOM | 2309 C | TYR | 238 | −7.787 | 3.898 | 54.819 | 1.00 | 12.10 |
| ATOM | 2310 O | TYR | 238 | −6.896 | 4.730 | 55.014 | 1.00 | 10.77 |
| ATOM | 2311 N | LEU | 239 | −8.739 | 3.636 | 55.709 | 1.00 | 12.47 |
| ATOM | 2312 H | LEU | 239 | −9.406 | 2.937 | 55.527 | 1.00 | 0.00 |
| ATOM | 2313 CA | LEU | 239 | −8.844 | 4.371 | 56.960 | 1.00 | 12.96 |
| ATOM | 2314 CB | LEU | 239 | −10.225 | 4.161 | 57.581 | 1.00 | 11.26 |
| ATOM | 2315 CG | LEU | 239 | −11.369 | 4.619 | 56.659 | 1.00 | 14.61 |
| ATOM | 2316 CD1 | LEU | 239 | −12.723 | 4.368 | 57.306 | 1.00 | 11.36 |
| ATOM | 2317 CD2 | LEU | 239 | −11.208 | 6.100 | 56.303 | 1.00 | 15.59 |
| ATOM | 2318 C | LEU | 239 | −7.713 | 4.045 | 57.938 | 1.00 | 15.09 |
| ATOM | 2319 O | LEU | 239 | −7.609 | 4.644 | 59.014 | 1.00 | 15.00 |
| ATOM | 2320 N | LYS | 240 | −6.881 | 3.073 | 57.572 | 1.00 | 15.14 |
| ATOM | 2321 H | LYS | 240 | −7.069 | 2.565 | 56.760 | 1.00 | 0.00 |
| ATOM | 2322 CA | LYS | 240 | −5.721 | 2.713 | 58.380 | 1.00 | 17.35 |
| ATOM | 2323 CB | LYS | 240 | −5.258 | 1.284 | 58.095 | 1.00 | 15.90 |
| ATOM | 2324 CG | LYS | 240 | −6.069 | 0.192 | 58.749 | 1.00 | 19.37 |
| ATOM | 2325 CD | LYS | 240 | −5.352 | −1.147 | 58.604 | 1.00 | 23.39 |
| ATOM | 2326 CE | LYS | 240 | −6.141 | −2.282 | 59.234 | 1.00 | 26.87 |
| ATOM | 2327 NZ | LYS | 240 | −5.449 | −3.592 | 59.076 | 1.00 | 27.64 |
| ATOM | 2328 HZ1 | LYS | 240 | −4.528 | −3.564 | 59.561 | 1.00 | 0.00 |
| ATOM | 2329 HZ2 | LYS | 240 | −5.303 | −3.797 | 58.066 | 1.00 | 0.00 |
| ATOM | 2330 HZ3 | LYS | 240 | −6.056 | −4.328 | 59.485 | 1.00 | 0.00 |
| ATOM | 2331 C | LYS | 240 | −4.602 | 3.674 | 57.988 | 1.00 | 18.17 |
| ATOM | 2332 O | LYS | 240 | −3.741 | 4.005 | 58.797 | 1.00 | 20.88 |
| ATOM | 2333 N | LEU | 241 | −4.624 | 4.119 | 56.737 | 1.00 | 19.69 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2334 | H | LEU | 241 | −5.346 | 3.850 | 56.132 | 1.00 | 0.00 |
| ATOM | 2335 | CA | LEU | 241 | −3.609 | 5.034 | 56.235 | 1.00 | 24.27 |
| ATOM | 2336 | CB | LEU | 241 | −3.499 | 4.927 | 54.708 | 1.00 | 27.48 |
| ATOM | 2337 | CG | LEU | 241 | −3.315 | 3.550 | 54.060 | 1.00 | 32.84 |
| ATOM | 2338 | CD1 | LEU | 241 | −3.353 | 3.698 | 52.541 | 1.00 | 33.90 |
| ATOM | 2339 | CD2 | LEU | 241 | −2.008 | 2.909 | 54.505 | 1.00 | 33.04 |
| ATOM | 2340 | C | LEU | 241 | −3.906 | 6.483 | 56.615 | 1.00 | 23.86 |
| ATOM | 2341 | O | LEU | 241 | −2.997 | 7.237 | 56.962 | 1.00 | 25.78 |
| ATOM | 2342 | N | LYS | 242 | −5.176 | 6.870 | 56.544 | 1.00 | 23.81 |
| ATOM | 2343 | H | LYS | 242 | −5.879 | 6.232 | 56.282 | 1.00 | 0.00 |
| ATOM | 2344 | CA | LYS | 242 | −5.581 | 8.237 | 56.851 | 1.00 | 22.58 |
| ATOM | 2345 | CB | LYS | 242 | −5.570 | 9.074 | 55.565 | 1.00 | 25.37 |
| ATOM | 2346 | CG | LYS | 242 | −6.401 | 8.478 | 54.432 | 1.00 | 27.76 |
| ATOM | 2347 | CD | LYS | 242 | −6.085 | 9.108 | 53.085 | 1.00 | 30.37 |
| ATOM | 2348 | CE | LYS | 242 | −4.720 | 8.701 | 52.554 | 1.00 | 28.46 |
| ATOM | 2349 | NZ | LYS | 242 | −4.450 | 9.342 | 51.238 | 1.00 | 27.65 |
| ATOM | 2350 | HZ1 | LYS | 242 | −4.507 | 10.369 | 51.346 | 1.00 | 0.00 |
| ATOM | 2351 | HZ2 | LYS | 242 | −5.152 | 9.021 | 50.544 | 1.00 | 0.00 |
| ATOM | 2352 | HZ3 | LYS | 242 | −3.496 | 9.081 | 50.914 | 1.00 | 0.00 |
| ATOM | 2353 | C | LYS | 242 | −6.955 | 8.287 | 57.512 | 1.00 | 19.10 |
| ATOM | 2354 | O | LYS | 242 | −7.853 | 7.535 | 57.142 | 1.00 | 17.80 |
| ATOM | 2355 | N | ALA | 243 | −7.110 | 9.917 | 58.473 | 1.00 | 18.84 |
| ATOM | 2356 | H | ALA | 243 | −6.329 | 9.765 | 58.680 | 1.00 | 0.00 |
| ATOM | 2357 | CA | ALA | 243 | −8.362 | 9.362 | 59.214 | 1.00 | 17.03 |
| ATOM | 2358 | CB | ALA | 243 | −8.233 | 10.489 | 60.240 | 1.00 | 14.93 |
| ATOM | 2359 | C | ALA | 243 | −9.540 | 9.620 | 58.285 | 1.00 | 16.79 |
| ATOM | 2360 | O | ALA | 243 | −10.632 | 9.098 | 58.503 | 1.00 | 15.85 |
| ATOM | 2361 | N | ASP | 244 | −9.332 | 10.486 | 57.295 | 1.00 | 17.15 |
| ATOM | 2362 | H | ASP | 244 | −8.459 | 10.915 | 57.232 | 1.00 | 0.00 |
| ATOM | 2363 | CA | ASP | 244 | −10.359 | 10.796 | 56.304 | 1.00 | 18.82 |
| ATOM | 2364 | CB | ASP | 244 | −10.481 | 9.599 | 55.347 | 1.00 | 18.91 |
| ATOM | 2365 | CG | ASP | 244 | −11.295 | 9.904 | 54.113 | 1.00 | 21.74 |
| ATOM | 2366 | OD1 | ASP | 244 | −12.087 | 9.030 | 53.712 | 1.00 | 23.51 |
| ATOM | 2367 | OD2 | ASP | 244 | −11.139 | 10.998 | 53.533 | 1.00 | 25.93 |
| ATOM | 2368 | C | ASP | 244 | −11.723 | 11.169 | 56.923 | 1.00 | 19.28 |
| ATOM | 2369 | O | ASP | 244 | −12.786 | 10.734 | 56.461 | 1.00 | 17.04 |
| ATOM | 2370 | N | GLY | 245 | −11.687 | 11.994 | 57.963 | 1.00 | 18.87 |
| ATOM | 2371 | H | GLY | 245 | −10.837 | 12.330 | 58.306 | 1.00 | 0.00 |
| ATOM | 2372 | CA | GLY | 245 | −12.920 | 12.402 | 58.613 | 1.00 | 18.84 |
| ATOM | 2373 | C | GLY | 245 | −13.123 | 11.779 | 59.982 | 1.00 | 18.77 |
| ATOM | 2374 | O | GLY | 245 | −13.863 | 12.319 | 60.804 | 1.00 | 18.51 |
| ATOM | 2375 | N | LEU | 246 | −12.503 | 10.625 | 60.218 | 1.00 | 18.35 |
| ATOM | 2376 | H | LEU | 246 | −11.973 | 10.209 | 59.505 | 1.00 | 0.00 |
| ATOM | 2377 | CA | LEU | 246 | −12.623 | 9.949 | 61.506 | 1.00 | 18.30 |
| ATOM | 2378 | CB | LEU | 246 | −12.066 | 8.519 | 61.442 | 1.00 | 17.23 |
| ATOM | 2379 | CG | LEU | 246 | −12.647 | 7.431 | 60.534 | 1.00 | 17.12 |
| ATOM | 2380 | CD1 | LEU | 246 | −11.849 | 6.151 | 60.746 | 1.00 | 18.63 |
| ATOM | 2381 | CD2 | LEU | 246 | −14.104 | 7.186 | 60.834 | 1.00 | 15.56 |
| ATOM | 2382 | C | LEU | 246 | −11.866 | 10.707 | 62.591 | 1.00 | 18.47 |
| ATOM | 2383 | O | LEU | 246 | −10.921 | 11.448 | 62.307 | 1.00 | 17.84 |
| ATOM | 2384 | N | ILE | 247 | −12.253 | 10.453 | 63.837 | 1.00 | 17.52 |
| ATOM | 2385 | H | ILE | 247 | −13.020 | 9.857 | 63.945 | 1.00 | 0.00 |
| ATOM | 2386 | CA | ILE | 247 | −11.636 | 11.072 | 65.005 | 1.00 | 18.73 |
| ATOM | 2387 | CB | ILE | 247 | −12.424 | 10.694 | 66.302 | 1.00 | 19.74 |
| ATOM | 2388 | CG2 | ILE | 247 | −12.209 | 9.225 | 66.664 | 1.00 | 17.58 |
| ATOM | 2389 | CG1 | ILE | 247 | −12.020 | 11.599 | 67.463 | 1.00 | 22.31 |
| ATOM | 2390 | CD | ILE | 247 | −12.501 | 13.023 | 67.320 | 1.00 | 25.66 |
| ATOM | 2391 | C | ILE | 247 | −10.163 | 10.651 | 65.129 | 1.00 | 20.39 |
| ATOM | 2392 | O | ILE | 247 | −9.340 | 11.381 | 65.680 | 1.00 | 20.44 |
| ATOM | 2393 | N | TYR | 248 | −9.840 | 9.475 | 64.598 | 1.00 | 20.63 |
| ATOM | 2394 | H | TYR | 248 | −10.512 | 8.919 | 64.159 | 1.00 | 0.00 |
| ATOM | 2395 | CA | TYR | 248 | −8.484 | 8.937 | 64.631 | 1.00 | 21.07 |
| ATOM | 2396 | CB | TYR | 248 | −8.174 | 8.391 | 66.030 | 1.00 | 20.66 |
| ATOM | 2397 | CG | TYR | 248 | −6.704 | 8.168 | 66.310 | 1.00 | 21.55 |
| ATOM | 2398 | CD1 | TYR | 248 | −6.212 | 6.894 | 66.590 | 1.00 | 23.90 |
| ATOM | 2399 | CE1 | TYR | 248 | −4.861 | 6.691 | 66.884 | 1.00 | 27.45 |
| ATOM | 2400 | CD2 | TYR | 248 | −5.810 | 9.235 | 66.237 | 1.00 | 24.95 |
| ATOM | 2401 | CE2 | TYR | 248 | −4.457 | 9.045 | 66.622 | 1.00 | 26.89 |
| ATOM | 2402 | CZ | TYR | 248 | −3.992 | 7.773 | 66.900 | 1.00 | 27.31 |
| ATOM | 2403 | OH | TYR | 248 | −2.664 | 7.588 | 67.209 | 1.00 | 32.39 |
| ATOM | 2404 | HH | TYR | 248 | −2.203 | 8.432 | 67.197 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2405 | C | TYR | 248 | −8.463 | 7.806 | 63.602 | 1.00 | 21.64 |
| ATOM | 2406 | O | TYR | 248 | −9.506 | 7.223 | 63.307 | 1.00 | 22.45 |
| ATOM | 2407 | N | CYS | 249 | −7.304 | 7.510 | 63.025 | 1.00 | 21.61 |
| ATOM | 2408 | H | CYS | 249 | −6.477 | 7.958 | 63.280 | 1.00 | 0.00 |
| ATOM | 2409 | CA | CYS | 249 | −7.252 | 6.444 | 62.035 | 1.00 | 22.88 |
| ATOM | 2410 | CB | CYS | 249 | −6.102 | 6.649 | 61.042 | 1.00 | 25.15 |
| ATOM | 2411 | SG | CYS | 249 | −4.471 | 6.722 | 61.779 | 1.00 | 42.25 |
| ATOM | 2412 | C | CYS | 249 | −7.189 | 5.068 | 62.692 | 1.00 | 21.47 |
| ATOM | 2413 | O | CYS | 249 | −6.787 | 4.929 | 63.853 | 1.00 | 20.61 |
| ATOM | 2414 | N | LEU | 250 | −7.642 | 4.065 | 61.952 | 1.00 | 20.77 |
| ATOM | 2415 | H | LEU | 250 | −7.945 | 4.257 | 61.037 | 1.00 | 0.00 |
| ATOM | 2416 | CA | LEU | 250 | −7.674 | 2.687 | 62.425 | 1.00 | 20.19 |
| ATOM | 2417 | CB | LEU | 250 | −8.416 | 1.820 | 61.405 | 1.00 | 18.49 |
| ATOM | 2418 | CG | LEU | 250 | −9.944 | 1.724 | 61.463 | 1.00 | 17.48 |
| ATOM | 2419 | CD1 | LEU | 250 | −10.596 | 2.988 | 61.983 | 1.00 | 17.55 |
| ATOM | 2420 | CD2 | LEU | 250 | −10.467 | 1.353 | 60.095 | 1.00 | 11.95 |
| ATOM | 2421 | C | LEU | 250 | −6.274 | 2.142 | 62.662 | 1.00 | 21.59 |
| ATOM | 2422 | O | LEU | 250 | −5.389 | 2.319 | 61.829 | 1.00 | 22.32 |
| ATOM | 2423 | N | LYS | 251 | −6.077 | 1.480 | 63.797 | 1.00 | 23.42 |
| ATOM | 2424 | H | LYS | 251 | −6.834 | 1.343 | 64.404 | 1.00 | 0.00 |
| ATOM | 2425 | CA | LYS | 251 | −4.776 | 0.913 | 64.136 | 1.00 | 27.72 |
| ATOM | 2426 | CB | LYS | 251 | −4.191 | 1.594 | 65.381 | 1.00 | 27.91 |
| ATOM | 2427 | CG | LYS | 251 | −3.938 | 3.085 | 65.239 | 1.00 | 29.20 |
| ATOM | 2428 | CD | LYS | 251 | −2.882 | 3.372 | 64.197 | 1.00 | 30.93 |
| ATOM | 2429 | CE | LYS | 251 | −2.677 | 4.859 | 64.038 | 1.00 | 33.75 |
| ATOM | 2430 | NZ | LYS | 251 | −1.669 | 5.159 | 62.987 | 1.00 | 38.98 |
| ATOM | 2431 | HZ1 | LYS | 251 | −1.976 | 4.774 | 62.070 | 1.00 | 0.00 |
| ATOM | 2432 | HZ2 | LYS | 251 | −0.753 | 4.744 | 63.253 | 1.00 | 0.00 |
| ATOM | 2433 | HZ3 | LYS | 251 | −1.561 | 6.191 | 62.908 | 1.00 | 0.00 |
| ATOM | 2434 | C | LYS | 251 | −4.837 | −0.603 | 64.353 | 1.00 | 31.01 |
| ATOM | 2435 | O | LYS | 251 | −4.768 | −1.385 | 63.401 | 1.00 | 34.63 |
| ATOM | 2436 | N | GLU | 252 | −4.991 | −1.013 | 65.606 | 1.00 | 31.53 |
| ATOM | 2437 | H | GLU | 252 | −5.146 | −0.377 | 66.329 | 1.00 | 0.00 |
| ATOM | 2438 | CA | GLU | 252 | −5.036 | −2.426 | 65.952 | 1.00 | 31.94 |
| ATOM | 2439 | CB | GLU | 252 | −4.535 | −2.629 | 67.383 | 1.00 | 36.37 |
| ATOM | 2440 | CG | GLU | 252 | −3.113 | −2.136 | 67.621 | 1.00 | 47.65 |
| ATOM | 2441 | CD | GLU | 252 | −2.878 | −1.678 | 69.053 | 1.00 | 53.28 |
| ATOM | 2442 | OE1 | GLU | 252 | −2.807 | −0.447 | 69.277 | 1.00 | 56.81 |
| ATOM | 2443 | OE2 | GLU | 252 | −2.770 | −2.542 | 69.952 | 1.00 | 56.39 |
| ATOM | 2444 | C | GLU | 252 | −6.440 | −2.993 | 65.817 | 1.00 | 30.12 |
| ATOM | 2445 | O | GLU | 252 | −7.419 | −2.361 | 66.213 | 1.00 | 29.12 |
| ATOM | 2446 | N | ALA | 253 | −6.527 | −4.182 | 65.237 | 1.00 | 26.83 |
| ATOM | 2447 | H | ALA | 253 | −5.716 | −4.627 | 64.930 | 1.00 | 0.00 |
| ATOM | 2448 | CA | ALA | 253 | −7.795 | −4.853 | 65.063 | 1.00 | 26.20 |
| ATOM | 2449 | CB | ALA | 253 | −7.698 | −5.868 | 63.944 | 1.00 | 25.70 |
| ATOM | 2450 | C | ALA | 253 | −8.149 | −5.554 | 66.361 | 1.00 | 28.42 |
| ATOM | 2451 | O | ALA | 253 | −7.276 | −6.096 | 67.036 | 1.00 | 28.38 |
| ATOM | 2452 | N | CYS | 254 | −9.414 | −5.473 | 66.746 | 1.00 | 31.05 |
| ATOM | 2453 | H | CYS | 254 | −10.046 | −4.955 | 66.206 | 1.00 | 0.00 |
| ATOM | 2454 | CA | CYS | 254 | −9.907 | −6.143 | 67.941 | 1.00 | 32.95 |
| ATOM | 2455 | CB | CYS | 254 | −11.087 | −5.361 | 68.533 | 1.00 | 34.98 |
| ATOM | 2456 | SG | CYS | 254 | −11.787 | −6.015 | 70.077 | 1.00 | 32.47 |
| ATOM | 2457 | C | CYS | 254 | −10.372 | −7.475 | 67.358 | 1.00 | 35.53 |
| ATOM | 2458 | O | CYS | 254 | −11.391 | −7.528 | 66.674 | 1.00 | 33.47 |
| ATOM | 2459 | N | PRO | 255 | −9.584 | −8.545 | 67.554 | 1.00 | 40.79 |
| ATOM | 2460 | CD | PRO | 255 | −8.346 | −8.542 | 68.352 | 1.00 | 42.81 |
| ATOM | 2461 | CA | PRO | 255 | −9.865 | −9.900 | 67.058 | 1.00 | 45.35 |
| ATOM | 2462 | CB | PRO | 255 | −8.780 | −10.738 | 67.733 | 1.00 | 46.01 |
| ATOM | 2463 | CG | PRO | 255 | −7.643 | −9.774 | 67.847 | 1.00 | 43.91 |
| ATOM | 2464 | C | PRO | 255 | −11.258 | −10.437 | 67.368 | 1.00 | 48.63 |
| ATOM | 2465 | O | PRO | 255 | −12.027 | −9.807 | 68.088 | 1.00 | 50.93 |
| ATOM | 2466 | N | ASN | 256 | −11.549 | −11.612 | 66.813 | 1.00 | 52.77 |
| ATOM | 2467 | H | ASN | 256 | −10.862 | −12.052 | 66.277 | 1.00 | 0.00 |
| ATOM | 2468 | CA | ASN | 256 | −12.825 | −12.314 | 66.965 | 1.00 | 56.77 |
| ATOM | 2469 | CB | ASN | 256 | −12.631 | −13.804 | 66.654 | 1.00 | 56.87 |
| ATOM | 2470 | CG | ASN | 256 | −11.494 | −14.430 | 67.455 | 1.00 | 58.22 |
| ATOM | 2471 | OD1 | ASN | 256 | −10.354 | −14.507 | 66.987 | 1.00 | 58.21 |
| ATOM | 2472 | ND2 | ASN | 256 | −11.798 | −14.874 | 68.666 | 1.00 | 60.09 |
| ATOM | 2473 | HD21 | ASN | 256 | −12.721 | −14.706 | 68.970 | 1.00 | 0.00 |
| ATOM | 2474 | HD22 | ASN | 256 | −11.107 | −15.313 | 69.188 | 1.00 | 0.00 |
| ATOM | 2475 | C | ASN | 256 | −13.545 | −12.159 | 68.308 | 1.00 | 59.22 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2476 | O | ASN | 256 | −12.888 | −12.281 | 69.365 | 1.00 | 60.95 |
| ATOM | 2477 | OT | ASN | 256 | −14.776 | −11.934 | 68.282 | 1.00 | 62.08 |
| ATOM | 2478 | CB | ASN | 301 | −31.365 | 5.229 | 63.299 | 1.00 | 56.01 |
| ATOM | 2479 | CG | ASN | 301 | −32.706 | 5.204 | 64.007 | 1.00 | 56.26 |
| ATOM | 2480 | OD1 | ASN | 301 | −33.338 | 4.151 | 64.119 | 1.00 | 54.90 |
| ATOM | 2481 | ND2 | ASN | 301 | −33.146 | 6.360 | 64.490 | 1.00 | 56.88 |
| ATOM | 2482 | HD21 | ASN | 301 | −32.620 | 7.179 | 64.396 | 1.00 | 0.00 |
| ATOM | 2483 | HD22 | ASN | 301 | −34.026 | 6.336 | 64.926 | 1.00 | 0.00 |
| ATOM | 2484 | C | ASN | 301 | −30.146 | 4.272 | 65.265 | 1.00 | 56.46 |
| ATOM | 2485 | O | ASN | 301 | −30.767 | 3.599 | 66.093 | 1.00 | 57.32 |
| ATOM | 2486 | HT1 | ASN | 301 | −31.950 | 2.747 | 64.009 | 1.00 | 0.00 |
| ATOM | 2487 | HT2 | ASN | 301 | −30.386 | 2.096 | 64.004 | 1.00 | 0.00 |
| ATOM | 2488 | N | ASN | 301 | −31.028 | 2.767 | 63.513 | 1.00 | 55.62 |
| ATOM | 2489 | HT3 | ASN | 301 | −31.104 | 2.517 | 62.501 | 1.00 | 0.00 |
| ATOM | 2490 | CA | ASN | 301 | −30.427 | 4.112 | 63.774 | 1.00 | 56.70 |
| ATOM | 2491 | N | GLN | 302 | −29.220 | 5.167 | 65.602 | 1.00 | 55.38 |
| ATOM | 2492 | H | GLN | 302 | −28.777 | 5.736 | 64.935 | 1.00 | 0.00 |
| ATOM | 2493 | CA | GLN | 302 | −28.849 | 5.397 | 66.995 | 1.00 | 52.01 |
| ATOM | 2494 | CB | GLN | 302 | −28.061 | 4.185 | 67.520 | 1.00 | 54.35 |
| ATOM | 2495 | CG | GLN | 302 | −28.174 | 3.927 | 69.017 | 1.00 | 56.79 |
| ATOM | 2496 | CD | GLN | 302 | −29.560 | 3.475 | 69.421 | 1.00 | 60.50 |
| ATOM | 2497 | OE1 | GLN | 302 | −30.386 | 4.280 | 69.859 | 1.00 | 63.09 |
| ATOM | 2498 | NE2 | GLN | 302 | −29.825 | 2.182 | 69.280 | 1.00 | 60.40 |
| ATOM | 2499 | HE21 | GLN | 302 | −29.131 | 1.575 | 68.950 | 1.00 | 0.00 |
| ATOM | 2500 | HE22 | GLN | 302 | −30.732 | 1.904 | 69.512 | 1.00 | 0.00 |
| ATOM | 2501 | C | GLN | 302 | −27.998 | 6.670 | 67.089 | 1.00 | 47.72 |
| ATOM | 2502 | O | GLN | 302 | −28.185 | 7.614 | 66.314 | 1.00 | 46.40 |
| ATOM | 2503 | N | LEU | 303 | −27.061 | 6.677 | 68.034 | 1.00 | 43.29 |
| ATOM | 2504 | H | LEU | 303 | −26.909 | 5.925 | 68.633 | 1.00 | 0.00 |
| ATOM | 2505 | CA | LEU | 303 | −26.165 | 7.802 | 68.260 | 1.00 | 36.89 |
| ATOM | 2506 | CB | LEU | 303 | −25.966 | 7.986 | 69.764 | 1.00 | 38.96 |
| ATOM | 2507 | CG | LEU | 303 | −27.251 | 7.951 | 70.594 | 1.00 | 42.01 |
| ATOM | 2508 | CD1 | LEU | 303 | −26.952 | 7.491 | 72.007 | 1.00 | 41.24 |
| ATOM | 2509 | CD2 | LEU | 303 | −27.926 | 9.316 | 70.572 | 1.00 | 43.88 |
| ATOM | 2510 | C | LEU | 303 | −24.824 | 7.489 | 67.595 | 1.00 | 31.37 |
| ATOM | 2511 | O | LEU | 303 | −23.917 | 6.942 | 68.228 | 1.00 | 31.51 |
| ATOM | 2512 | N | PTY | 304 | −24.712 | 7.799 | 66.309 | 1.00 | 25.51 |
| ATOM | 2513 | H | PTY | 304 | −25.443 | 8.263 | 65.853 | 1.00 | 0.00 |
| ATOM | 2514 | CA | PTY | 304 | −23.481 | 7.545 | 65.572 | 1.00 | 22.04 |
| ATOM | 2515 | CB | PTY | 304 | −23.774 | 6.882 | 64.224 | 1.00 | 18.08 |
| ATOM | 2516 | CG | PTY | 304 | −24.310 | 5.478 | 64.358 | 1.00 | 16.80 |
| ATOM | 2517 | CD1 | PTY | 304 | −23.459 | 4.375 | 64.296 | 1.00 | 15.50 |
| ATOM | 2518 | CE1 | PTY | 304 | −23.950 | 3.078 | 64.462 | 1.00 | 17.12 |
| ATOM | 2519 | CD2 | PTY | 304 | −25.662 | 5.253 | 64.580 | 1.00 | 18.22 |
| ATOM | 2520 | CE2 | PTY | 304 | −26.160 | 3.971 | 64.743 | 1.00 | 18.21 |
| ATOM | 2521 | CZ | PTY | 304 | −25.305 | 2.889 | 64.687 | 1.00 | 16.53 |
| ATOM | 2522 | OH | PTY | 304 | −25.840 | 1.637 | 64.857 | 1.00 | 15.66 |
| ATOM | 2523 | OR1 | PTY | 304 | −26.848 | 1.189 | 66.998 | 1.00 | 17.78 |
| ATOM | 2524 | OR2 | PTY | 304 | −24.474 | 1.199 | 66.960 | 1.00 | 13.33 |
| ATOM | 2525 | OR3 | PTY | 304 | −25.836 | −0.551 | 65.882 | 1.00 | 19.12 |
| ATOM | 2526 | PR | PTY | 304 | −25.659 | 0.847 | 66.222 | 1.00 | 16.13 |
| ATOM | 2527 | C | PTY | 304 | −22.717 | 8.839 | 65.375 | 1.00 | 20.65 |
| ATOM | 2528 | O | PTY | 304 | −23.313 | 9.909 | 65.272 | 1.00 | 23.13 |
| ATOM | 2529 | N | ASN | 305 | −21.396 | 8.741 | 65.358 | 1.00 | 18.57 |
| ATOM | 2530 | H | ASN | 305 | −21.009 | 7.863 | 65.445 | 1.00 | 0.00 |
| ATOM | 2531 | CA | ASN | 305 | −20.545 | 9.907 | 65.189 | 1.00 | 20.26 |
| ATOM | 2532 | CB | ASN | 305 | −19.157 | 9.625 | 65.764 | 1.00 | 19.11 |
| ATOM | 2533 | CG | ASN | 305 | −19.197 | 9.305 | 67.241 | 1.00 | 21.22 |
| ATOM | 2534 | OD1 | ASN | 305 | −19.003 | 10.180 | 68.084 | 1.00 | 24.78 |
| ATOM | 2535 | ND2 | ASN | 305 | −19.481 | 8.054 | 67.567 | 1.00 | 20.41 |
| ATOM | 2536 | HD21 | ASN | 305 | −19.675 | 7.444 | 66.829 | 1.00 | 0.00 |
| ATOM | 2537 | HD22 | ASN | 305 | −19.499 | 7.805 | 68.521 | 1.00 | 0.00 |
| ATOM | 2538 | C | ASN | 305 | −20.452 | 10.333 | 63.725 | 1.00 | 20.42 |
| ATOM | 2539 | O | ASN | 305 | −20.549 | 9.503 | 62.819 | 1.00 | 21.37 |
| ATOM | 2540 | N | GLU | 306 | −20.295 | 11.635 | 63.506 | 1.00 | 21.58 |
| ATOM | 2541 | H | GLU | 306 | −20.232 | 12.234 | 64.271 | 1.00 | 0.00 |
| ATOM | 2542 | CA | GLU | 306 | −20.191 | 12.203 | 62.165 | 1.00 | 22.52 |
| ATOM | 2543 | CB | GLU | 306 | −20.911 | 13.556 | 62.093 | 1.00 | 28.56 |
| ATOM | 2544 | CG | GLU | 306 | −22.411 | 13.510 | 62.344 | 1.00 | 37.30 |
| ATOM | 2545 | CD | GLU | 306 | −23.053 | 14.889 | 62.283 | 1.00 | 41.64 |
| ATOM | 2546 | OE1 | GLU | 306 | −22.761 | 15.719 | 63.169 | 1.00 | 43.36 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2547 | OE2 | GLU | 306 | −23.846 | 15.143 | 61.349 | 1.00 | 45.10 |
| ATOM | 2548 | C | GLU | 306 | −18.729 | 12.416 | 61.791 | 1.00 | 20.22 |
| ATOM | 2549 | O | GLU | 306 | −17.859 | 12.502 | 62.665 | 1.00 | 20.01 |
| ATOM | 2550 | N | LEU | 307 | −18.469 | 12.528 | 60.493 | 1.00 | 18.25 |
| ATOM | 2551 | H | LEU | 307 | −19.208 | 12.499 | 59.842 | 1.00 | 0.00 |
| ATOM | 2552 | CA | LEU | 307 | −17.118 | 12.747 | 60.005 | 1.00 | 16.72 |
| ATOM | 2553 | CB | LEU | 307 | −16.995 | 12.307 | 58.544 | 1.00 | 16.17 |
| ATOM | 2554 | CG | LEU | 307 | −17.056 | 10.831 | 58.166 | 1.00 | 13.26 |
| ATOM | 2555 | CD1 | LEU | 307 | −16.950 | 10.720 | 56.658 | 1.00 | 14.79 |
| ATOM | 2556 | CD2 | LEU | 307 | −15.921 | 10.075 | 58.829 | 1.00 | 12.43 |
| ATOM | 2557 | C | LEU | 307 | −16.778 | 14.223 | 60.080 | 1.00 | 18.93 |
| ATOM | 2558 | O | LEU | 307 | −17.632 | 15.075 | 59.843 | 1.00 | 19.72 |
| ATOM | 2559 | N | ASN | 308 | −15.544 | 14.529 | 60.455 | 1.00 | 18.95 |
| ATOM | 2560 | H | ASN | 308 | −14.946 | 13.819 | 60.757 | 1.00 | 0.00 |
| ATOM | 2561 | CA | ASN | 308 | −15.108 | 15.913 | 60.479 | 1.00 | 22.39 |
| ATOM | 2562 | CB | ASN | 308 | −13.848 | 16.076 | 61.324 | 1.00 | 22.65 |
| ATOM | 2563 | CG | ASN | 308 | −13.325 | 17.502 | 61.322 | 1.00 | 24.93 |
| ATOM | 2564 | OD1 | ASN | 308 | −13.764 | 18.348 | 60.540 | 1.00 | 23.61 |
| ATOM | 2565 | ND2 | ASN | 308 | −12.363 | 17.769 | 62.186 | 1.00 | 29.91 |
| ATOM | 2566 | HD21 | ASN | 308 | −12.039 | 17.026 | 62.740 | 1.00 | 0.00 |
| ATOM | 2567 | HD22 | ASN | 308 | −12.030 | 18.689 | 62.233 | 1.00 | 0.00 |
| ATOM | 2568 | C | ASN | 308 | −14.800 | 16.173 | 59.012 | 1.00 | 22.77 |
| ATOM | 2569 | O | ASN | 308 | −13.728 | 15.821 | 58.519 | 1.00 | 22.81 |
| ATOM | 2570 | N | LEU | 309 | −15.770 | 16.733 | 58.305 | 1.00 | 25.79 |
| ATOM | 2571 | H | LEU | 309 | −16.614 | 16.937 | 58.764 | 1.00 | 0.00 |
| ATOM | 2572 | CA | LEU | 309 | −15.624 | 17.002 | 56.884 | 1.00 | 29.56 |
| ATOM | 2573 | CB | LEU | 309 | −16.937 | 17.546 | 56.316 | 1.00 | 30.40 |
| ATOM | 2574 | CG | LEU | 309 | −18.120 | 16.573 | 56.465 | 1.00 | 31.06 |
| ATOM | 2575 | CD1 | LEU | 309 | −19.365 | 17.171 | 55.845 | 1.00 | 29.69 |
| ATOM | 2576 | CD2 | LEU | 309 | −17.802 | 15.229 | 55.814 | 1.00 | 28.45 |
| ATOM | 2577 | C | LEU | 309 | −14.433 | 17.879 | 56.496 | 1.00 | 32.74 |
| ATOM | 2578 | O | LEU | 309 | −13.980 | 17.840 | 55.352 | 1.00 | 34.00 |
| ATOM | 2579 | N | GLY | 310 | −13.896 | 18.628 | 57.453 | 1.00 | 34.39 |
| ATOM | 2580 | H | GLY | 310 | −14.259 | 18.618 | 58.363 | 1.00 | 0.00 |
| ATOM | 2581 | CA | GLY | 310 | −12.749 | 19.471 | 57.166 | 1.00 | 37.43 |
| ATOM | 2582 | C | GLY | 310 | −11.451 | 18.694 | 56.967 | 1.00 | 40.37 |
| ATOM | 2583 | O | GLY | 310 | −10.494 | 19.212 | 56.382 | 1.00 | 42.20 |
| ATOM | 2584 | N | ARG | 311 | −11.411 | 17.454 | 57.453 | 1.00 | 39.39 |
| ATOM | 2585 | H | ARG | 311 | −12.204 | 17.096 | 57.902 | 1.00 | 0.00 |
| ATOM | 2586 | CA | ARG | 311 | −10.220 | 16.613 | 57.334 | 1.00 | 37.84 |
| ATOM | 2587 | CB | ARG | 311 | −9.912 | 15.938 | 58.673 | 1.00 | 38.89 |
| ATOM | 2588 | CG | ARG | 311 | −9.364 | 16.864 | 59.737 | 1.00 | 42.25 |
| ATOM | 2589 | CD | ARG | 311 | −9.096 | 16.101 | 61.022 | 1.00 | 47.16 |
| ATOM | 2590 | NE | ARG | 311 | −10.323 | 15.546 | 61.587 | 1.00 | 51.46 |
| ATOM | 2591 | HE | ARG | 311 | −11.178 | 15.829 | 61.204 | 1.00 | 0.00 |
| ATOM | 2592 | CZ | ARG | 311 | −10.364 | 14.671 | 62.588 | 1.00 | 53.11 |
| ATOM | 2593 | NH1 | ARG | 311 | −9.242 | 14.231 | 63.145 | 1.00 | 54.45 |
| ATOM | 2594 | HH11 | ARG | 311 | −8.350 | 14.554 | 62.828 | 1.00 | 0.00 |
| ATOM | 2595 | HH12 | ARG | 311 | −9.301 | 13.580 | 63.901 | 1.00 | 0.00 |
| ATOM | 2596 | NH2 | ARG | 311 | −11.535 | 14.255 | 63.054 | 1.00 | 54.64 |
| ATOM | 2597 | HH21 | ARG | 311 | −12.383 | 14.597 | 62.652 | 1.00 | 0.00 |
| ATOM | 2598 | HH22 | ARG | 311 | −11.568 | 13.601 | 63.810 | 1.00 | 0.00 |
| ATOM | 2599 | C | ARG | 311 | −10.306 | 15.545 | 56.246 | 1.00 | 35.04 |
| ATOM | 2600 | O | ARG | 311 | −9.479 | 14.632 | 56.201 | 1.00 | 35.34 |
| ATOM | 2601 | N | ARG | 312 | −11.315 | 15.639 | 55.389 | 1.00 | 34.68 |
| ATOM | 2602 | H | ARG | 312 | −11.927 | 16.402 | 55.451 | 1.00 | 0.00 |
| ATOM | 2603 | CA | ARG | 312 | −11.484 | 14.668 | 54.316 | 1.00 | 34.78 |
| ATOM | 2604 | CB | ARG | 312 | −12.882 | 14.766 | 53.706 | 1.00 | 35.31 |
| ATOM | 2605 | CG | ARG | 312 | −13.947 | 13.942 | 54.403 | 1.00 | 36.14 |
| ATOM | 2606 | CD | ARG | 312 | −15.085 | 13.646 | 53.436 | 1.00 | 37.95 |
| ATOM | 2607 | NE | ARG | 312 | −14.597 | 12.970 | 52.232 | 1.00 | 37.17 |
| ATOM | 2608 | HE | ARG | 312 | −13.715 | 12.542 | 52.265 | 1.00 | 0.00 |
| ATOM | 2609 | CZ | ARG | 312 | −15.268 | 12.882 | 51.086 | 1.00 | 37.05 |
| ATOM | 2610 | NH1 | ARG | 312 | −16.473 | 13.423 | 50.966 | 1.00 | 38.97 |
| ATOM | 2611 | HH11 | ARG | 312 | −16.889 | 13.908 | 51.731 | 1.00 | 0.00 |
| ATOM | 2612 | HH12 | ARG | 312 | −16.956 | 13.348 | 50.094 | 1.00 | 0.00 |
| ATOM | 2613 | NH2 | ARG | 312 | −14.721 | 12.271 | 50.044 | 1.00 | 36.61 |
| ATOM | 2614 | HH21 | ARG | 312 | −13.804 | 11.879 | 50.127 | 1.00 | 0.00 |
| ATOM | 2615 | HH22 | ARG | 312 | −15.225 | 12.194 | 49.185 | 1.00 | 0.00 |
| ATOM | 2616 | C | ARG | 312 | −10.449 | 14.829 | 53.209 | 1.00 | 36.45 |
| ATOM | 2617 | O | ARG | 312 | −9.953 | 15.929 | 52.957 | 1.00 | 35.30 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2618 N | GLU | 313 | −10.121 | 13.715 | 52.560 | 1.00 | 37.25 |
| ATOM | 2619 H | GLU | 313 | −10.548 | 12.871 | 52.795 | 1.00 | 0.00 |
| ATOM | 2620 CA | GLU | 313 | −9.169 | 13.713 | 51.459 | 1.00 | 37.51 |
| ATOM | 2621 CB | GLU | 313 | −8.586 | 12.317 | 51.249 | 1.00 | 39.21 |
| ATOM | 2622 CG | GLU | 313 | −7.367 | 12.039 | 52.100 | 1.00 | 42.52 |
| ATOM | 2623 CD | GLU | 313 | −6.114 | 12.722 | 51.576 | 1.00 | 43.09 |
| ATOM | 2624 OE1 | GLU | 313 | −5.282 | 12.027 | 50.962 | 1.00 | 44.41 |
| ATOM | 2625 OE2 | GLU | 313 | −5.954 | 13.945 | 51.778 | 1.00 | 44.79 |
| ATOM | 2626 C | GLU | 313 | −9.903 | 14.162 | 50.214 | 1.00 | 35.75 |
| ATOM | 2627 O | GLU | 313 | −10.973 | 13.639 | 49.894 | 1.00 | 37.66 |
| ATOM | 2628 N | GLU | 314 | −9.332 | 15.139 | 49.523 | 1.00 | 33.41 |
| ATOM | 2629 H | GLU | 314 | −8.466 | 15.487 | 49.818 | 1.00 | 0.00 |
| ATOM | 2630 CA | GLU | 314 | −9.939 | 15.683 | 48.319 | 1.00 | 31.60 |
| ATOM | 2631 CB | GLU | 314 | −9.771 | 17.214 | 48.305 | 1.00 | 37.69 |
| ATOM | 2632 CG | GLU | 314 | −10.165 | 17.916 | 46.999 | 1.00 | 46.27 |
| ATOM | 2633 CD | GLU | 314 | −8.965 | 18.483 | 46.233 | 1.00 | 51.86 |
| ATOM | 2634 OE1 | GLU | 314 | −8.667 | 19.689 | 46.391 | 1.00 | 54.73 |
| ATOM | 2635 OE2 | GLU | 314 | −8.332 | 17.728 | 45.468 | 1.00 | 53.64 |
| ATOM | 2636 C | GLU | 314 | −9.363 | 15.083 | 47.043 | 1.00 | 25.93 |
| ATOM | 2637 O | GLU | 314 | −8.152 | 14.916 | 46.918 | 1.00 | 24.72 |
| ATOM | 2638 N | PTY | 315 | −10.249 | 14.729 | 46.119 | 1.00 | 21.35 |
| ATOM | 2639 H | PTY | 315 | −11.206 | 14.843 | 46.282 | 1.00 | 0.00 |
| ATOM | 2640 CA | PTY | 315 | −9.854 | 14.204 | 44.820 | 1.00 | 19.78 |
| ATOM | 2641 CB | PTY | 315 | −10.482 | 12.839 | 44.544 | 1.00 | 17.55 |
| ATOM | 2642 CG | PTY | 315 | −9.678 | 11.690 | 45.091 | 1.00 | 14.77 |
| ATOM | 2643 CD1 | PTY | 315 | −8.575 | 11.196 | 44.396 | 1.00 | 9.06 |
| ATOM | 2644 CE1 | PTY | 315 | −7.808 | 10.163 | 44.916 | 1.00 | 12.12 |
| ATOM | 2645 CD2 | PTY | 315 | −9.998 | 11.117 | 46.319 | 1.00 | 14.36 |
| ATOM | 2646 CE2 | PTY | 315 | −9.239 | 10.085 | 46.847 | 1.00 | 14.01 |
| ATOM | 2647 CZ | PTY | 315 | −8.146 | 9.612 | 46.145 | 1.00 | 14.96 |
| ATOM | 2648 OH | PTY | 315 | −7.408 | 8.580 | 46.682 | 1.00 | 15.26 |
| ATOM | 2649 OR1 | PTY | 315 | −6.224 | 9.301 | 48.730 | 1.00 | 15.27 |
| ATOM | 2650 OR2 | PTY | 315 | −5.231 | 9.872 | 46.712 | 1.00 | 14.33 |
| ATOM | 2651 OR3 | PTY | 315 | −5.246 | 7.621 | 47.409 | 1.00 | 16.50 |
| ATOM | 2652 PR | PTY | 315 | −6.018 | 8.864 | 47.331 | 1.00 | 14.86 |
| ATOM | 2653 C | PTY | 315 | −10.349 | 15.218 | 43.808 | 1.00 | 21.32 |
| ATOM | 2654 O | PTY | 315 | −11.354 | 15.892 | 44.034 | 1.00 | 22.46 |
| ATOM | 2655 N | ASP | 316 | −9.629 | 15.351 | 42.707 | 1.00 | 22.70 |
| ATOM | 2656 H | ASP | 316 | −8.875 | 14.753 | 42.558 | 1.00 | 0.00 |
| ATOM | 2657 CA | ASP | 316 | −10.009 | 16.306 | 41.684 | 1.00 | 24.09 |
| ATOM | 2658 CB | ASP | 316 | −8.770 | 16.826 | 40.954 | 1.00 | 24.94 |
| ATOM | 2659 CG | ASP | 316 | −7.853 | 17.622 | 41.860 | 1.00 | 28.90 |
| ATOM | 2660 OD1 | ASP | 316 | −7.849 | 18.865 | 41.756 | 1.00 | 32.00 |
| ATOM | 2661 OD2 | ASP | 316 | −7.140 | 17.004 | 42.681 | 1.00 | 29.88 |
| ATOM | 2662 C | ASP | 316 | −10.981 | 15.692 | 40.698 | 1.00 | 24.49 |
| ATOM | 2663 O | ASP | 316 | −11.148 | 14.473 | 40.646 | 1.00 | 23.60 |
| ATOM | 2664 N | VAL | 317 | −11.644 | 16.559 | 39.948 | 1.00 | 27.16 |
| ATOM | 2665 H | VAL | 317 | −11.475 | 17.521 | 40.029 | 1.00 | 0.00 |
| ATOM | 2666 CA | VAL | 317 | −12.605 | 16.155 | 38.934 | 1.00 | 32.09 |
| ATOM | 2667 CB | VAL | 317 | −14.069 | 16.266 | 39.437 | 1.00 | 35.09 |
| ATOM | 2668 CG1 | VAL | 317 | −14.375 | 15.156 | 40.343 | 1.00 | 36.22 |
| ATOM | 2669 CG2 | VAL | 317 | −14.314 | 17.636 | 40.066 | 1.00 | 36.89 |
| ATOM | 2670 C | VAL | 317 | −12.410 | 17.095 | 37.757 | 1.00 | 30.78 |
| ATOM | 2671 O | VAL | 317 | −11.807 | 18.159 | 37.906 | 1.00 | 28.67 |
| ATOM | 2672 N | LEU | 318 | −12.871 | 16.684 | 36.583 | 1.00 | 33.70 |
| ATOM | 2673 H | LEU | 318 | −13.315 | 15.816 | 36.543 | 1.00 | 0.00 |
| ATOM | 2674 CA | LEU | 318 | −12.745 | 17.513 | 35.395 | 1.00 | 36.88 |
| ATOM | 2675 CB | LEU | 318 | −13.044 | 16.699 | 34.138 | 1.00 | 34.38 |
| ATOM | 2676 CG | LEU | 318 | −12.133 | 15.505 | 33.854 | 1.00 | 32.08 |
| ATOM | 2677 CD1 | LEU | 318 | −12.560 | 14.864 | 32.553 | 1.00 | 33.40 |
| ATOM | 2678 CD2 | LEU | 318 | −10.678 | 15.939 | 33.775 | 1.00 | 30.49 |
| ATOM | 2679 C | LEU | 318 | −13.698 | 18.700 | 35.492 | 1.00 | 41.41 |
| ATOM | 2680 O | LEU | 318 | −14.768 | 18.604 | 36.108 | 1.00 | 41.34 |
| ATOM | 2681 N | ASP | 319 | −13.282 | 19.821 | 34.911 | 1.00 | 46.71 |
| ATOM | 2682 H | ASP | 319 | −12.447 | 19.843 | 34.406 | 1.00 | 0.00 |
| ATOM | 2683 CA | ASP | 319 | −14.072 | 21.048 | 34.913 | 1.00 | 51.29 |
| ATOM | 2684 CB | ASP | 319 | −13.204 | 22.239 | 35.340 | 1.00 | 53.24 |
| ATOM | 2685 CG | ASP | 319 | −11.958 | 22.400 | 34.479 | 1.00 | 55.43 |
| ATOM | 2686 OD1 | ASP | 319 | −12.065 | 22.950 | 33.361 | 1.00 | 58.31 |
| ATOM | 2687 OD2 | ASP | 319 | −10.868 | 21.982 | 34.923 | 1.00 | 58.61 |
| ATOM | 2688 C | ASP | 319 | −14.682 | 21.306 | 33.535 | 1.00 | 52.86 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2689 | O | ASP | 319 | −14.195 | 20.701 | 32.549 | 1.00 | 53.27 |
| ATOM | 2690 | OT | ASP | 319 | −15.634 | 22.114 | 33.459 | 1.00 | 54.58 |
| ATOM | 2691 | OH2 | H2O | 503 | −16.395 | 6.573 | 53.935 | 1.00 | 13.04 |
| ATOM | 2692 | H1 | H2O | 501 | −15.625 | 7.149 | 54.126 | 1.00 | 0.00 |
| ATOM | 2693 | H2 | H2O | 501 | −16.189 | 6.220 | 53.062 | 1.00 | 0.00 |
| ATOM | 2694 | OH2 | H2O | 502 | −6.900 | −1.703 | 48.537 | 1.00 | 15.81 |
| ATOM | 2695 | H1 | H2O | 502 | −6.073 | −2.133 | 48.827 | 1.00 | 0.00 |
| ATOM | 2696 | H2 | H2O | 502 | −7.012 | −1.023 | 49.224 | 1.00 | 0.00 |
| ATOM | 2697 | OH2 | H2O | 503 | −7.775 | 0.446 | 50.612 | 1.00 | 12.12 |
| ATOM | 2698 | H1 | H2O | 503 | −8.328 | 0.785 | 51.329 | 1.00 | 0.00 |
| ATOM | 2699 | H2 | H2O | 503 | −8.364 | 0.608 | 49.869 | 1.00 | 0.00 |
| ATOM | 2700 | OH2 | H2O | 504 | −5.965 | 5.376 | 45.701 | 1.00 | 13.82 |
| ATOM | 2701 | H1 | H2O | 504 | −5.838 | 6.191 | 46.188 | 1.00 | 0.00 |
| ATOM | 2702 | H2 | H2O | 504 | −5.040 | 5.192 | 45.431 | 1.00 | 0.00 |
| ATOM | 2703 | OH2 | H2O | 505 | −14.971 | −6.776 | 51.457 | 1.00 | 11.75 |
| ATOM | 2704 | H1 | H2O | 505 | −14.401 | −7.005 | 50.693 | 1.00 | 0.00 |
| ATOM | 2705 | H2 | H2O | 505 | −15.747 | −6.411 | 50.986 | 1.00 | 0.00 |
| ATOM | 2706 | OH2 | H2O | 506 | −7.399 | −1.565 | 45.723 | 1.00 | 20.80 |
| ATOM | 2707 | H1 | H2O | 506 | −6.869 | −0.820 | 45.388 | 1.00 | 0.00 |
| ATOM | 2708 | H2 | H2O | 506 | −7.127 | −1.603 | 46.669 | 1.00 | 0.00 |
| ATOM | 2709 | OH2 | H2O | 507 | −3.458 | 7.189 | 49.505 | 1.00 | 12.46 |
| ATOM | 2710 | H1 | H2O | 507 | −3.854 | 6.375 | 49.171 | 1.00 | 0.00 |
| ATOM | 2711 | H2 | H2O | 507 | −4.035 | 7.857 | 49.121 | 1.00 | 0.00 |
| ATOM | 2712 | OH2 | H2O | 508 | −19.524 | 4.162 | 75.938 | 1.00 | 31.54 |
| ATOM | 2713 | H1 | H2O | 508 | −20.107 | 4.703 | 76.513 | 1.00 | 0.00 |
| ATOM | 2714 | H2 | H2O | 508 | −19.510 | 4.732 | 75.158 | 1.00 | 0.00 |
| ATOM | 2715 | OH2 | H2O | 509 | 11.153 | 11.020 | 41.619 | 1.00 | 23.22 |
| ATOM | 2716 | H1 | H2O | 509 | 10.658 | 10.668 | 40.869 | 1.00 | 0.00 |
| ATOM | 2717 | H2 | H2O | 509 | 10.757 | 11.895 | 41.712 | 1.00 | 0.00 |
| ATOM | 2718 | OH2 | H2O | 510 | −17.729 | −5.463 | 50.658 | 1.00 | 8.16 |
| ATOM | 2719 | H1 | H2O | 510 | −18.166 | −5.105 | 49.866 | 1.00 | 0.00 |
| ATOM | 2720 | H2 | H2O | 510 | −18.454 | −6.018 | 50.978 | 1.00 | 0.00 |
| ATOM | 2721 | OH2 | H2O | 511 | −2.939 | 4.711 | 45.111 | 1.00 | 12.99 |
| ATOM | 2722 | H1 | H2O | 511 | −2.168 | 4.703 | 45.673 | 1.00 | 0.00 |
| ATOM | 2723 | H2 | H2O | 511 | −2.789 | 3.917 | 44.596 | 1.00 | 0.00 |
| ATOM | 2724 | OH2 | H2O | 512 | −14.697 | 8.482 | 54.840 | 1.00 | 28.53 |
| ATOM | 2725 | H1 | H2O | 512 | −15.286 | 8.807 | 55.530 | 1.00 | 0.00 |
| ATOM | 2726 | H2 | H2O | 512 | −13.856 | 8.877 | 55.112 | 1.00 | 0.00 |
| ATOM | 2727 | OH2 | H2O | 513 | −4.301 | −4.082 | 45.672 | 1.00 | 22.83 |
| ATOM | 2728 | H1 | H2O | 513 | −3.747 | −3.518 | 45.097 | 1.00 | 0.00 |
| ATOM | 2729 | H2 | H2O | 513 | −5.176 | −3.940 | 45.269 | 1.00 | 0.00 |
| ATOM | 2730 | OH2 | H2O | 514 | −21.713 | 7.798 | 61.095 | 1.00 | 18.35 |
| ATOM | 2731 | H1 | H2O | 514 | −21.035 | 7.798 | 61.588 | 1.00 | 0.00 |
| ATOM | 2732 | H2 | H2O | 514 | −22.251 | 8.537 | 60.778 | 1.00 | 0.00 |
| ATOM | 2733 | OH2 | H2O | 515 | −10.843 | 5.000 | 40.733 | 1.00 | 28.99 |
| ATOM | 2734 | H1 | H2O | 515 | −10.540 | 4.529 | 41.519 | 1.00 | 0.00 |
| ATOM | 2735 | H2 | H2O | 515 | −10.110 | 4.889 | 40.111 | 1.00 | 0.00 |
| ATOM | 2736 | OH2 | H2O | 516 | 1.069 | 6.001 | 27.806 | 1.00 | 27.31 |
| ATOM | 2737 | H1 | H2O | 516 | 1.435 | 6.888 | 27.776 | 1.00 | 0.00 |
| ATOM | 2738 | H2 | H2O | 516 | 0.143 | 6.122 | 27.559 | 1.00 | 0.00 |
| ATOM | 2739 | OH2 | H2O | 517 | −4.403 | −3.111 | 48.506 | 1.00 | 19.12 |
| ATOM | 2740 | H1 | H2O | 517 | −4.371 | −3.215 | 47.537 | 1.00 | 0.00 |
| ATOM | 2741 | H2 | H2O | 517 | −3.595 | −2.596 | 48.690 | 1.00 | 0.00 |
| ATOM | 2742 | OH2 | H2O | 518 | −20.848 | 12.059 | 58.636 | 1.00 | 30.17 |
| ATOM | 2743 | H1 | H2O | 518 | −20.732 | 12.086 | 57.675 | 1.00 | 0.00 |
| ATOM | 2744 | H2 | H2O | 518 | −21.337 | 11.237 | 58.756 | 1.00 | 0.00 |
| ATOM | 2745 | OH2 | H2O | 519 | −7.330 | −4.001 | 44.530 | 1.00 | 20.45 |
| ATOM | 2746 | H1 | H2O | 519 | −7.479 | −3.098 | 44.898 | 1.00 | 0.00 |
| ATOM | 2747 | H2 | H2O | 519 | −7.935 | −4.524 | 45.062 | 1.00 | 0.00 |
| ATOM | 2748 | OH2 | H2O | 520 | −12.664 | 0.989 | 38.964 | 1.00 | 15.59 |
| ATOM | 2749 | H1 | H2O | 520 | −12.180 | 0.157 | 39.070 | 1.00 | 0.00 |
| ATOM | 2750 | H2 | H2O | 520 | −13.550 | 0.682 | 39.238 | 1.00 | 0.00 |
| ATOM | 2751 | OH2 | H2O | 521 | −11.379 | 10.139 | 30.946 | 1.00 | 26.07 |
| ATOM | 2752 | H1 | H2O | 521 | −11.624 | 10.977 | 30.530 | 1.00 | 0.00 |
| ATOM | 2753 | H2 | H2O | 521 | −11.994 | 9.525 | 30.519 | 1.00 | 0.00 |
| ATOM | 2754 | OH2 | H2O | 522 | −15.662 | 9.282 | 47.198 | 1.00 | 17.30 |
| ATOM | 2755 | H1 | H2O | 522 | −15.240 | 9.703 | 46.450 | 1.00 | 0.00 |
| ATOM | 2756 | H2 | H2O | 522 | −16.316 | 9.967 | 47.478 | 1.00 | 0.00 |
| ATOM | 2757 | OH2 | H2O | 523 | −11.947 | −18.788 | 49.297 | 1.00 | 31.49 |
| ATOM | 2758 | H1 | H2O | 523 | −11.710 | −18.432 | 48.437 | 1.00 | 0.00 |
| ATOM | 2759 | H2 | H2O | 523 | −12.293 | −17.992 | 49.754 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | x | y | z | occ | temp factor |
|---|---|---|---|---|---|---|---|
| ATOM | 2760 OH2 | H2O 524 | 6.740 | 2.001 | 42.957 | 1.00 | 21.38 |
| ATOM | 2761 H1 | H2O 524 | 5.847 | 2.141 | 43.289 | 1.00 | 0.00 |
| ATOM | 2762 H2 | H2O 524 | 6.864 | 1.047 | 42.891 | 1.00 | 0.00 |
| ATOM | 2763 OH2 | H2O 525 | −8.682 | 6.518 | 44.398 | 1.00 | 27.19 |
| ATOM | 2764 H1 | H2O 525 | −7.791 | 6.155 | 44.453 | 1.00 | 0.00 |
| ATOM | 2765 H2 | H2O 525 | −8.649 | 7.215 | 45.061 | 1.00 | 0.00 |
| ATOM | 2766 OH2 | H2O 526 | −14.480 | 3.578 | 44.839 | 1.00 | 22.05 |
| ATOM | 2767 H1 | H2O 526 | −15.718 | 3.347 | 45.149 | 1.00 | 0.00 |
| ATOM | 2768 H2 | H2O 526 | −14.551 | 4.227 | 45.498 | 1.00 | 0.00 |
| ATOM | 2769 OH2 | H2O 527 | 4.492 | 23.057 | 38.874 | 1.00 | 25.33 |
| ATOM | 2770 H1 | H2O 527 | 4.800 | 22.472 | 38.173 | 1.00 | 0.00 |
| ATOM | 2771 H2 | H2O 527 | 5.246 | 22.944 | 39.473 | 1.00 | 0.00 |
| ATOM | 2772 OH2 | H2O 528 | 0.375 | −17.917 | 41.574 | 1.00 | 56.36 |
| ATOM | 2773 H1 | H2O 528 | −0.351 | −18.113 | 42.169 | 1.00 | 0.00 |
| ATOM | 2774 H2 | H2O 528 | −0.043 | −17.548 | 40.796 | 1.00 | 0.00 |
| ATOM | 2775 OH2 | H2O 529 | 7.016 | 14.850 | 51.046 | 1.00 | 20.70 |
| ATOM | 2776 H1 | H2O 529 | 6.142 | 14.448 | 50.870 | 1.00 | 0.00 |
| ATOM | 2777 H2 | H2O 529 | 6.980 | 15.645 | 50.511 | 1.00 | 0.00 |
| ATOM | 2778 OH2 | H2O 530 | −7.683 | −1.801 | 42.232 | 1.00 | 34.83 |
| ATOM | 2779 H1 | H2O 530 | −8.052 | −1.273 | 42.957 | 1.00 | 0.00 |
| ATOM | 2780 H2 | H2O 530 | −7.249 | −2.522 | 42.702 | 1.00 | 0.00 |
| ATOM | 2781 OH2 | H2O 531 | −21.235 | 6.653 | 69.461 | 1.00 | 40.97 |
| ATOM | 2782 H1 | H2O 531 | −22.089 | 6.966 | 69.119 | 1.00 | 0.00 |
| ATOM | 2783 H2 | H2O 531 | −21.371 | 6.744 | 70.411 | 1.00 | 0.00 |
| ATOM | 2784 OH2 | H2O 532 | 0.051 | −0.240 | 27.111 | 1.00 | 38.10 |
| ATOM | 2785 H1 | H2O 532 | −0.526 | −0.554 | 26.406 | 1.00 | 0.00 |
| ATOM | 2786 H2 | H2O 532 | 0.153 | 0.695 | 26.895 | 1.00 | 0.00 |
| ATOM | 2787 OH2 | H2O 533 | 4.720 | 13.526 | 50.274 | 1.00 | 24.25 |
| ATOM | 2788 H1 | H2O 533 | 3.779 | 13.360 | 50.353 | 1.00 | 0.00 |
| ATOM | 2789 H2 | H2O 533 | 5.030 | 12.691 | 49.901 | 1.00 | 0.00 |
| ATOM | 2790 OH2 | H2O 535 | −24.439 | −4.493 | 65.220 | 1.00 | 19.89 |
| ATOM | 2791 H1 | H2O 535 | −23.921 | −4.800 | 64.468 | 1.00 | 0.00 |
| ATOM | 2792 H2 | H2O 535 | −23.970 | −4.918 | 65.943 | 1.00 | 0.00 |
| ATOM | 2793 OH2 | H2O 536 | −24.821 | −8.124 | 64.414 | 1.00 | 26.52 |
| ATOM | 2794 H1 | H2O 536 | −25.733 | −8.277 | 64.141 | 1.00 | 0.00 |
| ATOM | 2795 H2 | H2O 536 | −24.637 | −7.232 | 64.092 | 1.00 | 0.00 |
| ATOM | 2796 OH2 | H2O 537 | −1.448 | 9.507 | 51.754 | 1.00 | 14.14 |
| ATOM | 2797 H1 | H2O 537 | −2.234 | 9.866 | 52.178 | 1.00 | 0.00 |
| ATOM | 2798 H2 | H2O 537 | −1.227 | 8.752 | 52.319 | 1.00 | 0.00 |
| ATOM | 2799 OH2 | H2O 538 | −19.810 | −23.909 | 45.616 | 1.00 | 42.72 |
| ATOM | 2800 H1 | H2O 538 | −20.226 | −24.776 | 45.518 | 1.00 | 0.00 |
| ATOM | 2801 H2 | H2O 538 | −19.298 | −24.029 | 46.420 | 1.00 | 0.00 |
| ATOM | 2802 OH2 | H2O 539 | −6.034 | −10.821 | 42.457 | 1.00 | 29.94 |
| ATOM | 2803 H1 | H2O 539 | −6.800 | −10.777 | 43.033 | 1.00 | 0.00 |
| ATOM | 2804 H2 | H2O 539 | −5.304 | −10.964 | 43.068 | 1.00 | 0.00 |
| ATOM | 2805 OH2 | H2O 540 | −20.033 | 10.958 | 50.001 | 1.00 | 31.83 |
| ATOM | 2806 H1 | H2O 540 | −19.256 | 10.718 | 50.512 | 1.00 | 0.00 |
| ATOM | 2807 H2 | H2O 540 | −20.491 | 10.121 | 49.920 | 1.00 | 0.00 |
| ATOM | 2808 OH2 | H2O 541 | −5.125 | −7.851 | 62.359 | 1.00 | 38.63 |
| ATOM | 2809 H1 | H2O 541 | −4.372 | −8.168 | 61.862 | 1.00 | 0.00 |
| ATOM | 2810 H2 | H2O 541 | −5.411 | −7.104 | 61.798 | 1.00 | 0.00 |
| ATOM | 2811 OH2 | H2O 542 | −1.080 | 20.333 | 46.689 | 1.00 | 26.15 |
| ATOM | 2812 H1 | H2O 542 | −1.337 | 19.477 | 47.057 | 1.00 | 0.00 |
| ATOM | 2813 H2 | H2O 542 | −1.916 | 20.809 | 46.638 | 1.00 | 0.00 |
| ATOM | 2814 OH2 | H2O 543 | 5.975 | 26.290 | 37.583 | 1.00 | 43.59 |
| ATOM | 2815 H1 | H2O 543 | 6.265 | 26.840 | 36.852 | 1.00 | 0.00 |
| ATOM | 2816 H2 | H2O 543 | 6.741 | 26.247 | 38.153 | 1.00 | 0.00 |
| ATOM | 2817 OH2 | H2O 544 | −13.632 | −13.848 | 50.081 | 1.00 | 27.21 |
| ATOM | 2818 H1 | H2O 544 | −13.441 | −13.263 | 50.817 | 1.00 | 0.00 |
| ATOM | 2819 H2 | H2O 544 | −13.685 | −13.228 | 49.342 | 1.00 | 0.00 |
| ATOM | 2820 OH2 | H2O 545 | 6.897 | 4.096 | 46.579 | 1.00 | 32.58 |
| ATOM | 2821 H1 | H2O 545 | 7.538 | 4.515 | 47.182 | 1.00 | 0.00 |
| ATOM | 2822 H2 | H2O 545 | 7.296 | 3.250 | 46.353 | 1.00 | 0.00 |
| ATOM | 2823 OH2 | H2O 546 | −19.007 | 6.577 | 73.627 | 1.00 | 51.06 |
| ATOM | 2824 H1 | H2O 546 | −18.833 | 7.495 | 73.390 | 1.00 | 0.00 |
| ATOM | 2825 H2 | H2O 546 | −18.795 | 6.148 | 72.791 | 1.00 | 0.00 |
| ATOM | 2826 OH2 | H2O 547 | −0.107 | 9.991 | 22.576 | 1.00 | 43.45 |
| ATOM | 2827 H1 | H2O 547 | −0.622 | 10.655 | 23.054 | 1.00 | 0.00 |
| ATOM | 2828 H2 | H2O 547 | 0.140 | 10.441 | 21.766 | 1.00 | 0.00 |
| ATOM | 2829 OH2 | H2O 549 | −20.845 | −8.815 | 51.470 | 1.00 | 32.88 |
| ATOM | 2830 H1 | H2O 549 | −20.910 | −9.731 | 51.186 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2831 | H2 | H2O | 549 | −20.734 | −8.346 | 50.637 | 1.00 | 0.00 |
| ATOM | 2832 | OH2 | H2O | 550 | −18.995 | −8.847 | 74.340 | 1.00 | 33.79 |
| ATOM | 2833 | H1 | H2O | 550 | −19.031 | −9.373 | 73.541 | 1.00 | 0.00 |
| ATOM | 2834 | H2 | H2O | 550 | −18.620 | −8.012 | 74.046 | 1.00 | 0.00 |
| ATOM | 2835 | OH2 | H2O | 551 | −29.193 | 1.529 | 65.322 | 1.00 | 28.70 |
| ATOM | 2836 | H1 | H2O | 551 | −29.521 | 1.026 | 66.091 | 1.00 | 0.00 |
| ATOM | 2837 | H2 | H2O | 551 | −28.243 | 1.541 | 65.504 | 1.00 | 0.00 |
| ATOM | 2838 | OH2 | H2O | 552 | −9.376 | −14.036 | 60.634 | 1.00 | 39.70 |
| ATOM | 2839 | H1 | H2O | 552 | −9.678 | −14.141 | 59.724 | 1.00 | 0.00 |
| ATOM | 2840 | H2 | H2O | 552 | −8.558 | −14.547 | 60.629 | 1.00 | 0.00 |
| ATOM | 2841 | OH2 | H2O | 553 | 15.303 | 7.535 | 43.610 | 1.00 | 43.10 |
| ATOM | 2842 | H1 | H2O | 553 | 15.256 | 8.508 | 43.528 | 1.00 | 0.00 |
| ATOM | 2843 | H2 | H2O | 553 | 14.945 | 7.223 | 42.779 | 1.00 | 0.00 |
| ATOM | 2844 | OH2 | H2O | 554 | −6.351 | −6.041 | 58.195 | 1.00 | 39.35 |
| ATOM | 2845 | H1 | H2O | 554 | −5.433 | −5.940 | 58.470 | 1.00 | 0.00 |
| ATOM | 2846 | H2 | H2O | 554 | −6.453 | −6.976 | 58.404 | 1.00 | 0.00 |
| ATOM | 2847 | OH2 | H2O | 555 | −26.688 | −2.898 | 68.239 | 1.00 | 26.60 |
| ATOM | 2848 | H1 | H2O | 555 | −27.261 | −2.128 | 68.123 | 1.00 | 0.00 |
| ATOM | 2849 | H2 | H2O | 555 | −26.730 | −3.318 | 67.372 | 1.00 | 0.00 |
| ATOM | 2850 | OH2 | H2O | 556 | −27.507 | −2.530 | 64.808 | 1.00 | 35.40 |
| ATOM | 2851 | H1 | H2O | 556 | −26.716 | −3.098 | 64.836 | 1.00 | 0.00 |
| ATOM | 2852 | H2 | H2O | 556 | −27.089 | −1.666 | 64.684 | 1.00 | 0.00 |
| ATOM | 2853 | OH2 | H2O | 557 | −3.466 | 0.091 | 55.103 | 1.00 | 31.58 |
| ATOM | 2854 | H1 | H2O | 557 | −4.116 | 0.662 | 54.672 | 1.00 | 0.00 |
| ATOM | 2855 | H2 | H2O | 557 | −3.730 | 0.129 | 56.022 | 1.00 | 0.00 |
| ATOM | 2856 | OH2 | H2O | 558 | −17.363 | 11.081 | 48.313 | 1.00 | 34.37 |
| ATOM | 2857 | H1 | H2O | 558 | −18.067 | 11.741 | 48.280 | 1.00 | 0.00 |
| ATOM | 2858 | H2 | H2O | 558 | −17.568 | 10.638 | 49.148 | 1.00 | 0.00 |
| ATOM | 2859 | OH2 | H2O | 559 | −5.182 | 1.100 | 51.170 | 1.00 | 35.10 |
| ATOM | 2860 | H1 | H2O | 559 | −6.102 | 0.891 | 50.910 | 1.00 | 0.00 |
| ATOM | 2861 | H2 | H2O | 559 | −4.870 | 0.273 | 51.539 | 1.00 | 0.00 |
| ATOM | 2862 | OH2 | H2O | 560 | −1.672 | −2.171 | 49.168 | 1.00 | 30.93 |
| ATOM | 2863 | H1 | H2O | 560 | −1.378 | −1.786 | 48.327 | 1.00 | 0.00 |
| ATOM | 2864 | H2 | H2O | 560 | −1.186 | −1.638 | 49.811 | 1.00 | 0.00 |
| ATOM | 2865 | OH2 | H2O | 561 | −12.968 | −16.434 | 50.268 | 1.00 | 38.85 |
| ATOM | 2866 | H1 | H2O | 561 | −13.869 | −16.305 | 49.955 | 1.00 | 0.00 |
| ATOM | 2867 | H2 | H2O | 561 | −12.756 | −15.504 | 50.450 | 1.00 | 0.00 |
| ATOM | 2868 | OH2 | H2O | 563 | 8.438 | 5.804 | 48.097 | 1.00 | 48.55 |
| ATOM | 2869 | H1 | H2O | 563 | 7.987 | 5.826 | 48.951 | 1.00 | 0.00 |
| ATOM | 2870 | H2 | H2O | 563 | 9.187 | 6.397 | 48.249 | 1.00 | 0.00 |
| ATOM | 2871 | OH2 | H2O | 569 | −18.518 | 8.907 | 70.572 | 1.00 | 33.67 |
| ATOM | 2872 | H1 | H2O | 569 | −19.475 | 8.882 | 70.611 | 1.00 | 0.00 |
| ATOM | 2873 | H2 | H2O | 569 | −18.362 | 9.599 | 69.917 | 1.00 | 0.00 |
| ATOM | 2874 | OH2 | H2O | 570 | −3.123 | 15.254 | 51.267 | 1.00 | 44.68 |
| ATOM | 2875 | H1 | H2O | 570 | −2.857 | 15.725 | 50.474 | 1.00 | 0.00 |
| ATOM | 2876 | H2 | H2O | 570 | −2.642 | 14.427 | 51.213 | 1.00 | 0.00 |
| ATOM | 2877 | OH2 | H2O | 572 | −4.725 | 17.961 | 46.351 | 1.00 | 28.78 |
| ATOM | 2878 | H1 | H2O | 572 | −5.641 | 18.255 | 46.416 | 1.00 | 0.00 |
| ATOM | 2879 | H2 | H2O | 572 | −4.454 | 18.331 | 45.500 | 1.00 | 0.00 |
| ATOM | 2880 | OH2 | H2O | 573 | −17.831 | −26.994 | 47.079 | 1.00 | 47.81 |
| ATOM | 2881 | H1 | H2O | 573 | −18.168 | −27.861 | 47.345 | 1.00 | 0.00 |
| ATOM | 2882 | H2 | H2O | 573 | −16.954 | −27.236 | 46.737 | 1.00 | 0.00 |
| ATOM | 2883 | OH2 | H2O | 574 | −11.347 | −10.955 | 43.461 | 1.00 | 27.59 |
| ATOM | 2884 | H1 | H2O | 574 | −12.285 | −11.031 | 43.636 | 1.00 | 0.00 |
| ATOM | 2885 | H2 | H2O | 574 | −11.302 | −10.452 | 42.652 | 1.00 | 0.00 |
| ATOM | 2886 | OH2 | H2O | 575 | −7.797 | 6.237 | 24.140 | 1.00 | 43.37 |
| ATOM | 2887 | H1 | H2O | 575 | −8.151 | 5.827 | 23.336 | 1.00 | 0.00 |
| ATOM | 2888 | H2 | H2O | 575 | −7.042 | 6.728 | 23.794 | 1.00 | 0.00 |
| ATOM | 2889 | OH2 | H2O | 576 | −2.183 | 3.330 | 69.045 | 1.00 | 33.93 |
| ATOM | 2890 | H1 | H2O | 576 | −3.094 | 3.131 | 68.802 | 1.00 | 0.00 |
| ATOM | 2891 | H2 | H2O | 576 | −1.964 | 4.076 | 68.483 | 1.00 | 0.00 |
| ATOM | 2892 | OH2 | H2O | 577 | −0.855 | −5.759 | 42.695 | 1.00 | 25.76 |
| ATOM | 2893 | H1 | H2O | 577 | −1.157 | −5.188 | 41.984 | 1.00 | 0.00 |
| ATOM | 2894 | H2 | H2O | 577 | −0.947 | −6.645 | 42.342 | 1.00 | 0.00 |
| ATOM | 2895 | OH2 | H2O | 579 | 3.333 | 6.242 | 53.401 | 1.00 | 50.25 |
| ATOM | 2896 | H1 | H2O | 579 | 3.451 | 5.332 | 53.701 | 1.00 | 0.00 |
| ATOM | 2897 | H2 | H2O | 579 | 4.217 | 6.487 | 53.105 | 1.00 | 0.00 |
| ATOM | 2898 | OH2 | H2O | 580 | −2.444 | 2.334 | 61.039 | 1.00 | 31.46 |
| ATOM | 2899 | H1 | H2O | 580 | −3.317 | 2.148 | 61.413 | 1.00 | 0.00 |
| ATOM | 2900 | H2 | H2O | 580 | −2.660 | 3.049 | 60.423 | 1.00 | 0.00 |
| ATOM | 2901 | OH2 | H2O | 581 | −15.655 | 7.091 | 35.775 | 1.00 | 37.09 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2902 | H1 | H2O | 581 | −14.694 | 7.066 | 35.713 | 1.00 | 0.00 |
| ATOM | 2903 | H2 | H2O | 581 | −5.902 | 6.185 | 35.548 | 1.00 | 0.00 |
| ATOM | 2904 | OH2 | H2O | 582 | 2.063 | 24.320 | 47.146 | 1.00 | 51.91 |
| ATOM | 2905 | H1 | H2O | 582 | 1.349 | 24.295 | 46.468 | 1.00 | 0.00 |
| ATOM | 2906 | H2 | H2O | 582 | 2.119 | 25.295 | 47.172 | 1.00 | 0.00 |
| ATOM | 2907 | OH2 | H2O | 583 | −6.779 | −2.271 | 28.633 | 1.00 | 40.33 |
| ATOM | 2908 | H1 | H2O | 583 | −6.999 | −1.707 | 27.886 | 1.00 | 0.00 |
| ATOM | 2909 | H2 | H2O | 583 | −7.664 | −2.443 | 28.970 | 1.00 | 0.00 |
| ATOM | 2910 | OH2 | H2O | 584 | 11.799 | 8.386 | 47.735 | 1.00 | 53.26 |
| ATOM | 2911 | H1 | H2O | 584 | 12.475 | 8.197 | 47.055 | 1.00 | 0.00 |
| ATOM | 2912 | H2 | H2O | 584 | 11.657 | 9.325 | 47.602 | 1.00 | 0.00 |
| ATOM | 2913 | OH2 | H2O | 585 | −13.524 | 6.050 | 40.840 | 1.00 | 43.92 |
| ATOM | 2914 | H1 | H2O | 585 | −12.588 | 5.799 | 40.707 | 1.00 | 0.00 |
| ATOM | 2915 | H2 | H2O | 585 | −13.692 | 5.671 | 41.705 | 1.00 | 0.00 |
| ATOM | 2916 | OH2 | H2O | 586 | −20.205 | −18.799 | 46.340 | 1.00 | 35.53 |
| ATOM | 2917 | H1 | H2O | 586 | −20.221 | −18.803 | 47.304 | 1.00 | 0.00 |
| ATOM | 2918 | H2 | H2O | 586 | −19.889 | −17.914 | 46.132 | 1.00 | 0.00 |
| ATOM | 2919 | OH2 | H2O | 587 | 9.685 | 9.586 | 28.857 | 1.00 | 23.20 |
| ATOM | 2920 | H1 | H2O | 587 | 8.918 | 9.519 | 28.276 | 1.00 | 0.00 |
| ATOM | 2921 | H2 | H2O | 587 | 10.422 | 9.526 | 28.241 | 1.00 | 0.00 |
| ATOM | 2922 | OH2 | H2O | 588 | −18.278 | 15.597 | 52.143 | 1.00 | 37.65 |
| ATOM | 2923 | H1 | H2O | 588 | −17.821 | 15.619 | 52.985 | 1.00 | 0.00 |
| ATOM | 2924 | H2 | H2O | 588 | −18.442 | 14.652 | 52.046 | 1.00 | 0.00 |
| ATOM | 2925 | OH2 | H2O | 589 | 12.004 | 9.442 | 43.787 | 1.00 | 36.10 |
| ATOM | 2926 | H1 | H2O | 589 | 11.783 | 9.993 | 43.008 | 1.00 | 0.00 |
| ATOM | 2927 | H2 | H2O | 589 | 12.929 | 9.683 | 43.951 | 1.00 | 0.00 |
| ATOM | 2928 | OH2 | H2O | 592 | −25.871 | −5.699 | 57.447 | 1.00 | 24.88 |
| ATOM | 2929 | H1 | H2O | 592 | −26.445 | −5.733 | 58.226 | 1.00 | 0.00 |
| ATOM | 2930 | H2 | H2O | 592 | −25.440 | −4.847 | 57.572 | 1.00 | 0.00 |
| ATOM | 2931 | OH2 | H2O | 593 | −13.120 | 10.109 | 38.496 | 1.00 | 33.36 |
| ATOM | 2932 | H1 | H2O | 593 | −12.211 | 9.803 | 38.544 | 1.00 | 0.00 |
| ATOM | 2933 | H2 | H2O | 593 | −13.553 | 9.578 | 39.173 | 1.00 | 0.00 |
| ATOM | 2934 | OH2 | H2O | 594 | −2.642 | 17.050 | 48.010 | 1.00 | 31.60 |
| ATOM | 2935 | H1 | H2O | 594 | −2.754 | 17.725 | 48.682 | 1.00 | 0.00 |
| ATOM | 2936 | H2 | H2O | 594 | −3.443 | 17.194 | 47.462 | 1.00 | 0.00 |
| ATOM | 2937 | OH2 | H2O | 595 | 13.645 | 7.886 | 45.763 | 1.00 | 41.58 |
| ATOM | 2938 | H1 | H2O | 595 | 14.505 | 7.762 | 46.191 | 1.00 | 0.00 |
| ATOM | 2939 | H2 | H2O | 595 | 13.921 | 7.739 | 44.837 | 1.00 | 0.00 |
| ATOM | 2940 | OH2 | H2O | 596 | 11.562 | 6.029 | 45.973 | 1.00 | 50.87 |
| ATOM | 2941 | H1 | H2O | 596 | 11.768 | 5.826 | 46.893 | 1.00 | 0.00 |
| ATOM | 2942 | H2 | H2O | 596 | 12.242 | 6.714 | 45.805 | 1.00 | 0.00 |
| ATOM | 2943 | OH2 | H2O | 597 | 8.860 | −0.601 | 32.747 | 1.00 | 41.20 |
| ATOM | 2944 | H1 | H2O | 597 | 8.422 | −0.896 | 31.940 | 1.00 | 0.00 |
| ATOM | 2945 | H2 | H2O | 597 | 8.194 | −0.773 | 33.420 | 1.00 | 0.00 |
| ATOM | 2946 | OH2 | H2O | 598 | 14.739 | 10.248 | 44.027 | 1.00 | 61.01 |
| ATOM | 2947 | H1 | H2O | 598 | 14.760 | 11.112 | 43.590 | 1.00 | 0.00 |
| ATOM | 2948 | H2 | H2O | 598 | 15.049 | 10.456 | 44.920 | 1.00 | 0.00 |
| ATOM | 2949 | OH2 | H2O | 599 | −14.578 | −0.522 | 39.901 | 1.00 | 47.63 |
| ATOM | 2950 | H1 | H2O | 599 | −15.399 | −0.544 | 39.178 | 1.00 | 0.00 |
| ATOM | 2951 | H2 | H2O | 599 | −14.534 | −1.454 | 39.996 | 1.00 | 0.00 |
| ATOM | 2952 | OH2 | H2O | 601 | 11.055 | 1.025 | 33.198 | 1.00 | 33.67 |
| ATOM | 2953 | H1 | H2O | 601 | 10.283 | 0.434 | 33.099 | 1.00 | 0.00 |
| ATOM | 2954 | H2 | H2O | 601 | 11.463 | 0.920 | 32.328 | 1.00 | 0.00 |
| ATOM | 2955 | OH2 | H2O | 602 | −7.939 | 5.076 | 74.158 | 1.00 | 35.51 |
| ATOM | 2956 | H1 | H2O | 602 | −7.267 | 5.133 | 74.849 | 1.00 | 0.00 |
| ATOM | 2957 | H2 | H2O | 602 | −7.784 | 4.156 | 73.888 | 1.00 | 0.00 |
| ATOM | 2958 | OH2 | H2O | 603 | −16.636 | −12.874 | 62.037 | 1.00 | 36.29 |
| ATOM | 2959 | H1 | H2O | 603 | −16.225 | −13.402 | 61.337 | 1.00 | 0.00 |
| ATOM | 2960 | H2 | H2O | 603 | −15.849 | −12.404 | 62.373 | 1.00 | 0.00 |
| ATOM | 2961 | OH2 | H2O | 604 | −18.358 | −20.653 | 39.617 | 1.00 | 36.43 |
| ATOM | 2962 | H1 | H2O | 604 | −17.998 | −20.559 | 40.507 | 1.00 | 0.00 |
| ATOM | 2963 | H2 | H2O | 604 | −17.638 | −20.31 | 39.059 | 1.00 | 0.00 |
| ATOM | 2964 | OH2 | H2O | 605 | −5.855 | −5.527 | 60.942 | 1.00 | 35.83 |
| ATOM | 2965 | H1 | H2O | 605 | −6.476 | −5.558 | 60.199 | 1.00 | 0.00 |
| ATOM | 2966 | H2 | H2O | 605 | −5.861 | −4.592 | 61.176 | 1.00 | 0.00 |
| ATOM | 2967 | OH2 | H2O | 606 | −7.119 | −2.334 | 35.830 | 1.00 | 31.03 |
| ATOM | 2968 | H1 | H2O | 606 | −7.787 | −1.638 | 35.776 | 1.00 | 0.00 |
| ATOM | 2969 | H2 | H2O | 606 | −7.562 | −3.033 | 35.342 | 1.00 | 0.00 |
| ATOM | 2970 | OH2 | H2O | 608 | −4.292 | 10.348 | 58.969 | 1.00 | 59.16 |
| ATOM | 2971 | H1 | H2O | 608 | −3.677 | 9.723 | 59.379 | 1.00 | 0.00 |
| ATOM | 2972 | H2 | H2O | 608 | −3.683 | 10.944 | 58.518 | 1.00 | 0.00 |

TABLE 21-continued

Coordinates for the 3D structure of ZAP-NC:ζ1*

REMARK FILENAME="test-slow.pdb"
REMARK TOPH19.pep -MACRO for protein sequence
created by user: marcos

| Atom Number | Atom type | amino acid residue | | x | y | z | occ | temp factor |
|---|---|---|---|---|---|---|---|---|
| ATOM | 2973 | OH2 | H2O | 609 | −4.131 | 23.593 | 29.611 | 1.00 | 48.52 |
| ATOM | 2974 | H1 | H2O | 609 | −4.310 | 24.395 | 30.105 | 1.00 | 0.00 |
| ATOM | 2975 | H2 | H2O | 609 | −4.950 | 23.104 | 39.684 | 1.00 | 0.00 |
| ATOM | 2976 | OH2 | H2O | 610 | −13.858 | −29.598 | 37.538 | 1.00 | 34.23 |
| ATOM | 2977 | H1 | H2O | 610 | −13.564 | −29.123 | 38.335 | 1.00 | 0.00 |
| ATOM | 2978 | H2 | H2O | 610 | −14.093 | −30.430 | 37.979 | 1.00 | 0.00 |
| ATOM | 2979 | OH2 | H2O | 611 | −20.921 | −9.179 | 55.419 | 1.00 | 26.60 |
| ATOM | 2980 | H1 | H2O | 611 | −21.180 | −9.388 | 56.337 | 1.00 | 0.00 |
| ATOM | 2981 | H2 | H2O | 611 | −21.260 | −9.951 | 54.942 | 1.00 | 0.00 |
| ATOM | 2982 | OH2 | H2O | 612 | −26.331 | −2.023 | 72.803 | 1.00 | 53.47 |
| ATOM | 2983 | H1 | H2O | 612 | −26.140 | −1.532 | 73.608 | 1.00 | 0.00 |
| ATOM | 2984 | H2 | H2O | 612 | −27.255 | −1.793 | 72.631 | 1.00 | 0.00 |
| ATOM | 2985 | OH2 | H2O | 613 | −13.525 | 13.983 | 37.069 | 1.00 | 50.82 |
| ATOM | 2986 | H1 | H2O | 613 | −14.442 | 14.000 | 36.781 | 1.00 | 0.00 |
| ATOM | 2987 | H2 | H2O | 613 | −13.355 | 13.043 | 37.165 | 1.00 | 0.00 |
| ATOM | 2988 | OH2 | H2O | 614 | −21.926 | 16.371 | 65.955 | 1.00 | 46.58 |
| ATOM | 2989 | H1 | H2O | 614 | −22.637 | 17.103 | 65.941 | 1.00 | 0.00 |
| ATOM | 2990 | H2 | H2O | 614 | −22.048 | 15.876 | 65.146 | 1.00 | 0.00 |
| ATOM | 2991 | OH2 | H2O | 615 | 1.690 | −5.302 | 31.945 | 1.00 | 33.74 |
| ATOM | 2992 | H1 | H2O | 615 | 1.397 | −6.113 | 31.506 | 1.00 | 0.00 |
| ATOM | 2993 | H2 | H2O | 615 | 2.121 | −5.661 | 32.733 | 1.00 | 0.00 |
| ATOM | 2994 | OH2 | H2O | 616 | −20.949 | −21.416 | 38.360 | 1.00 | 46.62 |
| ATOM | 2995 | H1 | H2O | 616 | −20.201 | −21.991 | 38.548 | 1.00 | 0.00 |
| ATOM | 2996 | H2 | H2O | 616 | −20.536 | −20.560 | 38.533 | 1.00 | 0.00 |
| ATOM | 2997 | OH2 | H2O | 617 | −12.061 | 10.750 | 73.270 | 1.00 | 33.05 |
| ATOM | 2998 | H1 | H2O | 617 | −12.819 | 11.023 | 72.742 | 1.00 | 0.00 |
| ATOM | 2999 | H2 | H2O | 617 | −11.922 | 9.855 | 72.958 | 1.00 | 0.00 |
| ATOM | 3000 | OH2 | H2O | 618 | −15.349 | 12.400 | 63.729 | 1.00 | 37.51 |
| ATOM | 3001 | H1 | H2O | 618 | −15.377 | 11.908 | 62.908 | 1.00 | 0.00 |
| ATOM | 3002 | H2 | H2O | 618 | −16.272 | 12.641 | 63.835 | 1.00 | 0.00 |
| ATOM | 3003 | OH2 | H2O | 619 | 0.949 | 7.386 | 53.643 | 1.00 | 49.12 |
| ATOM | 3004 | H1 | H2O | 619 | 1.002 | 7.867 | 54.473 | 1.00 | 0.00 |
| ATOM | 3005 | H2 | H2O | 619 | 1.831 | 6.951 | 53.624 | 1.00 | 0.00 |
| ATOM | 3006 | OH2 | H2O | 620 | −4.534 | −8.391 | 59.287 | 1.00 | 32.23 |
| ATOM | 3007 | H1 | H2O | 620 | −4.887 | −9.282 | 59.417 | 1.00 | 0.00 |
| ATOM | 3008 | H2 | H2O | 620 | −3.858 | −8.571 | 58.625 | 1.00 | 0.00 |
| ATOM | 3009 | OH2 | H2O | 621 | −25.465 | −6.264 | 54.211 | 1.00 | 48.91 |
| ATOM | 3010 | H1 | H2O | 621 | −24.522 | −6.048 | 54.259 | 1.00 | 0.00 |
| ATOM | 3011 | H2 | H2O | 621 | −25.496 | −6.709 | 53.362 | 1.00 | 0.00 |
| ATOM | 3012 | OH2 | H2O | 622 | −28.810 | −0.917 | 66.953 | 1.00 | 54.26 |
| ATOM | 3013 | H1 | H2O | 622 | −28.968 | −1.765 | 66.514 | 1.00 | 0.00 |
| ATOM | 3014 | H2 | H2O | 622 | −28.017 | −0.623 | 66.496 | 1.00 | 0.00 |
| ATOM | 3015 | OH2 | H2O | 623 | −1.838 | 20.090 | 25.125 | 1.00 | 53.05 |
| ATOM | 3016 | H1 | H2O | 623 | −1.624 | 20.918 | 24.699 | 1.00 | 0.00 |
| ATOM | 3017 | H2 | H2O | 623 | −2.056 | 19.496 | 24.392 | 1.00 | 0.00 |
| ATOM | 3018 | OH2 | H2O | 624 | 4.169 | 12.348 | 27.338 | 1.00 | 59.51 |
| ATOM | 3019 | H1 | H2O | 624 | 3.885 | 11.758 | 26.634 | 1.00 | 0.00 |
| ATOM | 3020 | H2 | H2O | 624 | 3.382 | 12.887 | 27.475 | 1.00 | 0.00 |
| ATOM | 3021 | OH2 | H2O | 625 | −20.172 | −12.484 | 57.970 | 1.00 | 48.36 |
| ATOM | 3022 | H1 | H2O | 625 | −20.919 | −12.902 | 58.402 | 1.00 | 0.00 |
| ATOM | 3023 | H2 | H2O | 625 | −19.544 | −12.424 | 58.696 | 1.00 | 0.00 |
| ATOM | 3024 | OH2 | H2O | 626 | −2.341 | −0.010 | 29.093 | 1.00 | 41.65 |
| ATOM | 3025 | H1 | H2O | 626 | −2.634 | −0.652 | 29.755 | 1.00 | 0.00 |
| ATOM | 3026 | H2 | H2O | 626 | −1.592 | −0.477 | 28.705 | 1.00 | 0.00 |
| ATOM | 3027 | OH2 | H2O | 627 | −5.808 | −1.656 | 39.529 | 1.00 | 30.08 |
| ATOM | 3028 | H1 | H2O | 627 | −6.395 | −1.472 | 38.788 | 1.00 | 0.00 |
| ATOM | 3029 | H2 | H2O | 627 | −5.340 | −0.821 | 39.617 | 1.00 | 0.00 |
| END | | | | | | | | | |

Note:
See copyright notice on page 1.

TABLE 22

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| | | | | | | | | |
|---|---|---|---|---|---|---|---|---|
| ATOM | 1 | CB | ASP | 3 | −1.930 | −4.782 | 36.991 | 1.00 | 37.05 |
| ATOM | 2 | CG | ASP | 3 | −2.570 | −3.408 | 37.176 | 1.00 | 38.16 |
| ATOM | 3 | OD1 | ASP | 3 | −2.370 | −2.527 | 36.311 | 1.00 | 37.36 |
| ATOM | 4 | OD2 | ASP | 3 | −3.265 | −3.205 | 38.197 | 1.00 | 37.01 |
| ATOM | 5 | C | ASP | 3 | −2.096 | −4.960 | 34.485 | 1.00 | 32.75 |
| ATOM | 6 | O | ASP | 3 | −0.916 | −4.974 | 34.145 | 1.00 | 31.91 |
| ATOM | 7 | HT1 | ASP | 3 | −1.022 | −6.965 | 35.742 | 1.00 | 0.00 |
| ATOM | 8 | HT2 | ASP | 3 | −2.470 | −7.515 | 35.059 | 1.00 | 0.00 |
| ATOM | 9 | N | ASP | 3 | −2.058 | −6.982 | 35.850 | 1.00 | 39.84 |
| ATOM | 10 | HT3 | ASP | 3 | −2.314 | −7.428 | 36.750 | 1.00 | 0.00 |
| ATOM | 11 | CA | ASP | 3 | −2.531 | −5.568 | 35.816 | 1.00 | 35.10 |
| ATOM | 12 | N | PRO | 4 | −3.057 | −4.449 | 33.704 | 1.00 | 29.48 |
| ATOM | 13 | CD | PRO | 4 | −4.493 | −4.558 | 34.013 | 1.00 | 31.76 |
| ATOM | 14 | CA | PRO | 4 | −2.860 | −3.823 | 32.394 | 1.00 | 27.70 |
| ATOM | 15 | CB | PRO | 4 | −4.273 | −3.399 | 32.011 | 1.00 | 30.04 |
| ATOM | 16 | CG | PRO | 4 | −5.115 | −4.444 | 32.653 | 1.00 | 32.47 |
| ATOM | 17 | C | PRO | 4 | −1.929 | −2.616 | 32.393 | 1.00 | 26.07 |
| ATOM | 18 | O | PRO | 4 | −1.563 | −2.119 | 31.324 | 1.00 | 27.89 |
| ATOM | 19 | N | ALA | 5 | −1.585 | −2.121 | 33.578 | 1.00 | 20.52 |
| ATOM | 20 | H | ALA | 5 | −1.962 | −2.491 | 34.379 | 1.00 | 0.00 |
| ATOM | 21 | CA | ALA | 5 | −0.713 | −0.963 | 33.682 | 1.00 | 15.66 |
| ATOM | 22 | CB | ALA | 5 | −1.363 | 0.104 | 34.546 | 1.00 | 12.37 |
| ATOM | 23 | C | ALA | 5 | 0.662 | −1.303 | 34.222 | 1.00 | 15.18 |
| ATOM | 24 | O | ALA | 5 | 1.560 | −0.474 | 34.167 | 1.00 | 15.42 |
| ATOM | 25 | N | ALA | 6 | 0.849 | −2.545 | 34.663 | 1.00 | 17.31 |
| ATOM | 26 | H | ALA | 6 | 0.133 | −3.204 | 34.566 | 1.00 | 0.00 |
| ATOM | 27 | CA | ALA | 6 | 2.118 | −2.982 | 35.250 | 1.00 | 15.36 |
| ATOM | 28 | CB | ALA | 6 | 2.037 | −4.448 | 35.644 | 1.00 | 16.18 |
| ATOM | 29 | C | ALA | 6 | 3.373 | −2.730 | 34.420 | 1.00 | 14.64 |
| ATOM | 30 | O | ALA | 6 | 4.455 | −2.560 | 34.970 | 1.00 | 15.69 |
| ATOM | 31 | N | HIS | 7 | 3.238 | −2.712 | 33.100 | 1.00 | 13.68 |
| ATOM | 32 | H | HIS | 7 | 2.333 | −2.845 | 32.758 | 1.00 | 0.00 |
| ATOM | 33 | CA | HIS | 7 | 4.393 | −2.487 | 32.234 | 1.00 | 11.91 |
| ATOM | 34 | CB | HIS | 7 | 4.199 | −3.186 | 30.884 | 1.00 | 11.56 |
| ATOM | 35 | CG | HIS | 7 | 2.990 | −2.727 | 30.134 | 1.00 | 6.98 |
| ATOM | 36 | CD2 | HIS | 7 | 2.861 | −1.908 | 29.064 | 1.00 | 8.55 |
| ATOM | 37 | ND1 | HIS | 7 | 1.712 | −3.118 | 30.470 | 1.00 | 6.26 |
| ATOM | 38 | HD1 | HIS | 7 | 1.443 | −3.762 | 31.161 | 1.00 | 0.00 |
| ATOM | 39 | CE1 | HIS | 7 | 0.848 | −2.558 | 29.642 | 1.00 | 9.39 |
| ATOM | 40 | NE2 | HIS | 7 | 1.524 | −1.820 | 28.778 | 1.00 | 9.77 |
| ATOM | 41 | HE2 | HIS | 7 | 1.115 | −1.305 | 28.037 | 1.00 | 0.00 |
| ATOM | 42 | C | HIS | 7 | 4.726 | −1.012 | 32.019 | 1.00 | 11.78 |
| ATOM | 43 | O | HIS | 7 | 5.780 | −0.688 | 31.479 | 1.00 | 15.61 |
| ATOM | 44 | N | LEU | 8 | 3.821 | −0.121 | 32.421 | 1.00 | 11.63 |
| ATOM | 45 | H | LEU | 8 | 3.016 | −0.410 | 32.904 | 1.00 | 0.00 |
| ATOM | 46 | CA | LEU | 8 | 4.035 | 1.317 | 32.271 | 1.00 | 11.65 |
| ATOM | 47 | CB | LEU | 8 | 2.733 | 2.076 | 32.536 | 1.00 | 12.00 |
| ATOM | 48 | CG | LEU | 8 | 1.807 | 2.318 | 31.340 | 1.00 | 14.44 |
| ATOM | 49 | CD1 | LEU | 8 | 2.031 | 1.303 | 30.248 | 1.00 | 14.24 |
| ATOM | 50 | CD2 | LEU | 8 | 0.373 | 2.309 | 31.804 | 1.00 | 13.16 |
| ATOM | 51 | C | LEU | 8 | 5.129 | 1.799 | 33.213 | 1.00 | 10.74 |
| ATOM | 52 | O | LEU | 8 | 5.059 | 1.576 | 34.419 | 1.00 | 13.97 |
| ATOM | 53 | N | PRO | 9 | 6.142 | 2.500 | 32.676 | 1.00 | 11.59 |
| ATOM | 54 | CD | PRO | 9 | 6.257 | 2.872 | 31.256 | 1.00 | 10.31 |
| ATOM | 55 | CA | PRO | 9 | 7.279 | 3.032 | 33.439 | 1.00 | 9.53 |
| ATOM | 56 | CB | PRO | 9 | 8.087 | 3.778 | 32.373 | 1.00 | 10.55 |
| ATOM | 57 | CG | PRO | 9 | 7.724 | 3.094 | 31.115 | 1.00 | 10.88 |
| ATOM | 58 | C | PRO | 9 | 6.867 | 3.997 | 34.548 | 1.00 | 8.58 |
| ATOM | 59 | O | PRO | 9 | 7.567 | 4.134 | 35.550 | 1.00 | 10.26 |
| ATOM | 60 | N | PHE | 10 | 5.752 | 4.688 | 34.340 | 1.00 | 7.17 |
| ATOM | 61 | H | PHE | 10 | 5.256 | 4.547 | 33.516 | 1.00 | 0.00 |
| ATOM | 62 | CA | PHE | 10 | 5.247 | 5.667 | 35.295 | 1.00 | 8.06 |
| ATOM | 63 | CB | PHE | 10 | 4.772 | 6.929 | 34.553 | 1.00 | 4.56 |
| ATOM | 64 | CG | PHE | 10 | 3.822 | 6.646 | 33.425 | 1.00 | 6.98 |
| ATOM | 65 | CD1 | PHE | 10 | 2.445 | 6.666 | 33.629 | 1.00 | 7.37 |
| ATOM | 66 | CD2 | PHE | 10 | 4.308 | 6.349 | 32.152 | 1.00 | 6.47 |
| ATOM | 67 | CE1 | PHE | 10 | 1.563 | 6.390 | 32.578 | 1.00 | 8.56 |
| ATOM | 68 | CE2 | PHE | 10 | 3.439 | 6.074 | 31.103 | 1.00 | 8.81 |
| ATOM | 69 | CZ | PHE | 10 | 2.060 | 6.095 | 31.315 | 1.00 | 8.30 |
| ATOM | 70 | C | PHE | 10 | 4.141 | 5.125 | 36.203 | 1.00 | 9.03 |
| ATOM | 71 | O | PHE | 10 | 3.387 | 5.898 | 36.795 | 1.00 | 9.71 |
| ATOM | 72 | N | PHE | 11 | 4.020 | 3.802 | 36.280 | 1.00 | 7.91 |
| ATOM | 73 | H | PHE | 11 | 4.649 | 3.204 | 35.823 | 1.00 | 0.00 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 74 | CA | PHE | 11 | 3.026 | 3.166 | 37.137 | 1.00 | 7.22 |
|---|---|---|---|---|---|---|---|---|---|
| ATOM | 75 | CB | PHE | 11 | 2.404 | 1.964 | 36.427 | 1.00 | 7.31 |
| ATOM | 76 | CG | PHE | 11 | 1.383 | 1.237 | 37.251 | 1.00 | 5.77 |
| ATOM | 77 | CD1 | PHE | 11 | 0.206 | 1.864 | 37.635 | 1.00 | 2.00 |
| ATOM | 78 | CD2 | PHE | 11 | 1.603 | -0.078 | 37.642 | 1.00 | 2.95 |
| ATOM | 79 | CE1 | PHE | 11 | -0.729 | 1.192 | 38.389 | 1.00 | 3.12 |
| ATOM | 80 | CE2 | PHE | 11 | 0.668 | -0.761 | 38.401 | 1.00 | 2.87 |
| ATOM | 81 | CZ | PHE | 11 | -0.497 | -0.130 | 38.775 | 1.00 | 2.00 |
| ATOM | 82 | C | PHE | 11 | 3.725 | 2.725 | 38.434 | 1.00 | 7.69 |
| ATOM | 83 | O | PHE | 11 | 4.710 | 1.983 | 38.400 | 1.00 | 5.93 |
| ATOM | 84 | N | TYR | 12 | 3.231 | 3.202 | 39.573 | 1.00 | 6.36 |
| ATOM | 85 | H | TYR | 12 | 2.469 | 3.818 | 39.520 | 1.00 | 0.00 |
| ATOM | 86 | CA | TYR | 12 | 3.836 | 2.870 | 40.860 | 1.00 | 5.86 |
| ATOM | 87 | CB | TYR | 12 | 3.996 | 4.130 | 41.706 | 1.00 | 7.27 |
| ATOM | 88 | CG | TYR | 12 | 5.066 | 5.063 | 41.193 | 1.00 | 8.07 |
| ATOM | 89 | CD1 | TYR | 12 | 4.862 | 5.836 | 40.051 | 1.00 | 7.30 |
| ATOM | 90 | CE1 | TYR | 12 | 5.858 | 6.672 | 39.569 | 1.00 | 7.12 |
| ATOM | 91 | CD2 | TYR | 12 | 6.294 | 5.156 | 41.840 | 1.00 | 7.58 |
| ATOM | 92 | CE2 | TYR | 12 | 7.289 | 5.987 | 41.367 | 1.00 | 7.70 |
| ATOM | 93 | CZ | TYR | 12 | 7.063 | 6.740 | 40.234 | 1.00 | 8.65 |
| ATOM | 94 | OH | TYR | 12 | 8.068 | 7.546 | 39.779 | 1.00 | 12.68 |
| ATOM | 95 | HH | TYR | 12 | 8.910 | 7.326 | 40.171 | 1.00 | 0.00 |
| ATOM | 96 | C | TYR | 12 | 3.114 | 1.805 | 41.662 | 1.00 | 5.87 |
| ATOM | 97 | O | TYR | 12 | 3.554 | 1.428 | 42.749 | 1.00 | 5.79 |
| ATOM | 98 | N | GLY | 13 | 2.000 | 1.325 | 41.139 | 1.00 | 5.99 |
| ATOM | 99 | H | GLY | 13 | 1.656 | 1.690 | 40.302 | 1.00 | 0.00 |
| ATOM | 100 | CA | GLY | 13 | 1.262 | 0.299 | 41.842 | 1.00 | 11.58 |
| ATOM | 101 | C | GLY | 13 | 0.420 | 0.849 | 42.974 | 1.00 | 13.90 |
| ATOM | 102 | O | GLY | 13 | -0.098 | 1.960 | 42.888 | 1.00 | 13.74 |
| ATOM | 103 | N | SER | 14 | 0.315 | 0.087 | 44.056 | 1.00 | 14.19 |
| ATOM | 104 | H | SER | 14 | 0.788 | -0.773 | 44.102 | 1.00 | 0.00 |
| ATOM | 105 | CA | SER | 14 | -0.496 | 0.492 | 45.190 | 1.00 | 15.17 |
| ATOM | 106 | CB | SER | 14 | -1.162 | -0.737 | 45.810 | 1.00 | 14.68 |
| ATOM | 107 | OG | SER | 14 | -2.009 | -0.370 | 46.884 | 1.00 | 23.05 |
| ATOM | 108 | HG | SER | 14 | -1.439 | -0.023 | 47.586 | 1.00 | 0.00 |
| ATOM | 109 | C | SER | 14 | 0.210 | 1.316 | 46.265 | 1.00 | 16.00 |
| ATOM | 110 | O | SER | 14 | 0.467 | 0.820 | 47.363 | 1.00 | 16.80 |
| ATOM | 111 | N | ILE | 15 | 0.522 | 2.570 | 45.950 | 1.00 | 15.37 |
| ATOM | 112 | H | ILE | 15 | 0.283 | 2.901 | 45.058 | 1.00 | 0.00 |
| ATOM | 113 | CA | ILE | 15 | 1.159 | 3.467 | 46.914 | 1.00 | 12.48 |
| ATOM | 114 | CB | ILE | 15 | 2.370 | 4.223 | 46.304 | 1.00 | 10.89 |
| ATOM | 115 | CG2 | ILE | 15 | 3.496 | 3.237 | 45.986 | 1.00 | 8.22 |
| ATOM | 116 | CG1 | ILE | 15 | 1.945 | 5.032 | 45.074 | 1.00 | 7.10 |
| ATOM | 117 | CD | ILE | 15 | 3.062 | 5.887 | 44.496 | 1.00 | 2.93 |
| ATOM | 118 | C | ILE | 15 | 0.120 | 4.473 | 47.426 | 1.00 | 12.27 |
| ATOM | 119 | O | ILE | 15 | -0.990 | 4.555 | 46.889 | 1.00 | 11.25 |
| ATOM | 120 | N | SER | 16 | 0.469 | 5.233 | 48.459 | 1.00 | 8.90 |
| ATOM | 121 | H | SER | 16 | 1.358 | 5.201 | 48.836 | 1.00 | 0.00 |
| ATOM | 122 | CA | SER | 16 | -0.459 | 6.215 | 49.010 | 1.00 | 10.27 |
| ATOM | 123 | CB | SER | 16 | -0.231 | 6.398 | 50.512 | 1.00 | 7.24 |
| ATOM | 124 | OG | SER | 16 | 1.051 | 6.950 | 50.758 | 1.00 | 11.57 |
| ATOM | 125 | HG | SER | 16 | 1.119 | 7.092 | 51.719 | 1.00 | 0.00 |
| ATOM | 126 | C | SER | 16 | -0.267 | 7.549 | 48.316 | 1.00 | 8.08 |
| ATOM | 127 | O | SER | 16 | 0.727 | 7.753 | 47.608 | 1.00 | 5.74 |
| ATOM | 128 | N | ARG | 17 | -1.209 | 8.461 | 48.549 | 1.00 | 8.03 |
| ATOM | 129 | H | ARG | 17 | -1.975 | 8.225 | 49.117 | 1.00 | 0.00 |
| ATOM | 130 | CA | ARG | 17 | -1.137 | 9.792 | 47.969 | 1.00 | 7.35 |
| ATOM | 131 | CB | ARG | 17 | -2.328 | 10.640 | 48.407 | 1.00 | 6.44 |
| ATOM | 132 | CG | ARG | 17 | -2.230 | 12.078 | 47.919 | 1.00 | 5.73 |
| ATOM | 133 | CD | ARG | 17 | -3.359 | 12.936 | 48.428 | 1.00 | 7.10 |
| ATOM | 134 | NE | ARG | 17 | -4.651 | 12.497 | 47.919 | 1.00 | 10.08 |
| ATOM | 135 | HE | ARG | 17 | -4.764 | 11.542 | 47.799 | 1.00 | 0.00 |
| ATOM | 136 | CZ | ARG | 17 | -5.667 | 13.308 | 47.651 | 1.00 | 12.64 |
| ATOM | 137 | NH1 | ARG | 17 | -5.547 | 14.615 | 47.839 | 1.00 | 14.72 |
| ATOM | 138 | HH11 | ARG | 17 | -4.683 | 14.986 | 48.174 | 1.00 | 0.00 |
| ATOM | 139 | HH12 | ARG | 17 | -6.311 | 15.229 | 47.642 | 1.00 | 0.00 |
| ATOM | 140 | NH2 | ARG | 17 | -6.807 | 12.807 | 47.199 | 1.00 | 14.47 |
| ATOM | 141 | HH21 | ARG | 17 | -6.903 | 11.820 | 47.061 | 1.00 | 0.00 |
| ATOM | 142 | HH22 | ARG | 17 | -7.576 | 13.416 | 47.005 | 1.00 | 0.00 |
| ATOM | 143 | C | ARG | 17 | 0.142 | 10.462 | 48.432 | 1.00 | 7.25 |
| ATOM | 144 | O | ARG | 17 | 0.814 | 11.133 | 47.657 | 1.00 | 11.16 |
| ATOM | 145 | N | ALA | 18 | 0.470 | 10.286 | 49.704 | 1.00 | 8.87 |
| ATOM | 146 | H | ALA | 18 | -0.131 | 9.780 | 50.291 | 1.00 | 0.00 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 147 | CA | ALA | 18 | 1.674 | 10.877 | 50.267 | 1.00 | 7.33 |
|---|---|---|---|---|---|---|---|---|---|
| ATOM | 148 | CB | ALA | 18 | 1.787 | 10.544 | 51.747 | 1.00 | 12.14 |
| ATOM | 149 | C | ALA | 18 | 2.904 | 10.405 | 49.526 | 1.00 | 7.31 |
| ATOM | 150 | O | ALA | 18 | 3.764 | 11.209 | 49.168 | 1.00 | 8.68 |
| ATOM | 151 | N | GLU | 19 | 2.987 | 9.100 | 49.292 | 1.00 | 8.47 |
| ATOM | 152 | H | GLU | 19 | 2.260 | 8.510 | 49.603 | 1.00 | 0.00 |
| ATOM | 153 | CA | GLU | 19 | 4.127 | 8.530 | 48.580 | 1.00 | 7.37 |
| ATOM | 154 | CB | GLU | 19 | 4.061 | 7.005 | 48.589 | 1.00 | 9.12 |
| ATOM | 155 | CG | GLU | 19 | 4.085 | 6.415 | 49.986 | 1.00 | 18.39 |
| ATOM | 156 | CD | GLU | 19 | 3.901 | 4.909 | 50.005 | 1.00 | 18.70 |
| ATOM | 157 | OE1 | GLU | 19 | 4.912 | 4.190 | 50.112 | 1.00 | 27.52 |
| ATOM | 158 | OE2 | GLU | 19 | 2.748 | 4.439 | 49.931 | 1.00 | 16.92 |
| ATOM | 159 | C | GLU | 19 | 4.166 | 9.050 | 47.150 | 1.00 | 8.14 |
| ATOM | 160 | O | GLU | 19 | 5.239 | 9.289 | 46.596 | 1.00 | 8.18 |
| ATOM | 161 | N | ALA | 20 | 2.987 | 9.229 | 46.560 | 1.00 | 8.26 |
| ATOM | 162 | H | ALA | 20 | 2.170 | 9.017 | 47.052 | 1.00 | 0.00 |
| ATOM | 163 | CA | ALA | 20 | 2.882 | 9.738 | 45.197 | 1.00 | 9.21 |
| ATOM | 164 | CB | ALA | 20 | 1.432 | 9.702 | 44.731 | 1.00 | 7.13 |
| ATOM | 165 | C | ALA | 20 | 3.421 | 11.165 | 45.122 | 1.00 | 7.93 |
| ATOM | 166 | O | ALA | 20 | 4.178 | 11.510 | 44.216 | 1.00 | 7.73 |
| ATOM | 167 | N | GLU | 21 | 3.042 | 11.981 | 46.097 | 1.00 | 8.72 |
| ATOM | 168 | H | GLU | 21 | 2.458 | 11.637 | 46.807 | 1.00 | 0.00 |
| ATOM | 169 | CA | GLU | 21 | 3.474 | 13.371 | 46.142 | 1.00 | 8.14 |
| ATOM | 170 | CB | GLU | 21 | 2.621 | 14.156 | 47.132 | 1.00 | 3.54 |
| ATOM | 171 | CG | GLU | 21 | 1.166 | 14.213 | 46.698 | 1.00 | 4.77 |
| ATOM | 172 | CD | GLU | 21 | 0.276 | 15.052 | 47.594 | 1.00 | 3.41 |
| ATOM | 173 | OE1 | GLU | 21 | −0.882 | 15.278 | 47.213 | 1.00 | 3.53 |
| ATOM | 174 | OE2 | GLU | 21 | 0.716 | 15.489 | 48.674 | 1.00 | 8.91 |
| ATOM | 175 | C | GLU | 21 | 4.960 | 13.520 | 46.434 | 1.00 | 7.55 |
| ATOM | 176 | O | GLU | 21 | 5.595 | 14.470 | 45.982 | 1.00 | 10.13 |
| ATOM | 177 | N | GLU | 22 | 5.521 | 12.563 | 47.159 | 1.00 | 6.89 |
| ATOM | 178 | H | GLU | 22 | 4.964 | 11.853 | 47.531 | 1.00 | 0.00 |
| ATOM | 179 | CA | GLU | 22 | 6.941 | 12.584 | 47.458 | 1.00 | 7.66 |
| ATOM | 180 | CB | GLU | 22 | 7.291 | 11.489 | 48.465 | 1.00 | 9.80 |
| ATOM | 181 | CG | GLU | 22 | 8.772 | 11.140 | 48.465 | 1.00 | 20.65 |
| ATOM | 182 | CD | GLU | 22 | 9.231 | 10.377 | 49.691 | 1.00 | 26.23 |
| ATOM | 183 | OE1 | GLU | 22 | 8.381 | 9.865 | 50.457 | 1.00 | 27.98 |
| ATOM | 184 | OE2 | GLU | 22 | 10.461 | 10.304 | 49.887 | 1.00 | 27.22 |
| ATOM | 185 | C | GLU | 22 | 7.754 | 12.407 | 46.173 | 1.00 | 8.48 |
| ATOM | 186 | O | GLU | 22 | 8.739 | 13.111 | 45.949 | 1.00 | 11.39 |
| ATOM | 187 | N | HIS | 23 | 7.330 | 11.473 | 45.326 | 1.00 | 10.23 |
| ATOM | 188 | H | HIS | 23 | 6.513 | 10.983 | 45.570 | 1.00 | 0.00 |
| ATOM | 189 | CA | HIS | 23 | 8.009 | 11.199 | 44.060 | 1.00 | 7.78 |
| ATOM | 190 | CB | HIS | 23 | 7.420 | 9.954 | 43.388 | 1.00 | 6.65 |
| ATOM | 191 | CG | HIS | 23 | 7.813 | 8.667 | 44.047 | 1.00 | 7.16 |
| ATOM | 192 | CD2 | HIS | 23 | 9.015 | 8.056 | 44.166 | 1.00 | 5.40 |
| ATOM | 193 | ND1 | HIS | 23 | 6.902 | 7.835 | 44.661 | 1.00 | 9.76 |
| ATOM | 194 | HD1 | HIS | 23 | 5.953 | 8.008 | 44.836 | 1.00 | 0.00 |
| ATOM | 195 | CE1 | HIS | 23 | 7.522 | 6.767 | 45.125 | 1.00 | 5.88 |
| ATOM | 196 | NE2 | HIS | 23 | 8.808 | 6.879 | 44.838 | 1.00 | 7.20 |
| ATOM | 197 | HE2 | HIS | 23 | 9.497 | 6.257 | 45.178 | 1.00 | 0.00 |
| ATOM | 198 | C | HIS | 23 | 7.923 | 12.380 | 43.102 | 1.00 | 7.58 |
| ATOM | 199 | O | HIS | 23 | 8.893 | 12.698 | 42.412 | 1.00 | 9.48 |
| ATOM | 200 | N | LEU | 24 | 6.758 | 13.016 | 43.049 | 1.00 | 8.34 |
| ATOM | 201 | H | LEU | 24 | 6.007 | 12.724 | 43.606 | 1.00 | 0.00 |
| ATOM | 202 | CA | LEU | 24 | 6.551 | 14.164 | 42.174 | 1.00 | 6.84 |
| ATOM | 203 | CB | LEU | 24 | 5.062 | 14.527 | 42.112 | 1.00 | 5.05 |
| ATOM | 204 | CG | LEU | 24 | 4.140 | 13.522 | 41.392 | 1.00 | 9.41 |
| ATOM | 205 | CD1 | LEU | 24 | 2.672 | 13.866 | 41.630 | 1.00 | 2.00 |
| ATOM | 206 | CD2 | LEU | 24 | 4.441 | 13.479 | 39.889 | 1.00 | 2.21 |
| ATOM | 207 | C | LEU | 24 | 7.401 | 15.340 | 42.654 | 1.00 | 8.80 |
| ATOM | 208 | O | LEU | 24 | 7.973 | 16.072 | 41.843 | 1.00 | 10.47 |
| ATOM | 209 | N | LYS | 25 | 7.521 | 15.497 | 43.969 | 1.00 | 9.78 |
| ATOM | 210 | H | LYS | 25 | 7.026 | 14.908 | 44.577 | 1.00 | 0.00 |
| ATOM | 211 | CA | LYS | 25 | 8.343 | 16.562 | 44.540 | 1.00 | 10.08 |
| ATOM | 212 | CB | LYS | 25 | 8.178 | 16.621 | 46.058 | 1.00 | 8.96 |
| ATOM | 213 | CG | LYS | 25 | 6.849 | 17.130 | 46.550 | 1.00 | 3.65 |
| ATOM | 214 | CD | LYS | 25 | 6.863 | 17.140 | 48.059 | 1.00 | 10.29 |
| ATOM | 215 | CE | LYS | 25 | 5.533 | 17.549 | 48.656 | 1.00 | 9.07 |
| ATOM | 216 | NZ | LYS | 25 | 5.612 | 17.513 | 50.147 | 1.00 | 12.20 |
| ATOM | 217 | HZ1 | LYS | 25 | 6.355 | 18.162 | 50.481 | 1.00 | 0.00 |
| ATOM | 218 | HZ2 | LYS | 25 | 5.830 | 16.546 | 50.457 | 1.00 | 0.00 |
| ATOM | 219 | HZ3 | LYS | 25 | 4.697 | 17.805 | 50.540 | 1.00 | 0.00 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 220 | C | LYS | 25 | 9.815 | 16.312 | 44.214 | 1.00 | 11.23 |
|---|---|---|---|---|---|---|---|---|---|
| ATOM | 221 | O | LYS | 25 | 10.518 | 17.204 | 43.741 | 1.00 | 11.13 |
| ATOM | 222 | N | LEU | 26 | 10.274 | 15.086 | 44.450 | 1.00 | 12.69 |
| ATOM | 223 | H | LEU | 26 | 9.655 | 14.414 | 44.817 | 1.00 | 0.00 |
| ATOM | 224 | CA | LEU | 26 | 11.664 | 14.721 | 44.188 | 1.00 | 11.54 |
| ATOM | 225 | CB | LEU | 26 | 11.967 | 13.322 | 44.730 | 1.00 | 9.05 |
| ATOM | 226 | CG | LEU | 26 | 12.030 | 13.127 | 46.421 | 1.00 | 7.75 |
| ATOM | 227 | CD1 | LEU | 26 | 12.144 | 11.659 | 46.545 | 1.00 | 10.85 |
| ATOM | 228 | CD2 | LEU | 26 | 13.196 | 13.880 | 46.822 | 1.00 | 8.02 |
| ATOM | 229 | C | LEU | 26 | 12.016 | 14.770 | 42.709 | 1.00 | 13.09 |
| ATOM | 230 | O | LEU | 26 | 13.194 | 14.788 | 42.353 | 1.00 | 13.85 |
| ATOM | 231 | N | ALA | 27 | 10.998 | 14.768 | 41.852 | 1.00 | 14.57 |
| ATOM | 232 | H | ALA | 27 | 10.076 | 14.716 | 42.182 | 1.00 | 0.00 |
| ATOM | 233 | CA | ALA | 27 | 11.207 | 14.809 | 40.409 | 1.00 | 14.74 |
| ATOM | 234 | CB | ALA | 27 | 10.114 | 14.036 | 39.690 | 1.00 | 11.97 |
| ATOM | 235 | C | ALA | 27 | 11.310 | 16.217 | 39.847 | 1.00 | 14.47 |
| ATOM | 236 | O | ALA | 27 | 11.450 | 16.388 | 38.637 | 1.00 | 18.58 |
| ATOM | 237 | N | GLY | 28 | 11.214 | 17.228 | 40.701 | 1.00 | 14.44 |
| ATOM | 238 | H | GLY | 28 | 11.100 | 17.075 | 41.663 | 1.00 | 0.00 |
| ATOM | 239 | CA | GLY | 28 | 11.322 | 18.588 | 40.208 | 1.00 | 16.06 |
| ATOM | 240 | C | GLY | 28 | 10.059 | 19.417 | 40.277 | 1.00 | 18.17 |
| ATOM | 241 | O | GLY | 28 | 10.121 | 20.638 | 40.125 | 1.00 | 20.12 |
| ATOM | 242 | N | SEM | 29 | 8.911 | 18.764 | 40.445 | 1.00 | 18.95 |
| ATOM | 243 | H | SEM | 29 | 8.916 | 17.783 | 40.530 | 1.00 | 0.00 |
| ATOM | 244 | CA | SEM | 29 | 7.633 | 19.461 | 40.560 | 1.00 | 19.29 |
| ATOM | 245 | CB | SEM | 29 | 7.691 | 20.394 | 41.774 | 1.00 | 26.13 |
| ATOM | 246 | CG | SEM | 29 | 6.357 | 20.714 | 42.386 | 1.00 | 38.67 |
| ATOM | 247 | A | SEM | 29 | 5.628 | 19.139 | 43.253 | 1.00 | 56.20 |
| ATOM | 248 | CE | SEM | 29 | 4.244 | 20.250 | 43.984 | 1.00 | 49.18 |
| ATOM | 249 | C | SEM | 29 | 7.244 | 20.262 | 39.307 | 1.00 | 17.59 |
| ATOM | 250 | O | SEM | 29 | 6.551 | 21.277 | 39.404 | 1.00 | 14.79 |
| ATOM | 251 | N | ALA | 30 | 7.661 | 19.799 | 38.132 | 1.00 | 17.50 |
| ATOM | 252 | H | ALA | 30 | 8.158 | 18.959 | 38.095 | 1.00 | 0.00 |
| ATOM | 253 | CA | ALA | 30 | 7.361 | 20.506 | 36.883 | 1.00 | 17.68 |
| ATOM | 254 | CB | ALA | 30 | 8.328 | 20.078 | 35.787 | 1.00 | 17.19 |
| ATOM | 255 | C | ALA | 30 | 5.920 | 20.303 | 36.427 | 1.00 | 18.58 |
| ATOM | 256 | O | ALA | 30 | 5.336 | 19.246 | 36.667 | 1.00 | 20.12 |
| ATOM | 257 | N | ASP | 31 | 5.345 | 21.323 | 35.786 | 1.00 | 19.30 |
| ATOM | 258 | H | ASP | 31 | 5.870 | 22.127 | 35.608 | 1.00 | 0.00 |
| ATOM | 259 | CA | ASP | 31 | 3.967 | 21.251 | 35.287 | 1.00 | 18.84 |
| ATOM | 260 | CB | ASP | 31 | 3.556 | 22.553 | 34.585 | 1.00 | 22.71 |
| ATOM | 261 | CG | ASP | 31 | 3.270 | 23.682 | 35.550 | 1.00 | 26.71 |
| ATOM | 262 | OD1 | ASP | 31 | 3.279 | 24.850 | 35.109 | 1.00 | 32.54 |
| ATOM | 263 | OD2 | ASP | 31 | 3.023 | 23.415 | 36.744 | 1.00 | 30.87 |
| ATOM | 264 | C | ASP | 31 | 3.822 | 20.110 | 34.298 | 1.00 | 15.55 |
| ATOM | 265 | O | ASP | 31 | 4.678 | 19.920 | 33.434 | 1.00 | 13.41 |
| ATOM | 266 | N | GLY | 32 | 2.727 | 19.371 | 34.413 | 1.00 | 13.36 |
| ATOM | 267 | H | GLY | 32 | 2.082 | 19.548 | 35.121 | 1.00 | 0.00 |
| ATOM | 268 | CA | GLY | 32 | 2.500 | 18.261 | 33.513 | 1.00 | 10.92 |
| ATOM | 269 | C | GLY | 32 | 3.215 | 17.002 | 33.956 | 1.00 | 10.21 |
| ATOM | 270 | O | GLY | 32 | 3.189 | 16.002 | 33.241 | 1.00 | 12.71 |
| ATOM | 271 | N | LEU | 33 | 3.920 | 17.063 | 35.084 | 1.00 | 10.73 |
| ATOM | 272 | H | LEU | 33 | 3.996 | 17.913 | 35.563 | 1.00 | 0.00 |
| ATOM | 273 | CA | LEU | 33 | 4.608 | 15.889 | 35.621 | 1.00 | 10.86 |
| ATOM | 274 | CB | LEU | 33 | 5.587 | 16.297 | 36.730 | 1.00 | 10.14 |
| ATOM | 275 | CG | LEU | 33 | 6.506 | 15.217 | 37.309 | 1.00 | 8.41 |
| ATOM | 276 | CD1 | LEU | 33 | 7.578 | 14.842 | 36.312 | 1.00 | 8.33 |
| ATOM | 277 | CD2 | LEU | 33 | 7.146 | 15.735 | 38.564 | 1.00 | 4.68 |
| ATOM | 278 | C | LEU | 33 | 3.486 | 15.015 | 36.193 | 1.00 | 11.04 |
| ATOM | 279 | O | LEU | 33 | 2.665 | 15.495 | 36.987 | 1.00 | 10.22 |
| ATOM | 280 | N | PHE | 34 | 3.431 | 13.751 | 35.786 | 1.00 | 8.86 |
| ATOM | 281 | H | PHE | 34 | 4.113 | 13.400 | 35.173 | 1.00 | 0.00 |
| ATOM | 282 | CA | PHE | 34 | 2.369 | 12.868 | 36.247 | 1.00 | 6.90 |
| ATOM | 283 | CB | PHE | 34 | 1.236 | 12.837 | 35.210 | 1.00 | 5.89 |
| ATOM | 284 | CG | PHE | 34 | 1.587 | 12.101 | 33.941 | 1.00 | 7.44 |
| ATOM | 285 | CD1 | PHE | 34 | 1.247 | 10.755 | 33.784 | 1.00 | 8.28 |
| ATOM | 286 | CD2 | PHE | 34 | 2.259 | 12.746 | 32.905 | 1.00 | 3.28 |
| ATOM | 287 | CE1 | PHE | 34 | 1.575 | 10.066 | 32.615 | 1.00 | 10.52 |
| ATOM | 288 | CE2 | PHE | 34 | 2.587 | 12.070 | 31.739 | 1.00 | 5.20 |
| ATOM | 289 | CZ | PHE | 34 | 2.247 | 10.727 | 31.589 | 1.00 | 7.45 |
| ATOM | 290 | C | PHE | 34 | 2.820 | 11.446 | 36.510 | 1.00 | 6.42 |
| ATOM | 291 | O | PHE | 34 | 3.861 | 11.003 | 36.026 | 1.00 | 7.20 |
| ATOM | 292 | N | LEU | 35 | 2.015 | 10.724 | 37.273 | 1.00 | 5.42 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 293 | H | LEU | 35 | 1.189 | 11.106 | 37.637 | 1.00 | 0.00 |
|---|---|---|---|---|---|---|---|---|---|
| ATOM | 294 | CA | LEU | 35 | 2.294 | 9.328 | 37.564 | 1.00 | 5.16 |
| ATOM | 295 | CB | LEU | 35 | 3.228 | 9.170 | 38.780 | 1.00 | 3.91 |
| ATOM | 296 | CG | LEU | 35 | 2.861 | 9.681 | 40.178 | 1.00 | 5.75 |
| ATOM | 297 | CD1 | LEU | 35 | 1.822 | 8.770 | 40.833 | 1.00 | 3.81 |
| ATOM | 298 | CD2 | LEU | 35 | 4.125 | 9.730 | 41.033 | 1.00 | 5.45 |
| ATOM | 299 | C | LEU | 35 | 0.950 | 8.638 | 37.759 | 1.00 | 5.01 |
| ATOM | 300 | O | LEU | 35 | −0.071 | 9.297 | 37.976 | 1.00 | 4.17 |
| ATOM | 301 | N | LEU | 36 | 0.947 | 7.321 | 36.628 | 1.00 | 5.84 |
| ATOM | 302 | H | LEU | 36 | 1.787 | 6.845 | 37.447 | 1.00 | 0.00 |
| ATOM | 303 | CA | LEU | 36 | −0.266 | 6.543 | 37.772 | 1.00 | 6.22 |
| ATOM | 304 | CB | LEU | 36 | −0.513 | 5.745 | 36.487 | 1.00 | 8.32 |
| ATOM | 305 | CG | LEU | 36 | −1.945 | 5.377 | 36.090 | 1.00 | 12.01 |
| ATOM | 306 | CD1 | LEU | 36 | −2.670 | 6.628 | 35.627 | 1.00 | 9.93 |
| ATOM | 307 | CD2 | LEU | 36 | −1.924 | 4.333 | 34.975 | 1.00 | 11.40 |
| ATOM | 308 | C | LEU | 36 | −0.093 | 5.587 | 38.942 | 1.00 | 5.04 |
| ATOM | 309 | O | LEU | 36 | 1.002 | 5.075 | 39.178 | 1.00 | 4.23 |
| ATOM | 310 | N | ARG | 37 | −1.156 | 5.396 | 39.712 | 1.00 | 5.30 |
| ATOM | 311 | H | ARG | 37 | −1.991 | 5.875 | 39.531 | 1.00 | 0.00 |
| ATOM | 312 | CA | ARG | 37 | −1.122 | 4.469 | 40.837 | 1.00 | 4.66 |
| ATOM | 313 | CB | ARG | 37 | −0.845 | 5.190 | 42.156 | 1.00 | 3.66 |
| ATOM | 314 | CG | ARG | 37 | −1.713 | 6.381 | 42.403 | 1.00 | 2.00 |
| ATOM | 315 | CD | ARG | 37 | −1.287 | 7.057 | 43.664 | 1.00 | 2.41 |
| ATOM | 316 | NE | ARG | 37 | −1.942 | 8.346 | 43.828 | 1.00 | 2.04 |
| ATOM | 317 | HE | ARG | 37 | −1.677 | 9.086 | 43.246 | 1.00 | 0.00 |
| ATOM | 318 | CZ | ARG | 37 | −2.891 | 8.584 | 44.719 | 1.00 | 3.03 |
| ATOM | 319 | NH1 | ARG | 37 | −3.308 | 7.614 | 45.526 | 1.00 | 2.03 |
| ATOM | 320 | HH11 | ARG | 37 | −2.923 | 6.697 | 45.464 | 1.00 | 0.00 |
| ATOM | 321 | HH12 | ARG | 37 | −4.022 | 7.812 | 46.194 | 1.00 | 0.00 |
| ATOM | 322 | NH2 | ARG | 37 | −3.400 | 9.798 | 44.824 | 1.00 | 2.00 |
| ATOM | 323 | HH21 | ARG | 37 | −3.054 | 10.515 | 44.228 | 1.00 | 0.00 |
| ATOM | 324 | HH22 | ARG | 37 | −4.109 | 9.997 | 45.488 | 1.00 | 0.00 |
| ATOM | 325 | C | ARG | 37 | −2.443 | 3.732 | 40.884 | 1.00 | 3.21 |
| ATOM | 326 | O | ARG | 37 | −3.387 | 4.105 | 40.195 | 1.00 | 4.62 |
| ATOM | 327 | N | GLN | 38 | −2.496 | 2.657 | 41.652 | 1.00 | 5.11 |
| ATOM | 328 | H | GLN | 38 | −1.732 | 2.444 | 42.213 | 1.00 | 0.00 |
| ATOM | 329 | CA | GLN | 38 | −3.708 | 1.858 | 41.758 | 1.00 | 8.69 |
| ATOM | 330 | CB | GLN | 38 | −3.356 | 0.428 | 42.169 | 1.00 | 9.37 |
| ATOM | 331 | CG | GLN | 38 | −4.540 | −0.505 | 42.289 | 1.00 | 12.33 |
| ATOM | 332 | CD | GLN | 38 | −4.101 | −1.914 | 42.594 | 1.00 | 16.53 |
| ATOM | 333 | OE1 | GLN | 38 | −3.915 | −2.283 | 43.750 | 1.00 | 20.00 |
| ATOM | 334 | NE2 | GLN | 38 | −3.892 | −2.698 | 41.555 | 1.00 | 19.17 |
| ATOM | 335 | HE21 | GLN | 38 | −4.078 | −2.315 | 40.666 | 1.00 | 0.00 |
| ATOM | 336 | HE22 | GLN | 38 | −3.579 | −3.605 | 41.714 | 1.00 | 0.00 |
| ATOM | 337 | C | GLN | 38 | −4.649 | 2.483 | 42.772 | 1.00 | 8.28 |
| ATOM | 338 | O | GLN | 38 | −4.209 | 2.975 | 43.802 | 1.00 | 11.23 |
| ATOM | 339 | N | CYS | 39 | −5.938 | 2.477 | 42.469 | 1.00 | 8.89 |
| ATOM | 340 | H | CYS | 39 | −6.237 | 2.044 | 41.640 | 1.00 | 0.00 |
| ATOM | 341 | CA | CYS | 39 | −6.933 | 3.049 | 43.361 | 1.00 | 8.08 |
| ATOM | 342 | CB | CYS | 39 | −8.266 | 3.168 | 42.638 | 1.00 | 5.67 |
| ATOM | 343 | SG | CYS | 39 | −9.520 | 4.051 | 43.539 | 1.00 | 10.90 |
| ATOM | 344 | C | CYS | 39 | −7.085 | 2.150 | 44.577 | 1.00 | 9.83 |
| ATOM | 345 | O | CYS | 39 | −7.116 | 0.921 | 44.451 | 1.00 | 7.19 |
| ATOM | 346 | N | LEU | 40 | −7.158 | 2.768 | 45.750 | 1.00 | 7.63 |
| ATOM | 347 | H | LEU | 40 | −7.089 | 3.751 | 45.775 | 1.00 | 0.00 |
| ATOM | 348 | CA | LEU | 40 | −7.310 | 2.036 | 46.994 | 1.00 | 9.31 |
| ATOM | 349 | CB | LEU | 40 | −6.505 | 2.722 | 48.103 | 1.00 | 9.89 |
| ATOM | 350 | CG | LEU | 40 | −4.997 | 2.799 | 47.891 | 1.00 | 9.01 |
| ATOM | 351 | CD1 | LEU | 40 | −4.374 | 3.725 | 48.921 | 1.00 | 11.37 |
| ATOM | 352 | CD2 | LEU | 40 | −4.388 | 1.407 | 47.975 | 1.00 | 9.89 |
| ATOM | 353 | C | LEU | 40 | −8.774 | 1.974 | 47.405 | 1.00 | 9.85 |
| ATOM | 354 | O | LEU | 40 | −9.115 | 1.337 | 48.399 | 1.00 | 11.71 |
| ATOM | 355 | N | ARG | 41 | −9.638 | 2.622 | 46.633 | 1.00 | 9.83 |
| ATOM | 356 | H | ARG | 41 | −9.326 | 3.073 | 45.825 | 1.00 | 0.00 |
| ATOM | 357 | CA | ARG | 41 | −11.060 | 2.681 | 46.952 | 1.00 | 9.49 |
| ATOM | 358 | CB | ARG | 41 | −11.519 | 4.138 | 47.000 | 1.00 | 8.44 |
| ATOM | 359 | CG | ARG | 41 | −10.675 | 5.023 | 47.900 | 1.00 | 5.66 |
| ATOM | 360 | CD | ARG | 41 | −11.147 | 6.449 | 47.830 | 1.00 | 8.87 |
| ATOM | 361 | NE | ARG | 41 | −11.038 | 6.990 | 46.481 | 1.00 | 11.49 |
| ATOM | 362 | HE | ARG | 41 | −10.148 | 7.039 | 46.102 | 1.00 | 0.00 |
| ATOM | 363 | CZ | ARG | 41 | −12.057 | 7.468 | 45.775 | 1.00 | 13.34 |
| ATOM | 364 | NH1 | ARG | 41 | −13.280 | 7.483 | 46.280 | 1.00 | 15.40 |
| ATOM | 365 | HH11 | ARG | 41 | −13.439 | 7.153 | 47.206 | 1.00 | 0.00 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 366 | HH12 | ARG | 41 | −14.048 | 7.854 | 45.750 | 1.00 | 0.00 |
|------|-----|------|-----|----|---------|-------|--------|------|------|
| ATOM | 367 | NH2  | ARG | 41 | −11.851 | 7.937 | 44.555 | 1.00 | 14.77 |
| ATOM | 368 | HH21 | ARG | 41 | −10.937 | 7.928 | 44.156 | 1.00 | 0.00 |
| ATOM | 369 | HH22 | ARG | 41 | −12.626 | 8.289 | 44.031 | 1.00 | 0.00 |
| ATOM | 370 | C    | ARG | 41 | −11.990 | 1.898 | 46.042 | 1.00 | 9.85 |
| ATOM | 371 | O    | ARG | 41 | −13.110 | 1.581 | 46.434 | 1.00 | 8.69 |
| ATOM | 372 | N    | SER | 42 | −11.550 | 1.604 | 44.827 | 1.00 | 10.68 |
| ATOM | 373 | H    | SER | 42 | −10.650 | 1.838 | 44.525 | 1.00 | 0.00 |
| ATOM | 374 | CA   | SER | 42 | −12.389 | 0.859 | 43.902 | 1.00 | 12.49 |
| ATOM | 375 | CB   | SER | 42 | −12.866 | 1.763 | 42.764 | 1.00 | 12.46 |
| ATOM | 376 | OG   | SER | 42 | −11.774 | 2.306 | 42.050 | 1.00 | 17.74 |
| ATOM | 377 | HG   | SER | 42 | −12.149 | 3.093 | 41.607 | 1.00 | 0.00 |
| ATOM | 378 | C    | SER | 42 | −11.651 | −0.349 | 43.352 | 1.00 | 14.30 |
| ATOM | 379 | O    | SER | 42 | −10.457 | −0.528 | 43.600 | 1.00 | 14.79 |
| ATOM | 380 | N    | LEU | 43 | −12.381 | −1.209 | 42.654 | 1.00 | 14.42 |
| ATOM | 381 | H    | LEU | 43 | −13.322 | −1.022 | 42.491 | 1.00 | 0.00 |
| ATOM | 382 | CA   | LEU | 43 | −11.795 | −2.400 | 42.062 | 1.00 | 14.72 |
| ATOM | 383 | CB   | LEU | 43 | −12.800 | −3.556 | 42.094 | 1.00 | 15.93 |
| ATOM | 384 | CG   | LEU | 43 | −13.008 | −4.241 | 43.445 | 1.00 | 17.87 |
| ATOM | 385 | CD1  | LEU | 43 | −14.314 | −5.017 | 43.441 | 1.00 | 18.61 |
| ATOM | 386 | CD2  | LEU | 43 | −11.835 | −5.158 | 43.740 | 1.00 | 19.73 |
| ATOM | 387 | C    | LEU | 43 | −11.390 | −2.091 | 40.623 | 1.00 | 14.52 |
| ATOM | 388 | O    | LEU | 43 | −12.165 | −1.496 | 39.867 | 1.00 | 14.42 |
| ATOM | 389 | N    | GLY | 44 | −10.148 | −2.418 | 40.283 | 1.00 | 15.19 |
| ATOM | 390 | H    | GLY | 44 | −9.563  | −2.772 | 40.986 | 1.00 | 0.00 |
| ATOM | 391 | CA   | GLY | 44 | −9.646  | −2.186 | 38.938 | 1.00 | 13.99 |
| ATOM | 392 | C    | GLY | 44 | −9.496  | −0.733 | 38.533 | 1.00 | 11.65 |
| ATOM | 393 | O    | GLY | 44 | −9.353  | −0.434 | 37.353 | 1.00 | 15.02 |
| ATOM | 394 | N    | GLY | 45 | −9.489  | 0.170  | 39.503 | 1.00 | 9.86 |
| ATOM | 395 | H    | GLY | 45 | −9.551  | −0.116 | 40.434 | 1.00 | 0.00 |
| ATOM | 396 | CA   | GLY | 45 | −9.360  | 1.580  | 39.192 | 1.00 | 5.54 |
| ATOM | 397 | C    | GLY | 45 | −7.943  | 2.071  | 39.371 | 1.00 | 5.84 |
| ATOM | 398 | O    | GLY | 45 | −7.088  | 1.360  | 39.899 | 1.00 | 6.52 |
| ATOM | 399 | N    | TYR | 46 | −7.705  | 3.312  | 38.978 | 1.00 | 5.35 |
| ATOM | 400 | H    | TYR | 46 | −8.441  | 3.865  | 38.629 | 1.00 | 0.00 |
| ATOM | 401 | CA   | TYR | 46 | −6.389  | 3.916  | 39.077 | 1.00 | 5.58 |
| ATOM | 402 | CB   | TYR | 46 | −5.709  | 3.954  | 37.694 | 1.00 | 5.14 |
| ATOM | 403 | CG   | TYR | 46 | −5.371  | 2.597  | 37.127 | 1.00 | 6.25 |
| ATOM | 404 | CD1  | TYR | 46 | −4.305  | 1.853  | 37.634 | 1.00 | 7.73 |
| ATOM | 405 | CE1  | TYR | 46 | −4.046  | 0.573  | 37.177 | 1.00 | 7.63 |
| ATOM | 406 | CD2  | TYR | 46 | −6.157  | 2.024  | 36.136 | 1.00 | 8.86 |
| ATOM | 407 | CE2  | TYR | 46 | −5.905  | 0.743  | 35.670 | 1.00 | 7.09 |
| ATOM | 408 | CZ   | TYR | 46 | −4.858  | 0.024  | 36.197 | 1.00 | 9.65 |
| ATOM | 409 | OH   | TYR | 46 | −4.640  | −1.262 | 35.765 | 1.00 | 14.03 |
| ATOM | 410 | HH   | TYR | 46 | −4.204  | −1.681 | 36.505 | 1.00 | 0.00 |
| ATOM | 411 | C    | TYR | 46 | −6.548  | 5.339  | 39.564 | 1.00 | 6.00 |
| ATOM | 412 | O    | TYR | 46 | −7.667  | 5.816  | 39.748 | 1.00 | 5.33 |
| ATOM | 413 | N    | VAL | 47 | −5.429  | 5.988  | 39.840 | 1.00 | 3.93 |
| ATOM | 414 | H    | VAL | 47 | −4.562  | 5.532  | 39.759 | 1.00 | 0.00 |
| ATOM | 415 | CA   | VAL | 47 | −5.440  | 7.384  | 40.223 | 1.00 | 6.45 |
| ATOM | 416 | CB   | VAL | 47 | −5.152  | 7.623  | 41.720 | 1.00 | 5.21 |
| ATOM | 417 | CG1  | VAL | 47 | −5.289  | 9.116  | 42.024 | 1.00 | 2.00 |
| ATOM | 418 | CG2  | VAL | 47 | −6.108  | 6.824  | 42.591 | 1.00 | 2.00 |
| ATOM | 419 | C    | VAL | 47 | −4.333  | 8.033  | 39.398 | 1.00 | 6.52 |
| ATOM | 420 | O    | VAL | 47 | −3.225  | 7.504  | 39.323 | 1.00 | 5.99 |
| ATOM | 421 | N    | LEU | 48 | −4.672  | 9.119  | 38.710 | 1.00 | 8.11 |
| ATOM | 422 | H    | LEU | 48 | −5.588  | 9.443  | 38.750 | 1.00 | 0.00 |
| ATOM | 423 | CA   | LEU | 48 | −3.720  | 9.870  | 37.903 | 1.00 | 8.79 |
| ATOM | 424 | CB   | LEU | 48 | −4.418  | 10.427 | 36.658 | 1.00 | 12.43 |
| ATOM | 425 | CG   | LEU | 48 | −3.677  | 10.764 | 35.353 | 1.00 | 14.11 |
| ATOM | 426 | CD1  | LEU | 48 | −4.438  | 11.888 | 34.674 | 1.00 | 14.34 |
| ATOM | 427 | CD2  | LEU | 48 | −2.240  | 11.183 | 35.576 | 1.00 | 10.17 |
| ATOM | 428 | C    | LEU | 48 | −3.277  | 11.039 | 38.779 | 1.00 | 11.50 |
| ATOM | 429 | O    | LEU | 48 | −4.102  | 11.873 | 39.162 | 1.00 | 9.63 |
| ATOM | 430 | N    | SER | 49 | −1.998  | 11.078 | 39.139 | 1.00 | 11.61 |
| ATOM | 431 | H    | SER | 49 | −1.392  | 10.383 | 38.818 | 1.00 | 0.00 |
| ATOM | 432 | CA   | SER | 49 | −1.479  | 12.166 | 39.960 | 1.00 | 8.18 |
| ATOM | 433 | CB   | SER | 49 | −0.683  | 11.611 | 41.144 | 1.00 | 7.55 |
| ATOM | 434 | OG   | SER | 49 | −1.495  | 10.791 | 41.969 | 1.00 | 3.18 |
| ATOM | 435 | HG   | SER | 49 | −1.674  | 10.001 | 41.438 | 1.00 | 0.00 |
| ATOM | 436 | C    | SER | 49 | −0.595  | 13.083 | 39.108 | 1.00 | 9.13 |
| ATOM | 437 | O    | SER | 49 | 0.371   | 12.625 | 38.498 | 1.00 | 10.70 |
| ATOM | 438 | N    | LEU | 50 | −0.951  | 14.363 | 39.031 | 1.00 | 10.96 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 439 | H | LEU | 50 | −1.751 | 14.686 | 39.502 | 1.00 | 0.00 |
|---|---|---|---|---|---|---|---|---|---|
| ATOM | 440 | CA | LEU | 50 | −0.170 | 15.315 | 38.252 | 1.00 | 12.63 |
| ATOM | 441 | CB | LEU | 50 | −0.735 | 15.498 | 36.827 | 1.00 | 16.12 |
| ATOM | 442 | CG | LEU | 50 | −2.127 | 15.995 | 36.426 | 1.00 | 17.82 |
| ATOM | 443 | CD1 | LEU | 50 | −3.182 | 15.206 | 37.167 | 1.00 | 23.32 |
| ATOM | 444 | CD2 | LEU | 50 | −2.275 | 17.479 | 36.672 | 1.00 | 17.92 |
| ATOM | 445 | C | LEU | 50 | 0.064 | 16.657 | 38.929 | 1.00 | 11.83 |
| ATOM | 446 | O | LEU | 50 | −0.663 | 17.056 | 39.845 | 1.00 | 8.52 |
| ATOM | 447 | N | VAL | 51 | 1.099 | 17.343 | 38.467 | 1.00 | 10.51 |
| ATOM | 448 | H | VAL | 51 | 1.613 | 16.980 | 37.717 | 1.00 | 0.00 |
| ATOM | 449 | CA | VAL | 51 | 1.471 | 18.635 | 39.007 | 1.00 | 10.18 |
| ATOM | 450 | CB | VAL | 51 | 3.000 | 18.704 | 39.283 | 1.00 | 9.58 |
| ATOM | 451 | CG1 | VAL | 51 | 3.369 | 20.031 | 39.938 | 1.00 | 5.85 |
| ATOM | 452 | CG2 | VAL | 51 | 3.445 | 17.520 | 40.138 | 1.00 | 8.60 |
| ATOM | 453 | C | VAL | 51 | 1.111 | 19.758 | 38.046 | 1.00 | 10.79 |
| ATOM | 454 | O | VAL | 51 | 1.283 | 19.637 | 36.833 | 1.00 | 11.95 |
| ATOM | 455 | N | HIS | 52 | 0.545 | 20.823 | 38.591 | 1.00 | 10.19 |
| ATOM | 456 | H | HIS | 52 | 0.343 | 20.832 | 39.556 | 1.00 | 0.00 |
| ATOM | 457 | CA | HIS | 52 | 0.231 | 22.005 | 37.814 | 1.00 | 13.16 |
| ATOM | 458 | CB | HIS | 52 | −1.148 | 21.937 | 37.167 | 1.00 | 16.99 |
| ATOM | 459 | CG | HIS | 52 | −1.460 | 23.127 | 36.308 | 1.00 | 19.12 |
| ATOM | 460 | CD2 | HIS | 52 | −2.483 | 24.011 | 36.344 | 1.00 | 19.25 |
| ATOM | 461 | ND1 | HIS | 52 | −0.645 | 23.530 | 35.269 | 1.00 | 21.39 |
| ATOM | 462 | HD1 | HIS | 52 | 0.164 | 23.066 | 34.951 | 1.00 | 0.00 |
| ATOM | 463 | CE1 | HIS | 52 | −1.154 | 24.607 | 34.702 | 1.00 | 18.57 |
| ATOM | 464 | NE2 | HIS | 52 | −2.271 | 24.919 | 35.335 | 1.00 | 20.49 |
| ATOM | 465 | HE2 | HIS | 52 | −2.880 | 25.642 | 35.070 | 1.00 | 0.00 |
| ATOM | 466 | C | HIS | 52 | 0.285 | 23.137 | 38.813 | 1.00 | 14.35 |
| ATOM | 467 | O | HIS | 52 | −0.304 | 23.033 | 39.884 | 1.00 | 14.87 |
| ATOM | 468 | N | ASP | 53 | 1.035 | 24.186 | 38.487 | 1.00 | 18.31 |
| ATOM | 469 | H | ASP | 53 | 1.499 | 24.235 | 37.643 | 1.00 | 0.00 |
| ATOM | 470 | CA | ASP | 53 | 1.182 | 25.341 | 39.370 | 1.00 | 21.21 |
| ATOM | 471 | CB | ASP | 53 | −0.156 | 26.062 | 39.523 | 1.00 | 25.36 |
| ATOM | 472 | CG | ASP | 53 | −0.260 | 27.272 | 38.643 | 1.00 | 33.50 |
| ATOM | 473 | OD1 | ASP | 53 | −0.918 | 27.174 | 37.586 | 1.00 | 39.21 |
| ATOM | 474 | OD2 | ASP | 53 | 0.314 | 28.321 | 39.016 | 1.00 | 35.58 |
| ATOM | 475 | C | ASP | 53 | 1.709 | 24.977 | 40.753 | 1.00 | 21.34 |
| ATOM | 476 | O | ASP | 53 | 1.213 | 25.490 | 41.759 | 1.00 | 20.63 |
| ATOM | 477 | N | VAL | 54 | 2.706 | 24.094 | 40.803 | 1.00 | 20.75 |
| ATOM | 478 | H | VAL | 54 | 3.064 | 23.729 | 39.964 | 1.00 | 0.00 |
| ATOM | 479 | CA | VAL | 54 | 3.298 | 23.650 | 42.072 | 1.00 | 21.10 |
| ATOM | 480 | CB | VAL | 54 | 4.081 | 24.806 | 42.777 | 1.00 | 22.31 |
| ATOM | 481 | CG1 | VAL | 54 | 4.962 | 24.261 | 43.892 | 1.00 | 21.47 |
| ATOM | 482 | CG2 | VAL | 54 | 4.943 | 25.546 | 41.773 | 1.00 | 25.32 |
| ATOM | 483 | C | VAL | 54 | 2.207 | 23.094 | 43.004 | 1.00 | 20.23 |
| ATOM | 484 | O | VAL | 54 | 2.325 | 23.144 | 44.234 | 1.00 | 21.96 |
| ATOM | 485 | N | ARG | 55 | 1.180 | 22.502 | 42.399 | 1.00 | 20.64 |
| ATOM | 486 | H | ARG | 55 | 1.149 | 22.431 | 41.425 | 1.00 | 0.00 |
| ATOM | 487 | CA | ARG | 55 | 0.049 | 21.936 | 43.127 | 1.00 | 20.79 |
| ATOM | 488 | CB | ARG | 55 | −1.166 | 22.862 | 42.982 | 1.00 | 24.88 |
| ATOM | 489 | CG | ARG | 55 | −2.454 | 22.303 | 43.543 | 1.00 | 37.51 |
| ATOM | 490 | CD | ARG | 55 | −2.330 | 22.040 | 45.036 | 1.00 | 47.31 |
| ATOM | 491 | NE | ARG | 55 | −3.385 | 21.152 | 45.519 | 1.00 | 52.82 |
| ATOM | 492 | HE | ARG | 55 | −4.305 | 21.346 | 45.243 | 1.00 | 0.00 |
| ATOM | 493 | CZ | ARG | 55 | −3.179 | 20.109 | 46.319 | 1.00 | 54.83 |
| ATOM | 494 | NH1 | ARG | 55 | −1.950 | 19.818 | 46.738 | 1.00 | 51.75 |
| ATOM | 495 | HH11 | ARG | 55 | −1.181 | 20.384 | 46.445 | 1.00 | 0.00 |
| ATOM | 496 | HH12 | ARG | 55 | −1.803 | 19.025 | 47.333 | 1.00 | 0.00 |
| ATOM | 497 | NH2 | ARG | 55 | −4.204 | 19.345 | 46.686 | 1.00 | 55.41 |
| ATOM | 498 | HH21 | ARG | 55 | −5.129 | 19.569 | 46.367 | 1.00 | 0.00 |
| ATOM | 499 | HH22 | ARG | 55 | −4.061 | 18.561 | 47.291 | 1.00 | 0.00 |
| ATOM | 500 | C | ARG | 55 | −0.278 | 20.539 | 42.586 | 1.00 | 17.44 |
| ATOM | 501 | O | ARG | 55 | −0.162 | 20.289 | 41.386 | 1.00 | 16.40 |
| ATOM | 502 | N | PHE | 56 | −0.697 | 19.642 | 43.472 | 1.00 | 12.91 |
| ATOM | 503 | H | PHE | 56 | −0.795 | 19.904 | 44.409 | 1.00 | 0.00 |
| ATOM | 504 | CA | PHE | 56 | −1.038 | 18.276 | 43.087 | 1.00 | 11.38 |
| ATOM | 505 | CB | PHE | 56 | −0.670 | 17.295 | 44.192 | 1.00 | 7.94 |
| ATOM | 506 | CG | PHE | 56 | 0.767 | 17.346 | 44.596 | 1.00 | 9.45 |
| ATOM | 507 | CD1 | PHE | 56 | 1.134 | 17.879 | 45.828 | 1.00 | 9.25 |
| ATOM | 508 | CD2 | PHE | 56 | 1.756 | 16.864 | 43.571 | 1.00 | 7.32 |
| ATOM | 509 | CE1 | PHE | 56 | 2.468 | 17.931 | 46.213 | 1.00 | 7.59 |
| ATOM | 510 | CE2 | PHE | 56 | 3.093 | 16.911 | 44.126 | 1.00 | 10.67 |
| ATOM | 511 | CZ | PHE | 56 | 3.449 | 17.448 | 45.362 | 1.00 | 7.88 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 512 | C   | PHE | 56 | -2.518  | 18.128 | 42.806 | 1.00 | 10.74 |
|------|-----|-----|-----|----|---------|--------|--------|------|-------|
| ATOM | 513 | O   | PHE | 56 | -3.354  | 18.696 | 43.502 | 1.00 | 11.90 |
| ATOM | 514 | N   | HIS | 57 | -2.835  | 17.346 | 41.786 | 1.00 | 12.61 |
| ATOM | 515 | H   | HIS | 57 | -2.116  | 16.929 | 41.249 | 1.00 | 0.00  |
| ATOM | 516 | CA  | HIS | 57 | -4.217  | 17.082 | 41.405 | 1.00 | 12.51 |
| ATOM | 517 | CB  | HIS | 57 | -4.550  | 17.771 | 40.076 | 1.00 | 15.95 |
| ATOM | 518 | CG  | HIS | 57 | -4.415  | 19.263 | 40.108 | 1.00 | 16.89 |
| ATOM | 519 | CD2 | HIS | 57 | -3.346  | 20.065 | 39.882 | 1.00 | 17.62 |
| ATOM | 520 | ND1 | HIS | 57 | -5.466  | 20.103 | 40.413 | 1.00 | 21.02 |
| ATOM | 521 | HD1 | HIS | 57 | -6.378  | 19.803 | 40.644 | 1.00 | 0.00  |
| ATOM | 522 | CE1 | HIS | 57 | -5.050  | 21.356 | 40.374 | 1.00 | 18.85 |
| ATOM | 523 | NE2 | HIS | 57 | -3.770  | 21.361 | 40.056 | 1.00 | 17.75 |
| ATOM | 524 | HE2 | HIS | 57 | -3.184  | 22.148 | 40.028 | 1.00 | 0.00  |
| ATOM | 525 | C   | HIS | 57 | -4.288  | 15.567 | 41.245 | 1.00 | 11.47 |
| ATOM | 526 | O   | HIS | 57 | -3.451  | 14.981 | 40.553 | 1.00 | 9.71  |
| ATOM | 527 | N   | HIS | 58 | -5.226  | 14.932 | 41.947 | 1.00 | 10.52 |
| ATOM | 528 | H   | HIS | 58 | -5.837  | 15.442 | 42.530 | 1.00 | 0.00  |
| ATOM | 529 | CA  | HIS | 58 | -5.387  | 13.478 | 41.892 | 1.00 | 7.58  |
| ATOM | 530 | CB  | HIS | 58 | -5.236  | 12.884 | 43.293 | 1.00 | 4.66  |
| ATOM | 531 | CG  | HIS | 58 | -3.964  | 13.291 | 43.973 | 1.00 | 4.02  |
| ATOM | 532 | CD2 | HIS | 58 | -3.707  | 14.285 | 44.855 | 1.00 | 2.46  |
| ATOM | 533 | ND1 | HIS | 58 | -2.748  | 12.703 | 43.697 | 1.00 | 3.15  |
| ATOM | 534 | HD1 | HIS | 58 | -2.585  | 11.924 | 43.109 | 1.00 | 0.00  |
| ATOM | 535 | CE1 | HIS | 58 | -1.799  | 13.318 | 44.372 | 1.00 | 2.00  |
| ATOM | 536 | NE2 | HIS | 58 | -2.354  | 14.281 | 45.082 | 1.00 | 3.60  |
| ATOM | 537 | HE2 | HIS | 58 | -1.914  | 14.927 | 45.656 | 1.00 | 0.00  |
| ATOM | 538 | C   | HIS | 58 | -6.734  | 13.130 | 41.302 | 1.00 | 6.91  |
| ATOM | 539 | O   | HIS | 58 | -7.773  | 13.391 | 41.905 | 1.00 | 10.26 |
| ATOM | 540 | N   | PHE | 59 | -6.704  | 12.588 | 40.093 | 1.00 | 8.54  |
| ATOM | 541 | H   | PHE | 59 | -5.843  | 12.465 | 39.640 | 1.00 | 0.00  |
| ATOM | 542 | CA  | PHE | 59 | -7.907  | 12.202 | 39.372 | 1.00 | 5.78  |
| ATOM | 543 | CB  | PHE | 59 | -7.816  | 12.653 | 37.915 | 1.00 | 7.34  |
| ATOM | 544 | CG  | PHE | 59 | -7.752  | 14.138 | 37.749 | 1.00 | 7.56  |
| ATOM | 545 | CD1 | PHE | 59 | -6.533  | 14.796 | 37.774 | 1.00 | 8.46  |
| ATOM | 546 | CD2 | PHE | 59 | -8.913  | 14.881 | 37.588 | 1.00 | 6.77  |
| ATOM | 547 | CE1 | PHE | 59 | -6.466  | 16.181 | 37.646 | 1.00 | 10.40 |
| ATOM | 548 | CE2 | PHE | 59 | -8.856  | 16.263 | 37.461 | 1.00 | 9.75  |
| ATOM | 549 | CZ  | PHE | 59 | -7.630  | 16.915 | 37.492 | 1.00 | 11.63 |
| ATOM | 550 | C   | PHE | 59 | -8.126  | 10.703 | 39.410 | 1.00 | 6.79  |
| ATOM | 551 | O   | PHE | 59 | -7.342  | 9.932  | 38.852 | 1.00 | 7.41  |
| ATOM | 552 | N   | PRO | 60 | -9.188  | 10.263 | 40.089 | 1.00 | 9.70  |
| ATOM | 553 | CD  | PRO | 60 | -10.180 | 11.018 | 40.877 | 1.00 | 6.89  |
| ATOM | 554 | CA  | PRO | 60 | -9.444  | 8.826  | 40.147 | 1.00 | 10.01 |
| ATOM | 555 | CB  | PRO | 60 | -10.483 | 8.718  | 41.258 | 1.00 | 10.34 |
| ATOM | 556 | CG  | PRO | 60 | -11.247 | 9.988  | 41.119 | 1.00 | 9.58  |
| ATOM | 557 | C   | PRO | 60 | -9.983  | 8.349  | 38.804 | 1.00 | 13.30 |
| ATOM | 558 | O   | PRO | 60 | -10.806 | 9.023  | 38.174 | 1.00 | 14.14 |
| ATOM | 559 | N   | ILE | 61 | -9.457  | 7.226  | 38.339 | 1.00 | 13.16 |
| ATOM | 560 | H   | ILE | 61 | -8.791  | 6.793  | 38.870 | 1.00 | 0.00  |
| ATOM | 561 | CA  | ILE | 61 | -9.857  | 6.625  | 37.079 | 1.00 | 13.78 |
| ATOM | 562 | CB  | ILE | 61 | -8.615  | 6.239  | 36.246 | 1.00 | 11.71 |
| ATOM | 563 | CG2 | ILE | 61 | -9.025  | 5.656  | 34.906 | 1.00 | 13.24 |
| ATOM | 564 | CG1 | ILE | 61 | -7.715  | 7.460  | 36.041 | 1.00 | 9.66  |
| ATOM | 565 | CD  | ILE | 61 | -6.386  | 7.129  | 35.387 | 1.00 | 6.22  |
| ATOM | 566 | C   | ILE | 61 | -10.651 | 5.366  | 37.432 | 1.00 | 15.81 |
| ATOM | 567 | O   | ILE | 61 | -10.165 | 4.499  | 38.167 | 1.00 | 14.88 |
| ATOM | 568 | N   | GLU | 62 | -11.883 | 5.286  | 36.947 | 1.00 | 19.32 |
| ATOM | 569 | H   | GLU | 62 | -12.238 | 6.005  | 36.378 | 1.00 | 0.00  |
| ATOM | 570 | CA  | GLU | 62 | -12.723 | 4.132  | 37.233 | 1.00 | 23.46 |
| ATOM | 571 | CB  | GLU | 62 | -14.100 | 4.575  | 38.253 | 1.00 | 28.96 |
| ATOM | 572 | CG  | GLU | 62 | -14.963 | 3.422  | 38.253 | 1.00 | 36.57 |
| ATOM | 573 | CD  | GLU | 62 | -16.337 | 3.864  | 38.716 | 1.00 | 40.63 |
| ATOM | 574 | OE1 | GLU | 62 | -17.320 | 3.612  | 37.980 | 1.00 | 41.74 |
| ATOM | 575 | OE2 | GLU | 62 | -16.434 | 4.450  | 39.819 | 1.00 | 41.68 |
| ATOM | 576 | C   | GLU | 62 | -12.884 | 3.230  | 36.021 | 1.00 | 21.41 |
| ATOM | 577 | O   | GLU | 62 | -12.984 | 3.707  | 34.892 | 1.00 | 21.22 |
| ATOM | 578 | N   | ARG | 63 | -12.867 | 1.925  | 36.262 | 1.00 | 21.79 |
| ATOM | 579 | H   | ARG | 63 | -12.783 | 1.600  | 37.186 | 1.00 | 0.00  |
| ATOM | 580 | CA  | ARG | 63 | -13.036 | 0.943  | 35.205 | 1.00 | 25.45 |
| ATOM | 581 | CB  | ARG | 63 | -12.425 | -0.391 | 35.615 | 1.00 | 27.80 |
| ATOM | 582 | CG  | ARG | 63 | -12.414 | -1.419 | 34.496 | 1.00 | 33.00 |
| ATOM | 583 | CD  | ARG | 63 | -11.931 | -2.760 | 34.997 | 1.00 | 33.41 |
| ATOM | 584 | NE  | ARG | 63 | -12.828 | -3.269 | 36.027 | 1.00 | 35.94 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 585 | HE | ARG | 63 | −13.722 | −2.876 | 36.094 | 1.00 | 0.00 |
|---|---|---|---|---|---|---|---|---|---|
| ATOM | 586 | CZ | ARG | 63 | −12.516 | −4.231 | 36.887 | 1.00 | 35.92 |
| ATOM | 587 | NH1 | ARG | 63 | −11.318 | −4.806 | 36.851 | 1.00 | 37.94 |
| ATOM | 588 | HH11 | ARG | 63 | −10.639 | −4.529 | 36.173 | 1.00 | 0.00 |
| ATOM | 589 | HH12 | ARG | 63 | −11.100 | −5.528 | 37.509 | 1.00 | 0.00 |
| ATOM | 590 | NH2 | ARG | 63 | −13.406 | −4.610 | 37.793 | 1.00 | 36.87 |
| ATOM | 591 | HH21 | ARG | 63 | −14.306 | −4.173 | 37.818 | 1.00 | 0.00 |
| ATOM | 592 | HH22 | ARG | 63 | −13.189 | −5.331 | 38.450 | 1.00 | 0.00 |
| ATOM | 593 | C | ARG | 63 | −14.529 | 0.767 | 34.999 | 1.00 | 26.74 |
| ATOM | 594 | O | ARG | 63 | −15.218 | 0.244 | 35.872 | 1.00 | 29.01 |
| ATOM | 595 | N | GLN | 64 | −15.028 | 1.218 | 33.856 | 1.00 | 29.10 |
| ATOM | 596 | H | GLN | 64 | −14.402 | 1.626 | 33.234 | 1.00 | 0.00 |
| ATOM | 597 | CA | GLN | 64 | −16.449 | 1.125 | 33.538 | 1.00 | 32.01 |
| ATOM | 598 | CB | GLN | 64 | −16.757 | 1.886 | 32.247 | 1.00 | 31.94 |
| ATOM | 599 | CG | GLN | 64 | −16.217 | 3.306 | 32.192 | 1.00 | 35.07 |
| ATOM | 600 | CD | GLN | 64 | −16.893 | 4.236 | 33.175 | 1.00 | 36.14 |
| ATOM | 601 | OE1 | GLN | 64 | −16.698 | 4.135 | 34.384 | 1.00 | 36.71 |
| ATOM | 602 | NE2 | GLN | 64 | −17.681 | 5.164 | 32.655 | 1.00 | 40.49 |
| ATOM | 603 | HE21 | GLN | 64 | −17.785 | 5.194 | 31.683 | 1.00 | 0.00 |
| ATOM | 604 | HE22 | GLN | 64 | −18.122 | 5.773 | 33.280 | 1.00 | 0.00 |
| ATOM | 605 | C | GLN | 64 | −16.911 | −0.318 | 33.385 | 1.00 | 35.23 |
| ATOM | 606 | O | GLN | 64 | −16.117 | −1.214 | 33.084 | 1.00 | 36.40 |
| ATOM | 607 | N | LEU | 65 | −18.215 | −0.523 | 33.551 | 1.00 | 39.04 |
| ATOM | 608 | H | LEU | 65 | −18.766 | 0.242 | 33.804 | 1.00 | 0.00 |
| ATOM | 609 | CA | LEU | 65 | −18.834 | −1.842 | 33.428 | 1.00 | 41.57 |
| ATOM | 610 | CB | LEU | 65 | −20.361 | −1.731 | 33.578 | 1.00 | 45.35 |
| ATOM | 611 | CG | LEU | 65 | −21.194 | −1.014 | 32.498 | 1.00 | 48.79 |
| ATOM | 612 | CD1 | LEU | 65 | −22.682 | −1.210 | 32.774 | 1.00 | 48.80 |
| ATOM | 613 | CD2 | LEU | 65 | −20.861 | 0.477 | 32.425 | 1.00 | 48.69 |
| ATOM | 614 | C | LEU | 65 | −18.490 | −2.498 | 32.089 | 1.00 | 40.88 |
| ATOM | 615 | O | LEU | 65 | −18.406 | −3.720 | 31.988 | 1.00 | 41.06 |
| ATOM | 616 | N | ASN | 66 | −18.281 | −1.670 | 31.070 | 1.00 | 40.78 |
| ATOM | 617 | H | ASN | 66 | −18.363 | −0.709 | 31.237 | 1.00 | 0.00 |
| ATOM | 618 | CA | ASN | 66 | −17.946 | −2.155 | 29.735 | 1.00 | 39.66 |
| ATOM | 619 | CB | ASN | 66 | −18.496 | −1.214 | 28.649 | 1.00 | 43.14 |
| ATOM | 620 | CG | ASN | 66 | −18.333 | 0.255 | 28.995 | 1.00 | 46.18 |
| ATOM | 621 | OD1 | ASN | 66 | −18.884 | 0.742 | 29.987 | 1.00 | 48.62 |
| ATOM | 622 | ND2 | ASN | 66 | −17.605 | 0.977 | 28.161 | 1.00 | 45.77 |
| ATOM | 623 | HD21 | ASN | 66 | −17.199 | 0.536 | 27.388 | 1.00 | 0.00 |
| ATOM | 624 | HD22 | ASN | 66 | −17.532 | 1.927 | 28.370 | 1.00 | 0.00 |
| ATOM | 625 | C | ASN | 66 | −16.464 | −2.440 | 29.505 | 1.00 | 36.70 |
| ATOM | 626 | O | ASN | 66 | −16.045 | −2.686 | 28.375 | 1.00 | 35.57 |
| ATOM | 627 | N | GLY | 67 | −15.676 | −2.408 | 30.577 | 1.00 | 35.06 |
| ATOM | 628 | H | GLY | 67 | −16.031 | −2.213 | 31.465 | 1.00 | 0.00 |
| ATOM | 629 | CA | GLY | 67 | −14.253 | −2.686 | 30.467 | 1.00 | 32.41 |
| ATOM | 630 | C | GLY | 67 | −13.349 | −1.520 | 30.106 | 1.00 | 30.31 |
| ATOM | 631 | O | GLY | 67 | −12.138 | −1.697 | 29.991 | 1.00 | 30.24 |
| ATOM | 632 | N | THR | 68 | −13.923 | −0.338 | 29.904 | 1.00 | 28.66 |
| ATOM | 633 | H | THR | 68 | −14.888 | −0.234 | 29.971 | 1.00 | 0.00 |
| ATOM | 634 | CA | THR | 68 | −13.128 | 0.838 | 29.574 | 1.00 | 25.46 |
| ATOM | 635 | CB | THR | 68 | −13.872 | 1.785 | 28.620 | 1.00 | 26.78 |
| ATOM | 636 | OG1 | THR | 68 | −15.186 | 2.052 | 29.127 | 1.00 | 27.70 |
| ATOM | 637 | HG1 | THR | 68 | −15.620 | 2.606 | 28.472 | 1.00 | 0.00 |
| ATOM | 638 | CG2 | THR | 68 | −13.957 | 1.180 | 27.230 | 1.00 | 27.47 |
| ATOM | 639 | C | THR | 68 | −12.746 | 1.596 | 30.838 | 1.00 | 23.00 |
| ATOM | 640 | O | THR | 68 | −13.144 | 1.220 | 31.938 | 1.00 | 22.61 |
| ATOM | 641 | N | TYR | 69 | −11.995 | 2.678 | 30.673 | 1.00 | 20.59 |
| ATOM | 642 | H | TYR | 69 | −11.718 | 2.938 | 29.778 | 1.00 | 0.00 |
| ATOM | 643 | CA | TYR | 69 | −11.551 | 3.483 | 31.796 | 1.00 | 15.58 |
| ATOM | 644 | CB | TYR | 69 | −10.047 | 3.328 | 31.978 | 1.00 | 12.63 |
| ATOM | 645 | CG | TYR | 69 | −9.664 | 1.936 | 32.386 | 1.00 | 12.79 |
| ATOM | 646 | CD1 | TYR | 69 | −9.485 | 0.934 | 31.433 | 1.00 | 10.68 |
| ATOM | 647 | CE1 | TYR | 69 | −9.189 | −0.370 | 31.815 | 1.00 | 13.20 |
| ATOM | 648 | CD2 | TYR | 69 | −9.533 | 1.601 | 33.731 | 1.00 | 9.78 |
| ATOM | 649 | CE2 | TYR | 69 | −9.236 | 0.308 | 34.119 | 1.00 | 11.49 |
| ATOM | 650 | CZ | TYR | 69 | −9.067 | −0.674 | 33.161 | 1.00 | 11.48 |
| ATOM | 651 | OH | TYR | 69 | −8.785 | −1.961 | 33.546 | 1.00 | 13.55 |
| ATOM | 652 | HH | TYR | 69 | −8.850 | −2.067 | 34.504 | 1.00 | 0.00 |
| ATOM | 653 | C | TYR | 69 | −11.897 | 4.936 | 31.583 | 1.00 | 15.95 |
| ATOM | 654 | O | TYR | 69 | −11.727 | 5.468 | 30.487 | 1.00 | 13.25 |
| ATOM | 655 | N | ALA | 70 | −12.361 | 5.591 | 32.638 | 1.00 | 17.69 |
| ATOM | 656 | H | ALA | 70 | −12.479 | 5.142 | 33.508 | 1.00 | 0.00 |
| ATOM | 657 | CA | ALA | 70 | −12.725 | 6.991 | 32.533 | 1.00 | 19.16 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 658 | CB | ALA | 70 | −14.150 | 7.121 | 31.981 | 1.00 | 18.87 |
|---|---|---|---|---|---|---|---|---|---|
| ATOM | 659 | C | ALA | 70 | −12.608 | 7.742 | 33.848 | 1.00 | 18.59 |
| ATOM | 660 | O | ALA | 70 | −12.844 | 7.184 | 34.925 | 1.00 | 19.11 |
| ATOM | 661 | N | ILE | 71 | −12.155 | 8.985 | 33.749 | 1.00 | 19.47 |
| ATOM | 662 | H | ILE | 71 | −11.906 | 9.337 | 32.870 | 1.00 | 0.00 |
| ATOM | 663 | CA | ILE | 71 | −12.048 | 9.864 | 34.897 | 1.00 | 19.95 |
| ATOM | 664 | CB | ILE | 71 | −11.037 | 10.989 | 34.645 | 1.00 | 21.71 |
| ATOM | 665 | CG2 | ILE | 71 | −11.010 | 11.948 | 35.814 | 1.00 | 20.85 |
| ATOM | 666 | CG1 | ILE | 71 | −9.644 | 10.405 | 34.428 | 1.00 | 21.25 |
| ATOM | 667 | CD | ILE | 71 | −8.597 | 11.453 | 34.109 | 1.00 | 23.55 |
| ATOM | 668 | C | ILE | 71 | −13.448 | 10.455 | 34.936 | 1.00 | 21.14 |
| ATOM | 669 | O | ILE | 71 | −14.049 | 10.673 | 33.888 | 1.00 | 19.95 |
| ATOM | 670 | N | ALA | 72 | −13.991 | 10.669 | 36.126 | 1.00 | 25.60 |
| ATOM | 671 | H | ALA | 72 | −13.484 | 10.472 | 36.937 | 1.00 | 0.00 |
| ATOM | 672 | CA | ALA | 72 | −15.335 | 11.220 | 36.240 | 1.00 | 30.18 |
| ATOM | 673 | CB | ALA | 72 | −15.679 | 11.495 | 37.698 | 1.00 | 31.23 |
| ATOM | 674 | C | ALA | 72 | −15.458 | 12.494 | 35.412 | 1.00 | 33.10 |
| ATOM | 675 | O | ALA | 72 | −14.651 | 13.418 | 35.551 | 1.00 | 34.99 |
| ATOM | 676 | N | GLY | 73 | −16.425 | 12.502 | 34.500 | 1.00 | 33.63 |
| ATOM | 677 | H | GLY | 73 | −16.972 | 11.706 | 34.360 | 1.00 | 0.00 |
| ATOM | 678 | CA | GLY | 73 | −16.643 | 13.663 | 33.658 | 1.00 | 34.45 |
| ATOM | 679 | C | GLY | 73 | −15.998 | 13.530 | 32.293 | 1.00 | 34.98 |
| ATOM | 680 | O | GLY | 73 | −16.470 | 14.113 | 31.317 | 1.00 | 36.54 |
| ATOM | 681 | N | GLY | 74 | −14.931 | 12.743 | 32.221 | 1.00 | 34.48 |
| ATOM | 682 | H | GLY | 74 | −14.615 | 12.263 | 33.010 | 1.00 | 0.00 |
| ATOM | 683 | CA | GLY | 74 | −14.230 | 12.558 | 30.996 | 1.00 | 32.55 |
| ATOM | 684 | C | GLY | 74 | −14.704 | 11.388 | 30.130 | 1.00 | 32.17 |
| ATOM | 685 | O | GLY | 74 | −15.632 | 10.666 | 30.493 | 1.00 | 32.72 |
| ATOM | 686 | N | LYS | 75 | −14.040 | 11.200 | 28.997 | 1.00 | 31.90 |
| ATOM | 687 | H | LYS | 75 | −13.309 | 11.813 | 28.811 | 1.00 | 0.00 |
| ATOM | 688 | CA | LYS | 75 | −14.361 | 10.125 | 28.075 | 1.00 | 30.83 |
| ATOM | 689 | CB | LYS | 75 | −14.002 | 10.536 | 26.645 | 1.00 | 34.04 |
| ATOM | 690 | CG | LYS | 75 | −12.604 | 11.124 | 26.486 | 1.00 | 37.94 |
| ATOM | 691 | CD | LYS | 75 | −12.207 | 11.203 | 25.022 | 1.00 | 40.86 |
| ATOM | 692 | CE | LYS | 75 | −12.088 | 9.811 | 24.408 | 1.00 | 44.39 |
| ATOM | 693 | NZ | LYS | 75 | −11.678 | 9.850 | 22.977 | 1.00 | 46.69 |
| ATOM | 694 | HZ1 | LYS | 75 | −10.759 | 10.330 | 22.888 | 1.00 | 0.00 |
| ATOM | 695 | HZ2 | LYS | 75 | −12.394 | 10.355 | 22.419 | 1.00 | 0.00 |
| ATOM | 696 | HZ3 | LYS | 75 | −11.601 | 8.873 | 22.628 | 1.00 | 0.00 |
| ATOM | 697 | C | LYS | 75 | −13.652 | 8.825 | 28.443 | 1.00 | 29.70 |
| ATOM | 698 | O | LYS | 75 | −12.567 | 8.840 | 29.035 | 1.00 | 29.72 |
| ATOM | 699 | N | ALA | 76 | −14.264 | 7.705 | 28.072 | 1.00 | 26.68 |
| ATOM | 700 | H | ALA | 76 | −15.096 | 7.775 | 27.566 | 1.00 | 0.00 |
| ATOM | 701 | CA | ALA | 76 | −13.711 | 6.388 | 28.352 | 1.00 | 26.38 |
| ATOM | 702 | CB | ALA | 76 | −14.813 | 5.334 | 28.327 | 1.00 | 26.29 |
| ATOM | 703 | C | ALA | 76 | −12.621 | 6.028 | 27.355 | 1.00 | 23.85 |
| ATOM | 704 | O | ALA | 76 | −12.590 | 6.542 | 26.241 | 1.00 | 23.96 |
| ATOM | 705 | N | HIS | 77 | −11.718 | 5.149 | 27.769 | 1.00 | 23.92 |
| ATOM | 706 | H | HIS | 77 | −11.794 | 4.779 | 28.678 | 1.00 | 0.00 |
| ATOM | 707 | CA | HIS | 77 | −10.624 | 4.715 | 26.915 | 1.00 | 23.21 |
| ATOM | 708 | CB | HIS | 77 | −9.349 | 5.468 | 27.270 | 1.00 | 22.18 |
| ATOM | 709 | CG | HIS | 77 | −9.466 | 6.947 | 27.097 | 1.00 | 22.49 |
| ATOM | 710 | CD2 | HIS | 77 | −9.273 | 7.732 | 26.012 | 1.00 | 23.47 |
| ATOM | 711 | ND1 | HIS | 77 | −9.870 | 7.784 | 28.111 | 1.00 | 25.61 |
| ATOM | 712 | HD1 | HIS | 77 | −10.123 | 7.524 | 29.028 | 1.00 | 0.00 |
| ATOM | 713 | CE1 | HIS | 77 | −9.920 | 9.025 | 27.662 | 1.00 | 25.59 |
| ATOM | 714 | NE2 | HIS | 77 | −9.563 | 9.020 | 26.390 | 1.00 | 24.65 |
| ATOM | 715 | HE2 | HIS | 77 | −9.544 | 9.793 | 25.792 | 1.00 | 0.00 |
| ATOM | 716 | C | HIS | 77 | −10.413 | 3.227 | 27.073 | 1.00 | 23.54 |
| ATOM | 717 | O | HIS | 77 | −10.833 | 2.640 | 28.067 | 1.00 | 22.48 |
| ATOM | 718 | N | CYS | 78 | −9.762 | 2.622 | 26.086 | 1.00 | 24.06 |
| ATOM | 719 | H | CYS | 78 | −9.468 | 3.146 | 25.315 | 1.00 | 0.00 |
| ATOM | 720 | CA | CYS | 78 | −9.500 | 1.186 | 26.089 | 1.00 | 25.49 |
| ATOM | 721 | CB | CYS | 78 | −8.831 | 0.762 | 24.782 | 1.00 | 28.48 |
| ATOM | 722 | SG | CYS | 78 | −9.718 | 1.274 | 23.311 | 1.00 | 45.92 |
| ATOM | 723 | C | CYS | 78 | −8.625 | 0.743 | 27.245 | 1.00 | 20.86 |
| ATOM | 724 | O | CYS | 78 | −8.675 | −0.413 | 27.649 | 1.00 | 21.75 |
| ATOM | 725 | N | GLY | 79 | −7.791 | 1.646 | 27.740 | 1.00 | 17.20 |
| ATOM | 726 | H | GLY | 79 | −7.750 | 2.555 | 27.393 | 1.00 | 0.00 |
| ATOM | 727 | CA | GLY | 79 | −6.919 | 1.297 | 28.839 | 1.00 | 13.97 |
| ATOM | 728 | C | GLY | 79 | −6.204 | 2.501 | 29.408 | 1.00 | 13.22 |
| ATOM | 729 | O | GLY | 79 | −6.291 | 3.600 | 28.848 | 1.00 | 12.24 |
| ATOM | 730 | N | PRO | 80 | −5.473 | 2.314 | 30.518 | 1.00 | 14.67 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| | | | | | | | | |
|---|---|---|---|---|---|---|---|---|
| ATOM | 731 | CD  | PRO | 80 | −5.345  | 1.022  | 31.222 | 1.00 | 16.84 |
| ATOM | 732 | CA  | PRO | 80 | −4.714  | 3.358  | 31.207 | 1.00 | 15.78 |
| ATOM | 733 | CB  | PRO | 80 | −4.108  | 2.610  | 32.402 | 1.00 | 17.64 |
| ATOM | 734 | CG  | PRO | 80 | −4.039  | 1.179  | 31.930 | 1.00 | 17.90 |
| ATOM | 735 | C   | PRO | 80 | −3.645  | 3.991  | 30.321 | 1.00 | 14.91 |
| ATOM | 736 | O   | PRO | 80 | −3.434  | 5.206  | 30.357 | 1.00 | 15.49 |
| ATOM | 737 | N   | ALA | 81 | −3.003  | 3.168  | 29.500 | 1.00 | 13.13 |
| ATOM | 738 | H   | ALA | 81 | −3.231  | 2.212  | 29.488 | 1.00 | 0.00 |
| ATOM | 739 | CA  | ALA | 81 | −1.969  | 3.645  | 28.594 | 1.00 | 13.20 |
| ATOM | 740 | CB  | ALA | 81 | −1.325  | 2.474  | 27.882 | 1.00 | 11.11 |
| ATOM | 741 | C   | ALA | 81 | −2.585  | 4.602  | 27.584 | 1.00 | 12.98 |
| ATOM | 742 | O   | ALA | 81 | −2.080  | 5.706  | 27.376 | 1.00 | 9.81 |
| ATOM | 743 | N   | GLU | 82 | −3.712  | 4.185  | 27.006 | 1.00 | 15.40 |
| ATOM | 744 | H   | GLU | 82 | −4.074  | 3.319  | 27.268 | 1.00 | 0.00 |
| ATOM | 745 | CA  | GLU | 82 | −4.432  | 4.975  | 26.007 | 1.00 | 16.50 |
| ATOM | 746 | CB  | GLU | 82 | −5.578  | 4.165  | 25.391 | 1.00 | 18.83 |
| ATOM | 747 | CG  | GLU | 82 | −5.143  | 3.076  | 24.417 | 1.00 | 22.18 |
| ATOM | 748 | CD  | GLU | 82 | −4.391  | 1.934  | 25.087 | 1.00 | 29.04 |
| ATOM | 749 | OE1 | GLU | 82 | −4.960  | 1.286  | 25.992 | 1.00 | 29.04 |
| ATOM | 750 | OE2 | GLU | 82 | −3.228  | 1.678  | 24.702 | 1.00 | 36.49 |
| ATOM | 751 | C   | GLU | 82 | −4.974  | 6.266  | 26.594 | 1.00 | 16.45 |
| ATOM | 752 | O   | GLU | 82 | −5.064  | 7.287  | 25.905 | 1.00 | 15.38 |
| ATOM | 753 | N   | LEU | 83 | −5.338  | 6.215  | 27.868 | 1.00 | 15.01 |
| ATOM | 754 | H   | LEU | 83 | −5.252  | 5.365  | 28.350 | 1.00 | 0.00 |
| ATOM | 755 | CA  | LEU | 83 | −5.863  | 7.378  | 28.567 | 1.00 | 13.23 |
| ATOM | 756 | CB  | LEU | 83 | −6.453  | 6.957  | 29.920 | 1.00 | 11.92 |
| ATOM | 757 | CG  | LEU | 83 | −7.191  | 8.010  | 30.748 | 1.00 | 9.05 |
| ATOM | 758 | CD1 | LEU | 83 | −8.321  | 7.365  | 31.526 | 1.00 | 6.47 |
| ATOM | 759 | CD2 | LEU | 83 | −6.217  | 8.729  | 31.669 | 1.00 | 8.09 |
| ATOM | 760 | C   | LEU | 83 | −4.770  | 8.431  | 28.743 | 1.00 | 12.70 |
| ATOM | 761 | O   | LEU | 83 | −4.964  | 9.603  | 28.415 | 1.00 | 13.58 |
| ATOM | 762 | N   | CYS | 84 | −3.608  | 8.013  | 29.228 | 1.00 | 12.46 |
| ATOM | 763 | H   | CYS | 84 | −3.484  | 7.068  | 29.473 | 1.00 | 0.00 |
| ATOM | 764 | CA  | CYS | 84 | −2.508  | 8.948  | 29.419 | 1.00 | 11.61 |
| ATOM | 765 | CB  | CYS | 84 | −1.387  | 8.289  | 30.207 | 1.00 | 10.43 |
| ATOM | 766 | SG  | CYS | 84 | −1.915  | 7.860  | 31.867 | 1.00 | 10.33 |
| ATOM | 767 | C   | CYS | 84 | −1.997  | 9.485  | 28.092 | 1.00 | 13.49 |
| ATOM | 768 | O   | CYS | 84 | −1.591  | 10.640 | 28.003 | 1.00 | 12.47 |
| ATOM | 769 | N   | GLU | 85 | −2.024  | 8.640  | 27.064 | 1.00 | 16.19 |
| ATOM | 770 | H   | GLU | 85 | −2.346  | 7.726  | 27.199 | 1.00 | 0.00 |
| ATOM | 771 | CA  | GLU | 85 | −1.590  | 9.035  | 25.729 | 1.00 | 18.26 |
| ATOM | 772 | CB  | GLU | 85 | −1.542  | 7.812  | 24.802 | 1.00 | 19.98 |
| ATOM | 773 | CG  | GLU | 85 | −0.393  | 6.843  | 25.144 | 1.00 | 26.96 |
| ATOM | 774 | CD  | GLU | 85 | −0.462  | 5.465  | 24.456 | 1.00 | 28.02 |
| ATOM | 775 | OE1 | GLU | 85 | 0.570   | 4.759  | 24.466 | 1.00 | 25.08 |
| ATOM | 776 | OE2 | GLU | 85 | −1.530  | 5.069  | 23.937 | 1.00 | 27.13 |
| ATOM | 777 | C   | GLU | 85 | −2.537  | 10.113 | 25.192 | 1.00 | 19.29 |
| ATOM | 778 | O   | GLU | 85 | −2.099  | 11.077 | 24.564 | 1.00 | 22.26 |
| ATOM | 779 | N   | PHE | 86 | −3.824  | 9.985  | 25.508 | 1.00 | 18.82 |
| ATOM | 780 | H   | PHE | 86 | −4.103  | 9.216  | 26.042 | 1.00 | 0.00 |
| ATOM | 781 | CA  | PHE | 86 | −4.839  | 10.948 | 25.080 | 1.00 | 15.74 |
| ATOM | 782 | CB  | PHE | 86 | −6.240  | 10.391 | 25.368 | 1.00 | 14.90 |
| ATOM | 783 | CG  | PHE | 86 | −7.350  | 11.360 | 25.084 | 1.00 | 17.05 |
| ATOM | 784 | CD1 | PHE | 86 | −7.867  | 11.487 | 23.801 | 1.00 | 20.88 |
| ATOM | 785 | CD2 | PHE | 86 | −7.867  | 12.167 | 26.096 | 1.00 | 17.90 |
| ATOM | 786 | CE1 | PHE | 86 | −8.883  | 12.407 | 23.529 | 1.00 | 21.36 |
| ATOM | 787 | CE2 | PHE | 86 | −8.878  | 13.089 | 25.834 | 1.00 | 16.83 |
| ATOM | 788 | CZ  | PHE | 86 | −9.387  | 13.209 | 24.551 | 1.00 | 20.44 |
| ATOM | 789 | C   | PHE | 86 | −4.674  | 12.313 | 25.762 | 1.00 | 15.39 |
| ATOM | 790 | O   | PHE | 86 | −4.705  | 13.355 | 25.104 | 1.00 | 9.31 |
| ATOM | 791 | N   | TYR | 87 | −4.511  | 12.302 | 27.082 | 1.00 | 14.05 |
| ATOM | 792 | H   | TYR | 87 | −4.518  | 11.448 | 27.562 | 1.00 | 0.00 |
| ATOM | 793 | CA  | TYR | 87 | −4.357  | 13.542 | 27.838 | 1.00 | 16.04 |
| ATOM | 794 | CB  | TYR | 87 | −4.645  | 13.303 | 29.316 | 1.00 | 15.23 |
| ATOM | 795 | CG  | TYR | 87 | −6.106  | 13.035 | 29.553 | 1.00 | 17.80 |
| ATOM | 796 | CD1 | TYR | 87 | −6.551  | 11.781 | 29.964 | 1.00 | 20.66 |
| ATOM | 797 | CE1 | TYR | 87 | −7.911  | 11.519 | 30.142 | 1.00 | 21.74 |
| ATOM | 798 | CD2 | TYR | 87 | −7.056  | 14.028 | 29.327 | 1.00 | 19.58 |
| ATOM | 799 | CE2 | TYR | 87 | −8.411  | 13.780 | 29.500 | 1.00 | 19.90 |
| ATOM | 800 | CZ  | TYR | 87 | −8.834  | 12.526 | 29.907 | 1.00 | 22.31 |
| ATOM | 801 | OH  | TYR | 87 | −10.179 | 12.284 | 30.070 | 1.00 | 24.09 |
| ATOM | 802 | HH  | TYR | 87 | −10.601 | 13.151 | 29.992 | 1.00 | 0.00 |
| ATOM | 803 | C   | TYR | 87 | −3.042  | 14.282 | 27.629 | 1.00 | 15.72 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 804 | O | TYR | 87 | −2.918 | 15.457 | 27.988 | 1.00 | 13.60 |
|---|---|---|---|---|---|---|---|---|---|
| ATOM | 805 | N | SER | 88 | −2.059 | 13.598 | 27.054 | 1.00 | 17.80 |
| ATOM | 806 | H | SER | 88 | −2.164 | 12.641 | 26.866 | 1.00 | 0.00 |
| ATOM | 807 | CA | SER | 88 | −0.775 | 14.222 | 26.763 | 1.00 | 23.25 |
| ATOM | 808 | CB | SER | 88 | 0.258 | 13.165 | 26.371 | 1.00 | 23.49 |
| ATOM | 809 | OG | SER | 88 | 0.617 | 12.360 | 27.480 | 1.00 | 33.23 |
| ATOM | 810 | HG | SER | 88 | 0.973 | 12.975 | 28.143 | 1.00 | 0.00 |
| ATOM | 811 | C | SER | 88 | −0.938 | 15.226 | 25.619 | 1.00 | 26.20 |
| ATOM | 812 | O | SER | 88 | −0.278 | 16.265 | 25.595 | 1.00 | 28.26 |
| ATOM | 813 | N | ARG | 89 | −1.822 | 14.908 | 24.677 | 1.00 | 30.06 |
| ATOM | 814 | H | ARG | 89 | −2.342 | 14.080 | 24.761 | 1.00 | 0.00 |
| ATOM | 815 | CA | ARG | 89 | −2.070 | 15.771 | 23.524 | 1.00 | 33.80 |
| ATOM | 816 | CB | ARG | 89 | −2.350 | 14.931 | 22.269 | 1.00 | 37.17 |
| ATOM | 817 | CG | ARG | 89 | −1.112 | 14.334 | 21.598 | 1.00 | 43.59 |
| ATOM | 818 | CD | ARG | 89 | −0.425 | 13.287 | 22.464 | 1.00 | 47.19 |
| ATOM | 819 | NE | ARG | 89 | 0.796 | 12.767 | 21.848 | 1.00 | 51.34 |
| ATOM | 820 | HE | ARG | 89 | 0.710 | 12.040 | 21.193 | 1.00 | 0.00 |
| ATOM | 821 | CZ | ARG | 89 | 2.023 | 13.219 | 22.103 | 1.00 | 53.00 |
| ATOM | 822 | NH1 | ARG | 89 | 2.212 | 14.212 | 22.967 | 1.00 | 53.42 |
| ATOM | 823 | HH11 | ARG | 89 | 1.435 | 14.633 | 23.434 | 1.00 | 0.00 |
| ATOM | 824 | HH12 | ARG | 89 | 3.142 | 14.533 | 23.154 | 1.00 | 0.00 |
| ATOM | 825 | NH2 | ARG | 89 | 3.070 | 12.664 | 21.503 | 1.00 | 54.73 |
| ATOM | 826 | HH21 | ARG | 89 | 2.936 | 11.899 | 20.870 | 1.00 | 0.00 |
| ATOM | 827 | HH22 | ARG | 89 | 3.993 | 13.004 | 21.690 | 1.00 | 0.00 |
| ATOM | 828 | C | ARG | 89 | −3.224 | 16.747 | 23.742 | 1.00 | 33.93 |
| ATOM | 829 | O | ARG | 89 | −3.220 | 17.849 | 23.195 | 1.00 | 35.37 |
| ATOM | 830 | N | ASP | 90 | −4.206 | 16.342 | 24.539 | 1.00 | 34.09 |
| ATOM | 831 | H | ASP | 90 | −4.177 | 15.460 | 24.968 | 1.00 | 0.00 |
| ATOM | 832 | CA | ASP | 90 | −5.370 | 17.181 | 24.797 | 1.00 | 32.55 |
| ATOM | 833 | CB | ASP | 90 | −6.533 | 16.707 | 23.907 | 1.00 | 34.44 |
| ATOM | 834 | CG | ASP | 90 | −7.780 | 17.576 | 24.028 | 1.00 | 37.74 |
| ATOM | 835 | OD1 | ASP | 90 | −8.865 | 17.075 | 23.662 | 1.00 | 42.07 |
| ATOM | 836 | OD2 | ASP | 90 | −7.688 | 18.749 | 24.464 | 1.00 | 36.32 |
| ATOM | 837 | C | ASP | 90 | −5.775 | 17.137 | 26.271 | 1.00 | 31.21 |
| ATOM | 838 | O | ASP | 90 | −6.160 | 16.086 | 26.784 | 1.00 | 29.06 |
| ATOM | 839 | N | PRO | 91 | −5.678 | 18.280 | 26.974 | 1.00 | 31.00 |
| ATOM | 840 | CD | PRO | 91 | −5.144 | 19.571 | 26.500 | 1.00 | 31.27 |
| ATOM | 841 | CA | PRO | 91 | −6.046 | 18.363 | 28.391 | 1.00 | 30.53 |
| ATOM | 842 | CB | PRO | 91 | −5.938 | 19.860 | 28.677 | 1.00 | 30.79 |
| ATOM | 843 | CG | PRO | 91 | −4.817 | 20.280 | 27.793 | 1.00 | 30.18 |
| ATOM | 844 | C | PRO | 91 | −7.479 | 17.869 | 28.576 | 1.00 | 30.82 |
| ATOM | 845 | O | PRO | 91 | −7.783 | 17.169 | 29.536 | 1.00 | 32.23 |
| ATOM | 846 | N | ASP | 92 | −8.358 | 18.287 | 27.664 | 1.00 | 31.25 |
| ATOM | 847 | H | ASP | 92 | −8.041 | 18.890 | 26.966 | 1.00 | 0.00 |
| ATOM | 848 | CA | ASP | 92 | −9.768 | 17.895 | 27.660 | 1.00 | 29.68 |
| ATOM | 849 | CB | ASP | 92 | −9.906 | 16.470 | 27.097 | 1.00 | 32.25 |
| ATOM | 850 | CG | ASP | 92 | −11.281 | 16.192 | 26.498 | 1.00 | 33.34 |
| ATOM | 851 | OD1 | ASP | 92 | −11.880 | 15.142 | 26.826 | 1.00 | 33.77 |
| ATOM | 852 | OD2 | ASP | 92 | −11.748 | 17.009 | 25.679 | 1.00 | 39.38 |
| ATOM | 853 | C | ASP | 92 | −10.423 | 18.005 | 29.043 | 1.00 | 30.56 |
| ATOM | 854 | O | ASP | 92 | −11.208 | 17.142 | 29.442 | 1.00 | 30.28 |
| ATOM | 855 | N | GLY | 93 | −10.099 | 19.079 | 29.762 | 1.00 | 29.01 |
| ATOM | 856 | H | GLY | 93 | −9.464 | 19.737 | 29.417 | 1.00 | 0.00 |
| ATOM | 857 | CA | GLY | 93 | −10.665 | 19.285 | 31.084 | 1.00 | 27.68 |
| ATOM | 858 | C | GLY | 93 | −9.654 | 19.345 | 32.218 | 1.00 | 27.53 |
| ATOM | 859 | O | GLY | 93 | −9.933 | 19.912 | 33.278 | 1.00 | 28.17 |
| ATOM | 860 | N | LEU | 94 | −8.488 | 18.737 | 32.020 | 1.00 | 25.94 |
| ATOM | 861 | H | LEU | 94 | −8.329 | 18.255 | 31.183 | 1.00 | 0.00 |
| ATOM | 862 | CA | LEU | 94 | −7.451 | 18.741 | 33.046 | 1.00 | 26.33 |
| ATOM | 863 | CB | LEU | 94 | −6.353 | 17.725 | 32.710 | 1.00 | 22.36 |
| ATOM | 864 | CG | LEU | 94 | −6.696 | 16.241 | 32.594 | 1.00 | 22.65 |
| ATOM | 865 | CD1 | LEU | 94 | −5.403 | 15.473 | 32.399 | 1.00 | 20.32 |
| ATOM | 866 | CD2 | LEU | 94 | −7.429 | 15.742 | 33.829 | 1.00 | 21.91 |
| ATOM | 867 | C | LEU | 94 | −6.830 | 20.133 | 33.167 | 1.00 | 27.78 |
| ATOM | 868 | O | LEU | 94 | −6.927 | 20.942 | 32.239 | 1.00 | 27.47 |
| ATOM | 869 | N | PRO | 95 | −6.175 | 20.423 | 34.310 | 1.00 | 26.98 |
| ATOM | 870 | CD | PRO | 95 | −6.077 | 19.560 | 35.502 | 1.00 | 26.89 |
| ATOM | 871 | CA | PRO | 95 | −5.526 | 21.715 | 34.558 | 1.00 | 26.62 |
| ATOM | 872 | CB | PRO | 95 | −4.898 | 21.518 | 35.939 | 1.00 | 24.83 |
| ATOM | 873 | CG | PRO | 95 | −5.821 | 20.556 | 36.598 | 1.00 | 24.86 |
| ATOM | 874 | C | PRO | 95 | −4.456 | 22.009 | 33.504 | 1.00 | 27.96 |
| ATOM | 875 | O | PRO | 95 | −4.073 | 23.163 | 33.301 | 1.00 | 29.86 |
| ATOM | 876 | N | CYS | 96 | −3.924 | 20.944 | 32.909 | 1.00 | 27.78 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 877 | H | CYS | 96 | −4.197 | 20.035 | 33.153 | 1.00 | 0.00 |
|---|---|---|---|---|---|---|---|---|---|
| ATOM | 878 | CA | CYS | 96 | −2.911 | 21.022 | 31.859 | 1.00 | 26.63 |
| ATOM | 879 | CB | CYS | 96 | −1.580 | 21.563 | 32.394 | 1.00 | 29.10 |
| ATOM | 880 | SG | CYS | 96 | −0.785 | 20.559 | 33.655 | 1.00 | 33.00 |
| ATOM | 881 | C | CYS | 96 | −2.715 | 19.626 | 31.285 | 1.00 | 25.83 |
| ATOM | 882 | O | CYS | 96 | −3.114 | 18.633 | 31.897 | 1.00 | 25.07 |
| ATOM | 883 | N | ASN | 97 | −2.145 | 19.547 | 30.092 | 1.00 | 24.09 |
| ATOM | 884 | H | ASN | 97 | −1.833 | 20.360 | 29.642 | 1.00 | 0.00 |
| ATOM | 885 | CA | ASN | 97 | −1.919 | 18.259 | 29.464 | 1.00 | 24.47 |
| ATOM | 886 | CB | ASN | 97 | −1.613 | 18.432 | 27.978 | 1.00 | 27.75 |
| ATOM | 887 | CG | ASN | 97 | −0.384 | 19.271 | 27.734 | 1.00 | 30.72 |
| ATOM | 888 | OD1 | ASN | 97 | −0.267 | 20.381 | 28.255 | 1.00 | 33.88 |
| ATOM | 889 | ND2 | ASN | 97 | 0.540 | 18.754 | 26.936 | 1.00 | 32.61 |
| ATOM | 890 | HD21 | ASN | 97 | 0.370 | 17.869 | 26.542 | 1.00 | 0.00 |
| ATOM | 891 | HD22 | ASN | 97 | 1.350 | 19.270 | 26.774 | 1.00 | 0.00 |
| ATOM | 892 | C | ASN | 97 | −0.779 | 17.526 | 30.154 | 1.00 | 22.90 |
| ATOM | 893 | O | ASN | 97 | 0.056 | 18.140 | 30.820 | 1.00 | 21.51 |
| ATOM | 894 | N | LEU | 98 | −0.756 | 16.207 | 29.990 | 1.00 | 20.54 |
| ATOM | 895 | H | LEU | 98 | −1.447 | 15.800 | 29.429 | 1.00 | 0.00 |
| ATOM | 896 | CA | LEU | 98 | 0.273 | 15.369 | 30.591 | 1.00 | 19.00 |
| ATOM | 897 | CB | LEU | 98 | −0.201 | 13.913 | 30.641 | 1.00 | 14.90 |
| ATOM | 898 | CG | LEU | 98 | −1.503 | 13.668 | 31.417 | 1.00 | 11.64 |
| ATOM | 899 | CD1 | LEU | 98 | −1.847 | 12.182 | 31.440 | 1.00 | 6.04 |
| ATOM | 900 | CD2 | LEU | 98 | −1.368 | 14.215 | 32.828 | 1.00 | 9.37 |
| ATOM | 901 | C | LEU | 98 | 1.568 | 15.498 | 29.790 | 1.00 | 20.67 |
| ATOM | 902 | O | LEU | 98 | 1.685 | 14.970 | 28.683 | 1.00 | 22.82 |
| ATOM | 903 | N | ARG | 99 | 2.545 | 16.180 | 30.372 | 1.00 | 20.51 |
| ATOM | 904 | H | ARG | 99 | 2.399 | 16.534 | 31.271 | 1.00 | 0.00 |
| ATOM | 905 | CA | ARG | 99 | 3.815 | 16.425 | 29.712 | 1.00 | 21.55 |
| ATOM | 906 | CB | ARG | 99 | 4.261 | 17.864 | 29.974 | 1.00 | 19.71 |
| ATOM | 907 | CG | ARG | 99 | 3.230 | 18.899 | 29.558 | 1.00 | 22.45 |
| ATOM | 908 | CD | ARG | 99 | 3.620 | 20.296 | 29.990 | 1.00 | 25.64 |
| ATOM | 909 | NE | ARG | 99 | 2.530 | 21.243 | 29.758 | 1.00 | 31.98 |
| ATOM | 910 | HE | ARG | 99 | 1.868 | 21.026 | 29.067 | 1.00 | 0.00 |
| ATOM | 911 | CZ | ARG | 99 | 2.366 | 22.383 | 30.426 | 1.00 | 35.95 |
| ATOM | 912 | NH1 | ARG | 99 | 3.224 | 22.733 | 31.380 | 1.00 | 38.13 |
| ATOM | 913 | HH11 | ARG | 99 | 4.000 | 22.139 | 31.586 | 1.00 | 0.00 |
| ATOM | 914 | HH12 | ARG | 99 | 3.111 | 23.583 | 31.889 | 1.00 | 0.00 |
| ATOM | 915 | NH2 | ARG | 99 | 1.342 | 23.177 | 30.139 | 1.00 | 35.02 |
| ATOM | 916 | HH21 | ARG | 99 | 0.700 | 22.940 | 29.416 | 1.00 | 0.00 |
| ATOM | 917 | HH22 | ARG | 99 | 1.238 | 24.034 | 30.643 | 1.00 | 0.00 |
| ATOM | 918 | C | ARG | 99 | 4.961 | 15.471 | 30.022 | 1.00 | 23.55 |
| ATOM | 919 | O | ARG | 99 | 5.461 | 14.789 | 29.125 | 1.00 | 28.87 |
| ATOM | 920 | N | LYS | 100 | 5.377 | 15.408 | 31.281 | 1.00 | 21.07 |
| ATOM | 921 | H | LYS | 100 | 4.912 | 15.896 | 31.993 | 1.00 | 0.00 |
| ATOM | 922 | CA | LYS | 100 | 6.507 | 14.564 | 31.644 | 1.00 | 18.54 |
| ATOM | 923 | CB | LYS | 100 | 7.575 | 15.441 | 32.304 | 1.00 | 20.05 |
| ATOM | 924 | CG | LYS | 100 | 8.939 | 14.799 | 32.507 | 1.00 | 27.37 |
| ATOM | 925 | CD | LYS | 100 | 9.891 | 15.784 | 33.196 | 1.00 | 29.35 |
| ATOM | 926 | CE | LYS | 100 | 11.321 | 15.259 | 33.266 | 1.00 | 32.53 |
| ATOM | 927 | NZ | LYS | 100 | 11.443 | 13.994 | 34.043 | 1.00 | 36.81 |
| ATOM | 928 | HZ1 | LYS | 100 | 10.853 | 13.266 | 33.597 | 1.00 | 0.00 |
| ATOM | 929 | HZ2 | LYS | 100 | 11.123 | 14.155 | 35.017 | 1.00 | 0.00 |
| ATOM | 930 | HZ3 | LYS | 100 | 12.438 | 13.683 | 34.047 | 1.00 | 0.00 |
| ATOM | 931 | C | LYS | 100 | 6.118 | 13.410 | 32.563 | 1.00 | 17.15 |
| ATOM | 932 | O | LYS | 100 | 5.586 | 13.627 | 33.647 | 1.00 | 16.18 |
| ATOM | 933 | N | PRO | 101 | 6.302 | 12.162 | 32.104 | 1.00 | 16.34 |
| ATOM | 934 | CD | PRO | 101 | 6.627 | 11.735 | 30.734 | 1.00 | 15.63 |
| ATOM | 935 | CA | PRO | 101 | 5.961 | 11.006 | 32.937 | 1.00 | 16.36 |
| ATOM | 936 | CB | PRO | 101 | 6.092 | 9.830 | 31.965 | 1.00 | 16.00 |
| ATOM | 937 | CG | PRO | 101 | 5.849 | 10.453 | 30.620 | 1.00 | 17.99 |
| ATOM | 938 | C | PRO | 101 | 6.987 | 10.883 | 34.064 | 1.00 | 15.83 |
| ATOM | 939 | O | PRO | 101 | 8.194 | 10.987 | 33.832 | 1.00 | 14.18 |
| ATOM | 940 | N | CYS | 102 | 6.510 | 10.718 | 35.287 | 1.00 | 14.78 |
| ATOM | 941 | H | CYS | 102 | 5.550 | 10.658 | 35.443 | 1.00 | 0.00 |
| ATOM | 942 | CA | CYS | 102 | 7.410 | 10.576 | 36.415 | 1.00 | 12.30 |
| ATOM | 943 | CB | CYS | 102 | 6.762 | 11.078 | 37.700 | 1.00 | 8.52 |
| ATOM | 944 | SG | CYS | 102 | 7.925 | 11.184 | 39.064 | 1.00 | 12.86 |
| ATOM | 945 | C | CYS | 102 | 7.714 | 9.097 | 36.511 | 1.00 | 13.33 |
| ATOM | 946 | O | CYS | 102 | 7.078 | 8.364 | 37.266 | 1.00 | 13.67 |
| ATOM | 947 | N | ASN | 103 | 8.662 | 8.661 | 35.693 | 1.00 | 13.67 |
| ATOM | 948 | H | ASN | 103 | 9.085 | 9.330 | 35.108 | 1.00 | 0.00 |
| ATOM | 949 | CA | ASN | 103 | 9.073 | 7.264 | 35.623 | 1.00 | 14.10 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 950 | CB | ASN | 103 | 10.013 | 7.041 | 34.444 | 1.00 | 15.80 |
|---|---|---|---|---|---|---|---|---|---|
| ATOM | 951 | CG | ASN | 103 | 9.374 | 7.399 | 33.124 | 1.00 | 18.98 |
| ATOM | 952 | OD1 | ASN | 103 | 8.206 | 7.101 | 32.888 | 1.00 | 19.82 |
| ATOM | 953 | ND2 | ASN | 103 | 10.132 | 8.056 | 32.259 | 1.00 | 24.80 |
| ATOM | 954 | HD21 | ASN | 103 | 11.054 | 8.272 | 32.491 | 1.00 | 0.00 |
| ATOM | 955 | HD22 | ASN | 103 | 9.730 | 8.327 | 31.394 | 1.00 | 0.00 |
| ATOM | 956 | C | ASN | 103 | 9.741 | 6.767 | 36.899 | 1.00 | 13.80 |
| ATOM | 957 | O | ASN | 103 | 10.513 | 7.843 | 37.537 | 1.00 | 14.29 |
| ATOM | 958 | N | ARG | 104 | 9.448 | 5.522 | 37.247 | 1.00 | 13.40 |
| ATOM | 959 | H | ARG | 104 | 8.826 | 5.010 | 36.697 | 1.00 | 0.00 |
| ATOM | 960 | CA | ARG | 104 | 10.018 | 4.896 | 38.426 | 1.00 | 14.48 |
| ATOM | 961 | CB | ARG | 104 | 9.501 | 3.464 | 38.556 | 1.00 | 14.01 |
| ATOM | 962 | CG | ARG | 104 | 8.089 | 3.354 | 39.074 | 1.00 | 11.01 |
| ATOM | 963 | CD | ARG | 104 | 7.691 | 1.901 | 39.222 | 1.00 | 13.56 |
| ATOM | 964 | NE | ARG | 104 | 7.262 | 1.324 | 37.951 | 1.00 | 18.89 |
| ATOM | 965 | HE | ARG | 104 | 6.380 | 1.537 | 37.599 | 1.00 | 0.00 |
| ATOM | 966 | CZ | ARG | 104 | 8.001 | 0.529 | 37.190 | 1.00 | 16.72 |
| ATOM | 967 | NH1 | ARG | 104 | 9.227 | 0.203 | 37.557 | 1.00 | 24.48 |
| ATOM | 968 | HH11 | ARG | 104 | 9.608 | 0.548 | 38.418 | 1.00 | 0.00 |
| ATOM | 969 | HH12 | ARG | 104 | 9.771 | −0.406 | 36.979 | 1.00 | 0.00 |
| ATOM | 970 | NH2 | ARG | 104 | 7.501 | 0.044 | 36.065 | 1.00 | 24.27 |
| ATOM | 971 | HH21 | ARG | 104 | 6.570 | 0.279 | 35.777 | 1.00 | 0.00 |
| ATOM | 972 | HH22 | ARG | 104 | 8.060 | −0.560 | 35.497 | 1.00 | 0.00 |
| ATOM | 973 | C | ARG | 104 | 11.545 | 4.871 | 38.363 | 1.00 | 17.95 |
| ATOM | 974 | O | ARG | 104 | 12.128 | 4.542 | 37.326 | 1.00 | 16.59 |
| ATOM | 975 | N | PRO | 105 | 12.211 | 5.235 | 39.473 | 1.00 | 21.58 |
| ATOM | 976 | CD | PRO | 105 | 11.622 | 5.709 | 40.738 | 1.00 | 24.11 |
| ATOM | 977 | CA | PRO | 105 | 13.674 | 5.248 | 39.548 | 1.00 | 24.61 |
| ATOM | 978 | CB | PRO | 105 | 13.933 | 5.750 | 40.970 | 1.00 | 25.94 |
| ATOM | 979 | CG | PRO | 105 | 12.713 | 6.566 | 41.285 | 1.00 | 26.77 |
| ATOM | 980 | C | PRO | 105 | 14.174 | 3.816 | 39.403 | 1.00 | 26.84 |
| ATOM | 981 | O | PRO | 105 | 13.493 | 2.884 | 39.829 | 1.00 | 29.03 |
| ATOM | 982 | N | SER | 106 | 15.348 | 3.629 | 38.805 | 1.00 | 29.28 |
| ATOM | 983 | H | SER | 106 | 15.851 | 4.400 | 34.484 | 1.00 | 0.00 |
| ATOM | 984 | CA | SER | 106 | 15.893 | 2.283 | 38.652 | 1.00 | 31.72 |
| ATOM | 985 | CB | SER | 106 | 17.306 | 2.329 | 38.074 | 1.00 | 34.84 |
| ATOM | 986 | OG | SER | 106 | 17.273 | 2.524 | 36.673 | 1.00 | 42.09 |
| ATOM | 987 | HG | SER | 106 | 16.759 | 3.302 | 36.439 | 1.00 | 0.00 |
| ATOM | 988 | C | SER | 106 | 15.904 | 1.572 | 40.002 | 1.00 | 31.31 |
| ATOM | 989 | O | SER | 106 | 16.301 | 2.154 | 41.017 | 1.00 | 32.32 |
| ATOM | 990 | N | GLY | 107 | 15.433 | 0.330 | 40.015 | 1.00 | 27.87 |
| ATOM | 991 | H | GLY | 107 | 15.089 | −0.065 | 39.190 | 1.00 | 0.00 |
| ATOM | 992 | CA | GLY | 107 | 15.391 | −0.420 | 41.252 | 1.00 | 27.05 |
| ATOM | 993 | C | GLY | 107 | 14.041 | −0.345 | 41.941 | 1.00 | 26.16 |
| ATOM | 994 | O | GLY | 107 | 13.837 | −0.989 | 42.971 | 1.00 | 26.25 |
| ATOM | 995 | N | LEU | 108 | 13.130 | 0.462 | 41.406 | 1.00 | 25.02 |
| ATOM | 996 | H | LEU | 108 | 13.318 | 1.005 | 40.610 | 1.00 | 0.00 |
| ATOM | 997 | CA | LEU | 108 | 11.800 | 0.577 | 41.986 | 1.00 | 22.01 |
| ATOM | 998 | CB | LEU | 108 | 11.375 | 2.044 | 42.127 | 1.00 | 20.37 |
| ATOM | 999 | CG | LEU | 108 | 10.061 | 2.277 | 42.885 | 1.00 | 19.84 |
| ATOM | 1000 | CD1 | LEU | 108 | 10.151 | 1.672 | 44.270 | 1.00 | 20.62 |
| ATOM | 1001 | CD2 | LEU | 108 | 9.749 | 3.758 | 42.985 | 1.00 | 19.42 |
| ATOM | 1002 | C | LEU | 108 | 10.831 | −0.173 | 41.087 | 1.00 | 22.30 |
| ATOM | 1003 | O | LEU | 108 | 10.848 | −0.020 | 39.865 | 1.00 | 22.42 |
| ATOM | 1004 | N | GLU | 109 | 10.022 | −1.027 | 41.699 | 1.00 | 23.39 |
| ATOM | 1005 | H | GLU | 109 | 10.052 | −1.102 | 42.673 | 1.00 | 0.00 |
| ATOM | 1006 | CA | GLU | 109 | 9.041 | −1.824 | 40.975 | 1.00 | 21.29 |
| ATOM | 1007 | CB | GLU | 109 | 9.231 | −3.310 | 41.306 | 1.00 | 28.00 |
| ATOM | 1008 | CG | GLU | 109 | 10.625 | −3.868 | 40.997 | 1.00 | 34.55 |
| ATOM | 1009 | CD | GLU | 109 | 11.018 | −3.719 | 39.536 | 1.00 | 39.08 |
| ATOM | 1010 | OE1 | GLU | 109 | 11.970 | −2.955 | 39.253 | 1.00 | 41.37 |
| ATOM | 1011 | OE2 | GLU | 109 | 10.378 | −4.363 | 38.672 | 1.00 | 40.88 |
| ATOM | 1012 | C | GLU | 109 | 7.655 | −1.385 | 41.414 | 1.00 | 17.67 |
| ATOM | 1013 | O | GLU | 109 | 7.516 | −.0686 | 42.420 | 1.00 | 17.75 |
| ATOM | 1014 | N | PRO | 110 | 6.619 | −1.718 | 40.628 | 1.00 | 13.39 |
| ATOM | 1015 | CD | PRO | 110 | 6.595 | −2.348 | 39.301 | 1.00 | 8.68 |
| ATOM | 1016 | CA | PRO | 110 | 5.274 | −1.316 | 41.038 | 1.00 | 11.28 |
| ATOM | 1017 | CB | PRO | 110 | 4.405 | −1.856 | 39.912 | 1.00 | 9.37 |
| ATOM | 1018 | CG | PRO | 110 | 5.315 | −1.825 | 38.737 | 1.00 | 9.71 |
| ATOM | 1019 | C | PRO | 110 | 4.988 | −2.029 | 42.357 | 1.00 | 13.59 |
| ATOM | 1020 | O | PRO | 110 | 5.280 | −3.213 | 42.503 | 1.00 | 15.70 |
| ATOM | 1021 | N | GLN | 111 | 4.451 | −1.293 | 43.320 | 1.00 | 14.83 |
| ATOM | 1022 | H | GLN | 111 | 4.224 | −0.362 | 43.128 | 1.00 | 0.00 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1023 | CA | GLN | 111 | 4.146 | −1.817 | 44.644 | 1.00 | 14.80 |
|---|---|---|---|---|---|---|---|---|---|
| ATOM | 1024 | CB | GLN | 111 | 3.914 | −0.630 | 45.588 | 1.00 | 19.62 |
| ATOM | 1025 | CG | GLN | 111 | 3.460 | −0.972 | 46.992 | 1.00 | 29.16 |
| ATOM | 1026 | CD | GLN | 111 | 4.507 | −1.733 | 47.779 | 1.00 | 35.22 |
| ATOM | 1027 | OE1 | GLN | 111 | 5.675 | −1.338 | 47.828 | 1.00 | 39.00 |
| ATOM | 1028 | NE2 | GLN | 111 | 4.096 | −2.841 | 48.393 | 1.00 | 38.02 |
| ATOM | 1029 | HE21 | GLN | 111 | 3.152 | −3.094 | 48.292 | 1.00 | 0.00 |
| ATOM | 1030 | HE22 | GLN | 111 | 4.763 | −3.331 | 48.921 | 1.00 | 0.00 |
| ATOM | 1031 | C | GLN | 111 | 2.921 | −2.732 | 44.631 | 1.00 | 13.55 |
| ATOM | 1032 | O | GLN | 111 | 1.858 | −2.337 | 44.164 | 1.00 | 13.13 |
| ATOM | 1033 | N | PRO | 112 | 3.064 | −3.980 | 45.117 | 1.00 | 15.54 |
| ATOM | 1034 | CD | PRO | 112 | 4.324 | −4.595 | 45.571 | 1.00 | 14.21 |
| ATOM | 1035 | CA | PRO | 112 | 1.962 | −4.954 | 45.169 | 1.00 | 14.46 |
| ATOM | 1036 | CB | PRO | 112 | 2.616 | −6.176 | 45.814 | 1.00 | 17.80 |
| ATOM | 1037 | CG | PRO | 112 | 4.043 | −6.060 | 45.391 | 1.00 | 18.52 |
| ATOM | 1038 | C | PRO | 112 | 0.818 | −4.424 | 46.036 | 1.00 | 12.81 |
| ATOM | 1039 | O | PRO | 112 | 1.044 | −3.924 | 47.140 | 1.00 | 13.23 |
| ATOM | 1040 | N | GLY | 113 | −0.406 | −4.590 | 45.550 | 1.00 | 13.74 |
| ATOM | 1041 | H | GLY | 113 | −0.506 | −5.038 | 44.681 | 1.00 | 0.00 |
| ATOM | 1042 | CA | GLY | 113 | −1.585 | −4.095 | 46.242 | 1.00 | 16.62 |
| ATOM | 1043 | C | GLY | 113 | −1.920 | −4.452 | 47.682 | 1.00 | 20.03 |
| ATOM | 1044 | O | GLY | 113 | −2.178 | −3.564 | 48.492 | 1.00 | 25.17 |
| ATOM | 1045 | N | VAL | 114 | −1.964 | −5.742 | 47.985 | 1.00 | 15.08 |
| ATOM | 1046 | H | VAL | 114 | −1.759 | −6.328 | 47.241 | 1.00 | 0.00 |
| ATOM | 1047 | CA | VAL | 114 | −2.325 | −6.279 | 49.308 | 1.00 | 15.99 |
| ATOM | 1048 | CB | VAL | 114 | −2.159 | −5.308 | 50.525 | 1.00 | 15.66 |
| ATOM | 1049 | CG1 | VAL | 114 | −2.735 | −5.944 | 51.787 | 1.00 | 15.95 |
| ATOM | 1050 | CG2 | VAL | 114 | −0.691 | −5.029 | 50.785 | 1.00 | 18.12 |
| ATOM | 1051 | C | VAL | 114 | −3.759 | −6.788 | 49.208 | 1.00 | 14.14 |
| ATOM | 1052 | O | VAL | 114 | −4.000 | −7.960 | 49.493 | 1.00 | 15.64 |
| ATOM | 1053 | N | PHE | 115 | −4.694 | −5.956 | 48.749 | 1.00 | 12.08 |
| ATOM | 1054 | H | PHE | 115 | −4.473 | −5.029 | 48.516 | 1.00 | 0.00 |
| ATOM | 1055 | CA | PHE | 115 | −6.065 | −6.429 | 48.583 | 1.00 | 8.80 |
| ATOM | 1056 | CB | PHE | 115 | −7.021 | −5.316 | 48.167 | 1.00 | 6.19 |
| ATOM | 1057 | CG | PHE | 115 | −8.474 | −5.719 | 48.214 | 1.00 | 3.76 |
| ATOM | 1058 | CD1 | PHE | 115 | −8.900 | −6.745 | 49.054 | 1.00 | 2.76 |
| ATOM | 1059 | CD2 | PHE | 115 | −9.423 | −5.046 | 47.451 | 1.00 | 6.51 |
| ATOM | 1060 | CE1 | PHE | 115 | −10.253 | −7.090 | 49.141 | 1.00 | 5.06 |
| ATOM | 1061 | CE2 | PHE | 115 | −10.781 | −5.382 | 47.528 | 1.00 | 6.67 |
| ATOM | 1062 | CZ | PHE | 115 | −11.197 | −6.405 | 48.376 | 1.00 | 6.27 |
| ATOM | 1063 | C | PHE | 115 | −5.997 | −7.464 | 47.471 | 1.00 | 9.14 |
| ATOM | 1064 | O | PHE | 115 | −6.553 | −8.548 | 47.592 | 1.00 | 12.04 |
| ATOM | 1065 | N | ASP | 116 | −5.287 | −7.128 | 46.398 | 1.00 | 9.44 |
| ATOM | 1066 | H | ASP | 116 | −4.943 | −6.208 | 46.326 | 1.00 | 0.00 |
| ATOM | 1067 | CA | ASP | 116 | −5.120 | −8.048 | 45.272 | 1.00 | 12.42 |
| ATOM | 1068 | CB | ASP | 116 | −4.240 | −7.420 | 44.181 | 1.00 | 15.62 |
| ATOM | 1069 | CG | ASP | 116 | −4.968 | −6.372 | 43.349 | 1.00 | 19.07 |
| ATOM | 1070 | OD1 | ASP | 116 | −6.205 | −6.246 | 43.445 | 1.00 | 23.47 |
| ATOM | 1071 | OD2 | ASP | 116 | −4.287 | −5.679 | 42.569 | 1.00 | 25.14 |
| ATOM | 1072 | C | ASP | 116 | −4.466 | −9.347 | 45.740 | 1.00 | 11.75 |
| ATOM | 1073 | O | ASP | 116 | −4.862 | −10.445 | 45.344 | 1.00 | 11.50 |
| ATOM | 1074 | N | CLE | 117 | −3.461 | −9.199 | 45.593 | 1.00 | 12.80 |
| ATOM | 1075 | H | CLE | 117 | −3.267 | −8.285 | 46.841 | 1.00 | 0.00 |
| ATOM | 1076 | CA | CLE | 117 | −2.717 | −10.321 | 47.135 | 1.00 | 14.11 |
| ATOM | 1077 | CB | CLE | 117 | −1.552 | −9.797 | 47.962 | 1.00 | 16.88 |
| ATOM | 1078 | SG | CLE | 117 | −0.415 | −11.054 | 48.533 | 1.00 | 22.90 |
| ATOM | 1079 | B | CLE | 117 | 1.110 | −9.552 | 50.024 | 1.00 | 31.80 |
| ATOM | 1080 | C | CLE | 117 | −3.607 | −11.241 | 47.971 | 1.00 | 16.15 |
| ATOM | 1081 | O | CLE | 117 | −3.484 | −12.466 | 47.899 | 1.00 | 17.64 |
| ATOM | 1082 | N | LEU | 118 | −4.509 | −10.653 | 48.753 | 1.00 | 15.34 |
| ATOM | 1083 | H | LEU | 118 | −4.574 | −9.678 | 48.794 | 1.00 | 0.00 |
| ATOM | 1084 | CA | LEU | 118 | −5.419 | −11.430 | 49.579 | 1.00 | 13.10 |
| ATOM | 1085 | CB | LEU | 118 | −5.994 | −10.574 | 50.711 | 1.00 | 12.53 |
| ATOM | 1086 | CG | LEU | 118 | −5.204 | −10.607 | 52.027 | 1.00 | 17.96 |
| ATOM | 1087 | CD1 | LEU | 118 | −3.763 | −10.149 | 51.845 | 1.00 | 20.79 |
| ATOM | 1088 | CD2 | LEU | 118 | −5.915 | −9.758 | 53.078 | 1.00 | 21.05 |
| ATOM | 1089 | C | LEU | 118 | −6.530 | −12.068 | 48.744 | 1.00 | 13.66 |
| ATOM | 1090 | O | LEU | 118 | −6.899 | −13.220 | 48.977 | 1.00 | 13.82 |
| ATOM | 1091 | N | ARG | 119 | −7.043 | −11.343 | 47.752 | 1.00 | 13.95 |
| ATOM | 1092 | H | ARG | 119 | −6.729 | −10.431 | 47.595 | 1.00 | 0.00 |
| ATOM | 1093 | CA | ARG | 119 | −8.097 | −11.890 | 46.891 | 1.00 | 16.99 |
| ATOM | 1094 | CB | ARG | 119 | −8.685 | −10.835 | 45.952 | 1.00 | 18.77 |
| ATOM | 1095 | CG | ARG | 119 | −9.292 | −9.633 | 46.630 | 1.00 | 21.75 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1096 | CD   | ARG | 119 | −10.186 | −8.859  | 45.671 | 1.00 | 24.22 |
|------|------|------|-----|-----|---------|---------|--------|------|-------|
| ATOM | 1097 | NE   | ARG | 119 | −9.634  | −8.710  | 44.325 | 1.00 | 25.20 |
| ATOM | 1098 | HE   | ARG | 119 | −9.753  | −9.441  | 43.686 | 1.00 | 0.00  |
| ATOM | 1099 | CZ   | ARG | 119 | −8.970  | −7.644  | 43.889 | 1.00 | 26.62 |
| ATOM | 1100 | NH1  | ARG | 119 | −8.751  | −6.613  | 44.692 | 1.00 | 26.88 |
| ATOM | 1101 | HH11 | ARG | 119 | −9.079  | −6.630  | 45.637 | 1.00 | 0.00  |
| ATOM | 1102 | HH12 | ARG | 119 | −8.258  | −5.813  | 44.357 | 1.00 | 0.00  |
| ATOM | 1103 | NH2  | ARG | 119 | −8.552  | −7.596  | 42.632 | 1.00 | 28.12 |
| ATOM | 1104 | HH21 | ARG | 119 | −8.731  | −8.366  | 42.018 | 1.00 | 0.00  |
| ATOM | 1105 | HH22 | ARG | 119 | −8.055  | −6.793  | 42.296 | 1.00 | 0.00  |
| ATOM | 1106 | C    | ARG | 119 | −7.573  | −13.042 | 46.050 | 1.00 | 16.34 |
| ATOM | 1107 | O    | ARG | 119 | −8.338  | −13.911 | 45.649 | 1.00 | 20.19 |
| ATOM | 1108 | N    | ASP | 120 | −6.279  | −13.038 | 45.747 | 1.00 | 16.82 |
| ATOM | 1109 | H    | ASP | 120 | −5.712  | −12.290 | 46.047 | 1.00 | 0.00  |
| ATOM | 1110 | CA   | ASP | 120 | −5.699  | −14.123 | 44.963 | 1.00 | 16.01 |
| ATOM | 1111 | CB   | ASP | 120 | −4.195  | −13.924 | 44.775 | 1.00 | 20.39 |
| ATOM | 1112 | CG   | ASP | 120 | −3.543  | −15.068 | 43.997 | 1.00 | 26.16 |
| ATOM | 1113 | OD1  | ASP | 120 | −3.897  | −15.260 | 42.813 | 1.00 | 29.33 |
| ATOM | 1114 | OD2  | ASP | 120 | −2.682  | −15.778 | 44.570 | 1.00 | 25.10 |
| ATOM | 1115 | C    | ASP | 120 | −5.972  | −15.449 | 45.668 | 1.00 | 12.54 |
| ATOM | 1116 | O    | ASP | 120 | −6.566  | −16.346 | 45.084 | 1.00 | 13.46 |
| ATOM | 1117 | N    | ALA | 121 | −5.572  | −15.539 | 46.935 | 1.00 | 10.31 |
| ATOM | 1118 | H    | ALA | 121 | −5.115  | −14.768 | 47.334 | 1.00 | 0.00  |
| ATOM | 1119 | CA   | ALA | 121 | −5.764  | −16.738 | 47.758 | 1.00 | 11.07 |
| ATOM | 1120 | CB   | ALA | 121 | −5.155  | −16.521 | 49.141 | 1.00 | 9.11  |
| ATOM | 1121 | C    | ALA | 121 | −7.237  | −17.132 | 47.903 | 1.00 | 9.94  |
| ATOM | 1122 | O    | ALA | 121 | −7.585  | −18.311 | 47.927 | 1.00 | 13.51 |
| ATOM | 1123 | N    | SEM | 122 | −8.103  | −16.140 | 48.016 | 1.00 | 9.68  |
| ATOM | 1124 | H    | SEM | 122 | −7.771  | −15.218 | 48.000 | 1.00 | 0.00  |
| ATOM | 1125 | CA   | SEM | 122 | −9.519  | −16.402 | 48.163 | 1.00 | 11.81 |
| ATOM | 1126 | CB   | SEM | 122 | −10.233 | −15.133 | 48.605 | 1.00 | 19.02 |
| ATOM | 1127 | CG   | SEM | 122 | −9.687  | −14.587 | 49.905 | 1.00 | 29.28 |
| ATOM | 1128 | A    | SEM | 122 | −10.585 | −13.021 | 50.550 | 1.00 | 42.69 |
| ATOM | 1129 | CE   | SEM | 122 | −9.376  | −12.528 | 51.958 | 1.00 | 36.95 |
| ATOM | 1130 | C    | SEM | 122 | −10.151 | −16.974 | 46.903 | 1.00 | 9.90  |
| ATOM | 1131 | O    | SEM | 122 | −11.056 | −17.804 | 46.988 | 1.00 | 10.61 |
| ATOM | 1132 | N    | VAL | 123 | −9.693  | −16.526 | 45.737 | 1.00 | 10.83 |
| ATOM | 1133 | H    | VAL | 123 | −8.993  | −15.829 | 45.711 | 1.00 | 0.00  |
| ATOM | 1134 | CA   | VAL | 123 | −10.223 | −17.029 | 44.471 | 1.00 | 10.83 |
| ATOM | 1135 | CB   | VAL | 123 | −9.796  | −16.144 | 43.277 | 1.00 | 11.82 |
| ATOM | 1136 | CG1  | VAL | 123 | −10.149 | −16.814 | 41.957 | 1.00 | 13.10 |
| ATOM | 1137 | CG2  | VAL | 123 | −10.489 | −14.799 | 43.358 | 1.00 | 12.23 |
| ATOM | 1138 | C    | VAL | 123 | −9.740  | −18.469 | 44.269 | 1.00 | 11.72 |
| ATOM | 1139 | O    | VAL | 123 | −10.492 | −19.332 | 43.820 | 1.00 | 11.90 |
| ATOM | 1140 | N    | ARG | 124 | −8.496  | −18.737 | 44.645 | 1.00 | 11.15 |
| ATOM | 1141 | H    | ARG | 124 | −7.934  | −18.012 | 44.992 | 1.00 | 0.00  |
| ATOM | 1142 | CA   | ARG | 124 | −7.952  | −20.078 | 44.521 | 1.00 | 10.74 |
| ATOM | 1143 | CB   | ARG | 124 | −6.496  | −20.113 | 44.958 | 1.00 | 13.48 |
| ATOM | 1144 | CG   | ARG | 124 | −5.588  | −19.228 | 44.150 | 1.00 | 22.67 |
| ATOM | 1145 | CD   | ARG | 124 | −4.164  | −19.371 | 44.639 | 1.00 | 30.29 |
| ATOM | 1146 | NE   | ARG | 124 | −3.677  | −20.737 | 44.462 | 1.00 | 34.80 |
| ATOM | 1147 | HE   | ARG | 124 | −3.798  | −21.375 | 45.202 | 1.00 | 0.00  |
| ATOM | 1148 | CZ   | ARG | 124 | −3.075  | −21.173 | 43.359 | 1.00 | 36.89 |
| ATOM | 1149 | NH1  | ARG | 124 | −2.885  | −20.352 | 42.330 | 1.00 | 35.72 |
| ATOM | 1150 | HH11 | ARG | 124 | −3.203  | −19.404 | 42.371 | 1.00 | 0.00  |
| ATOM | 1151 | HH12 | ARG | 124 | −2.428  | −20.690 | 41.503 | 1.00 | 0.00  |
| ATOM | 1152 | NH2  | ARG | 124 | −2.646  | −22.427 | 43.292 | 1.00 | 38.58 |
| ATOM | 1153 | HH21 | ARG | 124 | −2.777  | −23.034 | 44.072 | 1.00 | 0.00  |
| ATOM | 1154 | HH22 | ARG | 124 | −2.190  | −22.758 | 42.469 | 1.00 | 0.00  |
| ATOM | 1155 | C    | ARG | 124 | −8.750  | −20.989 | 45.426 | 1.00 | 9.71  |
| ATOM | 1156 | O    | ARG | 124 | −9.144  | −22.079 | 45.029 | 1.00 | 10.87 |
| ATOM | 1157 | N    | ASP | 125 | −9.004  | −20.526 | 46.644 | 1.00 | 11.13 |
| ATOM | 1158 | H    | ASP | 125 | −8.663  | −19.644 | 46.891 | 1.00 | 0.00  |
| ATOM | 1159 | CA   | ASP | 125 | −9.753  | −21.311 | 47.617 | 1.00 | 10.38 |
| ATOM | 1160 | CB   | ASP | 125 | −9.765  | −20.600 | 48.974 | 1.00 | 13.20 |
| ATOM | 1161 | CG   | ASP | 125 | −10.489 | −21.397 | 50.051 | 1.00 | 18.39 |
| ATOM | 1162 | OD1  | ASP | 125 | −11.393 | −20.831 | 50.706 | 1.00 | 21.49 |
| ATOM | 1163 | OD2  | ASP | 125 | −10.158 | −22.590 | 50.238 | 1.00 | 18.02 |
| ATOM | 1164 | C    | ASP | 125 | −11.174 | −21.617 | 47.140 | 1.00 | 8.61  |
| ATOM | 1165 | O    | ASP | 125 | −11.652 | −22.741 | 47.266 | 1.00 | 11.19 |
| ATOM | 1166 | N    | TYR | 126 | −11.840 | −20.621 | 46.579 | 1.00 | 10.44 |
| ATOM | 1167 | H    | TYR | 126 | −11.410 | −19.747 | 46.499 | 1.00 | 0.00  |
| ATOM | 1168 | CA   | TYR | 126 | −13.198 | −20.802 | 46.074 | 1.00 | 11.59 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| | | | | | | | | |
|---|---|---|---|---|---|---|---|---|
| ATOM | 1169 | CB   | TYR | 126 | −13.780 | −19.452 | 45.641 | 1.00 | 11.23 |
| ATOM | 1170 | CG   | TYR | 126 | −15.206 | −19.523 | 45.138 | 1.00 | 12.70 |
| ATOM | 1171 | CD1  | TYR | 126 | −16.275 | −19.332 | 46.009 | 1.00 | 14.14 |
| ATOM | 1172 | CE1  | TYR | 126 | −17.589 | −19.395 | 45.562 | 1.00 | 17.06 |
| ATOM | 1173 | CD2  | TYR | 126 | −15.488 | −19.784 | 43.794 | 1.00 | 13.43 |
| ATOM | 1174 | CE2  | TYR | 126 | −16.812 | −19.856 | 43.334 | 1.00 | 15.60 |
| ATOM | 1175 | CZ   | TYR | 126 | −17.858 | −19.655 | 44.228 | 1.00 | 16.20 |
| ATOM | 1176 | OH   | TYR | 126 | −19.173 | −19.702 | 43.806 | 1.00 | 16.29 |
| ATOM | 1177 | HH   | TYR | 126 | −19.739 | −19.596 | 44.573 | 1.00 |  0.00 |
| ATOM | 1178 | C    | TYR | 126 | −13.248 | −21.776 | 44.888 | 1.00 | 13.13 |
| ATOM | 1179 | O    | TYR | 126 | −14.131 | −22.629 | 44.815 | 1.00 | 11.60 |
| ATOM | 1180 | N    | VAL | 127 | −12.318 | −21.618 | 43.948 | 1.00 | 13.17 |
| ATOM | 1181 | H    | VAL | 127 | −11.653 | −20.905 | 44.039 | 1.00 |  0.00 |
| ATOM | 1182 | CA   | VAL | 127 | −12.272 | −22.469 | 42.764 | 1.00 | 13.56 |
| ATOM | 1183 | CB   | VAL | 127 | −11.275 | −21.918 | 41.712 | 1.00 | 13.44 |
| ATOM | 1184 | CG1  | VAL | 127 | −11.230 | −22.826 | 40.480 | 1.00 | 14.23 |
| ATOM | 1185 | CG2  | VAL | 127 | −11.684 | −20.512 | 41.302 | 1.00 | 10.59 |
| ATOM | 1186 | C    | VAL | 127 | −11.941 | −23.916 | 43.115 | 1.00 | 14.89 |
| ATOM | 1187 | O    | VAL | 127 | −12.527 | −24.843 | 42.560 | 1.00 | 16.19 |
| ATOM | 1188 | N    | ARG | 128 | −11.022 | −24.112 | 44.052 | 1.00 | 15.44 |
| ATOM | 1189 | H    | ARG | 128 | −10.583 | −23.335 | 44.470 | 1.00 |  0.00 |
| ATOM | 1190 | CA   | ARG | 128 | −10.640 | −25.450 | 44.473 | 1.00 | 15.05 |
| ATOM | 1191 | CB   | ARG | 128 |  −9.422 | −25.365 | 45.388 | 1.00 | 19.03 |
| ATOM | 1192 | CG   | ARG | 128 |  −8.887 | −26.701 | 45.848 | 1.00 | 24.57 |
| ATOM | 1193 | CD   | ARG | 128 |  −7.521 | −26.528 | 46.483 | 1.00 | 29.44 |
| ATOM | 1194 | NE   | ARG | 128 |  −7.551 | −25.528 | 47.544 | 1.00 | 32.78 |
| ATOM | 1195 | HE   | ARG | 128 |  −8.319 | −25.519 | 48.151 | 1.00 |  0.00 |
| ATOM | 1196 | CZ   | ARG | 128 |  −6.614 | −24.606 | 47.732 | 1.00 | 32.41 |
| ATOM | 1197 | NH1  | ARG | 128 |  −5.557 | −24.541 | 46.929 | 1.00 | 28.66 |
| ATOM | 1198 | HH11 | ARG | 128 |  −5.461 | −25.186 | 46.170 | 1.00 |  0.00 |
| ATOM | 1199 | HH12 | ARG | 128 |  −4.855 | −23.840 | 47.078 | 1.00 |  0.00 |
| ATOM | 1200 | NH2  | ARG | 128 |  −6.742 | −23.746 | 48.729 | 1.00 | 34.68 |
| ATOM | 1201 | HH21 | ARG | 128 |  −7.528 | −23.786 | 49.343 | 1.00 |  0.00 |
| ATOM | 1202 | HH22 | ARG | 128 |  −6.015 | −23.087 | 48.879 | 1.00 |  0.00 |
| ATOM | 1203 | C    | ARG | 128 | −11.806 | −26.118 | 45.196 | 1.00 | 16.91 |
| ATOM | 1204 | O    | ARG | 128 | −12.185 | −27.241 | 44.884 | 1.00 | 16.06 |
| ATOM | 1205 | N    | GLN | 129 | −12.386 | −25.399 | 46.149 | 1.00 | 17.04 |
| ATOM | 1206 | H    | GLN | 129 | −12.025 | −24.508 | 46.347 | 1.00 |  0.00 |
| ATOM | 1207 | CA   | GLN | 129 | −13.516 | −25.886 | 46.924 | 1.00 | 17.75 |
| ATOM | 1208 | CB   | GLN | 129 | −13.922 | −24.813 | 47.941 | 1.00 | 24.23 |
| ATOM | 1209 | CG   | GLN | 129 | −15.184 | −25.116 | 48.735 | 1.00 | 35.10 |
| ATOM | 1210 | CD   | GLN | 129 | −15.850 | −23.854 | 49.274 | 1.00 | 43.22 |
| ATOM | 1211 | OE1  | GLN | 129 | −16.998 | −23.547 | 48.934 | 1.00 | 45.61 |
| ATOM | 1212 | NE2  | GLN | 129 | −15.134 | −23.120 | 50.124 | 1.00 | 44.34 |
| ATOM | 1213 | HE21 | GLN | 129 | −14.232 | −23.402 | 50.371 | 1.00 |  0.00 |
| ATOM | 1214 | HE22 | GLN | 129 | −15.573 | −22.317 | 50.462 | 1.00 |  0.00 |
| ATOM | 1215 | C    | GLN | 129 | −14.707 | −26.215 | 46.024 | 1.00 | 14.94 |
| ATOM | 1216 | O    | GLN | 129 | −15.374 | −27.227 | 46.202 | 1.00 | 17.51 |
| ATOM | 1217 | N    | THR | 130 | −14.967 | −25.359 | 45.051 | 1.00 | 12.68 |
| ATOM | 1218 | H    | THR | 130 | −14.422 | −24.549 | 44.954 | 1.00 |  0.00 |
| ATOM | 1219 | CA   | THR | 130 | −16.094 | −25.547 | 44.151 | 1.00 | 14.74 |
| ATOM | 1220 | CB   | THR | 130 | −16.473 | −24.207 | 43.491 | 1.00 | 16.50 |
| ATOM | 1221 | OG1  | THR | 130 | −16.680 | −23.223 | 44.513 | 1.00 | 15.75 |
| ATOM | 1222 | HG1  | THR | 130 | −17.352 | −23.533 | 45.132 | 1.00 |  0.00 |
| ATOM | 1223 | CG2  | THR | 130 | −17.748 | −24.347 | 42.666 | 1.00 | 16.34 |
| ATOM | 1224 | C    | THR | 130 | −15.909 | −26.599 | 43.063 | 1.00 | 14.23 |
| ATOM | 1225 | O    | THR | 130 | −16.746 | −27.481 | 42.894 | 1.00 | 15.79 |
| ATOM | 1226 | N    | TRP | 131 | −14.812 | −26.507 | 42.329 | 1.00 | 13.82 |
| ATOM | 1227 | H    | TRP | 131 | −14.156 | −25.807 | 42.510 | 1.00 |  0.00 |
| ATOM | 1228 | CA   | TRP | 131 | −14.551 | −27.429 | 41.235 | 1.00 | 12.96 |
| ATOM | 1229 | CB   | TRP | 131 | −13.790 | −26.702 | 40.128 | 1.00 | 13.33 |
| ATOM | 1230 | CG   | TRP | 131 | −14.586 | −25.559 | 39.589 | 1.00 | 15.21 |
| ATOM | 1231 | CD2  | TRP | 131 | −15.383 | −25.551 | 38.398 | 1.00 | 16.02 |
| ATOM | 1232 | CE2  | TRP | 131 | −16.037 | −24.299 | 38.342 | 1.00 | 16.98 |
| ATOM | 1233 | CE3  | TRP | 131 | −15.610 | −26.483 | 37.375 | 1.00 | 19.06 |
| ATOM | 1234 | CD1  | TRP | 131 | −14.773 | −24.339 | 40.183 | 1.00 | 16.24 |
| ATOM | 1235 | NE1  | TRP | 131 | −15.650 | −23.583 | 39.444 | 1.00 | 19.42 |
| ATOM | 1236 | HE1  | TRP | 131 | −15.968 | −22.696 | 39.715 | 1.00 |  0.00 |
| ATOM | 1237 | CZ2  | TRP | 131 | −16.907 | −23.952 | 37.301 | 1.00 | 17.20 |
| ATOM | 1238 | CZ3  | TRP | 131 | −16.477 | −26.137 | 36.340 | 1.00 | 19.80 |
| ATOM | 1239 | CH2  | TRP | 131 | −17.114 | −24.880 | 36.312 | 1.00 | 18.84 |
| ATOM | 1240 | C    | TRP | 131 | −13.852 | −28.712 | 41.629 | 1.00 | 13.29 |
| ATOM | 1241 | O    | TRP | 131 | −13.892 | −29.692 | 40.883 | 1.00 | 12.51 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1242 | N   | LYS | 132 | −13.245 | −28.710 | 42.813 | 1.00 | 15.49 |
|------|------|-----|-----|-----|---------|---------|--------|------|-------|
| ATOM | 1243 | H   | LYS | 132 | −13.261 | −27.900 | 43.361 | 1.00 | 0.00  |
| ATOM | 1244 | CA  | LYS | 132 | −12.531 | −29.872 | 43.344 | 1.00 | 18.55 |
| ATOM | 1245 | CB  | LYS | 132 | −13.467 | −31.090 | 43.451 | 1.00 | 17.43 |
| ATOM | 1246 | CG  | LYS | 132 | −14.374 | −31.116 | 44.670 | 1.00 | 19.61 |
| ATOM | 1247 | CD  | LYS | 132 | −15.519 | −30.137 | 44.557 | 1.00 | 21.76 |
| ATOM | 1248 | CE  | LYS | 132 | −16.482 | −30.273 | 45.727 | 1.00 | 20.70 |
| ATOM | 1249 | NZ  | LYS | 132 | −15.842 | −29.954 | 47.029 | 1.00 | 23.81 |
| ATOM | 1250 | HZ1 | LYS | 132 | −15.472 | −28.987 | 47.004 | 1.00 | 0.00  |
| ATOM | 1251 | HZ2 | LYS | 132 | −15.060 | −30.615 | 47.195 | 1.00 | 0.00  |
| ATOM | 1252 | HZ3 | LYS | 132 | −16.535 | −30.033 | 47.800 | 1.00 | 0.00  |
| ATOM | 1253 | C   | LYS | 132 | −11.310 | −30.220 | 42.496 | 1.00 | 20.84 |
| ATOM | 1254 | O   | LYS | 132 | −10.973 | −31.392 | 42.325 | 1.00 | 21.28 |
| ATOM | 1255 | N   | LEU | 133 | −10.635 | −29.195 | 41.991 | 1.00 | 22.03 |
| ATOM | 1256 | H   | LEU | 133 | −10.915 | −28.292 | 42.231 | 1.00 | 0.00  |
| ATOM | 1257 | CA  | LEU | 133 | −9.459  | −29.383 | 41.149 | 1.00 | 23.93 |
| ATOM | 1258 | CB  | LEU | 133 | −9.539  | −28.464 | 39.930 | 1.00 | 22.92 |
| ATOM | 1259 | CG  | LEU | 133 | −10.724 | −28.710 | 38.993 | 1.00 | 21.45 |
| ATOM | 1260 | CD1 | LEU | 133 | −10.779 | −27.638 | 37.930 | 1.00 | 16.33 |
| ATOM | 1261 | CD2 | LEU | 133 | −10.608 | −30.091 | 38.365 | 1.00 | 18.90 |
| ATOM | 1262 | C   | LEU | 133 | −8.158  | −29.131 | 41.897 | 1.00 | 25.56 |
| ATOM | 1263 | O   | LEU | 133 | −8.137  | −28.456 | 42.921 | 1.00 | 24.95 |
| ATOM | 1264 | N   | GLU | 134 | −7.068  | −29.675 | 41.372 | 1.00 | 30.15 |
| ATOM | 1265 | H   | GLU | 134 | −7.120  | −30.201 | 40.549 | 1.00 | 0.00  |
| ATOM | 1266 | CA  | GLU | 134 | −5.758  | −29.501 | 41.983 | 1.00 | 35.39 |
| ATOM | 1267 | CB  | GLU | 134 | −5.418  | −30.687 | 42.899 | 1.00 | 40.72 |
| ATOM | 1268 | CG  | GLU | 134 | −6.137  | −30.693 | 44.262 | 1.00 | 47.74 |
| ATOM | 1269 | CD  | GLU | 134 | −5.572  | −29.689 | 45.276 | 1.00 | 52.02 |
| ATOM | 1270 | OE1 | GLU | 134 | −6.063  | −29.681 | 46.427 | 1.00 | 52.20 |
| ATOM | 1271 | OE2 | GLU | 134 | −4.643  | −28.916 | 44.940 | 1.00 | 54.41 |
| ATOM | 1272 | C   | GLU | 134 | −4.694  | −29.361 | 40.904 | 1.00 | 35.44 |
| ATOM | 1273 | O   | GLU | 134 | −4.968  | −29.569 | 39.719 | 1.00 | 35.63 |
| ATOM | 1274 | N   | GLY | 135 | −3.494  | −28.965 | 41.316 | 1.00 | 34.91 |
| ATOM | 1275 | H   | GLY | 135 | −3.374  | −28.756 | 42.265 | 1.00 | 0.00  |
| ATOM | 1276 | CA  | GLY | 135 | −2.392  | −28.807 | 40.382 | 1.00 | 34.73 |
| ATOM | 1277 | C   | GLY | 135 | −2.686  | −27.917 | 39.189 | 1.00 | 34.52 |
| ATOM | 1278 | O   | GLY | 135 | −3.416  | −26.927 | 39.297 | 1.00 | 34.03 |
| ATOM | 1279 | N   | GLU | 136 | −2.149  | −28.302 | 38.035 | 1.00 | 34.50 |
| ATOM | 1280 | H   | GLU | 136 | −1.609  | −29.117 | 38.031 | 1.00 | 0.00  |
| ATOM | 1281 | CA  | GLU | 136 | −2.324  | −27.544 | 36.799 | 1.00 | 34.12 |
| ATOM | 1282 | CB  | GLU | 136 | −1.543  | −28.203 | 35.658 | 1.00 | 38.90 |
| ATOM | 1283 | CG  | GLU | 136 | −1.203  | −27.256 | 34.511 | 1.00 | 43.32 |
| ATOM | 1284 | CD  | GLU | 136 | −0.456  | −26.009 | 34.980 | 1.00 | 46.70 |
| ATOM | 1285 | OE1 | GLU | 136 | 0.595   | −26.145 | 35.650 | 1.00 | 48.76 |
| ATOM | 1286 | OE2 | GLU | 136 | −0.930  | −24.889 | 34.686 | 1.00 | 46.11 |
| ATOM | 1287 | C   | GLU | 136 | −3.787  | −27.359 | 36.399 | 1.00 | 31.34 |
| ATOM | 1288 | O   | GLU | 136 | −4.148  | −26.351 | 35.787 | 1.00 | 28.55 |
| ATOM | 1289 | N   | ALA | 137 | −4.625  | −28.329 | 36.756 | 1.00 | 29.45 |
| ATOM | 1290 | H   | ALA | 137 | −4.285  | −29.104 | 37.238 | 1.00 | 0.00  |
| ATOM | 1291 | CA  | ALA | 137 | −6.048  | −28.258 | 36.440 | 1.00 | 26.31 |
| ATOM | 1292 | CB  | ALA | 137 | −6.740  | −29.548 | 36.842 | 1.00 | 26.49 |
| ATOM | 1293 | C   | ALA | 137 | −6.652  | −27.072 | 37.181 | 1.00 | 22.29 |
| ATOM | 1294 | O   | ALA | 137 | −7.442  | −26.317 | 36.622 | 1.00 | 22.04 |
| ATOM | 1295 | N   | LEU | 138 | −6.241  | −26.894 | 38.432 | 1.00 | 20.21 |
| ATOM | 1296 | H   | LEU | 138 | −5.577  | −27.514 | 38.813 | 1.00 | 0.00  |
| ATOM | 1297 | CA  | LEU | 138 | −6.725  | −25.792 | 39.249 | 1.00 | 20.63 |
| ATOM | 1298 | CB  | LEU | 138 | −6.223  | −25.941 | 40.686 | 1.00 | 17.38 |
| ATOM | 1299 | CG  | LEU | 138 | −6.519  | −24.807 | 41.670 | 1.00 | 17.34 |
| ATOM | 1300 | CD1 | LEU | 138 | −8.013  | −24.543 | 41.738 | 1.00 | 16.71 |
| ATOM | 1301 | CD2 | LEU | 138 | −5.986  | −25.170 | 43.040 | 1.00 | 15.22 |
| ATOM | 1302 | C   | LEU | 138 | −6.243  | −24.469 | 38.659 | 1.00 | 21.98 |
| ATOM | 1303 | O   | LEU | 138 | −7.027  | −23.528 | 38.513 | 1.00 | 21.24 |
| ATOM | 1304 | N   | GLU | 139 | −4.965  | −24.415 | 38.288 | 1.00 | 23.87 |
| ATOM | 1305 | H   | GLU | 139 | −4.423  | −25.227 | 38.393 | 1.00 | 0.00  |
| ATOM | 1306 | CA  | GLU | 139 | −4.372  | −23.209 | 37.713 | 1.00 | 25.73 |
| ATOM | 1307 | CB  | GLU | 139 | −2.914  | −23.454 | 37.334 | 1.00 | 28.07 |
| ATOM | 1308 | CG  | GLU | 139 | −2.052  | −23.944 | 38.479 | 1.00 | 33.00 |
| ATOM | 1309 | CD  | GLU | 139 | −2.216  | −23.110 | 39.733 | 1.00 | 37.06 |
| ATOM | 1310 | OE1 | GLU | 139 | −2.506  | −23.697 | 40.796 | 1.00 | 41.81 |
| ATOM | 1311 | OE2 | GLU | 139 | −2.062  | −21.872 | 39.662 | 1.00 | 39.33 |
| ATOM | 1312 | C   | GLU | 139 | −5.138  | −22.737 | 36.487 | 1.00 | 26.80 |
| ATOM | 1313 | O   | GLU | 139 | −5.462  | −21.555 | 36.362 | 1.00 | 25.34 |
| ATOM | 1314 | N   | GLN | 140 | −5.434  | −23.669 | 35.588 | 1.00 | 29.70 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1315 | H    | GLN | 140 | −5.140  | −24.594 | 35.755 | 1.00 | 0.00  |
|------|------|------|-----|-----|---------|---------|--------|------|-------|
| ATOM | 1316 | CA   | GLN | 140 | −6.172  | −23.361 | 34.369 | 1.00 | 31.92 |
| ATOM | 1317 | CB   | GLN | 140 | −6.270  | −24.605 | 33.479 | 1.00 | 38.06 |
| ATOM | 1318 | CG   | GLN | 140 | −4.935  | −25.155 | 32.994 | 1.00 | 45.35 |
| ATOM | 1319 | CD   | GLN | 140 | −5.088  | −26.459 | 32.218 | 1.00 | 52.31 |
| ATOM | 1320 | OE1  | GLN | 140 | −4.434  | −27.461 | 32.523 | 1.00 | 54.99 |
| ATOM | 1321 | NE2  | GLN | 140 | −5.958  | −26.453 | 31.212 | 1.00 | 53.53 |
| ATOM | 1322 | HE21 | GLN | 140 | −6.453  | −25.632 | 31.016 | 1.00 | 0.00  |
| ATOM | 1323 | HE22 | GLN | 140 | −6.057  | −27.290 | 30.723 | 1.00 | 0.00  |
| ATOM | 1324 | C    | GLN | 140 | −7.579  | −22.853 | 34.690 | 1.00 | 30.17 |
| ATOM | 1325 | O    | GLN | 140 | −8.068  | −21.914 | 34.058 | 1.00 | 29.36 |
| ATOM | 1326 | N    | ALA | 141 | −8.218  | −23.472 | 35.680 | 1.00 | 28.89 |
| ATOM | 1327 | H    | ALA | 141 | −7.777  | −24.201 | 36.166 | 1.00 | 0.00  |
| ATOM | 1328 | CA   | ALA | 141 | −9.572  | −23.099 | 36.084 | 1.00 | 27.36 |
| ATOM | 1329 | CB   | ALA | 141 | −10.154 | −24.143 | 37.028 | 1.00 | 25.84 |
| ATOM | 1330 | C    | ALA | 141 | −9.665  | −21.711 | 36.709 | 1.00 | 26.93 |
| ATOM | 1331 | O    | ALA | 141 | −10.584 | −20.963 | 36.396 | 1.00 | 25.78 |
| ATOM | 1332 | N    | ILE | 142 | −8.725  | −21.358 | 37.581 | 1.00 | 27.95 |
| ATOM | 1333 | H    | ILE | 142 | −8.010  | −22.001 | 37.791 | 1.00 | 0.00  |
| ATOM | 1334 | CA   | ILE | 142 | −8.771  | −20.043 | 38.209 | 1.00 | 30.29 |
| ATOM | 1335 | CB   | ILE | 142 | −7.703  | −19.856 | 39.321 | 1.00 | 32.16 |
| ATOM | 1336 | CG2  | ILE | 142 | −7.763  | −21.010 | 40.310 | 1.00 | 31.60 |
| ATOM | 1337 | CG1  | ILE | 142 | −6.303  | −19.742 | 38.722 | 1.00 | 38.22 |
| ATOM | 1338 | CD   | ILE | 142 | −5.205  | −19.539 | 39.750 | 1.00 | 41.97 |
| ATOM | 1339 | C    | ILE | 142 | −8.628  | −18.955 | 37.153 | 1.00 | 30.56 |
| ATOM | 1340 | O    | ILE | 142 | −9.256  | −17.911 | 37.253 | 1.00 | 32.19 |
| ATOM | 1341 | N    | ILE | 143 | −7.847  | −19.223 | 36.111 | 1.00 | 31.49 |
| ATOM | 1342 | H    | ILE | 143 | −7.382  | −20.088 | 36.069 | 1.00 | 0.00  |
| ATOM | 1343 | CA   | ILE | 143 | −7.656  | −18.246 | 35.044 | 1.00 | 32.26 |
| ATOM | 1344 | CB   | ILE | 143 | −6.618  | −18.736 | 34.000 | 1.00 | 34.28 |
| ATOM | 1345 | CG2  | ILE | 143 | −6.480  | −17.728 | 32.868 | 1.00 | 34.40 |
| ATOM | 1346 | CG1  | ILE | 143 | −5.254  | −18.975 | 34.661 | 1.00 | 36.63 |
| ATOM | 1347 | CD   | ILE | 143 | −4.561  | −17.724 | 35.179 | 1.00 | 39.46 |
| ATOM | 1348 | C    | ILE | 143 | −8.984  | −17.951 | 34.342 | 1.00 | 30.93 |
| ATOM | 1349 | O    | ILE | 143 | −9.295  | −16.799 | 34.052 | 1.00 | 30.08 |
| ATOM | 1350 | N    | SER | 144 | −9.776  | −18.989 | 34.100 | 1.00 | 30.90 |
| ATOM | 1351 | H    | SER | 144 | −9.524  | −19.901 | 34.367 | 1.00 | 0.00  |
| ATOM | 1352 | CA   | SER | 144 | −11.056 | −18.826 | 33.427 | 1.00 | 33.20 |
| ATOM | 1353 | CB   | SER | 144 | −11.434 | −20.123 | 32.704 | 1.00 | 35.30 |
| ATOM | 1354 | OG   | SER | 144 | −11.353 | −21.242 | 33.569 | 1.00 | 40.36 |
| ATOM | 1355 | HG   | SER | 144 | −11.540 | −22.026 | 33.050 | 1.00 | 0.00  |
| ATOM | 1356 | C    | SER | 144 | −12.197 | −18.375 | 34.343 | 1.00 | 34.38 |
| ATOM | 1357 | O    | SER | 144 | −13.103 | −17.653 | 33.920 | 1.00 | 34.88 |
| ATOM | 1358 | N    | GLN | 145 | −12.154 | −18.803 | 35.598 | 1.00 | 34.59 |
| ATOM | 1359 | H    | GLN | 145 | −11.420 | −19.393 | 35.855 | 1.00 | 0.00  |
| ATOM | 1360 | CA   | GLN | 145 | −13.189 | −18.444 | 36.557 | 1.00 | 33.70 |
| ATOM | 1361 | CB   | GLN | 145 | −13.383 | −19.572 | 37.571 | 1.00 | 33.70 |
| ATOM | 1362 | CG   | GLN | 145 | −13.934 | −20.859 | 36.978 | 1.00 | 35.74 |
| ATOM | 1363 | CD   | GLN | 145 | −15.369 | −20.728 | 36.503 | 1.00 | 37.42 |
| ATOM | 1364 | OE1  | GLN | 145 | −15.699 | −21.098 | 35.374 | 1.00 | 39.84 |
| ATOM | 1365 | NE2  | GLN | 145 | −16.238 | −20.227 | 37.374 | 1.00 | 38.81 |
| ATOM | 1366 | HE21 | GLN | 145 | −15.932 | −19.964 | 38.263 | 1.00 | 0.00  |
| ATOM | 1367 | HE22 | GLN | 145 | −17.171 | −20.156 | 37.086 | 1.00 | 0.00  |
| ATOM | 1368 | C    | GLN | 145 | −12.948 | −17.124 | 37.292 | 1.00 | 32.75 |
| ATOM | 1369 | O    | GLN | 145 | −13.905 | −16.450 | 37.668 | 1.00 | 33.82 |
| ATOM | 1370 | N    | ALA | 146 | −11.687 | −16.735 | 37.463 | 1.00 | 32.02 |
| ATOM | 1371 | H    | ALA | 146 | −10.979 | −17.277 | 37.078 | 1.00 | 0.00  |
| ATOM | 1372 | CA   | ALA | 146 | −11.343 | −15.500 | 38.179 | 1.00 | 34.00 |
| ATOM | 1373 | CB   | ALA | 146 | −9.858  | −15.167 | 38.003 | 1.00 | 32.05 |
| ATOM | 1374 | C    | ALA | 146 | −12.199 | −14.278 | 37.841 | 1.00 | 35.44 |
| ATOM | 1375 | O    | ALA | 146 | −12.710 | −13.607 | 38.742 | 1.00 | 36.48 |
| ATOM | 1376 | N    | PRO | 147 | −12.371 | −13.970 | 36.543 | 1.00 | 36.46 |
| ATOM | 1377 | CD   | PRO | 147 | −11.711 | −14.566 | 35.365 | 1.00 | 36.36 |
| ATOM | 1378 | CA   | PRO | 147 | −13.178 | −12.812 | 36.145 | 1.00 | 35.69 |
| ATOM | 1379 | CB   | PRO | 147 | −13.108 | −12.872 | 34.621 | 1.00 | 37.74 |
| ATOM | 1380 | CG   | PRO | 147 | −11.741 | −13.432 | 34.380 | 1.00 | 37.31 |
| ATOM | 1381 | C    | PRO | 147 | −14.627 | −12.823 | 36.632 | 1.00 | 35.01 |
| ATOM | 1382 | O    | PRO | 147 | −15.170 | −11.781 | 37.008 | 1.00 | 34.92 |
| ATOM | 1383 | N    | GLN | 148 | −15.232 | −14.005 | 36.662 | 1.00 | 34.44 |
| ATOM | 1384 | H    | GLN | 148 | −14.719 | −14.803 | 36.413 | 1.00 | 0.00  |
| ATOM | 1385 | CA   | GLN | 148 | −16.627 | −14.155 | 37.072 | 1.00 | 36.11 |
| ATOM | 1386 | CB   | GLN | 148 | −17.194 | −15.465 | 36.507 | 1.00 | 40.50 |
| ATOM | 1387 | CG   | GLN | 148 | −17.002 | −15.634 | 34.996 | 1.00 | 43.75 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1388 | CD   | GLN | 148 | −17.614 | −14.499 | 34.198 | 1.00 | 47.86 |
| ---- | ---- | ---- | --- | --- | ------- | ------- | ------ | ---- | ----- |
| ATOM | 1389 | OE1  | GLN | 148 | −16.915 | −13.779 | 33.482 | 1.00 | 49.23 |
| ATOM | 1390 | NE2  | GLN | 148 | −18.925 | −14.330 | 34.319 | 1.00 | 49.03 |
| ATOM | 1391 | HE21 | GLN | 148 | −19.440 | −14.926 | 34.897 | 1.00 | 0.00  |
| ATOM | 1392 | HE22 | GLN | 148 | −19.303 | −13.595 | 33.801 | 1.00 | 0.00  |
| ATOM | 1393 | C    | GLN | 148 | −16.892 | −14.083 | 38.581 | 1.00 | 34.17 |
| ATOM | 1394 | O    | GLN | 148 | −17.963 | −13.645 | 39.018 | 1.00 | 34.12 |
| ATOM | 1395 | N    | VAL | 149 | −15.924 | −14.518 | 39.378 | 1.00 | 30.55 |
| ATOM | 1396 | H    | VAL | 149 | −15.084 | −14.843 | 38.983 | 1.00 | 0.00  |
| ATOM | 1397 | CA   | VAL | 149 | −16.084 | −14.506 | 40.824 | 1.00 | 27.34 |
| ATOM | 1398 | CB   | VAL | 149 | −15.730 | −15.874 | 41.424 | 1.00 | 26.70 |
| ATOM | 1399 | CG1  | VAL | 149 | −16.628 | −16.942 | 40.829 | 1.00 | 27.05 |
| ATOM | 1400 | CG2  | VAL | 149 | −14.271 | −16.202 | 41.164 | 1.00 | 25.34 |
| ATOM | 1401 | C    | VAL | 149 | −15.258 | −13.418 | 41.506 | 1.00 | 27.10 |
| ATOM | 1402 | O    | VAL | 149 | −15.220 | −13.341 | 42.732 | 1.00 | 26.82 |
| ATOM | 1403 | N    | GLU | 150 | −14.622 | −12.565 | 40.708 | 1.00 | 27.77 |
| ATOM | 1404 | H    | GLU | 150 | −14.683 | −12.695 | 39.739 | 1.00 | 0.00  |
| ATOM | 1405 | CA   | GLU | 150 | −13.795 | −11.477 | 41.229 | 1.00 | 28.17 |
| ATOM | 1406 | CB   | GLU | 150 | −13.249 | −10.616 | 40.078 | 1.00 | 32.48 |
| ATOM | 1407 | CG   | GLU | 150 | −11.848 | −10.013 | 40.336 | 1.00 | 42.10 |
| ATOM | 1408 | CD   | GLU | 150 | −11.772 | −8.484  | 40.177 | 1.00 | 43.81 |
| ATOM | 1409 | OE1  | GLU | 150 | −12.480 | −7.918  | 39.313 | 1.00 | 41.18 |
| ATOM | 1410 | OE2  | GLU | 150 | −10.981 | −7.850  | 40.915 | 1.00 | 45.59 |
| ATOM | 1411 | C    | GLU | 150 | −14.585 | −10.600 | 42.201 | 1.00 | 24.18 |
| ATOM | 1412 | O    | GLU | 150 | −14.179 | −10.415 | 43.344 | 1.00 | 22.05 |
| ATOM | 1413 | N    | LYS | 151 | −15.721 | −10.083 | 41.749 | 1.00 | 21.94 |
| ATOM | 1414 | H    | LYS | 151 | −15.998 | −10.281 | 40.831 | 1.00 | 0.00  |
| ATOM | 1415 | CA   | LYS | 151 | −16.552 | −9.225  | 42.584 | 1.00 | 22.44 |
| ATOM | 1416 | CB   | LYS | 151 | −17.221 | −8.646  | 41.784 | 1.00 | 25.52 |
| ATOM | 1417 | CG   | LYS | 151 | −17.297 | −7.656  | 40.698 | 1.00 | 33.26 |
| ATOM | 1418 | CD   | LYS | 151 | −16.749 | −6.357  | 41.293 | 1.00 | 36.27 |
| ATOM | 1419 | CE   | LYS | 151 | −15.910 | −5.572  | 40.282 | 1.00 | 36.61 |
| ATOM | 1420 | NZ   | LYS | 151 | −14.684 | −6.337  | 39.897 | 1.00 | 38.17 |
| ATOM | 1421 | HZ1  | LYS | 151 | −14.965 | −7.218  | 39.418 | 1.00 | 0.00  |
| ATOM | 1422 | HZ2  | LYS | 151 | −14.135 | −6.581  | 40.747 | 1.00 | 0.00  |
| ATOM | 1423 | HZ3  | LYS | 151 | −14.080 | −5.784  | 39.256 | 1.00 | 0.00  |
| ATOM | 1424 | C    | LYS | 151 | −17.064 | −9.945  | 43.820 | 1.00 | 20.52 |
| ATOM | 1425 | O    | LYS | 151 | −16.935 | −9.430  | 44.925 | 1.00 | 21.76 |
| ATOM | 1426 | N    | LEU | 152 | −17.620 | −11.139 | 43.633 | 1.00 | 18.37 |
| ATOM | 1427 | H    | LEU | 152 | −17.693 | −11.501 | 42.726 | 1.00 | 0.00  |
| ATOM | 1428 | CA   | LEU | 152 | −18.147 | −11.936 | 44.471 | 1.00 | 17.20 |
| ATOM | 1429 | CB   | LEU | 152 | −18.532 | −13.336 | 44.249 | 1.00 | 18.20 |
| ATOM | 1430 | CG   | LEU | 152 | −18.958 | −14.382 | 45.287 | 1.00 | 23.16 |
| ATOM | 1431 | CD1  | LEU | 152 | −20.324 | −14.025 | 45.859 | 1.00 | 21.89 |
| ATOM | 1432 | CD2  | LEU | 152 | −18.993 | −15.771 | 44.648 | 1.00 | 22.05 |
| ATOM | 1433 | C    | LEU | 152 | −17.113 | −12.059 | 45.856 | 1.00 | 15.24 |
| ATOM | 1434 | O    | LEU | 152 | −17.408 | −11.798 | 47.023 | 1.00 | 14.43 |
| ATOM | 1435 | N    | ILE | 153 | −15.896 | −12.436 | 45.482 | 1.00 | 12.34 |
| ATOM | 1436 | H    | ILE | 153 | −15.725 | −12.621 | 44.531 | 1.00 | 0.00  |
| ATOM | 1437 | CA   | ILE | 153 | −14.817 | −12.595 | 46.441 | 1.00 | 13.12 |
| ATOM | 1438 | CB   | ILE | 153 | −13.580 | −13.261 | 45.792 | 1.00 | 12.78 |
| ATOM | 1439 | CG2  | ILE | 153 | −12.498 | −13.469 | 46.813 | 1.00 | 10.18 |
| ATOM | 1440 | CG1  | ILE | 153 | −13.962 | −14.611 | 45.182 | 1.00 | 13.04 |
| ATOM | 1441 | CD   | ILE | 153 | −14.603 | −15.557 | 46.135 | 1.00 | 12.82 |
| ATOM | 1442 | C    | ILE | 153 | −14.418 | −11.265 | 47.081 | 1.00 | 12.71 |
| ATOM | 1443 | O    | ILE | 153 | −14.266 | −11.189 | 48.297 | 1.00 | 14.81 |
| ATOM | 1444 | N    | ALA | 154 | −14.299 | −10.212 | 46.276 | 1.00 | 11.61 |
| ATOM | 1445 | H    | ALA | 154 | −14.478 | −10.311 | 45.317 | 1.00 | 0.00  |
| ATOM | 1446 | CA   | ALA | 154 | −13.914 | −8.897  | 46.789 | 1.00 | 11.24 |
| ATOM | 1447 | CB   | ALA | 154 | −13.702 | −7.932  | 45.643 | 1.00 | 8.04  |
| ATOM | 1448 | C    | ALA | 154 | −14.918 | −8.308  | 47.788 | 1.00 | 11.11 |
| ATOM | 1449 | O    | ALA | 154 | −14.547 | −7.850  | 48.872 | 1.00 | 8.33  |
| ATOM | 1450 | N    | THR | 155 | −16.192 | −8.345  | 47.432 | 1.00 | 11.93 |
| ATOM | 1451 | H    | THR | 155 | −16.462 | −8.779  | 46.599 | 1.00 | 0.00  |
| ATOM | 1452 | CA   | THR | 155 | −17.232 | −7.793  | 48.285 | 1.00 | 16.85 |
| ATOM | 1453 | CB   | THR | 155 | −18.566 | −7.654  | 47.509 | 1.00 | 19.45 |
| ATOM | 1454 | OG1  | THR | 155 | −19.034 | −8.949  | 47.108 | 1.00 | 23.26 |
| ATOM | 1455 | HG1  | THR | 155 | −19.810 | −8.856  | 46.545 | 1.00 | 0.00  |
| ATOM | 1456 | CG2  | THR | 155 | −18.366 | −6.795  | 46.261 | 1.00 | 19.86 |
| ATOM | 1457 | C    | THR | 155 | −17.450 | −8.583  | 49.578 | 1.00 | 17.70 |
| ATOM | 1458 | O    | THR | 155 | −18.015 | −8.059  | 50.454 | 1.00 | 16.86 |
| ATOM | 1459 | N    | THR | 156 | −16.945 | −9.812  | 49.622 | 1.00 | 17.24 |
| ATOM | 1460 | H    | THR | 156 | −16.483 | −10.203 | 48.844 | 1.00 | 0.00  |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| | | | | | | | | |
|---|---|---|---|---|---|---|---|---|
| ATOM | 1461 | CA   | THR | 156 | −17.110 | −10.641 | 50.805 | 1.00 | 16.73 |
| ATOM | 1462 | CB   | THR | 156 | −17.781 | −11.991 | 50.436 | 1.00 | 18.95 |
| ATOM | 1463 | OG1  | THR | 156 | −18.349 | −12.579 | 51.610 | 1.00 | 28.41 |
| ATOM | 1464 | HG1  | THR | 156 | −17.628 | −12.777 | 52.224 | 1.00 | 0.00 |
| ATOM | 1465 | CG2  | THR | 156 | −16.782 | −12.958 | 49.825 | 1.00 | 16.01 |
| ATOM | 1466 | C    | THR | 156 | −15.818 | −10.864 | 51.607 | 1.00 | 15.60 |
| ATOM | 1467 | O    | THR | 156 | −15.853 | −11.468 | 52.681 | 1.00 | 14.74 |
| ATOM | 1468 | N    | ALA | 157 | −14.712 | −10.291 | 51.134 | 1.00 | 11.48 |
| ATOM | 1469 | H    | ALA | 157 | −14.745 | −9.796  | 50.286 | 1.00 | 0.00 |
| ATOM | 1470 | CA   | ALA | 157 | −13.404 | −10.426 | 51.780 | 1.00 | 9.54 |
| ATOM | 1471 | CB   | ALA | 157 | −12.342 | −9.713  | 50.961 | 1.00 | 5.51 |
| ATOM | 1472 | C    | ALA | 157 | −13.312 | −9.981  | 53.239 | 1.00 | 8.69 |
| ATOM | 1473 | O    | ALA | 157 | −12.471 | −10.476 | 53.987 | 1.00 | 10.31 |
| ATOM | 1474 | N    | HIS | 158 | −14.150 | −9.037  | 53.648 | 1.00 | 10.04 |
| ATOM | 1475 | H    | HIS | 158 | −14.761 | −8.654  | 52.995 | 1.00 | 0.00 |
| ATOM | 1476 | CA   | HIS | 158 | −14.119 | −8.550  | 55.029 | 1.00 | 9.74 |
| ATOM | 1477 | CB   | HIS | 158 | −15.043 | −7.335  | 55.185 | 1.00 | 8.60 |
| ATOM | 1478 | CG   | HIS | 158 | −16.494 | −7.631  | 54.940 | 1.00 | 10.37 |
| ATOM | 1479 | CD2  | HIS | 158 | −17.508 | −7.875  | 55.801 | 1.00 | 6.93 |
| ATOM | 1480 | ND1  | HIS | 158 | −17.045 | −7.685  | 53.677 | 1.00 | 9.52 |
| ATOM | 1481 | HD1  | HIS | 158 | −16.621 | −7.506  | 52.814 | 1.00 | 0.00 |
| ATOM | 1482 | CE1  | HIS | 158 | −18.336 | −7.952  | 53.771 | 1.00 | 8.21 |
| ATOM | 1483 | NE2  | HIS | 158 | −18.641 | −8.073  | 55.052 | 1.00 | 7.61 |
| ATOM | 1484 | HE2  | HIS | 158 | −19.542 | −8.310  | 55.393 | 1.00 | 0.00 |
| ATOM | 1485 | C    | HIS | 158 | −14.463 | −9.621  | 56.070 | 1.00 | 11.48 |
| ATOM | 1486 | O    | HIS | 158 | −13.948 | −9.602  | 57.189 | 1.00 | 12.15 |
| ATOM | 1487 | N    | GLU | 159 | −15.292 | −10.580 | 55.673 | 1.00 | 12.68 |
| ATOM | 1488 | H    | GLU | 159 | −15.604 | −10.612 | 54.744 | 1.00 | 0.00 |
| ATOM | 1489 | CA   | GLU | 159 | −15.734 | −11.657 | 56.554 | 1.00 | 16.34 |
| ATOM | 1490 | CB   | GLU | 159 | −16.826 | −12.477 | 55.870 | 1.00 | 19.60 |
| ATOM | 1491 | CG   | GLU | 159 | −18.109 | −11.703 | 55.586 | 1.00 | 22.36 |
| ATOM | 1492 | CD   | GLU | 159 | −19.133 | −12.516 | 54.811 | 1.00 | 25.59 |
| ATOM | 1493 | OE1  | GLU | 159 | −18.923 | −13.733 | 54.614 | 1.00 | 27.02 |
| ATOM | 1494 | OE2  | GLU | 159 | −20.157 | −11.933 | 54.396 | 1.00 | 30.21 |
| ATOM | 1495 | C    | GLU | 159 | −14.648 | −12.601 | 57.041 | 1.00 | 17.61 |
| ATOM | 1496 | O    | GLU | 159 | −14.881 | −13.388 | 57.958 | 1.00 | 19.13 |
| ATOM | 1497 | N    | ARG | 160 | −13.480 | −12.552 | 56.413 | 1.00 | 18.47 |
| ATOM | 1498 | H    | ARG | 160 | −13.336 | −11.921 | 55.678 | 1.00 | 0.00 |
| ATOM | 1499 | CA   | ARG | 160 | −12.380 | −13.428 | 56.799 | 1.00 | 20.02 |
| ATOM | 1500 | CB   | ARG | 160 | −11.637 | −13.926 | 55.555 | 1.00 | 23.13 |
| ATOM | 1501 | CG   | ARG | 160 | −12.539 | −14.448 | 54.449 | 1.00 | 29.15 |
| ATOM | 1502 | CD   | ARG | 160 | −11.737 | −15.149 | 53.364 | 1.00 | 34.59 |
| ATOM | 1503 | NE   | ARG | 160 | −11.157 | −16.394 | 53.856 | 1.00 | 37.25 |
| ATOM | 1504 | HE   | ARG | 160 | −10.278 | −16.359 | 54.280 | 1.00 | 0.00 |
| ATOM | 1505 | CZ   | ARG | 160 | −11.735 | −17.585 | 53.744 | 1.00 | 39.25 |
| ATOM | 1506 | NH1  | ARG | 160 | −12.907 | −17.705 | 53.141 | 1.00 | 40.34 |
| ATOM | 1507 | HH11 | ARG | 160 | −13.373 | −16.903 | 52.774 | 1.00 | 0.00 |
| ATOM | 1508 | HH12 | ARG | 160 | −13.329 | −18.607 | 53.067 | 1.00 | 0.00 |
| ATOM | 1509 | NH2  | ARG | 160 | −11.177 | −18.647 | 54.308 | 1.00 | 43.48 |
| ATOM | 1510 | HH21 | ARG | 160 | −10.326 | −18.543 | 54.826 | 1.00 | 0.00 |
| ATOM | 1511 | HH22 | ARG | 160 | −11.612 | −19.546 | 54.229 | 1.00 | 0.00 |
| ATOM | 1512 | C    | ARG | 160 | −11.407 | −12.697 | 57.711 | 1.00 | 18.50 |
| ATOM | 1513 | O    | ARG | 160 | −10.500 | −13.298 | 58.284 | 1.00 | 17.09 |
| ATOM | 1514 | N    | SEM | 161 | −11.610 | −11.391 | 57.841 | 1.00 | 18.54 |
| ATOM | 1515 | H    | SEM | 161 | −12.394 | −10.969 | 57.430 | 1.00 | 0.00 |
| ATOM | 1516 | CA   | SEM | 161 | −10.746 | −10.550 | 58.651 | 1.00 | 16.58 |
| ATOM | 1517 | CB   | SEM | 161 | −10.814 | −9.109  | 58.146 | 1.00 | 18.99 |
| ATOM | 1518 | CG   | SEM | 161 | −10.507 | −8.961  | 56.669 | 1.00 | 21.84 |
| ATOM | 1519 | A    | SEM | 161 | −8.831  | −9.824  | 56.217 | 1.00 | 39.69 |
| ATOM | 1520 | CE   | SEM | 161 | −7.469  | −8.584  | 56.687 | 1.00 | 28.84 |
| ATOM | 1521 | C    | SEM | 161 | −11.119 | −10.620 | 60.125 | 1.00 | 15.27 |
| ATOM | 1522 | O    | SEM | 161 | −12.299 | −10.641 | 60.470 | 1.00 | 13.98 |
| ATOM | 1523 | N    | SEM | 161 | −10.111 | −10.624 | 61.018 | 1.00 | 15.37 |
| ATOM | 1524 | CD   | PRO | 162 | −8.671  | −10.585 | 60.713 | 1.00 | 16.16 |
| ATOM | 1525 | CA   | PRO | 162 | −10.329 | −10.689 | 62.467 | 1.00 | 15.23 |
| ATOM | 1526 | CB   | PRO | 162 | −8.905  | −10.745 | 63.027 | 1.00 | 15.71 |
| ATOM | 1527 | CG   | PRO | 162 | −8.091  | −10.035 | 61.988 | 1.00 | 15.90 |
| ATOM | 1528 | C    | PRO | 162 | −11.121 | −9.514  | 63.039 | 1.00 | 16.06 |
| ATOM | 1529 | O    | PRO | 162 | −11.734 | −9.640  | 64.096 | 1.00 | 15.21 |
| ATOM | 1530 | N    | TRP | 163 | −11.106 | −8.375  | 62.348 | 1.00 | 14.60 |
| ATOM | 1531 | H    | TRP | 163 | −10.610 | −8.340  | 61.509 | 1.00 | 0.00 |
| ATOM | 1532 | CA   | TRP | 163 | −11.833 | −7.199  | 62.813 | 1.00 | 10.63 |
| ATOM | 1533 | CB   | TRP | 163 | −11.211 | −5.906  | 62.271 | 1.00 | 9.82 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1534 | CG | TRP | 163 | −10.807 | −5.919 | 60.808 | 1.00 | 8.73 |
| ATOM | 1535 | CD2 | TRP | 163 | −11.667 | −5.754 | 59.667 | 1.00 | 4.19 |
| ATOM | 1536 | CE2 | TRP | 163 | −10.843 | −5.739 | 58.523 | 1.00 | 5.73 |
| ATOM | 1537 | CE3 | TRP | 163 | −13.049 | −5.616 | 59.503 | 1.00 | 7.68 |
| ATOM | 1538 | CD1 | TRP | 163 | −9.538 | −6.002 | 60.317 | 1.00 | 7.09 |
| ATOM | 1539 | NE1 | TRP | 163 | −9.550 | −5.890 | 58.946 | 1.00 | 7.80 |
| ATOM | 1540 | HE1 | TRP | 163 | −8.747 | −5.895 | 58.372 | 1.00 | 0.00 |
| ATOM | 1541 | CZ2 | TRP | 163 | −11.356 | −5.586 | 57.236 | 1.00 | 3.92 |
| ATOM | 1542 | CZ3 | TRP | 163 | −13.559 | −5.465 | 58.222 | 1.00 | 6.08 |
| ATOM | 1543 | CH2 | TRP | 163 | −12.713 | −5.453 | 57.106 | 1.00 | 6.60 |
| ATOM | 1544 | C | TRP | 163 | −13.333 | −7.236 | 62.546 | 1.00 | 10.74 |
| ATOM | 1545 | O | TRP | 163 | −14.068 | −6.410 | 63.069 | 1.00 | 11.52 |
| ATOM | 1546 | N | TYR | 164 | −13.798 | −8.207 | 61.764 | 1.00 | 12.03 |
| ATOM | 1547 | H | TYR | 164 | −13.212 | −8.893 | 61.386 | 1.00 | 0.00 |
| ATOM | 1548 | CA | TYR | 164 | −15.225 | −8.321 | 61.471 | 1.00 | 11.28 |
| ATOM | 1549 | CB | TYR | 164 | −15.458 | −8.736 | 60.021 | 1.00 | 10.37 |
| ATOM | 1550 | CG | TYR | 164 | −16.922 | −8.793 | 59.634 | 1.00 | 8.61 |
| ATOM | 1551 | CD1 | TYR | 164 | −17.645 | −7.631 | 59.372 | 1.00 | 6.05 |
| ATOM | 1552 | CE1 | TYR | 164 | −18.986 | −7.687 | 59.010 | 1.00 | 5.19 |
| ATOM | 1553 | CD2 | TYR | 164 | −17.583 | −10.013 | 59.523 | 1.00 | 8.20 |
| ATOM | 1554 | CE2 | TYR | 164 | −18.919 | −10.074 | 59.160 | 1.00 | 9.10 |
| ATOM | 1555 | CZ | TYR | 164 | −19.609 | −8.913 | 58.904 | 1.00 | 6.35 |
| ATOM | 1556 | OH | TYR | 164 | −20.920 | −8.989 | 58.504 | 1.00 | 15.30 |
| ATOM | 1557 | HH | TYR | 164 | −21.280 | −8.115 | 58.337 | 1.00 | 0.00 |
| ATOM | 1558 | C | TYR | 164 | −15.910 | −9.319 | 62.406 | 1.00 | 14.40 |
| ATOM | 1559 | O | TYR | 164 | −15.454 | −10.456 | 62.564 | 1.00 | 11.39 |
| ATOM | 1560 | N | HIS | 165 | −17.014 | −8.887 | 63.016 | 1.00 | 15.72 |
| ATOM | 1561 | H | HIS | 165 | −17.347 | −7.989 | 62.813 | 1.00 | 0.00 |
| ATOM | 1562 | CA | HIS | 165 | −17.769 | −9.724 | 63.945 | 1.00 | 15.88 |
| ATOM | 1563 | CB | HIS | 165 | −17.824 | −9.061 | 65.328 | 1.00 | 14.50 |
| ATOM | 1564 | CG | HIS | 165 | −16.476 | −8.812 | 65.939 | 1.00 | 13.27 |
| ATOM | 1565 | CD2 | HIS | 165 | −15.393 | −8.142 | 65.472 | 1.00 | 13.68 |
| ATOM | 1566 | ND1 | HIS | 165 | −16.117 | −9.296 | 67.181 | 1.00 | 13.92 |
| ATOM | 1567 | HD1 | HIS | 165 | −16.644 | −9.884 | 67.761 | 1.00 | 0.00 |
| ATOM | 1568 | CE1 | HIS | 165 | −14.872 | −8.937 | 67.448 | 1.00 | 9.42 |
| ATOM | 1569 | NE2 | HIS | 165 | −14.413 | −8.240 | 66.431 | 1.00 | 9.18 |
| ATOM | 1570 | HE2 | HIS | 165 | −13.496 | −7.895 | 66.349 | 1.00 | 0.00 |
| ATOM | 1571 | C | HIS | 165 | −19.170 | −9.952 | 63.382 | 1.00 | 18.23 |
| ATOM | 1572 | O | HIS | 165 | −19.962 | −9.017 | 63.273 | 1.00 | 19.85 |
| ATOM | 1573 | N | SER | 166 | −19.451 | −11.201 | 63.014 | 1.00 | 20.28 |
| ATOM | 1574 | H | SER | 166 | −18.770 | −11.903 | 63.124 | 1.00 | 0.00 |
| ATOM | 1575 | CA | SER | 166 | −20.723 | −11.619 | 62.420 | 1.00 | 21.65 |
| ATOM | 1576 | CB | SER | 166 | −20.708 | −13.130 | 62.191 | 1.00 | 20.69 |
| ATOM | 1577 | OG | SER | 166 | −19.443 | −13.555 | 61.714 | 1.00 | 32.02 |
| ATOM | 1578 | HG | SER | 166 | −19.263 | −13.122 | 60.873 | 1.00 | 0.00 |
| ATOM | 1579 | C | SER | 166 | −21.985 | −11.260 | 63.197 | 1.00 | 22.80 |
| ATOM | 1580 | O | SER | 166 | −23.005 | −10.924 | 62.597 | 1.00 | 23.80 |
| ATOM | 1581 | N | SER | 167 | −21.944 | −11.424 | 64.515 | 1.00 | 24.13 |
| ATOM | 1582 | H | SER | 167 | −21.139 | −11.759 | 64.954 | 1.00 | 0.00 |
| ATOM | 1583 | CA | SER | 167 | −23.089 | −11.117 | 65.364 | 1.00 | 26.47 |
| ATOM | 1584 | CB | SER | 167 | −23.831 | −12.391 | 65.775 | 1.00 | 26.47 |
| ATOM | 1585 | OG | SER | 167 | −24.476 | −12.991 | 64.664 | 1.00 | 33.37 |
| ATOM | 1586 | HG | SER | 167 | −25.120 | −13.631 | 64.981 | 1.00 | 0.00 |
| ATOM | 1587 | C | SER | 167 | −22.598 | −10.401 | 66.599 | 1.00 | 26.39 |
| ATOM | 1588 | O | SER | 167 | −22.019 | −11.016 | 67.492 | 1.00 | 31.31 |
| ATOM | 1589 | N | LEU | 168 | −22.788 | −9.089 | 66.616 | 1.00 | 25.40 |
| ATOM | 1590 | H | LEU | 168 | −23.244 | −8.656 | 65.859 | 1.00 | 0.00 |
| ATOM | 1591 | CA | LEU | 168 | −22.378 | −8.254 | 67.731 | 1.00 | 21.28 |
| ATOM | 1592 | CB | LEU | 168 | −20.975 | −7.692 | 67.514 | 1.00 | 19.91 |
| ATOM | 1593 | CG | LEU | 168 | −19.787 | −8.250 | 68.290 | 1.00 | 19.49 |
| ATOM | 1594 | CD1 | LEU | 168 | −18.688 | −7.208 | 68.269 | 1.00 | 17.54 |
| ATOM | 1595 | CD2 | LEU | 168 | −20.165 | −8.547 | 69.717 | 1.00 | 20.20 |
| ATOM | 1596 | C | LEU | 168 | −23.338 | −7.096 | 67.799 | 1.00 | 20.38 |
| ATOM | 1597 | O | LEU | 168 | −23.574 | −6.420 | 66.797 | 1.00 | 23.06 |
| ATOM | 1598 | N | THR | 169 | −23.935 | −6.897 | 68.961 | 1.00 | 18.27 |
| ATOM | 1599 | H | THR | 169 | −23.739 | −7.470 | 69.729 | 1.00 | 0.00 |
| ATOM | 1600 | CA | THR | 169 | −24.846 | −5.788 | 69.138 | 1.00 | 14.78 |
| ATOM | 1601 | CB | THR | 169 | −25.898 | −6.091 | 70.224 | 1.00 | 17.59 |
| ATOM | 1602 | OG1 | THR | 169 | −25.244 | −6.312 | 71.482 | 1.00 | 16.95 |
| ATOM | 1603 | HG1 | THR | 169 | −25.904 | −6.666 | 72.097 | 1.00 | 0.00 |
| ATOM | 1604 | CG2 | THR | 169 | −26.709 | −7.327 | 69.854 | 1.00 | 18.12 |
| ATOM | 1605 | C | THR | 169 | −23.962 | −4.647 | 69.612 | 1.00 | 14.12 |
| ATOM | 1606 | O | THR | 169 | −22.784 | −4.853 | 69.918 | 1.00 | 13.47 |

TABLE 22-continued

Coordinates for the 3D structure of ZAP-NCζ2*

REMARK FILENAME="tm1-zeta2-wat1-slow.pdb"
REMARK TOPH19.pep -MACRO for protein sequence
created by user: marcos

| ATOM | 1607 | N    | ARG | 170 | −24.532 | −3.453 | 69.683 | 1.00 | 13.49 |
|------|------|------|-----|-----|---------|--------|--------|------|-------|
| ATOM | 1608 | H    | ARG | 170 | −25.461 | −3.362 | 69.374 | 1.00 | 0.00  |
| ATOM | 1609 | CA   | ARG | 170 | −23.819 | −2.271 | 70.142 | 1.00 | 12.83 |
| ATOM | 1610 | CB   | ARG | 170 | −24.768 | −1.075 | 70.111 | 1.00 | 9.01  |
| ATOM | 1611 | CG   | ARG | 170 | −24.200 | 0.203  | 70.663 | 1.00 | 7.72  |
| ATOM | 1612 | CD   | ARG | 170 | −25.258 | 1.271  | 70.649 | 1.00 | 7.48  |
| ATOM | 1613 | NE   | ARG | 170 | −24.693 | 2.587  | 70.897 | 1.00 | 9.76  |
| ATOM | 1614 | HE   | ARG | 170 | −24.435 | 2.810  | 71.815 | 1.00 | 0.00  |
| ATOM | 1615 | CZ   | ARG | 170 | −24.515 | 3.512  | 69.962 | 1.00 | 9.38  |
| ATOM | 1616 | NH1  | ARG | 170 | −23.989 | 4.681  | 70.290 | 1.00 | 8.60  |
| ATOM | 1617 | HH11 | ARG | 170 | −23.732 | 4.855  | 71.242 | 1.00 | 0.00  |
| ATOM | 1618 | HH12 | ARG | 170 | −23.839 | 5.384  | 69.600 | 1.00 | 0.00  |
| ATOM | 1619 | NH2  | ARG | 170 | −24.872 | 3.277  | 68.705 | 1.00 | 6.68  |
| ATOM | 1620 | HH21 | ARG | 170 | −25.304 | 2.407  | 68.477 | 1.00 | 0.00  |
| ATOM | 1621 | HH22 | ARG | 170 | −24.748 | 3.982  | 68.003 | 1.00 | 0.00  |
| ATOM | 1622 | C    | ARG | 170 | −23.295 | −2.478 | 71.564 | 1.00 | 14.22 |
| ATOM | 1623 | O    | ARG | 170 | −22.162 | −2.113 | 71.876 | 1.00 | 15.95 |
| ATOM | 1624 | N    | GLU | 171 | −24.133 | −3.044 | 72.425 | 1.00 | 16.49 |
| ATOM | 1625 | H    | GLU | 171 | −25.006 | −3.316 | 72.108 | 1.00 | 0.00  |
| ATOM | 1626 | CA   | GLU | 171 | −23.764 | −3.294 | 73.815 | 1.00 | 18.76 |
| ATOM | 1627 | CB   | GLU | 171 | −24.946 | −3.879 | 74.596 | 1.00 | 23.85 |
| ATOM | 1628 | CG   | GLU | 171 | −26.031 | −2.873 | 74.999 | 1.00 | 33.82 |
| ATOM | 1629 | CD   | GLU | 171 | −26.910 | −2.398 | 73.838 | 1.00 | 38.04 |
| ATOM | 1630 | OE1  | GLU | 171 | −27.491 | −1.288 | 73.952 | 1.00 | 36.00 |
| ATOM | 1631 | OE2  | GLU | 171 | −27.034 | −3.132 | 72.826 | 1.00 | 37.18 |
| ATOM | 1632 | C    | GLU | 171 | −22.584 | −4.249 | 73.900 | 1.00 | 17.67 |
| ATOM | 1633 | O    | GLU | 171 | −21.632 | −4.009 | 74.645 | 1.00 | 17.85 |
| ATOM | 1634 | N    | GLU | 172 | −22.660 | −5.331 | 73.130 | 1.00 | 17.32 |
| ATOM | 1635 | H    | GLU | 172 | −23.444 | −5.443 | 72.559 | 1.00 | 0.00  |
| ATOM | 1636 | CA   | GLU | 172 | −21.606 | −6.340 | 73.090 | 1.00 | 15.02 |
| ATOM | 1637 | CB   | GLU | 172 | −22.061 | −7.542 | 72.267 | 1.00 | 15.64 |
| ATOM | 1638 | CG   | GLU | 172 | −23.194 | −8.329 | 72.899 | 1.00 | 19.91 |
| ATOM | 1639 | CD   | GLU | 172 | −23.906 | −9.255 | 71.918 | 1.00 | 25.18 |
| ATOM | 1640 | OE1  | GLU | 172 | −25.002 | −9.751 | 72.253 | 1.00 | 30.20 |
| ATOM | 1641 | OE2  | GLU | 172 | −23.390 | −9.481 | 70.804 | 1.00 | 27.42 |
| ATOM | 1642 | C    | GLU | 172 | −20.315 | −5.764 | 72.519 | 1.00 | 14.37 |
| ATOM | 1643 | O    | GLU | 172 | −19.221 | −6.107 | 72.970 | 1.00 | 15.38 |
| ATOM | 1644 | N    | ALA | 173 | −20.443 | −4.888 | 71.527 | 1.00 | 12.66 |
| ATOM | 1645 | H    | ALA | 173 | −21.328 | −4.667 | 71.181 | 1.00 | 0.00  |
| ATOM | 1646 | CA   | ALA | 173 | −19.282 | −4.250 | 70.913 | 1.00 | 10.27 |
| ATOM | 1647 | CB   | ALA | 173 | −19.709 | −3.376 | 69.747 | 1.00 | 9.98  |
| ATOM | 1648 | C    | ALA | 173 | −18.551 | −3.415 | 71.953 | 1.00 | 9.42  |
| ATOM | 1649 | O    | ALA | 173 | −17.339 | −3.527 | 72.102 | 1.00 | 10.18 |
| ATOM | 1650 | N    | GLU | 174 | −19.295 | −2.599 | 72.694 | 1.00 | 11.48 |
| ATOM | 1651 | H    | GLU | 174 | −20.266 | −2.557 | 72.540 | 1.00 | 0.00  |
| ATOM | 1652 | CA   | GLU | 174 | −18.697 | −1.761 | 73.725 | 1.00 | 11.44 |
| ATOM | 1653 | CB   | GLU | 174 | −19.727 | −0.810 | 74.322 | 1.00 | 10.86 |
| ATOM | 1654 | CG   | GLU | 174 | −20.082 | 0.331  | 73.398 | 1.00 | 13.06 |
| ATOM | 1655 | CD   | GLU | 174 | −20.959 | 1.383  | 74.050 | 1.00 | 15.17 |
| ATOM | 1656 | OE1  | GLU | 174 | −20.984 | 1.474  | 75.297 | 1.00 | 14.77 |
| ATOM | 1657 | OE2  | GLU | 174 | −21.622 | 2.132  | 73.306 | 1.00 | 15.98 |
| ATOM | 1658 | C    | GLU | 174 | −18.061 | −2.589 | 74.824 | 1.00 | 11.55 |
| ATOM | 1659 | O    | GLU | 174 | −17.005 | −2.237 | 75.345 | 1.00 | 15.49 |
| ATOM | 1660 | N    | ARG | 175 | −18.707 | −3.684 | 75.194 | 1.00 | 13.21 |
| ATOM | 1661 | H    | ARG | 175 | −19.572 | −3.890 | 74.766 | 1.00 | 0.00  |
| ATOM | 1662 | CA   | ARG | 175 | −18.169 | −4.550 | 76.232 | 1.00 | 15.31 |
| ATOM | 1663 | CB   | ARG | 175 | −19.136 | −5.693 | 76.514 | 1.00 | 16.15 |
| ATOM | 1664 | CG   | ARG | 175 | −18.747 | −6.564 | 77.685 | 1.00 | 24.24 |
| ATOM | 1665 | CD   | ARG | 175 | −19.658 | −7.776 | 77.764 | 1.00 | 31.62 |
| ATOM | 1666 | NE   | ARG | 175 | −21.073 | −7.405 | 77.758 | 1.00 | 38.21 |
| ATOM | 1667 | HE   | ARG | 175 | −21.507 | −7.272 | 76.885 | 1.00 | 0.00  |
| ATOM | 1668 | CZ   | ARG | 175 | −21.813 | −7.241 | 78.852 | 1.00 | 43.81 |
| ATOM | 1669 | NH1  | ARG | 175 | −21.276 | −7.421 | 80.056 | 1.00 | 42.92 |
| ATOM | 1670 | HH11 | ARG | 175 | −20.313 | −7.677 | 80.134 | 1.00 | 0.00  |
| ATOM | 1671 | HH12 | ARG | 175 | −21.827 | −7.290 | 80.881 | 1.00 | 0.00  |
| ATOM | 1672 | NH2  | ARG | 175 | −23.087 | −6.869 | 78.741 | 1.00 | 45.14 |
| ATOM | 1673 | HH21 | ARG | 175 | −23.483 | −6.719 | 77.836 | 1.00 | 0.00  |
| ATOM | 1674 | HH22 | ARG | 175 | −23.645 | −6.731 | 79.561 | 1.00 | 0.00  |
| ATOM | 1675 | C    | ARG | 175 | −16.808 | −5.102 | 75.808 | 1.00 | 15.70 |
| ATOM | 1676 | O    | ARG | 175 | −15.875 | −5.124 | 76.606 | 1.00 | 14.24 |
| ATOM | 1677 | N    | LYS | 176 | −16.691 | −5.522 | 74.550 | 1.00 | 15.99 |
| ATOM | 1678 | H    | LYS | 176 | −17.474 | −5.464 | 73.956 | 1.00 | 0.00  |
| ATOM | 1679 | CA   | LYS | 176 | −15.432 | −6.061 | 74.031 | 1.00 | 18.88 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1680 | CB | LYS | 176 | −15.643 | −6.727 | 72.672 | 1.00 | 20.03 |
|---|---|---|---|---|---|---|---|---|---|
| ATOM | 1681 | CG | LYS | 176 | −16.324 | −8.074 | 72.733 | 1.00 | 24.38 |
| ATOM | 1682 | CD | LYS | 176 | −16.319 | −8.737 | 71.365 | 1.00 | 28.28 |
| ATOM | 1683 | CE | LYS | 176 | −16.972 | −10.118 | 71.402 | 1.00 | 32.74 |
| ATOM | 1684 | NZ | LYS | 176 | −16.224 | −11.112 | 72.229 | 1.00 | 33.50 |
| ATOM | 1685 | HZ1 | LYS | 176 | −16.180 | −10.765 | 73.210 | 1.00 | 0.00 |
| ATOM | 1686 | HZ2 | LYS | 176 | −15.257 | −11.220 | 71.853 | 1.00 | 0.00 |
| ATOM | 1687 | HZ3 | LYS | 176 | −16.712 | −12.029 | 72.190 | 1.00 | 0.00 |
| ATOM | 1688 | C | LYS | 176 | −14.336 | −5.002 | 73.903 | 1.00 | 19.37 |
| ATOM | 1689 | O | LYS | 176 | −13.164 | −5.275 | 74.164 | 1.00 | 20.28 |
| ATOM | 1690 | N | LEU | 177 | −14.722 | −3.799 | 73.490 | 1.00 | 16.82 |
| ATOM | 1691 | H | LEU | 177 | −15.661 | −3.666 | 73.244 | 1.00 | 0.00 |
| ATOM | 1692 | CA | LEU | 177 | −13.776 | −2.704 | 73.325 | 1.00 | 15.13 |
| ATOM | 1693 | CB | LEU | 177 | −14.379 | −1.617 | 72.428 | 1.00 | 13.20 |
| ATOM | 1694 | CG | LEU | 177 | −14.633 | −2.023 | 70.973 | 1.00 | 11.03 |
| ATOM | 1695 | CD1 | LEU | 177 | −15.280 | −0.876 | 70.229 | 1.00 | 8.85 |
| ATOM | 1696 | CD2 | LEU | 177 | −13.329 | −2.429 | 70.302 | 1.00 | 5.60 |
| ATOM | 1697 | C | LEU | 177 | −13.315 | −2.111 | 74.654 | 1.00 | 16.41 |
| ATOM | 1698 | O | LEU | 177 | −12.157 | −1.730 | 74.800 | 1.00 | 16.11 |
| ATOM | 1699 | N | TYR | 178 | −14.227 | −2.014 | 75.615 | 1.00 | 17.85 |
| ATOM | 1700 | H | TYR | 178 | −15.136 | −2.325 | 75.444 | 1.00 | 0.00 |
| ATOM | 1701 | CA | TYR | 178 | −13.900 | −1.471 | 76.929 | 1.00 | 19.30 |
| ATOM | 1702 | CB | TYR | 178 | −15.174 | −1.068 | 77.676 | 1.00 | 15.30 |
| ATOM | 1703 | CG | TYR | 178 | −15.706 | 0.301 | 77.313 | 1.00 | 11.87 |
| ATOM | 1704 | CD1 | TYR | 178 | −14.866 | 1.413 | 77.301 | 1.00 | 9.08 |
| ATOM | 1705 | CE1 | TYR | 178 | −15.356 | 2.681 | 77.014 | 1.00 | 8.80 |
| ATOM | 1706 | CD2 | TYR | 178 | −17.051 | 0.493 | 77.023 | 1.00 | 8.22 |
| ATOM | 1707 | CE2 | TYR | 178 | −17.549 | 1.756 | 76.736 | 1.00 | 8.10 |
| ATOM | 1708 | CZ | TYR | 178 | −16.696 | 2.846 | 76.734 | 1.00 | 10.05 |
| ATOM | 1709 | OH | TYR | 178 | −17.183 | 4.110 | 76.465 | 1.00 | 12.49 |
| ATOM | 1710 | HH | TYR | 178 | −18.142 | 4.016 | 76.455 | 1.00 | 0.00 |
| ATOM | 1711 | C | TYR | 178 | −13.135 | −2.494 | 77.752 | 1.00 | 22.26 |
| ATOM | 1712 | O | TYR | 178 | −12.287 | −2.148 | 78.572 | 1.00 | 22.67 |
| ATOM | 1713 | N | SER | 179 | −13.432 | −3.764 | 77.514 | 1.00 | 28.96 |
| ATOM | 1714 | H | SER | 179 | −14.082 | −4.002 | 76.825 | 1.00 | 0.00 |
| ATOM | 1715 | CA | SER | 179 | −12.791 | −4.850 | 78.237 | 1.00 | 32.67 |
| ATOM | 1716 | CB | SER | 179 | −13.775 | −6.013 | 78.416 | 1.00 | 34.27 |
| ATOM | 1717 | OG | SER | 179 | −14.956 | −5.590 | 79.095 | 1.00 | 32.95 |
| ATOM | 1718 | HG | SER | 179 | −15.462 | −5.097 | 78.445 | 1.00 | 0.00 |
| ATOM | 1719 | C | SER | 179 | −11.518 | −5.320 | 77.544 | 1.00 | 34.73 |
| ATOM | 1720 | O | SER | 179 | −11.467 | −6.416 | 76.994 | 1.00 | 37.10 |
| ATOM | 1721 | N | GLY | 180 | −10.490 | −4.483 | 77.578 | 1.00 | 37.24 |
| ATOM | 1722 | H | GLY | 180 | −10.577 | −3.618 | 78.040 | 1.00 | 0.00 |
| ATOM | 1723 | CA | GLY | 180 | −9.230 | −4.834 | 76.951 | 1.00 | 39.63 |
| ATOM | 1724 | C | GLY | 180 | −8.163 | −3.809 | 77.266 | 1.00 | 41.09 |
| ATOM | 1725 | O | GLY | 180 | −8.217 | −3.151 | 78.305 | 1.00 | 41.30 |
| ATOM | 1726 | N | ALA | 181 | −7.201 | −3.659 | 76.361 | 1.00 | 43.10 |
| ATOM | 1727 | H | ALA | 181 | −7.216 | −4.226 | 75.564 | 1.00 | 0.00 |
| ATOM | 1728 | CA | ALA | 181 | −6.116 | −2.699 | 76.541 | 1.00 | 43.62 |
| ATOM | 1729 | CB | ALA | 181 | −5.003 | −2.975 | 75.547 | 1.00 | 44.37 |
| ATOM | 1730 | C | ALA | 181 | −6.608 | −1.261 | 76.393 | 1.00 | 44.60 |
| ATOM | 1731 | O | ALA | 181 | −5.962 | −0.327 | 76.865 | 1.00 | 47.43 |
| ATOM | 1732 | N | GLN | 182 | −7.749 | −1.091 | 75.731 | 1.00 | 42.79 |
| ATOM | 1733 | H | GLN | 182 | −8.217 | −1.875 | 75.390 | 1.00 | 0.00 |
| ATOM | 1734 | CA | GLN | 182 | −8.339 | 0.229 | 75.516 | 1.00 | 41.06 |
| ATOM | 1735 | CB | GLN | 182 | −8.819 | 0.840 | 76.837 | 1.00 | 40.78 |
| ATOM | 1736 | CG | GLN | 182 | −10.005 | 0.113 | 77.453 | 1.00 | 42.40 |
| ATOM | 1737 | CD | GLN | 182 | −10.574 | 0.836 | 78.661 | 1.00 | 45.06 |
| ATOM | 1738 | OE1 | GLN | 182 | −10.583 | 2.069 | 78.717 | 1.00 | 45.31 |
| ATOM | 1739 | NE2 | GLN | 182 | −11.067 | 0.075 | 79.626 | 1.00 | 44.73 |
| ATOM | 1740 | HE21 | GLN | 182 | −11.050 | −0.897 | 79.502 | 1.00 | 0.00 |
| ATOM | 1741 | HE22 | GLN | 182 | −11.427 | 0.496 | 80.437 | 1.00 | 0.00 |
| ATOM | 1742 | C | GLN | 182 | −7.405 | 1.189 | 74.784 | 1.00 | 39.41 |
| ATOM | 1743 | O | GLN | 182 | −7.449 | 2.406 | 74.994 | 1.00 | 39.06 |
| ATOM | 1744 | N | GLN | 182 | −6.580 | 0.625 | 73.908 | 1.00 | 38.44 |
| ATOM | 1745 | H | THR | 183 | −6.587 | −0.340 | 73.784 | 1.00 | 0.00 |
| ATOM | 1746 | CA | THR | 183 | −5.632 | 1.390 | 73.109 | 1.00 | 35.60 |
| ATOM | 1747 | CB | THR | 183 | −4.702 | 0.455 | 72.333 | 1.00 | 37.11 |
| ATOM | 1748 | OG1 | THR | 183 | −4.298 | −0.628 | 73.180 | 1.00 | 40.31 |
| ATOM | 1749 | HG1 | THR | 183 | −3.583 | −1.085 | 72.722 | 1.00 | 0.00 |
| ATOM | 1750 | CG2 | THR | 183 | −3.477 | 1.212 | 71.842 | 1.00 | 38.58 |
| ATOM | 1751 | C | THR | 183 | −6.398 | 2.212 | 72.081 | 1.00 | 32.82 |
| ATOM | 1752 | O | THR | 183 | −7.365 | 1.725 | 71.485 | 1.00 | 30.53 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1753 | N | ASP | 184 | −5.957 | 3.444 | 71.856 | 1.00 | 29.67 |
|---|---|---|---|---|---|---|---|---|---|
| ATOM | 1754 | H | ASP | 184 | −5.161 | 3.761 | 72.327 | 1.00 | 0.00 |
| ATOM | 1755 | CA | ASP | 184 | −6.616 | 4.312 | 70.889 | 1.00 | 27.05 |
| ATOM | 1756 | CB | ASP | 184 | −5.947 | 5.693 | 70.862 | 1.00 | 28.47 |
| ATOM | 1757 | CG | ASP | 184 | −6.205 | 6.506 | 72.126 | 1.00 | 30.50 |
| ATOM | 1758 | OD1 | ASP | 184 | −5.410 | 7.432 | 72.391 | 1.00 | 32.80 |
| ATOM | 1759 | OD2 | ASP | 184 | −7.198 | 6.244 | 72.844 | 1.00 | 29.45 |
| ATOM | 1760 | C | ASP | 184 | −6.582 | 3.679 | 69.495 | 1.00 | 24.36 |
| ATOM | 1761 | O | ASP | 184 | −5.569 | 3.109 | 69.089 | 1.00 | 21.86 |
| ATOM | 1762 | N | GLY | 185 | −7.707 | 3.752 | 68.790 | 1.00 | 20.06 |
| ATOM | 1763 | H | GLY | 185 | −8.508 | 4.173 | 69.171 | 1.00 | 0.00 |
| ATOM | 1764 | CA | GLY | 185 | −7.784 | 3.190 | 67.458 | 1.00 | 16.45 |
| ATOM | 1765 | C | GLY | 185 | −8.218 | 1.737 | 67.404 | 1.00 | 13.20 |
| ATOM | 1766 | O | GLY | 185 | −8.296 | 1.173 | 66.318 | 1.00 | 14.03 |
| ATOM | 1767 | N | LYS | 186 | −8.438 | 1.111 | 68.557 | 1.00 | 13.12 |
| ATOM | 1768 | H | LYS | 186 | −8.274 | 1.583 | 69.398 | 1.00 | 0.00 |
| ATOM | 1769 | CA | LYS | 186 | −8.888 | −0.282 | 68.606 | 1.00 | 13.63 |
| ATOM | 1770 | CB | LYS | 186 | −8.986 | −0.748 | 70.057 | 1.00 | 17.81 |
| ATOM | 1771 | CG | LYS | 186 | −8.738 | −2.226 | 70.287 | 1.00 | 22.20 |
| ATOM | 1772 | CD | LYS | 186 | −7.246 | −2.526 | 70.257 | 1.00 | 30.53 |
| ATOM | 1773 | CE | LYS | 186 | −6.949 | −3.956 | 70.685 | 1.00 | 34.36 |
| ATOM | 1774 | NZ | LYS | 186 | −5.493 | −4.283 | 70.606 | 1.00 | 33.77 |
| ATOM | 1775 | HZ1 | LYS | 186 | −4.967 | −3.644 | 71.232 | 1.00 | 0.00 |
| ATOM | 1776 | HZ2 | LYS | 186 | −5.150 | −4.182 | 69.632 | 1.00 | 0.00 |
| ATOM | 1777 | HZ3 | LYS | 186 | −5.356 | −5.264 | 70.919 | 1.00 | 0.00 |
| ATOM | 1778 | C | LYS | 186 | −10.282 | −0.245 | 67.980 | 1.00 | 10.77 |
| ATOM | 1779 | O | LYS | 186 | −11.107 | 0.573 | 68.376 | 1.00 | 10.89 |
| ATOM | 1780 | N | PHE | 187 | −10.563 | −1.139 | 67.038 | 1.00 | 9.58 |
| ATOM | 1781 | H | PHE | 187 | −9.906 | −1.827 | 66.789 | 1.00 | 0.00 |
| ATOM | 1782 | CA | PHE | 187 | −11.849 | −1.114 | 66.354 | 1.00 | 5.69 |
| ATOM | 1783 | CB | PHE | 187 | −11.718 | −0.276 | 65.066 | 1.00 | 6.05 |
| ATOM | 1784 | CG | PHE | 187 | −10.985 | −0.991 | 63.949 | 1.00 | 6.66 |
| ATOM | 1785 | CD1 | PHE | 187 | −11.684 | −1.540 | 62.876 | 1.00 | 5.77 |
| ATOM | 1786 | CD2 | PHE | 187 | −9.600 | −1.149 | 63.991 | 1.00 | 7.01 |
| ATOM | 1787 | CE1 | PHE | 187 | −11.022 | −2.240 | 61.868 | 1.00 | 6.32 |
| ATOM | 1788 | CE2 | PHE | 187 | −8.926 | −1.853 | 62.978 | 1.00 | 6.92 |
| ATOM | 1789 | CZ | PHE | 187 | −9.640 | −2.397 | 61.919 | 1.00 | 5.13 |
| ATOM | 1790 | C | PHE | 187 | −12.368 | −2.485 | 65.962 | 1.00 | 6.09 |
| ATOM | 1791 | O | PHE | 187 | −11.659 | −3.482 | 66.040 | 1.00 | 6.46 |
| ATOM | 1792 | N | LEU | 188 | −13.612 | −2.506 | 65.502 | 1.00 | 4.37 |
| ATOM | 1793 | H | LEU | 188 | −14.139 | −1.682 | 65.510 | 1.00 | 0.00 |
| ATOM | 1794 | CA | LEU | 188 | −14.253 | −3.711 | 65.018 | 1.00 | 4.97 |
| ATOM | 1795 | CB | LEU | 188 | −14.849 | −4.529 | 66.164 | 1.00 | 8.12 |
| ATOM | 1796 | CG | LEU | 188 | −15.937 | −3.971 | 67.079 | 1.00 | 6.99 |
| ATOM | 1797 | CD1 | LEU | 188 | −17.293 | −3.940 | 66.382 | 1.00 | 4.98 |
| ATOM | 1798 | CD2 | LEU | 188 | −16.005 | −4.869 | 68.296 | 1.00 | 9.58 |
| ATOM | 1799 | C | LEU | 188 | −15.328 | −3.269 | 64.044 | 1.00 | 4.81 |
| ATOM | 1800 | O | LEU | 188 | −15.705 | −2.099 | 64.021 | 1.00 | 7.29 |
| ATOM | 1801 | N | LEU | 189 | −15.776 | −4.185 | 63.201 | 1.00 | 4.31 |
| ATOM | 1802 | H | LEU | 189 | −15.415 | −5.099 | 63.217 | 1.00 | 0.00 |
| ATOM | 1803 | CA | LEU | 189 | −16.816 | −3.887 | 62.234 | 1.00 | 6.28 |
| ATOM | 1804 | CB | LEU | 189 | −16.289 | −3.999 | 60.806 | 1.00 | 6.37 |
| ATOM | 1805 | CG | LEU | 189 | −17.305 | −3.588 | 59.747 | 1.00 | 9.47 |
| ATOM | 1806 | CD1 | LEU | 189 | −17.422 | −2.078 | 59.738 | 1.00 | 13.86 |
| ATOM | 1807 | CD2 | LEU | 188 | −16.874 | −4.083 | 58.383 | 1.00 | 14.76 |
| ATOM | 1808 | C | LEU | 188 | −17.892 | −4.921 | 62.468 | 1.00 | 6.49 |
| ATOM | 1809 | O | LEU | 188 | −17.590 | −6.097 | 62.647 | 1.00 | 7.98 |
| ATOM | 1810 | N | ARG | 190 | −19.146 | −4.492 | 62.457 | 1.00 | 7.83 |
| ATOM | 1811 | H | ARG | 190 | −19.341 | −3.547 | 62.290 | 1.00 | 0.00 |
| ATOM | 1812 | CA | ARG | 190 | −20.249 | −5.407 | 62.706 | 1.00 | 8.00 |
| ATOM | 1813 | CB | ARG | 190 | −20.660 | −5.307 | 64.181 | 1.00 | 8.07 |
| ATOM | 1814 | CG | ARG | 190 | −21.012 | −3.879 | 64.610 | 1.00 | 5.07 |
| ATOM | 1815 | CD | ARG | 190 | −21.372 | −3.771 | 66.080 | 1.00 | 9.21 |
| ATOM | 1816 | NE | ARG | 190 | −21.369 | −2.379 | 66.535 | 1.00 | 9.70 |
| ATOM | 1817 | HE | ARG | 190 | −20.510 | −2.002 | 66.808 | 1.00 | 0.00 |
| ATOM | 1818 | CZ | ARG | 190 | −22.446 | −1.603 | 66.618 | 1.00 | 7.61 |
| ATOM | 1819 | NH1 | ARG | 190 | −23.644 | −2.069 | 66.288 | 1.00 | 9.52 |
| ATOM | 1820 | HH11 | ARG | 190 | −23.756 | −3.016 | 65.981 | 1.00 | 0.00 |
| ATOM | 1821 | HH12 | ARG | 190 | −24.437 | −1.466 | 66.366 | 1.00 | 0.00 |
| ATOM | 1822 | NH2 | ARG | 190 | −22.314 | −0.342 | 66.995 | 1.00 | 5.65 |
| ATOM | 1823 | HH21 | ARG | 190 | −21.402 | 0.008 | 67.211 | 1.00 | 0.00 |
| ATOM | 1824 | HH22 | ARG | 190 | −23.111 | 0.252 | 67.069 | 1.00 | 0.00 |
| ATOM | 1825 | C | ARG | 190 | −21.444 | −5.057 | 61.847 | 1.00 | 10.51 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1826 | O    | ARG | 190 | −21.683 | −3.880  | 61.565 | 1.00 | 14.83 |
|------|------|------|-----|-----|---------|---------|--------|------|-------|
| ATOM | 1827 | N    | PRO | 191 | −22.176 | −6.071  | 61.361 | 1.00 | 10.83 |
| ATOM | 1828 | CD   | PRO | 191 | −21.942 | −7.523  | 61.465 | 1.00 | 10.41 |
| ATOM | 1829 | CA   | PRO | 191 | −23.352 | −5.787  | 60.540 | 1.00 | 10.84 |
| ATOM | 1830 | CB   | PRO | 191 | −23.690 | −7.156  | 59.946 | 1.00 | 9.30  |
| ATOM | 1831 | CG   | PRO | 191 | −23.267 | −8.095  | 61.017 | 1.00 | 9.83  |
| ATOM | 1832 | C    | PRO | 191 | −24.462 | −5.298  | 61.471 | 1.00 | 12.64 |
| ATOM | 1833 | O    | PRO | 191 | −24.466 | −5.630  | 62.659 | 1.00 | 15.28 |
| ATOM | 1834 | N    | ARG | 192 | −25.363 | −4.469  | 60.963 | 1.00 | 12.45 |
| ATOM | 1835 | H    | ARG | 192 | −25.336 | −4.180  | 60.025 | 1.00 | 0.00  |
| ATOM | 1836 | CA   | ARG | 192 | −26.454 | −3.983  | 61.787 | 1.00 | 12.10 |
| ATOM | 1837 | CB   | ARG | 192 | −26.689 | −2.491  | 61.575 | 1.00 | 9.12  |
| ATOM | 1838 | CG   | ARG | 192 | −25.592 | −1.606  | 62.105 | 1.00 | 2.40  |
| ATOM | 1839 | CD   | ARG | 192 | −25.878 | −0.148  | 61.810 | 1.00 | 7.40  |
| ATOM | 1840 | NE   | ARG | 192 | −27.001 | 0.383   | 62.583 | 1.00 | 8.66  |
| ATOM | 1841 | HE   | ARG | 192 | −26.904 | 0.465   | 63.553 | 1.00 | 0.00  |
| ATOM | 1842 | CZ   | ARG | 192 | −28.172 | 0.743   | 62.064 | 1.00 | 8.48  |
| ATOM | 1843 | NH1  | ARG | 192 | −28.390 | 0.628   | 60.764 | 1.00 | 11.77 |
| ATOM | 1844 | HH11 | ARG | 192 | −27.658 | 0.282   | 60.181 | 1.00 | 0.00  |
| ATOM | 1845 | HH12 | ARG | 192 | −29.261 | 0.900   | 60.355 | 1.00 | 0.00  |
| ATOM | 1846 | NH2  | ARG | 192 | −29.121 | 1.243   | 62.841 | 1.00 | 11.80 |
| ATOM | 1847 | HH21 | ARG | 192 | −28.968 | 1.357   | 63.822 | 1.00 | 0.00  |
| ATOM | 1848 | HH21 | ARG | 192 | −29.999 | 1.507   | 62.438 | 1.00 | 0.00  |
| ATOM | 1849 | C    | ARG | 192 | −27.708 | −4.761  | 61.449 | 1.00 | 16.67 |
| ATOM | 1850 | O    | ARG | 192 | −27.713 | −5.581  | 60.530 | 1.00 | 16.54 |
| ATOM | 1851 | N    | LYS | 193 | −28.765 | −4.497  | 62.207 | 1.00 | 24.12 |
| ATOM | 1852 | H    | LYS | 193 | −28.664 | −3.846  | 62.939 | 1.00 | 0.00  |
| ATOM | 1853 | CA   | LYS | 193 | −30.052 | −5.154  | 62.021 | 1.00 | 27.69 |
| ATOM | 1854 | CB   | LYS | 193 | −31.054 | −4.605  | 63.040 | 1.00 | 30.58 |
| ATOM | 1855 | CG   | LYS | 193 | −32.442 | −5.207  | 62.954 | 1.00 | 36.83 |
| ATOM | 1856 | CD   | LYS | 193 | −33.390 | −4.538  | 63.950 | 1.00 | 42.21 |
| ATOM | 1857 | CE   | LYS | 193 | −34.851 | −4.902  | 63.677 | 1.00 | 43.76 |
| ATOM | 1858 | NZ   | LYS | 193 | −35.100 | −6.373  | 63.679 | 1.00 | 45.07 |
| ATOM | 1859 | HZ1  | LYS | 193 | −34.800 | −6.768  | 64.593 | 1.00 | 0.00  |
| ATOM | 1860 | HZ2  | LYS | 193 | −34.562 | −6.822  | 62.914 | 1.00 | 0.00  |
| ATOM | 1861 | HZ3  | LYS | 193 | −36.117 | −6.545  | 63.544 | 1.00 | 0.00  |
| ATOM | 1862 | C    | LYS | 193 | −30.595 | −5.004  | 60.595 | 1.00 | 29.29 |
| ATOM | 1863 | O    | LYS | 193 | −31.078 | −5.970  | 60.009 | 1.00 | 30.78 |
| ATOM | 1864 | N    | GLU | 194 | −30.505 | −3.803  | 60.027 | 1.00 | 30.08 |
| ATOM | 1865 | H    | GLU | 194 | −30.052 | −3.073  | 60.494 | 1.00 | 0.00  |
| ATOM | 1866 | CA   | GLU | 194 | −31.010 | −3.580  | 58.672 | 1.00 | 29.65 |
| ATOM | 1867 | CB   | GLU | 194 | −31.443 | −2.124  | 58.468 | 1.00 | 31.51 |
| ATOM | 1868 | CG   | GLU | 194 | −32.478 | −1.620  | 59.468 | 1.00 | 34.14 |
| ATOM | 1869 | CD   | GLU | 194 | −31.843 | −1.000  | 60.701 | 1.00 | 39.15 |
| ATOM | 1870 | OE1  | GLU | 194 | −32.144 | −1.447  | 61.828 | 1.00 | 43.02 |
| ATOM | 1871 | OE2  | GLU | 194 | −31.040 | −0.057  | 60.545 | 1.00 | 42.87 |
| ATOM | 1872 | C    | GLU | 194 | −29.996 | −3.978  | 57.608 | 1.00 | 29.35 |
| ATOM | 1873 | O    | GLU | 194 | −28.815 | −3.656  | 57.708 | 1.00 | 30.02 |
| ATOM | 1874 | N    | GLN | 195 | −30.475 | −4.676  | 56.585 | 1.00 | 27.79 |
| ATOM | 1875 | H    | GLN | 195 | −31.430 | −4.874  | 56.579 | 1.00 | 0.00  |
| ATOM | 1876 | CA   | GLN | 195 | −29.638 | −5.143  | 55.486 | 1.00 | 26.98 |
| ATOM | 1877 | CB   | GLN | 195 | −30.495 | −5.896  | 54.468 | 1.00 | 32.16 |
| ATOM | 1878 | CG   | GLN | 195 | −31.179 | −7.137  | 55.007 | 1.00 | 38.27 |
| ATOM | 1879 | CD   | GLN | 195 | −30.242 | −8.321  | 55.098 | 1.00 | 42.30 |
| ATOM | 1880 | OE1  | GLN | 195 | −29.244 | −8.286  | 55.816 | 1.00 | 46.88 |
| ATOM | 1881 | NE2  | GLN | 195 | −30.550 | −9.375  | 54.356 | 1.00 | 43.75 |
| ATOM | 1882 | HE21 | GLN | 195 | −31.346 | −9.348  | 53.792 | 1.00 | 0.00  |
| ATOM | 1883 | HE22 | GLN | 195 | −29.951 | −10.143 | 54.423 | 1.00 | 0.00  |
| ATOM | 1884 | C    | GLN | 195 | −28.949 | −3.987  | 54.779 | 1.00 | 23.15 |
| ATOM | 1885 | O    | GLN | 195 | −29.574 | −2.973  | 54.488 | 1.00 | 24.44 |
| ATOM | 1886 | N    | GLY | 196 | −27.661 | −4.142  | 54.502 | 1.00 | 20.21 |
| ATOM | 1887 | H    | GLY | 196 | −27.192 | −4.960  | 54.770 | 1.00 | 0.00  |
| ATOM | 1888 | CA   | GLY | 196 | −26.934 | −3.096  | 53.811 | 1.00 | 17.86 |
| ATOM | 1889 | C    | GLY | 196 | −26.347 | −2.009  | 54.687 | 1.00 | 17.20 |
| ATOM | 1890 | O    | GLY | 196 | −25.769 | −1.050  | 54.169 | 1.00 | 15.58 |
| ATOM | 1891 | N    | THR | 197 | −26.517 | −2.130  | 56.003 | 1.00 | 16.43 |
| ATOM | 1892 | H    | THR | 197 | −27.003 | −2.893  | 56.375 | 1.00 | 0.00  |
| ATOM | 1893 | CA   | THR | 197 | −25.966 | −1.160  | 56.944 | 1.00 | 12.41 |
| ATOM | 1894 | CB   | THR | 197 | −27.056 | −0.415  | 57.740 | 1.00 | 12.16 |
| ATOM | 1895 | OG1  | THR | 197 | −27.907 | −1.361  | 58.392 | 1.00 | 12.64 |
| ATOM | 1896 | HG1  | THR | 197 | −28.275 | −1.934  | 57.715 | 1.00 | 0.00  |
| ATOM | 1897 | CG2  | THR | 197 | −27.883 | 0.478   | 56.826 | 1.00 | 7.90  |
| ATOM | 1898 | C    | THR | 197 | −25.050 | −1.897  | 57.912 | 1.00 | 12.59 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1899 | O | THR | 197 | −25.333 | −3.033 | 58.312 | 1.00 | 13.67 |
|---|---|---|---|---|---|---|---|---|---|
| ATOM | 1900 | N | TYR | 198 | −29.933 | −1.259 | 58.244 | 1.00 | 8.91 |
| ATOM | 1901 | H | TYR | 198 | −23.787 | −0.345 | 57.907 | 1.00 | 0.00 |
| ATOM | 1902 | CA | TYR | 198 | −22.936 | −1.814 | 59.148 | 1.00 | 8.91 |
| ATOM | 1903 | CB | TYR | 198 | −21.686 | −2.239 | 58.363 | 1.00 | 6.61 |
| ATOM | 1904 | CG | TYR | 198 | −23.941 | −3.345 | 57.363 | 1.00 | 9.50 |
| ATOM | 1905 | CD1 | TYR | 198 | −22.509 | −3.072 | 56.118 | 1.00 | 6.46 |
| ATOM | 1906 | CE1 | TYR | 198 | −22.777 | −2.092 | 55.212 | 1.00 | 9.83 |
| ATOM | 1907 | CD2 | TYR | 198 | −21.643 | −4.671 | 57.675 | 1.00 | 9.33 |
| ATOM | 1908 | CE2 | TYR | 198 | −21.905 | −5.693 | 56.778 | 1.00 | 12.76 |
| ATOM | 1909 | CZ | TYR | 198 | −22.469 | −5.403 | 55.549 | 1.00 | 13.23 |
| ATOM | 1910 | OH | TYR | 198 | −22.692 | −6.430 | 54.649 | 1.00 | 15.25 |
| ATOM | 1911 | HH | TYR | 198 | −23.165 | −6.078 | 53.883 | 1.00 | 0.00 |
| ATOM | 1912 | C | TYR | 198 | −22.560 | −0.696 | 60.091 | 1.00 | 8.51 |
| ATOM | 1913 | O | TYR | 198 | −23.001 | 0.436 | 59.912 | 1.00 | 11.67 |
| ATOM | 1914 | N | ALA | 199 | −21.748 | −1.001 | 61.091 | 1.00 | 8.59 |
| ATOM | 1915 | H | ALA | 199 | −21.423 | −1.916 | 61.229 | 1.00 | 0.00 |
| ATOM | 1916 | CA | ALA | 199 | −21.306 | 0.025 | 62.017 | 1.00 | 6.98 |
| ATOM | 1917 | CB | ALA | 199 | −22.149 | 0.012 | 63.283 | 1.00 | 7.55 |
| ATOM | 1918 | C | ALA | 199 | −19.851 | −0.214 | 62.348 | 1.00 | 8.45 |
| ATOM | 1919 | O | ALA | 199 | −19.422 | −1.361 | 62.501 | 1.00 | 9.19 |
| ATOM | 1920 | N | LEU | 200 | −19.084 | 0.869 | 62.380 | 1.00 | 7.78 |
| ATOM | 1921 | H | LEU | 200 | −19.476 | 1.742 | 62.171 | 1.00 | 0.00 |
| ATOM | 1922 | CA | LEU | 200 | −17.674 | 0.821 | 62.715 | 1.00 | 7.79 |
| ATOM | 1923 | CB | LEU | 200 | −16.893 | 1.746 | 61.784 | 1.00 | 9.17 |
| ATOM | 1924 | CG | LEU | 200 | −15.369 | 1.757 | 61.924 | 1.00 | 15.15 |
| ATOM | 1925 | CD1 | LEU | 200 | −14.783 | 0.386 | 61.569 | 1.00 | 12.28 |
| ATOM | 1926 | CD2 | LEU | 200 | −14.793 | 2.844 | 61.012 | 1.00 | 13.36 |
| ATOM | 1927 | C | LEU | 200 | −17.571 | 1.313 | 64.158 | 1.00 | 9.38 |
| ATOM | 1928 | O | LEU | 200 | −17.970 | 2.433 | 64.461 | 1.00 | 13.05 |
| ATOM | 1929 | N | SER | 201 | −17.087 | 0.463 | 65.057 | 1.00 | 10.24 |
| ATOM | 1930 | H | SER | 201 | −16.753 | −0.412 | 64.768 | 1.00 | 0.00 |
| ATOM | 1931 | CA | SER | 201 | −16.961 | 0.824 | 66.466 | 1.00 | 8.31 |
| ATOM | 1932 | CB | SER | 201 | −17.707 | −0.196 | 67.339 | 1.00 | 6.89 |
| ATOM | 1933 | OG | SER | 201 | −19.077 | −0.311 | 66.977 | 1.00 | 7.26 |
| ATOM | 1934 | HG | SER | 201 | −19.090 | −0.707 | 66.093 | 1.00 | 0.00 |
| ATOM | 1935 | C | SER | 201 | −15.491 | 0.869 | 66.862 | 1.00 | 9.36 |
| ATOM | 1936 | O | SER | 201 | −14.765 | −0.104 | 66.653 | 1.00 | 9.48 |
| ATOM | 1937 | N | LEU | 202 | −15.051 | 1.984 | 67.439 | 1.00 | 10.31 |
| ATOM | 1938 | H | LEU | 202 | −15.662 | 2.736 | 67.609 | 1.00 | 0.00 |
| ATOM | 1939 | CA | LEU | 202 | −13.657 | 2.124 | 67.853 | 1.00 | 11.15 |
| ATOM | 1940 | CB | LEU | 202 | −12.835 | 2.838 | 66.771 | 1.00 | 11.80 |
| ATOM | 1941 | CG | LEU | 202 | −12.959 | 4.352 | 66.596 | 1.00 | 12.43 |
| ATOM | 1942 | CD1 | LEU | 202 | −11.634 | 5.027 | 66.905 | 1.00 | 15.63 |
| ATOM | 1943 | CD2 | LEU | 202 | −13.371 | 4.665 | 65.176 | 1.00 | 18.37 |
| ATOM | 1944 | C | LEU | 202 | −13.534 | 2.893 | 69.156 | 1.00 | 14.24 |
| ATOM | 1945 | O | LEU | 202 | −14.446 | 3.617 | 69.546 | 1.00 | 12.46 |
| ATOM | 1946 | N | ILE | 203 | −12.399 | 2.736 | 69.825 | 1.00 | 17.13 |
| ATOM | 1947 | H | ILE | 203 | −11.707 | 2.154 | 69.453 | 1.00 | 0.00 |
| ATOM | 1948 | CA | ILE | 203 | −12.162 | 3.433 | 71.081 | 1.00 | 18.71 |
| ATOM | 1949 | CB | ILE | 203 | −11.490 | 2.540 | 72.317 | 1.00 | 19.35 |
| ATOM | 1950 | CG2 | ILE | 203 | −11.866 | 3.011 | 73.529 | 1.00 | 21.06 |
| ATOM | 1951 | CG1 | ILE | 203 | −11.887 | 1.084 | 71.957 | 1.00 | 23.07 |
| ATOM | 1952 | CD | ILE | 203 | −10.981 | 0.139 | 72.713 | 1.00 | 26.33 |
| ATOM | 1953 | C | ILE | 203 | −11.195 | 4.580 | 70.853 | 1.00 | 19.13 |
| ATOM | 1954 | O | ILE | 203 | −10.265 | 4.481 | 70.046 | 1.00 | 20.24 |
| ATOM | 1955 | N | TYR | 204 | −11.419 | 5.667 | 71.571 | 1.00 | 19.51 |
| ATOM | 1956 | H | TYR | 204 | −12.205 | 5.723 | 72.147 | 1.00 | 0.00 |
| ATOM | 1957 | CA | TYR | 204 | −10.544 | 6.818 | 71.520 | 1.00 | 20.06 |
| ATOM | 1958 | CB | TYR | 204 | −10.831 | 7.714 | 70.324 | 1.00 | 21.97 |
| ATOM | 1959 | CG | TYR | 204 | −9.864 | 8.866 | 70.276 | 1.00 | 23.47 |
| ATOM | 1960 | CD1 | TYR | 204 | −8.493 | 8.637 | 70.173 | 1.00 | 24.19 |
| ATOM | 1961 | CE1 | TYR | 204 | −7.590 | 9.685 | 70.211 | 1.00 | 26.94 |
| ATOM | 1962 | CD2 | TYR | 204 | −10.307 | 10.177 | 70.411 | 1.00 | 24.45 |
| ATOM | 1963 | CE2 | TYR | 204 | −9.410 | 11.232 | 70.449 | 1.00 | 26.76 |
| ATOM | 1964 | CZ | TYR | 204 | −8.056 | 10.977 | 70.354 | 1.00 | 28.21 |
| ATOM | 1965 | OH | TYR | 204 | −7.160 | 12.014 | 70.424 | 1.00 | 37.45 |
| ATOM | 1966 | HH | TYR | 204 | −7.642 | 12.839 | 70.522 | 1.00 | 0.00 |
| ATOM | 1967 | C | TYR | 204 | −10.724 | 7.594 | 72.814 | 1.00 | 20.33 |
| ATOM | 1968 | O | TYR | 204 | −11.827 | 8.055 | 73.125 | 1.00 | 18.87 |
| ATOM | 1969 | N | GLY | 205 | −9.643 | 7.695 | 73.584 | 1.00 | 21.84 |
| ATOM | 1970 | H | GLY | 205 | −8.815 | 7.295 | 73.279 | 1.00 | 0.00 |
| ATOM | 1971 | CA | GLY | 205 | −9.684 | 8.394 | 74.858 | 1.00 | 20.17 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 1972 | C | GLY | 205 | −10.621 | 7.710 | 75.837 | 1.00 | 19.37 |
|---|---|---|---|---|---|---|---|---|---|
| ATOM | 1973 | O | GLY | 205 | −11.482 | 8.360 | 76.424 | 1.00 | 21.75 |
| ATOM | 1974 | N | LYS | 206 | −10.494 | 6.390 | 75.963 | 1.00 | 18.95 |
| ATOM | 1975 | H | LYS | 206 | −9.814 | 5.924 | 75.440 | 1.00 | 0.00 |
| ATOM | 1976 | CA | LYS | 206 | −11.330 | 5.597 | 76.886 | 1.00 | 21.57 |
| ATOM | 1977 | CB | LYS | 206 | −11.065 | 5.982 | 78.323 | 1.00 | 23.25 |
| ATOM | 1978 | CG | LYS | 206 | −9.920 | 5.239 | 78.982 | 1.00 | 27.37 |
| ATOM | 1979 | CD | LYS | 206 | −9.687 | 5.772 | 80.394 | 1.00 | 33.80 |
| ATOM | 1980 | CE | LYS | 206 | −9.061 | 4.730 | 81.315 | 1.00 | 35.90 |
| ATOM | 1981 | NZ | LYS | 206 | −10.000 | 3.606 | 81.620 | 1.00 | 37.25 |
| ATOM | 1982 | HZ1 | LYS | 206 | −10.264 | 3.129 | 80.773 | 1.00 | 0.00 |
| ATOM | 1983 | HZ2 | LYS | 206 | −10.854 | 3.986 | 82.078 | 1.00 | 0.00 |
| ATOM | 1984 | HZ3 | LYS | 206 | −9.536 | 2.926 | 82.259 | 1.00 | 0.00 |
| ATOM | 1985 | C | LYS | 206 | −12.829 | 5.688 | 76.577 | 1.00 | 21.03 |
| ATOM | 1986 | O | LYS | 206 | −13.649 | 5.298 | 77.403 | 1.00 | 22.71 |
| ATOM | 1987 | N | THR | 207 | −13.185 | 6.174 | 75.396 | 1.00 | 20.66 |
| ATOM | 1988 | H | THR | 207 | −12.532 | 6.456 | 74.735 | 1.00 | 0.00 |
| ATOM | 1989 | CA | THR | 207 | −14.582 | 6.297 | 75.020 | 1.00 | 20.40 |
| ATOM | 1990 | CB | THR | 207 | −14.992 | 7.782 | 74.907 | 1.00 | 23.55 |
| ATOM | 1991 | OG1 | THR | 207 | −14.482 | 8.507 | 76.033 | 1.00 | 25.33 |
| ATOM | 1992 | HG1 | THR | 207 | −13.533 | 8.667 | 75.914 | 1.00 | 0.00 |
| ATOM | 1993 | CG2 | THR | 207 | −16.507 | 7.919 | 74.890 | 1.00 | 24.82 |
| ATOM | 1994 | C | THR | 207 | −14.777 | 5.589 | 73.679 | 1.00 | 19.07 |
| ATOM | 1995 | O | THR | 207 | −13.893 | 5.630 | 72.824 | 1.00 | 20.35 |
| ATOM | 1996 | N | VAL | 208 | −15.906 | 4.900 | 73.531 | 1.00 | 16.81 |
| ATOM | 1997 | H | VAL | 208 | −16.535 | 4.881 | 74.280 | 1.00 | 0.00 |
| ATOM | 1998 | CA | VAL | 208 | −16.240 | 4.156 | 72.317 | 1.00 | 15.40 |
| ATOM | 1999 | CB | VAL | 208 | −16.952 | 2.803 | 72.665 | 1.00 | 12.63 |
| ATOM | 2000 | CG1 | VAL | 208 | −17.532 | 2.159 | 71.422 | 1.00 | 16.18 |
| ATOM | 2001 | CG2 | VAL | 208 | −15.972 | 1.841 | 73.316 | 1.00 | 8.54 |
| ATOM | 2002 | C | VAL | 208 | −17.115 | 4.965 | 71.355 | 1.00 | 15.91 |
| ATOM | 2003 | O | VAL | 208 | −18.159 | 5.483 | 71.748 | 1.00 | 16.07 |
| ATOM | 2004 | N | TYR | 209 | −16.668 | 5.061 | 70.100 | 1.00 | 17.15 |
| ATOM | 2005 | H | TYR | 209 | −15.820 | 4.658 | 69.884 | 1.00 | 0.00 |
| ATOM | 2006 | CA | TYR | 209 | −17.366 | 5.775 | 69.026 | 1.00 | 13.45 |
| ATOM | 2007 | CB | TYR | 209 | −16.393 | 6.701 | 68.298 | 1.00 | 12.87 |
| ATOM | 2008 | CG | TYR | 209 | −15.821 | 7.795 | 69.153 | 1.00 | 12.70 |
| ATOM | 2009 | CD1 | TYR | 209 | −16.246 | 9.107 | 69.005 | 1.00 | 14.59 |
| ATOM | 2010 | CE1 | TYR | 209 | −15.721 | 10.124 | 69.786 | 1.00 | 17.80 |
| ATOM | 2011 | CD2 | TYR | 209 | −14.851 | 7.523 | 70.108 | 1.00 | 12.27 |
| ATOM | 2012 | CE2 | TYR | 209 | −14.322 | 8.531 | 70.896 | 1.00 | 15.57 |
| ATOM | 2013 | CZ | TYR | 209 | −14.760 | 9.830 | 70.732 | 1.00 | 16.21 |
| ATOM | 2014 | OH | TYR | 209 | −14.250 | 10.837 | 71.519 | 1.00 | 16.78 |
| ATOM | 2015 | HH | TYR | 209 | −14.677 | 11.671 | 71.296 | 1.00 | 0.00 |
| ATOM | 2016 | C | TYR | 209 | −17.956 | 4.790 | 68.014 | 1.00 | 11.19 |
| ATOM | 2017 | O | TYR | 209 | −17.350 | 3.770 | 67.706 | 1.00 | 12.29 |
| ATOM | 2018 | N | HIS | 210 | −19.143 | 5.096 | 67.505 | 1.00 | 10.27 |
| ATOM | 2019 | H | HIS | 210 | −19.587 | 5.914 | 67.804 | 1.00 | 0.00 |
| ATOM | 2020 | CA | HIS | 210 | −19.811 | 4.244 | 66.525 | 1.00 | 9.28 |
| ATOM | 2021 | CB | HIS | 210 | −21.123 | 3.697 | 67.085 | 1.00 | 11.42 |
| ATOM | 2022 | CG | HIS | 210 | −20.981 | 2.980 | 68.390 | 1.00 | 13.02 |
| ATOM | 2023 | CD2 | HIS | 210 | −21.058 | 3.429 | 69.663 | 1.00 | 12.81 |
| ATOM | 2024 | ND1 | HIS | 210 | −20.751 | 1.624 | 68.474 | 1.00 | 12.75 |
| ATOM | 2025 | HD1 | HIS | 210 | −20.594 | 1.000 | 67.722 | 1.00 | 0.00 |
| ATOM | 2026 | CE1 | HIS | 210 | −20.696 | 1.268 | 69.744 | 1.00 | 13.87 |
| ATOM | 2027 | NE2 | HIS | 210 | −20.878 | 2.345 | 70.485 | 1.00 | 13.61 |
| ATOM | 2028 | HE2 | HIS | 210 | −20.870 | 2.365 | 71.458 | 1.00 | 0.00 |
| ATOM | 2029 | C | HIS | 210 | −20.143 | 5.074 | 65.301 | 1.00 | 9.07 |
| ATOM | 2030 | O | HIS | 210 | −20.690 | 6.165 | 65.430 | 1.00 | 11.99 |
| ATOM | 2031 | N | TYR | 211 | −19.839 | 4.550 | 64.119 | 1.00 | 9.30 |
| ATOM | 2032 | H | TYR | 211 | −19.408 | 3.671 | 64.065 | 1.00 | 0.00 |
| ATOM | 2033 | CA | TYR | 211 | −20.115 | 5.239 | 62.860 | 1.00 | 8.50 |
| ATOM | 2034 | CB | TYR | 211 | −18.810 | 5.602 | 62.136 | 1.00 | 7.82 |
| ATOM | 2035 | CG | TYR | 211 | −17.960 | 6.618 | 62.866 | 1.00 | 9.31 |
| ATOM | 2036 | CD1 | TYR | 211 | −17.064 | 6.224 | 63.862 | 1.00 | 10.88 |
| ATOM | 2037 | CE1 | TYR | 211 | −16.270 | 7.154 | 64.531 | 1.00 | 9.13 |
| ATOM | 2038 | CD2 | TYR | 211 | −18.043 | 7.973 | 62.559 | 1.00 | 10.28 |
| ATOM | 2039 | CE2 | TYR | 211 | −17.254 | 8.911 | 63.223 | 1.00 | 9.76 |
| ATOM | 2040 | CZ | TYR | 211 | −16.371 | 8.492 | 64.205 | 1.00 | 9.78 |
| ATOM | 2041 | OH | TYR | 211 | −15.579 | 9.405 | 64.857 | 1.00 | 11.29 |
| ATOM | 2042 | HH | TYR | 211 | −15.854 | 10.307 | 64.614 | 1.00 | 0.00 |
| ATOM | 2043 | C | TYR | 211 | −20.958 | 4.331 | 61.981 | 1.00 | 6.82 |
| ATOM | 2044 | O | TYR | 211 | −20.728 | 3.124 | 61.917 | 1.00 | 8.26 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2045 | N | LEU | 212 | −21.949 | 4.917 | 61.324 | 1.00 | 6.71 |
|---|---|---|---|---|---|---|---|---|---|
| ATOM | 2046 | H | LEU | 212 | −22.062 | 5.893 | 61.376 | 1.00 | 0.00 |
| ATOM | 2047 | CA | LEU | 212 | −22.852 | 4.185 | 60.451 | 1.00 | 5.46 |
| ATOM | 2048 | CB | LEU | 212 | −24.174 | 4.959 | 60.360 | 1.00 | 7.18 |
| ATOM | 2049 | CG | LEU | 212 | −25.494 | 4.395 | 59.818 | 1.00 | 9.03 |
| ATOM | 2050 | CD1 | LEU | 212 | −25.835 | 5.015 | 58.480 | 1.00 | 12.52 |
| ATOM | 2051 | CD2 | LEU | 212 | −25.475 | 2.889 | 59.756 | 1.00 | 11.67 |
| ATOM | 2052 | C | LEU | 212 | −22.226 | 4.035 | 59.065 | 1.00 | 6.62 |
| ATOM | 2053 | O | LEU | 212 | −21.636 | 4.975 | 58.535 | 1.00 | 5.44 |
| ATOM | 2054 | N | ILE | 213 | −22.275 | 2.827 | 58.521 | 1.00 | 7.03 |
| ATOM | 2055 | H | ILE | 213 | −22.665 | 2.078 | 59.020 | 1.00 | 0.00 |
| ATOM | 2056 | CA | ILE | 213 | −21.757 | 2.583 | 57.187 | 1.00 | 6.11 |
| ATOM | 2057 | CB | ILE | 213 | −20.691 | 1.477 | 57.174 | 1.00 | 8.10 |
| ATOM | 2058 | CG2 | ILE | 213 | −20.328 | 1.111 | 55.733 | 1.00 | 8.26 |
| ATOM | 2059 | CG1 | ILE | 213 | −19.446 | 1.940 | 57.935 | 1.00 | 7.79 |
| ATOM | 2060 | CD | ILE | 213 | −18.405 | 0.858 | 58.106 | 1.00 | 4.59 |
| ATOM | 2061 | C | ILE | 213 | −22.972 | 2.142 | 56.384 | 1.00 | 7.52 |
| ATOM | 2062 | O | ILE | 213 | −23.708 | 1.254 | 56.806 | 1.00 | 7.66 |
| ATOM | 2063 | N | SER | 214 | −23.212 | 2.781 | 55.250 | 1.00 | 8.29 |
| ATOM | 2064 | H | SER | 214 | −22.616 | 3.483 | 54.920 | 1.00 | 0.00 |
| ATOM | 2065 | CA | SER | 214 | −24.365 | 2.429 | 54.442 | 1.00 | 11.71 |
| ATOM | 2066 | CB | SER | 214 | −25.403 | 3.550 | 54.517 | 1.00 | 13.40 |
| ATOM | 2067 | OG | SER | 214 | −26.664 | 3.122 | 54.045 | 1.00 | 21.53 |
| ATOM | 2068 | HG | SER | 214 | −27.246 | 2.924 | 54.794 | 1.00 | 0.00 |
| ATOM | 2069 | C | SER | 214 | −23.944 | 2.183 | 53.000 | 1.00 | 13.39 |
| ATOM | 2070 | O | SER | 214 | −22.868 | 2.608 | 52.574 | 1.00 | 14.33 |
| ATOM | 2071 | N | GLN | 215 | −24.773 | 1.454 | 52.266 | 1.00 | 16.85 |
| ATOM | 2072 | H | GLN | 215 | −25.622 | 1.144 | 52.659 | 1.00 | 0.00 |
| ATOM | 2073 | CA | GLN | 215 | −24.501 | 1.145 | 50.870 | 1.00 | 21.53 |
| ATOM | 2074 | CB | GLN | 215 | −24.656 | −0.356 | 50.632 | 1.00 | 21.76 |
| ATOM | 2075 | CG | GLN | 215 | −24.198 | −0.815 | 49.265 | 1.00 | 25.99 |
| ATOM | 2076 | CD | GLN | 215 | −24.267 | −2.320 | 49.102 | 1.00 | 27.71 |
| ATOM | 2077 | OE1 | GLN | 215 | −24.990 | −3.002 | 49.825 | 1.00 | 31.50 |
| ATOM | 2078 | NE2 | GLN | 215 | −23.500 | −2.848 | 48.160 | 1.00 | 26.57 |
| ATOM | 2079 | HE21 | GLN | 215 | −22.916 | −2.272 | 47.626 | 1.00 | 0.00 |
| ATOM | 2080 | HE22 | GLN | 215 | −23.571 | −3.817 | 48.059 | 1.00 | 0.00 |
| ATOM | 2081 | C | GLN | 215 | −25.496 | 1.919 | 50.014 | 1.00 | 23.57 |
| ATOM | 2082 | O | GLN | 215 | −26.702 | 1.807 | 50.218 | 1.00 | 26.27 |
| ATOM | 2083 | N | ASP | 216 | −24.997 | 2.742 | 49.096 | 1.00 | 24.50 |
| ATOM | 2084 | H | ASP | 216 | −24.024 | 2.829 | 49.029 | 1.00 | 0.00 |
| ATOM | 2085 | CA | ASP | 216 | −25.878 | 3.523 | 48.239 | 1.00 | 25.05 |
| ATOM | 2086 | CB | ASP | 216 | −25.195 | 4.820 | 47.769 | 1.00 | 24.39 |
| ATOM | 2087 | CG | ASP | 216 | −23.933 | 4.580 | 46.941 | 1.00 | 24.49 |
| ATOM | 2088 | OD1 | ASP | 216 | −23.826 | 3.556 | 46.232 | 1.00 | 24.62 |
| ATOM | 2089 | OD2 | ASP | 216 | −23.041 | 5.451 | 46.986 | 1.00 | 22.90 |
| ATOM | 2090 | C | ASP | 216 | −26.447 | 2.743 | 47.055 | 1.00 | 26.80 |
| ATOM | 2091 | O | ASP | 216 | −26.222 | 1.539 | 46.923 | 1.00 | 27.31 |
| ATOM | 2092 | N | LYS | 217 | −27.143 | 3.454 | 46.173 | 1.00 | 30.69 |
| ATOM | 2093 | H | LYS | 217 | −27.270 | 4.407 | 46.343 | 1.00 | 0.00 |
| ATOM | 2094 | CA | LYS | 217 | −27.762 | 2.863 | 44.986 | 1.00 | 32.79 |
| ATOM | 2095 | CB | LYS | 217 | −28.498 | 3.946 | 44.189 | 1.00 | 36.64 |
| ATOM | 2096 | CG | LYS | 217 | −27.606 | 4.818 | 43.290 | 1.00 | 41.04 |
| ATOM | 2097 | CD | LYS | 217 | −26.611 | 5.688 | 44.067 | 1.00 | 45.48 |
| ATOM | 2098 | CE | LYS | 217 | −27.307 | 6.796 | 44.850 | 1.00 | 49.13 |
| ATOM | 2099 | NZ | LYS | 217 | −26.330 | 7.760 | 45.446 | 1.00 | 51.31 |
| ATOM | 2100 | HZ1 | LYS | 217 | −25.793 | 8.221 | 44.683 | 1.00 | 0.00 |
| ATOM | 2101 | HZ2 | LYS | 217 | −25.684 | 7.252 | 46.083 | 1.00 | 0.00 |
| ATOM | 2102 | HZ3 | LYS | 217 | −26.846 | 8.482 | 45.988 | 1.00 | 0.00 |
| ATOM | 2103 | C | LYS | 217 | −26.758 | 2.156 | 44.077 | 1.00 | 31.55 |
| ATOM | 2104 | O | LYS | 217 | −27.058 | 1.116 | 43.497 | 1.00 | 33.38 |
| ATOM | 2105 | N | ALA | 218 | −25.567 | 2.731 | 43.959 | 1.00 | 30.81 |
| ATOM | 2106 | H | ALA | 218 | −25.384 | 3.544 | 44.464 | 1.00 | 0.00 |
| ATOM | 2107 | CA | ALA | 218 | −24.517 | 2.175 | 43.113 | 1.00 | 28.71 |
| ATOM | 2108 | CB | ALA | 218 | −23.534 | 3.265 | 42.728 | 1.00 | 27.61 |
| ATOM | 2109 | C | ALA | 218 | −23.781 | 1.011 | 43.773 | 1.00 | 29.11 |
| ATOM | 2110 | O | ALA | 218 | −22.812 | 0.490 | 43.217 | 1.00 | 31.99 |
| ATOM | 2111 | N | GLY | 219 | −24.222 | 0.624 | 44.968 | 1.00 | 26.78 |
| ATOM | 2112 | H | GLY | 219 | −25.007 | 1.034 | 45.378 | 1.00 | 0.00 |
| ATOM | 2113 | CA | GLY | 219 | −23.588 | −0.472 | 45.674 | 1.00 | 22.67 |
| ATOM | 2114 | C | GLY | 219 | −22.322 | −0.078 | 46.411 | 1.00 | 22.34 |
| ATOM | 2115 | O | GLY | 219 | −21.617 | −0.937 | 46.943 | 1.00 | 22.37 |
| ATOM | 2116 | N | LYS | 220 | −22.043 | 1.218 | 46.472 | 1.00 | 18.20 |
| ATOM | 2117 | H | LYS | 220 | −22.639 | 1.850 | 46.038 | 1.00 | 0.00 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2118 | CA | LYS | 220 | −20.857 | 1.699 | 47.157 | 1.00 | 15.98 |
|---|---|---|---|---|---|---|---|---|---|
| ATOM | 2119 | CB | LYS | 220 | −20.334 | 2.951 | 46.464 | 1.00 | 19.42 |
| ATOM | 2120 | CG | LYS | 220 | −19.724 | 2.658 | 45.103 | 1.00 | 24.14 |
| ATOM | 2121 | CD | LYS | 220 | −19.446 | 3.937 | 44.349 | 1.00 | 30.32 |
| ATOM | 2122 | CE | LYS | 220 | −18.686 | 3.669 | 43.057 | 1.00 | 35.44 |
| ATOM | 2123 | NZ | LYS | 220 | −17.267 | 3.293 | 43.318 | 1.00 | 39.63 |
| ATOM | 2124 | HZ1 | LYS | 220 | −17.249 | 2.479 | 43.959 | 1.00 | 0.00 |
| ATOM | 2125 | HZ2 | LYS | 220 | −16.790 | 4.091 | 43.777 | 1.00 | 0.00 |
| ATOM | 2126 | HZ3 | LYS | 220 | −16.781 | 3.043 | 42.432 | 1.00 | 0.00 |
| ATOM | 2127 | C | LYS | 220 | −21.119 | 1.954 | 48.636 | 1.00 | 13.83 |
| ATOM | 2128 | O | LYS | 220 | −22.221 | 2.346 | 49.019 | 1.00 | 12.56 |
| ATOM | 2129 | N | TYR | 221 | −20.112 | 1.677 | 49.459 | 1.00 | 10.21 |
| ATOM | 2130 | H | TYR | 221 | −19.285 | 1.336 | 49.059 | 1.00 | 0.00 |
| ATOM | 2131 | CA | TYR | 221 | −20.194 | 1.863 | 50.903 | 1.00 | 9.57 |
| ATOM | 2132 | CB | TYR | 221 | −19.445 | 0.759 | 51.641 | 1.00 | 8.91 |
| ATOM | 2133 | CG | TYR | 221 | −19.910 | −0.632 | 51.334 | 1.00 | 9.85 |
| ATOM | 2134 | CD1 | TYR | 221 | −19.410 | −1.318 | 50.231 | 1.00 | 9.27 |
| ATOM | 2135 | CE1 | TYR | 221 | −19.782 | −2.629 | 49.974 | 1.00 | 13.17 |
| ATOM | 2136 | CD2 | TYR | 221 | −20.805 | −1.289 | 52.174 | 1.00 | 10.94 |
| ATOM | 2137 | CE2 | TYR | 221 | −21.185 | −2.605 | 51.928 | 1.00 | 13.53 |
| ATOM | 2138 | CZ | TYR | 221 | −20.665 | −3.267 | 50.826 | 1.00 | 12.86 |
| ATOM | 2139 | OH | TYR | 221 | −20.995 | −4.579 | 50.584 | 1.00 | 19.40 |
| ATOM | 2140 | HH | TYR | 221 | −20.857 | −4.758 | 49.645 | 1.00 | 0.00 |
| ATOM | 2141 | C | TYR | 221 | −19.574 | 3.174 | 51.330 | 1.00 | 10.79 |
| ATOM | 2142 | O | TYR | 221 | −18.616 | 3.651 | 50.714 | 1.00 | 10.37 |
| ATOM | 2143 | N | CYS | 222 | −20.090 | 3.724 | 52.422 | 1.00 | 9.88 |
| ATOM | 2144 | H | CYS | 222 | −20.863 | 3.315 | 52.870 | 1.00 | 0.00 |
| ATOM | 2145 | CA | CYS | 222 | −19.570 | 4.964 | 52.967 | 1.00 | 9.81 |
| ATOM | 2146 | CB | CYS | 222 | −19.774 | 6.126 | 51.986 | 1.00 | 10.60 |
| ATOM | 2147 | SG | CYS | 222 | −21.492 | 6.676 | 51.784 | 1.00 | 17.23 |
| ATOM | 2148 | C | CYS | 222 | −20.244 | 5.331 | 54.270 | 1.00 | 9.69 |
| ATOM | 2149 | O | CYS | 222 | −21.345 | 4.860 | 54.579 | 1.00 | 7.62 |
| ATOM | 2150 | N | ILE | 223 | −19.521 | 6.097 | 55.074 | 1.00 | 10.22 |
| ATOM | 2151 | H | ILE | 223 | −18.601 | 6.331 | 54.815 | 1.00 | 0.00 |
| ATOM | 2152 | CA | ILE | 223 | −20.059 | 6.638 | 56.306 | 1.00 | 9.93 |
| ATOM | 2153 | CB | ILE | 223 | −18.925 | 6.995 | 57.300 | 1.00 | 6.84 |
| ATOM | 2154 | CG2 | ILE | 223 | −19.475 | 7.742 | 58.498 | 1.00 | 5.29 |
| ATOM | 2155 | CG1 | ILE | 223 | −18.225 | 5.712 | 57.762 | 1.00 | 6.96 |
| ATOM | 2156 | CD | ILE | 223 | −16.938 | 5.946 | 58.525 | 1.00 | 9.34 |
| ATOM | 2157 | C | ILE | 223 | −20.697 | 7.902 | 55.706 | 1.00 | 11.78 |
| ATOM | 2158 | O | ILE | 223 | −20.109 | 8.528 | 54.823 | 1.00 | 12.45 |
| ATOM | 2159 | N | PRO | 224 | −21.936 | 8.234 | 56.102 | 1.00 | 13.13 |
| ATOM | 2160 | CD | PRO | 224 | −22.736 | 7.595 | 57.167 | 1.00 | 13.77 |
| ATOM | 2161 | CA | PRO | 224 | −22.621 | 9.422 | 55.572 | 1.00 | 12.77 |
| ATOM | 2162 | CB | PRO | 224 | −23.707 | 9.672 | 56.616 | 1.00 | 12.95 |
| ATOM | 2163 | CG | PRO | 224 | −24.088 | 8.271 | 57.014 | 1.00 | 13.82 |
| ATOM | 2164 | C | PRO | 224 | −21.715 | 10.647 | 55.374 | 1.00 | 11.50 |
| ATOM | 2165 | O | PRO | 224 | −21.090 | 11.126 | 56.315 | 1.00 | 9.13 |
| ATOM | 2166 | N | GLU | 225 | −21.645 | 11.124 | 54.132 | 1.00 | 14.71 |
| ATOM | 2167 | H | GLU | 225 | −22.179 | 10.664 | 53.448 | 1.00 | 0.00 |
| ATOM | 2168 | CA | GLU | 225 | −20.830 | 12.280 | 53.738 | 1.00 | 15.88 |
| ATOM | 2169 | CB | GLU | 225 | −21.055 | 13.465 | 54.680 | 1.00 | 20.79 |
| ATOM | 2170 | CG | GLU | 225 | −22.439 | 14.080 | 54.631 | 1.00 | 26.35 |
| ATOM | 2171 | CD | GLU | 225 | −22.526 | 15.306 | 55.516 | 1.00 | 32.15 |
| ATOM | 2172 | OE1 | GLU | 225 | −22.863 | 15.151 | 56.712 | 1.00 | 33.44 |
| ATOM | 2173 | OE2 | GLU | 225 | −22.228 | 16.418 | 55.020 | 1.00 | 34.61 |
| ATOM | 2174 | C | GLU | 225 | −19.330 | 12.006 | 53.641 | 1.00 | 13.50 |
| ATOM | 2175 | O | GLU | 225 | −18.536 | 12.937 | 53.502 | 1.00 | 14.62 |
| ATOM | 2176 | N | GLY | 226 | −18.939 | 10.740 | 53.707 | 1.00 | 10.60 |
| ATOM | 2177 | H | GLY | 226 | −19.593 | 10.021 | 53.791 | 1.00 | 0.00 |
| ATOM | 2178 | CA | GLY | 226 | −17.532 | 10.407 | 53.626 | 1.00 | 9.49 |
| ATOM | 2179 | C | GLY | 226 | −17.172 | 9.830 | 52.273 | 1.00 | 7.50 |
| ATOM | 2180 | O | GLY | 226 | −18.004 | 9.771 | 51.373 | 1.00 | 7.18 |
| ATOM | 2181 | N | THR | 227 | −15.926 | 9.395 | 52.140 | 1.00 | 11.32 |
| ATOM | 2182 | H | THR | 227 | −15.314 | 9.439 | 52.909 | 1.00 | 0.00 |
| ATOM | 2183 | CA | THR | 227 | −15.419 | 8.798 | 50.907 | 1.00 | 11.27 |
| ATOM | 2184 | CB | THR | 227 | −13.911 | 8.469 | 51.054 | 1.00 | 10.87 |
| ATOM | 2185 | OG1 | THR | 227 | −13.191 | 9.664 | 51.370 | 1.00 | 11.75 |
| ATOM | 2186 | HG1 | THR | 227 | −13.305 | 10.261 | 50.623 | 1.00 | 0.00 |
| ATOM | 2187 | CG2 | THR | 227 | −13.350 | 7.891 | 49.783 | 1.00 | 9.00 |
| ATOM | 2188 | C | THR | 227 | −16.191 | 7.513 | 50.609 | 1.00 | 11.40 |
| ATOM | 2189 | O | THR | 227 | −16.643 | 6.835 | 51.530 | 1.00 | 13.43 |
| ATOM | 2190 | N | LYS | 228 | −16.343 | 7.187 | 49.330 | 1.00 | 11.00 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2191 | H | LYS | 228 | −15.978 | 7.748 | 48.614 | 1.00 | 0.00 |
|---|---|---|---|---|---|---|---|---|---|
| ATOM | 2192 | CA | LYS | 228 | −17.056 | 5.986 | 48.927 | 1.00 | 11.19 |
| ATOM | 2193 | CB | LYS | 228 | −18.118 | 6.329 | 47.882 | 1.00 | 15.00 |
| ATOM | 2194 | CG | LYS | 228 | −19.153 | 7.293 | 48.448 | 1.00 | 11.92 |
| ATOM | 2195 | CD | LYS | 228 | −20.385 | 7.410 | 47.598 | 1.00 | 15.46 |
| ATOM | 2196 | CE | LYS | 228 | −21.505 | 8.048 | 48.399 | 1.00 | 16.88 |
| ATOM | 2197 | NZ | LYS | 228 | −21.135 | 9.394 | 48.914 | 1.00 | 26.16 |
| ATOM | 2198 | HZ1 | LYS | 228 | −20.889 | 10.007 | 48.111 | 1.00 | 0.00 |
| ATOM | 2199 | HZ2 | LYS | 228 | −20.321 | 9.311 | 49.557 | 1.00 | 0.00 |
| ATOM | 2200 | HZ3 | LYS | 228 | −21.945 | 9.804 | 49.428 | 1.00 | 0.00 |
| ATOM | 2201 | C | LYS | 228 | −16.114 | 4.890 | 48.452 | 1.00 | 10.75 |
| ATOM | 2202 | O | LYS | 228 | −15.136 | 5.153 | 47.745 | 1.00 | 8.11 |
| ATOM | 2203 | N | PHE | 229 | −16.412 | 3.661 | 48.866 | 1.00 | 8.50 |
| ATOM | 2204 | H | PHE | 229 | −17.223 | 3.514 | 49.399 | 1.00 | 0.00 |
| ATOM | 2205 | CA | PHE | 229 | −15.590 | 2.504 | 48.552 | 1.00 | 5.46 |
| ATOM | 2206 | CB | PHE | 229 | −14.963 | 1.973 | 49.843 | 1.00 | 4.60 |
| ATOM | 2207 | CG | PHE | 229 | −14.272 | 3.031 | 50.669 | 1.00 | 4.48 |
| ATOM | 2208 | CD1 | PHE | 229 | −14.983 | 3.792 | 51.590 | 1.00 | 7.15 |
| ATOM | 2209 | CD2 | PHE | 229 | −12.913 | 3.269 | 50.525 | 1.00 | 5.66 |
| ATOM | 2210 | CE1 | PHE | 229 | −14.350 | 4.767 | 52.352 | 1.00 | 4.56 |
| ATOM | 2211 | CE2 | PHE | 229 | −12.280 | 4.242 | 51.284 | 1.00 | 5.66 |
| ATOM | 2212 | CZ | PHE | 229 | −13.003 | 4.991 | 52.199 | 1.00 | 2.65 |
| ATOM | 2213 | C | PHE | 229 | −16.403 | 1.398 | 47.891 | 1.00 | 8.16 |
| ATOM | 2214 | O | PHE | 229 | −17.617 | 1.312 | 48.086 | 1.00 | 5.71 |
| ATOM | 2215 | N | ASP | 230 | −15.728 | 0.538 | 47.126 | 1.00 | 9.14 |
| ATOM | 2216 | H | ASP | 230 | −14.760 | 0.670 | 47.008 | 1.00 | 0.00 |
| ATOM | 2217 | CA | ASP | 230 | −16.394 | −0.574 | 46.445 | 1.00 | 9.38 |
| ATOM | 2218 | CB | ASP | 230 | −15.574 | −1.052 | 45.246 | 1.00 | 8.63 |
| ATOM | 2219 | CG | ASP | 230 | −15.869 | −0.274 | 43.981 | 1.00 | 8.43 |
| ATOM | 2220 | OD1 | ASP | 230 | −15.274 | −0.608 | 42.947 | 1.00 | 9.85 |
| ATOM | 2221 | OD2 | ASP | 230 | −16.698 | 0.654 | 43.998 | 1.00 | 11.91 |
| ATOM | 2222 | C | ASP | 230 | −16.651 | −1.761 | 47.363 | 1.00 | 10.64 |
| ATOM | 2223 | O | ASP | 230 | −17.541 | −2.573 | 47.108 | 1.00 | 11.10 |
| ATOM | 2224 | N | THR | 231 | −15.824 | −1.904 | 48.391 | 1.00 | 10.48 |
| ATOM | 2225 | H | THR | 231 | −15.090 | −1.275 | 48.547 | 1.00 | 0.00 |
| ATOM | 2226 | CA | THR | 231 | −15.971 | −3.007 | 49.321 | 1.00 | 6.74 |
| ATOM | 2227 | CB | THR | 231 | −14.953 | −4.131 | 49.036 | 1.00 | 7.00 |
| ATOM | 2228 | OG1 | THR | 231 | −13.627 | −3.614 | 49.171 | 1.00 | 8.09 |
| ATOM | 2229 | HG1 | THR | 231 | −13.496 | −3.068 | 48.382 | 1.00 | 0.00 |
| ATOM | 2230 | CG2 | THR | 231 | −15.127 | −4.692 | 47.635 | 1.00 | 9.33 |
| ATOM | 2231 | C | THR | 231 | −15.700 | −2.501 | 50.719 | 1.00 | 5.98 |
| ATOM | 2232 | O | THR | 231 | −15.050 | −1.477 | 50.898 | 1.00 | 4.61 |
| ATOM | 2233 | N | LEU | 232 | −16.211 | −3.224 | 51.704 | 1.00 | 7.05 |
| ATOM | 2234 | H | LEU | 232 | −16.795 | −3.989 | 51.481 | 1.00 | 0.00 |
| ATOM | 2235 | CA | LEU | 232 | −16.001 | −2.885 | 53.099 | 1.00 | 8.76 |
| ATOM | 2236 | CB | LEU | 232 | −16.881 | −3.761 | 53.994 | 1.00 | 6.96 |
| ATOM | 2237 | CG | LEU | 232 | −18.367 | −3.450 | 54.121 | 1.00 | 6.67 |
| ATOM | 2238 | CD1 | LEU | 232 | −19.044 | −4.612 | 54.828 | 1.00 | 7.35 |
| ATOM | 2239 | CD2 | LEU | 232 | −18.576 | −2.150 | 54.897 | 1.00 | 6.04 |
| ATOM | 2240 | C | LEU | 232 | −14.534 | −3.090 | 53.473 | 1.00 | 7.18 |
| ATOM | 2241 | O | LEU | 232 | −14.021 | −2.433 | 54.374 | 1.00 | 9.95 |
| ATOM | 2242 | N | TRP | 233 | −13.873 | −4.022 | 52.796 | 1.00 | 6.47 |
| ATOM | 2243 | H | TRP | 233 | −14.348 | −4.510 | 52.099 | 1.00 | 0.00 |
| ATOM | 2244 | CA | TRP | 233 | −12.464 | −4.305 | 53.057 | 1.00 | 6.87 |
| ATOM | 2245 | CB | TRP | 233 | −11.979 | −5.466 | 52.188 | 1.00 | 3.74 |
| ATOM | 2246 | CG | TRP | 233 | −10.687 | −6.058 | 52.650 | 1.00 | 4.57 |
| ATOM | 2247 | CD2 | TRP | 233 | −9.359 | −5.570 | 52.381 | 1.00 | 8.34 |
| ATOM | 2248 | CE2 | TRP | 233 | −8.458 | −6.423 | 53.060 | 1.00 | 6.83 |
| ATOM | 2249 | CE3 | TRP | 233 | −8.844 | −4.493 | 51.641 | 1.00 | 8.52 |
| ATOM | 2250 | CD1 | TRP | 233 | −10.536 | −7.154 | 53.440 | 1.00 | 5.21 |
| ATOM | 2251 | NE1 | TRP | 233 | −9.204 | −7.380 | 53.693 | 1.00 | 6.92 |
| ATOM | 2252 | HE1 | TRP | 233 | −8.861 | −8.107 | 54.265 | 1.00 | 0.00 |
| ATOM | 2253 | CZ2 | TRP | 233 | −7.073 | −6.237 | 53.021 | 1.00 | 8.01 |
| ATOM | 2254 | CZ3 | TRP | 233 | −7.458 | −4.308 | 51.601 | 1.00 | 6.16 |
| ATOM | 2255 | CH2 | TRP | 233 | −6.592 | −5.177 | 52.292 | 1.00 | 7.69 |
| ATOM | 2256 | C | TRP | 233 | −11.617 | −3.062 | 52.772 | 1.00 | 7.29 |
| ATOM | 2257 | O | TRP | 233 | −10.733 | −2.700 | 53.561 | 1.00 | 9.21 |
| ATOM | 2258 | N | GLN | 234 | −11.902 | −2.403 | 51.652 | 1.00 | 5.93 |
| ATOM | 2259 | H | GLN | 234 | −12.613 | −2.733 | 51.066 | 1.00 | 0.00 |
| ATOM | 2260 | CA | GLN | 234 | −11.169 | −1.204 | 51.262 | 1.00 | 4.78 |
| ATOM | 2261 | CB | GLN | 234 | −11.443 | −0.862 | 49.798 | 1.00 | 6.84 |
| ATOM | 2262 | CG | GLN | 234 | −10.836 | −1.880 | 48.848 | 1.00 | 10.82 |
| ATOM | 2263 | CD | GLN | 234 | −11.380 | −1.789 | 47.432 | 1.00 | 10.56 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2264 | OE1 | GLN | 234 | −12.586 | −1.878 | 47.209 | 1.00 | 8.62 |
|---|---|---|---|---|---|---|---|---|---|
| ATOM | 2265 | NE2 | GLN | 234 | −10.487 | −1.652 | 46.469 | 1.00 | 11.25 |
| ATOM | 2266 | HE21 | GLN | 234 | −9.531 | −1.629 | 46.708 | 1.00 | 0.00 |
| ATOM | 2267 | HE22 | GLN | 234 | −10.789 | −1.580 | 45.537 | 1.00 | 0.00 |
| ATOM | 2268 | C | GLN | 234 | −11.449 | −0.015 | 52.160 | 1.00 | 3.62 |
| ATOM | 2269 | O | GLN | 234 | −10.554 | 0.781 | 52.430 | 1.00 | 5.94 |
| ATOM | 2270 | N | LEU | 235 | −12.689 | 0.106 | 52.615 | 1.00 | 5.89 |
| ATOM | 2271 | H | LEU | 235 | −13.364 | −0.541 | 52.324 | 1.00 | 0.00 |
| ATOM | 2272 | CA | LEU | 235 | −13.081 | 1.190 | 53.511 | 1.00 | 4.73 |
| ATOM | 2273 | CB | LEU | 235 | −14.566 | 1.059 | 53.872 | 1.00 | 4.90 |
| ATOM | 2274 | CG | LEU | 235 | −15.185 | 2.047 | 54.874 | 1.00 | 6.15 |
| ATOM | 2275 | CD1 | LEU | 235 | −16.630 | 2.350 | 54.483 | 1.00 | 8.45 |
| ATOM | 2276 | CD2 | LEU | 235 | −15.109 | 1.496 | 56.298 | 1.00 | 4.62 |
| ATOM | 2277 | C | LEU | 235 | −12.216 | 1.146 | 54.769 | 1.00 | 5.64 |
| ATOM | 2278 | O | LEU | 235 | −11.579 | 2.133 | 55.134 | 1.00 | 6.99 |
| ATOM | 2279 | N | VAL | 236 | −12.158 | −0.025 | 55.390 | 1.00 | 5.96 |
| ATOM | 2280 | H | VAL | 236 | −12.661 | −0.789 | 55.026 | 1.00 | 0.00 |
| ATOM | 2281 | CA | VAL | 236 | −11.383 | −0.223 | 56.603 | 1.00 | 8.27 |
| ATOM | 2282 | CB | VAL | 236 | −11.604 | −1.650 | 57.157 | 1.00 | 9.38 |
| ATOM | 2283 | CG1 | VAL | 236 | −10.658 | −1.938 | 58.330 | 1.00 | 7.51 |
| ATOM | 2284 | CG2 | VAL | 236 | −13.042 | −1.816 | 57.587 | 1.00 | 5.71 |
| ATOM | 2285 | C | VAL | 236 | −9.892 | 0.031 | 56.406 | 1.00 | 9.49 |
| ATOM | 2286 | O | VAL | 236 | −9.270 | 0.731 | 57.197 | 1.00 | 12.68 |
| ATOM | 2287 | N | GLU | 237 | −9.317 | −0.524 | 55.347 | 1.00 | 10.79 |
| ATOM | 2288 | H | GLU | 237 | −9.854 | −1.062 | 54.733 | 1.00 | 0.00 |
| ATOM | 2289 | CA | GLU | 237 | −7.887 | −0.349 | 55.094 | 1.00 | 11.35 |
| ATOM | 2290 | CB | GLU | 237 | −7.430 | −1.272 | 53.976 | 1.00 | 16.61 |
| ATOM | 2291 | CG | GLU | 237 | −7.605 | −2.731 | 54.340 | 1.00 | 22.80 |
| ATOM | 2292 | CD | GLU | 237 | −6.787 | −3.144 | 55.547 | 1.00 | 24.22 |
| ATOM | 2293 | OE1 | GLU | 237 | −5.597 | −2.765 | 55.618 | 1.00 | 22.20 |
| ATOM | 2294 | OE2 | GLU | 237 | −7.340 | −3.852 | 56.416 | 1.00 | 23.12 |
| ATOM | 2295 | C | GLU | 237 | −7.474 | 1.076 | 54.796 | 1.00 | 9.15 |
| ATOM | 2296 | O | GLU | 237 | −6.380 | 1.498 | 55.156 | 1.00 | 12.17 |
| ATOM | 2297 | N | TYR | 238 | −8.355 | 1.809 | 54.128 | 1.00 | 9.53 |
| ATOM | 2298 | H | TYR | 238 | −9.205 | 1.398 | 53.859 | 1.00 | 0.00 |
| ATOM | 2299 | CA | TYR | 238 | −8.125 | 3.205 | 53.785 | 1.00 | 6.78 |
| ATOM | 2300 | CB | TYR | 238 | −9.226 | 3.674 | 52.835 | 1.00 | 5.11 |
| ATOM | 2301 | CG | TYR | 238 | −9.016 | 5.049 | 52.254 | 1.00 | 6.85 |
| ATOM | 2302 | CD1 | TYR | 238 | −8.241 | 5.232 | 51.112 | 1.00 | 6.52 |
| ATOM | 2303 | CE1 | TYR | 238 | −8.072 | 6.503 | 50.549 | 1.00 | 10.87 |
| ATOM | 2304 | CD2 | TYR | 238 | −9.619 | 6.169 | 52.830 | 1.00 | 9.19 |
| ATOM | 2305 | CE2 | TYR | 238 | −9.458 | 7.438 | 52.281 | 1.00 | 10.07 |
| ATOM | 2306 | CZ | TYR | 238 | −8.686 | 7.596 | 51.141 | 1.00 | 10.71 |
| ATOM | 2307 | OH | TYR | 238 | −8.540 | 8.843 | 50.592 | 1.00 | 14.33 |
| ATOM | 2308 | HH | TYR | 238 | −9.060 | 9.481 | 51.085 | 1.00 | 0.00 |
| ATOM | 2309 | C | TYR | 238 | −8.160 | 4.042 | 55.057 | 1.00 | 6.62 |
| ATOM | 2310 | O | TYR | 238 | −7.335 | 4.929 | 55.247 | 1.00 | 6.71 |
| ATOM | 2311 | N | LEU | 239 | −9.113 | 3.731 | 55.931 | 1.00 | 7.40 |
| ATOM | 2312 | H | LEU | 239 | −9.745 | 3.006 | 55.745 | 1.00 | 0.00 |
| ATOM | 2313 | CA | LEU | 239 | −9.276 | 4.443 | 57.191 | 1.00 | 9.62 |
| ATOM | 2314 | CB | LEU | 239 | −10.675 | 4.198 | 57.774 | 1.00 | 8.00 |
| ATOM | 2315 | CG | LEU | 239 | −11.814 | 4.773 | 56.918 | 1.00 | 8.26 |
| ATOM | 2316 | CD1 | LEU | 239 | −13.168 | 4.365 | 57.461 | 1.00 | 2.00 |
| ATOM | 2317 | CD2 | LEU | 239 | −11.696 | 6.285 | 56.865 | 1.00 | 6.62 |
| ATOM | 2318 | C | LEU | 239 | −8.170 | 4.092 | 58.187 | 1.00 | 11.33 |
| ATOM | 2319 | O | LEU | 239 | −8.076 | 4.689 | 59.261 | 1.00 | 11.19 |
| ATOM | 2320 | N | LYS | 240 | −7.360 | 3.091 | 57.848 | 1.00 | 12.90 |
| ATOM | 2321 | H | LYS | 240 | −7.552 | 2.545 | 57.064 | 1.00 | 0.00 |
| ATOM | 2322 | CA | LYS | 240 | −6.221 | 2.725 | 58.687 | 1.00 | 15.35 |
| ATOM | 2323 | CB | LYS | 240 | −5.709 | 1.326 | 58.368 | 1.00 | 12.42 |
| ATOM | 2324 | CG | LYS | 240 | −6.446 | 0.171 | 59.010 | 1.00 | 16.17 |
| ATOM | 2325 | CD | LYS | 240 | −5.570 | −1.069 | 58.865 | 1.00 | 18.37 |
| ATOM | 2326 | CE | LYS | 240 | −6.272 | −2.347 | 59.239 | 1.00 | 21.75 |
| ATOM | 2327 | NZ | LYS | 240 | −5.382 | −3.491 | 58.897 | 1.00 | 22.57 |
| ATOM | 2328 | HZ1 | LYS | 240 | −4.536 | −3.458 | 59.499 | 1.00 | 0.00 |
| ATOM | 2329 | HZ2 | LYS | 240 | −5.113 | −3.415 | 57.895 | 1.00 | 0.00 |
| ATOM | 2330 | HZ3 | LYS | 240 | −5.890 | −4.386 | 59.045 | 1.00 | 0.00 |
| ATOM | 2331 | C | LYS | 240 | −5.103 | 3.706 | 58.351 | 1.00 | 16.14 |
| ATOM | 2332 | O | LYS | 240 | −4.316 | 4.084 | 59.212 | 1.00 | 18.31 |
| ATOM | 2333 | N | LEU | 241 | −5.039 | 4.096 | 57.081 | 1.00 | 17.44 |
| ATOM | 2334 | H | LEU | 241 | −5.702 | 3.764 | 56.447 | 1.00 | 0.00 |
| ATOM | 2335 | CA | LEU | 241 | −4.023 | 5.015 | 56.584 | 1.00 | 20.78 |
| ATOM | 2336 | CB | LEU | 241 | −3.838 | 4.814 | 55.080 | 1.00 | 23.79 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2337 | CG  | LEU | 241 | −3.473  | 3.389  | 54.637 | 1.00 | 29.02 |
|------|------|-----|-----|-----|---------|--------|--------|------|-------|
| ATOM | 2338 | CD1 | LEU | 241 | −3.580  | 3.258  | 53.116 | 1.00 | 31.10 |
| ATOM | 2339 | CD2 | LEU | 241 | −2.072  | 3.023  | 55.123 | 1.00 | 29.32 |
| ATOM | 2340 | C   | LEU | 241 | −4.336  | 6.479  | 56.882 | 1.00 | 20.10 |
| ATOM | 2341 | O   | LEU | 241 | −3.430  | 7.271  | 57.127 | 1.00 | 22.00 |
| ATOM | 2342 | N   | LYS | 242 | −5.608  | 6.849  | 56.829 | 1.00 | 19.66 |
| ATOM | 2343 | H   | LYS | 242 | −6.313  | 6.208  | 56.582 | 1.00 | 0.00  |
| ATOM | 2344 | CA  | LYS | 242 | −5.996  | 8.224  | 57.114 | 1.00 | 19.53 |
| ATOM | 2345 | CB  | LYS | 242 | −5.892  | 9.082  | 55.844 | 1.00 | 22.06 |
| ATOM | 2346 | CG  | LYS | 242 | −6.778  | 8.639  | 54.688 | 1.00 | 24.44 |
| ATOM | 2347 | CD  | LYS | 242 | −6.367  | 9.308  | 53.386 | 1.00 | 24.79 |
| ATOM | 2348 | CE  | LYS | 242 | −5.120  | 8.664  | 52.808 | 1.00 | 23.03 |
| ATOM | 2349 | NZ  | LYS | 242 | −4.732  | 9.280  | 51.518 | 1.00 | 23.85 |
| ATOM | 2350 | HZ1 | LYS | 242 | −4.553  | 10.291 | 51.657 | 1.00 | 0.00  |
| ATOM | 2351 | HZ2 | LYS | 242 | −5.490  | 9.155  | 50.820 | 1.00 | 0.00  |
| ATOM | 2352 | HZ3 | LYS | 242 | −3.864  | 8.824  | 51.169 | 1.00 | 0.00  |
| ATOM | 2353 | C   | LYS | 242 | −7.395  | 8.279  | 57.716 | 1.00 | 16.00 |
| ATOM | 2354 | O   | LYS | 242 | −8.313  | 7.645  | 57.218 | 1.00 | 15.48 |
| ATOM | 2355 | N   | ALA | 243 | −7.540  | 9.047  | 58.793 | 1.00 | 18.41 |
| ATOM | 2356 | H   | ALA | 243 | −6.733  | 9.494  | 59.123 | 1.00 | 0.00  |
| ATOM | 2357 | CA  | ALA | 243 | −8.814  | 9.192  | 59.507 | 1.00 | 18.23 |
| ATOM | 2358 | CB  | ALA | 243 | −8.690  | 10.251 | 60.597 | 1.00 | 15.43 |
| ATOM | 2359 | C   | ALA | 243 | −10.018 | 9.497  | 58.620 | 1.00 | 18.79 |
| ATOM | 2360 | O   | ALA | 243 | −11.102 | 8.965  | 58.839 | 1.00 | 21.98 |
| ATOM | 2361 | N   | ASP | 244 | −9.834  | 10.408 | 57.669 | 1.00 | 18.70 |
| ATOM | 2362 | H   | ASP | 244 | −8.942  | 10.786 | 57.579 | 1.00 | 0.00  |
| ATOM | 2363 | CA  | ASP | 244 | −10.888 | 10.804 | 56.737 | 1.00 | 19.33 |
| ATOM | 2364 | CB  | ASP | 244 | −11.023 | 9.741  | 55.633 | 1.00 | 19.97 |
| ATOM | 2365 | CG  | ASP | 244 | −11.885 | 10.197 | 54.466 | 1.00 | 23.11 |
| ATOM | 2366 | OD1 | ASP | 244 | −12.653 | 9.359  | 53.958 | 1.00 | 27.17 |
| ATOM | 2367 | OD2 | ASP | 244 | −11.802 | 11.374 | 54.045 | 1.00 | 24.99 |
| ATOM | 2368 | C   | ASP | 244 | −12.245 | 11.108 | 57.402 | 1.00 | 19.28 |
| ATOM | 2369 | O   | ASP | 244 | −13.293 | 10.622 | 56.969 | 1.00 | 19.97 |
| ATOM | 2370 | N   | GLY | 245 | −12.219 | 11.934 | 58.445 | 1.00 | 19.45 |
| ATOM | 2371 | H   | GLY | 245 | −11.383 | 12.294 | 58.773 | 1.00 | 0.00  |
| ATOM | 2372 | CA  | GLY | 245 | −13.447 | 12.295 | 59.133 | 1.00 | 16.82 |
| ATOM | 2373 | C   | GLY | 245 | −13.591 | 11.656 | 60.499 | 1.00 | 15.03 |
| ATOM | 2374 | O   | GLY | 245 | −14.259 | 12.202 | 61.639 | 1.00 | 16.04 |
| ATOM | 2375 | N   | LEU | 246 | −13.000 | 10.482 | 60.676 | 1.00 | 13.51 |
| ATOM | 2376 | H   | LEU | 246 | −12.517 | 10.063 | 59.930 | 1.00 | 0.00  |
| ATOM | 2377 | CA  | LEU | 246 | −13.069 | 9.791  | 61.951 | 1.00 | 12.38 |
| ATOM | 2378 | CB  | LEU | 246 | −12.484 | 8.377  | 61.836 | 1.00 | 10.62 |
| ATOM | 2379 | CG  | LEU | 246 | −13.117 | 7.342  | 60.907 | 1.00 | 8.08  |
| ATOM | 2380 | CD1 | LEU | 246 | −12.370 | 6.037  | 61.059 | 1.00 | 7.46  |
| ATOM | 2381 | CD2 | LEU | 246 | −14.568 | 7.138  | 61.240 | 1.00 | 9.01  |
| ATOM | 2382 | C   | LEU | 246 | −12.311 | 10.576 | 63.019 | 1.00 | 12.72 |
| ATOM | 2383 | O   | LEU | 246 | −11.451 | 11.411 | 62.704 | 1.00 | 12.81 |
| ATOM | 2384 | N   | ILE | 247 | −12.627 | 10.288 | 64.279 | 1.00 | 13.47 |
| ATOM | 2385 | H   | ILE | 247 | −13.329 | 9.624  | 64.457 | 1.00 | 0.00  |
| ATOM | 2386 | CA  | ILE | 247 | −11.995 | 10.947 | 65.418 | 1.00 | 13.85 |
| ATOM | 2387 | CB  | ILE | 247 | −12.762 | 10.635 | 66.734 | 1.00 | 15.16 |
| ATOM | 2388 | CG2 | ILE | 247 | −12.608 | 9.163  | 67.118 | 1.00 | 12.79 |
| ATOM | 2389 | CG1 | ILE | 247 | −12.268 | 11.529 | 67.869 | 1.00 | 15.17 |
| ATOM | 2390 | CD  | ILE | 247 | −12.636 | 12.970 | 67.713 | 1.00 | 18.15 |
| ATOM | 2391 | C   | ILE | 247 | −10.542 | 10.502 | 65.550 | 1.00 | 15.68 |
| ATOM | 2392 | O   | ILE | 247 | −9.709  | 11.218 | 66.100 | 1.00 | 15.94 |
| ATOM | 2393 | N   | TYR | 248 | −10.244 | 9.320  | 65.020 | 1.00 | 17.12 |
| ATOM | 2394 | H   | TYR | 248 | −10.933 | 8.784  | 64.573 | 1.00 | 0.00  |
| ATOM | 2395 | CA  | TYR | 248 | −8.902  | 8.760  | 65.071 | 1.00 | 18.04 |
| ATOM | 2396 | CB  | TYR | 248 | −8.623  | 8.221  | 66.478 | 1.00 | 19.67 |
| ATOM | 2397 | CG  | TYR | 248 | −7.160  | 8.036  | 66.808 | 1.00 | 22.04 |
| ATOM | 2398 | CD1 | TYR | 248 | −6.666  | 6.795  | 67.194 | 1.00 | 21.97 |
| ATOM | 2399 | CE1 | TYR | 248 | −5.330  | 6.630  | 67.539 | 1.00 | 24.30 |
| ATOM | 2400 | CD2 | TYR | 248 | −6.277  | 9.113  | 66.770 | 1.00 | 25.29 |
| ATOM | 2401 | CE2 | TYR | 248 | −4.940  | 8.962  | 67.113 | 1.00 | 26.21 |
| ATOM | 2402 | CZ  | TYR | 248 | −4.471  | 7.720  | 67.498 | 1.00 | 26.00 |
| ATOM | 2403 | OH  | TYR | 248 | −3.147  | 7.572  | 67.853 | 1.00 | 27.81 |
| ATOM | 2404 | HH  | TYR | 248 | −2.695  | 8.422  | 67.810 | 1.00 | 0.00  |
| ATOM | 2405 | C   | TYR | 248 | −8.826  | 7.618  | 64.053 | 1.00 | 18.31 |
| ATOM | 2406 | O   | TYR | 248 | −9.839  | 6.992  | 63.737 | 1.00 | 15.87 |
| ATOM | 2407 | N   | CYS | 249 | −7.625  | 7.363  | 63.543 | 1.00 | 18.92 |
| ATOM | 2408 | H   | CYS | 249 | −6.862  | 7.889  | 63.852 | 1.00 | 0.00  |
| ATOM | 2409 | CA  | CYS | 249 | −7.402  | 6.305  | 62.651 | 1.00 | 22.24 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2410 | CB | CYS | 249 | −5.996 | 6.413 | 61.961 | 1.00 | 25.63 |
|---|---|---|---|---|---|---|---|---|---|
| ATOM | 2411 | SG | CYS | 249 | −5.786 | 7.763 | 60.701 | 1.00 | 35.34 |
| ATOM | 2412 | C | CYS | 249 | −7.554 | 4.915 | 63.162 | 1.00 | 21.45 |
| ATOM | 2413 | O | CYS | 249 | −7.292 | 4.709 | 64.350 | 1.00 | 22.48 |
| ATOM | 2414 | N | LEU | 250 | −7.940 | 3.963 | 62.321 | 1.00 | 19.48 |
| ATOM | 2415 | H | LEU | 250 | −8.101 | 4.207 | 61.383 | 1.00 | 0.00 |
| ATOM | 2416 | CA | LEU | 250 | −8.104 | 2.579 | 62.735 | 1.00 | 18.62 |
| ATOM | 2417 | CB | LEU | 250 | −8.828 | 1.801 | 61.643 | 1.00 | 14.55 |
| ATOM | 2418 | CG | LEU | 250 | −10.355 | 1.767 | 61.685 | 1.00 | 15.19 |
| ATOM | 2419 | CD1 | LEU | 250 | −10.924 | 2.936 | 62.474 | 1.00 | 15.11 |
| ATOM | 2420 | CD2 | LEU | 250 | −10.909 | 1.703 | 60.275 | 1.00 | 10.15 |
| ATOM | 2421 | C | LEU | 250 | −6.717 | 1.999 | 62.598 | 1.00 | 19.97 |
| ATOM | 2422 | O | LEU | 250 | −5.874 | 2.037 | 62.064 | 1.00 | 20.94 |
| ATOM | 2423 | N | LYS | 251 | −6.469 | 1.496 | 64.158 | 1.00 | 20.78 |
| ATOM | 2424 | H | LYS | 251 | −7.187 | 1.486 | 64.818 | 1.00 | 0.00 |
| ATOM | 2425 | CA | LYS | 251 | −5.167 | 0.937 | 64.479 | 1.00 | 22.81 |
| ATOM | 2426 | CB | LYS | 251 | −4.605 | 1.601 | 65.737 | 1.00 | 22.15 |
| ATOM | 2427 | CG | LYS | 251 | −4.299 | 3.082 | 65.586 | 1.00 | 27.38 |
| ATOM | 2428 | CD | LYS | 251 | −3.054 | 3.298 | 64.379 | 1.00 | 33.83 |
| ATOM | 2429 | CE | LYS | 251 | −2.720 | 4.776 | 64.587 | 1.00 | 36.07 |
| ATOM | 2430 | NZ | LYS | 251 | −3.778 | 5.512 | 63.835 | 1.00 | 39.79 |
| ATOM | 2431 | HZ1 | LYS | 251 | −4.678 | 5.441 | 64.346 | 1.00 | 0.00 |
| ATOM | 2432 | HZ2 | LYS | 251 | −3.889 | 5.099 | 62.891 | 1.00 | 0.00 |
| ATOM | 2433 | HZ3 | LYS | 251 | −3.501 | 6.511 | 63.746 | 1.00 | 0.00 |
| ATOM | 2434 | C | LYS | 251 | −5.217 | −0.574 | 64.657 | 1.00 | 24.22 |
| ATOM | 2435 | O | LYS | 251 | −5.026 | −1.329 | 63.703 | 1.00 | 27.36 |
| ATOM | 2436 | N | GLU | 252 | −5.516 | −1.013 | 65.871 | 1.00 | 24.92 |
| ATOM | 2437 | H | GLU | 252 | −5.766 | −0.390 | 66.588 | 1.00 | 0.00 |
| ATOM | 2438 | CA | GLU | 252 | −5.565 | −2.430 | 66.174 | 1.00 | 27.42 |
| ATOM | 2439 | CB | GLU | 252 | −5.012 | −2.671 | 67.577 | 1.00 | 32.86 |
| ATOM | 2440 | CG | GLU | 252 | −3.569 | −2.212 | 67.765 | 1.00 | 43.35 |
| ATOM | 2441 | CD | GLU | 252 | −3.268 | −1.746 | 69.186 | 1.00 | 49.35 |
| ATOM | 2442 | OE1 | GLU | 252 | −3.435 | −2.543 | 70.137 | 1.00 | 51.97 |
| ATOM | 2443 | OE2 | GLU | 252 | −2.858 | −0.575 | 69.348 | 1.00 | 50.94 |
| ATOM | 2444 | C | GLU | 252 | −6.978 | −2.977 | 66.071 | 1.00 | 26.08 |
| ATOM | 2445 | O | GLU | 252 | −7.929 | −2.360 | 66.550 | 1.00 | 25.56 |
| ATOM | 2446 | N | ALA | 253 | −7.108 | −4.132 | 65.432 | 1.00 | 24.39 |
| ATOM | 2447 | H | ALA | 253 | −6.318 | −4.560 | 65.066 | 1.00 | 0.00 |
| ATOM | 2448 | CA | ALA | 253 | −8.395 | −4.786 | 65.278 | 1.00 | 25.57 |
| ATOM | 2449 | CB | ALA | 253 | −8.343 | −5.756 | 64.123 | 1.00 | 24.04 |
| ATOM | 2450 | C | ALA | 253 | −8.747 | −5.537 | 66.555 | 1.00 | 27.38 |
| ATOM | 2451 | O | ALA | 253 | −7.876 | −6.121 | 67.194 | 1.00 | 27.58 |
| ATOM | 2452 | N | CYS | 254 | −10.014 | −5.479 | 66.949 | 1.00 | 31.53 |
| ATOM | 2453 | H | CYS | 254 | −10.650 | −4.969 | 66.417 | 1.00 | 0.00 |
| ATOM | 2454 | CA | CYS | 254 | −10.492 | −6.198 | 68.125 | 1.00 | 32.99 |
| ATOM | 2455 | CB | CYS | 254 | −11.780 | −5.561 | 68.652 | 1.00 | 33.76 |
| ATOM | 2456 | SG | CYS | 254 | −12.375 | −6.219 | 70.299 | 1.00 | 27.18 |
| ATOM | 2457 | C | CYS | 254 | −10.767 | −7.569 | 67.511 | 1.00 | 36.46 |
| ATOM | 2458 | O | CYS | 254 | −11.755 | −7.746 | 66.799 | 1.00 | 36.39 |
| ATOM | 2459 | N | PRO | 255 | −9.875 | −8.542 | 67.759 | 1.00 | 41.03 |
| ATOM | 2460 | CD | PRO | 255 | −8.830 | −8.385 | 68.790 | 1.00 | 42.01 |
| ATOM | 2461 | CA | PRO | 255 | −9.899 | −9.928 | 67.273 | 1.00 | 44.44 |
| ATOM | 2462 | CB | PRO | 255 | −8.601 | −10.493 | 67.840 | 1.00 | 45.11 |
| ATOM | 2463 | CG | PRO | 255 | −8.523 | −9.817 | 69.164 | 1.00 | 43.82 |
| ATOM | 2464 | C | PRO | 255 | −11.081 | −10.826 | 67.628 | 1.00 | 46.86 |
| ATOM | 2465 | O | PRO | 255 | −12.133 | −10.365 | 68.071 | 1.00 | 47.30 |
| ATOM | 2466 | N | ASN | 256 | −10.888 | −12.119 | 67.377 | 1.00 | 51.27 |
| ATOM | 2467 | H | ASN | 256 | −10.045 | −12.478 | 67.027 | 1.00 | 0.00 |
| ATOM | 2468 | CA | ASN | 256 | −11.871 | −13.161 | 67.655 | 1.00 | 53.98 |
| ATOM | 2469 | CB | ASN | 256 | −12.685 | −13.504 | 66.400 | 1.00 | 54.04 |
| ATOM | 2470 | CG | ASN | 256 | −13.596 | −12.375 | 65.964 | 1.00 | 53.84 |
| ATOM | 2471 | OD1 | ASN | 256 | −14.807 | −12.413 | 66.187 | 1.00 | 53.28 |
| ATOM | 2472 | ND2 | ASN | 256 | −13.021 | −11.366 | 65.336 | 1.00 | 52.61 |
| ATOM | 2473 | HD21 | ASN | 256 | −12.055 | −11.405 | 65.202 | 1.00 | 0.00 |
| ATOM | 2474 | HD22 | ASN | 256 | −13.555 | −10.623 | 65.004 | 1.00 | 0.00 |
| ATOM | 2475 | C | ASN | 256 | −11.085 | −14.393 | 68.105 | 1.00 | 55.88 |
| ATOM | 2476 | O | ASN | 256 | −11.316 | −14.859 | 69.241 | 1.00 | 56.61 |
| ATOM | 2477 | OT | ASN | 256 | −10.212 | −14.846 | 67.326 | 1.00 | 57.33 |
| ATOM | 2478 | C | GLY | 301 | −28.599 | 6.538 | 66.632 | 1.00 | 34.96 |
| ATOM | 2479 | O | GLY | 301 | −28.689 | 7.658 | 66.126 | 1.00 | 35.59 |
| ATOM | 2480 | HT1 | GLY | 301 | −29.755 | 6.289 | 64.304 | 1.00 | 0.00 |
| ATOM | 2481 | HT2 | GLY | 301 | −30.909 | 6.664 | 65.460 | 1.00 | 0.00 |
| ATOM | 2482 | N | GLY | 301 | −30.363 | 5.888 | 65.043 | 1.00 | 38.32 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2483 | HT3 | GLY | 301 | −30.941 | 5.100 | 64.692 | 1.00 | 0.00 |
|---|---|---|---|---|---|---|---|---|---|
| ATOM | 2484 | CA | GLY | 301 | −29.470 | 5.406 | 66.131 | 1.00 | 35.83 |
| ATOM | 2485 | N | LEU | 302 | −27.760 | 6.248 | 67.620 | 1.00 | 32.78 |
| ATOM | 2486 | H | LEU | 302 | −27.741 | 5.327 | 67.985 | 1.00 | 0.00 |
| ATOM | 2487 | CA | LEU | 302 | −26.861 | 7.240 | 68.203 | 1.00 | 28.83 |
| ATOM | 2488 | CB | LEU | 302 | −26.840 | 7.061 | 69.721 | 1.00 | 30.89 |
| ATOM | 2489 | CG | LEU | 302 | −26.726 | 8.304 | 70.601 | 1.00 | 35.75 |
| ATOM | 2490 | CD1 | LEU | 302 | −27.093 | 7.919 | 72.026 | 1.00 | 34.77 |
| ATOM | 2491 | CD2 | LEU | 302 | −25.328 | 8.914 | 70.520 | 1.00 | 36.69 |
| ATOM | 2492 | C | LEU | 302 | −25.465 | 7.028 | 67.613 | 1.00 | 24.31 |
| ATOM | 2493 | O | LEU | 302 | −24.620 | 6.352 | 68.205 | 1.00 | 22.95 |
| ATOM | 2494 | N | PTY | 303 | −25.236 | 7.580 | 66.427 | 1.00 | 20.12 |
| ATOM | 2495 | H | PTY | 303 | −25.916 | 8.143 | 65.984 | 1.00 | 0.00 |
| ATOM | 2496 | CA | PTY | 303 | −23.952 | 7.422 | 65.758 | 1.00 | 17.44 |
| ATOM | 2497 | CB | PTY | 303 | −24.137 | 6.739 | 64.399 | 1.00 | 15.28 |
| ATOM | 2498 | CG | PTY | 303 | −24.685 | 5.341 | 64.531 | 1.00 | 11.57 |
| ATOM | 2499 | CD1 | PTY | 303 | −23.836 | 4.247 | 64.652 | 1.00 | 14.15 |
| ATOM | 2500 | CE1 | PTY | 303 | −24.342 | 2.959 | 64.848 | 1.00 | 14.74 |
| ATOM | 2501 | CD2 | PTY | 303 | −26.053 | 5.121 | 64.602 | 1.00 | 14.21 |
| ATOM | 2502 | CE2 | PTY | 303 | −26.570 | 3.847 | 64.796 | 1.00 | 14.14 |
| ATOM | 2503 | CZ | PTY | 303 | −25.714 | 2.772 | 64.918 | 1.00 | 15.16 |
| ATOM | 2504 | OH | PTY | 303 | −26.257 | 1.519 | 65.078 | 1.00 | 16.76 |
| ATOM | 2505 | OR1 | PTY | 303 | −27.377 | 1.226 | 67.142 | 1.00 | 15.99 |
| ATOM | 2506 | OR2 | PTY | 303 | −24.983 | 1.051 | 67.202 | 1.00 | 15.90 |
| ATOM | 2507 | OR3 | PTY | 303 | −26.327 | −0.668 | 66.144 | 1.00 | 16.79 |
| ATOM | 2508 | PR | PTY | 303 | −26.181 | 0.776 | 66.437 | 1.00 | 13.90 |
| ATOM | 2509 | C | PTY | 303 | −23.217 | 8.735 | 65.605 | 1.00 | 16.36 |
| ATOM | 2510 | O | PTY | 303 | −23.831 | 9.795 | 65.484 | 1.00 | 19.96 |
| ATOM | 2511 | N | ASN | 304 | −21.895 | 8.660 | 65.620 | 1.00 | 15.34 |
| ATOM | 2512 | H | ASN | 304 | −21.498 | 7.781 | 65.684 | 1.00 | 0.00 |
| ATOM | 2513 | CA | ASN | 304 | −21.062 | 9.841 | 65.492 | 1.00 | 17.74 |
| ATOM | 2514 | CB | ASN | 304 | −19.676 | 9.569 | 66.078 | 1.00 | 17.48 |
| ATOM | 2515 | CG | ASN | 304 | −19.731 | 9.186 | 67.544 | 1.00 | 21.95 |
| ATOM | 2516 | OD1 | ASN | 304 | −19.541 | 10.024 | 68.421 | 1.00 | 25.74 |
| ATOM | 2517 | ND2 | ASN | 304 | −20.008 | 7.918 | 67.818 | 1.00 | 20.37 |
| ATOM | 2518 | HD21 | ASN | 304 | −20.117 | 7.310 | 67.059 | 1.00 | 0.00 |
| ATOM | 2519 | HD22 | ASN | 304 | −20.130 | 7.655 | 68.755 | 1.00 | 0.00 |
| ATOM | 2520 | C | ASN | 304 | −20.959 | 10.277 | 64.033 | 1.00 | 18.33 |
| ATOM | 2521 | O | ASN | 304 | −20.992 | 9.450 | 63.118 | 1.00 | 19.64 |
| ATOM | 2522 | N | GLU | 305 | −20.917 | 11.583 | 63.814 | 1.00 | 19.12 |
| ATOM | 2523 | H | GLU | 305 | −20.936 | 12.208 | 64.568 | 1.00 | 0.00 |
| ATOM | 2524 | CA | GLU | 305 | −20.802 | 12.114 | 62.463 | 1.00 | 22.88 |
| ATOM | 2525 | CB | GLU | 305 | −21.555 | 13.441 | 62.336 | 1.00 | 28.44 |
| ATOM | 2526 | CG | GLU | 305 | −23.071 | 13.318 | 62.315 | 1.00 | 37.99 |
| ATOM | 2527 | CD | GLU | 305 | −23.767 | 14.669 | 62.216 | 1.00 | 43.48 |
| ATOM | 2528 | OE1 | GLU | 305 | −24.877 | 14.800 | 62.775 | 1.00 | 46.82 |
| ATOM | 2529 | OE2 | GLU | 305 | −23.214 | 15.597 | 61.580 | 1.00 | 45.74 |
| ATOM | 2530 | C | GLU | 305 | −19.329 | 12.339 | 62.158 | 1.00 | 21.37 |
| ATOM | 2531 | O | GLU | 305 | −18.504 | 12.412 | 63.068 | 1.00 | 21.67 |
| ATOM | 2532 | N | LEU | 306 | −19.002 | 12.437 | 60.878 | 1.00 | 19.52 |
| ATOM | 2533 | H | LEU | 306 | −19.698 | 12.382 | 60.192 | 1.00 | 0.00 |
| ATOM | 2534 | CA | LEU | 306 | −17.628 | 12.667 | 60.469 | 1.00 | 17.30 |
| ATOM | 2535 | CB | LEU | 306 | −17.451 | 12.319 | 58.992 | 1.00 | 16.06 |
| ATOM | 2536 | CG | LEU | 306 | −17.537 | 10.838 | 58.627 | 1.00 | 12.83 |
| ATOM | 2537 | CD1 | LEU | 306 | −17.235 | 10.669 | 57.151 | 1.00 | 16.69 |
| ATOM | 2538 | CD2 | LEU | 306 | −16.555 | 10.040 | 59.462 | 1.00 | 10.12 |
| ATOM | 2539 | C | LEU | 306 | −17.251 | 14.119 | 60.706 | 1.00 | 17.36 |
| ATOM | 2540 | O | LEU | 306 | −18.070 | 15.014 | 60.519 | 1.00 | 17.26 |
| ATOM | 2541 | N | GLN | 307 | −16.019 | 14.341 | 61.147 | 1.00 | 18.44 |
| ATOM | 2542 | H | GLN | 307 | −15.442 | 13.576 | 61.304 | 1.00 | 0.00 |
| ATOM | 2543 | CA | GLN | 307 | −15.509 | 15.685 | 61.396 | 1.00 | 23.01 |
| ATOM | 2544 | CB | GLN | 307 | −14.187 | 15.618 | 62.167 | 1.00 | 25.06 |
| ATOM | 2545 | CG | GLN | 307 | −14.138 | 14.590 | 63.278 | 1.00 | 29.12 |
| ATOM | 2546 | CD | GLN | 307 | −14.549 | 15.148 | 64.618 | 1.00 | 30.60 |
| ATOM | 2547 | OE1 | GLN | 307 | −15.721 | 15.453 | 64.849 | 1.00 | 34.83 |
| ATOM | 2548 | NE2 | GLN | 307 | −13.583 | 15.285 | 65.517 | 1.00 | 31.12 |
| ATOM | 2549 | HE21 | GLN | 307 | −12.680 | 15.007 | 65.262 | 1.00 | 0.00 |
| ATOM | 2550 | HE22 | GLN | 307 | −13.830 | 15.662 | 66.384 | 1.00 | 0.00 |
| ATOM | 2551 | C | GLN | 307 | −15.219 | 16.248 | 60.017 | 1.00 | 24.16 |
| ATOM | 2552 | O | GLN | 307 | −14.087 | 16.149 | 59.546 | 1.00 | 20.19 |
| ATOM | 2553 | N | LYS | 308 | −16.245 | 16.781 | 59.354 | 1.00 | 30.35 |
| ATOM | 2554 | H | LYS | 308 | −17.125 | 16.772 | 59.791 | 1.00 | 0.00 |
| ATOM | 2555 | CA | LYS | 308 | −16.110 | 17.348 | 58.004 | 1.00 | 33.42 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2556 | CB   | LYS | 308 | −17.486 | 17.666 | 57.388 | 1.00 | 34.90 |
|------|------|------|-----|-----|---------|--------|--------|------|-------|
| ATOM | 2557 | CG   | LYS | 308 | −18.534 | 16.560 | 57.453 | 1.00 | 35.45 |
| ATOM | 2558 | CD   | LYS | 308 | −19.567 | 16.860 | 58.532 | 1.00 | 36.09 |
| ATOM | 2559 | CE   | LYS | 308 | −20.215 | 18.229 | 58.316 | 1.00 | 37.61 |
| ATOM | 2560 | NZ   | LYS | 308 | −21.196 | 18.594 | 59.391 | 1.00 | 37.36 |
| ATOM | 2561 | HZ1  | LYS | 308 | −20.771 | 18.602 | 60.310 | 1.00 | 0.00  |
| ATOM | 2562 | HZ2  | LYS | 308 | −21.961 | 17.891 | 59.403 | 1.00 | 0.00  |
| ATOM | 2563 | HZ3  | LYS | 308 | −21.589 | 19.535 | 59.193 | 1.00 | 0.00  |
| ATOM | 2564 | C    | LYS | 308 | −15.296 | 18.632 | 58.059 | 1.00 | 34.50 |
| ATOM | 2565 | O    | LYS | 308 | −15.720 | 19.675 | 57.561 | 1.00 | 36.22 |
| ATOM | 2566 | N    | ASP | 309 | −14.110 | 18.542 | 58.637 | 1.00 | 34.96 |
| ATOM | 2567 | H    | ASP | 309 | −13.714 | 17.697 | 58.867 | 1.00 | 0.00  |
| ATOM | 2568 | CA   | ASP | 309 | −13.247 | 19.684 | 58.786 | 1.00 | 40.11 |
| ATOM | 2569 | CB   | ASP | 309 | −13.833 | 20.653 | 59.825 | 1.00 | 43.76 |
| ATOM | 2570 | CG   | ASP | 309 | −12.937 | 21.857 | 60.076 | 1.00 | 49.11 |
| ATOM | 2571 | OD1  | ASP | 309 | −12.285 | 21.902 | 61.147 | 1.00 | 50.11 |
| ATOM | 2572 | OD2  | ASP | 309 | −12.878 | 22.752 | 59.198 | 1.00 | 53.22 |
| ATOM | 2573 | C    | ASP | 309 | −11.919 | 19.147 | 59.266 | 1.00 | 41.03 |
| ATOM | 2574 | O    | ASP | 309 | −11.021 | 18.889 | 58.468 | 1.00 | 42.47 |
| ATOM | 2575 | N    | LYS | 310 | −11.848 | 18.882 | 60.565 | 1.00 | 42.27 |
| ATOM | 2576 | H    | LYS | 310 | −12.637 | 19.008 | 61.117 | 1.00 | 0.00  |
| ATOM | 2577 | CA   | LYS | 310 | −10.634 | 18.385 | 61.192 | 1.00 | 43.52 |
| ATOM | 2578 | CB   | LYS | 310 | −10.941 | 17.848 | 62.595 | 1.00 | 42.96 |
| ATOM | 2579 | CG   | LYS | 310 | −11.586 | 18.868 | 63.525 | 1.00 | 42.02 |
| ATOM | 2580 | CD   | LYS | 310 | −11.779 | 18.312 | 64.933 | 1.00 | 41.98 |
| ATOM | 2581 | CE   | LYS | 310 | −10.445 | 18.138 | 65.654 | 1.00 | 41.82 |
| ATOM | 2582 | NZ   | LYS | 310 | −10.613 | 17.544 | 67.012 | 1.00 | 40.90 |
| ATOM | 2583 | HZ1  | LYS | 310 | −11.030 | 16.595 | 66.920 | 1.00 | 0.00  |
| ATOM | 2584 | HZ2  | LYS | 310 | −11.238 | 18.146 | 67.589 | 1.00 | 0.00  |
| ATOM | 2585 | HZ3  | LYS | 310 | −9.684  | 17.470 | 67.471 | 1.00 | 0.00  |
| ATOM | 2586 | C    | LYS | 310 | −9.895  | 17.331 | 60.372 | 1.00 | 43.43 |
| ATOM | 2587 | O    | LYS | 310 | −8.664  | 17.323 | 60.353 | 1.00 | 46.61 |
| ATOM | 2588 | N    | ARG | 311 | −10.629 | 16.461 | 59.680 | 1.00 | 42.01 |
| ATOM | 2589 | H    | ARG | 311 | −11.604 | 16.507 | 59.665 | 1.00 | 0.00  |
| ATOM | 2590 | CA   | ARG | 311 | −9.982  | 15.415 | 58.891 | 1.00 | 42.72 |
| ATOM | 2591 | CB   | ARG | 311 | −10.023 | 14.081 | 59.644 | 1.00 | 44.23 |
| ATOM | 2592 | CG   | ARG | 311 | −10.718 | 14.119 | 61.003 | 1.00 | 45.03 |
| ATOM | 2593 | CD   | ARG | 311 | −9.748  | 14.485 | 62.100 | 1.00 | 45.93 |
| ATOM | 2594 | NE   | ARG | 311 | −10.418 | 14.685 | 63.378 | 1.00 | 48.24 |
| ATOM | 2595 | HE   | ARG | 311 | −11.373 | 14.913 | 63.367 | 1.00 | 0.00  |
| ATOM | 2596 | CZ   | ARG | 311 | −9.818  | 14.577 | 64.561 | 1.00 | 51.76 |
| ATOM | 2597 | NH1  | ARG | 311 | −8.530  | 14.264 | 64.635 | 1.00 | 54.63 |
| ATOM | 2598 | HH11 | ARG | 311 | −7.990  | 14.102 | 63.808 | 1.00 | 0.00  |
| ATOM | 2599 | HH12 | ARG | 311 | −8.100  | 14.179 | 65.535 | 1.00 | 0.00  |
| ATOM | 2600 | NH2  | ARG | 311 | −10.503 | 14.798 | 65.675 | 1.00 | 53.00 |
| ATOM | 2601 | HH21 | ARG | 311 | −11.469 | 15.047 | 65.619 | 1.00 | 0.00  |
| ATOM | 2602 | HH22 | ARG | 311 | −10.059 | 14.715 | 66.567 | 1.00 | 0.00  |
| ATOM | 2603 | C    | ARG | 311 | −10.555 | 15.212 | 57.491 | 1.00 | 42.09 |
| ATOM | 2604 | O    | ARG | 311 | −11.725 | 14.856 | 57.346 | 1.00 | 40.29 |
| ATOM | 2605 | N    | ALA | 312 | −9.714  | 15.389 | 56.469 | 1.00 | 44.22 |
| ATOM | 2606 | H    | ALA | 312 | −8.797  | 15.704 | 56.637 | 1.00 | 0.00  |
| ATOM | 2607 | CA   | ALA | 312 | −10.130 | 15.204 | 55.077 | 1.00 | 45.11 |
| ATOM | 2608 | CB   | ALA | 312 | −11.440 | 15.947 | 54.818 | 1.00 | 46.77 |
| ATOM | 2609 | C    | ALA | 312 | −9.086  | 15.616 | 54.024 | 1.00 | 47.98 |
| ATOM | 2610 | O    | ALA | 312 | −8.221  | 16.462 | 54.283 | 1.00 | 50.03 |
| ATOM | 2611 | N    | GLU | 313 | −9.168  | 14.980 | 52.852 | 1.00 | 45.77 |
| ATOM | 2612 | H    | GLU | 313 | −9.890  | 14.332 | 52.717 | 1.00 | 0.00  |
| ATOM | 2613 | CA   | GLU | 313 | −8.306  | 15.252 | 51.693 | 1.00 | 43.28 |
| ATOM | 2614 | CB   | GLU | 313 | −7.513  | 14.005 | 51.283 | 1.00 | 46.48 |
| ATOM | 2615 | CG   | GLU | 313 | −6.297  | 13.659 | 52.143 | 1.00 | 46.91 |
| ATOM | 2616 | CD   | GLU | 313 | −5.519  | 12.454 | 51.605 | 1.00 | 46.04 |
| ATOM | 2617 | OE1  | GLU | 313 | −6.023  | 11.761 | 50.692 | 1.00 | 44.53 |
| ATOM | 2618 | OE2  | GLU | 313 | −4.397  | 12.198 | 52.097 | 1.00 | 45.88 |
| ATOM | 2619 | C    | GLU | 313 | −9.314  | 15.575 | 50.583 | 1.00 | 42.06 |
| ATOM | 2620 | O    | GLU | 313 | −10.513 | 15.680 | 50.869 | 1.00 | 45.47 |
| ATOM | 2621 | N    | ALA | 314 | −8.870  | 15.668 | 49.329 | 1.00 | 31.51 |
| ATOM | 2622 | H    | ALA | 314 | −7.925  | 15.544 | 49.104 | 1.00 | 0.00  |
| ATOM | 2623 | CA   | ALA | 314 | −9.801  | 15.967 | 48.239 | 1.00 | 27.16 |
| ATOM | 2624 | CB   | ALA | 314 | −10.156 | 17.447 | 48.238 | 1.00 | 25.68 |
| ATOM | 2625 | C    | ALA | 314 | −9.311  | 15.545 | 46.858 | 1.00 | 24.26 |
| ATOM | 2626 | O    | ALA | 314 | −8.204  | 15.896 | 46.447 | 1.00 | 26.34 |
| ATOM | 2627 | N    | PTY | 315 | −10.127 | 14.766 | 46.158 | 1.00 | 18.14 |
| ATOM | 2628 | H    | PTY | 315 | −11.001 | 14.528 | 46.522 | 1.00 | 0.00  |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2629 | CA  | PTY | 315 | −9.787  | 14.306 | 44.814 | 1.00 | 17.87 |
|------|------|-----|-----|-----|---------|--------|--------|------|-------|
| ATOM | 2630 | CB  | PTY | 315 | −10.410 | 12.934 | 44.531 | 1.00 | 16.23 |
| ATOM | 2631 | CG  | PTY | 315 | −9.653  | 11.782 | 45.147 | 1.00 | 13.44 |
| ATOM | 2632 | CD1 | PTY | 315 | −8.546  | 11.233 | 44.504 | 1.00 | 10.57 |
| ATOM | 2633 | CE1 | PTY | 315 | −7.821  | 10.199 | 45.083 | 1.00 | 12.46 |
| ATOM | 2634 | CD2 | PTY | 315 | −10.024 | 11.261 | 46.388 | 1.00 | 14.63 |
| ATOM | 2635 | CE2 | PTY | 315 | −9.308  | 10.226 | 46.977 | 1.00 | 12.19 |
| ATOM | 2636 | CZ  | PTY | 315 | −8.207  | 9.702  | 46.319 | 1.00 | 14.21 |
| ATOM | 2637 | OH  | PTY | 315 | −7.508  | 8.671  | 46.869 | 1.00 | 10.17 |
| ATOM | 2638 | OR1 | PTY | 315 | −6.491  | 9.535  | 48.913 | 1.00 | 12.42 |
| ATOM | 2639 | OR2 | PTY | 315 | −5.416  | 9.978  | 46.850 | 1.00 | 12.44 |
| ATOM | 2640 | OR3 | PTY | 315 | −5.389  | 7.728  | 47.750 | 1.00 | 8.98  |
| ATOM | 2641 | PR  | PTY | 315 | −6.156  | 8.991  | 47.608 | 1.00 | 11.81 |
| ATOM | 2642 | C   | PTY | 315 | −10.273 | 15.318 | 43.781 | 1.00 | 18.42 |
| ATOM | 2643 | O   | PTY | 315 | −11.328 | 15.928 | 43.950 | 1.00 | 18.97 |
| ATOM | 2644 | N   | SER | 316 | −9.500  | 15.502 | 42.718 | 1.00 | 18.72 |
| ATOM | 2645 | H   | SER | 316 | −8.700  | 14.957 | 42.602 | 1.00 | 0.00  |
| ATOM | 2646 | CA  | SER | 316 | −9.871  | 16.443 | 41.676 | 1.00 | 17.28 |
| ATOM | 2647 | CB  | SER | 316 | −8.642  | 16.849 | 40.874 | 1.00 | 16.40 |
| ATOM | 2648 | OG  | SER | 316 | −7.653  | 17.434 | 41.705 | 1.00 | 23.25 |
| ATOM | 2649 | HG  | SER | 316 | −7.610  | 16.969 | 42.563 | 1.00 | 0.00  |
| ATOM | 2650 | C   | SER | 316 | −10.895 | 15.799 | 40.762 | 1.00 | 17.80 |
| ATOM | 2651 | O   | SER | 316 | −11.065 | 14.581 | 40.763 | 1.00 | 18.76 |
| ATOM | 2652 | N   | GLU | 317 | −11.578 | 16.619 | 39.978 | 1.00 | 21.98 |
| ATOM | 2653 | H   | GLU | 317 | −11.430 | 17.585 | 39.995 | 1.00 | 0.00  |
| ATOM | 2654 | CA  | GLU | 317 | −12.577 | 16.113 | 39.048 | 1.00 | 26.81 |
| ATOM | 2655 | CB  | GLU | 317 | −13.956 | 16.070 | 39.718 | 1.00 | 28.26 |
| ATOM | 2656 | CG  | GLU | 317 | −14.954 | 15.164 | 39.010 | 1.00 | 34.96 |
| ATOM | 2657 | CD  | GLU | 317 | −16.232 | 14.947 | 39.803 | 1.00 | 40.11 |
| ATOM | 2658 | OE1 | GLU | 317 | −17.320 | 14.948 | 39.180 | 1.00 | 42.24 |
| ATOM | 2659 | OE2 | GLU | 317 | −16.153 | 14.763 | 41.041 | 1.00 | 42.30 |
| ATOM | 2660 | C   | GLU | 317 | −12.594 | 17.020 | 37.826 | 1.00 | 27.50 |
| ATOM | 2661 | O   | GLU | 317 | −12.160 | 18.170 | 37.908 | 1.00 | 28.44 |
| ATOM | 2662 | N   | ILE | 318 | −12.985 | 16.479 | 36.676 | 1.00 | 30.01 |
| ATOM | 2663 | H   | ILE | 318 | −13.247 | 15.532 | 36.647 | 1.00 | 0.00  |
| ATOM | 2664 | CA  | ILE | 318 | −13.052 | 17.287 | 35.463 | 1.00 | 32.57 |
| ATOM | 2665 | CB  | ILE | 318 | −12.991 | 16.428 | 34.176 | 1.00 | 31.13 |
| ATOM | 2666 | CG2 | ILE | 318 | −13.313 | 17.282 | 32.955 | 1.00 | 30.52 |
| ATOM | 2667 | CG1 | ILE | 318 | −11.598 | 15.824 | 34.009 | 1.00 | 29.07 |
| ATOM | 2668 | CD  | ILE | 318 | −11.436 | 15.012 | 32.736 | 1.00 | 29.47 |
| ATOM | 2669 | C   | ILE | 318 | −14.368 | 18.051 | 35.510 | 1.00 | 36.48 |
| ATOM | 2670 | O   | ILE | 318 | −15.438 | 17.474 | 35.299 | 1.00 | 37.22 |
| ATOM | 2671 | N   | GLY | 319 | −14.281 | 19.335 | 35.841 | 1.00 | 40.36 |
| ATOM | 2672 | H   | GLY | 319 | −13.427 | 19.760 | 36.061 | 1.00 | 0.00  |
| ATOM | 2673 | CA  | GLY | 319 | −15.461 | 20.174 | 35.922 | 1.00 | 45.03 |
| ATOM | 2674 | C   | GLY | 319 | −15.094 | 21.595 | 36.305 | 1.00 | 47.82 |
| ATOM | 2675 | O   | GLY | 319 | −14.951 | 22.445 | 35.395 | 1.00 | 50.47 |
| ATOM | 2676 | OT  | GLY | 319 | −14.941 | 21.860 | 37.516 | 1.00 | 49.68 |
| ATOM | 2677 | OH2 | H2O | 501 | −16.699 | 6.688  | 54.302 | 1.00 | 10.61 |
| ATOM | 2678 | H1  | H2O | 501 | −16.511 | 6.418  | 53.393 | 1.00 | 0.00  |
| ATOM | 2679 | H2  | H2O | 501 | −16.240 | 7.548  | 54.364 | 1.00 | 0.00  |
| ATOM | 2680 | OH2 | H2O | 502 | −7.254  | −1.610 | 48.935 | 1.00 | 17.08 |
| ATOM | 2681 | H1  | H2O | 502 | −6.444  | −2.072 | 49.204 | 1.00 | 0.00  |
| ATOM | 2682 | H2  | H2O | 502 | −7.404  | −0.987 | 49.670 | 1.00 | 0.00  |
| ATOM | 2683 | OH2 | H2O | 503 | −8.059  | 0.563  | 50.782 | 1.00 | 14.29 |
| ATOM | 2684 | H1  | H2O | 503 | −8.518  | 0.793  | 49.971 | 1.00 | 0.00  |
| ATOM | 2685 | H2  | H2O | 503 | −8.748  | 0.792  | 51.423 | 1.00 | 0.00  |
| ATOM | 2686 | OH2 | H2O | 504 | −6.332  | 5.449  | 46.114 | 1.00 | 17.64 |
| ATOM | 2687 | H1  | H2O | 504 | −5.403  | 5.611  | 45.858 | 1.00 | 0.00  |
| ATOM | 2688 | H2  | H2O | 504 | −6.621  | 6.329  | 46.396 | 1.00 | 0.00  |
| ATOM | 2689 | OH2 | H2O | 505 | −15.290 | −6.823 | 51.705 | 1.00 | 5.22  |
| ATOM | 2690 | H1  | H2O | 505 | −15.570 | −6.668 | 50.860 | 1.00 | 0.00  |
| ATOM | 2691 | H2  | H2O | 505 | −14.376 | −6.905 | 51.376 | 1.00 | 0.00  |
| ATOM | 2692 | OH2 | H2O | 506 | −7.617  | −1.501 | 46.161 | 1.00 | 17.32 |
| ATOM | 2693 | H1  | H2O | 506 | −7.518  | −1.538 | 47.137 | 1.00 | 0.00  |
| ATOM | 2694 | H2  | H2O | 506 | −6.696  | −1.494 | 45.885 | 1.00 | 0.00  |
| ATOM | 2695 | OH2 | H2O | 507 | −3.651  | 7.250  | 49.955 | 1.00 | 15.71 |
| ATOM | 2696 | H1  | H2O | 507 | −4.520  | 7.609  | 50.184 | 1.00 | 0.00  |
| ATOM | 2697 | H2  | H2O | 507 | −3.891  | 6.758  | 49.154 | 1.00 | 0.00  |
| ATOM | 2698 | OH2 | H2O | 508 | −19.945 | 3.732  | 76.340 | 1.00 | 29.44 |
| ATOM | 2699 | H1  | H2O | 508 | −20.832 | 3.744  | 75.964 | 1.00 | 0.00  |
| ATOM | 2700 | H2  | H2O | 508 | −19.954 | 4.642  | 76.685 | 1.00 | 0.00  |
| ATOM | 2701 | OH2 | H2O | 509 | 10.902  | 10.846 | 41.751 | 1.00 | 27.04 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2702 | H1  | H2O | 509 | 10.681  | 10.574  | 40.852 | 1.00 | 0.00  |
|------|------|-----|-----|-----|---------|---------|--------|------|-------|
| ATOM | 2703 | H2  | H2O | 509 | 10.412  | 11.675  | 41.818 | 1.00 | 0.00  |
| ATOM | 2704 | OH2 | H2O | 510 | −18.163 | −5.347  | 50.709 | 1.00 | 9.29  |
| ATOM | 2705 | H1  | H2O | 510 | −18.386 | −6.283  | 50.714 | 1.00 | 0.00  |
| ATOM | 2706 | H2  | H2O | 510 | −19.045 | −4.964  | 50.769 | 1.00 | 0.00  |
| ATOM | 2707 | OH2 | H2O | 511 | −3.361  | 4.879   | 45.414 | 1.00 | 16.59 |
| ATOM | 2708 | H1  | H2O | 511 | −3.647  | 4.007   | 45.146 | 1.00 | 0.00  |
| ATOM | 2709 | H2  | H2O | 511 | −2.506  | 4.681   | 45.802 | 1.00 | 0.00  |
| ATOM | 2710 | OH2 | H2O | 512 | −15.018 | 8.551   | 55.143 | 1.00 | 25.00 |
| ATOM | 2711 | H1  | H2O | 512 | −14.918 | 7.843   | 55.793 | 1.00 | 0.00  |
| ATOM | 2712 | H2  | H2O | 512 | −14.547 | 9.270   | 55.600 | 1.00 | 0.00  |
| ATOM | 2713 | OH2 | H2O | 513 | −4.825  | −3.898  | 46.077 | 1.00 | 26.22 |
| ATOM | 2714 | H1  | H2O | 513 | −4.880  | −3.377  | 46.901 | 1.00 | 0.00  |
| ATOM | 2715 | H2  | H2O | 513 | −4.485  | −3.251  | 45.428 | 1.00 | 0.00  |
| ATOM | 2716 | OH2 | H2O | 514 | −22.319 | 7.998   | 61.532 | 1.00 | 14.50 |
| ATOM | 2717 | H1  | H2O | 514 | −21.517 | 8.530   | 61.422 | 1.00 | 0.00  |
| ATOM | 2718 | H2  | H2O | 514 | −22.478 | 8.172   | 62.465 | 1.00 | 0.00  |
| ATOM | 2719 | OH2 | H2O | 515 | −10.803 | 5.341   | 41.005 | 1.00 | 25.05 |
| ATOM | 2720 | H1  | H2O | 515 | −10.171 | 5.135   | 40.303 | 1.00 | 0.00  |
| ATOM | 2721 | H2  | H2O | 515 | −10.270 | 5.263   | 41.804 | 1.00 | 0.00  |
| ATOM | 2722 | OH2 | H2O | 516 | 0.902   | 5.902   | 27.902 | 1.00 | 36.64 |
| ATOM | 2723 | H1  | H2O | 516 | 0.214   | 6.451   | 28.280 | 1.00 | 0.00  |
| ATOM | 2724 | H2  | H2O | 516 | 1.440   | 6.522   | 27.390 | 1.00 | 0.00  |
| ATOM | 2725 | OH2 | H2O | 517 | −4.715  | −2.823  | 48.594 | 1.00 | 17.95 |
| ATOM | 2726 | H1  | H2O | 517 | −4.476  | −1.913  | 48.357 | 1.00 | 0.00  |
| ATOM | 2727 | H2  | H2O | 517 | −3.933  | −3.025  | 49.141 | 1.00 | 0.00  |
| ATOM | 2728 | OH2 | H2O | 518 | −24.803 | 12.426  | 65.782 | 1.00 | 40.32 |
| ATOM | 2729 | H1  | H2O | 518 | −25.338 | 11.990  | 66.447 | 1.00 | 0.00  |
| ATOM | 2730 | H2  | H2O | 518 | −24.368 | 11.668  | 65.372 | 1.00 | 0.00  |
| ATOM | 2731 | OH2 | H2O | 519 | −7.490  | −3.895  | 44.639 | 1.00 | 17.54 |
| ATOM | 2732 | H1  | H2O | 519 | −7.799  | −3.087  | 45.072 | 1.00 | 0.00  |
| ATOM | 2733 | H2  | H2O | 519 | −6.561  | −3.711  | 44.492 | 1.00 | 0.00  |
| ATOM | 2734 | OH2 | H2O | 520 | −12.970 | 1.075   | 39.173 | 1.00 | 19.76 |
| ATOM | 2735 | H1  | H2O | 520 | −12.945 | 0.105   | 39.195 | 1.00 | 0.00  |
| ATOM | 2736 | H2  | H2O | 520 | −12.514 | 1.300   | 39.992 | 1.00 | 0.00  |
| ATOM | 2737 | OH2 | H2O | 521 | −11.261 | 10.026  | 31.185 | 1.00 | 20.36 |
| ATOM | 2738 | H1  | H2O | 521 | −11.026 | 10.800  | 30.672 | 1.00 | 0.00  |
| ATOM | 2739 | H2  | H2O | 521 | −11.878 | 9.547   | 30.622 | 1.00 | 0.00  |
| ATOM | 2740 | OH2 | H2O | 522 | −16.253 | 9.623   | 47.575 | 1.00 | 22.54 |
| ATOM | 2741 | H1  | H2O | 522 | −16.330 | 10.315  | 46.911 | 1.00 | 0.00  |
| ATOM | 2742 | H2  | H2O | 522 | −16.945 | 9.935   | 48.191 | 1.00 | 0.00  |
| ATOM | 2743 | OH2 | H2O | 523 | −13.184 | −18.559 | 49.110 | 1.00 | 32.97 |
| ATOM | 2744 | H1  | H2O | 523 | −13.959 | −18.613 | 48.452 | 1.00 | 0.00  |
| ATOM | 2745 | H2  | H2O | 523 | −12.455 | −18.533 | 48.480 | 1.00 | 0.00  |
| ATOM | 2746 | OH2 | H2O | 524 | 6.370   | 1.830   | 43.428 | 1.00 | 20.14 |
| ATOM | 2747 | H1  | H2O | 524 | 5.423   | 1.688   | 43.475 | 1.00 | 0.00  |
| ATOM | 2748 | H2  | H2O | 524 | 6.738   | 0.978   | 43.159 | 1.00 | 0.00  |
| ATOM | 2749 | OH2 | H2O | 525 | −8.942  | 6.660   | 44.772 | 1.00 | 32.99 |
| ATOM | 2750 | H1  | H2O | 525 | −8.594  | 7.220   | 44.081 | 1.00 | 0.00  |
| ATOM | 2751 | H2  | H2O | 525 | −8.778  | 7.191   | 45.563 | 1.00 | 0.00  |
| ATOM | 2752 | OH2 | H2O | 526 | −15.180 | 4.706   | 44.777 | 1.00 | 35.71 |
| ATOM | 2753 | H1  | H2O | 526 | −15.373 | 4.421   | 45.677 | 1.00 | 0.00  |
| ATOM | 2754 | H2  | H2O | 526 | −14.575 | 5.433   | 44.939 | 1.00 | 0.00  |
| ATOM | 2755 | OH2 | H2O | 527 | 4.557   | 22.831  | 38.913 | 1.00 | 25.19 |
| ATOM | 2756 | H1  | H2O | 527 | 4.963   | 22.258  | 38.254 | 1.00 | 0.00  |
| ATOM | 2757 | H2  | H2O | 527 | 5.249   | 22.752  | 39.588 | 1.00 | 0.00  |
| ATOM | 2758 | OH2 | H2O | 528 | 0.327   | −18.441 | 40.849 | 1.00 | 63.62 |
| ATOM | 2759 | H1  | H2O | 528 | 0.588   | −18.051 | 40.013 | 1.00 | 0.00  |
| ATOM | 2760 | H2  | H2O | 528 | −0.242  | −17.781 | 41.246 | 1.00 | 0.00  |
| ATOM | 2761 | OH2 | H2O | 529 | 6.903   | 14.794  | 51.066 | 1.00 | 29.24 |
| ATOM | 2762 | H1  | H2O | 529 | 7.219   | 15.307  | 50.322 | 1.00 | 0.00  |
| ATOM | 2763 | H2  | H2O | 529 | 5.950   | 14.776  | 50.943 | 1.00 | 0.00  |
| ATOM | 2764 | OH2 | H2O | 530 | −7.974  | −1.103  | 42.817 | 1.00 | 34.83 |
| ATOM | 2765 | H1  | H2O | 530 | −7.354  | −0.435  | 43.127 | 1.00 | 0.00  |
| ATOM | 2766 | H2  | H2O | 530 | −8.438  | −1.272  | 43.650 | 1.00 | 0.00  |
| ATOM | 2767 | OH2 | H2O | 531 | −21.992 | 6.566   | 69.376 | 1.00 | 33.58 |
| ATOM | 2768 | H1  | H2O | 531 | −22.876 | 6.479   | 68.981 | 1.00 | 0.00  |
| ATOM | 2769 | H2  | H2O | 531 | −22.202 | 7.118   | 70.144 | 1.00 | 0.00  |
| ATOM | 2770 | OH2 | H2O | 532 | −0.211  | −0.329  | 27.193 | 1.00 | 35.34 |
| ATOM | 2771 | H1  | H2O | 532 | −1.107  | −0.247  | 27.545 | 1.00 | 0.00  |
| ATOM | 2772 | H2  | H2O | 532 | −0.184  | 0.393   | 26.558 | 1.00 | 0.00  |
| ATOM | 2773 | OH2 | H2O | 533 | −14.231 | 14.927  | 55.731 | 1.00 | 22.94 |
| ATOM | 2774 | H1  | H2O | 533 | −14.283 | 14.056  | 55.341 | 1.00 | 0.00  |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2775 | H2  | H2O | 533 | −13.463 | 14.883  | 56.317 | 1.00 | 0.00  |
|------|------|-----|-----|-----|---------|---------|--------|------|-------|
| ATOM | 2776 | OH2 | H2O | 535 | −24.946 | −4.13   | 65.364 | 1.00 | 21.19 |
| ATOM | 2777 | H1  | H2O | 535 | −24.728 | −4.688  | 64.466 | 1.00 | 0.00  |
| ATOM | 2778 | H2  | H2O | 535 | −24.390 | −5.033  | 65.854 | 1.00 | 0.00  |
| ATOM | 2779 | OH2 | H2O | 536 | −25.179 | −8.028  | 64.357 | 1.00 | 22.68 |
| ATOM | 2780 | H1  | H2O | 536 | −25.799 | −8.497  | 63.785 | 1.00 | 0.00  |
| ATOM | 2781 | H2  | H2O | 536 | −24.887 | −7.298  | 63.794 | 1.00 | 0.00  |
| ATOM | 2782 | OH2 | H2O | 537 | −1.848  | 9.665   | 51.881 | 1.00 | 19.01 |
| ATOM | 2783 | H1  | H2O | 537 | −2.268  | 8.825   | 51.657 | 1.00 | 0.00  |
| ATOM | 2784 | H2  | H2O | 537 | −2.023  | 9.739   | 52.829 | 1.00 | 0.00  |
| ATOM | 2785 | OH2 | H2O | 538 | −20.606 | −24.004 | 46.721 | 1.00 | 48.06 |
| ATOM | 2786 | H1  | H2O | 538 | −19.935 | −24.681 | 46.905 | 1.00 | 0.00  |
| ATOM | 2787 | H2  | H2O | 538 | −21.387 | −24.399 | 47.126 | 1.00 | 0.00  |
| ATOM | 2788 | OH2 | H2O | 539 | −6.036  | −10.488 | 42.753 | 1.00 | 24.63 |
| ATOM | 2789 | H1  | H2O | 539 | −6.570  | −11.253 | 42.552 | 1.00 | 0.00  |
| ATOM | 2790 | H2  | H2O | 539 | −5.637  | −10.712 | 43.597 | 1.00 | 0.00  |
| ATOM | 2791 | OH2 | H2O | 540 | −20.360 | 12.924  | 50.060 | 1.00 | 44.45 |
| ATOM | 2792 | H1  | H2O | 540 | −20.542 | 13.863  | 50.173 | 1.00 | 0.00  |
| ATOM | 2793 | H2  | H2O | 540 | −20.438 | 12.583  | 50.953 | 1.00 | 0.00  |
| ATOM | 2794 | OH2 | H2O | 541 | −5.385  | −8.053  | 62.249 | 1.00 | 38.68 |
| ATOM | 2795 | H1  | H2O | 541 | −5.543  | −7.543  | 63.043 | 1.00 | 0.00  |
| ATOM | 2796 | H2  | H2O | 541 | −5.697  | −7.436  | 61.567 | 1.00 | 0.00  |
| ATOM | 2797 | OH2 | H2O | 542 | −0.772  | 18.789  | 49.390 | 1.00 | 42.13 |
| ATOM | 2798 | H1  | H2O | 542 | −1.284  | 18.533  | 50.147 | 1.00 | 0.00  |
| ATOM | 2799 | H2  | H2O | 542 | −1.010  | 18.089  | 48.776 | 1.00 | 0.00  |
| ATOM | 2800 | OH2 | H2O | 543 | 5.290   | 26.308  | 37.785 | 1.00 | 44.00 |
| ATOM | 2801 | H1  | H2O | 543 | 5.875   | 26.038  | 38.496 | 1.00 | 0.00  |
| ATOM | 2802 | H2  | H2O | 543 | 5.853   | 26.326  | 37.011 | 1.00 | 0.00  |
| ATOM | 2803 | OH2 | H2O | 544 | −13.634 | −13.651 | 50.337 | 1.00 | 32.32 |
| ATOM | 2804 | H1  | H2O | 544 | −13.622 | −14.594 | 50.588 | 1.00 | 0.00  |
| ATOM | 2805 | H2  | H2O | 544 | −14.365 | −13.576 | 49.736 | 1.00 | 0.00  |
| ATOM | 2806 | OH2 | H2O | 545 | 6.675   | 4.419   | 46.648 | 1.00 | 30.02 |
| ATOM | 2807 | H1  | H2O | 545 | 7.290   | 4.690   | 47.341 | 1.00 | 0.00  |
| ATOM | 2808 | H2  | H2O | 545 | 6.944   | 3.519   | 46.428 | 1.00 | 0.00  |
| ATOM | 2809 | OH2 | H2O | 546 | −19.308 | 6.081   | 75.052 | 1.00 | 51.03 |
| ATOM | 2810 | H1  | H2O | 546 | −19.538 | 6.138   | 74.117 | 1.00 | 0.00  |
| ATOM | 2811 | H2  | H2O | 546 | −18.372 | 5.871   | 75.036 | 1.00 | 0.00  |
| ATOM | 2812 | OH2 | H2O | 547 | −0.121  | 9.589   | 22.739 | 1.00 | 39.87 |
| ATOM | 2813 | H1  | H2O | 547 | 0.690   | 10.066  | 22.559 | 1.00 | 0.00  |
| ATOM | 2814 | H2  | H2O | 547 | −0.740  | 10.279  | 23.010 | 1.00 | 0.00  |
| ATOM | 2815 | OH2 | H2O | 549 | −21.186 | −9.641  | 52.393 | 1.00 | 33.61 |
| ATOM | 2816 | H1  | H2O | 549 | −21.706 | −9.261  | 51.676 | 1.00 | 0.00  |
| ATOM | 2817 | H2  | H2O | 549 | −20.925 | −10.499 | 52.022 | 1.00 | 0.00  |
| ATOM | 2818 | OH2 | H2O | 550 | −19.368 | −9.513  | 74.224 | 1.00 | 42.38 |
| ATOM | 2819 | H1  | H2O | 550 | −19.314 | −8.555  | 74.189 | 1.00 | 0.00  |
| ATOM | 2820 | H2  | H2O | 550 | −18.853 | −9.794  | 73.467 | 1.00 | 0.00  |
| ATOM | 2821 | OH2 | H2O | 551 | −29.465 | 1.964   | 65.682 | 1.00 | 30.82 |
| ATOM | 2822 | H1  | H2O | 551 | −28.568 | 1.698   | 65.445 | 1.00 | 0.00  |
| ATOM | 2823 | H2  | H2O | 551 | −29.959 | 1.156   | 65.517 | 1.00 | 0.00  |
| ATOM | 2824 | OH2 | H2O | 552 | −11.132 | −14.092 | 61.004 | 1.00 | 44.69 |
| ATOM | 2825 | H1  | H2O | 552 | −11.162 | −13.825 | 60.080 | 1.00 | 0.00  |
| ATOM | 2826 | H2  | H2O | 552 | −10.792 | −14.983 | 60.930 | 1.00 | 0.00  |
| ATOM | 2827 | OH2 | H2O | 553 | 15.549  | 7.780   | 43.275 | 1.00 | 41.22 |
| ATOM | 2828 | H1  | H2O | 553 | 16.001  | 7.569   | 42.453 | 1.00 | 0.00  |
| ATOM | 2829 | H2  | H2O | 553 | 15.451  | 8.759   | 43.198 | 1.00 | 0.00  |
| ATOM | 2830 | OH2 | H2O | 554 | −6.955  | −6.005  | 57.945 | 1.00 | 42.99 |
| ATOM | 2831 | H1  | H2O | 554 | −6.261  | −6.655  | 58.193 | 1.00 | 0.00  |
| ATOM | 2832 | H2  | H2O | 554 | −6.769  | −5.912  | 57.007 | 1.00 | 0.00  |
| ATOM | 2833 | OH2 | H2O | 555 | −26.977 | −3.406  | 67.817 | 1.00 | 32.14 |
| ATOM | 2834 | H1  | H2O | 555 | −26.901 | −2.533  | 67.411 | 1.00 | 0.00  |
| ATOM | 2835 | H2  | H2O | 555 | −26.567 | −3.960  | 67.122 | 1.00 | 0.00  |
| ATOM | 2836 | OH2 | H2O | 556 | −28.411 | −2.810  | 64.708 | 1.00 | 30.05 |
| ATOM | 2837 | H1  | H2O | 556 | −28.703 | −3.042  | 65.597 | 1.00 | 0.00  |
| ATOM | 2838 | H2  | H2O | 556 | −27.572 | −2.359  | 64.889 | 1.00 | 0.00  |
| ATOM | 2839 | OH2 | H2O | 557 | −3.769  | 0.192   | 55.470 | 1.00 | 36.92 |
| ATOM | 2840 | H1  | H2O | 557 | −3.997  | 0.505   | 54.588 | 1.00 | 0.00  |
| ATOM | 2841 | H2  | H2O | 557 | −4.594  | 0.325   | 55.939 | 1.00 | 0.00  |
| ATOM | 2842 | OH2 | H2O | 558 | −18.369 | 11.227  | 49.122 | 1.00 | 40.83 |
| ATOM | 2843 | H1  | H2O | 558 | −19.062 | 11.911  | 49.168 | 1.00 | 0.00  |
| ATOM | 2844 | H2  | H2O | 558 | −18.590 | 10.704  | 49.898 | 1.00 | 0.00  |
| ATOM | 2845 | OH2 | H2O | 559 | −5.557  | 1.430   | 51.259 | 1.00 | 37.40 |
| ATOM | 2846 | H1  | H2O | 559 | −6.379  | 0.902   | 51.227 | 1.00 | 0.00  |
| ATOM | 2847 | H2  | H2O | 559 | −5.811  | 2.195   | 50.750 | 1.00 | 0.00  |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2848 | OH2 | H2O | 560 | −1.244  | −1.789  | 50.252 | 1.00 | 42.03 |
|------|------|-----|-----|-----|---------|---------|--------|------|-------|
| ATOM | 2849 | H1  | H2O | 560 | −1.114  | −2.419  | 49.540 | 1.00 | 0.00  |
| ATOM | 2850 | H2  | H2O | 560 | −0.486  | −1.214  | 50.163 | 1.00 | 0.00  |
| ATOM | 2851 | OH2 | H2O | 561 | −13.464 | −16.412 | 50.896 | 1.00 | 40.41 |
| ATOM | 2852 | H1  | H2O | 561 | −13.891 | −17.167 | 51.134 | 1.00 | 0.00  |
| ATOM | 2853 | H2  | H2O | 561 | −12.907 | −16.874 | 50.251 | 1.00 | 0.00  |
| ATOM | 2854 | OH2 | H2O | 563 | 8.297   | 7.021   | 48.013 | 1.00 | 45.26 |
| ATOM | 2855 | H1  | H2O | 563 | 9.916   | 6.664   | 48.079 | 1.00 | 0.00  |
| ATOM | 2856 | H2  | H2O | 563 | 8.400   | 7.891   | 48.412 | 1.00 | 0.00  |
| ATOM | 2857 | OH2 | H2O | 569 | −18.672 | 9.411   | 70.985 | 1.00 | 42.69 |
| ATOM | 2858 | H1  | H2O | 569 | −18.454 | 10.301  | 70.720 | 1.00 | 0.00  |
| ATOM | 2859 | H2  | H2O | 569 | −19.299 | 9.181   | 70.297 | 1.00 | 0.00  |
| ATOM | 2860 | OH2 | H2O | 570 | −4.013  | 16.605  | 50.811 | 1.00 | 50.36 |
| ATOM | 2861 | H1  | H2O | 570 | −3.642  | 15.998  | 51.464 | 1.00 | 0.00  |
| ATOM | 2862 | H2  | H2O | 570 | −4.727  | 17.023  | 51.309 | 1.00 | 0.00  |
| ATOM | 2863 | OH2 | H2O | 572 | −6.268  | 16.662  | 44.180 | 1.00 | 24.25 |
| ATOM | 2864 | H1  | H2O | 572 | −6.777  | 16.796  | 45.000 | 1.00 | 0.00  |
| ATOM | 2865 | H2  | H2O | 572 | −5.615  | 17.379  | 44.261 | 1.00 | 0.00  |
| ATOM | 2866 | OH2 | H2O | 573 | −18.387 | −26.644 | 47.160 | 1.00 | 49.62 |
| ATOM | 2867 | H1  | H2O | 573 | −17.586 | −26.570 | 46.621 | 1.00 | 0.00  |
| ATOM | 2868 | H2  | H2O | 573 | −18.382 | −27.600 | 47.318 | 1.00 | 0.00  |
| ATOM | 2869 | OH2 | H2O | 574 | −11.225 | −10.882 | 43.386 | 1.00 | 28.82 |
| ATOM | 2870 | H1  | H2O | 574 | −12.100 | −10.489 | 43.454 | 1.00 | 0.00  |
| ATOM | 2871 | H2  | H2O | 574 | −11.400 | −11.765 | 43.056 | 1.00 | 0.00  |
| ATOM | 2872 | OH2 | H2O | 575 | −7.241  | 6.911   | 24.257 | 1.00 | 46.54 |
| ATOM | 2873 | H1  | H2O | 575 | −6.378  | 7.294   | 24.478 | 1.00 | 0.00  |
| ATOM | 2874 | H2  | H2O | 575 | −7.127  | 6.659   | 23.334 | 1.00 | 0.00  |
| ATOM | 2875 | OH2 | H2O | 576 | −2.732  | 3.489   | 69.646 | 1.00 | 35.00 |
| ATOM | 2876 | H1  | H2O | 576 | −2.509  | 3.272   | 68.740 | 1.00 | 0.00  |
| ATOM | 2877 | H2  | H2O | 576 | −3.201  | 4.317   | 69.547 | 1.00 | 0.00  |
| ATOM | 2878 | OH2 | H2O | 577 | −1.004  | −5.395  | 42.848 | 1.00 | 31.83 |
| ATOM | 2879 | H1  | H2O | 577 | −1.718  | −5.183  | 42.244 | 1.00 | 0.00  |
| ATOM | 2880 | H2  | H2O | 577 | −0.242  | −5.437  | 42.261 | 1.00 | 0.00  |
| ATOM | 2881 | OH2 | H2O | 579 | 2.618   | 6.038   | 53.054 | 1.00 | 53.16 |
| ATOM | 2882 | H1  | H2O | 579 | 2.206   | 5.196   | 53.266 | 1.00 | 0.00  |
| ATOM | 2883 | H2  | H2O | 579 | 3.530   | 5.782   | 52.875 | 1.00 | 0.00  |
| ATOM | 2884 | OH2 | H2O | 580 | −3.109  | 1.708   | 61.212 | 1.00 | 32.77 |
| ATOM | 2885 | H1  | H2O | 580 | −4.013  | 1.787   | 61.547 | 1.00 | 0.00  |
| ATOM | 2886 | H2  | H2O | 580 | −3.145  | 2.263   | 60.427 | 1.00 | 0.00  |
| ATOM | 2887 | OH2 | H2O | 581 | −15.517 | 7.216   | 36.498 | 1.00 | 45.24 |
| ATOM | 2888 | H1  | H2O | 581 | −14.609 | 7.036   | 36.239 | 1.00 | 0.00  |
| ATOM | 2889 | H2  | H2O | 581 | −15.977 | 6.404   | 36.259 | 1.00 | 0.00  |
| ATOM | 2890 | OH2 | H2O | 582 | 4.831   | 21.847  | 47.571 | 1.00 | 53.78 |
| ATOM | 2891 | H1  | H2O | 582 | 5.295   | 22.312  | 46.821 | 1.00 | 0.00  |
| ATOM | 2892 | H2  | H2O | 582 | 5.264   | 20.951  | 47.474 | 1.00 | 0.00  |
| ATOM | 2893 | OH2 | H2O | 583 | −7.370  | −2.505  | 28.449 | 1.00 | 43.85 |
| ATOM | 2894 | H1  | H2O | 583 | −7.859  | −2.031  | 27.773 | 1.00 | 0.00  |
| ATOM | 2895 | H2  | H2O | 583 | −8.070  | −2.637  | 29.095 | 1.00 | 0.00  |
| ATOM | 2896 | OH2 | H2O | 584 | 11.021  | 8.553   | 47.239 | 1.00 | 55.00 |
| ATOM | 2897 | H1  | H2O | 584 | 11.035  | 9.388   | 47.727 | 1.00 | 0.00  |
| ATOM | 2898 | H2  | H2O | 584 | 11.358  | 8.841   | 46.355 | 1.00 | 0.00  |
| ATOM | 2899 | OH2 | H2O | 585 | −13.463 | 4.859   | 41.287 | 1.00 | 51.26 |
| ATOM | 2900 | H1  | H2O | 585 | −13.800 | 5.285   | 42.041 | 1.00 | 0.00  |
| ATOM | 2901 | H2  | H2O | 585 | −12.578 | 5.274   | 41.218 | 1.00 | 0.00  |
| ATOM | 2902 | OH2 | H2O | 586 | −21.459 | −21.141 | 46.452 | 1.00 | 38.96 |
| ATOM | 2903 | H1  | H2O | 586 | −20.860 | −20.849 | 47.150 | 1.00 | 0.00  |
| ATOM | 2904 | H2  | H2O | 586 | −21.155 | −22.070 | 46.466 | 1.00 | 0.00  |
| ATOM | 2905 | OH2 | H2O | 587 | 9.552   | 9.085   | 29.404 | 1.00 | 21.31 |
| ATOM | 2906 | H1  | H2O | 587 | 10.017  | 9.328   | 28.595 | 1.00 | 0.00  |
| ATOM | 2907 | H2  | H2O | 587 | 8.874   | 8.487   | 29.061 | 1.00 | 0.00  |
| ATOM | 2908 | OH2 | H2O | 588 | −18.589 | 16.079  | 53.026 | 1.00 | 47.95 |
| ATOM | 2909 | H1  | H2O | 588 | −17.885 | 16.496  | 53.527 | 1.00 | 0.00  |
| ATOM | 2910 | H2  | H2O | 588 | −18.406 | 15.135  | 53.154 | 1.00 | 0.00  |
| ATOM | 2911 | OH2 | H2O | 589 | 11.877  | 9.205   | 44.689 | 1.00 | 37.00 |
| ATOM | 2912 | H1  | H2O | 589 | 12.160  | 9.585   | 43.847 | 1.00 | 0.00  |
| ATOM | 2913 | H2  | H2O | 589 | 12.543  | 8.490   | 44.824 | 1.00 | 0.00  |
| ATOM | 2914 | OH2 | H2O | 592 | −26.188 | −5.587  | 57.097 | 1.00 | 33.07 |
| ATOM | 2915 | H1  | H2O | 592 | −26.971 | −5.989  | 57.502 | 1.00 | 0.00  |
| ATOM | 2916 | H2  | H2O | 592 | −26.094 | −4.777  | 57.619 | 1.00 | 0.00  |
| ATOM | 2917 | OH2 | H2O | 593 | −12.898 | 10.911  | 38.656 | 1.00 | 46.97 |
| ATOM | 2918 | H1  | H2O | 593 | −12.354 | 10.108  | 38.666 | 1.00 | 0.00  |
| ATOM | 2919 | H2  | H2O | 593 | −13.273 | 10.940  | 39.540 | 1.00 | 0.00  |
| ATOM | 2920 | OH2 | H2O | 594 | −2.882  | 16.968  | 48.295 | 1.00 | 30.83 |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2921 | H1  | H2O | 594 | -3.396  | 17.749  | 48.079 | 1.00 | 0.00  |
|------|------|-----|-----|-----|---------|---------|--------|------|-------|
| ATOM | 2922 | H2  | H2O | 594 | -3.313  | 16.697  | 49.134 | 1.00 | 0.00  |
| ATOM | 2923 | OH2 | H2O | 595 | 13.656  | 7.244   | 45.221 | 1.00 | 39.29 |
| ATOM | 2924 | H1  | H2O | 595 | 14.189  | 7.235   | 44.397 | 1.00 | 0.00  |
| ATOM | 2925 | H2  | H2O | 595 | 14.368  | 7.167   | 45.864 | 1.00 | 0.00  |
| ATOM | 2926 | OH2 | H2O | 596 | 10.754  | 5.887   | 46.780 | 1.00 | 58.01 |
| ATOM | 2927 | H1  | H2O | 596 | 10.942  | 6.831   | 46.995 | 1.00 | 0.00  |
| ATOM | 2928 | H2  | H2O | 596 | 11.653  | 5.535   | 46.772 | 1.00 | 0.00  |
| ATOM | 2929 | OH2 | H2O | 597 | 8.570   | -1.874  | 32.277 | 1.00 | 42.55 |
| ATOM | 2930 | H1  | H2O | 597 | 8.461   | -2.699  | 31.792 | 1.00 | 0.00  |
| ATOM | 2931 | H2  | H2O | 597 | 7.661   | -1.660  | 32.512 | 1.00 | 0.00  |
| ATOM | 2932 | OH2 | H2O | 598 | 15.043  | 10.456  | 42.923 | 1.00 | 62.88 |
| ATOM | 2933 | H1  | H2O | 598 | 14.279  | 10.904  | 43.307 | 1.00 | 0.00  |
| ATOM | 2934 | H2  | H2O | 598 | 25.457  | 11.173  | 42.429 | 1.00 | 0.00  |
| ATOM | 2935 | OH2 | H2O | 599 | -15.660 | 0.506   | 40.466 | 1.00 | 47.74 |
| ATOM | 2936 | H1  | H2O | 599 | -16.222 | 0.052   | 39.836 | 1.00 | 0.00  |
| ATOM | 2937 | H2  | H2O | 599 | -15.144 | 1.096   | 39.903 | 1.00 | 0.00  |
| ATOM | 2938 | OH2 | H2O | 601 | 10.395  | 0.423   | 33.259 | 1.00 | 37.60 |
| ATOM | 2939 | H1  | H2O | 601 | 10.006  | 0.653   | 34.105 | 1.00 | 0.00  |
| ATOM | 2940 | H2  | H2O | 601 | 9.821   | -0.291  | 32.928 | 1.00 | 0.00  |
| ATOM | 2941 | OH2 | H2O | 602 | -8.774  | 4.671   | 74.569 | 1.00 | 26.62 |
| ATOM | 2942 | H1  | H2O | 602 | -8.038  | 4.434   | 75.158 | 1.00 | 0.00  |
| ATOM | 2943 | H2  | H2O | 602 | -8.979  | 3.782   | 74.258 | 1.00 | 0.00  |
| ATOM | 2944 | OH2 | H2O | 603 | -17.104 | -12.783 | 62.725 | 1.00 | 37.86 |
| ATOM | 2945 | H1  | H2O | 603 | -16.954 | -13.496 | 62.099 | 1.00 | 0.00  |
| ATOM | 2946 | H2  | H2O | 603 | -16.217 | -12.397 | 62.806 | 1.00 | 0.00  |
| ATOM | 2947 | OH2 | H2O | 604 | -18.900 | -20.100 | 39.570 | 1.00 | 34.28 |
| ATOM | 2948 | H1  | H2O | 604 | -18.978 | -19.931 | 40.517 | 1.00 | 0.00  |
| ATOM | 2949 | H2  | H2O | 604 | -19.834 | -20.252 | 39.318 | 1.00 | 0.00  |
| ATOM | 2950 | OH2 | H2O | 605 | -5.985  | -5.412  | 60.745 | 1.00 | 36.79 |
| ATOM | 2951 | H1  | H2O | 605 | -5.650  | -4.512  | 60.798 | 1.00 | 0.00  |
| ATOM | 2952 | H2  | H2O | 605 | -6.609  | -5.537  | 60.001 | 1.00 | 0.00  |
| ATOM | 2953 | OH2 | H2O | 606 | -7.708  | -2.084  | 36.092 | 1.00 | 21.56 |
| ATOM | 2954 | H1  | H2O | 606 | -6.902  | -1.784  | 35.650 | 1.00 | 0.00  |
| ATOM | 2955 | H2  | H2O | 606 | -8.190  | -1.262  | 36.233 | 1.00 | 0.00  |
| ATOM | 2956 | OH2 | H2O | 608 | -3.614  | 10.212  | 57.878 | 1.00 | 65.19 |
| ATOM | 2957 | H1  | H2O | 608 | -3.452  | 9.262   | 57.744 | 1.00 | 0.00  |
| ATOM | 2958 | H2  | H2O | 608 | -3.027  | 10.425  | 58.606 | 1.00 | 0.00  |
| ATOM | 2959 | OH2 | H2O | 609 | -3.860  | 23.973  | 29.811 | 1.00 | 50.06 |
| ATOM | 2960 | H1  | H2O | 609 | -3.959  | 23.569  | 28.947 | 1.00 | 0.00  |
| ATOM | 2961 | H2  | H2O | 609 | -4.765  | 24.102  | 30.103 | 1.00 | 0.00  |
| ATOM | 2962 | OH2 | H2O | 610 | -14.484 | -29.114 | 38.149 | 1.00 | 37.42 |
| ATOM | 2963 | H1  | H2O | 610 | -13.947 | -29.402 | 38.898 | 1.00 | 0.00  |
| ATOM | 2964 | H2  | H2O | 610 | -15.333 | -29.510 | 38.352 | 1.00 | 0.00  |
| ATOM | 2965 | OH2 | H2O | 611 | -21.240 | -8.832  | 55.096 | 1.00 | 28.35 |
| ATOM | 2966 | H1  | H2O | 611 | -21.322 | -9.290  | 54.233 | 1.00 | 0.00  |
| ATOM | 2967 | H2  | H2O | 611 | -21.978 | -8.198  | 55.041 | 1.00 | 0.00  |
| ATOM | 2968 | OH2 | H2O | 612 | -28.312 | 0.830   | 71.261 | 1.00 | 57.03 |
| ATOM | 2969 | H1  | H2O | 612 | -27.631 | 0.653   | 70.617 | 1.00 | 0.00  |
| ATOM | 2970 | H2  | H2O | 612 | -28.949 | 0.130   | 70.091 | 1.00 | 0.00  |
| ATOM | 2971 | OH2 | H2O | 613 | -12.785 | 13.825  | 37.299 | 1.00 | 58.02 |
| ATOM | 2972 | H1  | H2O | 613 | -13.581 | 13.348  | 37.068 | 1.00 | 0.00  |
| ATOM | 2973 | H2  | H2O | 613 | -12.320 | 13.191  | 37.859 | 1.00 | 0.00  |
| ATOM | 2974 | OH2 | H2O | 614 | -26.951 | 9.367   | 64.841 | 1.00 | 44.43 |
| ATOM | 2975 | H1  | H2O | 614 | -27.479 | 9.463   | 64.039 | 1.00 | 0.00  |
| ATOM | 2976 | H2  | H2O | 614 | -27.225 | 10.150  | 65.326 | 1.00 | 0.00  |
| ATOM | 2977 | OH2 | H2O | 615 | 0.669   | -5.217  | 31.942 | 1.00 | 34.30 |
| ATOM | 2978 | H1  | H2O | 615 | 1.054   | -5.954  | 32.433 | 1.00 | 0.00  |
| ATOM | 2979 | H2  | H2O | 615 | -0.020  | -5.664  | 31.430 | 1.00 | 0.00  |
| ATOM | 2980 | OH2 | H2O | 616 | -21.268 | -20.889 | 38.280 | 1.00 | 52.02 |
| ATOM | 2981 | H1  | H2O | 616 | -20.821 | -20.660 | 37.462 | 1.00 | 0.00  |
| ATOM | 2982 | H2  | H2O | 616 | -21.549 | -21.801 | 38.127 | 1.00 | 0.00  |
| ATOM | 2983 | OH2 | H2O | 617 | -12.839 | 10.577  | 73.997 | 1.00 | 32.65 |
| ATOM | 2984 | H1  | H2O | 617 | -13.386 | 10.619  | 73.198 | 1.00 | 0.00  |
| ATOM | 2985 | H2  | H2O | 617 | -12.500 | 9.678   | 73.936 | 1.00 | 0.00  |
| ATOM | 2986 | OH2 | H2O | 618 | -16.254 | 12.102  | 64.699 | 1.00 | 39.97 |
| ATOM | 2987 | H1  | H2O | 618 | -16.278 | 12.774  | 65.388 | 1.00 | 0.00  |
| ATOM | 2988 | H2  | H2O | 618 | -16.940 | 12.440  | 64.106 | 1.00 | 0.00  |
| ATOM | 2989 | OH2 | H2O | 619 | 0.609   | 7.758   | 53.655 | 1.00 | 59.42 |
| ATOM | 2990 | H1  | H2O | 619 | 1.450   | 7.256   | 53.684 | 1.00 | 0.00  |
| ATOM | 2991 | H2  | H2O | 619 | 0.683   | 8.342   | 54.416 | 1.00 | 0.00  |
| ATOM | 2992 | OH2 | H2O | 620 | -4.989  | -8.010  | 58.309 | 1.00 | 38.58 |
| ATOM | 2993 | H1  | H2O | 620 | -5.068  | -8.214  | 59.248 | 1.00 | 0.00  |

TABLE 22-continued

Coordinates for the 3D structure of ZAP-NC:ζ2*

REMARK FILENAME="tm1-zeta2-wat1-slow.pdb"
REMARK TOPH19.pep -MACRO for protein sequence
created by user: marcos

| ATOM | 2994 | H2 | H2O | 620 | −4.822 | −8.893 | 57.952 | 1.00 | 0.00 |
|---|---|---|---|---|---|---|---|---|---|
| ATOM | 2995 | OH2 | H2O | 621 | −26.221 | −7.530 | 53.875 | 1.00 | 52.25 |
| ATOM | 2996 | H1 | H2O | 621 | −25.549 | −8.202 | 53.730 | 1.00 | 0.00 |
| ATOM | 2997 | H2 | H2O | 621 | −26.714 | −7.882 | 54.627 | 1.00 | 0.00 |
| ATOM | 2998 | OH2 | H2O | 622 | −28.638 | 3.741 | 68.846 | 1.00 | 59.40 |
| ATOM | 2999 | H1 | H2O | 622 | −28.605 | 3.555 | 68.794 | 1.00 | 0.00 |
| ATOM | 3000 | H2 | H2O | 622 | −28.709 | 2.848 | 68.480 | 1.00 | 0.00 |
| ATOM | 3001 | OH2 | H2O | 623 | −2.090 | 21.292 | 26.341 | 1.00 | 57.48 |
| ATOM | 3002 | H1 | H2O | 623 | −1.329 | 21.457 | 26.918 | 1.00 | 0.00 |
| ATOM | 3003 | H2 | H2O | 623 | −1.757 | 21.533 | 25.471 | 1.00 | 0.00 |
| ATOM | 3004 | OH2 | H2O | 624 | 2.746 | 10.956 | 28.128 | 1.00 | 62.18 |
| ATOM | 3005 | H1 | H2O | 624 | 2.977 | 11.822 | 27.786 | 1.00 | 0.00 |
| ATOM | 3006 | H2 | H2O | 624 | 1.817 | 10.899 | 27.885 | 1.00 | 0.00 |
| ATOM | 3007 | OH2 | H2O | 625 | −21.125 | −12.685 | 57.962 | 1.00 | 56.36 |
| ATOM | 3008 | H1 | H2O | 625 | −22.032 | −12.954 | 57.802 | 1.00 | 0.00 |
| ATOM | 3009 | H2 | H2O | 625 | −21.176 | −11.723 | 57.883 | 1.00 | 0.00 |
| ATOM | 3010 | OH2 | H2O | 626 | −3.498 | 0.232 | 28.222 | 1.00 | 45.90 |
| ATOM | 3011 | H1 | H2O | 626 | −3.396 | −0.544 | 28.792 | 1.00 | 0.00 |
| ATOM | 3012 | H2 | H2O | 626 | −4.076 | −0.127 | 27.533 | 1.00 | 0.00 |
| ATOM | 3013 | OH2 | H2O | 627 | −6.243 | −1.618 | 39.632 | 1.00 | 33.00 |
| ATOM | 3014 | H1 | H2O | 627 | −6.546 | −0.718 | 39.813 | 1.00 | 0.00 |
| ATOM | 3015 | H2 | H2O | 627 | −6.989 | −2.019 | 39.186 | 1.00 | 0.00 |
| END | | | | | | | | | |

Note:
See copyright notice on page 1.

TABLE 23

Coordinates for the 3D structure of ZAP-NC:ζ1 "dimer" structure
(two molecules of complex per unit cell)*

REMARK FILENAME="tzape-zetal-reb7-wat-slow:pdb"
REMARK TOPH19.pep -MACRO for protein sequence
created by user: marcos

| ATOM | 1 | CB | ASP | 3 | 3.023 | −3.462 | 13.100 | 1.00 | 13.09 |
|---|---|---|---|---|---|---|---|---|---|
| ATOM | 2 | CG | ASP | 3 | 3.616 | −2.223 | 12.417 | 1.00 | 20.07 |
| ATOM | 3 | OD1 | ASP | 3 | 3.875 | −2.263 | 11.212 | 1.00 | 23.94 |
| ATOM | 4 | OD2 | ASP | 3 | 3.795 | −1.198 | 13.066 | 1.00 | 20.96 |
| ATOM | 5 | C | ASP | 3 | 3.125 | −2.930 | 15.585 | 1.00 | 11.37 |
| ATOM | 6 | O | ASP | 3 | 1.915 | −2.908 | 15.816 | 1.00 | 14.62 |
| ATOM | 7 | HT1 | ASP | 3 | 1.919 | −4.746 | 15.191 | 1.00 | 0.00 |
| ATOM | 8 | HT2 | ASP | 3 | 3.317 | −5.471 | 15.778 | 1.00 | 0.00 |
| ATOM | 9 | N | ASP | 3 | 2.872 | −5.087 | 14.923 | 1.00 | 17.39 |
| ATOM | 10 | HT3 | ASP | 3 | 2.808 | −5.797 | 14.172 | 1.00 | 0.00 |
| ATOM | 11 | CA | ASP | 3 | 3.564 | −3.885 | 14.482 | 1.00 | 13.78 |
| ATOM | 12 | N | PRO | 4 | 3.958 | −2.177 | 16.299 | 1.00 | 6.97 |
| ATOM | 13 | CD | PRO | 4 | 5.405 | −2.209 | 16.150 | 1.00 | 10.48 |
| ATOM | 14 | CA | PRO | 4 | 3.556 | −1.192 | 17.314 | 1.00 | 10.28 |
| ATOM | 15 | CB | PRO | 4 | 4.853 | −0.568 | 17.733 | 1.00 | 9.59 |
| ATOM | 16 | CG | PRO | 4 | 5.881 | −1.611 | 17.455 | 1.00 | 10.34 |
| ATOM | 17 | C | PRO | 4 | 2.524 | −0.151 | 16.856 | 1.00 | 12.09 |
| ATOM | 18 | O | PRO | 4 | 1.665 | 0.351 | 17.601 | 1.00 | 15.40 |
| ATOM | 19 | N | ALA | 5 | 2.568 | 0.146 | 15.556 | 1.00 | 14.44 |
| ATOM | 20 | H | ALA | 5 | 3.317 | −0.168 | 15.008 | 1.00 | 0.00 |
| ATOM | 21 | CA | ALA | 5 | 1.662 | 1.120 | 14.996 | 1.00 | 11.85 |
| ATOM | 22 | CB | ALA | 5 | 2.291 | 1.818 | 13.819 | 1.00 | 11.48 |
| ATOM | 23 | C | ALA | 5 | 0.348 | 0.580 | 14.532 | 1.00 | 12.81 |
| ATOM | 24 | O | ALA | 5 | −0.543 | 1.361 | 14.246 | 1.00 | 14.41 |
| ATOM | 25 | N | ALA | 6 | 0.126 | −0.726 | 14.574 | 1.00 | 10.58 |
| ATOM | 26 | H | ALA | 6 | 0.778 | −1.310 | 15.006 | 1.00 | 0.00 |
| ATOM | 27 | CA | ALA | 6 | −1.089 | −1.294 | 14.028 | 1.00 | 14.14 |
| ATOM | 28 | CB | ALA | 6 | −1.098 | −2.784 | 14.300 | 1.00 | 16.49 |
| ATOM | 29 | C | ALA | 6 | −2.394 | −0.721 | 14.540 | 1.00 | 16.09 |
| ATOM | 30 | O | ALA | 6 | −3.390 | −0.608 | 13.844 | 1.00 | 21.55 |
| ATOM | 31 | N | HIS | 7 | −2.376 | −0.363 | 15.806 | 1.00 | 17.76 |
| ATOM | 32 | H | HIS | 7 | −1.541 | −0.482 | 16.284 | 1.00 | 0.00 |
| ATOM | 33 | CA | HIS | 7 | −3.533 | 0.171 | 16.488 | 1.00 | 16.60 |
| ATOM | 34 | CB | HIS | 7 | −3.352 | −0.066 | 18.009 | 1.00 | 22.31 |
| ATOM | 35 | CG | HIS | 7 | −2.219 | 0.769 | 18.644 | 1.00 | 27.59 |
| ATOM | 36 | CD2 | HIS | 7 | −2.489 | 1.750 | 19.576 | 1.00 | 28.93 |

TABLE 23-continued

Coordinates for the 3D structure of ZAP-NC:ζ1 "dimer" structure
(two molecules of complex per unit cell)*

| ATOM | 37 | ND1 | HIS | 7 | −0.885 | 0.783 | 18.461 | 1.00 | 25.24 |
|---|---|---|---|---|---|---|---|---|---|
| ATOM | 38 | HD1 | HIS | 7 | −0.298 | 0.154 | 17.994 | 1.00 | 0.00 |
| ATOM | 39 | CE1 | HIS | 7 | −0.376 | 1.717 | 19.227 | 1.00 | 28.14 |
| ATOM | 40 | NE2 | HIS | 7 | −1.347 | 2.282 | 19.884 | 1.00 | 26.99 |
| ATOM | 41 | HE2 | HIS | 7 | −1.204 | 2.905 | 20.638 | 1.00 | 0.00 |
| ATOM | 42 | C | HIS | 7 | −3.741 | 1.658 | 16.209 | 1.00 | 13.37 |
| ATOM | 43 | O | HIS | 7 | −4.720 | 2.243 | 16.644 | 1.00 | 14.49 |
| ATOM | 44 | N | LEU | 8 | −2.817 | 2.341 | 15.557 | 1.00 | 10.78 |
| ATOM | 45 | H | LEU | 8 | −2.221 | 1.861 | 14.946 | 1.00 | 0.00 |
| ATOM | 46 | CA | LEU | 8 | −2.871 | 3.783 | 15.423 | 1.00 | 7.84 |
| ATOM | 47 | CB | LEU | 8 | −1.436 | 4.278 | 15.161 | 1.00 | 6.56 |
| ATOM | 48 | CG | LEU | 8 | −0.575 | 4.915 | 16.234 | 1.00 | 3.50 |
| ATOM | 49 | CD1 | LEU | 8 | −1.174 | 4.730 | 17.610 | 1.00 | 6.85 |
| ATOM | 50 | CD2 | LEU | 8 | 0.801 | 4.382 | 16.098 | 1.00 | 2.00 |
| ATOM | 51 | C | LEU | 8 | −3.808 | 4.079 | 14.265 | 1.00 | 8.93 |
| ATOM | 52 | O | LEU | 8 | −3.580 | 3.600 | 13.154 | 1.00 | 10.23 |
| ATOM | 53 | N | PRO | 9 | −4.863 | 4.873 | 14.434 | 1.00 | 9.86 |
| ATOM | 54 | CD | PRO | 9 | −5.197 | 5.551 | 15.693 | 1.00 | 9.32 |
| ATOM | 55 | CA | PRO | 9 | −5.849 | 5.081 | 13.389 | 1.00 | 8.41 |
| ATOM | 56 | CB | PRO | 9 | −6.966 | 5.752 | 14.144 | 1.00 | 10.72 |
| ATOM | 57 | CG | PRO | 9 | −6.309 | 6.490 | 15.289 | 1.00 | 11.80 |
| ATOM | 58 | C | PRO | 9 | −5.355 | 5.835 | 12.149 | 1.00 | 12.47 |
| ATOM | 59 | O | PRO | 9 | −6.026 | 5.867 | 11.110 | 1.00 | 18.23 |
| ATOM | 60 | N | PHE | 10 | −4.162 | 6.430 | 12.259 | 1.00 | 9.59 |
| ATOM | 61 | H | PHE | 10 | −3.692 | 6.342 | 13.107 | 1.00 | 0.00 |
| ATOM | 62 | CA | PHE | 10 | −3.498 | 7.181 | 11.203 | 1.00 | 7.32 |
| ATOM | 63 | CB | PHE | 10 | −3.024 | 8.538 | 11.737 | 1.00 | 4.10 |
| ATOM | 64 | CG | PHE | 10 | −2.321 | 8.453 | 13.094 | 1.00 | 4.21 |
| ATOM | 65 | CD1 | PHE | 10 | −0.943 | 8.232 | 13.179 | 1.00 | 4.43 |
| ATOM | 66 | CD2 | PHE | 10 | −3.058 | 8.624 | 14.267 | 1.00 | 2.00 |
| ATOM | 67 | CE1 | PHE | 10 | −0.301 | 8.182 | 14.416 | 1.00 | 2.00 |
| ATOM | 68 | CE2 | PHE | 10 | −2.417 | 8.580 | 15.500 | 1.00 | 2.51 |
| ATOM | 69 | CZ | PHE | 10 | −1.047 | 8.362 | 15.583 | 1.00 | 2.00 |
| ATOM | 70 | C | PHE | 10 | −2.294 | 6.405 | 10.696 | 1.00 | 7.70 |
| ATOM | 71 | O | PHE | 10 | −1.349 | 7.007 | 10.175 | 1.00 | 7.52 |
| ATOM | 72 | N | PHE | 11 | −2.224 | 5.088 | 10.921 | 1.00 | 6.80 |
| ATOM | 73 | H | PHE | 11 | −2.965 | 4.597 | 11.332 | 1.00 | 0.00 |
| ATOM | 74 | CA | PHE | 11 | −1.120 | 4.299 | 10.415 | 1.00 | 7.59 |
| ATOM | 75 | CB | PHE | 11 | −0.705 | 3.238 | 11.425 | 1.00 | 5.71 |
| ATOM | 76 | CG | PHE | 11 | 0.248 | 2.165 | 10.884 | 1.00 | 7.61 |
| ATOM | 77 | CD1 | PHE | 11 | 1.519 | 2.510 | 10.393 | 1.00 | 2.06 |
| ATOM | 78 | CD2 | PHE | 11 | −0.165 | 0.821 | 10.874 | 1.00 | 2.94 |
| ATOM | 79 | CE1 | PHE | 11 | 2.370 | 1.522 | 9.895 | 1.00 | 2.00 |
| ATOM | 80 | CE2 | PHE | 11 | 0.700 | −0.160 | 10.373 | 1.00 | 3.03 |
| ATOM | 81 | CZ | PHE | 11 | 1.962 | 0.191 | 9.888 | 1.00 | 4.25 |
| ATOM | 82 | C | PHE | 11 | −1.686 | 3.663 | 9.154 | 1.00 | 7.98 |
| ATOM | 83 | O | PHE | 11 | −2.784 | 3.126 | 9.188 | 1.00 | 9.38 |
| ATOM | 84 | N | TYR | 12 | −1.000 | 3.774 | 8.025 | 1.00 | 4.03 |
| ATOM | 85 | H | TYR | 12 | −0.170 | 4.294 | 8.022 | 1.00 | 0.00 |
| ATOM | 86 | CA | TYR | 12 | −1.522 | 3.259 | 6.774 | 1.00 | 7.69 |
| ATOM | 87 | CB | TYR | 12 | −1.455 | 4.329 | 5.714 | 1.00 | 4.20 |
| ATOM | 88 | CG | TYR | 12 | −2.582 | 5.340 | 5.795 | 1.00 | 3.37 |
| ATOM | 89 | CD1 | TYR | 12 | −2.543 | 6.332 | 6.766 | 1.00 | 2.00 |
| ATOM | 90 | CE1 | TYR | 12 | −3.532 | 7.297 | 6.818 | 1.00 | 2.00 |
| ATOM | 91 | CD2 | TYR | 12 | −3.617 | 5.301 | 4.872 | 1.00 | 2.00 |
| ATOM | 92 | CE2 | TYR | 12 | −4.609 | 6.269 | 4.918 | 1.00 | 3.76 |
| ATOM | 93 | CZ | TYR | 12 | −4.557 | 7.263 | 5.891 | 1.00 | 5.13 |
| ATOM | 94 | OH | TYR | 12 | −5.521 | 8.242 | 5.911 | 1.00 | 6.92 |
| ATOM | 95 | HH | TYR | 12 | −5.379 | 8.771 | 6.713 | 1.00 | 0.00 |
| ATOM | 96 | C | TYR | 12 | −0.793 | 2.041 | 6.249 | 1.00 | 10.10 |
| ATOM | 97 | O | TYR | 12 | −1.154 | 1.494 | 5.206 | 1.00 | 10.16 |
| ATOM | 98 | N | GLY | 13 | 0.290 | 1.623 | 6.899 | 1.00 | 4.96 |
| ATOM | 99 | H | GLY | 13 | 0.676 | 2.192 | 7.592 | 1.00 | 0.00 |
| ATOM | 100 | CA | GLY | 13 | 0.993 | 0.444 | 6.465 | 1.00 | 5.01 |
| ATOM | 101 | C | GLY | 13 | 1.962 | 0.782 | 5.361 | 1.00 | 9.03 |
| ATOM | 102 | O | GLY | 13 | 2.466 | 1.911 | 5.324 | 1.00 | 9.88 |
| ATOM | 103 | N | SER | 14 | 2.248 | −0.181 | 4.484 | 1.00 | 6.75 |
| ATOM | 104 | H | SER | 14 | 1.835 | −1.069 | 4.566 | 1.00 | 0.00 |
| ATOM | 105 | CA | SER | 14 | 3.216 | −0.042 | 3.425 | 1.00 | 6.38 |
| ATOM | 106 | CB | SER | 14 | 3.761 | −1.433 | 3.160 | 1.00 | 12.45 |
| ATOM | 107 | OG | SER | 14 | 4.042 | −2.137 | 4.368 | 1.00 | 14.84 |
| ATOM | 108 | HG | SER | 14 | 4.988 | −2.032 | 4.504 | 1.00 | 0.00 |
| ATOM | 109 | C | SER | 14 | 2.646 | 0.592 | 2.163 | 1.00 | 9.03 |
| ATOM | 110 | O | SER | 14 | 2.597 | −0.003 | 1.083 | 1.00 | 6.91 |
| ATOM | 111 | N | ILE | 15 | 2.120 | 1.812 | 2.312 | 1.00 | 12.05 |
| ATOM | 112 | H | ILE | 15 | 2.188 | 2.238 | 3.193 | 1.00 | 0.00 |

TABLE 23-continued

Coordinates for the 3D structure of ZAP-NC:ζ1 "dimer" structure
(two molecules of complex per unit cell)*

| ATOM | 113 | CA | ILE | 15 | 1.610 | 2.588 | 1.187 | 1.00 | 4.84 |
|------|-----|------|------|----|--------|--------|--------|------|-------|
| ATOM | 114 | CB | ILE | 15 | 0.538 | 3.627 | 1.605 | 1.00 | 6.22 |
| ATOM | 115 | CG2 | ILE | 15 | −0.680 | 2.860 | 2.116 | 1.00 | 2.00 |
| ATOM | 116 | CG1 | ILE | 15 | 1.075 | 4.612 | 2.629 | 1.00 | 4.45 |
| ATOM | 117 | CD | ILE | 15 | 0.057 | 5.720 | 2.801 | 1.00 | 2.00 |
| ATOM | 118 | C | ILE | 15 | 2.798 | 3.326 | 0.597 | 1.00 | 4.88 |
| ATOM | 119 | O | ILE | 15 | 3.861 | 3.382 | 1.221 | 1.00 | 9.72 |
| ATOM | 120 | N | SER | 16 | 2.707 | 3.871 | −0.603 | 1.00 | 2.18 |
| ATOM | 121 | H | SER | 16 | 1.875 | 3.823 | −1.116 | 1.00 | 0.00 |
| ATOM | 122 | CA | SER | 16 | 3.788 | 4.641 | −1.154 | 1.00 | 2.42 |
| ATOM | 123 | CB | SER | 16 | 3.704 | 4.505 | −2.673 | 1.00 | 8.87 |
| ATOM | 124 | OG | SER | 16 | 2.388 | 4.754 | −3.152 | 1.00 | 3.44 |
| ATOM | 125 | HG | SER | 16 | 2.047 | 3.891 | −3.426 | 1.00 | 0.00 |
| ATOM | 126 | C | SER | 16 | 3.687 | 6.106 | −0.714 | 1.00 | 2.00 |
| ATOM | 127 | O | SER | 16 | 2.675 | 6.502 | −0.132 | 1.00 | 2.00 |
| ATOM | 128 | N | ARG | 17 | 4.699 | 6.935 | −0.968 | 1.00 | 2.93 |
| ATOM | 129 | H | ARG | 17 | 5.537 | 6.524 | −1.277 | 1.00 | 0.00 |
| ATOM | 130 | CA | ARG | 17 | 4.648 | 8.381 | −0.757 | 1.00 | 7.56 |
| ATOM | 131 | CB | ARG | 17 | 5.924 | 9.017 | −1.273 | 1.00 | 6.05 |
| ATOM | 132 | CG | ARG | 17 | 5.862 | 10.510 | −1.338 | 1.00 | 5.21 |
| ATOM | 133 | CD | ARG | 17 | 7.154 | 11.123 | −1.775 | 1.00 | 3.35 |
| ATOM | 134 | NE | ARG | 17 | 8.227 | 10.897 | −0.825 | 1.00 | 4.91 |
| ATOM | 135 | HE | ARG | 17 | 8.208 | 10.065 | −0.338 | 1.00 | 0.00 |
| ATOM | 136 | CZ | ARG | 17 | 9.140 | 11.829 | −0.522 | 1.00 | 4.06 |
| ATOM | 137 | NH1 | ARG | 17 | 9.090 | 13.040 | −1.078 | 1.00 | 11.79 |
| ATOM | 138 | HH11 | ARG | 17 | 8.351 | 13.280 | −1.704 | 1.00 | 0.00 |
| ATOM | 139 | HH12 | ARG | 17 | 9.767 | 13.730 | −0.827 | 1.00 | 0.00 |
| ATOM | 140 | NH2 | ARG | 17 | 10.160 | 11.543 | 0.279 | 1.00 | 2.00 |
| ATOM | 141 | HH21 | ARG | 17 | 10.267 | 10.623 | 0.648 | 1.00 | 0.00 |
| ATOM | 142 | HH22 | ARG | 17 | 10.826 | 12.246 | 0.515 | 1.00 | 0.00 |
| ATOM | 143 | C | ARG | 17 | 3.467 | 9.007 | −1.478 | 1.00 | 9.96 |
| ATOM | 144 | O | ARG | 17 | 2.767 | 9.855 | −0.912 | 1.00 | 18.22 |
| ATOM | 145 | N | ALA | 18 | 3.226 | 8.597 | −2.725 | 1.00 | 8.79 |
| ATOM | 146 | H | ALA | 18 | 3.866 | 7.978 | −3.146 | 1.00 | 0.00 |
| ATOM | 147 | CA | ALA | 18 | 2.127 | 9.126 | −3.517 | 1.00 | 6.30 |
| ATOM | 148 | CB | ALA | 18 | 2.157 | 8.565 | −4.946 | 1.00 | 6.16 |
| ATOM | 149 | C | ALA | 18 | 0.752 | 8.856 | −2.957 | 1.00 | 6.92 |
| ATOM | 150 | O | ALA | 18 | −0.107 | 9.754 | −2.973 | 1.00 | 7.53 |
| ATOM | 151 | N | GLU | 19 | 0.506 | 7.652 | −2.443 | 1.00 | 7.90 |
| ATOM | 152 | H | GLU | 19 | 1.209 | 6.967 | −2.446 | 1.00 | 0.00 |
| ATOM | 153 | CA | GLU | 19 | −0.782 | 7.381 | −1.814 | 1.00 | 9.39 |
| ATOM | 154 | CB | GLU | 19 | −0.933 | 5.916 | −1.471 | 1.00 | 10.49 |
| ATOM | 155 | CG | GLU | 19 | −2.377 | 5.601 | −1.128 | 1.00 | 19.14 |
| ATOM | 156 | CD | GLU | 19 | −2.645 | 4.173 | −0.680 | 1.00 | 20.65 |
| ATOM | 157 | OE1 | GLU | 19 | −3.479 | 3.996 | 0.201 | 1.00 | 17.14 |
| ATOM | 158 | OE2 | GLU | 19 | −2.030 | 3.243 | −1.201 | 1.00 | 24.68 |
| ATOM | 159 | C | GLU | 19 | −0.919 | 8.177 | −0.532 | 1.00 | 3.96 |
| ATOM | 160 | O | GLU | 19 | −2.017 | 8.678 | −0.270 | 1.00 | 8.60 |
| ATOM | 161 | N | ALA | 20 | 0.158 | 8.264 | 0.270 | 1.00 | 7.91 |
| ATOM | 162 | H | ALA | 20 | 0.966 | 7.756 | 0.027 | 1.00 | 0.00 |
| ATOM | 163 | CA | ALA | 20 | 0.211 | 9.052 | 1.508 | 1.00 | 5.76 |
| ATOM | 164 | CB | ALA | 20 | 1.649 | 9.038 | 2.045 | 1.00 | 2.00 |
| ATOM | 165 | C | ALA | 20 | −0.241 | 10.487 | 1.209 | 1.00 | 4.60 |
| ATOM | 166 | O | ALA | 20 | −1.206 | 10.973 | 1.808 | 1.00 | 5.16 |
| ATOM | 167 | N | GLU | 21 | 0.379 | 11.097 | 0.190 | 1.00 | 4.13 |
| ATOM | 168 | H | GLU | 21 | 1.116 | 10.617 | −0.239 | 1.00 | 0.00 |
| ATOM | 169 | CA | GLU | 21 | 0.040 | 12.416 | −0.312 | 1.00 | 2.10 |
| ATOM | 170 | CB | GLU | 21 | 1.020 | 12.792 | −1.412 | 1.00 | 4.68 |
| ATOM | 171 | CG | GLU | 21 | 2.397 | 13.047 | −0.773 | 1.00 | 2.00 |
| ATOM | 172 | CD | GLU | 21 | 3.519 | 13.499 | −1.669 | 1.00 | 2.00 |
| ATOM | 173 | OE1 | GLU | 21 | 4.557 | 13.853 | −1.142 | 1.00 | 5.32 |
| ATOM | 174 | OE2 | GLU | 21 | 3.407 | 13.490 | −2.883 | 1.00 | 13.97 |
| ATOM | 175 | C | GLU | 21 | −1.380 | 12.520 | −0.818 | 1.00 | 6.29 |
| ATOM | 176 | O | GLU | 21 | −2.019 | 13.528 | −0.527 | 1.00 | 10.48 |
| ATOM | 177 | N | GLU | 22 | −1.962 | 11.533 | −1.497 | 1.00 | 8.02 |
| ATOM | 178 | H | GLU | 22 | −1.426 | 10.751 | −1.745 | 1.00 | 0.00 |
| ATOM | 179 | CA | GLU | 22 | −3.372 | 11.572 | −1.859 | 1.00 | 7.52 |
| ATOM | 180 | CB | GLU | 22 | −3.832 | 10.346 | −2.661 | 1.00 | 7.05 |
| ATOM | 181 | CG | GLU | 22 | −3.392 | 10.345 | −4.114 | 1.00 | 14.40 |
| ATOM | 182 | CG | GLU | 22 | −3.683 | 11.637 | −4.867 | 1.00 | 8.48 |
| ATOM | 183 | CD | GLU | 22 | −4.835 | 11.930 | −5.138 | 1.00 | 9.34 |
| ATOM | 184 | OE2 | GLU | 22 | −2.752 | 12.353 | −5.183 | 1.00 | 11.08 |
| ATOM | 185 | C | GLU | 22 | −4.273 | 11.631 | −0.641 | 1.00 | 6.86 |
| ATOM | 186 | O | GLU | 22 | −5.253 | 12.378 | −0.613 | 1.00 | 5.32 |
| ATOM | 187 | N | HIS | 23 | −3.959 | 10.856 | 0.392 | 1.00 | 5.94 |
| ATOM | 188 | H | HIS | 23 | −3.140 | 10.318 | 0.345 | 1.00 | 0.00 |

TABLE 23-continued

Coordinates for the 3D structure of ZAP-NC:ζ1 "dimer" structure
(two molecules of complex per unit cell)*

| ATOM | 189 | CA | HIS | 23 | −4.755 | 10.908 | 1.612 | 1.00 | 5.56 |
|---|---|---|---|---|---|---|---|---|---|
| ATOM | 190 | CB | HIS | 23 | −4.321 | 9.773 | 2.499 | 1.00 | 2.00 |
| ATOM | 191 | CG | HIS | 23 | −4.867 | 8.436 | 2.044 | 1.00 | 2.00 |
| ATOM | 192 | CD2 | HIS | 23 | −6.203 | 8.130 | 1.947 | 1.00 | 2.00 |
| ATOM | 193 | ND1 | HIS | 23 | −4.118 | 7.361 | 1.687 | 1.00 | 3.99 |
| ATOM | 194 | HD1 | HIS | 23 | −3.210 | 7.263 | 1.722 | 1.00 | 0.00 |
| ATOM | 195 | CE1 | HIS | 23 | −5.036 | 6.418 | 1.389 | 1.00 | 4.29 |
| ATOM | 196 | NE2 | HIS | 23 | −6.245 | 6.892 | 1.547 | 1.00 | 2.00 |
| ATOM | 197 | HE2 | HIS | 23 | −7.054 | 6.418 | 1.246 | 1.00 | 0.00 |
| ATOM | 198 | C | HIS | 23 | −4.635 | 12.252 | 2.349 | 1.00 | 4.09 |
| ATOM | 199 | O | HIS | 23 | −5.626 | 12.842 | 2.795 | 1.00 | 6.37 |
| ATOM | 200 | N | LEU | 24 | −3.421 | 12.790 | 2.458 | 1.00 | 3.53 |
| ATOM | 201 | H | LEU | 24 | −2.646 | 12.264 | 2.177 | 1.00 | 0.00 |
| ATOM | 202 | CA | LEU | 24 | −3.206 | 14.085 | 3.063 | 1.00 | 5.01 |
| ATOM | 203 | CB | LEU | 24 | −1.701 | 14.303 | 3.096 | 1.00 | 2.00 |
| ATOM | 204 | CG | LEU | 24 | −0.823 | 14.200 | 4.370 | 1.00 | 6.54 |
| ATOM | 205 | CD1 | LEU | 24 | −1.454 | 13.379 | 5.465 | 1.00 | 7.05 |
| ATOM | 206 | CD2 | LEU | 24 | 0.498 | 13.624 | 3.967 | 1.00 | 2.00 |
| ATOM | 207 | C | LEU | 24 | −3.973 | 15.138 | 2.252 | 1.00 | 11.01 |
| ATOM | 208 | O | LEU | 24 | −4.652 | 15.982 | 2.852 | 1.00 | 12.49 |
| ATOM | 209 | N | LYS | 25 | −4.000 | 15.036 | 0.904 | 1.00 | 10.63 |
| ATOM | 210 | H | LYS | 25 | −3.462 | 14.341 | 0.474 | 1.00 | 0.00 |
| ATOM | 211 | CA | LYS | 25 | −4.774 | 15.932 | 0.043 | 1.00 | 7.14 |
| ATOM | 212 | CB | LYS | 25 | −4.496 | 15.670 | −1.428 | 1.00 | 8.00 |
| ATOM | 213 | CG | LYS | 25 | −3.153 | 16.255 | −1.839 | 1.00 | 5.27 |
| ATOM | 214 | CD | LYS | 25 | −2.581 | 15.554 | −3.051 | 1.00 | 3.30 |
| ATOM | 215 | CE | LYS | 25 | −3.260 | 15.890 | −4.355 | 1.00 | 10.38 |
| ATOM | 216 | NZ | LYS | 25 | −2.559 | 15.231 | −5.444 | 1.00 | 11.78 |
| ATOM | 217 | HZ1 | LYS | 25 | −3.027 | 14.321 | −5.634 | 1.00 | 0.00 |
| ATOM | 218 | HZ2 | LYS | 25 | −1.570 | 15.066 | −5.169 | 1.00 | 0.00 |
| ATOM | 219 | HZ3 | LYS | 25 | −2.588 | 15.821 | −6.298 | 1.00 | 0.00 |
| ATOM | 220 | C | LYS | 25 | −6.265 | 15.828 | 0.258 | 1.00 | 10.22 |
| ATOM | 221 | O | LYS | 25 | −6.897 | 16.878 | 0.404 | 1.00 | 9.54 |
| ATOM | 222 | N | LEU | 26 | −6.838 | 14.617 | 0.301 | 1.00 | 11.16 |
| ATOM | 223 | H | LEU | 26 | −6.273 | 13.839 | 0.106 | 1.00 | 0.00 |
| ATOM | 224 | CA | LEU | 26 | −8.251 | 14.406 | 0.623 | 1.00 | 9.37 |
| ATOM | 225 | CB | LEU | 26 | −8.620 | 12.933 | 0.400 | 1.00 | 11.52 |
| ATOM | 226 | CG | LEU | 26 | −8.869 | 12.403 | −1.006 | 1.00 | 15.81 |
| ATOM | 227 | CD1 | LEU | 26 | −8.667 | 10.906 | −1.070 | 1.00 | 12.44 |
| ATOM | 228 | CD2 | LEU | 26 | −10.274 | 12.781 | −1.405 | 1.00 | 14.24 |
| ATOM | 229 | C | LEU | 26 | −8.631 | 14.799 | 2.069 | 1.00 | 10.95 |
| ATOM | 230 | O | LEU | 26 | −9.801 | 15.111 | 2.355 | 1.00 | 14.32 |
| ATOM | 231 | N | ALA | 27 | −7.692 | 14.822 | 3.024 | 1.00 | 11.08 |
| ATOM | 232 | H | ALA | 27 | −6.777 | 14.533 | 2.808 | 1.00 | 0.00 |
| ATOM | 233 | CA | ALA | 27 | −7.994 | 15.224 | 4.386 | 1.00 | 11.08 |
| ATOM | 234 | CB | ALA | 27 | −7.036 | 14.511 | 5.304 | 1.00 | 10.64 |
| ATOM | 235 | C | ALA | 27 | −7.953 | 16.734 | 4.652 | 1.00 | 7.17 |
| ATOM | 236 | O | ALA | 27 | −8.111 | 17.181 | 5.782 | 1.00 | 11.67 |
| ATOM | 237 | N | GLY | 28 | −7.739 | 17.589 | 3.664 | 1.00 | 12.48 |
| ATOM | 238 | H | GLY | 28 | −7.484 | 17.253 | 2.781 | 1.00 | 0.00 |
| ATOM | 239 | CA | GLY | 28 | −7.896 | 19.028 | 3.827 | 1.00 | 7.75 |
| ATOM | 240 | C | GLY | 28 | −6.628 | 19.840 | 3.923 | 1.00 | 4.07 |
| ATOM | 241 | O | GLY | 28 | −6.690 | 21.035 | 4.200 | 1.00 | 6.51 |
| ATOM | 242 | N | MET | 29 | −5.473 | 19.214 | 3.803 | 1.00 | 2.00 |
| ATOM | 243 | H | MET | 29 | −5.490 | 18.237 | 3.712 | 1.00 | 0.00 |
| ATOM | 244 | CA | MET | 29 | −4.190 | 19.893 | 3.778 | 1.00 | 8.42 |
| ATOM | 245 | CB | MET | 29 | −3.995 | 20.563 | 2.387 | 1.00 | 10.20 |
| ATOM | 246 | CG | MET | 29 | −3.777 | 19.617 | 1.225 | 1.00 | 2.00 |
| ATOM | 247 | SD | MET | 29 | −2.291 | 18.598 | 1.382 | 1.00 | 8.85 |
| ATOM | 248 | CE | MET | 29 | −1.010 | 19.682 | 0.859 | 1.00 | 2.00 |
| ATOM | 249 | C | MET | 29 | −3.856 | 20.922 | 4.854 | 1.00 | 10.87 |
| ATOM | 250 | O | MET | 29 | −2.966 | 21.768 | 4.665 | 1.00 | 10.88 |
| ATOM | 251 | N | ALA | 30 | −4.500 | 20.905 | 6.021 | 1.00 | 11.57 |
| ATOM | 252 | H | ALA | 30 | −5.182 | 20.223 | 6.167 | 1.00 | 0.00 |
| ATOM | 253 | CA | ALA | 30 | −4.164 | 21.845 | 7.095 | 1.00 | 10.40 |
| ATOM | 254 | CB | ALA | 30 | −5.179 | 21.738 | 8.228 | 1.00 | 6.30 |
| ATOM | 255 | C | ALA | 30 | −2.775 | 21.578 | 7.669 | 1.00 | 10.33 |
| ATOM | 256 | O | ALA | 30 | −2.295 | 20.435 | 7.630 | 1.00 | 13.22 |
| ATOM | 257 | N | ASP | 30 | −2.076 | 22.614 | 8.163 | 1.00 | 12.01 |
| ATOM | 258 | H | ASP | 30 | −2.486 | 23.499 | 8.124 | 1.00 | 0.00 |
| ATOM | 259 | CA | ASP | 30 | −0.776 | 22.454 | 8.823 | 1.00 | 12.46 |
| ATOM | 260 | CB | ALA | 30 | −0.288 | 23.751 | 9.448 | 1.00 | 13.37 |
| ATOM | 261 | CG | ASP | 31 | 0.098 | 24.844 | 8.474 | 1.00 | 21.50 |
| ATOM | 262 | OD1 | ASP | 31 | 0.146 | 25.992 | 8.888 | 1.00 | 24.55 |
| ATOM | 263 | OD2 | ASP | 31 | 0.365 | 24.563 | 7.309 | 1.00 | 20.09 |
| ATOM | 264 | C | ASP | 31 | −0.900 | 21.447 | 9.952 | 1.00 | 7.22 |

TABLE 23-continued

Coordinates for the 3D structure of ZAP-NC:ζ1 "dimer" structure
(two molecules of complex per unit cell)*

| ATOM | 265 | O | ASP | 31 | −1.854 | 21.484 | 10.668 | 1.00 | 4.46 |
|---|---|---|---|---|---|---|---|---|---|
| ATOM | 266 | N | GLY | 32 | 0.048 | 20.550 | 10.124 | 1.00 | 10.27 |
| ATOM | 267 | H | GLY | 32 | 0.798 | 20.509 | 0.504 | 1.00 | 0.00 |
| ATOM | 268 | CA | GLY | 32 | −0.033 | 10.590 | 11.205 | 1.00 | 8.51 |
| ATOM | 269 | C | GLY | 32 | −0.823 | 18.338 | 10.859 | 1.00 | 7.26 |
| ATOM | 270 | O | GLY | 32 | −0.854 | 17.457 | 11.714 | 1.00 | 8.25 |
| ATOM | 271 | N | LEU | 33 | −1.475 | 18.224 | 9.681 | 1.00 | 11.32 |
| ATOM | 272 | H | LEU | 33 | −1.447 | 18.977 | 9.055 | 1.00 | 0.00 |
| ATOM | 273 | CA | LEU | 33 | −2.163 | 17.020 | 9.241 | 1.00 | 7.48 |
| ATOM | 274 | CB | LEU | 33 | −2.958 | 17.285 | 7.052 | 1.00 | 6.35 |
| ATOM | 275 | CG | LEU | 33 | −3.782 | 16.168 | 7.277 | 1.00 | 6.57 |
| ATOM | 276 | CD1 | LEU | 33 | −5.026 | 15.832 | 8.081 | 1.00 | 2.00 |
| ATOM | 277 | CD2 | LEU | 33 | −4.230 | 16.632 | 5.924 | 1.00 | 2.00 |
| ATOM | 278 | C | LEU | 33 | −1.040 | 16.019 | 8.975 | 1.00 | 6.22 |
| ATOM | 279 | O | LEU | 33 | −0.088 | 16.324 | 8.255 | 1.00 | 6.43 |
| ATOM | 280 | N | PHE | 34 | −1.096 | 14.827 | 9.559 | 1.00 | 8.18 |
| ATOM | 281 | H | PHE | 34 | −1.873 | 14.606 | 10.113 | 1.00 | 0.00 |
| ATOM | 282 | CA | PHE | 34 | −0.031 | 13.841 | 9.449 | 1.00 | 6.96 |
| ATOM | 283 | CB | PHE | 34 | 0.906 | 13.955 | 10.668 | 1.00 | 9.24 |
| ATOM | 284 | CG | PHE | 34 | 0.293 | 13.474 | 12.001 | 1.00 | 11.41 |
| ATOM | 285 | CD1 | PHE | 34 | 0.609 | 12.195 | 12.511 | 1.00 | 10.54 |
| ATOM | 286 | CD2 | PHE | 34 | −0.598 | 14.301 | 12.705 | 1.00 | 6.42 |
| ATOM | 287 | CE1 | PHE | 34 | 0.036 | 11.755 | 13.703 | 1.00 | 2.02 |
| ATOM | 288 | CE2 | PHE | 34 | −1.171 | 13.850 | 13.902 | 1.00 | 7.27 |
| ATOM | 289 | CZ | PHE | 34 | −0.851 | 12.578 | 14.396 | 1.00 | 6.84 |
| ATOM | 290 | C | PHE | 34 | −0.567 | 12.412 | 9.374 | 1.00 | 5.22 |
| ATOM | 291 | O | PHE | 34 | −1.726 | 12.147 | 9.661 | 1.00 | 3.39 |
| ATOM | 292 | N | LEU | 35 | 0.268 | 11.458 | 9.034 | 1.00 | 5.72 |
| ATOM | 293 | H | LEU | 35 | 1.189 | 11.706 | 8.790 | 1.00 | 0.00 |
| ATOM | 294 | CA | LEU | 35 | −0.072 | 10.050 | 9.046 | 1.00 | 4.60 |
| ATOM | 295 | CB | LEU | 35 | −0.724 | 9.614 | 7.712 | 1.00 | 8.73 |
| ATOM | 296 | CG | LEU | 35 | −0.088 | 9.773 | 6.319 | 1.00 | 3.40 |
| ATOM | 297 | CD1 | LEU | 35 | 0.959 | 8.732 | 5.950 | 1.00 | 2.00 |
| ATOM | 298 | CD2 | LEU | 35 | −1.244 | 9.677 | 5.386 | 1.00 | 2.00 |
| ATOM | 299 | C | LEU | 35 | 1.245 | 9.317 | 9.250 | 1.00 | 3.92 |
| ATOM | 300 | O | LEU | 35 | 2.324 | 9.933 | 9.225 | 1.00 | 2.00 |
| ATOM | 301 | N | LEU | 36 | 1.191 | 8.005 | 9.422 | 1.00 | 5.92 |
| ATOM | 302 | H | LEU | 36 | 0.323 | 7.551 | 9.390 | 1.00 | 0.00 |
| ATOM | 303 | CA | LEU | 36 | 2.380 | 7.184 | 9.594 | 1.00 | 8.39 |
| ATOM | 304 | CB | LEU | 36 | 2.363 | 6.596 | 10.986 | 1.00 | 11.32 |
| ATOM | 305 | CG | LEU | 36 | 3.640 | 6.400 | 11.741 | 1.00 | 14.05 |
| ATOM | 306 | CD1 | LEU | 36 | 4.436 | 7.705 | 11.802 | 1.00 | 16.00 |
| ATOM | 307 | CD2 | LEU | 36 | 3.265 | 5.884 | 13.125 | 1.00 | 9.12 |
| ATOM | 308 | C | LEU | 36 | 2.337 | 6.074 | 8.546 | 1.00 | 7.14 |
| ATOM | 309 | O | LEU | 36 | 1.281 | 5.554 | 8.193 | 1.00 | 5.23 |
| ATOM | 310 | N | ARG | 37 | 3.451 | 5.641 | 8.002 | 1.00 | 7.21 |
| ATOM | 311 | H | ARG | 37 | 4.319 | 6.012 | 8.281 | 1.00 | 0.00 |
| ATOM | 312 | CA | ARG | 37 | 3.436 | 4.601 | 7.001 | 1.00 | 6.63 |
| ATOM | 313 | CB | ARG | 37 | 3.347 | 5.207 | 5.570 | 1.00 | 6.69 |
| ATOM | 314 | CG | ARG | 37 | 4.431 | 6.217 | 5.175 | 1.00 | 7.51 |
| ATOM | 315 | CD | ARG | 37 | 4.113 | 6.877 | 3.834 | 1.00 | 3.14 |
| ATOM | 316 | NE | ARG | 37 | 4.999 | 7.996 | 3.521 | 1.00 | 2.00 |
| ATOM | 317 | HE | ARG | 37 | 4.751 | 8.885 | 3.842 | 1.00 | 0.00 |
| ATOM | 318 | CZ | ARG | 37 | 6.090 | 7.884 | 2.784 | 1.00 | 2.00 |
| ATOM | 319 | NH1 | ARG | 37 | 6.467 | 6.714 | 2.287 | 1.00 | 9.05 |
| ATOM | 320 | HH11 | ARG | 37 | 5.927 | 5.895 | 2.467 | 1.00 | 0.00 |
| ATOM | 321 | HH12 | ARG | 37 | 7.293 | 6.665 | 1.729 | 1.00 | 0.00 |
| ATOM | 322 | NH2 | ARG | 37 | 6.826 | 8.967 | 2.509 | 1.00 | 2.00 |
| ATOM | 323 | HH21 | ARG | 37 | 6.527 | 9.860 | 2.843 | 1.00 | 0.00 |
| ATOM | 324 | HH22 | ARG | 37 | 7.645 | 8.898 | 1.946 | 1.00 | 0.00 |
| ATOM | 325 | C | ARG | 37 | 4.742 | 3.896 | 7.236 | 1.00 | 4.63 |
| ATOM | 326 | O | ARG | 37 | 5.673 | 4.451 | 7.813 | 1.00 | 6.35 |
| ATOM | 327 | N | GLN | 38 | 4.774 | 2.634 | 6.860 | 1.00 | 5.04 |
| ATOM | 328 | H | GLN | 38 | 4.022 | 2.306 | 6.330 | 1.00 | 0.00 |
| ATOM | 329 | CA | GLN | 38 | 5.938 | 1.799 | 7.031 | 1.00 | 7.58 |
| ATOM | 330 | CB | GLN | 38 | 5.595 | 0.351 | 6.761 | 1.00 | 7.74 |
| ATOM | 331 | CG | GLN | 38 | 6.806 | −0.558 | 6.935 | 1.00 | 13.64 |
| ATOM | 332 | CD | GLN | 38 | 6.483 | −2.001 | 6.637 | 1.00 | 14.53 |
| ATOM | 333 | OE1 | GLN | 38 | 6.523 | −2.458 | 5.497 | 1.00 | 12.05 |
| ATOM | 334 | NE1 | GLN | 38 | 6.109 | −2.747 | 7.656 | 1.00 | 18.12 |
| ATOM | 335 | HE21 | GLN | 38 | 6.074 | −2.344 | 8.548 | 1.00 | 0.00 |
| ATOM | 336 | HE22 | GLN | 38 | 5.914 | −3.686 | 7.478 | 1.00 | 0.00 |
| ATOM | 337 | C | GLN | 38 | 6.999 | 2.228 | 6.044 | 1.00 | 10.26 |
| ATOM | 338 | O | GLN | 38 | 6.685 | 2.463 | 4.877 | 1.00 | 17.97 |
| ATOM | 339 | N | CYS | 39 | 8.249 | 2.259 | 6.487 | 1.00 | 5.47 |
| ATOM | 340 | H | CYS | 39 | 8.430 | 1.978 | 7.409 | 1.00 | 0.00 |

TABLE 23-continued

Coordinates for the 3D structure of ZAP-NC:ζ1 "dimer" structure
(two molecules of complex per unit cell)*

| ATOM | 341 | CA | CYS | 39 | 9.348 | 2.636 | 5.640 | 1.00 | 5.68 |
|------|-----|------|-----|----|--------|--------|--------|------|-------|
| ATOM | 342 | CB | CYS | 39 | 10.486 | 3.061 | 6.507 | 1.00 | 2.00 |
| ATOM | 343 | SG | CYS | 39 | 11.920 | 3.657 | 5.614 | 1.00 | 7.85 |
| ATOM | 344 | C | CYS | 39 | 9.677 | 1.390 | 4.861 | 1.00 | 8.60 |
| ATOM | 345 | O | CYS | 39 | 9.841 | 0.306 | 5.419 | 1.00 | 7.46 |
| ATOM | 346 | N | LEU | 40 | 9.732 | 1.534 | 3.551 | 1.00 | 9.77 |
| ATOM | 347 | H | LEU | 40 | 9.503 | 2.417 | 3.173 | 1.00 | 0.00 |
| ATOM | 348 | CA | LEU | 40 | 10.016 | 3.061 | 6.507 | 1.00 | 8.59 |
| ATOM | 349 | CB | LEU | 40 | 11.920 | 3.657 | 5.614 | 1.00 | 6.71 |
| ATOM | 350 | CG | LEU | 40 | 9.677 | 1.390 | 4.861 | 1.00 | 11.30 |
| ATOM | 351 | CD1 | LEU | 40 | 9.841 | 0.306 | 5.419 | 1.00 | 8.08 |
| ATOM | 352 | CD2 | LEU | 40 | 9.732 | 1.534 | 3.551 | 1.00 | 11.61 |
| ATOM | 353 | C | LEU | 40 | 9.503 | 2.417 | 3.173 | 1.00 | 5.73 |
| ATOM | 354 | O | LEU | 40 | 10.016 | 0.439 | 2.642 | 1.00 | 9.26 |
| ATOM | 355 | N | ARG | 41 | 12.309 | 1.209 | 2.962 | 1.00 | 8.34 |
| ATOM | 356 | H | ARG | 41 | 11.897 | 1.977 | 3.405 | 1.00 | 0.00 |
| ATOM | 357 | CA | ARG | 41 | 13.763 | 1.249 | 2.813 | 1.00 | 2.90 |
| ATOM | 358 | CB | ARG | 41 | 14.210 | 2.666 | 2.555 | 1.00 | 2.00 |
| ATOM | 359 | CG | ARG | 41 | 13.454 | 3.361 | 1.465 | 1.00 | 2.98 |
| ATOM | 360 | CD | ARG | 41 | 13.444 | 4.854 | 1.636 | 1.00 | 2.00 |
| ATOM | 361 | NE | ARG | 41 | 14.799 | 5.288 | 1.685 | 1.00 | 8.56 |
| ATOM | 362 | HE | ARG | 41 | 15.451 | 4.892 | 1.068 | 1.00 | 0.00 |
| ATOM | 363 | CZ | ARG | 41 | 15.236 | 6.186 | 2.575 | 1.00 | 12.54 |
| ATOM | 364 | NH1 | ARG | 41 | 14.464 | 6.783 | 3.503 | 1.00 | 5.62 |
| ATOM | 365 | HH11 | ARG | 41 | 13.491 | 6.577 | 3.561 | 1.00 | 0.00 |
| ATOM | 366 | HH12 | ARG | 41 | 14.875 | 7.443 | 4.131 | 1.00 | 0.00 |
| ATOM | 367 | NH2 | ARG | 41 | 16.541 | 6.418 | 3.555 | 1.00 | 9.56 |
| ATOM | 368 | HH21 | ARG | 41 | 17.122 | 5.945 | 1.892 | 1.00 | 0.00 |
| ATOM | 369 | HH22 | ARG | 41 | 16.939 | 7.080 | 3.189 | 1.00 | 0.00 |
| ATOM | 370 | C | ARG | 41 | 14.546 | 0.749 | 4.026 | 1.00 | 3.10 |
| ATOM | 371 | O | ARG | 41 | 15.738 | 0.442 | 3.924 | 1.00 | 6.59 |
| ATOM | 372 | N | SER | 42 | 13.886 | 0.603 | 5.172 | 1.00 | 6.64 |
| ATOM | 373 | H | SER | 42 | 12.914 | 0.695 | 5.196 | 1.00 | 0.00 |
| ATOM | 374 | CA | SER | 42 | 14.523 | 0.260 | 6.436 | 1.00 | 10.06 |
| ATOM | 375 | CB | SER | 42 | 14.450 | 1.447 | 7.379 | 1.00 | 7.22 |
| ATOM | 376 | OG | SER | 42 | 15.317 | 2.451 | 6.893 | 1.00 | 18.52 |
| ATOM | 377 | HG | SER | 42 | 15.130 | 3.248 | 7.414 | 1.00 | 0.00 |
| ATOM | 378 | C | SER | 42 | 13.877 | −0.927 | 7.130 | 1.00 | 13.90 |
| ATOM | 379 | O | SER | 42 | 12.722 | −1.258 | 6.862 | 1.00 | 18.52 |
| ATOM | 380 | N | LEU | 43 | 14.615 | −1.614 | 7.985 | 1.00 | 14.21 |
| ATOM | 381 | H | LEU | 43 | 15.551 | −1.367 | 8.099 | 1.00 | 0.00 |
| ATOM | 382 | CA | LEU | 43 | 14.096 | −2.659 | 8.842 | 1.00 | 12.11 |
| ATOM | 383 | CB | LEU | 43 | 15.245 | −3.504 | 9.359 | 1.00 | 12.29 |
| ATOM | 384 | CG | LEU | 43 | 15.525 | −4.925 | 8.908 | 1.00 | 14.37 |
| ATOM | 385 | CD1 | LEU | 43 | 14.425 | −5.442 | 7.984 | 1.00 | 15.27 |
| ATOM | 386 | CD2 | LEU | 43 | 16.915 | −4.921 | 8.302 | 1.00 | 3.04 |
| ATOM | 387 | C | LEU | 43 | 13.405 | −1.982 | 10.027 | 1.00 | 11.13 |
| ATOM | 388 | O | LEU | 43 | 14.057 | −1.224 | 10.754 | 1.00 | 10.97 |
| ATOM | 389 | N | GLY | 44 | 12.099 | −2.164 | 10.184 | 1.00 | 7.84 |
| ATOM | 390 | H | GLY | 44 | 11.625 | −2.683 | 9.498 | 1.00 | 0.00 |
| ATOM | 391 | CA | GLY | 44 | 11.327 | −1.661 | 11.321 | 1.00 | 11.90 |
| ATOM | 392 | C | GLY | 44 | 11.099 | −0.147 | 11.447 | 1.00 | 14.98 |
| ATOM | 393 | O | GLY | 44 | 10.677 | 0.352 | 12.508 | 1.00 | 9.21 |
| ATOM | 394 | N | GLY | 45 | 11.279 | 0.615 | 10.380 | 1.00 | 14.81 |
| ATOM | 395 | H | GLY | 45 | 11.397 | 0.182 | 9.512 | 1.00 | 0.00 |
| ATOM | 396 | CA | GLY | 45 | 11.122 | 2.047 | 10.463 | 1.00 | 9.74 |
| ATOM | 397 | CB | GLY | 45 | 9.769 | 2.464 | 9.936 | 1.00 | 8.20 |
| ATOM | 398 | CG | GLY | 45 | 8.978 | 1.687 | 9.395 | 1.00 | 6.62 |
| ATOM | 399 | N | TYR | 46 | 9.511 | 3.752 | 10.057 | 1.00 | 9.51 |
| ATOM | 400 | H | TYR | 46 | 10.194 | 4.332 | 10.458 | 1.00 | 0.00 |
| ATOM | 401 | CA | TYR | 46 | 8.295 | 4.356 | 9.555 | 1.00 | 4.24 |
| ATOM | 402 | CB | TYR | 46 | 7.347 | 4.752 | 10.689 | 1.00 | 2.68 |
| ATOM | 403 | CG | TYR | 46 | 6.921 | 3.588 | 11.564 | 1.00 | 8.82 |
| ATOM | 404 | CD1 | TYR | 46 | 5.812 | 2.830 | 11.220 | 1.00 | 2.00 |
| ATOM | 405 | CE1 | TYR | 46 | 5.463 | 1.728 | 11.982 | 1.00 | 7.74 |
| ATOM | 406 | CD2 | TYR | 46 | 7.684 | 3.255 | 12.684 | 1.00 | 6.02 |
| ATOM | 407 | CE2 | TYR | 46 | 7.343 | 2.147 | 13.453 | 1.00 | 11.00 |
| ATOM | 408 | CZ | TYR | 46 | 6.233 | 1.388 | 13.092 | 1.00 | 10.98 |
| ATOM | 409 | OH | TYR | 46 | 5.905 | 0.267 | 13.825 | 1.00 | 8.20 |
| ATOM | 410 | HH | TYR | 46 | 6.725 | −0.036 | 14.250 | 1.00 | 0.00 |
| ATOM | 411 | C | TYR | 46 | 8.678 | 5.610 | 8.796 | 1.00 | 2.66 |
| ATOM | 412 | O | TYR | 46 | 9.856 | 5.975 | 8.722 | 1.00 | 2.00 |
| ATOM | 413 | N | VAL | 47 | 7.691 | 6.266 | 8.217 | 1.00 | 2.00 |
| ATOM | 414 | H | VAL | 47 | 6.772 | 5.925 | 8.251 | 1.00 | 0.00 |
| ATOM | 415 | CA | VAL | 47 | 7.906 | 7.564 | 7.655 | 1.00 | 3.35 |
| ATOM | 416 | CB | VAL | 47 | 7.904 | 7.582 | 6.088 | 1.00 | 4.68 |

TABLE 23-continued

Coordinates for the 3D structure of ZAP-NC:ζ1 "dimer" structure
(two molecules of complex per unit cell)*

| ATOM | 417 | CG1 | VAL | 47 | 8.233 | 9.004 | 5.674 | 1.00 | 2.00 |
|---|---|---|---|---|---|---|---|---|---|
| ATOM | 418 | CG2 | VAL | 47 | 8.969 | 6.694 | 5.445 | 1.00 | 2.00 |
| ATOM | 419 | C | VAL | 47 | 6.702 | 8.327 | 8.198 | 1.00 | 5.16 |
| ATOM | 420 | O | VAL | 47 | 5.560 | 7.842 | 8.202 | 1.00 | 2.00 |
| ATOM | 421 | N | LEU | 48 | 7.015 | 7.842 | 8.772 | 1.00 | 8.17 |
| ATOM | 422 | H | LEU | 48 | 7.954 | 9.505 | 8.830 | 1.00 | 0.00 |
| ATOM | 423 | CA | LEU | 48 | 6.001 | 9.773 | 9.273 | 1.00 | 6.70 |
| ATOM | 424 | CB | LEU | 48 | 6.544 | 10.432 | 10.506 | 1.00 | 3.33 |
| ATOM | 425 | CG | LEU | 48 | 5.855 | 11.178 | 11.014 | 1.00 | 10.59 |
| ATOM | 426 | CD1 | LEU | 48 | 4.443 | 12.184 | 11.481 | 1.00 | 2.00 |
| ATOM | 427 | CD2 | LEU | 48 | 6.688 | 13.032 | 12.151 | 1.00 | 10.81 |
| ATOM | 428 | C | LEU | 48 | 5.732 | 11.393 | 8.125 | 1.00 | 2.00 |
| ATOM | 429 | O | LEU | 48 | 6.652 | 12.078 | 7.681 | 1.00 | 2.00 |
| ATOM | 430 | N | SER | 49 | 4.518 | 11.432 | 7.592 | 1.00 | 5.52 |
| ATOM | 431 | H | SER | 49 | 3.795 | 10.929 | 8.028 | 1.00 | 0.00 |
| ATOM | 432 | CA | SER | 49 | 4.204 | 12.312 | 6.464 | 1.00 | 7.99 |
| ATOM | 433 | CB | SER | 49 | 3.533 | 11.538 | 5.339 | 1.00 | 5.20 |
| ATOM | 434 | OG | SER | 49 | 4.472 | 10.608 | 4.804 | 1.00 | 4.26 |
| ATOM | 435 | HG | SER | 49 | 4.258 | 9.763 | 5.230 | 1.00 | 0.00 |
| ATOM | 436 | C | SER | 49 | 3.279 | 13.402 | 6.946 | 1.00 | 4.36 |
| ATOM | 437 | O | SER | 49 | 2.207 | 13.129 | 7.476 | 1.00 | 2.46 |
| ATOM | 438 | N | LEU | 50 | 3.692 | 14.646 | 6.740 | 1.00 | 11.49 |
| ATOM | 439 | H | LEU | 50 | 4.500 | 14.827 | 6.218 | 1.00 | 0.00 |
| ATOM | 440 | CA | LEU | 50 | 2.981 | 15.773 | 7.301 | 1.00 | 10.89 |
| ATOM | 441 | CB | LEU | 50 | 3.736 | 16.081 | 8.614 | 1.00 | 13.17 |
| ATOM | 442 | CG | LEU | 50 | 4.269 | 17.435 | 9.006 | 1.00 | 11.02 |
| ATOM | 443 | CD1 | LEU | 50 | 3.244 | 18.149 | 9.876 | 1.00 | 15.66 |
| ATOM | 444 | CD2 | LEU | 50 | 5.557 | 17.249 | 9.743 | 1.00 | 10.25 |
| ATOM | 445 | C | LEU | 50 | 2.862 | 16.965 | 6.360 | 1.00 | 5.13 |
| ATOM | 446 | O | LEU | 50 | 3.836 | 17.222 | 5.517 | 1.00 | 5.58 |
| ATOM | 447 | N | VAL | 51 | 1.734 | 17.659 | 6.517 | 1.00 | 5.20 |
| ATOM | 448 | H | VAL | 51 | 1.077 | 17.332 | 7.162 | 1.00 | 0.00 |
| ATOM | 449 | CA | VAL | 51 | 1.444 | 18.873 | 5.778 | 1.00 | 6.94 |
| ATOM | 450 | CB | VAL | 51 | −0.037 | 18.938 | 5.369 | 1.00 | 5.57 |
| ATOM | 451 | CG1 | VAL | 51 | −0.313 | 20.171 | 4.539 | 1.00 | 5.27 |
| ATOM | 452 | CG2 | VAL | 51 | −0.363 | 17.755 | 4.502 | 1.00 | 8.48 |
| ATOM | 453 | C | VAL | 51 | 1.767 | 20.115 | 6.605 | 1.00 | 6.19 |
| ATOM | 454 | O | VAL | 51 | 1.419 | 20.266 | 7.779 | 1.00 | 6.38 |
| ATOM | 455 | N | HIS | 52 | 2.496 | 21.014 | 5.956 | 1.00 | 7.67 |
| ATOM | 456 | H | HIS | 52 | 2.779 | 20.789 | 5.041 | 1.00 | 0.00 |
| ATOM | 457 | CA | HIS | 52 | 2.805 | 22.326 | 6.469 | 1.00 | 5.57 |
| ATOM | 458 | CB | HIS | 52 | 4.074 | 22.315 | 7.320 | 1.00 | 4.68 |
| ATOM | 459 | CG | HIS | 52 | 4.302 | 23.714 | 7.897 | 1.00 | 2.00 |
| ATOM | 460 | CD2 | HIS | 52 | 5.319 | 24.547 | 7.535 | 1.00 | 5.06 |
| ATOM | 461 | ND1 | HIS | 52 | 3.552 | 24.372 | 8.768 | 1.00 | 6.19 |
| ATOM | 462 | HD1 | HIS | 52 | 2.809 | 24.027 | 9.315 | 1.00 | 0.00 |
| ATOM | 463 | CE1 | HIS | 52 | 4.076 | 25.555 | 8.929 | 1.00 | 2.82 |
| ATOM | 464 | NE2 | HIS | 52 | 5.135 | 25.652 | 8.189 | 1.00 | 2.00 |
| ATOM | 465 | HE2 | HIS | 52 | 5.832 | 26.325 | 8.378 | 1.00 | 0.00 |
| ATOM | 466 | C | HIS | 52 | 3.011 | 23.224 | 5.233 | 1.00 | 6.14 |
| ATOM | 467 | O | HIS | 52 | 3.752 | 22.848 | 4.326 | 1.00 | 7.03 |
| ATOM | 468 | N | ASP | 53 | 2.344 | 24.398 | 5.203 | 1.00 | 7.04 |
| ATOM | 469 | H | ASP | 53 | 1.756 | 24.593 | 5.946 | 1.00 | 0.00 |
| ATOM | 470 | CA | ASP | 53 | 2.319 | 25.378 | 4.128 | 1.00 | 7.19 |
| ATOM | 471 | CB | ASP | 53 | 3.692 | 26.074 | 2.077 | 1.00 | 13.83 |
| ATOM | 472 | CG | ASP | 53 | 3.752 | 27.331 | 3.203 | 1.00 | 19.58 |
| ATOM | 473 | OD1 | ASP | 53 | 4.872 | 27.597 | 2.695 | 1.00 | 24.03 |
| ATOM | 474 | OD2 | ASP | 53 | 2.790 | 28.048 | 3.030 | 1.00 | 20.95 |
| ATOM | 475 | C | ASP | 53 | 1.944 | 24.749 | 2.783 | 1.00 | 7.16 |
| ATOM | 476 | O | ASP | 53 | 2.571 | 24.963 | 1.752 | 1.00 | 4.53 |
| ATOM | 477 | N | VAL | 54 | 0.844 | 23.980 | 2.869 | 1.00 | 8.53 |
| ATOM | 478 | H | VAL | 54 | 0.390 | 23.945 | 3.737 | 1.00 | 0.00 |
| ATOM | 479 | CA | VAL | 54 | 0.204 | 23.208 | 1.800 | 1.00 | 8.93 |
| ATOM | 480 | CB | VAL | 54 | −0.627 | 24.166 | 0.849 | 1.00 | 12.04 |
| ATOM | 481 | CG1 | VAL | 54 | −1.678 | 23.357 | 0.060 | 1.00 | 7.47 |
| ATOM | 482 | CG2 | VAL | 54 | −1.419 | 25.201 | 1.664 | 1.00 | 8.15 |
| ATOM | 483 | C | VAL | 54 | 1.224 | 22.395 | 1.006 | 1.00 | 9.82 |
| ATOM | 484 | O | VAL | 54 | 1.087 | 22.119 | −0.185 | 1.00 | 9.21 |
| ATOM | 485 | N | ARG | 55 | 2.250 | 21.903 | 1.704 | 1.00 | 8.33 |
| ATOM | 486 | H | ARG | 55 | 2.287 | 33.011 | 2.677 | 1.00 | 0.00 |
| ATOM | 487 | CA | ARG | 55 | 3.322 | 21.141 | 1.094 | 1.00 | 9.23 |
| ATOM | 488 | CB | ARG | 55 | 4.611 | 21.966 | 1.055 | 1.00 | 6.97 |
| ATOM | 489 | CG | ARG | 55 | 4.532 | 23.059 | 0.020 | 1.00 | 10.44 |
| ATOM | 490 | CD | ARG | 55 | 5.795 | 23.872 | 0.061 | 1.00 | 12.13 |
| ATOM | 491 | NE | ARG | 55 | 5.926 | 24.706 | −1.136 | 1.00 | 18.61 |
| ATOM | 492 | HE | ARG | 55 | 6.452 | 24.356 | −1.888 | 1.00 | 0.00 |

TABLE 23-continued

Coordinates for the 3D structure of ZAP-NC:ζ1 "dimer" structure
(two molecules of complex per unit cell)*

| ATOM | 493 | CZ | ARG | 55 | 5.350 | 25.913 | -1.280 | 1.00 | 15.59 |
|------|-----|------|-----|----|--------|--------|--------|------|-------|
| ATOM | 494 | NH1  | ARG | 55 | 4.586  | 26.464 | -0.336 | 1.00 | 10.00 |
| ATOM | 495 | HH11 | ARG | 55 | 4.408  | 25.984 | 0.524  | 1.00 | 0.00  |
| ATOM | 496 | HH12 | ARG | 55 | 4.189  | 27.367 | -0.490 | 1.00 | 0.00  |
| ATOM | 497 | NH2  | ARG | 55 | 5.584  | 26.607 | -2.390 | 1.00 | 14.76 |
| ATOM | 498 | HH21 | ARG | 55 | 6.170  | 26.232 | -3.108 | 1.00 | 0.00  |
| ATOM | 499 | HH22 | ARG | 55 | 5.161  | 27.505 | -2.516 | 1.00 | 0.00  |
| ATOM | 500 | C    | ARG | 55 | 3.524  | 19.911 | 1.961  | 1.00 | 9.89  |
| ATOM | 501 | O    | ARG | 55 | 3.145  | 19.914 | 3.136  | 1.00 | 7.57  |
| ATOM | 502 | N    | PHE | 56 | 4.170  | 18.888 | 1.414  | 1.00 | 11.16 |
| ATOM | 503 | H    | PHE | 56 | 4.544  | 18.997 | 0.510  | 1.00 | 0.00  |
| ATOM | 504 | CA   | PHE | 56 | 4.340  | 17.617 | 2.096  | 1.00 | 10.07 |
| ATOM | 505 | CB   | PHE | 56 | 4.098  | 16.569 | 1.151  | 1.00 | 10.65 |
| ATOM | 506 | CG   | PHE | 56 | 2.742  | 16.558 | 0.505  | 1.00 | 5.39  |
| ATOM | 507 | CD1  | PHE | 56 | 2.644  | 16.978 | -0.820 | 1.00 | 7.49  |
| ATOM | 508 | CD2  | PHE | 56 | 1.625  | 16.180 | 1.224  | 1.00 | 2.00  |
| ATOM | 509 | CE1  | PHE | 56 | 1.397  | 17.010 | -1.440 | 1.00 | 2.00  |
| ATOM | 510 | CE2  | PHE | 56 | 0.387  | 16.217 | 0.593  | 1.00 | 4.37  |
| ATOM | 511 | CZ   | PHE | 56 | 0.271  | 16.629 | -0.735 | 1.00 | 3.23  |
| ATOM | 512 | C    | PHE | 56 | 5.720  | 17.453 | 2.654  | 1.00 | 7.33  |
| ATOM | 513 | O    | PHE | 56 | 6.669  | 17.846 | 1.989  | 1.00 | 3.76  |
| ATOM | 514 | N    | HIS | 57 | 5.911  | 16.893 | 3.847  | 1.00 | 7.78  |
| ATOM | 515 | H    | HIS | 57 | 5.145  | 16.575 | 3.476  | 1.00 | 0.00  |
| ATOM | 516 | CA   | HIS | 57 | 7.243  | 16.753 | 4.422  | 1.00 | 9.13  |
| ATOM | 517 | CB   | HIS | 57 | 7.410  | 17.781 | 5.554  | 1.00 | 9.13  |
| ATOM | 518 | CG   | HIS | 57 | 7.101  | 19.214 | 5.116  | 1.00 | 5.87  |
| ATOM | 519 | CD2  | HIS | 57 | 5.851  | 19.759 | 5.157  | 1.00 | 4.86  |
| ATOM | 520 | ND1  | HIS | 57 | 7.905  | 20.137 | 4.602  | 1.00 | 5.61  |
| ATOM | 521 | HD1  | HIS | 57 | 8.788  | 19.977 | 4.213  | 1.00 | 0.00  |
| ATOM | 522 | CE1  | HIS | 57 | 7.208  | 21.202 | 4.328  | 1.00 | 2.00  |
| ATOM | 523 | NE2  | HIS | 57 | 5.978  | 20.952 | 4.666  | 1.00 | 8.92  |
| ATOM | 524 | HE2  | HIS | 57 | 5.233  | 21.552 | 4.438  | 1.00 | 0.00  |
| ATOM | 525 | C    | HIS | 57 | 7.295  | 15.330 | 4.945  | 1.00 | 7.66  |
| ATOM | 526 | O    | HIS | 57 | 6.364  | 14.882 | 5.611  | 1.00 | 11.39 |
| ATOM | 527 | N    | HIS | 58 | 8.296  | 14.567 | 4.535  | 1.00 | 9.95  |
| ATOM | 528 | H    | HIS | 58 | 9.012  | 14.961 | 3.981  | 1.00 | 0.00  |
| ATOM | 529 | CA   | HIS | 58 | 8.411  | 13.173 | 4.887  | 1.00 | 7.60  |
| ATOM | 530 | CB   | HIS | 58 | 8.491  | 12.344 | 3.620  | 1.00 | 3.50  |
| ATOM | 531 | CG   | HIS | 58 | 7.195  | 12.474 | 2.834  | 1.00 | 2.00  |
| ATOM | 532 | CD2  | HIS | 58 | 7.013  | 13.360 | 1.813  | 1.00 | 2.00  |
| ATOM | 533 | ND1  | HIS | 58 | 6.051  | 11.828 | 2.960  | 1.00 | 4.99  |
| ATOM | 534 | HD1  | HIS | 58 | 5.844  | 11.123 | 3.619  | 1.00 | 0.00  |
| ATOM | 535 | CE1  | HIS | 58 | 5.196  | 12.273 | 2.087  | 1.00 | 2.00  |
| ATOM | 536 | NE2  | HIS | 58 | 5.794  | 13.197 | 1.403  | 1.00 | 2.00  |
| ATOM | 537 | HE2  | HIS | 58 | 5.390  | 13.727 | 0.691  | 1.00 | 0.00  |
| ATOM | 538 | C    | HIS | 58 | 9.636  | 12.966 | 5.731  | 1.00 | 7.66  |
| ATOM | 539 | O    | HIS | 58 | 10.756 | 13.187 | 5.271  | 1.00 | 6.10  |
| ATOM | 540 | N    | PHE | 59 | 9.418  | 12.580 | 6.985  | 1.00 | 4.13  |
| ATOM | 541 | H    | PHE | 59 | 8.490  | 12.492 | 7.283  | 1.00 | 0.00  |
| ATOM | 542 | CA   | PHE | 59 | 10.476 | 12.333 | 7.958  | 1.00 | 5.36  |
| ATOM | 543 | CB   | PHE | 59 | 10.097 | 13.014 | 9.295  | 1.00 | 5.09  |
| ATOM | 544 | CG   | PHE | 59 | 10.111 | 14.519 | 9.155  | 1.00 | 2.00  |
| ATOM | 545 | CD1  | PHE | 59 | 8.934  | 15.182 | 8.879  | 1.00 | 2.00  |
| ATOM | 546 | CD2  | PHE | 59 | 11.332 | 15.206 | 9.253  | 1.00 | 3.34  |
| ATOM | 547 | CE1  | PHE | 59 | 8.987  | 16.571 | 8.688  | 1.00 | 8.91  |
| ATOM | 548 | CE2  | PHE | 59 | 11.371 | 16.549 | 9.060  | 1.00 | 2.00  |
| ATOM | 549 | C2   | PHE | 59 | 10.203 | 17.246 | 8.780  | 1.00 | 2.00  |
| ATOM | 550 | C    | PHE | 59 | 10.707 | 10.846 | 8.189  | 1.00 | 3.82  |
| ATOM | 551 | O    | PHE | 59 | 9.802  | 10.183 | 8.724  | 1.00 | 4.17  |
| ATOM | 552 | N    | PRO | 60 | 11.822 | 10.239 | 7.802  | 1.00 | 4.66  |
| ATOM | 553 | CD   | PRO | 60 | 12.871 | 10.838 | 6.989  | 1.00 | 7.48  |
| ATOM | 554 | CA   | PRO | 60 | 12.139 | 8.867  | 8.165  | 1.00 | 6.70  |
| ATOM | 555 | CB   | PRO | 60 | 13.388 | 8.558  | 7.392  | 1.00 | 4.95  |
| ATOM | 556 | CG   | PRO | 60 | 13.453 | 9.621  | 6.300  | 1.00 | 5.79  |
| ATOM | 557 | C    | PRO | 60 | 12.313 | 8.715  | 9.672  | 1.00 | 10.66 |
| ATOM | 558 | O    | PRO | 60 | 12.935 | 9.532  | 10.350 | 1.00 | 8.35  |
| ATOM | 559 | N    | ILE | 61 | 11.681 | 7.687  | 10.217 | 1.00 | 11.15 |
| ATOM | 560 | H    | ILE | 61 | 11.116 | 7.128  | 9.646  | 1.00 | 0.00  |
| ATOM | 561 | CA   | ILE | 61 | 11.807 | 7.337  | 11.621 | 1.00 | 7.78  |
| ATOM | 562 | CB   | ILE | 61 | 10.408 | 7.155  | 12.247 | 1.00 | 6.02  |
| ATOM | 563 | CG2  | ILE | 61 | 10.620 | 6.819  | 13.710 | 1.00 | 4.07  |
| ATOM | 564 | CG1  | ILE | 61 | 9.524  | 8.398  | 12.103 | 1.00 | 4.03  |
| ATOM | 565 | CD   | ILE | 61 | 8.035  | 8.155  | 12.396 | 1.00 | 2.00  |
| ATOM | 566 | C    | ILE | 61 | 12.563 | 6.013  | 11.574 | 1.00 | 8.52  |
| ATOM | 567 | O    | ILE | 61 | 12.018 | 5.034  | 11.047 | 1.00 | 9.02  |
| ATOM | 568 | N    | GLU | 62 | 13.816 | 5.975  | 12.022 | 1.00 | 9.62  |

TABLE 23-continued

Coordinates for the 3D structure of ZAP-NC:ζ1 "dimer" structure
(two molecules of complex per unit cell)*

| ATOM | 569 | H | GLU | 62 | 14.202 | 6.797 | 12.395 | 1.00 | 0.00 |
|------|-----|---|-----|-----|--------|-------|--------|------|-------|
| ATOM | 570 | CA | GLU | 62 | 14.612 | 4.856 | 12.035 | 1.00 | 8.61 |
| ATOM | 571 | CB | GLU | 62 | 16.077 | 5.015 | 11.900 | 1.00 | 8.30 |
| ATOM | 572 | CG | GLU | 62 | 16.575 | 5.629 | 10.615 | 1.00 | 29.69 |
| ATOM | 573 | CD | GLU | 62 | 18.027 | 6.097 | 10.749 | 1.00 | 43.17 |
| ATOM | 574 | OE1 | GLU | 62 | 18.878 | 5.304 | 11.173 | 1.00 | 46.59 |
| ATOM | 575 | OE2 | GLU | 62 | 18.305 | 7.262 | 10.441 | 1.00 | 47.06 |
| ATOM | 576 | C | GLU | 62 | 14.464 | 4.023 | 13.358 | 1.00 | 9.33 |
| ATOM | 577 | O | GLU | 62 | 14.321 | 4.691 | 14.365 | 1.00 | 11.22 |
| ATOM | 578 | N | ARG | 63 | 14.460 | 2.698 | 13.370 | 1.00 | 9.50 |
| ATOM | 579 | H | ARG | 63 | 14.448 | 2.228 | 12.514 | 1.00 | 0.00 |
| ATOM | 580 | CA | ARG | 63 | 14.508 | 1.918 | 14.597 | 1.00 | 11.99 |
| ATOM | 581 | CB | ARG | 63 | 13.851 | 0.583 | 14.339 | 1.00 | 16.38 |
| ATOM | 582 | CG | ARG | 63 | 13.612 | −0.203 | 15.604 | 1.00 | 20.52 |
| ATOM | 583 | CD | ARG | 63 | 12.825 | −1.422 | 15.224 | 1.00 | 27.53 |
| ATOM | 584 | NE | ARG | 63 | 12.614 | −2.334 | 16.332 | 1.00 | 36.69 |
| ATOM | 585 | HE | ARG | 63 | 11.709 | −2.419 | 16.697 | 1.00 | 0.00 |
| ATOM | 586 | CZ | ARG | 63 | 13.596 | −3.072 | 16.878 | 1.00 | 39.35 |
| ATOM | 587 | NH1 | ARG | 63 | 14.864 | −3.031 | 16.463 | 1.00 | 42.71 |
| ATOM | 588 | HH11 | ARG | 63 | 15.125 | −2.426 | 15.711 | 1.00 | 0.00 |
| ATOM | 589 | HH12 | ARG | 63 | 15.553 | −3.603 | 16.909 | 1.00 | 0.00 |
| ATOM | 590 | NH2 | ARG | 63 | 13.293 | −3.915 | 17.858 | 1.00 | 41.76 |
| ATOM | 591 | HH21 | ARG | 63 | 12.349 | −3.985 | 18.185 | 1.00 | 0.00 |
| ATOM | 592 | HH22 | ARG | 63 | 14.009 | −4.480 | 18.269 | 1.00 | 0.00 |
| ATOM | 593 | C | ARG | 63 | 15.992 | 1.760 | 14.998 | 1.00 | 14.55 |
| ATOM | 594 | O | ARG | 63 | 16.882 | 1.405 | 14.210 | 1.00 | 15.00 |
| ATOM | 595 | N | GLN | 64 | 16.312 | 2.083 | 16.247 | 1.00 | 13.04 |
| ATOM | 596 | H | GLN | 64 | 15.586 | 2.240 | 16.876 | 1.00 | 0.00 |
| ATOM | 597 | CA | GLN | 64 | 17.692 | 2.150 | 16.724 | 1.00 | 14.92 |
| ATOM | 598 | CB | GLN | 64 | 17.809 | 3.120 | 17.901 | 1.00 | 13.12 |
| ATOM | 599 | CG | GLN | 64 | 17.253 | 4.507 | 17.632 | 1.00 | 20.26 |
| ATOM | 600 | CD | GLN | 64 | 18.029 | 5.265 | 16.569 | 1.00 | 26.72 |
| ATOM | 601 | OE1 | GLN | 64 | 17.579 | 5.524 | 15.453 | 1.00 | 32.53 |
| ATOM | 602 | NE2 | GLN | 64 | 19.246 | 5.681 | 16.873 | 1.00 | 31.43 |
| ATOM | 603 | HE21 | GLN | 64 | 19.593 | 5.484 | 17.766 | 1.00 | 0.00 |
| ATOM | 604 | HE22 | GLN | 64 | 19.721 | 6.197 | 16.189 | 1.00 | 0.00 |
| ATOM | 605 | C | GLN | 64 | 18.196 | 0.803 | 17.200 | 1.00 | 14.42 |
| ATOM | 606 | O | GLN | 64 | 17.384 | −0.097 | 17.379 | 1.00 | 15.52 |
| ATOM | 607 | N | LEU | 65 | 19.498 | 0.702 | 17.519 | 1.00 | 19.29 |
| ATOM | 608 | H | LEU | 65 | 20.086 | 1.426 | 17.230 | 1.00 | 0.00 |
| ATOM | 609 | CA | LEU | 65 | 20.112 | −0.477 | 18.145 | 1.00 | 22.45 |
| ATOM | 610 | CB | LEU | 65 | 21.589 | −0.172 | 18.629 | 1.00 | 28.25 |
| ATOM | 611 | CG | LEU | 65 | 22.134 | 0.937 | 19.638 | 1.00 | 36.97 |
| ATOM | 612 | CD1 | LEU | 65 | 21.972 | 0.566 | 21.105 | 1.00 | 35.85 |
| ATOM | 613 | CD2 | LEU | 65 | 23.666 | 1.012 | 19.553 | 1.00 | 31.59 |
| ATOM | 614 | C | LEU | 65 | 19.306 | −0.988 | 17.337 | 1.00 | 19.74 |
| ATOM | 615 | O | LEU | 65 | 19.098 | −2.185 | 19.514 | 1.00 | 22.52 |
| ATOM | 616 | N | ASN | 66 | 18.737 | −0.082 | 20.122 | 1.00 | 16.94 |
| ATOM | 617 | H | ASN | 66 | 18.751 | 0.854 | 19.850 | 1.00 | 0.00 |
| ATOM | 618 | CA | ASN | 66 | 18.035 | −0.443 | 21.344 | 1.00 | 14.28 |
| ATOM | 619 | CB | ASN | 66 | 18.408 | 0.567 | 22.433 | 1.00 | 17.49 |
| ATOM | 620 | CG | ASN | 66 | 18.149 | 2.027 | 22.091 | 1.00 | 18.94 |
| ATOM | 621 | OD1 | ASN | 66 | 17.411 | 2.357 | 21.159 | 1.00 | 20.48 |
| ATOM | 622 | ND2 | ASN | 66 | 18.776 | 2.964 | 22.771 | 1.00 | 26.84 |
| ATOM | 623 | HD21 | ASN | 66 | 19.427 | 2.694 | 23.459 | 1.00 | 0.00 |
| ATOM | 624 | HD22 | ASN | 66 | 18.577 | 3.906 | 22.593 | 1.00 | 0.00 |
| ATOM | 625 | C | ASN | 66 | 18.631 | −0.557 | 21.223 | 1.00 | 13.50 |
| ATOM | 626 | O | ASN | 66 | 15.822 | −0.693 | 22.219 | 1.00 | 11.14 |
| ATOM | 627 | N | GLY | 67 | 16.013 | −0.514 | 19.997 | 1.00 | 10.89 |
| ATOM | 628 | H | GLY | 67 | 16.594 | −0.368 | 19.219 | 1.00 | 0.00 |
| ATOM | 629 | CA | GLY | 67 | 14.604 | −0.731 | 19.757 | 1.00 | 5.16 |
| ATOM | 630 | C | GLY | 67 | 13.780 | 0.521 | 19.903 | 1.00 | 5.50 |
| ATOM | 631 | O | GLY | 67 | 12.551 | 0.429 | 19.953 | 1.00 | 4.32 |
| ATOM | 632 | N | THR | 68 | 14.402 | 1.679 | 20.083 | 1.00 | 5.74 |
| ATOM | 633 | H | THR | 68 | 15.364 | 1.730 | 20.241 | 1.00 | 0.00 |
| ATOM | 634 | CA | THR | 68 | 13.602 | 2.891 | 20.096 | 1.00 | 10.10 |
| ATOM | 635 | CB | THR | 68 | 14.274 | 3.962 | 21.038 | 1.00 | 7.70 |
| ATOM | 636 | OG1 | THR | 68 | 15.602 | 4.200 | 20.634 | 1.00 | 6.50 |
| ATOM | 637 | HG1 | THR | 68 | 16.204 | 3.718 | 21.205 | 1.00 | 0.00 |
| ATOM | 638 | CG2 | THR | 68 | 14.284 | 3.486 | 22.482 | 1.00 | 6.39 |
| ATOM | 639 | C | THR | 68 | 13.465 | 3.376 | 18.643 | 1.00 | 10.84 |
| ATOM | 640 | O | THR | 68 | 14.033 | 2.800 | 17.706 | 1.00 | 8.07 |
| ATOM | 641 | N | THR | 68 | 12.687 | 4.417 | 18.438 | 1.00 | 11.31 |
| ATOM | 642 | H | TYR | 69 | 12.312 | 4.893 | 19.205 | 1.00 | 0.00 |
| ATOM | 643 | CA | TYR | 69 | 12.398 | 1.956 | 17.143 | 1.00 | 8.56 |
| ATOM | 644 | CB | TYR | 69 | 10.914 | 1.793 | 16.881 | 1.00 | 10.27 |

TABLE 23-continued

Coordinates for the 3D structure of ZAP-NC:ζ1 "dimer" structure
(two molecules of complex per unit cell)*

| ATOM | 645 | CG | TYR | 69 | 10.494 | 3.343 | 18.604 | 1.00 | 9.08 |
|------|-----|-----|-----|----|--------|-------|--------|------|-------|
| ATOM | 646 | CD1 | TYR | 69 | 10.116 | 2.661 | 17.959 | 1.00 | 11.62 |
| ATOM | 647 | CE1 | TYR | 69 | 9.736 | 1.316 | 17.883 | 1.00 | 15.89 |
| ATOM | 648 | CD2 | TYR | 69 | 10.525 | 2.691 | 15.571 | 1.00 | 12.19 |
| ATOM | 649 | CE2 | TYR | 69 | 10.178 | 1.342 | 15.490 | 1.00 | 16.67 |
| ATOM | 650 | CZ | TYR | 69 | 9.798 | 0.654 | 16.647 | 1.00 | 20.73 |
| ATOM | 651 | OH | TYR | 69 | 9.417 | 0.682 | 16.573 | 1.00 | 17.13 |
| ATOM | 652 | HH | TYR | 69 | 9.258 | 0.922 | 15.649 | 1.00 | 0.00 |
| ATOM | 653 | C | TYR | 69 | 12.784 | 6.416 | 17.202 | 1.00 | 10.11 |
| ATOM | 654 | O | TYR | 69 | 12.428 | 7.111 | 18.163 | 1.00 | 14.34 |
| ATOM | 655 | N | ALA | 70 | 13.510 | 6.930 | 16.225 | 1.00 | 12.39 |
| ATOM | 656 | H | ALA | 70 | 13.836 | 6.347 | 15.502 | 1.00 | 0.00 |
| ATOM | 657 | CA | ALA | 70 | 13.886 | 8.334 | 16.185 | 1.00 | 10.82 |
| ATOM | 658 | CB | ALA | 70 | 15.239 | 8.583 | 16.848 | 1.00 | 2.00 |
| ATOM | 659 | C | ALA | 70 | 14.013 | 8.833 | 14.753 | 1.00 | 12.46 |
| ATOM | 660 | O | ALA | 70 | 14.523 | 8.112 | 13.875 | 1.00 | 13.59 |
| ATOM | 661 | N | ILE | 71 | 13.533 | 10.060 | 14.503 | 1.00 | 12.16 |
| ATOM | 662 | H | ILE | 71 | 13.071 | 10.526 | 15.230 | 1.00 | 0.00 |
| ATOM | 663 | CA | ILE | 71 | 13.773 | 10.777 | 13.252 | 1.00 | 8.89 |
| ATOM | 664 | CB | ILE | 71 | 12.896 | 12.060 | 13.195 | 1.00 | 8.93 |
| ATOM | 665 | CG2 | ILE | 71 | 13.255 | 12.885 | 11.969 | 1.00 | 7.48 |
| ATOM | 666 | CG1 | ILE | 71 | 11.433 | 11.675 | 13.158 | 1.00 | 2.00 |
| ATOM | 667 | CD | ILE | 71 | 10.520 | 12.881 | 13.246 | 1.00 | 4.76 |
| ATOM | 668 | C | ILE | 71 | 15.260 | 11.117 | 13.332 | 1.00 | 11.20 |
| ATOM | 669 | O | ILE | 71 | 15.714 | 11.412 | 14.446 | 1.00 | 13.25 |
| ATOM | 670 | N | ALA | 72 | 16.085 | 11.069 | 12.277 | 1.00 | 11.89 |
| ATOM | 671 | H | ALA | 72 | 15.694 | 10.895 | 11.392 | 1.00 | 0.00 |
| ATOM | 672 | CA | ALA | 72 | 17.517 | 11.313 | 12.436 | 1.00 | 14.12 |
| ATOM | 673 | CB | ALA | 72 | 18.258 | 11.340 | 11.128 | 1.00 | 12.87 |
| ATOM | 674 | C | ALA | 72 | 17.808 | 12.650 | 13.095 | 1.00 | 15.57 |
| ATOM | 675 | O | ALA | 72 | 17.219 | 13.669 | 12.737 | 1.00 | 13.25 |
| ATOM | 676 | N | GLY | 73 | 18.672 | 12.625 | 14.108 | 1.00 | 16.33 |
| ATOM | 677 | H | GLY | 73 | 19.112 | 11.771 | 14.299 | 1.00 | 0.00 |
| ATOM | 678 | CA | GLY | 73 | 19.052 | 13.798 | 14.882 | 1.00 | 11.52 |
| ATOM | 679 | C | GLY | 73 | 17.960 | 14.265 | 15.834 | 1.00 | 14.51 |
| ATOM | 680 | O | GLY | 73 | 18.049 | 15.366 | 16.389 | 1.00 | 17.12 |
| ATOM | 681 | N | GLY | 73 | 16.920 | 13.456 | 16.033 | 1.00 | 13.85 |
| ATOM | 682 | H | GLY | 73 | 16.913 | 12.572 | 15.613 | 1.00 | 0.00 |
| ATOM | 683 | CA | GLY | 73 | 15.824 | 13.787 | 16.906 | 1.00 | 9.77 |
| ATOM | 684 | C | GLY | 73 | 15.825 | 12.895 | 18.126 | 1.00 | 13.72 |
| ATOM | 685 | O | GLY | 73 | 16.649 | 11.983 | 18.268 | 1.00 | 12.11 |
| ATOM | 686 | N | LYS | 75 | 14.817 | 13.150 | 18.960 | 1.00 | 12.83 |
| ATOM | 687 | H | LYS | 75 | 14.144 | 13.806 | 18.678 | 1.00 | 0.00 |
| ATOM | 688 | CA | LYS | 75 | 14.668 | 12.437 | 20.215 | 1.00 | 14.60 |
| ATOM | 689 | CB | LYS | 75 | 13.695 | 13.172 | 21.136 | 1.00 | 15.05 |
| ATOM | 690 | CG | LYS | 75 | 14.384 | 14.383 | 21.707 | 1.00 | 11.11 |
| ATOM | 691 | CD | LYS | 75 | 13.518 | 15.120 | 22.693 | 1.00 | 13.01 |
| ATOM | 692 | CE | LYS | 75 | 14.260 | 16.420 | 22.919 | 1.00 | 12.46 |
| ATOM | 693 | NZ | LYS | 75 | 13.448 | 17.330 | 23.676 | 1.00 | 21.36 |
| ATOM | 694 | HZ1 | LYS | 75 | 12.515 | 17.427 | 23.225 | 1.00 | 0.00 |
| ATOM | 695 | HZ2 | LYS | 75 | 13.918 | 18.257 | 23.714 | 1.00 | 0.00 |
| ATOM | 696 | HZ3 | LYS | 75 | 13.329 | 16.962 | 24.643 | 1.00 | 0.00 |
| ATOM | 697 | C | LYS | 75 | 14.189 | 11.018 | 20.033 | 1.00 | 16.16 |
| ATOM | 698 | O | LYS | 75 | 13.270 | 10.809 | 19.220 | 1.00 | 17.70 |
| ATOM | 699 | N | ALA | 76 | 14.934 | 10.048 | 20.761 | 1.00 | 13.81 |
| ATOM | 700 | H | ALA | 76 | 15.503 | 10.266 | 21.322 | 1.00 | 0.00 |
| ATOM | 701 | CA | ALA | 76 | 14.257 | 86.84 | 20.683 | 1.00 | 10.95 |
| ATOM | 702 | CB | ALA | 76 | 15.391 | 77.21 | 21.213 | 1.00 | 11.99 |
| ATOM | 703 | C | ALA | 76 | 12.977 | 84.77 | 21.464 | 1.00 | 10.10 |
| ATOM | 704 | O | ALA | 76 | 12.625 | 9.208 | 22.399 | 1.00 | 11.36 |
| ATOM | 705 | N | HIS | 77 | 12.180 | 7.515 | 21.037 | 1.00 | 6.45 |
| ATOM | 706 | H | HIS | 77 | 12.464 | 6.969 | 30.258 | 1.00 | 0.00 |
| ATOM | 707 | CA | HIS | 77 | 10.911 | 7.205 | 21.658 | 1.00 | 8.09 |
| ATOM | 708 | CB | HIS | 77 | 9.751 | 7.778 | 20.879 | 1.00 | 8.53 |
| ATOM | 709 | CG | HIS | 77 | 9.907 | 9.264 | 20.582 | 1.00 | 8.60 |
| ATOM | 710 | CD2 | HIS | 77 | 9.429 | 10.268 | 21.371 | 1.00 | 9.12 |
| ATOM | 711 | ND1 | HIS | 77 | 10.514 | 9.833 | 19.550 | 1.00 | 9.19 |
| ATOM | 712 | HD1 | HIS | 77 | 11.053 | 9.394 | 18.851 | 1.00 | 0.00 |
| ATOM | 713 | CE1 | HIS | 77 | 10.418 | 11.122 | 19.680 | 1.00 | 2.93 |
| ATOM | 714 | NE2 | HIS | 77 | 9.768 | 11.359 | 20.778 | 1.00 | 9.32 |
| ATOM | 715 | HE2 | HIS | 77 | 9.596 | 12.266 | 21.126 | 1.00 | 0.00 |
| ATOM | 716 | C | HIS | 77 | 10.745 | 5.702 | 21.692 | 1.00 | 11.51 |
| ATOM | 717 | O | HIS | 77 | 11.253 | 4.990 | 30.834 | 1.00 | 12.04 |
| ATOM | 718 | N | CYS | 78 | 10.033 | 5.169 | 22.660 | 1.00 | 12.82 |
| ATOM | 719 | H | CYS | 78 | 9.625 | 5.747 | 23.326 | 1.00 | 0.00 |
| ATOM | 720 | CA | CYS | 78 | 9.884 | 3.735 | 22.776 | 1.00 | 14.28 |

TABLE 23-continued

Coordinates for the 3D structure of ZAP-NC:ζ1 "dimer" structure
(two molecules of complex per unit cell)*

| ATOM | 721 | CB | CYS | 78 | 9.381 | 3.354 | 24.184 | 1.00 | 11.77 |
|---|---|---|---|---|---|---|---|---|---|
| ATOM | 722 | SG | CYS | 78 | 10.796 | 3.369 | 25.280 | 1.00 | 9.90 |
| ATOM | 723 | C | CYS | 78 | 8.960 | 3.126 | 21.757 | 1.00 | 16.98 |
| ATOM | 724 | O | CYS | 78 | 9.005 | 1.908 | 21.558 | 1.00 | 17.80 |
| ATOM | 725 | N | GLY | 79 | 8.128 | 3.943 | 21.113 | 1.00 | 15.68 |
| ATOM | 726 | H | GLY | 79 | 8.169 | 4.912 | 21.228 | 1.00 | 0.00 |
| ATOM | 727 | CA | GLY | 79 | 7.212 | 3.410 | 20.145 | 1.00 | 11.88 |
| ATOM | 728 | C | GLY | 79 | 6.762 | 4.509 | 19.210 | 1.00 | 14.80 |
| ATOM | 729 | O | GLY | 79 | 7.015 | 5.682 | 19.512 | 1.00 | 12.62 |
| ATOM | 730 | N | PRO | 80 | 6.089 | 4.186 | 18.089 | 1.00 | 16.78 |
| ATOM | 731 | CD | PRO | 80 | 6.052 | 2.849 | 17.491 | 1.00 | 13.56 |
| ATOM | 732 | CA | PRO | 80 | 5.496 | 5.158 | 17.187 | 1.00 | 15.14 |
| ATOM | 733 | CB | PRO | 80 | 5.005 | 4.318 | 16.015 | 1.00 | 18.70 |
| ATOM | 734 | CG | PRO | 80 | 4.852 | 2.933 | 16.571 | 1.00 | 14.52 |
| ATOM | 735 | C | PRO | 80 | 4.425 | 6.013 | 17.827 | 1.00 | 13.25 |
| ATOM | 736 | O | PRO | 80 | 4.390 | 7.209 | 17.551 | 1.00 | 13.75 |
| ATOM | 737 | N | ALA | 81 | 3.582 | 5.470 | 18.715 | 1.00 | 11.81 |
| ATOM | 738 | H | ALA | 81 | 3.658 | 4.511 | 18.927 | 1.00 | 0.00 |
| ATOM | 739 | CA | ALA | 81 | 2.560 | 6.256 | 19.378 | 1.00 | 8.01 |
| ATOM | 740 | CB | ALA | 81 | 1.696 | 5.401 | 20.259 | 1.00 | 10.17 |
| ATOM | 741 | C | ALA | 81 | 3.127 | 7.301 | 20.270 | 1.00 | 14.13 |
| ATOM | 742 | O | ALA | 81 | 2.759 | 8.447 | 20.315 | 1.00 | 19.64 |
| ATOM | 743 | N | GLU | 82 | 4.317 | 6.966 | 20.950 | 1.00 | 8.88 |
| ATOM | 744 | H | GLU | 82 | 4.685 | 6.068 | 20.827 | 1.00 | 0.00 |
| ATOM | 745 | CA | GLU | 82 | 4.998 | 7.900 | 21.810 | 1.00 | 8.22 |
| ATOM | 746 | CB | GLU | 82 | 6.055 | 7.211 | 22.673 | 1.00 | 12.54 |
| ATOM | 747 | CG | GLU | 82 | 5.510 | 6.345 | 23.801 | 1.00 | 15.92 |
| ATOM | 748 | CD | GLU | 82 | 5.248 | 4.903 | 23.391 | 1.00 | 21.01 |
| ATOM | 749 | OE1 | GLU | 82 | 5.898 | 4.019 | 23.922 | 1.00 | 19.20 |
| ATOM | 750 | OE2 | GLU | 82 | 4.403 | 4.643 | 22.545 | 1.00 | 30.40 |
| ATOM | 751 | C | GLU | 82 | 5.683 | 8.982 | 21.007 | 1.00 | 7.91 |
| ATOM | 752 | O | GLU | 82 | 5.772 | 10.112 | 21.492 | 1.00 | 8.06 |
| ATOM | 753 | N | LEU | 83 | 6.177 | 8.672 | 19.799 | 1.00 | 9.05 |
| ATOM | 754 | H | LEU | 83 | 6.060 | 7.759 | 19.462 | 1.00 | 0.00 |
| ATOM | 755 | CA | LEU | 83 | 6.804 | 9.659 | 18.928 | 1.00 | 4.91 |
| ATOM | 756 | CB | LEU | 83 | 7.521 | 8.966 | 17.736 | 1.00 | 3.58 |
| ATOM | 757 | CG | LEU | 83 | 8.272 | 9.829 | 16.683 | 1.00 | 7.47 |
| ATOM | 758 | CD1 | LEU | 83 | 9.480 | 9.086 | 16.219 | 1.00 | 2.00 |
| ATOM | 759 | CD2 | LEU | 83 | 7.357 | 10.216 | 15.524 | 1.00 | 2.00 |
| ATOM | 760 | C | LEU | 83 | 5.752 | 10.640 | 18.449 | 1.00 | 4.63 |
| ATOM | 761 | O | LEU | 83 | 5.988 | 11.849 | 18.544 | 1.00 | 5.60 |
| ATOM | 762 | N | CYS | 84 | 4.602 | 10.164 | 17.973 | 1.00 | 8.55 |
| ATOM | 763 | H | CYS | 84 | 4.494 | 9.162 | 17.890 | 1.00 | 0.00 |
| ATOM | 764 | CA | CYS | 84 | 2.548 | 11.027 | 17.482 | 1.00 | 8.64 |
| ATOM | 765 | CB | CYS | 84 | 2.503 | 10.168 | 16.756 | 1.00 | 5.54 |
| ATOM | 766 | SG | CYS | 84 | 3.177 | 9.486 | 15.221 | 1.00 | 11.42 |
| ATOM | 767 | C | CYS | 84 | 2.926 | 11.826 | 18.615 | 1.00 | 12.17 |
| ATOM | 768 | O | CYS | 84 | 2.575 | 12.979 | 18.399 | 1.00 | 11.99 |
| ATOM | 769 | N | GLU | 85 | 2.806 | 11.294 | 19.835 | 1.00 | 15.31 |
| ATOM | 770 | H | GLU | 85 | 3.004 | 10.339 | 19.935 | 1.00 | 0.00 |
| ATOM | 771 | CA | GLU | 85 | 2.350 | 12.030 | 21.007 | 1.00 | 12.31 |
| ATOM | 772 | CB | GLU | 85 | 2.212 | 11.121 | 22.207 | 1.00 | 19.90 |
| ATOM | 773 | CG | GLU | 85 | 0.815 | 10.555 | 22.406 | 1.00 | 31.63 |
| ATOM | 774 | CD | GLU | 85 | 0.658 | 9.495 | 23.503 | 1.00 | 39.27 |
| ATOM | 775 | OE1 | GLU | 85 | −0.477 | 9.081 | 23.738 | 1.00 | 41.21 |
| ATOM | 776 | OE2 | GLU | 85 | 1.642 | 9.071 | 24.118 | 1.00 | 42.94 |
| ATOM | 777 | C | GLU | 85 | 3.333 | 13.125 | 21.372 | 1.00 | 6.87 |
| ATOM | 778 | O | GLU | 85 | 2.920 | 14.260 | 21.571 | 1.00 | 10.13 |
| ATOM | 779 | N | PHE | 86 | 4.631 | 12.861 | 21.416 | 1.00 | 4.59 |
| ATOM | 780 | H | PHE | 86 | 4.937 | 11.944 | 21.248 | 1.00 | 0.00 |
| ATOM | 781 | CA | PHE | 86 | 5.603 | 13.891 | 21.725 | 1.00 | 6.95 |
| ATOM | 782 | CB | PHE | 86 | 6.999 | 13.293 | 21.764 | 1.00 | 4.93 |
| ATOM | 783 | CG | PHE | 86 | 8.114 | 14.317 | 21.932 | 1.00 | 5.40 |
| ATOM | 784 | CD1 | PHE | 86 | 8.400 | 14.831 | 23.201 | 1.00 | 2.19 |
| ATOM | 785 | CD2 | PHE | 86 | 8.808 | 14.781 | 20.807 | 1.00 | 2.76 |
| ATOM | 786 | CE1 | PHE | 86 | 9.375 | 15.816 | 23.336 | 1.00 | 2.93 |
| ATOM | 787 | CE2 | PHE | 86 | 9.781 | 15.765 | 20.944 | 1.00 | 2.30 |
| ATOM | 788 | CZ | PHE | 86 | 10.064 | 16.284 | 22.212 | 1.00 | 5.55 |
| ATOM | 789 | C | PHE | 86 | 5.575 | 15.027 | 20.720 | 1.00 | 9.00 |
| ATOM | 790 | O | PHE | 86 | 5.446 | 16.187 | 21.109 | 1.00 | 14.30 |
| ATOM | 791 | N | TYR | 87 | 5.653 | 14.760 | 19.418 | 1.00 | 11.37 |
| ATOM | 792 | H | TYR | 87 | 5.691 | 13.826 | 19.113 | 1.00 | 0.00 |
| ATOM | 793 | CA | TYR | 87 | 5.666 | 15.833 | 18.446 | 1.00 | 6.03 |
| ATOM | 794 | CB | TYR | 87 | 6.110 | 15.254 | 17.139 | 1.00 | 3.16 |
| ATOM | 795 | CG | TYR | 87 | 7.591 | 14.946 | 17.117 | 1.00 | 2.00 |
| ATOM | 796 | CD1 | TYR | 87 | 8.021 | 13.631 | 17.046 | 1.00 | 5.05 |

TABLE 23-continued

Coordinates for the 3D structure of ZAP-NC:ζ1 "dimer" structure
(two molecules of complex per unit cell)*

| ATOM | 797 | CE1 | TYR | 87 | 9.391 | 13.345 | 16.974 | 1.00 | 8.26 |
|---|---|---|---|---|---|---|---|---|---|
| ATOM | 798 | CD2 | TYR | 87 | 8.525 | 15.979 | 17.117 | 1.00 | 2.00 |
| ATOM | 799 | CE2 | TYR | 87 | 9.891 | 15.713 | 17.043 | 1.00 | 2.00 |
| ATOM | 800 | CZ | TYR | 87 | 10.316 | 14.396 | 16.974 | 1.00 | 6.27 |
| ATOM | 801 | OH | TYR | 87 | 11.668 | 14.102 | 16.932 | 1.00 | 7.53 |
| ATOM | 802 | HH | TYR | 87 | 12.181 | 14.910 | 17.066 | 1.00 | 0.00 |
| ATOM | 803 | C | TYR | 87 | 4.352 | 16.586 | 18.305 | 1.00 | 3.38 |
| ATOM | 804 | O | TYR | 87 | 4.619 | 17.653 | 17.702 | 1.00 | 5.53 |
| ATOM | 805 | N | SER | 88 | 3.248 | 16.094 | 18.857 | 1.00 | 7.17 |
| ATOM | 806 | H | SER | 88 | 3.264 | 15.179 | 19.207 | 1.00 | 0.00 |
| ATOM | 807 | CA | SER | 88 | 2.009 | 16.852 | 18.979 | 1.00 | 6.67 |
| ATOM | 808 | CB | SER | 88 | 0.860 | 15.969 | 19.425 | 1.00 | 6.09 |
| ATOM | 809 | OG | SER | 88 | 0.561 | 14.907 | 18.539 | 1.00 | 23.12 |
| ATOM | 810 | HG | SER | 88 | 1.351 | 14.368 | 18.429 | 1.00 | 0.00 |
| ATOM | 811 | C | SER | 88 | 2.160 | 17.942 | 20.036 | 1.00 | 9.31 |
| ATOM | 812 | O | SER | 88 | 1.486 | 18.970 | 19.995 | 1.00 | 5.17 |
| ATOM | 813 | N | ARG | 89 | 3.017 | 17.673 | 21.027 | 1.00 | 15.78 |
| ATOM | 814 | H | ARG | 89 | 3.530 | 16.838 | 20.985 | 1.00 | 0.00 |
| ATOM | 815 | CA | ARG | 89 | 3.262 | 18.543 | 22.175 | 1.00 | 19.64 |
| ATOM | 816 | CB | ARG | 89 | 3.587 | 17.742 | 23.444 | 1.00 | 18.92 |
| ATOM | 817 | CG | ARG | 89 | 2.563 | 16.693 | 23.853 | 1.00 | 28.31 |
| ATOM | 818 | CD | ARG | 89 | 3.997 | 15.861 | 25.067 | 1.00 | 36.85 |
| ATOM | 819 | NE | ARG | 89 | 4.239 | 15.083 | 24.955 | 1.00 | 42.21 |
| ATOM | 820 | HE | ARG | 89 | 5.061 | 15.540 | 24.679 | 1.00 | 0.00 |
| ATOM | 821 | CZ | ARG | 89 | 4.296 | 13.764 | 25.223 | 1.00 | 44.61 |
| ATOM | 822 | NH1 | ARG | 89 | 3.207 | 13.079 | 25.601 | 1.00 | 46.06 |
| ATOM | 823 | HH11 | ARG | 89 | 2.324 | 13.538 | 25.696 | 1.00 | 0.00 |
| ATOM | 824 | HH12 | ARG | 89 | 3.280 | 12.100 | 25.792 | 1.00 | 0.00 |
| ATOM | 825 | NH2 | ARG | 89 | 5.469 | 13.119 | 25.157 | 1.00 | 44.47 |
| ATOM | 826 | HH21 | ARG | 89 | 6.295 | 13.619 | 24.899 | 1.00 | 0.00 |
| ATOM | 827 | HH22 | ARG | 89 | 5.518 | 12.140 | 25.357 | 1.00 | 0.00 |
| ATOM | 828 | C | ARG | 89 | 4.444 | 19.469 | 21.928 | 1.00 | 18.88 |
| ATOM | 829 | O | ARG | 89 | 4.507 | 20.553 | 22.493 | 1.00 | 20.00 |
| ATOM | 830 | N | ASP | 90 | 5.421 | 19.082 | 21.131 | 1.00 | 18.60 |
| ATOM | 831 | H | ASP | 90 | 5.407 | 18.181 | 20.728 | 1.00 | 0.00 |
| ATOM | 832 | CA | ASP | 90 | 5.483 | 19.891 | 20.903 | 1.00 | 16.39 |
| ATOM | 833 | CB | ASP | 90 | 7.626 | 19.502 | 21.966 | 1.00 | 12.09 |
| ATOM | 834 | CG | ASP | 90 | 8.925 | 20.286 | 22.048 | 1.00 | 10.44 |
| ATOM | 835 | OD1 | ASP | 90 | 9.737 | 19.962 | 22.905 | 1.00 | 21.16 |
| ATOM | 836 | OD2 | ASP | 90 | 9.156 | 21.203 | 21.267 | 1.00 | 19.94 |
| ATOM | 837 | C | ASP | 90 | 7.039 | 19.587 | 19.478 | 1.00 | 19.96 |
| ATOM | 838 | O | ASP | 90 | 7.512 | 18.482 | 19.202 | 1.00 | 20.24 |
| ATOM | 839 | N | PRO | 91 | 6.917 | 20.560 | 18.560 | 1.00 | 15.46 |
| ATOM | 840 | CD | PRO | 91 | 6.233 | 21.831 | 18.781 | 1.00 | 17.20 |
| ATOM | 841 | CA | PRO | 91 | 7.434 | 20.495 | 17.196 | 1.00 | 14.01 |
| ATOM | 842 | CB | PRO | 91 | 7.387 | 21.916 | 16.672 | 1.00 | 16.08 |
| ATOM | 843 | CG | PRO | 91 | 7.060 | 22.761 | 17.913 | 1.00 | 12.13 |
| ATOM | 844 | C | PRO | 91 | 8.844 | 19.968 | 17.102 | 1.00 | 14.28 |
| ATOM | 845 | O | PRO | 91 | 9.173 | 19.194 | 16.210 | 1.00 | 16.05 |
| ATOM | 846 | N | ASP | 92 | 9.683 | 20.419 | 18.195 | 1.00 | 12.31 |
| ATOM | 847 | H | ASP | 92 | 9.364 | 21.117 | 18.631 | 1.00 | 0.00 |
| ATOM | 848 | CA | ASP | 92 | 11.043 | 19.991 | 18.195 | 1.00 | 10.93 |
| ATOM | 849 | CB | ASP | 92 | 11.007 | 18.818 | 19.198 | 1.00 | 5.10 |
| ATOM | 850 | CG | ASP | 92 | 12.355 | 18.438 | 19.826 | 1.00 | 8.25 |
| ATOM | 851 | OD1 | ASP | 92 | 13.246 | 19.264 | 20.003 | 1.00 | 14.68 |
| ATOM | 852 | OD2 | ASP | 92 | 12.549 | 17.285 | 20.136 | 1.00 | 12.78 |
| ATOM | 853 | C | ASP | 92 | 11.829 | 19.653 | 16.932 | 1.00 | 12.54 |
| ATOM | 854 | O | GLY | 93 | 12.501 | 18.619 | 16.798 | 1.00 | 13.03 |
| ATOM | 855 | N | GLY | 93 | 11.772 | 20.607 | 16.009 | 1.00 | 12.18 |
| ATOM | 856 | H | GLY | 93 | 11.235 | 21.419 | 16.141 | 1.00 | 0.00 |
| ATOM | 857 | CA | GLY | 93 | 12.563 | 20.488 | 14.786 | 1.00 | 13.73 |
| ATOM | 858 | C | GLY | 93 | 11.725 | 20.330 | 13.537 | 1.00 | 8.10 |
| ATOM | 859 | O | GLY | 93 | 12.192 | 20.497 | 12.408 | 1.00 | 11.87 |
| ATOM | 860 | N | LEU | 94 | 10.493 | 19.914 | 13.762 | 1.00 | 4.57 |
| ATOM | 861 | H | LEU | 94 | 10.225 | 19.703 | 14.675 | 1.00 | 0.00 |
| ATOM | 862 | CA | LEU | 94 | 9.523 | 19.788 | 12.708 | 1.00 | 10.89 |
| ATOM | 863 | CB | LEU | 94 | 8.308 | 19.012 | 13.188 | 1.00 | 3.94 |
| ATOM | 864 | CG | LEU | 94 | 8.411 | 17.587 | 13.597 | 1.00 | 3.94 |
| ATOM | 865 | CD1 | LEU | 94 | 7.031 | 17.090 | 13.966 | 1.00 | 2.31 |
| ATOM | 866 | CD2 | LEU | 94 | 8.999 | 16.780 | 12.463 | 1.00 | 11.05 |
| ATOM | 867 | C | LEU | 94 | 9.063 | 21.176 | 12.237 | 1.00 | 13.55 |
| ATOM | 868 | O | LEU | 94 | 9.223 | 22.166 | 12.969 | 1.00 | 11.66 |
| ATOM | 869 | N | PRO | 95 | 8.485 | 21.309 | 11.034 | 1.00 | 14.27 |
| ATOM | 870 | CD | PRO | 95 | 8.563 | 20.350 | 9.925 | 1.00 | 7.51 |
| ATOM | 871 | CA | PRO | 95 | 7.915 | 22.559 | 10.591 | 1.00 | 13.61 |
| ATOM | 872 | CB | PRO | 95 | 7.452 | 22.217 | 9.186 | 1.00 | 10.57 |

TABLE 23-continued

Coordinates for the 3D structure of ZAP-NC:ζ1 "dimer" structure
(two molecules of complex per unit cell)*

| ATOM | 873 | CG | PRO | 95 | 7.358 | 20.732 | 9.137 | 1.00 | 8.09 |
|---|---|---|---|---|---|---|---|---|---|
| ATOM | 874 | C | PRO | 95 | 6.847 | 23.113 | 11.518 | 1.00 | 13.42 |
| ATOM | 875 | O | PRO | 95 | 6.668 | 24.329 | 11.347 | 1.00 | 16.04 |
| ATOM | 876 | N | CYS | 96 | 6.072 | 22.244 | 12.136 | 1.00 | 14.57 |
| ATOM | 877 | H | CYS | 96 | 6.248 | 21.287 | 12.011 | 1.00 | 0.00 |
| ATOM | 878 | CA | CYS | 96 | 5.039 | 22.624 | 13.080 | 1.00 | 12.49 |
| ATOM | 879 | CB | CYS | 96 | 3.753 | 23.076 | 13.224 | 1.00 | 13.81 |
| ATOM | 880 | SG | CYS | 96 | 2.809 | 22.013 | 11.202 | 1.00 | 10.86 |
| ATOM | 881 | C | CYS | 96 | 4.764 | 21.420 | 13.974 | 1.00 | 11.03 |
| ATOM | 882 | O | CYS | 96 | 5.459 | 20.411 | 13.826 | 1.00 | 10.72 |
| ATOM | 883 | N | ASN | 97 | 3.839 | 21.448 | 14.931 | 1.00 | 8.03 |
| ATOM | 884 | H | ASN | 97 | 3.208 | 22.196 | 15.012 | 1.00 | 0.00 |
| ATOM | 885 | CA | ASN | 97 | 3.559 | 20.279 | 15.739 | 1.00 | 7.35 |
| ATOM | 886 | CB | ASN | 97 | 3.041 | 20.641 | 17.155 | 1.00 | 4.07 |
| ATOM | 887 | CG | ASN | 97 | 1.691 | 21.326 | 17.216 | 1.00 | 6.44 |
| ATOM | 888 | OD1 | ASN | 97 | 1.546 | 22.385 | 16.618 | 1.00 | 17.31 |
| ATOM | 889 | ND2 | ASN | 97 | 0.651 | 20.865 | 17.900 | 1.00 | 6.94 |
| ATOM | 890 | HD21 | ASN | 97 | 0.764 | 20.069 | 18.469 | 1.00 | 0.00 |
| ATOM | 891 | HD22 | ASN | 97 | −0.206 | 21.300 | 17.743 | 1.00 | 0.00 |
| ATOM | 892 | C | ASN | 97 | 2.486 | 19.489 | 15.026 | 1.00 | 8.28 |
| ATOM | 893 | O | ASN | 97 | 1.770 | 19.991 | 14.156 | 1.00 | 10.98 |
| ATOM | 894 | N | LEU | 98 | 2.347 | 18.236 | 15.423 | 1.00 | 12.14 |
| ATOM | 895 | H | LEU | 98 | 2.886 | 17.927 | 16.180 | 1.00 | 0.00 |
| ATOM | 896 | CA | LEU | 98 | 1.356 | 17.353 | 14.839 | 1.00 | 10.83 |
| ATOM | 897 | CB | LEU | 98 | 1.685 | 15.889 | 15.187 | 1.00 | 7.32 |
| ATOM | 898 | CG | LEU | 98 | 3.068 | 15.393 | 14.737 | 1.00 | 6.54 |
| ATOM | 899 | CD1 | LEU | 98 | 3.206 | 13.928 | 15.097 | 1.00 | 7.62 |
| ATOM | 900 | CD2 | LEU | 98 | 3.254 | 15.611 | 13.231 | 1.00 | 2.41 |
| ATOM | 901 | C | LEU | 98 | 0.019 | 17.761 | 15.393 | 1.00 | 9.96 |
| ATOM | 902 | O | LEU | 98 | −0.1.7 | 17.920 | 16.599 | 1.00 | 14.76 |
| ATOM | 903 | N | ARG | 99 | −0.969 | 17.998 | 14.552 | 1.00 | 12.00 |
| ATOM | 904 | H | ARG | 99 | −0.853 | 17.785 | 13.605 | 1.00 | 0.00 |
| ATOM | 905 | CA | ARG | 99 | −2.257 | 18.422 | 15.030 | 1.00 | 11.66 |
| ATOM | 906 | CB | ARG | 99 | −2.520 | 19.819 | 14.458 | 1.00 | 12.20 |
| ATOM | 907 | CG | ARG | 99 | −1.461 | 20.810 | 14.959 | 1.00 | 9.52 |
| ATOM | 908 | CD | ARG | 99 | −1.525 | 22.166 | 14.292 | 1.00 | 10.29 |
| ATOM | 909 | NE | ARG | 99 | −0.269 | 22.879 | 14.499 | 1.00 | 11.13 |
| ATOM | 910 | HE | ARG | 99 | 0.463 | 22.410 | 14.946 | 1.00 | 0.00 |
| ATOM | 911 | CZ | ARG | 99 | −0.038 | 24.108 | 14.024 | 1.00 | 6.20 |
| ATOM | 912 | NH1 | ARG | 99 | −0.942 | 24.777 | 13.321 | 1.00 | 10.93 |
| ATOM | 913 | HH11 | ARG | 99 | −1.836 | 24.374 | 13.127 | 1.00 | 0.00 |
| ATOM | 914 | HH12 | ARG | 99 | −0.723 | 25.694 | 12.986 | 1.00 | 0.00 |
| ATOM | 915 | NH2 | ARG | 99 | 1.126 | 24.694 | 14.265 | 1.00 | 4.38 |
| ATOM | 916 | HH21 | ARG | 99 | 1.813 | 24.226 | 14.820 | 1.00 | 0.00 |
| ATOM | 917 | HH22 | ARG | 99 | 1.302 | 25.617 | 13.927 | 1.00 | 0.00 |
| ATOM | 918 | C | ARG | 99 | −3.269 | 17.374 | 14.595 | 1.00 | 16.11 |
| ATOM | 919 | O | ARG | 99 | −3.328 | 16.338 | 15.272 | 1.00 | 19.03 |
| ATOM | 920 | N | LYS | 100 | −4.050 | 17.477 | 13.516 | 1.00 | 16.69 |
| ATOM | 921 | H | LYS | 100 | −3.918 | 18.213 | 12.869 | 1.00 | 0.00 |
| ATOM | 922 | CA | LYS | 100 | −5.053 | 16.439 | 13.215 | 1.00 | 20.22 |
| ATOM | 923 | CB | LYS | 100 | −6.150 | 17.030 | 12.293 | 1.00 | 22.25 |
| ATOM | 924 | CG | LYS | 100 | −7.259 | 16.096 | 11.791 | 1.00 | 30.42 |
| ATOM | 925 | CD | LYS | 100 | −7.988 | 16.782 | 10.629 | 1.00 | 38.20 |
| ATOM | 926 | CE | LYS | 100 | −8.924 | 15.887 | 9.811 | 1.00 | 42.38 |
| ATOM | 927 | NZ | LYS | 100 | −8.227 | 14.874 | 9.034 | 1.00 | 46.25 |
| ATOM | 928 | HZ1 | LYS | 100 | −7.665 | 14.285 | 9.681 | 1.00 | 0.00 |
| ATOM | 929 | HZ2 | LYS | 100 | −7.598 | 15.329 | 8.342 | 1.00 | 0.00 |
| ATOM | 930 | HZ3 | LYS | 100 | −8.923 | 14.282 | 8.536 | 1.00 | 0.00 |
| ATOM | 931 | C | LYS | 100 | −4.432 | 15.183 | 12.566 | 1.00 | 16.85 |
| ATOM | 932 | O | LYS | 100 | −3.696 | 15.275 | 11.569 | 1.00 | 15.54 |
| ATOM | 933 | N | PRO | 101 | −4.669 | 13.987 | 13.131 | 1.00 | 13.08 |
| ATOM | 934 | CD | PRO | 101 | −5.370 | 13.784 | 14.388 | 1.00 | 7.49 |
| ATOM | 935 | CA | PRO | 101 | −4.277 | 12.708 | 12.564 | 1.00 | 11.31 |
| ATOM | 936 | CB | PRO | 101 | −4.602 | 11.755 | 13.678 | 1.00 | 6.33 |
| ATOM | 937 | CG | PRO | 101 | −5.819 | 12.361 | 14.308 | 1.00 | 3.78 |
| ATOM | 938 | C | PRO | 101 | −5.030 | 12.465 | 11.269 | 1.00 | 10.35 |
| ATOM | 939 | O | PRO | 101 | −6.262 | 12.590 | 11.215 | 1.00 | 12.69 |
| ATOM | 940 | N | CYS | 102 | −4.343 | 12.176 | 10.182 | 1.00 | 9.14 |
| ATOM | 941 | H | CYS | 102 | −3.391 | 12.015 | 10.264 | 1.00 | 0.00 |
| ATOM | 942 | CA | CYS | 102 | −5.048 | 11.857 | 8.941 | 1.00 | 11.88 |
| ATOM | 943 | CB | CYS | 102 | −4.153 | 12.171 | 7.768 | 1.00 | 11.92 |
| ATOM | 944 | SG | CYS | 102 | −4.935 | 11.867 | 6.165 | 1.00 | 13.71 |
| ATOM | 945 | C | CYS | 102 | −5.393 | 10.362 | 9.002 | 1.00 | 12.91 |
| ATOM | 946 | O | CYS | 102 | −4.678 | 9.431 | 8.600 | 1.00 | 11.19 |
| ATOM | 947 | N | ASN | 103 | −6.550 | 10.168 | 9.618 | 1.00 | 10.89 |
| ATOM | 948 | H | ASN | 103 | −7.043 | 10.958 | 9.927 | 1.00 | 0.00 |

TABLE 23-continued

Coordinates for the 3D structure of ZAP-NC:ζ1 "dimer" structure
(two molecules of complex per unit cell)*

| ATOM | 949 | CA | ASN | 103 | −7.044 | 8.843 | 9.919 | 1.00 | 11.19 |
|---|---|---|---|---|---|---|---|---|---|
| ATOM | 950 | CB | ASN | 103 | −8.144 | 8.940 | 10.978 | 1.00 | 8.17 |
| ATOM | 951 | CG | ASN | 103 | −7.592 | 9.244 | 12.364 | 1.00 | 8.17 |
| ATOM | 952 | OD1 | ASN | 103 | −6.421 | 9.068 | 12.663 | 1.00 | 15.63 |
| ATOM | 953 | ND2 | ASN | 103 | −8.372 | 9.703 | 13.314 | 1.00 | 15.55 |
| ATOM | 954 | HD21 | ASN | 103 | −9.323 | 9.825 | 13.123 | 1.00 | 0.00 |
| ATOM | 955 | HD22 | ASN | 103 | −7.943 | 9.918 | 14.169 | 1.00 | 0.00 |
| ATOM | 956 | C | ARG | 104 | −7.569 | 8.118 | 8.716 | 1.00 | 8.63 |
| ATOM | 957 | O | ARG | 104 | −8.330 | 9.700 | 7.939 | 1.00 | 9.71 |
| ATOM | 958 | N | ARG | 104 | −7.178 | 6.847 | 8.614 | 1.00 | 9.83 |
| ATOM | 959 | H | ARG | 104 | −6.631 | 6.474 | 9.337 | 1.00 | 0.00 |
| ATOM | 960 | CA | ARG | 104 | −7.597 | 5.971 | 7.538 | 1.00 | 6.25 |
| ATOM | 961 | CB | ARG | 104 | −7.267 | 4.514 | 7.782 | 1.00 | 8.62 |
| ATOM | 962 | CG | ARG | 104 | −5.860 | 3.941 | 7.783 | 1.00 | 3.24 |
| ATOM | 963 | CD | ARG | 104 | −6.139 | 2.498 | 8.209 | 1.00 | 10.70 |
| ATOM | 964 | NE | ARG | 104 | −5.367 | 2.175 | 9.396 | 1.00 | 18.79 |
| ATOM | 965 | HE | ARG | 104 | −4.399 | 2.204 | 9.337 | 1.00 | 0.00 |
| ATOM | 966 | CZ | ARG | 104 | −5.879 | 1.729 | 10.539 | 1.00 | 21.66 |
| ATOM | 967 | NH1 | ARG | 104 | −7.180 | 1.522 | 10.699 | 1.00 | 28.57 |
| ATOM | 968 | HH11 | ARG | 104 | −7.808 | 1.680 | 9.936 | 1.00 | 0.00 |
| ATOM | 969 | HH12 | ARG | 104 | −7.523 | 1.167 | 11.568 | 1.00 | 0.00 |
| ATOM | 970 | NH2 | ARG | 104 | −5.056 | 1.550 | 11.575 | 1.00 | 30.06 |
| ATOM | 971 | HH21 | ARG | 104 | −4.083 | 1.765 | 11.484 | 1.00 | 0.00 |
| ATOM | 972 | HH22 | ARG | 104 | −5.413 | 1.212 | 12.445 | 1.00 | 0.00 |
| ATOM | 973 | C | ARG | 104 | −9.101 | 6.043 | 7.449 | 1.00 | 9.23 |
| ATOM | 974 | O | ARG | 104 | −9.787 | 6.062 | 8.477 | 1.00 | 11.51 |
| ATOM | 975 | N | PRO | 105 | −9.660 | 6.168 | 8.249 | 1.00 | 13.97 |
| ATOM | 976 | H | PRO | 105 | −8.924 | 6.498 | 5.033 | 1.00 | 10.44 |
| ATOM | 977 | CA | PRO | 105 | −11.091 | 6.079 | 6.010 | 1.00 | 14.04 |
| ATOM | 978 | CB | PRO | 105 | −11.213 | 6.227 | 4.521 | 1.00 | 16.08 |
| ATOM | 979 | CG | PRO | 105 | −10.017 | 7.060 | 4.161 | 1.00 | 15.10 |
| ATOM | 980 | C | PRO | 105 | −11.695 | 4.775 | 6.517 | 1.00 | 18.06 |
| ATOM | 981 | O | PRO | 105 | −10.991 | 3.768 | 6.660 | 1.00 | 18.50 |
| ATOM | 982 | N | SER | 106 | −12.999 | 4.738 | 6.776 | 1.00 | 21.15 |
| ATOM | 983 | H | SER | 106 | −13.535 | 5.558 | 7.846 | 1.00 | 0.00 |
| ATOM | 984 | CA | SER | 106 | −13.664 | 3.505 | 7.149 | 1.00 | 21.87 |
| ATOM | 985 | CB | SER | 106 | −15.140 | 3.789 | 7.401 | 1.00 | 22.16 |
| ATOM | 986 | OG | SER | 106 | −15.313 | 4.735 | 8.445 | 1.00 | 25.97 |
| ATOM | 987 | HG | SER | 106 | −14.780 | 4.508 | 9.214 | 1.00 | 0.00 |
| ATOM | 988 | C | SER | 106 | −13.520 | 2.430 | 6.063 | 1.00 | 23.43 |
| ATOM | 989 | O | SER | 106 | −13.672 | 2.683 | 4.865 | 1.00 | 20.97 |
| ATOM | 990 | N | GLY | 107 | −13.132 | 1.232 | 6.509 | 1.00 | 21.55 |
| ATOM | 991 | H | GLY | 107 | −12.849 | 1.128 | 7.440 | 1.00 | 0.00 |
| ATOM | 992 | CA | GLY | 107 | −12.980 | 0.119 | 4.509 | 1.00 | 20.51 |
| ATOM | 993 | C | GLY | 107 | −11.576 | 0.059 | 5.036 | 1.00 | 24.96 |
| ATOM | 994 | O | GLY | 107 | −11.188 | −0.959 | 4.456 | 1.00 | 27.67 |
| ATOM | 995 | N | LEU | 108 | −10.765 | 1.111 | 5.178 | 1.00 | 22.03 |
| ATOM | 996 | H | LEU | 108 | −11.032 | 1.900 | 5.691 | 1.00 | 0.00 |
| ATOM | 997 | CA | LEU | 108 | −9.414 | 1.042 | 4.673 | 1.00 | 16.09 |
| ATOM | 998 | CB | LEU | 108 | −8.874 | 2.413 | 4.278 | 1.00 | 12.09 |
| ATOM | 999 | CG | LEU | 108 | −7.414 | 2.431 | 3.836 | 1.00 | 10.25 |
| ATOM | 1000 | CD1 | LEU | 108 | −7.261 | 1.578 | 3.512 | 1.00 | 11.68 |
| ATOM | 1001 | CD2 | LEU | 108 | −6.960 | 3.852 | 3.576 | 1.00 | 12.09 |
| ATOM | 1002 | C | LEU | 108 | −8.654 | 0.500 | 5.862 | 1.00 | 12.99 |
| ATOM | 1003 | O | LEU | 108 | −8.771 | 0.954 | 7.001 | 1.00 | 12.44 |
| ATOM | 1004 | N | GLU | 109 | −7.921 | −0.543 | 5.533 | 1.00 | 14.56 |
| ATOM | 1005 | H | GLU | 109 | −7.853 | −0.782 | 4.585 | 1.00 | 0.00 |
| ATOM | 1006 | CA | GLU | 109 | −7.127 | −1.275 | 6.481 | 1.00 | 13.90 |
| ATOM | 1007 | CB | GLU | 109 | −7.309 | −2.773 | 6.230 | 1.00 | 19.29 |
| ATOM | 1008 | CG | GLU | 109 | −8.738 | −3.284 | 6.141 | 1.00 | 29.48 |
| ATOM | 1009 | CD | GLU | 109 | −9.520 | −3.230 | 7.441 | 1.00 | 40.66 |
| ATOM | 1010 | OE1 | GLU | 109 | −10.270 | −2.277 | 7.666 | 1.00 | 45.63 |
| ATOM | 1011 | OE2 | GLU | 109 | −9.388 | −4.168 | 8.223 | 1.00 | 51.26 |
| ATOM | 1012 | C | GLU | 109 | −5.695 | −0.866 | 6.231 | 1.00 | 8.40 |
| ATOM | 1013 | O | GLU | 109 | −5.398 | −0.456 | 5.114 | 1.00 | 10.50 |
| ATOM | 1014 | N | PRO | 110 | −4.758 | −0.979 | 7.155 | 1.00 | 5.95 |
| ATOM | 1015 | CD | PRO | 110 | −4.984 | −1.282 | 8.564 | 1.00 | 5.24 |
| ATOM | 1016 | CA | PRO | 110 | −3.339 | −0.915 | 6.861 | 1.00 | 10.05 |
| ATOM | 1017 | CB | PRO | 110 | −2.674 | −1.303 | 8.175 | 1.00 | 4.68 |
| ATOM | 1018 | CG | PRO | 110 | −3.664 | −0.827 | 9.198 | 1.00 | 4.54 |
| ATOM | 1019 | C | PRO | 110 | −2.896 | −1.785 | 5.680 | 1.00 | 7.66 |
| ATOM | 1020 | O | PRO | 110 | −3.310 | −2.924 | 5.536 | 1.00 | 11.84 |
| ATOM | 1021 | N | GLN | 111 | −2.008 | −1.294 | 4.838 | 1.00 | 10.25 |
| ATOM | 1022 | H | GLN | 111 | −1.653 | −0.395 | 5.008 | 1.00 | 0.00 |
| ATOM | 1023 | CA | GLN | 111 | −1.593 | −1.998 | 3.637 | 1.00 | 8.90 |
| ATOM | 1024 | CB | GLN | 111 | −1.157 | −0.944 | 2.610 | 1.00 | 2.00 |

TABLE 23-continued

Coordinates for the 3D structure of ZAP-NC:ζ1 "dimer" structure
(two molecules of complex per unit cell)*

| ATOM | 1025 | CG | GLN | 111 | −0.638 | −1.453 | 1.268 | 1.00 | 8.79 |
|---|---|---|---|---|---|---|---|---|---|
| ATOM | 1026 | CD | GLN | 111 | −1.646 | −2.233 | 0.449 | 1.00 | 5.34 |
| ATOM | 1027 | OE1 | GLN | 111 | −2.850 | −2.233 | 0.684 | 1.00 | 5.86 |
| ATOM | 1028 | NE2 | GLN | 111 | −1.177 | −2.954 | 0.536 | 1.00 | 6.33 |
| ATOM | 1029 | HE21 | GLN | 111 | −0.210 | −2.930 | 0.716 | 1.00 | 0.00 |
| ATOM | 1030 | HE22 | GLN | 111 | −1.812 | −3.537 | 1.006 | 1.00 | 0.00 |
| ATOM | 1031 | C | GLN | 111 | −0.493 | −3.010 | 3.891 | 1.00 | 8.54 |
| ATOM | 1032 | O | GLN | 111 | 0.573 | −2.599 | 4.345 | 1.00 | 5.96 |
| ATOM | 1033 | N | PRO | 112 | −0.673 | −4.308 | 3.579 | 1.00 | 9.29 |
| ATOM | 1034 | CD | PRO | 112 | −1.931 | −5.872 | 3.075 | 1.00 | 7.95 |
| ATOM | 1035 | CA | PRO | 112 | 0.366 | −5.332 | 3.622 | 1.00 | 5.72 |
| ATOM | 1036 | CB | PRO | 112 | −0.244 | −6.558 | 2.999 | 1.00 | 5.42 |
| ATOM | 1037 | CG | PRO | 112 | −1.719 | −6.364 | 3.178 | 1.00 | 5.05 |
| ATOM | 1038 | C | PRO | 112 | 1.647 | −4.955 | 2.921 | 1.00 | 6.46 |
| ATOM | 1039 | O | PRO | 112 | 1.636 | −4.369 | 1.839 | 1.00 | 6.87 |
| ATOM | 1040 | N | GLY | 113 | 2.766 | −5.354 | 3.510 | 1.00 | 6.40 |
| ATOM | 1041 | H | GLY | 113 | 2.703 | −5.962 | 4.274 | 1.00 | 0.00 |
| ATOM | 1042 | CA | GLY | 113 | 4.046 | −6.056 | 2.945 | 1.00 | 6.46 |
| ATOM | 1043 | C | GLY | 113 | 4.653 | −6.303 | 2.353 | 1.00 | 8.56 |
| ATOM | 1044 | O | GLY | 113 | 4.674 | −7.344 | 3.011 | 1.00 | 13.23 |
| ATOM | 1045 | N | VAL | 114 | 5.213 | −6.187 | 1.155 | 1.00 | 4.67 |
| ATOM | 1046 | H | VAL | 114 | 5.187 | −5.284 | 0.757 | 1.00 | 0.00 |
| ATOM | 1047 | CA | VAL | 114 | 5.865 | −7.249 | 0.419 | 1.00 | 4.61 |
| ATOM | 1048 | CB | VAL | 114 | 6.315 | −6.694 | 0.990 | 1.00 | 3.22 |
| ATOM | 1049 | CG1 | VAL | 114 | 7.105 | −7.719 | 1.741 | 1.00 | 3.86 |
| ATOM | 1050 | CG2 | VAL | 114 | 5.102 | −6.401 | 1.877 | 1.00 | 2.00 |
| ATOM | 1051 | C | VAL | 114 | 7.035 | −7.793 | 1.206 | 1.00 | 4.93 |
| ATOM | 1052 | O | VAL | 114 | 7.054 | −9.006 | 1.413 | 1.00 | 10.35 |
| ATOM | 1053 | N | PHE | 115 | 7.975 | −7.002 | 1.730 | 1.00 | 6.39 |
| ATOM | 1054 | H | PHE | 115 | 7.899 | −6.003 | 1.601 | 1.00 | 0.00 |
| ATOM | 1055 | CA | PHE | 115 | 9.090 | −7.562 | 2.483 | 1.00 | 6.83 |
| ATOM | 1056 | CB | PHE | 115 | 10.118 | −6.486 | 2.878 | 1.00 | 7.30 |
| ATOM | 1057 | CG | PHE | 115 | 11.542 | −6.975 | 3.148 | 1.00 | 2.90 |
| ATOM | 1058 | CD1 | PHE | 115 | 12.012 | −8.211 | 2.690 | 1.00 | 2.00 |
| ATOM | 1059 | CD2 | PHE | 115 | 12.423 | −6.132 | 3.827 | 1.00 | 7.94 |
| ATOM | 1060 | CE1 | PHE | 115 | 13.340 | −8.584 | 2.900 | 1.00 | 2.00 |
| ATOM | 1061 | CE2 | PHE | 115 | 13.756 | −6.511 | 4.036 | 1.00 | 4.71 |
| ATOM | 1062 | CZ | PHE | 115 | 14.213 | −7.732 | 3.568 | 1.00 | 4.45 |
| ATOM | 1063 | C | PHE | 115 | 8.579 | −8.229 | 3.744 | 1.00 | 6.82 |
| ATOM | 1064 | O | PHE | 115 | 9.145 | −9.245 | 4.138 | 1.00 | 10.26 |
| ATOM | 1065 | N | CYS | 116 | 7.515 | −7.717 | 4.372 | 1.00 | 7.65 |
| ATOM | 1066 | H | CYS | 116 | 7.189 | −6.839 | 4.083 | 1.00 | 0.00 |
| ATOM | 1067 | CA | CYS | 116 | 6.901 | −8.348 | 5.543 | 1.00 | 9.49 |
| ATOM | 1068 | CB | CYS | 116 | 5.707 | −7.554 | 6.057 | 1.00 | 3.65 |
| ATOM | 1069 | CG | CYS | 116 | 5.989 | −6.246 | 6.768 | 1.00 | 10.72 |
| ATOM | 1070 | OD1 | CYS | 116 | 7.132 | −5.815 | 6.873 | 1.00 | 10.46 |
| ATOM | 1071 | OD2 | CYS | 116 | 5.026 | −5.683 | 7.242 | 1.00 | 12.59 |
| ATOM | 1072 | C | CYS | 116 | 6.394 | −9.762 | 5.878 | 1.00 | 8.07 |
| ATOM | 1073 | O | CYS | 116 | 6.621 | −10.666 | 6.092 | 1.00 | 8.78 |
| ATOM | 1074 | N | CYS | 116 | 5.675 | −9.910 | 4.162 | 1.00 | 5.88 |
| ATOM | 1075 | H | CYS | 116 | 5.429 | −9.194 | 3.680 | 1.00 | 0.00 |
| ATOM | 1076 | CA | CYS | 116 | 5.170 | −11.181 | 3.662 | 1.00 | 7.52 |
| ATOM | 1077 | CB | CYS | 116 | 4.341 | −10.980 | 2.386 | 1.00 | 2.00 |
| ATOM | 1078 | SG | CYS | 116 | 2.747 | −10.208 | 2.720 | 1.00 | 5.27 |
| ATOM | 1079 | C | CYS | 116 | 6.332 | −12.097 | 3.342 | 1.00 | 5.36 |
| ATOM | 1080 | O | CYS | 117 | 6.327 | −13.261 | 3.729 | 1.00 | 12.91 |
| ATOM | 1081 | N | LEU | 118 | 7.372 | −11.579 | 2.716 | 1.00 | 2.00 |
| ATOM | 1082 | H | LEU | 118 | 7.373 | −10.622 | 2.486 | 1.00 | 0.00 |
| ATOM | 1083 | CA | LEU | 118 | 8.534 | −12.362 | 2.404 | 1.00 | 3.80 |
| ATOM | 1084 | CB | LEU | 118 | 9.533 | −11.502 | 1.607 | 1.00 | 7.77 |
| ATOM | 1085 | CG | LEU | 118 | 10.691 | −12.257 | 0.967 | 1.00 | 2.00 |
| ATOM | 1086 | CD1 | LEU | 118 | 10.302 | −12.739 | −0.416 | 1.00 | 10.01 |
| ATOM | 1087 | CD2 | LEU | 118 | 11.873 | −11.362 | 0.852 | 1.00 | 2.00 |
| ATOM | 1088 | C | LEU | 118 | 9.207 | −12.888 | 3.672 | 1.00 | 7.78 |
| ATOM | 1089 | O | LEU | 118 | 9.371 | −14.097 | 3.878 | 1.00 | 14.19 |
| ATOM | 1090 | N | ARG | 119 | 9.570 | −11.996 | 4.586 | 1.00 | 8.62 |
| ATOM | 1091 | H | ARG | 119 | 9.355 | −11.059 | 4.427 | 1.00 | 0.00 |
| ATOM | 1092 | CA | ARG | 119 | 10.267 | −12.355 | 5.802 | 1.00 | 6.69 |
| ATOM | 1093 | CB | ARG | 119 | 10.642 | −11.148 | 6.609 | 1.00 | 3.95 |
| ATOM | 1094 | CG | ARG | 119 | 11.653 | −10.284 | 5.927 | 1.00 | 4.79 |
| ATOM | 1095 | CD | ARG | 119 | 11.994 | −9.159 | 6.864 | 1.00 | 10.98 |
| ATOM | 1096 | NE | ARG | 119 | 10.818 | −8.346 | 7.066 | 1.00 | 16.70 |
| ATOM | 1097 | HE | ARG | 119 | 10.122 | −8.329 | 6.375 | 1.00 | 0.00 |
| ATOM | 1098 | CZ | ARG | 119 | 10.663 | −7.617 | 8.160 | 1.00 | 19.41 |
| ATOM | 1099 | NH1 | ARG | 119 | 11.579 | −7.589 | 9.132 | 1.00 | 24.20 |
| ATOM | 1100 | HH11 | ARG | 119 | 12.412 | −8.139 | 9.057 | 1.00 | 0.00 |

TABLE 23-continued

Coordinates for the 3D structure of ZAP-NC:ζ1 "dimer" structure
(two molecules of complex per unit cell)*

| | | | | | | | | |
|---|---|---|---|---|---|---|---|---|
| ATOM | 1101 | HH12 | ARG | 119 | 11.421 | −7.034 | 9.948 | 1.00 | 0.00 |
| ATOM | 1102 | NH2 | ARG | 119 | 9.541 | −6.930 | 8.271 | 1.00 | 17.87 |
| ATOM | 1103 | HH21 | ARG | 119 | 8.858 | −6.988 | 7.541 | 1.00 | 0.00 |
| ATOM | 1104 | HH22 | ARG | 119 | 9.373 | −6.357 | 9.072 | 1.00 | 0.00 |
| ATOM | 1105 | C | ARG | 119 | 9.472 | −13.239 | 6.700 | 1.00 | 7.52 |
| ATOM | 1106 | O | ARG | 119 | 10.066 | −14.043 | 7.407 | 1.00 | 12.31 |
| ATOM | 1107 | N | ASP | 120 | 8.151 | −13.126 | 6.680 | 1.00 | 9.60 |
| ATOM | 1108 | H | ASP | 120 | 7.743 | −12.422 | 6.133 | 1.00 | 0.00 |
| ATOM | 1109 | CA | ASP | 120 | 7.299 | −13.966 | 7.478 | 1.00 | 7.93 |
| ATOM | 1110 | CB | ASP | 120 | 5.844 | −13.534 | 7.320 | 1.00 | 7.93 |
| ATOM | 1111 | CG | ASP | 120 | 4.844 | −14.338 | 8.161 | 1.00 | 15.41 |
| ATOM | 1112 | OD1 | ASP | 120 | 4.818 | −14.250 | 9.396 | 1.00 | 15.27 |
| ATOM | 1113 | OD2 | ASP | 120 | 4.075 | −15.076 | 7.561 | 1.00 | 17.76 |
| ATOM | 1114 | C | ASP | 120 | 7.480 | −15.388 | 6.996 | 1.00 | 13.71 |
| ATOM | 1115 | O | ASP | 120 | 7.696 | −16.290 | 7.814 | 1.00 | 12.77 |
| ATOM | 1116 | N | ALA | 121 | 7.454 | −15.565 | 5.667 | 1.00 | 9.90 |
| ATOM | 1117 | H | ALA | 121 | 7.350 | −14.790 | 5.071 | 1.00 | 0.00 |
| ATOM | 1118 | CA | ALA | 121 | 7.575 | −16.873 | 5.067 | 1.00 | 8.78 |
| ATOM | 1119 | CB | ALA | 121 | 7.243 | −16.761 | 3.570 | 1.00 | 4.63 |
| ATOM | 1120 | C | ALA | 121 | 8.965 | −17.446 | 5.267 | 1.00 | 6.18 |
| ATOM | 1121 | O | ALA | 121 | 9.119 | −18.625 | 5.604 | 1.00 | 11.46 |
| ATOM | 1122 | N | MET | 122 | 10.012 | −16.646 | 5.142 | 1.00 | 9.21 |
| ATOM | 1123 | H | MET | 122 | 9.854 | −15.711 | 4.890 | 1.00 | 0.00 |
| ATOM | 1124 | CA | MET | 122 | 11.368 | −17.142 | 5.331 | 1.00 | 12.95 |
| ATOM | 1125 | CB | MET | 122 | 12.397 | −16.141 | 4.868 | 1.00 | 13.19 |
| ATOM | 1126 | CG | MET | 122 | 12.235 | −15.697 | 3.430 | 1.00 | 6.17 |
| ATOM | 1127 | SD | MET | 122 | 13.633 | −14.669 | 2.923 | 1.00 | 13.61 |
| ATOM | 1128 | CE | MET | 122 | 13.348 | −13.208 | 3.865 | 1.00 | 22.78 |
| ATOM | 1129 | C | MET | 122 | 11.665 | −17.462 | 6.785 | 1.00 | 15.80 |
| ATOM | 1130 | O | MET | 122 | 12.376 | −18.420 | 7.076 | 1.00 | 18.09 |
| ATOM | 1131 | N | VAL | 123 | 11.153 | −16.686 | 7.730 | 1.00 | 17.27 |
| ATOM | 1132 | H | VAL | 123 | 10.655 | −15.882 | 7.474 | 1.00 | 0.00 |
| ATOM | 1133 | CA | VAL | 123 | 11.331 | −16.955 | 9.146 | 1.00 | 18.34 |
| ATOM | 1134 | CB | VAL | 123 | 10.805 | −15.703 | 9.903 | 1.00 | 14.82 |
| ATOM | 1135 | CG1 | VAL | 123 | 10.469 | −15.927 | 11.378 | 1.00 | 7.76 |
| ATOM | 1136 | CG2 | VAL | 123 | 11.945 | −14.692 | 9.816 | 1.00 | 11.65 |
| ATOM | 1137 | C | VAL | 123 | 10.594 | −18.255 | 9.500 | 1.00 | 20.45 |
| ATOM | 1138 | O | VAL | 123 | 11.187 | −19.111 | 10.163 | 1.00 | 22.11 |
| ATOM | 1139 | N | ARG | 124 | 9.342 | −18.449 | 9.049 | 1.00 | 18.15 |
| ATOM | 1140 | H | ARG | 124 | 8.898 | −17.702 | 8.593 | 1.00 | 0.00 |
| ATOM | 1141 | CA | ARG | 124 | 8.594 | −19.687 | 9.247 | 1.00 | 15.36 |
| ATOM | 1142 | CB | ARG | 124 | 7.245 | −19.585 | 8.554 | 1.00 | 11.87 |
| ATOM | 1143 | CG | ARG | 124 | 6.392 | −20.857 | 8.581 | 1.00 | 12.47 |
| ATOM | 1144 | CD | ARG | 124 | 4.913 | −20.641 | 8.301 | 1.00 | 8.51 |
| ATOM | 1145 | NE | ARG | 124 | 4.393 | −19.885 | 9.383 | 1.00 | 12.39 |
| ATOM | 1146 | HE | ARG | 124 | 4.020 | −20.375 | 10.184 | 1.00 | 0.00 |
| ATOM | 1147 | CZ | ARG | 124 | 4.085 | −18.568 | 9.313 | 1.00 | 13.51 |
| ATOM | 1148 | NH1 | ARG | 124 | 4.424 | −17.850 | 8.232 | 1.00 | 11.97 |
| ATOM | 1149 | HH11 | ARG | 124 | 4.843 | −18.283 | 7.433 | 1.00 | 0.00 |
| ATOM | 1150 | HH12 | ASP | 125 | 4.251 | −16.869 | 8.234 | 1.00 | 0.00 |
| ATOM | 1151 | NH2 | ASP | 125 | 3.587 | −17.946 | 10.370 | 1.00 | 41.34 |
| ATOM | 1152 | HH21 | ASP | 125 | 3.381 | −18.461 | 11.201 | 1.00 | 0.00 |
| ATOM | 1153 | HH22 | ASP | 125 | 3.424 | −16.959 | 10.340 | 1.00 | 0.00 |
| ATOM | 1154 | C | ASP | 125 | 9.360 | −20.879 | 8.713 | 1.00 | 15.60 |
| ATOM | 1155 | O | ASP | 125 | 9.503 | −21.882 | 9.406 | 1.00 | 18.62 |
| ATOM | 1156 | N | ASP | 125 | 9.926 | −20.747 | 7.519 | 1.00 | 20.33 |
| ATOM | 1157 | H | ASP | 125 | 9.827 | −19.897 | 7.038 | 1.00 | 0.00 |
| ATOM | 1158 | CA | ASP | 125 | 10.715 | −21.802 | 6.909 | 1.00 | 21.31 |
| ATOM | 1159 | CB | ASP | 125 | 11.096 | −21.802 | 5.486 | 1.00 | 21.39 |
| ATOM | 1160 | CG | ASP | 125 | 11.702 | −21.389 | 4.645 | 1.00 | 27.25 |
| ATOM | 1161 | OD1 | ASP | 125 | 10.972 | −22.503 | 4.269 | 1.00 | 34.81 |
| ATOM | 1162 | OD2 | TYR | 126 | 12.899 | −23.416 | 4.358 | 1.00 | 31.46 |
| ATOM | 1163 | C | TYR | 126 | 11.970 | −22.469 | 7.727 | 1.00 | 23.47 |
| ATOM | 1164 | O | TYR | 126 | 12.253 | −22.077 | 8.042 | 1.00 | 24.12 |
| ATOM | 1165 | N | TYR | 126 | 12.745 | −21.070 | 8.118 | 1.00 | 21.49 |
| ATOM | 1166 | H | TYR | 126 | 12.467 | −20.160 | 7.902 | 1.00 | 0.00 |
| ATOM | 1167 | CA | TYR | 126 | 13.942 | −21.267 | 8.901 | 1.00 | 19.50 |
| ATOM | 1168 | CB | TYR | 126 | 14.635 | −19.916 | 9.133 | 1.00 | 25.90 |
| ATOM | 1169 | CG | TYR | 126 | 15.783 | −19.899 | 10.150 | 1.00 | 29.35 |
| ATOM | 1170 | CD1 | TYR | 126 | 17.104 | −20.144 | 9.730 | 1.00 | 27.77 |
| ATOM | 1171 | CE1 | TYR | 126 | 18.145 | −20.102 | 10.667 | 1.00 | 31.52 |
| ATOM | 1172 | CD2 | TYR | 126 | 15.511 | −19.613 | 11.506 | 1.00 | 28.26 |
| ATOM | 1173 | CE2 | TYR | 126 | 16.546 | −19.577 | 12.439 | 1.00 | 30.56 |
| ATOM | 1174 | CZ | TYR | 126 | 17.861 | −19.813 | 12.012 | 1.00 | 35.32 |
| ATOM | 1175 | OH | TYR | 126 | 18.902 | −19.727 | 12.929 | 1.00 | 40.70 |
| ATOM | 1176 | HH | TYR | 126 | 19.731 | −19.774 | 12.446 | 1.00 | 0.00 |

TABLE 23-continued

Coordinates for the 3D structure of ZAP-NC:ζ1 "dimer" structure
(two molecules of complex per unit cell)*

| ATOM | 1177 | C    | TYR | 126 | 13.646 | −21.923 | 10.239 | 1.00 | 21.90 |
|------|------|------|-----|-----|--------|---------|--------|------|-------|
| ATOM | 1178 | O    | TYR | 126 | 14.406 | −22.816 | 10.619 | 1.00 | 25.30 |
| ATOM | 1179 | N    | VAL | 127 | 12.631 | −21.526 | 11.013 | 1.00 | 19.39 |
| ATOM | 1180 | H    | VAL | 127 | 12.049 | −20.807 | 10.687 | 1.00 | 0.00  |
| ATOM | 1181 | CA   | VAL | 127 | 12.377 | −22.137 | 12.317 | 1.00 | 19.85 |
| ATOM | 1182 | CB   | VAL | 127 | 11.246 | −21.401 | 13.053 | 1.00 | 17.19 |
| ATOM | 1183 | CG1  | VAL | 127 | 10.876 | −22.108 | 14.356 | 1.00 | 16.84 |
| ATOM | 1184 | CG2  | VAL | 127 | 11.731 | −20.002 | 13.403 | 1.00 | 17.80 |
| ATOM | 1185 | C    | VAL | 127 | 12.011 | −23.603 | 12.144 | 1.00 | 22.88 |
| ATOM | 1186 | O    | VAL | 127 | 12.647 | −24.446 | 12.772 | 1.00 | 22.13 |
| ATOM | 1187 | N    | VAL | 127 | 11.060 | −23.912 | 11.258 | 1.00 | 24.55 |
| ATOM | 1188 | H    | ARG | 128 | 10.583 | −23.176 | 10.812 | 1.00 | 0.00  |
| ATOM | 1189 | CA   | ARG | 128 | 10.661 | −25.264 | 10.923 | 1.00 | 22.77 |
| ATOM | 1190 | CB   | ARG | 128 | 9.644  | −25.176 | 9.804  | 1.00 | 23.22 |
| ATOM | 1191 | CG   | ARG | 128 | 9.414  | −26.500 | 9.265  | 1.00 | 26.51 |
| ATOM | 1192 | CD   | ARG | 128 | 8.025  | −26.280 | 8.265  | 1.00 | 26.64 |
| ATOM | 1193 | NE   | ARG | 128 | 8.493  | −25.548 | 7.104  | 1.00 | 31.22 |
| ATOM | 1194 | HE   | ARG | 128 | 9.341  | −25.807 | 6.688  | 1.00 | 0.00  |
| ATOM | 1195 | CZ   | ARG | 128 | 7.797  | −24.530 | 6.581  | 1.00 | 35.88 |
| ATOM | 1196 | NH1  | ARG | 128 | 6.632  | −24.107 | 7.082  | 1.00 | 34.74 |
| ATOM | 1197 | HH11 | ARG | 128 | 6.238  | −24.538 | 7.894  | 1.00 | 0.00  |
| ATOM | 1198 | HH22 | ARG | 128 | 6.166  | −23.334 | 6.649  | 1.00 | 0.00  |
| ATOM | 1199 | NH2  | ARG | 128 | 8.284  | −23.930 | 5.502  | 1.00 | 40.92 |
| ATOM | 1200 | HH21 | ARG | 128 | 9.152  | −24.244 | 5.115  | 1.00 | 0.00  |
| ATOM | 1201 | HH22 | ARG | 128 | 7.797  | −23.165 | 5.082  | 1.00 | 0.00  |
| ATOM | 1202 | C    | ARG | 128 | 11.859 | −26.103 | 10.505 | 1.00 | 25.38 |
| ATOM | 1203 | O    | ARG | 128 | 11.996 | −27.258 | 10.905 | 1.00 | 31.19 |
| ATOM | 1204 | N    | GLN | 129 | 12.763 | −25.555 | 9.706  | 1.00 | 27.63 |
| ATOM | 1205 | H    | GLN | 129 | 12.611 | −24.646 | 9.375  | 1.00 | 0.00  |
| ATOM | 1206 | CA   | GLN | 129 | 13.945 | −26.270 | 9.289  | 1.00 | 30.34 |
| ATOM | 1207 | CB   | GLN | 129 | 14.576 | −25.497 | 8.155  | 1.00 | 29.95 |
| ATOM | 1208 | CG   | GLN | 129 | 13.868 | −25.769 | 6.847  | 1.00 | 32.24 |
| ATOM | 1209 | CD   | GLN | 129 | 14.365 | −27.031 | 6.177  | 1.00 | 38.31 |
| ATOM | 1210 | OE1  | GLN | 129 | 14.088 | −28.153 | 6.591  | 1.00 | 43.39 |
| ATOM | 1211 | NE2  | GLN | 129 | 15.146 | −26.896 | 5.116  | 1.00 | 41.97 |
| ATOM | 1212 | HE21 | GLN | 129 | 15.362 | −25.995 | 4.785  | 1.00 | 0.00  |
| ATOM | 1213 | HE22 | GLN | 129 | 15.498 | −27.716 | 4.717  | 1.00 | 0.00  |
| ATOM | 1214 | C    | GLN | 129 | 14.931 | −26.488 | 10.436 | 1.00 | 35.26 |
| ATOM | 1215 | O    | GLN | 129 | 15.086 | −27.639 | 10.857 | 1.00 | 35.05 |
| ATOM | 1216 | N    | THR | 130 | 15.534 | −25.453 | 11.045 | 1.00 | 39.04 |
| ATOM | 1217 | H    | THR | 130 | 15.356 | −24.543 | 10.735 | 1.00 | 0.00  |
| ATOM | 1218 | CA   | THR | 130 | 16.514 | −25.655 | 12.114 | 1.00 | 38.84 |
| ATOM | 1219 | CB   | THR | 130 | 17.282 | −24.342 | 12.434 | 1.00 | 41.46 |
| ATOM | 1220 | OG1  | THR | 130 | 16.840 | −23.271 | 11.602 | 1.00 | 35.92 |
| ATOM | 1221 | HG1  | THR | 130 | 15.925 | −23.048 | 11.823 | 1.00 | 0.00  |
| ATOM | 1222 | CG2  | THR | 130 | 18.766 | −24.585 | 12.221 | 1.00 | 39.34 |
| ATOM | 1223 | C    | THR | 130 | 15.985 | −26.204 | 13.436 | 1.00 | 37.73 |
| ATOM | 1224 | O    | THR | 130 | 16.698 | −26.948 | 14.113 | 1.00 | 40.99 |
| ATOM | 1225 | N    | TRP | 131 | 14.773 | −25.865 | 13.868 | 1.00 | 34.87 |
| ATOM | 1226 | H    | TRP | 131 | 14.215 | −25.292 | 13.309 | 1.00 | 0.00  |
| ATOM | 1227 | CA   | TRP | 131 | 14.227 | −26.388 | 15.111 | 1.00 | 35.73 |
| ATOM | 1228 | CB   | TRP | 131 | 13.480 | −25.284 | 15.867 | 1.00 | 36.36 |
| ATOM | 1229 | CG   | TRP | 131 | 14.343 | −24.072 | 16.164 | 1.00 | 38.36 |
| ATOM | 1230 | CD2  | TRP | 131 | 15.380 | −24.020 | 17.052 | 1.00 | 39.04 |
| ATOM | 1231 | CE2  | TRP | 131 | 15.821 | −22.709 | 16.869 | 1.00 | 40.13 |
| ATOM | 1232 | CE3  | TRP | 131 | 16.020 | −24.847 | 17.975 | 1.00 | 44.19 |
| ATOM | 1233 | CD1  | TRP | 131 | 14.152 | −22.898 | 15.494 | 1.00 | 38.77 |
| ATOM | 1234 | NE1  | TRP | 131 | 15.071 | −22.093 | 15.951 | 1.00 | 37.02 |
| ATOM | 1235 | HE1  | TRP | 131 | 15.199 | −21.145 | 15.686 | 1.00 | 0.00  |
| ATOM | 1236 | CZ2  | TRP | 131 | 16.901 | −22.200 | 17.596 | 1.00 | 44.06 |
| ATOM | 1237 | CZ3  | TRP | 131 | 17.105 | −24.344 | 18.706 | 1.00 | 43.68 |
| ATOM | 1238 | CH2  | TRP | 131 | 17.542 | −23.029 | 18.517 | 1.00 | 41.50 |
| ATOM | 1239 | C    | TRP | 131 | 13.273 | −27.560 | 14.873 | 1.00 | 38.05 |
| ATOM | 1240 | O    | TRP | 131 | 12.439 | −27.871 | 15.725 | 1.00 | 36.61 |
| ATOM | 1241 | N    | LYS | 132 | 13.346 | −28.194 | 13.694 | 1.00 | 43.57 |
| ATOM | 1242 | H    | LYS | 132 | 13.985 | −27.860 | 13.032 | 1.00 | 0.00  |
| ATOM | 1243 | CA   | LYS | 132 | 12.551 | −29.349 | 13.270 | 1.00 | 47.47 |
| ATOM | 1244 | CB   | LYS | 132 | 13.283 | −30.640 | 13.676 | 1.00 | 48.07 |
| ATOM | 1245 | CG   | LYS | 132 | 14.216 | −31.184 | 12.593 | 1.00 | 49.73 |
| ATOM | 1246 | CD   | LYS | 132 | 15.521 | −30.405 | 12.488 | 1.00 | 53.88 |
| ATOM | 1247 | CE   | LYS | 132 | 16.307 | −30.757 | 11.227 | 1.00 | 55.30 |
| ATOM | 1248 | NZ   | LYS | 132 | 17.576 | −30.049 | 11.211 | 1.00 | 57.90 |
| ATOM | 1249 | HZ1  | LYS | 132 | 18.153 | −30.357 | 12.021 | 1.00 | 0.00  |
| ATOM | 1250 | HZ2  | LYS | 132 | 17.398 | −29.026 | 11.289 | 1.00 | 0.00  |
| ATOM | 1251 | HZ3  | LYS | 132 | 18.082 | −30.248 | 10.325 | 1.00 | 0.00  |
| ATOM | 1252 | C    | LYS | 132 | 11.082 | −29.544 | 13.629 | 1.00 | 49.55 |

TABLE 23-continued

Coordinates for the 3D structure of ZAP-NC:ζ1 "dimer" structure
(two molecules of complex per unit cell)*

| ATOM | 1253 | O | LYS | 132 | 10.526 | −30.587 | 13.267 | 1.00 | 53.16 |
|---|---|---|---|---|---|---|---|---|---|
| ATOM | 1254 | N | LEU | 133 | 10.364 | −28.657 | 14.311 | 1.00 | 53.10 |
| ATOM | 1255 | H | LEU | 133 | 10.767 | −27.821 | 14.621 | 1.00 | 0.00 |
| ATOM | 1256 | CA | LEU | 133 | 8.971 | −28.915 | 14.607 | 1.00 | 57.74 |
| ATOM | 1257 | CB | LEU | 133 | 8.743 | −28.920 | 16.126 | 1.00 | 62.97 |
| ATOM | 1258 | CG | LEU | 133 | 8.758 | −30.282 | 16.864 | 1.00 | 66.61 |
| ATOM | 1259 | CD1 | LEU | 133 | 7.846 | −31.256 | 16.107 | 1.00 | 66.25 |
| ATOM | 1260 | CD2 | LEU | 133 | 10.173 | −30.854 | 16.951 | 1.00 | 67.72 |
| ATOM | 1261 | C | LEU | 133 | 8.011 | −27.941 | 13.957 | 1.00 | 56.96 |
| ATOM | 1262 | O | LEU | 133 | 8.185 | −26.726 | 13.984 | 1.00 | 60.52 |
| ATOM | 1263 | N | GLU | 134 | 6.998 | −28.531 | 13.340 | 1.00 | 54.79 |
| ATOM | 1264 | H | GLU | 134 | 6.959 | −29.504 | 13.399 | 1.00 | 0.00 |
| ATOM | 1265 | CA | GLU | 134 | 5.955 | −27.814 | 12.637 | 1.00 | 52.86 |
| ATOM | 1266 | CB | GLU | 134 | 5.538 | −28.675 | 11.420 | 1.00 | 55.90 |
| ATOM | 1267 | CG | GLU | 134 | 4.795 | −30.029 | 11.620 | 1.00 | 60.27 |
| ATOM | 1268 | CD | GLU | 134 | 5.592 | −31.292 | 11.981 | 1.00 | 62.82 |
| ATOM | 1269 | OE1 | GLU | 134 | 5.830 | −31.530 | 13.167 | 1.00 | 66.15 |
| ATOM | 1270 | OE2 | GLU | 134 | 5.947 | −32.059 | 11.081 | 1.00 | 59.19 |
| ATOM | 1271 | C | GLU | 134 | 4.756 | −27.492 | 13.544 | 1.00 | 50.75 |
| ATOM | 1272 | O | GLU | 134 | 4.844 | −27.559 | 14.775 | 1.00 | 51.08 |
| ATOM | 1273 | N | GLY | 135 | 3.620 | −27.059 | 12.992 | 1.00 | 48.62 |
| ATOM | 1274 | H | GLY | 135 | 3.650 | −26.799 | 12.050 | 1.00 | 0.00 |
| ATOM | 1275 | CA | GLY | 135 | 2.363 | −16.848 | 13.724 | 1.00 | 46.72 |
| ATOM | 1276 | C | GLY | 135 | 2.302 | −15.664 | 14.678 | 1.00 | 44.51 |
| ATOM | 1277 | O | GLY | 135 | 3.004 | −14.664 | 14.536 | 1.00 | 46.83 |
| ATOM | 1278 | N | GLU | 136 | 1.450 | −15.759 | 15.693 | 1.00 | 46.52 |
| ATOM | 1279 | H | GLU | 136 | 0.871 | −26.545 | 15.747 | 1.00 | 0.00 |
| ATOM | 1280 | CA | GLU | 136 | 1.327 | −24.710 | 16.710 | 1.00 | 49.02 |
| ATOM | 1281 | CB | GLU | 136 | 0.262 | −25.059 | 17.763 | 1.00 | 51.89 |
| ATOM | 1282 | CG | GLU | 136 | −0.931 | −24.090 | 17.857 | 1.00 | 52.06 |
| ATOM | 1283 | CD | GLY | 136 | −0.588 | −22.646 | 18.218 | 1.00 | 54.10 |
| ATOM | 1284 | OE1 | GLY | 136 | −0.616 | −21.791 | 17.329 | 1.00 | 57.12 |
| ATOM | 1285 | OE2 | GLY | 136 | −0.300 | −22.376 | 19.384 | 1.00 | 51.65 |
| ATOM | 1286 | C | GLY | 136 | 2.645 | −24.489 | 17.440 | 1.00 | 46.65 |
| ATOM | 1287 | O | GLY | 136 | 2.944 | −23.398 | 17.936 | 1.00 | 46.30 |
| ATOM | 1288 | N | ALA | 137 | 3.437 | −25.556 | 17.502 | 1.00 | 45.19 |
| ATOM | 1289 | H | ALA | 137 | 3.139 | −26.407 | 17.128 | 1.00 | 0.00 |
| ATOM | 1290 | CA | ALA | 137 | 4.765 | −25.477 | 18.061 | 1.00 | 44.22 |
| ATOM | 1291 | CB | ALA | 137 | 5.442 | −26.837 | 17.034 | 1.00 | 45.58 |
| ATOM | 1292 | C | ALA | 137 | 5.559 | −24.509 | 17.196 | 1.00 | 42.82 |
| ATOM | 1293 | O | ALA | 137 | 6.139 | −23.610 | 17.799 | 1.00 | 47.38 |
| ATOM | 1294 | N | ALA | 137 | 5.513 | −24.597 | 15.847 | 1.00 | 36.97 |
| ATOM | 1295 | H | LEU | 138 | 5.012 | −25.341 | 15.455 | 1.00 | 0.00 |
| ATOM | 1296 | CA | LEU | 138 | 6.214 | −23.700 | 14.925 | 1.00 | 31.88 |
| ATOM | 1297 | CB | LEU | 138 | 5.865 | −23.934 | 13.461 | 1.00 | 27.69 |
| ATOM | 1298 | CG | LEU | 138 | 6.930 | −24.048 | 12.355 | 1.00 | 28.20 |
| ATOM | 1299 | CD1 | LEU | 138 | 6.191 | −24.029 | 11.030 | 1.00 | 18.29 |
| ATOM | 1300 | CD2 | LEU | 138 | 7.918 | −22.914 | 12.347 | 1.00 | 21.98 |
| ATOM | 1301 | C | LEU | 138 | 5.821 | −22.269 | 15.197 | 1.00 | 29.00 |
| ATOM | 1302 | O | LEU | 138 | 6.672 | −21.402 | 15.377 | 1.00 | 27.80 |
| ATOM | 1303 | N | GLU | 139 | 4.526 | −22.008 | 15.247 | 1.00 | 29.67 |
| ATOM | 1304 | H | GLU | 139 | 2.896 | −22.746 | 15.108 | 1.00 | 0.00 |
| ATOM | 1305 | CA | GLU | 139 | 4.053 | −20.660 | 15.464 | 1.00 | 34.50 |
| ATOM | 1306 | CB | GLU | 139 | 2.538 | −20.665 | 15.451 | 1.00 | 38.42 |
| ATOM | 1307 | CG | GLU | 139 | 1.945 | −20.289 | 14.082 | 1.00 | 44.60 |
| ATOM | 1308 | CD | GLU | 139 | 2.501 | −21.012 | 12.851 | 1.00 | 46.22 |
| ATOM | 1309 | OE1 | GLU | 139 | 3.301 | −20.401 | 12.149 | 1.00 | 43.80 |
| ATOM | 1310 | OE2 | GLU | 139 | 2.135 | −22.162 | 12.583 | 1.00 | 48.63 |
| ATOM | 1311 | C | GLU | 139 | 4.587 | −20.109 | 16.760 | 1.00 | 36.52 |
| ATOM | 1312 | O | GLU | 139 | 5.196 | −19.037 | 16.774 | 1.00 | 39.38 |
| ATOM | 1313 | N | GLN | 140 | 4.479 | −20.876 | 17.839 | 1.00 | 38.33 |
| ATOM | 1314 | H | GLN | 140 | 4.053 | −21.755 | 17.765 | 1.00 | 0.00 |
| ATOM | 1315 | CA | GLN | 140 | 5.037 | −20.439 | 19.100 | 1.00 | 37.72 |
| ATOM | 1316 | CB | GLN | 140 | 4.724 | −21.476 | 20.168 | 1.00 | 45.54 |
| ATOM | 1317 | CG | GLN | 140 | 3.307 | −21.321 | 20.713 | 1.00 | 56.23 |
| ATOM | 1318 | CD | GLN | 140 | 2.957 | −22.366 | 21.770 | 1.00 | 65.59 |
| ATOM | 1319 | OE1 | GLN | 140 | 3.103 | −22.167 | 22.987 | 1.00 | 66.51 |
| ATOM | 1320 | NE2 | GLN | 140 | 2.470 | −23.531 | 21.354 | 1.00 | 67.31 |
| ATOM | 1321 | HE21 | GLN | 140 | 2.379 | −23.670 | 20.391 | 1.00 | 0.00 |
| ATOM | 1322 | HE22 | GLN | 140 | 2.259 | −24.177 | 22.050 | 1.00 | 0.00 |
| ATOM | 1323 | C | GLN | 140 | 6.573 | −20.224 | 18.975 | 1.00 | 33.59 |
| ATOM | 1324 | O | GLN | 140 | 7.032 | −19.142 | 19.323 | 1.00 | 31.72 |
| ATOM | 1325 | N | ALA | 141 | 7.291 | −21.155 | 18.388 | 1.00 | 25.14 |
| ATOM | 1326 | H | ALA | 141 | 6.848 | −21.926 | 17.991 | 1.00 | 0.00 |
| ATOM | 1327 | CA | ALA | 141 | 8.725 | −21.022 | 18.220 | 1.00 | 25.84 |
| ATOM | 1328 | CB | ALA | 141 | 9.300 | −22.343 | 17.683 | 1.00 | 28.13 |

TABLE 23-continued

Coordinates for the 3D structure of ZAP-NC:ζ1 "dimer" structure
(two molecules of complex per unit cell)*

| ATOM | 1329 | C | ALA | 141 | 9.137 | −19.872 | 17.290 | 1.00 | 28.14 |
|---|---|---|---|---|---|---|---|---|---|
| ATOM | 1330 | O | ALA | 141 | 10.287 | −19.437 | 17.344 | 1.00 | 30.78 |
| ATOM | 1331 | N | ILE | 142 | 8.266 | −19.316 | 16.429 | 1.00 | 30.84 |
| ATOM | 1332 | H | ILE | 142 | 7.402 | −19.863 | 16.297 | 1.00 | 0.00 |
| ATOM | 1333 | CA | ILE | 142 | 8.571 | −18.125 | 15.627 | 1.00 | 25.85 |
| ATOM | 1334 | CB | ILE | 142 | 7.449 | −17.965 | 14.547 | 1.00 | 18.89 |
| ATOM | 1335 | CG2 | ILE | 142 | 7.432 | −16.583 | 13.908 | 1.00 | 21.04 |
| ATOM | 1336 | CG1 | ILE | 142 | 7.732 | −18.967 | 13.428 | 1.00 | 20.14 |
| ATOM | 1337 | CD | ILE | 142 | 6.556 | −19.269 | 12.492 | 1.00 | 15.71 |
| ATOM | 1338 | C | ILE | 142 | 8.660 | −16.923 | 16.573 | 1.00 | 29.99 |
| ATOM | 1339 | O | ILE | 142 | 9.565 | −16.097 | 16.493 | 1.00 | 31.41 |
| ATOM | 1340 | N | ILE | 143 | 7.736 | −16.887 | 17.532 | 1.00 | 35.52 |
| ATOM | 1341 | H | ILE | 143 | 7.119 | −17.638 | 17.588 | 1.00 | 0.00 |
| ATOM | 1342 | CA | ILE | 143 | 7.613 | −15.810 | 18.518 | 1.00 | 37.48 |
| ATOM | 1343 | CB | ILE | 143 | 6.199 | −15.808 | 19.126 | 1.00 | 37.49 |
| ATOM | 1344 | CG2 | ILE | 143 | 5.947 | −14.427 | 19.699 | 1.00 | 39.63 |
| ATOM | 1345 | CG1 | ILE | 143 | 5.114 | −16.077 | 18.092 | 1.00 | 40.16 |
| ATOM | 1346 | CD | ILE | 143 | 3.812 | −16.651 | 18.686 | 1.00 | 41.67 |
| ATOM | 1347 | C | ILE | 143 | 8.625 | −16.006 | 19.641 | 1.00 | 41.27 |
| ATOM | 1348 | O | SER | 144 | 9.047 | −15.041 | 20.273 | 1.00 | 41.07 |
| ATOM | 1349 | N | SER | 144 | 8.976 | −17.255 | 19.949 | 1.00 | 47.79 |
| ATOM | 1350 | H | SER | 144 | 8.616 | −17.986 | 19.410 | 1.00 | 0.00 |
| ATOM | 1351 | CA | SER | 144 | 9.893 | −17.576 | 21.033 | 1.00 | 52.28 |
| ATOM | 1352 | CB | SER | 144 | 9.534 | −18.976 | 21.632 | 1.00 | 52.29 |
| ATOM | 1353 | OG | SER | 144 | 8.145 | −19.030 | 21.895 | 1.00 | 53.23 |
| ATOM | 1354 | HG | SER | 144 | 7.612 | −18.881 | 21.109 | 1.00 | 0.00 |
| ATOM | 1355 | C | SER | 144 | 11.370 | −17.481 | 20.651 | 1.00 | 55.20 |
| ATOM | 1356 | O | SER | 144 | 12.205 | −17.066 | 21.467 | 1.00 | 58.47 |
| ATOM | 1357 | N | GLN | 145 | 11.769 | −17.860 | 19.438 | 1.00 | 58.14 |
| ATOM | 1358 | H | GLN | 145 | 11.133 | −18.245 | 18.798 | 1.00 | 0.00 |
| ATOM | 1359 | CA | GLN | 145 | 13.142 | −17.681 | 18.996 | 1.00 | 59.26 |
| ATOM | 1360 | CB | GLN | 145 | 13.637 | −18.900 | 18.186 | 1.00 | 58.99 |
| ATOM | 1361 | CG | GLN | 145 | 14.116 | −20.105 | 19.015 | 1.00 | 51.70 |
| ATOM | 1362 | CD | GLN | 145 | 13.040 | −20.987 | 19.634 | 1.00 | 46.51 |
| ATOM | 1363 | OE1 | GLN | 145 | 12.040 | −20.526 | 20.174 | 1.00 | 46.63 |
| ATOM | 1364 | NE2 | GLN | 145 | 13.205 | −22.301 | 19.603 | 1.00 | 42.17 |
| ATOM | 1365 | HE21 | GLN | 145 | 14.014 | −22.649 | 19.174 | 1.00 | 0.00 |
| ATOM | 1366 | HE22 | GLN | 145 | 12.505 | −22.846 | 20.014 | 1.00 | 0.00 |
| ATOM | 1367 | C | ALA | 146 | 13.086 | −16.436 | 18.121 | 1.00 | 59.37 |
| ATOM | 1368 | O | ALA | 146 | 12.441 | −16.418 | 17.066 | 1.00 | 59.11 |
| ATOM | 1369 | N | ALA | 146 | 13.761 | −15.381 | 18.584 | 1.00 | 57.95 |
| ATOM | 1370 | H | ALA | 146 | 14.348 | −15.502 | 19.358 | 1.00 | 0.00 |
| ATOM | 1371 | CA | ALA | 146 | 13.716 | −14.068 | 17.955 | 1.00 | 54.83 |
| ATOM | 1372 | CB | ALA | 146 | 12.490 | −13.332 | 18.513 | 1.00 | 51.86 |
| ATOM | 1373 | C | ALA | 146 | 15.014 | −13.314 | 18.266 | 1.00 | 50.12 |
| ATOM | 1374 | O | ALA | 146 | 16.019 | −13.982 | 18.529 | 1.00 | 50.90 |
| ATOM | 1375 | N | PRO | 147 | 15.147 | −11.984 | 18.217 | 1.00 | 45.39 |
| ATOM | 1376 | CD | PRO | 147 | 15.344 | −11.200 | 19.436 | 1.00 | 46.16 |
| ATOM | 1377 | CA | PRO | 147 | 14.760 | −11.112 | 17.111 | 1.00 | 40.33 |
| ATOM | 1378 | CB | PRO | 147 | 14.220 | −98.84 | 17.808 | 1.00 | 42.32 |
| ATOM | 1379 | CG | PRO | 147 | 15.140 | −97.50 | 18.996 | 1.00 | 43.96 |
| ATOM | 1380 | C | PRO | 147 | 15.855 | −10.796 | 16.102 | 1.00 | 37.26 |
| ATOM | 1381 | O | PRO | 147 | 15.560 | −10.361 | 14.988 | 1.00 | 38.02 |
| ATOM | 1382 | N | GLN | 148 | 17.131 | −11.025 | 16.427 | 1.00 | 34.30 |
| ATOM | 1383 | H | GLN | 148 | 17.343 | −11.320 | 17.344 | 1.00 | 0.00 |
| ATOM | 1384 | CA | GLN | 148 | 18.237 | −10.822 | 15.500 | 1.00 | 29.73 |
| ATOM | 1385 | CB | GLN | 148 | 19.609 | −11.094 | 16.111 | 1.00 | 33.42 |
| ATOM | 1386 | CG | GLN | 148 | 20.143 | −10.081 | 17.095 | 1.00 | 38.19 |
| ATOM | 1387 | CD | GLN | 148 | 19.410 | −10.075 | 18.428 | 1.00 | 44.05 |
| ATOM | 1388 | OE1 | GLN | 148 | 18.677 | −10.999 | 18.795 | 1.00 | 44.63 |
| ATOM | 1389 | NE2 | GLN | 148 | 19.566 | −9.020 | 19.207 | 1.00 | 47.86 |
| ATOM | 1390 | HE21 | GLN | 148 | 20.127 | −8.273 | 18.912 | 1.00 | 0.00 |
| ATOM | 1391 | HE22 | GLN | 148 | 19.121 | −9.038 | 20.078 | 1.00 | 0.00 |
| ATOM | 1392 | C | GLN | 148 | 18.122 | −11.771 | 14.327 | 1.00 | 25.44 |
| ATOM | 1393 | O | VAL | 149 | 18.647 | −11.478 | 13.258 | 1.00 | 25.23 |
| ATOM | 1394 | N | VAL | 149 | 17.436 | −12.905 | 14.497 | 1.00 | 23.42 |
| ATOM | 1395 | H | VAL | 149 | 17.174 | −13.141 | 15.408 | 1.00 | 0.00 |
| ATOM | 1396 | CA | VAL | 149 | 17.228 | −13.855 | 13.417 | 1.00 | 22.10 |
| ATOM | 1397 | CB | VAL | 149 | 16.571 | −15.172 | 13.960 | 1.00 | 21.97 |
| ATOM | 1398 | CG1 | VAL | 149 | 17.492 | −15.765 | 15.008 | 1.00 | 21.05 |
| ATOM | 1399 | CG2 | VAL | 149 | 15.220 | −14.937 | 14.591 | 1.00 | 22.67 |
| ATOM | 1400 | C | VAL | 149 | 16.368 | −13.249 | 12.309 | 1.00 | 20.80 |
| ATOM | 1401 | O | VAL | 149 | 16.646 | −13.427 | 11.129 | 1.00 | 21.04 |
| ATOM | 1402 | N | GLU | 150 | 15.360 | −12.455 | 12.650 | 1.00 | 22.05 |
| ATOM | 1403 | H | GLU | 150 | 15.224 | −12.254 | 13.595 | 1.00 | 0.00 |
| ATOM | 1404 | CA | GLU | 150 | 14.490 | −11.803 | 11.691 | 1.00 | 23.41 |

TABLE 23-continued

Coordinates for the 3D structure of ZAP-NC:ζ1 "dimer" structure
(two molecules of complex per unit cell)*

| ATOM | 1405 | CB | GLU | 150 | 13.373 | −11.162 | 12.511 | 1.00 | 27.75 |
|---|---|---|---|---|---|---|---|---|---|
| ATOM | 1406 | CG | GLU | 150 | 12.420 | −10.140 | 11.875 | 1.00 | 40.15 |
| ATOM | 1407 | CD | GLU | 150 | 11.567 | −10.618 | 10.706 | 1.00 | 40.12 |
| ATOM | 1408 | OE1 | GLU | 150 | 12.136 | −11.023 | 9.695 | 1.00 | 42.37 |
| ATOM | 1409 | OE2 | GLU | 150 | 10.338 | −10.554 | 10.791 | 1.00 | 43.49 |
| ATOM | 1410 | C | GLU | 150 | 15.292 | −10.801 | 10.858 | 1.00 | 24.41 |
| ATOM | 1411 | O | GLU | 150 | 15.156 | −10.712 | 9.633 | 1.00 | 25.40 |
| ATOM | 1412 | N | LYS | 151 | 16.208 | −10.100 | 11.535 | 1.00 | 22.99 |
| ATOM | 1413 | H | LYS | 151 | 16.231 | −10.204 | 12.506 | 1.00 | 0.00 |
| ATOM | 1414 | CA | LYS | 151 | 17.115 | −9.138 | 10.931 | 1.00 | 19.15 |
| ATOM | 1415 | CB | LYS | 151 | 17.760 | −8.384 | 12.094 | 1.00 | 17.32 |
| ATOM | 1416 | CG | LYS | 151 | 18.552 | −7.125 | 11.791 | 1.00 | 20.52 |
| ATOM | 1417 | CD | LYS | 151 | 18.701 | −6.401 | 13.121 | 1.00 | 26.52 |
| ATOM | 1418 | CE | LYS | 151 | 19.509 | −5.113 | 13.089 | 1.00 | 31.53 |
| ATOM | 1419 | NZ | LYS | 151 | 20.920 | −5.393 | 12.889 | 1.00 | 44.71 |
| ATOM | 1420 | HZ1 | LYS | 151 | 21.255 | −6.004 | 13.662 | 1.00 | 0.00 |
| ATOM | 1421 | HZ2 | LYS | 151 | 21.473 | −4.513 | 12.884 | 1.00 | 0.00 |
| ATOM | 1422 | HZ3 | LYS | 151 | 21.048 | −5.890 | 11.985 | 1.00 | 0.00 |
| ATOM | 1423 | C | LYS | 151 | 18.127 | −9.852 | 10.036 | 1.00 | 16.31 |
| ATOM | 1424 | O | LYS | 151 | 18.480 | −9.389 | 8.955 | 1.00 | 12.19 |
| ATOM | 1425 | N | LEU | 152 | 18.601 | −11.015 | 10.444 | 1.00 | 16.09 |
| ATOM | 1426 | H | LEU | 152 | 18.331 | −11.332 | 11.331 | 1.00 | 0.00 |
| ATOM | 1427 | CA | LEU | 152 | 19.524 | −11.849 | 9.703 | 1.00 | 12.00 |
| ATOM | 1428 | CB | LEU | 152 | 19.855 | −13.040 | 10.500 | 1.00 | 15.88 |
| ATOM | 1429 | CG | LEU | 152 | 21.222 | −13.560 | 10.639 | 1.00 | 16.05 |
| ATOM | 1430 | CD1 | LEU | 152 | 21.077 | −14.775 | 11.546 | 1.00 | 16.90 |
| ATOM | 1431 | CD2 | LEU | 152 | 21.866 | −13.869 | 9.301 | 1.00 | 11.67 |
| ATOM | 1432 | C | LEU | 152 | 18.870 | −12.335 | 8.438 | 1.00 | 13.18 |
| ATOM | 1433 | O | LEU | 152 | 19.497 | −12.346 | 7.383 | 1.00 | 18.93 |
| ATOM | 1434 | N | ILE | 153 | 17.631 | −12.796 | 8.537 | 1.00 | 12.61 |
| ATOM | 1435 | H | ILE | 153 | 17.208 | −12.810 | 9.421 | 1.00 | 0.00 |
| ATOM | 1436 | CA | ILE | 153 | 16.874 | −13.277 | 7.392 | 1.00 | 18.32 |
| ATOM | 1437 | CB | ILE | 153 | 15.603 | −13.925 | 8.013 | 1.00 | 19.63 |
| ATOM | 1438 | CG2 | ILE | 153 | 14.479 | −14.062 | 7.006 | 1.00 | 15.55 |
| ATOM | 1439 | CG1 | ILE | 153 | 16.011 | −15.280 | 8.620 | 1.00 | 20.47 |
| ATOM | 1440 | CD | ILE | 153 | 16.260 | −16.471 | 7.679 | 1.00 | 22.78 |
| ATOM | 1441 | C | ILE | 153 | 16.613 | −12.117 | 6.406 | 1.00 | 16.99 |
| ATOM | 1442 | O | ILE | 153 | 16.784 | −12.260 | 5.192 | 1.00 | 14.84 |
| ATOM | 1443 | N | ALA | 154 | 16.283 | −10.929 | 6.906 | 1.00 | 14.59 |
| ATOM | 1444 | H | ALA | 154 | 16.079 | −10.868 | 7.864 | 1.00 | 0.00 |
| ATOM | 1445 | CA | ALA | 154 | 16.129 | −9.740 | 6.087 | 1.00 | 14.27 |
| ATOM | 1446 | CB | ALA | 154 | 15.654 | −8.595 | 6.980 | 1.00 | 11.41 |
| ATOM | 1447 | C | ALA | 154 | 17.402 | −9.316 | 5.362 | 1.00 | 13.07 |
| ATOM | 1448 | O | ALA | 154 | 17.394 | −9.006 | 4.159 | 1.00 | 13.71 |
| ATOM | 1449 | N | THR | 155 | 18.526 | −9.306 | 6.099 | 1.00 | 12.27 |
| ATOM | 1450 | H | THR | 155 | 18.467 | −9.606 | 7.029 | 1.00 | 0.00 |
| ATOM | 1451 | CA | THR | 155 | 19.830 | −8.914 | 5.559 | 1.00 | 10.44 |
| ATOM | 1452 | CB | THR | 155 | 20.887 | −8.906 | 6.713 | 1.00 | 9.80 |
| ATOM | 1453 | OG1 | THR | 155 | 20.456 | −7.925 | 7.663 | 1.00 | 18.84 |
| ATOM | 1454 | HG1 | THR | 155 | 19.665 | −8.275 | 8.091 | 1.00 | 0.00 |
| ATOM | 1455 | CG2 | THR | 155 | 22.278 | −8.550 | 6.270 | 1.00 | 9.45 |
| ATOM | 1456 | C | THR | 155 | 20.236 | −9.883 | 4.440 | 1.00 | 14.92 |
| ATOM | 1457 | O | THR | 155 | 20.778 | −9.460 | 3.403 | 1.00 | 15.13 |
| ATOM | 1458 | N | THR | 156 | 19.900 | −11.172 | 4.578 | 1.00 | 17.24 |
| ATOM | 1459 | H | THR | 156 | 19.422 | −11.506 | 5.372 | 1.00 | 0.00 |
| ATOM | 1460 | CA | THR | 156 | 20.317 | −12.165 | 3.609 | 1.00 | 17.42 |
| ATOM | 1461 | CB | THR | 156 | 20.778 | −13.424 | 4.387 | 1.00 | 21.01 |
| ATOM | 1462 | OG1 | THR | 156 | 19.701 | −13.847 | 5.216 | 1.00 | 18.15 |
| ATOM | 1463 | HG1 | THR | 156 | 20.090 | −14.396 | 5.915 | 1.00 | 0.00 |
| ATOM | 1464 | CG2 | THR | 156 | 22.010 | −13.145 | 5.222 | 1.00 | 17.36 |
| ATOM | 1465 | C | THR | 156 | 19.286 | −12.525 | 2.548 | 1.00 | 16.54 |
| ATOM | 1466 | O | THR | 156 | 19.675 | −13.151 | 1.556 | 1.00 | 16.61 |
| ATOM | 1467 | N | ALA | 157 | 18.021 | −12.082 | 2.648 | 1.00 | 11.96 |
| ATOM | 1468 | H | ALA | 157 | 17.765 | −11.593 | 3.460 | 1.00 | 0.00 |
| ATOM | 1469 | CA | ALA | 157 | 16.978 | −12.353 | 1.665 | 1.00 | 8.10 |
| ATOM | 1470 | CB | ALA | 157 | 15.792 | −11.463 | 1.875 | 1.00 | 5.22 |
| ATOM | 1471 | C | ALA | 157 | 17.334 | −12.205 | 0.203 | 1.00 | 11.31 |
| ATOM | 1472 | O | ALA | 157 | 16.768 | −12.899 | −0.628 | 1.00 | 12.82 |
| ATOM | 1473 | N | HIS | 158 | 18.272 | −11.321 | −0.131 | 1.00 | 11.13 |
| ATOM | 1474 | H | HIS | 158 | 18.588 | −10.744 | 0.590 | 1.00 | 0.00 |
| ATOM | 1475 | CA | HIS | 158 | 18.748 | −11.150 | −1.490 | 1.00 | 13.55 |
| ATOM | 1476 | CB | HIS | 158 | 19.697 | −9.955 | −1.599 | 1.00 | 12.74 |
| ATOM | 1477 | CG | HIS | 158 | 20.963 | −9.981 | −0.760 | 1.00 | 6.21 |
| ATOM | 1478 | CD2 | HIS | 158 | 22.226 | −10.209 | −1.250 | 1.00 | 5.93 |
| ATOM | 1479 | ND1 | HIS | 158 | 21.062 | −9.767 | 0.543 | 1.00 | 9.66 |
| ATOM | 1480 | HD1 | HIS | 158 | 20.370 | −9.464 | 1.176 | 1.00 | 0.00 |

TABLE 23-continued

Coordinates for the 3D structure of ZAP-NC:ζ1 "dimer" structure
(two molecules of complex per unit cell)*

| ATOM | 1481 | CE1 | HIS | 158 | 22.335 | −9.850 | 0.857 | 1.00 | 7.67 |
|---|---|---|---|---|---|---|---|---|---|
| ATOM | 1482 | NE2 | HIS | 158 | 23.027 | −10.113 | −0.218 | 1.00 | 9.31 |
| ATOM | 1483 | HE2 | HIS | 158 | 24.008 | −10.028 | −0.233 | 1.00 | 0.00 |
| ATOM | 1484 | C | HIS | 158 | 19.481 | −12.359 | −2.052 | 1.00 | 1.619 |
| ATOM | 1485 | O | HIS | 158 | 19.448 | −12.632 | −3.236 | 1.00 | 2.047 |
| ATOM | 1486 | N | GLU | 159 | 20.175 | −13.107 | −1.216 | 1.00 | 1.723 |
| ATOM | 1487 | H | GLU | 159 | 20.072 | −12.955 | −0.257 | 1.00 | 0.00 |
| ATOM | 1488 | CA | GLU | 159 | 20.940 | −14.254 | −1.657 | 1.00 | 20.55 |
| ATOM | 1489 | CB | GLU | 159 | 21.657 | −14.764 | −0.429 | 1.00 | 20.24 |
| ATOM | 1490 | CG | GLU | 159 | 22.843 | −13.822 | −0.229 | 1.00 | 27.41 |
| ATOM | 1491 | CD | GLU | 159 | 23.580 | −13.832 | 1.103 | 1.00 | 25.05 |
| ATOM | 1492 | OE1 | GLU | 159 | 24.583 | −13.120 | 1.190 | 1.00 | 41.39 |
| ATOM | 1493 | OE2 | GLU | 159 | 23.163 | −14.513 | 2.045 | 1.00 | 37.57 |
| ATOM | 1494 | C | GLU | 159 | 20.124 | −15.341 | −2.356 | 1.00 | 20.03 |
| ATOM | 1495 | O | GLU | 159 | 20.575 | −15.957 | −3.322 | 1.00 | 23.76 |
| ATOM | 1496 | N | ARG | 160 | 18.879 | −15.517 | −1.936 | 1.00 | 16.92 |
| ATOM | 1497 | H | ARG | 160 | 18.494 | −14.915 | −1.266 | 1.00 | 0.00 |
| ATOM | 1498 | CA | ARG | 160 | 18.031 | −16.500 | −2.555 | 1.00 | 16.29 |
| ATOM | 1499 | CB | ARG | 160 | 17.147 | −17.180 | −1.499 | 1.00 | 18.52 |
| ATOM | 1500 | CG | ARG | 160 | 16.251 | −16.276 | −0.682 | 1.00 | 24.37 |
| ATOM | 1501 | CD | ARG | 160 | 16.483 | −16.570 | 0.783 | 1.00 | 31.61 |
| ATOM | 1502 | NE | ARG | 160 | 15.708 | −17.723 | 1.197 | 1.00 | 22.80 |
| ATOM | 1503 | HE | ARG | 160 | 15.197 | −18.221 | 0.523 | 1.00 | 0.00 |
| ATOM | 1504 | CZ | ARG | 160 | 15.689 | −18.141 | 2.467 | 1.00 | 35.13 |
| ATOM | 1505 | NH1 | ARG | 160 | 16.392 | −17.532 | 3.449 | 1.00 | 23.68 |
| ATOM | 1506 | HH11 | ARG | 160 | 16.962 | −16.736 | 3.244 | 1.00 | 0.00 |
| ATOM | 1507 | HH12 | ARG | 160 | 16.341 | −17.882 | 4.384 | 1.00 | 0.00 |
| ATOM | 1508 | NH2 | ARG | 160 | 14.895 | −19.179 | 2.743 | 1.00 | 34.48 |
| ATOM | 1509 | HH21 | ARG | 160 | 14.346 | −19.596 | 2.018 | 1.00 | 0.00 |
| ATOM | 1510 | HH22 | ARG | 160 | 14.848 | −19.541 | 3.672 | 1.00 | 0.00 |
| ATOM | 1511 | C | ARG | 160 | 17.175 | −15.879 | −3.625 | 1.00 | 13.93 |
| ATOM | 1512 | O | ARG | 160 | 16.168 | −16.457 | −4.043 | 1.00 | 18.72 |
| ATOM | 1513 | N | MET | 161 | 17.530 | −14.702 | −4.103 | 1.00 | 13.50 |
| ATOM | 1514 | H | MET | 161 | 18.413 | −14.316 | −3.923 | 1.00 | 0.00 |
| ATOM | 1515 | CA | MET | 161 | 16.690 | −14.069 | −5.093 | 1.00 | 14.46 |
| ATOM | 1516 | CB | MET | 161 | 16.666 | −12.575 | −5.874 | 1.00 | 13.73 |
| ATOM | 1517 | CG | MET | 161 | 15.916 | −12.130 | −3.637 | 1.00 | 7.08 |
| ATOM | 1518 | SD | MET | 161 | 14.135 | −12.358 | −3.669 | 1.00 | 12.33 |
| ATOM | 1519 | CE | MET | 161 | 14.041 | −13.525 | −2.328 | 1.00 | 2.25 |
| ATOM | 1520 | C | MET | 161 | 17.226 | −14.378 | −6.475 | 1.00 | 14.92 |
| ATOM | 1521 | O | MET | 161 | 18.442 | −14.348 | −6.651 | 1.00 | 15.63 |
| ATOM | 1522 | N | MET | 161 | 16.412 | −14.649 | −7.509 | 1.00 | 16.02 |
| ATOM | 1523 | CD | MET | 161 | 14.961 | −14.709 | −7.458 | 1.00 | 14.38 |
| ATOM | 1524 | CA | MET | 161 | 16.873 | −15.010 | −8.847 | 1.00 | 17.79 |
| ATOM | 1525 | CB | MET | 161 | 15.602 | −15.227 | −9.619 | 1.00 | 17.80 |
| ATOM | 1526 | CG | MET | 161 | 14.600 | −14.377 | −8.889 | 1.00 | 17.12 |
| ATOM | 1527 | C | MET | 161 | 17.806 | −14.015 | −9.519 | 1.00 | 19.05 |
| ATOM | 1528 | O | PRO | 162 | 18.647 | −14.391 | −10.328 | 1.00 | 21.41 |
| ATOM | 1529 | N | TRP | 163 | 17.661 | −12.733 | −9.167 | 1.00 | 19.49 |
| ATOM | 1530 | H | TRP | 163 | 17.016 | −12.516 | −8.470 | 1.00 | 0.00 |
| ATOM | 1531 | CA | TRP | 163 | 18.493 | −11.669 | −9.712 | 1.00 | 14.79 |
| ATOM | 1532 | CB | TRP | 163 | 17.765 | −10.334 | −8.563 | 1.00 | 16.38 |
| ATOM | 1533 | CG | TRP | 163 | 17.026 | −10.040 | −8.251 | 1.00 | 15.65 |
| ATOM | 1534 | CD2 | TRP | 163 | 17.590 | −6.306 | −7.061 | 1.00 | 18.28 |
| ATOM | 1535 | CE2 | TRP | 163 | 16.439 | −6.447 | −6.263 | 1.00 | 16.96 |
| ATOM | 1536 | CE3 | TRP | 163 | 18.862 | −6.320 | −6.520 | 1.00 | 14.05 |
| ATOM | 1537 | CD1 | TRP | 163 | 15.661 | −10.145 | −8.186 | 1.00 | 11.47 |
| ATOM | 1538 | NE1 | TRP | 163 | 15.341 | −9.775 | −6.971 | 1.00 | 13.57 |
| ATOM | 1539 | HE1 | TRP | 163 | 14.423 | −9.631 | −6.647 | 1.00 | 0.00 |
| ATOM | 1540 | CZ2 | TRP | 163 | 16.543 | −8.999 | −4.933 | 1.00 | 14.05 |
| ATOM | 1541 | CZ3 | TRP | 163 | 18.963 | −8.873 | −5.184 | 1.00 | 13.85 |
| ATOM | 1542 | CH2 | TRP | 163 | 17.808 | −8.715 | −4.398 | 1.00 | 9.31 |
| ATOM | 1543 | C | TRP | 163 | 19.827 | −11.574 | −9.065 | 1.00 | 14.37 |
| ATOM | 1544 | O | TRP | 163 | 20.704 | −10.868 | −9.562 | 1.00 | 18.36 |
| ATOM | 1545 | N | TYR | 164 | 20.068 | −12.259 | −7.958 | 1.00 | 12.49 |
| ATOM | 1546 | H | TYR | 164 | 19.506 | −13.007 | −7.676 | 1.00 | 0.00 |
| ATOM | 1547 | CA | TYR | 164 | 21.355 | −12.130 | −7.333 | 1.00 | 13.07 |
| ATOM | 1548 | CB | TYR | 164 | 21.230 | −12.357 | −5.831 | 1.00 | 12.72 |
| ATOM | 1549 | CG | TYR | 164 | 22.544 | −12.125 | −5.109 | 1.00 | 10.10 |
| ATOM | 1550 | CD1 | TYR | 164 | 23.138 | −10.875 | −5.204 | 1.00 | 13.14 |
| ATOM | 1551 | CE1 | TYR | 164 | 24.358 | −10.634 | −4.587 | 1.00 | 14.29 |
| ATOM | 1552 | CD2 | TYR | 164 | 23.168 | −13.149 | −4.388 | 1.00 | 13.03 |
| ATOM | 1553 | CE2 | TYR | 164 | 24.392 | −12.907 | −3.762 | 1.00 | 11.06 |
| ATOM | 1554 | CZ | TYR | 164 | 24.966 | −11.647 | −3.873 | 1.00 | 10.57 |
| ATOM | 1555 | OH | TYR | 164 | 26.144 | −11.333 | −3.245 | 1.00 | 21.87 |
| ATOM | 1556 | HH | TYR | 164 | 26.452 | −12.073 | −2.702 | 1.00 | 0.00 |

TABLE 23-continued

Coordinates for the 3D structure of ZAP-NC:ζ1 "dimer" structure
(two molecules of complex per unit cell)*

| ATOM | 1557 | C    | TYR | 164 | 22.208 | −13.205 | −7.980  | 1.00 | 18.71 |
|------|------|------|-----|-----|--------|---------|---------|------|-------|
| ATOM | 1558 | O    | TYR | 164 | 21.751 | −14.324 | −8.226  | 1.00 | 17.75 |
| ATOM | 1559 | N    | HIS | 165 | 23.435 | −12.870 | −8.377  | 1.00 | 22.75 |
| ATOM | 1560 | H    | HIS | 165 | 23.729 | −11.938 | −8.262  | 1.00 | 0.00  |
| ATOM | 1561 | CA   | HIS | 165 | 24.344 | −13.855 | −8.923  | 1.00 | 24.59 |
| ATOM | 1562 | CB   | HIS | 165 | 24.598 | −13.627 | −10.422 | 1.00 | 23.90 |
| ATOM | 1563 | CG   | HIS | 165 | 23.397 | −13.904 | −11.315 | 1.00 | 26.19 |
| ATOM | 1564 | CD2  | HIS | 165 | 22.254 | −13.135 | −11.335 | 1.00 | 27.29 |
| ATOM | 1565 | ND1  | HIS | 165 | 23.221 | −14.894 | −12.184 | 1.00 | 27.47 |
| ATOM | 1566 | HD1  | HIS | 165 | 23.783 | −15.675 | −12.397 | 1.00 | 0.00  |
| ATOM | 1567 | CE1  | HIS | 165 | 22.034 | −14.736 | −12.698 | 1.00 | 25.41 |
| ATOM | 1568 | NE2  | HIS | 165 | 21.456 | −13.688 | −12.189 | 1.00 | 21.53 |
| ATOM | 1569 | HE2  | HIS | 165 | 20.486 | −13.539 | −12.228 | 1.00 | 0.00  |
| ATOM | 1570 | C    | HIS | 165 | 25.633 | −13.656 | −8.156  | 1.00 | 26.23 |
| ATOM | 1571 | O    | HIS | 165 | 26.362 | −12.687 | −8.378  | 1.00 | 31.62 |
| ATOM | 1572 | N    | SER | 166 | 25.946 | −14.547 | −7.232  | 1.00 | 25.87 |
| ATOM | 1573 | H    | SER | 166 | 25.362 | −15.319 | −7.058  | 1.00 | 0.00  |
| ATOM | 1574 | CA   | SER | 166 | 27.160 | −14.490 | −6.428  | 1.00 | 30.85 |
| ATOM | 1575 | CB   | SER | 166 | 27.023 | −15.535 | −5.320  | 1.00 | 33.11 |
| ATOM | 1576 | OG   | SER | 166 | 26.099 | −16.587 | −5.652  | 1.00 | 40.48 |
| ATOM | 1577 | HG   | SER | 166 | 25.779 | −16.955 | −4.812  | 1.00 | 0.00  |
| ATOM | 1578 | C    | SER | 166 | 28.485 | −14.691 | −7.166  | 1.00 | 32.77 |
| ATOM | 1579 | O    | SER | 166 | 29.556 | −14.546 | −5.487  | 1.00 | 34.67 |
| ATOM | 1580 | N    | SER | 167 | 28.439 | −15.017 | −8.444  | 1.00 | 32.96 |
| ATOM | 1581 | H    | SER | 167 | 27.581 | −15.108 | −8.895  | 1.00 | 0.00  |
| ATOM | 1582 | CA   | SER | 167 | 29.597 | −15.394 | −9.219  | 1.00 | 32.24 |
| ATOM | 1583 | CB   | SER | 167 | 29.281 | −16.777 | −9.733  | 1.00 | 35.47 |
| ATOM | 1584 | OG   | SER | 167 | 27.912 | −16.819 | −10.196 | 1.00 | 38.74 |
| ATOM | 1585 | HG   | SER | 167 | 27.744 | −17.703 | −10.543 | 1.00 | 0.00  |
| ATOM | 1586 | C    | SER | 167 | 20.007 | −14.475 | −10.363 | 1.00 | 31.65 |
| ATOM | 1587 | O    | SER | 167 | 31.116 | −14.603 | −10.885 | 1.00 | 35.00 |
| ATOM | 1588 | N    | LEU | 168 | 29.170 | −13.535 | −10.796 | 1.00 | 29.62 |
| ATOM | 1589 | H    | LEU | 168 | 28.501 | −13.148 | −10.198 | 1.00 | 0.00  |
| ATOM | 1590 | CA   | LEU | 168 | 29.473 | −12.889 | −12.053 | 1.00 | 29.98 |
| ATOM | 1591 | CB   | LEU | 168 | 28.202 | −12.382 | −12.708 | 1.00 | 27.12 |
| ATOM | 1592 | CG   | LEU | 168 | 27.207 | −13.436 | −13.139 | 1.00 | 23.43 |
| ATOM | 1593 | CD1  | LEU | 168 | 26.136 | −13.746 | −13.947 | 1.00 | 12.17 |
| ATOM | 1594 | CD2  | LEU | 168 | 27.873 | −14.525 | −13.992 | 1.00 | 22.78 |
| ATOM | 1595 | C    | LEU | 168 | 30.445 | −11.753 | −11.974 | 1.00 | 32.36 |
| ATOM | 1596 | O    | LEU | 168 | 30.379 | −10.917 | −11.074 | 1.00 | 36.48 |
| ATOM | 1597 | N    | THR | 160 | 31.400 | −11.777 | −12.898 | 1.00 | 31.71 |
| ATOM | 1598 | H    | THR | 169 | 31.509 | −12.555 | −13.479 | 1.00 | 0.00  |
| ATOM | 1599 | CA   | THR | 169 | 32.287 | −10.639 | −13.076 | 1.00 | 30.85 |
| ATOM | 1600 | CB   | THR | 169 | 33.596 | −11.055 | −13.767 | 1.00 | 32.01 |
| ATOM | 1601 | OG1  | THR | 169 | 33.258 | −11.649 | −15.020 | 1.00 | 34.34 |
| ATOM | 1602 | HG1  | THR | 169 | 34.045 | −12.124 | −15.328 | 1.00 | 0.00  |
| ATOM | 1603 | CG2  | THR | 169 | 34.415 | −12.014 | −12.917 | 1.00 | 33.00 |
| ATOM | 1604 | C    | THR | 169 | 31.478 | −9.695  | −13.973 | 1.00 | 29.05 |
| ATOM | 1605 | O    | THR | 169 | 30.372 | −10.044 | −14.417 | 1.00 | 26.29 |
| ATOM | 1606 | N    | ARG | 170 | 32.041 | −8.525  | −14.294 | 1.00 | 30.94 |
| ATOM | 1607 | H    | ARG | 170 | 32.861 | −8.261  | −13.824 | 1.00 | 0.00  |
| ATOM | 1608 | CA   | ARG | 170 | 31.421 | −7.557  | −15.199 | 1.00 | 27.92 |
| ATOM | 1609 | CB   | ARG | 170 | 32.320 | −6.316  | −15.323 | 1.00 | 25.77 |
| ATOM | 1610 | CG   | ARG | 170 | 31.766 | −5.288  | −16.289 | 1.00 | 22.36 |
| ATOM | 1611 | CD   | ARG | 170 | 32.742 | −4.160  | −16.541 | 1.00 | 21.88 |
| ATOM | 1612 | NE   | ARG | 170 | 32.560 | −3.097  | −15.587 | 1.00 | 23.01 |
| ATOM | 1613 | HE   | ARG | 170 | 32.924 | −3.206  | −14.684 | 1.00 | 0.00  |
| ATOM | 1614 | CZ   | ARG | 170 | 31.958 | −1.951  | −15.896 | 1.00 | 26.69 |
| ATOM | 1616 | NH1  | ARG | 170 | 31.809 | −1.036  | −14.946 | 1.00 | 32.94 |
| ATOM | 1616 | HH11 | ARG | 170 | 32.161 | −1.213  | −14.027 | 1.00 | 0..00 |
| ATOM | 1617 | HH12 | ARG | 170 | 31.349 | −0.170  | −15.144 | 1.00 | 0..00 |
| ATOM | 1618 | NH2  | ARG | 170 | 31.505 | −1.660  | −17.112 | 1.00 | 25.12 |
| ATOM | 1619 | HH21 | ARG | 170 | 31.615 | −2.316  | −17.858 | 1.00 | 0.00  |
| ATOM | 1620 | HH22 | ARG | 170 | 31.055 | −0.782  | −17.278 | 1.00 | 0.00  |
| ATOM | 1621 | C    | ARG | 170 | 31.201 | −8.165  | −16.577 | 1.00 | 25.49 |
| ATOM | 1622 | O    | ARG | 170 | 30.132 | −8.046  | −17.178 | 1.00 | 28.82 |
| ATOM | 1623 | N    | GLU | 171 | 32.220 | −8.866  | −17.047 | 1.00 | 25.45 |
| ATOM | 1624 | H    | GLU | 171 | 32.978 | −8.985  | −16.448 | 1.00 | 0.00  |
| ATOM | 1625 | CA   | GLU | 171 | 32.195 | −9.477  | −18.364 | 1.00 | 28.63 |
| ATOM | 1626 | CB   | GLU | 171 | 33.580 | −10.054 | −18.735 | 1.00 | 34.71 |
| ATOM | 1627 | CG   | GLU | 171 | 34.771 | −10.040 | −17.736 | 1.00 | 46.27 |
| ATOM | 1628 | CD   | GLU | 171 | 25.272 | −8.696  | −17.177 | 1.00 | 49.62 |
| ATOM | 1629 | OE1  | GLU | 171 | 35.099 | −7.641  | −17.803 | 1.00 | 49.52 |
| ATOM | 1630 | OE2  | GLU | 171 | 35.845 | −8.717  | −16.084 | 1.00 | 52.83 |
| ATOM | 1631 | C    | GLU | 171 | 31.154 | −10.579 | −18.416 | 1.00 | 24.95 |
| ATOM | 1632 | O    | GLU | 171 | 30.279 | −10.593 | −19.294 | 1.00 | 23.81 |

TABLE 23-continued

Coordinates for the 3D structure of ZAP-NC:ζ1 "dimer" structure
(two molecules of complex per unit cell)*

| ATOM | 1633 | N | GLU | 171 | 31.181 | −11.445 | −17.405 | 1.00 | 22.24 |
|---|---|---|---|---|---|---|---|---|---|
| ATOM | 1634 | H | GLU | 172 | 31.828 | −11.331 | −16.679 | 1.00 | 0.00 |
| ATOM | 1635 | CA | GLU | 172 | 30.210 | −12.516 | −17.343 | 1.00 | 24.18 |
| ATOM | 1636 | CB | GLU | 172 | 30.508 | −13.429 | −16.192 | 1.00 | 27.98 |
| ATOM | 1637 | CG | GLU | 172 | 31.858 | −14.079 | −16.392 | 1.00 | 32.11 |
| ATOM | 1638 | CD | GLU | 172 | 32.251 | −15.088 | −15.337 | 1.00 | 37.30 |
| ATOM | 1639 | OE1 | GLU | 172 | 32.039 | −14.841 | −14.149 | 1.00 | 41.49 |
| ATOM | 1640 | OE2 | GLU | 172 | 32.785 | −16.129 | −15.716 | 1.00 | 45.22 |
| ATOM | 1641 | C | GLU | 172 | 28.797 | −12.006 | −17.199 | 1.00 | 26.45 |
| ATOM | 1642 | O | GLU | 172 | 27.888 | −12.558 | −17.827 | 1.00 | 32.90 |
| ATOM | 1643 | N | ALA | 173 | 28.592 | −10.941 | −16.416 | 1.00 | 25.95 |
| ATOM | 1644 | H | ALA | 173 | 29.348 | −10.540 | −15.948 | 1.00 | 0.00 |
| ATOM | 1645 | CA | ALA | 173 | 27.280 | −10.335 | −16.264 | 1.00 | 23.01 |
| ATOM | 1646 | CB | ALA | 173 | 27.311 | −9.190 | −15.242 | 1.00 | 20.11 |
| ATOM | 1647 | C | ALA | 173 | 26.819 | −9.766 | −17.598 | 1.00 | 23.39 |
| ATOM | 1648 | O | ALA | 173 | 25.661 | −9.963 | −17.977 | 1.00 | 25.28 |
| ATOM | 1649 | N | GLU | 174 | 27.695 | −9.077 | −18.346 | 1.00 | 24.22 |
| ATOM | 1650 | H | GLU | 174 | 28.605 | −8.964 | −18.004 | 1.00 | 0.00 |
| ATOM | 1651 | CA | GLU | 174 | 27.350 | −8.542 | −19.663 | 1.00 | 25.70 |
| ATOM | 1652 | CB | GLU | 174 | 28.531 | −7.822 | −20.244 | 1.00 | 21.46 |
| ATOM | 1653 | CG | GLU | 174 | 28.706 | −6.545 | −19.477 | 1.00 | 24.32 |
| ATOM | 1654 | CD | GLU | 174 | 29.944 | −5.776 | −19.873 | 1.00 | 31.18 |
| ATOM | 1655 | OE1 | GLU | 174 | 31.017 | −6.383 | −20.010 | 1.00 | 37.96 |
| ATOM | 1656 | OE2 | GLU | 174 | 29.824 | −4.560 | −20.021 | 1.00 | 30.27 |
| ATOM | 1657 | C | GLU | 174 | 26.919 | −9.632 | −20.632 | 1.00 | 26.95 |
| ATOM | 1658 | O | GLU | 174 | 25.868 | −9.544 | −21.276 | 1.00 | 27.65 |
| ATOM | 1659 | N | ARG | 175 | 27.699 | −10.711 | −20.690 | 1.00 | 30.32 |
| ATOM | 1660 | H | ARG | 175 | 28.513 | −10.712 | −20.144 | 1.00 | 0.00 |
| ATOM | 1661 | CA | ARG | 175 | 27.374 | −11.870 | −21.517 | 1.00 | 32.32 |
| ATOM | 1662 | CB | ARG | 175 | 28.389 | −12.991 | −21.253 | 1.00 | 37.30 |
| ATOM | 1663 | CG | ARG | 175 | 29.859 | −12.688 | −21.529 | 1.00 | 45.49 |
| ATOM | 1664 | CD | ARG | 175 | 30.745 | −13.832 | −21.022 | 1.00 | 51.37 |
| ATOM | 1665 | NE | ARG | 175 | 32.019 | −13.336 | −20.499 | 1.00 | 55.15 |
| ATOM | 1666 | HE | ARG | 175 | 32.252 | −12.393 | −20.637 | 1.00 | 0.00 |
| ATOM | 1667 | CZ | ARG | 175 | 32.890 | −14.117 | −19.832 | 1.00 | 59.00 |
| ATOM | 1668 | NH1 | ARG | 175 | 32.656 | −15.414 | −19.599 | 1.00 | 58.66 |
| ATOM | 1669 | HH11 | ARG | 175 | 31.812 | −15.837 | −19.926 | 1.00 | 0.00 |
| ATOM | 1670 | HH12 | ARG | 175 | 33.332 | −15.959 | −19.102 | 1.00 | 0.00 |
| ATOM | 1671 | NH2 | ARG | 175 | 34.024 | −13.588 | −19.361 | 1.00 | 61.91 |
| ATOM | 1672 | HH21 | ARG | 175 | 34.213 | −12.616 | −19.502 | 1.00 | 0.00 |
| ATOM | 1673 | HH22 | ARG | 175 | 34.681 | −14.160 | −18.872 | 1.00 | 0.00 |
| ATOM | 1674 | C | ARG | 175 | 25.963 | −12.388 | −21.213 | 1.00 | 30.27 |
| ATOM | 1675 | O | ARG | 175 | 25.110 | −12.551 | −22.088 | 1.00 | 32.04 |
| ATOM | 1676 | N | LYS | 176 | 25.702 | −12.560 | −19.921 | 1.00 | 32.42 |
| ATOM | 1677 | H | LYS | 176 | 26.414 | −12.342 | −19.277 | 1.00 | 0.00 |
| ATOM | 1678 | CA | LYS | 176 | 24.452 | −13.071 | −19.401 | 1.00 | 32.03 |
| ATOM | 1679 | CB | LYS | 176 | 24.531 | −13.145 | −17.892 | 1.00 | 35.56 |
| ATOM | 1680 | CG | LYS | 176 | 23.547 | −14.115 | −17.250 | 1.00 | 44.13 |
| ATOM | 1681 | CD | LYS | 176 | 24.055 | −15.547 | −17.412 | 1.00 | 48.57 |
| ATOM | 1682 | CE | LYS | 176 | 25.324 | −15.720 | −16.575 | 1.00 | 52.52 |
| ATOM | 1683 | NZ | LYS | 176 | 25.941 | −17.022 | −16.754 | 1.00 | 52.83 |
| ATOM | 1684 | HZ1 | LYS | 176 | 26.298 | −17.096 | −17.728 | 1.00 | 0.00 |
| ATOM | 1685 | HZ2 | LYS | 176 | 25.235 | −17.766 | −16.585 | 1.00 | 0.00 |
| ATOM | 1686 | HZ3 | LYS | 176 | 26.728 | −17.135 | −16.083 | 1.00 | 0.00 |
| ATOM | 1687 | C | LYS | 176 | 23.285 | −12.195 | −19.791 | 1.00 | 31.06 |
| ATOM | 1688 | O | LYS | 176 | 22.269 | −12.672 | −20.284 | 1.00 | 31.58 |
| ATOM | 1689 | N | LEU | 177 | 23.436 | −10.892 | −19.595 | 1.00 | 34.11 |
| ATOM | 1690 | H | LEU | 177 | 24.296 | −10.569 | −19.251 | 1.00 | 0.00 |
| ATOM | 1691 | CA | LEU | 177 | 22.383 | −9.922 | −19.855 | 1.00 | 32.25 |
| ATOM | 1692 | CB | LEU | 177 | 22.814 | −8.567 | −19.282 | 1.00 | 30.73 |
| ATOM | 1693 | CG | LEU | 177 | 22.271 | −7.948 | −17.963 | 1.00 | 31.54 |
| ATOM | 1694 | CD1 | LEU | 177 | 21.559 | −8.933 | −17.048 | 1.00 | 26.77 |
| ATOM | 1695 | CD2 | LEU | 177 | 23.468 | −7.352 | −17.267 | 1.00 | 24.48 |
| ATOM | 1696 | C | LEU | 177 | 22.080 | −9.800 | −21.333 | 1.00 | 32.45 |
| ATOM | 1697 | O | LEU | 177 | 20.930 | −9.592 | −21.719 | 1.00 | 34.39 |
| ATOM | 1698 | N | TYR | 178 | 23.085 | −9.914 | −22.199 | 1.00 | 34.48 |
| ATOM | 1699 | H | TYR | 178 | 23.995 | −10.079 | −21.869 | 1.00 | 0.00 |
| ATOM | 1700 | CA | TYR | 178 | 22.838 | −9.805 | −23.628 | 1.00 | 36.68 |
| ATOM | 1701 | CB | TYR | 178 | 24.156 | −9.530 | −24.341 | 1.00 | 35.30 |
| ATOM | 1702 | CG | TYR | 178 | 24.568 | −8.071 | −24.223 | 1.00 | 31.08 |
| ATOM | 1703 | CD1 | TYR | 178 | 23.631 | −7.081 | −24.509 | 1.00 | 30.05 |
| ATOM | 1704 | CE1 | TYR | 178 | 23.995 | −5.745 | −24.396 | 1.00 | 30.73 |
| ATOM | 1705 | CD2 | TYR | 178 | 25.867 | −7.715 | −23.825 | 1.00 | 29.53 |
| ATOM | 1706 | CE2 | TYR | 178 | 26.232 | −6.366 | −23.709 | 1.00 | 26.18 |
| ATOM | 1707 | CZ | TYR | 178 | 25.282 | −5.387 | −23.999 | 1.00 | 25.96 |
| ATOM | 1708 | OH | TYR | 178 | 25.580 | −4.043 | −23.874 | 1.00 | 25.36 |

TABLE 23-continued

Coordinates for the 3D structure of ZAP-NC:ζ1 "dimer" structure
(two molecules of complex per unit cell)*

| ATOM | 1709 | HH | TYR | 178 | 25.002 | −3.585 | −24.505 | 1.00 | 0.00 |
|------|------|----|-----|-----|--------|--------|---------|------|------|
| ATOM | 1710 | C | TYR | 178 | 22.172 | −11.038 | −24.219 | 1.00 | 38.35 |
| ATOM | 1711 | O | TYR | 178 | 21.576 | −11.020 | −25.307 | 1.00 | 37.60 |
| ATOM | 1712 | N | SER | 179 | 22.300 | −12.135 | −23.481 | 1.00 | 40.20 |
| ATOM | 1713 | H | SER | 179 | 22.747 | −12.098 | −22.611 | 1.00 | 0.00 |
| ATOM | 1714 | CA | SER | 179 | 21.693 | −13.366 | −23.885 | 1.00 | 40.95 |
| ATOM | 1715 | CB | SER | 179 | 22.147 | −14.488 | −22.964 | 1.00 | 38.18 |
| ATOM | 1716 | OG | SER | 179 | 23.552 | −14.693 | −23.097 | 1.00 | 42.54 |
| ATOM | 1717 | HG | SER | 179 | 24.014 | −13.865 | −22.917 | 1.00 | 0.00 |
| ATOM | 1718 | C | SER | 179 | 20.181 | −13.236 | −23.859 | 1.00 | 44.69 |
| ATOM | 1719 | O | SER | 179 | 19.507 | −12.850 | −22.897 | 1.00 | 43.01 |
| ATOM | 1720 | N | GLY | 180 | 19.685 | −13.487 | −25.059 | 1.00 | 49.23 |
| ATOM | 1721 | H | GLY | 180 | 20.289 | −13.525 | −25.832 | 1.00 | 0.00 |
| ATOM | 1722 | CA | GLY | 180 | 18.273 | −13.576 | −25.269 | 1.00 | 50.39 |
| ATOM | 1723 | C | GLY | 180 | 17.657 | −12.238 | −25.579 | 1.00 | 53.13 |
| ATOM | 1724 | O | GLY | 180 | 18.179 | −11.405 | −26.325 | 1.00 | 52.03 |
| ATOM | 1725 | N | ALA | 181 | 16.551 | −12.099 | −24.852 | 1.00 | 55.03 |
| ATOM | 1726 | H | ALA | 181 | 16.426 | −12.708 | −24.086 | 1.00 | 0.00 |
| ATOM | 1727 | CA | ALA | 181 | 15.575 | −11.041 | −25.034 | 1.00 | 54.94 |
| ATOM | 1728 | CB | ALA | 181 | 14.436 | −11.279 | −24.044 | 1.00 | 45.02 |
| ATOM | 1729 | C | ALA | 181 | 16.003 | −9.584 | −24.928 | 1.00 | 54.22 |
| ATOM | 1730 | O | ALA | 181 | 15.448 | −8.741 | −25.638 | 1.00 | 56.20 |
| ATOM | 1731 | N | GLN | 182 | 16.947 | −9.267 | −24.032 | 1.00 | 49.18 |
| ATOM | 1732 | H | GLN | 182 | 17.366 | −9.999 | −23.535 | 1.00 | 0.00 |
| ATOM | 1733 | CA | GLN | 182 | 17.430 | −7.908 | −23.794 | 1.00 | 44.29 |
| ATOM | 1734 | CB | GLN | 182 | 18.314 | −7.462 | −24.967 | 1.00 | 41.96 |
| ATOM | 1735 | CG | GLN | 182 | 19.551 | −8.314 | −25.058 | 1.00 | 41.18 |
| ATOM | 1736 | CD | GLN | 182 | 20.483 | −7.844 | −26.148 | 1.00 | 44.47 |
| ATOM | 1737 | OE1 | GLN | 182 | 20.784 | −6.664 | −26.295 | 1.00 | 48.23 |
| ATOM | 1738 | NE2 | GLN | 182 | 21.012 | −8.740 | −26.949 | 1.00 | 50.67 |
| ATOM | 1739 | HE21 | GLN | 182 | 20.793 | −9.686 | −26.786 | 1.00 | 0.00 |
| ATOM | 1740 | HE22 | GLN | 182 | 21.587 | −8.410 | −27.662 | 1.00 | 0.00 |
| ATOM | 1741 | C | GLN | 182 | 16.324 | −6.875 | −23.552 | 1.00 | 40.00 |
| ATOM | 1742 | O | GLN | 182 | 16.323 | −5.731 | −24.026 | 1.00 | 41.01 |
| ATOM | 1743 | N | THR | 183 | 15.365 | −7.391 | −22.735 | 1.00 | 35.70 |
| ATOM | 1744 | H | THR | 183 | 15.390 | −8.208 | −22.393 | 1.00 | 0.00 |
| ATOM | 1745 | CA | THR | 183 | 14.255 | −6.456 | −22.308 | 1.00 | 33.60 |
| ATOM | 1746 | CB | THR | 183 | 13.298 | −7.378 | −21.503 | 1.00 | 36.83 |
| ATOM | 1747 | OG1 | THR | 183 | 13.223 | −8.626 | −22.202 | 1.00 | 40.13 |
| ATOM | 1748 | HG1 | THR | 183 | 12.742 | −8.509 | −23.029 | 1.00 | 0.00 |
| ATOM | 1749 | CG2 | THR | 183 | 11.906 | −6.789 | −21.348 | 1.00 | 38.03 |
| ATOM | 1750 | C | THR | 183 | 14.790 | −5.271 | −21.471 | 1.00 | 32.43 |
| ATOM | 1751 | O | THR | 183 | 15.797 | −5.393 | −20.764 | 1.00 | 30.96 |
| ATOM | 1752 | N | ASP | 184 | 14.166 | −4.091 | −21.553 | 1.00 | 30.47 |
| ATOM | 1753 | H | ASP | 184 | 13.379 | −4.025 | −22.126 | 1.00 | 0.00 |
| ATOM | 1754 | CA | ASP | 184 | 14.538 | −2.916 | −20.779 | 1.00 | 28.11 |
| ATOM | 1755 | CB | ASP | 184 | 13.670 | −1.722 | −21.181 | 1.00 | 28.38 |
| ATOM | 1756 | CG | ASP | 184 | 14.010 | −0.944 | −22.457 | 1.00 | 32.20 |
| ATOM | 1757 | OD1 | ASP | 184 | 13.124 | −0.235 | −22.959 | 1.00 | 29.32 |
| ATOM | 1758 | OD2 | ASP | 184 | 15.144 | −1.024 | −22.938 | 1.00 | 30.40 |
| ATOM | 1759 | C | ASP | 184 | 14.336 | −3.192 | −19.285 | 1.00 | 26.83 |
| ATOM | 1760 | O | ASP | 184 | 13.322 | −3.777 | −18.894 | 1.00 | 24.72 |
| ATOM | 1761 | N | GLY | 185 | 15.294 | −2.826 | −18.441 | 1.00 | 25.09 |
| ATOM | 1762 | H | GLY | 185 | 16.080 | −2.372 | −18.798 | 1.00 | 0.00 |
| ATOM | 1763 | CA | GLY | 185 | 15.206 | −3.060 | −17.010 | 1.00 | 25.19 |
| ATOM | 1764 | C | GLY | 185 | 15.37 | −4.484 | −16.606 | 1.00 | 20.65 |
| ATOM | 1765 | O | GLY | 185 | 15.341 | −4.837 | −15.450 | 1.00 | 20.02 |
| ATOM | 1766 | N | LYS | 186 | 16.057 | −5.333 | −17.498 | 1.00 | 21.61 |
| ATOM | 1767 | H | LYS | 186 | 16.285 | −4.995 | −18.386 | 1.00 | 0.00 |
| ATOM | 1768 | CA | LYS | 186 | 16.388 | −6.706 | −17.155 | 1.00 | 21.03 |
| ATOM | 1769 | CB | LYS | 186 | 16.592 | −7.514 | −18.405 | 1.00 | 22.80 |
| ATOM | 1770 | CG | LYS | 186 | 17.021 | −8.954 | −18.261 | 1.00 | 23.15 |
| ATOM | 1771 | CD | LYS | 186 | 17.304 | −9.312 | −19.716 | 1.00 | 24.01 |
| ATOM | 1772 | CE | LYS | 186 | 18.073 | −10.597 | −19.860 | 1.00 | 25.57 |
| ATOM | 1773 | NZ | LYS | 186 | 18.360 | −10.834 | −21.258 | 1.00 | 26.92 |
| ATOM | 1774 | HZ1 | LYS | 186 | 18.897 | −10.028 | −21.638 | 1.00 | 0.00 |
| ATOM | 1775 | HZ2 | LYS | 186 | 17.473 | −10.945 | −21.789 | 1.00 | 0.00 |
| ATOM | 1776 | HZ3 | LYS | 186 | 18.932 | −11.698 | −21.346 | 1.00 | 0.00 |
| ATOM | 1777 | C | LYS | 186 | 17.678 | −6.569 | −16.401 | 1.00 | 20.18 |
| ATOM | 1778 | O | LYS | 186 | 18.632 | −5.993 | −16.932 | 1.00 | 22.74 |
| ATOM | 1779 | N | LYS | 186 | 17.736 | −7.127 | −15.209 | 1.00 | 18.17 |
| ATOM | 1780 | H | PHE | 187 | 17.018 | −7.724 | −14.905 | 1.00 | 0.00 |
| ATOM | 1781 | CA | PHE | 187 | 18.835 | −6.825 | −14.323 | 1.00 | 15.32 |
| ATOM | 1782 | CB | PHE | 187 | 18.343 | −5.741 | −13.341 | 1.00 | 13.75 |
| ATOM | 1783 | CG | PHE | 187 | 17.375 | −6.215 | −12.254 | 1.00 | 10.60 |
| ATOM | 1784 | CD1 | PHE | 187 | 17.851 | −6.516 | −10.963 | 1.00 | 4.59 |

TABLE 23-continued

Coordinates for the 3D structure of ZAP-NC:ζ1 "dimer" structure
(two molecules of complex per unit cell)*

| ATOM | 1785 | CD2 | PHE | 187 | 16.027 | −6.375 | −12.550 | 1.00 | 6.32 |
|---|---|---|---|---|---|---|---|---|---|
| ATOM | 1786 | CE1 | PHE | 187 | 16.975 | −6.978 | −10.000 | 1.00 | 3.69 |
| ATOM | 1787 | CE2 | PHE | 187 | 15.161 | −6.840 | −11.564 | 1.00 | 8.44 |
| ATOM | 1788 | CZ | PHE | 187 | 15.630 | −7.146 | −10.294 | 1.00 | 5.46 |
| ATOM | 1789 | C | LEU | 188 | 19.404 | −7.979 | −13.538 | 1.00 | 12.65 |
| ATOM | 1790 | O | LEU | 188 | 18.770 | −9.031 | −13.434 | 1.00 | 19.75 |
| ATOM | 1791 | N | LEU | 188 | 20.550 | −8.850 | −12.906 | 1.00 | 11.33 |
| ATOM | 1792 | H | LEU | 188 | 21.054 | −6.926 | −13.096 | 1.00 | 0.00 |
| ATOM | 1793 | CA | LEU | 188 | 21.065 | −8.647 | −11.899 | 1.00 | 11.79 |
| ATOM | 1794 | CB | LEU | 188 | 21.938 | −9.744 | −12.521 | 1.00 | 15.47 |
| ATOM | 1795 | CG | LEU | 188 | 23.210 | −9.476 | −13.324 | 1.00 | 15.83 |
| ATOM | 1796 | CD1 | LEU | 188 | 24.466 | −9.304 | −12.465 | 1.00 | 8.89 |
| ATOM | 1797 | CD2 | LEU | 188 | 23.364 | −10.695 | −14.223 | 1.00 | 13.24 |
| ATOM | 1798 | C | LEU | 188 | 21.892 | −7.838 | −10.908 | 1.00 | 13.76 |
| ATOM | 1799 | O | LEU | 188 | 22.306 | −6.706 | −11.206 | 1.00 | 9.67 |
| ATOM | 1800 | N | LEU | 189 | 22.156 | −8.386 | −9.726 | 1.00 | 11.91 |
| ATOM | 1801 | H | LEU | 189 | 21.844 | −9.285 | −9.525 | 1.00 | 0.00 |
| ATOM | 1802 | CA | LEU | 189 | 23.002 | −7.720 | −8.770 | 1.00 | 11.04 |
| ATOM | 1803 | CB | LEU | 189 | 22.139 | −7.371 | −7.533 | 1.00 | 10.60 |
| ATOM | 1804 | CG | LEU | 189 | 22.718 | −6.409 | −6.467 | 1.00 | 10.76 |
| ATOM | 1805 | CD1 | LEU | 189 | 21.591 | −5.775 | −5.699 | 1.00 | 16.31 |
| ATOM | 1806 | CD2 | LEU | 189 | 23.580 | −7.144 | −5.462 | 1.00 | 11.36 |
| ATOM | 1807 | C | LEU | 189 | 24.090 | −8.751 | −8.511 | 1.00 | 10.52 |
| ATOM | 1808 | O | LEU | 189 | 23.821 | −9.956 | −8.487 | 1.00 | 15.16 |
| ATOM | 1809 | N | ARG | 190 | 25.335 | −8.355 | −8.354 | 1.00 | 9.93 |
| ATOM | 1810 | H | ARG | 190 | 25.548 | −7.398 | −8.329 | 1.00 | 0.00 |
| ATOM | 1811 | CA | ARG | 190 | 26.417 | −9.296 | −8.148 | 1.00 | 15.26 |
| ATOM | 1812 | CB | ARG | 190 | 27.158 | −9.565 | −9.487 | 1.00 | 19.74 |
| ATOM | 1813 | CG | ARG | 190 | 27.523 | −8.309 | −10.276 | 1.00 | 18.73 |
| ATOM | 1814 | CD | ARG | 190 | 28.210 | −8.529 | −11.615 | 1.00 | 19.13 |
| ATOM | 1815 | NE | ARG | 190 | 28.258 | −7.264 | −12.327 | 1.00 | 15.71 |
| ATOM | 1816 | HE | ARG | 190 | 27.488 | −7.013 | −12.880 | 1.00 | 0.00 |
| ATOM | 1817 | CZ | ARG | 190 | 29.300 | −6.427 | −12.264 | 1.00 | 12.44 |
| ATOM | 1818 | NH1 | ARG | 190 | 30.398 | −6.661 | −11.557 | 1.00 | 12.24 |
| ATOM | 1819 | HH11 | ARG | 190 | 30.484 | −8.401 | −11.020 | 1.00 | 0.00 |
| ATOM | 1820 | HH12 | ARG | 190 | 31.138 | −5.988 | −11.551 | 1.00 | 0.00 |
| ATOM | 1821 | NH2 | ARG | 190 | 29.204 | −5.365 | −12.874 | 1.00 | 19.14 |
| ATOM | 1822 | HH21 | ARG | 190 | 28.357 | −5.038 | −13.349 | 1.00 | 0.00 |
| ATOM | 1823 | HH22 | ARG | 190 | 29.953 | −4.608 | −12.846 | 1.00 | 0.00 |
| ATOM | 1824 | C | ARG | 190 | 27.363 | −8.675 | −7.128 | 1.00 | 17.85 |
| ATOM | 1825 | O | ARG | 190 | 27.428 | −7.441 | −7.051 | 1.00 | 17.12 |
| ATOM | 1826 | N | PRO | 191 | 28.063 | −9.426 | −6.269 | 1.00 | 19.25 |
| ATOM | 1827 | CD | PRO | 191 | 27.823 | −10.832 | −5.993 | 1.00 | 15.67 |
| ATOM | 1828 | CA | PRO | 191 | 29.087 | −8.896 | −5.386 | 1.00 | 18.77 |
| ATOM | 1829 | CB | PRO | 191 | 29.348 | −9.996 | −4.377 | 1.00 | 17.25 |
| ATOM | 1830 | CG | PRO | 191 | 29.015 | −11.250 | −5.129 | 1.00 | 13.46 |
| ATOM | 1831 | C | PRO | 191 | 30.314 | −8.517 | −6.174 | 1.00 | 22.81 |
| ATOM | 1832 | O | PRO | 191 | 30.605 | −9.074 | −7.241 | 1.00 | 22.89 |
| ATOM | 1833 | N | ARG | 192 | 31.057 | −7.551 | −5.672 | 1.00 | 25.23 |
| ATOM | 1834 | H | ARG | 192 | 30.882 | −7.165 | −4.790 | 1.00 | 0.00 |
| ATOM | 1835 | CA | ARG | 192 | 32.254 | −7.192 | −6.372 | 1.00 | 27.78 |
| ATOM | 1836 | CB | ARG | 192 | 32.321 | −5.708 | −6.573 | 1.00 | 23.97 |
| ATOM | 1837 | CG | ARG | 192 | 31.329 | −5.258 | −7.639 | 1.00 | 20.97 |
| ATOM | 1838 | CD | ARG | 192 | 31.708 | −3.925 | −8.349 | 1.00 | 21.89 |
| ATOM | 1839 | NE | ARG | 192 | 32.301 | −3.053 | −7.259 | 1.00 | 29.17 |
| ATOM | 1840 | HE | ARG | 192 | 31.803 | −2.865 | −6.436 | 1.00 | 0.00 |
| ATOM | 1841 | CZ | ARG | 192 | 33.503 | −2.487 | −7.403 | 1.00 | 33.01 |
| ATOM | 1842 | NH1 | ARG | 192 | 34.277 | −2.657 | −8.478 | 1.00 | 27.14 |
| ATOM | 1843 | HH11 | ARG | 192 | 33.966 | −3.223 | −9.241 | 1.00 | 0.00 |
| ATOM | 1844 | HH12 | ARG | 192 | 35.166 | −2.200 | −8.525 | 1.00 | 0.00 |
| ATOM | 1845 | NH2 | ARG | 192 | 33.960 | −1.776 | −6.376 | 1.00 | 40.84 |
| ATOM | 1846 | HH21 | ARG | 192 | 33.406 | −1.692 | −5.548 | 1.00 | 0.00 |
| ATOM | 1847 | HH22 | ARG | 192 | 34.853 | −1.330 | −6.427 | 1.00 | 0.00 |
| ATOM | 1848 | C | ARG | 192 | 33.425 | −76.68 | −5.557 | 1.00 | 34.57 |
| ATOM | 1849 | O | ARG | 192 | 33.324 | −78.56 | −4.339 | 1.00 | 37.12 |
| ATOM | 1850 | N | LYS | 193 | 34.526 | −78.81 | −6.289 | 1.00 | 42.26 |
| ATOM | 1851 | H | LYS | 193 | 34.467 | −76.55 | −4.256 | 1.00 | 0.00 |
| ATOM | 1852 | CA | LYS | 193 | 34.795 | −84.03 | −5.795 | 1.00 | 47.15 |
| ATOM | 1853 | CB | LYS | 193 | 35.904 | −80.81 | −6.793 | 1.00 | 52.06 |
| ATOM | 1854 | CG | LYS | 193 | 36.997 | −88.76 | −8.091 | 1.00 | 54.92 |
| ATOM | 1855 | CD | LYS | 193 | 36.281 | −85.41 | −8.878 | 1.00 | 55.99 |
| ATOM | 1856 | CE | LYS | 193 | 38.618 | −89.36 | −8.217 | 1.00 | 58.17 |
| ATOM | 1857 | NZ | LYS | 193 | 39.052 | −80.33 | −7.156 | 1.00 | 59.70 |
| ATOM | 1858 | HZ1 | LYS | 193 | 40.351 | −80.30 | −6.388 | 1.00 | 0.00 |
| ATOM | 1859 | HZ2 | LYS | 193 | 39.147 | −70.69 | −8.637 | 1.00 | 0.00 |
| ATOM | 1860 | HZ3 | LYS | 193 | 40.973 | −83.45 | −6.784 | 1.00 | 0.00 |

TABLE 23-continued

Coordinates for the 3D structure of ZAP-NC:ζ1 "dimer" structure
(two molecules of complex per unit cell)*

| ATOM | 1861 | C | LYS | 193 | 36.264 | −79.23 | −4.427 | 1.00 | 48.59 |
|---|---|---|---|---|---|---|---|---|---|
| ATOM | 1862 | O | LYS | 193 | 36.714 | −87.01 | −3.585 | 1.00 | 48.16 |
| ATOM | 1863 | N | GLU | 194 | 36.139 | −66.21 | −4.202 | 1.00 | 48.68 |
| ATOM | 1864 | H | GLU | 194 | 35.613 | −61.12 | −4.842 | 1.00 | 0.00 |
| ATOM | 1865 | CA | GLU | 194 | 36.536 | −59.82 | −2.962 | 1.00 | 52.35 |
| ATOM | 1866 | CB | GLU | 194 | 36.997 | −45.37 | −3.272 | 1.00 | 55.36 |
| ATOM | 1867 | CG | GLU | 194 | 36.171 | −36.49 | −4.234 | 1.00 | 57.27 |
| ATOM | 1868 | CD | GLU | 194 | 36.365 | −38.91 | −5.731 | 1.00 | 56.04 |
| ATOM | 1869 | OE1 | GLU | 194 | 37.277 | −32.98 | −6.310 | 1.00 | 56.94 |
| ATOM | 1870 | OE2 | GLU | 194 | 35.595 | −46.52 | −6.319 | 1.00 | 54.29 |
| ATOM | 1871 | C | GLU | 194 | 35.267 | −60.45 | −2.121 | 1.00 | 52.06 |
| ATOM | 1872 | O | GLU | 194 | 34.474 | −51.09 | −2.048 | 1.00 | 51.19 |
| ATOM | 1873 | N | GLN | 195 | 35.081 | −72.32 | −1.545 | 1.00 | 54.38 |
| ATOM | 1874 | H | GLN | 195 | 35.805 | −78.85 | −1.636 | 1.00 | 0.00 |
| ATOM | 1875 | CA | GLN | 195 | 33.858 | −76.19 | −0.850 | 1.00 | 55.92 |
| ATOM | 1876 | CB | GLN | 195 | 34.139 | −88.95 | −0.051 | 1.00 | 59.23 |
| ATOM | 1877 | CG | GLN | 195 | 34.284 | −10.113 | −0.980 | 1.00 | 61.52 |
| ATOM | 1878 | CD | GLN | 195 | 33.058 | −10.451 | −1.830 | 1.00 | 64.33 |
| ATOM | 1879 | OE1 | GLN | 195 | 31.897 | −10.254 | −1.457 | 1.00 | 66.50 |
| ATOM | 1880 | NE2 | GLN | 195 | 33.269 | −11.005 | −3.011 | 1.00 | 64.00 |
| ATOM | 1881 | HE21 | GLN | 195 | 34.194 | −11.170 | −3.287 | 1.00 | 0.00 |
| ATOM | 1882 | HE22 | GLN | 195 | 32.482 | −11.228 | −3.547 | 1.00 | 0.00 |
| ATOM | 1883 | C | GLN | 195 | 33.171 | −6.599 | 0.039 | 1.00 | 52.83 |
| ATOM | 1884 | O | GLN | 195 | 33.784 | −5.715 | 0.646 | 1.00 | 54.52 |
| ATOM | 1885 | N | GLY | 196 | 31.851 | −6.727 | 0.086 | 1.00 | 48.51 |
| ATOM | 1886 | H | GLY | 196 | 31.410 | −7.490 | −0.347 | 1.00 | 0.00 |
| ATOM | 1887 | CA | GLY | 196 | 31.058 | −5.704 | 0.734 | 1.00 | 43.01 |
| ATOM | 1888 | C | GLY | 196 | 30.677 | −4.644 | −0.298 | 1.00 | 28.41 |
| ATOM | 1889 | O | GLY | 196 | 29.901 | −3.751 | 0.029 | 1.00 | 39.57 |
| ATOM | 1890 | N | THR | 197 | 31.232 | −4.650 | −1.524 | 1.00 | 34.03 |
| ATOM | 1891 | H | THR | 197 | 31.954 | −5.266 | −1.758 | 1.00 | 0.00 |
| ATOM | 1892 | CA | THR | 197 | 30.740 | −3.783 | −2.574 | 1.00 | 26.80 |
| ATOM | 1893 | CB | THR | 197 | 31.858 | −3.075 | −3.375 | 1.00 | 27.15 |
| ATOM | 1894 | OG1 | THR | 197 | 32.759 | −4.048 | −3.873 | 1.00 | 29.46 |
| ATOM | 1895 | HG1 | THR | 197 | 33.343 | −4.227 | −3.145 | 1.00 | 0.00 |
| ATOM | 1896 | CG2 | THR | 197 | 32.554 | −2.032 | −2.514 | 1.00 | 27.29 |
| ATOM | 1897 | C | THR | 197 | 29.972 | −4.717 | −3.498 | 1.00 | 24.98 |
| ATOM | 1898 | O | THR | 197 | 30.181 | −5.945 | −3.493 | 1.00 | 23.20 |
| ATOM | 1899 | N | THR | 198 | 29.030 | −4.130 | −4.243 | 1.00 | 21.47 |
| ATOM | 1900 | H | THR | 198 | 28.957 | −3.149 | −4.246 | 1.00 | 0.00 |
| ATOM | 1901 | CA | THR | 198 | 28.129 | −4.849 | −5.118 | 1.00 | 18.56 |
| ATOM | 1902 | CB | THR | 198 | 26.753 | −5.073 | −4.426 | 1.00 | 12.78 |
| ATOM | 1903 | CG | THR | 198 | 26.823 | −5.927 | −3.146 | 1.00 | 22.01 |
| ATOM | 1904 | CD1 | THR | 198 | 27.142 | −5.362 | −1.895 | 1.00 | 20.02 |
| ATOM | 1905 | CE1 | THR | 198 | 27.264 | −6.166 | −0.747 | 1.00 | 22.60 |
| ATOM | 1906 | CD2 | THR | 198 | 26.618 | −7.306 | −3.214 | 1.00 | 19.95 |
| ATOM | 1907 | CE2 | THR | 198 | 26.741 | −8.114 | −3.071 | 1.00 | 25.51 |
| ATOM | 1908 | CZ | THR | 198 | 27.065 | −7.544 | −0.837 | 1.00 | 23.70 |
| ATOM | 1909 | OH | THR | 198 | 27.201 | −8.359 | 0.286 | 1.00 | 31.49 |
| ATOM | 1910 | HH | THR | 198 | 27.735 | −9.132 | 0.008 | 1.00 | 0.00 |
| ATOM | 1911 | C | THR | 198 | 27.965 | −3.975 | −6.365 | 1.00 | 21.17 |
| ATOM | 1912 | O | THR | 198 | 28.322 | −2.782 | −6.377 | 1.00 | 18.78 |
| ATOM | 1913 | N | ALA | 199 | 27.514 | −4.574 | −7.465 | 1.00 | 17.77 |
| ATOM | 1914 | H | ALA | 199 | 27.340 | −5.539 | −7.472 | 1.00 | 0.00 |
| ATOM | 1915 | CA | ALA | 199 | 27.203 | −3.802 | −8.639 | 1.00 | 17.47 |
| ATOM | 1916 | CB | ALA | 199 | 28.194 | −4.003 | −9.759 | 1.00 | 16.18 |
| ATOM | 1917 | C | ALA | 199 | 25.877 | −4.356 | −9.092 | 1.00 | 18.13 |
| ATOM | 1918 | O | ALA | 199 | 25.602 | −5.564 | −8.991 | 1.00 | 22.08 |
| ATOM | 1919 | N | LEU | 200 | 25.047 | −3.427 | −9.530 | 1.00 | 14.97 |
| ATOM | 1920 | H | LEU | 200 | 25.351 | −2.496 | −9.531 | 1.00 | 0.00 |
| ATOM | 1921 | CA | LEU | 200 | 23.747 | −3.719 | −10.080 | 1.00 | 17.06 |
| ATOM | 1922 | CB | LEU | 200 | 22.780 | −2.719 | −9.450 | 1.00 | 12.56 |
| ATOM | 1923 | CG | LEU | 200 | 21.249 | −2.769 | −9.466 | 1.00 | 21.69 |
| ATOM | 1924 | CD1 | LEU | 200 | 20.765 | −1.518 | −10.193 | 1.00 | 17.31 |
| ATOM | 1925 | CD2 | LEU | 200 | 20.710 | −4.042 | −10.105 | 1.00 | 16.41 |
| ATOM | 1926 | C | LEU | 200 | 23.964 | −3.527 | −11.591 | 1.00 | 15.53 |
| ATOM | 1927 | O | LEU | 200 | 24.416 | −2.467 | −12.025 | 1.00 | 11.97 |
| ATOM | 1928 | N | SER | 201 | 23.746 | −4.526 | −12.434 | 1.00 | 17.37 |
| ATOM | 1929 | H | SER | 201 | 23.328 | −5.350 | −12.112 | 1.00 | 0.00 |
| ATOM | 1930 | CA | SER | 201 | 23.939 | −4.381 | −13.867 | 1.00 | 18.19 |
| ATOM | 1931 | CB | SER | 201 | 24.899 | −5.455 | −14.323 | 1.00 | 15.29 |
| ATOM | 1932 | OG | SER | 201 | 26.098 | −5.406 | −13.557 | 1.00 | 13.30 |
| ATOM | 1933 | HG | SER | 201 | 25.836 | −5.633 | −12.651 | 1.00 | 0.00 |
| ATOM | 1934 | C | SER | 201 | 22.594 | −4.535 | −14.549 | 1.00 | 16.35 |
| ATOM | 1935 | O | SER | 201 | 21.864 | −6.552 | −14.163 | 1.00 | 17.51 |
| ATOM | 1936 | N | LEU | 202 | 22.194 | −3.704 | −15.513 | 1.00 | 20.48 |

TABLE 23-continued

Coordinates for the 3D structure of ZAP-NC:ζ1 "dimer" structure
(two molecules of complex per unit cell)*

| ATOM | 1937 | H | LEU | 202 | 22.784 | −2.981 | −15.814 | 1.00 | 0.00 |
|---|---|---|---|---|---|---|---|---|---|
| ATOM | 1938 | CA | LEU | 202 | 20.906 | −2.879 | −16.184 | 1.00 | 20.46 |
| ATOM | 1939 | CB | LEU | 202 | 19.826 | −2.932 | −15.635 | 1.00 | 18.55 |
| ATOM | 1940 | CG | LEU | 202 | 19.923 | −1.415 | −15.745 | 1.00 | 20.47 |
| ATOM | 1941 | CD1 | LEU | 202 | 18.554 | −0.802 | −15.515 | 1.00 | 26.80 |
| ATOM | 1942 | CD2 | LEU | 202 | 20.916 | −0.888 | −14.726 | 1.00 | 24.17 |
| ATOM | 1943 | C | LEU | 202 | 20.997 | −3.636 | −17.679 | 1.00 | 24.32 |
| ATOM | 1944 | O | LEU | 202 | 22.026 | −3.156 | −18.168 | 1.00 | 22.66 |
| ATOM | 1945 | N | ILE | 203 | 19.929 | −3.998 | −18.393 | 1.00 | 25.50 |
| ATOM | 1946 | H | ILE | 203 | 19.187 | −4.430 | −17.925 | 1.00 | 0.00 |
| ATOM | 1947 | CA | ILE | 203 | 19.801 | −3.775 | −19.817 | 1.00 | 23.41 |
| ATOM | 1948 | CB | ILE | 203 | 19.185 | −5.025 | −20.488 | 1.00 | 24.34 |
| ATOM | 1949 | CG2 | ILE | 203 | 18.668 | −4.683 | −21.880 | 1.00 | 29.27 |
| ATOM | 1950 | CG1 | ILE | 203 | 20.225 | −6.114 | −20.595 | 1.00 | 20.19 |
| ATOM | 1951 | CD | ILE | 203 | 21.302 | −5.877 | −21.688 | 1.00 | 27.26 |
| ATOM | 1952 | C | ILE | 203 | 18.902 | −2.567 | −20.030 | 1.00 | 24.65 |
| ATOM | 1953 | O | ILE | 203 | 17.835 | −2.440 | −19.411 | 1.00 | 26.06 |
| ATOM | 1954 | N | TYR | 204 | 19.326 | −1.667 | −20.901 | 1.00 | 23.00 |
| ATOM | 1955 | H | TYR | 204 | 20.252 | −1.690 | −21.219 | 1.00 | 0.00 |
| ATOM | 1956 | CA | TYR | 204 | 18.505 | −0.566 | −21.310 | 1.00 | 22.39 |
| ATOM | 1957 | CB | TYR | 204 | 18.691 | −0.638 | −20.392 | 1.00 | 23.53 |
| ATOM | 1958 | CG | TYR | 204 | 17.817 | −1.779 | −20.871 | 1.00 | 19.38 |
| ATOM | 1959 | CD1 | TYR | 204 | 16.435 | −1.597 | −20.888 | 1.00 | 21.27 |
| ATOM | 1960 | CE1 | TYR | 204 | 15.613 | −2.589 | −21.400 | 1.00 | 23.27 |
| ATOM | 1961 | CD2 | TYR | 204 | 18.389 | −2.952 | −21.353 | 1.00 | 17.37 |
| ATOM | 1962 | CE2 | TYR | 204 | 17.566 | −3.946 | −21.872 | 1.00 | 20.74 |
| ATOM | 1963 | CZ | TYR | 204 | 16.189 | −3.749 | −21.888 | 1.00 | 22.21 |
| ATOM | 1964 | OH | TYR | 204 | 15.364 | −4.701 | −22.428 | 1.00 | 35.35 |
| ATOM | 1965 | HH | TYR | 204 | 15.823 | −5.551 | −22.421 | 1.00 | 0.00 |
| ATOM | 1966 | C | TYR | 204 | 18.951 | −0.202 | −22.712 | 1.00 | 24.33 |
| ATOM | 1967 | O | TYR | 204 | 20.108 | −0.141 | −22.948 | 1.00 | 23.64 |
| ATOM | 1968 | N | GLY | 205 | 18.026 | −0.296 | −23.672 | 1.00 | 27.09 |
| ATOM | 1969 | H | GLY | 205 | 17.167 | −0.691 | −23.456 | 1.00 | 0.00 |
| ATOM | 1970 | CA | GLY | 205 | 18.331 | −0.022 | −25.063 | 1.00 | 28.04 |
| ATOM | 1971 | C | GLY | 205 | 19.445 | −0.886 | −25.568 | 1.00 | 28.26 |
| ATOM | 1972 | O | GLY | 205 | 20.434 | −0.425 | −26.129 | 1.00 | 29.56 |
| ATOM | 1973 | N | LYS | 206 | 19.310 | −2.183 | −25.274 | 1.00 | 30.20 |
| ATOM | 1974 | H | LYS | 206 | 18.469 | −2.463 | −24.853 | 1.00 | 0.00 |
| ATOM | 1975 | CA | LYS | 206 | 20.310 | −3.204 | −25.576 | 1.00 | 30.88 |
| ATOM | 1976 | CB | LYS | 206 | 20.348 | −3.437 | −27.106 | 1.00 | 39.67 |
| ATOM | 1977 | CG | LYS | 206 | 19.208 | −4.284 | −27.668 | 1.00 | 46.40 |
| ATOM | 1978 | CD | LYS | 206 | 19.427 | −4.533 | −29.171 | 1.00 | 58.59 |
| ATOM | 1979 | CE | LYS | 206 | 18.857 | −5.858 | −29.733 | 1.00 | 59.73 |
| ATOM | 1980 | NZ | LYS | 206 | 17.414 | −5.981 | −29.599 | 1.00 | 60.63 |
| ATOM | 1981 | HZ1 | LYS | 206 | 17.100 | −6.871 | −30.034 | 1.00 | 0.00 |
| ATOM | 1982 | HZ2 | LYS | 206 | 16.942 | −5.181 | −30.367 | 1.00 | 0.00 |
| ATOM | 1983 | HZ3 | LYS | 206 | 17.164 | −5.984 | −28.588 | 1.00 | 0.00 |
| ATOM | 1984 | C | LYS | 206 | 21.713 | −2.885 | −25.048 | 1.00 | 27.65 |
| ATOM | 1985 | O | LYS | 206 | 22.715 | −3.453 | −25.484 | 1.00 | 26.71 |
| ATOM | 1986 | N | THR | 207 | 21.854 | −1.988 | −24.075 | 1.00 | 27.08 |
| ATOM | 1987 | H | THR | 207 | 21.093 | −1.475 | −23.736 | 1.00 | 0.00 |
| ATOM | 1988 | CA | THR | 207 | 23.157 | −1.686 | −23.497 | 1.00 | 29.48 |
| ATOM | 1989 | CB | THR | 207 | 23.513 | −0.193 | −23.705 | 1.00 | 26.97 |
| ATOM | 1990 | OG1 | THR | 207 | 23.486 | 0.043 | −25.101 | 1.00 | 30.98 |
| ATOM | 1991 | HG1 | THR | 207 | 22.576 | −0.039 | −25.421 | 1.00 | 0.00 |
| ATOM | 1992 | CG2 | THR | 207 | 24.897 | −0.172 | −23.191 | 1.00 | 21.13 |
| ATOM | 1993 | C | THR | 207 | 23.126 | −2.009 | −22.006 | 1.00 | 31.62 |
| ATOM | 1994 | O | THR | 207 | 22.104 | −1.825 | −21.322 | 1.00 | 29.33 |
| ATOM | 1995 | N | VAL | 208 | 24.243 | −2.586 | −21.544 | 1.00 | 32.82 |
| ATOM | 1996 | H | VAL | 208 | 24.983 | −2.778 | −22.157 | 1.00 | 0.00 |
| ATOM | 1997 | CA | VAL | 208 | 24.418 | −2.923 | −20.146 | 1.00 | 27.75 |
| ATOM | 1998 | CB | VAL | 208 | 25.352 | −4.142 | −19.988 | 1.00 | 26.11 |
| ATOM | 1999 | CG1 | VAL | 208 | 25.598 | −4.433 | −18.520 | 1.00 | 25.10 |
| ATOM | 2000 | CG2 | VAL | 208 | 24.688 | −5.371 | −20.555 | 1.00 | 21.70 |
| ATOM | 2001 | C | VAL | 208 | 25.030 | −1.705 | −19.479 | 1.00 | 21.70 |
| ATOM | 2002 | O | VAL | 208 | 26.021 | −1.153 | −19.973 | 1.00 | 26.14 |
| ATOM | 2003 | N | TYR | 209 | 24.398 | −1.315 | −18.369 | 1.00 | 24.51 |
| ATOM | 2004 | H | TYR | 209 | 23.600 | −1.825 | −18.102 | 1.00 | 24.22 |
| ATOM | 2005 | CA | TYR | 209 | 24.819 | −0.206 | −17.528 | 1.00 | 0.00 |
| ATOM | 2006 | CB | TYR | 209 | 23.703 | 0.788 | −17.413 | 1.00 | 20.40 |
| ATOM | 2007 | CG | TYR | 209 | 23.416 | 1.508 | −18.712 | 1.00 | 21.23 |
| ATOM | 2008 | CD1 | TYR | 209 | 24.275 | 2.526 | −19.114 | 1.00 | 25.84 |
| ATOM | 2009 | CE1 | TYR | 209 | 24.025 | 3.264 | −20.261 | 1.00 | 27.02 |
| ATOM | 2010 | CD2 | TYR | 209 | 22.293 | 1.197 | −19.473 | 1.00 | 30.87 |
| ATOM | 2011 | CE2 | TYR | 209 | 22.033 | 1.929 | −20.960 | 1.00 | 25.74 |
| ATOM | 2012 | CZ | TYR | 209 | 22.899 | 2.958 | −21.010 | 1.00 | 33.37 |

TABLE 23-continued

Coordinates for the 3D structure of ZAP-NC:ζ1 "dimer" structure
(two molecules of complex per unit cell)*

| ATOM | 2013 | OH | TYR | 209 | 22.636 | 3.699 | −22.143 | 1.00 | 43.26 |
|---|---|---|---|---|---|---|---|---|---|
| ATOM | 2014 | HH | TYR | 209 | 22.811 | 4.641 | −21.974 | 1.00 | 0.00 |
| ATOM | 2015 | C | TYR | 209 | 25.151 | −0.751 | −16.144 | 1.00 | 18.17 |
| ATOM | 2016 | O | TYR | 209 | 24.410 | −1.594 | −15.633 | 1.00 | 17.18 |
| ATOM | 2017 | N | HIS | 210 | 26.256 | −0.371 | −15.515 | 1.00 | 17.72 |
| ATOM | 2018 | H | HIS | 210 | 26.826 | 0.337 | −15.894 | 1.00 | 0.00 |
| ATOM | 2019 | CA | HIS | 210 | 26.609 | −0.918 | −14.218 | 1.00 | 19.24 |
| ATOM | 2020 | CB | HIS | 210 | 28.008 | −1.531 | −14.215 | 1.00 | 21.16 |
| ATOM | 2021 | CG | HIS | 210 | 28.135 | −2.724 | −15.153 | 1.00 | 23.97 |
| ATOM | 2022 | CD2 | HIS | 210 | 28.543 | −2.656 | −16.468 | 1.00 | 24.36 |
| ATOM | 2023 | ND1 | HIS | 210 | 27.881 | −2.996 | −14.891 | 1.00 | 22.98 |
| ATOM | 2024 | HD1 | HIS | 210 | 27.529 | −4.364 | −14.053 | 1.00 | 0.00 |
| ATOM | 2025 | CE1 | HIS | 210 | 28.110 | −4.701 | −15.967 | 1.00 | 22.54 |
| ATOM | 2026 | NE2 | HIS | 210 | 28.506 | −2.884 | −16.907 | 1.00 | 21.56 |
| ATOM | 2027 | HE2 | HIS | 210 | 28.750 | −4.161 | −17.817 | 1.00 | 0.00 |
| ATOM | 2028 | C | HIS | 210 | 26.581 | 0.182 | −13.181 | 1.00 | 18.72 |
| ATOM | 2029 | O | HIS | 210 | 27.158 | 1.225 | −13.437 | 1.00 | 17.56 |
| ATOM | 2030 | N | TYR | 211 | 25.888 | −0.025 | −12.059 | 1.00 | 17.28 |
| ATOM | 2031 | H | TYR | 211 | 25.420 | −0.876 | −11.933 | 1.00 | 0.00 |
| ATOM | 2032 | CA | TYR | 211 | 25.817 | 0.927 | −10.966 | 1.00 | 15.79 |
| ATOM | 2033 | CB | TYR | 211 | 24.404 | 1.190 | −10.547 | 1.00 | 10.05 |
| ATOM | 2034 | CG | TYR | 211 | 23.724 | 2.032 | −11.583 | 1.00 | 12.14 |
| ATOM | 2035 | CD1 | TYR | 211 | 23.025 | 1.419 | −12.615 | 1.00 | 14.77 |
| ATOM | 2036 | CE1 | TYR | 211 | 22.378 | 2.205 | −13.476 | 1.00 | 17.95 |
| ATOM | 2037 | CD2 | TYR | 211 | 23.793 | 3.422 | −11.497 | 1.00 | 13.82 |
| ATOM | 2038 | CE2 | TYR | 211 | 23.146 | 4.214 | −12.450 | 1.00 | 14.13 |
| ATOM | 2039 | CZ | TYR | 211 | 22.440 | 3.600 | −13.487 | 1.00 | 17.28 |
| ATOM | 2040 | OH | TYR | 211 | 21.765 | 4.360 | −14.428 | 1.00 | 14.60 |
| ATOM | 2041 | HH | TYR | 211 | 22.097 | 5.271 | −14.394 | 1.00 | 0.00 |
| ATOM | 2042 | C | TYR | 211 | 26.528 | 0.305 | −9.795 | 1.00 | 17.49 |
| ATOM | 2043 | O | LEU | 212 | 26.378 | −0.900 | −9.552 | 1.00 | 20.48 |
| ATOM | 2044 | N | LEU | 212 | 27.312 | 1.111 | −9.090 | 1.00 | 17.95 |
| ATOM | 2045 | H | LEU | 212 | 27.306 | 2.074 | −9.285 | 1.00 | 0.00 |
| ATOM | 2046 | CA | LEU | 212 | 28.100 | 0.653 | −7.961 | 1.00 | 15.94 |
| ATOM | 2047 | CB | LEU | 212 | 29.274 | 1.590 | −7.816 | 1.00 | 16.35 |
| ATOM | 2048 | CG | LEU | 212 | 20.459 | 1.166 | −7.014 | 1.00 | 17.69 |
| ATOM | 2049 | CD1 | LEU | 212 | 20.986 | −0.162 | −7.495 | 1.00 | 21.17 |
| ATOM | 2050 | CD2 | LEU | 212 | 31.528 | 2.213 | −7.189 | 1.00 | 23.05 |
| ATOM | 2051 | C | LEU | 212 | 27.230 | 0.663 | −6.724 | 1.00 | 15.43 |
| ATOM | 2052 | O | LEU | 212 | 26.326 | 1.493 | −6.647 | 1.00 | 17.00 |
| ATOM | 2053 | N | ILE | 213 | 27.397 | −0.243 | −5.765 | 1.00 | 14.45 |
| ATOM | 2054 | H | ILE | 213 | 28.088 | −0.934 | −5.854 | 1.00 | 0.00 |
| ATOM | 2055 | CA | ILE | 213 | 26.591 | −0.197 | −4.566 | 1.00 | 12.29 |
| ATOM | 2056 | CB | ILE | 213 | 25.504 | −1.310 | −4.579 | 1.00 | 10.74 |
| ATOM | 2057 | CG2 | ILE | 213 | 24.772 | −1.292 | −3.234 | 1.00 | 8.99 |
| ATOM | 2058 | CG1 | ILE | 213 | 24.504 | −1.100 | −5.725 | 1.00 | 9.15 |
| ATOM | 2059 | CD | ILE | 213 | 23.386 | −2.155 | −5.837 | 1.00 | 2.00 |
| ATOM | 2060 | C | ILE | 213 | 27.581 | −0.409 | −3.440 | 1.00 | 12.99 |
| ATOM | 2061 | O | ILE | 213 | 28.458 | −1.266 | −3.511 | 1.00 | 13.44 |
| ATOM | 2062 | N | SER | 214 | 27.539 | 0.409 | −2.406 | 1.00 | 15.58 |
| ATOM | 2063 | H | SER | 214 | 26.849 | 1.103 | −2.368 | 1.00 | 0.00 |
| ATOM | 2064 | CA | SER | 214 | 28.435 | 0.266 | −1.286 | 1.00 | 18.78 |
| ATOM | 2065 | CB | SER | 214 | 29.515 | 0.409 | −1.367 | 1.00 | 18.30 |
| ATOM | 2066 | OG | SER | 214 | 30.131 | 1.374 | −2.657 | 1.00 | 26.17 |
| ATOM | 2067 | HG | SER | 214 | 29.992 | 0.512 | −3.070 | 1.00 | 0.00 |
| ATOM | 2068 | C | SER | 214 | 27.595 | 0.401 | −0.020 | 1.00 | 21.15 |
| ATOM | 2069 | O | SER | 214 | 26.462 | 0.921 | 0.001 | 1.00 | 18.71 |
| ATOM | 2070 | N | GLN | 215 | 28.159 | −0.172 | 1.035 | 1.00 | 23.98 |
| ATOM | 2071 | H | GLN | 215 | 29.053 | −0.568 | 0.974 | 1.00 | 0.00 |
| ATOM | 2072 | CA | GLN | 215 | 27.546 | −0.162 | 2.338 | 1.00 | 28.50 |
| ATOM | 2073 | CB | GLN | 215 | 27.528 | −1.599 | 2.792 | 1.00 | 22.80 |
| ATOM | 2074 | CG | GLN | 215 | 26.814 | −1.698 | 4.085 | 1.00 | 25.14 |
| ATOM | 2075 | CD | GLN | 215 | 26.746 | −3.095 | 4.636 | 1.00 | 29.02 |
| ATOM | 2076 | OE1 | GLN | 215 | 27.642 | −3.924 | 4.521 | 1.00 | 34.28 |
| ATOM | 2077 | NE2 | GLN | 215 | 25.627 | −3.395 | 5.265 | 1.00 | 30.80 |
| ATOM | 2078 | HE21 | GLN | 215 | 24.898 | −2.740 | 5.289 | 1.00 | 0.00 |
| ATOM | 2079 | HE22 | GLN | 215 | 25.607 | −4.263 | 5.713 | 1.00 | 0.00 |
| ATOM | 2080 | C | GLN | 215 | 28.362 | 0.757 | 3.262 | 1.00 | 33.95 |
| ATOM | 2081 | O | GLN | 215 | 29.604 | 0.709 | 3.248 | 1.00 | 36.63 |
| ATOM | 2082 | N | ASP | 216 | 27.723 | 1.654 | 4.016 | 1.00 | 34.60 |
| ATOM | 2083 | H | ASP | 216 | 26.758 | 1.767 | 3.899 | 1.00 | 0.00 |
| ATOM | 2084 | CA | ASP | 216 | 28.456 | 2.492 | 4.953 | 1.00 | 40.28 |
| ATOM | 2085 | CB | ASP | 216 | 27.723 | 3.833 | 5.154 | 1.00 | 43.67 |
| ATOM | 2086 | CG | ASP | 216 | 26.240 | 3.802 | 5.557 | 1.00 | 45.13 |
| ATOM | 2087 | OD1 | ASP | 216 | 25.830 | 2.926 | 6.315 | 1.00 | 44.28 |
| ATOM | 2088 | OD2 | ASP | 216 | 25.488 | 4.673 | 5.118 | 1.00 | 44.20 |

TABLE 23-continued

Coordinates for the 3D structure of ZAP-NC:ζ1 "dimer" structure
(two molecules of complex per unit cell)*

| ATOM | 2089 | C   | ASP | 216 | 28.625 | 1.783  | 6.295  | 1.00 | 43.90 |
|------|------|-----|-----|-----|--------|--------|--------|------|-------|
| ATOM | 2090 | O   | ASP | 216 | 27.872 | 0.851  | 6.578  | 1.00 | 47.97 |
| ATOM | 2091 | N   | LYS | 217 | 29.514 | 2.220  | 7.201  | 1.00 | 45.32 |
| ATOM | 2092 | H   | LYS | 217 | 30.087 | 2.958  | 6.916  | 1.00 | 0.00  |
| ATOM | 2093 | CA  | LYS | 217 | 29.754 | 1.599  | 8.517  | 1.00 | 41.99 |
| ATOM | 2094 | CB  | LYS | 217 | 30.698 | 2.467  | 9.376  | 1.00 | 42.40 |
| ATOM | 2095 | CG  | LYS | 217 | 30.279 | 3.912  | 9.649  | 1.00 | 46.37 |
| ATOM | 2096 | CD  | LYS | 217 | 30.563 | 4.860  | 8.484  | 1.00 | 46.52 |
| ATOM | 2097 | CE  | LYS | 217 | 29.906 | 6.201  | 8.735  | 1.00 | 48.92 |
| ATOM | 2098 | NZ  | LYS | 217 | 30.394 | 7.190  | 7.799  | 1.00 | 49.37 |
| ATOM | 2099 | HZ1 | LYS | 217 | 30.186 | 6.881  | 6.828  | 1.00 | 0.00  |
| ATOM | 2100 | HZ2 | LYS | 217 | 31.422 | 7.301  | 7.916  | 1.00 | 0.00  |
| ATOM | 2101 | HZ3 | LYS | 217 | 29.924 | 8.099  | 7.985  | 1.00 | 0.00  |
| ATOM | 2102 | C   | LYS | 217 | 28.518 | 1.306  | 9.356  | 1.00 | 39.51 |
| ATOM | 2103 | O   | LYS | 217 | 28.443 | 0.314  | 10.088 | 1.00 | 36.58 |
| ATOM | 2104 | N   | ALA | 218 | 27.521 | 2.178  | 9.183  | 1.00 | 38.15 |
| ATOM | 2105 | H   | ALA | 218 | 27.665 | 2.928  | 8.576  | 1.00 | 0.00  |
| ATOM | 2106 | CA  | ALA | 218 | 26.221 | 2.054  | 9.829  | 1.00 | 36.79 |
| ATOM | 2107 | CB  | ALA | 218 | 25.535 | 3.423  | 9.784  | 1.00 | 34.86 |
| ATOM | 2108 | C   | ALA | 218 | 25.314 | 0.991  | 9.178  | 1.00 | 35.43 |
| ATOM | 2109 | O   | ALA | 218 | 24.112 | 0.914  | 9.449  | 1.00 | 34.77 |
| ATOM | 2110 | N   | GLY | 219 | 25.840 | 0.184  | 8.255  | 1.00 | 32.78 |
| ATOM | 2111 | H   | GLY | 219 | 26.444 | 0.284  | 8.010  | 1.00 | 0.00  |
| ATOM | 2112 | CA  | GLY | 219 | 25.102 | -0.907 | 7.644  | 1.00 | 30.47 |
| ATOM | 2113 | C   | GLY | 219 | 24.190 | -0.554 | 6.484  | 1.00 | 26.67 |
| ATOM | 2114 | O   | GLY | 219 | 23.627 | -1.481 | 5.904  | 1.00 | 27.94 |
| ATOM | 2115 | N   | LYS | 220 | 24.069 | 0.703  | 6.077  | 1.00 | 21.58 |
| ATOM | 2116 | H   | LYS | 220 | 24.534 | 0.383  | 6.592  | 1.00 | 0.00  |
| ATOM | 2117 | CA  | LYS | 220 | 23.171 | 1.111  | 5.001  | 1.00 | 18.65 |
| ATOM | 2118 | CB  | LYS | 220 | 22.620 | 2.478  | 5.324  | 1.00 | 19.50 |
| ATOM | 2119 | CG  | LYS | 220 | 21.841 | 2.359  | 6.621  | 1.00 | 24.09 |
| ATOM | 2120 | CD  | LYS | 220 | 21.455 | 3.712  | 7.137  | 1.00 | 29.01 |
| ATOM | 2121 | CE  | LYS | 220 | 20.193 | 4.202  | 6.464  | 1.00 | 34.13 |
| ATOM | 2122 | NZ  | LYS | 220 | 19.009 | 3.547  | 6.978  | 1.00 | 33.94 |
| ATOM | 2123 | HZ1 | LYS | 220 | 18.175 | 4.046  | 6.615  | 1.00 | 0.00  |
| ATOM | 2124 | HZ2 | LYS | 220 | 19.007 | 3.607  | 8.017  | 1.00 | 0.00  |
| ATOM | 2125 | HZ3 | LYS | 220 | 18.983 | 2.550  | 6.684  | 1.00 | 0.00  |
| ATOM | 2126 | C   | LYS | 220 | 23.772 | 1.126  | 3.609  | 1.00 | 14.52 |
| ATOM | 2127 | O   | LYS | 220 | 24.863 | 1.647  | 3.367  | 1.00 | 14.63 |
| ATOM | 2128 | N   | TYR | 221 | 23.019 | 0.538  | 2.695  | 1.00 | 9.58  |
| ATOM | 2129 | H   | TYR | 221 | 22.127 | 0.234  | 2.956  | 1.00 | 0.00  |
| ATOM | 2130 | CA  | TYR | 221 | 23.425 | 0.359  | 1.315  | 1.00 | 10.18 |
| ATOM | 2131 | CB  | TYR | 221 | 22.866 | -0.930 | 0.735  | 1.00 | 10.07 |
| ATOM | 2132 | CG  | TYR | 221 | 23.293 | -2.194 | 1.445  | 1.00 | 7.80  |
| ATOM | 2133 | CD1 | TYR | 221 | 22.523 | -2.686 | 2.492  | 1.00 | 12.85 |
| ATOM | 2134 | CE1 | TYR | 221 | 22.859 | -3.901 | 3.088  | 1.00 | 17.08 |
| ATOM | 2135 | CD2 | TYR | 221 | 24.411 | -2.891 | 1.000  | 1.00 | 9.44  |
| ATOM | 2136 | CE2 | TYR | 221 | 24.755 | -4.104 | 1.596  | 1.00 | 18.12 |
| ATOM | 2137 | CZ  | TYR | 221 | 23.969 | -4.609 | 2.635  | 1.00 | 18.06 |
| ATOM | 2138 | OH  | TYR | 221 | 24.244 | -5.857 | 3.182  | 1.00 | 27.12 |
| ATOM | 2139 | HH  | TYR | 221 | 24.730 | -5.725 | 4.011  | 1.00 | 0.00  |
| ATOM | 2140 | C   | TYR | 221 | 22.930 | 1.477  | 0.439  | 1.00 | 9.37  |
| ATOM | 2141 | O   | TYR | 221 | 21.825 | 2.001  | 0.636  | 1.00 | 8.55  |
| ATOM | 2142 | N   | CYS | 222 | 23.749 | 1.851  | 0.528  | 1.00 | 10.43 |
| ATOM | 2143 | H   | CYS | 222 | 24.666 | 1.495  | 0.600  | 1.00 | 0.00  |
| ATOM | 2144 | CA  | CYS | 222 | 23.333 | 2.838  | 1.489  | 1.00 | 13.36 |
| ATOM | 2145 | CB  | CYS | 222 | 23.355 | 4.241  | 0.865  | 1.00 | 8.71  |
| ATOM | 2146 | SG  | CYS | 222 | 24.969 | 4.951  | 0.501  | 1.00 | 10.62 |
| ATOM | 2147 | C   | CYS | 222 | 24.254 | 2.809  | 2.697  | 1.00 | 13.50 |
| ATOM | 2148 | O   | CYS | 222 | 25.380 | 2.292  | 2.653  | 1.00 | 14.26 |
| ATOM | 2149 | N   | ILE | 223 | 23.725 | 3.267  | 3.824  | 1.00 | 16.58 |
| ATOM | 2150 | H   | ILE | 223 | 22.785 | 3.537  | 3.825  | 1.00 | 0.00  |
| ATOM | 2151 | CA  | ILE | 223 | 24.519 | 3.485  | 5.026  | 1.00 | 17.67 |
| ATOM | 2152 | CB  | ILE | 223 | 23.572 | 3.587  | 6.273  | 1.00 | 21.79 |
| ATOM | 2153 | CG2 | ILE | 223 | 24.356 | 3.926  | 7.550  | 1.00 | 19.55 |
| ATOM | 2154 | CG1 | ILE | 223 | 22.849 | 2.257  | 6.436  | 1.00 | 20.47 |
| ATOM | 2155 | CD  | ILE | 223 | 21.823 | 2.181  | 7.581  | 1.00 | 25.28 |
| ATOM | 2156 | C   | ILE | 223 | 25.198 | 4.818  | 4.710  | 1.00 | 15.39 |
| ATOM | 2157 | O   | ILE | 223 | 24.544 | 5.635  | 4.036  | 1.00 | 13.54 |
| ATOM | 2158 | N   | PRO | 224 | 26.451 | 5.139  | 5.094  | 1.00 | 16.61 |
| ATOM | 2159 | CD  | PRO | 224 | 27.410 | 4.262  | 5.761  | 1.00 | 11.44 |
| ATOM | 2160 | CA  | PRO | 224 | 27.092 | 6.417  | 4.799  | 1.00 | 19.91 |
| ATOM | 2161 | CB  | PRO | 224 | 28.376 | 6.383  | 5.626  | 1.00 | 19.31 |
| ATOM | 2162 | CG  | PRO | 224 | 28.751 | 4.926  | 5.508  | 1.00 | 17.17 |
| ATOM | 2163 | C   | PRO | 224 | 26.176 | 7.590  | 5.112  | 1.00 | 22.71 |
| ATOM | 2164 | O   | PRO | 224 | 25.757 | 7.771  | 6.260  | 1.00 | 25.97 |

TABLE 23-continued

Coordinates for the 3D structure of ZAP-NC:ζ1 "dimer" structure
(two molecules of complex per unit cell)*

| ATOM | 2165 | N   | GLU | 225 | 25.830 | 8.255  | 3.999  | 1.00 | 22.58 |
|------|------|-----|-----|-----|--------|--------|--------|------|-------|
| ATOM | 2166 | H   | GLU | 225 | 26.153 | 7.878  | 3.160  | 1.00 | 0.00  |
| ATOM | 2167 | CA  | GLU | 225 | 24.988 | 9.443  | 3.895  | 1.00 | 19.95 |
| ATOM | 2168 | CB  | GLU | 225 | 25.333 | 10.437 | 5.051  | 1.00 | 28.14 |
| ATOM | 2169 | CG  | GLU | 225 | 26.809 | 10.930 | 5.182  | 1.00 | 38.98 |
| ATOM | 2170 | CD  | GLU | 225 | 27.461 | 10.929 | 6.588  | 1.00 | 44.42 |
| ATOM | 2171 | OE1 | GLY | 226 | 26.803 | 11.226 | 7.594  | 1.00 | 38.07 |
| ATOM | 2172 | OE2 | GLY | 226 | 28.656 | 10.618 | 6.678  | 1.00 | 48.45 |
| ATOM | 2173 | C   | GLY | 226 | 23.490 | 7.114  | 3.902  | 1.00 | 14.73 |
| ATOM | 2174 | O   | GLY | 226 | 22.657 | 10.016 | 4.033  | 1.00 | 13.50 |
| ATOM | 2175 | N   | GLY | 226 | 23.089 | 7.859  | 3.659  | 1.00 | 10.41 |
| ATOM | 2176 | H   | GLY | 226 | 23.732 | 7.202  | 3.336  | 1.00 | 0.00  |
| ATOM | 2177 | CA  | GLY | 226 | 21.697 | 7.463  | 3.776  | 1.00 | 7.22  |
| ATOM | 2178 | C   | GLY | 226 | 20.986 | 7.289  | 2.455  | 1.00 | 8.63  |
| ATOM | 2179 | O   | GLY | 226 | 21.524 | 7.576  | 1.378  | 1.00 | 14.32 |
| ATOM | 2180 | N   | THR | 227 | 19.735 | 6.849  | 2.535  | 1.00 | 10.35 |
| ATOM | 2181 | H   | THR | 227 | 19.304 | 6.740  | 3.409  | 1.00 | 0.00  |
| ATOM | 2182 | CA  | THR | 227 | 18.909 | 6.566  | 1.373  | 1.00 | 7.32  |
| ATOM | 2183 | CB  | THR | 227 | 17.544 | 6.211  | 1.937  | 1.00 | 3.12  |
| ATOM | 2184 | OG1 | THR | 227 | 17.248 | 7.345  | 2.725  | 1.00 | 12.83 |
| ATOM | 2185 | HG1 | THR | 227 | 16.969 | 8.067  | 2.140  | 1.00 | 0.00  |
| ATOM | 2186 | CG1 | THR | 227 | 16.382 | 6.076  | 0.988  | 1.00 | 2.69  |
| ATOM | 2187 | C   | THR | 227 | 19.563 | 5.440  | 0.562  | 1.00 | 8.27  |
| ATOM | 2188 | O   | THR | 227 | 20.207 | 4.542  | 1.117  | 1.00 | 8.17  |
| ATOM | 2189 | N   | LYS | 228 | 19.465 | 5.533  | 0.758  | 1.00 | 9.07  |
| ATOM | 2190 | H   | LYS | 228 | 18.953 | 6.274  | 1.161  | 1.00 | 0.00  |
| ATOM | 2191 | CA  | LYS | 228 | 20.027 | 4.523  | 1.630  | 1.00 | 10.14 |
| ATOM | 2192 | CB  | LYS | 228 | 20.479 | 5.067  | 2.971  | 1.00 | 15.14 |
| ATOM | 2193 | CG  | LYS | 228 | 21.337 | 6.290  | 3.029  | 1.00 | 19.45 |
| ATOM | 2194 | CD  | LYS | 228 | 22.464 | 6.201  | 2.058  | 1.00 | 21.10 |
| ATOM | 2195 | CE  | LYS | 228 | 23.498 | 7.216  | 2.476  | 1.00 | 29.17 |
| ATOM | 2196 | NZ  | LYS | 228 | 24.486 | 6.542  | 3.294  | 1.00 | 35.96 |
| ATOM | 2197 | HZ1 | LYS | 228 | 25.167 | 7.233  | 3.663  | 1.00 | 0.00  |
| ATOM | 2198 | HZ2 | LYS | 228 | 24.987 | 5.841  | 2.712  | 1.00 | 0.00  |
| ATOM | 2199 | HZ3 | LYS | 228 | 24.014 | 6.058  | 4.086  | 1.00 | 0.00  |
| ATOM | 2200 | C   | LYS | 228 | 18.945 | 3.509  | 1.947  | 1.00 | 8.99  |
| ATOM | 2201 | O   | LYS | 228 | 17.772 | 3.879  | 2.070  | 1.00 | 2.97  |
| ATOM | 2202 | N   | PHE | 229 | 19.335 | 2.239  | 2.074  | 1.00 | 7.55  |
| ATOM | 2203 | H   | PHE | 229 | 20.283 | 2.022  | 1.957  | 1.00 | 0.00  |
| ATOM | 2204 | CA  | PHE | 229 | 18.434 | 1.143  | 2.403  | 1.00 | 7.13  |
| ATOM | 2205 | CB  | PHE | 229 | 18.161 | 0.236  | 1.202  | 1.00 | 7.86  |
| ATOM | 2206 | CG  | PHE | 229 | 17.602 | 1.035  | 0.047  | 1.00 | 2.00  |
| ATOM | 2207 | CD1 | PHE | 229 | 18.451 | 1.524  | 0.944  | 1.00 | 8.70  |
| ATOM | 2208 | CD2 | PHE | 229 | 16.255 | 1.330  | 0.001  | 1.00 | 4.73  |
| ATOM | 2209 | CE1 | PHE | 229 | 17.958 | 2.314  | 1.976  | 1.00 | 7.18  |
| ATOM | 2210 | CE2 | PHE | 229 | 15.758 | 2.122  | 1.033  | 1.00 | 7.26  |
| ATOM | 2211 | CZ  | PHE | 229 | 16.599 | 2.612  | 2.016  | 1.00 | 2.00  |
| ATOM | 2212 | C   | PHE | 229 | 19.133 | 0.306  | 3.455  | 1.00 | 9.26  |
| ATOM | 2213 | O   | PHE | 229 | 20.356 | 0.321  | 3.597  | 1.00 | 8.05  |
| ATOM | 2214 | N   | ASP | 230 | 18.393 | 0.461  | 4.215  | 1.00 | 9.93  |
| ATOM | 2215 | H   | ASP | 230 | 17.419 | 0.468  | 4.097  | 1.00 | 0.00  |
| ATOM | 2216 | CA  | ASP | 230 | 19.041 | 1.318  | 5.183  | 1.00 | 11.63 |
| ATOM | 2217 | CB  | ASP | 230 | 18.125 | 1.490  | 6.382  | 1.00 | 7.41  |
| ATOM | 2218 | CG  | ASP | 230 | 18.175 | 0.350  | 7.397  | 1.00 | 10.95 |
| ATOM | 2219 | OD1 | ASP | 230 | 19.033 | 0.524  | 7.281  | 1.00 | 10.94 |
| ATOM | 2220 | OD2 | ASP | 230 | 17.358 | 0.353  | 8.326  | 1.00 | 12.05 |
| ATOM | 2221 | C   | ASP | 230 | 19.424 | 2.679  | 4.643  | 1.00 | 12.18 |
| ATOM | 2222 | O   | ASP | 230 | 20.264 | 3.360  | 5.220  | 1.00 | 15.45 |
| ATOM | 2223 | N   | THR | 231 | 18.797 | 3.145  | 3.565  | 1.00 | 14.62 |
| ATOM | 2224 | H   | THR | 231 | 18.165 | 2.584  | 3.072  | 1.00 | 0.00  |
| ATOM | 2225 | CA  | THR | 231 | 19.108 | 4.445  | 3.000  | 1.00 | 11.96 |
| ATOM | 2226 | CB  | THR | 231 | 17.962 | 5.429  | 3.266  | 1.00 | 6.38  |
| ATOM | 2227 | OG1 | THR | 231 | 16.791 | 4.882  | 2.696  | 1.00 | 8.91  |
| ATOM | 2228 | HG1 | THR | 231 | 16.387 | 4.307  | 3.370  | 1.00 | 0.00  |
| ATOM | 2229 | CG2 | THR | 231 | 17.723 | 5.654  | 4.750  | 1.00 | 8.69  |
| ATOM | 2230 | C   | THR | 231 | 19.293 | 4.277  | 1.508  | 1.00 | 9.43  |
| ATOM | 2231 | O   | THR | 231 | 18.720 | 3.348  | 0.929  | 1.00 | 10.77 |
| ATOM | 2232 | N   | LEU | 232 | 20.040 | −5.146 | 0.840  | 1.00 | 6.23  |
| ATOM | 2233 | H   | LEU | 232 | 20.535 | −5.828 | 1.341  | 1.00 | 0.00  |
| ATOM | 2234 | CA  | LEU | 232 | 20.134 | −5.089 | −0.598 | 1.00 | 2.95  |
| ATOM | 2235 | CB  | LEU | 232 | 21.146 | −6.078 | −1.084 | 1.00 | 2.00  |
| ATOM | 2236 | CG  | LEU | 232 | 22.538 | −5.695 | −1.570 | 1.00 | 7.83  |
| ATOM | 2237 | CD1 | LEU | 232 | 22.670 | −4.204 | −1.804 | 1.00 | 6.14  |
| ATOM | 2238 | CD2 | LEU | 232 | 23.519 | −6.259 | −0.588 | 1.00 | 5.92  |
| ATOM | 2239 | C   | LEU | 232 | 18.788 | −5.422 | −1.210 | 1.00 | 3.62  |
| ATOM | 2240 | O   | LEU | 232 | 18.446 | −4.879 | −2.256 | 1.00 | 11.85 |

TABLE 23-continued

Coordinates for the 3D structure of ZAP-NC:ζ1 "dimer" structure
(two molecules of complex per unit cell)*

| ATOM | 2241 | N | TRP | 233 | 17.959 | −6.266 | −0.590 | 1.00 | 7.60 |
|---|---|---|---|---|---|---|---|---|---|
| ATOM | 2242 | H | TRP | 233 | 18.236 | −6.662 | 0.263 | 1.00 | 0.00 |
| ATOM | 2243 | CA | TRP | 233 | 15.560 | −6.611 | −1.119 | 1.00 | 3.89 |
| ATOM | 2244 | CB | TRP | 233 | 15.903 | −7.634 | −0.232 | 1.00 | 5.05 |
| ATOM | 2245 | CG | TRP | 233 | 14.559 | −8.122 | −0.793 | 1.00 | 3.68 |
| ATOM | 2246 | CD2 | TRP | 233 | 13.319 | −7.504 | −0.707 | 1.00 | 7.30 |
| ATOM | 2247 | CE2 | TRP | 233 | 12.416 | −8.393 | −1.406 | 1.00 | 2.00 |
| ATOM | 2248 | CE3 | TRP | 233 | 12.743 | −6.346 | −0.161 | 1.00 | 5.75 |
| ATOM | 2249 | CD1 | TRP | 233 | 14.503 | −9.298 | −1.485 | 1.00 | 2.00 |
| ATOM | 2250 | NE1 | TRP | 233 | 13.249 | −9.419 | −1.834 | 1.00 | 2.00 |
| ATOM | 2251 | HE1 | TRP | 233 | 12.886 | −10.159 | −2.387 | 1.00 | 0.00 |
| ATOM | 2252 | CZ2 | TRP | 233 | 11.156 | −8.154 | −1.566 | 1.00 | 5.63 |
| ATOM | 2253 | CZ3 | TRP | 233 | 11.386 | −6.098 | −0.314 | 1.00 | 2.00 |
| ATOM | 2254 | CH2 | TRP | 233 | 10.597 | −7.001 | −1.012 | 1.00 | 11.94 |
| ATOM | 2255 | C | TRP | 233 | 15.776 | −5.389 | −1.218 | 1.00 | 8.61 |
| ATOM | 2256 | O | TRP | 233 | 15.050 | −5.243 | −2.208 | 1.00 | 5.31 |
| ATOM | 2257 | N | GLN | 234 | 15.757 | −4.569 | −0.160 | 1.00 | 7.54 |
| ATOM | 2258 | H | GLN | 234 | 16.278 | −4.789 | −0.645 | 1.00 | 0.00 |
| ATOM | 2259 | CA | GLN | 234 | 14.936 | −3.379 | −0.181 | 1.00 | 5.71 |
| ATOM | 2260 | CB | GLN | 234 | 14.898 | −2.731 | 1.182 | 1.00 | 8.39 |
| ATOM | 2261 | CG | GLN | 234 | 13.956 | −2.432 | 2.121 | 1.00 | 10.31 |
| ATOM | 2262 | CD | GLN | 234 | 14.065 | −2.931 | 3.557 | 1.00 | 11.00 |
| ATOM | 2263 | OE1 | GLN | 234 | 15.131 | −3.022 | 4.161 | 1.00 | 6.43 |
| ATOM | 2264 | N32 | GLN | 234 | 13.010 | −2.409 | 4.171 | 1.00 | 6.16 |
| ATOM | 2265 | HE21 | GLN | 234 | 12.163 | −2.384 | 3.672 | 1.00 | 0.00 |
| ATOM | 2266 | HE22 | GLN | 234 | 13.119 | −2.107 | 5.091 | 1.00 | 0.00 |
| ATOM | 2267 | C | GLN | 234 | 15.479 | −2.388 | −1.194 | 1.00 | 3.99 |
| ATOM | 2268 | O | GLN | 234 | 14.693 | −1.634 | −1.757 | 1.00 | 8.14 |
| ATOM | 2269 | N | LEU | 235 | 16.775 | −2.345 | −1.489 | 1.00 | 5.43 |
| ATOM | 2270 | H | LEU | 235 | 17.407 | −2.893 | −0.976 | 1.00 | 0.00 |
| ATOM | 2271 | CA | LEU | 235 | 17.285 | −1.460 | −2.527 | 1.00 | 8.35 |
| ATOM | 2272 | CB | LEU | 235 | 18.831 | −1.563 | −2.577 | 1.00 | 2.00 |
| ATOM | 2273 | CG | LEU | 235 | 19.649 | −0.729 | −3.596 | 1.00 | 2.00 |
| ATOM | 2274 | CD1 | LEU | 235 | 20.947 | −0.300 | −2.980 | 1.00 | 2.00 |
| ATOM | 2275 | CD2 | LEU | 235 | 20.012 | −1.545 | −4.817 | 1.00 | 4.96 |
| ATOM | 2276 | C | LEU | 235 | 16.659 | −1.826 | −3.873 | 1.00 | 45.15 |
| ATOM | 2277 | O | LEU | 235 | 16.060 | −0.967 | −4.545 | 1.00 | 13.16 |
| ATOM | 2278 | N | VAL | 236 | 16.710 | −3.120 | −4.220 | 1.00 | 8.74 |
| ATOM | 2279 | H | VAL | 236 | 17.132 | −3.757 | −3.603 | 1.00 | 0.00 |
| ATOM | 2280 | CA | VAL | 236 | 16.185 | −3.580 | −5.494 | 1.00 | 9.17 |
| ATOM | 2281 | CB | VAL | 236 | 16.477 | −5.079 | −5.682 | 1.00 | 8.00 |
| ATOM | 2282 | CG1 | VAL | 236 | 15.742 | −5.655 | −6.880 | 1.00 | 9.58 |
| ATOM | 2283 | CG2 | VAL | 236 | 17.968 | −5.216 | −5.949 | 1.00 | 3.72 |
| ATOM | 2284 | C | VAL | 236 | 14.707 | −3.320 | −5.616 | 1.00 | 9.31 |
| ATOM | 2285 | O | VAL | 236 | 14.278 | −2.681 | −6.586 | 1.00 | 17.05 |
| ATOM | 2286 | N | GLU | 237 | 13.942 | −3.715 | −4.602 | 1.00 | 7.98 |
| ATOM | 2287 | H | GLU | 237 | 14.359 | −4.221 | −3.874 | 1.00 | 0.00 |
| ATOM | 2288 | CA | GLU | 237 | 12.507 | −3.526 | −4.598 | 1.00 | 5.37 |
| ATOM | 2289 | CB | GLU | 237 | 11.923 | −4.003 | −3.284 | 1.00 | 4.42 |
| ATOM | 2290 | CG | GLU | 237 | 10.399 | −4.242 | −3.284 | 1.00 | 9.65 |
| ATOM | 2291 | CD | GLU | 237 | 9.844 | −5.417 | −4.113 | 1.00 | 13.56 |
| ATOM | 2292 | OE1 | GLU | 237 | 8.630 | −5.457 | −4.307 | 1.00 | 22.81 |
| ATOM | 2293 | OE2 | GLU | 237 | 10.589 | −6.290 | −4.562 | 1.00 | 14.84 |
| ATOM | 2294 | C | GLU | 237 | 12.079 | −2.091 | −4.814 | 1.00 | 8.53 |
| ATOM | 2295 | O | GLU | 237 | 11.084 | −1.831 | −5.485 | 1.00 | 11.94 |
| ATOM | 2299 | CB | TYR | 238 | 13.315 | 1.018 | −3.400 | 1.00 | 12.67 |
| ATOM | 2300 | CG | TYR | 238 | 12.969 | 2.471 | −3.148 | 1.00 | 12.96 |
| ATOM | 2301 | CD1 | TYR | 238 | 12.065 | 2.796 | −2.126 | 1.00 | 6.34 |
| ATOM | 2302 | CE1 | TYR | 238 | 11.766 | 4.141 | −1.884 | 1.00 | 8.90 |
| ATOM | 2303 | CD2 | TYR | 238 | 13.576 | 3.482 | −3.925 | 1.00 | 12.47 |
| ATOM | 2304 | CE2 | TYR | 238 | 13.277 | 4.823 | −3.672 | 1.00 | 7.42 |
| ATOM | 2305 | CZ | TYR | 238 | 12.380 | 5.142 | −2.656 | 1.00 | 8.04 |
| ATOM | 2306 | OH | TYR | 238 | 12.118 | 6.469 | −2.398 | 1.00 | 10.73 |
| ATOM | 2307 | HH | TYR | 238 | 11.600 | 6.534 | −1.589 | 1.00 | 0.00 |
| ATOM | 2308 | C | TYR | 238 | 12.658 | 0.760 | −5.827 | 1.00 | 10.55 |
| ATOM | 2309 | O | TYR | 238 | 11.825 | 1.506 | −6.348 | 1.00 | 9.33 |
| ATOM | 2310 | N | LEU | 239 | 13.764 | 0.323 | −6.443 | 1.00 | 12.05 |
| ATOM | 2311 | H | LEU | 239 | 14.358 | −0.294 | −5.962 | 1.00 | 0.00 |
| ATOM | 2312 | CA | LEU | 239 | 14.169 | 0.725 | −7.784 | 1.00 | 10.14 |
| ATOM | 2313 | CB | LEU | 239 | 15.631 | 0.379 | −8.015 | 1.00 | 11.39 |
| ATOM | 2314 | CG | LEU | 239 | 16.612 | 1.015 | −7.051 | 1.00 | 9.45 |
| ATOM | 2315 | CD1 | LEU | 239 | 18.003 | 0.616 | −7.428 | 1.00 | 4.78 |
| ATOM | 2316 | CD2 | LEU | 239 | 16.458 | 2.515 | −7.075 | 1.00 | 11.26 |
| ATOM | 2317 | C | LEU | 239 | 13.357 | 0.078 | −8.873 | 1.00 | 9.57 |
| ATOM | 2318 | O | LEU | 239 | 13.533 | 0.339 | −10.054 | 1.00 | 9.15 |
| ATOM | 2319 | N | LYS | 240 | 12.525 | −0.867 | −8.476 | 1.00 | 15.55 |

TABLE 23-continued

Coordinates for the 3D structure of ZAP-NC:ζ1 "dimer" structure
(two molecules of complex per unit cell)*

| | | | | | | | | | |
|---|---|---|---|---|---|---|---|---|---|
| ATOM | 2320 | H | LYS | 240 | 12.628 | −1.226 | −7.572 | 1.00 | 0.00 |
| ATOM | 2321 | CA | LYS | 240 | 11.598 | −1.526 | −9.359 | 1.00 | 17.48 |
| ATOM | 2322 | CB | LYS | 240 | 11.086 | −2.846 | −8.804 | 1.00 | 17.46 |
| ATOM | 2323 | CG | LYS | 240 | 12.080 | −3.968 | −8.744 | 1.00 | 15.22 |
| ATOM | 2324 | CD | LYS | 240 | 11.241 | −5.061 | −8.143 | 1.00 | 14.34 |
| ATOM | 2325 | CE | LYS | 240 | 12.104 | −6.285 | −7.941 | 1.00 | 18.77 |
| ATOM | 2326 | NZ | LYS | 240 | 11.320 | −7.303 | −7.288 | 1.00 | 14.93 |
| ATOM | 2327 | HZ1 | LYS | 240 | 10.510 | −7.562 | −7.887 | 1.00 | 0.00 |
| ATOM | 2328 | HZ2 | LYS | 240 | 10.971 | −6.935 | −6.381 | 1.00 | 0.00 |
| ATOM | 2329 | HZ3 | LYS | 240 | 11.912 | −8.142 | −7.119 | 1.00 | 0.00 |
| ATOM | 2330 | C | LYS | 240 | 10.393 | −0.647 | −9.532 | 1.00 | 21.00 |
| ATOM | 2331 | O | LYS | 240 | 9.710 | −0.714 | −10.561 | 1.00 | 24.63 |
| ATOM | 2332 | N | LEU | 241 | 10.121 | 0.155 | −8.496 | 1.00 | 22.22 |
| ATOM | 2333 | H | LEU | 241 | 10.722 | 0.171 | −7.725 | 1.00 | 0.00 |
| ATOM | 2334 | CA | LEU | 241 | 8.936 | 0.992 | −8.503 | 1.00 | 21.50 |
| ATOM | 2335 | CB | LEU | 241 | 8.312 | 0.984 | −7.111 | 1.00 | 22.84 |
| ATOM | 2336 | CG | LEU | 241 | 8.099 | −0.392 | −6.506 | 1.00 | 25.03 |
| ATOM | 2337 | CD1 | LEU | 241 | 7.695 | −0.270 | −5.047 | 1.00 | 28.03 |
| ATOM | 2338 | CD2 | LEU | 241 | 7.086 | −1.136 | −7.365 | 1.00 | 27.90 |
| ATOM | 2339 | C | LEU | 241 | 9.240 | 2.402 | −8.922 | 1.00 | 20.05 |
| ATOM | 2340 | O | LEU | 241 | 8.443 | 2.970 | −9.660 | 1.00 | 27.60 |
| ATOM | 2341 | N | LYS | 242 | 10.365 | 2.968 | −8.472 | 1.00 | 18.36 |
| ATOM | 2342 | H | LYS | 242 | 11.030 | 2.419 | −8.002 | 1.00 | 0.00 |
| ATOM | 2343 | CA | LYS | 242 | 10.736 | 4.355 | −8.708 | 1.00 | 18.26 |
| ATOM | 2344 | CB | LYS | 242 | 10.562 | 5.193 | −7.429 | 1.00 | 19.41 |
| ATOM | 2345 | CG | LYS | 242 | 9.096 | 5.447 | −7.114 | 1.00 | 17.62 |
| ATOM | 2346 | CD | LYS | 242 | 8.908 | 6.480 | −6.033 | 1.00 | 14.02 |
| ATOM | 2347 | CE | LYS | 242 | 9.326 | 5.989 | −4.671 | 1.00 | 10.78 |
| ATOM | 2348 | NZ | LYS | 242 | 8.973 | 6.952 | −3.638 | 1.00 | 12.29 |
| ATOM | 2349 | HZ1 | LYS | 242 | 7.964 | 7.198 | −3.716 | 1.00 | 0.00 |
| ATOM | 2350 | HZ2 | LYS | 242 | 9.549 | 7.808 | −3.757 | 1.00 | 0.00 |
| ATGM | 2351 | HZ3 | LYS | 242 | 9.156 | 6.528 | −2.709 | 1.00 | 0.00 |
| ATOM | 2352 | C | LYS | 242 | 12.192 | 4.371 | −9.123 | 1.00 | 18.38 |
| ATOM | 2353 | O | LYS | 242 | 13.044 | 3.948 | −8.340 | 1.00 | 23.83 |
| ATOM | 2354 | N | ALA | 243 | 12.492 | 4.869 | −10.327 | 1.00 | 18.80 |
| ATOM | 2355 | H | ALA | 243 | 11.770 | 5.267 | −10.850 | 1.00 | 0.00 |
| ATOM | 2356 | CA | ALA | 243 | 13.841 | 4.812 | −10.887 | 1.00 | 19.06 |
| ATOM | 2357 | CB | ALA | 243 | 13.949 | 5.553 | −12.237 | 1.00 | 15.73 |
| ATOM | 2358 | C | ALA | 243 | 14.883 | 5.412 | −9.975 | 1.00 | 16.76 |
| ATOM | 2359 | O | ALA | 243 | 16.030 | 4.971 | −10.012 | 1.00 | 16.14 |
| ATOM | 2360 | N | ASP | 244 | 14.528 | 6.456 | −9.214 | 1.00 | 13.41 |
| ATOM | 2361 | H | ASP | 244 | 13.631 | 6.846 | −9.318 | 1.00 | 0.00 |
| ATOM | 2362 | CA | ASP | 244 | 15.399 | 7.026 | −8.202 | 1.00 | 14.59 |
| ATOM | 2363 | CB | ASP | 244 | 15.314 | 6.027 | −7.034 | 1.00 | 18.56 |
| ATOM | 2364 | CG | ASP | 244 | 15.807 | 6.513 | −5.697 | 1.00 | 15.45 |
| ATOM | 2365 | OD1 | ASP | 244 | 15.432 | 7.607 | −5.302 | 1.00 | 14.61 |
| ATOM | 2366 | OD2 | ASP | 244 | 16.551 | 5.779 | −5.058 | 1.00 | 15.49 |
| ATOM | 2367 | C | ASP | 244 | 16.834 | 7.347 | −8.637 | 1.00 | 14.32 |
| ATOM | 2368 | O | ASP | 244 | 17.841 | 7.119 | −7.947 | 1.00 | 17.05 |
| ATOM | 2369 | N | GLY | 245 | 16.948 | 7.902 | −9.840 | 1.00 | 17.98 |
| ATOM | 2370 | H | GLY | 245 | 16.134 | 8.056 | −10.361 | 1.00 | 0.00 |
| ATOM | 2371 | CA | GLY | 245 | 18.239 | 8.279 | −10.368 | 1.00 | 10.81 |
| ATOM | 2372 | C | GLY | 245 | 18.811 | 7.304 | −11.369 | 1.00 | 11.69 |
| ATOM | 2373 | O | GLY | 245 | 19.760 | 7.670 | −12.059 | 1.00 | 14.24 |
| ATOM | 2374 | N | LEU | 246 | 18.279 | 6.091 | −11.484 | 1.00 | 15.09 |
| ATOM | 2375 | H | LEU | 246 | 17.538 | 5.845 | −10.890 | 1.00 | 0.00 |
| ATOM | 2376 | CA | LEU | 246 | 18.736 | 5.089 | −12.451 | 1.00 | 16.67 |
| ATOM | 2377 | CB | LEU | 246 | 18.123 | 3.729 | −12.247 | 1.00 | 12.64 |
| ATOM | 2378 | CG | LEU | 246 | 18.387 | 2.880 | −11.055 | 1.00 | 12.13 |
| ATOM | 2379 | CD1 | LEU | 246 | 17.581 | 1.601 | −11.239 | 1.00 | 16.26 |
| ATOM | 2380 | CD2 | LEU | 246 | 19.866 | 2.604 | −10.896 | 1.00 | 7.94 |
| ATOM | 2381 | C | LEU | 246 | 18.322 | 5.465 | −13.861 | 1.00 | 17.17 |
| ATOM | 2382 | O | LEU | 246 | 17.378 | 6.237 | −14.033 | 1.00 | 16.84 |
| ATOM | 2383 | N | ILE | 247 | 19.004 | 4.899 | −14.859 | 1.00 | 18.24 |
| ATOM | 2384 | H | ILE | 247 | 19.848 | 4.448 | −14.647 | 1.00 | 0.00 |
| ATOM | 2385 | CA | ILE | 247 | 18.640 | 5.084 | −16.243 | 1.00 | 19.23 |
| ATOM | 2386 | CB | ILE | 247 | 19.743 | 4.443 | −17.166 | 1.00 | 21.02 |
| ATOM | 2387 | CG2 | ILE | 247 | 19.762 | 2.933 | −17.037 | 1.00 | 18.75 |
| ATOM | 2388 | CG1 | ILE | 247 | 19.461 | 4.744 | −18.623 | 1.00 | 18.10 |
| ATOM | 2389 | CD | ILE | 247 | 19.246 | 6.228 | −18.940 | 1.00 | 26.97 |
| ATOM | 2390 | C | ILE | 247 | 17.267 | 4.479 | −16.501 | 1.00 | 24.15 |
| ATOM | 2391 | O | ILE | 247 | 16.548 | 4.963 | −17.381 | 1.00 | 27.80 |
| ATOM | 2392 | N | TYR | 248 | 16.839 | 3.453 | −15.764 | 1.00 | 22.21 |
| ATOM | 2393 | H | TYR | 248 | 17.362 | 3.113 | −15.008 | 1.00 | 0.00 |
| ATOM | 2394 | CA | TYR | 248 | 15.562 | 2.810 | −16.014 | 1.00 | 21.62 |
| ATOM | 2395 | CB | TYR | 248 | 15.690 | 1.863 | −17.222 | 1.00 | 21.58 |

TABLE 23-continued

Coordinates for the 3D structure of ZAP-NC:ζ1 "dimer" structure
(two molecules of complex per unit cell)*

| ATOM | 2396 | CG | TYR | 248 | 14.358 | 1.459 | −17.836 | 1.00 | 22.46 |
|---|---|---|---|---|---|---|---|---|---|
| ATOM | 2397 | CD1 | TYR | 248 | 13.932 | 0.136 | −17.768 | 1.00 | 25.31 |
| ATOM | 2398 | CE1 | TYR | 248 | 12.710 | −0.232 | −18.321 | 1.00 | 25.82 |
| ATOM | 2399 | CD2 | TYR | 248 | 13.564 | 2.420 | −18.464 | 1.00 | 24.69 |
| ATOM | 2400 | CE2 | TYR | 248 | 12.343 | 2.057 | −19.030 | 1.00 | 20.76 |
| ATOM | 2401 | CZ | TYR | 248 | 11.926 | 0.733 | −18.952 | 1.00 | 22.54 |
| ATOM | 2402 | OH | TYR | 248 | 10.723 | 0.368 | −19.518 | 1.00 | 26.05 |
| ATOM | 2403 | HH | TYR | 248 | 10.182 | 1.145 | −19.684 | 1.00 | 0.00 |
| ATOM | 2404 | C | TYR | 248 | 15.197 | 2.013 | −14.771 | 1.00 | 20.39 |
| ATOM | 2405 | O | TYR | 248 | 16.116 | 1.543 | −14.091 | 1.00 | 21.20 |
| ATOM | 2406 | N | CYS | 249 | 13.897 | 1.885 | −14.469 | 1.00 | 16.84 |
| ATOM | 2407 | H | CYS | 249 | 13.238 | 2.385 | −14.998 | 1.00 | 0.00 |
| ATOM | 2408 | CA | CYS | 249 | 13.422 | 1.032 | −13.382 | 1.00 | 15.26 |
| ATOM | 2409 | CB | CYS | 249 | 11.901 | 1.106 | −13.174 | 1.00 | 14.09 |
| ATOM | 2410 | SG | CYS | 249 | 11.404 | 2.626 | −12.300 | 1.00 | 18.14 |
| ATOM | 2411 | C | CYS | 249 | 13.753 | −0.412 | −13.666 | 1.00 | 14.21 |
| ATOM | 2412 | O | CYS | 249 | 13.773 | −0.843 | −14.823 | 1.00 | 14.52 |
| ATOM | 2413 | N | LEU | 250 | 14.025 | −1.151 | −12.589 | 1.00 | 13.28 |
| ATOM | 2414 | H | LEU | 250 | 13.948 | −0.736 | −11.703 | 1.00 | 0.00 |
| ATOM | 2415 | CA | LEU | 250 | 14.352 | −2.561 | −12.686 | 1.00 | 15.78 |
| ATOM | 2416 | CB | LEU | 250 | 14.919 | −3.094 | −11.360 | 1.00 | 6.33 |
| ATOM | 2417 | CG | LEU | 250 | 16.117 | −2.358 | −10.789 | 1.00 | 6.54 |
| ATOM | 2418 | CD1 | LEU | 250 | 16.561 | −3.102 | −9.557 | 1.00 | 5.37 |
| ATOM | 2419 | CD2 | LEU | 250 | 17.241 | −2.245 | −11.807 | 1.00 | 8.52 |
| ATOM | 2420 | C | LEU | 250 | 13.064 | −3.292 | −13.029 | 1.00 | 18.36 |
| ATOM | 2421 | O | LEU | 250 | 11.987 | −2.905 | −12.563 | 1.00 | 20.40 |
| ATOM | 2422 | N | LYS | 251 | 13.147 | −4.314 | −13.870 | 1.00 | 21.41 |
| ATOM | 2423 | H | LYS | 251 | 14.026 | −4.664 | −14.120 | 1.00 | 0.00 |
| ATOM | 2424 | CA | LYS | 251 | 11.974 | −5.035 | −14.309 | 1.00 | 29.19 |
| ATOM | 2425 | CB | LYS | 251 | 11.594 | −4.599 | −15.727 | 1.00 | 31.81 |
| ATOM | 2426 | CG | LYS | 251 | 10.932 | −3.252 | −15.911 | 1.00 | 36.36 |
| ATOM | 2427 | CD | LYS | 251 | 10.358 | −3.321 | −17.316 | 1.00 | 46.04 |
| ATOM | 2428 | CE | LYS | 251 | 9.335 | −2.219 | −17.552 | 1.00 | 49.77 |
| ATOM | 2429 | NE | LYS | 251 | 8.508 | −2.570 | −18.689 | 1.00 | 47.05 |
| ATOM | 2430 | HZ1 | LYS | 251 | 8.015 | −3.461 | −18.478 | 1.00 | 0.00 |
| ATOM | 2431 | HZ2 | LYS | 251 | 9.095 | −2.696 | −19.538 | 1.00 | 0.00 |
| ATOM | 2432 | HZ3 | LYS | 251 | 7.805 | −1.824 | −18.854 | 1.00 | 0.00 |
| ATOM | 2433 | C | LYS | 251 | 12.281 | −6.529 | −14.273 | 1.00 | 31.19 |
| ATOM | 2434 | O | LYS | 251 | 12.298 | −7.107 | −13.187 | 1.00 | 32.83 |
| ATOM | 2435 | N | GLU | 252 | 12.577 | −4.221 | −15.372 | 1.00 | 27.48 |
| ATOM | 2436 | H | GLU | 252 | 12.735 | −6.759 | −16.224 | 1.00 | 0.00 |
| ATOM | 2437 | CA | GLU | 252 | 12.808 | −8.649 | −15.349 | 1.00 | 27.78 |
| ATOM | 2438 | CB | GLU | 252 | 12.753 | −9.113 | −16.799 | 1.00 | 33.80 |
| ATOM | 2439 | CG | GLU | 252 | 12.915 | −10.598 | −17.097 | 1.00 | 42.74 |
| ATOM | 2440 | CD | GLU | 252 | 13.832 | −10.890 | −18.277 | 1.00 | 44.39 |
| ATOM | 2441 | OE1 | GLU | 252 | 13.632 | −10.336 | −19.360 | 1.00 | 48.44 |
| ATOM | 2442 | OE2 | GLU | 252 | 14.760 | −11.678 | −18.098 | 1.00 | 45.82 |
| ATOM | 2443 | C | GLU | 252 | 14.140 | −9.005 | −14.690 | 1.00 | 24.46 |
| ATOM | 2444 | O | GLU | 252 | 15.182 | −8.416 | −14.990 | 1.00 | 23.91 |
| ATOM | 2445 | N | ALA | 253 | 14.133 | −9.980 | −13.786 | 1.00 | 22.26 |
| ATOM | 2446 | H | ALA | 253 | 13.277 | −10.377 | −13.540 | 1.00 | 0.00 |
| ATOM | 2447 | CA | ALA | 253 | 15.354 | −10.499 | −13.186 | 1.00 | 23.18 |
| ATOM | 2448 | CB | ALA | 253 | 15.051 | −11.274 | −11.919 | 1.00 | 20.69 |
| ATOM | 2449 | SG | ALA | 253 | 16.032 | −11.469 | −14.153 | 1.00 | 25.29 |
| ATOM | 2450 | C | ALA | 253 | 15.406 | −12.393 | −14.672 | 1.00 | 25.19 |
| ATOM | 2451 | O | ALA | 253 | 17.302 | −11.209 | −14.458 | 1.00 | 28.10 |
| ATOM | 2452 | N | CYS | 254 | 17.789 | −10.541 | −14.055 | 1.00 | 0.00 |
| ATOM | 2453 | CA | CYS | 254 | 18.009 | −12.221 | −15.306 | 1.00 | 32.61 |
| ATOM | 2454 | CB | CYS | 254 | 19.237 | −11.516 | −15.870 | 1.00 | 31.75 |
| ATOM | 2455 | SG | CYS | 254 | 20.443 | −12.611 | −16.651 | 1.00 | 32.44 |
| ATOM | 2456 | C | CYS | 254 | 18.385 | −13.402 | −14.414 | 1.00 | 36.58 |
| ATOM | 2457 | O | CYS | 254 | 19.302 | −13.243 | −13.604 | 1.00 | 32.66 |
| ATOM | 2458 | N | CYS | 254 | 17.736 | −14.582 | −14.469 | 1.00 | 42.06 |
| ATOM | 2459 | CD | PRO | 255 | 16.816 | −15.010 | −15.511 | 1.00 | 44.90 |
| ATOM | 2460 | CA | PRO | 255 | 17.881 | −15.667 | −13.508 | 1.00 | 46.64 |
| ATOM | 2461 | CB | PRO | 255 | 16.693 | −16.572 | −13.752 | 1.00 | 45.44 |
| ATOM | 2462 | CG | PRO | 255 | 15.803 | −15.772 | −14.666 | 1.00 | 45.18 |
| ATOM | 2463 | C | PRO | 255 | 19.209 | −16.379 | −13.699 | 1.00 | 52.71 |
| ATOM | 2464 | O | PRO | 255 | 19.967 | −16.514 | −12.736 | 1.00 | 51.83 |
| ATOM | 2465 | N | ASN | 256 | 19.423 | −16.849 | −14.938 | 1.00 | 57.99 |
| ATOM | 2466 | H | ASN | 256 | 18.668 | −16.918 | −15.559 | 1.00 | 0.00 |
| ATOM | 2467 | CA | ASN | 256 | 20.623 | −17.469 | −15.488 | 1.00 | 62.54 |
| ATOM | 2468 | CB | ASN | 256 | 21.441 | −18.299 | −14.490 | 1.00 | 65.25 |
| ATOM | 2469 | CG | ASN | 256 | 22.929 | −18.083 | −14.712 | 1.00 | 66.81 |
| ATOM | 2470 | OD1 | ASN | 256 | 23.634 | −17.431 | −13.921 | 1.00 | 57.18 |
| ATOM | 2471 | ND2 | ASN | 256 | 23.440 | −18.585 | −15.825 | 1.00 | 57.52 |

TABLE 23-continued

Coordinates for the 3D structure of ZAP-NC:ζ1 "dimer" structure
(two molecules of complex per unit cell)*

| | | | | | | | | |
|---|---|---|---|---|---|---|---|---|
| ATOM | 2472 | HD21 | ASN | 256 | 22.782 | −18.992 | −16.444 | 1.00 | 0.00 |
| ATOM | 2473 | HD22 | ASN | 256 | 24.395 | −18.528 | −15.990 | 1.00 | 0.00 |
| ATOM | 2474 | C | ASN | 256 | 20.177 | −18.438 | −16.589 | 1.00 | 64.50 |
| ATOM | 2475 | O | ASN | 256 | 20.971 | −18.719 | −17.481 | 1.00 | 67.70 |
| ATOM | 2476 | OT | ASN | 301 | 19.021 | −18.861 | −16.603 | 1.00 | 65.26 |
| ATOM | 2477 | CB | ASN | 301 | 36.860 | −2.320 | −19.345 | 1.00 | 69.57 |
| ATOM | 2478 | CG | ASN | 301 | 36.797 | −2.379 | −20.870 | 1.00 | 73.37 |
| ATOM | 2479 | OD1 | ASN | 301 | 35.914 | −1.729 | −21.445 | 1.00 | 74.19 |
| ATOM | 2480 | ND2 | ASN | 301 | 37.648 | −3.095 | −21.595 | 1.00 | 71.92 |
| ATOM | 2481 | HD21 | ASN | 301 | 38.347 | −3.615 | −21.146 | 1.00 | 0.00 |
| ATOM | 2482 | HD22 | ASN | 301 | 37.539 | −3.068 | −22.570 | 1.00 | 0.00 |
| ATOM | 2483 | C | ASN | 301 | 35.546 | −1.915 | −17.229 | 1.00 | 62.96 |
| ATOM | 2484 | O | ASN | 301 | 35.538 | −2.834 | −16.427 | 1.00 | 64.29 |
| ATOM | 2485 | HT1 | ASN | 301 | 35.437 | −0.113 | −19.057 | 1.00 | 0.00 |
| ATOM | 2486 | HT2 | ASN | 301 | 33.944 | −3.750 | −18.698 | 1.00 | 0.00 |
| ATOM | 2487 | N | ASN | 301 | 34.823 | −0.927 | −19.230 | 1.00 | 62.99 |
| ATOM | 2488 | HT2 | ASN | 301 | 34.663 | −1.030 | −20.256 | 1.00 | 0.00 |
| ATOM | 2489 | CA | ASN | 301 | 35.463 | −2.137 | −18.724 | 1.00 | 65.07 |
| ATOM | 2490 | N | GLN | 302 | 35.788 | −0.672 | −16.851 | 1.00 | 60.20 |
| ATOM | 2491 | H | GLN | 302 | 36.395 | −0.113 | −17.375 | 1.00 | 0.00 |
| ATOM | 2492 | CA | GLN | 302 | 35.444 | −0.176 | −15.522 | 1.00 | 56.74 |
| ATOM | 2493 | CB | GLN | 302 | 36.677 | 0.491 | −14.883 | 1.00 | 57.90 |
| ATOM | 2494 | CG | GLN | 302 | 37.907 | −0.432 | −14.691 | 1.00 | 63.47 |
| ATOM | 2495 | CD | GLN | 302 | 38.599 | −1.034 | −15.937 | 1.00 | 65.28 |
| ATOM | 2496 | OE1 | GLN | 302 | 38.352 | −0.683 | −17.103 | 1.00 | 66.79 |
| ATOM | 2497 | NE2 | GLN | 302 | 39.485 | −2.004 | −15.770 | 1.00 | 65.62 |
| ATOM | 2498 | HE21 | GLN | 302 | 39.677 | −2.304 | −14.860 | 1.00 | 0.00 |
| ATOM | 2499 | HE22 | GLN | 302 | 39.918 | −2.371 | −16.565 | 1.00 | 0.00 |
| ATOM | 2500 | C | GLN | 302 | 34.361 | 0.845 | −15.961 | 1.00 | 53.62 |
| ATOM | 2501 | O | GLN | 302 | 33.831 | 0.670 | −17.088 | 1.00 | 54.45 |
| ATOM | 2502 | N | LEU | 303 | 34.058 | 1.917 | −15.204 | 1.00 | 44.49 |
| ATOM | 2503 | H | LEU | 303 | 34.536 | 2.006 | −15.354 | 1.00 | 0.00 |
| ATOM | 2504 | CA | LEU | 303 | 33.028 | 2.927 | −15.484 | 1.00 | 34.84 |
| ATOM | 2505 | CB | LEU | 303 | 32.632 | 3.417 | −16.940 | 1.00 | 31.82 |
| ATOM | 2506 | CG | LEU | 303 | 33.369 | 4.825 | −17.292 | 1.00 | 30.98 |
| ATOM | 2507 | CD1 | LEU | 303 | 34.886 | 4.916 | −17.295 | 1.00 | 31.39 |
| ATOM | 2508 | CD2 | LEU | 303 | 32.860 | 5.183 | −18.676 | 1.00 | 32.60 |
| ATOM | 2509 | C | LEU | 303 | 31.624 | 2.471 | −15.160 | 1.00 | 31.46 |
| ATOM | 2510 | O | LEU | 303 | 30.919 | 1.703 | −15.820 | 1.00 | 30.31 |
| ATOM | 2511 | N | PTY | 304 | 31.253 | 2.987 | −14.015 | 1.00 | 29.09 |
| ATOM | 2512 | H | PTY | 304 | 31.821 | 3.642 | −13.563 | 1.00 | 0.00 |
| ATOM | 2513 | CA | PTY | 304 | 29.936 | 2.775 | −13.481 | 1.00 | 25.08 |
| ATOM | 2514 | CB | PTY | 304 | 30.043 | 2.545 | −11.983 | 1.00 | 22.52 |
| ATOM | 2515 | CG | PTY | 304 | 30.722 | 1.239 | −11.678 | 1.00 | 20.76 |
| ATOM | 2516 | CD1 | PTY | 304 | 29.995 | 0.026 | −11.631 | 1.00 | 19.61 |
| ATOM | 2517 | CE1 | PTY | 304 | 30.618 | −1.204 | −11.387 | 1.00 | 18.55 |
| ATOM | 2518 | CD2 | PTY | 304 | 32.114 | 1.170 | −11.468 | 1.00 | 23.88 |
| ATOM | 2519 | CE2 | PTY | 304 | 32.746 | −0.058 | −11.223 | 1.00 | 28.36 |
| ATOM | 2520 | CZ | PTY | 304 | 32.004 | −1.261 | −11.185 | 1.00 | 23.76 |
| ATOM | 2521 | OH | PTY | 304 | 32.693 | −2.423 | −10.923 | 1.00 | 28.36 |
| ATOM | 2522 | OR1 | PTY | 304 | 32.971 | −4.897 | −11.058 | 1.00 | 28.97 |
| ATOM | 2523 | OR2 | PTY | 304 | 34.118 | −3.534 | −12.638 | 1.00 | 33.20 |
| ATOM | 2524 | OR3 | PTY | 304 | 31.717 | −3.857 | −12.879 | 1.00 | 30.35 |
| ATOM | 2525 | PR | PTY | 304 | 32.822 | −3.701 | −11.913 | 1.00 | 29.14 |
| ATOM | 2526 | C | PTY | 304 | 29.189 | 4.049 | −13.805 | 1.00 | 24.98 |
| ATOM | 2527 | O | PTY | 304 | 29.765 | 5.121 | −14.023 | 1.00 | 32.82 |
| ATOM | 2528 | N | ASN | 305 | 27.890 | 3.929 | −13.870 | 1.00 | 23.83 |
| ATOM | 2529 | H | ASN | 305 | 27.489 | 3.081 | −13.594 | 1.00 | 0.00 |
| ATOM | 2530 | CA | ASN | 305 | 27.030 | 5.042 | −14.190 | 1.00 | 24.41 |
| ATOM | 2531 | CB | ASN | 305 | 25.758 | 4.572 | −14.824 | 1.00 | 26.42 |
| ATOM | 2532 | CG | ASN | 305 | 25.898 | 3.944 | −16.184 | 1.00 | 24.24 |
| ATOM | 2533 | OD1 | ASN | 305 | 25.035 | 4.171 | −17.007 | 1.00 | 33.32 |
| ATOM | 2534 | ND2 | ASN | 305 | 26.883 | 3.141 | −16.534 | 1.00 | 27.31 |
| ATOM | 2535 | HD21 | ASN | 305 | 27.568 | 2.878 | −15.888 | 1.00 | 0.00 |
| ATOM | 2536 | HD22 | ASN | 305 | 26.910 | 2.846 | −17.468 | 1.00 | 0.00 |
| ATOM | 2537 | C | ASN | 305 | 26.646 | 5.788 | −12.931 | 1.00 | 26.89 |
| ATOM | 2538 | O | ASN | 305 | 26.463 | 5.181 | −11.870 | 1.00 | 26.21 |
| ATOM | 2539 | N | GLU | 306 | 26.502 | 7.098 | −13.029 | 1.00 | 26.87 |
| ATOM | 2540 | H | GLU | 306 | 26.619 | 7.529 | −13.901 | 1.00 | 0.00 |
| ATOM | 2541 | CA | GLU | 306 | 26.053 | 7.888 | −11.905 | 1.00 | 29.02 |
| ATOM | 2542 | CB | GLU | 306 | 26.708 | 9.275 | −11.886 | 1.00 | 32.98 |
| ATOM | 2543 | CG | GLU | 306 | 26.553 | 10.101 | −13.156 | 1.00 | 35.35 |
| ATOM | 2544 | CD | GLU | 306 | 26.731 | 11.581 | −12.905 | 1.00 | 36.20 |
| ATOM | 2545 | OE1 | GLU | 306 | 25.760 | 12.318 | −13.089 | 1.00 | 39.79 |
| ATOM | 2546 | OE2 | GLU | 306 | 27.833 | 11.985 | −12.528 | 1.00 | 39.08 |
| ATOM | 2547 | C | GLU | 306 | 24.554 | 8.067 | −12.017 | 1.00 | 26.18 |

TABLE 23-continued

Coordinates for the 3D structure of ZAP-NC:ζ1 "dimer" structure
(two molecules of complex per unit cell)*

| ATOM | 2548 | O | GLU | 306 | 23.999 | 7.923 | −13.109 | 1.00 | 26.43 |
|---|---|---|---|---|---|---|---|---|---|
| ATOM | 2549 | N | LEU | 307 | 23.926 | 8.432 | −10.904 | 1.00 | 26.19 |
| ATOM | 2550 | H | LEU | 307 | 24.434 | 8.578 | −10.080 | 1.00 | 0.00 |
| ATOM | 2551 | CA | LEU | 307 | 22.512 | 8.679 | −10.915 | 1.00 | 26.40 |
| ATOM | 2552 | CB | LEU | 307 | 21.819 | 8.244 | −9.639 | 1.00 | 28.26 |
| ATOM | 2553 | CG | LEU | 307 | 22.362 | 8.248 | −8.253 | 1.00 | 30.34 |
| ATOM | 2554 | CD1 | LEU | 307 | 21.230 | 8.042 | −7.267 | 1.00 | 31.01 |
| ATOM | 2555 | CD2 | LEU | 307 | 23.357 | 7.136 | −8.115 | 1.00 | 28.88 |
| ATOM | 2556 | C | LEU | 307 | 22.119 | 10.118 | −11.130 | 1.00 | 25.17 |
| ATOM | 2557 | O | LEU | 307 | 22.824 | 11.077 | −10.810 | 1.00 | 25.91 |
| ATOM | 2558 | N | ASN | 308 | 20.929 | 10.231 | −11.692 | 1.00 | 23.16 |
| ATOM | 2559 | H | ASN | 308 | 20.474 | 9.395 | −11.916 | 1.00 | 0.00 |
| ATOM | 2560 | CA | ASN | 308 | 20.285 | 11.497 | −11.977 | 1.00 | 22.52 |
| ATOM | 2561 | CB | ASN | 308 | 19.149 | 11.318 | −12.993 | 1.00 | 22.41 |
| ATOM | 2562 | CG | ASN | 308 | 19.569 | 10.764 | −14.349 | 1.00 | 17.49 |
| ATOM | 2563 | OD1 | ASN | 308 | 20.482 | 11.269 | −15.006 | 1.00 | 18.25 |
| ATOM | 2564 | ND2 | ASN | 308 | 18.899 | 97.12 | −14.812 | 1.00 | 12.44 |
| ATOM | 2565 | HD21 | ASN | 308 | 18.211 | 92.90 | −14.262 | 1.00 | 0.00 |
| ATOM | 2566 | HD22 | ASN | 308 | 19.116 | 94.03 | −15.722 | 1.00 | 0.00 |
| ATOM | 2567 | C | LEU | 309 | 19.714 | 11.910 | −10.638 | 1.00 | 23.34 |
| ATOM | 2568 | O | LEU | 309 | 18.580 | 11.582 | −10.279 | 1.00 | 19.95 |
| ATOM | 2569 | N | LEU | 309 | 20.511 | 12.640 | −9.874 | 1.00 | 29.40 |
| ATOM | 2570 | H | LEU | 309 | 21.402 | 12.862 | −10.222 | 1.00 | 0.00 |
| ATOM | 2571 | CA | LEU | 309 | 20.143 | 13.022 | −8.516 | 1.00 | 31.98 |
| ATOM | 2572 | CB | LEU | 309 | 21.281 | 13.803 | −7.886 | 1.00 | 31.78 |
| ATOM | 2573 | CG | LEU | 309 | 22.549 | 13.034 | −7.551 | 1.00 | 30.04 |
| ATOM | 2574 | CD1 | LEU | 309 | 23.498 | 13.976 | −6.828 | 1.00 | 32.49 |
| ATOM | 2575 | CD2 | LEU | 309 | 22.233 | 11.839 | −6.670 | 1.00 | 29.67 |
| ATOM | 2576 | C | LEU | 309 | 18.857 | 13.811 | −8.352 | 1.00 | 32.71 |
| ATOM | 2577 | O | LEU | 309 | 18.184 | 1.367 | −7.327 | 1.00 | 33.18 |
| ATOM | 2578 | N | GLY | 310 | 18.453 | 14.571 | −9.376 | 1.00 | 29.51 |
| ATOM | 2579 | H | GLY | 310 | 18.976 | 14.564 | −10.197 | 1.00 | 0.00 |
| ATOM | 2580 | CA | GLY | 310 | 17.179 | 15.284 | −9.330 | 1.00 | 27.02 |
| ATOM | 2581 | C | GLY | 310 | 15.983 | 14.351 | −9.552 | 1.00 | 26.12 |
| ATOM | 2582 | O | GLY | 310 | 14.841 | 14.792 | −9.660 | 1.00 | 24.61 |
| ATOM | 2583 | N | ARG | 311 | 16.223 | 13.050 | −9.692 | 1.00 | 26.37 |
| ATOM | 2584 | H | ARG | 311 | 17.136 | 12.716 | −9.635 | 1.00 | 0.00 |
| ATOM | 2585 | CA | ARG | 311 | 15.167 | 12.087 | −9.890 | 1.00 | 26.85 |
| ATOM | 2586 | CB | ARG | 311 | 15.520 | 11.222 | −11.115 | 1.00 | 28.37 |
| ATOM | 2587 | CG | ARG | 311 | 15.337 | 11.959 | −12.441 | 1.00 | 22.17 |
| ATOM | 2588 | CD | ARG | 311 | 13.858 | 12.286 | −12.617 | 1.00 | 20.22 |
| ATOM | 2589 | NE | ARG | 311 | 13.085 | 11.087 | −12.889 | 1.00 | 22.46 |
| ATOM | 2590 | HE | ARG | 311 | 13.270 | 10.598 | −13.718 | 1.00 | 0.00 |
| ATOM | 2591 | CZ | ARG | 311 | 12.120 | 10.608 | −12.098 | 1.00 | 30.68 |
| ATOM | 2592 | NH1 | ARG | 311 | 11.757 | 11.199 | −10.944 | 1.00 | 37.34 |
| ATOM | 2593 | HH11 | ARG | 311 | 12.203 | 12.040 | −10.636 | 1.00 | 00.0 |
| ATOM | 2594 | HH12 | ARG | 311 | 11.030 | 10.791 | −10.389 | 1.00 | 00.0 |
| ATOM | 2595 | NH2 | ARG | 311 | 11.490 | 9.497 | −12.482 | 1.00 | 24.13 |
| ATOM | 2596 | HH21 | ARG | 311 | 11.739 | 9.048 | −13.337 | 1.00 | 0.00 |
| ATOM | 2597 | HH22 | ARG | 311 | 10.779 | 9.100 | −11.899 | 1.00 | 0.00 |
| ATOM | 2598 | C | ARG | 311 | 14.970 | 11.229 | −8.650 | 1.00 | 26.76 |
| ATOM | 2599 | O | ARG | 311 | 14.321 | 10.178 | −8.704 | 1.00 | 27.21 |
| ATOM | 2600 | N | ARG | 312 | 15.562 | 11.638 | −7.528 | 1.00 | 24.91 |
| ATOM | 2601 | H | ARG | 312 | 16.027 | 12.501 | −7.525 | 1.00 | 00.0 |
| ATOM | 2602 | CA | ARG | 312 | 15.398 | 10.930 | −6.245 | 1.00 | 19.46 |
| ATOM | 2603 | CB | ARG | 312 | 16.685 | 10.983 | −5.444 | 1.00 | 18.55 |
| ATOM | 2604 | CG | ARG | 312 | 17.790 | 10.119 | −6.047 | 1.00 | 18.34 |
| ATOM | 2605 | CD | ARG | 312 | 19.017 | 10.171 | −5.167 | 1.00 | 16.42 |
| ATOM | 2606 | NE | ARG | 312 | 18.651 | 10.046 | −3.764 | 1.00 | 12.29 |
| ATOM | 2607 | HE | ARG | 312 | 17.873 | 9.507 | −3.514 | 1.00 | 00.0 |
| ATOM | 2608 | CZ | ARG | 312 | 19.374 | 10.627 | −2.804 | 1.00 | 18.47 |
| ATOM | 2609 | NH1 | ARG | 312 | 20.476 | 11.346 | −3.081 | 1.00 | 12.42 |
| ATOM | 2610 | HH11 | ARG | 312 | 20.781 | 11.451 | −4.026 | 1.00 | 0.00 |
| ATOM | 2611 | HH12 | ARG | 312 | 20.990 | 11.774 | −2.338 | 1.00 | 0.00 |
| ATOM | 2612 | NH2 | ARG | 312 | 18.965 | 10.470 | −1.542 | 1.00 | 17.98 |
| ATOM | 2613 | HH21 | ARG | 312 | 18.143 | 99.932 | −1.353 | 1.00 | 0.00 |
| ATOM | 2614 | HH22 | ARG | 312 | 19.483 | 10.878 | −0.791 | 1.00 | 0.00 |
| ATOM | 2615 | C | ARG | 312 | 14.335 | 11.688 | −5.435 | 1.00 | 16.16 |
| ATOM | 2616 | O | ARG | 312 | 14.101 | 12.879 | −5.676 | 1.00 | 12.19 |
| ATOM | 2617 | N | GLU | 313 | 13.665 | 10.995 | −4.505 | 1.00 | 13.42 |
| ATOM | 2618 | H | GLU | 313 | 13.870 | 10.047 | −4.350 | 1.00 | 0.00 |
| ATOM | 2619 | CA | GLU | 313 | 12.720 | 11.659 | −3.609 | 1.00 | 11.44 |
| ATOM | 2620 | CB | GLU | 313 | 11.866 | 10.690 | −2.822 | 1.00 | 8.28 |
| ATOM | 2621 | CG | GLU | 313 | 10.908 | 9.792 | −3.562 | 1.00 | 12.05 |
| ATOM | 2622 | CD | GLU | 313 | 9.671 | 10.432 | −4.151 | 1.00 | 13.52 |
| ATOM | 2623 | OE1 | GLU | 313 | 9.666 | 11.623 | −4.445 | 1.00 | 17.14 |

TABLE 23-continued

Coordinates for the 3D structure of ZAP-NC:ζ1 "dimer" structure
(two molecules of complex per unit cell)*

| ATOM | 2624 | OE2 | GLU | 313 | 8.694 | 9.715 | −4.345 | 1.00 | 12.82 |
|---|---|---|---|---|---|---|---|---|---|
| ATOM | 2625 | C | GLU | 313 | 13.465 | 12.489 | −2.568 | 1.00 | 8.47 |
| ATOM | 2626 | O | GLU | 313 | 14.571 | 12.145 | −2.119 | 1.00 | 10.79 |
| ATOM | 2627 | N | GLU | 314 | 12.855 | 13.568 | −2.125 | 1.00 | 11.58 |
| ATOM | 2628 | H | GLU | 314 | 11.943 | 13.768 | −2.434 | 1.00 | 0.00 |
| ATOM | 2629 | CA | GLU | 314 | 13.460 | 14.406 | −1.119 | 1.00 | 17.11 |
| ATOM | 2630 | CB | GLU | 314 | 13.182 | 15.876 | −1.474 | 1.00 | 27.79 |
| ATOM | 2631 | CG | GLU | 314 | 14.202 | 16.886 | −0.930 | 1.00 | 39.55 |
| ATOM | 2632 | CD | GLU | 314 | 13.586 | 18.089 | −0.219 | 1.00 | 47.02 |
| ATOM | 2633 | OE1 | GLU | 314 | 13.940 | 18.333 | −0.940 | 1.00 | 45.05 |
| ATOM | 2634 | OE2 | GLU | 314 | 12.756 | 18.772 | −0.825 | 1.00 | 50.75 |
| ATOM | 2635 | C | GLU | 314 | 12.835 | 14.037 | −0.226 | 1.00 | 11.85 |
| ATOM | 2636 | O | GLU | 314 | 11.606 | 13.917 | −0.331 | 1.00 | 7.93 |
| ATOM | 2637 | N | GLU | 314 | 13.660 | 13.816 | −1.254 | 1.00 | 12.01 |
| ATOM | 2638 | H | GLU | 314 | 14.628 | 13.926 | −1.152 | 1.00 | 0.00 |
| ATOM | 2539 | CA | PTY | 315 | 13.156 | 13.592 | 2.607 | 1.00 | 12.93 |
| ATOM | 2640 | CB | PTY | 315 | 13.178 | 12.317 | 3.224 | 1.00 | 12.89 |
| ATOM | 2641 | CG | PTY | 315 | 13.105 | 11.093 | 2.629 | 1.00 | 10.77 |
| ATOM | 2642 | CD1 | PTY | 315 | 11.907 | 10.560 | 3.135 | 1.00 | 4.78 |
| ATOM | 2643 | CE1 | PTY | 315 | 11.301 | 9.445 | 2.546 | 1.00 | 10.51 |
| ATOM | 2644 | CD2 | PTY | 315 | 13.680 | 10.470 | 1.504 | 1.00 | 10.84 |
| ATOM | 2645 | CE2 | PTY | 315 | 13.085 | 9.361 | 0.895 | 1.00 | 11.24 |
| ATOM | 2646 | CZ | PTY | 315 | 11.887 | 8.828 | 1.407 | 1.00 | 12.06 |
| ATOM | 2647 | OH | PTY | 315 | 11.369 | 7.695 | 0.799 | 1.00 | 10.74 |
| ATOM | 2648 | OR1 | PTY | 315 | 9.804 | 6.760 | −0.809 | 1.00 | 19.02 |
| ATOM | 2649 | OR2 | PTY | 315 | 9.041 | 8.574 | 0.508 | 1.00 | 16.68 |
| ATOM | 2650 | OR3 | PTY | 315 | 9.423 | 6.511 | 1.512 | 1.00 | 18.31 |
| ATOM | 2651 | PR | PTY | 315 | 9.871 | 7.408 | 0.478 | 1.00 | 5.42 |
| ATOM | 2652 | C | PTY | 315 | 13.603 | 14.774 | 3.451 | 1.00 | 12.45 |
| ATOM | 2653 | O | ASP | 316 | 14.708 | 15.396 | 3.294 | 1.00 | 12.95 |
| ATOM | 2654 | N | ASP | 316 | 12.738 | 15.212 | 4.343 | 1.00 | 15.05 |
| ATOM | 2655 | H | ASP | 316 | 11.936 | 14.675 | 4.511 | 1.00 | 0.00 |
| ATOM | 2656 | CA | ASP | 316 | 13.002 | 16.360 | 5.173 | 1.00 | 13.90 |
| ATOM | 2657 | CB | ASP | 316 | 11.688 | 16.931 | 5.649 | 1.00 | 16.18 |
| ATOM | 2658 | CG | ASP | 316 | 10.975 | 17.923 | 4.741 | 1.00 | 20.73 |
| ATOM | 2659 | OD1 | ASP | 316 | 10.924 | 17.743 | 3.529 | 1.00 | 19.42 |
| ATOM | 2660 | OD2 | ASP | 316 | 10.443 | 18.893 | 5.274 | 1.00 | 27.82 |
| ATOM | 2661 | C | ASP | 316 | 13.866 | 15.995 | 6.357 | 1.00 | 14.41 |
| ATOM | 2662 | O | ASP | 316 | 13.970 | 14.838 | 6.776 | 1.00 | 15.75 |
| ATOM | 2663 | N | VAL | 317 | 14.519 | 17.004 | 6.913 | 1.00 | 15.30 |
| ATOM | 2664 | H | VAL | 317 | 14.334 | 17.922 | 6.631 | 1.00 | 0.00 |
| ATOM | 2665 | CA | VAL | 317 | 15.385 | 16.846 | 8.073 | 1.00 | 14.94 |
| ATOM | 2666 | CB | VAL | 317 | 16.858 | 17.146 | 7.739 | 1.00 | 14.44 |
| ATOM | 2667 | CG1 | VAL | 317 | 17.448 | 15.947 | 7.004 | 1.00 | 15.76 |
| ATOM | 2668 | CG2 | VAL | 317 | 16.981 | 18.357 | 6.832 | 1.00 | 16.92 |
| ATOM | 2669 | C | VAL | 317 | 14.871 | 17.842 | 9.083 | 1.00 | 14.10 |
| ATOM | 2670 | O | VAL | 317 | 14.248 | 18.845 | 8.712 | 1.00 | 17.30 |
| ATOM | 2671 | N | LEU | 318 | 15.029 | 17.480 | 10.349 | 1.00 | 12.16 |
| ATOM | 2672 | H | LEU | 318 | 15.548 | 16.671 | 10.535 | 1.00 | 0.00 |
| ATOM | 2673 | CA | LEU | 318 | 14.624 | 18.329 | 11.451 | 1.00 | 14.05 |
| ATOM | 2674 | CB | LEU | 318 | 14.818 | 17.637 | 12.790 | 1.00 | 13.29 |
| ATOM | 2675 | CG | LEU | 318 | 14.067 | 16.364 | 13.069 | 1.00 | 4.19 |
| ATOM | 2676 | CD1 | LEU | 318 | 14.669 | 15.703 | 14.270 | 1.00 | 3.04 |
| ATOM | 2677 | CD2 | LEU | 318 | 12.625 | 16.643 | 13.287 | 1.00 | 2.00 |
| ATOM | 2678 | C | LEU | 318 | 15.537 | 19.537 | 11.433 | 1.00 | 16.18 |
| ATOM | 2679 | O | LEU | 318 | 16.665 | 19.398 | 10.961 | 1.00 | 13.67 |
| ATOM | 2680 | N | ASP | 319 | 15.117 | 20.707 | 11.882 | 1.00 | 26.49 |
| ATOM | 2681 | H | ASP | 319 | 14.247 | 20.848 | 12.302 | 1.00 | 0.00 |
| ATOM | 2682 | CA | ASP | 319 | 16.062 | 21.792 | 11.942 | 1.00 | 34.53 |
| ATOM | 2683 | CB | ASP | 319 | 15.636 | 22.871 | 10.880 | 1.00 | 39.93 |
| ATOM | 2684 | CG | ASP | 319 | 14.637 | 23.977 | 11.210 | 1.00 | 46.93 |
| ATOM | 2685 | OD1 | ASP | 319 | 13.509 | 23.928 | 10.710 | 1.00 | 52.84 |
| ATOM | 2686 | OD2 | ASP | 319 | 15.003 | 24.906 | 11.941 | 1.00 | 52.04 |
| ATOM | 2687 | C | ASP | 319 | 16.064 | 22.270 | 13.401 | 1.00 | 36.49 |
| ATOM | 2688 | O | ASP | 319 | 14.996 | 22.586 | 13.944 | 1.00 | 37.04 |
| ATOM | 2689 | OT | ASP | 319 | 17.140 | 22.239 | 14.004 | 1.00 | 36.34 |
| ATOM | 2690 | CB | ASP | 1003 | 43.142 | −13.016 | 13.156 | 1.00 | 53.93 |
| ATOM | 2691 | CG | ASP | 1003 | 43.106 | −12.430 | 14.568 | 1.00 | 55.01 |
| ATOM | 2692 | OD1 | ASP | 1003 | 44.109 | −11.869 | 15.000 | 1.00 | 54.01 |
| ATOM | 2693 | OD2 | ASP | 1003 | 42.091 | −12.567 | 15.252 | 1.00 | 58.11 |
| ATOM | 2694 | C | ASP | 1003 | 44.166 | −11.129 | 11.729 | 1.00 | 46.97 |
| ATOM | 2695 | O | ASP | 1003 | 45.204 | −11.666 | 11.320 | 1.00 | 50.37 |
| ATOM | 2696 | HT1 | ASP | 1003 | 44.012 | −13.030 | 10.569 | 1.00 | 0.00 |
| ATOM | 2697 | HT2 | ASP | 1003 | 42.591 | −12.376 | 9.952 | 1.00 | 0.00 |
| ATOM | 2698 | N | ASP | 1003 | 42.996 | −12.885 | 10.758 | 1.00 | 53.96 |
| ATOM | 2699 | HT3 | ASP | 1003 | 42.524 | −13.800 | 10.916 | 1.00 | 0.00 |

TABLE 23-continued

Coordinates for the 3D structure of ZAP-NC:ζ1 "dimer" structure
(two molecules of complex per unit cell)*

| ATOM | 2700 | CA  | ASP | 1003 | 42.970 | −12.063 | 11.955 | 1.00 | 49.69 |
|------|------|-----|-----|------|--------|---------|--------|------|-------|
| ATOM | 2701 | N   | PRO | 1004 | 44.151 | −9.802  | 11.904 | 1.00 | 43.37 |
| ATOM | 2702 | CD  | PRO | 1004 | 42.945 | −8.991  | 12.008 | 1.00 | 42.38 |
| ATOM | 2703 | CA  | PRO | 1004 | 45.344 | −8.948  | 11.771 | 1.00 | 42.64 |
| ATOM | 2704 | CB  | PRO | 1004 | 44.794 | −7.522  | 11.801 | 1.00 | 39.86 |
| ATOM | 2705 | CG  | PRO | 1004 | 43.467 | −7.643  | 12.503 | 1.00 | 40.49 |
| ATOM | 2706 | C   | PRO | 1004 | 46.477 | −9.175  | 12.780 | 1.00 | 41.41 |
| ATOM | 2707 | O   | PRO | 1004 | 47.559 | −8.570  | 12.685 | 1.00 | 39.94 |
| ATOM | 2708 | N   | ALA | 1005 | 46.242 | −10.044 | 13.772 | 1.00 | 39.65 |
| ATOM | 2709 | H   | ALA | 1005 | 45.323 | −10.276 | 14.007 | 1.00 | 0.00  |
| ATOM | 2710 | CA  | ALA | 1005 | 47.290 | −10.440 | 14.688 | 1.00 | 31.86 |
| ATOM | 2711 | CB  | ALA | 1005 | 46.785 | −10.334 | 16.117 | 1.00 | 30.50 |
| ATOM | 2712 | C   | ALA | 1005 | 47.801 | −11.850 | 14.451 | 1.00 | 28.13 |
| ATOM | 2713 | O   | ALA | 1005 | 48.889 | −12.126 | 14.931 | 1.00 | 27.62 |
| ATOM | 2714 | N   | ALA | 1006 | 47.227 | −12.783 | 13.671 | 1.00 | 30.30 |
| ATOM | 2715 | H   | ALA | 1006 | 46.450 | −12.533 | 13.136 | 1.00 | 0.00  |
| ATOM | 2716 | CA  | ALA | 1006 | 47.757 | −14.165 | 13.610 | 1.00 | 29.17 |
| ATOM | 2717 | CB  | ALA | 1006 | 46.836 | −15.035 | 12.767 | 1.00 | 31.01 |
| ATOM | 2718 | C   | ALA | 1006 | 49.186 | −14.409 | 13.109 | 1.00 | 29.99 |
| ATOM | 2719 | O   | ALA | 1006 | 49.832 | −15.435 | 13.328 | 1.00 | 30.85 |
| ATOM | 2720 | N   | HIS | 1007 | 49.713 | −13.387 | 12.465 | 1.00 | 29.64 |
| ATOM | 2721 | H   | HIS | 1007 | 49.168 | −12.584 | 12.420 | 1.00 | 0.00  |
| ATOM | 2722 | CA  | HIS | 1007 | 51.077 | −13.401 | 11.952 | 1.00 | 31.60 |
| ATOM | 2723 | CB  | HIS | 1007 | 51.162 | −12.602 | 10.648 | 1.00 | 32.94 |
| ATOM | 2724 | CG  | HIS | 1007 | 50.861 | −11.131 | 10.902 | 1.00 | 36.73 |
| ATOM | 2725 | CD2 | HIS | 1007 | 49.606 | −10.560 | 10.876 | 1.00 | 38.63 |
| ATOM | 2726 | ND1 | HIS | 1007 | 51.734 | −10.193 | 11.247 | 1.00 | 39.17 |
| ATOM | 2727 | HD1 | HIS | 1007 | 52.690 | −10.342 | 11.446 | 1.00 | 0.00  |
| ATOM | 2728 | CE1 | HIS | 1007 | 51.062 | −9.078  | 11.434 | 1.00 | 41.04 |
| ATOM | 2729 | NE2 | HIS | 1007 | 49.789 | −9.313  | 11.213 | 1.00 | 40.15 |
| ATOM | 2730 | HE2 | HIS | 1007 | 49.059 | −8.678  | 11.422 | 1.00 | 0.00  |
| ATOM | 2731 | C   | HIS | 1007 | 52.050 | −12.781 | 12.946 | 1.00 | 30.36 |
| ATOM | 2732 | O   | HIS | 1007 | 53.158 | −12.386 | 12.576 | 1.00 | 31.97 |
| ATOM | 2733 | N   | LEU | 1008 | 51.592 | −12.480 | 14.151 | 1.00 | 26.41 |
| ATOM | 2734 | H   | LEU | 1008 | 50.742 | −12.852 | 14.476 | 1.00 | 0.00  |
| ATOM | 2735 | CA  | LEU | 1008 | 52.427 | −11.828 | 15.126 | 1.00 | 24.03 |
| ATOM | 2736 | CB  | LEU | 1008 | 51.558 | −10.849 | 15.911 | 1.00 | 20.44 |
| ATOM | 2737 | CG  | LEU | 1008 | 51.829 | −9.348  | 15.835 | 1.00 | 19.01 |
| ATOM | 2738 | CD1 | LEU | 1008 | 52.484 | −8.962  | 14.531 | 1.00 | 15.31 |
| ATOM | 2739 | CD2 | LEU | 1008 | 50.513 | −8.620  | 16.018 | 1.00 | 18.56 |
| ATOM | 2740 | C   | LEU | 1008 | 52.963 | −12.958 | 15.979 | 1.00 | 24.31 |
| ATOM | 2741 | O   | LEU | 1008 | 52.181 | −13.829 | 16.350 | 1.00 | 21.63 |
| ATOM | 2742 | N   | PRO | 1009 | 54.245 | −13.032 | 16.334 | 1.00 | 25.92 |
| ATOM | 2743 | CD  | PRO | 1009 | 55.280 | −12.055 | 15.973 | 1.00 | 29.07 |
| ATOM | 2744 | CA  | PRO | 1009 | 54.787 | −14.159 | 17.084 | 1.00 | 26.60 |
| ATOM | 2745 | CB  | PRO | 1009 | 56.285 | −14.047 | 16.806 | 1.00 | 28.94 |
| ATOM | 2746 | CG  | PRO | 1009 | 56.538 | −12.546 | 16.691 | 1.00 | 27.11 |
| ATOM | 2747 | C   | PRO | 1009 | 54.405 | −14.163 | 18.566 | 1.00 | 24.10 |
| ATOM | 2748 | O   | PRO | 1009 | 54.692 | −15.112 | 19.397 | 1.00 | 25.51 |
| ATOM | 2749 | N   | PHE | 1010 | 53.788 | −13.089 | 19.060 | 1.00 | 20.53 |
| ATOM | 2750 | H   | PHE | 1010 | 53.497 | −12.388 | 18.445 | 1.00 | 0.00  |
| ATOM | 2751 | CA  | PHE | 1010 | 53.398 | −12.960 | 20.459 | 1.00 | 20.39 |
| ATOM | 2752 | CB  | PHE | 1010 | 53.950 | −11.636 | 21.035 | 1.00 | 19.73 |
| ATOM | 2753 | CG  | PHE | 1010 | 53.756 | −10.406 | 20.161 | 1.00 | 16.45 |
| ATOM | 2754 | CD1 | PHE | 1010 | 52.546 | −97.28   | 20.140 | 1.00 | 17.02 |
| ATOM | 2755 | CD2 | PHE | 1010 | 54.816 | −99.58   | 19.376 | 1.00 | 23.44 |
| ATOM | 2756 | CE1 | PHE | 1010 | 52.397 | −85.99   | 19.332 | 1.00 | 21.75 |
| ATOM | 2757 | CE2 | PHE | 1010 | 54.667 | −88.27   | 18.567 | 1.00 | 21.56 |
| ATOM | 2758 | C   | PHE | 1010 | 53.456 | −81.42   | 18.544 | 1.00 | 18.10 |
| ATOM | 2759 | O   | PHE | 1010 | 61.888 | −13.006 | 20.636 | 1.00 | 20.98 |
| ATOM | 2760 | N   | PHE | 1010 | 51.374 | −12.658 | 21.699 | 1.00 | 20.72 |
| ATOM | 2761 | H   | PHE | 1011 | 51.182 | −13.399 | 19.565 | 1.00 | 15.13 |
| ATOM | 2762 | CA  | PHE | 1011 | 51.635 | −13.830 | 18.814 | 1.00 | 0.00  |
| ATOM | 2763 | CB  | PHE | 1011 | 59.748 | −13.457 | 19.567 | 1.00 | 11.64 |
| ATOM | 2764 | CG  | PHE | 1011 | 49.224 | −13.105 | 18.175 | 1.00 | 93.9  |
| ATOM | 2765 | CG  | PHE | 1011 | 47.716 | −13.279 | 18.066 | 1.00 | 10.72 |
| ATOM | 2766 | CD1 | PHE | 1011 | 46.856 | −12.628 | 18.960 | 1.00 | 78.5  |
| ATOM | 2767 | CD2 | PHE | 1011 | 47.200 | −14.136 | 17.096 | 1.00 | 90.6  |
| ATOM | 2768 | CE1 | PHE | 1011 | 45.488 | −12.846 | 18.889 | 1.00 | 45.5  |
| ATOM | 2769 | CE2 | PHE | 1011 | 45.824 | −14.347 | 17.029 | 1.00 | 93.7  |
| ATOM | 2770 | CZ  | PHE | 1011 | 44.974 | −13.702 | 17.929 | 1.00 | 7.19  |
| ATOM | 2771 | C   | PHE | 1011 | 49.413 | −14.891 | 19.933 | 1.00 | 13.64 |
| ATOM | 2772 | O   | PHE | 1011 | 49.963 | −15.834 | 19.365 | 1.00 | 13.56 |
| ATOM | 2773 | N   | TYR | 1012 | 48.496 | −15.092 | 20.870 | 1.00 | 13.88 |
| ATOM | 2774 | H   | TYR | 1012 | 48.085 | −14.317 | 21.306 | 1.00 | 0.00  |
| ATOM | 2775 | CA  | TYR | 1012 | 48.204 | −16.427 | 21.346 | 1.00 | 14.06 |

TABLE 23-continued

Coordinates for the 3D structure of ZAP-NC:ζ1 "dimer" structure
(two molecules of complex per unit cell)*

| ATOM | 2776 | CB | TYR | 1012 | 48.456 | −16.449 | 22.842 | 1.00 | 13.70 |
|---|---|---|---|---|---|---|---|---|---|
| ATOM | 2777 | CG | TYR | 1012 | 49.930 | −16.553 | 23.172 | 1.00 | 10.19 |
| ATOM | 2778 | CD1 | TYR | 1012 | 50.738 | −15.427 | 23.116 | 1.00 | 8.33 |
| ATOM | 2779 | CD2 | TYR | 1012 | 52.086 | −15.504 | 23.417 | 1.00 | 11.13 |
| ATOM | 2780 | CD2 | TYR | 1012 | 50.464 | −17.783 | 23.531 | 1.00 | 15.69 |
| ATOM | 2781 | CE2 | TYR | 1012 | 51.830 | −17.871 | 23.839 | 1.00 | 18.91 |
| ATOM | 2782 | CZ | TYR | 1012 | 52.612 | −16.728 | 23.782 | 1.00 | 17.41 |
| ATOM | 2783 | OH | TYR | 1012 | 53.929 | −16.816 | 24.155 | 1.00 | 19.18 |
| ATOM | 2784 | HH | TYR | 1012 | 54.334 | −15.949 | 23.998 | 1.00 | 0.00 |
| ATOM | 2785 | C | TYR | 1012 | 46.821 | −16.971 | 21.048 | 1.00 | 14.86 |
| ATOM | 2786 | O | TYR | 1012 | 46.537 | −18.146 | 21.309 | 1.00 | 14.54 |
| ATOM | 2787 | N | GLY | 1013 | 45.948 | −16.193 | 20.413 | 1.00 | 15.74 |
| ATOM | 2788 | H | GLY | 1013 | 46.199 | −15.277 | 20.194 | 1.00 | 00.0 |
| ATOM | 2789 | CA | GLY | 1013 | 44.602 | −16.654 | 20.123 | 1.00 | 12.83 |
| ATOM | 2790 | C | GLY | 1013 | 43.768 | −16.522 | 21.380 | 1.00 | 13.78 |
| ATOM | 2791 | O | GLY | 1013 | 44.088 | −15.717 | 22.260 | 1.00 | 12.71 |
| ATOM | 2792 | N | SER | 1014 | 42.692 | −17.277 | 21.461 | 1.00 | 14.40 |
| ATOM | 2793 | H | SER | 1014 | 42.460 | −17.891 | 20.729 | 1.00 | 0.00 |
| ATOM | 2794 | CA | SER | 1014 | 41.790 | −17.228 | 22.572 | 1.00 | 19.95 |
| ATOM | 2795 | CB | SER | 1014 | 40.446 | −17.759 | 22.077 | 1.00 | 21.51 |
| ATOM | 2796 | OG | SER | 1014 | 40.140 | −17.212 | 20.789 | 1.00 | 23.00 |
| ATOM | 2797 | HG | SER | 1014 | 39.581 | −16.430 | 20.875 | 1.00 | 0.00 |
| ATOM | 2798 | C | SER | 1014 | 42.335 | −18.038 | 23.735 | 1.00 | 21.75 |
| ATOM | 2799 | O | SER | 1014 | 42.025 | −19.222 | 23.887 | 1.00 | 27.85 |
| ATOM | 2800 | N | ILE | 1015 | 43.242 | −17.436 | 24.506 | 1.00 | 22.37 |
| ATOM | 2801 | H | ILE | 1015 | 43.553 | −16.542 | 24.252 | 1.00 | 00.0 |
| ATOM | 2802 | CA | ILE | 1015 | 43.755 | −18.030 | 25.737 | 1.00 | 18.94 |
| ATOM | 2803 | CB | ILE | 1015 | 45.300 | −17.928 | 25.823 | 1.00 | 14.49 |
| ATOM | 2804 | CG2 | ILE | 1015 | 45.816 | −18.827 | 24.712 | 1.00 | 10.66 |
| ATOM | 2805 | CG1 | ILE | 1015 | 45.828 | −16.508 | 25.738 | 1.00 | 5.38 |
| ATOM | 2806 | CD | ILE | 1015 | 47.306 | −16.402 | 26.087 | 1.00 | 4.01 |
| ATOM | 2807 | C | ILE | 1015 | 43.133 | −17.261 | 26.894 | 1.00 | 18.07 |
| ATOM | 2808 | O | ILE | 1015 | 43.731 | −16.114 | 26.688 | 1.00 | 15.23 |
| ATOM | 2809 | N | SER | 1016 | 43.011 | −17.835 | 28.091 | 1.00 | 47.60 |
| ATOM | 2810 | H | SER | 1016 | 43.360 | −18.737 | 28.240 | 1.00 | 0.00 |
| ATOM | 2811 | CA | SER | 1016 | 42.414 | −17.128 | 29.211 | 1.00 | 17.39 |
| ATOM | 2812 | CB | SER | 1016 | 41.797 | −18.106 | 30.225 | 1.00 | 13.17 |
| ATOM | 2813 | OG | SER | 1016 | 42.766 | −19.003 | 30.737 | 1.00 | 18.24 |
| ATOM | 2814 | HG | SER | 1016 | 42.913 | −19.673 | 30.356 | 1.00 | 0.00 |
| ATOM | 2815 | C | SER | 1016 | 43.474 | −16.305 | 29.907 | 1.00 | 15.97 |
| ATOM | 2816 | O | SER | 1016 | 44.662 | −16.478 | 29.609 | 1.00 | 20.64 |
| ATOM | 2817 | N | ARG | 1017 | 43.088 | −15.451 | 30.866 | 1.00 | 18.56 |
| ATOM | 2818 | H | ARG | 1017 | 42.137 | −15.409 | 31.087 | 1.00 | 0.00 |
| ATOM | 2819 | CA | ARG | 1017 | 44.027 | −14.653 | 31.653 | 1.00 | 16.01 |
| ATOM | 2820 | CB | ARG | 1017 | 43.262 | −13.808 | 32.672 | 1.00 | 17.86 |
| ATOM | 2821 | CG | ARG | 1017 | 44.157 | −12.902 | 22.519 | 1.00 | 10.59 |
| ATOM | 2822 | CD | ARG | 1017 | 43.366 | −12.149 | 24.570 | 1.00 | 8.03 |
| ATOM | 2823 | NE | ARG | 1017 | 42.474 | −11.197 | 33.952 | 1.00 | 11.62 |
| ATOM | 2824 | HE | ARG | 1017 | 42.024 | −11.439 | 33.117 | 1.00 | 0.00 |
| ATOM | 2825 | CZ | ARG | 1017 | 42.184 | −10.026 | 34.498 | 1.00 | 13.10 |
| ATOM | 2826 | NH1 | ARG | 1017 | 42.697 | −9.643 | 35.658 | 1.00 | 14.59 |
| ATOM | 2827 | HH11 | ARG | 1017 | 43.328 | −10.244 | 36.148 | 1.00 | 0.00 |
| ATOM | 2828 | HH12 | ARG | 1017 | 42.461 | −8.748 | 36.037 | 1.00 | 0.00 |
| ATOM | 2829 | NH2 | ARG | 1017 | 41.347 | −9.229 | 33.854 | 1.00 | 15.19 |
| ATOM | 2830 | HH21 | ARG | 1017 | 40.952 | −9.522 | 32.984 | 1.00 | 0.00 |
| ATOM | 2831 | HH22 | ARG | 1017 | 41.112 | −8.334 | 34.236 | 1.00 | 0.00 |
| ATOM | 2832 | C | ARG | 1017 | 45.001 | −15.567 | 32.383 | 1.00 | 16.72 |
| ATOM | 2833 | O | ARG | 1017 | 46.202 | −15.294 | 32.469 | 1.00 | 22.39 |
| ATOM | 2834 | N | ALA | 1018 | 44.481 | −16.675 | 32.906 | 1.00 | 21.82 |
| ATOM | 2835 | H | ALA | 1018 | 43.505 | −16.792 | 32.879 | 1.00 | 0.00 |
| ATOM | 2836 | CA | ALA | 1018 | 45.274 | −17.667 | 33.611 | 1.00 | 19.48 |
| ATOM | 2837 | CB | ALA | 1018 | 44.380 | −18.824 | 34.070 | 1.00 | 18.63 |
| ATOM | 2838 | C | ALA | 1018 | 46.356 | −18.208 | 32.707 | 1.00 | 20.25 |
| ATOM | 2839 | O | ALA | 1018 | 47.531 | −18.209 | 33.097 | 1.00 | 23.41 |
| ATOM | 2840 | N | GLU | 1019 | 46.018 | −18.541 | 31.453 | 1.00 | 26.17 |
| ATOM | 2841 | H | GLU | 1019 | 45.097 | −18.382 | 31.148 | 1.00 | 0.00 |
| ATOM | 2842 | CA | GLU | 1019 | 47.007 | −19.117 | 30.559 | 1.00 | 25.54 |
| ATOM | 2843 | CB | GLU | 1019 | 46.331 | −19.816 | 29.366 | 1.00 | 32.42 |
| ATOM | 2844 | CG | GLU | 1019 | 47.353 | −20.841 | 28.796 | 1.00 | 58.31 |
| ATOM | 2845 | CD | GLU | 1019 | 69.40 | −21.712 | 27.601 | 1.00 | 54.58 |
| ATOM | 2846 | OE1 | GLU | 1019 | 45.954 | −22.447 | 27.709 | 1.00 | 61.36 |
| ATOM | 2847 | OE2 | GLU | 1019 | 47.618 | −21.681 | 26.568 | 1.00 | 56.27 |
| ATOM | 2848 | C | GLU | 1019 | 47.976 | −18.080 | 30.045 | 1.00 | 20.28 |
| ATOM | 2849 | O | GLU | 1019 | 49.125 | −18.401 | 29.708 | 1.00 | 22.96 |
| ATOM | 2850 | N | ALA | 1020 | 47.535 | −16.831 | 29.929 | 1.00 | 20.31 |
| ATOM | 2851 | H | ALA | 1020 | 46.592 | −16.654 | 30.134 | 1.00 | 0.00 |

TABLE 23-continued

Coordinates for the 3D structure of ZAP-NC:ζ1 "dimer" structure
(two molecules of complex per unit cell)*

| ATOM | 2852 | CA | ALA | 1020 | 48.372 | −15.704 | 29.515 | 1.00 | 14.33 |
|---|---|---|---|---|---|---|---|---|---|
| ATOM | 2853 | CB | ALA | 1020 | 47.532 | −14.431 | 29.359 | 1.00 | 10.33 |
| ATOM | 2854 | C | ALA | 1020 | 49.424 | −15.451 | 30.587 | 1.00 | 17.38 |
| ATOM | 2855 | O | ALA | 1020 | 50.621 | −15.470 | 30.283 | 1.00 | 20.66 |
| ATOM | 2856 | N | GLU | 1021 | 48.992 | −15.301 | 31.843 | 1.00 | 20.59 |
| ATOM | 2857 | H | GLU | 1021 | 48.029 | −15.342 | 32.004 | 1.00 | 0.00 |
| ATOM | 2858 | CA | GLU | 1021 | 49.877 | −15.110 | 32.982 | 1.00 | 23.11 |
| ATOM | 2859 | CB | GLU | 1021 | 49.070 | −14.931 | 34.246 | 1.00 | 22.53 |
| ATOM | 2860 | CG | GLU | 1021 | 48.343 | −13.605 | 34.247 | 1.00 | 17.51 |
| ATOM | 2861 | CD | GLU | 1021 | 47.521 | −13.292 | 35.485 | 1.00 | 22.86 |
| ATOM | 2862 | OE1 | GLU | 1021 | 47.081 | −12.150 | 35.589 | 1.00 | 26.96 |
| ATOM | 2863 | OE2 | GLU | 1021 | 47.303 | −14.160 | 36.338 | 1.00 | 31.30 |
| ATOM | 2864 | C | GLU | 1021 | 50.831 | −16.271 | 33.181 | 1.00 | 22.56 |
| ATOM | 2865 | O | GLU | 1021 | 51.999 | −16.024 | 33.469 | 1.00 | 24.82 |
| ATOM | 2866 | N | GLU | 1022 | 50.422 | −17.533 | 32.999 | 1.00 | 26.01 |
| ATOM | 2867 | H | GLU | 1022 | 49.465 | −17.718 | 32.877 | 1.00 | 0.00 |
| ATOM | 2868 | CA | GLU | 1022 | 51.361 | −18.649 | 33.072 | 1.00 | 28.78 |
| ATOM | 2869 | CB | GLU | 1022 | 50.708 | −20.001 | 32.767 | 1.00 | 32.14 |
| ATOM | 2870 | CG | GLU | 1022 | 49.564 | −20.417 | 33.691 | 1.00 | 41.37 |
| ATOM | 2871 | CD | GLU | 1022 | 49.750 | −20.078 | 35.168 | 1.00 | 47.97 |
| ATOM | 2872 | OE1 | GLU | 1022 | 50.608 | −20.686 | 35.813 | 1.00 | 50.55 |
| ATOM | 2873 | OE2 | GLU | 1022 | 49.036 | −19.195 | 35.663 | 1.00 | 51.22 |
| ATOM | 2874 | C | GLU | 1022 | 52.488 | −18.469 | 32.080 | 1.00 | 29.05 |
| ATOM | 2875 | O | GLU | 1022 | 53.647 | −18.612 | 32.469 | 1.00 | 30.51 |
| ATOM | 2876 | N | HIS | 1023 | 53.147 | −18.072 | 30.835 | 1.00 | 29.07 |
| ATOM | 2877 | H | HIS | 1023 | 51.192 | −17.931 | 30.663 | 1.00 | 0.00 |
| ATOM | 2878 | CA | HIS | 1023 | 53.09 | −17.785 | 29.768 | 1.00 | 23.70 |
| ATOM | 2879 | CB | HIS | 1023 | 52.402 | −17.389 | 28.463 | 1.00 | 26.84 |
| ATOM | 2880 | CG | HIS | 1023 | 51.754 | −18.539 | 27.700 | 1.00 | 21.08 |
| ATOM | 2881 | CD2 | HIS | 1023 | 52.452 | −19.570 | 27.112 | 1.00 | 19.12 |
| ATOM | 2882 | ND1 | HIS | 1023 | 50.457 | −18.741 | 27.451 | 1.00 | 18.71 |
| ATOM | 2883 | HD1 | HIS | 1023 | 49.706 | −18.258 | 27.867 | 1.00 | 0.00 |
| ATOM | 2884 | CE1 | HIS | 1023 | 50.345 | −19.836 | 26.738 | 1.00 | 15.87 |
| ATOM | 2885 | NE2 | HIS | 1023 | 51.548 | −20.329 | 26.541 | 1.00 | 17.83 |
| ATOM | 2886 | HE2 | HIS | 1023 | 51.752 | −21.134 | 26.020 | 1.00 | 0.00 |
| ATOM | 2887 | C | HIS | 1023 | 54.043 | −16.662 | 30.107 | 1.00 | 20.78 |
| ATOM | 2888 | O | HIS | 1023 | 55.247 | −16.815 | 29.895 | 1.00 | 24.83 |
| ATOM | 2889 | N | LEU | 1024 | 53.578 | −15.531 | 30.628 | 1.00 | 22.60 |
| ATOM | 2890 | H | LEU | 1024 | 52.612 | −15.418 | 30.757 | 1.00 | 0.00 |
| ATOM | 2891 | CA | LEU | 1024 | 54.489 | −14.462 | 31.036 | 1.00 | 24.27 |
| ATOM | 2892 | CB | LEU | 1024 | 53.753 | −13.210 | 31.558 | 1.00 | 24.96 |
| ATOM | 2893 | CG | LEU | 1024 | 53.085 | −12.073 | 30.735 | 1.00 | 22.86 |
| ATOM | 2894 | CD1 | LEU | 1024 | 53.723 | −12.000 | 29.373 | 1.00 | 19.34 |
| ATOM | 2895 | CD2 | LEU | 1024 | 51.605 | −12.301 | 30.571 | 1.00 | 18.19 |
| ATOM | 2896 | C | LEU | 1024 | 55.404 | −14.940 | 32.163 | 1.00 | 28.32 |
| ATOM | 2897 | O | LEU | 1024 | 56.605 | −14.641 | 32.186 | 1.00 | 30.07 |
| ATOM | 2898 | N | LYS | 1025 | 54.863 | −15.712 | 33.115 | 1.00 | 33.91 |
| ATOM | 2899 | H | LYS | 1025 | 53.911 | −15.931 | 33.060 | 1.00 | 0.00 |
| ATOM | 2900 | CA | LYS | 1025 | 55.640 | −16.233 | 34.239 | 1.00 | 35.35 |
| ATOM | 2901 | CB | LYS | 1025 | 54.782 | −17.080 | 35.183 | 1.00 | 38.19 |
| ATOM | 2902 | CG | LYS | 1025 | 53.976 | −16.173 | 36.102 | 1.00 | 40.50 |
| ATOM | 2903 | CD | LYS | 1025 | 53.101 | −16.863 | 37.152 | 1.00 | 42.76 |
| ATOM | 2904 | CE | LYS | 1025 | 51.986 | −17.672 | 36.534 | 1.00 | 40.89 |
| ATOM | 2905 | NZ | LYS | 1025 | 51.138 | −18.245 | 37.560 | 1.00 | 45.64 |
| ATOM | 2906 | HZ1 | LYS | 1025 | 50.393 | −18.818 | 37.119 | 1.00 | 0.00 |
| ATOM | 2907 | HZ2 | LYS | 1025 | 50.696 | −17.477 | 38.105 | 1.00 | 0.00 |
| ATOM | 2908 | HZ3 | LYS | 1025 | 51.705 | −18.843 | 38.193 | 1.00 | 0.00 |
| ATOM | 2909 | C | LYS | 1025 | 56.770 | −17.090 | 33.763 | 1.00 | 34.63 |
| ATOM | 2910 | O | LYS | 1025 | 57.936 | −16.854 | 34.046 | 1.00 | 36.50 |
| ATOM | 2911 | N | LEU | 1026 | 56.426 | −18.031 | 32.857 | 1.00 | 37.51 |
| ATOM | 2912 | H | LEU | 1026 | 55.483 | −18.128 | 32.621 | 1.00 | 0.00 |
| ATOM | 2913 | CA | LEU | 1026 | 57.402 | −18.908 | 32.245 | 1.00 | 35.08 |
| ATOM | 2914 | CB | LEU | 1026 | 56.671 | −19.965 | 31.406 | 1.00 | 35.34 |
| ATOM | 2915 | CG | LEU | 1026 | 55.672 | −20.873 | 32.167 | 1.00 | 34.52 |
| ATOM | 2916 | CD1 | LEU | 1026 | 55.241 | −22.004 | 31.260 | 1.00 | 34.74 |
| ATOM | 2917 | CD2 | LEU | 1026 | 56.397 | −21.471 | 33.418 | 1.00 | 31.16 |
| ATOM | 2918 | C | LEU | 1026 | 58.388 | −18.115 | 31.408 | 1.00 | 34.31 |
| ATOM | 2919 | O | ALA | 1027 | 59.576 | −18.431 | 31.418 | 1.00 | 37.02 |
| ATOM | 2920 | N | ALA | 1027 | 58.007 | −17.022 | 30.749 | 1.00 | 36.27 |
| ATOM | 2921 | H | ALA | 1027 | 57.062 | −16.764 | 30.756 | 1.00 | 0.00 |
| ATOM | 2922 | CA | ALA | 1027 | 58.969 | −16.177 | 30.032 | 1.00 | 38.06 |
| ATOM | 2923 | CB | ALA | 1027 | 58.185 | −15.258 | 29.091 | 1.00 | 39.20 |
| ATOM | 2924 | C | ALA | 1027 | 59.879 | −15.327 | 30.956 | 1.00 | 40.05 |
| ATOM | 2925 | O | ALA | 1027 | 60.436 | −14.391 | 30.568 | 1.00 | 42.49 |
| ATOM | 2926 | N | GLY | 1028 | 60.042 | −15.701 | 32.228 | 1.00 | 42.21 |
| ATOM | 2927 | H | GLY | 1028 | 59.563 | −16.479 | 32.578 | 1.00 | 0.00 |

TABLE 23-continued

Coordinates for the 3D structure of ZAP-NC:ζ1 "dimer" structure
(two molecules of complex per unit cell)*

| ATOM | 2928 | CA | GLY | 1028 | 60.911 | −15.002 | 33.146 | 1.00 | 41.60 |
|---|---|---|---|---|---|---|---|---|---|
| ATOM | 2929 | C | GLY | 1028 | 60.320 | −13.705 | 33.688 | 1.00 | 42.47 |
| ATOM | 2930 | O | GLY | 1028 | 61.123 | −12.858 | 34.082 | 1.00 | 45.26 |
| ATOM | 2931 | N | MET | 1029 | 58.999 | −13.445 | 33.704 | 1.00 | 39.68 |
| ATOM | 2932 | H | MET | 1029 | 58.405 | −14.085 | 33.254 | 1.00 | 0.00 |
| ATOM | 2933 | CA | MET | 1029 | 58.415 | −12.229 | 34.396 | 1.00 | 39.81 |
| ATOM | 2934 | CB | MET | 1029 | 58.204 | −12.492 | 35.780 | 1.00 | 37.74 |
| ATOM | 2935 | CG | MET | 1029 | 57.191 | −13.558 | 36.080 | 1.00 | 34.82 |
| ATOM | 2936 | SD | MET | 1030 | 55.548 | −13.160 | 35.465 | 1.00 | 37.33 |
| ATOM | 2937 | CE | MET | 1030 | 55.139 | −11.863 | 36.592 | 1.00 | 28.27 |
| ATOM | 2938 | C | MET | 1030 | 59.106 | −10.850 | 34.145 | 1.00 | 41.56 |
| ATOM | 2939 | O | MET | 1030 | 58.931 | −9.913 | 34.953 | 1.00 | 43.62 |
| ATOM | 2940 | N | ALA | 1030 | 59.893 | −10.700 | 33.074 | 1.00 | 41.39 |
| ATOM | 2941 | H | ALA | 1030 | 59.990 | −11.464 | 32.474 | 1.00 | 0.00 |
| ATOM | 2942 | CA | ALA | 1030 | 60.625 | −9.484 | 32.791 | 1.00 | 39.08 |
| ATOM | 2943 | CB | ALA | 1030 | 61.401 | −9.669 | 31.495 | 1.00 | 37.10 |
| ATOM | 2944 | C | ALA | 1030 | 59.718 | −8.269 | 32.674 | 1.00 | 40.79 |
| ATOM | 2945 | O | ALA | 1030 | 58.540 | −8.363 | 32.315 | 1.00 | 39.87 |
| ATOM | 2946 | N | ASP | 1031 | 60.262 | −7.100 | 32.994 | 1.00 | 43.06 |
| ATOM | 2947 | H | ASP | 1031 | 61.220 | −7.065 | 33.170 | 1.00 | 0.00 |
| ATOM | 2948 | CA | ASP | 1031 | 59.483 | −5.883 | 32.928 | 1.00 | 46.24 |
| ATOM | 2949 | CB | ASP | 1031 | 60.222 | −4.768 | 33.674 | 1.00 | 50.38 |
| ATOM | 2950 | CG | ASP | 1031 | 59.322 | −3.657 | 34.202 | 1.00 | 52.70 |
| ATOM | 2951 | OD1 | ASP | 1031 | 59.536 | −3.217 | 35.330 | 1.00 | 55.84 |
| ATOM | 2952 | OD2 | ASP | 1031 | 58.406 | −3.232 | 33.502 | 1.00 | 54.94 |
| ATOM | 2953 | C | ASP | 1031 | 59.342 | −5.564 | 31.446 | 1.00 | 45.89 |
| ATOM | 2954 | O | ASP | 1031 | 60.282 | −5.798 | 30.682 | 1.00 | 48.59 |
| ATOM | 2955 | N | GLY | 1032 | 58.159 | −5.114 | 31.029 | 1.00 | 45.12 |
| ATOM | 2956 | H | GLY | 1032 | 57.428 | −5.032 | 31.670 | 1.00 | 0.00 |
| ATOM | 2957 | CA | GLY | 1032 | 57.872 | −4.794 | 29.638 | 1.00 | 39.58 |
| ATOM | 2958 | C | GLY | 1032 | 57.597 | −6.031 | 28.788 | 1.00 | 37.39 |
| ATOM | 2959 | O | GLY | 1032 | 57.438 | −5.940 | 27.563 | 1.00 | 36.99 |
| ATOM | 2960 | N | LEU | 1033 | 57.585 | −7.218 | 29.397 | 1.00 | 33.89 |
| ATOM | 2961 | H | LEU | 1033 | 57.724 | −7.251 | 30.367 | 1.00 | 0.00 |
| ATOM | 2962 | CA | LEU | 1033 | 57.259 | −8.459 | 28.716 | 1.00 | 28.02 |
| ATOM | 2963 | CB | LEU | 1033 | 57.502 | −9.640 | 29.646 | 1.00 | 26.51 |
| ATOM | 2964 | CG | LEU | 1033 | 57.337 | −11.085 | 29.224 | 1.00 | 22.78 |
| ATOM | 2965 | CD1 | LEU | 1033 | 58.468 | −11.545 | 28.347 | 1.00 | 18.85 |
| ATOM | 2966 | CD2 | LEU | 1033 | 57.322 | −11.918 | 30.487 | 1.00 | 19.74 |
| ATOM | 2967 | C | PHE | 1034 | 55.776 | −8.298 | 28.427 | 1.00 | 26.53 |
| ATOM | 2968 | O | PHE | 1034 | 55.029 | −7.838 | 29.302 | 1.00 | 23.41 |
| ATOM | 2969 | N | PHE | 1034 | 55.363 | −8.589 | 27.198 | 1.00 | 24.15 |
| ATOM | 2970 | H | PHE | 1034 | 56.006 | −8.911 | 26.539 | 1.00 | 0.00 |
| ATOM | 2971 | CA | PHE | 1034 | 53.976 | −8.439 | 26.822 | 1.00 | 21.19 |
| ATOM | 2972 | CB | PHE | 1034 | 53.761 | −7.092 | 26.100 | 1.00 | 21.77 |
| ATOM | 2973 | CG | PHE | 1034 | 54.457 | −6.953 | 24.744 | 1.00 | 23.54 |
| ATOM | 2974 | OD1 | PHE | 1034 | 53.722 | −7.110 | 23.570 | 1.00 | 27.19 |
| ATOM | 2975 | OD2 | PHE | 1034 | 55.818 | −6.664 | 24.665 | 1.00 | 24.54 |
| ATOM | 2976 | CE1 | PHE | 1034 | 54.343 | −6.983 | 22.333 | 1.00 | 25.67 |
| ATOM | 2977 | CE2 | PHE | 1034 | 56.436 | −6.534 | 23.422 | 1.00 | 24.17 |
| ATOM | 2978 | CZ | PHE | 1034 | 55.702 | −6.694 | 22.259 | 1.00 | 24.71 |
| ATOM | 2979 | C | PHE | 1034 | 53.571 | −9.571 | 25.908 | 1.00 | 20.13 |
| ATOM | 2980 | O | PHE | 1034 | 54.417 | −10.319 | 25.405 | 1.00 | 20.20 |
| ATOM | 2981 | N | LEU | 1035 | 52.284 | −9.686 | 25.641 | 1.00 | 21.17 |
| ATOM | 2982 | H | LEU | 1035 | 51.633 | −9.098 | 26.081 | 1.00 | 0.00 |
| ATOM | 2983 | CA | LEU | 1035 | 51.775 | −10.647 | 24.685 | 1.00 | 19.77 |
| ATOM | 2984 | CB | LEU | 1035 | 51.654 | −12.048 | 25.333 | 1.00 | 20.30 |
| ATOM | 2985 | CG | LEU | 1035 | 50.695 | −12.462 | 26.447 | 1.00 | 12.94 |
| ATOM | 2986 | CD1 | LEU | 1035 | 49.314 | −12.804 | 25.946 | 1.00 | 14.01 |
| ATOM | 2987 | CD2 | LEU | 1035 | 51.181 | −13.777 | 26.987 | 1.00 | 12.52 |
| ATOM | 2988 | C | LEU | 1035 | 50.415 | −10.122 | 24.256 | 1.00 | 18.47 |
| ATOM | 2989 | O | LEU | 1035 | 49.817 | −9.268 | 24.935 | 1.00 | 13.42 |
| ATOM | 2990 | N | LEU | 1036 | 49.905 | −10.668 | 23.154 | 1.00 | 17.71 |
| ATOM | 2991 | H | LEU | 1036 | 50.390 | −11.397 | 22.713 | 1.00 | 0.00 |
| ATOM | 2992 | CA | LEU | 1036 | 58.602 | −10.296 | 22.636 | 1.00 | 17.41 |
| ATOM | 2993 | CB | LEU | 1036 | 58.862 | −9.725 | 21.252 | 1.00 | 15.80 |
| ATOM | 2994 | CG | LEU | 1036 | 47.848 | −8.867 | 20.504 | 1.00 | 21.02 |
| ATOM | 2995 | CD1 | LEU | 1036 | 47.484 | −7.615 | 21.281 | 1.00 | 12.72 |
| ATOM | 2996 | CD2 | LEU | 1036 | 48.479 | −8.470 | 19.168 | 1.00 | 21.07 |
| ATOM | 2997 | C | LEU | 1036 | 47.675 | −11.526 | 22.636 | 1.00 | 15.31 |
| ATOM | 2998 | O | LEU | 1036 | 48.100 | −12.643 | 22.317 | 1.00 | 14.62 |
| ATOM | 2999 | N | ARG | 1037 | 46.401 | −11.417 | 23.034 | 1.00 | 14.85 |
| ATOM | 3000 | H | ARG | 1037 | 46.037 | −10.536 | 23.270 | 1.00 | 0.00 |
| ATOM | 3001 | CA | ARG | 1037 | 56.486 | −12.558 | 23.011 | 1.00 | 14.73 |
| ATOM | 3002 | CB | ARG | 1037 | 45.303 | −13.143 | 24.403 | 1.00 | 12.40 |
| ATOM | 3003 | CG | ARG | 1037 | 44.799 | −12.232 | 25.502 | 1.00 | 11.81 |

TABLE 23-continued

Coordinates for the 3D structure of ZAP-NC:ζ1 "dimer" structure
(two molecules of complex per unit cell)*

| ATOM | 3004 | CD | ARG | 1037 | 44.980 | −13.004 | 26.799 | 1.00 | 18.71 |
|---|---|---|---|---|---|---|---|---|---|
| ATOM | 3005 | NE | ARG | 1037 | 45.018 | −12.174 | 27.995 | 1.00 | 13.00 |
| ATOM | 3006 | HE | ARG | 1037 | 45.850 | −11.703 | 28.210 | 1.00 | 0.00 |
| ATOM | 3007 | CZ | ARG | 1037 | 43.963 | −12.015 | 28.790 | 1.00 | 8.56 |
| ATOM | 3008 | NH1 | ARG | 1037 | 42.788 | −12.578 | 28.579 | 1.00 | 4.18 |
| ATOM | 3009 | HH11 | ARG | 1037 | 42.647 | −13.162 | 27.780 | 1.00 | 0.00 |
| ATOM | 3010 | HH12 | ARG | 1037 | 42.038 | −12.409 | 29.219 | 1.00 | 0.00 |
| ATOM | 3011 | NH2 | ARG | 1037 | 44.111 | −11.263 | 29.863 | 1.00 | 15.54 |
| ATOM | 3012 | HH21 | ARG | 1037 | 45.000 | −10.842 | 30.042 | 1.00 | 0.00 |
| ATOM | 3013 | HH22 | ARG | 1037 | 43.362 | −11.129 | 30.503 | 1.00 | 0.00 |
| ATOM | 3014 | C | ARG | 1037 | 44.144 | −12.076 | 22.487 | 1.00 | 15.15 |
| ATOM | 3015 | O | ARG | 1037 | 43.870 | −10.880 | 22.529 | 1.00 | 18.16 |
| ATOM | 3016 | N | GLN | 1038 | 43.274 | −12.913 | 21.947 | 1.00 | 15.48 |
| ATOM | 3017 | H | GLN | 1038 | 43.461 | −13.872 | 21.999 | 1.00 | 0.00 |
| ATOM | 3018 | CA | GLN | 1038 | 41.997 | −12.454 | 21.426 | 1.00 | 14.10 |
| ATOM | 3019 | CB | GLN | 1038 | 41.373 | −13.521 | 20.540 | 1.00 | 18.15 |
| ATOM | 3020 | CG | GLN | 1038 | 40.006 | −13.156 | 19.989 | 1.00 | 28.15 |
| ATOM | 3021 | CD | GLN | 1038 | 39.307 | −14.246 | 19.187 | 1.00 | 34.24 |
| ATOM | 3022 | OE1 | GLN | 1038 | 38.715 | −15.187 | 19.728 | 1.00 | 38.06 |
| ATOM | 3023 | OE2 | GLN | 1038 | 39.311 | −14.134 | 17.871 | 1.00 | 37.72 |
| ATOM | 3024 | HE21 | GLN | 1038 | 39.718 | −13.321 | 17.496 | 1.00 | 0.00 |
| ATOM | 3025 | HE22 | GLN | 1038 | 38.909 | −14.848 | 17.342 | 1.00 | 0.00 |
| ATOM | 3026 | C | GLN | 1038 | 41.101 | −12.214 | 22.617 | 1.00 | 16.07 |
| ATOM | 3027 | O | GLN | 1038 | 41.119 | −13.003 | 23.573 | 1.00 | 18.21 |
| ATOM | 3028 | N | CYS | 1039 | 40.296 | −11.154 | 22.554 | 1.00 | 12.03 |
| ATOM | 3029 | H | CYS | 1039 | 40.277 | −10.599 | 21.746 | 1.00 | 0.00 |
| ATOM | 3030 | CA | CYS | 1039 | 39.372 | −10.872 | 23.623 | 1.00 | 13.04 |
| ATOM | 3031 | CB | CYS | 1039 | 38.926 | −9.451 | 23.477 | 1.00 | 9.29 |
| ATOM | 3032 | SG | CYS | 1039 | 37.883 | −8.919 | 24.843 | 1.00 | 18.16 |
| ATOM | 3033 | C | CYS | 1039 | 38.179 | −11.826 | 23.602 | 1.00 | 14.04 |
| ATOM | 3034 | O | CYS | 1039 | 37.519 | −12.057 | 22.579 | 1.00 | 14.09 |
| ATOM | 3035 | N | LEU | 1040 | 37.900 | −12.406 | 24.768 | 1.00 | 15.22 |
| ATOM | 3036 | H | LEU | 1040 | 38.502 | −12.212 | 25.526 | 1.00 | 0.00 |
| ATOM | 3037 | CA | LEU | 1040 | 36.787 | −13.319 | 24.969 | 1.00 | 9.91 |
| ATOM | 3038 | CB | LEU | 1040 | 37.085 | −14.214 | 26.168 | 1.00 | 12.52 |
| ATOM | 3039 | CG | LEU | 1040 | 37.745 | −15.585 | 26.056 | 1.00 | 11.84 |
| ATOM | 3040 | CD1 | LEU | 1040 | 38.554 | −15.722 | 24.770 | 1.00 | 13.81 |
| ATOM | 3041 | CD2 | LEU | 1040 | 38.451 | −15.784 | 27.339 | 1.00 | 13.23 |
| ATOM | 3042 | C | LEU | 1040 | 35.454 | −12.620 | 25.195 | 1.00 | 11.13 |
| ATOM | 3043 | O | LEU | 1040 | 34.418 | −13.274 | 25.228 | 1.00 | 13.17 |
| ATOM | 3044 | N | ARG | 1041 | 35.377 | −11.311 | 25.374 | 1.00 | 12.13 |
| ATOM | 3045 | H | ARG | 1041 | 36.187 | −10.764 | 25.346 | 1.00 | 0.00 |
| ATOM | 3046 | CA | ARG | 1041 | 34.111 | −10.669 | 25.679 | 1.00 | 10.99 |
| ATOM | 3047 | CB | ARG | 1041 | 34.288 | −9.748 | 26.874 | 1.00 | 12.91 |
| ATOM | 3048 | CG | ARG | 1041 | 35.011 | −10.409 | 28.044 | 1.00 | 15.73 |
| ATOM | 3049 | CD | ARG | 1041 | 35.147 | −9.425 | 29.170 | 1.00 | 18.18 |
| ATOM | 3050 | NE | ARG | 1041 | 36.250 | −8.523 | 28.926 | 1.00 | 19.90 |
| ATOM | 3051 | HE | ARG | 1041 | 37.154 | −8.890 | 28.998 | 1.00 | 0.00 |
| ATOM | 3052 | CZ | ARG | 1041 | 36.099 | −7.224 | 28.699 | 1.00 | 14.29 |
| ATOM | 3053 | NH1 | ARG | 1041 | 34.902 | −6.630 | 28.678 | 1.00 | 18.27 |
| ATOM | 3054 | HH11 | ARG | 1041 | 34.070 | −7.163 | 28.831 | 1.00 | 0.00 |
| ATOM | 3055 | HH12 | ARG | 1041 | 34.836 | −5.648 | 28.501 | 1.00 | 0.00 |
| ATOM | 3056 | NH2 | ARG | 1041 | 37.194 | −6.525 | 28.474 | 1.00 | 14.40 |
| ATOM | 3057 | HH21 | ARG | 1041 | 38.088 | −6.972 | 28.482 | 1.00 | 0.00 |
| ATOM | 3058 | HH22 | ARG | 1041 | 37.125 | −5.546 | 28.291 | 1.00 | 0.00 |
| ATOM | 3059 | C | ARG | 1041 | 33.576 | −9.862 | 24.530 | 1.00 | 13.52 |
| ATOM | 3060 | O | ARG | 1041 | 32.381 | −9.559 | 24.485 | 1.00 | 14.23 |
| ATOM | 3061 | N | SER | 1042 | 34.423 | −9.463 | 23.581 | 1.00 | 15.67 |
| ATOM | 3062 | H | SER | 1042 | 35.377 | −9.669 | 23.602 | 1.00 | 0.00 |
| ATOM | 3063 | CA | SER | 1042 | 33.974 | −8.656 | 22.476 | 1.00 | 20.42 |
| ATOM | 3064 | CB | SER | 1042 | 34.508 | −7.256 | 22.661 | 1.00 | 25.01 |
| ATOM | 3065 | OG | SER | 1042 | 35.923 | −7.614 | 22.764 | 1.00 | 29.54 |
| ATOM | 3066 | HG | SER | 1042 | 36.266 | −6.507 | 23.176 | 1.00 | 0.00 |
| ATOM | 3067 | C | SER | 1042 | 34.426 | −9.212 | 21.146 | 1.00 | 21.18 |
| ATOM | 3068 | O | SER | 1042 | 35.579 | −9.627 | 21.026 | 1.00 | 25.17 |
| ATOM | 3069 | N | LEU | 1043 | 33.518 | −9.254 | 20.173 | 1.00 | 19.97 |
| ATOM | 3070 | H | LEU | 1043 | 32.600 | −9.025 | 20.392 | 1.00 | 0.00 |
| ATOM | 3071 | CA | LEU | 1043 | 33.811 | −9.648 | 18.798 | 1.00 | 24.42 |
| ATOM | 3072 | CB | LEU | 1043 | 32.509 | −9.609 | 17.961 | 1.00 | 24.11 |
| ATOM | 3073 | CG | LEU | 1043 | 31.223 | −10.342 | 18.414 | 1.00 | 26.18 |
| ATOM | 3074 | CD1 | LEU | 1043 | 30.091 | −10.041 | 17.441 | 1.00 | 20.08 |
| ATOM | 3075 | CD2 | LEU | 1043 | 31.458 | −11.837 | 18.459 | 1.00 | 27.15 |
| ATOM | 3076 | C | LEU | 1043 | 34.852 | −8.703 | 18.164 | 1.00 | 23.94 |
| ATOM | 3077 | O | LEU | 1043 | 34.643 | −7.491 | 18.066 | 1.00 | 27.05 |
| ATOM | 3078 | N | GLY | 1044 | 36.012 | −9.201 | 17.770 | 1.00 | 24.33 |
| ATOM | 3079 | H | GLY | 1044 | 36.200 | −10.150 | 17.951 | 1.00 | 0.00 |

TABLE 23-continued

Coordinates for the 3D structure of ZAP-NC:ζ1 "dimer" structure
(two molecules of complex per unit cell)*

| ATOM | 3080 | CA  | GLY | 1044 | 36.996 | −8.377  | 17.087 | 1.00 | 22.34 |
|------|------|-----|-----|------|--------|---------|--------|------|-------|
| ATOM | 3081 | C   | GLY | 1044 | 38.082 | −7.770  | 17.961 | 1.00 | 22.83 |
| ATOM | 3082 | O   | GLY | 1044 | 39.124 | −7.396  | 17.418 | 1.00 | 29.16 |
| ATOM | 3083 | N   | GLY | 1045 | 37.935 | −7.661  | 19.282 | 1.00 | 22.47 |
| ATOM | 3084 | H   | GLY | 1045 | 37.152 | −8.068  | 19.709 | 1.00 | 0.00  |
| ATOM | 3085 | CA  | GLY | 1045 | 38.959 | −7.050  | 20.113 | 1.00 | 17.57 |
| ATOM | 3086 | C   | GLY | 1045 | 40.081 | −8.005  | 20.519 | 1.00 | 17.34 |
| ATOM | 3087 | O   | GLY | 1045 | 40.034 | −9.226  | 20.291 | 1.00 | 17.24 |
| ATOM | 3088 | N   | TYR | 1046 | 41.082 | −7.446  | 21.183 | 1.00 | 13.57 |
| ATOM | 3089 | H   | TYR | 1046 | 40.988 | −6.507  | 21.467 | 1.00 | 0.00  |
| ATOM | 3090 | CA  | TYR | 1046 | 42.234 | −8.182  | 21.672 | 1.00 | 15.71 |
| ATOM | 3091 | CB  | TYR | 1046 | 43.490 | −7.848  | 20.902 | 1.00 | 21.28 |
| ATOM | 3092 | CG  | TYR | 1046 | 43.413 | −8.275  | 19.457 | 1.00 | 24.29 |
| ATOM | 3093 | CD1 | TYR | 1046 | 43.708 | −9.590  | 19.084 | 1.00 | 22.08 |
| ATOM | 3094 | CE1 | TYR | 1046 | 43.609 | −9.958  | 17.742 | 1.00 | 29.88 |
| ATOM | 3095 | CD2 | TYR | 1046 | 43.023 | −7.327  | 18.518 | 1.00 | 23.41 |
| ATOM | 3096 | CE2 | TYR | 1046 | 42.924 | −7.693  | 17.184 | 1.00 | 32.25 |
| ATOM | 3097 | CZ  | TYR | 1046 | 43.217 | −8.998  | 16.801 | 1.00 | 31.62 |
| ATOM | 3098 | OH  | TYR | 1046 | 43.118 | −9.302  | 15.457 | 1.00 | 31.31 |
| ATOM | 3099 | HH  | TYR | 1046 | 42.631 | −8.575  | 15.048 | 1.00 | 0.00  |
| ATOM | 3100 | C   | TYR | 1046 | 42.491 | −7.793  | 23.112 | 1.00 | 13.63 |
| ATOM | 3101 | O   | TYR | 1046 | 41.744 | −6.969  | 23.620 | 1.00 | 14.97 |
| ATOM | 3102 | N   | VAL | 1047 | 43.467 | −8.354  | 23.828 | 1.00 | 16.06 |
| ATOM | 3103 | H   | VAL | 1047 | 43.984 | −9.086  | 23.428 | 1.00 | 0.00  |
| ATOM | 3104 | CA  | VAL | 1047 | 43.835 | −7.929  | 25.178 | 1.00 | 15.04 |
| ATOM | 3105 | CB  | VAL | 1047 | 43.330 | −8.920  | 26.310 | 1.00 | 12.79 |
| ATOM | 3106 | CG1 | VAL | 1047 | 43.721 | −8.413  | 27.705 | 1.00 | 5.01  |
| ATOM | 3107 | CG2 | VAL | 1047 | 41.820 | −8.948  | 26.381 | 1.00 | 3.47  |
| ATOM | 3108 | C   | VAL | 1047 | 45.362 | −7.939  | 25.119 | 1.00 | 15.77 |
| ATOM | 3109 | O   | VAL | 1047 | 45.953 | −8.849  | 24.517 | 1.00 | 10.22 |
| ATOM | 3110 | N   | LEU | 1048 | 45.977 | −6.880  | 15.663 | 1.00 | 19.22 |
| ATOM | 3111 | H   | LEU | 1048 | 45.429 | −6.147  | 26.016 | 1.00 | 0.00  |
| ATOM | 3112 | CA  | LEU | 1048 | 47.427 | −6.758  | 25.804 | 1.00 | 20.69 |
| ATOM | 3113 | CB  | LEU | 1048 | 47.865 | −6.299  | 25.610 | 1.00 | 24.41 |
| ATOM | 3114 | OG  | LEU | 1048 | 49.229 | −4.886  | 25.045 | 1.00 | 24.96 |
| ATOM | 3115 | CD1 | LEU | 1048 | 50.347 | −5.852  | 25.414 | 1.00 | 25.43 |
| ATOM | 3116 | CD2 | LEU | 1048 | 49.106 | −4.886  | 23.533 | 1.00 | 30.87 |
| ATOM | 3117 | C   | LEU | 1048 | 47.754 | −7.185  | 27.239 | 1.00 | 19.63 |
| ATOM | 3118 | O   | LEU | 1048 | 47.194 | −6.597  | 28.175 | 1.00 | 20.94 |
| ATOM | 3119 | N   | SER | 1049 | 48.578 | −8.212  | 27.451 | 1.00 | 18.81 |
| ATOM | 3120 | H   | SER | 1049 | 48.977 | −8.679  | 26.690 | 1.00 | 0.00  |
| ATOM | 3121 | CA  | SER | 1049 | 48.975 | −8.629  | 28.776 | 1.00 | 19.55 |
| ATOM | 3122 | CB  | SER | 1049 | 48.671 | −10.116 | 28.985 | 1.00 | 13.59 |
| ATOM | 3123 | OG  | SER | 1049 | 57.263 | −10.393 | 28.987 | 1.00 | 12.90 |
| ATOM | 3124 | HG  | SER | 1049 | 57.044 | −10.337 | 28.034 | 1.00 | 0.00  |
| ATOM | 3125 | C   | SER | 1049 | 50.465 | −8.350  | 28.857 | 1.00 | 23.25 |
| ATOM | 3126 | O   | SER | 1049 | 51.279 | −8.800  | 28.051 | 1.00 | 27.44 |
| ATOM | 3127 | N   | SER | 1049 | 50.806 | −7.549  | 29.843 | 1.00 | 29.25 |
| ATOM | 3128 | H   | LEU | 1050 | 50.116 | −7.296  | 30.492 | 1.00 | 0.00  |
| ATOM | 3129 | CA  | LEU | 1050 | 53.137 | −7.031  | 30.060 | 1.00 | 28.57 |
| ATOM | 3130 | CB  | LEU | 1050 | 51.960 | −5.562  | 29.602 | 1.00 | 24.11 |
| ATOM | 3131 | CG  | LEU | 1050 | 52.540 | −4.304  | 30.228 | 1.00 | 25.47 |
| ATOM | 3132 | CD1 | LEU | 1050 | 54.012 | −4.129  | 29.911 | 1.00 | 25.51 |
| ATOM | 3133 | CD2 | LEU | 1050 | 51.830 | −3.120  | 29.611 | 1.00 | 27.22 |
| ATOM | 3134 | C   | LEU | 1050 | 52.561 | −7.280  | 31.529 | 1.00 | 30.12 |
| ATOM | 3135 | O   | LEU | 1050 | 51.730 | −8.499  | 32.430 | 1.00 | 28.70 |
| ATOM | 3136 | N   | VAL | 1051 | 53.860 | −7.287  | 31.806 | 1.00 | 31.79 |
| ATOM | 3137 | H   | VAL | 1051 | 54.494 | −7.177  | 31.065 | 1.00 | 0.00  |
| ATOM | 3138 | CA  | VAL | 1051 | 54.401 | −7.422  | 33.150 | 1.00 | 34.62 |
| ATOM | 3139 | CB  | VAL | 1051 | 55.474 | −8.537  | 33.264 | 1.00 | 34.04 |
| ATOM | 3140 | CG1 | VAL | 1051 | 55.903 | −8.689  | 34.701 | 1.00 | 36.53 |
| ATOM | 3141 | CG2 | VAL | 1051 | 54.926 | −9.868  | 32.830 | 1.00 | 35.98 |
| ATOM | 3142 | C   | VAL | 1051 | 55.091 | −6.086  | 33.424 | 1.00 | 38.18 |
| ATOM | 3143 | O   | VAL | 1051 | 55.879 | −5.549  | 32.634 | 1.00 | 35.79 |
| ATOM | 3144 | N   | HIS | 1052 | 54.811 | −5.468  | 34.551 | 1.00 | 42.38 |
| ATOM | 3145 | H   | HIS | 1052 | 54.198 | −5.900  | 35.181 | 1.00 | 0.00  |
| ATOM | 3146 | CA  | HIS | 1052 | 55.526 | −4.270  | 34.925 | 1.00 | 46.55 |
| ATOM | 3147 | CB  | HIS | 1052 | 54.622 | −3.054  | 34.980 | 1.00 | 47.71 |
| ATOM | 3148 | CG  | HIS | 1052 | 55.292 | −1.796  | 35.514 | 1.00 | 51.97 |
| ATOM | 3149 | CD2 | HIS | 1052 | 56.403 | −1.215  | 34.957 | 1.00 | 50.95 |
| ATOM | 3150 | ND1 | HIS | 1052 | 54.920 | −1.038  | 36.542 | 1.00 | 53.03 |
| ATOM | 3151 | HD1 | HIS | 1052 | 54.229 | −1.225  | 37.214 | 1.00 | 0.00  |
| ATOM | 3152 | CE1 | HIS | 1052 | 55.751 | −0.028  | 36.615 | 1.00 | 52.41 |
| ATOM | 3153 | NE2 | HIS | 1052 | 56.637 | −0.145  | 35.657 | 1.00 | 52.66 |
| ATOM | 3154 | HE2 | HIS | 1052 | 59.240 | −0.580  | 35.383 | 1.00 | 0.00  |
| ATOM | 3155 | C   | ASP | 1053 | 55.905 | −4.696  | 36.308 | 1.00 | 48.34 |

TABLE 23-continued

Coordinates for the 3D structure of ZAP-NC:ζ1 "dimer" structure
(two molecules of complex per unit cell)*

| ATOM | 3156 | O    | ASP | 1053 | 55.023 | -4.788  | 37.157  | 1.00 | 50.78 |
|------|------|------|-----|------|--------|---------|---------|------|-------|
| ATOM | 3157 | N    | ASP | 1053 | 57.194 | -5.005  | 36.440  | 1.00 | 51.11 |
| ATOM | 3158 | H    | ASP | 1053 | 57.743 | -4.976  | 35.634  | 1.00 | 0.00  |
| ATOM | 3159 | CA   | ASP | 1053 | 57.851 | -5.483  | 37.655  | 1.00 | 54.60 |
| ATOM | 3160 | CB   | ASP | 1053 | 58.239 | -4.287  | 38.603  | 1.00 | 57.17 |
| ATOM | 3161 | CG   | ASP | 1053 | 57.191 | -3.278  | 39.068  | 1.00 | 55.92 |
| ATOM | 3162 | OD1  | ASP | 1053 | 57.343 | -2.104  | 38.741  | 1.00 | 58.38 |
| ATOM | 3163 | OD2  | ASP | 1053 | 56.244 | -3.647  | 39.761  | 1.00 | 55.18 |
| ATOM | 3164 | C    | ASP | 1053 | 57.098 | -6.535  | 38.462  | 1.00 | 54.40 |
| ATOM | 3165 | O    | ASP | 1053 | 56.537 | -6.320  | 39.534  | 1.00 | 56.76 |
| ATOM | 3166 | N    | VAL | 1054 | 57.101 | -7.737  | 37.882  | 1.00 | 51.08 |
| ATOM | 3167 | H    | VAL | 1054 | 57.591 | -7.850  | 37.043  | 1.00 | 0.00  |
| ATOM | 3168 | CA   | VAL | 1054 | 56.472 | -8.926  | 38.449  | 1.00 | 45.93 |
| ATOM | 3169 | CB   | VAL | 1054 | 57.278 | -9.313  | 39.763  | 1.00 | 46.32 |
| ATOM | 3170 | CG1  | VAL | 1054 | 56.979 | -1.075  | 40.164  | 1.00 | 48.05 |
| ATOM | 3171 | CG2  | VAL | 1054 | 58.788 | -9.253  | 39.532  | 1.00 | 42.02 |
| ATOM | 3172 | C    | VAL | 1054 | 54.953 | -8.767  | 38.693  | 1.00 | 43.30 |
| ATOM | 3173 | O    | VAL | 1054 | 54.306 | -9.578  | 39.358  | 1.00 | 39.79 |
| ATOM | 3174 | N    | ARG | 1055 | 54.397 | -7.760  | 38.117  | 1.00 | 44.36 |
| ATOM | 3175 | H    | ARG | 1055 | 54.798 | -7.059  | 37.658  | 1.00 | 0.00  |
| ATOM | 3176 | CA   | ARG | 1055 | 53.851 | -7.588  | 38.236  | 1.00 | 44.68 |
| ATOM | 3177 | CB   | ARG | 1055 | 53.474 | -6.272  | 38.916  | 1.00 | 50.69 |
| ATOM | 3178 | CG   | ARG | 1055 | 53.105 | -6.377  | 40.387  | 1.00 | 57.61 |
| ATOM | 3179 | CD   | ARG | 1055 | 51.635 | -5.024  | 40.913  | 1.00 | 61.91 |
| ATOM | 3180 | NE   | ARG | 1055 | 53.729 | -4.130  | 41.282  | 1.00 | 68.12 |
| ATOM | 3181 | HE   | ARG | 1055 | 53.219 | -4.311  | 42.112  | 1.00 | 0.00  |
| ATOM | 3182 | CZ   | ARG | 1055 | 53.110 | -3.074  | 40.553  | 1.00 | 69.52 |
| ATOM | 3183 | NH1  | ARG | 1055 | 53.535 | -2.744  | 39.394  | 1.00 | 69.57 |
| ATOM | 3184 | HH11 | ARG | 1055 | 51.767 | -3.294  | 39.044  | 1.00 | 0.00  |
| ATOM | 3185 | HH12 | ARG | 1055 | 52.844 | -1.945  | 38.882  | 1.00 | 0.00  |
| ATOM | 3186 | NH2  | ARG | 1055 | 54.075 | -2.287  | 41.039  | 1.00 | 69.36 |
| ATOM | 3187 | HH21 | ARG | 1055 | 54.496 | -2.495  | 41.922  | 1.00 | 0.00  |
| ATOM | 3188 | HH22 | ARG | 1055 | 54.380 | -1.490  | 40.518  | 1.00 | 0.00  |
| ATOM | 3189 | C    | ARG | 1055 | 52.273 | -7.553  | 36.837  | 1.00 | 39.48 |
| ATOM | 3190 | O    | ARG | 1055 | 52.702 | -6.718  | 36.031  | 1.00 | 35.41 |
| ATOM | 3191 | N    | PHE | 1056 | 51.277 | -8.400  | 36.577  | 1.00 | 35.03 |
| ATOM | 3192 | H    | PHE | 1056 | 50.896 | -8.907  | 37.325  | 1.00 | 0.00  |
| ATOM | 3193 | CA   | PHE | 1056 | 50.643 | -8.531  | 35.270  | 1.00 | 30.23 |
| ATOM | 3194 | CB   | PHE | 1056 | 49.910 | -9.817  | 35.090  | 1.00 | 28.55 |
| ATOM | 3195 | CG   | PHE | 1056 | 50.728 | -11.041 | 35.3341 | 1.00 | 24.98 |
| ATOM | 3196 | CD1  | PHE | 1056 | 50.515 | -11.749 | 36.5139 | 1.00 | 25.55 |
| ATOM | 3197 | CD2  | PHE | 1056 | 51.617 | -11.476 | 34.3656 | 1.00 | 20.60 |
| ATOM | 3198 | CE1  | PHE | 1056 | 51.206 | -12.935 | 36.4215 | 1.00 | 27.31 |
| ATOM | 3199 | CE2  | PHE | 1056 | 52.305 | -12.661 | 34.5791 | 1.00 | 25.47 |
| ATOM | 3200 | CZ   | PHE | 1056 | 52.099 | -13.388 | 35.7518 | 1.00 | 27.08 |
| ATOM | 3201 | C    | PHE | 1056 | 49.584 | -7.487  | 35.083  | 1.00 | 26.03 |
| ATOM | 3202 | O    | PHE | 1056 | 48.861 | -7.198  | 36.038  | 1.00 | 28.66 |
| ATOM | 3203 | N    | HIS | 1057 | 49.427 | -6.944  | 33.888  | 1.00 | 23.48 |
| ATOM | 3204 | H    | HIS | 1057 | 49.959 | -7.281  | 33.131  | 1.00 | 0.00  |
| ATOM | 3205 | CA   | HIS | 1057 | 48.428 | -5.900  | 33.635  | 1.00 | 27.72 |
| ATOM | 3206 | CB   | HIS | 1057 | 49.127 | -4.511  | 33.499  | 1.00 | 27.65 |
| ATOM | 3207 | CG   | HIS | 1057 | 19.955 | -4.158  | 34.715  | 1.00 | 26.44 |
| ATOM | 3208 | CD2  | HIS | 1057 | 51.296 | -4.523  | 34.820  | 1.00 | 26.73 |
| ATOM | 3209 | ND1  | HIS | 1057 | 49.638 | -3.584  | 35.870  | 1.00 | 26.22 |
| ATOM | 3210 | HD1  | HIS | 1057 | 49.729 | -3.352  | 36.167  | 1.00 | 0.00  |
| ATOM | 3211 | CE1  | HIS | 1057 | 50.693 | -3.611  | 36.650  | 1.00 | 23.17 |
| ATOM | 3212 | NE2  | HIS | 1057 | 51.689 | -4.182  | 36.017  | 1.00 | 22.82 |
| ATOM | 3213 | HE2  | HIS | 1057 | 52.470 | -4.597  | 36.455  | 1.00 | 0.00  |
| ATOM | 3214 | C    | HIS | 1057 | 47.737 | -6.298  | 32.332  | 1.00 | 26.04 |
| ATOM | 3215 | O    | HIS | 1057 | 48.401 | -6.849  | 31.445  | 1.00 | 26.55 |
| ATOM | 3216 | N    | HIS | 1058 | 46.422 | -6.107  | 32.193  | 1.00 | 23.29 |
| ATOM | 3217 | H    | HIS | 1058 | 45.925 | -5.566  | 32.839  | 1.00 | 0.00  |
| ATOM | 3218 | CA   | HIS | 1058 | 45.668 | -6.592  | 31.043  | 1.00 | 17.86 |
| ATOM | 3219 | CB   | HIS | 1058 | 44.669 | -7.714  | 31.412  | 1.00 | 17.03 |
| ATOM | 3220 | CG   | HIS | 1058 | 45.393 | -8.892  | 32.027  | 1.00 | 12.01 |
| ATOM | 3221 | CD2  | HIS | 1058 | 45.577 | -9.067  | 33.378  | 1.00 | 14.01 |
| ATOM | 3222 | ND1  | HIS | 1058 | 46.059 | -9.845  | 31.407  | 1.00 | 15.39 |
| ATOM | 3223 | HD1  | HIS | 1058 | 46.150 | -9.979  | 30.433  | 1.00 | 0.00  |
| ATOM | 3224 | CE1  | HIS | 1058 | 46.656 | -10.577 | 32.308  | 1.00 | 18.06 |
| ATOM | 3225 | NE2  | HIS | 1058 | 46.362 | -10.102 | 33.495  | 1.00 | 14.69 |
| ATOM | 3226 | HE2  | HIS | 1058 | 46.704 | -10.441 | 34.346  | 1.00 | 00.0  |
| ATOM | 3227 | C    | HIS | 1058 | 44.872 | -5.433  | 30.553  | 1.00 | 14.50 |
| ATOM | 3228 | O    | HIS | 1058 | 44.041 | -4.949  | 31.314  | 1.00 | 16.31 |
| ATOM | 3229 | N    | PHE | 1059 | 45.101 | -4.956  | 29.343  | 1.00 | 16.76 |
| ATOM | 3230 | H    | PHE | 1059 | 45.771 | -5.375  | 28.760  | 1.00 | 0.00  |
| ATOM | 3231 | CA   | PHE | 1059 | 44.326 | -3.837  | 28.839  | 1.00 | 19.96 |

TABLE 23-continued

Coordinates for the 3D structure of ZAP-NC:ζ1 "dimer" structure
(two molecules of complex per unit cell)*

| ATOM | 3232 | CB | PHE | 1059 | 45.215 | −2.681 | 28.409 | 1.00 | 17.38 |
|---|---|---|---|---|---|---|---|---|---|
| ATOM | 3233 | CG | PHE | 1059 | 46.192 | −2.226 | 29.477 | 1.00 | 19.10 |
| ATOM | 3234 | CD1 | PHE | 1059 | 47.284 | −3.039 | 29.834 | 1.00 | 15.32 |
| ATOM | 3235 | CD2 | PHE | 1059 | 46.007 | −0.976 | 30.070 | 1.00 | 15.59 |
| ATOM | 3236 | CE1 | PHE | 1059 | 48.194 | −2.599 | 30.785 | 1.00 | 13.47 |
| ATOM | 3237 | CE2 | PHE | 1059 | 46.932 | −0.550 | 31.023 | 1.00 | 14.40 |
| ATOM | 3238 | CZ | PHE | 1059 | 48.014 | −1.354 | 31.378 | 1.00 | 10.86 |
| ATOM | 3239 | C | PHE | 1059 | 43.564 | −4.334 | 27.628 | 1.00 | 21.22 |
| ATOM | 3240 | O | PHE | 1059 | 44.160 | −4.900 | 26.703 | 1.00 | 22.35 |
| ATOM | 3241 | N | PRO | 1060 | 42.240 | −4.224 | 27.616 | 1.00 | 22.92 |
| ATOM | 3242 | H | PRO | 1060 | 41.428 | −3.723 | 28.719 | 1.00 | 22.08 |
| ATOM | 3243 | CA | PRO | 1060 | 41.428 | −4.568 | 26.461 | 1.00 | 25.16 |
| ATOM | 3244 | CB | PRO | 1060 | 39.998 | −4.422 | 26.931 | 1.00 | 23.49 |
| ATOM | 3245 | CG | PRO | 1060 | 40.122 | −4.448 | 28.443 | 1.00 | 26.03 |
| ATOM | 3246 | C | PRO | 1060 | 41.767 | −3.632 | 25.307 | 1.00 | 27.91 |
| ATOM | 3247 | O | PRO | 1060 | 42.169 | −3.482 | 25.523 | 1.00 | 30.97 |
| ATOM | 3248 | N | PRO | 1060 | 41.617 | −4.135 | 24.085 | 1.00 | 27.10 |
| ATOM | 3249 | H | ILE | 1061 | 41.291 | −5.059 | 24.000 | 1.00 | 0.00 |
| ATOM | 3250 | CA | ILE | 1061 | 41.815 | −3.388 | 22.860 | 1.00 | 22.55 |
| ATOM | 3251 | CB | ILE | 1061 | 42.985 | −3.990 | 22.042 | 1.00 | 21.40 |
| ATOM | 3252 | CG2 | ILE | 1061 | 42.986 | −3.497 | 20.593 | 1.00 | 19.96 |
| ATOM | 3253 | CG1 | ILE | 1061 | 44.285 | −3.620 | 22.748 | 1.00 | 14.21 |
| ATOM | 3254 | CD | ILE | 1061 | 45.456 | −4.517 | 22.333 | 1.00 | 12.69 |
| ATOM | 3255 | C | ILE | 1061 | 40.466 | −3.649 | 22.221 | 1.00 | 26.54 |
| ATOM | 3256 | O | ILE | 1061 | 39.996 | −4.775 | 22.014 | 1.00 | 29.17 |
| ATOM | 3257 | N | GLU | 1062 | 39.804 | −2.541 | 21.999 | 1.00 | 30.58 |
| ATOM | 3258 | H | GLU | 1062 | 40.243 | −1.681 | 22.171 | 1.00 | 0.00 |
| ATOM | 3259 | CA | GLU | 1062 | 38.499 | −2.520 | 21.402 | 1.00 | 32.23 |
| ATOM | 3260 | CB | GLU | 1062 | 37.689 | −1.410 | 22.034 | 1.00 | 41.61 |
| ATOM | 3261 | CG | GLU | 1062 | 37.527 | −1.439 | 23.557 | 1.00 | 49.21 |
| ATOM | 3262 | CD | GLU | 1062 | 36.164 | −1.951 | 24.011 | 1.00 | 58.98 |
| ATOM | 3263 | OE1 | GLU | 1062 | 35.889 | −3.143 | 23.843 | 1.00 | 61.43 |
| ATOM | 3264 | OE2 | GLU | 1062 | 35.378 | −1.148 | 24.529 | 1.00 | 63.31 |
| ATOM | 3265 | C | GLU | 1062 | 38.743 | −2.217 | 19.930 | 1.00 | 32.90 |
| ATOM | 3266 | O | GLU | 1062 | 39.729 | −1.570 | 19.549 | 1.00 | 32.88 |
| ATOM | 3267 | N | ARG | 1063 | 37.832 | −2.696 | 19.103 | 1.00 | 32.93 |
| ATOM | 3268 | H | ARG | 1063 | 37.039 | −3.150 | 19.448 | 1.00 | 0.00 |
| ATOM | 3269 | CA | ARG | 1063 | 37.857 | −2.429 | 17.687 | 1.00 | 35.42 |
| ATOM | 3270 | CB | ARG | 1063 | 37.598 | −3.727 | 16.960 | 1.00 | 35.48 |
| ATOM | 3271 | CG | ARG | 1063 | 37.655 | −3.611 | 15.450 | 1.00 | 37.92 |
| ATOM | 3272 | CD | ARG | 1063 | 37.188 | −4.928 | 14.870 | 1.00 | 38.55 |
| ATOM | 3273 | NE | ARG | 1063 | 37.008 | −4.830 | 13.432 | 1.00 | 44.21 |
| ATOM | 3274 | HE | ARG | 1063 | 37.719 | −5.155 | 12.841 | 1.00 | 0.00 |
| ATOM | 3275 | CZ | ARG | 1063 | 35.907 | −4.309 | 12.878 | 1.00 | 44.14 |
| ATOM | 3276 | NH1 | ARG | 1063 | 34.898 | −3.837 | 13.604 | 1.00 | 46.11 |
| ATOM | 3277 | HH11 | ARG | 1063 | 34.940 | −3.864 | 14.601 | 1.00 | 0.00 |
| ATOM | 3278 | HH12 | ARG | 1063 | 34.093 | −3.460 | 13.148 | 1.00 | 0.00 |
| ATOM | 3279 | NH2 | ARG | 1063 | 35.797 | −4.302 | 11.555 | 1.00 | 44.51 |
| ATOM | 3280 | HH21 | ARG | 1063 | 36.523 | −4.696 | 10.991 | 1.00 | 0.00 |
| ATOM | 3281 | HH22 | ARG | 1063 | 34.977 | −3.925 | 11.124 | 1.00 | 0.00 |
| ATOM | 3282 | C | ARG | 1063 | 36.713 | −1.428 | 17.503 | 1.00 | 38.94 |
| ATOM | 3283 | O | ARG | 1063 | 35.627 | −1.620 | 18.073 | 1.00 | 38.58 |
| ATOM | 3284 | N | GLN | 1064 | 36.909 | −0.313 | 16.804 | 1.00 | 43.24 |
| ATOM | 3285 | H | GLN | 1064 | 37.762 | −0.182 | 16.341 | 1.00 | 0.00 |
| ATOM | 3286 | CA | GLN | 1064 | 35.830 | 0.639 | 16.639 | 1.00 | 46.48 |
| ATOM | 3287 | CB | GLN | 1064 | 36.352 | 2.068 | 16.566 | 1.00 | 45.17 |
| ATOM | 3288 | CG | GLN | 1064 | 36.851 | 2.699 | 17.853 | 1.00 | 50.93 |
| ATOM | 3289 | CD | GLN | 1064 | 38.196 | 2.187 | 18.326 | 1.00 | 51.83 |
| ATOM | 3290 | OE1 | GLN | 1064 | 39.182 | 2.160 | 17.590 | 1.00 | 56.19 |
| ATOM | 3291 | NE2 | GLN | 1064 | 38.299 | 1.777 | 19.573 | 1.00 | 51.87 |
| ATOM | 3292 | HE21 | GLN | 1064 | 37.505 | 1.835 | 20.148 | 1.00 | 0.00 |
| ATOM | 3293 | HE22 | GLN | 1064 | 39.155 | 1.420 | 19.872 | 1.00 | 0.00 |
| ATOM | 3294 | C | GLN | 1064 | 35.088 | 0.328 | 15.353 | 1.00 | 51.07 |
| ATOM | 3295 | O | GLN | 1064 | 35.558 | −0.469 | 14.524 | 1.00 | 52.23 |
| ATOM | 3296 | N | LEU | 1065 | 33.918 | 0.946 | 15.133 | 1.00 | 55.53 |
| ATOM | 3297 | H | LEU | 1065 | 33.595 | 1.616 | 15.766 | 1.00 | 0.00 |
| ATOM | 3298 | CA | LEU | 1065 | 33.198 | 0.759 | 13.881 | 1.00 | 57.02 |
| ATOM | 3299 | CB | LEU | 1065 | 31.724 | 1.156 | 13.984 | 1.00 | 61.19 |
| ATOM | 3300 | CG | LEU | 1065 | 30.663 | 0.137 | 13.534 | 1.00 | 64.64 |
| ATOM | 3301 | CD1 | LEU | 1065 | 29.344 | 0.884 | 13.414 | 1.00 | 67.26 |
| ATOM | 3302 | CD2 | LEU | 1065 | 30.997 | −0.502 | 12.182 | 1.00 | 66.64 |
| ATOM | 3303 | C | LEU | 1065 | 33.898 | 1.707 | 12.925 | 1.00 | 56.04 |
| ATOM | 3304 | O | ASN | 1066 | 33.752 | 2.930 | 12.997 | 1.00 | 55.83 |
| ATOM | 3305 | N | ASN | 1066 | 34.778 | 1.049 | 12.172 | 1.00 | 54.44 |
| ATOM | 3306 | H | ASN | 1066 | 34.903 | 0.102 | 12.392 | 1.00 | 0.00 |
| ATOM | 3307 | CA | ASN | 1066 | 35.648 | 1.603 | 11.142 | 1.00 | 54.22 |

TABLE 23-continued

Coordinates for the 3D structure of ZAP-NC:ζ1 "dimer" structure
(two molecules of complex per unit cell)*

| ATOM | 3308 | CB | ASN | 1066 | 36.216 | 3.006 | 11.467 | 1.00 | 55.90 |
|---|---|---|---|---|---|---|---|---|---|
| ATOM | 3309 | CG | ASN | 1066 | 36.994 | 3.104 | 12.771 | 1.00 | 56.20 |
| ATOM | 3310 | OD1 | ASN | 1066 | 37.012 | 2.166 | 13.563 | 1.00 | 58.50 |
| ATOM | 3311 | ND2 | ASN | 1066 | 37.655 | 4.203 | 13.086 | 1.00 | 56.65 |
| ATOM | 3312 | HD21 | ASN | 1066 | 37.613 | 4.977 | 12.494 | 1.00 | 0.00 |
| ATOM | 3313 | HD22 | ASN | 1066 | 38.176 | 4.166 | 13.918 | 1.00 | 0.00 |
| ATOM | 3314 | C | ASN | 1066 | 36.849 | 0.671 | 11.002 | 1.00 | 53.31 |
| ATOM | 3315 | O | ASN | 1066 | 37.506 | 0.679 | 9.961 | 1.00 | 54.36 |
| ATOM | 3316 | N | GLY | 1067 | 37.187 | −0.137 | 12.010 | 1.00 | 50.83 |
| ATOM | 3317 | H | GLY | 1067 | 36.761 | −0.023 | 12.889 | 1.00 | 0.00 |
| ATOM | 3318 | CA | GLY | 1067 | 38.314 | −1.048 | 11.901 | 1.00 | 48.53 |
| ATOM | 3319 | C | GLY | 1067 | 39.560 | −0.517 | 12.601 | 1.00 | 47.35 |
| ATOM | 3320 | O | GLY | 1067 | 40.656 | −1.066 | 12.421 | 1.00 | 49.79 |
| ATOM | 3321 | N | TYR | 1068 | 39.470 | 0.566 | 13.373 | 1.00 | 45.38 |
| ATOM | 3322 | H | TYR | 1068 | 38.638 | 1.064 | 13.499 | 1.00 | 0.00 |
| ATOM | 3323 | CA | TYR | 1068 | 40.632 | 0.976 | 14.124 | 1.00 | 43.80 |
| ATOM | 3324 | CB | TYR | 1068 | 40.595 | 2.519 | 14.300 | 1.00 | 45.85 |
| ATOM | 3325 | OG1 | TYR | 1068 | 39.344 | 2.942 | 14.840 | 1.00 | 47.48 |
| ATOM | 3326 | HG1 | TYR | 1068 | 39.235 | 2.533 | 15.712 | 1.00 | 0.00 |
| ATOM | 3327 | CG2 | TYR | 1068 | 40.883 | 3.172 | 12.947 | 1.00 | 40.16 |
| ATOM | 3328 | C | TYR | 1068 | 40.612 | 0.199 | 15.446 | 1.00 | 42.99 |
| ATOM | 3329 | O | TYR | 1068 | 39.592 | −0.421 | 15.800 | 1.00 | 43.98 |
| ATOM | 3330 | N | TYR | 1069 | 41.743 | 0.183 | 16.158 | 1.00 | 28.49 |
| ATOM | 3331 | H | TYR | 1069 | 42.458 | 1.791 | 15.905 | 1.00 | 0.00 |
| ATOM | 3332 | CA | TYR | 1069 | 41.953 | −0.608 | 17.359 | 1.00 | 33.53 |
| ATOM | 3333 | CB | TYR | 1069 | 42.953 | −1.740 | 17.095 | 1.00 | 29.74 |
| ATOM | 3334 | CG | TYR | 1069 | 42.345 | −2.842 | 16.238 | 1.00 | 30.58 |
| ATOM | 3335 | CD1 | TYR | 1069 | 42.488 | −2.831 | 14.844 | 1.00 | 27.87 |
| ATOM | 3336 | CE1 | TYR | 1069 | 41.922 | −3.846 | 14.074 | 1.00 | 27.82 |
| ATOM | 3337 | CD2 | TYR | 1069 | 41.636 | −2.871 | 16.859 | 1.00 | 28.51 |
| ATOM | 3338 | CE2 | TYR | 1069 | 41.071 | −4.887 | 16.093 | 1.00 | 27.96 |
| ATOM | 3339 | CZ | TYR | 1069 | 41.217 | −4.864 | 14.711 | 1.00 | 27.78 |
| ATOM | 3340 | OH | TYR | 1069 | 40.626 | −5.861 | 13.973 | 1.00 | 33.15 |
| ATOM | 3341 | HH | TYR | 1069 | 39.963 | −6.295 | 14.520 | 1.00 | 0.00 |
| ATOM | 3342 | C | TYR | 1069 | 42.520 | 0.307 | 18.415 | 1.00 | 33.52 |
| ATOM | 3343 | O | TYR | 1069 | 43.558 | 0.946 | 18.210 | 1.00 | 33.82 |
| ATOM | 3344 | N | ALA | 1070 | 41.900 | 0.347 | 19.580 | 1.00 | 32.06 |
| ATOM | 3345 | H | ALA | 1070 | 41.151 | −0.261 | 19.769 | 1.00 | 0.00 |
| ATOM | 3346 | CA | ALA | 1070 | 42.324 | 1.263 | 20.603 | 1.00 | 28.04 |
| ATOM | 3347 | CB | ALA | 1070 | 41.605 | 2.580 | 20.437 | 1.00 | 26.29 |
| ATOM | 3348 | C | ALA | 1070 | 41.992 | 0.722 | 21.976 | 1.00 | 27.69 |
| ATOM | 3349 | O | ALA | 1070 | 40.919 | 0.153 | 22.184 | 1.00 | 29.45 |
| ATOM | 3350 | N | ILE | 1071 | 42.935 | 0.860 | 22.905 | 1.00 | 26.64 |
| ATOM | 3351 | H | ILE | 1071 | 43.779 | 1.277 | 22.641 | 1.00 | 0.00 |
| ATOM | 3352 | CA | ILE | 1071 | 43.709 | 0.579 | 24.313 | 1.00 | 27.04 |
| ATOM | 3353 | CB | ILE | 1071 | 44.032 | 0.635 | 25.117 | 1.00 | 25.62 |
| ATOM | 3354 | CG2 | ILE | 1071 | 43.730 | 0.441 | 26.608 | 1.00 | 25.21 |
| ATOM | 3355 | CG1 | ILE | 1071 | 45.003 | −0.438 | 24.603 | 1.00 | 26.34 |
| ATOM | 3356 | CD | ILE | 1071 | 46.364 | −0.464 | 25.318 | 1.00 | 23.97 |
| ATOM | 3357 | C | ILE | 1071 | 41.806 | 1.739 | 24.694 | 1.00 | 31.25 |
| ATOM | 3358 | O | ILE | 1071 | 42.087 | 2.874 | 24.292 | 1.00 | 35.46 |
| ATOM | 3359 | N | ALA | 1072 | 40.711 | 1.527 | 25.413 | 1.00 | 38.50 |
| ATOM | 3360 | H | ALA | 1072 | 10.567 | 0.631 | 25.776 | 1.00 | 0.00 |
| ATOM | 3361 | CA | ALA | 1072 | 39.775 | 2.603 | 25.750 | 1.00 | 43.90 |
| ATOM | 3362 | CB | ALA | 1072 | 38.653 | 2.053 | 26.636 | 1.00 | 44.68 |
| ATOM | 3363 | C | ALA | 1072 | 40.407 | 3.805 | 26.464 | 1.00 | 45.61 |
| ATOM | 3364 | O | ALA | 1072 | 41.009 | 3.680 | 27.536 | 1.00 | 45.17 |
| ATOM | 3365 | N | GLY | 1073 | 40.290 | 4.959 | 25.796 | 1.00 | 16.20 |
| ATOM | 3366 | H | GLY | 1073 | 39.880 | 4.931 | 24.912 | 1.00 | 0.00 |
| ATOM | 3367 | CA | GLY | 1073 | 40.820 | 6.231 | 26.267 | 1.00 | 44.42 |
| ATOM | 3368 | C | GLY | 1073 | 42.222 | 6.531 | 25.730 | 1.00 | 43.18 |
| ATOM | 3369 | O | GLY | 1073 | 42.806 | 7.578 | 26.027 | 1.00 | 46.40 |
| ATOM | 3370 | N | GLY | 1073 | 42.812 | 5.634 | 24.947 | 1.00 | 39.43 |
| ATOM | 3371 | H | GLY | 1073 | 42.335 | 4.822 | 24.678 | 1.00 | 0.00 |
| ATOM | 3372 | CA | GLY | 1073 | 44.139 | 5.851 | 24.424 | 1.00 | 34.46 |
| ATOM | 3373 | C | GLY | 1073 | 44.037 | 6.104 | 22.947 | 1.00 | 34.61 |
| ATOM | 3374 | O | GLY | 1073 | 42.964 | 6.354 | 22.378 | 1.00 | 36.50 |
| ATOM | 3375 | N | LYS | 1074 | 45.187 | 5.951 | 22.314 | 1.00 | 37.26 |
| ATOM | 3376 | H | LYS | 1074 | 45.948 | 5.572 | 22.802 | 1.00 | 0.00 |
| ATOM | 3377 | CA | LYS | 1074 | 45.300 | 6.215 | 20.896 | 1.00 | 39.16 |
| ATOM | 3378 | CB | LYS | 1074 | 46.760 | 6.409 | 20.566 | 1.00 | 42.86 |
| ATOM | 3379 | CG | LYS | 1074 | 47.012 | 7.475 | 19.510 | 1.00 | 45.51 |
| ATOM | 3380 | CD | LYS | 1074 | 48.403 | 8.077 | 19.775 | 1.00 | 51.14 |
| ATOM | 3381 | CE | LYS | 1074 | 48.647 | 8.663 | 21.198 | 1.00 | 48.74 |
| ATOM | 3382 | NZ | LYS | 1074 | 47.819 | 9.817 | 21.511 | 1.00 | 46.00 |
| ATOM | 3383 | HZ1 | LYS | 1074 | 46.818 | 9.539 | 21.522 | 1.00 | 0.00 |

TABLE 23-continued

Coordinates for the 3D structure of ZAP-NC:ζ1 "dimer" structure
(two molecules of complex per unit cell)*

| ATOM | 3384 | HZ2 | LYS | 1075 | 47.969 | 10.554 | 20.793 | 1.00 | 0.00 |
|------|------|-----|-----|------|--------|--------|--------|------|------|
| ATOM | 3385 | HZ3 | LYS | 1075 | 48.087 | 10.187 | 22.444 | 1.00 | 0.00 |
| ATOM | 3386 | C | LYS | 1075 | 44.719 | 5.125 | 20.005 | 1.00 | 40.24 |
| ATOM | 3387 | O | LYS | 1075 | 44.968 | 3.916 | 20.185 | 1.00 | 37.79 |
| ATOM | 3388 | N | ALA | 1076 | 43.983 | 5.616 | 19.003 | 1.00 | 40.40 |
| ATOM | 3389 | H | ALA | 1076 | 43.867 | 6.585 | 18.930 | 1.00 | 0.00 |
| ATOM | 3390 | CA | ALA | 1076 | 43.411 | 4.772 | 17.969 | 1.00 | 39.60 |
| ATOM | 3391 | CB | ALA | 1076 | 42.390 | 5.517 | 17.112 | 1.00 | 40.11 |
| ATOM | 3392 | C | ALA | 1076 | 44.577 | 4.383 | 17.084 | 1.00 | 38.92 |
| ATOM | 3393 | O | ALA | 1076 | 45.597 | 5.070 | 16.985 | 1.00 | 40.33 |
| ATOM | 3394 | N | HIS | 1077 | 44.485 | 3.196 | 16.522 | 1.00 | 39.15 |
| ATOM | 3395 | H | HIS | 1077 | 43.653 | 2.682 | 16.622 | 1.00 | 0.00 |
| ATOM | 3396 | CA | HIS | 1077 | 45.516 | 2.622 | 15.693 | 1.00 | 41.38 |
| ATOM | 3397 | CB | HIS | 1077 | 46.386 | 1.682 | 16.493 | 1.00 | 38.84 |
| ATOM | 3398 | CG | HIS | 1077 | 47.188 | 2.367 | 17.574 | 1.00 | 37.80 |
| ATOM | 3399 | CD2 | HIS | 1077 | 48.402 | 2.946 | 17.353 | 1.00 | 37.54 |
| ATOM | 3400 | ND1 | HIS | 1077 | 46.898 | 2.502 | 18.866 | 1.00 | 41.89 |
| ATOM | 3401 | HD1 | HIS | 1077 | 46.011 | 2.402 | 19.292 | 1.00 | 0.00 |
| ATOM | 3402 | CE1 | HIS | 1077 | 47.889 | 3.129 | 19.438 | 1.00 | 40.69 |
| ATOM | 3403 | NE2 | HIS | 1077 | 48.786 | 3.391 | 18.517 | 1.00 | 42.21 |
| ATOM | 3404 | HE2 | HIS | 1077 | 49.577 | 3.946 | 18.657 | 1.00 | 0.00 |
| ATOM | 3405 | C | HIS | 1077 | 44.771 | 1.821 | 14.644 | 1.00 | 44.66 |
| ATOM | 3406 | O | HIS | 1077 | 43.544 | 1.699 | 14.698 | 1.00 | 43.75 |
| ATOM | 3407 | N | CYS | 1078 | 45.467 | 1.272 | 13.664 | 1.00 | 49.78 |
| ATOM | 3408 | H | CYS | 1078 | 46.439 | 1.382 | 13.603 | 1.00 | 0.00 |
| ATOM | 3409 | CA | CYS | 1078 | 44.853 | 0.414 | 12.666 | 1.00 | 54.24 |
| ATOM | 3410 | CB | CYS | 1078 | 45.069 | 0.998 | 11.256 | 1.00 | 58.19 |
| ATOM | 3411 | SG | CYS | 1078 | 44.397 | 2.671 | 11.011 | 1.00 | 71.36 |
| ATOM | 3412 | C | CYS | 1078 | 45.693 | −0.832 | 12.890 | 1.00 | 51.82 |
| ATOM | 3413 | O | CYS | 1078 | 46.927 | −0.752 | 12.852 | 1.00 | 55.71 |
| ATOM | 3414 | N | GLY | 1079 | 45.083 | −1.969 | 13.190 | 1.00 | 47.69 |
| ATOM | 3415 | H | GLY | 1079 | 44.104 | −1.984 | 13.206 | 1.00 | 0.00 |
| ATOM | 3416 | CA | GLY | 1079 | 45.849 | −3.185 | 13.436 | 1.00 | 43.67 |
| ATOM | 3417 | C | GLY | 1079 | 46.508 | −3.249 | 14.823 | 1.00 | 40.20 |
| ATOM | 3418 | O | GLY | 1079 | 47.123 | −2.286 | 15.309 | 1.00 | 40.36 |
| ATOM | 3419 | N | PRO | 1080 | 46.431 | −4.401 | 15.503 | 1.00 | 37.25 |
| ATOM | 3420 | CD | PRO | 1080 | 45.738 | −8.599 | 15.044 | 1.00 | 36.81 |
| ATOM | 3421 | CA | PRO | 1080 | A7.049 | −4.627 | 16.812 | 1.00 | 34.51 |
| ATOM | 3422 | CB | PRO | 1080 | 46.520 | −5.965 | 17.245 | 1.00 | 35.28 |
| ATOM | 3423 | CG | PRO | 1080 | 46.349 | −6.680 | 15.921 | 1.00 | 37.15 |
| ATOM | 3424 | C | PRO | 1080 | 48.559 | −4.583 | 16.707 | 1.00 | 31.54 |
| ATOM | 3425 | O | PRO | 1080 | 49.245 | −4.177 | 17.651 | 1.00 | 31.30 |
| ATOM | 3426 | N | ALA | 1081 | 49.084 | −4.958 | 15.528 | 1.00 | 30.26 |
| ATOM | 3427 | H | ALA | 1081 | 48.480 | −5.268 | 14.829 | 1.00 | 0.00 |
| ATOM | 3428 | CA | ALA | 1081 | 50.515 | −4.940 | 15.256 | 1.00 | 30.04 |
| ATOM | 3429 | CB | ALA | 1081 | 80.778 | −5.435 | 13.827 | 1.00 | 29.58 |
| ATOM | 3430 | C | ALA | 1081 | 51.109 | −3.545 | 15.416 | 1.00 | 30.25 |
| ATOM | 3431 | O | ALA | 1081 | 52.098 | −3.360 | 16.136 | 1.00 | 31.27 |
| ATOM | 3432 | N | GLU | 1082 | 50.462 | −2.534 | 14.822 | 1.00 | 32.52 |
| ATOM | 3433 | H | GLU | 1082 | 49.612 | −2.707 | 14.365 | 1.00 | 0.00 |
| ATOM | 3434 | CA | GLU | 1082 | 50.923 | −1.146 | 14.906 | 1.00 | 31.86 |
| ATOM | 3435 | CB | GLU | 1082 | 50.117 | −0.257 | 13.961 | 1.00 | 33.49 |
| ATOM | 3436 | CG | GLU | 1082 | 50.445 | −0.415 | 12.480 | 1.00 | 34.68 |
| ATOM | 3437 | CD | GLU | 1082 | 50.414 | −1.848 | 11.968 | 1.00 | 38.35 |
| ATOM | 3438 | OE1 | GLU | 1082 | 49.335 | −2.445 | 11.933 | 1.00 | 38.71 |
| ATOM | 3439 | OE2 | GLU | 1082 | 51.485 | −2.364 | 11.638 | 1.00 | 41.55 |
| ATOM | 3440 | C | GLU | 1082 | 50.755 | −0.649 | 16.328 | 1.00 | 29.07 |
| ATOM | 3441 | O | GLU | 1082 | 51.671 | −0.026 | 16.874 | 1.00 | 28.55 |
| ATOM | 3442 | N | LEU | 1083 | 49.605 | −0.991 | 16.942 | 1.00 | 27.23 |
| ATOM | 3443 | H | LEU | 1083 | 48.939 | −1.519 | 16.448 | 1.00 | 0.00 |
| ATOM | 3444 | CA | LEU | 1083 | 49.329 | −0.592 | 18.309 | 1.00 | 26.74 |
| ATOM | 3445 | CB | LEU | 1083 | 48.008 | −1.212 | 18.799 | 1.00 | 25.43 |
| ATOM | 3446 | CG | LEU | 1083 | 47.531 | −0.830 | 20.215 | 1.00 | 21.57 |
| ATOM | 3447 | CD1 | LEU | 1083 | 46.038 | −0.643 | 20.202 | 1.00 | 20.84 |
| ATOM | 3448 | CD2 | LEU | 1083 | 47.943 | −1.898 | 21.226 | 1.00 | 19.23 |
| ATOM | 3449 | C | LEU | 1083 | 50.466 | −0.996 | 19.227 | 1.00 | 29.37 |
| ATOM | 3450 | O | LEU | 1083 | 50.966 | −0.135 | 19.966 | 1.00 | 31.06 |
| ATOM | 3451 | N | CYS | 1084 | 50.930 | −2.252 | 19.124 | 1.00 | 32.62 |
| ATOM | 3452 | H | CYS | 1084 | 50.514 | −2.867 | 18.482 | 1.00 | 0.00 |
| ATOM | 3453 | CA | CYS | 1084 | 51.988 | −2.721 | 20.002 | 1.00 | 31.81 |
| ATOM | 3454 | CB | CYS | 1084 | 52.242 | −4.221 | 19.865 | 1.00 | 31.52 |
| ATOM | 3455 | SG | CYS | 1084 | 50.901 | −5.192 | 20.592 | 1.00 | 29.87 |
| ATOM | 3456 | C | CYS | 1084 | 53.283 | −2.018 | 19.722 | 1.00 | 31.85 |
| ATOM | 3457 | O | CYS | 1084 | 53.989 | −1.702 | 20.679 | 1.00 | 31.54 |
| ATOM | 3458 | N | GLU | 1085 | 53.588 | −1.719 | 18.447 | 1.00 | 33.95 |
| ATOM | 3459 | H | GLU | 1085 | 52.937 | −1.899 | 17.737 | 1.00 | 0.00 |

TABLE 23-continued

Coordinates for the 3D structure of ZAP-NC:ζ1 "dimer" structure
(two molecules of complex per unit cell)*

| ATOM | 3460 | CA | GLU | 1085 | 54.856 | −1.083 | 18.105 | 1.00 | 35.05 |
|---|---|---|---|---|---|---|---|---|---|
| ATOM | 3461 | CB | GLU | 1085 | 55.035 | −1.981 | 16.595 | 1.00 | 40.13 |
| ATOM | 3462 | CG | GLU | 1085 | 56.513 | −1.026 | 16.217 | 1.00 | 49.97 |
| ATOM | 3463 | CD | GLU | 1085 | 56.801 | −0.768 | 14.736 | 1.00 | 60.29 |
| ATOM | 3464 | OE1 | GLU | 1085 | 57.850 | −0.176 | 14.444 | 1.00 | 68.30 |
| ATOM | 3465 | OE2 | GLU | 1085 | 55.991 | −1.138 | 13.874 | 1.00 | 62.08 |
| ATOM | 3466 | C | GLU | 1085 | 54.869 | 0.306 | 18.701 | 1.00 | 32.52 |
| ATOM | 3467 | O | GLU | 1085 | 55.861 | 0.678 | 19.333 | 1.00 | 33.29 |
| ATOM | 3468 | N | PHE | 1086 | 53.721 | 1.005 | 18.599 | 1.00 | 31.71 |
| ATOM | 3469 | H | PHE | 1086 | 52.970 | 0.583 | 18.135 | 1.00 | 0.00 |
| ATOM | 3470 | CA | PHE | 1086 | 53.545 | 2.341 | 19.136 | 1.00 | 31.07 |
| ATOM | 3471 | CB | PHE | 1086 | 52.090 | 2.777 | 18.895 | 1.00 | 29.64 |
| ATOM | 3472 | CG | PHE | 1086 | 51.772 | 4.100 | 19.578 | 1.00 | 34.51 |
| ATOM | 3473 | CD1 | PHE | 1086 | 52.277 | 5.298 | 19.057 | 1.00 | 38.20 |
| ATOM | 3474 | CD2 | PHE | 1086 | 51.030 | 4.112 | 20.770 | 1.00 | 37.01 |
| ATOM | 3475 | CE1 | PHE | 1086 | 52.045 | 6.494 | 19.739 | 1.00 | 37.34 |
| ATOM | 3476 | CE2 | PHE | 1086 | 50.798 | 5.308 | 21.451 | 1.00 | 33.21 |
| ATOM | 3477 | CZ | PHE | 1086 | 51.308 | 6.495 | 20.934 | 1.00 | 39.15 |
| ATOM | 3478 | C | PHE | 1086 | 53.901 | 2.373 | 20.627 | 1.00 | 32.70 |
| ATOM | 3479 | O | PHE | 1086 | 54.661 | 3.239 | 21.084 | 1.00 | 36.52 |
| ATOM | 3480 | N | TYR | 1087 | 53.396 | 1.415 | 21.399 | 1.00 | 32.45 |
| ATOM | 3481 | H | TYR | 1087 | 52.828 | 0.726 | 20.994 | 1.00 | 0.00 |
| ATOM | 3482 | CA | TYR | 1087 | 53.662 | 1.372 | 22.842 | 1.00 | 28.99 |
| ATOM | 3483 | CB | TYR | 1087 | 52.527 | 0.572 | 23.496 | 1.00 | 29.23 |
| ATOM | 3484 | CG | TYR | 1087 | 51.192 | 1.346 | 23.507 | 1.00 | 28.38 |
| ATOM | 3485 | CD1 | TYR | 1087 | 50.221 | 1.141 | 22.520 | 1.00 | 28.31 |
| ATOM | 3486 | CE1 | TYR | 1087 | 49.005 | 1.835 | 22.550 | 1.00 | 26.26 |
| ATOM | 3487 | CD2 | TYR | 1087 | 50.924 | 2.266 | 24.538 | 1.00 | 29.02 |
| ATOM | 3488 | CE2 | TYR | 1087 | 49.703 | 2.963 | 24.572 | 1.00 | 24.57 |
| ATOM | 3489 | CZ | TYR | 1087 | 48.746 | 2.744 | 23.580 | 1.00 | 26.40 |
| ATOM | 3490 | OH | TYR | 1087 | 47.531 | 3.426 | 23.619 | 1.00 | 26.78 |
| ATOM | 3491 | HH | TYR | 1087 | 47.453 | 3.794 | 24.512 | 1.00 | 0.00 |
| ATOM | 3492 | C | TYR | 1087 | 55.036 | 0.814 | 23.165 | 1.00 | 30.34 |
| ATOM | 3493 | O | TYR | 1087 | 55.537 | 0.983 | 24.290 | 1.00 | 30.02 |
| ATOM | 3494 | N | SER | 1088 | 55.716 | 0.129 | 22.241 | 1.00 | 33.87 |
| ATOM | 3495 | H | SER | 1088 | 55.266 | −0.198 | 21.430 | 1.00 | 0.00 |
| ATOM | 3496 | CA | SER | 1088 | 57.099 | −0.270 | 22.439 | 1.00 | 37.71 |
| ATOM | 3497 | CB | SER | 1088 | 57.538 | −1.150 | 21.271 | 1.00 | 40.54 |
| ATOM | 3498 | OG | SER | 1088 | 56.747 | −2.337 | 21.159 | 1.00 | 40.91 |
| ATOM | 3499 | HG | SER | 1088 | 57.236 | −3.023 | 21.637 | 1.00 | 0.00 |
| ATOM | 3500 | C | SER | 1088 | 57.985 | 0.978 | 22.531 | 1.00 | 41.25 |
| ATOM | 3501 | O | SER | 1088 | 59.047 | 0.995 | 23.183 | 1.00 | 38.81 |
| ATOM | 3502 | N | ARG | 1089 | 57.570 | 2.047 | 21.843 | 1.00 | 44.94 |
| ATOM | 3503 | H | ARG | 1089 | 56.773 | 1.973 | 21.274 | 1.00 | 0.00 |
| ATOM | 3504 | CA | ARG | 1089 | 58.272 | 3.314 | 21.934 | 1.00 | 48.42 |
| ATOM | 3505 | CB | ARG | 1089 | 58.161 | 4.166 | 20.656 | 1.00 | 49.53 |
| ATOM | 3506 | CG | ARG | 1089 | 58.895 | 3.689 | 19.410 | 1.00 | 47.71 |
| ATOM | 3507 | CD | ARG | 1089 | 58.041 | 2.725 | 18.614 | 1.00 | 48.46 |
| ATOM | 3508 | NE | ARG | 1089 | 56.856 | 3.372 | 18.073 | 1.00 | 51.23 |
| ATOM | 3509 | HE | ARG | 1089 | 56.280 | 3.894 | 18.668 | 1.00 | 0.00 |
| ATOM | 3510 | CZ | ARG | 1089 | 56.517 | 3.268 | 16.778 | 1.00 | 54.05 |
| ATOM | 3511 | NH1 | ARG | 1089 | 57.265 | 2.560 | 15.912 | 1.00 | 52.77 |
| ATOM | 3512 | HH11 | ARG | 1089 | 58.098 | 2.101 | 16.219 | 1.00 | 0.00 |
| ATOM | 3513 | HH12 | ARG | 1089 | 56.995 | 2.514 | 14.951 | 1.00 | 0.00 |
| ATOM | 3514 | NH2 | ARG | 1089 | 55.391 | 2.865 | 16.355 | 1.00 | 50.10 |
| ATOM | 3515 | HH21 | ARG | 1089 | 54.825 | 4.373 | 17.002 | 1.00 | 0.00 |
| ATOM | 3516 | HH22 | ARG | 1089 | 55.130 | 3.814 | 15.391 | 1.00 | 0.00 |
| ATOM | 3517 | C | ARG | 1089 | 57.655 | 4.107 | 23.072 | 1.00 | 48.92 |
| ATOM | 3518 | O | ARG | 1089 | 58.270 | 4.220 | 24.138 | 1.00 | 49.60 |
| ATOM | 3519 | N | ASP | 1090 | 56.422 | 4.580 | 22.877 | 1.00 | 50.51 |
| ATOM | 3520 | H | ASP | 1090 | 55.905 | 4.297 | 22.092 | 1.00 | 0.00 |
| ATOM | 3521 | CA | ASP | 1090 | 55.753 | 4.557 | 23.834 | 1.00 | 55.15 |
| ATOM | 3522 | CB | ASP | 1090 | 55.177 | 6.659 | 23.071 | 1.00 | 56.05 |
| ATOM | 3523 | CG | ASP | 1090 | 54.281 | 7.584 | 23.889 | 1.00 | 55.59 |
| ATOM | 3524 | OD1 | ASP | 1090 | 53.104 | 7.678 | 23.550 | 1.00 | 57.02 |
| ATOM | 3525 | OD2 | ASP | 1090 | 54.748 | 8.189 | 24.854 | 1.00 | 57.74 |
| ATOM | 3526 | C | ASP | 1090 | 54.653 | 4.774 | 24.659 | 1.00 | 55.94 |
| ATOM | 3527 | O | ASP | 1090 | 53.592 | 4.432 | 24.115 | 1.00 | 55.42 |
| ATOM | 3528 | N | PRO | 1091 | 54.835 | 4.624 | 25.984 | 1.00 | 55.78 |
| ATOM | 3529 | H | PRO | 1091 | 56.135 | 4.706 | 26.655 | 1.00 | 55.19 |
| ATOM | 3530 | CA | PRO | 1091 | 53.801 | 4.154 | 26.897 | 1.00 | 55.95 |
| ATOM | 3531 | CB | PRO | 1091 | 54.598 | 3.706 | 28.114 | 1.00 | 56.04 |
| ATOM | 3532 | CG | PRO | 1091 | 55.792 | 4.624 | 28.138 | 1.00 | 55.88 |
| ATOM | 3533 | C | PRO | 1091 | 52.688 | 5.146 | 27.220 | 1.00 | 56.97 |
| ATOM | 3534 | O | PRO | 1091 | 52.486 | 5.489 | 28.389 | 1.00 | 57.39 |
| ATOM | 3535 | N | ASP | 1092 | 51.933 | 5.654 | 26.238 | 1.00 | 58.64 |

TABLE 23-continued

Coordinates for the 3D structure of ZAP-NC:ζ1 "dimer" structure
(two molecules of complex per unit cell)*

| ATOM | 3536 | H | ASP | 1092 | 52.090 | 5.339 | 25.318 | 1.00 | 0.00 |
|---|---|---|---|---|---|---|---|---|---|
| ATOM | 3537 | CA | ASP | 1092 | 50.820 | 6.556 | 26.519 | 1.00 | 58.90 |
| ATOM | 3538 | CB | ASP | 1092 | 50.155 | 7.027 | 25.210 | 1.00 | 63.88 |
| ATOM | 3539 | CG | ASP | 1092 | 48.815 | 7.764 | 25.350 | 1.00 | 70.81 |
| ATOM | 3540 | OD1 | ASP | 1092 | 47.831 | 7.289 | 34.774 | 1.00 | 74.91 |
| ATOM | 3541 | OD2 | ASP | 1092 | 48.747 | 8.794 | 26.029 | 1.00 | 70.73 |
| ATOM | 3542 | C | ASP | 1092 | 49.792 | 5.826 | 27.385 | 1.00 | 57.19 |
| ATOM | 3543 | O | ASP | 1092 | 48.978 | 5.011 | 26.942 | 1.00 | 56.76 |
| ATOM | 3544 | N | GLY | 1093 | 49.932 | 6.112 | 28.666 | 1.00 | 55.12 |
| ATOM | 3545 | H | GLY | 1093 | 50.717 | 6.617 | 28.959 | 1.00 | 0.00 |
| ATOM | 3546 | CA | GLY | 1093 | 49.040 | 5.592 | 29.665 | 1.00 | 53.01 |
| ATOM | 3547 | C | GLY | 1093 | 49.403 | 4.161 | 30.026 | 1.00 | 48.92 |
| ATOM | 3548 | O | GLY | 1093 | 48.533 | 3.358 | 30.360 | 1.00 | 52.72 |
| ATOM | 3549 | N | LEU | 1094 | 50.665 | 3.777 | 29.993 | 1.00 | 45.02 |
| ATOM | 3550 | H | LEU | 1094 | 51.386 | 4.424 | 29.840 | 1.00 | 0.00 |
| ATOM | 3551 | CA | LEU | 1094 | 50.984 | 2.413 | 31.330 | 1.00 | 40.34 |
| ATOM | 3552 | CB | LEU | 1094 | 51.649 | 1.749 | 29.132 | 1.00 | 38.94 |
| ATOM | 3553 | CG | LEU | 1094 | 50.921 | 0.611 | 28.409 | 1.00 | 36.60 |
| ATOM | 3554 | CD1 | LEU | 1094 | 49.570 | 1.068 | 27.871 | 1.00 | 31.39 |
| ATOM | 3555 | CD2 | LEU | 1094 | 51.824 | 0.120 | 27.283 | 1.00 | 37.39 |
| ATOM | 3556 | C | LEU | 1094 | 51.880 | 2.366 | 31.555 | 1.00 | 39.95 |
| ATOM | 3557 | O | LEU | 1094 | 53.543 | 3.351 | 31.881 | 1.00 | 39.55 |
| ATOM | 3558 | N | PRO | 1095 | 51.866 | 1.249 | 32.290 | 1.00 | 40.07 |
| ATOM | 3559 | CD | PRO | 1095 | 50.737 | 0.328 | 32.367 | 1.00 | 42.05 |
| ATOM | 3560 | CA | PRO | 1095 | 52.888 | 0.848 | 33.241 | 1.00 | 41.65 |
| ATOM | 3561 | CB | PRO | 1095 | 52.491 | 0.578 | 33.571 | 1.00 | 41.38 |
| ATOM | 3562 | CG | PRO | 1095 | 50.991 | 0.476 | 33.630 | 1.00 | 41.02 |
| ATOM | 3563 | C | PRO | 1095 | 54.342 | 0.990 | 32.799 | 1.00 | 42.06 |
| ATOM | 3564 | O | PRO | 1095 | 55.202 | 1.307 | 33.630 | 1.00 | 45.34 |
| ATOM | 3565 | N | CYS | 1096 | 54.666 | 0.605 | 31.565 | 1.00 | 40.67 |
| ATOM | 3566 | H | CYS | 1096 | 53.997 | 0.185 | 30.981 | 1.00 | 0.00 |
| ATOM | 3567 | CA | CYS | 1096 | 55.982 | 0.797 | 30.961 | 1.00 | 38.40 |
| ATOM | 3568 | CB | CYS | 1096 | 57.041 | 0.184 | 31.463 | 1.00 | 39.77 |
| ATOM | 3569 | SG | CYS | 1096 | 56.640 | 1.942 | 31.408 | 1.00 | 39.49 |
| ATOM | 3570 | C | CYS | 1096 | 55.800 | 0.558 | 27.486 | 1.00 | 37.14 |
| ATOM | 3571 | O | CYS | 1096 | 54.686 | 0.204 | 29.075 | 1.00 | 36.74 |
| ATOM | 3572 | N | ASN | 1097 | 56.824 | 0.800 | 28.670 | 1.00 | 37.32 |
| ATOM | 3573 | H | ASN | 1097 | 57.719 | 0.998 | 29.013 | 1.00 | 0.00 |
| ATOM | 3574 | CA | ASN | 1097 | 56.696 | 0.535 | 28.245 | 1.00 | 36.40 |
| ATOM | 3575 | CB | ASN | 1097 | 57.775 | 1.260 | 26.443 | 1.00 | 33.25 |
| ATOM | 3576 | CG | ASN | 1097 | 59.179 | 0.822 | 26.788 | 1.00 | 32.16 |
| ATOM | 3577 | OD1 | ASN | 1097 | 29.559 | 0.769 | 27.957 | 1.00 | 34.46 |
| ATOM | 3578 | ND2 | ASN | 1097 | 59.996 | 0.486 | 25.810 | 1.00 | 35.25 |
| ATOM | 3579 | HD21 | ASN | 1097 | 59.662 | 0.517 | 24.892 | 1.00 | 0.00 |
| ATOM | 3580 | HD22 | ASN | 1097 | 60.893 | 0.203 | 26.064 | 1.00 | 0.00 |
| ATOM | 3581 | C | ASN | 1097 | 56.843 | −0.968 | 27.051 | 1.00 | 38.24 |
| ATOM | 3582 | O | ASN | 1097 | 57.278 | −1.726 | 27.938 | 1.00 | 40.46 |
| ATOM | 3583 | N | LEU | 1098 | 56.431 | −1.443 | 25.886 | 1.00 | 35.38 |
| ATOM | 3584 | H | LEU | 1098 | 56.119 | −0.821 | 25.196 | 1.00 | 0.00 |
| ATOM | 3585 | CA | LEU | 1098 | 56.504 | −2.861 | 25.619 | 1.00 | 30.02 |
| ATOM | 3586 | CB | LEU | 1098 | 55.537 | −3.194 | 24.494 | 1.00 | 29.07 |
| ATOM | 3587 | CG | LEU | 1098 | 54.094 | −2.729 | 24.669 | 1.00 | 26.84 |
| ATOM | 3588 | CD1 | LEU | 1098 | 53.306 | −3.185 | 23.475 | 1.00 | 27.25 |
| ATOM | 3589 | CD2 | LEU | 1098 | 53.496 | −3.273 | 25.960 | 1.00 | 31.57 |
| ATOM | 3590 | C | LEU | 1098 | 57.941 | −3.103 | 25.237 | 1.00 | 29.99 |
| ATOM | 3591 | O | LEU | 1098 | 58.515 | −2.385 | 24.418 | 1.00 | 30.27 |
| ATOM | 3592 | N | ARG | 1099 | 58.565 | −4.056 | 25.901 | 1.00 | 32.01 |
| ATOM | 3593 | H | ARG | 1099 | 58.053 | −4.563 | 26.551 | 1.00 | 0.00 |
| ATOM | 3594 | CA | ARG | 1099 | 59.951 | −4.369 | 25.656 | 1.00 | 33.13 |
| ATOM | 3595 | CB | ARG | 1099 | 60.768 | −4.250 | 26.964 | 1.00 | 33.84 |
| ATOM | 3596 | CG | ARG | 1099 | 60.776 | −2.845 | 27.586 | 1.00 | 37.15 |
| ATOM | 3597 | CD | ARG | 1099 | 61.588 | −2.775 | 28.889 | 1.00 | 42.03 |
| ATOM | 3598 | NE | ARG | 1099 | 61.307 | −1.550 | 29.650 | 1.00 | 45.59 |
| ATOM | 3599 | HE | ARG | 1099 | 60.933 | −0.777 | 29.176 | 1.00 | 0.00 |
| ATOM | 3600 | CZ | ARG | 1099 | 61.545 | −1.435 | 30.972 | 1.00 | 44.75 |
| ATOM | 3601 | NH1 | ARG | 1099 | 62.068 | −2.432 | 31.691 | 1.00 | 47.19 |
| ATOM | 3602 | HH11 | ARG | 1099 | 62.294 | −3.306 | 31.262 | 1.00 | 0.00 |
| ATOM | 3603 | HH12 | ARG | 1099 | 62.221 | −2.304 | 32.670 | 1.00 | 0.00 |
| ATOM | 3604 | NH2 | ARG | 1099 | 61.216 | −0.312 | 31.612 | 1.00 | 41.73 |
| ATOM | 3605 | HH21 | ARG | 1099 | 60.796 | −0.443 | 31.108 | 1.00 | 0.00 |
| ATOM | 3606 | HH22 | ARG | 1099 | 61.379 | −0.226 | 32.594 | 1.00 | 0.00 |
| ATOM | 3607 | C | ARG | 1099 | 60.063 | −5.778 | 25.093 | 1.00 | 35.07 |
| ATOM | 3608 | O | ARG | 1099 | 60.240 | −5.942 | 23.881 | 1.00 | 35.29 |
| ATOM | 3609 | N | LYS | 1100 | 59.781 | −6.841 | 25.868 | 1.00 | 34.71 |
| ATOM | 3610 | H | LYS | 1100 | 59.427 | −6.750 | 26.727 | 1.00 | 0.00 |
| ATOM | 3611 | CA | LYS | 1100 | 60.158 | −8.157 | 25.324 | 1.00 | 37.09 |

TABLE 23-continued

Coordinates for the 3D structure of ZAP-NC:ζ1 "dimer" structure
(two molecules of complex per unit cell)*

| ATOM | 3612 | CB | LYS | 1100 | 60.795 | −9.008 | 26.411 | 1.00 | 42.93 |
|---|---|---|---|---|---|---|---|---|---|
| ATOM | 3613 | CG | LYS | 1100 | 61.396 | −10.344 | 25.868 | 1.00 | 53.06 |
| ATOM | 3614 | CD | LYS | 1100 | 61.978 | −11.153 | 26.969 | 1.00 | 57.15 |
| ATOM | 3615 | CE | LYS | 1100 | 62.305 | −12.569 | 26.488 | 1.00 | 61.71 |
| ATOM | 3616 | NZ | LYS | 1100 | 60.103 | −13.375 | 26.322 | 1.00 | 65.62 |
| ATOM | 3617 | HZ1 | LYS | 1100 | 60.468 | −12.912 | 25.642 | 1.00 | 0.00 |
| ATOM | 3618 | HZ2 | LYS | 1100 | 60.623 | −13.475 | 27.240 | 1.00 | 0.00 |
| ATOM | 3619 | HZ3 | LYS | 1100 | 61.370 | −14.316 | 25.969 | 1.00 | 0.00 |
| ATOM | 3620 | C | LYS | 1100 | 58.848 | −8.765 | 24.833 | 1.00 | 37.79 |
| ATOM | 3621 | O | LYS | 1100 | 57.914 | −8.899 | 25.637 | 1.00 | 39.77 |
| ATOM | 3622 | N | PRO | 1101 | 58.672 | −9.097 | 23.543 | 1.00 | 34.56 |
| ATOM | 3623 | H | PRO | 1101 | 59.557 | −8.728 | 22.448 | 1.00 | 32.70 |
| ATOM | 3624 | CA | PRO | 1101 | 57.514 | −9.832 | 23.050 | 1.00 | 33.16 |
| ATOM | 3625 | CB | PRO | 1101 | 57.701 | −9.840 | 21.556 | 1.00 | 34.82 |
| ATOM | 3626 | CG | PRO | 1101 | 58.594 | −8.657 | 21.285 | 1.00 | 34.87 |
| ATOM | 3627 | C | PRO | 1101 | 57.539 | −11.213 | 23.683 | 1.00 | 30.83 |
| ATOM | 3628 | O | PRO | 1101 | 58.573 | −11.890 | 23.614 | 1.00 | 33.53 |
| ATOM | 3629 | N | CYS | 1102 | 56.480 | −11.707 | 24.317 | 1.00 | 29.51 |
| ATOM | 3630 | H | CYS | 1102 | 55.634 | −11.216 | 24.333 | 1.00 | 0.00 |
| ATOM | 3631 | CA | CYS | 1102 | 56.534 | −13.050 | 24.891 | 1.00 | 27.74 |
| ATOM | 3632 | CB | CYS | 1102 | 55.525 | −13.239 | 26.041 | 1.00 | 24.93 |
| ATOM | 3633 | SG | CYS | 1102 | 55.550 | −14.875 | 26.838 | 1.00 | 25.54 |
| ATOM | 3634 | C | CYS | 1102 | 56.120 | −13.868 | 23.679 | 1.00 | 28.20 |
| ATOM | 3635 | O | CYS | 1102 | 54.939 | −14.057 | 23.356 | 1.00 | 24.55 |
| ATOM | 3636 | N | ASN | 1103 | 57.153 | −14.223 | 22.921 | 1.00 | 25.01 |
| ATOM | 3637 | H | ASN | 1103 | 58.060 | −13.985 | 23.213 | 1.00 | 0.00 |
| ATOM | 3638 | CA | ASN | 1103 | 56.945 | −14.999 | 21.730 | 1.00 | 27.34 |
| ATOM | 3639 | CB | ASN | 1103 | 58.160 | −14.805 | 20.822 | 1.00 | 25.34 |
| ATOM | 3640 | CG | ASN | 1103 | 58.030 | −13.536 | 19.974 | 1.00 | 24.69 |
| ATOM | 3641 | OD1 | ASN | 1103 | 58.871 | −13.209 | 19.144 | 1.00 | 31.34 |
| ATOM | 3642 | ND2 | ASN | 1103 | 57.000 | −12.709 | 20.053 | 1.00 | 27.90 |
| ATOM | 3643 | HD21 | ASN | 1103 | 56.232 | −12.920 | 20.617 | 1.00 | 0.00 |
| ATOM | 3644 | HD22 | ASN | 1103 | 57.117 | −11.875 | 19.552 | 1.00 | 0.00 |
| ATOM | 3645 | C | ASN | 1103 | 56.668 | −16.460 | 22.044 | 1.00 | 27.74 |
| ATOM | 3646 | O | ASN | 1103 | 57.148 | −17.042 | 23.027 | 1.00 | 27.94 |
| ATOM | 3647 | N | ARG | 1104 | 55.745 | −16.955 | 21.217 | 1.00 | 26.87 |
| ATOM | 3648 | H | ARG | 1104 | 55.445 | −16.404 | 20.468 | 1.00 | 0.00 |
| ATOM | 3649 | CA | ARG | 1104 | 55.177 | −18.280 | 21.333 | 1.00 | 26.33 |
| ATOM | 3650 | CB | ARG | 1104 | 54.266 | −18.536 | 20.161 | 1.00 | 24.23 |
| ATOM | 3651 | CG | ARG | 1104 | 52.888 | −18.950 | 20.569 | 1.00 | 25.72 |
| ATOM | 3652 | CD | ARG | 1104 | 51.989 | −19.095 | 19.367 | 1.00 | 24.23 |
| ATOM | 3653 | NE | ARG | 1104 | 51.863 | −17.832 | 18.700 | 1.00 | 24.12 |
| ATOM | 3654 | HE | ARG | 1104 | 51.489 | −17.084 | 19.203 | 1.00 | 0.00 |
| ATOM | 3655 | CZ | ARG | 1104 | 52.257 | −17.629 | 17.447 | 1.00 | 24.35 |
| ATOM | 3656 | HN1 | ARG | 1104 | 52.803 | −18.572 | 16.669 | 1.00 | 22.87 |
| ATOM | 3657 | HH11 | ARG | 1104 | 52.937 | −19.496 | 17.023 | 1.00 | 0.00 |
| ATOM | 3658 | HH12 | ARG | 1104 | 53.075 | −18.349 | 15.734 | 1.00 | 0.00 |
| ATOM | 3659 | NH2 | ARG | 1104 | 52.098 | −16.401 | 16.999 | 1.00 | 26.96 |
| ATOM | 3660 | HD21 | ARG | 1104 | 51.687 | −15.710 | 17.595 | 1.00 | 0.00 |
| ATOM | 3661 | HD22 | ARG | 1104 | 52.368 | −16.154 | 16.074 | 1.00 | 0.00 |
| ATOM | 3662 | C | ARG | 1104 | 56.248 | −19.341 | 21.367 | 1.00 | 25.95 |
| ATOM | 3663 | O | ARG | 1104 | 57.056 | −19.403 | 30.438 | 1.00 | 25.69 |
| ATOM | 3664 | N | PRO | 1105 | 56.321 | −20.176 | 33.402 | 1.00 | 26.74 |
| ATOM | 3665 | H | PRO | 1105 | 55.548 | −20.058 | 23.635 | 1.00 | 29.26 |
| ATOM | 3666 | CA | PRO | 1105 | 57.209 | −21.331 | 22.426 | 1.00 | 32.94 |
| ATOM | 3667 | CB | PRO | 1105 | 56.899 | −21.986 | 23.770 | 1.00 | 28.93 |
| ATOM | 3668 | CG | PRO | 1105 | 55.515 | −21.495 | 24.134 | 1.00 | 30.42 |
| ATOM | 3669 | C | PRO | 1105 | 56.960 | −22.209 | 21.197 | 1.00 | 38.12 |
| ATOM | 3670 | O | PRO | 1105 | 55.865 | −22.738 | 21.004 | 1.00 | 38.58 |
| ATOM | 3671 | N | SER | 1106 | 57.945 | −22.269 | 20.306 | 1.00 | 43.86 |
| ATOM | 3672 | H | SER | 1106 | 58.734 | −21.704 | 20.434 | 1.00 | 0.00 |
| ATOM | 3673 | CA | SER | 1106 | 57.886 | −23.014 | 19.058 | 1.00 | 49.42 |
| ATOM | 3674 | CB | SER | 1106 | 59.331 | −23.177 | 18.574 | 1.00 | 51.93 |
| ATOM | 3675 | OG | SER | 1106 | 59.964 | −21.896 | 18.565 | 1.00 | 55.67 |
| ATOM | 3676 | HG | SER | 1106 | 60.814 | −21.945 | 18.119 | 1.00 | 0.00 |
| ATOM | 3677 | C | SER | 1106 | 57.161 | −24.356 | 19.157 | 1.00 | 49.17 |
| ATOM | 3678 | O | SER | 1106 | 57.443 | −25.230 | 19.979 | 1.00 | 51.15 |
| ATOM | 3679 | N | GLY | 1107 | 56.127 | −24.464 | 18.336 | 1.00 | 47.64 |
| ATOM | 3680 | H | GLY | 1107 | 55.849 | −23.683 | 17.814 | 1.00 | 0.00 |
| ATOM | 3681 | CA | GLY | 1107 | 55.285 | −25.640 | 18.361 | 1.00 | 43.01 |
| ATOM | 3682 | C | GLY | 1107 | 53.901 | −25.219 | 18.826 | 1.00 | 39.30 |
| ATOM | 3683 | O | GLY | 1107 | 52.903 | −25.817 | 18.411 | 1.00 | 42.80 |
| ATOM | 3684 | N | LEU | 1108 | 53.845 | −24.188 | 19.667 | 1.00 | 30.41 |
| ATOM | 3685 | H | LEU | 1108 | 54.668 | −23.763 | 19.977 | 1.00 | 0.00 |
| ATOM | 3686 | CA | LEU | 1108 | 52.603 | −23.628 | 20.133 | 1.00 | 24.96 |
| ATOM | 3687 | CB | LEU | 1108 | 52.839 | −22.863 | 21.434 | 1.00 | 28.86 |

TABLE 23-continued

Coordinates for the 3D structure of ZAP-NC:ζ1 "dimer" structure
(two molecules of complex per unit cell)*

| ATOM | 3688 | CG | LEU | 1108 | 51.627 | −22.255 | 22.107 | 1.00 | 26.69 |
|---|---|---|---|---|---|---|---|---|---|
| ATOM | 3689 | CD1 | LEU | 1108 | 50.821 | −23.356 | 22.737 | 1.00 | 30.10 |
| ATOM | 3690 | CD2 | LEU | 1108 | 52.036 | −21.299 | 23.185 | 1.00 | 29.77 |
| ATOM | 3691 | C | LEU | 1108 | 52.108 | −22.688 | 19.037 | 1.00 | 19.07 |
| ATOM | 3692 | O | LEU | 1108 | 52.868 | −21.897 | 18.471 | 1.00 | 19.17 |
| ATOM | 3693 | N | GLU | 1109 | 50.839 | −22.822 | 18.731 | 1.00 | 11.01 |
| ATOM | 3694 | H | GLU | 1109 | 50.292 | −23.421 | 19.287 | 1.00 | 0.00 |
| ATOM | 3695 | CA | GLU | 1109 | 50.141 | −22.052 | 17.715 | 1.00 | 13.68 |
| ATOM | 3696 | CB | GLU | 1109 | 49.349 | −22.970 | 16.765 | 1.00 | 15.71 |
| ATOM | 3697 | CG | GLU | 1109 | 50.244 | −23.684 | 15.754 | 1.00 | 3.36 |
| ATOM | 3698 | CD | GLU | 1109 | 50.907 | −22.718 | 14.771 | 1.00 | 14.34 |
| ATOM | 3699 | OE1 | GLU | 1109 | 52.127 | −22.779 | 14.666 | 1.00 | 14.12 |
| ATOM | 3700 | OE2 | GLU | 1109 | 50.226 | −21.925 | 14.101 | 1.00 | 18.46 |
| ATOM | 3701 | C | GLU | 1109 | 49.168 | −21.137 | 18.425 | 1.00 | 15.87 |
| ATOM | 3702 | O | GLU | 1109 | 48.936 | −21.367 | 19.623 | 1.00 | 17.90 |
| ATOM | 3703 | N | PRO | 1110 | 48.573 | −20.099 | 17.794 | 1.00 | 12.87 |
| ATOM | 3704 | CD | PRO | 1110 | 49.101 | −19.362 | 16.640 | 1.00 | 9.54 |
| ATOM | 3705 | CA | PRO | 1110 | 47.375 | −19.456 | 18.309 | 1.00 | 10.18 |
| ATOM | 3706 | CB | PRO | 1110 | 47.003 | −18.460 | 17.242 | 1.00 | 11.89 |
| ATOM | 3707 | CG | PRO | 1110 | 48.342 | −18.025 | 16.680 | 1.00 | 12.40 |
| ATOM | 3708 | C | PRO | 1110 | 46.311 | −20.503 | 18.583 | 1.00 | 13.76 |
| ATOM | 3709 | O | PRO | 1110 | 46.240 | −21.529 | 17.895 | 1.00 | 18.10 |
| ATOM | 3710 | N | GLN | 1111 | 45.539 | −20.283 | 19.648 | 1.00 | 14.71 |
| ATOM | 3711 | H | GLN | 1111 | 45.659 | −19.457 | 20.161 | 1.00 | 0.00 |
| ATOM | 3712 | CA | GLN | 1111 | 44.477 | −21.190 | 20.058 | 1.00 | 17.01 |
| ATOM | 3713 | CB | GLN | 1111 | 44.351 | −21.103 | 21.584 | 1.00 | 18.38 |
| ATOM | 3714 | CG | GLN | 1111 | 43.385 | −22.049 | 22.286 | 1.00 | 23.45 |
| ATOM | 3715 | CD | GLN | 1111 | 43.676 | −23.532 | 22.089 | 1.00 | 28.59 |
| ATOM | 3716 | OE1 | GLN | 1111 | 42.757 | −24.348 | 21.959 | 1.00 | 29.01 |
| ATOM | 3717 | NE2 | GLN | 1111 | 44.929 | −23.965 | 22.030 | 1.00 | 27.57 |
| ATOM | 3718 | HE21 | GLN | 1111 | 45.691 | −23.340 | 22.074 | 1.00 | 0.00 |
| ATOM | 3719 | HE22 | GLN | 1111 | 45.064 | −24.928 | 21.948 | 1.00 | 0.00 |
| ATOM | 3720 | C | GLN | 1111 | 43.206 | −20.728 | 19.348 | 1.00 | 20.44 |
| ATOM | 3721 | O | PRO | 1112 | 42.856 | −19.555 | 19.522 | 1.00 | 21.59 |
| ATOM | 3722 | N | PRO | 1112 | 42.514 | −21.525 | 18.509 | 1.00 | 23.22 |
| ATOM | 3723 | CD | PRO | 1112 | 42.844 | −22.911 | 18.181 | 1.00 | 23.13 |
| ATOM | 3724 | CA | PRO | 1112 | 41.305 | −21.123 | 17.811 | 1.00 | 20.52 |
| ATOM | 3725 | CB | PRO | 1112 | 40.998 | −22.286 | 16.909 | 1.00 | 22.54 |
| ATOM | 3726 | CG | PRO | 1112 | 41.526 | −23.474 | 17.670 | 1.00 | 23.92 |
| ATOM | 3727 | C | PRO | 1112 | 40.213 | −20.825 | 18.815 | 1.00 | 24.15 |
| ATOM | 3728 | O | PRO | 1112 | 40.200 | −21.368 | 19.930 | 1.00 | 30.52 |
| ATOM | 3729 | N | GLY | 1113 | 39.267 | −19.977 | 18.447 | 1.00 | 23.10 |
| ATOM | 3730 | H | GLY | 1113 | 39.267 | −19.606 | 17.544 | 1.00 | 0.00 |
| ATOM | 3731 | CA | GLY | 1113 | 29.234 | −19.632 | 19.391 | 1.00 | 19.43 |
| ATOM | 3732 | C | GLY | 1113 | 37.089 | −20.616 | 19.363 | 1.00 | 16.65 |
| ATOM | 3733 | O | GLY | 1113 | 36.646 | −21.008 | 18.289 | 1.00 | 18.76 |
| ATOM | 3734 | N | VAL | 1114 | 36.534 | −30.984 | 20.510 | 1.00 | 13.19 |
| ATOM | 3735 | H | VAL | 1114 | 37.000 | −20.757 | 21.341 | 1.00 | 0.00 |
| ATOM | 3736 | CA | VAL | 1114 | 35.340 | −21.823 | 20.532 | 1.00 | 14.63 |
| ATOM | 3737 | CB | VAL | 1114 | 34.907 | −22.210 | 21.964 | 1.00 | 15.86 |
| ATOM | 3738 | CG1 | VAL | 1114 | 33.601 | −22.998 | 21.950 | 1.00 | 12.00 |
| ATOM | 3739 | CG2 | VAL | 1114 | 35.981 | −23.080 | 22.586 | 1.00 | 18.74 |
| ATOM | 3740 | C | VAL | 1114 | 34.182 | −21.083 | 19.902 | 1.00 | 13.31 |
| ATOM | 3741 | O | VAL | 1114 | 33.443 | −21.670 | 19.117 | 1.00 | 17.48 |
| ATOM | 3742 | N | PHE | 1115 | 33.998 | −19.804 | 20.235 | 1.00 | 11.59 |
| ATOM | 3743 | H | PHE | 1115 | 34.572 | −19.392 | 20.907 | 1.00 | 0.00 |
| ATOM | 3744 | CA | PHE | 1115 | 32.902 | −19.029 | 19.669 | 1.00 | 14.67 |
| ATOM | 3745 | CB | PHE | 1115 | 32.909 | −17.600 | 20.244 | 1.00 | 10.62 |
| ATOM | 3746 | CG | PHE | 1115 | 31.577 | −16.871 | 20.131 | 1.00 | 9.10 |
| ATOM | 3747 | CD1 | PHE | 1115 | 30.397 | −17.551 | 19.840 | 1.00 | 7.14 |
| ATOM | 3748 | CD2 | PHE | 1115 | 31.537 | −15.490 | 20.321 | 1.00 | 11.41 |
| ATOM | 3749 | CE1 | PHE | 1115 | 29.199 | −16.865 | 19.742 | 1.00 | 9.87 |
| ATOM | 3750 | CE2 | PHE | 1115 | 30.328 | −14.805 | 20.222 | 1.00 | 9.09 |
| ATOM | 3751 | CZ | PHE | 1115 | 29.161 | −15.488 | 19.934 | 1.00 | 7.44 |
| ATOM | 3752 | C | PHE | 1115 | 33.025 | −18.962 | 18.146 | 1.00 | 17.73 |
| ATOM | 3753 | O | PHE | 1115 | 32.066 | −19.184 | 17.415 | 1.00 | 16.85 |
| ATOM | 3754 | N | ASP | 1116 | 34.234 | −18.697 | 17.657 | 1.00 | 18.54 |
| ATOM | 3755 | H | ASP | 1116 | 34.964 | −18.588 | 18.291 | 1.00 | 0.00 |
| ATOM | 3756 | CA | ASP | 1116 | 34.524 | −18.601 | 16.242 | 1.00 | 21.41 |
| ATOM | 3757 | CB | ASP | 1116 | 36.045 | −18.374 | 16.039 | 1.00 | 26.96 |
| ATOM | 3758 | CG | ASP | 1116 | 36.719 | −17.147 | 16.693 | 1.00 | 29.54 |
| ATOM | 3759 | OD1 | ASP | 1116 | 37.891 | −16.890 | 16.396 | 1.00 | 32.73 |
| ATOM | 3760 | OD2 | ASP | 1116 | 36.110 | −16.449 | 17.506 | 1.00 | 33.86 |
| ATOM | 3761 | C | CYS | 1117 | 34.076 | −19.895 | 15.576 | 1.00 | 18.86 |
| ATOM | 3762 | O | CYS | 1117 | 33.320 | −19.831 | 14.610 | 1.00 | 20.05 |
| ATOM | 3763 | N | CYS | 1117 | 34.413 | −21.061 | 16.139 | 1.00 | 18.63 |

TABLE 23-continued

Coordinates for the 3D structure of ZAP-NC:ζ1 "dimer" structure
(two molecules of complex per unit cell)*

| ATOM | 3764 | H | CYS | 1117 | 34.979 | −21.075 | 16.939 | 1.00 | 0.00 |
|---|---|---|---|---|---|---|---|---|---|
| ATOM | 3765 | CA | CYS | 1117 | 34.034 | −22.350 | 15.572 | 1.00 | 17.24 |
| ATOM | 3766 | CB | CYS | 1117 | 34.723 | −23.478 | 16.348 | 1.00 | 18.30 |
| ATOM | 3767 | SG | CYS | 1117 | 36.536 | −23.316 | 16.425 | 1.00 | 26.14 |
| ATOM | 3768 | C | CYS | 1117 | 32.531 | −22.513 | 15.634 | 1.00 | 14.66 |
| ATOM | 3769 | O | CYS | 1117 | 31.923 | −23.045 | 14.701 | 1.00 | 21.58 |
| ATOM | 3770 | N | LEU | 1118 | 31.881 | −21.997 | 16.680 | 1.00 | 16.74 |
| ATOM | 3771 | H | LEU | 1118 | 32.402 | −21.553 | 17.381 | 1.00 | 0.00 |
| ATOM | 3772 | CA | LEU | 1118 | 30.431 | −22.098 | 16.849 | 1.00 | 14.92 |
| ATOM | 3773 | CB | LEU | 1118 | 29.978 | −21.517 | 18.192 | 1.00 | 15.40 |
| ATOM | 3774 | CG | LEU | 1118 | 28.763 | −22.045 | 18.959 | 1.00 | 19.35 |
| ATOM | 3775 | CD1 | LEU | 1118 | 28.307 | −20.886 | 19.786 | 1.00 | 20.69 |
| ATOM | 3776 | CD2 | LEU | 1118 | 27.544 | −22.433 | 18.126 | 1.00 | 19.69 |
| ATOM | 3777 | C | LEU | 1118 | 29.739 | −21.314 | 15.755 | 1.00 | 13.42 |
| ATOM | 3778 | O | LEU | 1118 | 28.874 | −21.856 | 15.066 | 1.00 | 17.93 |
| ATOM | 3779 | N | ARG | 1119 | 30.103 | −20.049 | 15.560 | 1.00 | 18.04 |
| ATOM | 3780 | H | ARG | 1119 | 30.822 | −19.690 | 16.116 | 1.00 | 0.00 |
| ATOM | 3781 | CA | ARG | 1119 | 29.506 | −19.188 | 14.549 | 1.00 | 20.03 |
| ATOM | 3782 | CB | ARG | 1119 | 30.169 | −17.814 | 14.511 | 1.00 | 23.89 |
| ATOM | 3783 | CG | ARG | 1119 | 29.866 | −16.868 | 15.654 | 1.00 | 23.86 |
| ATOM | 3784 | CD | ARG | 1119 | 30.650 | −15.585 | 15.352 | 1.00 | 24.54 |
| ATOM | 3785 | NE | ARG | 1119 | 31.494 | −15.252 | 16.483 | 1.00 | 27.03 |
| ATOM | 3786 | HE | ARG | 1119 | 31.083 | −15.218 | 17.373 | 1.00 | 0.00 |
| ATOM | 3787 | CZ | ARG | 1119 | 32.793 | −14.973 | 16.400 | 1.00 | 27.13 |
| ATOM | 3788 | NH1 | ARG | 1119 | 33.472 | −14.963 | 15.257 | 1.00 | 28.80 |
| ATOM | 3789 | HH11 | ARG | 1119 | 33.013 | −15.183 | 14.396 | 1.00 | 0.00 |
| ATOM | 3790 | HH12 | ARG | 1119 | 34.449 | −14.751 | 15.265 | 1.00 | 0.00 |
| ATOM | 3791 | NH2 | ARG | 1119 | 33.442 | −14.720 | 17.532 | 1.00 | 36.40 |
| ATOM | 3792 | HH21 | ARG | 1119 | 32.949 | −14.741 | 18.402 | 1.00 | 0.00 |
| ATOM | 3793 | HH22 | ARG | 1119 | 34.418 | −14.503 | 17.515 | 1.00 | 0.00 |
| ATOM | 3794 | C | ARG | 1119 | 29.674 | −19.828 | 13.182 | 1.00 | 20.52 |
| ATOM | 3795 | O | ARG | 1119 | 28.718 | −19.836 | 12.404 | 1.00 | 22.98 |
| ATOM | 3796 | N | ASP | 1120 | 30.848 | −20.406 | 12.885 | 1.00 | 23.48 |
| ATOM | 3797 | H | ASP | 1120 | 31.568 | −20.357 | 13.552 | 1.00 | 0.00 |
| ATOM | 3798 | CA | ASP | 1120 | 31.101 | −21.113 | 11.627 | 1.00 | 22.85 |
| ATOM | 3799 | CB | ASP | 1120 | 32.511 | −21.706 | 11.604 | 1.00 | 21.65 |
| ATOM | 3800 | CG | ASP | 1120 | 33.616 | −20.731 | 11.243 | 1.00 | 24.26 |
| ATOM | 3801 | OD1 | ASP | 1120 | 33.434 | −19.945 | 10.315 | 1.00 | 32.04 |
| ATOM | 3802 | OD2 | ASP | 1120 | 34.670 | −20.772 | 11.878 | 1.00 | 26.48 |
| ATOM | 3803 | C | ASP | 1120 | 30.113 | −22.243 | 11.386 | 1.00 | 24.84 |
| ATOM | 3804 | O | ASP | 1120 | 29.540 | −22.365 | 10.390 | 1.00 | 24.21 |
| ATOM | 3805 | N | ALA | 1121 | 29.888 | −23.054 | 12.430 | 1.00 | 22.80 |
| ATOM | 3806 | H | ALA | 1121 | 30.393 | −22.917 | 13.262 | 1.00 | 0.00 |
| ATOM | 3807 | CA | ALA | 1121 | 28.937 | −24.140 | 12.339 | 1.00 | 22.02 |
| ATOM | 3808 | CB | ALA | 1121 | 28.945 | −24.943 | 13.637 | 1.00 | 22.11 |
| ATOM | 3809 | C | ALA | 1121 | 27.545 | −23.577 | 12.085 | 1.00 | 23.31 |
| ATOM | 3810 | O | ALA | 1121 | 26.809 | −24.130 | 11.262 | 1.00 | 24.82 |
| ATOM | 3811 | N | MET | 1122 | 27.156 | −22.459 | 12.713 | 1.00 | 21.97 |
| ATOM | 3812 | H | MET | 1122 | 27.767 | −22.050 | 13.365 | 1.00 | 0.00 |
| ATOM | 3813 | CA | MET | 1122 | 25.854 | −21.832 | 12.467 | 1.00 | 18.45 |
| ATOM | 3814 | CB | MET | 1122 | 25.613 | −20.720 | 13.492 | 1.00 | 17.14 |
| ATOM | 3815 | CG | MET | 1122 | 25.432 | −21.261 | 14.904 | 1.00 | 19.15 |
| ATOM | 3816 | SD | MET | 1122 | 25.599 | −20.024 | 16.221 | 1.00 | 18.27 |
| ATOM | 3817 | CE | MET | 1122 | 24.071 | −19.187 | 15.883 | 1.00 | 11.73 |
| ATOM | 3818 | C | MET | 1122 | 25.766 | −21.255 | 11.042 | 1.00 | 17.93 |
| ATOM | 3819 | O | MET | 1122 | 24.772 | −21.488 | 10.354 | 1.00 | 14.65 |
| ATOM | 3820 | N | VAL | 1123 | 26.755 | −20.516 | 10.533 | 1.00 | 19.13 |
| ATOM | 3821 | H | VAL | 1123 | 27.531 | −20.361 | 11.101 | 1.00 | 0.00 |
| ATOM | 3822 | CA | VAL | 1123 | 26.772 | −20.019 | 9.158 | 1.00 | 26.08 |
| ATOM | 3823 | CB | VAL | 1123 | 28.184 | −19.388 | 8.881 | 1.00 | 28.32 |
| ATOM | 3824 | CG1 | VAL | 1123 | 28.276 | −18.942 | 7.432 | 1.00 | 29.68 |
| ATOM | 3825 | CG2 | VAL | 1123 | 28.427 | −18.162 | 9.766 | 1.00 | 28.12 |
| ATOM | 3826 | C | VAL | 1123 | 26.469 | −21.191 | 8.193 | 1.00 | 27.65 |
| ATOM | 3827 | O | VAL | 1123 | 25.512 | −21.163 | 7.406 | 1.00 | 28.82 |
| ATOM | 3828 | N | ARG | 1124 | 27.237 | −22.266 | 8.331 | 1.00 | 29.08 |
| ATOM | 3829 | H | ARG | 1124 | 27.954 | −22.226 | 9.002 | 1.00 | 0.00 |
| ATOM | 3830 | CA | ARG | 1124 | 27.114 | −23.478 | 7.540 | 1.00 | 32.51 |
| ATOM | 3831 | CB | ARG | 1124 | 28.229 | −24.419 | 8.025 | 1.00 | 34.11 |
| ATOM | 3832 | CG | ARG | 1124 | 28.670 | −25.610 | 7.190 | 1.00 | 34.35 |
| ATOM | 3833 | CD | ARG | 1124 | 30.198 | −25.740 | 7.290 | 1.00 | 37.42 |
| ATOM | 3834 | NE | ARG | 1124 | 30.680 | −25.911 | 8.658 | 1.00 | 44.31 |
| ATOM | 3835 | HE | ARG | 1124 | 30.151 | −26.458 | 9.275 | 1.00 | 0.00 |
| ATOM | 3836 | CZ | ARG | 1124 | 31.813 | −25.353 | 9.121 | 1.00 | 46.35 |
| ATOM | 3837 | NH1 | ARG | 1124 | 32.599 | −24.585 | 8.349 | 1.00 | 44.58 |
| ATOM | 3838 | HH11 | ARG | 1124 | 32.350 | −24.406 | 7.397 | 1.00 | 0.00 |
| ATOM | 3839 | HH12 | ARG | 1124 | 33.435 | −24.188 | 8.726 | 1.00 | 0.00 |

TABLE 23-continued

Coordinates for the 3D structure of ZAP-NC:ζ1 "dimer" structure
(two molecules of complex per unit cell)*

| ATOM | 3840 | NH2 | ARG | 1124 | 32.150 | −25.573 | 10.396 | 1.00 | 41.78 |
|---|---|---|---|---|---|---|---|---|---|
| ATOM | 3841 | HH21 | ARG | 1124 | 31.564 | −26.138 | 10.975 | 1.00 | 0.00 |
| ATOM | 3842 | HH22 | ARG | 1124 | 32.989 | −25.172 | 10.767 | 1.00 | 0.00 |
| ATOM | 3843 | C | ARG | 1124 | 25.742 | −24.136 | 7.608 | 1.00 | 32.81 |
| ATOM | 3844 | O | ARG | 1124 | 25.047 | −24.237 | 6.596 | 1.00 | 32.98 |
| ATOM | 3845 | N | ASP | 1125 | 25.291 | −24.527 | 8.793 | 1.00 | 34.45 |
| ATOM | 3846 | H | ASP | 1125 | 25.833 | −24.328 | 9.586 | 1.00 | 0.00 |
| ATOM | 3847 | CA | ASP | 1125 | 24.018 | −25.200 | 8.971 | 1.00 | 40.31 |
| ATOM | 3848 | CB | ASP | 1125 | 23.838 | −25.398 | 10.479 | 1.00 | 45.28 |
| ATOM | 3849 | CG | ASP | 1125 | 22.618 | −26.178 | 10.965 | 1.00 | 53.34 |
| ATOM | 3850 | OD1 | ASP | 1125 | 22.200 | −27.129 | 10.297 | 1.00 | 58.74 |
| ATOM | 3851 | OD2 | ASP | 1125 | 22.095 | −25.835 | 12.031 | 1.00 | 56.41 |
| ATOM | 3852 | C | ASP | 1125 | 22.850 | −24.434 | 8.347 | 1.00 | 42.48 |
| ATOM | 3853 | O | ASP | 1125 | 21.921 | −25.020 | 7.779 | 1.00 | 43.18 |
| ATOM | 3854 | N | TYR | 1126 | 22.936 | −23.104 | 8.375 | 1.00 | 43.78 |
| ATOM | 3855 | H | TYR | 1126 | 23.736 | −22.681 | 8.755 | 1.00 | 0.00 |
| ATOM | 3856 | CA | TYR | 1126 | 21.869 | −22.272 | 7.859 | 1.00 | 45.00 |
| ATOM | 3857 | CB | TYR | 1126 | 21.936 | −20.897 | 8.576 | 1.00 | 49.30 |
| ATOM | 3858 | CG | TYR | 1126 | 21.814 | −20.119 | 10.117 | 1.00 | 56.17 |
| ATOM | 3859 | CD1 | TYR | 1126 | 21.368 | −22.198 | 10.731 | 1.00 | 55.50 |
| ATOM | 3860 | CE1 | TYR | 1126 | 21.340 | −22.338 | 12.118 | 1.00 | 54.12 |
| ATOM | 3861 | CD2 | TYR | 1126 | 22.220 | −19.948 | 10.943 | 1.00 | 58.14 |
| ATOM | 3862 | CE2 | TYR | 1126 | 22.191 | −20.084 | 12.341 | 1.00 | 57.63 |
| ATOM | 3863 | CZ | TYR | 1126 | 21.753 | −21.282 | 12.916 | 1.00 | 55.36 |
| ATOM | 3864 | OH | TYR | 1126 | 21.728 | −21.434 | 14.286 | 1.00 | 52.52 |
| ATOM | 3865 | HH | TYR | 1126 | 21.465 | −22.334 | 14.501 | 1.00 | 0.00 |
| ATOM | 3866 | C | TYR | 1126 | 21.978 | −22.174 | 6.348 | 1.00 | 43.40 |
| ATOM | 3867 | O | TYR | 1126 | 20.947 | −22.293 | 5.687 | 1.00 | 42.11 |
| ATOM | 3868 | N | VAL | 1127 | 23.156 | −22.080 | 5.722 | 1.00 | 43.86 |
| ATOM | 3869 | H | VAL | 1127 | 23.975 | −22.025 | 6.260 | 1.00 | 0.00 |
| ATOM | 3870 | CA | VAL | 1127 | 23.349 | −22.080 | 4.256 | 1.00 | 41.19 |
| ATOM | 3871 | CB | VAL | 1127 | 34.703 | −21.748 | 3.848 | 1.00 | 38.42 |
| ATOM | 3872 | CG1 | VAL | 1127 | 24.955 | −22.021 | 2.377 | 1.00 | 40.55 |
| ATOM | 3873 | CG2 | VAL | 1127 | 24.935 | −20.249 | 4.079 | 1.00 | 34.48 |
| ATOM | 3874 | C | VAL | 1127 | 22.799 | −23.440 | 3.720 | 1.00 | 42.71 |
| ATOM | 3875 | O | VAL | 1127 | 22.056 | −23.517 | 2.743 | 1.00 | 44.92 |
| ATOM | 3876 | N | ARG | 1128 | 23.170 | −24.522 | 4.388 | 1.00 | 44.87 |
| ATOM | 3877 | H | ARG | 1128 | 23.800 | −24.401 | 5.126 | 1.00 | 0.00 |
| ATOM | 3878 | CA | ARG | 1128 | 22.815 | −25.869 | 4.086 | 1.00 | 47.89 |
| ATOM | 3879 | CB | ARG | 1128 | 23.211 | −26.815 | 5.184 | 1.00 | 48.33 |
| ATOM | 3880 | CG | ARG | 1128 | 24.324 | −27.807 | 4.876 | 1.00 | 49.48 |
| ATOM | 3881 | CD | ARG | 1128 | 23.765 | −29.032 | 4.161 | 1.00 | 52.30 |
| ATOM | 3882 | NE | ARG | 1128 | 24.794 | −30.002 | 3.801 | 1.00 | 55.87 |
| ATOM | 3883 | HE | ARG | 1128 | 25.620 | −30.046 | 4.326 | 1.00 | 0.00 |
| ATOM | 3884 | CZ | ARG | 1128 | 24.648 | −30.839 | 2.762 | 1.00 | 57.66 |
| ATOM | 3885 | NH1 | ARG | 1128 | 23.554 | −30.837 | 1.996 | 1.00 | 56.79 |
| ATOM | 3886 | HH11 | ARG | 1128 | 22.801 | −30.206 | 2.186 | 1.00 | 0.00 |
| ATOM | 3887 | HH12 | ARG | 1128 | 23.484 | −31.474 | 1.228 | 1.00 | 0.00 |
| ATOM | 3888 | NH2 | ARG | 1128 | 25.621 | −31.699 | 2.468 | 1.00 | 58.17 |
| ATOM | 3889 | HH21 | ARG | 1128 | 26.455 | −31.725 | 3.020 | 1.00 | 0.00 |
| ATOM | 3890 | HH22 | ARG | 1128 | 25.511 | −32.324 | 1.697 | 1.00 | 0.00 |
| ATOM | 3891 | C | ARG | 1128 | 21.187 | −25.967 | 3.988 | 1.00 | 25.36 |
| ATOM | 3892 | O | ARG | 1128 | 20.653 | −26.862 | 3.328 | 1.00 | 25.10 |
| ATOM | 3893 | N | GLN | 1129 | 20.433 | −25.085 | 4.643 | 1.00 | 57.83 |
| ATOM | 3894 | H | GLN | 1129 | 20.853 | −24.370 | 5.162 | 1.00 | 0.00 |
| ATOM | 3895 | CA | GLN | 1129 | 18.987 | −25.157 | 4.581 | 1.00 | 61.29 |
| ATOM | 3896 | CB | GLN | 1129 | 18.425 | −25.478 | 5.972 | 1.00 | 62.70 |
| ATOM | 3897 | CG | GLN | 1129 | 18.802 | −24.439 | 7.009 | 1.00 | 68.83 |
| ATOM | 3898 | CD | GLN | 1129 | 18.109 | −24.567 | 8.352 | 1.00 | 72.86 |
| ATOM | 3899 | OE1 | GLN | 1129 | 18.096 | −25.602 | 9.015 | 1.00 | 75.79 |
| ATOM | 3900 | NE2 | GLN | 1129 | 17.487 | −23.483 | 8.785 | 1.00 | 74.31 |
| ATOM | 3901 | HE21 | GLN | 1129 | 17.461 | −22.696 | 8.206 | 1.00 | 0.00 |
| ATOM | 3902 | HE22 | GLN | 1129 | 17.131 | −23.512 | 9.698 | 1.00 | 0.00 |
| ATOM | 3903 | C | GLN | 1129 | 18.289 | −23.917 | 4.038 | 1.00 | 61.62 |
| ATOM | 3904 | O | GLN | 1129 | 17.064 | −23.999 | 3.915 | 1.00 | 63.97 |
| ATOM | 3905 | N | THR | 1130 | 18.924 | −22.761 | 3.784 | 1.00 | 61.19 |
| ATOM | 3906 | H | THR | 1130 | 19.871 | −22.634 | 4.007 | 1.00 | 0.00 |
| ATOM | 3907 | CA | THR | 1130 | 18.211 | −21.648 | 3.172 | 1.00 | 62.61 |
| ATOM | 3908 | CB | THR | 1130 | 18.647 | −20.261 | 3.800 | 1.00 | 62.24 |
| ATOM | 3909 | OG1 | THR | 1130 | 20.069 | −20.145 | 3.708 | 1.00 | 62.26 |
| ATOM | 3910 | HG2 | THR | 1130 | 20.285 | −19.197 | 3.660 | 1.00 | 0.00 |
| ATOM | 3911 | CG2 | THR | 1130 | 18.183 | −20.116 | 5.249 | 1.00 | 62.20 |
| ATOM | 3912 | C | THR | 1130 | 18.529 | −21.708 | 1.670 | 1.00 | 65.28 |
| ATOM | 3913 | O | THR | 1130 | 17.842 | −22.402 | 0.907 | 1.00 | 66.03 |
| ATOM | 3914 | N | TRP | 1131 | 19.601 | −21.071 | 1.173 | 1.00 | 65.49 |
| ATOM | 3915 | H | TRP | 1131 | 20.224 | −20.655 | 1.806 | 1.00 | 0.00 |

TABLE 23-continued

Coordinates for the 3D structure of ZAP-NC:ζ1 "dimer" structure
(two molecules of complex per unit cell)*

| ATOM | 3916 | CA  | TRP | 1131 | 19.960 | −21.099 | 1.236  | 1.00 | 65.51 |
|------|------|-----|-----|------|--------|---------|--------|------|-------|
| ATOM | 3917 | CB  | TRP | 1131 | 20.573 | −19.749 | 0.617  | 1.00 | 65.52 |
| ATOM | 3918 | CG  | TRP | 1131 | 20.672 | −19.437 | 2.110  | 1.00 | 69.50 |
| ATOM | 3919 | CD2 | TRP | 1131 | 19.692 | −19.558 | 3.075  | 1.00 | 70.86 |
| ATOM | 3920 | CE2 | TRP | 1131 | 20.344 | −19.011 | 4.192  | 1.00 | 71.04 |
| ATOM | 3921 | NE2 | TRP | 1131 | 18.375 | −20.015 | 3.203  | 1.00 | 74.56 |
| ATOM | 3922 | CE3 | TRP | 1131 | 21.824 | −18.885 | 2.606  | 1.00 | 71.98 |
| ATOM | 3923 | NE1 | TRP | 1131 | 21.587 | −18.632 | 3.868  | 1.00 | 72.22 |
| ATOM | 3924 | HE1 | TRP | 1131 | 22.168 | −18.111 | 4.465  | 1.00 | 0.00  |
| ATOM | 3925 | CZ2 | TRP | 1131 | 19.709 | −18.910 | 5.429  | 1.00 | 69.80 |
| ATOM | 3926 | CZ3 | TRP | 1131 | 17.731 | −19.914 | 4.442  | 1.00 | 71.09 |
| ATOM | 3927 | CH2 | TRP | 1131 | 18.395 | −19.365 | 5.546  | 1.00 | 71.65 |
| ATOM | 3928 | C   | TRP | 1131 | 20.973 | −22.232 | 0.317  | 1.00 | 65.31 |
| ATOM | 3929 | O   | TRP | 1131 | 22.183 | −21.998 | 0.366  | 1.00 | 68.03 |
| ATOM | 3930 | N   | LYS | 1132 | 20.440 | −23.455 | 0.271  | 1.00 | 63.74 |
| ATOM | 3931 | H   | LYS | 1132 | 19.461 | −23.497 | 0.202  | 1.00 | 0.00  |
| ATOM | 3932 | CA  | LYS | 1132 | 21.175 | −24.716 | 0.242  | 1.00 | 63.56 |
| ATOM | 3933 | CB  | LYS | 1132 | 20.189 | −25.850 | 0.533  | 1.00 | 62.60 |
| ATOM | 3934 | CG  | LYS | 1132 | 19.225 | −26.249 | 0.555  | 1.00 | 61.93 |
| ATOM | 3935 | CD  | LYS | 1132 | 18.699 | −27.624 | 0.181  | 1.00 | 62.47 |
| ATOM | 3936 | CE  | LYS | 1132 | 17.702 | −28.156 | 1.197  | 1.00 | 66.22 |
| ATOM | 3937 | NZ  | LYS | 1132 | 16.467 | −27.393 | 1.165  | 1.00 | 69.52 |
| ATOM | 3938 | HZ1 | LYS | 1132 | 16.046 | −27.465 | 0.217  | 1.00 | 0.00  |
| ATOM | 3939 | HZ2 | LYS | 1132 | 16.673 | −26.395 | 1.379  | 1.00 | 0.00  |
| ATOM | 3940 | HZ3 | LYS | 1132 | 15.800 | −27.767 | 1.870  | 1.00 | 0.00  |
| ATOM | 3941 | C   | LYS | 1132 | 22.422 | −24.947 | 1.106  | 1.00 | 65.13 |
| ATOM | 3942 | O   | LYS | 1132 | 22.493 | −25.877 | 1.923  | 1.00 | 58.19 |
| ATOM | 3943 | N   | LEU | 1133 | 23.484 | −24.171 | 0.954  | 1.00 | 63.90 |
| ATOM | 3944 | H   | LEU | 1133 | 23.479 | −23.489 | 0.250  | 1.00 | 0.00  |
| ATOM | 3945 | CA  | LEU | 1133 | 24.674 | −24.387 | 1.743  | 1.00 | 63.65 |
| ATOM | 3946 | CB  | LEU | 1133 | 25.465 | −23.079 | 1.895  | 1.00 | 64.57 |
| ATOM | 3947 | CG  | LEU | 1133 | 24.808 | −21.770 | 2.401  | 1.00 | 63.39 |
| ATOM | 3948 | CD  | LEU | 1133 | 25.918 | −20.803 | 2.797  | 1.00 | 60.88 |
| ATOM | 3949 | CD1 | LEU | 1133 | 23.920 | −22.009 | 3.616  | 1.00 | 62.28 |
| ATOM | 3950 | CD2 | LEU | 1133 | 25.426 | −25.401 | 0.901  | 1.00 | 65.76 |
| ATOM | 3951 | C   | LEU | 1133 | 25.843 | −25.085 | 0.212  | 1.00 | 68.00 |
| ATOM | 3952 | O   | LEU | 1133 | 25.537 | −26.646 | 1.361  | 1.00 | 66.71 |
| ATOM | 3953 | N   | GLU | 1134 | 25.157 | −26.844 | 2.241  | 1.00 | 0.00  |
| ATOM | 3954 | H   | GLU | 1134 | 26.201 | −27.707 | 0.605  | 1.00 | 65.88 |
| ATOM | 3955 | CA  | GLU | 1134 | 25.354 | −28.997 | 0.610  | 1.00 | 67.01 |
| ATOM | 3956 | CB  | GLU | 1134 | 23.846 | −28.933 | 0.907  | 1.00 | 68.05 |
| ATOM | 3957 | CG  | GLU | 1134 | 22.932 | −28.316 | 0.146  | 1.00 | 69.18 |
| ATOM | 3958 | OE1 | GLU | 1134 | 23.314 | −27.338 | 0.789  | 1.00 | 69.90 |
| ATOM | 3959 | OE2 | GLU | 1134 | 21.816 | −28.815 | 0.308  | 1.00 | 67.93 |
| ATOM | 3960 | C   | GLU | 1134 | 27.576 | −28.031 | −1.190 | 1.00 | 64.86 |
| ATOM | 3961 | O   | GLU | 1134 | 28.087 | −27.284 | −2.032 | 1.00 | 65.19 |
| ATOM | 3962 | N   | GLY | 1135 | 28.237 | −29.113 | −0.748 | 1.00 | 63.94 |
| ATOM | 3963 | H   | GLY | 1135 | 27.890 | −29.572 | 0.041  | 1.00 | 0.00  |
| ATOM | 3964 | CA  | GLY | 1135 | 29.510 | −29.581 | −1.300 | 1.00 | 64.32 |
| ATGM | 3965 | C   | GLY | 1135 | 30.626 | −28.564 | −1.134 | 1.00 | 65.04 |
| ATOM | 3966 | O   | GLY | 1135 | 30.865 | −28.078 | −0.027 | 1.00 | 69.14 |
| ATOM | 3967 | N   | GLU | 1136 | 31.305 | −28.230 | −2.232 | 1.00 | 65.55 |
| ATOM | 3968 | H   | GLU | 1136 | 31.118 | −28.749 | −3.038 | 1.00 | 0.00  |
| ATOM | 3969 | CA  | GLU | 1136 | 32.335 | −27.183 | −2.250 | 1.00 | 63.31 |
| ATOM | 3970 | CB  | GLU | 1136 | 33.131 | −27.142 | −3.579 | 1.00 | 67.04 |
| ATOM | 3971 | CG  | GLU | 1136 | 32.638 | −27.887 | −4.845 | 1.00 | 70.75 |
| ATOM | 3972 | CD  | GLU | 1136 | 31.274 | −27.511 | −5.428 | 1.00 | 72.63 |
| ATOM | 3973 | OE1 | GLU | 1136 | 30.272 | −28.090 | −4.999 | 1.00 | 72.08 |
| ATOM | 3974 | OE2 | GLU | 1136 | 31.218 | −26.661 | −6.321 | 1.00 | 72.72 |
| ATOM | 3975 | C   | GLU | 1136 | 31.703 | −25.810 | −2.070 | 1.00 | 58.99 |
| ATOM | 3976 | O   | GLU | 1136 | 32.147 | −24.983 | −1.268 | 1.00 | 56.93 |
| ATOM | 3977 | N   | ALA | 1137 | 30.581 | −25.625 | −2.766 | 1.00 | 56.11 |
| ATOM | 3978 | H   | ALA | 1137 | 30.196 | −26.378 | −3.254 | 1.00 | 0.00  |
| ATOM | 3979 | CA  | ALA | 1137 | 29.850 | −24.377 | −2.767 | 1.00 | 56.06 |
| ATOM | 3980 | CB  | ALA | 1137 | 28.617 | −24.541 | −3.663 | 1.00 | 55.23 |
| ATOM | 3981 | C   | ALA | 1137 | 29.446 | −23.931 | −1.362 | 1.00 | 55.98 |
| ATOM | 3982 | O   | ALA | 1137 | 29.361 | −22.731 | −1.087 | 1.00 | 54.23 |
| ATOM | 3983 | N   | LEU | 1138 | 29.238 | −24.894 | −0.464 | 1.00 | 57.71 |
| ATOM | 3984 | H   | LEU | 1138 | 29.212 | −25.815 | −0.787 | 1.00 | 0.00  |
| ATOM | 3985 | CA  | LEU | 1138 | 28.985 | −24.630 | 0.947  | 1.00 | 60.29 |
| ATOM | 3986 | CB  | LEU | 1138 | 28.623 | −25.949 | 1.639  | 1.00 | 55.39 |
| ATOM | 3987 | CG  | LEU | 1138 | 28.039 | −26.034 | 3.047  | 1.00 | 54.97 |
| ATOM | 3988 | CD1 | LEU | 1138 | 26.745 | −25.238 | 3.210  | 1.00 | 49.34 |
| ATOM | 3989 | CD2 | LEU | 1138 | 27.782 | −27.510 | 3.310  | 1.00 | 52.82 |
| ATOM | 3990 | C   | LEU | 1138 | 30.257 | −24.016 | 1.541  | 1.00 | 61.97 |
| ATOM | 3991 | O   | LEU | 1138 | 30.199 | −22.866 | 1.993  | 1.00 | 62.86 |

TABLE 23-continued

Coordinates for the 3D structure of ZAP-NC:ζ1 "dimer" structure
(two molecules of complex per unit cell)*

| ATOM | 3992 | N | GLU | 1139 | 31.421 | −24.691 | 1.488 | 1.00 | 61.86 |
|---|---|---|---|---|---|---|---|---|---|
| ATOM | 3993 | H | GLU | 1139 | 31.407 | −25.596 | 1.112 | 1.00 | 0.00 |
| ATOM | 3994 | CA | GLU | 1139 | 32.702 | −24.191 | 2.000 | 1.00 | 62.74 |
| ATOM | 3995 | CB | GLU | 1139 | 33.815 | −25.131 | 1.497 | 1.00 | 61.24 |
| ATOM | 3996 | CG | GLU | 1139 | 35.261 | −24.889 | 1.948 | 1.00 | 57.30 |
| ATOM | 3997 | CD | GLU | 1139 | 36.311 | −25.774 | 1.269 | 1.00 | 55.83 |
| ATOM | 3998 | OE1 | GLU | 1139 | 36.544 | −25.580 | 0.074 | 1.00 | 57.77 |
| ATOM | 3999 | OE2 | GLU | 1139 | 36.899 | −26.646 | 1.924 | 1.00 | 50.09 |
| ATOM | 4000 | C | GLU | 1139 | 32.984 | −22.739 | 1.587 | 1.00 | 65.63 |
| ATOM | 4001 | O | GLU | 1139 | 33.420 | −21.921 | 2.417 | 1.00 | 66.43 |
| ATOM | 4002 | N | GLN | 1140 | 32.682 | −22.377 | 0.325 | 1.00 | 65.95 |
| ATOM | 4003 | H | GLN | 1140 | 32.365 | −23.071 | −0.297 | 1.00 | 0.00 |
| ATOM | 4004 | CA | GLN | 1140 | 32.876 | −21.003 | −0.136 | 1.00 | 66.03 |
| ATOM | 4005 | CB | GLN | 1140 | 32.967 | −20.930 | −1.681 | 1.00 | 67.56 |
| ATOM | 4006 | CG | GLN | 1140 | 31.674 | −20.780 | −2.496 | 1.00 | 72.83 |
| ATOM | 4007 | CD | GLN | 1140 | 31.587 | −21.593 | −3.783 | 1.00 | 77.61 |
| ATOM | 4008 | OE1 | GLN | 1140 | 32.482 | −22.341 | −4.178 | 1.00 | 79.83 |
| ATOM | 4009 | NE2 | GLN | 1140 | 30.460 | −21.524 | −4.480 | 1.00 | 79.79 |
| ATOM | 4010 | HE21 | GLN | 1140 | 29.726 | −20.982 | −4.126 | 1.00 | 0.00 |
| ATOM | 4011 | HE22 | GLN | 1140 | 30.439 | −22.013 | −5.326 | 1.00 | 0.00 |
| ATOM | 4012 | C | GLN | 1140 | 31.738 | −20.111 | 0.344 | 1.00 | 65.43 |
| ATOM | 4013 | O | GLN | 1140 | 32.001 | −18.966 | 0.717 | 1.00 | 65.89 |
| ATOM | 4014 | N | ALA | 1141 | 30.484 | −20.593 | 0.404 | 1.00 | 64.48 |
| ATOM | 4015 | H | ALA | 1141 | 30.331 | −21.536 | 0.181 | 1.00 | 0.00 |
| ATOM | 4016 | CA | ALA | 1141 | 29.327 | −19.805 | 0.819 | 1.00 | 63.19 |
| ATOM | 4017 | CB | ALA | 1141 | 28.077 | −20.670 | 0.840 | 1.00 | 60.31 |
| ATOM | 4018 | C | ALA | 1141 | 29.515 | −19.218 | 2.209 | 1.00 | 61.63 |
| ATOM | 4019 | O | ALA | 1141 | 29.156 | −18.073 | 2.488 | 1.00 | 60.18 |
| ATOM | 4020 | N | ILE | 1142 | 30.160 | −20.006 | 3.067 | 1.00 | 61.25 |
| ATOM | 4021 | H | ILE | 1142 | 30.402 | −20.903 | 2.746 | 1.00 | 0.00 |
| ATOM | 4022 | CA | ILE | 1142 | 30.484 | −19.641 | 4.435 | 1.00 | 59.83 |
| ATOM | 4023 | CB | ILE | 1142 | 31.157 | −20.900 | 5.095 | 1.00 | 60.04 |
| ATOM | 4024 | CG2 | ILE | 1142 | 32.084 | −20.514 | 6.259 | 1.00 | 63.09 |
| ATOM | 4025 | CG1 | ILE | 1142 | 30.376 | −21.816 | 5.665 | 1.00 | 58.69 |
| ATOM | 4026 | CD | ILE | 1142 | 29.000 | −22.397 | 4.736 | 1.00 | 54.31 |
| ATOM | 4027 | C | ILE | 1142 | 31.367 | −18.397 | 4.469 | 1.00 | 59.27 |
| ATOM | 4028 | O | ILE | 1142 | 31.114 | −17.476 | 5.251 | 1.00 | 57.70 |
| ATOM | 4029 | N | ILE | 1143 | 32.397 | −18.305 | 3.631 | 1.00 | 60.19 |
| ATOM | 4030 | H | ILE | 1143 | 32.567 | −19.013 | 2.972 | 1.00 | 0.00 |
| ATOM | 4031 | CA | ILE | 1143 | 33.242 | −17.128 | 3.679 | 1.00 | 61.81 |
| ATOM | 4032 | CB | ILE | 1143 | 34.659 | −17.470 | 3.078 | 1.00 | 64.29 |
| ATOM | 4033 | CG2 | ILE | 1143 | 34.620 | −17.636 | 1.554 | 1.00 | 63.53 |
| ATOM | 4034 | CG1 | ILE | 1143 | 35.640 | −16.335 | 3.454 | 1.00 | 66.15 |
| ATOM | 4035 | CD | ILE | 1143 | 35.960 | −16.121 | 4.963 | 1.00 | 61.98 |
| ATOM | 4036 | C | ILE | 1143 | 32.552 | −15.992 | 2.941 | 1.00 | 61.53 |
| ATOM | 4037 | O | ILE | 1143 | 32.769 | −14.816 | 3.240 | 1.00 | 62.25 |
| ATOM | 4038 | N | SER | 1144 | 31.642 | −18.318 | 2.030 | 1.00 | 63.73 |
| ATOM | 4039 | H | SER | 1144 | 31.415 | −17.258 | 1.876 | 1.00 | 0.00 |
| ATOM | 4040 | CA | SER | 1144 | 30.940 | −15.310 | 1.265 | 1.00 | 64.99 |
| ATOM | 4041 | CB | SER | 1144 | 30.516 | −15.998 | −0.048 | 1.00 | 65.52 |
| ATOM | 4042 | OG | SER | 1144 | 31.608 | −16.655 | −0.702 | 1.00 | 60.59 |
| ATOM | 4043 | HG | SER | 1144 | 32.049 | −17.235 | −0.076 | 1.00 | 0.00 |
| ATOM | 4044 | C | SER | 1144 | 29.758 | −14.731 | 2.067 | 1.00 | 65.32 |
| ATOM | 4045 | O | SER | 1144 | 28.634 | −14.623 | 1.559 | 1.00 | 59.14 |
| ATOM | 4046 | N | GLN | 1145 | 29.938 | −14.325 | 3.335 | 1.00 | 63.50 |
| ATOM | 4047 | H | GLN | 1145 | 30.843 | −14.279 | 3.712 | 1.00 | 0.00 |
| ATOM | 4048 | CA | GLN | 1145 | 28.809 | −13.809 | 4.091 | 1.00 | 60.48 |
| ATOM | 4049 | CB | GLN | 1145 | 28.723 | −14.494 | 5.452 | 1.00 | 56.62 |
| ATOM | 4050 | CG | GLN | 1145 | 28.142 | −15.910 | 5.299 | 1.00 | 53.05 |
| ATOM | 4051 | CD | GLN | 1145 | 26.825 | −16.090 | 4.525 | 1.00 | 51.72 |
| ATOM | 4052 | OE1 | GLN | 1145 | 25.802 | −15.428 | 4.735 | 1.00 | 53.41 |
| ATOM | 4053 | NE2 | GLN | 1145 | 26.771 | −17.024 | 3.593 | 1.00 | 46.83 |
| ATOM | 4054 | HE21 | GLN | 1145 | 27.582 | −17.547 | 3.429 | 1.00 | 0.00 |
| ATOM | 4055 | HE22 | GLN | 1145 | 25.935 | −17.136 | 3.098 | 1.00 | 0.00 |
| ATOM | 4056 | C | GLN | 1145 | 28.790 | −12.311 | 4.280 | 1.00 | 58.63 |
| ATOM | 4057 | O | GLN | 1145 | 29.778 | −11.635 | 4.576 | 1.00 | 56.87 |
| ATOM | 4058 | N | ALA | 1146 | 27.578 | −11.849 | 3.981 | 1.00 | 59.12 |
| ATOM | 4059 | H | ALA | 1146 | 26.897 | −12.510 | 3.738 | 1.00 | 0.00 |
| ATOM | 4060 | CA | ALA | 1146 | 27.193 | −10.451 | 4.009 | 1.00 | 62.34 |
| ATOM | 4061 | CB | ALA | 1146 | 25.679 | −10.365 | 3.809 | 1.00 | 59.64 |
| ATOM | 4062 | CG | ALA | 1146 | 27.582 | −97.59 | 5.314 | 1.00 | 65.19 |
| ATOM | 4063 | C | ALA | 1146 | 27.167 | −10.223 | 6.375 | 1.00 | 68.05 |
| ATOM | 4064 | O | ALA | 1146 | 28.322 | −86.45 | 5.329 | 1.00 | 66.24 |
| ATOM | 4065 | N | PRO | 1147 | 28.322 | −76.61 | 4.250 | 1.00 | 68.36 |
| ATOM | 4066 | H | PRO | 1147 | 29.113 | −81.66 | 6.468 | 1.00 | 65.49 |
| ATOM | 4067 | CA | PRO | 1147 | 29.549 | −67.86 | 6.027 | 1.00 | 66.85 |

TABLE 23-continued

Coordinates for the 3D structure of ZAP-NC:ζ1 "dimer" structure
(two molecules of complex per unit cell)*

| ATOM | 4068 | CB | PRO | 1147 | 29.610 | −69.07 | 4.523 | 1.00 | 68.63 |
|---|---|---|---|---|---|---|---|---|---|
| ATOM | 4069 | C | PRO | 1147 | 28.493 | −81.63 | 7.871 | 1.00 | 63.34 |
| ATOM | 4070 | O | PRO | 1147 | 29.080 | −86.99 | 8.816 | 1.00 | 61.92 |
| ATOM | 4071 | N | GLN | 1148 | 27.298 | −76.05 | 8.089 | 1.00 | 59.39 |
| ATOM | 4072 | H | GLN | 1148 | 26.805 | −72.35 | 7.326 | 1.00 | 0.00 |
| ATOM | 4073 | CA | GLN | 1148 | 26.750 | −75.91 | 9.436 | 1.00 | 54.07 |
| ATOM | 4074 | CB | GLN | 1148 | 25.679 | −64.84 | 9.581 | 1.00 | 54.31 |
| ATOM | 4075 | CG | GLN | 1148 | 24.390 | −65.16 | 8.766 | 1.00 | 56.67 |
| ATOM | 4076 | CD | GLN | 1148 | 24.445 | −59.27 | 7.356 | 1.00 | 56.23 |
| ATOM | 4077 | OE1 | GLN | 1148 | 25.198 | −63.60 | 6.475 | 1.00 | 57.34 |
| ATOM | 4078 | NE2 | GLN | 1148 | 23.635 | −49.17 | 7.079 | 1.00 | 51.65 |
| ATOM | 4079 | HE21 | GLN | 1148 | 23.090 | −45.54 | 7.811 | 1.00 | 0.00 |
| ATOM | 4080 | HE22 | GLN | 1148 | 23.553 | −45.91 | 6.160 | 1.00 | 0.00 |
| ATOM | 4081 | C | GLN | 1148 | 26.164 | −89.29 | 9.884 | 1.00 | 50.94 |
| ATOM | 4082 | O | GLN | 1148 | 25.824 | −90.64 | 11.061 | 1.00 | 47.58 |
| ATOM | 4083 | N | VAL | 1149 | 26.097 | −99.91 | 9.063 | 1.00 | 49.04 |
| ATOM | 4084 | H | VAL | 1149 | 26.493 | −99.40 | 8.186 | 1.00 | 0.00 |
| ATOM | 4085 | CA | VAL | 1149 | 25.492 | −11.239 | 9.524 | 1.00 | 45.67 |
| ATOM | 4086 | CB | VAL | 1149 | 25.146 | −12.262 | 8.372 | 1.00 | 41.33 |
| ATOM | 4087 | CG1 | VAL | 1149 | 24.379 | −11.486 | 7.327 | 1.00 | 44.52 |
| ATOM | 4088 | CG2 | VAL | 1149 | 26.342 | −12.968 | 7.782 | 1.00 | 37.34 |
| ATOM | 4089 | C | VAL | 1149 | 26.393 | −11.954 | 10.518 | 1.00 | 43.99 |
| ATOM | 4090 | O | VAL | 1149 | 25.900 | −12.667 | 11.386 | 1.00 | 41.36 |
| ATOM | 4091 | N | GLU | 1150 | 27.705 | −11.733 | 10.479 | 1.00 | 42.85 |
| ATOM | 4092 | H | GLU | 1150 | 28.054 | −11.109 | 9.808 | 1.00 | 0.00 |
| ATOM | 4093 | CA | GLU | 1150 | 28.618 | −12.389 | 11.398 | 1.00 | 42.22 |
| ATOM | 4094 | CB | GLU | 1150 | 30.050 | −12.009 | 11.046 | 1.00 | 46.21 |
| ATOM | 4095 | CG | GLU | 1150 | 30.495 | −12.414 | 9.621 | 1.00 | 57.47 |
| ATOM | 4096 | CD | GLU | 1150 | 30.205 | −11.422 | 8.478 | 1.00 | 62.05 |
| ATOM | 4097 | OE1 | GLU | 1150 | 31.050 | −10.572 | 8.182 | 1.00 | 67.14 |
| ATOM | 4098 | OE2 | GLU | 1150 | 29.142 | −11.493 | 7.865 | 1.00 | 61.78 |
| ATOM | 4099 | C | GLU | 1150 | 28.255 | −11.931 | 12.803 | 1.00 | 38.38 |
| ATOM | 4100 | O | GLU | 1150 | 27.993 | −12.741 | 13.689 | 1.00 | 42.57 |
| ATOM | 4101 | N | LYS | 1151 | 28.058 | −10.619 | 12.937 | 1.00 | 35.01 |
| ATOM | 4102 | H | LYS | 1151 | 28.150 | −10.069 | 12.135 | 1.00 | 0.00 |
| ATOM | 4103 | CA | LYS | 1151 | 27.642 | −9.981 | 14.175 | 1.00 | 30.94 |
| ATOM | 4104 | CB | LYS | 1151 | 27.567 | −8.423 | 14.081 | 1.00 | 34.99 |
| ATOM | 4105 | CG | LYS | 1151 | 28.827 | −7.591 | 13.773 | 1.00 | 39.28 |
| ATOM | 4106 | CD | LYS | 1151 | 29.258 | −7.778 | 12.320 | 1.00 | 44.76 |
| ATOM | 4107 | CE | LYS | 1151 | 30.649 | −7.256 | 12.041 | 1.00 | 47.25 |
| ATOM | 4108 | NZ | LYS | 1151 | 31.121 | −7.818 | 10.788 | 1.00 | 45.73 |
| ATOM | 4109 | HZ1 | LYS | 1151 | 30.467 | −7.579 | 10.016 | 1.00 | 0.00 |
| ATOM | 4110 | HZ2 | LYS | 1151 | 31.179 | −8.852 | 10.886 | 1.00 | 0.00 |
| ATOM | 4111 | HZ3 | LYS | 1151 | 32.067 | −7.440 | 10.576 | 1.00 | 0.00 |
| ATOM | 4112 | C | LYS | 1151 | 26.241 | −10.466 | 14.517 | 1.00 | 25.99 |
| ATOM | 4113 | O | LYS | 1151 | 25.943 | −10.676 | 15.685 | 1.00 | 27.16 |
| ATOM | 4114 | N | LEU | 1152 | 25.357 | −10.684 | 13.540 | 1.00 | 22.11 |
| ATOM | 4115 | H | LEU | 1152 | 25.620 | −10.478 | 12.621 | 1.00 | 0.00 |
| ATOM | 4116 | CA | LEU | 1152 | 23.993 | −11.114 | 13.813 | 1.00 | 16.23 |
| ATOM | 4117 | CB | LEU | 1152 | 23.177 | −10.957 | 12.515 | 1.00 | 9.86 |
| ATOM | 4118 | CG | LEU | 1152 | 22.906 | −9.504 | 12.080 | 1.00 | 11.37 |
| ATOM | 4119 | CD1 | LEU | 1152 | 22.338 | −9.492 | 10.678 | 1.00 | 9.78 |
| ATOM | 4120 | CD2 | LEU | 1152 | 21.910 | −8.841 | 13.005 | 1.00 | 11.47 |
| ATOM | 4121 | C | LEU | 1152 | 23.896 | −12.523 | 14.371 | 1.00 | 10.24 |
| ATOM | 4122 | O | LEU | 1152 | 23.131 | −12.774 | 15.299 | 1.00 | 9.17 |
| ATOM | 4123 | N | ILE | 1153 | 24.727 | −13.419 | 13.841 | 1.00 | 13.04 |
| ATOM | 4124 | H | ILE | 1153 | 25.319 | −13.098 | 13.132 | 1.00 | 0.00 |
| ATOM | 4125 | CA | ILE | 1153 | 24.864 | −14.828 | 14.218 | 1.00 | 12.12 |
| ATOM | 4126 | CB | ILE | 1153 | 25.744 | −15.474 | 13.121 | 1.00 | 15.18 |
| ATOM | 4127 | CG2 | ILE | 1153 | 26.453 | −16.748 | 13.547 | 1.00 | 14.74 |
| ATOM | 4128 | CG1 | ILE | 1153 | 24.803 | −15.737 | 11.964 | 1.00 | 15.60 |
| ATOM | 4129 | CD | ILE | 1153 | 25.554 | −16.002 | 10.657 | 1.00 | 27.01 |
| ATOM | 4130 | C | ILE | 1153 | 25.457 | −14.936 | 15.614 | 1.00 | 12.01 |
| ATOM | 4131 | O | ILE | 1153 | 24.938 | −15.653 | 16.468 | 1.00 | 12.84 |
| ATOM | 4132 | N | ALA | 1154 | 26.552 | −14.241 | 15.879 | 1.00 | 10.22 |
| ATOM | 4133 | H | ALA | 1154 | 27.021 | −13.803 | 15.135 | 1.00 | 0.00 |
| ATOM | 4134 | CA | ALA | 1154 | 27.123 | −14.168 | 17.201 | 1.00 | 11.63 |
| ATOM | 4135 | CB | ALA | 1154 | 28.259 | −13.194 | 17.110 | 1.00 | 8.82 |
| ATOM | 4136 | C | ALA | 1154 | 26.107 | −13.747 | 18.276 | 1.00 | 18.06 |
| ATOM | 4137 | O | ALA | 1154 | 25.901 | −14.458 | 19.281 | 1.00 | 22.58 |
| ATOM | 4138 | N | THR | 1155 | 25.380 | −12.645 | 18.103 | 1.00 | 17.52 |
| ATOM | 4139 | H | THR | 1155 | 25.577 | −12.028 | 17.358 | 1.00 | 0.00 |
| ATOM | 4140 | CA | THR | 1155 | 24.349 | −12.242 | 19.065 | 1.00 | 18.83 |
| ATOM | 4141 | CB | THR | 1155 | 23.904 | −10.801 | 18.598 | 1.00 | 22.02 |
| ATOM | 4142 | OG1 | THR | 1155 | 25.086 | −9.989 | 18.654 | 1.00 | 25.75 |
| ATOM | 4143 | HG1 | THR | 1155 | 25.450 | −9.946 | 19.545 | 1.00 | 0.00 |

TABLE 23-continued

Coordinates for the 3D structure of ZAP-NC:ζ1 "dimer" structure
(two molecules of complex per unit cell)*

| ATOM | 4144 | CG2 | THR | 1155 | 22.905 | −10.096 | 19.487 | 1.00 | 26.93 |
|---|---|---|---|---|---|---|---|---|---|
| ATOM | 4145 | C | THR | 1155 | 23.190 | −13.272 | 19.190 | 1.00 | 20.86 |
| ATOM | 4146 | O | THR | 1155 | 22.481 | −13.310 | 20.208 | 1.00 | 18.89 |
| ATOM | 4147 | N | THR | 1156 | 22.963 | −14.161 | 18.207 | 1.00 | 21.15 |
| ATOM | 4148 | H | THR | 1156 | 23.450 | −14.028 | 17.364 | 1.00 | 0.00 |
| ATOM | 4149 | CA | THR | 1156 | 21.961 | −15.233 | 18.199 | 1.00 | 18.52 |
| ATOM | 4150 | CB | THR | 1156 | 21.500 | −15.438 | 16.684 | 1.00 | 19.00 |
| ATOM | 4152 | HG1 | THR | 1156 | 19.941 | −14.355 | 17.088 | 1.00 | 0.00 |
| ATOM | 4153 | CG2 | ALA | 1157 | 20.789 | −16.746 | 16.399 | 1.00 | 21.79 |
| ATOM | 4154 | C | ALA | 1157 | 22.487 | −16.548 | 18.816 | 1.00 | 15.90 |
| ATOM | 4155 | O | ALA | 1157 | 21.664 | −17.362 | 19.249 | 1.00 | 13.44 |
| ATOM | 4156 | N | ALA | 1157 | 23.812 | −16.756 | 18.993 | 1.00 | 15.78 |
| ATOM | 4157 | H | ALA | 1157 | 24.421 | −16.012 | 18.786 | 1.00 | 0.00 |
| ATOM | 4158 | CA | ALA | 1157 | 24.391 | −18.060 | 19.349 | 1.00 | 13.25 |
| ATOM | 4159 | CB | ALA | 1157 | 25.908 | −17.958 | 19.445 | 1.00 | 7.54 |
| ATOM | 4160 | C | ALA | 1157 | 23.912 | −18.755 | 20.604 | 1.00 | 13.91 |
| ATOM | 4161 | O | ALA | 1157 | 23.814 | −19.974 | 20.635 | 1.00 | 15.61 |
| ATOM | 4162 | N | HIS | 1158 | 23.520 | −17.991 | 21.622 | 1.00 | 14.45 |
| ATOM | 4163 | H | HIS | 1158 | 23.688 | −17.032 | 21.529 | 1.00 | 0.00 |
| ATOM | 4164 | CA | HIS | 1158 | 22.988 | −18.518 | 22.830 | 1.00 | 10.20 |
| ATOM | 4165 | CB | HIS | 1158 | 22.621 | −17.348 | 23.802 | 1.00 | 8.12 |
| ATOM | 4166 | CG | HIS | 1158 | 21.657 | −16.322 | 23.213 | 1.00 | 8.39 |
| ATOM | 4167 | CD2 | HIS | 1158 | 20.290 | −16.362 | 23.334 | 1.00 | 4.48 |
| ATOM | 4168 | ND1 | HIS | 1158 | 21.946 | −15.266 | 22.462 | 1.00 | 8.59 |
| ATOM | 4169 | HD1 | HIS | 1158 | 22.832 | −14.924 | 22.195 | 1.00 | 0.00 |
| ATOM | 4170 | CE1 | HIS | 1158 | 20.813 | −14.687 | 22.128 | 1.00 | 5.15 |
| ATOM | 4171 | NE2 | HIS | 1158 | 19.829 | −15.355 | 22.654 | 1.00 | 6.40 |
| ATOM | 4172 | HE2 | HIS | 1158 | 18.888 | −15.059 | 22.617 | 1.00 | 0.00 |
| ATOM | 4173 | C | HIS | 1158 | 21.781 | −19.429 | 22.668 | 1.00 | 14.20 |
| ATOM | 4174 | O | HIS | 1158 | 21.585 | −20.322 | 23.515 | 1.00 | 15.95 |
| ATOM | 4175 | N | GLU | 1159 | 20.960 | −19.294 | 21.636 | 1.00 | 18.68 |
| ATOM | 4176 | H | GLU | 1159 | 21.217 | −18.718 | 20.883 | 1.00 | 0.00 |
| ATOM | 4177 | CA | GLU | 1159 | 19.753 | −20.112 | 21.496 | 1.00 | 20.00 |
| ATOM | 4178 | CB | GLU | 1159 | 18.877 | −19.607 | 20.388 | 1.00 | 24.35 |
| ATOM | 4179 | CG | GLU | 1159 | 18.247 | −18.240 | 30.637 | 1.00 | 31.35 |
| ATOM | 4180 | CD | GLU | 1159 | 17.302 | −17.760 | 19.540 | 1.00 | 32.75 |
| ATOM | 4181 | OE1 | GLU | 1159 | 17.281 | −18.339 | 18.449 | 1.00 | 32.14 |
| ATOM | 4182 | OE2 | GLU | 1159 | 16.581 | −16.790 | 19.788 | 1.00 | 38.48 |
| ATOM | 4183 | C | GLU | 1159 | 19.979 | −21.585 | 21.214 | 1.00 | 23.06 |
| ATOM | 4184 | O | GLU | 1159 | 19.147 | −22.458 | 21.491 | 1.00 | 23.92 |
| ATOM | 4185 | N | ARG | 1160 | 21.159 | −21.818 | 20.657 | 1.00 | 25.06 |
| ATOM | 4186 | H | ARG | 1160 | 21.803 | −21.086 | 20.550 | 1.00 | 0.00 |
| ATOM | 4187 | CA | ARG | 1160 | 21.574 | −23.139 | 20.254 | 1.00 | 29.23 |
| ATOM | 4188 | CB | ARG | 1160 | 22.616 | −23.065 | 19.111 | 1.00 | 30.90 |
| ATOM | 4189 | CG | ARG | 1160 | 22.364 | −22.145 | 17.916 | 1.00 | 31.60 |
| ATOM | 4190 | CD | ARG | 1160 | 21.047 | −22.440 | 17.215 | 1.00 | 35.44 |
| ATOM | 4191 | NE | ARG | 1160 | 20.988 | −23.796 | 16.705 | 1.00 | 41.49 |
| ATOM | 4192 | HE | ARG | 1160 | 21.639 | −24.458 | 17.019 | 1.00 | 0.00 |
| ATOM | 4193 | CZ | ARG | 1160 | 20.070 | −24.189 | 15.816 | 1.00 | 44.62 |
| ATOM | 4194 | NH1 | ARG | 1160 | 19.143 | −23.355 | 15.329 | 1.00 | 48.17 |
| ATOM | 4195 | HH11 | ARG | 1160 | 19.110 | −22.401 | 15.626 | 1.00 | 0.00 |
| ATOM | 4196 | HH12 | ARG | 1160 | 18.471 | −23.690 | 14.669 | 1.00 | 0.00 |
| ATOM | 4197 | NH2 | ARG | 1160 | 20.066 | −25.468 | 15.428 | 1.00 | 46.65 |
| ATOM | 4198 | HH21 | ARG | 1160 | 20.734 | −26.107 | 15.803 | 1.00 | 0.00 |
| ATOM | 4199 | HH22 | ARG | 1160 | 19.398 | −25.781 | 14.752 | 1.00 | 0.00 |
| ATOM | 4200 | C | ARG | 1160 | 22.214 | −23.843 | 21.437 | 1.00 | 27.73 |
| ATOM | 4201 | O | ARG | 1160 | 22.669 | −24.984 | 21.293 | 1.00 | 30.26 |
| ATOM | 4202 | N | MET | 1161 | 22.309 | −23.215 | 22.614 | 1.00 | 25.32 |
| ATOM | 4203 | H | MET | 1161 | 21.769 | −22.422 | 22.814 | 1.00 | 0.00 |
| ATOM | 4204 | CA | MET | 1161 | 23.045 | −23.835 | 23.701 | 1.00 | 18.76 |
| ATOM | 4205 | CB | MET | 1161 | 23.790 | −22.792 | 24.485 | 1.00 | 11.53 |
| ATOM | 4206 | CG | MET | 1161 | 24.778 | −22.042 | 23.647 | 1.00 | 13.13 |
| ATOM | 4207 | SD | MET | 1161 | 25.964 | −23.089 | 22.771 | 1.00 | 26.11 |
| ATOM | 4208 | CE | MET | 1161 | 27.076 | −23.610 | 24.041 | 1.00 | 21.15 |
| ATOM | 4209 | C | MET | 1161 | 22.056 | −24.545 | 24.593 | 1.00 | 12.35 |
| ATOM | 4210 | O | MET | 1161 | 20.927 | −24.071 | 24.734 | 1.00 | 12.85 |
| ATOM | 4211 | N | PRO | 1162 | 22.425 | −25.665 | 25.233 | 1.00 | 12.69 |
| ATOM | 4212 | CD | PRO | 1162 | 23.679 | −26.372 | 24.996 | 1.00 | 9.78 |
| ATOM | 4213 | CA | PRO | 1162 | 21.579 | −26.392 | 26.190 | 1.00 | 10.28 |
| ATOM | 4214 | CB | PRO | 1162 | 22.456 | −27.563 | 26.550 | 1.00 | 9.48 |
| ATOM | 4215 | CG | PRO | 1162 | 23.862 | −27.082 | 26.321 | 1.00 | 10.73 |
| ATOM | 4216 | C | PRO | 1162 | 21.044 | −25.611 | 27.407 | 1.00 | 9.82 |
| ATOM | 4217 | O | PRO | 1162 | 20.058 | −25.944 | 28.062 | 1.00 | 12.50 |
| ATOM | 4218 | N | TRP | 1163 | 21.718 | −24.527 | 27.743 | 1.00 | 11.52 |
| ATOM | 4219 | H | TRP | 1163 | 22.473 | −24.268 | 27.184 | 1.00 | 0.00 |
| ATOM | 4220 | CA | TRP | 1163 | 21.372 | −23.683 | 28.862 | 1.00 | 10.72 |

TABLE 23-continued

Coordinates for the 3D structure of ZAP-NC:ζ1 "dimer" structure
(two molecules of complex per unit cell)*

| ATOM | 4221 | CB | TRP | 1163 | 22.663 | −23.045 | 29.405 | 1.00 | 4.48 |
|---|---|---|---|---|---|---|---|---|---|
| ATOM | 4222 | CG | TRP | 1163 | 23.679 | −22.401 | 28.454 | 1.00 | 4.54 |
| ATOM | 4223 | CD2 | TRP | 1163 | 23.669 | −21.123 | 27.880 | 1.00 | 5.04 |
| ATOM | 4224 | CE2 | TRP | 1163 | 24.925 | −21.090 | 27.255 | 1.00 | 5.29 |
| ATOM | 4225 | CE3 | TRP | 1163 | 22.844 | −19.996 | 27.775 | 1.00 | 2.00 |
| ATOM | 4226 | CD1 | TRP | 1163 | 24.838 | −23.082 | 28.176 | 1.00 | 2.28 |
| ATOM | 4227 | NE1 | TRP | 1163 | 25.575 | −22.263 | 27..457 | 1.00 | 6.80 |
| ATOM | 4228 | HE1 | TRP | 1163 | 26.499 | −22.436 | 27.155 | 1.00 | 0.00 |
| ATOM | 4229 | CZ2 | TRP | 1163 | 25.363 | −19.959 | 26.540 | 1.00 | 6.60 |
| ATOM | 4230 | CZ3 | TRP | 1163 | 23.282 | −18.873 | 27.055 | 1.00 | 2.00 |
| ATOM | 4231 | CH2 | TRP | 1163 | 24.533 | −18.845 | 26.441 | 1.00 | 2.00 |
| ATOM | 4232 | C | TRP | 1163 | 20.345 | −22.622 | 28.520 | 1.00 | 11.70 |
| ATOM | 4233 | O | TRP | 1163 | 19.793 | −22.041 | 29.456 | 1.00 | 11.21 |
| ATOM | 4234 | N | TYR | 1164 | 19.988 | −22.349 | 27.258 | 1.00 | 12.21 |
| ATOM | 4235 | H | TYR | 1164 | 20.226 | −22.947 | 26.519 | 1.00 | 0.00 |
| ATOM | 4236 | CA | TYR | 1164 | 19.053 | −21.280 | 26.979 | 1.00 | 9.05 |
| ATOM | 4237 | CB | TYR | 1164 | 19.387 | −20.582 | 25.667 | 1.00 | 11.55 |
| ATOM | 4238 | CG | TYR | 1164 | 18.493 | −19.365 | 25.402 | 1.00 | 9.69 |
| ATOM | 4239 | CD1 | TYR | 1164 | 18.541 | −18.245 | 26.254 | 1.00 | 8.89 |
| ATOM | 4240 | CE1 | TYR | 1164 | 17.687 | −17.155 | 26.012 | 1.00 | 12.44 |
| ATOM | 4241 | CD2 | TYR | 1164 | 17.602 | −19.386 | 24.314 | 1.00 | 8.85 |
| ATOM | 4242 | CE2 | TYR | 1164 | 16.756 | −18.301 | 24.069 | 1.00 | 8.29 |
| ATOM | 4243 | CZ | TYR | 1164 | 16.806 | −17.192 | 24.921 | 1.00 | 13.30 |
| ATOM | 4244 | OH | TYR | 1164 | 15.993 | −16.110 | 24.673 | 1.00 | 15.18 |
| ATOM | 4245 | HH | TYR | 1164 | 15.388 | −16.300 | 23.946 | 1.00 | 0.00 |
| ATOM | 4246 | C | TYR | 1164 | 17.676 | −21.864 | 26.897 | 1.00 | 13.42 |
| ATOM | 4247 | O | TYR | 1164 | 17.449 | −22.907 | 26.271 | 1.00 | 16.65 |
| ATOM | 4248 | N | HIS | 1165 | 16.757 | −21.238 | 27.625 | 1.00 | 10.41 |
| ATOM | 4249 | H | HIS | 1165 | 17.023 | −20.453 | 28.157 | 1.00 | 0.00 |
| ATOM | 4250 | CA | HIS | 1165 | 15.386 | −21.680 | 27.657 | 1.00 | 9.19 |
| ATOM | 4251 | CB | HIS | 1165 | 15.046 | −22.242 | 29.025 | 1.00 | 8.07 |
| ATOM | 4252 | CG | HIS | 1165 | 15.822 | −23.476 | 29.470 | 1.00 | 6.13 |
| ATOM | 4253 | CD2 | HIS | 1165 | 17.188 | −23.531 | 29.603 | 1.00 | 3.28 |
| ATOM | 4254 | ND1 | HIS | 1165 | 15.360 | −24.673 | 29.834 | 1.00 | 5.83 |
| ATOM | 4255 | HD1 | HIS | 1165 | 14.432 | −24.992 | 29.833 | 1.00 | 0.00 |
| ATOM | 4256 | CE1 | HIS | 1165 | 16.389 | −25.423 | 30.172 | 1.00 | 2.00 |
| ATOM | 4257 | NE2 | HIS | 1165 | 17.481 | −24.727 | 30.026 | 1.00 | 3.94 |
| ATOM | 4258 | HE2 | HIS | 1165 | 18.390 | −25.104 | 30.044 | 1.00 | 0.00 |
| ATOM | 4259 | C | HIS | 1165 | 14.499 | −20.488 | 27.359 | 1.00 | 12.21 |
| ATOM | 4260 | O | HIS | 1165 | 14.122 | −19.735 | 28.246 | 1.00 | 15.69 |
| ATOM | 4261 | N | SER | 1166 | 14.123 | −20.310 | 26.096 | 1.00 | 18.69 |
| ATOM | 4262 | H | SER | 1166 | 14.377 | −20.990 | 25.433 | 1.00 | 0.00 |
| ATOM | 4263 | CA | SER | 1166 | 13.275 | −19.235 | 25.580 | 1.00 | 22.32 |
| ATOM | 4264 | CB | SER | 1166 | 13.142 | −19.448 | 24.077 | 1.00 | 24.30 |
| ATOM | 4265 | OG | SER | 1166 | 12.997 | −20.850 | 23.816 | 1.00 | 27.37 |
| ATOM | 4266 | HG | SER | 1166 | 13.693 | −21.116 | 23.199 | 1.00 | 0.00 |
| ATOM | 4267 | C | SER | 1166 | 11.883 | −19.119 | 26.201 | 1.00 | 25.68 |
| ATOM | 4268 | O | SER | 1166 | 11.229 | −18.073 | 26.253 | 1.00 | 28.35 |
| ATOM | 4269 | N | SER | 1167 | 11.484 | −20.297 | 26.640 | 1.00 | 28.43 |
| ATOM | 4270 | H | SER | 1167 | 12.094 | −21.052 | 26.534 | 1.00 | 0.00 |
| ATOM | 4271 | CA | SER | 1167 | 10.186 | −20.640 | 27.174 | 1.00 | 30.35 |
| ATOM | 4272 | CB | SER | 1167 | 9.981 | −22.064 | 26.593 | 1.00 | 35.08 |
| ATOM | 4273 | OG | SER | 1167 | 11.206 | −22.853 | 26.583 | 1.00 | 35.86 |
| ATOM | 4274 | HG | SER | 1167 | 11.021 | −23.626 | 26.039 | 1.00 | 0.00 |
| ATOM | 4275 | C | SER | 1167 | 9.887 | −20.535 | 28.688 | 1.00 | 27.36 |
| ATOM | 4276 | O | SER | 1167 | 8.729 | −20.731 | 29.066 | 1.00 | 25.18 |
| ATOM | 4277 | N | LEU | 1168 | 10.815 | −20.231 | 29.614 | 1.00 | 24.64 |
| ATOM | 4278 | H | LEU | 1168 | 11.680 | −19.865 | 29.328 | 1.00 | 0.00 |
| ATOM | 4279 | CA | LEU | 1168 | 10.498 | −20.295 | 31.044 | 1.00 | 22.29 |
| ATOM | 4280 | CB | LEU | 1168 | 11.557 | −21.101 | 31.794 | 1.00 | 19.48 |
| ATOM | 4281 | CG | LEU | 1168 | 12.002 | −22.465 | 31.275 | 1.00 | 19.31 |
| ATOM | 4282 | CD1 | LEU | 1168 | 13.095 | −22.977 | 32.202 | 1.00 | 21.06 |
| ATOM | 4283 | CD2 | LEU | 1168 | 10.868 | −23.462 | 31.244 | 1.00 | 14.54 |
| ATOM | 4284 | C | LEU | 1168 | 10.306 | −19.012 | 31.634 | 1.00 | 17.29 |
| ATOM | 4285 | O | LEU | 1168 | 11.015 | −18.020 | 31.664 | 1.00 | 18.35 |
| ATOM | 4266 | N | THR | 1169 | 9.313 | −19.044 | 32.722 | 1.00 | 18.42 |
| ATOM | 4287 | H | THR | 1169 | 8.737 | −19.830 | 32.790 | 1.00 | 0.00 |
| ATOM | 4288 | CA | THR | 1169 | 9.095 | −17.971 | 33.682 | 1.00 | 17.82 |
| ATOM | 4289 | CB | THR | 1169 | 7.653 | −17.980 | 34.221 | 1.00 | 19.72 |
| ATOM | 4290 | OG1 | THR | 1169 | 7.429 | −19.264 | 34.804 | 1.00 | 19.56 |
| ATOM | 4291 | HG1 | THR | 1169 | 6.475 | −19.419 | 34.793 | 1.00 | 0.00 |
| ATOM | 4292 | CG2 | THR | 1169 | 6.636 | −17.685 | 33.152 | 1.00 | 18.55 |
| ATOM | 4293 | C | THR | 1169 | 10.043 | −18.209 | 34.852 | 1.00 | 10.98 |
| ATOM | 4294 | O | THR | 1169 | 10.641 | −19.285 | 34.937 | 1.00 | 13.16 |
| ATOM | 4295 | N | ARG | 1170 | 10.164 | −17.270 | 35.781 | 1.00 | 12.27 |
| ATOM | 4296 | H | ARG | 1170 | 9.759 | −16.397 | 35.585 | 1.00 | 0.00 |

TABLE 23-continued

Coordinates for the 3D structure of ZAP-NC:ζ1 "dimer" structure
(two molecules of complex per unit cell)*

| ATOM | 4297 | CA | ARG | 1170 | 10.945 | −17.431 | 36.998 | 1.00 | 13.63 |
|---|---|---|---|---|---|---|---|---|---|
| ATOM | 4298 | CB | ARG | 1170 | 10.726 | −16.204 | 37.885 | 1.00 | 9.48 |
| ATOM | 4299 | CG | ARG | 1170 | 11.337 | −16.386 | 39.259 | 1.00 | 11.46 |
| ATOM | 4300 | CD | ARG | 1170 | 10.964 | −15.269 | 40.208 | 1.00 | 11.17 |
| ATOM | 4301 | NE | ARG | 1170 | 11.912 | −14.216 | 39.978 | 1.00 | 15.66 |
| ATOM | 4302 | HE | ARG | 1170 | 11.832 | −13.703 | 39.151 | 1.00 | 0.00 |
| ATOM | 4303 | CZ | ARG | 1170 | 12.818 | −13.829 | 40.866 | 1.00 | 13.85 |
| ATOM | 4304 | NH1 | ARG | 1170 | 13.634 | −12.864 | 40.468 | 1.00 | 13.48 |
| ATOM | 4305 | HH11 | ARG | 1170 | 13.543 | −12.488 | 39.546 | 1.00 | 0.00 |
| ATOM | 4306 | HH12 | ARG | 1170 | 14.351 | −12.528 | 41.072 | 1.00 | 0.00 |
| ATOM | 4307 | NH2 | ARG | 1170 | 12.878 | −14.317 | 42.111 | 1.00 | 15.64 |
| ATOM | 4308 | HH21 | ARG | 1170 | 12.202 | −14.988 | 42.417 | 1.00 | 0.00 |
| ATOM | 4309 | HH22 | ARG | 1170 | 13.578 | −13.986 | 42.747 | 1.00 | 0.00 |
| ATOM | 4310 | C | ARG | 1170 | 10.584 | −18.709 | 37.768 | 1.00 | 14.28 |
| ATOM | 4311 | O | ARG | 1170 | 11.437 | −19.520 | 38.145 | 1.00 | 15.79 |
| ATOM | 4312 | N | GLU | 1171 | 9.292 | −18.934 | 37.913 | 1.00 | 12.16 |
| ATOM | 4313 | H | GLU | 1171 | 8.675 | −18.340 | 37.445 | 1.00 | 0.00 |
| ATOM | 4314 | CA | GLU | 1171 | 8.792 | −20.075 | 38.632 | 1.00 | 16.73 |
| ATOM | 4315 | CB | GLU | 1171 | 7.269 | −20.067 | 38.688 | 1.00 | 24.50 |
| ATOM | 4316 | CG | GLU | 1171 | 6.607 | −18.830 | 39.300 | 1.00 | 39.58 |
| ATOM | 4317 | CD | GLU | 1171 | 6.664 | −17.554 | 38.452 | 1.00 | 46.40 |
| ATOM | 4318 | OE1 | GLU | 1171 | 7.176 | −16.541 | 38.935 | 1.00 | 48.99 |
| ATOM | 4319 | OE2 | GLU | 1171 | 6.203 | −17.579 | 37.308 | 1.00 | 53.13 |
| ATOM | 4320 | C | GLU | 1171 | 9.232 | −21.344 | 37.952 | 1.00 | 16.53 |
| ATOM | 4321 | O | GLU | 1171 | 9.811 | −22.204 | 38.602 | 1.00 | 19.25 |
| ATOM | 4322 | N | GLU | 1172 | 9.021 | −21.438 | 36.633 | 1.00 | 20.89 |
| ATOM | 4323 | H | GLU | 1172 | 8.697 | −20.643 | 36.157 | 1.00 | 0.00 |
| ATOM | 4324 | CA | GLU | 1172 | 9.338 | −22.632 | 35.849 | 1.00 | 17.91 |
| ATOM | 4325 | CB | GLU | 1172 | 8.892 | −22.458 | 34.416 | 1.00 | 17.90 |
| ATOM | 4326 | CG | GLU | 1172 | 7.369 | −22.486 | 34.271 | 1.00 | 27.69 |
| ATOM | 4327 | CD | GLU | 1172 | 6.780 | −21.903 | 32.984 | 1.00 | 27.08 |
| ATOM | 4328 | OE1 | GLU | 1172 | 7.359 | −22.058 | 31.915 | 1.00 | 34.51 |
| ATOM | 4329 | OE2 | GLU | 1172 | 5.723 | −21.282 | 33.052 | 1.00 | 32.11 |
| ATOM | 4330 | C | GLU | 1172 | 10.814 | −22.927 | 35.866 | 1.00 | 15.95 |
| ATOM | 4331 | O | GLU | 1172 | 11.207 | −24.083 | 35.976 | 1.00 | 18.39 |
| ATOM | 4332 | N | ALA | 1173 | 11.643 | −21.889 | 35.819 | 1.00 | 17.72 |
| ATOM | 4333 | H | ALA | 1173 | 11.266 | −20.991 | 35.737 | 1.00 | 0.00 |
| ATOM | 4334 | CA | ALA | 1173 | 13.088 | −22.029 | 35.894 | 1.00 | 17.23 |
| ATOM | 4335 | CB | ALA | 1173 | 13.744 | −20.657 | 35.803 | 1.00 | 16.89 |
| ATOM | 4336 | C | ALA | 1173 | 13.504 | −22.681 | 37.208 | 1.00 | 14.94 |
| ATOM | 4337 | O | ALA | 1173 | 14.228 | −23.673 | 37.220 | 1.00 | 17.02 |
| ATOM | 4338 | N | GLU | 1174 | 13.008 | −22.180 | 38.330 | 1.00 | 15.36 |
| ATOM | 4339 | H | GLU | 1174 | 12.387 | −21.420 | 38.258 | 1.00 | 0.00 |
| ATOM | 4340 | CA | GLU | 1174 | 13.300 | −22.759 | 39.637 | 1.00 | 15.72 |
| ATOM | 4341 | CB | GLU | 1174 | 12.528 | −22.007 | 40.702 | 1.00 | 14.38 |
| ATOM | 4342 | CG | GLU | 1174 | 12.963 | −20.560 | 40.838 | 1.00 | 17.68 |
| ATOM | 4343 | CD | GLU | 1174 | 12.413 | −19.797 | 42.032 | 1.00 | 20.98 |
| ATOM | 4344 | OE1 | GLU | 1174 | 11.503 | −20.278 | 42.705 | 1.00 | 28.76 |
| ATOM | 4345 | OE2 | GLU | 1174 | 12.902 | −18.701 | 42.293 | 1.00 | 17.73 |
| ATOM | 4346 | C | GLU | 1174 | 12.906 | −24.235 | 39.680 | 1.00 | 17.50 |
| ATOM | 4347 | O | GLU | 1174 | 13.703 | −25.090 | 40.077 | 1.00 | 15.79 |
| ATOM | 4348 | N | ARG | 1175 | 11.703 | −24.578 | 39.198 | 1.00 | 19.83 |
| ATOM | 4349 | H | ARG | 1175 | 11.118 | −23.863 | 38.863 | 1.00 | 0.00 |
| ATOM | 4350 | CA | ARG | 1175 | 11.240 | −25.958 | 39.149 | 1.00 | 17.46 |
| ATOM | 4351 | CB | ARG | 1175 | 9.812 | −26.015 | 38.618 | 1.00 | 22.12 |
| ATOM | 4352 | CG | ARG | 1175 | 8.805 | −25.491 | 39.647 | 1.00 | 31.07 |
| ATOM | 4353 | CD | ARG | 1175 | 7.351 | −25.744 | 39.250 | 1.00 | 37.43 |
| ATOM | 4354 | NE | ARG | 1175 | 6.593 | −24.512 | 39.055 | 1.00 | 40.92 |
| ATOM | 4355 | HE | ARG | 1175 | 6.444 | −23.921 | 39.823 | 1.00 | 0.00 |
| ATOM | 4356 | CZ | ARG | 1175 | 6.092 | −24.160 | 37.862 | 1.00 | 43.85 |
| ATOM | 4357 | NH1 | ARG | 1175 | 6.260 | −24.923 | 36.776 | 1.00 | 44.41 |
| ATOM | 4358 | HH11 | ARG | 1175 | 6.773 | −25.779 | 36.831 | 1.00 | 0.00 |
| ATOM | 4359 | HH12 | ARG | 1175 | 5.870 | −24.633 | 35.902 | 1.00 | 0.00 |
| ATOM | 4360 | NH2 | ARG | 1175 | 5.419 | −23.010 | 37.746 | 1.00 | 41.58 |
| ATOM | 4361 | HH21 | ARG | 1175 | 5.312 | −22.413 | 38.541 | 1.00 | 0.00 |
| ATOM | 4362 | HH22 | ARG | 1175 | 5.048 | −22.735 | 36.860 | 1.00 | 0.00 |
| ATOM | 4363 | C | ARG | 1175 | 12.139 | −26.831 | 38.290 | 1.00 | 18.03 |
| ATOM | 4364 | O | ARG | 1175 | 12.465 | −27.951 | 38.681 | 1.00 | 19.18 |
| ATOM | 4365 | N | LYS | 1176 | 12.646 | −26.307 | 37.179 | 1.00 | 19.95 |
| ATOM | 4366 | H | LYS | 1176 | 12.409 | −25.382 | 36.946 | 1.00 | 0.00 |
| ATOM | 4367 | CA | LYS | 1176 | 13.523 | −27.040 | 36.277 | 1.00 | 19.66 |
| ATOM | 4368 | CB | LYS | 1176 | 13.704 | −26.240 | 34.968 | 1.00 | 24.70 |
| ATOM | 4369 | CG | LYS | 1176 | 14.239 | −27.027 | 33.766 | 1.00 | 27.63 |
| ATOM | 4370 | CD | LYS | 1176 | 13.192 | −27.947 | 33.130 | 1.00 | 33.14 |
| ATOM | 4371 | CE | LYS | 1176 | 12.084 | −27.187 | 32.375 | 1.00 | 32.52 |
| ATOM | 4372 | NZ | LYS | 1176 | 11.254 | −28.098 | 31.601 | 1.00 | 30.45 |

TABLE 23-continued

Coordinates for the 3D structure of ZAP-NC:ζ1 "dimer" structure
(two molecules of complex per unit cell)*

| ATOM | 4373 | HZ1 | LYS | 1176 | 10.824 | −28.804 | 32.232 | 1.00 | 0.00 |
|---|---|---|---|---|---|---|---|---|---|
| ATOM | 4374 | HZ2 | LYS | 1176 | 11.850 | −28.586 | 30.900 | 1.00 | 0.00 |
| ATOM | 4375 | HZ3 | LYS | 1176 | 10.508 | −27.570 | 31.106 | 1.00 | 0.00 |
| ATOM | 4376 | C | LYS | 1176 | 14.866 | −27.273 | 36.741 | 1.00 | 15.53 |
| ATOM | 4377 | O | LYS | 1176 | 15.351 | −28.400 | 36.968 | 1.00 | 18.60 |
| ATOM | 4378 | N | LEU | 1177 | 15.433 | −26.223 | 37.531 | 1.00 | 20.13 |
| ATOM | 4379 | H | LEU | 1177 | 14.945 | −25.377 | 37.490 | 1.00 | 0.00 |
| ATOM | 4380 | CA | LEU | 1177 | 16.715 | −26.242 | 38.225 | 1.00 | 18.75 |
| ATOM | 4381 | CB | LEU | 1177 | 17.004 | −24.782 | 38.564 | 1.00 | 17.17 |
| ATOM | 4382 | CG | LEU | 1177 | 18.184 | −23.971 | 38.029 | 1.00 | 15.05 |
| ATOM | 4383 | CD1 | LEU | 1177 | 18.762 | −24.567 | 36.777 | 1.00 | 13.44 |
| ATOM | 4384 | CD2 | LEU | 1177 | 17.697 | −22.560 | 37.810 | 1.00 | 7.89 |
| ATOM | 4385 | C | LEU | 1177 | 16.744 | −27.158 | 39.461 | 1.00 | 17.88 |
| ATOM | 4366 | O | LEU | 1177 | 17.759 | −17.761 | 39.804 | 1.00 | 16.88 |
| ATOM | 4387 | N | TYR | 1178 | 15.637 | −27.251 | 40.193 | 1.00 | 19.77 |
| ATOM | 4388 | H | TYR | 1178 | 14.887 | −26.668 | 39.963 | 1.00 | 0.00 |
| ATOM | 4389 | CA | TYR | 1178 | 15.521 | −28.151 | 41.329 | 1.00 | 24.93 |
| ATOM | 4390 | CB | TYR | 1178 | 14.301 | −27.775 | 42.188 | 1.00 | 22.12 |
| ATOM | 4391 | CG | TYR | 1178 | 14.517 | −26.530 | 43.029 | 1.00 | 24.04 |
| ATOM | 4392 | CD1 | TYR | 1178 | 15.626 | −26.436 | 43.875 | 1.00 | 25.26 |
| ATOM | 4393 | CE1 | TYR | 1178 | 15.821 | −25.289 | 44.649 | 1.00 | 29.64 |
| ATOM | 4394 | CD2 | TYR | 1178 | 13.605 | −25.479 | 42.958 | 1.00 | 20.32 |
| ATOM | 4395 | CE2 | TYR | 1178 | 13.795 | −24.326 | 43.729 | 1.00 | 25.80 |
| ATOM | 4396 | CZ | TYR | 1178 | 14.906 | −24.231 | 44.576 | 1.00 | 28.67 |
| ATOM | 4397 | OH | TYR | 1178 | 15.105 | −23.078 | 45.334 | 1.00 | 28.90 |
| ATOM | 4398 | HH | TYR | 1178 | 14.279 | −22.583 | 45.370 | 1.00 | 0.00 |
| ATOM | 4399 | C | TYR | 1178 | 15.397 | −29.624 | 40.939 | 1.00 | 27.89 |
| ATOM | 4400 | O | TYR | 1178 | 15.565 | −30.502 | 41.793 | 1.00 | 28.32 |
| ATOM | 4401 | N | SER | 1179 | 15.080 | −29.931 | 39.671 | 1.00 | 30.11 |
| ATOM | 4402 | H | SER | 1179 | 15.087 | −29.234 | 38.985 | 1.00 | 0.00 |
| ATOM | 4403 | CA | SER | 1179 | 14.933 | −31.307 | 39.223 | 1.00 | 28.15 |
| ATOM | 4404 | CB | SER | 1179 | 14.183 | −31.423 | 37.897 | 1.00 | 28.43 |
| ATOM | 4405 | OG | SER | 1179 | 12.801 | −31.106 | 38.019 | 1.00 | 41.95 |
| ATOM | 4406 | HG | SER | 1179 | 12.751 | −30.143 | 38.120 | 1.00 | 0.00 |
| ATOM | 4407 | C | SER | 1179 | 16.303 | −31.898 | 39.010 | 1.00 | 26.65 |
| ATOM | 4408 | O | SER | 1179 | 17.190 | −31.306 | 38.393 | 1.00 | 23.06 |
| ATOM | 4409 | N | GLY | 1180 | 16.475 | −33.096 | 39.533 | 1.00 | 24.46 |
| ATOM | 4410 | H | GLY | 1180 | 15.843 | −33.441 | 40.193 | 1.00 | 0.00 |
| ATOM | 4411 | CA | GLY | 1180 | 17.719 | −33.778 | 39.337 | 1.00 | 24.52 |
| ATOM | 4412 | C | GLY | 1180 | 18.692 | −33.270 | 40.364 | 1.00 | 26.59 |
| ATOM | 4413 | O | GLY | 1180 | 18.351 | −32.970 | 41.505 | 1.00 | 27.29 |
| ATOM | 4414 | N | ALA | 1181 | 19.879 | −33.121 | 39.810 | 1.00 | 29.30 |
| ATOM | 4415 | H | ALA | 1181 | 19.932 | −33.275 | 38.847 | 1.00 | 0.00 |
| ATOM | 4416 | CA | ALA | 1181 | 21.082 | −32.730 | 40.497 | 1.00 | 31.94 |
| ATOM | 4417 | CB | ALA | 1181 | 22.129 | −32.393 | 39.454 | 1.00 | 38.26 |
| ATOM | 4418 | C | ALA | 1181 | 21.143 | −31.629 | 41.539 | 1.00 | 33.00 |
| ATOM | 4419 | O | ALA | 1181 | 21.590 | −31.937 | 42.643 | 1.00 | 40.36 |
| ATOM | 4420 | N | GLN | 1182 | 20.762 | −30.374 | 41.309 | 1.00 | 29.27 |
| ATOM | 4421 | H | GLN | 1182 | 20.272 | −30.169 | 40.490 | 1.00 | 0.00 |
| ATOM | 4422 | CA | GLN | 1182 | 20.962 | −29.298 | 42.309 | 1.00 | 28.61 |
| ATOM | 4423 | CB | GLN | 1182 | 20.064 | −29.532 | 43.545 | 1.00 | 23.51 |
| ATOM | 4424 | CG | GLN | 1182 | 18.601 | −29.269 | 43.273 | 1.00 | 29.62 |
| ATOM | 4425 | CD | GLN | 1182 | 17.692 | −29.877 | 44.324 | 1.00 | 35.92 |
| ATOM | 4426 | OE1 | GLN | 1182 | 17.243 | −29.245 | 45.289 | 1.00 | 37.09 |
| ATOM | 4427 | NE2 | GLN | 1182 | 17.413 | −31.156 | 44.135 | 1.00 | 45.00 |
| ATOM | 4428 | HE21 | GLN | 1182 | 17.810 | −31.600 | 43.352 | 1.00 | 0.00 |
| ATOM | 4429 | HE22 | GLN | 1182 | 16.769 | −31.597 | 44.723 | 1.00 | 0.00 |
| ATOM | 4430 | C | GLN | 1182 | 22.417 | −29.095 | 42.787 | 1.00 | 23.87 |
| ATOM | 4431 | O | GLN | 1182 | 22.746 | −28.817 | 43.947 | 1.00 | 22.97 |
| ATOM | 4432 | N | THR | 1183 | 23.336 | −29.158 | 41.837 | 1.00 | 18.65 |
| ATOM | 4433 | H | THR | 1183 | 23.097 | −29.276 | 40.898 | 1.00 | 0.00 |
| ATOM | 4434 | CA | THR | 1183 | 24.738 | −28.955 | 42.096 | 1.00 | 16.92 |
| ATOM | 4435 | CB | THR | 1183 | 25.517 | −29.736 | 41.010 | 1.00 | 18.51 |
| ATOM | 4436 | OG1 | THR | 1183 | 24.892 | −29.453 | 39.753 | 1.00 | 17.00 |
| ATOM | 4437 | HG1 | THR | 1183 | 25.621 | −29.318 | 39.122 | 1.00 | 0.00 |
| ATOM | 4438 | CG2 | THR | 1183 | 25.531 | −31.245 | 41.285 | 1.00 | 18.60 |
| ATOM | 4439 | C | THR | 1183 | 25.053 | −27.462 | 42.074 | 1.00 | 14.68 |
| ATOM | 4440 | O | THR | 1183 | 24.370 | −26.721 | 41.361 | 1.00 | 18.03 |
| ATOM | 4441 | N | ASP | 1184 | 26.065 | −26.961 | 42.779 | 1.00 | 13.66 |
| ATOM | 4442 | H | ASP | 1184 | 26.579 | −27.569 | 43.353 | 1.00 | 0.00 |
| ATOM | 4443 | CA | ASP | 1184 | 26.404 | −25.549 | 42.741 | 1.00 | 15.21 |
| ATOM | 4444 | CB | ASP | 1184 | 27.536 | −25.242 | 43.695 | 1.00 | 10.46 |
| ATOM | 4445 | CG | ASP | 1184 | 27.176 | −25.188 | 45.170 | 1.00 | 12.60 |
| ATOM | 4446 | OD1 | ASP | 1184 | 28.084 | −25.277 | 46.010 | 1.00 | 10.75 |
| ATOM | 4447 | OD2 | ASP | 1184 | 25.990 | −25.054 | 45.471 | 1.00 | 12.16 |
| ATOM | 4448 | C | ASP | 1184 | 26.828 | −25.115 | 41.356 | 1.00 | 16.93 |

TABLE 23-continued

Coordinates for the 3D structure of ZAP-NC:ζ1 "dimer" structure
(two molecules of complex per unit cell)*

| ATOM | 4449 | O | ASP | 1184 | 27.602 | −25.817 | 40.695 | 1.00 | 21.40 |
|---|---|---|---|---|---|---|---|---|---|
| ATOM | 4450 | N | GLY | 1185 | 26.262 | −23.997 | 40.918 | 1.00 | 14.05 |
| ATOM | 4451 | H | GLY | 1185 | 25.633 | −23.519 | 41.496 | 1.00 | 0.00 |
| ATOM | 4452 | CA | GLY | 1185 | 26.561 | −23.443 | 39.614 | 1.00 | 14.01 |
| ATOM | 4453 | C | GLY | 1185 | 25.741 | −24.063 | 38.499 | 1.00 | 15.04 |
| ATOM | 4454 | O | GLY | 1185 | 26.035 | −23.832 | 37.331 | 1.00 | 13.07 |
| ATOM | 4455 | N | LYS | 1186 | 24.734 | −24.889 | 38.778 | 1.00 | 14.59 |
| ATOM | 4456 | H | LYS | 1186 | 24.547 | −25.122 | 39.711 | 1.00 | 0.00 |
| ATOM | 4457 | CA | LYS | 1186 | 23.860 | −25.398 | 37.737 | 1.00 | 14.21 |
| ATOM | 4458 | CB | LYS | 1186 | 23.012 | −26.505 | 38.326 | 1.00 | 12.61 |
| ATOM | 4459 | CG | LYS | 1186 | 22.022 | −27.129 | 37.379 | 1.00 | 14.10 |
| ATOM | 4460 | CD | LYS | 1186 | 21.252 | −27.977 | 38.361 | 1.00 | 22.79 |
| ATOM | 4461 | CE | LYS | 1186 | 20.043 | −28.626 | 37.721 | 1.00 | 27.95 |
| ATOM | 4462 | NZ | LYS | 1186 | 19.440 | −29.535 | 38.677 | 1.00 | 30.90 |
| ATOM | 4463 | HZ1 | LYS | 1186 | 20.110 | −30.295 | 38.908 | 1.00 | 0.00 |
| ATOM | 4464 | HZ2 | LYS | 1186 | 18.582 | −29.942 | 38.257 | 1.00 | 0.00 |
| ATOM | 4465 | HZ3 | LYS | 1186 | 19.194 | −29.024 | 39.548 | 1.00 | 0.00 |
| ATOM | 4466 | C | LYS | 1186 | 23.024 | −24.186 | 37.303 | 1.00 | 14.69 |
| ATOM | 4467 | O | LYS | 1186 | 22.539 | −23.457 | 38.176 | 1.00 | 12.22 |
| ATOM | 4468 | N | PHE | 1187 | 22.836 | −23.931 | 36.007 | 1.00 | 11.37 |
| ATOM | 4469 | H | PHE | 1187 | 23.152 | −24.577 | 35.337 | 1.00 | 0.00 |
| ATOM | 4470 | CA | PHE | 1187 | 22.222 | −22.688 | 35.554 | 1.00 | 11.00 |
| ATOM | 4471 | CB | PHE | 1187 | 23.316 | −21.609 | 35.354 | 1.00 | 3.59 |
| ATOM | 4472 | CG | PHE | 1187 | 24.161 | −21.823 | 34.092 | 1.00 | 10.48 |
| ATOM | 4473 | CD1 | PHE | 1187 | 23.895 | −21.065 | 32.936 | 1.00 | 4.12 |
| ATOM | 4474 | CD2 | PHE | 1187 | 25.167 | −22.802 | 34.076 | 1.00 | 4.77 |
| ATOM | 4475 | CE1 | PHE | 1187 | 24.631 | −21.297 | 31.788 | 1.00 | 2.00 |
| ATOM | 4476 | CE2 | PHE | 1187 | 25.904 | −23.023 | 32.918 | 1.00 | 3.39 |
| ATOM | 4477 | CZ | PHE | 1187 | 25.639 | −22.275 | 31.776 | 1.00 | 2.00 |
| ATOM | 4478 | C | PHE | 1187 | 21.441 | −22.811 | 34.251 | 1.00 | 12.70 |
| ATOM | 4479 | O | PHE | 1187 | 21.629 | −23.757 | 33.469 | 1.00 | 14.29 |
| ATOM | 4480 | N | LEU | 1188 | 20.617 | −21.805 | 33.980 | 1.00 | 15.30 |
| ATOM | 4481 | H | LEU | 1188 | 20.500 | −21.083 | 34.639 | 1.00 | 0.00 |
| ATOM | 4482 | CA | LEU | 1188 | 19.932 | −21.659 | 32.705 | 1.00 | 13.51 |
| ATOM | 4483 | CB | LEU | 1188 | 18.537 | −22.312 | 32.777 | 1.00 | 9.23 |
| ATOM | 4484 | CG | LEU | 1188 | 17.434 | −21.857 | 33.728 | 1.00 | 8.72 |
| ATOM | 4485 | CD1 | LEU | 1188 | 16.675 | −20.662 | 33.151 | 1.00 | 6.00 |
| ATOM | 4486 | CD2 | LEU | 1188 | 16.444 | −22.984 | 33.915 | 1.00 | 3.86 |
| ATOM | 4487 | C | LEU | 1188 | 19.834 | −20.148 | 32.432 | 1.00 | 17.33 |
| ATOM | 4488 | O | LEU | 1188 | 19.923 | −19.335 | 33.384 | 1.00 | 16.73 |
| ATOM | 4489 | N | LEU | 1189 | 19.732 | −19.698 | 31.178 | 1.00 | 11.00 |
| ATOM | 4490 | H | LEU | 1189 | 19.712 | −20.341 | 30.439 | 1.00 | 0.00 |
| ATOM | 4491 | CA | LEU | 1189 | 19.464 | −18.312 | 30.886 | 1.00 | 8.88 |
| ATOM | 4492 | CB | LEU | 1189 | 20.505 | −17.761 | 29.951 | 1.00 | 9.47 |
| ATOM | 4493 | CG | LEU | 1189 | 20.749 | −16.264 | 29.994 | 1.00 | 11.16 |
| ATOM | 4494 | CD1 | LEU | 1189 | 22.234 | −15.989 | 29.946 | 1.00 | 14.98 |
| ATOM | 4495 | CD2 | LEU | 1189 | 20.093 | −15.606 | 28.818 | 1.00 | 17.03 |
| ATOM | 4496 | C | LEU | 1189 | 18.105 | −18.311 | 30.221 | 1.00 | 10.34 |
| ATOM | 4497 | O | LEU | 1189 | 17.787 | −19.243 | 29.481 | 1.00 | 11.32 |
| ATOM | 4498 | N | ARG | 1190 | 17.246 | −17.316 | 30.494 | 1.00 | 11.83 |
| ATOM | 4499 | H | ARG | 1190 | 17.569 | −16.616 | 31.112 | 1.00 | 0.00 |
| ATOM | 4500 | CA | ARG | 1190 | 15.940 | −17.192 | 29.930 | 1.00 | 12.55 |
| ATOM | 4501 | CB | ARG | 1190 | 14.872 | −17.742 | 30.924 | 1.00 | 10.80 |
| ATOM | 4502 | CG | ARG | 1190 | 14.816 | −16.996 | 32.246 | 1.00 | 16.94 |
| ATOM | 4503 | CD | ARG | 1190 | 13.866 | −17.619 | 33.244 | 1.00 | 10.51 |
| ATOM | 4504 | NE | ARG | 1190 | 14.272 | −17.195 | 34.574 | 1.00 | 14.51 |
| ATOM | 4505 | HE | ARG | 1190 | 14.905 | −17.754 | 35.065 | 1.00 | 0.00 |
| ATOM | 4506 | CZ | ARG | 1190 | 13.838 | −16.071 | 35.155 | 1.00 | 11.97 |
| ATOM | 4507 | NH1 | ARG | 1190 | 12.979 | −15.236 | 34.576 | 1.00 | 8.12 |
| ATOM | 4508 | HH11 | ARG | 1190 | 12.632 | −15.428 | 33.659 | 1.00 | 0.00 |
| ATOM | 4509 | HH12 | ARG | 1190 | 12.684 | −14.419 | 35.066 | 1.00 | 0.00 |
| ATOM | 4510 | NH2 | ARG | 1190 | 14.345 | −15.731 | 36.323 | 1.00 | 8.29 |
| ATOM | 4511 | HH21 | ARG | 1190 | 15.053 | −16.316 | 36.734 | 1.00 | 0.00 |
| ATOM | 4512 | HH22 | ARG | 1190 | 14.070 | −14.895 | 36.785 | 1.00 | 0.00 |
| ATOM | 4513 | C | ARG | 1190 | 15.654 | −15.715 | 29.608 | 1.00 | 14.97 |
| ATOM | 4514 | O | ARG | 1190 | 16.245 | −14.815 | 30.226 | 1.00 | 15.61 |
| ATOM | 4515 | N | PRO | 1191 | 14.809 | −15.374 | 28.625 | 1.00 | 14.74 |
| ATOM | 4516 | H | PRO | 1191 | 14.125 | −16.305 | 27.724 | 1.00 | 14.72 |
| ATOM | 4517 | CA | PRO | 1191 | 14.427 | −14.014 | 28.335 | 1.00 | 15.50 |
| ATOM | 4518 | CB | PRO | 1191 | 13.942 | −14.095 | 26.902 | 1.00 | 20.02 |
| ATOM | 4519 | CG | PRO | 1191 | 13.230 | −15.430 | 26.849 | 1.00 | 12.74 |
| ATOM | 4520 | C | PRO | 1191 | 13.377 | −13.599 | 29.354 | 1.00 | 17.84 |
| ATOM | 4521 | O | PRO | 1191 | 12.559 | −14.420 | 29.789 | 1.00 | 18.29 |
| ATOM | 4522 | N | ARG | 1192 | 13.392 | −12.351 | 29.787 | 1.00 | 16.50 |
| ATOM | 4523 | H | ARG | 1192 | 14.020 | −11.697 | 29.417 | 1.00 | 0.00 |
| ATOM | 4524 | CA | ARG | 1192 | 12.390 | −11.919 | 30.731 | 1.00 | 19.93 |

TABLE 23-continued

Coordinates for the 3D structure of ZAP-NC:ζ1 "dimer" structure
(two molecules of complex per unit cell)*

| ATOM | 4525 | CB | ARG | 1192 | 12.896 | −10.822 | 31.655 | 1.00 | 16.49 |
|---|---|---|---|---|---|---|---|---|---|
| ATOM | 4526 | CG | ARG | 1192 | 14.046 | −11.166 | 32.595 | 1.00 | 10.36 |
| ATOM | 4527 | CD | ARG | 1192 | 14.060 | −10.221 | 33.763 | 1.00 | 10.83 |
| ATOM | 4528 | NE | ARG | 1192 | 14.004 | −8.826 | 33.365 | 1.00 | 21.58 |
| ATOM | 4529 | HE | ARG | 1192 | 14.571 | −8.533 | 32.622 | 1.00 | 0.00 |
| ATOM | 4530 | CZ | ARG | 1192 | 13.214 | −7.909 | 33.937 | 1.00 | 17.94 |
| ATOM | 4531 | NH1 | ARG | 1192 | 12.378 | −8.164 | 34.943 | 1.00 | 12.97 |
| ATOM | 4532 | HH11 | ARG | 1192 | 12.311 | −9.088 | 35.321 | 1.00 | 0.00 |
| ATOM | 4533 | HH12 | ARG | 1192 | 11.830 | −7.426 | 35.322 | 1.00 | 0.00 |
| ATOM | 4534 | NH2 | ARG | 1192 | 13.296 | −6.674 | 33.467 | 1.00 | 21.28 |
| ATOM | 4535 | HH21 | ARG | 1192 | 13.919 | −6.471 | 32.711 | 1.00 | 0.00 |
| ATOM | 4536 | HH22 | ARG | 1192 | 12.741 | −5.948 | 33.873 | 1.00 | 0.00 |
| ATOM | 4537 | C | ARG | 1192 | 11.241 | −11.367 | 29.915 | 1.00 | 28.96 |
| ATOM | 4538 | O | ARG | 1192 | 11.345 | −11.120 | 28.703 | 1.00 | 32.17 |
| ATOM | 4539 | N | LYS | 1193 | 10.133 | −11.182 | 30.620 | 1.00 | 35.58 |
| ATOM | 4540 | H | LYS | 1193 | 10.123 | −11.503 | 31.549 | 1.00 | 0.00 |
| ATOM | 4541 | CA | LYS | 1193 | 8.919 | −10.627 | 30.059 | 1.00 | 39.90 |
| ATOM | 4542 | CB | LYS | 1193 | 7.862 | −10.552 | 31.167 | 1.00 | 44.44 |
| ATOM | 4543 | CG | LYS | 1193 | 8.242 | −9.817 | 32.469 | 1.00 | 50.54 |
| ATOM | 4544 | CD | LYS | 1193 | 7.395 | −10.421 | 33.597 | 1.00 | 54.35 |
| ATOM | 4545 | CE | LYS | 1193 | 7.441 | −9.651 | 34.907 | 1.00 | 50.38 |
| ATOM | 4546 | NZ | LYS | 1193 | 6.716 | −8.403 | 34.764 | 1.00 | 50.92 |
| ATOM | 4547 | HZ1 | LYS | 1193 | 5.768 | −8.597 | 34.383 | 1.00 | 0.00 |
| ATOM | 4548 | HZ2 | LYS | 1193 | 7.230 | −7.776 | 34.112 | 1.00 | 0.00 |
| ATOM | 4549 | HZ3 | LYS | 1193 | 6.627 | −7.945 | 35.693 | 1.00 | 0.00 |
| ATOM | 4550 | C | LYS | 1193 | 9.200 | −9.258 | 29.465 | 1.00 | 42.01 |
| ATOM | 4551 | O | LYS | 1193 | 8.681 | −8.919 | 28.400 | 1.00 | 45.17 |
| ATOM | 4552 | N | GLU | 1194 | 10.063 | −8.465 | 30.107 | 1.00 | 43.21 |
| ATOM | 4553 | H | GLU | 1194 | 10.545 | −8.826 | 30.876 | 1.00 | 0.00 |
| ATOM | 4554 | CA | GLU | 1194 | 10.422 | −7.154 | 29.598 | 1.00 | 42.46 |
| ATOM | 4555 | CB | GLU | 1194 | 11.099 | −6.342 | 30.699 | 1.00 | 45.15 |
| ATOM | 4556 | CG | GLU | 1194 | 10.161 | −6.091 | 31.888 | 1.00 | 51.05 |
| ATOM | 4557 | CD | GLU | 1194 | 10.620 | −5.135 | 32.997 | 1.00 | 54.40 |
| ATOM | 4558 | OE1 | GLU | 1194 | 11.621 | −4.428 | 32.841 | 1.00 | 51.74 |
| ATOM | 4559 | OE2 | GLU | 1194 | 9.960 | −5.106 | 34.040 | 1.00 | 53.43 |
| ATOM | 4560 | C | GLU | 1194 | 11.374 | −7.449 | 28.450 | 1.00 | 41.34 |
| ATOM | 4561 | O | GLN | 1195 | 12.693 | −8.111 | 28.620 | 1.00 | 41.69 |
| ATOM | 4562 | N | GLN | 1195 | 11.021 | −7.015 | 27.252 | 1.00 | 41.74 |
| ATOM | 4563 | H | GLN | 1195 | 10.212 | −6.475 | 27.187 | 1.00 | 0.00 |
| ATOM | 4564 | CA | GLN | 1195 | 11.787 | −7.317 | 26.052 | 1.00 | 41.57 |
| ATOM | 4565 | CB | GLN | 1195 | 10.993 | −6.804 | 24.850 | 1.00 | 49.15 |
| ATOM | 4566 | CG | GLN | 1195 | 9.692 | −7.586 | 24.621 | 1.00 | 57.96 |
| ATOM | 4567 | CD | GLN | 1195 | 9.918 | −9.056 | 24.262 | 1.00 | 62.70 |
| ATOM | 4568 | OE1 | GLN | 1195 | 10.451 | −9.376 | 23.198 | 1.00 | 67.19 |
| ATOM | 4569 | NE2 | GLN | 1195 | 9.529 | −10.002 | 25.108 | 1.00 | 63.28 |
| ATOM | 4570 | HE21 | GLN | 1195 | 9.110 | −9.750 | 25.959 | 1.00 | 0.00 |
| ATOM | 4571 | HE22 | GLN | 1195 | 9.686 | −10.930 | 24.842 | 1.00 | 0.00 |
| ATOM | 4572 | C | GLN | 1195 | 13.201 | −6.763 | 26.036 | 1.00 | 36.58 |
| ATOM | 4573 | O | GLN | 1195 | 13.410 | −5.634 | 26.442 | 1.00 | 38.41 |
| ATOM | 4574 | N | GLY | 1196 | 14.180 | −7.567 | 25.631 | 1.00 | 33.45 |
| ATOM | 4575 | H | GLY | 1196 | 13.953 | −8.505 | 25.441 | 1.00 | 0.00 |
| ATOM | 4576 | CA | GLY | 1196 | 15.579 | −7.149 | 25.576 | 1.00 | 27.92 |
| ATOM | 4577 | C | GLY | 1196 | 16.373 | −7.473 | 26.850 | 1.00 | 20.50 |
| ATOM | 4578 | O | GLY | 1196 | 17.596 | −7.331 | 26.896 | 1.00 | 17.86 |
| ATOM | 4579 | N | THR | 1197 | 15.713 | −7.930 | 27.912 | 1.00 | 21.77 |
| ATOM | 4580 | H | THR | 1197 | 14.758 | −8.129 | 27.852 | 1.00 | 0.00 |
| ATOM | 4581 | CA | THR | 1197 | 16.376 | −8.267 | 29.151 | 1.00 | 15.76 |
| ATOM | 4582 | CB | THR | 1197 | 15.701 | −7.539 | 30.329 | 1.00 | 16.54 |
| ATOM | 4583 | OG1 | THR | 1197 | 14.355 | −7.984 | 30.455 | 1.00 | 18.76 |
| ATOM | 4584 | HG1 | THR | 1197 | 13.876 | −7.758 | 29.653 | 1.00 | 0.00 |
| ATOM | 4585 | CG2 | THR | 1197 | 15.758 | −6.037 | 30.127 | 1.00 | 15.13 |
| ATOM | 4586 | C | THR | 1197 | 16.300 | −9.769 | 29.328 | 1.00 | 16.59 |
| ATOM | 4587 | O | THR | 1197 | 15.438 | −10.452 | 28.738 | 1.00 | 17.00 |
| ATOM | 4588 | N | TYR | 1198 | 17.204 | −10.298 | 30.140 | 1.00 | 14.48 |
| ATOM | 4589 | H | TYR | 1198 | 17.739 | −9.719 | 30.720 | 1.00 | 0.00 |
| ATOM | 4590 | CA | TYR | 1198 | 17.356 | −11.719 | 30.325 | 1.00 | 16.70 |
| ATOM | 4591 | CB | TYR | 1198 | 18.556 | −12.201 | 29.519 | 1.00 | 17.59 |
| ATOM | 4592 | CG | TYR | 1198 | 18.374 | −12.049 | 28.008 | 1.00 | 21.32 |
| ATOM | 4593 | CD1 | TYR | 1198 | 18.820 | −10.916 | 27.326 | 1.00 | 16.75 |
| ATOM | 4594 | CE1 | TYR | 1198 | 18.609 | −10.791 | 25.950 | 1.00 | 19.88 |
| ATOM | 4595 | CD2 | TYR | 1198 | 17.725 | −13.072 | 27.304 | 1.00 | 25.15 |
| ATOM | 4596 | CE2 | TYR | 1198 | 17.509 | −12.964 | 25.929 | 1.00 | 25.33 |
| ATOM | 4597 | CZ | TYR | 1198 | 17.954 | −11.824 | 25.263 | 1.00 | 26.49 |
| ATOM | 4598 | OH | TYR | 1198 | 17.748 | −11.741 | 23.894 | 1.00 | 36.63 |
| ATOM | 4599 | HH | TYR | 1198 | 17.993 | −10.861 | 23.598 | 1.00 | 0.00 |
| ATOM | 4600 | C | TYR | 1198 | 17.589 | −11.975 | 31.791 | 1.00 | 14.67 |

TABLE 23-continued

Coordinates for the 3D structure of ZAP-NC:ζ1 "dimer" structure
(two molecules of complex per unit cell)*

| ATOM | 4601 | O | TYR | 1198 | 18.007 | −11.074 | 35.512 | 1.00 | 18.92 |
|---|---|---|---|---|---|---|---|---|---|
| ATOM | 4602 | N | ALA | 1199 | 17.351 | −13.168 | 32.283 | 1.00 | 12.49 |
| ATOM | 4603 | H | ALA | 1199 | 17.003 | −13.882 | 31.710 | 1.00 | 0.00 |
| ATOM | 4604 | CA | ALA | 1199 | 17.694 | −13.466 | 33.659 | 1.00 | 10.60 |
| ATOM | 4605 | CB | ALA | 1199 | 16.446 | −13.646 | 34.500 | 1.00 | 3.99 |
| ATOM | 4606 | C | ALA | 1199 | 18.501 | −14.755 | 33.690 | 1.00 | 9.64 |
| ATOM | 4607 | O | ALA | 1199 | 18.152 | −15.740 | 33.036 | 1.00 | 11.40 |
| ATOM | 4608 | N | LEU | 1200 | 19.653 | −14.684 | 34.355 | 1.00 | 6.80 |
| ATOM | 4609 | H | LEU | 1200 | 19.907 | −13.807 | 34.720 | 1.00 | 0.00 |
| ATOM | 4610 | CA | LEU | 1200 | 20.499 | −15.823 | 34.655 | 1.00 | 9.47 |
| ATOM | 4611 | CB | LEU | 1200 | 21.895 | −15.345 | 34.915 | 1.00 | 8.55 |
| ATOM | 4612 | CG | LEU | 1200 | 23.093 | −15.967 | 34.261 | 1.00 | 12.62 |
| ATOM | 4613 | CD1 | LEU | 1200 | 24.235 | −15.618 | 35.215 | 1.00 | 4.18 |
| ATOM | 4614 | CD2 | LEU | 1200 | 22.921 | −17.455 | 33.940 | 1.00 | 2.53 |
| ATOM | 4615 | C | LEU | 1200 | 19.975 | −16.527 | 35.934 | 1.00 | 10.31 |
| ATOM | 4616 | O | LEU | 1200 | 19.911 | −15.893 | 37.002 | 1.00 | 9.18 |
| ATOM | 4617 | N | SER | 1201 | 19.539 | −17.787 | 35.929 | 1.00 | 8.80 |
| ATOM | 4618 | H | SER | 1201 | 19.637 | −18.340 | 35.125 | 1.00 | 0.00 |
| ATOM | 4619 | CA | SER | 1201 | 19.073 | −18.416 | 37.154 | 1.00 | 10.37 |
| ATOM | 4620 | CB | SER | 1201 | 17.702 | −18.992 | 36.893 | 1.00 | 11.67 |
| ATOM | 4621 | OG | SER | 1201 | 16.765 | −17.981 | 32.654 | 1.00 | 13.11 |
| ATOM | 4622 | HG | SER | 1201 | 17.018 | −17.717 | 35.640 | 1.00 | 0.00 |
| ATOM | 4623 | C | SER | 1201 | 20.091 | −19.498 | 37.493 | 1.00 | 13.77 |
| ATOM | 4624 | O | SER | 1201 | 20.425 | −20.250 | 36.565 | 1.00 | 13.42 |
| ATOM | 4625 | N | LEU | 1202 | 20.600 | −19.589 | 38.739 | 1.00 | 10.94 |
| ATOM | 4626 | H | LEU | 1202 | 20.254 | −19.000 | 39.443 | 1.00 | 0.00 |
| ATOM | 4627 | CA | LEU | 1202 | 21.622 | −20.553 | 39.113 | 1.00 | 10.67 |
| ATOM | 4628 | CB | LEU | 1202 | 23.010 | −19.859 | 39.184 | 1.00 | 16.39 |
| ATOM | 4629 | CG | LEU | 1202 | 23.690 | −19.359 | 40.485 | 1.00 | 15.58 |
| ATOM | 4630 | CD1 | LEU | 1202 | 25.112 | −19.872 | 40.531 | 1.00 | 18.14 |
| ATOM | 4631 | CD2 | LEU | 1202 | 23.778 | −17.875 | 40.526 | 1.00 | 14.38 |
| ATOM | 4632 | C | LEU | 1202 | 21.341 | −21.242 | 40.449 | 1.00 | 11.37 |
| ATOM | 4633 | O | LEU | 1202 | 20.596 | −20.712 | 41.265 | 1.00 | 13.60 |
| ATOM | 4634 | N | ILE | 1203 | 21.873 | −22.422 | 40.728 | 1.00 | 13.31 |
| ATOM | 4635 | H | ILE | 1203 | 22.435 | −22.841 | 40.047 | 1.00 | 0.00 |
| ATOM | 4636 | CA | ILE | 1203 | 21.704 | −23.099 | 41.999 | 1.00 | 11.49 |
| ATOM | 4637 | CB | ILE | 1203 | 21.585 | −24.650 | 41.781 | 1.00 | 18.26 |
| ATOM | 4638 | CG2 | ILE | 1203 | 22.002 | −25.404 | 43.049 | 1.00 | 15.92 |
| ATOM | 4639 | CG1 | ILE | 1203 | 20.156 | −25.035 | 41.396 | 1.00 | 20.04 |
| ATOM | 4640 | CD | ILE | 1203 | 19.137 | −25.145 | 42.573 | 1.00 | 21.80 |
| ATOM | 4641 | C | ILE | 1203 | 22.939 | −22.781 | 42.819 | 1.00 | 7.80 |
| ATOM | 4642 | O | ILE | 1203 | 24.056 | −22.800 | 42.306 | 1.00 | 10.96 |
| ATOM | 4643 | N | TYR | 1204 | 22.777 | −22.459 | 44.090 | 1.00 | 10.54 |
| ATOM | 4644 | H | TYR | 1204 | 21.887 | −22.190 | 44.403 | 1.00 | 0.00 |
| ATOM | 4645 | CA | TYR | 1204 | 23.881 | −22.380 | 45.021 | 1.00 | 6.13 |
| ATOM | 4646 | CB | TYR | 1204 | 24.481 | −20.973 | 45.109 | 1.00 | 10.48 |
| ATOM | 4647 | CG | TYR | 1204 | 25.533 | −20.915 | 46.211 | 1.00 | 7.50 |
| ATOM | 4648 | CD1 | TYR | 1204 | 26.792 | −21.469 | 45.978 | 1.00 | 2.91 |
| ATOM | 4649 | CE1 | TYR | 1204 | 27.736 | −21.503 | 47.007 | 1.00 | 6.56 |
| ATOM | 4650 | CD2 | TYR | 1204 | 25.219 | −20.383 | 47.473 | 1.00 | 6.54 |
| ATOM | 4651 | CE2 | TYR | 1204 | 26.162 | −20.425 | 48.499 | 1.00 | 4.63 |
| ATOM | 4652 | CZ | TYR | 1204 | 27.407 | −20.991 | 48.257 | 1.00 | 5.40 |
| ATOM | 4653 | OH | TYR | 1204 | 28.302 | −21.141 | 49.285 | 1.00 | 6.28 |
| ATOM | 4654 | HH | TYR | 1204 | 29.180 | −20.904 | 48.957 | 1.00 | 0.00 |
| ATOM | 4655 | C | TYR | 1204 | 23.230 | −22.728 | 46.322 | 1.00 | 8.98 |
| ATOM | 4656 | O | TYR | 1204 | 22.156 | −22.157 | 46.640 | 1.00 | 9.89 |
| ATOM | 4657 | N | GLY | 1205 | 23.708 | −23.725 | 47.057 | 1.00 | 10.19 |
| ATOM | 4658 | H | GLY | 1205 | 24.387 | −24.311 | 46.661 | 1.00 | 0.00 |
| ATOM | 4659 | CA | GLY | 1205 | 23.143 | −24.100 | 48.356 | 1.00 | 5.00 |
| ATOM | 4660 | C | GLY | 1205 | 21.709 | −24.580 | 48.227 | 1.00 | 9.19 |
| ATOM | 4661 | O | GLY | 1205 | 20.825 | −24.345 | 49.073 | 1.00 | 10.18 |
| ATOM | 4662 | N | LYS | 1206 | 21.503 | −25.225 | 47.068 | 1.00 | 8.86 |
| ATOM | 4663 | H | LYS | 1206 | 22.286 | −25.417 | 46.504 | 1.00 | 0.00 |
| ATOM | 4664 | CA | LYS | 1206 | 20.208 | −25.701 | 46.603 | 1.00 | 4.66 |
| ATOM | 4665 | CB | LYS | 1206 | 19.836 | −26.968 | 47.357 | 1.00 | 6.05 |
| ATOM | 4666 | CG | LYS | 1206 | 20.929 | −28.011 | 47.201 | 1.00 | 4.25 |
| ATOM | 4667 | CD | LYS | 1206 | 20.424 | −29.318 | 47.766 | 1.00 | 10.92 |
| ATOM | 4668 | CE | LYS | 1206 | 21.540 | −30.357 | 47.758 | 1.00 | 10.58 |
| ATOM | 4669 | NZ | LYS | 1206 | 20.937 | −31.658 | 47.933 | 1.00 | 19.07 |
| ATOM | 4670 | HZ1 | LYS | 1206 | 20.351 | −31.871 | 47.101 | 1.00 | 0.00 |
| ATOM | 4671 | HZ2 | LYS | 1206 | 20.337 | −31.657 | 48.783 | 1.00 | 0.00 |
| ATOM | 4672 | HZ3 | LYS | 1206 | 21.669 | −32.389 | 48.030 | 1.00 | 0.00 |
| ATOM | 4673 | C | LYS | 1206 | 19.114 | −24.648 | 46.728 | 1.00 | 4.89 |
| ATOM | 4674 | O | LYS | 1206 | 17.957 | −24.880 | 47.090 | 1.00 | 7.21 |
| ATOM | 4675 | N | THR | 1207 | 19.538 | −23.433 | 46.388 | 1.00 | 8.77 |
| ATOM | 4676 | H | THR | 1207 | 20.471 | −23.265 | 46.151 | 1.00 | 0.00 |

TABLE 23-continued

Coordinates for the 3D structure of ZAP-NC:ζ1 "dimer" structure
(two molecules of complex per unit cell)*

| | | | | | | | | | |
|---|---|---|---|---|---|---|---|---|---|
| ATOM | 4677 | CA | THR | 1207 | 18.654 | −22.282 | 46.347 | 1.00 | 11.18 |
| ATOM | 4678 | CB | THR | 1207 | 18.993 | −21.309 | 47.469 | 1.00 | 8.66 |
| ATOM | 4679 | OG1 | THR | 1207 | 19.044 | −22.042 | 48.695 | 1.00 | 18.34 |
| ATOM | 4680 | HG1 | THR | 1207 | 19.657 | −22.792 | 48.654 | 1.00 | 0.00 |
| ATOM | 4681 | CG2 | THR | 1207 | 17.935 | −20.225 | 47.600 | 1.00 | 2.00 |
| ATOM | 4682 | C | THR | 1207 | 18.933 | −21.646 | 44.964 | 1.00 | 8.75 |
| ATOM | 4683 | O | THR | 1207 | 20.094 | −21.520 | 44.566 | 1.00 | 11.11 |
| ATOM | 4684 | N | VAL | 1208 | 17.897 | −21.317 | 44.203 | 1.00 | 11.99 |
| ATOM | 4685 | H | VAL | 1208 | 16.986 | −21.474 | 44.529 | 1.00 | 0.00 |
| ATOM | 4686 | CA | VAL | 1208 | 18.092 | −20.657 | 42.924 | 1.00 | 11.25 |
| ATOM | 4687 | CB | VAL | 1208 | 16.848 | −20.878 | 42.006 | 1.00 | 13.46 |
| ATOM | 4688 | CG1 | VAL | 1208 | 17.103 | −20.322 | 40.612 | 1.00 | 10.87 |
| ATOM | 4689 | CG2 | VAL | 1208 | 16.583 | −22.363 | 41.833 | 1.00 | 8.09 |
| ATOM | 4690 | C | VAL | 1208 | 18.313 | −19.169 | 43.185 | 1.00 | 9.93 |
| ATOM | 4691 | O | VAL | 1208 | 17.641 | −18.561 | 44.021 | 1.00 | 12.68 |
| ATOM | 4692 | N | TYR | 1209 | 19.289 | −18.559 | 42.538 | 1.00 | 10.99 |
| ATOM | 4693 | H | TYR | 1209 | 19.866 | −19.105 | 41.961 | 1.00 | 0.00 |
| ATOM | 4694 | CA | TYR | 1209 | 19.643 | −17.127 | 42.598 | 1.00 | 9.13 |
| ATOM | 4695 | CB | TYR | 1209 | 21.023 | −16.904 | 42.917 | 1.00 | 7.91 |
| ATOM | 4696 | CG | TYR | 1209 | 21.281 | −17.214 | 44.376 | 1.00 | 13.41 |
| ATOM | 4697 | CD1 | TYR | 1209 | 21.096 | −16.209 | 45.327 | 1.00 | 16.92 |
| ATOM | 4698 | CE1 | TYR | 1209 | 21.199 | −16.504 | 46.682 | 1.00 | 22.64 |
| ATOM | 4699 | CD2 | TYR | 1209 | 21.591 | −18.512 | 44.783 | 1.00 | 13.00 |
| ATOM | 4700 | CE1 | TYR | 1209 | 21.691 | −18.807 | 46.138 | 1.00 | 14.79 |
| ATOM | 4701 | CZ | TYR | 1209 | 21.492 | −17.805 | 47.080 | 1.00 | 18.04 |
| ATOM | 4702 | OH | TYR | 1209 | 21.555 | −18.089 | 48.425 | 1.00 | 16.55 |
| ATOM | 4703 | HH | TYR | 1209 | 21.525 | −19.044 | 48.552 | 1.00 | 0.00 |
| ATOM | 4704 | C | TYR | 1209 | 19.176 | −16.557 | 41.227 | 1.00 | 9.15 |
| ATOM | 4705 | O | TYR | 1209 | 19.307 | −17.306 | 40.258 | 1.00 | 9.61 |
| ATOM | 4706 | N | HIS | 1210 | 18.677 | −15.326 | 41.036 | 1.00 | 9.91 |
| ATOM | 4707 | H | HIS | 1210 | 18.622 | −14.715 | 41.807 | 1.00 | 0.00 |
| ATOM | 4708 | CA | HIS | 1210 | 18.366 | −14.805 | 39.699 | 1.00 | 7.08 |
| ATOM | 4709 | CB | HIS | 1210 | 16.886 | −14.536 | 39.478 | 1.00 | 9.03 |
| ATOM | 4710 | CG | HIS | 1210 | 16.007 | −15.770 | 39.564 | 1.00 | 8.44 |
| ATOM | 4711 | CD2 | HIS | 1210 | 15.433 | −16.228 | 40.731 | 1.00 | 10.80 |
| ATOM | 4712 | ND1 | HIS | 1210 | 15.657 | −16.621 | 37.613 | 1.00 | 11.46 |
| ATOM | 4713 | HD1 | HIS | 1210 | 15.996 | −16.657 | 37.689 | 1.00 | 0.00 |
| ATOM | 4714 | CE1 | HIS | 1210 | 14.908 | −17.563 | 39.136 | 1.00 | 7.08 |
| ATOM | 4715 | NE2 | HIS | 1210 | 14.785 | −17.314 | 40.416 | 1.00 | 10.12 |
| ATOM | 4716 | HE2 | HIS | 1210 | 14.360 | −17.908 | 41.068 | 1.00 | 0.00 |
| ATOM | 4717 | C | HIS | 1210 | 19.057 | −13.487 | 39.455 | 1.00 | 9.93 |
| ATOM | 4718 | O | TYR | 1211 | 18.956 | −12.579 | 40.269 | 1.00 | 8.85 |
| ATOM | 4719 | N | TYR | 1211 | 19.794 | −13.329 | 38.372 | 1.00 | 10.56 |
| ATOM | 4720 | H | TYR | 1211 | 19.870 | −14.074 | 37.737 | 1.00 | 0.00 |
| ATOM | 4721 | CA | TYR | 1211 | 20.501 | −12.089 | 38.069 | 1.00 | 14.64 |
| ATOM | 4722 | CB | TYR | 1211 | 21.990 | −12.387 | 37.885 | 1.00 | 8.91 |
| ATOM | 4723 | CG | TYR | 1211 | 22.642 | −12.837 | 39.175 | 1.00 | 13.49 |
| ATOM | 4724 | CD1 | TYR | 1211 | 22.545 | −14.176 | 39.587 | 1.00 | 11.64 |
| ATOM | 4725 | CE1 | TYR | 1211 | 23.138 | −14.579 | 40.782 | 1.00 | 8.95 |
| ATOM | 4726 | CD2 | TYR | 1211 | 23.333 | −11.897 | 39.950 | 1.00 | 10.65 |
| ATOM | 4727 | CE2 | TYR | 1211 | 23.928 | −12.305 | 41.144 | 1.00 | 8.87 |
| ATOM | 4728 | CZ | TYR | 1211 | 23.829 | −13.642 | 41.549 | 1.00 | 11.65 |
| ATOM | 4729 | OH | TYR | 1211 | 24.419 | −14.055 | 51.720 | 1.00 | 10.12 |
| ATOM | 4730 | HH | TYR | 1211 | 24.763 | −13.294 | 43.222 | 1.00 | 0.00 |
| ATOM | 4731 | C | TYR | 1211 | 19.940 | −11.461 | 36.795 | 1.00 | 12.65 |
| ATOM | 4732 | O | TYR | 1211 | 19.623 | −12.200 | 35.866 | 1.00 | 15.74 |
| ATOM | 4733 | N | LEU | 1212 | 19.779 | −10.150 | 36.679 | 1.00 | 14.20 |
| ATOM | 4734 | H | LEU | 1212 | 20.110 | −9.570 | 37.399 | 1.00 | 0.00 |
| ATOM | 4735 | CA | LEU | 1212 | 19.216 | −9.514 | 35.488 | 1.00 | 13.88 |
| ATOM | 4736 | CB | LEU | 1212 | 18.486 | −8.205 | 35.850 | 1.00 | 17.25 |
| ATOM | 4737 | CG | LEU | 1212 | 17.893 | −7.281 | 34.785 | 1.00 | 11.92 |
| ATOM | 4738 | CD1 | LEU | 1212 | 16.934 | −8.055 | 33.937 | 1.00 | 15.10 |
| ATOM | 4739 | CD2 | LEU | 1212 | 17.122 | −6.164 | 35.416 | 1.00 | 16.39 |
| ATOM | 4740 | C | LEU | 1212 | 20.350 | −9.193 | 34.556 | 1.00 | 11.08 |
| ATOM | 4741 | O | LEU | 1212 | 21.414 | −8.791 | 35.005 | 1.00 | 15.63 |
| ATOM | 4742 | N | ILE | 1213 | 20.155 | −9.402 | 33.274 | 1.00 | 11.41 |
| ATOM | 4743 | H | ILE | 1213 | 19.286 | −9.744 | 32.985 | 1.00 | 0.00 |
| ATOM | 4744 | CA | ILE | 1213 | 21.132 | −9.052 | 32.258 | 1.00 | 11.27 |
| ATOM | 4745 | CB | ILE | 1213 | 21.647 | −10.301 | 31.495 | 1.00 | 10.65 |
| ATOM | 4746 | CG2 | ILE | 1213 | 22.612 | −98.51 | 30.394 | 1.00 | 2.00 |
| ATOM | 4747 | CG1 | ILE | 1213 | 22.333 | −11.271 | 32.457 | 1.00 | 8.10 |
| ATOM | 4748 | CD | ILE | 1213 | 22.178 | −12.708 | 31.951 | 1.00 | 6.60 |
| ATOM | 4749 | C | ILE | 1213 | 20.300 | −8.185 | 31.319 | 1.00 | 12.26 |
| ATOM | 4750 | O | ILE | 1213 | 19.143 | −8.504 | 31.032 | 1.00 | 11.97 |
| ATOM | 4751 | N | SER | 1214 | 20.850 | −7.068 | 30.870 | 1.00 | 15.76 |
| ATOM | 4752 | H | SER | 1214 | 21.733 | −6.808 | 31.218 | 1.00 | 0.00 |

TABLE 23-continued

Coordinates for the 3D structure of ZAP-NC:ζ1 "dimer" structure
(two molecules of complex per unit cell)*

| ATOM | 4753 | CA | SER | 1214 | 20.219 | −6.188 | 29.898 | 1.00 | 11.43 |
|---|---|---|---|---|---|---|---|---|---|
| ATOM | 4754 | CB | SER | 1214 | 19.346 | −5.168 | 30.653 | 1.00 | 8.83 |
| ATOM | 4755 | OG | SER | 1214 | 19.967 | −4.636 | 31.807 | 1.00 | 13.26 |
| ATOM | 4756 | HG | SER | 1214 | 30.764 | −4.188 | 31.502 | 1.00 | 0.00 |
| ATOM | 4757 | C | SER | 1214 | 21.344 | −5.515 | 29.112 | 1.00 | 12.87 |
| ATOM | 4758 | O | SER | 1214 | 22.539 | −5.704 | 29.420 | 1.00 | 9.60 |
| ATOM | 4759 | N | GLN | 1215 | 21.012 | −4.789 | 28.040 | 1.00 | 13.37 |
| ATOM | 4760 | H | GLN | 1215 | 20.071 | −4.719 | 27.781 | 1.00 | 0.00 |
| ATOM | 4761 | CA | GLN | 1215 | 22.007 | −4.049 | 27.261 | 1.00 | 16.58 |
| ATOM | 4762 | CB | GLN | 1215 | 21.641 | −3.996 | 25.761 | 1.00 | 15.14 |
| ATOM | 4763 | CG | GLN | 1215 | 21.706 | −5.377 | 25.155 | 1.00 | 19.92 |
| ATOM | 4764 | CD | GLN | 1215 | 21.354 | −5.525 | 23.684 | 1.00 | 23.57 |
| ATOM | 4765 | OE1 | GLN | 1215 | 20.229 | −5.858 | 23.301 | 1.00 | 25.08 |
| ATOM | 4766 | NE2 | GLN | 1215 | 22.322 | −5.400 | 22.793 | 1.00 | 24.06 |
| ATOM | 4767 | HE21 | GLN | 1215 | 23.233 | −5.230 | 23.113 | 1.00 | 0.00 |
| ATOM | 4768 | HE22 | GLN | 1215 | 22.094 | −5.496 | 21.847 | 1.00 | 0.00 |
| ATOM | 4769 | C | GLN | 1215 | 22.069 | −2.625 | 27.789 | 1.00 | 16.06 |
| ATOM | 4770 | O | GLN | 1215 | 21.025 | −2.008 | 28.024 | 1.00 | 19.32 |
| ATOM | 4771 | N | ASP | 1216 | 23.268 | −2.124 | 28.048 | 1.00 | 17.64 |
| ATOM | 4772 | H | ASP | 1216 | 24.038 | −2.731 | 27.960 | 1.00 | 0.00 |
| ATOM | 4773 | CA | ASP | 1216 | 23.475 | −0.736 | 26.747 | 1.00 | 21.35 |
| ATOM | 4774 | CB | ASP | 1216 | 24.925 | −0.587 | 28.401 | 1.00 | 20.33 |
| ATOM | 4775 | CG | ASP | 1216 | 26.085 | −0.812 | 27.275 | 1.00 | 18.82 |
| ATOM | 4776 | OD1 | ASP | 1216 | 25.889 | −0.887 | 26.157 | 1.00 | 18.33 |
| ATOM | 4777 | OD2 | ASP | 1216 | 27.226 | −0.886 | 28.401 | 1.00 | 15.08 |
| ATOM | 4778 | C | ASP | 1216 | 23.211 | −0.206 | 27.275 | 1.00 | 22.60 |
| ATOM | 4779 | O | ASP | 1216 | 23.013 | −0.268 | 26.157 | 1.00 | 24.68 |
| ATOM | 4780 | N | LYS | 1217 | 23.334 | −1.527 | 27.414 | 1.00 | 27.26 |
| ATOM | 4781 | H | LYS | 1217 | 23.459 | −1.868 | 28.323 | 1.00 | 0.00 |
| ATOM | 4782 | CA | LYS | 1217 | 23.128 | −2.473 | 26.312 | 1.00 | 26.76 |
| ATOM | 4783 | CB | LYS | 1217 | 23.521 | −3.892 | 26.747 | 1.00 | 28.33 |
| ATOM | 4784 | CG | LYS | 1217 | 24.974 | −4.178 | 27.188 | 1.00 | 40.57 |
| ATOM | 4785 | CD | LYS | 1217 | 25.357 | −3.646 | 28.595 | 1.00 | 49.59 |
| ATOM | 4786 | CE | LYS | 1217 | 26.753 | −4.133 | 28.992 | 1.00 | 51.93 |
| ATOM | 4787 | NZ | LYS | 1217 | 27.053 | −3.846 | 30.383 | 1.00 | 52.30 |
| ATOM | 4788 | HZ1 | LYS | 1217 | 26.961 | −2.826 | 30.561 | 1.00 | 0.00 |
| ATOM | 4789 | HZ2 | LYS | 1217 | 26.396 | −4.369 | 31.000 | 1.00 | 0.00 |
| ATOM | 4790 | HZ3 | LYS | 1217 | 28.028 | −4.149 | 30.584 | 1.00 | 0.00 |
| ATOM | 4791 | C | LYS | 1217 | 23.856 | −2.171 | 24.973 | 1.00 | 23.75 |
| ATOM | 4792 | O | LYS | 1217 | 23.414 | 2.526 | 23.881 | 1.00 | 22.76 |
| ATOM | 4793 | N | ALA | 1218 | 24.992 | 1.488 | 25.066 | 1.00 | 19.56 |
| ATOM | 4794 | H | ALA | 1218 | 25.278 | 1.175 | 25.942 | 1.00 | 0.00 |
| ATOM | 4795 | CA | ALA | 1218 | 25.789 | 1.160 | 23.913 | 1.00 | 18.97 |
| ATOM | 4796 | CB | ALA | 1218 | 27.250 | 1.338 | 24.283 | 1.00 | 12.65 |
| ATOM | 4797 | C | ALA | 1218 | 25.574 | −0.245 | 23.355 | 1.00 | 20.40 |
| ATOM | 4798 | O | ALA | 1218 | 26.304 | −0.658 | 22.447 | 1.00 | 24.06 |
| ATOM | 4799 | N | GLY | 1219 | 24.611 | −1.018 | 23.852 | 1.00 | 17.93 |
| ATOM | 4700 | H | GLY | 1219 | 23.927 | −0.641 | 24.458 | 1.00 | 0.00 |
| ATOM | 4801 | CA | GLY | 1219 | 24.399 | −2.368 | 23.337 | 1.00 | 18.40 |
| ATOM | 4802 | C | GLY | 1219 | 25.163 | −3.491 | 24.043 | 1.00 | 12.63 |
| ATOM | 4803 | O | GLY | 1219 | 24.891 | −4.659 | 23.791 | 1.00 | 14.94 |
| ATOM | 4804 | N | LYS | 1220 | 26.090 | −3.212 | 24.938 | 1.00 | 9.76 |
| ATOM | 4805 | H | LYS | 1220 | 26.312 | −2.276 | 25.072 | 1.00 | 0.00 |
| ATOM | 4806 | CA | LYS | 1220 | 26.804 | −4.244 | 25.668 | 1.00 | 12.80 |
| ATOM | 4807 | CB | LYS | 1220 | 28.063 | −3.669 | 26.313 | 1.00 | 11.80 |
| ATOM | 4808 | CG | LYS | 1220 | 29.005 | −3.055 | 25.284 | 1.00 | 13.40 |
| ATOM | 4809 | CD | LYS | 1220 | 30.498 | −3.312 | 25.537 | 1.00 | 31.03 |
| ATOM | 4810 | CE | LYS | 1220 | 30.945 | −4.758 | 25.267 | 1.00 | 36.30 |
| ATOM | 4811 | NZ | LYS | 1220 | 32.384 | −4.971 | 25.363 | 1.00 | 35.49 |
| ATOM | 4812 | HZ1 | LYS | 1220 | 32.708 | −4.762 | 26.328 | 1.00 | 0.00 |
| ATOM | 4813 | HZ2 | LYS | 1220 | 32.874 | −4.347 | 24.690 | 1.00 | 0.00 |
| ATOM | 4814 | HZ3 | LYS | 1220 | 32.599 | −5.961 | 25.132 | 1.00 | 0.00 |
| ATOM | 4815 | C | LYS | 1220 | 25.940 | −4.884 | 26.745 | 1.00 | 14.51 |
| ATOM | 4816 | O | LYS | 1220 | 25.205 | −4.205 | 27.477 | 1.00 | 15.43 |
| ATOM | 4817 | N | TYR | 1221 | 25.990 | −6.217 | 26.744 | 1.00 | 12.28 |
| ATOM | 4818 | H | TYR | 1221 | 26.544 | −6.646 | 26.066 | 1.00 | 0.00 |
| ATOM | 4819 | CA | TYR | 1221 | 25.273 | −7.069 | 27.673 | 1.00 | 10.89 |
| ATOM | 4820 | CB | TYR | 1221 | 25.187 | −8.490 | 27.087 | 1.00 | 7.55 |
| ATOM | 4821 | CG | TYR | 1221 | 24.259 | −8.599 | 25.884 | 1.00 | 6.89 |
| ATOM | 4822 | CD1 | TYR | 1221 | 24.784 | −8.501 | 24.600 | 1.00 | 5.33 |
| ATOM | 4823 | CE1 | TYR | 1221 | 23.964 | −8.672 | 23.486 | 1.00 | 11.81 |
| ATOM | 4824 | CD2 | TYR | 1221 | 22.902 | −8.856 | 26.051 | 1.00 | 10.91 |
| ATOM | 4825 | CE2 | TYR | 1221 | 22.075 | −9.031 | 24.930 | 1.00 | 9.53 |
| ATOM | 4826 | CZ | TYR | 1221 | 22.612 | −8.950 | 23.645 | 1.00 | 12.73 |
| ATOM | 4827 | OH | TYR | 1221 | 21.836 | −9.245 | 22.524 | 1.00 | 13.45 |
| ATOM | 4828 | HH | TYR | 1221 | 21.836 | −8.487 | 21.914 | 1.00 | 0.00 |

TABLE 23-continued

Coordinates for the 3D structure of ZAP-NC:ζ1 "dimer" structure
(two molecules of complex per unit cell)*

| ATOM | 4829 | C | TYR | 1221 | 25.965 | −7.106 | 29.035 | 1.00 | 9.20 |
|---|---|---|---|---|---|---|---|---|---|
| ATOM | 4830 | O | TYR | 1221 | 27.197 | −7.211 | 29.109 | 1.00 | 13.58 |
| ATOM | 4831 | N | CYS | 1222 | 25.345 | −6.957 | 30.127 | 1.00 | 8.73 |
| ATOM | 4832 | H | CYS | 1222 | 24.293 | −6.678 | 30.068 | 1.00 | 0.00 |
| ATOM | 4833 | CA | CYS | 1222 | 25.842 | −7.089 | 31.435 | 1.00 | 11.15 |
| ATOM | 4834 | CB | CYS | 1222 | 26.711 | −5.878 | 31.730 | 1.00 | 13.63 |
| ATOM | 4835 | SG | CYS | 1222 | 25.843 | −4.300 | 31.769 | 1.00 | 15.70 |
| ATOM | 4836 | C | CYS | 1222 | 24.800 | −7.225 | 32.519 | 1.00 | 9.43 |
| ATOM | 4837 | O | CYS | 1222 | 23.617 | −6.955 | 32.302 | 1.00 | 13.63 |
| ATOM | 4838 | N | ILE | 1223 | 25.180 | −7.769 | 33.671 | 1.00 | 13.65 |
| ATOM | 4839 | H | ILE | 1223 | 26.097 | −8.112 | 33.760 | 1.00 | 0.00 |
| ATOM | 4840 | CA | ILE | 1223 | 24.318 | −7.763 | 34.866 | 1.00 | 11.24 |
| ATOM | 4841 | CB | ILE | 1223 | 24.724 | −8.944 | 35.792 | 1.00 | 12.90 |
| ATOM | 4842 | CG2 | ILE | 1223 | 24.025 | −8.884 | 37.166 | 1.00 | 8.32 |
| ATOM | 4843 | CG1 | ILE | 1223 | 24.377 | −1.0221 | 35.054 | 1.00 | 12.18 |
| ATOM | 4844 | CD | ILE | 1223 | 25.066 | −1.1480 | 35.556 | 1.00 | 14.74 |
| ATOM | 4845 | C | ILE | 1223 | 24.614 | −6.396 | 35.509 | 1.00 | 10.19 |
| ATOM | 4846 | O | ILE | 1223 | 25.728 | −5.880 | 35.285 | 1.00 | 9.63 |
| ATOM | 4847 | N | PRO | 1224 | 23.748 | −5.694 | 36.263 | 1.00 | 11.43 |
| ATOM | 4848 | CD | PRO | 1224 | 22.306 | −5.965 | 36.414 | 1.00 | 7.97 |
| ATOM | 4849 | CA | PRO | 1224 | 24.084 | −4.405 | 36.834 | 1.00 | 7.55 |
| ATOM | 4850 | CB | PRO | 1224 | 22.861 | −4.093 | 37.629 | 1.00 | 9.42 |
| ATOM | 4851 | CG | PRO | 1224 | 21.742 | −4.611 | 36.743 | 1.00 | 3.67 |
| ATOM | 4852 | C | PRO | 1224 | 25.385 | −4.433 | 37.614 | 1.00 | 14.05 |
| ATOM | 4853 | O | PRO | 1224 | 25.603 | −5.267 | 38.490 | 1.00 | 18.66 |
| ATOM | 4854 | N | GLU | 1225 | 26.275 | −3.545 | 37.179 | 1.00 | 13.58 |
| ATOM | 4855 | H | GLU | 1225 | 26.005 | −2.981 | 36.426 | 1.00 | 0.00 |
| ATOM | 4856 | CA | GLU | 1225 | 27.663 | −3.336 | 37.680 | 1.00 | 14.68 |
| ATOM | 4857 | CB | GLU | 1225 | 27.681 | −3.285 | 39.233 | 1.00 | 17.95 |
| ATOM | 4858 | CG | GLU | 1225 | 26.836 | −2.196 | 39.917 | 1.00 | 24.12 |
| ATOM | 4859 | CD | GLU | 1225 | 27.068 | −0.782 | 39.391 | 1.00 | 61.41 |
| ATOM | 4860 | OE1 | GLU | 1225 | 28.228 | −0.304 | 39.447 | 1.00 | 30.20 |
| ATOM | 4861 | OE2 | GLU | 1225 | 26.122 | −0.169 | 38.917 | 1.00 | 36.60 |
| ATOM | 4862 | C | GLU | 1225 | 28.603 | −4.402 | 37.208 | 1.00 | 12.36 |
| ATOM | 4863 | O | GLU | 1225 | 29.715 | −4.474 | 37.705 | 1.00 | 10.48 |
| ATOM | 4864 | N | GLY | 1226 | 28.247 | −5.202 | 36.203 | 1.00 | 15.65 |
| ATOM | 4865 | H | GLY | 1226 | 27.411 | −5.024 | 35.728 | 1.00 | 0.00 |
| ATOM | 4866 | CA | GLY | 1226 | 29.065 | −6.317 | 35.745 | 1.00 | 16.29 |
| ATOM | 4867 | C | GLY | 1226 | 29.877 | −6.033 | 34.498 | 1.00 | 14.66 |
| ATOM | 4868 | O | GLY | 1226 | 29.805 | −4.940 | 33.920 | 1.00 | 13.35 |
| ATOM | 4869 | N | THR | 1227 | 30.726 | −7.018 | 34.159 | 1.00 | 15.24 |
| ATOM | 4870 | H | THR | 1227 | 30.795 | −7.807 | 34.735 | 1.00 | 0.00 |
| ATOM | 4871 | CA | THR | 1227 | 31.568 | −3.688 | 32.958 | 1.00 | 10.28 |
| ATOM | 4872 | CB | THR | 1227 | 32.377 | −8.293 | 32.879 | 1.00 | 9.42 |
| ATOM | 4873 | OG1 | THR | 1227 | 33.033 | −8.487 | 34.126 | 1.00 | 13.78 |
| ATOM | 4874 | HG1 | THR | 1227 | 33.642 | −9.231 | 34.046 | 1.00 | 0.00 |
| ATOM | 4875 | CG2 | THR | 1227 | 33.443 | −8.243 | 31.825 | 1.00 | 4.54 |
| ATOM | 4876 | C | THR | 1227 | 30.659 | −6.839 | 31.749 | 1.00 | 3.83 |
| ATOM | 4877 | O | THR | 1227 | 29.553 | −7.372 | 31.758 | 1.00 | 5.43 |
| ATOM | 4878 | N | LYS | 1228 | 31.095 | −6.072 | 30.768 | 1.00 | 9.81 |
| ATOM | 4879 | H | LYS | 1228 | 32.012 | −5.718 | 30.808 | 1.00 | 0.00 |
| ATOM | 4880 | CA | LYS | 1228 | 30.345 | −5.772 | 29.551 | 1.00 | 11.73 |
| ATOM | 4881 | CB | LYS | 1228 | 30.720 | −4.416 | 28.983 | 1.00 | 11.23 |
| ATOM | 4882 | CG | LYS | 1228 | 30.633 | −3.200 | 29.882 | 1.00 | 10.19 |
| ATOM | 4883 | CD | LYS | 1228 | 29.203 | −2.969 | 30.270 | 1.00 | 15.20 |
| ATOM | 4884 | CE | LYS | 1228 | 29.100 | −1.660 | 31.047 | 1.00 | 14.54 |
| ATOM | 4885 | NZ | LYS | 1228 | 27.704 | −1.421 | 31.359 | 1.00 | 16.02 |
| ATOM | 4886 | HZ1 | LYS | 1228 | 27.340 | −2.244 | 31.880 | 1.00 | 0.00 |
| ATOM | 4887 | HZ2 | LYS | 1228 | 27.171 | −1.309 | 30.473 | 1.00 | 0.00 |
| ATOM | 4888 | HZ3 | LYS | 1228 | 27.599 | −0.564 | 31.940 | 1.00 | 0.00 |
| ATOM | 4889 | C | LYS | 1228 | 30.707 | −6.795 | 28.493 | 1.00 | 8.65 |
| ATOM | 4890 | O | LYS | 1228 | 31.897 | −7.072 | 28.329 | 1.00 | 8.25 |
| ATOM | 4891 | N | PHE | 1229 | 29.740 | −7.331 | 27.756 | 1.00 | 7.57 |
| ATOM | 4892 | H | PHE | 1229 | 28.806 | −7.093 | 27.938 | 1.00 | 0.00 |
| ATOM | 4893 | CA | PHE | 1229 | 29.996 | −8.334 | 26.722 | 1.00 | 11.09 |
| ATOM | 4894 | CB | PHE | 1229 | 29.483 | −9.753 | 27.086 | 1.00 | 6.70 |
| ATOM | 4895 | CG | PHE | 1229 | 29.986 | −1.0207 | 28.450 | 1.00 | 7.81 |
| ATOM | 4896 | CD1 | PHE | 1229 | 29.251 | −9.901 | 29.599 | 1.00 | 4.30 |
| ATOM | 4897 | CD2 | PHE | 1229 | 31.184 | −10.912 | 28.546 | 1.00 | 5.18 |
| ATOM | 4898 | CE1 | PHE | 1229 | 29.723 | −10.303 | 30.841 | 1.00 | 4.39 |
| ATOM | 4899 | CE2 | PHE | 1229 | 31.642 | −11.307 | 29.794 | 1.00 | 2.00 |
| ATOM | 4900 | CZ | PHE | 1229 | 30.916 | −11.005 | 30.936 | 1.00 | 2.00 |
| ATOM | 4901 | C | PHE | 1229 | 29.243 | −7.961 | 25.467 | 1.00 | 9.05 |
| ATOM | 4902 | O | PHE | 1229 | 28.174 | −7.361 | 25.535 | 1.00 | 6.36 |
| ATOM | 4903 | N | ASP | 1230 | 29.752 | −8.369 | 24.316 | 1.00 | 11.64 |
| ATOM | 4904 | H | ASP | 1230 | 30.616 | −8.832 | 24.322 | 1.00 | 0.00 |

TABLE 23-continued

Coordinates for the 3D structure of ZAP-NC:ζ1 "dimer" structure
(two molecules of complex per unit cell)*

| ATOM | 4905 | CA | ASP | 1230 | 29.041 | −8.183 | 23.062 | 1.00 | 10.17 |
|---|---|---|---|---|---|---|---|---|---|
| ATOM | 4906 | CB | ASP | 1230 | 20.961 | −8.319 | 21.875 | 1.00 | 13.12 |
| ATOM | 4907 | CG | ASP | 1230 | 30.845 | −7.122 | 21.591 | 1.00 | 12.53 |
| ATOM | 4908 | OD1 | ASP | 1230 | 30.818 | −6.121 | 22.303 | 1.00 | 18.42 |
| ATOM | 4909 | OD2 | ASP | 1230 | 31.566 | −7.190 | 20.610 | 1.00 | 16.16 |
| ATOM | 4910 | C | ASP | 1230 | 27.944 | −9.184 | 22.853 | 1.00 | 4.73 |
| ATOM | 4911 | O | ASP | 1230 | 26.995 | −8.933 | 22.121 | 1.00 | 10.59 |
| ATOM | 4912 | N | THR | 1231 | 28.020 | −10.298 | 23.534 | 1.00 | 4.42 |
| ATOM | 4913 | H | THR | 1231 | 28.644 | −10.378 | 24.281 | 1.00 | 0.00 |
| ATOM | 4914 | CA | THR | 1231 | 27.133 | −11.398 | 23.265 | 1.00 | 8.22 |
| ATOM | 4915 | CB | THR | 1231 | 27.987 | −12.342 | 22.365 | 1.00 | 10.46 |
| ATOM | 4916 | OG1 | THR | 1231 | 27.951 | −11.835 | 21.031 | 1.00 | 16.76 |
| ATOM | 4917 | HG1 | THR | 1231 | 28.848 | −11.875 | 20.682 | 1.00 | 0.00 |
| ATOM | 4918 | CG2 | THR | 1231 | 27.455 | −13.705 | 22.267 | 1.00 | 19.25 |
| ATOM | 4919 | C | THR | 1231 | 26.663 | −12.002 | 24.573 | 1.00 | 7.92 |
| ATOM | 4920 | O | THR | 1231 | 27.349 | −11.890 | 25.595 | 1.00 | 12.71 |
| ATOM | 4921 | N | LEU | 1232 | 25.496 | −12.649 | 24.574 | 1.00 | 9.70 |
| ATOM | 4922 | H | LEU | 1232 | 24.892 | −12.549 | 23.803 | 1.00 | 0.00 |
| ATOM | 4923 | CA | LEU | 1232 | 25.040 | −13.393 | 25.742 | 1.00 | 11.19 |
| ATOM | 4924 | CB | LEU | 1232 | 23.588 | −13.738 | 25.630 | 1.00 | 6.17 |
| ATOM | 4925 | CG | LEU | 1232 | 22.651 | −12.624 | 25.993 | 1.00 | 7.65 |
| ATOM | 4926 | CD1 | LEU | 1232 | 21.261 | −13.177 | 25.824 | 1.00 | 10.36 |
| ATOM | 4927 | CD2 | LEU | 1232 | 22.852 | −12.135 | 27.444 | 1.00 | 6.21 |
| ATOM | 4928 | C | LEU | 1232 | 25.815 | −14.682 | 25.902 | 1.00 | 11.62 |
| ATOM | 4929 | O | LEU | 1232 | 26.187 | −15.071 | 27.019 | 1.00 | 11.82 |
| ATOM | 4930 | N | TRP | 1233 | 26.123 | −15.312 | 24.730 | 1.00 | 9.01 |
| ATOM | 4931 | H | TRP | 1233 | 25.729 | −14.988 | 23.927 | 1.00 | 0.00 |
| ATOM | 4932 | CA | TRP | 1233 | 26.953 | −16.503 | 24.740 | 1.00 | 7.78 |
| ATOM | 4933 | CB | TRP | 1233 | 27.308 | −16.919 | 23.298 | 1.00 | 6.14 |
| ATOM | 4934 | CG | TRP | 1233 | 27.978 | −18.285 | 23.197 | 1.00 | 2.05 |
| ATOM | 4935 | CD2 | TRP | 1233 | 29.323 | −18.581 | 23.221 | 1.00 | 2.00 |
| ATOM | 4936 | CE2 | TRP | 1233 | 29.292 | −19.979 | 23.111 | 1.00 | 2.00 |
| ATOM | 4937 | CE3 | TRP | 1233 | 30.547 | −17.921 | 23.315 | 1.00 | 2.00 |
| ATOM | 4938 | CD1 | TRP | 1233 | 27.191 | −19.400 | 23.080 | 1.00 | 2.03 |
| ATOM | 4939 | NE1 | TRP | 1233 | 28.021 | −20.410 | 23.028 | 1.00 | 6.75 |
| ATOM | 4940 | HE1 | TRP | 1233 | 27.741 | −21.338 | 22.871 | 1.00 | 0.00 |
| ATOM | 4941 | CZ2 | TRP | 1233 | 30.463 | −20.737 | 23.097 | 1.00 | 2.00 |
| ATOM | 4942 | CZ3 | TRP | 1233 | 31.728 | −18.659 | 23.305 | 1.00 | 5.65 |
| ATOM | 4943 | CH2 | TRP | 1233 | 31.685 | −20.056 | 23.196 | 1.00 | 8.83 |
| ATOM | 4944 | C | TRP | 1233 | 28.248 | −16.248 | 25.501 | 1.00 | 6.51 |
| ATOM | 4945 | O | TRP | 1233 | 28.604 | −16.992 | 26.411 | 1.00 | 8.36 |
| ATOM | 4946 | N | GLN | 1234 | 28.927 | −15.161 | 25.118 | 1.00 | 6.74 |
| ATOM | 4947 | H | GLN | 1234 | 28.578 | −14.655 | 24.365 | 1.00 | 0.00 |
| ATOM | 4948 | CA | GLN | 1234 | 30.182 | −14.723 | 25.713 | 1.00 | 6.24 |
| ATOM | 4949 | CB | GLN | 1234 | 30.769 | −13.507 | 24.949 | 1.00 | 6.13 |
| ATOM | 4950 | CG | GLN | 1234 | 31.525 | −13.836 | 23.664 | 1.00 | 7.76 |
| ATOM | 4951 | CD | GLN | 1234 | 31.929 | −12.648 | 22.780 | 1.00 | 12.06 |
| ATOM | 4952 | OE1 | GLN | 1234 | 31.120 | −11.778 | 22.460 | 1.00 | 11.95 |
| ATOM | 4953 | NE2 | GLN | 1234 | 33.160 | −12.557 | 22.297 | 1.00 | 8.30 |
| ATOM | 4954 | HE21 | GLN | 1234 | 33.803 | −13.271 | 22.504 | 1.00 | 0.00 |
| ATOM | 4955 | HE22 | GLN | 1234 | 33.377 | −11.805 | 21.722 | 1.00 | 0.00 |
| ATOM | 4956 | C | GLN | 1234 | 30.026 | −14.340 | 27.182 | 1.00 | 5.81 |
| ATOM | 4957 | O | GLN | 1234 | 30.995 | −14.494 | 27.937 | 1.00 | 7.22 |
| ATOM | 4958 | N | LEU | 1235 | 28.850 | −13.859 | 27.606 | 1.00 | 4.55 |
| ATOM | 4959 | H | LEU | 1235 | 28.120 | −13.713 | 26.974 | 1.00 | 0.00 |
| ATOM | 4960 | CA | LEU | 1235 | 28.497 | −13.569 | 28.994 | 1.00 | 8.63 |
| ATOM | 4961 | CB | LEU | 1235 | 27.231 | −12.857 | 29.140 | 1.00 | 9.71 |
| ATOM | 4962 | CG | LEU | 1235 | 26.722 | −12.482 | 30.569 | 1.00 | 7.20 |
| ATOM | 4963 | CD1 | LEU | 1235 | 25.924 | −11.192 | 30.485 | 1.00 | 2.81 |
| ATOM | 4964 | CD2 | LEU | 1235 | 25.848 | −13.594 | 31.163 | 1.00 | 6.19 |
| ATOM | 4965 | C | LEU | 1235 | 28.625 | −14.879 | 29.772 | 1.00 | 9.27 |
| ATOM | 4966 | O | LEU | 1235 | 29.360 | −14.988 | 30.753 | 1.00 | 10.18 |
| ATOM | 4967 | N | VAL | 1236 | 27.889 | −15.910 | 29.353 | 1.00 | 12.76 |
| ATOM | 4968 | H | VAL | 1236 | 27.318 | −15.788 | 28.566 | 1.00 | 0.00 |
| ATOM | 4969 | CA | VAL | 1236 | 27.901 | −17.188 | 30.044 | 1.00 | 11.18 |
| ATOM | 4970 | CB | VAL | 1236 | 26.875 | −18.083 | 29.370 | 1.00 | 6.81 |
| ATOM | 4971 | CG1 | VAL | 1236 | 27.052 | −19.548 | 29.745 | 1.00 | 4.71 |
| ATOM | 4972 | CG2 | VAL | 1236 | 25.526 | −17.624 | 29.837 | 1.00 | 2.00 |
| ATOM | 4973 | C | VAL | 1236 | 29.293 | −17.815 | 30.042 | 1.00 | 12.39 |
| ATOM | 4974 | O | VAL | 1236 | 29.800 | −18.173 | 31.112 | 1.00 | 16.48 |
| ATOM | 4975 | N | GLU | 1237 | 29.966 | −17.869 | 28.888 | 1.00 | 7.45 |
| ATOM | 4976 | H | GLU | 1237 | 29.542 | −17.501 | 28.083 | 1.00 | 0.00 |
| ATOM | 4977 | CA | GLU | 1237 | 31.285 | −18.450 | 28.794 | 1.00 | 5.69 |
| ATOM | 4978 | CB | GLU | 1237 | 31.731 | −18.299 | 27.366 | 1.00 | 12.37 |
| ATOM | 4979 | CG | GLU | 1237 | 32.556 | −19.469 | 26.872 | 1.00 | 21.76 |
| ATOM | 4980 | CD | GLU | 1237 | 31.960 | −20.854 | 27.108 | 1.00 | 21.61 |

TABLE 23-continued

Coordinates for the 3D structure of ZAP-NC:ζ1 "dimer" structure
(two molecules of complex per unit cell)*

| ATOM | 4981 | OE1 | GLU | 1237 | 32.730 | −21.731 | 27.468 | 1.00 | 29.48 |
|---|---|---|---|---|---|---|---|---|---|
| ATOM | 4982 | OE2 | GLU | 1237 | 30.754 | −21.067 | 26.960 | 1.00 | 24.95 |
| ATOM | 4983 | C | GLU | 1237 | 32.303 | −17.857 | 29.750 | 1.00 | 9.53 |
| ATOM | 4984 | O | GLU | 1237 | 33.099 | −18.560 | 30.379 | 1.00 | 8.53 |
| ATOM | 4985 | N | TYR | 1238 | 32.261 | −16.545 | 29.937 | 1.00 | 11.77 |
| ATOM | 4986 | H | TYR | 1238 | 31.610 | −16.008 | 29.438 | 1.00 | 0.00 |
| ATOM | 4987 | CA | TYR | 1238 | 33.181 | −15.884 | 30.855 | 1.00 | 12.69 |
| ATOM | 4988 | CB | TYR | 1238 | 33.102 | −14.389 | 30.537 | 1.00 | 11.45 |
| ATOM | 4989 | CG | TYR | 1238 | 34.083 | −13.475 | 31.255 | 1.00 | 10.47 |
| ATOM | 4990 | CD1 | TYR | 1238 | 35.341 | −13.231 | 30.716 | 1.00 | 9.86 |
| ATOM | 4991 | CE1 | TYR | 1238 | 36.222 | −12.369 | 31.370 | 1.00 | 13.93 |
| ATOM | 4992 | CD2 | TYR | 1238 | 33.714 | −12.862 | 32.460 | 1.00 | 8.70 |
| ATOM | 4993 | CE2 | TYR | 1238 | 34.589 | −12.001 | 33.122 | 1.00 | 7.89 |
| ATOM | 4994 | CZ | TYR | 1238 | 25.840 | −11.757 | 32.571 | 1.00 | 11.90 |
| ATOM | 4995 | OH | TYR | 1238 | 36.698 | −10.874 | 33.204 | 1.00 | 16.71 |
| ATOM | 4996 | HH | TYR | 1238 | 37.612 | −11.155 | 33.062 | 1.00 | 0.00 |
| ATOM | 4997 | C | TYR | 1238 | 32.828 | −16.208 | 32.320 | 1.00 | 11.56 |
| ATOM | 4998 | O | TYR | 1238 | 33.719 | −16.478 | 33.140 | 1.00 | 13.31 |
| ATOM | 4999 | N | LEU | 1239 | 31.544 | −16.300 | 32.689 | 1.00 | 10.97 |
| ATOM | 5000 | H | LEU | 1239 | 30.845 | −16.189 | 32.007 | 1.00 | 0.00 |
| ATOM | 5001 | CA | LEU | 1239 | 31.164 | −16.540 | 34.075 | 1.00 | 7.36 |
| ATOM | 5002 | CB | LEU | 1239 | 29.747 | −16.092 | 34.317 | 1.00 | 5.23 |
| ATOM | 5003 | CG | LEU | 1239 | 29.391 | −14.668 | 33.989 | 1.00 | 9.04 |
| ATOM | 5004 | CD1 | LEU | 1239 | 27.892 | −14.500 | 34.192 | 1.00 | 7.48 |
| ATOM | 5005 | CD2 | LEU | 1239 | 30.230 | −13.709 | 34.820 | 1.00 | 9.75 |
| ATOM | 5006 | C | LEU | 1239 | 31.285 | −17.990 | 34.484 | 1.00 | 6.04 |
| ATOM | 5007 | O | LEU | 1239 | 31.016 | −18.368 | 35.620 | 1.00 | 9.78 |
| ATOM | 5008 | N | LYS | 1240 | 31.625 | −18.847 | 33.532 | 1.00 | 10.64 |
| ATOM | 5009 | H | LYS | 1240 | 31.561 | −18.558 | 32.596 | 1.00 | 0.00 |
| ATOM | 5010 | CA | LYS | 1240 | 31.970 | −20.225 | 33.816 | 1.00 | 9.28 |
| ATOM | 5011 | CB | LYS | 1240 | 31.917 | −21.088 | 32.558 | 1.00 | 3.87 |
| ATOM | 5012 | CG | LYS | 1240 | 30.545 | −21.458 | 32.032 | 1.00 | 4.02 |
| ATOM | 5013 | CD | LYS | 1240 | 30.731 | −22.176 | 30.691 | 1.00 | 8.38 |
| ATOM | 5014 | CE | LYS | 1240 | 29.404 | −22.644 | 30.101 | 1.00 | 11.25 |
| ATOM | 5015 | NZ | LYS | 1240 | 29.581 | −23.179 | 28.763 | 1.00 | 17.56 |
| ATOM | 5016 | HZ1 | LYS | 1240 | 30.253 | −23.972 | 28.793 | 1.00 | 0.00 |
| ATOM | 5017 | HZ2 | LYS | 1240 | 29.957 | −22.435 | 28.144 | 1.00 | 0.00 |
| ATOM | 5018 | HZ3 | LYS | 1240 | 28.667 | −23.511 | 28.392 | 1.00 | 0.00 |
| ATOM | 5019 | C | LYS | 1240 | 33.399 | −20.241 | 34.343 | 1.00 | 14.71 |
| ATOM | 5020 | O | LYS | 1240 | 33.787 | −21.138 | 35.094 | 1.00 | 21.55 |
| ATOM | 5021 | N | LEU | 1241 | 34.217 | −19.259 | 33.962 | 1.00 | 13.94 |
| ATOM | 5022 | H | LEU | 1241 | 33.862 | −18.519 | 33.428 | 1.00 | 0.00 |
| ATOM | 5023 | CA | LEU | 1241 | 35.600 | −19.248 | 34.355 | 1.00 | 14.58 |
| ATOM | 5024 | CB | LEU | 1241 | 36.457 | −18.634 | 33.282 | 1.00 | 22.23 |
| ATOM | 5025 | CG | LEU | 1241 | 36.223 | −18.933 | 31.805 | 1.00 | 31.30 |
| ATOM | 5026 | CD1 | LEU | 1241 | 37.045 | −17.959 | 30.950 | 1.00 | 30.14 |
| ATOM | 5027 | CD2 | LEU | 1241 | 36.540 | −20.398 | 31.541 | 1.00 | 28.41 |
| ATOM | 5028 | C | LEU | 1241 | 35.805 | −18.442 | 35.625 | 1.00 | 18.17 |
| ATOM | 5029 | O | LEU | 1241 | 36.656 | −18.766 | 36.475 | 1.00 | 19.31 |
| ATOM | 5030 | N | LYS | 1242 | 35.110 | −17.310 | 35.729 | 1.00 | 18.53 |
| ATOM | 5031 | H | LYS | 1242 | 34.467 | −17.041 | 35.035 | 1.00 | 0.00 |
| ATOM | 5032 | CA | LYS | 1242 | 35.258 | −16.445 | 36.891 | 1.00 | 18.29 |
| ATOM | 5033 | CB | LYS | 1242 | 36.053 | −15.163 | 36.596 | 1.00 | 17.78 |
| ATOM | 5034 | CG | LYS | 1242 | 37.404 | −15.288 | 35.877 | 1.00 | 20.93 |
| ATOM | 5035 | CD | LYS | 1242 | 37.182 | −15.155 | 34.356 | 1.00 | 26.47 |
| ATOM | 5036 | CE | LYS | 1242 | 29.487 | −15.277 | 33.558 | 1.00 | 28.84 |
| ATOM | 5037 | NZ | LYS | 1242 | 39.399 | −14.166 | 33.786 | 1.00 | 31.56 |
| ATOM | 5038 | HZ1 | LYS | 1242 | 39.650 | −14.113 | 34.794 | 1.00 | 0.00 |
| ATOM | 5039 | HZ2 | LYS | 1242 | 28.931 | −13.284 | 33.496 | 1.00 | 0.00 |
| ATOM | 5040 | HZ3 | LYS | 1242 | 40.258 | −14.304 | 33.217 | 1.00 | 0.00 |
| ATOM | 5041 | C | LYS | 1242 | 33.857 | −16.045 | 37.277 | 1.00 | 14.54 |
| ATOM | 5042 | O | LYS | 1242 | 33.082 | −15.650 | 36.417 | 1.00 | 14.69 |
| ATOM | 5043 | N | ALA | 1243 | 33.500 | −16.159 | 38.560 | 1.00 | 16.03 |
| ATOM | 5044 | H | ALA | 1243 | 34.150 | −16.545 | 39.191 | 1.00 | 0.00 |
| ATOM | 5045 | CA | ALA | 1243 | 32.167 | −15.817 | 39.016 | 1.00 | 10.30 |
| ATOM | 5046 | CB | ALA | 1243 | 32.003 | −16.130 | 40.481 | 1.00 | 10.45 |
| ATOM | 5047 | C | ALA | 1243 | 31.876 | −14.351 | 38.822 | 1.00 | 11.11 |
| ATOM | 5048 | O | ALA | 1243 | 30.729 | −13.955 | 38.615 | 1.00 | 18.39 |
| ATOM | 5049 | N | ASP | 1244 | 32.901 | −13.511 | 38.964 | 1.00 | 13.67 |
| ATOM | 5050 | H | ASP | 1244 | 33.748 | −13.880 | 39.280 | 1.00 | 0.00 |
| ATOM | 5051 | CA | ASP | 1244 | 32.808 | −12.097 | 38.658 | 1.00 | 12.02 |
| ATOM | 5052 | CB | ASP | 1244 | 32.796 | −12.085 | 37.119 | 1.00 | 17.69 |
| ATOM | 5053 | CG | ASP | 1244 | 32.971 | −10.744 | 36.408 | 1.00 | 21.88 |
| ATOM | 5054 | OD1 | ASP | 1244 | 32.043 | −10.598 | 35.445 | 1.00 | 22.59 |
| ATOM | 5055 | OD2 | ASP | 1244 | 33.537 | −9.863 | 36.812 | 1.00 | 16.27 |
| ATOM | 5056 | C | ASP | 1244 | 31.633 | −11.379 | 39.334 | 1.00 | 11.11 |

TABLE 23-continued

Coordinates for the 3D structure of ZAP-NC:ζ1 "dimer" structure
(two molecules of complex per unit cell)*

| ATOM | 5057 | O | ASP | 1244 | 30.905 | −10.591 | 38.733 | 1.00 | 12.88 |
|---|---|---|---|---|---|---|---|---|---|
| ATOM | 5058 | N | GLY | 1245 | 31.431 | −11.645 | 40.623 | 1.00 | 11.66 |
| ATOM | 5059 | H | GLY | 1245 | 32.035 | −12.271 | 41.067 | 1.00 | 0.00 |
| ATOM | 5060 | CA | GLY | 1245 | 30.360 | −11.047 | 41.394 | 1.00 | 4.05 |
| ATOM | 5061 | C | GLY | 1245 | 29.186 | −11.970 | 41.654 | 1.00 | 6.06 |
| ATOM | 5062 | O | GLY | 1245 | 28.328 | −11.641 | 42.478 | 1.00 | 4.56 |
| ATOM | 5063 | N | LEU | 1246 | 29.027 | −13.078 | 40.924 | 1.00 | 6.26 |
| ATOM | 5064 | H | LEU | 1246 | 29.670 | −13.274 | 40.209 | 1.00 | 0.00 |
| ATOM | 5065 | CA | LEU | 1246 | 27.937 | −14.037 | 41.135 | 1.00 | 8.93 |
| ATOM | 5066 | CB | LEU | 1246 | 27.839 | −15.104 | 10.067 | 1.00 | 5.31 |
| ATOM | 5067 | CG | LEU | 1246 | 27.674 | −14.752 | 38.606 | 1.00 | 5.46 |
| ATOM | 5068 | CD1 | LEU | 1246 | 27.924 | −16.009 | 37.796 | 1.00 | 2.14 |
| ATOM | 5069 | CD2 | LEU | 1246 | 26.331 | −14.139 | 38.380 | 1.00 | 2.00 |
| ATOM | 5070 | C | LEU | 1246 | 28.187 | −14.819 | 42.407 | 1.00 | 11.01 |
| ATOM | 5071 | O | LEU | 1246 | 29.351 | −14.975 | 42.786 | 1.00 | 13.17 |
| ATOM | 5072 | N | ILE | 1247 | 27.168 | −15.397 | 43.047 | 1.00 | 11.83 |
| ATOM | 5073 | H | ILE | 1247 | 26.238 | −15.238 | 42.765 | 1.00 | 0.00 |
| ATOM | 5074 | CA | ILE | 1247 | 27.448 | −16.185 | 44.231 | 1.00 | 12.55 |
| ATOM | 5075 | CB | ILE | 1247 | 26.078 | −16.432 | 44.900 | 1.00 | 11.32 |
| ATOM | 5076 | CG2 | ILE | 1247 | 25.248 | −17.439 | 44.094 | 1.00 | 11.69 |
| ATOM | 5077 | CG1 | ILE | 1247 | 26.338 | −16.845 | 46.362 | 1.00 | 4.92 |
| ATOM | 5078 | CD | ILE | 1247 | 25.094 | −16.664 | 47.211 | 1.00 | 2.58 |
| ATOM | 5079 | C | ILE | 1247 | 28.257 | −17.473 | 43.954 | 1.00 | 16.34 |
| ATOM | 5080 | O | ILE | 1247 | 28.841 | −18.047 | 44.880 | 1.00 | 13.40 |
| ATOM | 5081 | N | TYR | 1248 | 28.363 | −17.894 | 42.676 | 1.00 | 15.02 |
| ATOM | 5082 | H | TYR | 1248 | 27.947 | −17.387 | 41.950 | 1.00 | 0.00 |
| ATOM | 5083 | CA | TYR | 1248 | 29.092 | −19.088 | 42.274 | 1.00 | 12.39 |
| ATOM | 5084 | CB | TYR | 1248 | 28.289 | −20.366 | 42.625 | 1.00 | 9.23 |
| ATOM | 5085 | CG | TYR | 1248 | 29.191 | −21.564 | 42.880 | 1.00 | 8.97 |
| ATOM | 5086 | CD1 | TYR | 1248 | 29.429 | −22.516 | 41.885 | 1.00 | 10.00 |
| ATOM | 5087 | CE1 | TYR | 1248 | 30.306 | −23.572 | 42.130 | 1.00 | 8.55 |
| ATOM | 5088 | CD2 | TYR | 1248 | 29.824 | −21.676 | 44.119 | 1.00 | 9.95 |
| ATOM | 5089 | CE2 | TYR | 1248 | 30.701 | −22.732 | 44.368 | 1.00 | 6.09 |
| ATOM | 5090 | OH | TYR | 1248 | 30.935 | −23.669 | 43.374 | 1.00 | 3.83 |
| ATOM | 5091 | HH | TYR | 1248 | 31.815 | −24.695 | 43.637 | 1.00 | 12.23 |
| ATOM | 5092 | HH | TYR | 1248 | 31.879 | −25.262 | 42.861 | 1.00 | 0.00 |
| ATOM | 5093 | C | TYR | 1248 | 29.277 | −19.017 | 40.768 | 1.00 | 11.96 |
| ATOM | 5094 | O | CYS | 1249 | 28.492 | −18.350 | 40.093 | 1.00 | 10.19 |
| ATOM | 5095 | N | CYS | 1249 | 30.301 | −19.689 | 40.247 | 1.00 | 12.38 |
| ATOM | 5096 | H | CYS | 1249 | 30.939 | −20.117 | 40.855 | 1.00 | 0.00 |
| ATOM | 5097 | CA | CYS | 1249 | 30.535 | −19.856 | 38.815 | 1.00 | 17.03 |
| ATOM | 5098 | CB | CYS | 1249 | 31.812 | −20.599 | 38.512 | 1.00 | 14.50 |
| ATOM | 5099 | SG | CYS | 1249 | 33.232 | −19.521 | 38.611 | 1.00 | 29.55 |
| ATOM | 5100 | C | CYS | 1249 | 29.460 | −20.670 | 38.127 | 1.00 | 14.34 |
| ATOM | 5101 | O | CYS | 1249 | 28.821 | −21.562 | 38.699 | 1.00 | 15.48 |
| ATOM | 5102 | N | LEU | 1250 | 29.284 | −20.385 | 36.853 | 1.00 | 13.47 |
| ATOM | 5103 | H | LEU | 1250 | 29.860 | −19.715 | 36.427 | 1.00 | 0.00 |
| ATOM | 5104 | CA | LEU | 1250 | 28.363 | −21.157 | 36.061 | 1.00 | 14.95 |
| ATOM | 5105 | CB | LEU | 1250 | 28.039 | −20.406 | 34.787 | 1.00 | 7.93 |
| ATOM | 5106 | CG | LEU | 1250 | 27.434 | −19.026 | 34.950 | 1.00 | 3.87 |
| ATOM | 5107 | CD1 | LEU | 1250 | 26.912 | −18.579 | 33.605 | 1.00 | 2.00 |
| ATOM | 5108 | CD2 | LEU | 1250 | 26.318 | −19.043 | 35.979 | 1.00 | 8.53 |
| ATOM | 5109 | C | LEU | 1250 | 29.134 | −22.439 | 35.790 | 1.00 | 15.93 |
| ATOM | 5110 | O | LEU | 1250 | 30.301 | −22.424 | 35.407 | 1.00 | 19.86 |
| ATOM | 5111 | N | LYS | 1251 | 28.504 | −23.545 | 36.126 | 1.00 | 17.94 |
| ATOM | 5112 | H | LYS | 1251 | 27.570 | −23.472 | 36.389 | 1.00 | 0.00 |
| ATOM | 5113 | CA | LYS | 1251 | 29.104 | −24.851 | 36.032 | 1.00 | 21.49 |
| ATOM | 5114 | CB | LYS | 1251 | 29.070 | −25.527 | 37.415 | 1.00 | 19.69 |
| ATOM | 5115 | CG | LYS | 1251 | 30.428 | −25.703 | 38.058 | 1.00 | 24.61 |
| ATOM | 5116 | CD | LYS | 1251 | 31.108 | −24.378 | 38.326 | 1.00 | 26.63 |
| ATOM | 5117 | CE | LYS | 1251 | 32.563 | −24.607 | 38.683 | 1.00 | 32.65 |
| ATOM | 5118 | NZ | LYS | 1251 | 32.687 | −25.364 | 39.912 | 1.00 | 38.55 |
| ATOM | 5119 | HZ1 | LYS | 1251 | 32.281 | −26.314 | 39.795 | 1.00 | 0.00 |
| ATOM | 5120 | HZ2 | LYS | 1251 | 32.183 | −24.861 | 40.672 | 1.00 | 0.00 |
| ATOM | 5121 | HZ3 | LYS | 1251 | 33.695 | −25.446 | 40.160 | 1.00 | 0.00 |
| ATOM | 5122 | C | LYS | 1251 | 28.355 | −25.684 | 35.012 | 1.00 | 21.80 |
| ATOM | 5123 | O | LYS | 1251 | 28.712 | −25.723 | 33.829 | 1.00 | 26.89 |
| ATOM | 5124 | N | GLU | 1252 | 27.241 | −26.266 | 35.447 | 1.00 | 18.32 |
| ATOM | 5125 | H | GLU | 1252 | 26.845 | −25.961 | 36.290 | 1.00 | 0.00 |
| ATOM | 5126 | CA | GLU | 1252 | 26.502 | −27.236 | 34.685 | 1.00 | 16.59 |
| ATOM | 5127 | CB | GLU | 1252 | 26.147 | −28.341 | 35.653 | 1.00 | 24.16 |
| ATOM | 5128 | CG | GLU | 1252 | 25.066 | −29.361 | 35.347 | 1.00 | 37.83 |
| ATOM | 5129 | CD | GLU | 1252 | 24.682 | −30.193 | 36.571 | 1.00 | 46.82 |
| ATOM | 5130 | OE1 | GLU | 1252 | 25.571 | −30.646 | 37.298 | 1.00 | 52.14 |
| ATOM | 5131 | OE2 | GLU | 1252 | 23.487 | −30.392 | 36.804 | 1.00 | 53.93 |
| ATOM | 5132 | C | GLU | 1252 | 25.294 | −26.579 | 34.093 | 1.00 | 15.45 |

TABLE 23-continued

Coordinates for the 3D structure of ZAP-NC:ζ1 "dimer" structure
(two molecules of complex per unit cell)*

| ATOM | 5133 | O    | GLU | 1252 | 24.542 | −25.938 | 34.821 | 1.00 | 12.45 |
|------|------|------|-----|------|--------|---------|--------|------|-------|
| ATOM | 5134 | N    | ALA | 1253 | 25.134 | −26.714 | 32.776 | 1.00 | 15.62 |
| ATOM | 5135 | H    | ALA | 1253 | 25.821 | −27.186 | 32.272 | 1.00 | 0.00  |
| ATOM | 5136 | CA   | ALA | 1253 | 23.974 | −26.228 | 32.050 | 1.00 | 12.65 |
| ATOM | 5137 | CB   | ALA | 1253 | 24.130 | −26.360 | 30.548 | 1.00 | 5.87  |
| ATOM | 5138 | C    | ALA | 1253 | 22.785 | −27.080 | 32.420 | 1.00 | 14.00 |
| ATOM | 5139 | O    | ALA | 1253 | 22.886 | −28.304 | 32.502 | 1.00 | 17.74 |
| ATOM | 5140 | N    | CYS | 1254 | 21.668 | −26.433 | 32.709 | 1.00 | 16.80 |
| ATOM | 5141 | H    | CYS | 1254 | 21.680 | −25.457 | 32.687 | 1.00 | 0.0   |
| ATOM | 5142 | CA   | CYS | 1254 | 20.428 | −27.114 | 32.952 | 1.00 | 14.88 |
| ATOM | 5143 | CB   | CYS | 1254 | 19.533 | −26.275 | 33.838 | 1.00 | 7.31  |
| ATOM | 5144 | SG   | CYS | 1254 | 17.934 | −27.060 | 34.181 | 1.00 | 11.48 |
| ATOM | 5145 | C    | CYS | 1254 | 19.843 | −27.234 | 31.545 | 1.00 | 19.32 |
| ATOM | 5146 | O    | CYS | 1254 | 19.494 | −26.207 | 30.956 | 1.00 | 20.54 |
| ATOM | 5147 | N    | PRO | 1255 | 19.737 | −28.427 | 30.937 | 1.00 | 24.66 |
| ATOM | 5148 | CD   | PRO | 1255 | 19.747 | −29.716 | 31.620 | 1.00 | 23.90 |
| ATOM | 5149 | CA   | PRO | 1255 | 19.454 | −28.617 | 29.552 | 1.00 | 25.94 |
| ATOM | 5150 | CB   | PRO | 1255 | 19.916 | −30.024 | 29.277 | 1.00 | 25.59 |
| ATOM | 5151 | CG   | PRO | 1255 | 19.392 | −30.703 | 30.520 | 1.00 | 25.86 |
| ATOM | 5152 | C    | PRO | 1255 | 17.998 | −28.370 | 29.178 | 1.00 | 27.93 |
| ATOM | 5153 | O    | PRO | 1255 | 17.101 | −28.478 | 30.031 | 1.00 | 28.94 |
| ATOM | 5154 | N    | ASN | 1256 | 17.819 | −27.884 | 27.961 | 1.00 | 33.02 |
| ATOM | 5155 | H    | ASN | 1256 | 18.564 | −27.819 | 27.329 | 1.00 | 0.00  |
| ATOM | 5156 | CA   | ASN | 1256 | 16.494 | −27.679 | 27.418 | 1.00 | 36.15 |
| ATOM | 5157 | CB   | ASN | 1256 | 16.500 | −26.480 | 26.412 | 1.00 | 40.46 |
| ATOM | 5158 | CG   | ASN | 1256 | 17.538 | −26.371 | 25.280 | 1.00 | 43.38 |
| ATOM | 5159 | OD1  | ASN | 1256 | 18.465 | −27.162 | 25.085 | 1.00 | 49.15 |
| ATOM | 5160 | ND2  | ASN | 1256 | 17.492 | −25.289 | 24.509 | 1.00 | 47.41 |
| ATOM | 5161 | HD21 | ASN | 1256 | 16.828 | −24.602 | 24.706 | 1.00 | 0.00  |
| ATOM | 5162 | HD22 | ASN | 1256 | 18.165 | −25.229 | 23.805 | 1.00 | 0.00  |
| ATOM | 5163 | C    | ASN | 1256 | 16.026 | −28.969 | 26.747 | 1.00 | 37.74 |
| ATOM | 5164 | O    | ASN | 1256 | 14.817 | −29.127 | 26.588 | 1.00 | 40.27 |
| ATOM | 5165 | OT   | ASN | 1301 | 16.858 | −29.832 | 26.440 | 1.00 | 37.85 |
| ATOM | 5166 | CB   | ASN | 1301 | 9.323  | −7.474  | 39.011 | 1.00 | 72.83 |
| ATOM | 5167 | CG   | ASN | 1301 | 8.164  | −8.460  | 38.892 | 1.00 | 75.21 |
| ATOM | 5168 | OD1  | ASN | 1301 | 8.313  | −9.453  | 38.175 | 1.00 | 77.67 |
| ATOM | 5169 | ND2  | ASN | 1301 | 7.018  | −8.265  | 39.523 | 1.00 | 73.86 |
| ATOM | 5170 | HD21 | ASN | 1301 | 6.864  | −7.453  | 40.049 | 1.00 | 0.00  |
| ATOM | 5171 | HD22 | ASN | 1301 | 6.359  | −8.991  | 39.479 | 1.00 | 0.00  |
| ATOM | 5172 | C    | ASN | 1301 | 10.948 | −9.156  | 40.037 | 1.00 | 69.93 |
| ATOM | 5173 | O    | ASN | 1301 | 44.680 | −10.106 | 39.750 | 1.00 | 71.07 |
| ATOM | 5174 | HT1  | ASN | 1301 | 10.055 | −9.516  | 37.599 | 1.00 | 0.00  |
| ATOM | 5175 | HD2  | ASN | 1301 | 11.673 | −9.582  | 37.951 | 1.00 | 0.00  |
| ATOM | 5176 | N    | ASN | 1301 | 10.898 | −8.913  | 37.721 | 1.00 | 71.59 |
| ATOM | 5177 | HT3  | ASN | 1301 | 11.124 | −8.372  | 36.873 | 1.00 | 0.00  |
| ATOM | 5178 | CA   | ASN | 1301 | 10.741 | −8.118  | 38.933 | 1.00 | 71.90 |
| ATOM | 5179 | N    | GLN | 1302 | 10.329 | −9.121  | 41.226 | 1.00 | 66.66 |
| ATOM | 5180 | H    | GLN | 1302 | 9.648  | −8.440  | 41.394 | 1.00 | 0.00  |
| ATOM | 5181 | CA   | GLN | 1302 | 10.612 | −10.013 | 42.356 | 1.00 | 61.49 |
| ATOM | 5182 | CB   | GLN | 1302 | 10.414 | −11.513 | 41.988 | 1.00 | 62.07 |
| ATOM | 5183 | CG   | GLN | 1302 | 9.203  | −11.902 | 41.135 | 1.00 | 62.59 |
| ATOM | 5184 | CD   | GLN | 1302 | 7.876  | −11.373 | 41.651 | 1.00 | 64.61 |
| ATOM | 5185 | OE1  | GLN | 1302 | 7.588  | −10.173 | 41.632 | 1.00 | 60.30 |
| ATOM | 5186 | NE2  | GLN | 1302 | 7.015  | −12.263 | 42.117 | 1.00 | 66.75 |
| ATOM | 5187 | HE21 | GLN | 1302 | 7.256  | −13.211 | 42.101 | 1.00 | 0.00  |
| ATOM | 5188 | HE22 | GLN | 1302 | 6.171  | −11.916 | 42.471 | 1.00 | 0.00  |
| ATOM | 5189 | C    | GLN | 1302 | 12.043 | −9.756  | 42.803 | 1.00 | 56.80 |
| ATOM | 5190 | O    | GLN | 1302 | 12.552 | −8.645  | 42.573 | 1.00 | 58.90 |
| ATOM | 5191 | N    | LEU | 1303 | 12.761 | −10.678 | 43.432 | 1.00 | 49.38 |
| ATOM | 5192 | H    | LEU | 1303 | 12.476 | −11.612 | 43.456 | 1.00 | 0.00  |
| ATOM | 5193 | CA   | LEU | 1303 | 14.082 | −10.350 | 43.932 | 1.00 | 43.43 |
| ATOM | 5194 | CB   | LEU | 1303 | 14.394 | −11.073 | 45.273 | 1.00 | 51.18 |
| ATOM | 5195 | CG   | LEU | 1303 | 13.555 | −11.102 | 46.592 | 1.00 | 54.39 |
| ATOM | 5196 | CD1  | LEU | 1303 | 13.147 | −9.676  | 46.963 | 1.00 | 55.27 |
| ATOM | 5197 | CD2  | LEU | 1303 | 12.345 | −12.030 | 46.439 | 1.00 | 52.47 |
| ATOM | 5198 | C    | LEU | 1303 | 15.145 | −10.760 | 42.930 | 1.00 | 35.27 |
| ATOM | 5199 | O    | LEU | 1303 | 15.238 | −11.950 | 42.605 | 1.00 | 32.58 |
| ATOM | 5200 | N    | PTY | 1304 | 15.912 | −9.820  | 42.382 | 1.00 | 27.69 |
| ATOM | 5201 | H    | PTY | 1304 | 15.739 | −8.867  | 42.521 | 1.00 | 0.00  |
| ATOM | 5202 | CA   | PTY | 1304 | 17.072 | −10.190 | 41.594 | 1.00 | 21.92 |
| ATOM | 5203 | CB   | PTY | 1304 | 17.224 | −9.402  | 40.276 | 1.00 | 20.89 |
| ATOM | 5204 | CG   | PTY | 1304 | 16.247 | −9.844  | 39.214 | 1.00 | 15.14 |
| ATOM | 5205 | CD1  | PTY | 1304 | 16.425 | −11.042 | 28.469 | 1.00 | 9.03  |
| ATOM | 5206 | CE1  | PTY | 1304 | 15.461 | −11.487 | 37.558 | 1.00 | 7.86  |
| ATOM | 5207 | CD2  | PTY | 1304 | 15.081 | −9.117  | 38.994 | 1.00 | 14.16 |
| ATOM | 5208 | CE2  | PTY | 1304 | 14.127 | −9.556  | 38.083 | 1.00 | 16.68 |

TABLE 23-continued

Coordinates for the 3D structure of ZAP-NC:ζ1 "dimer" structure
(two molecules of complex per unit cell)*

| ATOM | 5209 | CZ | PTY | 1304 | 14.290 | −10.742 | 37.368 | 1.00 | 12.39 |
|---|---|---|---|---|---|---|---|---|---|
| ATOM | 5210 | OH | PTY | 1304 | 13.224 | −11.076 | 36.557 | 1.00 | 13.70 |
| ATOM | 5211 | OR1 | PTY | 1304 | 11.117 | −11.770 | 37.454 | 1.00 | 13.77 |
| ATOM | 5212 | OR2 | PTY | 1304 | 12.831 | −13.521 | 37.365 | 1.00 | 17.79 |
| ATOM | 5213 | OR3 | PTY | 1304 | 11.748 | −12.738 | 35.436 | 1.00 | 12.59 |
| ATOM | 5214 | PR | PTY | 1304 | 12.271 | −12.339 | 36.718 | 1.00 | 16.46 |
| ATOM | 5215 | C | PTY | 1304 | 18.265 | −9.885 | 42.458 | 1.00 | 17.57 |
| ATOM | 5216 | O | PTY | 1304 | 18.382 | −8.871 | 43.148 | 1.00 | 20.06 |
| ATOM | 5217 | N | ASN | 1305 | 19.163 | −10.830 | 42.439 | 1.00 | 11.57 |
| ATOM | 5218 | H | ASN | 1305 | 19.013 | −11.584 | 41.839 | 1.00 | 0.00 |
| ATOM | 5219 | CA | ASN | 1305 | 20.348 | −10.769 | 43.231 | 1.00 | 10.89 |
| ATOM | 5220 | CB | ASN | 1305 | 20.897 | −12.206 | 43.301 | 1.00 | 9.69 |
| ATOM | 5221 | CG | ASN | 1305 | 19.929 | −13.128 | 44.046 | 1.00 | 12.13 |
| ATOM | 5222 | OD1 | ASN | 1305 | 19.026 | −13.796 | 43.514 | 1.00 | 8.54 |
| ATOM | 5223 | ND2 | ASN | 1305 | 20.109 | −13.180 | 45.355 | 1.00 | 20.02 |
| ATOM | 5224 | HD21 | ASN | 1305 | 20.850 | −12.685 | 45.758 | 1.00 | 0.00 |
| ATOM | 5225 | HD22 | ASN | 1305 | 19.470 | −13.717 | 45.882 | 1.00 | 0.00 |
| ATOM | 5226 | C | ASN | 1305 | 21.314 | −9.761 | 42.640 | 1.00 | 13.84 |
| ATOM | 5227 | O | ASN | 1305 | 21.316 | −9.521 | 41.431 | 1.00 | 14.72 |
| ATOM | 5228 | N | GLU | 1306 | 22.119 | −9.125 | 43.500 | 1.00 | 17.11 |
| ATOM | 5229 | H | GLU | 1306 | 22.146 | −9.423 | 44.427 | 1.00 | 0.00 |
| ATOM | 5230 | CA | GLU | 1306 | 23.059 | −8.084 | 43.133 | 1.00 | 15.21 |
| ATOM | 5231 | CB | GLU | 1306 | 23.022 | −7.000 | 44.220 | 1.00 | 20.16 |
| ATOM | 5232 | CG | GLU | 1306 | 23.202 | −5.502 | 43.874 | 1.00 | 35.24 |
| ATOM | 5233 | CD | GLU | 1306 | 24.611 | −4.903 | 43.721 | 1.00 | 40.84 |
| ATOM | 5234 | OE1 | GLU | 1306 | 24.823 | −4.103 | 42.797 | 1.00 | 43.49 |
| ATOM | 5235 | OE2 | GLU | 1306 | 25.484 | −5.205 | 44.539 | 1.00 | 37.95 |
| ATOM | 5236 | C | GLU | 1306 | 24.401 | −8.777 | 43.086 | 1.00 | 13.63 |
| ATOM | 5237 | O | GLU | 1306 | 24.599 | −9.803 | 43.747 | 1.00 | 14.90 |
| ATOM | 5238 | N | LEU | 1307 | 25.352 | −8.248 | 42.332 | 1.00 | 11.69 |
| ATOM | 5239 | H | LEU | 1307 | 25.164 | −7.407 | 41.864 | 1.00 | 0.00 |
| ATOM | 5240 | CA | LEU | 1307 | 26.670 | −8.833 | 42.280 | 1.00 | 11.19 |
| ATOM | 5241 | CB | LEU | 1307 | 27.404 | −8.414 | 40.995 | 1.00 | 10.57 |
| ATOM | 5242 | CG | LEU | 1307 | 26.812 | −8.812 | 39.637 | 1.00 | 11.70 |
| ATOM | 5243 | CD1 | LEU | 1307 | 27.636 | −8.170 | 38.547 | 1.00 | 7.23 |
| ATOM | 5244 | CD2 | LEU | 1307 | 26.848 | −10.319 | 39.429 | 1.00 | 3.92 |
| ATOM | 5245 | C | LEU | 1307 | 27.492 | −8.390 | 43.481 | 1.00 | 12.34 |
| ATOM | 5246 | O | LEU | 1307 | 27.324 | −7.310 | 44.041 | 1.00 | 8.93 |
| ATOM | 5247 | N | ASN | 1308 | 58.429 | −9.220 | 43.898 | 1.00 | 13.03 |
| ATOM | 5248 | H | ASN | 1308 | 28.504 | −10.085 | 43.458 | 1.00 | 0.00 |
| ATOM | 5249 | CA | ASN | 1308 | 29.361 | −8.907 | 44.955 | 1.00 | 14.89 |
| ATOM | 5250 | CB | ASN | 1308 | 29.793 | −10.191 | 45.614 | 1.00 | 14.55 |
| ATOM | 5251 | CG | ASN | 1308 | 30.548 | −10.004 | 46.911 | 1.00 | 16.39 |
| ATOM | 5252 | OD1 | ASN | 1308 | 31.546 | −9.285 | 46.976 | 1.00 | 17.52 |
| ATOM | 5253 | ND2 | ASN | 1308 | 30.128 | −10.694 | 47.966 | 1.00 | 16.30 |
| ATOM | 5254 | HD21 | ASN | 1308 | 29.391 | −11.337 | 47.816 | 1.00 | 0.00 |
| ATOM | 5255 | HD22 | ASN | 1308 | 30.558 | −10.549 | 48.836 | 1.00 | 0.00 |
| ATOM | 5256 | C | ASN | 1308 | 30.526 | −8.231 | 44.239 | 1.00 | 19.27 |
| ATOM | 5257 | O | ASN | 1308 | 31.398 | −8.849 | 43.604 | 1.00 | 16.77 |
| ATOM | 5258 | N | LEU | 1309 | 30.458 | −6.902 | 44.309 | 1.00 | 19.96 |
| ATOM | 5259 | H | LEU | 1309 | 29.675 | −6.517 | 44.757 | 1.00 | 0.00 |
| ATOM | 5260 | CA | LEU | 1309 | 31.392 | −5.992 | 43.662 | 1.00 | 18.16 |
| ATOM | 5261 | CB | LEU | 1309 | 30.962 | −4.545 | 43.948 | 1.00 | 14.91 |
| ATOM | 5262 | CG | LEU | 1309 | 29.980 | −3.827 | 43.984 | 1.00 | 20.31 |
| ATOM | 5263 | CD1 | LEU | 1309 | 28.777 | −4.662 | 42.645 | 1.00 | 20.12 |
| ATOM | 5264 | CD2 | LEU | 1309 | 29.492 | −2.563 | 43.662 | 1.00 | 22.61 |
| ATOM | 5265 | C | LEU | 1309 | 32.841 | −6.177 | 44.027 | 1.00 | 18.95 |
| ATOM | 5266 | O | LEU | 1309 | 33.700 | −5.840 | 43.220 | 1.00 | 19.70 |
| ATOM | 5267 | N | GLY | 1310 | 33.179 | −6.740 | 45.192 | 1.00 | 24.64 |
| ATOM | 5268 | H | GLY | 1310 | 32.490 | −7.028 | 45.825 | 1.00 | 0.00 |
| ATOM | 5269 | CA | GLY | 1310 | 34.577 | −7.013 | 45.518 | 1.00 | 21.96 |
| ATOM | 5270 | C | GLY | 1310 | 35.074 | −8.325 | 44.899 | 1.00 | 25.29 |
| ATOM | 5271 | O | GLY | 1310 | 36.249 | −8.662 | 45.035 | 1.00 | 25.13 |
| ATOM | 5272 | N | ARG | 1311 | 34.210 | −9.106 | 44.230 | 1.00 | 25.06 |
| ATOM | 5273 | H | ARG | 1311 | 33.270 | −8.844 | 44.178 | 1.00 | 0.00 |
| ATOM | 5274 | CA | ARG | 1311 | 34.616 | −10.357 | 43.608 | 1.00 | 28.30 |
| ATOM | 5275 | CB | ARG | 1311 | 33.672 | −11.452 | 44.107 | 1.00 | 34.71 |
| ATOM | 5276 | CG | ARG | 1311 | 34.141 | −12.201 | 45.357 | 1.00 | 39.05 |
| ATOM | 5277 | CD | ARG | 1311 | 35.342 | −13.058 | 44.978 | 1.00 | 48.06 |
| ATOM | 5278 | NE | ARG | 1311 | 35.599 | −14.117 | 45.937 | 1.00 | 55.93 |
| ATOM | 5279 | HE | ARG | 1311 | 34.910 | −14.798 | 46.082 | 1.00 | 0.00 |
| ATOM | 5280 | CZ | ARG | 1311 | 36.749 | −14.216 | 46.617 | 1.00 | 63.14 |
| ATOM | 5281 | NH1 | ARG | 1311 | 37.744 | −13.337 | 46.455 | 1.00 | 67.95 |
| ATOM | 5282 | HH11 | ARG | 1311 | 37.646 | −12.581 | 45.806 | 1.00 | 0.00 |
| ATOM | 5283 | HH12 | ARG | 1311 | 38.588 | −13.433 | 46.982 | 1.00 | 0.00 |
| ATOM | 5284 | NH2 | ARG | 1311 | 36.902 | −15.213 | 47.494 | 1.00 | 66.62 |

TABLE 23-continued

Coordinates for the 3D structure of ZAP-NC:ζ1 "dimer" structure
(two molecules of complex per unit cell)*

| ATOM | 5285 | HH21 | ARG | 1311 | 36.168 | −15.876 | 47.633 | 1.00 | 0.00 |
|---|---|---|---|---|---|---|---|---|---|
| ATOM | 5286 | HH22 | ARG | 1311 | 37.757 | −15.394 | 48.007 | 1.00 | 0.0 |
| ATOM | 5287 | C | ARG | 1311 | 34.620 | −10.284 | 42.079 | 1.00 | 27.99 |
| ATOM | 5288 | O | ARG | 1311 | 34.700 | −11.280 | 41.345 | 1.00 | 30.80 |
| ATOM | 5289 | N | ARG | 1312 | 34.487 | −9.062 | 70.589 | 1.00 | 25.90 |
| ATOM | 5290 | H | ARG | 1312 | 34.477 | −8.309 | 42.214 | 1.00 | 0.00 |
| ATOM | 5291 | CA | ARG | 1312 | 34.500 | −8.764 | 40.177 | 1.00 | 21.56 |
| ATOM | 5292 | CB | ARG | 1312 | 33.926 | −7.381 | 39.926 | 1.00 | 20.04 |
| ATOM | 5293 | CG | ARG | 1312 | 32.424 | −7.339 | 39.718 | 1.00 | 21.41 |
| ATOM | 5294 | CD | ARG | 1312 | 32.166 | −6.440 | 38.507 | 1.00 | 25.51 |
| ATOM | 5295 | NE | ARG | 1312 | 33.042 | −6.760 | 37.375 | 1.00 | 23.48 |
| ATOM | 5296 | HE | ARG | 1312 | 33.472 | −7.639 | 37.346 | 1.00 | 0.00 |
| ATOM | 5297 | CZ | ARG | 1312 | 33.309 | −5.896 | 36.376 | 1.00 | 30.45 |
| ATOM | 5298 | NH1 | ARG | 1312 | 32.789 | −4.660 | 36.302 | 1.00 | 24.19 |
| ATOM | 5299 | HH11 | ARG | 1312 | 32.161 | −4.342 | 37.011 | 1.00 | 0.00 |
| ATOM | 5300 | HH12 | ARG | 1312 | 33.024 | −4.067 | 35.532 | 1.00 | 0.00 |
| ATOM | 5301 | NH2 | ARG | 1312 | 34.166 | −6.270 | 35.429 | 1.00 | 29.90 |
| ATOM | 5302 | HH21 | ARG | 1312 | 34.591 | −7.174 | 35.474 | 1.00 | 0.00 |
| ATOM | 5303 | HH22 | ARG | 1312 | 34.377 | −5.651 | 34.673 | 1.00 | 0.00 |
| ATOM | 5304 | C | ARG | 1312 | 35.910 | −8.811 | 39.631 | 1.00 | 19.53 |
| ATOM | 5305 | O | ARG | 1312 | 36.887 | −8.561 | 40.322 | 1.00 | 19.04 |
| ATOM | 5306 | N | GLU | 1313 | 35.998 | −9.116 | 38.349 | 1.00 | 24.10 |
| ATOM | 5307 | H | GLU | 1313 | 35.184 | −9.226 | 37.837 | 1.00 | 0.00 |
| ATOM | 5308 | CA | GLU | 1313 | 37.247 | −9.118 | 37.613 | 1.00 | 26.25 |
| ATOM | 5309 | CB | GLU | 1313 | 37.151 | −1.0038 | 36.397 | 1.00 | 26.68 |
| ATOM | 5310 | CG | GLU | 1313 | 37.071 | −1.1516 | 36.754 | 1.00 | 25.25 |
| ATOM | 5311 | CD | GLU | 1313 | 38.287 | −1.2043 | 37.507 | 1.00 | 22.33 |
| ATOM | 5312 | OE1 | GLU | 1313 | 39.408 | −1.1876 | 37.032 | 1.00 | 26.23 |
| ATOM | 5313 | OE2 | GLU | 1313 | 38.107 | −1.2629 | 38.571 | 1.00 | 22.65 |
| ATOM | 5314 | C | GLU | 1313 | 37.498 | −7.693 | 37.150 | 1.00 | 24.87 |
| ATOM | 5315 | O | GLU | 1313 | 36.574 | −6.939 | 36.825 | 1.00 | 24.77 |
| ATOM | 5316 | N | GLU | 1314 | 38.752 | −7.294 | 37.114 | 1.00 | 27.62 |
| ATOM | 5317 | H | GLU | 1314 | 39.462 | −7.941 | 37.273 | 1.00 | 0.00 |
| ATOM | 5318 | CA | GLU | 1314 | 39.104 | −5.958 | 36.726 | 1.00 | 30.26 |
| ATOM | 5319 | CB | GLU | 1314 | 39.571 | −5.105 | 37.919 | 1.00 | 37.89 |
| ATOM | 5320 | CG | GLU | 1314 | 38.557 | −4.762 | 39.039 | 1.00 | 50.13 |
| ATOM | 5321 | CD | GLU | 1314 | 37.237 | −4.057 | 38.679 | 1.00 | 55.69 |
| ATOM | 5322 | OE1 | GLU | 1314 | 37.178 | −3.262 | 37.735 | 1.00 | 57.25 |
| ATOM | 5323 | OE2 | GLU | 1314 | 36.249 | −4.304 | 39.374 | 1.00 | 56.57 |
| ATOM | 5324 | C | GLU | 1314 | 40.240 | −6.072 | 35.744 | 1.00 | 28.05 |
| ATOM | 5325 | O | GLU | 1314 | 41.141 | −6.909 | 35.842 | 1.00 | 26.42 |
| ATOM | 5326 | N | PTY | 1315 | 40.132 | −5.180 | 34.778 | 1.00 | 28.11 |
| ATOM | 5327 | H | PTY | 1315 | 39.447 | −4.489 | 34.849 | 1.00 | 0.00 |
| ATOM | 5328 | CA | PTY | 1315 | 41.118 | −5.037 | 33.732 | 1.00 | 26.87 |
| ATOM | 5329 | CB | PTY | 1315 | 40.404 | −4.824 | 32.419 | 1.00 | 20.01 |
| ATOM | 5330 | CG | PTY | 1315 | 40.128 | −6.149 | 31.786 | 1.00 | 11.21 |
| ATOM | 5331 | CD1 | PTY | 1315 | 41.120 | −6.812 | 31.054 | 1.00 | 7.33 |
| ATOM | 5332 | CE1 | PTY | 1315 | 40.892 | −8.077 | 30.509 | 1.00 | 12.31 |
| ATOM | 5333 | CD2 | PTY | 1315 | 38.889 | −6.802 | 31.949 | 1.00 | 9.76 |
| ATOM | 5334 | CE2 | PTY | 1315 | 38.650 | −8.070 | 31.403 | 1.00 | 6.98 |
| ATOM | 5335 | CZ | PTY | 1315 | 39.647 | −8.728 | 30.680 | 1.00 | 12.20 |
| ATOM | 5336 | OH | PTY | 1315 | 39.377 | −9.962 | 30.126 | 1.00 | 11.60 |
| ATOM | 5337 | OR1 | PTY | 1315 | 39.480 | −11.598 | 32.039 | 1.00 | 23.46 |
| ATOM | 5338 | OR2 | PTY | 1315 | 41.612 | −10.940 | 31.097 | 1.00 | 22.23 |
| ATOM | 5339 | OR3 | PTY | 1315 | 40.109 | −12.344 | 29.936 | 1.00 | 21.17 |
| ATOM | 5340 | PR | PTY | 1315 | 40.190 | −11.164 | 30.804 | 1.00 | 16.43 |
| ATOM | 5341 | C | PTY | 1315 | 41.937 | −3.825 | 34.101 | 1.00 | 28.24 |
| ATOM | 5342 | O | PTY | 1315 | 41.713 | −3.239 | 35.167 | 1.00 | 34.41 |
| ATOM | 5343 | N | ASP | 1316 | 42.895 | −3.433 | 33.300 | 1.00 | 30.96 |
| ATOM | 5344 | H | ASP | 1316 | 42.989 | −3.813 | 32.405 | 1.00 | 0.00 |
| ATOM | 5345 | CA | ASP | 1316 | 43.655 | −2.257 | 33.639 | 1.00 | 37.10 |
| ATOM | 5346 | CB | ASP | 1316 | 45.127 | −2.491 | 33.430 | 1.00 | 41.47 |
| ATOM | 5347 | CG | ASP | 1316 | 45.767 | −3.314 | 34.519 | 1.00 | 45.09 |
| ATOM | 5348 | OD1 | ASP | 1316 | 16.533 | −2.742 | 35.291 | 1.00 | 51.31 |
| ATOM | 5349 | OD2 | ASP | 1316 | 45.509 | −4.514 | 34.583 | 1.00 | 47.70 |
| ATOM | 5350 | C | ASP | 1316 | 43.193 | −1.143 | 32.733 | 1.00 | 39.53 |
| ATOM | 5351 | O | ASP | 1316 | 42.724 | −1.390 | 31.615 | 1.00 | 45.74 |
| ATOM | 5352 | N | VAL | 1317 | 43.280 | 0.085 | 33.299 | 1.00 | 41.83 |
| ATOM | 5353 | H | VAL | 1317 | 43.722 | 0.236 | 34.088 | 1.00 | 0.00 |
| ATOM | 5354 | CA | VAL | 1317 | 42.948 | 1.243 | 32.418 | 1.00 | 44.85 |
| ATOM | 5355 | CB | VAL | 1317 | 41.791 | 2.049 | 33.116 | 1.00 | 43.64 |
| ATOM | 5356 | CG1 | VAL | 1317 | 42.225 | 2.723 | 34.411 | 1.00 | 46.74 |
| ATOM | 5357 | CG2 | VAL | 1317 | 40.280 | 3.069 | 32.112 | 1.00 | 46.56 |
| ATOM | 5358 | C | VAL | 1317 | 44.269 | 2.008 | 32.319 | 1.00 | 45.31 |
| ATOM | 5359 | O | VAL | 1317 | 45.215 | 1.781 | 33.089 | 1.00 | 41.69 |
| ATOM | 5360 | N | LEU | 1318 | 44.340 | 2.869 | 31.308 | 1.00 | 45.11 |

TABLE 23-continued

Coordinates for the 3D structure of ZAP-NC:ζ1 "dimer" structure
(two molecules of complex per unit cell)*

| ATOM | 5361 | H | LEU | 1318 | 43.558 | 2.982 | 30.733 | 1.00 | 0.00 |
|---|---|---|---|---|---|---|---|---|---|
| ATOM | 5362 | CA | LEU | 1318 | 45.520 | 3.675 | 31.063 | 1.00 | 47.99 |
| ATOM | 5363 | CB | LEU | 1318 | 45.299 | 4.414 | 29.757 | 1.00 | 42.85 |
| ATOM | 5364 | CG | LEU | 1318 | 44.989 | 3.532 | 28.554 | 1.00 | 38.00 |
| ATOM | 5365 | CD1 | LEU | 1318 | 44.192 | 4.345 | 27.606 | 1.00 | 32.68 |
| ATOM | 5366 | CD2 | LEU | 1318 | 46.238 | 3.003 | 27.888 | 1.00 | 34.68 |
| ATOM | 5367 | C | LEU | 1318 | 45.793 | 4.633 | 32.222 | 1.00 | 53.72 |
| ATOM | 5368 | O | LEU | 1318 | 44.861 | 5.114 | 32.887 | 1.00 | 53.92 |
| ATOM | 5369 | N | ASP | 1319 | 47.101 | 4.744 | 32.471 | 1.00 | 60.15 |
| ATOM | 5370 | H | ASP | 1319 | 47.696 | 4.244 | 31.885 | 1.00 | 0.00 |
| ATOM | 5371 | CA | ASP | 1319 | 47.709 | 5.555 | 33.519 | 1.00 | 67.37 |
| ATOM | 5372 | CB | ASP | 1319 | 49.218 | 5.246 | 33.704 | 1.00 | 71.97 |
| ATOM | 5373 | CG | ASP | 1319 | 49.622 | 3.840 | 34.143 | 1.00 | 75.12 |
| ATOM | 5374 | OD1 | ASP | 1319 | 50.486 | 3.737 | 35.019 | 1.00 | 75.09 |
| ATOM | 5375 | OD2 | ASP | 1319 | 49.104 | 2.855 | 33.607 | 1.00 | 75.64 |
| ATOM | 5376 | C | ASP | 1319 | 48.559 | 7.036 | 33.206 | 1.00 | 69.96 |
| ATOM | 5377 | O | ASP | 1319 | 48.000 | 7.450 | 32.113 | 1.00 | 72.41 |
| ATOM | 5378 | OT | ASP | 1319 | 47.117 | 7.758 | 34.075 | 1.00 | 72.49 |
| ATOM | 5379 | OH2 | H2O | 2091 | 11.613 | 6.292 | 3.790 | 1.00 | 9.15 |
| ATOM | 5380 | H1 | H2O | 2091 | 11.021 | 6.247 | 3.030 | 1.00 | 0.00 |
| ATOM | 5381 | H2 | H2O | 2091 | 12.286 | 6.908 | 3.506 | 1.00 | 0.00 |
| ATOM | 5382 | OH2 | H2O | 2289 | −0.606 | 1.712 | 22.323 | 1.00 | 38.94 |
| ATOM | 5383 | H1 | H2O | 2289 | −0.216 | 1.680 | 23.198 | 1.00 | 0.00 |
| ATOM | 5384 | H2 | H2O | 2289 | −1.566 | 1.715 | 22.535 | 1.00 | 0.00 |
| ATOM | 5385 | OH2 | H2O | 2003 | −4.862 | −2.850 | 17.008 | 1.00 | 55.78 |
| ATOM | 5386 | H1 | H2O | 2003 | −5.578 | −2.602 | 16.416 | 1.00 | 0.00 |
| ATOM | 5387 | H2 | H2O | 2003 | −5.228 | −3.616 | 17.461 | 1.00 | 0.00 |
| ATOM | 5388 | OH2 | H2O | 2035 | 0.404 | 8.828 | 19.112 | 1.00 | 32.59 |
| ATOM | 5389 | H1 | H2O | 2035 | 0.960 | 8.879 | 19.902 | 1.00 | 0.00 |
| ATOM | 5390 | H2 | H2O | 2035 | −0.430 | 9.187 | 19.400 | 1.00 | 0.00 |
| ATOM | 5391 | OH2 | H2O | 2230 | −3.731 | 1.596 | 4.235 | 1.00 | 7.64 |
| ATOM | 5392 | H1 | H2O | 2230 | −3.892 | 1.670 | 3.275 | 1.00 | 0.00 |
| ATOM | 5393 | H2 | H2O | 2230 | −2.780 | 1.688 | 4.279 | 1.00 | 0.00 |
| ATOM | 5394 | OH2 | H2O | 2226 | 4.474 | −1.056 | −2.417 | 1.00 | 39.20 |
| ATOM | 5395 | H1 | H2O | 2226 | 3.910 | −1.250 | −1.642 | 1.00 | 0.00 |
| ATOM | 5396 | H2 | H2O | 2226 | 4.883 | −1.923 | −2.534 | 1.00 | 0.00 |
| ATOM | 5397 | OH2 | H2O | 2235 | 5.069 | 1.440 | −3.371 | 1.00 | 34.16 |
| ATOM | 5398 | H1 | H2O | 2235 | 4.530 | 1.009 | −4.064 | 1.00 | 0.00 |
| ATOM | 5399 | H2 | H2O | 2235 | 5.003 | 0.712 | −2.714 | 1.00 | 0.00 |
| ATOM | 5400 | OH2 | H2O | 2367 | 6.779 | 5.277 | −2.088 | 1.00 | 14.63 |
| ATOM | 5401 | H1 | H2O | 2367 | 6.838 | 4.525 | −2.722 | 1.00 | 0.00 |
| ATOM | 5402 | H2 | H2O | 2367 | 7.586 | 5.141 | −1.574 | 1.00 | 0.00 |
| ATOM | 5403 | OH2 | H2O | 2277 | 0.582 | 2.614 | −1.861 | 1.00 | 15.62 |
| ATOM | 5404 | H1 | H2O | 2277 | 0.905 | 1.731 | −1.641 | 1.00 | 0.00 |
| ATOM | 5405 | H2 | H2O | 2277 | −0.256 | 2.437 | −2.298 | 1.00 | 0.00 |
| ATOM | 5406 | OH2 | H2O | 2217 | 2.900 | −2.745 | −0.055 | 1.00 | 18.30 |
| ATOM | 5407 | H1 | H2O | 2217 | 3.827 | −2.865 | 0.230 | 1.00 | 0.00 |
| ATOM | 5408 | H2 | H2O | 2217 | 2.421 | −3.213 | 0.635 | 1.00 | 0.00 |
| ATOM | 5409 | OH2 | H2O | 2021 | 5.582 | −3.229 | 0.413 | 1.00 | 12.00 |
| ATOM | 5410 | H1 | H2O | 2021 | 6.399 | −3.389 | 0.934 | 1.00 | 0.00 |
| ATOM | 5411 | H2 | H2O | 2021 | 6.035 | −2.957 | −0.416 | 1.00 | 0.00 |
| ATOM | 5412 | OH2 | H2O | 2265 | 7.276 | −2.450 | −1.549 | 1.00 | 19.34 |
| ATOM | 5413 | H1 | H2O | 2265 | 7.061 | −1.547 | −1.814 | 1.00 | 0.00 |
| ATOM | 5414 | H2 | H2O | 2265 | 8.249 | −2.355 | −1.576 | 1.00 | 0.00 |
| ATOM | 5415 | OH2 | H2O | 2050 | 9.531 | −1.039 | −1.954 | 1.00 | 15.27 |
| ATOM | 5416 | H1 | H2O | 2050 | 9.759 | −0.600 | −2.781 | 1.00 | 0.00 |
| ATOM | 5417 | H2 | H2O | 2050 | 10.415 | −1.132 | −1.532 | 1.00 | 0.00 |
| ATOM | 5418 | OH2 | H2O | 2188 | 7.944 | −3.913 | 1.547 | 1.00 | 6.13 |
| ATOM | 5419 | H1 | H2O | 2188 | 8.919 | −3.847 | 1.542 | 1.00 | 0.00 |
| ATOM | 5420 | H2 | H2O | 2188 | 7.781 | −4.090 | 2.502 | 1.00 | 0.00 |
| ATOM | 5421 | OH2 | H2O | 2106 | 11.995 | −1.225 | 0.912 | 1.00 | 10.49 |
| ATOM | 5422 | H1 | H2O | 2106 | 12.822 | −1.128 | 1.708 | 1.00 | 0.00 |
| ATOM | 5423 | H2 | H2O | 2106 | 12.292 | −1.014 | −0.019 | 1.00 | 0.00 |
| ATOM | 5424 | OH2 | H2O | 2263 | 10.556 | −3.103 | 2.014 | 1.00 | 16.72 |
| ATOM | 5425 | H1 | H2O | 2263 | 9.920 | −2.379 | 2.027 | 1.00 | 0.00 |
| ATOM | 5426 | H2 | H2O | 2263 | 11.186 | −2.784 | 1.353 | 1.00 | 0.00 |
| ATOM | 5427 | OH2 | H2O | 2369 | 7.366 | −4.615 | 4.091 | 1.00 | 8.30 |
| ATOM | 5428 | H1 | H2O | 2369 | 6.788 | −3.949 | 4.488 | 1.00 | 0.00 |
| ATOM | 5429 | H2 | H2O | 2369 | 8.158 | −4.482 | 4.669 | 1.00 | 0.00 |
| ATOM | 5430 | OH2 | H2O | 2336 | 2.623 | −5.870 | 6.276 | 1.00 | 8.51 |
| ATOM | 5431 | H1 | H2O | 2336 | 3.445 | −5.538 | 5.917 | 1.00 | 0.00 |
| ATOM | 5432 | H2 | H2O | 2336 | 2.231 | −5.086 | 6.672 | 1.00 | 0.00 |
| ATOM | 5433 | OH2 | H2O | 2005 | 6.010 | 3.922 | 2.813 | 1.00 | 5.77 |
| ATOM | 5434 | H1 | H2O | 2005 | 5.210 | 3.992 | 2.283 | 1.00 | 0.00 |
| ATOM | 5435 | H2 | H2O | 2005 | 5.836 | 3.150 | 3.362 | 1.00 | 0.00 |
| ATOM | 5436 | OH2 | H2O | 2013 | 8.688 | 3.977 | 2.421 | 1.00 | 4.93 |

TABLE 23-continued

Coordinates for the 3D structure of ZAP-NC:ζ1 "dimer" structure
(two molecules of complex per unit cell)*

| ATOM | 5437 | H1 | H2O | 2013 | 7.716 | 3.844 | 2.522 | 1.00 | 0.00 |
|---|---|---|---|---|---|---|---|---|---|
| ATOM | 5438 | H2 | H2O | 2013 | 8.704 | 4.934 | 2.501 | 1.00 | 0.00 |
| ATOM | 5439 | OH2 | H2O | 2210 | −1.947 | 22.873 | 18.487 | 1.00 | 21.45 |
| ATOM | 5440 | H1 | H2O | 2210 | −1.077 | 23.018 | 18.107 | 1.00 | 0.00 |
| ATOM | 5441 | H2 | H2O | 2210 | −1.901 | 21.999 | 18.875 | 1.00 | 0.00 |
| ATOM | 5442 | OH2 | H2O | 2397 | 6.940 | 3.302 | −4.007 | 1.00 | 14.99 |
| ATOM | 5443 | H1 | H2O | 2397 | 6.259 | 2.617 | −3.809 | 1.00 | 0.00 |
| ATOM | 5444 | H2 | H2O | 2397 | 7.709 | 2.739 | −4.215 | 1.00 | 0.00 |
| ATOM | 5445 | OH2 | H2O | 2211 | 5.320 | 7.091 | −4.231 | 1.00 | 5.91 |
| ATOM | 5446 | H1 | H2O | 2211 | 5.164 | 6.691 | −5.096 | 1.00 | 0.00 |
| ATOM | 5447 | H2 | H2O | 2211 | 5.887 | 6.432 | −3.794 | 1.00 | 0.00 |
| ATOM | 5448 | OH2 | H2O | 2088 | 6.170 | 9.583 | −5.206 | 1.00 | 3.99 |
| ATOM | 5449 | H1 | H2O | 2088 | 5.979 | 9.263 | −6.114 | 1.00 | 0.00 |
| ATOM | 5450 | H2 | H2O | 2088 | 3.024 | 8.768 | −4.695 | 1.00 | 0.00 |
| ATOM | 5451 | OH2 | H2O | 2127 | 4.543 | 11.747 | −5.012 | 1.00 | 17.56 |
| ATOM | 5452 | H1 | H2O | 2127 | 4.355 | 11.872 | −5.943 | 1.00 | 0.00 |
| ATOM | 5453 | H2 | H2O | 2127 | 5.174 | 10.996 | −5.020 | 1.00 | 0.00 |
| ATOM | 5454 | OH2 | H2O | 2393 | 4.660 | 15.853 | −4.263 | 1.00 | 17.70 |
| ATOM | 5455 | H1 | H2O | 2393 | 4.191 | 16.391 | −3.624 | 1.00 | 0.00 |
| ATOM | 5456 | H2 | H2O | 2393 | 3.945 | 15.378 | −4.706 | 1.00 | 0.00 |
| ATOM | 5457 | OH2 | H2O | 2363 | 1.201 | 14.180 | −4.789 | 1.00 | 14.09 |
| ATOM | 5458 | H1 | H2O | 2363 | 0.982 | 14.252 | −3.860 | 1.00 | 0.00 |
| ATOM | 5459 | H2 | H2O | 2363 | 0.630 | 13.434 | −5.056 | 1.00 | 0.00 |
| ATOM | 5460 | OH2 | H2O | 2252 | 7.730 | 13.503 | −4.221 | 1.00 | 26.93 |
| ATOM | 5461 | H1 | H2O | 2252 | 7.376 | 12.604 | −4.201 | 1.00 | 0.00 |
| ATOM | 5462 | H2 | H2O | 2252 | 6.918 | 14.021 | −4.319 | 1.00 | 0.00 |
| ATOM | 5463 | OH2 | H2O | 2337 | −0.119 | 11.846 | −4.785 | 1.00 | 11.20 |
| ATOM | 5464 | H1 | H2O | 2337 | −0.770 | 11.321 | −4.302 | 1.00 | 0.00 |
| ATOM | 5465 | H2 | H2O | 2337 | 0.699 | 11.419 | −4.499 | 1.00 | 0.00 |
| ATOM | 5466 | OH2 | H2O | 2447 | −0.079 | 10.337 | −7.542 | 1.00 | 40.91 |
| ATOM | 5467 | H1 | H2O | 2447 | −0.141 | 11.081 | −6.922 | 1.00 | 0.00 |
| ATOM | 5468 | H2 | H2O | 2447 | −0.776 | 9.752 | −7.213 | 1.00 | 0.00 |
| ATOM | 5469 | OH2 | H2O | 2131 | −2.231 | 7.960 | −6.047 | 1.00 | 23.04 |
| ATOM | 5470 | H1 | H2O | 2131 | −2.931 | 7.867 | −5.394 | 1.00 | 0.00 |
| ATOM | 5471 | H2 | H2O | 2131 | −2.407 | 7.253 | −6.673 | 1.00 | 0.00 |
| ATOM | 5472 | OH2 | H2O | 2012 | −7.124 | 7.460 | −2.263 | 1.00 | 20.39 |
| ATOM | 5473 | H1 | H2O | 2012 | −7.847 | 8.045 | −1.992 | 1.00 | 0.00 |
| ATOM | 5474 | H2 | H2O | 2012 | −6.813 | 7.923 | −3.054 | 1.00 | 0.00 |
| ATOM | 5475 | OH2 | H2O | 2323 | −7.338 | 5.501 | −0.353 | 1.00 | 64.57 |
| ATOM | 5476 | H1 | H2O | 2323 | −7.697 | 4.705 | −0.764 | 1.00 | 0.00 |
| ATOM | 5477 | H2 | H2O | 232 | −7.245 | 6.096 | −1.135 | 1.00 | 0.00 |
| ATOM | 5478 | OH2 | H2O | 2037 | −7.188 | 10.431 | −4.834 | 1.00 | 18.12 |
| ATOM | 5479 | H1 | H2O | 2037 | −7.947 | 11.011 | −4.942 | 1.00 | 0.00 |
| ATOM | 5480 | H2 | H2O | 2037 | −6.730 | 10.509 | −5.672 | 1.00 | 0.00 |
| ATOM | 5481 | OH2 | H2O | 2428 | −10.421 | 9.838 | 2.454 | 1.00 | 48.35 |
| ATOM | 5482 | H1 | H2O | 2428 | −9.470 | 9.846 | 2.679 | 1.00 | 0.00 |
| ATOM | 5483 | H2 | H2O | 2428 | −10.709 | 10.567 | 3.029 | 1.00 | 0.00 |
| ATOM | 5484 | OH2 | H2O | 2017 | −8.108 | 10.668 | 3.645 | 1.00 | 7.28 |
| ATOM | 5485 | H1 | H2O | 2017 | −8.845 | 11.291 | 3.785 | 1.00 | 0.00 |
| ATOM | 5486 | H2 | H2O | 2017 | −7.664 | 10.692 | 4.498 | 1.00 | 0.00 |
| ATOM | 5487 | OH2 | H2O | 2219 | −10.483 | 12.122 | 3.962 | 1.00 | 33.10 |
| ATOM | 5488 | H1 | H2O | 2219 | −11.182 | 12.413 | 3.328 | 1.00 | 0.00 |
| ATOM | 5489 | H2 | H2O | 2219 | −10.338 | 12.947 | 4.438 | 1.00 | 0.00 |
| ATOM | 5490 | OH2 | H2O | 2262 | −12.360 | 13.300 | 2.252 | 1.00 | 20.55 |
| ATOM | 5491 | H1 | H2O | 2262 | −11.954 | 14.149 | 2.024 | 1.00 | 0.00 |
| ATOM | 5492 | H2 | H2O | 2262 | −13.288 | 13.532 | 2.382 | 1.00 | 0.00 |
| ATOM | 5493 | OH2 | H2O | 2381 | −11.522 | 8.285 | 0.417 | 1.00 | 28.89 |
| ATOM | 5494 | H1 | H2O | 2381 | −11.065 | 8.791 | 1.123 | 1.00 | 0.00 |
| ATOM | 5495 | H2 | H2O | 2381 | −12.392 | 8.682 | 0.427 | 1.00 | 0.00 |
| ATOM | 5496 | OH2 | H2O | 2245 | −9.256 | 20.762 | 7.011 | 1.00 | 26.26 |
| ATOM | 5497 | H1 | H2O | 2245 | −10.180 | 21.032 | 6.982 | 1.00 | 0.00 |
| ATOM | 5498 | H2 | H2O | 2245 | −9.310 | 19.800 | 6.966 | 1.00 | 0.00 |
| ATOM | 5499 | OH2 | H2O | 2339 | −6.000 | 18.865 | 9.435 | 1.00 | 27.95 |
| ATOM | 5400 | H1 | H2O | 2339 | −6.072 | 17.927 | 9.222 | 1.00 | 0.00 |
| ATOM | 5501 | H2 | H2O | 2339 | −6.887 | 19.186 | 9.244 | 1.00 | 0.00 |
| ATOM | 5502 | OH2 | H2O | 2224 | −9.178 | 21.950 | 4.490 | 1.00 | 14.21 |
| ATOM | 5503 | H1 | H2O | 2224 | −8.297 | 22.121 | 4.123 | 1.00 | 0.00 |
| ATOM | 5504 | H2 | H2O | 2224 | −8.945 | 21.700 | 5.404 | 1.00 | 0.00 |
| ATOM | 5505 | OH2 | H2O | 2157 | 11.171 | −10.628 | −3.794 | 1.00 | 7.88 |
| ATOM | 5506 | H1 | H2O | 2157 | 10.586 | −9.879 | −4.046 | 1.00 | 0.00 |
| ATOM | 5507 | H2 | H2O | 2157 | 10.577 | −11.117 | −3.221 | 1.00 | 0.00 |
| ATOM | 5508 | OH2 | H2O | 2248 | −6.862 | 19.924 | 0.800 | 1.00 | 20.11 |
| ATOM | 5509 | H1 | H2O | 2248 | −7.017 | 19.074 | 0.361 | 1.00 | 0.00 |
| ATOM | 5510 | H2 | H2O | 2248 | −6.417 | 20.445 | 0.127 | 1.00 | 0.00 |
| ATOM | 5511 | OH2 | H2O | 2283 | −4.214 | 19.691 | 11.429 | 1.00 | 12.06 |
| ATOM | 5512 | H1 | H2O | 2283 | −4.833 | 19.464 | 10.706 | 1.00 | 0.00 |

TABLE 23-continued

Coordinates for the 3D structure of ZAP-NC:ζ1 "dimer" structure
(two molecules of complex per unit cell)*

| ATOM | 5513 | H2 | H2O | 2283 | −3.531 | 20.196 | 10.967 | 1.00 | 0.00 |
|---|---|---|---|---|---|---|---|---|---|
| ATOM | 5514 | OH2 | H2O | 2255 | −3.770 | 23.422 | 11.688 | 1.00 | 11.13 |
| ATOM | 5515 | H1 | H2O | 2255 | −3.036 | 22.810 | 11.546 | 1.00 | 0.00 |
| ATOM | 5516 | H2 | H2O | 2255 | −4.446 | 22.840 | 12.045 | 1.00 | 0.00 |
| ATOM | 5517 | OH2 | H2O | 2237 | −1.087 | 23.450 | 7.984 | 1.00 | 5.75 |
| ATOM | 5518 | H1 | H2O | 2237 | −1.236 | 22.495 | 5.008 | 1.00 | 0.00 |
| ATOM | 5519 | H2 | H2O | 2237 | −1.995 | 23.718 | 4.776 | 1.00 | 0.00 |
| ATOM | 5520 | OH2 | H2O | 2236 | −2.200 | 7.603 | 3.264 | 1.00 | 94.00 |
| ATOM | 5521 | H1 | H2O | 2236 | −1.248 | 7.737 | 3.328 | 1.00 | 0.00 |
| ATOM | 5522 | H2 | H2O | 2236 | −2.478 | 7.806 | 4.166 | 1.00 | 0.00 |
| ATOM | 5523 | OH2 | H2O | 2032 | 9.637 | −4.335 | 5.775 | 1.00 | 22.19 |
| ATOM | 5524 | H1 | H2O | 2032 | 9.837 | −4.315 | 6.735 | 1.00 | 0.00 |
| ATOM | 5525 | H2 | H2O | 2032 | 10.503 | −4.129 | 5.414 | 1.00 | 0.00 |
| ATOM | 5526 | OH2 | H2O | 2384 | 8.433 | −8.053 | 11.060 | 1.00 | 58.89 |
| ATOM | 5527 | H1 | H2O | 2384 | 8.776 | −8.614 | 10.352 | 1.00 | 0.00 |
| ATOM | 5528 | H2 | H2O | 2384 | 7.535 | −8.400 | 11.097 | 1.00 | 0.00 |
| ATOM | 5529 | OH2 | H2O | 2008 | 10.386 | −0.880 | 7.792 | 1.00 | 3.56 |
| ATOM | 5530 | H1 | H2O | 2008 | 10.921 | −1.130 | 7.031 | 1.00 | 0.00 |
| ATOM | 5531 | H2 | H2O | 2008 | 9.704 | −0.366 | 7.345 | 1.00 | 0.00 |
| ATOM | 5532 | OH2 | H2O | 2019 | 10.216 | −3.653 | 8.487 | 1.00 | 19.93 |
| ATOM | 5533 | H1 | H2O | 2019 | 9.397 | −3.758 | 9.015 | 1.00 | 0.00 |
| ATOM | 5534 | H2 | H2O | 2019 | 10.150 | −2.713 | 8.232 | 1.00 | 0.00 |
| ATOM | 5535 | OH2 | H2O | 2048 | 13.175 | 4.924 | 8.006 | 1.00 | 15.14 |
| ATOM | 5536 | H1 | H2O | 2048 | 12.391 | 5.233 | 7.536 | 1.00 | 0.00 |
| ATOM | 5537 | H2 | H2O | 2048 | 12.850 | 4.832 | 8.910 | 1.00 | 0.00 |
| ATOM | 5538 | OH2 | H2O | 2028 | 14.613 | −6.647 | 11.993 | 1.00 | 18.49 |
| ATOM | 5539 | H1 | H2O | 2028 | 13.928 | −6.819 | 11.337 | 1.00 | 0.00 |
| ATOM | 5540 | H2 | H2O | 2028 | 14.201 | −5.975 | 12.541 | 1.00 | 0.00 |
| ATOM | 5541 | OH2 | H2O | 2051 | 14.444 | 1.483 | 10.802 | 1.00 | 2.00 |
| ATOM | 5542 | H1 | H2O | 2051 | 14.489 | 0.558 | 11.082 | 1.00 | 0.00 |
| ATOM | 5543 | H2 | H2O | 2051 | 15.329 | 1.607 | 10.393 | 1.00 | 0.00 |
| ATOM | 5544 | OH2 | H2O | 2390 | 7.071 | 26.689 | 10.142 | 1.00 | 64.54 |
| ATOM | 5545 | H1 | H2O | 2390 | 7.620 | 27.385 | 10.523 | 1.00 | 0.00 |
| ATOM | 5546 | H2 | H2O | 2390 | 7.141 | 26.008 | 10.831 | 1.00 | 0.00 |
| ATOM | 5547 | OH2 | H2O | 2416 | 7.110 | 24.301 | 5.255 | 1.00 | 25.90 |
| ATOM | 5548 | H1 | H2O | 2416 | 7.917 | 24.786 | 5.458 | 1.00 | 0.00 |
| ATOM | 5549 | H2 | H2O | 2416 | 6.872 | 24.654 | 4.389 | 1.00 | 0.00 |
| ATOM | 5550 | OH2 | H2O | 2278 | 2.347 | 20.840 | −2.242 | 1.00 | 25.42 |
| ATOM | 5551 | H1 | H2O | 2278 | 1.432 | 20.561 | −2.127 | 1.00 | 0.00 |
| ATOM | 5552 | H2 | H2O | 2278 | 2.313 | 21.668 | −1.736 | 1.00 | 0.00 |
| ATOM | 5553 | OH2 | H2O | 2241 | 4.928 | 19.565 | −1.717 | 1.00 | 13.89 |
| ATOM | 5554 | H1 | H2O | 2241 | 4.055 | 19.952 | −1.941 | 1.00 | 0.00 |
| ATOM | 5555 | H2 | H2O | 2241 | 5.389 | 19.661 | −2.552 | 1.00 | 0.00 |
| ATOM | 5556 | OH2 | H2O | 2330 | 5.495 | 19.739 | 11.311 | 1.00 | 89.21 |
| ATOM | 5557 | H1 | H2O | 2330 | 5.618 | 19.333 | 12.203 | 1.00 | 0.00 |
| ATOM | 5558 | H2 | H2O | 2330 | 4.537 | 19.756 | 11.269 | 1.00 | 0.00 |
| ATOM | 5559 | OH2 | H2O | 2319 | 9.830 | 15.311 | 2.100 | 1.00 | 15.29 |
| ATOM | 5560 | H1 | H2O | 2319 | 10.441 | 14.835 | 1.515 | 1.00 | 0.00 |
| ATOM | 5561 | H2 | H2O | 2319 | 9.294 | 15.773 | 1.419 | 1.00 | 0.00 |
| ATOM | 5562 | OH2 | H2O | 2129 | 8.201 | 16.349 | 0.185 | 1.00 | 20.32 |
| ATOM | 5563 | H1 | H2O | 2129 | 7.738 | 17.108 | 1.561 | 1.00 | 0.00 |
| ATOM | 5564 | H2 | H2O | 2129 | 8.316 | 16.597 | −0.737 | 1.00 | 0.00 |
| ATOM | 5565 | OH2 | H2O | 2405 | 10.491 | 14.246 | −3.600 | 1.00 | 13.44 |
| ATOM | 5566 | H1 | H2O | 2405 | 10.534 | 14.843 | −4.349 | 1.00 | 0.00 |
| ATOM | 5567 | H2 | H2O | 2405 | 9.584 | 13.891 | −3.697 | 1.00 | 0.00 |
| ATOM | 5568 | OH2 | H2O | 2002 | 15.029 | 10.845 | 9.558 | 1.00 | 3.64 |
| ATOM | 5569 | H1 | H2O | 2002 | 15.184 | 11.736 | 9.185 | 1.00 | 0.00 |
| ATOM | 5570 | H2 | H2O | 2002 | 15.740 | 10.321 | 9.146 | 1.00 | 0.00 |
| ATOM | 5571 | OH2 | H2O | 2104 | 15.471 | 13.315 | 8.633 | 1.00 | 17.22 |
| ATOM | 5572 | H1 | H2O | 2104 | 14.807 | 13.835 | 8.155 | 1.00 | 0.00 |
| ATOM | 5573 | H2 | H2O | 2104 | 15.759 | 13.928 | 9.338 | 1.00 | 0.00 |
| ATOM | 5574 | OH2 | H2O | 2437 | 17.011 | 9.295 | 8.530 | 1.00 | 20.44 |
| ATOM | 5575 | H1 | H2O | 2437 | 16.669 | 8.421 | 8.295 | 1.00 | 0.00 |
| ATOM | 5576 | H2 | H2O | 2437 | 17.919 | 9.230 | 8.217 | 1.00 | 0.00 |
| ATOM | 5577 | OH2 | H2O | 2128 | 17.124 | 10.103 | 3.658 | 1.00 | 38.97 |
| ATOM | 5578 | H1 | H2O | 2128 | 16.954 | 10.675 | 4.434 | 1.00 | 0.00 |
| ATOM | 5579 | H2 | H2O | 2128 | 17.281 | 10.773 | 2.990 | 1.00 | 0.00 |
| ATOM | 5580 | OH2 | H2O | 2083 | 18.716 | 6.786 | 5.655 | 1.00 | 38.25 |
| ATOM | 5581 | H1 | H2O | 2083 | 18.094 | 6.062 | 5.812 | 1.00 | 0.00 |
| ATOM | 5582 | H2 | H2O | 2083 | 18.449 | 7.120 | 4.794 | 1.00 | 0.00 |
| ATOM | 5583 | OH2 | H2O | 2167 | 18.412 | 8.237 | 1.848 | 1.00 | 17.94 |
| ATOM | 5584 | H1 | H2O | 2167 | 17.942 | 8.754 | 2.529 | 1.00 | 0.00 |
| ATOM | 5585 | H2 | H2O | 2167 | 19.202 | 8.789 | 1.688 | 1.00 | 0.00 |
| ATOM | 5586 | OH2 | H2O | 2026 | 15.879 | 5.673 | 7.246 | 1.00 | 48.02 |
| ATOM | 5587 | H1 | H2O | 2026 | 14.941 | 5.437 | 7.369 | 1.00 | 0.00 |
| ATOM | 5588 | H2 | H2O | 2026 | 16.175 | 5.047 | 6.554 | 1.00 | 0.00 |

TABLE 23-continued

Coordinates for the 3D structure of ZAP-NC:ζ1 "dimer" structure
(two molecules of complex per unit cell)*

| ATOM | 5589 | OH2 | H2O | 2049 | 17.314 | 7.977 | 13.797 | 1.00 | 16.58 |
|---|---|---|---|---|---|---|---|---|---|
| ATOM | 5590 | H1 | H2O | 2049 | 16.400 | 8.007 | 13.482 | 1.00 | 0.00 |
| ATOM | 5591 | H2 | H2O | 2049 | 17.375 | 7.066 | 14.141 | 1.00 | 0.00 |
| ATOM | 5592 | OH2 | H2O | 2228 | 20.491 | 10.527 | 13.557 | 1.00 | 79.19 |
| ATOM | 5593 | H1 | H2O | 2228 | 21.024 | 9.803 | 13.223 | 1.00 | 0.00 |
| ATOM | 5594 | H2 | H2O | 2228 | 19.983 | 10.083 | 14.274 | 1.00 | 0.00 |
| ATOM | 5595 | OH2 | H2O | 2247 | 18.848 | 9.457 | 15.383 | 1.00 | 28.02 |
| ATOM | 5596 | H1 | H2O | 2247 | 18.287 | 8.895 | 14.791 | 1.00 | 0.00 |
| ATOM | 5597 | H2 | H2O | 2247 | 18.206 | 9.713 | 16.054 | 1.00 | 0.00 |
| ATOM | 5598 | OH2 | H2O | 2189 | 7.177 | 0.098 | 20.558 | 1.00 | 12.38 |
| ATOM | 5599 | H1 | H2O | 2189 | 7.667 | −0.699 | 20.329 | 1.00 | 0.00 |
| ATOM | 5600 | H2 | H2O | 2189 | 7.855 | 0.612 | 21.009 | 1.00 | 0.00 |
| ATOM | 5601 | OH2 | H2O | 2153 | 10.987 | −2.027 | 19.374 | 1.00 | 30.53 |
| ATOM | 5602 | H1 | H2O | 2153 | 11.365 | −1.186 | 19.661 | 1.00 | 0.00 |
| ATOM | 5603 | H2 | H2O | 2153 | 10.534 | −1.780 | 18.559 | 1.00 | 0.00 |
| ATOM | 5604 | OH2 | H2O | 2387 | 15.573 | −5.220 | 22.034 | 1.00 | 26.88 |
| ATOM | 5605 | H1 | H2O | 2387 | 15.420 | −4.414 | 22.537 | 1.00 | 0.00 |
| ATOM | 5606 | H2 | H2O | 2387 | 15.880 | −4.902 | 21.183 | 1.00 | 0.00 |
| ATOM | 5607 | OH2 | H2O | 2081 | 11.585 | 0.443 | 22.679 | 1.00 | 18.85 |
| ATOM | 5608 | H1 | H2O | 2081 | 10.705 | 0.405 | 22.293 | 1.00 | 0.00 |
| ATOM | 5609 | H2 | H2O | 2081 | 12.133 | 0.412 | 21.891 | 1.00 | 0.00 |
| ATOM | 5610 | OH2 | H2O | 2065 | 12.324 | 11.499 | 16.673 | 1.00 | 6.58 |
| ATOM | 5611 | H1 | H2O | 2065 | 12.905 | 11.565 | 17.437 | 1.00 | 0.00 |
| ATOM | 5612 | H2 | H2O | 2065 | 12.163 | 12.420 | 16.446 | 1.00 | 0.00 |
| ATOM | 5613 | OH2 | H2O | 2307 | 13.497 | 15.746 | 18.110 | 1.00 | 21.94 |
| ATOM | 5614 | H1 | H2O | 2307 | 13.198 | 16.526 | 17.607 | 1.00 | 0.00 |
| ATOM | 5615 | H2 | H2O | 2307 | 14.125 | 16.164 | 18.711 | 1.00 | 0.00 |
| ATOM | 5616 | OH2 | H2O | 2174 | 16.345 | 14.884 | 10.755 | 1.00 | 12.56 |
| ATOM | 5617 | H1 | H2O | 2174 | 15.955 | 14.561 | 11.582 | 1.00 | 0.00 |
| ATOM | 5618 | H2 | H2O | 2174 | 17.276 | 14.775 | 10.999 | 1.00 | 0.00 |
| ATOM | 5619 | OH2 | H2O | 2080 | 16.899 | 10.708 | 22.439 | 1.00 | 18.59 |
| ATOM | 5620 | H1 | H2O | 2080 | 16.192 | 10.707 | 23.107 | 1.00 | 0.00 |
| ATOM | 5621 | H2 | H2O | 2080 | 17.504 | 10.070 | 22.839 | 1.00 | 0.00 |
| ATOM | 5622 | OH2 | H2O | 2145 | 8.985 | 6.741 | 24.686 | 1.00 | 10.42 |
| ATOM | 5623 | H1 | H2O | 2145 | 8.457 | 7.507 | 24.413 | 1.00 | 0.00 |
| ATOM | 5624 | H2 | H2O | 2145 | 8.932 | 6.789 | 25.642 | 1.00 | 0.00 |
| ATOM | 5625 | OH2 | H2O | 2234 | −1.344 | 12.735 | 21.035 | 1.00 | 32.56 |
| ATOM | 5626 | H1 | H2O | 2234 | −1.446 | 12.294 | 20.176 | 1.00 | 0.00 |
| ATOM | 5627 | H2 | H2O | 2234 | −1.081 | 13.620 | 20.775 | 1.00 | 0.00 |
| ATOM | 5628 | OH2 | H2O | 2389 | −1.529 | 11.859 | 18.208 | 1.00 | 25.81 |
| ATOM | 5629 | H1 | H2O | 2389 | −1.103 | 11.457 | 17.445 | 1.00 | 0.00 |
| ATOM | 5630 | H2 | H2O | 2389 | −1.683 | 12.782 | 17.891 | 1.00 | 0.00 |
| ATOM | 5631 | OH2 | H2O | 2442 | −4.227 | 11.513 | 17.909 | 1.00 | 40.21 |
| ATOM | 5632 | H1 | H2O | 2442 | −4.311 | 12.468 | 17.887 | 1.00 | 0.00 |
| ATOM | 5633 | H2 | H2O | 2442 | −3.299 | 11.412 | 18.188 | 1.00 | 0.00 |
| ATOM | 5634 | OH2 | H2O | 2294 | −1.737 | 4.678 | 21.101 | 1.00 | 50.85 |
| ATOM | 5635 | H1 | H2O | 2294 | −1.391 | 5.578 | 21.112 | 1.00 | 0.00 |
| ATOM | 5636 | H2 | H2O | 2294 | −2.553 | 4.753 | 21.611 | 1.00 | 0.00 |
| ATOM | 5637 | OH2 | H2O | 2436 | 3.968 | 2.794 | 20.047 | 1.00 | 20.89 |
| ATOM | 5638 | H1 | H2O | 2436 | 4.484 | 1.976 | 19.985 | 1.00 | 0.00 |
| ATOM | 5639 | H2 | H2O | 2436 | 3.362 | 2.571 | 20.765 | 1.00 | 0.00 |
| ATOM | 5640 | OH2 | H2O | 2195 | −2.103 | 14.513 | 17.363 | 1.00 | 45.39 |
| ATOM | 5641 | H1 | H2O | 2195 | −1.333 | 15.013 | 17.684 | 1.00 | 0.00 |
| ATOM | 5642 | H2 | H2O | 2195 | −2.463 | 15.110 | 16.687 | 1.00 | 0.00 |
| ATOM | 5643 | OH2 | H2O | 2292 | 4.660 | 24.323 | 21.790 | 1.00 | 31.24 |
| ATOM | 5644 | H1 | H2O | 2292 | 3.750 | 24.146 | 21.548 | 1.00 | 0.00 |
| ATOM | 5645 | H2 | H2O | 2292 | 4.768 | 23.824 | 22.603 | 1.00 | 0.00 |
| ATOM | 5646 | OH2 | H2O | 2445 | 7.938 | 18.020 | 26.568 | 1.00 | 33.41 |
| ATOM | 5647 | H1 | H2O | 2445 | 8.797 | 18.087 | 27.007 | 1.00 | 0.00 |
| ATOM | 5648 | H2 | H2O | 2445 | 7.479 | 17.386 | 27.129 | 1.00 | 0.00 |
| ATOM | 5649 | OH2 | H2O | 2400 | 10.560 | 23.286 | 20.157 | 1.00 | 25.80 |
| ATOM | 5650 | H1 | H2O | 2400 | 10.053 | 24.081 | 19.966 | 1.00 | 0.00 |
| ATOM | 5651 | H2 | H2O | 2400 | 11.445 | 23.627 | 20.311 | 1.00 | 0.00 |
| ATOM | 5652 | OH2 | H2O | 2427 | 10.358 | 23.548 | 15.422 | 1.00 | 19.65 |
| ATOM | 5653 | H1 | H2O | 2427 | 9.950 | 23.212 | 14.607 | 1.00 | 0.00 |
| ATOM | 5654 | H2 | H2O | 2427 | 10.834 | 24.319 | 15.099 | 1.00 | 0.00 |
| ATOM | 5655 | OH2 | H2O | 2275 | −11.995 | 7.700 | 8.856 | 1.00 | 56.20 |
| ATOM | 5656 | H1 | H2O | 2275 | −11.299 | 7.070 | 9.091 | 1.00 | 0.00 |
| ATOM | 5657 | H2 | H2O | 2275 | −11.495 | 8.399 | 8.430 | 1.00 | 0.00 |
| ATOM | 5658 | OH2 | H2O | 2253 | −10.228 | 1.870 | 9.007 | 1.00 | 15.68 |
| ATOM | 5659 | H1 | H2O | 2253 | −9.398 | 1.562 | 8.616 | 1.00 | 0.00 |
| ATOM | 5660 | H2 | H2O | 2253 | −10.313 | 2.724 | 8.562 | 1.00 | 0.00 |
| ATOM | 5661 | OH2 | H2O | 2076 | 7.254 | −10.240 | 9.154 | 1.00 | 13.69 |
| ATOM | 5662 | H1 | H2O | 2076 | 7.440 | −11.075 | 9.629 | 1.00 | 0.00 |
| ATOM | 5663 | H2 | H2O | 2076 | 6.948 | −10.557 | 8.294 | 1.00 | 0.00 |
| ATOM | 5664 | OH2 | H2O | 2191 | 14.696 | −18.919 | 5.506 | 1.00 | 21.42 |

TABLE 23-continued

Coordinates for the 3D structure of ZAP-NC:ζ1 "dimer" structure
(two molecules of complex per unit cell)*

| ATOM | 5665 | H1 | H2O | 2191 | 13.932 | −18.906 | 6.088 | 1.00 | 0.00 |
|---|---|---|---|---|---|---|---|---|---|
| ATOM | 5666 | H2 | H2O | 2191 | 14.993 | −17.999 | 5.512 | 1.00 | 0.00 |
| ATOM | 5667 | OH2 | H2O | 2025 | 13.620 | −17.448 | 15.050 | 1.00 | 16.30 |
| ATOM | 5668 | H1 | H2O | 2025 | 13.150 | −16.664 | 15.367 | 1.00 | 0.00 |
| ATOM | 5669 | H2 | H2O | 2025 | 12.888 | −18.073 | 15.081 | 1.00 | 0.00 |
| ATOM | 5670 | OH2 | H2O | 2184 | 19.050 | −19.408 | 16.078 | 1.00 | 37.17 |
| ATOM | 5671 | H1 | H2O | 2184 | 18.624 | −19.737 | 15.276 | 1.00 | 0.00 |
| ATOM | 5672 | H2 | H2O | 2184 | 19.972 | −19.612 | 15.906 | 1.00 | 0.00 |
| ATOM | 5673 | OH2 | H2O | 2429 | 11.300 | −29.483 | 9.061 | 1.00 | 46.58 |
| ATOM | 5674 | H1 | H2O | 2429 | 12.135 | −29.548 | 8.589 | 1.00 | 0.00 |
| ATOM | 5675 | H2 | H2O | 2429 | 11.528 | −28.904 | 9.800 | 1.00 | 0.00 |
| ATOM | 5676 | OH2 | H2O | 2196 | 4.962 | −12.445 | 14.206 | 1.00 | 55.45 |
| ATOM | 5677 | H1 | H2O | 2196 | 4.086 | −12.167 | 14.476 | 1.00 | 0.00 |
| ATOM | 5678 | H2 | H2O | 2196 | 5.364 | −11.658 | 13.839 | 1.00 | 0.00 |
| ATOM | 5679 | OH2 | H2O | 2426 | 7.900 | −12.611 | 10.746 | 1.00 | 23.66 |
| ATOM | 5680 | H1 | H2O | 2426 | 8.783 | −12.871 | 11.025 | 1.00 | 0.00 |
| ATOM | 5681 | H2 | H2O | 2426 | 7.348 | −13.325 | 11.080 | 1.00 | 0.00 |
| ATOM | 5682 | OH2 | H2O | 2052 | 10.898 | −6.045 | 11.814 | 1.00 | 25.42 |
| ATOM | 5683 | H1 | H2O | 2052 | 10.209 | −6.592 | 11.412 | 1.00 | 0.00 |
| ATOM | 5684 | H2 | H2O | 2052 | 10.931 | −6.401 | 12.704 | 1.00 | 0.00 |
| ATOM | 5685 | OH2 | H2O | 2103 | 15.818 | −19.257 | 15.652 | 1.00 | 72.28 |
| ATOM | 5686 | H1 | H2O | 2103 | 15.184 | −18.542 | 15.441 | 1.00 | 0.00 |
| ATOM | 5687 | H2 | H2O | 2103 | 16.640 | −18.781 | 15.841 | 1.00 | 0.00 |
| ATOM | 5688 | OH2 | H2O | 2388 | 17.485 | −7.351 | 16.533 | 1.00 | 39.92 |
| ATOM | 5689 | H1 | H2O | 2388 | 17.641 | −6.500 | 16.116 | 1.00 | 0.00 |
| ATOM | 5690 | H2 | H2O | 2388 | 16.879 | −7.780 | 15.920 | 1.00 | 0.00 |
| ATOM | 5691 | OH2 | H2O | 2350 | 20.265 | −5.720 | 9.455 | 1.00 | 41.89 |
| ATOM | 5692 | H1 | H2O | 2350 | 20.758 | −6.394 | 8.969 | 1.00 | 0.00 |
| ATOM | 5693 | H2 | H2O | 2350 | 19.357 | −6.018 | 9.356 | 1.00 | 0.00 |
| ATOM | 5694 | OH2 | H2O | 2183 | 17.171 | −14.901 | 4.225 | 1.00 | 28.26 |
| ATOM | 5695 | H1 | H2O | 2183 | 16.436 | −14.447 | 3.806 | 1.00 | 0.00 |
| ATOM | 5696 | H2 | H2O | 2183 | 17.728 | −14.161 | 4.506 | 1.00 | 0.00 |
| ATOM | 5697 | OH2 | H2O | 2151 | 24.700 | −8.316 | 1.652 | 1.00 | 100.47 |
| ATOM | 5698 | H1 | H2O | 2151 | 24.695 | −7.542 | 2.237 | 1.00 | 0.00 |
| ATOM | 5699 | H2 | H2O | 2151 | 25.603 | −8.257 | 1.302 | 1.00 | 0.00 |
| ATOM | 5700 | OH2 | H2O | 2138 | 21.387 | −6.900 | 2.709 | 1.00 | 8.74 |
| ATOM | 5701 | H1 | H2O | 2138 | 21.332 | −6.835 | 3.670 | 1.00 | 0.00 |
| ATOM | 5702 | H2 | H2O | 2138 | 22.351 | −6.980 | 2.613 | 1.00 | 0.00 |
| ATOM | 5703 | OH2 | H2O | 2004 | 18.730 | −8.591 | 1.591 | 1.00 | 7.03 |
| ATOM | 5704 | H1 | H2O | 2004 | 19.326 | −8.205 | 2.261 | 1.00 | 0.00 |
| ATOM | 5705 | H2 | H2O | 2004 | 17.917 | −8.662 | 2.128 | 1.00 | 0.00 |
| ATOM | 5706 | OH2 | H2O | 2218 | 20.874 | −17.466 | 2.643 | 1.00 | 55.49 |
| ATOM | 5707 | H1 | H2O | 2218 | 21.747 | −17.302 | 3.056 | 1.00 | 0.00 |
| ATOM | 5708 | H2 | H2O | 2218 | 20.481 | −16.588 | 2.671 | 1.00 | 0.00 |
| ATOM | 5709 | OH2 | H2O | 2419 | 20.819 | −17.988 | 7.921 | 1.00 | 29.43 |
| ATOM | 5710 | H1 | H2O | 2419 | 20.456 | −17.393 | 7.234 | 1.00 | 0.00 |
| ATOM | 5711 | H2 | H2O | 2419 | 21.769 | −17.913 | 7.729 | 1.00 | 0.00 |
| ATOM | 5712 | OH2 | H2O | 2031 | 19.578 | −16.187 | 6.433 | 1.00 | 34.49 |
| ATOM | 5713 | H1 | H2O | 2031 | 18.984 | −16.029 | 5.679 | 1.00 | 0.00 |
| ATOM | 5714 | H2 | H2O | 2031 | 18.968 | −16.183 | 7.182 | 1.00 | 0.00 |
| ATOM | 5715 | OH2 | H2O | 2238 | 23.558 | −17.675 | 7.540 | 1.00 | 52.94 |
| ATOM | 5716 | H1 | H2O | 2238 | 23.974 | −17.229 | 8.286 | 1.00 | 0.00 |
| ATOM | 5717 | H2 | H2O | 2238 | 23.895 | −18.577 | 7.600 | 1.00 | 0.00 |
| ATOM | 5718 | OH2 | H2O | 2314 | 23.469 | −16.836 | 3.905 | 1.00 | 40.23 |
| ATOM | 5719 | H1 | H2O | 2314 | 23.490 | −17.175 | 4.811 | 1.00 | 0.00 |
| ATOM | 5720 | H2 | H2O | 2314 | 24.143 | −16.139 | 3.965 | 1.00 | 0.00 |
| ATOM | 5721 | OH2 | H2O | 2430 | 24.508 | −16.953 | −2.476 | 1.00 | 39.10 |
| ATOM | 5722 | H1 | H2O | 2430 | 23.560 | −16.935 | −2.629 | 1.00 | 0.00 |
| ATOM | 5723 | H2 | H2O | 2430 | 24.557 | −17.528 | −1.683 | 1.00 | 0.00 |
| ATOM | 5724 | OH2 | H2O | 2398 | 31.756 | −8.627 | −9.918 | 1.00 | 31.65 |
| ATOM | 5725 | H1 | H2O | 2398 | 31.272 | −9.319 | −10.392 | 1.00 | 0.00 |
| ATOM | 5726 | H2 | H2O | 2398 | 31.395 | −8.751 | −9.028 | 1.00 | 0.00 |
| ATOM | 5727 | OH2 | H2O | 2357 | 35.235 | −6.559 | −13.025 | 1.00 | 36.71 |
| ATOM | 5728 | H1 | H2O | 2357 | 35.237 | −6.279 | −12.103 | 1.00 | 0.00 |
| ATOM | 5729 | H2 | H2O | 2357 | 35.388 | −5.723 | −13.483 | 1.00 | 0.00 |
| ATOM | 5730 | OH2 | H2O | 2096 | 28.378 | 0.965 | −16.864 | 1.00 | 30.28 |
| ATOM | 5731 | H1 | H2O | 2096 | 28.314 | 1.415 | −17.728 | 1.00 | 0.00 |
| ATOM | 5732 | H2 | H2O | 2096 | 29.306 | 1.134 | −16.635 | 1.00 | 0.00 |
| ATOM | 5733 | OH2 | H2O | 2386 | 22.098 | −15.122 | −27.193 | 1.00 | 30.97 |
| ATOM | 5734 | H1 | H2O | 2386 | 22.328 | −15.611 | −27.986 | 1.00 | 0.00 |
| ATOM | 5735 | H2 | H2O | 2386 | 22.946 | −14.810 | −26.865 | 1.00 | 0.00 |
| ATOM | 5736 | OH2 | H2O | 2401 | 19.525 | −16.915 | −19.140 | 1.00 | 60.66 |
| ATOM | 5737 | H1 | H2O | 2401 | 19.053 | −17.603 | −18.636 | 1.00 | 0.00 |
| ATOM | 5738 | H2 | H2O | 2401 | 20.414 | −17.217 | −18.897 | 1.00 | 0.00 |
| ATOM | 5739 | OH2 | H2O | 2112 | 13.236 | −6.440 | −18.191 | 1.00 | 30.00 |
| ATOM | 5740 | H1 | H2O | 2112 | 12.946 | −5.540 | −18.395 | 1.00 | 0.00 |

TABLE 23-continued

Coordinates for the 3D structure of ZAP-NC:ζ1 "dimer" structure
(two molecules of complex per unit cell)*

| ATOM | 5741 | H2  | H2O | 2112 | 14.149 | −6.441  | −18.482 | 1.00 | 0.00  |
|------|------|-----|-----|------|--------|---------|---------|------|-------|
| ATOM | 5742 | OH2 | H2O | 2099 | 16.728 | −3.157  | −24.065 | 1.00 | 31.03 |
| ATOM | 5743 | H1  | H2O | 2099 | 16.632 | −3.797  | −23.348 | 1.00 | 0.00  |
| ATOM | 5744 | H2  | H2O | 2099 | 16.491 | −3.755  | −24.792 | 1.00 | 0.00  |
| ATOM | 5745 | OH2 | H2O | 2368 | 16.789 | −13.334 | −22.170 | 1.00 | 58.09 |
| ATOM | 5746 | H1  | H2O | 2368 | 16.718 | −13.705 | −21.278 | 1.00 | 0.00  |
| ATOM | 5747 | H2  | H2O | 2368 | 17.727 | −13.076 | −22.156 | 1.00 | 0.00  |
| ATOM | 5748 | OH2 | H2O | 2377 | 29.291 | −10.210 | −0.300  | 1.00 | 50.66 |
| ATOM | 5749 | H1  | H2O | 2377 | 29.956 | −10.411 | −0.974  | 1.00 | 0.00  |
| ATOM | 5750 | H2  | H2O | 2377 | 29.866 | −9.834  | 0.395   | 1.00 | 0.00  |
| ATOM | 5751 | OH2 | H2O | 2424 | 34.504 | −6.760  | −9.490  | 1.00 | 27.48 |
| ATOM | 5752 | H1  | H2O | 2424 | 34.199 | −5.886  | −9.757  | 1.00 | 0.00  |
| ATOM | 5753 | H2  | H2O | 2424 | 22.787 | −7.317  | −9.834  | 1.00 | 0.00  |
| ATOM | 5754 | OH2 | H2O | 2023 | 15.631 | 5.950   | −19.680 | 1.00 | 12.26 |
| ATOM | 5755 | H1  | H2O | 2023 | 16.126 | 5.955   | −18.848 | 1.00 | 0.00  |
| ATOM | 5756 | H2  | H2O | 2023 | 15.137 | 5.128   | −19.588 | 1.00 | 0.00  |
| ATOM | 5757 | OH2 | H2O | 2155 | 27.699 | 2.486   | −19.359 | 1.00 | 26.98 |
| ATOM | 5758 | H1  | H2O | 2155 | 27.056 | 3.116   | −19.697 | 1.00 | 0.00  |
| ATOM | 5759 | H2  | H2O | 2155 | 27.833 | 1.887   | −20.103 | 1.00 | 0.00  |
| ATOM | 5760 | OH2 | H2O | 2040 | 21.670 | 7.029   | −14.364 | 1.00 | 19.72 |
| ATOM | 5761 | H1  | H2O | 2040 | 22.395 | 7.459   | −13.806 | 1.00 | 0.00  |
| ATOM | 5762 | H2  | H2O | 2040 | 20.930 | 7.613   | −14.073 | 1.00 | 0.00  |
| ATOM | 5763 | OH2 | H2O | 2034 | 27.535 | 4.082   | −9.593  | 1.00 | 11.33 |
| ATOM | 5764 | H1  | H2O | 2034 | 27.066 | 4.295   | −10.404 | 1.00 | 0.00  |
| ATOM | 5765 | H2  | H2O | 2034 | 27.618 | 4.944   | −9.184  | 1.00 | 0.00  |
| ATOM | 5766 | OH2 | H2O | 2146 | 26.621 | 3.630   | 1.891   | 1.00 | 30.47 |
| ATOM | 5767 | H1  | H2O | 2146 | 26.375 | 3.894   | 1.000   | 1.00 | 0.00  |
| ATOM | 5768 | H2  | H2O | 2146 | 25.859 | 3.131   | 2.201   | 1.00 | 0.00  |
| ATOM | 5769 | OH2 | H2O | 2068 | 20.920 | 3.904   | −3.760  | 1.00 | 7.73  |
| ATOM | 5770 | H1  | H2O | 2068 | 20.187 | 4.266   | −4.277  | 1.00 | 0.00  |
| ATOM | 5771 | H2  | H2O | 2068 | 20.537 | 3.848   | −2.870  | 1.00 | 0.00  |
| ATOM | 5772 | OH2 | H2O | 2364 | 27.480 | −2.239  | 11.630  | 1.00 | 42.03 |
| ATOM | 5773 | H1  | H2O | 2364 | 28.335 | −2.674  | 11.627  | 1.00 | 0.00  |
| ATOM | 5774 | H2  | H2O | 2364 | 27.679 | −1.400  | 11.186  | 1.00 | 0.00  |
| ATOM | 5775 | OH2 | H2O | 2343 | 24.938 | −3.397  | 12.441  | 1.00 | 63.93 |
| ATOM | 5776 | H1  | H2O | 2343 | 25.826 | −3.111  | 12.155  | 1.00 | 0.00  |
| ATOM | 5777 | H2  | H2O | 2343 | 24.545 | −2.572  | 12.718  | 1.00 | 0.00  |
| ATOM | 5778 | OH2 | H2O | 2113 | 20.780 | 9.545   | 0.873   | 1.00 | 21.71 |
| ATOM | 5779 | H1  | H2O | 2113 | 21.269 | 10.305  | 0.549   | 1.00 | 0.00  |
| ATOM | 5780 | H2  | H2O | 2113 | 21.101 | 8.844   | 0.281   | 1.00 | 0.00  |
| ATOM | 5781 | OH2 | H2O | 2045 | 19.024 | 5.919   | −5.656  | 1.00 | 15.08 |
| ATOM | 5782 | H1  | H2O | 2045 | 18.298 | 5.988   | −6.294  | 1.00 | 0.00  |
| ATOM | 5783 | H2  | H2O | 2045 | 19.582 | 6.638   | −5.959  | 1.00 | 0.00  |
| ATOM | 5784 | OH2 | H2O | 2065 | 21.114 | 5.417   | −9.307  | 1.00 | 22.18 |
| ATOM | 5785 | H1  | H2O | 2065 | 20.193 | 5.540   | −9.064  | 1.00 | 0.00  |
| ATOM | 5786 | H2  | H2O | 2065 | 21.468 | 4.912   | −8.570  | 1.00 | 0.00  |
| ATOM | 5787 | OH2 | H2O | 2342 | 13.713 | −6.970  | −4.121  | 1.00 | 12.52 |
| ATOM | 5788 | H1  | H2O | 2342 | 14.059 | −6.564  | −3.321  | 1.00 | 0.00  |
| ATOM | 5789 | H2  | H2O | 2342 | 13.327 | −7.788  | −3.792  | 1.00 | 0.00  |
| ATOM | 5790 | OH2 | H2O | 2109 | 13.864 | 8.376   | −3.158  | 1.00 | 12.93 |
| ATOM | 5791 | H1  | H2O | 2109 | 14.640 | 8.635   | −2.622  | 1.00 | 0.00  |
| ATOM | 5792 | H2  | H2O | 2109 | 13.501 | 7.844   | −2.646  | 1.00 | 0.00  |
| ATOM | 5793 | OH2 | H2O | 2098 | 11.925 | 3.812   | −15.931 | 1.00 | 18.96 |
| ATOM | 5794 | H1  | H2O | 2098 | 11.075 | 3.560   | −16.296 | 1.00 | 0.00  |
| ATOM | 5795 | H2  | H2O | 2098 | 12.285 | 4.414   | −16.600 | 1.00 | 0.00  |
| ATOM | 5796 | OH2 | H2O | 2365 | 9.223  | −0.496  | −14.217 | 1.00 | 54.84 |
| ATOM | 5797 | H1  | H2O | 2365 | 9.824  | −1.238  | −14.398 | 1.00 | 0.00  |
| ATOM | 5798 | H2  | H2O | 2365 | 9.151  | −0.395  | −13.258 | 1.00 | 0.00  |
| ATOM | 5799 | OH2 | H2O | 2404 | 12.428 | 8.296   | −6.209  | 1.00 | 9.63  |
| ATOM | 5800 | H1  | H2O | 2404 | 13.062 | 8.041   | −5.522  | 1.00 | 0.00  |
| ATOM | 5801 | H2  | H2O | 2404 | 11.618 | 8.368   | −5.696  | 1.00 | 0.00  |
| ATOM | 5802 | OH2 | H2O | 2156 | 12.447 | 8.353   | −8.928  | 1.00 | 14.17 |
| ATOM | 5803 | H1  | H2O | 2156 | 12.431 | 8.321   | −7.945  | 1.00 | 0.00  |
| ATOM | 5804 | H2  | H2O | 2156 | 12.713 | 9.272   | −9.054  | 1.00 | 0.00  |
| ATOM | 5805 | OH2 | H2O | 2423 | 11.556 | 21.534  | 9.898   | 1.00 | 47.08 |
| ATOM | 5806 | H1  | H2O | 2423 | 11.961 | 21.494  | 10.776  | 1.00 | 0.00  |
| ATOM | 5807 | H2  | H2O | 2423 | 12.201 | 21.063  | 9.362   | 1.00 | 0.00  |
| ATOM | 5808 | OH2 | H2O | 2299 | 16.641 | 12.291  | 5.375   | 1.00 | 46.28 |
| ATOM | 5809 | H1  | H2O | 2299 | 16.261 | 13.167  | 5.230   | 1.00 | 0.00  |
| ATOM | 5810 | H2  | H2O | 2299 | 16.480 | 12.192  | 6.327   | 1.00 | 0.00  |
| ATOM | 5811 | OH2 | H2O | 2232 | 53.010 | −16.149 | 14.337  | 1.00 | 24.27 |
| ATOM | 5812 | H1  | H2O | 2232 | 52.288 | −15.839 | 14.896  | 1.00 | 0.00  |
| ATOM | 5813 | H2  | H2O | 2232 | 52.553 | −16.366 | 13.518  | 1.00 | 0.00  |
| ATOM | 5814 | OH2 | H2O | 2100 | 57.480 | −6.928  | 18.196  | 1.00 | 40.81 |
| ATOM | 5815 | H1  | H2O | 2100 | 57.150 | −6.086  | 18.572  | 1.00 | 0.00  |
| ATOM | 5816 | H2  | H2O | 2100 | 56.946 | −6.989  | 17.402  | 1.00 | 0.00  |

TABLE 23-continued

Coordinates for the 3D structure of ZAP-NC:ζ1 "dimer" structure
(two molecules of complex per unit cell)*

| ATOM | 5817 | OH2 | H2O | 2111 | 54.138 | −5.214 | 16.024 | 1.00 | 25.96 |
|------|------|-----|-----|------|--------|--------|--------|------|-------|
| ATOM | 5818 | H1  | H2O | 2111 | 53.742 | −4.396 | 15.713 | 1.00 | 0.00  |
| ATOM | 5819 | H2  | H2O | 2111 | 53.615 | −5.424 | 16.797 | 1.00 | 0.00  |
| ATOM | 5820 | OH2 | H2O | 2137 | 48.495 | −20.103| 22.150 | 1.00 | 23.95 |
| ATOM | 5821 | H1  | H2O | 2137 | 48.754 | −20.324| 21.248 | 1.00 | 0.00  |
| ATOM | 5822 | H2  | H2O | 2137 | 47.706 | −19.564| 22.023 | 1.00 | 0.00  |
| ATOM | 5823 | OH2 | H2O | 2018 | 41.599 | −13.711| 26.160 | 1.00 | 17.34 |
| ATOM | 5824 | H1  | H2O | 2018 | 42.183 | −14.405| 26.481 | 1.00 | 0.00  |
| ATOM | 5825 | H2  | H2O | 2018 | 41.682 | −13.790| 25.203 | 1.00 | 0.00  |
| ATOM | 5826 | OH2 | H2O | 2220 | 39.734 | −11.952| 27.025 | 1.00 | 13.25 |
| ATOM | 5827 | H1  | H2O | 2220 | 39.941 | −11.999| 27.961 | 1.00 | 0.00  |
| ATOM | 5828 | H2  | H2O | 2220 | 40.429 | −12.556| 26.668 | 1.00 | 0.00  |
| ATOM | 5829 | OH2 | H2O | 2007 | 38.551 | −8.691 | 27.629 | 1.00 | 11.59 |
| ATOM | 5830 | H1  | H2O | 2007 | 38.595 | −9.046 | 28.528 | 1.00 | 0.00  |
| ATOM | 5831 | H2  | H2O | 2007 | 39.156 | −9.276 | 27.166 | 1.00 | 0.00  |
| ATOM | 5832 | OH2 | H2O | 2338 | 39.902 | −21.211| 23.898 | 1.00 | 42.52 |
| ATOM | 5833 | H1  | H2O | 2338 | 40.074 | −21.614| 23.041 | 1.00 | 0.00  |
| ATOM | 5834 | H2  | H2O | 2338 | 40.667 | −20.628| 23.991 | 1.00 | 0.00  |
| ATOM | 5835 | OH2 | H2O | 2170 | 37.082 | −11.430| 19.932 | 1.00 | 8.72  |
| ATOM | 5836 | H1  | H2O | 2170 | 37.916 | −10.964| 20.031 | 1.00 | 0.00  |
| ATOM | 5837 | H2  | H2O | 2170 | 36.648 | −11.216| 20.773 | 1.00 | 0.00  |
| ATOM | 5838 | OH2 | H2O | 2291 | 35.762 | −12.267| 17.716 | 1.00 | 29.90 |
| ATOM | 5839 | H1  | H2O | 2291 | 35.672 | −13.215| 17.815 | 1.00 | 0.00  |
| ATOM | 5840 | H2  | H2O | 2291 | 36.292 | −12.037| 18.513 | 1.00 | 0.00  |
| ATOM | 5841 | OH2 | H2O | 2272 | 39.915 | −10.797| 17.685 | 1.00 | 44.60 |
| ATOM | 5842 | H1  | H2O | 2272 | 39.983 | −10.215| 16.922 | 1.00 | 0.00  |
| ATOM | 5843 | H2  | H2O | 2272 | 40.129 | −10.212| 18.420 | 1.00 | 0.00  |
| ATOM | 5844 | OH2 | H2O | 2197 | 43.409 | −20.674| 28.340 | 1.00 | 42.19 |
| ATOM | 5845 | H1  | H2O | 2197 | 43.896 | −21.187| 27.683 | 1.00 | 0.00  |
| ATOM | 5846 | H2  | H2O | 2197 | 42.571 | −21.155| 28.384 | 1.00 | 0.00  |
| ATOM | 5847 | OH2 | H2O | 2121 | 39.304 | −19.820| 27.794 | 1.00 | 27.99 |
| ATOM | 5848 | H1  | H2O | 2121 | 39.361 | −20.164| 26.895 | 1.00 | 0.00  |
| ATOM | 5849 | H2  | H2O | 2121 | 38.371 | −19.897| 27.999 | 1.00 | 0.00  |
| ATOM | 5850 | OH2 | H2O | 2407 | 51.999 | −9.716 | 41.121 | 1.00 | 70.95 |
| ATOM | 5851 | H1  | H2O | 2407 | 52.431 | −9.793 | 41.974 | 1.00 | 0.00  |
| ATOM | 5852 | H2  | H2O | 2407 | 52.746 | −9.752 | 40.505 | 1.00 | 0.00  |
| ATOM | 5853 | OH2 | H2O | 2359 | 43.346 | −4.177 | 37.568 | 1.00 | 42.93 |
| ATOM | 5854 | H1  | H2O | 2359 | 42.843 | −3.822 | 36.819 | 1.00 | 0.00  |
| ATOM | 5855 | H2  | H2O | 2359 | 43.092 | −3.596 | 38.289 | 1.00 | 0.00  |
| ATOM | 5856 | OH2 | H2O | 2391 | 55.832 | −19.322| 27.628 | 1.00 | 23.55 |
| ATOM | 5857 | H1  | H2O | 2391 | 55.780 | −18.633| 26.968 | 1.00 | 0.00  |
| ATOM | 5858 | H2  | H2O | 2391 | 56.673 | −19.147| 28.044 | 1.00 | 0.00  |
| ATOM | 5859 | OH2 | H2O | 2047 | 50.968 | −7.693 | 22.248 | 1.00 | 96.94 |
| ATOM | 5860 | H1  | H2O | 2047 | 50.442 | −7.529 | 21.462 | 1.00 | 0.00  |
| ATOM | 5861 | H2  | H2O | 2047 | 51.298 | −6.818 | 22.456 | 1.00 | 0.00  |
| ATOM | 5862 | OH2 | H2O | 2055 | 35.378 | −14.080| 21.765 | 1.00 | 49.87 |
| ATOM | 5863 | H1  | H2O | 2055 | 35.625 | −14.970| 21.492 | 1.00 | 0.00  |
| ATOM | 5864 | H2  | H2O | 2055 | 36.179 | −13.577| 21.544 | 1.00 | 0.00  |
| ATOM | 5865 | OH2 | H2O | 2006 | 34.501 | −16.131| 23.435 | 1.00 | 11.58 |
| ATOM | 5866 | H1  | H2O | 2006 | 34.648 | −15.191| 23.259 | 1.00 | 0.00  |
| ATOM | 5867 | H2  | H2O | 2006 | 34.190 | −16.133| 24.347 | 1.00 | 0.00  |
| ATOM | 5868 | OH2 | H2O | 2438 | 44.149 | −6.639 | 36.075 | 1.00 | 31.31 |
| ATOM | 5869 | H1  | H2O | 2438 | 43.202 | −6.824 | 36.071 | 1.00 | 0.00  |
| ATOM | 5870 | H2  | H2O | 2438 | 44.191 | −5.912 | 36.717 | 1.00 | 0.00  |
| ATOM | 5871 | OH2 | H2O | 2354 | 36.028 | −4.916 | 25.879 | 1.00 | 29.54 |
| ATOM | 5872 | H1  | H2O | 2354 | 35.896 | −4.591 | 26.772 | 1.00 | 0.00  |
| ATOM | 5873 | H2  | H2O | 2354 | 35.939 | −5.866 | 25.990 | 1.00 | 0.00  |
| ATOM | 5874 | OH2 | H2O | 2308 | 33.617 | −4.709 | 31.374 | 1.00 | 21.34 |
| ATOM | 5875 | H1  | H2O | 2308 | 34.430 | −5.022 | 31.830 | 1.00 | 0.00  |
| ATOM | 5876 | H2  | H2O | 2308 | 33.358 | −3.976 | 31.956 | 1.00 | 0.00  |
| ATOM | 5877 | OH2 | H2O | 2420 | 37.905 | 7.003  | 18.893 | 1.00 | 37.09 |
| ATOM | 5878 | H1  | H2O | 2420 | 38.486 | 6.250  | 19.034 | 1.00 | 0.00  |
| ATOM | 5879 | H2  | H2O | 2420 | 38.528 | 7.722  | 18.774 | 1.00 | 0.00  |
| ATOM | 5880 | OH2 | H2O | 2185 | 41.075 | 7.225  | 20.364 | 1.00 | 48.82 |
| ATOM | 5881 | H1  | H2O | 2185 | 40.346 | 7.335  | 20.976 | 1.00 | 0.00  |
| ATOM | 5882 | H2  | H2O | 2185 | 41.785 | 6.958  | 20.967 | 1.00 | 0.00  |
| ATOM | 5883 | OH2 | H2O | 2402 | 57.143 | −2.340 | 11.369 | 1.00 | 27.22 |
| ATOM | 5884 | H1  | H2O | 2402 | 57.652 | −1.628 | 11.759 | 1.00 | 0.00  |
| ATOM | 5885 | H2  | H2O | 2402 | 56.387 | −1.842 | 10.998 | 1.00 | 0.00  |
| ATOM | 5886 | OH2 | H2O | 2090 | 58.792 | −4.704 | 21.220 | 1.00 | 45.35 |
| ATOM | 5887 | H1  | H2O | 2090 | 59.176 | −4.804 | 22.105 | 1.00 | 0.00  |
| ATOM | 5888 | H2  | H2O | 2090 | 59.358 | −5.288 | 20.716 | 1.00 | 0.00  |
| ATOM | 5889 | OH2 | H2O | 2214 | 61.585 | 1.744  | 22.791 | 1.00 | 66.01 |
| ATOM | 5890 | H1  | H2O | 2214 | 60.908 | 1.086  | 22.576 | 1.00 | 0.00  |
| ATOM | 5891 | H2  | H2O | 2214 | 61.115 | 2.206  | 23.499 | 1.00 | 0.00  |
| ATOM | 5892 | OH2 | H2O | 2180 | 47.497 | −23.533| 21.262 | 1.00 | 19.46 |

TABLE 23-continued

Coordinates for the 3D structure of ZAP-NC:ζ1 "dimer" structure
(two molecules of complex per unit cell)*

| ATOM | 5893 | H1 | H2O | 2180 | 48.118 | −24.053 | 20.714 | 1.00 | 0.00 |
|---|---|---|---|---|---|---|---|---|---|
| ATOM | 5894 | H2 | H2O | 2180 | 47.939 | −22.672 | 21.265 | 1.00 | 0.00 |
| ATOM | 5895 | OH2 | H2O | 2208 | 45.577 | −25.548 | 24.777 | 1.00 | 34.69 |
| ATOM | 5896 | H1 | H2O | 2208 | 44.707 | −25.952 | 24.684 | 1.00 | 0.00 |
| ATOM | 5897 | H2 | H2O | 2208 | 46.149 | −26.159 | 24.313 | 1.00 | 0.00 |
| ATOM | 5898 | OH2 | H2O | 2033 | 24.690 | −14.893 | 21.736 | 1.00 | 5.32 |
| ATOM | 5899 | H1 | H2O | 2033 | 25.308 | −15.101 | 21.006 | 1.00 | 0.00 |
| ATOM | 5900 | H2 | H2O | 2033 | 24.598 | −13.934 | 21.584 | 1.00 | 0.00 |
| ATOM | 5901 | OH2 | H2O | 2160 | 30.810 | 9.362 | 18.06 | 1.00 | 63.50 |
| ATOM | 5902 | H1 | H2O | 2160 | 31.326 | −8.858 | 24.43 | 1.00 | 0.00 |
| ATOM | 5903 | H2 | H2O | 2160 | 30.705 | −10.213 | 22.59 | 1.00 | 0.00 |
| ATOM | 5904 | OH2 | H2O | 2194 | 31.416 | −15.610 | 74.47 | 1.00 | 65.23 |
| ATOM | 5905 | H1 | H2O | 2194 | 31.229 | −16.277 | 67.72 | 1.00 | 0.00 |
| ATOM | 5906 | H2 | H2O | 2194 | 32.035 | −15.023 | 70.10 | 1.00 | 0.00 |
| ATOM | 5907 | OH2 | H2O | 2370 | 31.999 | −15.570 | 12.535 | 1.00 | 24.67 |
| ATOM | 5908 | H1 | H2O | 2370 | 32.407 | −16.359 | 12.895 | 1.00 | 0.00 |
| ATOM | 5909 | H2 | H2O | 2370 | 31.786 | −15.803 | 11.629 | 1.00 | 0.00 |
| ATOM | 5910 | OH2 | H2O | 2136 | 29.123 | −28.115 | 11.438 | 1.00 | 35.74 |
| ATOM | 5911 | H1 | H2O | 2136 | 29.011 | −28.804 | 10.776 | 1.00 | 0.00 |
| ATOM | 5912 | H2 | H2O | 2136 | 28.613 | −27.383 | 11.083 | 1.00 | 0.00 |
| ATOM | 5913 | OH2 | H2O | 2030 | 23.452 | −11.832 | 22.557 | 1.00 | 10.50 |
| ATOM | 5914 | H1 | H2O | 2030 | 22.530 | −11.594 | 22.374 | 1.00 | 0.00 |
| ATOM | 5915 | H2 | H2O | 2030 | 23.864 | −10.993 | 22.317 | 1.00 | 0.00 |
| ATOM | 5916 | OH2 | H2O | 2412 | 20.673 | −7.099 | 20.940 | 1.00 | 56.26 |
| ATOM | 5917 | H1 | H2O | 2412 | 20.237 | −7.012 | 21.808 | 1.00 | 0.00 |
| ATOM | 5918 | H2 | H2O | 2412 | 20.180 | −6.433 | 20.446 | 1.00 | 0.00 |
| ATOM | 5919 | OH2 | H2O | 2089 | 15.819 | −22.003 | 23.299 | 1.00 | 35.26 |
| ATOM | 5920 | H1 | H2O | 2089 | 15.795 | −22.742 | 22.683 | 1.00 | 0.00 |
| ATOM | 5921 | H2 | H2O | 2089 | 16.771 | −21.953 | 23.470 | 1.00 | 0.00 |
| ATOM | 5922 | OH2 | H2O | 2072 | 11.320 | −15.295 | 32.192 | 1.00 | 20.48 |
| ATOM | 5923 | H1 | H2O | 2072 | 11.654 | −15.091 | 31.308 | 1.00 | 0.00 |
| ATOM | 5924 | H2 | H2O | 2072 | 11.384 | −16.258 | 32.186 | 1.00 | 0.00 |
| ATOM | 5925 | OH2 | H2O | 2316 | 10.042 | −12.494 | 33.237 | 1.00 | 24.17 |
| ATOM | 5926 | H1 | H2O | 2316 | 10.406 | −13.370 | 32.999 | 1.00 | 0.00 |
| ATOM | 5927 | H2 | H2O | 2316 | 10.289 | −12.453 | 34.164 | 1.00 | 0.00 |
| ATOM | 5928 | OH2 | H2O | 2399 | 8.603 | −14.948 | 35.233 | 1.00 | 23.99 |
| ATOM | 5929 | H1 | H2O | 2399 | 8.313 | −14.487 | 36.053 | 1.00 | 0.00 |
| ATOM | 5930 | H2 | H2O | 2399 | 8.473 | −14.262 | 34.569 | 1.00 | 0.00 |
| ATOM | 5931 | OH2 | H2O | 2192 | 7.916 | −13.636 | 37.451 | 1.00 | 70.33 |
| ATOM | 5932 | H1 | H2O | 2192 | 7.104 | −13.217 | 37.761 | 1.00 | 0.00 |
| ATOM | 5933 | H2 | H2O | 2192 | 8.601 | −13.075 | 37.836 | 1.00 | 0.00 |
| ATOM | 5934 | OH2 | H2O | 2231 | 8.067 | −13.460 | 23.591 | 1.00 | 38.21 |
| ATOM | 5935 | H1 | H2O | 2231 | 8.632 | −14.192 | 23.328 | 1.00 | 0.00 |
| ATOM | 5936 | H2 | H2O | 2231 | 7.984 | −12.955 | 22.777 | 1.00 | 0.00 |
| ATOM | 5937 | OH2 | H2O | 2161 | 16.836 | −33.080 | 34.391 | 1.00 | 54.29 |
| ATOM | 5938 | H1 | H2O | 2161 | 16.968 | −33.045 | 35.343 | 1.00 | 0.00 |
| ATOM | 5939 | H2 | H2O | 2161 | 17.012 | −32.166 | 34.136 | 1.00 | 0.00 |
| ATOM | 5940 | OH2 | H2O | 2140 | 26.971 | −29.009 | 44.630 | 1.00 | 9.87 |
| ATOM | 5941 | H1 | H2O | 2140 | 26.721 | −29.930 | 44.498 | 1.00 | 0.00 |
| ATOM | 5942 | H2 | H2O | 2140 | 27.184 | −28.985 | 45.569 | 1.00 | 0.00 |
| ATOM | 5943 | OH2 | H2O | 2246 | 23.752 | −26.455 | 45.524 | 1.00 | 8.02 |
| ATOM | 5944 | H1 | H2O | 2246 | 24.151 | −27.078 | 46.149 | 1.00 | 0.00 |
| ATOM | 5945 | H2 | H2O | 2246 | 23.459 | −27.079 | 44.834 | 1.00 | 0.00 |
| ATOM | 5946 | OH2 | H2O | 2440 | 13.303 | −10.401 | 26.635 | 1.00 | 52.80 |
| ATOM | 5947 | H1 | H2O | 2440 | 13.963 | −10.537 | 27.326 | 1.00 | 0.00 |
| ATOM | 5948 | H2 | H2O | 2440 | 12.478 | −10.553 | 27.125 | 1.00 | 0.00 |
| ATOM | 5949 | OH2 | H2O | 2331 | 15.775 | −24.807 | 48.886 | 1.00 | 17.34 |
| ATOM | 5950 | H1 | H2O | 2331 | 16.212 | −25.108 | 48.074 | 1.00 | 0.00 |
| ATOM | 5951 | H2 | H2O | 2331 | 16.323 | −24.056 | 49.119 | 1.00 | 0.00 |
| ATOM | 5952 | OH2 | H2O | 2070 | 15.042 | −18.872 | 44.584 | 1.00 | 18.63 |
| ATOM | 5953 | H1 | H2O | 2070 | 15.952 | −18.620 | 44.779 | 1.00 | 0.00 |
| ATOM | 5954 | H2 | H2O | 2070 | 14.605 | −18.849 | 45.437 | 1.00 | 0.00 |
| ATOM | 5955 | OH2 | H2O | 2271 | 17.717 | −14.518 | 46.249 | 1.00 | 47.83 |
| ATOM | 5956 | H1 | H2O | 2271 | 17.672 | −14.366 | 45.394 | 1.00 | 0.00 |
| ATOM | 5957 | H2 | H2O | 2271 | 17.046 | −15.189 | 46.389 | 1.00 | 0.00 |
| ATOM | 5958 | OH2 | H2O | 2379 | 25.821 | −12.138 | 44.278 | 1.00 | 32.22 |
| ATOM | 5959 | H1 | H2O | 2379 | 26.013 | −11.483 | 43.596 | 1.00 | 0.00 |
| ATOM | 5960 | H2 | H2O | 2379 | 25.466 | −11.558 | 44.966 | 1.00 | 0.00 |
| ATOM | 5961 | OH2 | H2O | 2108 | 20.565 | −9.761 | 39.099 | 1.00 | 2.25 |
| ATOM | 5962 | H1 | H2O | 2108 | 21.504 | −8.707 | 39.314 | 1.00 | 0.00 |
| ATOM | 5963 | H2 | H2O | 2108 | 20.219 | −8.866 | 39.994 | 1.00 | 0.00 |
| ATOM | 5964 | OH2 | H2O | 2328 | 24.406 | −6.118 | 40.654 | 1.00 | 14.45 |
| ATOM | 5965 | H1 | H2O | 2328 | 23.863 | −5.355 | 40.422 | 1.00 | 0.00 |
| ATOM | 5966 | H2 | H2O | 2328 | 25.189 | −5.982 | 40.114 | 1.00 | 0.00 |
| ATOM | 5967 | OH2 | H2O | 2425 | 21.666 | −3.377 | 40.429 | 1.00 | 52.73 |
| ATOM | 5968 | H1 | H2O | 2425 | 21.213 | −3.720 | 41.204 | 1.00 | 0.00 |

TABLE 23-continued

Coordinates for the 3D structure of ZAP-NC:ζ1 "dimer" structure
(two molecules of complex per unit cell)*

| ATOM | 5969 | H2  | H2O | 2425 | 20.930 | −3.079  | 39.862 | 1.00 | 0.00  |
|------|------|-----|-----|------|--------|---------|--------|------|-------|
| ATOM | 5970 | OH2 | H2O | 2205 | 21.184 | −1.374  | 23.368 | 1.00 | 17.33 |
| ATOM | 5971 | H1  | H2O | 2205 | 20.516 | −1.305  | 24.082 | 1.00 | 0.00  |
| ATOM | 5972 | H2  | H2O | 2205 | 20.771 | −1.991  | 22.764 | 1.00 | 0.00  |
| ATOM | 5973 | OH2 | H2O | 2362 | 19.416 | −1.273  | 25.451 | 1.00 | 28.10 |
| ATOM | 5974 | H1  | H2O | 2362 | 20.154 | −0.939  | 25.985 | 1.00 | 0.00  |
| ATOM | 5975 | H2  | H2O | 2362 | 18.683 | −1.148  | 26.064 | 1.00 | 0.00  |
| ATOM | 5976 | OH2 | H2O | 2061 | 24.677 | −1.554  | 32.306 | 1.00 | 11.86 |
| ATOM | 5977 | H1  | H2O | 2061 | 24.757 | −0.836  | 32.940 | 1.00 | 0.00  |
| ATOM | 5978 | H2  | H2O | 2061 | 24.437 | −2.296  | 32.864 | 1.00 | 0.00  |
| ATOM | 5979 | OH2 | H2O | 2119 | 27.988 | −8.763  | 33.829 | 1.00 | 17.60 |
| ATOM | 5980 | H1  | H2O | 2119 | 28.536 | −8.635  | 33.040 | 1.00 | 0.00  |
| ATOM | 5981 | H2  | H2O | 2119 | 28.598 | −9.196  | 34.463 | 1.00 | 0.00  |
| ATOM | 5982 | OH2 | H2O | 2348 | 32.711 | −3.145  | 40.465 | 1.00 | 16.04 |
| ATOM | 5983 | H1  | H2O | 2348 | 32.068 | −3.312  | 39.768 | 1.00 | 0.00  |
| ATOM | 5984 | H2  | H2O | 2348 | 33.008 | −4.037  | 40.705 | 1.00 | 0.00  |
| ATOM | 5985 | OH2 | H2O | 2312 | 32.395 | −3.078  | 33.580 | 1.00 | 31.42 |
| ATOM | 5986 | H1  | H2O | 2312 | 31.958 | −3.871  | 33.911 | 1.00 | 0.00  |
| ATOM | 5987 | H2  | H2O | 2312 | 31.799 | −2.392  | 33.903 | 1.00 | 0.00  |
| ATOM | 5988 | OH2 | H2O | 2344 | 33.317 | −0.119  | 30.693 | 1.00 | 56.56 |
| ATOM | 5989 | H1  | H2O | 2344 | 34.118 | −0.155  | 31.142 | 1.00 | 0.00  |
| ATOM | 5990 | H2  | H2O | 2344 | 32.652 | −0.479  | 31.039 | 1.00 | 0.00  |
| ATOM | 5991 | OH2 | H2O | 2333 | 35.576 | −5.496  | 33.034 | 1.00 | 18.08 |
| ATOM | 5992 | H1  | H2O | 2333 | 35.635 | −6.428  | 33.271 | 1.00 | 0.00  |
| ATOM | 5993 | H2  | H2O | 2333 | 35.578 | −5.071  | 33.898 | 1.00 | 0.00  |
| ATOM | 5994 | OH2 | H2O | 2077 | 33.384 | −15.305 | 26.976 | 1.00 | 20.62 |
| ATOM | 5995 | H1  | H2O | 2077 | 33.638 | −14.532 | 26.459 | 1.00 | 0.00  |
| ATOM | 5996 | H2  | H2O | 2077 | 32.779 | −14.932 | 37.622 | 1.00 | 0.00  |
| ATOM | 5997 | OH2 | H2O | 2172 | 26.897 | −25.114 | 28.985 | 1.00 | 30.56 |
| ATOM | 5998 | H1  | H2O | 2172 | 27.162 | −24.490 | 28.305 | 1.00 | 0.00  |
| ATOM | 5999 | H2  | H2O | 2172 | 27.491 | −24.907 | 29.710 | 1.00 | 0.00  |
| ATOM | 6000 | OH2 | H2O | 2446 | 44.010 | −15.901 | 36.613 | 1.00 | 37.57 |
| ATOM | 6001 | H1  | H2O | 2446 | 44.830 | −15.428 | 36.448 | 1.00 | 0.00  |
| ATOM | 6002 | H2  | H2O | 2446 | 44.123 | −16.235 | 37.506 | 1.00 | 0.00  |
| ATOM | 6003 | OH2 | H2O | 2433 | 38.438 | −17.405 | 38.176 | 1.00 | 48.29 |
| ATOM | 6004 | H1  | H2O | 2433 | 39.273 | −17.807 | 37.928 | 1.00 | 0.00  |
| ATOM | 6005 | H2  | H2O | 2433 | 37.797 | −17.920 | 37.666 | 1.00 | 0.00  |
| ATOM | 6006 | OH2 | H2O | 2067 | 29.631 | −9.895  | 35.716 | 1.00 | 14.12 |
| ATOM | 6007 | H1  | H2O | 2067 | 29.864 | −9.637  | 36.590 | 1.00 | 0.00  |
| ATOM | 6008 | H2  | H2O | 2067 | 29.434 | −10.847 | 35.846 | 1.00 | 0.00  |
| ATOM | 6009 | OH2 | H2O | 2321 | 35.644 | −17.632 | 40.417 | 1.00 | 20.37 |
| ATOM | 6010 | H1  | H2O | 2321 | 35.574 | −18.582 | 40.274 | 1.00 | 0.00  |
| ATOM | 6011 | H2  | H2O | 2321 | 36.571 | −17.459 | 40.197 | 1.00 | 0.00  |
| ATOM | 6012 | OH2 | H2O | 2063 | 24.202 | −17.470 | 37.624 | 1.00 | 45.80 |
| ATOM | 6013 | H1  | H2O | 2063 | 24.163 | −18.245 | 37.065 | 1.00 | 0.00  |
| ATOM | 6014 | H2  | H2O | 2063 | 25.140 | −17.311 | 37.751 | 1.00 | 0.00  |
| ATOM | 6015 | OH2 | H2O | 2130 | 13.699 | −5.868  | 38.824 | 1.00 | 30.28 |
| ATOM | 6016 | H1  | H2O | 2130 | 14.554 | −6.277  | 39.001 | 1.00 | 0.00  |
| ATOM | 6017 | H2  | H2O | 2130 | 13.728 | −5.092  | 39.392 | 1.00 | 0.00  |
| ATOM | 6018 | OH2 | H2O | 2154 | 9.242  | −14.997 | 28.355 | 1.00 | 24.97 |
| ATOM | 6019 | H1  | H2O | 2154 | 9.669  | −14.959 | 27.498 | 1.00 | 0.00  |
| ATOM | 6020 | H2  | H2O | 2154 | 9.793  | −15.603 | 28.854 | 1.00 | 0.00  |
| ATOM | 6021 | OH2 | H2O | 2249 | 25.464 | −8.982  | 47.160 | 1.00 | 21.25 |
| ATOM | 6022 | H1  | H2O | 2249 | 25.372 | −8.692  | 48.068 | 1.00 | 0.00  |
| ATOM | 6023 | H2  | H2O | 2249 | 25.631 | −8.176  | 46.668 | 1.00 | 0.00  |
| ATOM | 6024 | OH2 | H2O | 2300 | 29.028 | −2.245  | 34.431 | 1.00 | 41.04 |
| ATOM | 6025 | H1  | H2O | 2300 | 29.282 | −3.175  | 34.367 | 1.00 | 0.00  |
| ATOM | 6026 | H2  | H2O | 2300 | 28.487 | −2.123  | 33.650 | 1.00 | 0.00  |
| ATOM | 6027 | OH2 | H2O | 2204 | 33.950 | −9.271  | 48.503 | 1.00 | 28.17 |
| ATOM | 6028 | H1  | H2O | 2204 | 33.742 | −9.522  | 49.406 | 1.00 | 0.00  |
| ATOM | 6029 | H2  | H2O | 2204 | 33.127 | −9.462  | 48.040 | 1.00 | 0.00  |
| ATOM | 6030 | OH2 | H2O | 2288 | 40.485 | −9.257  | 37.985 | 1.00 | 13.77 |
| ATOM | 6031 | H1  | H2O | 2288 | 41.241 | −9.027  | 37.430 | 1.00 | 0.00  |
| ATOM | 6032 | H2  | H2O | 2288 | 40.854 | −9.285  | 38.872 | 1.00 | 0.00  |
| ATOM | 6033 | OH2 | H2O | 2141 | 40.365 | −14.937 | 30.859 | 1.00 | 20.91 |
| ATOM | 6034 | H1  | H2O | 2141 | 40.009 | −14.090 | 31.144 | 1.00 | 0.00  |
| ATOM | 6035 | H2  | H2O | 2141 | 39.970 | −15.022 | 29.984 | 1.00 | 0.00  |
| ATOM | 6036 | OH2 | H2O | 2101 | 45.271 | 6.055   | 35.780 | 1.00 | 63.28 |
| ATOM | 6037 | H1  | H2O | 2101 | 45.897 | 6.745   | 35.495 | 1.00 | 0.00  |
| ATOM | 6038 | H2  | H2O | 2101 | 12.071 | 5.698   | 34.903 | 1.00 | 0.00  |
| ATOM | 6039 | OH2 | H2O | 2010 | 32.554 | 4.915   | −4.911 | 1.00 | 28.06 |
| ATOM | 6040 | H1  | H2O | 2010 | 32.927 | 5.785   | −4.780 | 1.00 | 0.00  |
| ATOM | 6041 | H2  | H2O | 2010 | 32.828 | 4.445   | −4.101 | 1.00 | 0.00  |
| ATOM | 6042 | OH2 | H2O | 2015 | 21.877 | −20.746 | 49.067 | 1.00 | 8.80  |
| ATOM | 6043 | H1  | H2O | 2015 | 22.711 | −20.839 | 49.547 | 1.00 | 0.00  |
| ATOM | 6044 | H2  | H2O | 2015 | 22.034 | −21.259 | 48.267 | 1.00 | 0.00  |

TABLE 23-continued

Coordinates for the 3D structure of ZAP-NC:ζ1 "dimer" structure
(two molecules of complex per unit cell)*

| ATOM | 6045 | OH2 | H2O | 3191 | −3.078 | −4.252 | 10.967 | 1.00 | 16.19 |
|---|---|---|---|---|---|---|---|---|---|
| ATOM | 6046 | H1 | H2O | 3191 | −3.469 | −3.684 | 11.636 | 1.00 | 0.00 |
| ATOM | 6047 | H2 | H2O | 3191 | −3.834 | −4.669 | 10.551 | 1.00 | 0.00 |
| ATOM | 6048 | OH2 | H2O | 3147 | 8.060 | −4.377 | 9.828 | 1.00 | 16.74 |
| ATOM | 6049 | H1 | H2O | 3147 | 8.121 | −4.590 | 10.768 | 1.00 | 0.00 |
| ATOM | 6050 | H2 | H2O | 3147 | 8.142 | −5.258 | 94.35 | 1.00 | 0.00 |
| ATOM | 6051 | OH2 | H2O | 3098 | 5.207 | 8.717 | −7.692 | 1.00 | 30.64 |
| ATOM | 6052 | H1 | H2O | 3098 | 4.246 | 8.849 | −7.841 | 1.00 | 0.00 |
| ATOM | 6053 | H2 | H2O | 3098 | 5.523 | 8.644 | −8.595 | 1.00 | 0.00 |
| ATOM | 6054 | OH2 | H2O | 3156 | 2.425 | 9.047 | −8.391 | 1.00 | 29.49 |
| ATOM | 6055 | H1 | H2O | 3156 | 1.889 | 8.446 | −8.916 | 1.00 | 0.00 |
| ATOM | 6056 | H2 | H2O | 3156 | 1.733 | 9.656 | −8.061 | 1.00 | 0.00 |
| ATOM | 6057 | OH2 | H2O | 3104 | 9.654 | 2.444 | −4.630 | 1.00 | 38.50 |
| ATOM | 6058 | H1 | H2O | 3104 | 9.692 | 3.402 | −4.681 | 1.00 | 0.00 |
| ATOM | 6059 | H2 | H2O | 3104 | 10.346 | 2.182 | −5.249 | 1.00 | 0.00 |
| ATOM | 6060 | OH2 | H2O | 3212 | 15.589 | 9.732 | −1.575 | 1.00 | 19.23 |
| ATOM | 6061 | H1 | H2O | 3212 | 14.759 | 10.169 | −1.343 | 1.00 | 0.00 |
| ATOM | 6062 | H2 | H2O | 3212 | 16.112 | 10.516 | −1.784 | 1.00 | 0.00 |
| ATOM | 6063 | OH2 | H2O | 3181 | −3.743 | 1.638 | 1.512 | 1.00 | 27.00 |
| ATOM | 6064 | H1 | H2O | 3181 | −2.961 | 1.156 | 1.243 | 1.00 | 0.00 |
| ATOM | 6065 | H2 | H2O | 3181 | −4.400 | 1.099 | 1.015 | 1.00 | 0.00 |
| ATOM | 6066 | OH2 | H2O | 3019 | −4.806 | −0.424 | 0.247 | 1.00 | 26.95 |
| ATOM | 6067 | H1 | H2O | 3019 | −4.368 | −1.251 | 0.014 | 1.00 | 0.00 |
| ATOM | 6068 | H2 | H2O | 3019 | −5.295 | −0.744 | 1.049 | 1.00 | 0.00 |
| ATOM | 6069 | OH2 | H2O | 3178 | −5.835 | −1.383 | 2.620 | 1.00 | 25.81 |
| ATOM | 6070 | H1 | H2O | 3178 | −5.525 | −2.113 | 3.165 | 1.00 | 0.00 |
| ATOM | 6071 | H2 | H2O | 3178 | −5.630 | −0.630 | 3.204 | 1.00 | 0.00 |
| ATOM | 6072 | OH2 | H2O | 3141 | 31.801 | −27.442 | 2.541 | 1.00 | 42.64 |
| ATOM | 6073 | H1 | H2O | 3141 | 31.519 | −27.882 | 1.730 | 1.00 | 0.00 |
| ATOM | 6074 | H2 | H2O | 3141 | 32.479 | −28.053 | 2.863 | 1.00 | 0.00 |
| ATOM | 6075 | OH2 | H2O | 3125 | 0.814 | 26.814 | 11.397 | 1.00 | 42.53 |
| ATOM | 6076 | H1 | H2O | 3125 | 0.885 | 27.670 | 11.830 | 1.00 | 0.00 |
| ATOM | 6077 | H2 | H2O | 3125 | −0.088 | 26.558 | 11.618 | 1.00 | 0.00 |
| ATOM | 6078 | OH2 | H2O | 3013 | 8.353 | −1.014 | 13.721 | 1.00 | 39.02 |
| ATOM | 6079 | H1 | H2O | 3013 | 9.135 | −0.527 | 13.410 | 1.00 | 0.00 |
| ATOM | 6080 | H2 | H2O | 3013 | 7.943 | −1.259 | 12.884 | 1.00 | 0.00 |
| ATOM | 6081 | OH2 | H2O | 3029 | 16.903 | 3.887 | 5.300 | 1.00 | 15.87 |
| ATOM | 6082 | H1 | H2O | 3029 | 16.700 | 3.026 | 5.691 | 1.00 | 0.00 |
| ATOM | 6083 | H2 | H2O | 3029 | 16.844 | 3.720 | 4.351 | 1.00 | 0.00 |
| ATOM | 6084 | OH2 | H2O | 3064 | 8.191 | 20.675 | 1.300 | 1.00 | 33.79 |
| ATOM | 6085 | H1 | H2O | 3064 | 8.643 | 21.164 | 0.604 | 1.00 | 0.00 |
| ATOM | 6086 | H2 | H2O | 3064 | 7.835 | 19.914 | 0.829 | 1.00 | 0.00 |
| ATOM | 6087 | OH2 | H2O | 3090 | −2.265 | 27.363 | 13.784 | 1.00 | 57.66 |
| ATOM | 6088 | H1 | H2O | 3090 | −2.320 | 26.647 | 14.421 | 1.00 | 0.00 |
| ATOM | 6089 | H2 | H2O | 3090 | −3.039 | 27.231 | 13.231 | 1.00 | 0.00 |
| ATOM | 6090 | OH2 | H2O | 3199 | 17.013 | 1.765 | 10.108 | 1.00 | 33.28 |
| ATOM | 6091 | H1 | H2O | 3199 | 17.299 | 1.776 | 11.032 | 1.00 | 0.00 |
| ATOM | 6092 | H2 | H2O | 3199 | 17.836 | 1.578 | 9.644 | 1.00 | 0.00 |
| ATOM | 6093 | OH2 | H2O | 3058 | 19.287 | −2.958 | 9.801 | 1.00 | 35.84 |
| ATOM | 6094 | H1 | H2O | 3058 | 19.593 | −3.850 | 10.036 | 1.00 | 0.00 |
| ATOM | 6095 | H2 | H2O | 3058 | 19.775 | −2.798 | 8.991 | 1.00 | 0.00 |
| ATOM | 6096 | OH2 | H2O | 3223 | −9.812 | −0.517 | 10.459 | 1.00 | 66.07 |
| ATOM | 6097 | H1 | H2O | 3223 | −9.918 | 0.387 | 10.100 | 1.00 | 0.00 |
| ATOM | 6098 | H2 | H2O | 3223 | −10.701 | −0.862 | 10.362 | 1.00 | 0.00 |
| ATOM | 6099 | OH2 | H2O | 3194 | 24.050 | −18.614 | 0.304 | 1.00 | 32.20 |
| ATOM | 6100 | H1 | H2O | 3194 | 23.909 | −19.568 | 0.359 | 1.00 | 0.00 |
| ATOM | 6101 | H2 | H2O | 3194 | 23.458 | −18.365 | 0.415 | 1.00 | 0.00 |
| ATOM | 6102 | OH2 | H2O | 3137 | 18.552 | −14.358 | 19.355 | 1.00 | 64.23 |
| ATOM | 6103 | H1 | H2O | 3137 | 19.371 | −13.903 | 19.578 | 1.00 | 0.00 |
| ATOM | 6104 | H2 | H2O | 3137 | 18.856 | −15.295 | 19.328 | 1.00 | 0.00 |
| ATOM | 6105 | OH2 | H2O | 3108 | 22.639 | 14.497 | 11.334 | 1.00 | 51.77 |
| ATOM | 6106 | H1 | H2O | 3108 | 22.763 | 14.199 | 12.248 | 1.00 | 0.00 |
| ATOM | 6107 | H2 | H2O | 3108 | 23.235 | 13.880 | 10.879 | 1.00 | 0.00 |
| ATOM | 6108 | OH2 | H2O | 3091 | 56.601 | −4.492 | 19.249 | 1.00 | 48.51 |
| ATOM | 6109 | H1 | H2O | 3091 | 27.268 | −4.523 | 19.963 | 1.00 | 0.00 |
| ATOM | 6110 | H2 | H2O | 3094 | 56.163 | −3.659 | 19.474 | 1.00 | 0.00 |
| ATOM | 6111 | OH2 | H2O | 3017 | 47.313 | −10.322 | 26.171 | 1.00 | 102.08 |
| ATOM | 6112 | H1 | H2O | 3017 | 48.025 | −10.044 | 25.576 | 1.00 | 0.00 |
| ATOM | 6113 | H2 | H2O | 3017 | 46.553 | −10.276 | 25.584 | 1.00 | 0.00 |
| ATOM | 6114 | OH2 | H2O | 3117 | 36.098 | 1.714 | 21.377 | 1.00 | 39.42 |
| ATOM | 6115 | H1 | H2O | 3117 | 35.588 | 0.898 | 21.398 | 1.00 | 0.00 |
| ATOM | 6116 | H2 | H2O | 3117 | 35.861 | 2.135 | 22.207 | 1.00 | 0.00 |
| ATOM | 6117 | OH2 | H2O | 3200 | 9.862 | −19.643 | 45.852 | 1.00 | 43.84 |
| ATOM | 6118 | H1 | H2O | 3200 | 9.445 | −19.512 | 44.999 | 1.00 | 0.00 |
| ATOM | 6119 | H2 | H2O | 3200 | 9.166 | −19.458 | 46.485 | 1.00 | 0.00 |
| ATOM | 6120 | OH2 | H2O | 3040 | 28.246 | −22.043 | 26.268 | 1.00 | 21.05 |

TABLE 23-continued

Coordinates for the 3D structure of ZAP-NC:ζ1 "dimer" structure
(two molecules of complex per unit cell)*

| ATOM | 6121 | H1 | H2O | 3040 | 29.090 | −22.212 | 25.842 | 1.00 | 0.00 |
|---|---|---|---|---|---|---|---|---|---|
| ATOM | 6122 | H2 | H2O | 3040 | 28.110 | −21.103 | 26.103 | 1.00 | 0.00 |
| ATOM | 6123 | OH2 | H2O | 3047 | 32.378 | −20.251 | 42.121 | 1.00 | 20.98 |
| ATOM | 6124 | H1 | H2O | 3047 | 32.631 | −19.373 | 42.435 | 1.00 | 0.00 |
| ATOM | 6125 | H2 | H2O | 3047 | 32.745 | −20.828 | 42.799 | 1.00 | 0.00 |
| ATOM | 6126 | OH2 | H2O | 3061 | 26.628 | −27.624 | 38.628 | 1.00 | 16.19 |
| ATOM | 6127 | H1 | H2O | 3061 | 25.753 | −27.319 | 38.895 | 1.00 | 0.00 |
| ATOM | 6128 | H2 | H2O | 3061 | 27.210 | −27.114 | 39.215 | 1.00 | 0.00 |
| ATOM | 6129 | OH2 | H2O | 3206 | 15.002 | −7.120 | 42.223 | 1.00 | 29.38 |
| ATOM | 6130 | H1 | H2O | 3206 | 14.082 | −7.406 | 42.327 | 1.00 | 0.00 |
| ATOM | 6131 | H2 | H2O | 3206 | 15.150 | −6.557 | 42.986 | 1.00 | 0.00 |
| ATOM | 6132 | OH2 | H2O | 3045 | 41.800 | −16.544 | 33.852 | 1.00 | 33.08 |
| ATOM | 6133 | H1 | H2O | 3045 | 40.959 | −16.083 | 33.908 | 1.00 | 0.00 |
| ATOM | 6134 | H2 | H2O | 3045 | 42.155 | −16.453 | 34.748 | 1.00 | 0.00 |
| END | | | | | | | | | |

*Note: See copyright notice on page 1.

TABLE 24

Coordinates for the 3D structure of SYK-C:peptide complex
created by user: dave

| ATOM | 1 | N | THR | 1 | 4.888 | 9.383 | 9.370 | 1.00 | 1.25 | PEP |
|---|---|---|---|---|---|---|---|---|---|---|
| ATOM | 2 | HN | THR | 1 | 4.897 | 8.671 | 10.072 | 1.00 | 1.30 | PEP |
| ATOM | 3 | CA | THR | 1 | 5.664 | 9.239 | 8.157 | 1.00 | 1.17 | PEP |
| ATOM | 4 | HA | THR | 1 | 6.160 | 10.195 | 7.974 | 1.00 | 1.22 | PEP |
| ATOM | 5 | CB | THR | 1 | 6.679 | 8.116 | 8.338 | 1.00 | 1.23 | PEP |
| ATOM | 6 | HB | THR | 1 | 6.327 | 7.446 | 9.117 | 1.00 | 1.29 | PEP |
| ATOM | 7 | OG1 | THR | 1 | 7.908 | 8.651 | 8.766 | 1.00 | 1.37 | PEP |
| ATOM | 8 | HG1 | THR | 1 | 8.091 | 8.269 | 9.614 | 1.00 | 1.72 | PEP |
| ATOM | 9 | CG2 | THR | 1 | 6.889 | 7.323 | 7.048 | 1.00 | 1.13 | PEP |
| ATOM | 10 | HG21 | THR | 1 | 6.764 | 7.967 | 6.175 | 1.00 | 1.37 | PEP |
| ATOM | 11 | HG22 | THR | 1 | 7.885 | 6.893 | 7.012 | 1.00 | 1.59 | PEP |
| ATOM | 12 | HG23 | THR | 1 | 6.165 | 6.511 | 6.970 | 1.00 | 1.49 | PEP |
| ATOM | 13 | C | THR | 1 | 4.724 | 8.926 | 6.998 | 1.00 | 1.00 | PEP |
| ATOM | 14 | O | THR | 1 | 4.484 | 7.776 | 6.650 | 1.00 | 0.99 | PEP |
| ATOM | 15 | CT2 | THR | 1 | 3.263 | 10.438 | 10.767 | 1.00 | 1.39 | PEP |
| ATOM | 16 | HT21 | THR | 1 | 2.897 | 9.423 | 10.918 | 1.00 | 1.48 | PEP |
| ATOM | 17 | HT22 | THR | 1 | 3.830 | 10.744 | 11.645 | 1.00 | 1.89 | PEP |
| ATOM | 18 | HT23 | THR | 1 | 2.412 | 11.106 | 10.644 | 1.00 | 1.82 | PEP |
| ATOM | 19 | CNT | THR | 1 | 4.150 | 10.492 | 9.528 | 1.00 | 1.28 | PEP |
| ATOM | 20 | ONT | THR | 1 | 4.157 | 11.458 | 8.775 | 1.00 | 1.27 | PEP |
| ATOM | 21 | N | PTYR | 2 | 4.187 | 10.014 | 6.438 | 1.00 | 0.94 | PEP |
| ATOM | 22 | HN | PTYR | 2 | 4.382 | 10.915 | 6.792 | 1.00 | 1.03 | PEP |
| ATOM | 23 | CA | PTYR | 2 | 3.272 | 9.812 | 5.331 | 1.00 | 0.82 | PEP |
| ATOM | 24 | HA | PTYR | 2 | 3.596 | 8.897 | 4.834 | 1.00 | 0.77 | PEP |
| ATOM | 25 | CB | PTYR | 2 | 1.861 | 9.638 | 5.864 | 1.00 | 0.82 | PEP |
| ATOM | 26 | HB1 | PTYR | 2 | 1.549 | 10.512 | 6.435 | 1.00 | 0.91 | PEP |
| ATOM | 27 | HB2 | PTYR | 2 | 1.151 | 9.496 | 5.049 | 1.00 | 0.76 | PEP |
| ATOM | 28 | CG | PTYR | 2 | 1.861 | 8.447 | 6.740 | 1.00 | 0.84 | PEP |
| ATOM | 29 | CD1 | PTYR | 2 | 1.804 | 7.154 | 6.171 | 1.00 | 0.75 | PEP |
| ATOM | 30 | HD1 | PTYR | 2 | 1.650 | 7.036 | 5.110 | 1.00 | 0.67 | PEP |
| ATOM | 31 | CE1 | PTYR | 2 | 1.984 | 6.023 | 6.974 | 1.00 | 0.82 | PEP |
| ATOM | 32 | HE1 | PTYR | 2 | 1.976 | 5.051 | 6.522 | 1.00 | 0.78 | PEP |
| ATOM | 33 | CD2 | PTYR | 2 | 2.091 | 8.598 | 8.127 | 1.00 | 1.00 | PEP |
| ATOM | 34 | HD2 | PTYR | 2 | 2.160 | 9.584 | 8.557 | 1.00 | 1.09 | PEP |
| ATOM | 35 | CE2 | PTYR | 2 | 2.275 | 7.471 | 8.938 | 1.00 | 1.06 | PEP |
| ATOM | 36 | HE2 | PTYR | 2 | 2.506 | 7.601 | 9.977 | 1.00 | 1.20 | PEP |
| ATOM | 37 | CZ | PTYR | 2 | 2.218 | 6.185 | 8.359 | 1.00 | 0.97 | PEP |
| ATOM | 38 | OH | PTYR | 2 | 2.396 | 5.057 | 9.180 | 1.00 | 1.07 | PEP |
| ATOM | 39 | PO4 | PTYR | 2 | 2.748 | 3.685 | 8.518 | 1.00 | 1.77 | PEP |
| ATOM | 40 | OC1 | PTYR | 2 | 1.375 | 3.038 | 8.201 | 1.00 | 2.43 | PEP |
| ATOM | 41 | OC2 | PTYR | 2 | 3.442 | 2.874 | 9.642 | 1.00 | 2.32 | PEP |
| ATOM | 42 | OT | PTYR | 2 | 3.609 | 3.836 | 7.299 | 1.00 | 2.72 | PEP |
| ATOM | 43 | C | PTYR | 2 | 3.336 | 10.946 | 4.334 | 1.00 | 0.81 | PEP |
| ATOM | 44 | O | PTYR | 2 | 2.857 | 12.052 | 4.556 | 1.00 | 0.95 | PEP |
| ATOM | 45 | N | GLU | 3 | 3.965 | 10.574 | 3.218 | 1.00 | 0.77 | PEP |
| ATOM | 46 | HN | GLU | 3 | 4.351 | 9.647 | 3.139 | 1.00 | 0.83 | PEP |
| ATOM | 47 | CA | GLU | 3 | 4.047 | 11.530 | 2.143 | 1.00 | 0.78 | PEP |
| ATOM | 48 | HA | GLU | 3 | 4.702 | 12.335 | 2.480 | 1.00 | 0.88 | PEP |
| ATOM | 49 | CB | GLU | 3 | 4.684 | 10.868 | 0.932 | 1.00 | 0.74 | PEP |
| ATOM | 50 | HB1 | GLU | 3 | 4.092 | 10.004 | 0.646 | 1.00 | 0.73 | PEP |
| ATOM | 51 | HB2 | GLU | 3 | 4.669 | 11.558 | 0.089 | 1.00 | 0.82 | PEP |

TABLE 24-continued

Coordinates for the 3D structure of SYK-C:peptide complex
created by user: dave

| ATOM | 52 | CG | GLU | 2 | 6.115 | 10.435 | 1.220 | 1.00 | 0.91 | PEP |
|---|---|---|---|---|---|---|---|---|---|---|
| ATOM | 53 | HG1 | GLU | 3 | 6.134 | 9.445 | 1.669 | 1.00 | 1.30 | PEP |
| ATOM | 54 | HG2 | GLU | 3 | 6.666 | 10.389 | 0.306 | 1.00 | 1.26 | PEP |
| ATOM | 55 | CD | GLU | 3 | 6.811 | 11.423 | 2.161 | 1.00 | 1.64 | PEP |
| ATOM | 56 | OE1 | GLU | 3 | 7.497 | 12.317 | 1.671 | 1.00 | 2.20 | PEP |
| ATOM | 57 | OE2 | GLU | 3 | 6.658 | 11.284 | 3.374 | 1.00 | 2.38 | PEP |
| ATOM | 58 | C | GLU | 3 | 2.683 | 12.066 | 1.850 | 1.00 | 0.76 | PEP |
| ATOM | 59 | O | GLU | 3 | 1.683 | 11.545 | 2.327 | 1.00 | 0.74 | PEP |
| ATOM | 60 | N | THR | 4 | 2.676 | 13.136 | 1.047 | 1.00 | 0.80 | PEP |
| ATOM | 61 | HN | THR | 4 | 3.522 | 13.511 | 0.673 | 1.00 | 0.86 | PEP |
| ATOM | 62 | CA | THR | 4 | 1.393 | 13.722 | 0.739 | 1.00 | 0.78 | PEP |
| ATOM | 63 | HA | THR | 4 | 0.670 | 13.269 | 1.432 | 1.00 | 0.75 | PEP |
| ATOM | 64 | CB | THR | 4 | 1.459 | 15.232 | 0.916 | 1.00 | 0.90 | PEP |
| ATOM | 65 | HB | THR | 4 | 0.752 | 15.698 | 0.241 | 1.00 | 1.28 | PEP |
| ATOM | 66 | OG1 | THR | 4 | 2.741 | 15.694 | 0.561 | 1.00 | 1.59 | PEP |
| ATOM | 67 | HG1 | THR | 4 | 2.614 | 16.446 | −0.002 | 1.00 | 2.03 | PEP |
| ATOM | 68 | CG2 | THR | 4 | 1.145 | 15.651 | 2.353 | 1.00 | 1.71 | PEP |
| ATOM | 69 | HG21 | THR | 4 | 1.866 | 15.224 | 3.049 | 1.00 | 2.14 | PEP |
| ATOM | 70 | HG22 | THR | 4 | 0.151 | 15.313 | 2.647 | 1.00 | 2.33 | PEP |
| ATOM | 71 | HG23 | THR | 4 | 1.176 | 16.735 | 2.458 | 1.00 | 2.26 | PEP |
| ATOM | 72 | C | THR | 4 | 0.969 | 13.357 | −0.668 | 1.00 | 0.72 | PEP |
| ATOM | 73 | O | THR | 4 | 1.550 | 13.759 | −1.668 | 1.00 | 0.77 | PEP |
| ATOM | 74 | N | LEU | 5 | −0.094 | 12.553 | −0.635 | 1.00 | 0.65 | PEP |
| ATOM | 75 | HN | LEU | 5 | −0.485 | 12.282 | 0.242 | 1.00 | 0.67 | PEP |
| ATOM | 76 | HA | LEU | 5 | 0.126 | 11.614 | −2.443 | 1.00 | 0.63 | PEP |
| ATOM | 77 | CB | LEU | 5 | −1.709 | 11.032 | −1.462 | 1.00 | 0.59 | PEP |
| ATOM | 78 | HB1 | LEU | 5 | −1.792 | 10.968 | −0.376 | 1.00 | 0.64 | PEP |
| ATOM | 79 | HB2 | LEU | 5 | −2.682 | 11.326 | −1.842 | 1.00 | 0.68 | PEP |
| ATOM | 80 | CG | LEU | 5 | −1.318 | 9.692 | −2.026 | 1.00 | 0.46 | PEP |
| ATOM | 81 | HG | LEU | 5 | −0.240 | 9.683 | −2.166 | 1.00 | 0.52 | PEP |
| ATOM | 82 | CD1 | LEU | 5 | −1.705 | 8.560 | −1.097 | 1.00 | 0.42 | PEP |
| ATOM | 83 | HD11 | LEU | 5 | −2.721 | 8.227 | −1.304 | 1.00 | 1.11 | PEP |
| ATOM | 84 | HD12 | LEU | 5 | −1.037 | 7.710 | −1.230 | 1.00 | 1.12 | PEP |
| ATOM | 85 | HD13 | LEU | 5 | −1.654 | 8.878 | −0.060 | 1.00 | 1.10 | PEP |
| ATOM | 86 | CD2 | LEU | 5 | −1.988 | 9.514 | −3.356 | 1.00 | 0.52 | PEP |
| ATOM | 87 | HD21 | LEU | 5 | −2.029 | 10.457 | −3.888 | 1.00 | 1.11 | PEP |
| ATOM | 88 | HD22 | LEU | 5 | −1.451 | 8.810 | −3.959 | 1.00 | 1.26 | PEP |
| ATOM | 89 | HD23 | LEU | 5 | −3.002 | 9.149 | −3.225 | 1.00 | 1.00 | PEP |
| ATOM | 90 | C | LEU | 5 | −1.322 | 13.231 | −2.604 | 1.00 | 0.72 | PEP |
| ATOM | 91 | O | LEU | 5 | −2.536 | 13.382 | −2.640 | 1.00 | 1.31 | PEP |
| ATOM | 92 | NCT | LEU | 5 | −0.427 | 14.037 | −3.203 | 1.00 | 1.13 | PEP |
| ATOM | 93 | HCT1 | LEU | 5 | 0.554 | 13.850 | −3.136 | 1.00 | 1.72 | PEP |
| ATOM | 94 | HCT2 | LEU | 5 | −0.727 | 14.836 | −3.724 | 1.00 | 1.61 | PEP |
| ATOM | 95 | CA | LEU | 5 | −0.675 | 12.071 | −1.845 | 1.00 | 0.63 | PEP |
| ATOM | 96 | N | GLY | 1 | −21.702 | −18.923 | 0.217 | 1.00 | 11.53 | ACSY |
| ATOM | 97 | HT1 | GLY | 1 | −21.532 | −19.938 | 0.069 | 1.00 | 11.78 | ACSY |
| ATOM | 98 | HT2 | GLY | 1 | −21.935 | −18.753 | 1.216 | 1.00 | 11.73 | ACSY |
| ATOM | 99 | HT3 | GLY | 1 | −22.495 | −18.614 | −0.381 | 1.00 | 11.61 | ACSY |
| ATOM | 100 | CA | GLY | 1 | −20.504 | −18.172 | −0.138 | 1.00 | 11.06 | ACSY |
| ATOM | 101 | HA1 | GLY | 1 | −20.709 | −17.110 | 0.000 | 1.00 | 11.33 | ACSY |
| ATOM | 102 | HA2 | GLY | 1 | −20.287 | −18.347 | −1.191 | 1.00 | 11.13 | ACSY |
| ATOM | 103 | C | GLY | 1 | −19.296 | −18.576 | 0.710 | 1.00 | 10.41 | ACSY |
| ATOM | 104 | O | GLY | 1 | −18.259 | −18.988 | 0.205 | 1.00 | 10.65 | ACSY |
| ATOM | 105 | N | SER | 2 | −19.508 | −18.427 | 2.030 | 1.00 | 9.79 | ACSY |
| ATOM | 106 | HN | SER | 2 | −20.383 | −18.084 | 2.371 | 1.00 | 9.80 | ACSY |
| ATOM | 107 | CA | SER | 2 | −18.439 | −18.776 | 2.950 | 1.00 | 9.36 | ACSY |
| ATOM | 108 | HA | SER | 2 | −18.713 | −18.382 | 3.932 | 1.00 | 9.73 | ACSY |
| ATOM | 109 | CB | SER | 2 | −18.285 | −20.294 | 2.997 | 1.00 | 9.43 | ACSY |
| ATOM | 110 | HB1 | SER | 2 | −17.509 | −20.584 | 3.707 | 1.00 | 9.49 | ACSY |
| ATOM | 111 | HB2 | SER | 2 | −19.216 | −20.770 | 3.304 | 1.00 | 9.38 | ACSY |
| ATOM | 112 | OG | SER | 2 | −17.932 | −20.796 | 1.734 | 1.00 | 9.82 | ACSY |
| ATOM | 113 | HG | SER | 2 | −17.058 | −21.152 | 1.816 | 1.00 | 9.92 | ACSY |
| ATOM | 114 | C | SER | 2 | −17.138 | −18.119 | 2.492 | 1.00 | 8.68 | ACSY |
| ATOM | 115 | O | SER | 2 | −16.353 | −18.690 | 1.743 | 1.00 | 8.72 | ACSY |
| ATOM | 116 | N | ARG | 3 | −16.966 | −16.884 | 2.99S | 1.00 | 8.32 | ACSY |
| ATOM | 117 | HN | ARG | 3 | −17.651 | −16.480 | 3.602 | 1.00 | 8.52 | ACSY |
| ATOM | 118 | CA | ARG | 3 | −15.762 | −16.148 | 2.637 | 1.00 | 7.90 | ACSY |
| ATOM | 119 | HA | ARG | 3 | −14.911 | −16.807 | 2.821 | 1.00 | 8.17 | ACSY |
| ATOM | 120 | CB | ARG | 3 | −15.827 | −15.760 | 1.166 | 1.00 | 8.52 | ACSY |
| ATOM | 121 | HB1 | ARG | 3 | −15.054 | −15.025 | 0.947 | 1.00 | 8.76 | ACSY |
| ATOM | 122 | HB2 | ARG | 3 | −15.616 | −16.634 | 0.549 | 1.00 | 8.65 | ACSY |
| ATOM | 123 | CG | ARG | 3 | −17.196 | −15.193 | 0.797 | 1.00 | 9.04 | ACSY |
| ATOM | 124 | HG1 | ARG | 3 | −17.381 | −14.282 | 1.366 | 1.00 | 9.17 | ACSY |
| ATOM | 125 | HG2 | ARG | 3 | −17.973 | −15.903 | 1.079 | 1.00 | 9.09 | ACSY |
| ATOM | 126 | CD | ARG | 3 | −17.293 | −14.895 | −0.696 | 1.00 | 9.72 | ACSY |
| ATOM | 127 | HD1 | ARG | 3 | −18.320 | −14.681 | −0.993 | 1.00 | 9.94 | ACSY |

TABLE 24-continued

Coordinates for the 3D structure of SYK-C:peptide complex
created by user: dave

| ATOM | 128 | HD2 | ARG | 3 | −16.924 | −15.723 | −1.297 | 1.00 | 9.81 | ACSY |
|---|---|---|---|---|---|---|---|---|---|---|
| ATOM | 129 | NE | ARG | 3 | −16.493 | −13.729 | −1.032 | 1.00 | 10.34 | ACSY |
| ATOM | 130 | HE | ARG | 3 | −16.896 | −12.814 | −1.019 | 1.00 | 10.40 | ACSY |
| ATOM | 131 | CZ | ARG | 3 | −15.197 | −13.899 | −1.359 | 1.00 | 11.04 | ACSY |
| ATOM | 132 | NH1 | ARG | 3 | −14.447 | −12.843 | −1.665 | 1.00 | 11.79 | ACSY |
| ATOM | 133 | HH11 | ARG | 3 | −14.846 | −11.927 | −1.652 | 1.00 | 11.84 | ACSY |
| ATOM | 134 | HH12 | ARG | 3 | −13.485 | −12.967 | −1.907 | 1.00 | 12.39 | ACSY |
| ATOM | 135 | NH2 | ARG | 3 | −14.663 | −15.118 | −1.378 | 1.00 | 11.17 | ACSY |
| ATOM | 136 | HH21 | ARG | 3 | −15.225 | −15.913 | −1.149 | 1.00 | 10.74 | ACSY |
| ATOM | 137 | HH22 | ARG | 3 | −13.701 | −15.239 | −1.621 | 1.00 | 11.80 | ACSY |
| ATOM | 138 | C | ARG | 3 | −15.624 | −14.897 | 3.514 | 1.00 | 6.86 | ACSY |
| ATOM | 139 | O | ARG | 3 | −15.148 | −13.857 | 3.076 | 1.00 | 6.84 | ACSY |
| ATOM | 140 | N | ARG | 4 | −16.064 | −15.073 | 4.776 | 1.00 | 6.28 | ACSY |
| ATOM | 141 | HN | ARG | 4 | −16.437 | −15.953 | 5.067 | 1.00 | 6.63 | ACSY |
| ATOM | 142 | CA | ARG | 4 | −15.985 | −13.957 | 5.703 | 1.00 | 5.44 | ACSY |
| ATOM | 143 | HA | ARG | 4 | −16.530 | −14.246 | 6.606 | 1.00 | 5.54 | ACSY |
| ATOM | 144 | CB | ARG | 4 | −14.520 | −13.668 | 6.024 | 1.00 | 5.41 | ACSY |
| ATOM | 145 | HB1 | ARG | 4 | −14.059 | −14.556 | 6.455 | 1.00 | 5.79 | ACSY |
| ATOM | 146 | HB2 | ARG | 4 | −13.980 | −13.448 | 5.104 | 1.00 | 5.72 | ACSY |
| ATOM | 147 | CG | ARG | 4 | −14.380 | −12.495 | 6.996 | 1.00 | 5.07 | ACSY |
| ATOM | 148 | HG1 | ARG | 4 | −14.567 | −11.560 | 6.470 | 1.00 | 5.15 | ACSY |
| ATOM | 149 | HG2 | ARG | 4 | −15.138 | −12.57S | 7.775 | 1.00 | 5.27 | ACSY |
| ATOM | 150 | CD | ARG | 4 | −12.993 | −12.456 | 7.637 | 1.00 | 5.03 | ACSY |
| ATOM | 151 | HD1 | ARG | 4 | −12.207 | −12.345 | 6.888 | 1.00 | 5.01 | ACSY |
| ATOM | 152 | HD2 | ARG | 4 | −12.794 | −13.352 | 8.221 | 1.00 | 5.05 | ACSY |
| ATOM | 153 | NE | ARG | 4 | −12.894 | −11.325 | 8.543 | 1.00 | 5.65 | ACSY |
| ATOM | 154 | HE | ARG | 4 | −13.490 | −10.530 | 8.432 | 1.00 | 6.04 | ACSY |
| ATOM | 155 | CZ | ARG | 4 | −11.987 | −11.367 | 9.537 | 1.00 | 6.06 | ACSY |
| ATOM | 156 | NH1 | ARG | 4 | −11.882 | −10.345 | 10.382 | 1.00 | 6.93 | ACSY |
| ATOM | 157 | HH11 | ARG | 4 | −12.476 | −9.547 | 10.277 | 1.00 | 7.26 | ACSY |
| ATOM | 158 | HH12 | ARG | 4 | −11.209 | −10.374 | 11.121 | 1.00 | 7.42 | ACSY |
| ATOM | 159 | NH2 | ARG | 4 | −11.195 | −12.428 | 9.677 | 1.00 | 5.95 | ACSY |
| ATOM | 160 | HH21 | ARG | 4 | −11.273 | −13.197 | 9.043 | 1.00 | 5.52 | ACSY |
| ATOM | 161 | HH22 | ARG | 4 | −10.523 | −12.456 | 10.417 | 1.00 | 6.5i | ACSY |
| ATOM | 162 | C | ARG | 4 | −16.656 | −12.730 | 5.086 | 1.00 | 5.05 | ACSY |
| ATOM | 163 | O | ARG | 4 | −16.958 | −12.683 | 3.900 | 1.00 | 5.27 | ACSY |
| ATOM | 164 | N | ALA | 5 | −16.875 | −11.746 | 5.977 | 1.00 | 4.86 | ACSY |
| ATOM | 165 | HN | ALA | 5 | −16.613 | −11.857 | 6.934 | 1.00 | 5.05 | ACSY |
| ATOM | 166 | CA | ALA | 5 | −17.506 | −10.521 | 5.519 | 1.00 | 4.79 | ACSY |
| ATOM | 167 | HA | ALA | 5 | −18.191 | −10.793 | 4.713 | 1.00 | 5.29 | ACSY |
| ATOM | 168 | CB | ALA | 5 | −18.263 | −9.875 | 6.678 | 1.00 | 5.32 | ACSY |
| ATOM | 169 | HB1 | ALA | 5 | −18.761 | −8.960 | 6.355 | 1.00 | 5.57 | ACSY |
| ATOM | 170 | HB2 | ALA | 5 | −19.023 | −10.550 | 7.071 | 1.00 | 5.59 | ACSY |
| ATOM | 171 | HB3 | ALA | 5 | −17.585 | −9.619 | 7.492 | 1.00 | 5.61 | ACSY |
| ATOM | 172 | C | ALA | 5 | −16.439 | −9.573 | 4.968 | 1.00 | 3.98 | ACSY |
| ATOM | 173 | O | ALA | 5 | −16.103 | −9.594 | 3.790 | 1.00 | 4.06 | ACSY |
| ATOM | 174 | N | SER | 6 | −15.935 | −8.743 | 5.899 | 1.00 | 3.66 | ACSY |
| ATOM | 175 | HN | SER | 6 | −16.257 | −8.782 | 6.844 | 1.00 | 4.09 | ACSY |
| ATOM | 176 | CA | SER | 6 | −14.912 | −7.790 | 5.500 | 1.00 | 3.17 | ACSY |
| ATOM | 177 | HA | SER | 6 | −15.261 | −7.303 | 4.586 | 1.00 | 3.31 | ACSY |
| ATOM | 178 | CB | SER | 6 | −14.706 | −6.768 | 6.615 | 1.00 | 3.61 | ACSY |
| ATOM | 179 | HB1 | SER | 6 | −13.988 | −6.005 | 6.314 | 1.00 | 3.90 | ACSY |
| ATOM | 180 | HB2 | SER | 6 | −15.643 | −6.268 | 6.863 | 1.00 | 3.95 | ACSY |
| ATOM | 181 | OG | SER | 6 | −14.221 | −7.391 | 7.777 | 1.00 | 4.03 | ACSY |
| ATOM | 182 | HG | SER | 6 | −13.626 | −6.778 | 8.187 | 1.00 | 4.34 | ACSY |
| ATOM | 183 | C | SER | 6 | −13.610 | −8.534 | 5.207 | 1.00 | 2.86 | ACSY |
| ATOM | 184 | O | SER | 6 | −13.354 | −9.618 | 5.717 | 1.00 | 3.29 | ACSY |
| ATOM | 185 | N | VAL | 7 | −12.810 | −7.873 | 4.350 | 1.00 | 2.60 | ACSY |
| ATOM | 186 | HN | VAL | 7 | −13.088 | −6.990 | 3.973 | 1.00 | 2.58 | ACSY |
| ATOM | 187 | CA | VAL | 7 | −11.537 | −8.470 | 3.983 | 1.00 | 2.97 | ACSY |
| ATOM | 188 | HA | VAL | 7 | −11.748 | −9.286 | 3.286 | 1.00 | 3.40 | ACSY |
| ATOM | 189 | CB | VAL | 7 | −10.652 | −7.413 | 3.328 | 1.00 | 3.63 | ACSY |
| ATOM | 190 | HB | VAL | 7 | −11.128 | −7.090 | 2.401 | 1.00 | 3.85 | ACSY |
| ATOM | 191 | CG1 | VAL | 7 | −10.501 | −6.199 | 4.243 | 1.00 | 3.87 | ACSY |
| ATOM | 192 | HG11 | VAL | 7 | −10.042 | −6.480 | 5.191 | 1.00 | 4.23 | ACSY |
| ATOM | 193 | HG12 | VAL | 7 | −11.471 | −5.751 | 4.459 | 1.00 | 4.18 | ACSY |
| ATOM | 194 | HG13 | VAL | 7 | −9.874 | −5.437 | 3.779 | 1.00 | 3.99 | ACSY |
| ATOM | 195 | CG2 | VAL | 7 | −9.279 | −8.000 | 2.997 | 1.00 | 4.53 | ACSY |
| ATOM | 196 | HG21 | VAL | 7 | −8.800 | −8.397 | 3.892 | 1.00 | 5.05 | ACSY |
| ATOM | 197 | HG22 | VAL | 7 | −9.366 | −8.811 | 2.273 | 1.00 | 4.84 | ACSY |
| ATOM | 198 | HG23 | VAL | 7 | −8.623 | −7.239 | 2.573 | 1.00 | 4.79 | ACSY |
| ATOM | 199 | C | VAL | 7 | −10.858 | −9.039 | 5.229 | 1.00 | 2.97 | ACSY |
| ATOM | 200 | O | VAL | 7 | −10.543 | −8.329 | 6.176 | 1.00 | 3.56 | ACSY |
| ATOM | 201 | N | GLY | 8 | −10.659 | −10.367 | 5.157 | 1.00 | 2.78 | ACSY |
| ATOM | 202 | HN | GLY | 8 | −10.943 | −10.882 | 4.349 | 1.00 | 2.72 | ACSY |
| ATOM | 203 | CA | GLY | 8 | −10.020 | −11.034 | 6.274 | 1.00 | 3.21 | ACSY |

TABLE 24-continued

Coordinates for the 3D structure of SYK-C:peptide complex
created by user: dave

| ATOM | 204 | HA1 | GLY | 8 | −10.329 | −12.080 | 6.256 | 1.00 | 3.70 | ACSY |
|---|---|---|---|---|---|---|---|---|---|---|
| ATOM | 205 | HA2 | GLY | 8 | −10.383 | −10.568 | 7.190 | 1.00 | 3.50 | ACSY |
| ATOM | 206 | C | GLY | 8 | −8.498 | −10.921 | 6.180 | 1.00 | 3.25 | ACSY |
| ATOM | 207 | O | GLY | 8 | −7.769 | −11.903 | 6.258 | 1.00 | 3.70 | ACSY |
| ATOM | 208 | N | SER | 9 | −8.075 | −9.656 | 6.006 | 1.00 | 3.25 | ACSY |
| ATOM | 209 | HN | SER | 9 | −8.730 | −8.902 | 5.954 | 1.00 | 3.31 | ACSY |
| ATOM | 210 | CA | SER | 9 | −6.649 | −9.410 | 5.899 | 1.00 | 3.63 | ACSY |
| ATOM | 211 | HA | SER | 9 | −6.521 | −8.404 | 5.489 | 1.00 | 3.96 | ACSY |
| ATOM | 212 | CB | SER | 9 | −6.011 | −9.518 | 7.281 | 1.00 | 4.53 | ACSY |
| ATOM | 213 | HB1 | SER | 9 | −6.479 | −8.823 | 7.977 | 1.00 | 4.87 | ACSY |
| ATOM | 214 | HB2 | SER | 9 | −4.947 | −9.286 | 7.238 | 1.00 | 4.92 | ACSY |
| ATOM | 215 | OG | SER | 9 | −6.157 | −10.817 | 7.794 | 1.00 | 5.09 | ACSY |
| ATOM | 216 | HG | SER | 9 | −6.454 | −10.725 | 8.689 | 1.00 | 5.60 | ACSY |
| ATOM | 217 | C | SER | 9 | −6.030 | −10.425 | 4.941 | 1.00 | 3.30 | ACSY |
| ATOM | 218 | O | SER | 9 | −5.335 | −11.352 | 5.339 | 1.00 | 3.79 | ACSY |
| ATOM | 219 | N | HIS | 10 | −6.330 | −10.180 | 3.653 | 1.00 | 3.01 | ACSY |
| ATOM | 220 | HN | HIS | 10 | −6.900 | −9.398 | 3.403 | 1.00 | 3.18 | ACSY |
| ATOM | 221 | CA | HIS | 10 | −5.808 | −11.075 | 2.636 | 1.00 | 3.08 | ACSY |
| ATOM | 222 | HA | HIS | 10 | −6.017 | −12.098 | 2.963 | 1.00 | 3.58 | ACSY |
| ATOM | 223 | CB | HIS | 10 | −6.488 | −10.781 | 1.301 | 1.00 | 3.80 | ACSY |
| ATOM | 224 | HB1 | HIS | 10 | −6.423 | −9.719 | 1.065 | 1.00 | 4.15 | ACSY |
| ATOM | 225 | HB2 | HIS | 10 | −5.999 | −11.329 | 0.496 | 1.00 | 4.03 | ACSY |
| ATOM | 226 | CG | HIS | 10 | −7.941 | −11.190 | 1.371 | 1.00 | 4.47 | ACSY |
| ATOM | 227 | CD2 | HIS | 10 | −8.741 | −11.366 | 2.516 | 1.00 | 5.19 | ACSY |
| ATOM | 228 | HD2 | HIS | 10 | −8.433 | −11.236 | 3.542 | 1.00 | 5.38 | ACSY |
| ATOM | 229 | ND1 | HIS | 10 | −8.700 | −11.451 | 0.285 | 1.00 | 4.99 | ACSY |
| ATOM | 230 | HD1 | HIS | 10 | −8.417 | −11.412 | −0.653 | 1.00 | 5.01 | ACSY |
| ATOM | 231 | CE1 | HIS | 10 | −9.921 | −11.776 | 0.743 | 1.00 | 5.85 | ACSY |
| ATOM | 232 | HE1 | HIS | 10 | −10.757 | −12.039 | 0.111 | 1.00 | 6.59 | ACSY |
| ATOM | 233 | NE2 | HIS | 10 | −9.970 | −11.732 | 2.086 | 1.00 | 5.97 | ACSY |
| ATOM | 234 | C | HIS | 10 | −4.297 | −10.887 | 2.519 | 1.00 | 2.47 | ACSY |
| ATOM | 235 | O | HIS | 10 | −3.798 | −10.190 | 1.644 | 1.00 | 2.49 | ACSY |
| ATOM | 236 | N | GLU | 11 | −3.608 | −11.560 | 3.458 | 1.00 | 2.40 | ACSY |
| ATOM | 237 | HN | GLU | 11 | −4.074 | −12.116 | 4.140 | 1.00 | 2.73 | ACSY |
| ATOM | 238 | CA | GLU | 11 | −2.170 | −11.475 | 3.463 | 1.00 | 2.34 | ACSY |
| ATOM | 239 | HA | GLU | 11 | −1.900 | −10.433 | 3.639 | 1.00 | 2.44 | ACSY |
| ATOM | 240 | CB | GLU | 11 | −1.652 | −12.378 | 4.570 | 1.00 | 2.96 | ACSY |
| ATOM | 241 | HB1 | GLU | 11 | −2.480 | −12.680 | 5.208 | 1.00 | 3.18 | ACSY |
| ATOM | 242 | HB2 | GLU | 11 | −1.249 | −13.287 | 4.136 | 1.00 | 3.13 | ACSY |
| ATOM | 243 | CG | GLU | 11 | −0.588 | −11.678 | 5.406 | 1.00 | 3.54 | ACSY |
| ATOM | 244 | HG1 | GLU | 11 | 0.236 | −11.351 | 4.775 | 1.00 | 3.67 | ACSY |
| ATOM | 245 | HG2 | GLU | 11 | −1.007 | −10.797 | 5.892 | 1.00 | 3.72 | ACSY |
| ATOM | 246 | CD | GLU | 11 | −0.052 | −12.631 | 6.476 | 1.00 | 4.24 | ACSY |
| ATOM | 247 | OE1 | GLU | 11 | −0.462 | −12.509 | 7.629 | 1.00 | 4.62 | ACSY |
| ATOM | 248 | OE2 | GLU | 11 | 0.770 | −13.484 | 6.144 | 1.00 | 4.74 | ACSY |
| ATOM | 249 | C | GLU | 11 | −1.631 | −11.926 | 2.112 | 1.00 | 2.16 | ACSY |
| ATOM | 250 | O | GLU | 11 | −0.885 | −11.225 | 1.439 | 1.00 | 2.18 | ACSY |
| ATOM | 251 | N | LYS | 12 | −2.068 | −13.151 | 1.778 | 1.00 | 2.44 | ACSY |
| ATOM | 252 | HN | LYS | 12 | −2.665 | −13.656 | 2.403 | 1.00 | 2.76 | ACSY |
| ATOM | 253 | CA | LYS | 12 | −1.651 | −13.737 | 0.511 | 1.00 | 2.66 | ACSY |
| ATOM | 254 | HA | LYS | 12 | −0.660 | −14.174 | 0.665 | 1.00 | 3.12 | ACSY |
| ATOM | 255 | CB | LYS | 12 | −2.657 | −14.809 | 0.099 | 1.00 | 3.44 | ACSY |
| ATOM | 256 | HB1 | LYS | 12 | −3.618 | −14.343 | −0.118 | 1.00 | 3.47 | ACSY |
| ATOM | 257 | HB2 | LYS | 12 | −2.325 | −15.289 | −0.822 | 1.00 | 3.71 | ACSY |
| ATOM | 258 | CG | LYS | 12 | −2.836 | −15.863 | 1.192 | 1.00 | 4.37 | ACSY |
| ATOM | 259 | HG1 | LYS | 12 | −1.928 | −16.461 | 1.277 | 1.00 | 4.60 | ACSY |
| ATOM | 260 | HG2 | LYS | 12 | −2.979 | −15.371 | 2.154 | 1.00 | 4.75 | ACSY |
| ATOM | 261 | CD | LYS | 12 | −4.028 | −16.776 | 0.902 | 1.00 | 5.03 | ACSY |
| ATOM | 262 | HD1 | LYS | 12 | −4.122 | −17.517 | 1.695 | 1.00 | 5.34 | ACSY |
| ATOM | 263 | HD2 | LYS | 12 | −4.947 | −16.189 | 0.909 | 1.00 | 4.95 | ACSY |
| ATOM | 264 | CE | LYS | 12 | −3.880 | −17.482 | −0.446 | 1.00 | 5.94 | ACSY |
| ATOM | 265 | HE1 | LYS | 12 | −3.757 | −16.755 | −1.249 | 1.00 | 6.28 | ACSY |
| ATOM | 266 | HE2 | LYS | 12 | −3.003 | −18.129 | −0.447 | 1.00 | 6.22 | ACSY |
| ATOM | 267 | NZ | LYS | 12 | −5.039 | −18.306 | −0.770 | 1.00 | 6.49 | ACSY |
| ATOM | 268 | HZ1 | LYS | 12 | −4.893 | −18.761 | −1.694 | 1.00 | 6.68 | ACSY |
| ATOM | 269 | HZ2 | LYS | 12 | −5.161 | −19.036 | −0.039 | 1.00 | 6.91 | ACSY |
| ATOM | 270 | HZ3 | LYS | 12 | −5.889 | −17.708 | −0.808 | 1.00 | 6.61 | ACSY |
| ATOM | 271 | C | LYS | 12 | −1.559 | −12.653 | −0.563 | 1.00 | 2.13 | ACSY |
| ATOM | 272 | O | LYS | 12 | −2.557 | −12.154 | −1.057 | 1.00 | 2.63 | ACSY |
| ATOM | 273 | N | MET | 13 | −0.285 | −12.340 | −0.873 | 1.00 | 1.83 | ACSY |
| ATOM | 274 | HN | MET | 13 | 0.468 | −12.807 | −0.411 | 1.00 | 2.22 | ACSY |
| ATOM | 275 | CA | MET | 13 | −0.002 | −11.321 | −1.882 | 1.00 | 1.83 | ACSY |
| ATOM | 276 | HA | MET | 13 | 0.048 | −11.826 | −2.848 | 1.00 | 2.37 | ACSY |
| ATOM | 277 | CB | MET | 13 | −1.083 | −10.233 | −1.879 | 1.00 | 2.34 | ACSY |
| ATOM | 278 | HB1 | MET | 13 | −1.621 | −10.253 | −0.932 | 1.00 | 2.33 | ACSY |
| ATOM | 279 | HB2 | MET | 13 | −0.604 | −9.256 | −1.940 | 1.00 | 2.63 | ACSY |

TABLE 24-continued

Coordinates for the 3D structure of SYK-C:peptide complex
created by user: dave

| ATOM | 280 | CG | MET | 13 | −2.079 | −10.379 | −3.044 | 1.00 | 3.26 | ACSY |
|---|---|---|---|---|---|---|---|---|---|---|
| ATOM | 281 | HG1 | MET | 13 | −2.825 | −11.136 | −2.820 | 1.00 | 3.64 | ACSY |
| ATOM | 282 | HG2 | MET | 13 | −2.613 | −9.441 | −3.194 | 1.00 | 3.50 | ACSY |
| ATOM | 283 | SD | MET | 13 | −1.252 | −10.822 | −4.580 | 1.00 | 4.25 | ACSY |
| ATOM | 284 | CE | MET | 13 | −1.731 | −12.557 | −4.631 | 1.00 | 4.96 | ACSY |
| ATOM | 285 | HE1 | MET | 13 | −0.919 | −13.162 | −5.035 | 1.00 | 5.13 | ACSY |
| ATOM | 286 | HE2 | MET | 13 | −2.610 | −12.689 | −5.261 | 1.00 | 5.43 | ACSY |
| ATOM | 287 | HE3 | MET | 13 | −1.964 | −12.914 | −3.628 | 1.00 | 5.19 | ACSY |
| ATOM | 288 | C | MET | 13 | 1.366 | −10.713 | −1.555 | 1.00 | 1.57 | ACSY |
| ATOM | 289 | O | MET | 13 | 1.843 | −10.785 | −0.430 | 1.00 | 1.67 | ACSY |
| ATOM | 290 | N | PRO | 14 | 1.978 | −10.111 | −2.602 | 1.00 | 1.40 | ACSY |
| ATOM | 291 | CD | PRO | 14 | 1.417 | −10.040 | −3.937 | 1.00 | 1.46 | ACSY |
| ATOM | 292 | HD1 | PRO | 14 | 0.542 | −9.391 | −3.941 | 1.00 | 1.49 | ACSY |
| ATOM | 293 | HD2 | PRO | 14 | 1.120 | −11.027 | −4.274 | 1.00 | 1.69 | ACSY |
| ATOM | 294 | CA | PRO | 14 | 3.279 | −9.483 | −2.491 | 1.00 | 1.35 | ACSY |
| ATOM | 295 | HA | PRO | 14 | 3.942 | −10.074 | −1.865 | 1.00 | 1.54 | ACSY |
| ATOM | 296 | CB | PRO | 14 | 3.782 | −9.370 | −3.928 | 1.00 | 1.38 | ACSY |
| ATOM | 297 | HB1 | PRO | 14 | 4.298 | −8.423 | −4.086 | 1.00 | 1.44 | ACSY |
| ATOM | 298 | HB2 | PRO | 14 | 4.482 | −10.175 | −4.155 | 1.00 | 1.60 | ACSY |
| ATOM | 299 | CG | PRO | 14 | 2.535 | −9.470 | −4.817 | 1.00 | 1.40 | ACSY |
| ATOM | 300 | HG1 | PRO | 14 | 2.258 | −8.490 | −5.202 | 1.00 | 1.44 | ACSY |
| ATOM | 301 | HG2 | PRO | 14 | 2.720 | −10.108 | −5.663 | 1.00 | 1.60 | ACSY |
| ATOM | 302 | C | PRO | 14 | 3.148 | −8.078 | −1.937 | 1.00 | 1.26 | ACSY |
| ATOM | 303 | O | PRO | 14 | 3.558 | −7.757 | −0.831 | 1.00 | 1.41 | ACSY |
| ATOM | 304 | N | TRP | 15 | 2.515 | −7.281 | −2.805 | 1.00 | 1.17 | ACSY |
| ATOM | 305 | HN | TRP | 15 | 2.196 | −7.649 | −3.689 | 1.00 | 1.17 | ACSY |
| ATOM | 306 | CA | TRP | 15 | 2.298 | −5.880 | −2.458 | 1.00 | 1.26 | ACSY |
| ATOM | 307 | HA | TRP | 15 | 3.264 | −5.479 | −2.133 | 1.00 | 1.41 | ACSY |
| ATOM | 308 | CB | TRP | 15 | 1.788 | −5.095 | −3.682 | 1.00 | 1.44 | ACSY |
| ATOM | 309 | HB1 | TRP | 15 | 1.338 | −4.163 | −3.358 | 1.00 | 1.41 | ACSY |
| ATOM | 310 | HB2 | TRP | 15 | 2.617 | −4.840 | −4.338 | 1.00 | 1.60 | ACSY |
| ATOM | 311 | CG | TRP | 15 | 0.749 | −5.891 | −4.464 | 1.00 | 1.71 | ACSY |
| ATOM | 312 | CD2 | TRP | 15 | 0.397 | −5.729 | −5.840 | 1.00 | 2.23 | ACSY |
| ATOM | 313 | CE2 | TRP | 15 | −0.624 | −6.690 | −6.124 | 1.00 | 2.46 | ACSY |
| ATOM | 314 | CE3 | TRP | 15 | 0.850 | −4.872 | −6.832 | 1.00 | 2.89 | ACSY |
| ATOM | 315 | HE3 | TRP | 15 | 1.621 | −4.148 | −6.614 | 1.00 | 2.88 | ACSY |
| ATOM | 316 | CD1 | TRP | 15 | −0.041 | −6.920 | −3.958 | 1.00 | 2.00 | ACSY |
| ATOM | 317 | HD1 | TRP | 15 | 0.019 | −7.304 | −2.955 | 1.00 | 2.35 | ACSY |
| ATOM | 318 | NE1 | TRP | 15 | −0.860 | −7.395 | −4.942 | 1.00 | 2.25 | ACSY |
| ATOM | 319 | HE1 | TRP | 15 | −1.511 | −8.119 | −4.835 | 1.00 | 2.53 | ACSY |
| ATOM | 320 | CZ2 | TRP | 15 | −1.175 | −6.776 | −7.396 | 1.00 | 3.15 | ACSY |
| ATOM | 321 | HZ2 | TRP | 15 | −1.946 | −7.503 | −7.606 | 1.00 | 3.33 | ACSY |
| ATOM | 322 | CZ3 | TRP | 15 | 0.294 | −4.951 | −8.134 | 1.00 | 3.75 | ACSY |
| ATOM | 323 | HZ3 | TRP | 15 | 0.643 | −4.288 | −8.912 | 1.00 | 4.43 | ACSY |
| ATOM | 324 | CH2 | TRP | 15 | −0.720 | −5.904 | −8.416 | 1.00 | 3.82 | ACSY |
| ATOM | 325 | HH2 | TRP | 15 | −1.143 | −5.965 | −9.408 | 1.00 | 4.49 | ACSY |
| ATOM | 326 | C | TRP | 15 | 1.304 | −5.744 | −1.294 | 1.00 | 1.18 | ACSY |
| ATOM | 327 | O | TRP | 15 | 0.867 | −4.651 | −0.965 | 1.00 | 1.21 | ACSY |
| ATOM | 328 | N | PHE | 16 | 0.973 | −6.903 | −0.692 | 1.00 | 1.17 | ACSY |
| ATOM | 329 | HN | PHE | 16 | 1.327 | −7.775 | −1.019 | 1.00 | 1.22 | ACSY |
| ATOM | 330 | CA | PHE | 16 | 0.059 | −6.845 | 0.428 | 1.00 | 1.18 | ACSY |
| ATOM | 331 | HA | PHE | 16 | 0.044 | −5.809 | 0.779 | 1.00 | 1.12 | ACSY |
| ATOM | 332 | CB | PHE | 16 | −1.326 | −7.277 | −0.014 | 1.00 | 1.33 | ACSY |
| ATOM | 333 | HB1 | PHE | 16 | −1.600 | −6.763 | −0.930 | 1.00 | 1.39 | ACSY |
| ATOM | 334 | HB2 | PHE | 16 | −1.339 | −8.347 | −0.224 | 1.00 | 1.50 | ACSY |
| ATOM | 335 | CG | PHE | 16 | −2.330 | −6.975 | 1.064 | 1.00 | 1.35 | ACSY |
| ATOM | 336 | CD1 | PHE | 16 | −2.511 | −7.882 | 2.139 | 1.00 | 1.69 | ACSY |
| ATOM | 337 | HD1 | PHE | 16 | −1.952 | −8.802 | 2.163 | 1.00 | 2.35 | ACSY |
| ATOM | 338 | CD2 | PHE | 16 | −3.078 | −5.770 | 1.044 | 1.00 | 1.93 | ACSY |
| ATOM | 339 | HD2 | PHE | 16 | −2.949 | −5.068 | 0.233 | 1.00 | 2.63 | ACSY |
| ATOM | 340 | CE1 | PHE | 16 | −3.421 | −7.589 | 3.179 | 1.00 | 1.71 | ACSY |
| ATOM | 341 | HE1 | PHE | 16 | −3.542 | −8.282 | 4.000 | 1.00 | 2.35 | ACSY |
| ATOM | 342 | CE2 | PHE | 16 | −3.989 | −5.481 | 2.087 | 1.00 | 1.99 | ACSY |
| ATOM | 343 | HE2 | PHE | 16 | −4.552 | −4.562 | 2.072 | 1.00 | 2.73 | ACSY |
| ATOM | 344 | CZ | PHE | 16 | −4.160 | −6.390 | 3.152 | 1.00 | 1.47 | ACSY |
| ATOM | 345 | HZ | PHE | 16 | −4.856 | −6.167 | 3.947 | 1.00 | 1.53 | ACSY |
| ATOM | 346 | C | PHE | 16 | 0.548 | −7.740 | 1.558 | 1.00 | 1.37 | ACSY |
| ATOM | 347 | O | PHE | 16 | 0.132 | −8.881 | 1.707 | 1.00 | 1.98 | ACSY |
| ATOM | 348 | N | HIS | 17 | 1.463 | −7.147 | 2.337 | 1.00 | 1.18 | ACSY |
| ATOM | 349 | HN | HIS | 17 | 1.791 | −6.227 | 2.135 | 1.00 | 1.30 | ACSY |
| ATOM | 350 | CA | HIS | 17 | 1.977 | −7.883 | 3.467 | 1.00 | 1.33 | ACSY |
| ATOM | 351 | HA | HIS | 17 | 1.547 | −8.888 | 3.425 | 1.00 | 1.64 | ACSY |
| ATOM | 352 | CB | HIS | 17 | 3.491 | −7.940 | 3.414 | 1.00 | 1.75 | ACSY |
| ATOM | 353 | HB1 | HIS | 17 | 3.901 | −7.013 | 3.013 | 1.00 | 1.78 | ACSY |
| ATOM | 354 | HB2 | HIS | 17 | 3.887 | −8.073 | 4.414 | 1.00 | 2.06 | ACSY |
| ATOM | 355 | CG | HIS | 17 | 3.919 | −9.100 | 2.548 | 1.00 | 2.50 | ACSY |

TABLE 24-continued

Coordinates for the 3D structure of SYK-C:peptide complex
created by user: dave

| ATOM | 356 | CD2 | HIS | 17 | 3.426 | −9.460 | 1.282 | 1.00 | 3.04 | ACSY |
|------|-----|-----|-----|----|-------|--------|-------|------|------|------|
| ATOM | 357 | HD2 | HIS | 17 | 2.655 | −8.949 | 0.723 | 1.00 | 2.88 | ACSY |
| ATOM | 358 | ND1 | HIS | 17 | 4.869 | −9.993 | 2.899 | 1.00 | 3.11 | ACSY |
| ATOM | 359 | HD1 | HIS | 17 | 5.391 | −10.000 | 3.728 | 1.00 | 3.08 | ACSY |
| ATOM | 360 | CE1 | HIS | 17 | 4.957 | −10.872 | 1.886 | 1.00 | 3.95 | ACSY |
| ATOM | 361 | HE1 | HIS | 17 | 5.634 | −11.713 | 1.868 | 1.00 | 4.63 | ACSY |
| ATOM | 362 | NE2 | HIS | 17 | 4.096 | −10.571 | 0.897 | 1.00 | 3.96 | ACSY |
| ATOM | 363 | C | HIS | 17 | 1.514 | −7.196 | 4.746 | 1.00 | 1.30 | ACSY |
| ATOM | 364 | O | HIS | 17 | 1.908 | −6.081 | 5.067 | 1.00 | 1.46 | ACSY |
| ATOM | 365 | N | GLY | 18 | 0.651 | −7.943 | 5.443 | 1.00 | 1.54 | ACSY |
| ATOM | 366 | HN | GLY | 18 | 0.407 | −8.855 | 5.127 | 1.00 | 1.71 | ACSY |
| ATOM | 367 | CA | GLY | 18 | 0.114 | −7.413 | 6.682 | 1.00 | 1.88 | ACSY |
| ATOM | 368 | HA1 | GLY | 18 | −0.900 | −7.799 | 6.792 | 1.00 | 2.11 | ACSY |
| ATOM | 369 | HA2 | GLY | 18 | 0.077 | −6.328 | 6.587 | 1.00 | 1.95 | ACSY |
| ATOM | 370 | C | GLY | 18 | 0.987 | −7.817 | 7.877 | 1.00 | 2.10 | ACSY |
| ATOM | 371 | O | GLY | 18 | 0.506 | −8.052 | 8.979 | 1.00 | 2.46 | ACSY |
| ATOM | 372 | N | LYS | 19 | 2.297 | −7.881 | 7.57S | 1.00 | 1.96 | ACSY |
| ATOM | 373 | HN | LYS | 19 | 2.613 | −7.677 | 6.648 | 1.00 | 1.76 | ACSY |
| ATOM | 374 | CA | LYS | 19 | 3.239 | −8.257 | 8.614 | 1.00 | 2.25 | ACSY |
| ATOM | 375 | HA | LYS | 19 | 2.679 | −8.337 | 9.549 | 1.00 | 2.47 | ACSY |
| ATOM | 376 | CB | LYS | 19 | 3.882 | −9.592 | 8.246 | 1.00 | 2.42 | ACSY |
| ATOM | 377 | HB1 | LYS | 19 | 3.105 | −10.332 | 8.058 | 1.00 | 2.52 | ACSY |
| ATOM | 378 | HB2 | LYS | 19 | 4.443 | −9.483 | 7.318 | 1.00 | 2.47 | ACSY |
| ATOM | 379 | CG | LYS | 19 | 4.813 | −10.095 | 9.350 | 1.00 | 2.83 | ACSY |
| ATOM | 380 | HG1 | LYS | 19 | 5.543 | −9.323 | 9.593 | 1.00 | 3.35 | ACSY |
| ATOM | 381 | HG2 | LYS | 19 | 4.238 | −10.281 | 10.257 | 1.00 | 3.28 | ACSY |
| ATOM | 382 | CD | LYS | 19 | 5.538 | −11.373 | 8.929 | 1.00 | 2.77 | ACSY |
| ATOM | 383 | HD1 | LYS | 19 | 4.808 | −12.149 | 8.700 | 1.00 | 2.91 | ACSY |
| ATOM | 384 | HD2 | LYS | 19 | 6.099 | −11.190 | 8.012 | 1.00 | 3.00 | ACSY |
| ATOM | 385 | CE | LYS | 19 | 6.487 | −11.868 | 10.020 | 1.00 | 3.23 | ACSY |
| ATOM | 386 | HE1 | LYS | 19 | 7.245 | −11.116 | 10.239 | 1.00 | 3.73 | ACSY |
| ATOM | 387 | HE2 | LYS | 19 | 5.940 | −12.067 | 10.942 | 1.00 | 3.52 | ACSY |
| ATOM | 388 | NZ | LYS | 19 | 7.176 | −13.095 | 9.640 | 1.00 | 3.46 | ACSY |
| ATOM | 389 | HZ1 | LYS | 19 | 7.720 | −12.932 | 8.769 | 1.00 | 3.67 | ACSY |
| ATOM | 390 | HZ2 | LYS | 19 | 6.478 | −13.849 | 9.476 | 1.00 | 3.66 | ACSY |
| ATOM | 391 | HZ3 | LYS | 19 | 7.822 | −13.381 | 10.403 | 1.00 | 3.79 | ACSY |
| ATOM | 392 | C | LYS | 19 | 4.306 | −7.172 | 8.755 | 1.00 | 2.17 | ACSY |
| ATOM | 393 | O | LYS | 19 | 4.560 | −6.650 | 9.834 | 1.00 | 2.83 | ACSY |
| ATOM | 394 | N | ILE | 20 | 4.908 | −6.874 | 7.589 | 1.00 | 1.56 | ACSY |
| ATOM | 395 | HN | ILE | 20 | 4.644 | −7.343 | 6.747 | 1.00 | 1.50 | ACSY |
| ATOM | 396 | CA | ILE | 20 | 5.949 | −5.857 | 7.578 | 1.00 | 1.44 | ACSY |
| ATOM | 397 | HA | ILE | 20 | 6.849 | −6.312 | 7.999 | 1.00 | 1.51 | ACSY |
| ATOM | 398 | CB | ILE | 20 | 6.204 | −5.391 | 6.146 | 1.00 | 1.24 | ACSY |
| ATOM | 399 | HB | ILE | 20 | 6.595 | −4.374 | 6.180 | 1.00 | 1.31 | ACSY |
| ATOM | 400 | CG2 | ILE | 20 | 7.246 | −6.285 | 5.477 | 1.00 | 1.23 | ACSY |
| ATOM | 401 | HG21 | ILE | 20 | 8.154 | −6.339 | 6.079 | 1.00 | 1.53 | ACSY |
| ATOM | 402 | HG22 | ILE | 20 | 6.865 | −7.299 | 5.352 | 1.00 | 1.60 | ACSY |
| ATOM | 403 | HG23 | ILE | 20 | 7.516 | −5.901 | 4.495 | 1.00 | 1.66 | ACSY |
| ATOM | 404 | CG1 | ILE | 20 | 4.901 | −5.391 | 5.341 | 1.00 | 1.26 | ACSY |
| ATOM | 405 | HG11 | ILE | 20 | 4.514 | −6.407 | 5.274 | 1.00 | 1.41 | ACSY |
| ATOM | 406 | HG12 | ILE | 20 | 4.148 | −4.803 | 5.865 | 1.00 | 1.71 | ACSY |
| ATOM | 407 | CD1 | ILE | 20 | 5.106 | −4.826 | 3.935 | 1.00 | 1.07 | ACSY |
| ATOM | 408 | HD11 | ILE | 20 | 5.308 | −3.756 | 3.974 | 1.00 | 1.34 | ACSY |
| ATOM | 409 | HD12 | ILE | 20 | 5.947 | −5.310 | 3.439 | 1.00 | 1.53 | ACSY |
| ATOM | 410 | HD13 | ILE | 20 | 4.219 | −4.979 | 3.321 | 1.00 | 1.29 | ACSY |
| ATOM | 411 | C | ILE | 20 | 5.535 | −4.680 | 8.456 | 1.00 | 1.49 | ACSY |
| ATOM | 412 | O | ILE | 20 | 4.379 | −4.521 | 8.830 | 1.00 | 1.58 | ACSY |
| ATOM | 413 | N | SER | 21 | 6.567 | −3.873 | 8.754 | 1.00 | 1.47 | ACSY |
| ATOM | 414 | HN | SER | 21 | 7.483 | −4.069 | 8.405 | 1.00 | 1.41 | ACSY |
| ATOM | 415 | CA | SER | 21 | 6.325 | −2.711 | 9.590 | 1.00 | 1.57 | ACSY |
| ATOM | 416 | HA | SER | 21 | 5.490 | −2.945 | 10.233 | 1.00 | 1.67 | ACSY |
| ATOM | 417 | CB | SER | 21 | 7.572 | −2.415 | 10.418 | 1.00 | 1.63 | ACSY |
| ATOM | 418 | HB1 | SER | 21 | 7.829 | −3.265 | 11.051 | 1.00 | 1.95 | ACSY |
| ATOM | 419 | HB2 | SER | 21 | 8.425 | −2.205 | 9.774 | 1.00 | 1.66 | ACSY |
| ATOM | 420 | OG | SER | 21 | 7.364 | −1.299 | 11.246 | 1.00 | 2.23 | ACSY |
| ATOM | 421 | HG | SER | 21 | 8.215 | −0.910 | 11.397 | 1.00 | 2.35 | ACSY |
| ATOM | 422 | C | SER | 21 | 5.969 | −1.511 | 8.719 | 1.00 | 1.51 | ACSY |
| ATOM | 423 | O | SER | 21 | 4.830 | −1.066 | 8.637 | 1.00 | 1.58 | ACSY |
| ATOM | 424 | N | ARG | 22 | 7.041 | −1.037 | 8.086 | 1.00 | 1.44 | ACSY |
| ATOM | 425 | HN | ARG | 22 | 7.928 | −1.480 | 8.213 | 1.00 | 1.46 | ACSY |
| ATOM | 426 | CA | ARG | 22 | 6.929 | 0.118 | 7.212 | 1.00 | 1.40 | ACSY |
| ATOM | 427 | HA | ARG | 22 | 6.228 | −0.136 | 6.413 | 1.00 | 1.34 | ACSY |
| ATOM | 428 | CB | ARG | 22 | 6.454 | 1.329 | 8.012 | 1.00 | 1.57 | ACSY |
| ATOM | 429 | HB1 | ARG | 22 | 5.552 | 1.070 | 8.568 | 1.00 | 1.98 | ACSY |
| ATOM | 430 | HB2 | ARG | 22 | 7.211 | 1.597 | 8.747 | 1.00 | 1.53 | ACSY |
| ATOM | 431 | CG | ARG | 22 | 6.172 | 2.525 | 7.105 | 1.00 | 1.89 | ACSY |

TABLE 24-continued

Coordinates for the 3D structure of SYK-C:peptide complex
created by user: dave

| ATOM | 432 | HG1 | ARG | 22 | 6.960 | 2.609 | 6.357 | 1.00 | 2.11 | ACSY |
|---|---|---|---|---|---|---|---|---|---|---|
| ATOM | 433 | HG2 | ARG | 22 | 5.241 | 2.360 | 6.562 | 1.00 | 2.13 | ACSY |
| ATOM | 434 | CD | ARG | 22 | 6.079 | 3.830 | 7.898 | 1.00 | 2.36 | ACSY |
| ATOM | 435 | HD1 | ARG | 22 | 5.505 | 3.705 | 8.815 | 1.00 | 2.77 | ACSY |
| ATOM | 436 | HD2 | ARG | 22 | 5.619 | 4.623 | 7.309 | 1.00 | 2.76 | ACSY |
| ATOM | 437 | NE | ARG | 22 | 7.408 | 4.298 | 8.262 | 1.00 | 2.61 | ACSY |
| ATOM | 438 | HE | ARG | 22 | 7.953 | 4.826 | 7.612 | 1.00 | 2.68 | ACSY |
| ATOM | 439 | CZ | ARG | 22 | 7.899 | 4.012 | 9.487 | 1.00 | 3.36 | ACSY |
| ATOM | 440 | NH1 | ARG | 22 | 9.114 | 4.436 | 9.823 | 1.00 | 3.96 | ACSY |
| ATOM | 441 | HH11 | ARG | 22 | 9.658 | 4.964 | 9.171 | 1.00 | 3.94 | ACSY |
| ATOM | 442 | HH12 | ARG | 22 | 9.484 | 4.227 | 10.729 | 1.00 | 4.64 | ACSY |
| ATOM | 443 | NH2 | ARG | 22 | 7.180 | 3.311 | 10.359 | 1.00 | 3.92 | ACSY |
| ATOM | 444 | HH21 | ARG | 22 | 6.266 | 2.990 | 10.110 | 1.00 | 3.79 | ACSY |
| ATOM | 445 | HH22 | ARG | 22 | 7.553 | 3.104 | 11.264 | 1.00 | 4.68 | ACSY |
| ATOM | 446 | C | ARG | 22 | 8.316 | 0.372 | 6.623 | 1.00 | 1.31 | ACSY |
| ATOM | 447 | O | ARG | 22 | 8.490 | 0.687 | 5.452 | 1.00 | 1.22 | ACSY |
| ATOM | 448 | N | GLU | 23 | 9.283 | 0.196 | 7.543 | 1.00 | 1.36 | ACSY |
| ATOM | 449 | HN | GLU | 23 | 9.048 | −0.060 | 8.479 | 1.00 | 1.46 | ACSY |
| ATOM | 450 | CA | GLU | 23 | 10.663 | 0.345 | 7.179 | 1.00 | 1.31 | ACSY |
| ATOM | 451 | HA | GLU | 23 | 10.745 | 1.195 | 6.502 | 1.00 | 1.29 | ACSY |
| ATOM | 452 | CB | GLU | 23 | 11.448 | 0.560 | 8.468 | 1.00 | 1.43 | ACSY |
| ATOM | 453 | HB1 | GLU | 23 | 12.274 | 1.226 | 8.280 | 1.00 | 1.45 | ACSY |
| ATOM | 454 | HB2 | GLU | 23 | 10.800 | 1.042 | 9.187 | 1.00 | 1.54 | ACSY |
| ATOM | 455 | CG | GLU | 23 | 11.969 | −0.737 | 9.080 | 1.00 | 1.43 | ACSY |
| ATOM | 456 | HG1 | GLU | 23 | 11.142 | −1.361 | 9.421 | 1.00 | 1.45 | ACSY |
| ATOM | 457 | HG2 | GLU | 23 | 12.530 | −1.304 | 8.349 | 1.00 | 1.33 | ACSY |
| ATOM | 458 | CD | GLU | 23 | 12.877 | −0.422 | 10.271 | 1.00 | 1.56 | ACSY |
| ATOM | 459 | OE1 | GLU | 23 | 14.004 | −0.913 | 10.294 | 1.00 | 1.99 | ACSY |
| ATOM | 460 | OE2 | GLU | 23 | 12.446 | 0.310 | 11.160 | 1.00 | 1.89 | ACSY |
| ATOM | 461 | C | GLU | 23 | 11.103 | −0.934 | 6.485 | 1.00 | 1.18 | ACSY |
| ATOM | 462 | O | GLU | 23 | 11.758 | −0.940 | 5.451 | 1.00 | 1.08 | ACSY |
| ATOM | 463 | N | GLU | 24 | 10.675 | −2.009 | 7.156 | 1.00 | 1.21 | ACSY |
| ATOM | 464 | HN | GLU | 24 | 10.161 | −1.880 | 8.019 | 1.00 | 1.31 | ACSY |
| ATOM | 465 | CA | GLU | 24 | 10.984 | −3.332 | 6.657 | 1.00 | 1.15 | ACSY |
| ATOM | 466 | HA | GLU | 24 | 12.057 | −3.491 | 6.800 | 1.00 | 1.16 | ACSY |
| ATOM | 467 | CB | GLU | 24 | 10.176 | −4.351 | 7.450 | 1.00 | 1.26 | ACSY |
| ATOM | 468 | HB1 | GLU | 24 | 9.127 | −4.292 | 7.161 | 1.00 | 1.25 | ACSY |
| ATOM | 469 | HB2 | GLU | 24 | 10.513 | −5.3S4 | 7.207 | 1.00 | 1.24 | ACSY |
| ATOM | 470 | CG | GLU | 24 | 10.308 | −4.113 | 8.9S4 | 1.00 | 1.44 | ACSY |
| ATOM | 471 | HG1 | GLU | 24 | 10.108 | −3.069 | 9.197 | 1.00 | 1.79 | ACSY |
| ATOM | 472 | HG2 | GLU | 24 | 9.595 | −4.725 | 9.506 | 1.00 | 1.59 | ACSY |
| ATOM | 473 | CD | GLU | 24 | 11.725 | −4.465 | 9.413 | 1.00 | 1.80 | ACSY |
| ATOM | 474 | OE1 | GLU | 24 | 11.986 | −4.399 | 10.613 | 1.00 | 2.37 | ACSY |
| ATOM | 475 | OE2 | GLU | 24 | 12.549 | −4.800 | 8.564 | 1.00 | 2.30 | ACSY |
| ATOM | 476 | C | GLU | 24 | 10.657 | −3.423 | 5.163 | 1.00 | 0.99 | ACSY |
| ATOM | 477 | O | GLU | 24 | 11.391 | −4.009 | 4.378 | 1.00 | 0.94 | ACSY |
| ATOM | 478 | N | SER | 25 | 9.516 | −2.794 | 4.828 | 1.00 | 0.96 | ACSY |
| ATOM | 479 | HN | SER | 25 | 8.975 | −2.319 | 5.521 | 1.00 | 1.04 | ACSY |
| ATOM | 480 | CA | SER | 25 | 9.086 | −2.818 | 3.435 | 1.00 | 0.84 | ACSY |
| ATOM | 481 | HA | SER | 25 | 9.332 | −3.806 | 3.039 | 1.00 | 0.83 | ACSY |
| ATOM | 482 | CB | SER | 25 | 7.581 | −2.585 | 3.382 | 1.00 | 0.86 | ACSY |
| ATOM | 483 | HB1 | SER | 25 | 7.144 | −3.083 | 2.519 | 1.00 | 1.16 | ACSY |
| ATOM | 484 | HB2 | SER | 25 | 7.098 | −2.976 | 4.277 | 1.00 | 1.37 | ACSY |
| ATOM | 485 | OG | SER | 25 | 7.292 | −1.213 | 3.290 | 1.00 | 1.53 | ACSY |
| ATOM | 486 | HG | SER | 25 | 6.367 | −1.143 | 3.093 | 1.00 | 1.79 | ACSY |
| ATOM | 487 | C | SER | 25 | 9.826 | −1.755 | 2.607 | 1.00 | 0.75 | ACSY |
| ATOM | 488 | O | SER | 25 | 9.979 | −1.879 | 1.398 | 1.00 | 0.67 | ACSY |
| ATOM | 489 | N | GLU | 26 | 10.269 | −0.710 | 3.331 | 1.00 | 0.83 | ACSY |
| ATOM | 490 | HN | GLU | 26 | 10.126 | −0.668 | 4.312 | 1.00 | 0.92 | ACSY |
| ATOM | 491 | CA | GLU | 26 | 10.973 | 0.359 | 2.667 | 1.00 | 0.81 | ACSY |
| ATOM | 492 | HA | GLU | 26 | 10.449 | 0.553 | 1.728 | 1.00 | 0.73 | ACSY |
| ATOM | 493 | CB | GLU | 26 | 10.916 | 1.574 | 3.588 | 1.00 | 0.92 | ACSY |
| ATOM | 494 | HB1 | GLU | 26 | 10.192 | 2.279 | 3.205 | 1.00 | 0.91 | ACSY |
| ATOM | 495 | HB2 | GLU | 26 | 10.555 | 1.265 | 4.566 | 1.00 | 0.99 | ACSY |
| ATOM | 496 | CG | GLU | 26 | 12.275 | 2.244 | 3.747 | 1.00 | 0.99 | ACSY |
| ATOM | 497 | HG1 | GLU | 26 | 13.013 | 1.509 | 4.042 | 1.00 | 1.02 | ACSY |
| ATOM | 498 | HG2 | GLU | 26 | 12.602 | 2.689 | 2.808 | 1.00 | 0.96 | ACSY |
| ATOM | 499 | CD | GLU | 26 | 12.200 | 3.331 | 4.823 | 1.00 | 1.11 | ACSY |
| ATOM | 500 | OE1 | GLU | 26 | 13.249 | 3.748 | 5.310 | 1.00 | 1.46 | ACSY |
| ATOM | 501 | OE2 | GLU | 26 | 11.092 | 3.745 | 5.163 | 1.00 | 1.59 | ACSY |
| ATOM | 502 | C | GLU | 26 | 12.418 | −0.061 | 2.350 | 1.00 | 0.81 | ACSY |
| ATOM | 503 | O | GLU | 26 | 13.065 | 0.487 | 1.465 | 1.00 | 0.80 | ACSY |
| ATOM | 504 | N | GLN | 27 | 12.875 | −1.065 | 3.123 | 1.00 | 0.86 | ACSY |
| ATOM | 505 | HN | GLN | 27 | 12.277 | −1.507 | 3.790 | 1.00 | 0.90 | ACSY |
| ATOM | 506 | CA | GLN | 27 | 14.219 | −1.566 | 2.882 | 1.00 | 0.87 | ACSY |
| ATOM | 507 | HA | GLN | 27 | 14.835 | −0.723 | 2.559 | 1.00 | 0.91 | ACSY |

TABLE 24-continued

Coordinates for the 3D structure of SYK-C:peptide complex
created by user: dave

| ATOM | 508 | CB | GLN | 27 | 14.790 | −2.213 | 4.143 | 1.00 | 0.96 | ACSY |
| --- | --- | --- | --- | --- | --- | --- | --- | --- | --- | --- |
| ATOM | 509 | HB1 | GLN | 27 | 15.731 | −2.709 | 3.904 | 1.00 | 0.98 | ACSY |
| ATOM | 510 | HB2 | GLN | 27 | 15.021 | −1.440 | 4.876 | 1.00 | 1.16 | ACSY |
| ATOM | 511 | CG | GLN | 27 | 13.821 | −3.221 | 4.753 | 1.00 | 1.16 | ACSY |
| ATOM | 512 | HG1 | GLN | 27 | 12.932 | −2.717 | 5.129 | 1.00 | 1.40 | ACSY |
| ATOM | 513 | HG2 | GLN | 27 | 13.503 | −3.949 | 4.006 | 1.00 | 1.25 | ACSY |
| ATOM | 514 | CD | GLN | 27 | 14.498 | −3.959 | 5.910 | 1.00 | 1.50 | ACSY |
| ATOM | 515 | OE1 | GLN | 27 | 14.807 | −5.142 | 5.831 | 1.00 | 1.87 | ACSY |
| ATOM | 516 | NE2 | GLN | 27 | 14.704 | −3.176 | 6.983 | 1.00 | 2.20 | ACSY |
| ATOM | 517 | HE21 | GLN | 27 | 14.425 | −2.215 | 6.976 | 1.00 | 2.69 | ACSY |
| ATOM | 518 | HE22 | GLN | 27 | 15.141 | −3.541 | 7.806 | 1.00 | 2.54 | ACSY |
| ATOM | 519 | C | GLN | 27 | 14.113 | −2.574 | 1.741 | 1.00 | 0.78 | ACSY |
| ATOM | 520 | O | GLN | 27 | 15.035 | −2.796 | 0.970 | 1.00 | 0.79 | ACSY |
| ATOM | 521 | N | ILE | 28 | 12.907 | −3.163 | 1.690 | 1.00 | 0.73 | ACSY |
| ATOM | 522 | HN | ILE | 28 | 12.196 | −2.957 | 2.367 | 1.00 | 0.75 | ACSY |
| ATOM | 523 | CA | ILE | 28 | 12.636 | −4.086 | 0.648 | 1.00 | 0.69 | ACSY |
| ATOM | 524 | HA | ILE | 28 | 13.465 | −4.779 | 0.605 | 1.00 | 0.73 | ACSY |
| ATOM | 525 | CB | ILE | 28 | 11.323 | −4.742 | 0.999 | 1.00 | 0.72 | ACSY |
| ATOM | 526 | HB | ILE | 28 | 10.679 | −3.974 | 1.446 | 1.00 | 0.74 | ACSY |
| ATOM | 527 | CG2 | ILE | 28 | 10.654 | −5.289 | −0.242 | 1.00 | 0.76 | ACSY |
| ATOM | 528 | HG21 | ILE | 28 | 9.998 | −4.544 | −0.686 | 1.00 | 1.25 | ACSY |
| ATOM | 529 | HG22 | ILE | 28 | 11.397 | −5.577 | −0.983 | 1.00 | 1.29 | ACSY |
| ATOM | 530 | HG23 | ILE | 28 | 10.060 | −6.167 | 0.002 | 1.00 | 1.25 | ACSY |
| ATOM | 531 | CG1 | ILE | 28 | 11.527 | −5.847 | 2.019 | 1.00 | 0.80 | ACSY |
| ATOM | 532 | HG11 | ILE | 28 | 11.891 | −6.741 | 1.517 | 1.00 | 0.84 | ACSY |
| ATOM | 533 | HG12 | ILE | 28 | 12.292 | −5.547 | 2.732 | 1.00 | 0.83 | ACSY |
| ATOM | 534 | CD1 | ILE | 28 | 10.227 | −6.157 | 2.754 | 1.00 | 0.89 | ACSY |
| ATOM | 535 | HD11 | ILE | 28 | 9.367 | −6.002 | 2.101 | 1.00 | 1.37 | ACSY |
| ATOM | 536 | HD12 | ILE | 28 | 10.211 | −7.189 | 3.096 | 1.00 | 1.38 | ACSY |
| ATOM | 537 | HD13 | ILE | 28 | 10.107 | −5.513 | 3.623 | 1.00 | 1.36 | ACSY |
| ATOM | 538 | C | ILE | 28 | 12.543 | −3.320 | −0.664 | 1.00 | 0.63 | ACSY |
| ATOM | 539 | O | ILE | 28 | 12.982 | −3.763 | −1.718 | 1.00 | 0.66 | ACSY |
| ATOM | 540 | N | VAL | 29 | 11.918 | −2.146 | −0.520 | 1.00 | 0.58 | ACSY |
| ATOM | 541 | HN | VAL | 29 | 11.536 | −1.878 | 0.370 | 1.00 | 0.60 | ACSY |
| ATOM | 542 | CA | VAL | 29 | 11.809 | −1.280 | −1.670 | 1.00 | 0.57 | ACSY |
| ATOM | 543 | HA | VAL | 29 | 11.361 | −1.861 | −2.473 | 1.00 | 0.58 | ACSY |
| ATOM | 544 | CB | VAL | 29 | 10.981 | −0.052 | −1.273 | 1.00 | 0.55 | ACSY |
| ATOM | 545 | HB | VAL | 29 | 11.060 | 0.060 | −0.190 | 1.00 | 0.57 | ACSY |
| ATOM | 546 | CG1 | VAL | 29 | 11.526 | 1.224 | −1.915 | 1.00 | 0.66 | ACSY |
| ATOM | 547 | HG11 | VAL | 29 | 12.578 | 1.367 | −1.670 | 1.00 | 1.22 | ACSY |
| ATOM | 548 | HG12 | VAL | 29 | 11.435 | 1.184 | −3.001 | 1.00 | 1.36 | ACSY |
| ATOM | 549 | HG13 | VAL | 29 | 10.983 | 2.094 | −1.559 | 1.00 | 1.09 | ACSY |
| ATOM | 550 | CG2 | VAL | 29 | 9.507 | −0.234 | −1.635 | 1.00 | 0.54 | ACSY |
| ATOM | 551 | HG21 | VAL | 29 | 9.396 | −0.564 | −2.668 | 1.00 | 1.13 | ACSY |
| ATOM | 552 | HG22 | VAL | 29 | 9.035 | −0.972 | −0.988 | 1.00 | 1.22 | ACSY |
| ATOM | 553 | HG23 | VAL | 29 | 8.962 | 0.704 | −1.523 | 1.00 | 0.99 | ACSY |
| ATOM | 554 | C | VAL | 29 | 13.206 | −0.864 | −2.106 | 1.00 | 0.67 | ACSY |
| ATOM | 555 | O | VAL | 29 | 13.469 | −0.587 | −3.269 | 1.00 | 0.73 | ACSY |
| ATOM | 556 | N | LEU | 30 | 14.075 | −0.834 | −1.093 | 1.00 | 0.72 | ACSY |
| ATOM | 557 | HN | LEU | 30 | 13.817 | −1.124 | −0.169 | 1.00 | 0.70 | ACSY |
| ATOM | 558 | CA | LEU | 30 | 15.421 | −0.478 | −1.362 | 1.00 | 0.84 | ACSY |
| ATOM | 559 | HA | LEU | 30 | 15.423 | 0.538 | −1.771 | 1.00 | 0.88 | ACSY |
| ATOM | 560 | CB | LEU | 30 | 16.145 | −0.569 | −0.025 | 1.00 | 0.90 | ACSY |
| ATOM | 561 | HB1 | LEU | 30 | 16.657 | 0.357 | 0.175 | 1.00 | 1.00 | ACSY |
| ATOM | 562 | HB2 | LEU | 30 | 15.407 | −0.688 | 0.757 | 1.00 | 0.86 | ACSY |
| ATOM | 563 | CG | LEU | 30 | 17.108 | −1.741 | 0.048 | 1.00 | 0.94 | ACSY |
| ATOM | 564 | HG | LEU | 30 | 16.646 | −2.586 | −0.437 | 1.00 | 0.87 | ACSY |
| ATOM | 565 | CD1 | LEU | 30 | 18.413 | −1.409 | −0.653 | 1.00 | 1.06 | ACSY |
| ATOM | 566 | HD11 | LEU | 30 | 19.102 | −2.251 | −0.606 | 1.00 | 1.65 | ACSY |
| ATOM | 567 | HD12 | LEU | 30 | 18.240 | −1.168 | −1.699 | 1.00 | 1.39 | ACSY |
| ATOM | 568 | HD13 | LEU | 30 | 18.894 | −0.551 | −0.182 | 1.00 | 1.42 | ACSY |
| ATOM | 569 | CD2 | LEU | 30 | 17.369 | −2.128 | 1.488 | 1.00 | 1.00 | ACSY |
| ATOM | 570 | HD21 | LEU | 30 | 17.485 | −3.209 | 1.573 | 1.00 | 1.36 | ACSY |
| ATOM | 571 | HD22 | LEU | 30 | 18.273 | −1.656 | 1.856 | 1.00 | 1.42 | ACSY |
| ATOM | 572 | HD23 | LEU | 30 | 16.538 | −1.826 | 2.122 | 1.00 | 1.42 | ACSY |
| ATOM | 573 | C | LEU | 30 | 15.967 | −1.468 | −2.387 | 1.00 | 0.86 | ACSY |
| ATOM | 574 | O | LEU | 30 | 16.749 | −1.139 | −3.271 | 1.00 | 0.96 | ACSY |
| ATOM | 575 | N | ILE | 31 | 15.479 | −2.709 | −2.188 | 1.00 | 0.79 | ACSY |
| ATOM | 576 | HN | ILE | 31 | 14.863 | −2.897 | −1.411 | 1.00 | 0.74 | ACSY |
| ATOM | 577 | CA | ILE | 31 | 15.885 | −3.766 | −3.057 | 1.00 | 0.85 | ACSY |
| ATOM | 578 | HA | ILE | 31 | 16.980 | −3.793 | −3.064 | 1.00 | 0.91 | ACSY |
| ATOM | 579 | CB | ILE | 31 | 15.294 | −5.098 | −2.599 | 1.00 | 0.83 | ACSY |
| ATOM | 580 | HB | ILE | 31 | 14.366 | −5.267 | −3.138 | 1.00 | 0.82 | ACSY |
| ATOM | 581 | CG2 | ILE | 31 | 16.223 | −6.208 | −2.978 | 1.00 | 0.92 | ACSY |
| ATOM | 582 | HG21 | ILE | 31 | 16.406 | −6.191 | −4.052 | 1.00 | 1.28 | ACSY |
| ATOM | 583 | HG22 | ILE | 31 | 17.173 | −6.098 | −2.465 | 1.00 | 1.41 | ACSY |

TABLE 24-continued

Coordinates for the 3D structure of SYK-C:peptide complex
created by user: dave

| ATOM | 584 | HG23 | ILE | 31 | 15.792 | −7.168 | −2.718 | 1.00 | 1.39 | ACSY |
|---|---|---|---|---|---|---|---|---|---|---|
| ATOM | 585 | CG1 | ILE | 31 | 14.972 | −5.149 | −1.116 | 1.00 | 0.78 | ACSY |
| ATOM | 586 | HG11 | ILE | 31 | 14.811 | −4.156 | −0.725 | 1.00 | 0.75 | ACSY |
| ATOM | 587 | HG12 | ILE | 31 | 14.028 | −5.671 | −1.003 | 1.00 | 0.77 | ACSY |
| ATOM | 588 | CD1 | ILE | 31 | 16.065 | −5.856 | −0.312 | 1.00 | 0.85 | ACSY |
| ATOM | 589 | HD11 | ILE | 31 | 16.217 | −6.873 | −0.675 | 1.00 | 1.28 | ACSY |
| ATOM | 590 | HD12 | ILE | 31 | 17.013 | −5.324 | −0.393 | 1.00 | 1.27 | ACSY |
| ATOM | 591 | HD13 | ILE | 31 | 15.797 | −5.912 | 0.743 | 1.00 | 1.42 | ACSY |
| ATOM | 592 | C | ILE | 31 | 15.353 | −3.501 | −4.439 | 1.00 | 0.88 | ACSY |
| ATOM | 593 | O | ILE | 31 | 16.071 | −3.241 | −5.396 | 1.00 | 0.98 | ACSY |
| ATOM | 594 | N | GLY | 32 | 14.020 | −3.598 | −4.448 | 1.00 | 0.83 | ACSY |
| ATOM | 595 | HN | GLY | 32 | 13.520 | −3.793 | −3.580 | 1.00 | 0.77 | ACSY |
| ATOM | 596 | CA | GLY | 32 | 13.328 | −3.443 | −5.701 | 1.00 | 0.89 | ACSY |
| ATOM | 597 | HA1 | GLY | 32 | 12.611 | −4.259 | −5.764 | 1.00 | 0.91 | ACSY |
| ATOM | 598 | HA2 | GLY | 32 | 14.070 | −3.566 | −6.486 | 1.00 | 0.97 | ACSY |
| ATOM | 599 | C | GLY | 32 | 12.628 | −2.089 | −5.833 | 1.00 | 0.92 | ACSY |
| ATOM | 600 | O | GLY | 32 | 12.104 | −1.537 | −4.876 | 1.00 | 1.40 | ACSY |
| ATOM | 601 | N | SER | 33 | 12.672 | −1.624 | −7.104 | 1.00 | 0.97 | ACSY |
| ATOM | 602 | HN | SER | 33 | 13.132 | −2.162 | −7.810 | 1.00 | 1.35 | ACSY |
| ATOM | 603 | A | SER | 33 | 12.054 | −0.346 | −7.460 | 1.00 | 0.96 | ACSY |
| ATOM | 604 | HA | SER | 33 | 11.133 | −0.582 | −7.989 | 1.00 | 0.99 | ACSY |
| ATOM | 605 | CB | SER | 33 | 11.750 | 0.491 | −6.214 | 1.00 | 0.90 | ACSY |
| ATOM | 606 | HB1 | SER | 33 | 10.952 | 0.035 | −5.627 | 1.00 | 1.26 | ACSY |
| ATOM | 607 | HB2 | SER | 33 | 12.629 | 0.580 | −5.578 | 1.00 | 1.21 | ACSY |
| ATOM | 608 | OG | SER | 33 | 11.329 | 1.783 | −6.570 | 1.00 | 1.66 | ACSY |
| ATOM | 609 | HG | SER | 33 | 11.623 | 2.365 | −5.881 | 1.00 | 1.90 | ACSY |
| ATOM | 610 | C | SER | 33 | 12.984 | 0.384 | −8.436 | 1.00 | 1.11 | ACSY |
| ATOM | 611 | O | SER | 33 | 13.387 | −0.169 | −9.452 | 1.00 | 1.60 | ACSY |
| ATOM | 612 | N | LYS | 34 | 13.294 | 1.649 | −8.076 | 1.00 | 1.03 | ACSY |
| ATOM | 613 | HN | LYS | 34 | 12.926 | 2.046 | −7.236 | 1.00 | 1.20 | ACSY |
| ATOM | 614 | CA | LYS | 34 | 14.178 | 2.419 | −8.940 | 1.00 | 1.14 | ACSY |
| ATOM | 615 | HA | LYS | 34 | 14.631 | 3.213 | −8.341 | 1.00 | 1.17 | ACSY |
| ATOM | 616 | CB | LYS | 34 | 15.231 | 1.487 | −9.523 | 1.00 | 1.27 | ACSY |
| ATOM | 617 | HB1 | LYS | 34 | 15.416 | 0.670 | −8.836 | 1.00 | 1.39 | ACSY |
| ATOM | 618 | HB2 | LYS | 34 | 14.848 | 1.039 | −10.443 | 1.00 | 1.59 | ACSY |
| ATOM | 619 | CG | LYS | 34 | 16.526 | 2.227 | −9.830 | 1.00 | 1.56 | ACSY |
| ATOM | 620 | HG1 | LYS | 34 | 16.882 | 1.932 | −10.816 | 1.00 | 1.98 | ACSY |
| ATOM | 621 | HG2 | LYS | 34 | 16.327 | 3.297 | −9.873 | 1.00 | 2.07 | ACSY |
| ATOM | 622 | CD | LYS | 34 | 17.604 | 1.940 | −8.785 | 1.00 | 1.57 | ACSY |
| ATOM | 623 | HD1 | LYS | 34 | 18.466 | 2.583 | −8.965 | 1.00 | 2.08 | ACSY |
| ATOM | 624 | HD2 | LYS | 34 | 17.229 | 2.189 | −7.793 | 1.00 | 1.79 | ACSY |
| ATOM | 625 | CE | LYS | 34 | 18.042 | 0.476 | −8.819 | 1.00 | 1.98 | ACSY |
| ATOM | 626 | HE1 | LYS | 34 | 17.222 | −0.176 | −8.516 | 1.00 | 2.46 | ACSY |
| ATOM | 627 | HE2 | LYS | 34 | 18.340 | 0.189 | −9.827 | 1.00 | 2.35 | ACSY |
| ATOM | 628 | NZ | LYS | 34 | 19.169 | 0.213 | −7.932 | 1.00 | 2.48 | ACSY |
| ATOM | 629 | HZ1 | LYS | 34 | 18.904 | 0.450 | −6.955 | 1.00 | 2.82 | ACSY |
| ATOM | 630 | HZ2 | LYS | 34 | 19.427 | −0.793 | −7.988 | 1.00 | 2.83 | ACSY |
| ATOM | 631 | HZ3 | LYS | 34 | 19.980 | 0.796 | −8.223 | 1.00 | 2.84 | ACSY |
| ATOM | 632 | C | LYS | 34 | 13.392 | 3.022 | −10.090 | 1.00 | 1.20 | ACSY |
| ATOM | 633 | O | LYS | 34 | 13.360 | 4.225 | −10.315 | 1.00 | 1.30 | ACSY |
| ATOM | 634 | N | THR | 35 | 12.770 | 2.071 | −10.791 | 1.00 | 1.22 | ACSY |
| ATOM | 635 | HN | THR | 35 | 12.840 | 1.119 | −10.507 | 1.00 | 1.19 | ACSY |
| ATOM | 636 | CA | THR | 35 | 11.996 | 2.414 | −11.968 | 1.00 | 1.35 | ACSY |
| ATOM | 637 | HA | THR | 35 | 12.674 | 2.903 | −12.659 | 1.00 | 1.51 | ACSY |
| ATOM | 638 | CB | THR | 35 | 11.463 | 1.118 | −12.553 | 1.00 | 1.47 | ACSY |
| ATOM | 639 | HB | THR | 35 | 10.411 | 1.028 | −12.316 | 1.00 | 1.54 | ACSY |
| ATOM | 640 | OG1 | THR | 35 | 12.112 | 0.017 | −11.959 | 1.00 | 1.54 | ACSY |
| ATOM | 641 | HG1 | THR | 35 | 11.493 | −0.372 | −11.356 | 1.00 | 1.78 | ACSY |
| ATOM | 642 | CG2 | THR | 35 | 11.664 | 1.065 | −14.055 | 1.00 | 1.88 | ACSY |
| ATOM | 643 | HG21 | THR | 35 | 12.725 | 1.122 | −14.301 | 1.00 | 2.17 | ACSY |
| ATOM | 644 | HG22 | THR | 35 | 11.270 | 0.138 | −14.465 | 1.00 | 2.18 | ACSY |
| ATOM | 645 | HG23 | THR | 35 | 11.159 | 1.897 | −14.541 | 1.00 | 2.38 | ACSY |
| ATOM | 646 | C | THR | 35 | 10.838 | 3.371 | −11.673 | 1.00 | 1.26 | ACSY |
| ATOM | 647 | O | THR | 35 | 10.049 | 3.716 | −12.545 | 1.00 | 1.40 | ACSY |
| ATOM | 648 | N | ASN | 36 | 10.791 | 3.768 | −10.408 | 1.00 | 1.13 | ACSY |
| ATOM | 649 | HN | ASN | 36 | 11.467 | 3.432 | −9.765 | 1.00 | 1.11 | ACSY |
| ATOM | 650 | CA | ASN | 36 | 9.743 | 4.682 | −10.001 | 1.00 | 1.11 | ACSY |
| ATOM | 651 | HA | ASN | 36 | 9.774 | 4.746 | −8.912 | 1.00 | 1.03 | ACSY |
| ATOM | 652 | CB | ASN | 36 | 9.982 | 6.051 | −10.639 | 1.00 | 1.32 | ACSY |
| ATOM | 653 | HB1 | ASN | 36 | 10.927 | 6.472 | −10.296 | 1.00 | 1.36 | ACSY |
| ATOM | 654 | HB2 | ASN | 36 | 10.037 | 5.961 | −11.724 | 1.00 | 1.46 | ACSY |
| ATOM | 655 | CG | ASN | 36 | 8.849 | 7.021 | −10.280 | 1.00 | 1.40 | ACSY |
| ATOM | 656 | OD1 | ASN | 36 | 8.578 | 7.982 | −10.989 | 1.00 | 1.87 | ACSY |
| ATOM | 657 | ND2 | ASN | 36 | 8.214 | 6.704 | −9.135 | 1.00 | 1.73 | ACSY |
| ATOM | 658 | HD21 | ASN | 36 | 8.489 | 5.903 | −8.604 | 1.00 | 2.24 | ACSY |
| ATOM | 659 | HD22 | ASN | 36 | 7.458 | 7.265 | −8.799 | 1.00 | 1.89 | ACSY |

TABLE 24-continued

Coordinates for the 3D structure of SYK-C:peptide complex
created by user: dave

| ATOM | 660 | C    | ASN | 36 | 8.395  | 4.111  | −10.421 | 1.00 | 1.10 | ACSY |
|------|-----|------|-----|-----|--------|--------|---------|------|------|------|
| ATOM | 661 | O    | ASN | 36 | 7.967  | 4.217  | −11.564 | 1.00 | 1.56 | ACSY |
| ATOM | 662 | N    | GLY | 37 | 7.767  | 3.500  | −9.408  | 1.00 | 0.86 | ACSY |
| ATOM | 663 | HN   | GLY | 37 | 8.185  | 3.468  | −8.500  | 1.00 | 1.02 | ACSY |
| ATOM | 664 | CA   | GLY | 37 | 6.471  | 2.894  | −9.647  | 1.00 | 0.82 | ACSY |
| ATOM | 665 | HA1  | GLY | 37 | 6.414  | 2.630  | −10.702 | 1.00 | 0.97 | ACSY |
| ATOM | 666 | HA2  | GLY | 37 | 5.713  | 3.645  | −9.425  | 1.00 | 0.91 | ACSY |
| ATOM | 667 | C    | GLY | 37 | 6.256  | 1.646  | −8.779  | 1.00 | 0.74 | ACSY |
| ATOM | 668 | O    | GLY | 37 | 5.163  | 1.097  | −8.720  | 1.00 | 0.76 | ACSY |
| ATOM | 669 | N    | LYS | 38 | 7.357  | 1.229  | −8.112  | 1.00 | 0.69 | ACSY |
| ATOM | 670 | HN   | LYS | 38 | 8.230  | 1.727  | −8.173  | 1.00 | 0.73 | ACSY |
| ATOM | 671 | CA   | LYS | 38 | 7.224  | 0.062  | −7.272  | 1.00 | 0.63 | ACSY |
| ATOM | 672 | HA   | LYS | 38 | 6.650  | −0.681 | −7.836  | 1.00 | 0.66 | ACSY |
| ATOM | 673 | CB   | LYS | 38 | 8.600  | −0.465 | −6.891  | 1.00 | 0.64 | ACSY |
| ATOM | 674 | HB1  | LYS | 38 | 9.286  | −0.306 | −7.717  | 1.00 | 0.72 | ACSY |
| ATOM | 675 | HB2  | LYS | 38 | 8.978  | 0.107  | −6.049  | 1.00 | 0.62 | ACSY |
| ATOM | 676 | CG   | LYS | 38 | 8.571  | −1.950 | −6.521  | 1.00 | 0.65 | ACSY |
| ATOM | 677 | HG1  | LYS | 38 | 9.029  | −2.087 | −5.542  | 1.00 | 0.85 | ACSY |
| ATOM | 678 | HG2  | LYS | 38 | 7.540  | −2.286 | −6.434  | 1.00 | 0.96 | ACSY |
| ATOM | 679 | CD   | LYS | 38 | 9.309  | −2.806 | −7.551  | 1.00 | 1.12 | ACSY |
| ATOM | 680 | HD1  | LYS | 38 | 8.686  | −2.936 | −8.433  | 1.00 | 1.85 | ACSY |
| ATOM | 681 | HD2  | LYS | 38 | 10.210 | −2.291 | −7.877  | 1.00 | 1.68 | ACSY |
| ATOM | 682 | CE   | LYS | 38 | 9.685  | −4.175 | −6.983  | 1.00 | 1.08 | ACSY |
| ATOM | 683 | HE1  | LYS | 38 | 10.256 | −4.063 | −6.061  | 1.00 | 1.37 | ACSY |
| ATOM | 684 | HE2  | LYS | 38 | 8.792  | −4.752 | −6.751  | 1.00 | 1.51 | ACSY |
| ATOM | 685 | NZ   | LYS | 38 | 10.491 | −4.959 | −7.911  | 1.00 | 1.82 | ACSY |
| ATOM | 686 | HZ1  | LYS | 38 | 9.949  | −5.130 | −8.782  | 1.00 | 2.15 | ACSY |
| ATOM | 687 | HZ2  | LYS | 38 | 11.362 | −4.439 | −8.141  | 1.00 | 2.24 | ACSY |
| ATOM | 688 | HZ3  | LYS | 38 | 10.737 | −5.869 | −7.471  | 1.00 | 2.41 | ACSY |
| ATOM | 689 | C    | LYS | 38 | 6.450  | 0.467  | −6.036  | 1.00 | 0.53 | ACSY |
| ATOM | 690 | O    | LYS | 38 | 6.551  | 1.586  | −5.548  | 1.00 | 0.51 | ACSY |
| ATOM | 691 | N    | PHE | 39 | 5.675  | −0.506 | −5.563  | 1.00 | 0.49 | ACSY |
| ATOM | 692 | HN   | PHE | 39 | 5.671  | −1.410 | −6.000  | 1.00 | 0.53 | ACSY |
| ATOM | 693 | CA   | PHE | 39 | 4.872  | −0.202 | −4.389  | 1.00 | 0.42 | ACSY |
| ATOM | 694 | HA   | PHE | 39 | 5.507  | 0.383  | −3.710  | 1.00 | 0.38 | ACSY |
| ATOM | 695 | CB   | PHE | 39 | 3.655  | 0.623  | −4.820  | 1.00 | 0.44 | ACSY |
| ATOM | 696 | HB1  | PHE | 39 | 3.227  | 1.128  | −3.956  | 1.00 | 0.64 | ACSY |
| ATOM | 697 | HB2  | PHE | 39 | 3.952  | 1.391  | −5.533  | 1.00 | 0.54 | ACSY |
| ATOM | 698 | CG   | PHE | 39 | 2.587  | −0.237 | −5.437  | 1.00 | 0.48 | ACSY |
| ATOM | 699 | CD1  | PHE | 39 | 1.456  | −0.603 | −4.673  | 1.00 | 0.50 | ACSY |
| ATOM | 700 | HD1  | PHE | 39 | 1.369  | −0.265 | −3.652  | 1.00 | 0.48 | ACSY |
| ATOM | 701 | CD2  | PHE | 39 | 2.698  | −0.689 | −6.774  | 1.00 | 0.55 | ACSY |
| ATOM | 702 | HD2  | PHE | 39 | 3.559  | −0.414 | −7.365  | 1.00 | 0.57 | ACSY |
| ATOM | 703 | CE1  | PHE | 39 | 0.444  | −1.410 | −5.233  | 1.00 | 0.57 | ACSY |
| ATOM | 704 | HE1  | PHE | 39 | −0.418 | −1.677 | −4.643  | 1.00 | 0.61 | ACSY |
| ATOM | 705 | CE2  | PHE | 39 | 1.685  | −1.499 | −7.337  | 1.00 | 0.61 | ACSY |
| ATOM | 706 | HE2  | PHE | 39 | 1.773  | −1.842 | −8.357  | 1.00 | 0.67 | ACSY |
| ATOM | 707 | CZ   | PHE | 39 | 0.558  | −1.858 | −6.566  | 1.00 | 0.62 | ACSY |
| ATOM | 708 | HZ   | PHE | 39 | −0.217 | −2.477 | −6.996  | 1.00 | 0.69 | ACSY |
| ATOM | 709 | C    | PHE | 39 | 4.407  | −1.469 | −3.673  | 1.00 | 0.42 | ACSY |
| ATOM | 710 | O    | PHE | 39 | 4.351  | −2.552 | −4.232  | 1.00 | 0.52 | ACSY |
| ATOM | 711 | N    | LEU | 40 | 4.039  | −1.224 | −2.406  | 1.00 | 0.42 | ACSY |
| ATOM | 712 | HN   | LEU | 40 | 4.138  | −0.306 | −2.021  | 1.00 | 0.45 | ACSY |
| ATOM | 713 | CA   | LEU | 40 | 3.524  | −2.311 | −1.595  | 1.00 | 0.49 | ACSY |
| ATOM | 714 | HA   | LEU | 40 | 2.895  | −2.930 | −2.240  | 1.00 | 0.56 | ACSY |
| ATOM | 715 | CB   | LEU | 40 | 4.673  | −3.120 | −1.014  | 1.00 | 0.52 | ACSY |
| ATOM | 716 | HB1  | LEU | 40 | 4.298  | −4.060 | −0.618  | 1.00 | 0.67 | ACSY |
| ATOM | 717 | HB2  | LEU | 40 | 5.372  | −3.376 | −1.801  | 1.00 | 0.70 | ACSY |
| ATOM | 718 | CG   | LEU | 40 | 5.388  | −2.340 | 0.087   | 1.00 | 0.48 | ACSY |
| ATOM | 719 | HG   | LEU | 40 | 5.379  | −1.282 | −0.181  | 1.00 | 0.45 | ACSY |
| ATOM | 720 | CD1  | LEU | 40 | 4.660  | −2.505 | 1.422   | 1.00 | 0.58 | ACSY |
| ATOM | 721 | HD11 | LEU | 40 | 5.225  | −3.148 | 2.094   | 1.00 | 1.04 | ACSY |
| ATOM | 722 | HD12 | LEU | 40 | 4.523  | −1.541 | 1.912   | 1.00 | 1.23 | ACSY |
| ATOM | 723 | HD13 | LEU | 40 | 3.678  | −2.954 | 1.278   | 1.00 | 1.20 | ACSY |
| ATOM | 724 | CD2  | LEU | 40 | 6.839  | −2.800 | 0.211   | 1.00 | 0.52 | ACSY |
| ATOM | 725 | HD21 | LEU | 40 | 7.312  | −2.860 | −0.767  | 1.00 | 1.19 | ACSY |
| ATOM | 726 | HD22 | LEU | 40 | 7.415  | −2.105 | 0.821   | 1.00 | 1.08 | ACSY |
| ATOM | 727 | HD23 | LEU | 40 | 6.896  | −3.784 | 0.674   | 1.00 | 1.14 | ACSY |
| ATOM | 728 | C    | LEU | 40 | 2.671  | −1.720 | −0.476  | 1.00 | 0.52 | ACSY |
| ATOM | 729 | O    | LEU | 40 | 3.115  | −0.883 | 0.300   | 1.00 | 0.53 | ACSY |
| ATOM | 730 | N    | ILE | 41 | 1.422  | −2.208 | −0.448  | 1.00 | 0.64 | ACSY |
| ATOM | 731 | HN   | ILE | 41 | 1.124  | −2.889 | −1.117  | 1.00 | 0.74 | ACSY |
| ATOM | 732 | CA   | ILE | 41 | 0.516  | −1.724 | 0.576   | 1.00 | 0.70 | ACSY |
| ATOM | 733 | HA   | ILE | 41 | 0.826  | −0.707 | 0.829   | 1.00 | 0.67 | ACSY |
| ATOM | 734 | CB   | ILE | 41 | −0.911 | −1.738 | 0.042   | 1.00 | 0.80 | ACSY |
| ATOM | 735 | HB   | ILE | 41 | −0.977 | −1.034 | −0.788  | 1.00 | 0.83 | ACSY |

TABLE 24-continued

Coordinates for the 3D structure of SYK-C:peptide complex
created by user: dave

| ATOM | 736 | CG2 | ILE | 41 | −1.278 | −3.128 | −0.472 | 1.00 | 0.90 | ACSY |
|------|-----|-----|-----|-----|--------|--------|--------|------|------|------|
| ATOM | 737 | HG21 | ILE | 41 | −0.995 | −3.896 | 0.249 | 1.00 | 1.49 | ACSY |
| ATOM | 738 | HG22 | ILE | 41 | −2.350 | −3.208 | −0.646 | 1.00 | 1.13 | ACSY |
| ATOM | 739 | HG23 | ILE | 41 | −0.768 | −3.341 | −1.410 | 1.00 | 1.37 | ACSY |
| ATOM | 740 | CG1 | ILE | 41 | −1.891 | −1.304 | 1.131 | 1.00 | 0.86 | ACSY |
| ATOM | 741 | HG11 | ILE | 41 | −2.902 | −1.319 | 0.733 | 1.00 | 1.11 | ACSY |
| ATOM | 742 | HG12 | ILE | 41 | −1.866 | −2.020 | 1.954 | 1.00 | 1.31 | ACSY |
| ATOM | 743 | CD1 | ILE | 41 | −1.568 | 0.096 | 1.653 | 1.00 | 1.08 | ACSY |
| ATOM | 744 | HD11 | ILE | 41 | −0.538 | 0.152 | 2.002 | 1.00 | 1.64 | ACSY |
| ATOM | 745 | HD12 | ILE | 41 | −1.699 | 0.842 | 0.870 | 1.00 | 1.56 | ACSY |
| ATOM | 746 | HD13 | ILE | 41 | −2.220 | 0.361 | 2.484 | 1.00 | 1.42 | ACSY |
| ATOM | 747 | C | ILE | 41 | 0.639 | −2.607 | 1.817 | 1.00 | 0.78 | ACSY |
| ATOM | 748 | O | ILE | 41 | 0.994 | −3.777 | 1.748 | 1.00 | 0.85 | ACSY |
| ATOM | 749 | N | ARG | 42 | 0.322 | −1.960 | 2.951 | 1.00 | 0.80 | ACSY |
| ATOM | 750 | HN | ARG | 42 | 0.033 | −1.004 | 2.926 | 1.00 | 0.76 | ACSY |
| ATOM | 751 | CA | ARG | 42 | 0.399 | −2.679 | 4.210 | 1.00 | 0.91 | ACSY |
| ATOM | 752 | HA | ARG | 42 | 0.520 | −3.740 | 3.974 | 1.00 | 0.94 | ACSY |
| ATOM | 753 | CB | ARG | 42 | 1.587 | −2.161 | 5.019 | 1.00 | 1.00 | ACSY |
| ATOM | 754 | HB1 | ARG | 42 | 2.518 | −2.477 | 4.547 | 1.00 | 1.43 | ACSY |
| ATOM | 755 | HB2 | ARG | 42 | 1.585 | −1.071 | 5.013 | 1.00 | 1.42 | ACSY |
| ATOM | 756 | CG | ARG | 42 | 1.545 | −2.666 | 6.462 | 1.00 | 1.50 | ACSY |
| ATOM | 757 | HG1 | ARG | 42 | 0.576 | −2.430 | 6.902 | 1.00 | 2.14 | ACSY |
| ATOM | 758 | HG2 | ARG | 42 | 1.639 | −3.752 | 6.473 | 1.00 | 2.02 | ACSY |
| ATOM | 759 | CD | ARG | 42 | 2.656 | −2.045 | 7.308 | 1.00 | 1.83 | ACSY |
| ATOM | 760 | HD1 | ARG | 42 | 2.625 | −0.955 | 7.276 | 1.00 | 2.28 | ACSY |
| ATOM | 761 | HD2 | ARG | 42 | 3.642 | −2.375 | 6.986 | 1.00 | 2.31 | ACSY |
| ATOM | 762 | NE | ARG | 42 | 2.509 | −2.442 | 8.697 | 1.00 | 2.09 | ACSY |
| ATOM | 763 | HE | ARG | 42 | 3.147 | −3.091 | 9.113 | 1.00 | 2.61 | ACSY |
| ATOM | 764 | CZ | ARG | 42 | 1.494 | −1.924 | 9.413 | 1.00 | 2.42 | ACSY |
| ATOM | 765 | NH1 | ARG | 42 | 1.330 | −2.277 | 10.684 | 1.00 | 3.12 | ACSY |
| ATOM | 766 | HH11 | ARG | 42 | 1.960 | −2.927 | 11.108 | 1.00 | 3.45 | ACSY |
| ATOM | 767 | HH12 | ARG | 42 | 0.575 | −1.892 | 11.216 | 1.00 | 3.59 | ACSY |
| ATOM | 768 | NH2 | ARG | 42 | 0.655 | −1.058 | 8.850 | 1.00 | 2.75 | ACSY |
| ATOM | 769 | HH21 | ARG | 42 | 0.779 | −0.791 | 7.894 | 1.00 | 2.71 | ACSY |
| ATOM | 770 | HH22 | ARG | 42 | −0.099 | −0.674 | 9.382 | 1.00 | 3.42 | ACSY |
| ATOM | 771 | C | ARG | 42 | −0.901 | −2.482 | 4.987 | 1.00 | 0.99 | ACSY |
| ATOM | 772 | O | ARG | 42 | −1.425 | −1.380 | 5.100 | 1.00 | 0.97 | ACSY |
| ATOM | 773 | N | ALA | 43 | −1.381 | −3.624 | 5.509 | 1.00 | 1.16 | ACSY |
| ATOM | 774 | HN | ALA | 43 | −0.899 | −4.490 | 5.373 | 1.00 | 1.23 | ACSY |
| ATOM | 775 | CA | ALA | 43 | −2.614 | −3.571 | 6.274 | 1.00 | 1.30 | ACSY |
| ATOM | 776 | HA | ALA | 43 | −2.573 | −2.672 | 6.895 | 1.00 | 1.24 | ACSY |
| ATOM | 777 | CB | ALA | 43 | −3.804 | −3.518 | 5.318 | 1.00 | 1.53 | ACSY |
| ATOM | 778 | HB1 | ALA | 43 | −3.818 | −4.391 | 4.666 | 1.00 | 2.07 | ACSY |
| ATOM | 779 | HB2 | ALA | 43 | −4.744 | −3.493 | 5.869 | 1.00 | 1.83 | ACSY |
| ATOM | 780 | HB3 | ALA | 43 | −3.758 | −2.628 | 4.689 | 1.00 | 1.84 | ACSY |
| ATOM | 781 | C | ALA | 43 | −2.708 | −4.799 | 7.179 | 1.00 | 1.63 | ACSY |
| ATOM | 782 | O | ALA | 43 | −2.897 | −5.922 | 6.729 | 1.00 | 2.22 | ACSY |
| ATOM | 783 | N | ARG | 44 | −2.562 | −4.502 | 8.483 | 1.00 | 1.75 | ACSY |
| ATOM | 784 | HN | ARG | 44 | −2.409 | −3.559 | 8.777 | 1.00 | 1.96 | ACSY |
| ATOM | 785 | CA | ARG | 44 | −2.633 | −5.581 | 9.453 | 1.00 | 2.10 | ACSY |
| ATOM | 786 | HA | ARG | 44 | −2.194 | −6.468 | 8.987 | 1.00 | 2.37 | ACSY |
| ATOM | 787 | CB | ARG | 44 | −1.859 | −5.188 | 10.710 | 1.00 | 2.62 | ACSY |
| ATOM | 788 | HB1 | ARG | 44 | −2.249 | −4.248 | 11.101 | 1.00 | 2.91 | ACSY |
| ATOM | 789 | HB2 | ARG | 44 | −2.013 | −5.939 | 11.484 | 1.00 | 3.07 | ACSY |
| ATOM | 790 | CG | ARG | 44 | −0.363 | −5.046 | 10.433 | 1.00 | 3.13 | ACSY |
| ATOM | 791 | HG1 | ARG | 44 | 0.004 | −5.946 | 9.939 | 1.00 | 3.33 | ACSY |
| ATOM | 792 | HG2 | ARG | 44 | −0.192 | −4.217 | 9.746 | 1.00 | 3.36 | ACSY |
| ATOM | 793 | CD | ARG | 44 | 0.421 | −4.815 | 11.724 | 1.00 | 3.97 | ACSY |
| ATOM | 794 | HD1 | ARG | 44 | 0.214 | −3.832 | 12.150 | 1.00 | 4.35 | ACSY |
| ATOM | 795 | HD2 | ARG | 44 | 1.495 | −4.908 | 11.568 | 1.00 | 4.27 | ACSY |
| ATOM | 796 | NE | ARG | 44 | 0.050 | −5.805 | 12.719 | 1.00 | 4.54 | ACSY |
| ATOM | 797 | HE | ARG | 44 | −0.714 | −6.430 | 12.557 | 1.00 | 4.82 | ACSY |
| ATOM | 798 | CZ | ARG | 44 | 0.752 | −5.865 | 13.866 | 1.00 | 5.05 | ACSY |
| ATOM | 799 | NH1 | ARG | 44 | 0.430 | −6.761 | 14.795 | 1.00 | 5.75 | ACSY |
| ATOM | 800 | HH11 | ARG | 44 | −0.333 | −7.389 | 14.640 | 1.00 | 5.94 | ACSY |
| ATOM | 801 | HH12 | ARG | 44 | 0.951 | −6.807 | 15.647 | 1.00 | 6.24 | ACSY |
| ATOM | 802 | NH2 | ARG | 44 | 1.767 | −5.029 | 14.072 | 1.00 | 5.19 | ACSY |
| ATOM | 803 | HH21 | ARG | 44 | 2.008 | −4.354 | 13.375 | 1.00 | 4.89 | ACSY |
| ATOM | 804 | HH22 | ARG | 44 | 2.287 | −5.075 | 14.925 | 1.00 | 5.82 | ACSY |
| ATOM | 805 | C | ARG | 44 | −4.097 | −5.864 | 9.791 | 1.00 | 2.44 | ACSY |
| ATOM | 806 | O | ARG | 44 | −5.004 | −5.588 | 9.015 | 1.00 | 2.92 | ACSY |
| ATOM | 807 | N | ASP | 45 | −4.259 | −6.430 | 11.001 | 1.00 | 2.85 | ACSY |
| ATOM | 808 | HN | ASP | 45 | −3.469 | −6.628 | 11.581 | 1.00 | 2.99 | ACSY |
| ATOM | 809 | CA | ASP | 45 | −5.603 | −6.750 | 11.446 | 1.00 | 3.58 | ACSY |
| ATOM | 810 | HA | ASP | 45 | −6.245 | −5.905 | 11.181 | 1.00 | 3.95 | ACSY |
| ATOM | 811 | CB | ASP | 45 | −6.073 | −8.029 | 10.760 | 1.00 | 4.38 | ACSY |

TABLE 24-continued

Coordinates for the 3D structure of SYK-C:peptide complex
created by user: dave

| ATOM | 812 | HB1  | ASP | 45 | −6.013 | −7.927 | 9.677  | 1.00 | 4.56 | ACSY |
|------|-----|------|-----|----|--------|--------|--------|------|------|------|
| ATOM | 813 | HB2  | ASP | 45 | −5.448 | −8.873 | 11.050 | 1.00 | 4.52 | ACSY |
| ATOM | 814 | CG   | ASP | 45 | −7.521 | −8.326 | 11.151 | 1.00 | 5.32 | ACSY |
| ATOM | 815 | OD1  | ASP | 45 | −8.418 | −7.677 | 10.617 | 1.00 | 5.79 | ACSY |
| ATOM | 816 | OD2  | ASP | 45 | −7.735 | −9.206 | 11.984 | 1.00 | 5.88 | ACSY |
| ATOM | 817 | C    | ASP | 45 | −5.605 | −6.925 | 12.963 | 1.00 | 3.64 | ACSY |
| ATOM | 818 | O    | ASP | 45 | −5.493 | −8.026 | 13.488 | 1.00 | 3.97 | ACSY |
| ATOM | 819 | N    | ASN | 46 | −5.740 | −5.763 | 13.627 | 1.00 | 3.82 | ACSY |
| ATOM | 820 | HN   | ASN | 46 | −5.829 | −4.899 | 13.131 | 1.00 | 4.02 | ACSY |
| ATOM | 821 | CA   | ASN | 46 | −5.756 | −5.792 | 15.078 | 1.00 | 4.17 | ACSY |
| ATOM | 822 | HA   | ASN | 46 | −6.532 | −6.500 | 15.382 | 1.00 | 4.53 | ACSY |
| ATOM | 823 | CB   | ASN | 46 | −4.387 | −6.233 | 15.592 | 1.00 | 4.87 | ACSY |
| ATOM | 824 | HB1  | ASN | 46 | −4.122 | −7.211 | 15.189 | 1.00 | 5.11 | ACSY |
| ATOM | 825 | HB2  | ASN | 46 | −3.615 | −5.528 | 15.284 | 1.00 | 5.08 | ACSY |
| ATOM | 826 | CG   | ASN | 46 | −4.406 | −6.314 | 17.119 | 1.00 | 5.51 | ACSY |
| ATOM | 827 | OD1  | ASN | 46 | −4.394 | −7.387 | 17.711 | 1.00 | 5.75 | ACSY |
| ATOM | 828 | ND2  | ASN | 46 | −4.436 | −5.106 | 17.708 | 1.00 | 6.13 | ACSY |
| ATOM | 829 | HD21 | ASN | 46 | −4.444 | −4.271 | 17.159 | 1.00 | 6.18 | ACSY |
| ATOM | 830 | HD22 | ASN | 46 | −4.451 | −5.024 | 18.704 | 1.00 | 6.74 | ACSY |
| ATOM | 831 | C    | ASN | 46 | −6.109 | −4.403 | 15.611 | 1.00 | 3.81 | ACSY |
| ATOM | 832 | O    | ASN | 46 | −7.032 | −4.227 | 16.395 | 1.00 | 4.09 | ACSY |
| ATOM | 833 | N    | ASN | 47 | −5.309 | −3.436 | 15.126 | 1.00 | 3.65 | ACSY |
| ATOM | 834 | HN   | ASN | 47 | −4.574 | −3.656 | 14.484 | 1.00 | 3.92 | ACSY |
| ATOM | 835 | CA   | ASN | 47 | −5.536 | −2.065 | 15.553 | 1.00 | 3.57 | ACSY |
| ATOM | 836 | HA   | ASN | 47 | −6.526 | −1.772 | 15.194 | 1.00 | 3.82 | ACSY |
| ATOM | 837 | CB   | ASN | 47 | −5.464 | −1.986 | 17.076 | 1.00 | 4.12 | ACSY |
| ATOM | 838 | HB1  | ASN | 47 | −6.266 | −2.567 | 17.530 | 1.00 | 4.49 | ACSY |
| ATOM | 839 | HB2  | ASN | 47 | −4.517 | −2.387 | 17.437 | 1.00 | 4.36 | ACSY |
| ATOM | 840 | CG   | ASN | 47 | −5.591 | −0.529 | 17.525 | 1.00 | 4.50 | ACSY |
| ATOM | 841 | OD1  | ASN | 47 | −4.710 | 0.294  | 17.309 | 1.00 | 4.69 | ACSY |
| ATOM | 842 | ND2  | ASN | 47 | −6.746 | −0.275 | 18.164 | 1.00 | 5.07 | ACSY |
| ATOM | 843 | HD21 | ASN | 47 | −7.421 | −0.999 | 18.305 | 1.00 | 5.25 | ACSY |
| ATOM | 844 | HD22 | ASN | 47 | −6.949 | 0.643  | 18.507 | 1.00 | 5.55 | ACSY |
| ATOM | 845 | C    | ASN | 47 | −4.484 | −1.156 | 14.919 | 1.00 | 3.20 | ACSY |
| ATOM | 846 | O    | ASN | 47 | −3.291 | −1.435 | 14.936 | 1.00 | 3.63 | ACSY |
| ATOM | 847 | N    | GLY | 48 | −5.012 | −0.052 | 14.360 | 1.00 | 2.90 | ACSY |
| ATOM | 848 | HN   | GLY | 48 | −5.998 | 0.109  | 14.383 | 1.00 | 3.10 | ACSY |
| ATOM | 849 | CA   | GLY | 48 | −4.120 | 0.898  | 13.722 | 1.00 | 2.89 | ACSY |
| ATOM | 850 | HA1  | GLY | 48 | −3.167 | 0.397  | 13.555 | 1.00 | 3.50 | ACSY |
| ATOM | 851 | HA2  | GLY | 48 | −3.974 | 1.729  | 14.413 | 1.00 | 3.36 | ACSY |
| ATOM | 852 | C    | GLY | 48 | −4.706 | 1.396  | 12.399 | 1.00 | 2.07 | ACSY |
| ATOM | 853 | O    | GLY | 48 | −5.874 | 1.751  | 12.303 | 1.00 | 2.14 | ACSY |
| ATOM | 854 | N    | SER | 49 | −3.813 | 1.393  | 11.393 | 1.00 | 1.70 | ACSY |
| ATOM | 855 | HN   | SER | 49 | −2.872 | 1.089  | 11.546 | 1.00 | 2.10 | ACSY |
| ATOM | 856 | CA   | SER | 49 | −4.246 | 1.842  | 10.081 | 1.00 | 1.20 | ACSY |
| ATOM | 857 | HA   | SER | 49 | −5.249 | 1.439  | 9.915  | 1.00 | 1.42 | ACSY |
| ATOM | 858 | CB   | SER | 49 | −4.264 | 3.368  | 10.044 | 1.00 | 1.53 | ACSY |
| ATOM | 859 | HB1  | SER | 49 | −4.616 | 3.729  | 9.077  | 1.00 | 2.11 | ACSY |
| ATOM | 860 | HB2  | SER | 49 | −4.924 | 3.768  | 10.813 | 1.00 | 2.00 | ACSY |
| ATOM | 861 | OG   | SER | 49 | −2.976 | 3.886  | 10.260 | 1.00 | 2.00 | ACSY |
| ATOM | 862 | HG   | SER | 49 | −3.047 | 4.829  | 10.192 | 1.00 | 2.35 | ACSY |
| ATOM | 863 | C    | SER | 49 | −3.303 | 1.289  | 9.012  | 1.00 | 1.13 | ACSY |
| ATOM | 864 | O    | SER | 49 | −2.209 | 0.816  | 9.294  | 1.00 | 1.26 | ACSY |
| ATOM | 865 | N    | TYR | 50 | −3.810 | 1.382  | 7.770  | 1.00 | 1.03 | ACSY |
| ATOM | 866 | HN   | TYR | 50 | −4.714 | 1.782  | 7.618  | 1.00 | 1.07 | ACSY |
| ATOM | 867 | CA   | TYR | 50 | −3.016 | 0.893  | 6.651  | 1.00 | 0.97 | ACSY |
| ATOM | 868 | HA   | TYR | 50 | −2.326 | 0.140  | 7.042  | 1.00 | 1.03 | ACSY |
| ATOM | 869 | CB   | TYR | 50 | −3.935 | 0.293  | 5.576  | 1.00 | 1.02 | ACSY |
| ATOM | 870 | HB1  | TYR | 50 | −4.479 | 1.088  | 5.067  | 1.00 | 1.00 | ACSY |
| ATOM | 871 | HB2  | TYR | 50 | −3.339 | −0.221 | 4.822  | 1.00 | 1.04 | ACSY |
| ATOM | 872 | CG   | TYR | 50 | −4.930 | −0.680 | 6.154  | 1.00 | 1.14 | ACSY |
| ATOM | 873 | CD1  | TYR | 50 | −4.662 | −1.349 | 7.375  | 1.00 | 1.94 | ACSY |
| ATOM | 874 | HD1  | TYR | 50 | −3.731 | −1.169 | 7.893  | 1.00 | 2.71 | ACSY |
| ATOM | 875 | CE1  | TYR | 50 | −5.606 | −2.250 | 7.919  | 1.00 | 2.04 | ACSY |
| ATOM | 876 | HE1  | TYR | 50 | −5.396 | −2.755 | 8.851  | 1.00 | 2.86 | ACSY |
| ATOM | 877 | CD2  | TYR | 50 | −6.154 | −0.927 | 5.486  | 1.00 | 1.46 | ACSY |
| ATOM | 878 | HD2  | TYR | 50 | −6.368 | −0.424 | 4.554  | 1.00 | 2.15 | ACSY |
| ATOM | 879 | CE2  | TYR | 50 | −7.098 | −1.828 | 6.030  | 1.00 | 1.54 | ACSY |
| ATOM | 880 | HE2  | TYR | 50 | −8.030 | −2.010 | 5.515  | 1.00 | 2.22 | ACSY |
| ATOM | 881 | CZ   | TYR | 50 | −6.823 | −2.489 | 7.246  | 1.00 | 1.40 | ACSY |
| ATOM | 882 | OH   | TYR | 50 | −7.745 | −3.368 | 7.778  | 1.00 | 1.54 | ACSY |
| ATOM | 883 | HH   | TYR | 50 | −7.413 | −3.721 | 8.593  | 1.00 | 1.79 | ACSY |
| ATOM | 884 | C    | TYR | 50 | −2.218 | 2.061  | 6.073  | 1.00 | 0.86 | ACSY |
| ATOM | 885 | O    | TYR | 50 | −2.370 | 3.204  | 6.485  | 1.00 | 0.99 | ACSY |
| ATOM | 886 | N    | ALA | 51 | −1.359 | 1.706  | 5.099  | 1.00 | 0.73 | ACSY |
| ATOM | 887 | HN   | ALA | 51 | −1.271 | 0.753  | 4.808  | 1.00 | 0.79 | ACSY |

TABLE 24-continued

Coordinates for the 3D structure of SYK-C:peptide complex
created by user: dave

| ATOM | 888 | CA   | ALA | 51 | -0.566 | 2.758 | 4.484  | 1.00 | 0.64 | ACSY |
|------|-----|------|-----|----|--------|-------|--------|------|------|------|
| ATOM | 889 | HA   | ALA | 51 | -1.267 | 3.533 | 4.166  | 1.00 | 0.63 | ACSY |
| ATOM | 890 | CB   | ALA | 51 | 0.423  | 3.321 | 5.501  | 1.00 | 0.70 | ACSY |
| ATOM | 891 | HB1  | ALA | 51 | 1.028  | 4.111 | 5.056  | 1.00 | 1.06 | ACSY |
| ATOM | 892 | HB2  | ALA | 51 | -0.100 | 3.742 | 6.360  | 1.00 | 1.35 | ACSY |
| ATOM | 893 | HB3  | ALA | 51 | 1.096  | 2.545 | 5.864  | 1.00 | 1.32 | ACSY |
| ATOM | 894 | C    | ALA | 51 | 0.170  | 2.230 | 3.251  | 1.00 | 0.57 | ACSY |
| ATOM | 895 | O    | ALA | 51 | 0.835  | 1.202 | 3.275  | 1.00 | 0.65 | ACSY |
| ATOM | 896 | N    | LEU | 52 | -0.001 | 3.026 | 2.179  | 1.00 | 0.47 | ACSY |
| ATOM | 897 | HN   | LEU | 52 | -0.580 | 3.841 | 2.248  | 1.00 | 0.49 | ACSY |
| ATOM | 898 | CA   | LEU | 52 | 0.636  | 2.681 | 0.915  | 1.00 | 0.41 | ACSY |
| ATOM | 899 | HA   | LEU | 52 | 0.565  | 1.597 | 0.793  | 1.00 | 0.45 | ACSY |
| ATOM | 900 | CB   | LEU | 52 | -0.091 | 3.413 | -0.211 | 1.00 | 0.42 | ACSY |
| ATOM | 901 | HB1  | LEU | 52 | -0.946 | 2.821 | -0.539 | 1.00 | 0.51 | ACSY |
| ATOM | 902 | HB2  | LEU | 52 | -0.486 | 4.355 | 0.166  | 1.00 | 0.45 | ACSY |
| ATOM | 903 | CG   | LEU | 52 | 0.825  | 3.693 | -1.401 | 1.00 | 0.37 | ACSY |
| ATOM | 904 | HG   | LEU | 52 | 1.597  | 4.411 | -1.091 | 1.00 | 0.35 | ACSY |
| ATOM | 905 | CD1  | LEU | 52 | 1.502  | 2.404 | -1.871 | 1.00 | 0.43 | ACSY |
| ATOM | 906 | HD11 | LEU | 52 | 1.255  | 1.571 | -1.212 | 1.00 | 1.05 | ACSY |
| ATOM | 907 | HD12 | LEU | 52 | 1.179  | 2.140 | -2.879 | 1.00 | 1.13 | ACSY |
| ATOM | 908 | HD13 | LEU | 52 | 2.586  | 2.514 | -1.883 | 1.00 | 1.16 | ACSY |
| ATOM | 909 | CD2  | LEU | 52 | 0.016  | 4.312 | -2.537 | 1.00 | 0.42 | ACSY |
| ATOM | 910 | HD21 | LEU | 52 | -0.414 | 5.264 | -2.229 | 1.00 | 0.95 | ACSY |
| ATOM | 911 | HD22 | LEU | 52 | 0.642  | 4.488 | -3.409 | 1.00 | 1.11 | ACSY |
| ATOM | 912 | HD23 | LEU | 52 | -0.801 | 3.655 | -2.835 | 1.00 | 1.13 | ACSY |
| ATOM | 913 | C    | LEU | 52 | 2.106  | 3.096 | 0.949  | 1.00 | 0.36 | ACSY |
| ATOM | 914 | O    | LEU | 52 | 2.448  | 4.200 | 1.334  | 1.00 | 0.39 | ACSY |
| ATOM | 915 | N    | CYS | 53 | 2.947  | 2.145 | 0.501  | 1.00 | 0.38 | ACSY |
| ATOM | 916 | HN   | CYS | 53 | 2.601  | 1.265 | 0.177  | 1.00 | 0.44 | ACSY |
| ATOM | 917 | CA   | CYS | 53 | 4.373  | 2.434 | 0.500  | 1.00 | 0.38 | ACSY |
| ATOM | 918 | HA   | CYS | 53 | 4.490  | 3.501 | 0.712  | 1.00 | 0.40 | ACSY |
| ATOM | 919 | CB   | CYS | 53 | 5.058  | 1.592 | 1.573  | 1.00 | 0.49 | ACSY |
| ATOM | 920 | HB1  | CYS | 53 | 4.979  | 0.535 | 1.318  | 1.00 | 0.73 | ACSY |
| ATOM | 921 | HB2  | CYS | 53 | 6.121  | 1.832 | 1.609  | 1.00 | 0.87 | ACSY |
| ATOM | 922 | SG   | CYS | 53 | 4.353  | 1.841 | 3.222  | 1.00 | 1.14 | ACSY |
| ATOM | 923 | HG   | CYS | 53 | 3.090  | 1.409 | 3.236  | 1.00 | 1.74 | ACSY |
| ATOM | 924 | C    | CYS | 53 | 4.976  | 2.130 | -0.872 | 1.00 | 0.34 | ACSY |
| ATOM | 925 | O    | CYS | 53 | 5.041  | 0.989 | -1.310 | 1.00 | 0.44 | ACSY |
| ATOM | 926 | N    | LEU | 54 | 5.419  | 3.230 | -1.512 | 1.00 | 0.33 | ACSY |
| ATOM | 927 | HN   | LEU | 54 | 5.333  | 4.135 | -1.089 | 1.00 | 0.38 | ACSY |
| ATOM | 928 | CA   | LEU | 54 | 6.035  | 3.068 | -2.825 | 1.00 | 0.36 | ACSY |
| ATOM | 929 | HA   | LEU | 54 | 6.309  | 2.013 | -2.913 | 1.00 | 0.36 | ACSY |
| ATOM | 930 | CB   | LEU | 54 | 5.054  | 2.452 | -3.942 | 1.00 | 0.45 | ACSY |
| ATOM | 931 | HB1  | LEU | 54 | 5.563  | 3.378 | -4.902 | 1.00 | 1.31 | ACSY |
| ATOM | 932 | HB2  | LEU | 54 | 4.248  | 2.724 | -3.965 | 1.00 | 0.57 | ACSY |
| ATOM | 933 | CG   | LEU | 54 | 4.454  | 4.861 | -3.799 | 1.00 | 0.42 | ACSY |
| ATOM | 934 | HG   | LEU | 54 | 4.083  | 5.165 | -4.779 | 1.00 | 0.72 | ACSY |
| ATOM | 935 | CD1  | LEU | 54 | 3.272  | 4.856 | -2.832 | 1.00 | 0.55 | ACSY |
| ATOM | 936 | HD11 | LEU | 54 | 2.754  | 5.815 | -2.849 | 1.00 | 1.22 | ACSY |
| ATOM | 937 | HD12 | LEU | 54 | 2.555  | 4.083 | -3.102 | 1.00 | 1.16 | ACSY |
| ATOM | 938 | HD13 | LEU | 54 | 3.601  | 4.671 | "1.811 | 1.00 | 1.05 | ACSY |
| ATOM | 939 | CD2  | LEU | 54 | 5.504  | 5.873 | -3.48  | 1.00 | 0.59 | ACSY |
| ATOM | 940 | HD21 | LEU | 54 | 6.391  | 5.824 | -3.978 | 1.00 | 1.17 | ACSY |
| ATOM | 941 | HD22 | LEU | 54 | 5.111  | 6.889 | -3.397 | 1.00 | 1.25 | ACSY |
| ATOM | 942 | HD23 | LEU | 54 | 5.806  | 5.679 | -2.323 | 1.00 | 1.10 | ACSY |
| ATOM | 943 | C    | LEU | 54 | 7.313  | 3.900 | -2.883 | 1.00 | 0.43 | ACSY |
| ATOM | 944 | O    | LEU | 54 | 7.617  | 4.666 | -1.980 | 1.00 | 0.49 | ACSY |
| ATOM | 945 | N    | LEU | 55 | 8.059  | 3.691 | -3.986 | 1.00 | 0.50 | ACSY |
| ATOM | 946 | HN   | LEU | 55 | 7.787  | 3.019 | -4.690 | 1.00 | 0.53 | ACSY |
| ATOM | 947 | CA   | LEU | 55 | 9.293  | 4.449 | -4.103 | 1.00 | 0.62 | ACSY |
| ATOM | 948 | HA   | LEU | 55 | 9.333  | 5.134 | -3.251 | 1.00 | 0.63 | ACSY |
| ATOM | 949 | CB   | LEU | 55 | 10.473 | 3.493 | -4.072 | 1.00 | 0.65 | ACSY |
| ATOM | 950 | HB1  | LEU | 55 | 10.385 | 2.842 | -3.211 | 1.00 | 0.59 | ACSY |
| ATOM | 951 | HB2  | LEU | 55 | 10.442 | 2.853 | -4.952 | 1.00 | 0.69 | ACSY |
| ATOM | 952 | CG   | LEU | 55 | 11.805 | 4.248 | -4.033 | 1.00 | 0.77 | ACSY |
| ATOM | 953 | HG   | LEU | 55 | 11.627 | 5.274 | -4.349 | 1.00 | 0.84 | ACSY |
| ATOM | 954 | CD1  | LEU | 55 | 12.397 | 4.274 | -2.631 | 1.00 | 0.77 | ACSY |
| ATOM | 955 | HD11 | LEU | 55 | 11.642 | 4.062 | -1.883 | 1.00 | 1.27 | ACSY |
| ATOM | 956 | HD12 | LEU | 55 | 13.190 | 3.534 | -2.535 | 1.00 | 1.29 | ACSY |
| ATOM | 957 | HD13 | LEU | 55 | 12.827 | 5.249 | -2.414 | 1.00 | 1.20 | ACSY |
| ATOM | 958 | CD2  | LEU | 55 | 12.802 | 3.605 | -4.983 | 1.00 | 0.84 | ACSY |
| ATOM | 959 | HD21 | LEU | 55 | 12.925 | 2.547 | -4.750 | 1.00 | 1.24 | ACSY |
| ATOM | 960 | HD22 | LEU | 55 | 12.468 | 3.690 | -6.013 | 1.00 | 1.34 | ACSY |
| ATOM | 961 | HD23 | LEU | 55 | 13.777 | 4.084 | -4.898 | 1.00 | 1.32 | ACSY |
| ATOM | 962 | C    | LEU | 55 | 9.307  | 5.264 | -5.390 | 1.00 | 0.74 | ACSY |
| ATOM | 963 | O    | LEU | 55 | 8.897  | 4.810 | -6.451 | 1.00 | 0.79 | ACSY |

TABLE 24-continued

Coordinates for the 3D structure of SYK-C:peptide complex
created by user: dave

| ATOM | 964 | N | HIS | 56 | 9.811 | 6.501 | −5.216 | 1.00 | 0.84 | ACSY |
|---|---|---|---|---|---|---|---|---|---|---|
| ATOM | 965 | HN | HIS | 56 | 10.099 | 6.815 | −4.309 | 1.00 | 0.83 | ACSY |
| ATOM | 966 | CA | HIS | 56 | 9.899 | 7.379 | −6.367 | 1.00 | 0.97 | ACSY |
| ATOM | 967 | HA | HIS | 56 | 8.998 | 7.214 | −6.965 | 1.00 | 1.01 | ACSY |
| ATOM | 968 | CB | HIS | 56 | 9.974 | 8.830 | −5.895 | 1.00 | 1.00 | ACSY |
| ATOM | 969 | HB1 | HIS | 56 | 9.096 | 9.085 | −5.301 | 1.00 | 1.00 | ACSY |
| ATOM | 970 | HB2 | HIS | 56 | 10.853 | 8.985 | −5.270 | 1.00 | 1.10 | ACSY |
| ATOM | 971 | CG | HIS | 56 | 10.047 | 9.742 | −7.096 | 1.00 | 1.31 | ACSY |
| ATOM | 972 | CD2 | HIS | 56 | 10.678 | 10.996 | −7.193 | 1.00 | 2.03 | ACSY |
| ATOM | 973 | HD2 | HIS | 56 | 11.213 | 11.508 | −6.408 | 1.00 | 2.72 | ACSY |
| ATOM | 974 | ND1 | HIS | 56 | 9.492 | 9.456 | −8.294 | 1.00 | 1.62 | ACSY |
| ATOM | 975 | HD1 | HIS | 56 | 8.987 | 8.651 | −8.529 | 1.00 | 2.07 | ACSY |
| ATOM | 976 | CE1 | HIS | 56 | 9.771 | 10.495 | −9.099 | 1.00 | 1.85 | ACSY |
| ATOM | 977 | HE1 | HIS | 56 | 9.460 | 10.565 | −10.131 | 1.00 | 2.24 | ACSY |
| ATOM | 978 | NE2 | HIS | 56 | 10.485 | 11.437 | −8.458 | 1.00 | 2.10 | ACSY |
| ATOM | 979 | C | HIS | 56 | 11.135 | 7.004 | −7.202 | 1.00 | 1.26 | ACSY |
| ATOM | 980 | O | HIS | 56 | 11.119 | 6.071 | −7.991 | 1.00 | 2.14 | ACSY |
| ATOM | 981 | N | GLU | 57 | 12.204 | 7.789 | −6.970 | 1.00 | 1.18 | ACSY |
| ATOM | 982 | HN | GLU | 57 | 12.150 | 8.542 | −6.314 | 1.00 | 1.66 | ACSY |
| ATOM | 983 | CA | GLU | 57 | 13.440 | 7.535 | −7.711 | 1.00 | 1.28 | ACSY |
| ATOM | 984 | HA | GLU | 57 | 13.248 | 6.710 | −8.403 | 1.00 | 1.36 | ACSY |
| ATOM | 985 | CB | GLU | 57 | 13.801 | 8.802 | −8.459 | 1.00 | 1.42 | ACSY |
| ATOM | 986 | HB1 | GLU | 57 | 14.040 | 9.577 | −7.732 | 1.00 | 1.46 | ACSY |
| ATOM | 987 | HB2 | GLU | 57 | 14.698 | 8.639 | −9.057 | 1.00 | 1.58 | ACSY |
| ATOM | 988 | CG | GLU | 57 | 12.656 | 9.272 | −9.356 | 1.00 | 1.51 | ACSY |
| ATOM | 989 | HG1 | GLU | 57 | 11.705 | 8.866 | −9.011 | 1.00 | 1.60 | ACSY |
| ATOM | 990 | HG2 | GLU | 57 | 12.577 | 10.357 | −9.338 | 1.00 | 1.73 | ACSY |
| ATOM | 991 | CD | GLU | 57 | 12.899 | 8.812 | −10.795 | 1.00 | 1.74 | ACSY |
| ATOM | 992 | OE1 | GLU | 57 | 12.048 | 8.110 | −11.339 | 1.00 | 2.07 | ACSY |
| ATOM | 993 | OE2 | GLU | 57 | 13.937 | 9.161 | −11.355 | 1.00 | 2.29 | ACSY |
| ATOM | 994 | C | GLU | 57 | 14.594 | 7.156 | −6.767 | 1.00 | 1.28 | ACSY |
| ATOM | 995 | O | GLU | 57 | 15.756 | 7.113 | −7.156 | 1.00 | 1.56 | ACSY |
| ATOM | 996 | N | GLY | 58 | 14.195 | 6.890 | −5.517 | 1.00 | 1.15 | ACSY |
| ATOM | 997 | HN | GLY | 58 | 13.230 | 6.933 | −5.286 | 1.00 | 1.21 | ACSY |
| ATOM | 998 | CA | GLY | 58 | 15.182 | 6.535 | −4.511 | 1.00 | 1.14 | ACSY |
| ATOM | 999 | HA1 | GLY | 58 | 16.152 | 6.846 | −4.876 | 1.00 | 1.29 | ACSY |
| ATOM | 1000 | HA2 | GLY | 58 | 15.169 | 5.451 | −4.404 | 1.00 | 1.17 | ACSY |
| ATOM | 1001 | C | GLY | 58 | 14.867 | 7.213 | −3.169 | 1.00 | 1.10 | ACSY |
| ATOM | 1002 | O | GLY | 58 | 15.744 | 7.559 | −2.388 | 1.00 | 1.20 | ACSY |
| ATOM | 1003 | N | LYS | 59 | 13.549 | 7.370 | −2.981 | 1.00 | 0.98 | ACSY |
| ATOM | 1004 | HN | LYS | 59 | 12.907 | 7.044 | −3.661 | 1.00 | 0.94 | ACSY |
| ATOM | 1005 | CA | LYS | 59 | 13.050 | 7.969 | −1.778 | 1.00 | 0.96 | ACSY |
| ATOM | 1006 | HA | LYS | 59 | 13.756 | 7.745 | −0.975 | 1.00 | 1.00 | ACSY |
| ATOM | 1007 | CB | LYS | 59 | 12.862 | 9.468 | −1.964 | 1.00 | 1.06 | ACSY |
| ATOM | 1008 | HB1 | ;YS | 59 | 11.954 | 9.650 | −2.536 | 1.00 | 1.09 | ACSY |
| ATOM | 1009 | HB2 | LYS | 59 | 12.720 | 9.936 | −0.990 | 1.00 | 1.09 | ACSY |
| ATOM | 1010 | CG | LYS | 59 | 14.055 | 10.106 | −2.673 | 1.00 | 1.30 | ACSY |
| ATOM | 1011 | HG1 | LYS | 59 | 14.129 | 11.154 | −2.388 | 1.00 | 1.73 | ACSY |
| ATOM | 1012 | HG2 | LYS | 59 | 14.977 | 9.624 | −2.346 | 1.00 | 1.75 | ACSY |
| ATOM | 1013 | CD | LYS | 59 | 13.932 | 9.999 | −4.194 | 1.00 | 1.40 | ACSY |
| ATOM | 1014 | HD1 | LYS | 59 | 14.530 | 9.161 | −4.552 | 1.00 | 1.77 | ACSY |
| ATOM | 1015 | HD2 | LYS | 59 | 12.897 | 9.785 | −4.462 | 1.00 | 1.75 | ACSY |
| ATOM | 1016 | CE | LYS | 59 | 14.385 | 11.287 | −4.884 | 1.00 | 1.71 | ACSY |
| ATOM | 1017 | HE1 | LYS | 59 | 14.363 | 11.169 | −5.967 | 1.00 | 2.09 | ACSY |
| ATOM | 1018 | HE2 | LYS | 59 | 13.721 | 12.112 | −4.627 | 1.00 | 2.06 | ACSY |
| ATOM | 1019 | NZ | LYS | 59 | 15.739 | 11.674 | −4.507 | 1.00 | 2.39 | ACSY |
| ATOM | 1020 | HZ1 | LYS | 59 | 16.406 | 10.933 | −4.802 | 1.00 | 2.76 | ACSY |
| ATOM | 1021 | HZ2 | LYS | 59 | 15.986 | 12.570 | −4.974 | 1.00 | 2.67 | ACSY |
| ATOM | 1022 | HZ3 | LYS | 59 | 15.790 | 11.796 | −3.475 | 1.00 | 2.93 | ACSY |
| ATOM | 1023 | C | LYS | 59 | 11.723 | 7.291 | −1.506 | 1.00 | 0.83 | ACSY |
| ATOM | 1024 | O | LYS | 59 | 10.697 | 7.603 | −2.101 | 1.00 | 0.79 | ACSY |
| ATOM | 1025 | N | VAL | 60 | 11.819 | 6.338 | −0.584 | 1.00 | 0.78 | ACSY |
| ATOM | 1026 | HN | VAL | 60 | 12.690 | 6.150 | −0.142 | 1.00 | 0.83 | ACSY |
| ATOM | 1027 | CA | VAL | 60 | 10.630 | 5.584 | −0.267 | 1.00 | 0.66 | ACSY |
| ATOM | 1028 | HA | VAL | 60 | 10.224 | 5.206 | −1.216 | 1.00 | 0.62 | ACSY |
| ATOM | 1029 | CB | VAL | 60 | 10.972 | 4.437 | 0.674 | 1.00 | 0.66 | ACSY |
| ATOM | 1030 | HB | VAL | 60 | 11.963 | 4.058 | 0.423 | 1.00 | 0.70 | ACSY |
| ATOM | 1031 | CG1 | VAL | 60 | 10.982 | 4.933 | 2.114 | 1.00 | 0.73 | ACSY |
| ATOM | 1032 | HG11 | VAL | 60 | 11.681 | 5.759 | 2.235 | 1.00 | 1.16 | ACSY |
| ATOM | 1033 | HG12 | VAL | 60 | 9.991 | 5.285 | 2.406 | 1.00 | 1.28 | ACSY |
| ATOM | 1034 | HG13 | VAL | 60 | 11.269 | 4.139 | 2.794 | 1.00 | 1.17 | ACSY |
| ATOM | 1035 | CG2 | VAL | 60 | 9.955 | 3.308 | 0.532 | 1.00 | 0.57 | ACSY |
| ATOM | 1036 | HG21 | VAL | 60 | 10.351 | 2.376 | 0.933 | 1.00 | 1.16 | ACSY |
| ATOM | 1037 | HG22 | VAL | 60 | 9.037 | 3.544 | 1.072 | 1.00 | 1.12 | ACSY |
| ATOM | 1038 | HG23 | VAL | 60 | 9.697 | 3.146 | −0.512 | 1.00 | 1.05 | ACSY |
| ATOM | 1039 | C | VAL | 60 | 9.616 | 6.499 | 0.393 | 1.00 | 0.66 | ACSY |

TABLE 24-continued

Coordinates for the 3D structure of SYK-C:peptide complex
created by user: dave

| ATOM | 1040 | O | VAL | 60 | 9.941 | 7.393 | 1.164 | 1.00 | 0.75 | ACSY |
|---|---|---|---|---|---|---|---|---|---|---|
| ATOM | 1041 | N | LEU | 61 | 8.370 | 6.186 | 0.048 | 1.00 | 0.56 | ACSY |
| ATOM | 1042 | HN | LEU | 61 | 8.204 | 5.437 | −0.570 | 1.00 | 0.51 | ACSY |
| ATOM | 1043 | CA | LEU | 61 | 7.285 | 6.965 | 0.591 | 1.00 | 0.57 | ACSY |
| ATOM | 1044 | HA | LEU | 61 | 7.710 | 7.604 | 1.366 | 1.00 | 0.65 | ACSY |
| ATOM | 1045 | CB | LEU | 61 | 6.641 | 7.796 | −0.508 | 1.00 | 0.58 | ACSY |
| ATOM | 1046 | HB1 | LEU | 61 | 6.023 | 7.167 | −1.146 | 1.00 | 0.53 | ACSY |
| ATOM | 1047 | HB2 | LEU | 61 | 5.976 | 8.534 | −0.069 | 1.00 | 0.62 | ACSY |
| ATOM | 1048 | CG | LEU | 61 | 7.710 | 8.492 | −1.323 | 1.00 | 0.68 | ACSY |
| ATOM | 1049 | HG | LEU | 61 | 8.308 | 7.738 | −1.835 | 1.00 | 0.66 | ACSY |
| ATOM | 1050 | CD1 | LEU | 61 | 7.090 | 9.413 | −2.368 | 1.00 | 0.75 | ACSY |
| ATOM | 1051 | HD11 | LEU | 61 | 7.859 | 9.995 | −2.878 | 1.00 | 1.33 | ACSY |
| ATOM | 1052 | HD12 | LEU | 61 | 6.552 | 8.835 | −3.117 | 1.00 | 1.20 | ACSY |
| ATOM | 1053 | HD13 | LEU | 61 | 6.389 | 10.109 | −1.908 | 1.00 | 1.22 | ACSY |
| ATOM | 1054 | CD2 | LEU | 61 | 8.609 | 9.268 | −0.376 | 1.00 | 0.78 | ACSY |
| ATOM | 1055 | HD21 | LEU | 61 | 8.692 | 10.304 | −0.682 | 1.00 | 1.25 | ACSY |
| ATOM | 1056 | HD22 | LEU | 61 | 8.209 | 9.248 | 0.639 | 1.00 | 1.39 | ACSY |
| ATOM | 1057 | HD23 | LEU | 61 | 9.605 | 8.834 | −0.350 | 1.00 | 1.15 | ACSY |
| ATOM | 1058 | C | LEU | 61 | 6.252 | 6.080 | 1.228 | 1.00 | 0.50 | ACSY |
| ATOM | 1059 | O | LEU | 61 | 6.206 | 4.868 | 1.051 | 1.00 | 0.47 | ACSY |
| ATOM | 1060 | N | HIS | 62 | 5.422 | 6.800 | 1.975 | 1.00 | 0.51 | ACSY |
| ATOM | 1061 | HN | HIS | 62 | 5.550 | 7.798 | 2.044 | 1.00 | 0.57 | ACSY |
| ATOM | 1062 | CA | HIS | 62 | 4.350 | 6.118 | 2.676 | 1.00 | 0.51 | ACSY |
| ATOM | 1063 | HA | HIS | 62 | 4.120 | 5.215 | 2.103 | 1.00 | 0.44 | ACSY |
| ATOM | 1064 | CB | HIS | 62 | 4.795 | 5.762 | 4.102 | 1.00 | 0.64 | ACSY |
| ATOM | 1065 | HB1 | HIS | 62 | 4.885 | 6.663 | 4.708 | 1.00 | 0.73 | ACSY |
| ATOM | 1066 | HB2 | HIS | 62 | 4.058 | 5.117 | 4.581 | 1.00 | 0.73 | ACSY |
| ATOM | 1067 | CG | HIS | 62 | 6.135 | 5.049 | 4.069 | 1.00 | 0.68 | ACSY |
| ATOM | 1068 | CD2 | HIS | 62 | 7.412 | 5.625 | 3.932 | 1.00 | 1.28 | ACSY |
| ATOM | 1069 | HD2 | HIS | 62 | 7.634 | 6.678 | 3.835 | 1.00 | 1.97 | ACSY |
| ATOM | 1070 | ND1 | HIS | 62 | 6.288 | 3.709 | 4.159 | 1.00 | 0.98 | ACSY |
| ATOM | 1071 | HD1 | HIS | 62 | 5.578 | 3.043 | 4.263 | 1.00 | 1.60 | ACSY |
| ATOM | 1072 | CE1 | HIS | 62 | 7.611 | 3.471 | 4.080 | 1.00 | 0.81 | ACSY |
| ATOM | 1073 | HE1 | HIS | 62 | 8.058 | 2.487 | 4.121 | 1.00 | 1.04 | ACSY |
| ATOM | 1074 | NE2 | HIS | 62 | 8.208 | 4.612 | 3.942 | 1.00 | 1.17 | ACSY |
| ATOM | 1075 | C | HIS | 62 | 3.122 | 7.030 | 2.698 | 1.00 | 0.53 | ACSY |
| ATOM | 1076 | O | HIS | 62 | 3.223 | 8.236 | 2.842 | 1.00 | 0.81 | ACSY |
| ATOM | 1077 | N | TYR | 63 | 1.961 | 6.378 | 2.529 | 1.00 | 0.51 | ACSY |
| ATOM | 1078 | HN | TYR | 63 | 1.939 | 5.396 | 2.393 | 1.00 | 0.72 | ACSY |
| ATOM | 1079 | CA | TYR | 63 | 0.733 | 7.136 | 2.531 | 1.00 | 0.52 | ACSY |
| ATOM | 1080 | HA | TYR | 63 | 0.957 | 8.138 | 2.910 | 1.00 | 0.55 | ACSY |
| ATOM | 1081 | CB | TYR | 63 | 0.182 | 7.177 | 1.114 | 1.00 | 0.47 | ACSY |
| ATOM | 1082 | HB1 | TYR | 63 | 0.152 | 6.170 | 0.699 | 1.00 | 0.93 | ACSY |
| ATOM | 1083 | HB2 | TYR | 63 | −0.831 | 7.543 | 1.129 | 1.00 | 0.77 | ACSY |
| ATOM | 1084 | CG | TYR | 63 | 1.010 | 8.044 | 0.211 | 1.00 | 0.45 | ACSY |
| ATOM | 1085 | CD1 | TYR | 63 | 1.729 | 7.461 | −0.860 | 1.00 | 1.28 | ACSY |
| ATOM | 1086 | HD1 | TYR | 63 | 1.670 | 6.403 | −1.030 | 1.00 | 2.17 | ACSY |
| ATOM | 1087 | CE1 | TYR | 63 | 2.514 | 8.256 | −1.715 | 1.00 | 1.28 | ACSY |
| ATOM | 1088 | HE1 | TYR | 63 | 3.059 | 7.796 | −2.524 | 1.00 | 2.14 | ACSY |
| ATOM | 1089 | CD2 | TYR | 63 | 1.089 | 9.446 | 0.412 | 1.00 | 1.28 | ACSY |
| ATOM | 1090 | HD2 | TYR | 63 | 0.540 | 9.915 | 1.216 | 1.00 | 2.15 | ACSY |
| ATOM | 1091 | CE2 | TYR | 63 | 1.877 | 10.240 | −0.446 | 1.00 | 1.33 | ACSY |
| ATOM | 1092 | HE2 | TYR | 63 | 1.947 | 11.294 | −0.276 | 1.00 | 2.22 | ACSY |
| ATOM | 1093 | CZ | TYR | 63 | 2.589 | 9.648 | −1.510 | 1.00 | 0.58 | ACSY |
| ATOM | 1094 | OH | TYR | 63 | 3.359 | 10.430 | −2.347 | 1.00 | 0.68 | ACSY |
| ATOM | 1095 | HH | TYR | 63 | 3.797 | 9.878 | −2.982 | 1.00 | 1.05 | ACSY |
| ATOM | 1096 | C | TYR | 63 | −0.273 | 6.447 | 3.445 | 1.00 | 0.60 | ACSY |
| ATOM | 1097 | O | TYR | 63 | −0.650 | 5.306 | 3.228 | 1.00 | 0.80 | ACSY |
| ATOM | 1098 | N | ARG | 64 | −0.695 | 7.211 | 4.466 | 1.00 | 0.59 | ACSY |
| ATOM | 1099 | HN | ARG | 64 | −0.363 | 8.147 | 4.582 | 1.00 | 0.65 | ACSY |
| ATOM | 1100 | CA | ARG | 64 | −1.658 | 6.634 | 5.389 | 1.00 | 0.67 | ACSY |
| ATOM | 1101 | HA | ARG | 64 | −1.238 | 5.684 | 5.739 | 1.00 | 0.70 | ACSY |
| ATOM | 1102 | CB | ARG | 64 | −1.914 | 7.570 | 6.566 | 1.00 | 0.72 | ACSY |
| ATOM | 1103 | HB1 | ARG | 64 | −2.959 | 7.495 | 6.864 | 1.00 | 1.09 | ACSY |
| ATOM | 1104 | HB2 | ARG | 64 | −1.325 | 7.240 | 7.418 | 1.00 | 1.24 | ACSY |
| ATOM | 1105 | CG | ARG | 64 | −1.584 | 9.028 | 6.234 | 1.00 | 1.73 | ACSY |
| ATOM | 1106 | HG1 | ARG | 64 | −0.504 | 9.170 | 6.237 | 1.00 | 2.39 | ACSY |
| ATOM | 1107 | HG2 | ARG | 64 | −1.929 | 9.258 | 5.226 | 1.00 | 2.33 | ACSY |
| ATOM | 1108 | CD | ARG | 64 | −2.234 | 9.991 | 7.228 | 1.00 | 1.95 | ACSY |
| ATOM | 1109 | HD1 | ARG | 64 | −1.823 | 9.873 | 8.231 | 1.00 | 2.17 | ACSY |
| ATOM | 1110 | HD2 | ARG | 64 | −3.312 | 9.850 | 7.277 | 1.00 | 2.56 | ACSY |
| ATOM | 1111 | NE | ARG | 64 | −2.007 | 11.366 | 6.820 | 1.00 | 2.22 | ACSY |
| ATOM | 1112 | HE | ARG | 64 | −2.669 | 11.842 | 6.242 | 1.00 | 2.64 | ACSY |
| ATOM | 1113 | CZ | ARG | 64 | −0.886 | 11.990 | 7.232 | 1.00 | 2.59 | ACSY |
| ATOM | 1114 | NH1 | ARG | 64 | −0.655 | 13.248 | 6.869 | 1.00 | 3.34 | ACSY |
| ATOM | 1115 | HH11 | ARG | 64 | −1.313 | 13.730 | 6.290 | 1.00 | 3.74 | ACSY |

TABLE 24-continued

Coordinates for the 3D structure of SYK-C:peptide complex
created by user: dave

| ATOM | 1116 | HH12 | ARG | 64 | 0.176 | 13.712 | 7.174 | 1.00 | 3.75 | ACSY |
|---|---|---|---|---|---|---|---|---|---|---|
| ATOM | 1117 | NH2 | ARG | 64 | −0.010 | 11.350 | 8.002 | 1.00 | 2.83 | ACSY |
| ATOM | 1118 | HH21 | ARG | 64 | −0.181 | 10.404 | 8.276 | 1.00 | 2.84 | ACSY |
| ATOM | 1119 | HH22 | ARG | 64 | 0.821 | 11.816 | 8.306 | 1.00 | 3.37 | ACSY |
| ATOM | 1120 | C | ARG | 64 | −2.958 | 6.358 | 4.645 | 1.00 | 0.74 | ACSY |
| ATOM | 1121 | O | ARG | 64 | −3.435 | 7.160 | 3.852 | 1.00 | 1.34 | ACSY |
| ATOM | 1122 | N | ILE | 65 | −3.492 | 5.169 | 4.959 | 1.00 | 0.74 | ACSY |
| ATOM | 1123 | HN | ILE | 65 | −3.032 | 4.563 | 5.603 | 1.00 | 1.15 | ACSY |
| ATOM | 1124 | CA | ILE | 65 | −4.732 | 4.777 | 4.314 | 1.00 | 0.78 | ACSY |
| ATOM | 1125 | HA | ILE | 65 | −5.128 | 5.657 | 3.800 | 1.00 | 0.75 | ACSY |
| ATOM | 1126 | CB | ILE | 65 | −4.436 | 3.661 | 3.325 | 1.00 | 0.81 | ACSY |
| ATOM | 1127 | HB | ILE | 65 | −3.710 | 2.983 | 3.779 | 1.00 | 0.81 | ACSY |
| ATOM | 1128 | CG2 | ILE | 65 | −5.704 | 2.870 | 3.001 | 1.00 | 1.05 | ACSY |
| ATOM | 1129 | HG21 | ILE | 65 | −6.468 | 3.519 | 2.573 | 1.00 | 1.66 | ACSY |
| ATOM | 1130 | HG22 | ILE | 65 | −5.495 | 2.077 | 2.283 | 1.00 | 1.37 | ACSY |
| ATOM | 1131 | HG23 | ILE | 65 | −6.117 | 2.411 | 3.899 | 1.00 | 1.48 | ACSY |
| ATOM | 1132 | CG1 | ILE | 65 | −3.831 | 4.228 | 2.051 | 1.00 | 0.82 | ACSY |
| ATOM | 1133 | HG11 | ILE | 65 | −4.622 | 4.508 | 1.357 | 1.00 | 1.30 | ACSY |
| ATOM | 1134 | HG12 | ILE | 65 | −3.272 | 5.135 | 2.281 | 1.00 | 1.25 | ACSY |
| ATOM | 1135 | CD1 | ILE | 65 | −2.911 | 3.207 | 1.403 | 1.00 | 0.86 | ACSY |
| ATOM | 1136 | HD11 | ILE | 65 | −3.485 | 2.448 | 0.875 | 1.00 | 1.50 | ACSY |
| ATOM | 1137 | HD12 | ILE | 65 | −2.243 | 3.684 | 0.692 | 1.00 | 1.23 | ACSY |
| ATOM | 1138 | HD13 | ILE | 65 | −2.305 | 2.705 | 2.157 | 1.00 | 1.39 | ACSY |
| ATOM | 1139 | C | ILE | 65 | −5.757 | 4.295 | 5.339 | 1.00 | 0.96 | ACSY |
| ATOM | 1140 | O | ILE | 65 | −5.561 | 3.310 | 6.040 | 1.00 | 1.18 | ACSY |
| ATOM | 1141 | N | ASP | 66 | −6.863 | 5.059 | 5.367 | 1.00 | 0.95 | ACSY |
| ATOM | 1142 | HN | ASP | 66 | −6.934 | 5.874 | 4.797 | 1.00 | 0.90 | ACSY |
| ATOM | 1143 | CA | ASP | 66 | −7.942 | 4.692 | 6.257 | 1.00 | 1.13 | ACSY |
| ATOM | 1144 | HA | ASP | 66 | −7.945 | 3.602 | 6.335 | 1.00 | 1.31 | ACSY |
| ATOM | 1145 | CB | ASP | 66 | −7.759 | 5.335 | 7.618 | 1.00 | 1.41 | ACSY |
| ATOM | 1146 | HB1 | ASP | 66 | −6.738 | 5.221 | 7.963 | 1.00 | 1.63 | ACSY |
| ATOM | 1147 | HB2 | ASP | 66 | −7.981 | 6.395 | 7.560 | 1.00 | 1.51 | ACSY |
| ATOM | 1148 | CG | ASP | 66 | −8.703 | 4.684 | 8.631 | 1.00 | 1.74 | ACSY |
| ATOM | 1149 | OD1 | ASP | 66 | −8.651 | 3.465 | 8.783 | 1.00 | 2.12 | ACSY |
| ATOM | 1150 | OD2 | ASP | 66 | −9.478 | 5.405 | 9.258 | 1.00 | 2.27 | ACSY |
| ATOM | 1151 | C | ASP | 66 | −9.252 | 5.150 | 5.645 | 1.00 | 1.07 | ACSY |
| ATOM | 1152 | O | ASP | 66 | −9.294 | 5.809 | 4.617 | 1.00 | 1.32 | ACSY |
| ATOM | 1153 | N | LYS | 67 | −10.308 | 4.788 | 6.373 | 1.00 | 1.25 | ACSY |
| ATOM | 1154 | HN | LYS | 67 | −10.183 | 4.303 | 7.235 | 1.00 | 1.58 | ACSY |
| ATOM | 1155 | CA | LYS | 67 | −11.628 | 5.141 | 5.899 | 1.00 | 1.22 | ACSY |
| ATOM | 1156 | HA | LYS | 67 | −11.573 | 5.207 | 4.808 | 1.00 | 1.15 | ACSY |
| ATOM | 1157 | CB | LYS | 67 | −12.617 | 4.064 | 6.335 | 1.00 | 1.34 | ACSY |
| ATOM | 1158 | HB1 | LYS | 67 | −13.618 | 4.324 | 5.992 | 1.00 | 1.51 | ACSY |
| ATOM | 1159 | HB2 | LYS | 67 | −12.359 | 3.114 | 5.867 | 1.00 | 1.51 | ACSY |
| ATOM | 1160 | CG | LYS | 67 | −12.623 | 3.907 | 7.851 | 1.00 | 1.53 | ACSY |
| ATOM | 1161 | HG1 | LYS | 67 | −12.083 | 4.738 | 8.301 | 1.00 | 2.00 | ACSY |
| ATOM | 1162 | HG2 | LYS | 67 | −13.641 | 3.962 | 8.219 | 1.00 | 1.67 | ACSY |
| ATOM | 1163 | CD | LYS | 67 | −11.994 | 2.582 | 8.283 | 1.00 | 1.92 | ACSY |
| ATOM | 1164 | HD1 | LYS | 67 | −11.023 | 2.464 | 7.803 | 1.00 | 2.32 | ACSY |
| ATOM | 1165 | HD2 | LYS | 67 | −11.816 | 2.596 | 9.357 | 1.00 | 2.35 | ACSY |
| ATOM | 1166 | CE | LYS | 67 | −12.889 | 1.395 | 7.929 | 1.00 | 2.17 | ACSY |
| ATOM | 1167 | HE1 | LYS | 67 | −13.820 | 1.435 | 8.495 | 1.00 | 2.50 | ACSY |
| ATOM | 1168 | HE2 | LYS | 67 | −13.144 | 1.409 | 6.870 | 1.00 | 2.34 | ACSY |
| ATOM | 1169 | NZ | LYS | 67 | −12.252 | 0.115 | 8.214 | 1.00 | 2.57 | ACSY |
| ATOM | 1170 | HZ1 | LYS | 67 | −11.401 | 0.013 | 7.626 | 1.00 | 2.87 | ACSY |
| ATOM | 1171 | HZ2 | LYS | 67 | −11.986 | 0.076 | 9.219 | 1.00 | 3.05 | ACSY |
| ATOM | 1172 | HZ3 | LYS | 67 | −12.915 | −0.658 | 8.001 | 1.00 | 2.72 | ACSY |
| ATOM | 1173 | C | LYS | 67 | −12.033 | 6.501 | 6.464 | 1.00 | 1.37 | ACSY |
| ATOM | 1174 | O | LYS | 67 | −11.204 | 7.351 | 6.768 | 1.00 | 1.56 | ACSY |
| ATOM | 1175 | N | ASP | 68 | −13.364 | 6.639 | 6.581 | 1.00 | 1.41 | ACSY |
| ATOM | 1176 | HN | ASP | 68 | −13.980 | 5.895 | 6.309 | 1.00 | 1.41 | ACSY |
| ATOM | 1177 | CA | ASP | 68 | −13.896 | 7.882 | 7.105 | 1.00 | 1.62 | ACSY |
| ATOM | 1178 | HA | ASP | 68 | −13.129 | 8.329 | 7.741 | 1.00 | 1.70 | ACSY |
| ATOM | 1179 | CB | ASP | 68 | −14.254 | 8.797 | 5.942 | 1.00 | 1.72 | ACSY |
| ATOM | 1180 | HB1 | ASP | 68 | −14.300 | 8.231 | 5.011 | 1.00 | 1.61 | ACSY |
| ATOM | 1181 | HB2 | ASP | 68 | −15.230 | 9.250 | 6.101 | 1.00 | 2.02 | ACSY |
| ATOM | 1182 | CG | ASP | 68 | −13.205 | 9.902 | 5.804 | 1.00 | 1.96 | ACSY |
| ATOM | 1183 | OD1 | ASP | 68 | −12.020 | 9.607 | 5.945 | 1.00 | 2.32 | ACSY |
| ATOM | 1184 | OD2 | ASP | 68 | −13.586 | 11.046 | 5.557 | 1.00 | 2.39 | ACSY |
| ATOM | 1185 | C | ASP | 68 | −15.134 | 7.572 | 7.938 | 1.00 | 1.77 | ACSY |
| ATOM | 1186 | O | ASP | 68 | −16.196 | 8.158 | 7.766 | 1.00 | 2.22 | ACSY |
| ATOM | 1187 | N | LYS | 69 | −14.920 | 6.607 | 8.848 | 1.00 | 1.68 | ACSY |
| ATOM | 1188 | HN | LYS | 69 | −14.018 | 6.186 | 8.942 | 1.00 | 1.77 | ACSY |
| ATOM | 1189 | CA | LYS | 69 | −16.030 | 6.185 | 9.693 | 1.00 | 1.82 | ACSY |
| ATOM | 1190 | HA | LYS | 69 | −15.737 | 5.232 | 10.143 | 1.00 | 1.87 | ACSY |
| ATOM | 1191 | CB | LYS | 69 | −16.293 | 7.239 | 10.764 | 1.00 | 2.01 | ACSY |

TABLE 24-continued

Coordinates for the 3D structure of SYK-C:peptide complex
created by user: dave

| ATOM | 1192 | HB1 | LYS | 69 | −16.568 | 8.182 | 10.293 | 1.00 | 2.15 | ACSY |
|---|---|---|---|---|---|---|---|---|---|---|
| ATOM | 1193 | HB2 | LYS | 69 | −17.140 | 6.933 | 11.377 | 1.00 | 2.17 | ACSY |
| ATOM | 1194 | CG | LYS | 69 | −15.066 | 7.443 | 11.650 | 1.00 | 2.50 | ACSY |
| ATOM | 1195 | HG1 | LYS | 69 | −14.395 | 8.167 | 11.187 | 1.00 | 2.75 | ACSY |
| ATOM | 1196 | HG2 | LYS | 69 | −15.371 | 7.864 | 12.608 | 1.00 | 2.88 | ACSY |
| ATOM | 1197 | CD | LYS | 69 | −14.323 | 6.127 | 11.878 | 1.00 | 3.02 | ACSY |
| ATOM | 1198 | HD1 | LYS | 69 | −15.023 | 5.368 | 12.226 | 1.00 | 3.24 | ACSY |
| ATOM | 1199 | HD2 | LYS | 69 | −13.917 | 5.769 | 10.930 | 1.00 | 3.05 | ACSY |
| ATOM | 1200 | CE | LYS | 69 | −13.191 | 6.287 | 12.893 | 1.00 | 3.77 | ACSY |
| ATOM | 1201 | HE1 | LYS | 69 | −12.472 | 7.032 | 12.552 | 1.00 | 4.07 | ACSY |
| ATOM | 1202 | HE2 | LYS | 69 | −13.583 | 6.620 | 13.854 | 1.00 | 4.08 | ACSY |
| ATOM | 1203 | NZ | LYS | 69 | −12.467 | 5.041 | 13.117 | 1.00 | 4.38 | ACSY |
| ATOM | 1204 | HZ1 | LYS | 69 | −13.126 | 4.316 | 13.466 | 1.00 | 4.70 | ACSY |
| ATOM | 1205 | HZ2 | LYS | 69 | −12.042 | 4.722 | 12.224 | 1.00 | 4.59 | ACSY |
| ATOM | 1206 | HZ3 | LYS | 69 | −11.718 | 5.198 | 13.822 | 1.00 | 4.74 | ACSY |
| ATOM | 1207 | C | LYS | 69 | −17.277 | 5.944 | 8.837 | 1.00 | 1.81 | ACSY |
| ATOM | 1208 | O | LYS | 69 | −18.411 | 6.099 | 9.273 | 1.00 | 2.01 | ACSY |
| ATOM | 1209 | N | THR | 70 | −16.968 | 5.553 | 7.593 | 1.00 | 1.66 | ACSY |
| ATOM | 1210 | HN | THR | 70 | −16.014 | 5.483 | 7.311 | 1.00 | 1.60 | ACSY |
| ATOM | 1211 | CA | THR | 70 | −18.004 | 5.255 | 6.645 | 1.00 | 1.68 | ACSY |
| ATOM | 1212 | HA | THR | 70 | −18.964 | 5.528 | 7.089 | 1.00 | 1.83 | ACSY |
| ATOM | 1213 | CB | THR | 70 | −17.709 | 6.052 | 5.385 | 1.00 | 1.63 | ACSY |
| ATOM | 1214 | HB | THR | 70 | −16.640 | 6.255 | 5.341 | 1.00 | 1.55 | ACSY |
| ATOM | 1215 | OG1 | THR | 70 | −18.371 | 7.291 | 5.441 | 1.00 | 1.81 | ACSY |
| ATOM | 1216 | HG1 | THR | 70 | −19.295 | 7.103 | 5.531 | 1.00 | 1.95 | ACSY |
| ATOM | 1217 | CG2 | THR | 70 | −18.118 | 5.300 | 4.130 | 1.00 | 1.62 | ACSY |
| ATOM | 1218 | HG21 | THR | 70 | −17.566 | 4.363 | 4.051 | 1.00 | 1.96 | ACSY |
| ATOM | 1219 | HG22 | THR | 70 | −19.180 | 5.066 | 4.149 | 1.00 | 1.86 | ACSY |
| ATOM | 1220 | HG23 | THR | 70 | −17.911 | 5.891 | 3.241 | 1.00 | 1.91 | ACSY |
| ATOM | 1221 | C | THR | 70 | −17.968 | 3.755 | 6.336 | 1.00 | 1.67 | ACSY |
| ATOM | 1222 | O | THR | 70 | −18.974 | 3.128 | 6.025 | 1.00 | 1.79 | ACSY |
| ATOM | 1223 | N | GLY | 71 | −16.728 | 3.235 | 6.447 | 1.00 | 1.59 | ACSY |
| ATOM | 1224 | HN | GLY | 71 | −15.964 | 3.809 | 6.749 | 1.00 | 1.53 | ACSY |
| ATOM | 1225 | CA | GLY | 71 | −16.532 | 1.833 | 6.169 | 1.00 | 1.67 | ACSY |
| ATOM | 1226 | HA1 | GLY | 71 | −17.512 | 1.401 | 6.014 | 1.00 | 1.80 | ACSY |
| ATOM | 1227 | HA2 | GLY | 71 | −16.075 | 1.396 | 7.050 | 1.00 | 1.79 | ACSY |
| ATOM | 1228 | C | GLY | 71 | −15.651 | 1.599 | 4.933 | 1.00 | 1.52 | ACSY |
| ATOM | 1229 | O | GLY | 71 | −15.118 | 0.517 | 4.717 | 1.00 | 1.62 | ACSY |
| ATOM | 1230 | N | LYS | 72 | −15.539 | 2.681 | 4.146 | 1.00 | 1.36 | ACSY |
| ATOM | 1231 | HN | LYS | 72 | −15.986 | 3.536 | 4.401 | 1.00 | 1.37 | ACSY |
| ATOM | 1232 | CA | LYS | 72 | −14.737 | 2.586 | 2.939 | 1.00 | 1.28 | ACSY |
| ATOM | 1233 | HA | LYS | 72 | −14.667 | 1.528 | 2.679 | 1.00 | 1.36 | ACSY |
| ATOM | 1234 | CB | LYS | 72 | −15.400 | 3.380 | 1.816 | 1.00 | 1.29 | ACSY |
| ATOM | 1235 | HB1 | LYS | 72 | −15.365 | 4.444 | 2.053 | 1.00 | 1.38 | ACSY |
| ATOM | 1236 | HB2 | LYS | 72 | −14.836 | 3.246 | 0.893 | 1.00 | 1.42 | ACSY |
| ATOM | 1237 | CG | LYS | 72 | −16.851 | 2.951 | 1.599 | 1.00 | 1.65 | ACSY |
| ATOM | 1238 | HG1 | LYS | 72 | −16.890 | 1.883 | 1.387 | 1.00 | 1.80 | ACSY |
| ATOM | 1239 | HG2 | LYS | 72 | −17.421 | 3.112 | 2.513 | 1.00 | 1.99 | ACSY |
| ATOM | 1240 | CD | LYS | 72 | −17.496 | 3.727 | 0.450 | 1.00 | 2.27 | ACSY |
| ATOM | 1241 | HD1 | LYS | 72 | −17.213 | 4.778 | 0.515 | 1.00 | 2.73 | ACSY |
| ATOM | 1242 | HD2 | LYS | 72 | −17.114 | 3.357 | −0.502 | 1.00 | 2.64 | ACSY |
| ATOM | 1243 | CE | LYS | 72 | −19.020 | 3.605 | 0.475 | 1.00 | 2.74 | ACSY |
| ATOM | 1244 | HE1 | LYS | 72 | −19.321 | 2.558 | 0.439 | 1.00 | 2.96 | ACSY |
| ATOM | 1245 | HE2 | LYS | 72 | −19.422 | 4.035 | 1.392 | 1.00 | 3.17 | ACSY |
| ATOM | 1246 | NZ | LYS | 72 | −19.651 | 4.286 | −0.649 | 1.00 | 3.27 | ACSY |
| ATOM | 1247 | HZ1 | LYS | 72 | −20.686 | 4.215 | −0.561 | 1.00 | 3.63 | ACSY |
| ATOM | 1248 | HZ2 | LYS | 72 | −19.371 | 5.289 | −0.648 | 1.00 | 3.46 | ACSY |
| ATOM | 1249 | HZ3 | LYS | 72 | −19.346 | 3.842 | −1.539 | 1.00 | 3.62 | ACSY |
| ATOM | 1250 | C | LYS | 72 | −13.342 | 3.128 | 3.221 | 1.00 | 1.20 | ACSY |
| ATOM | 1251 | O | LYS | 72 | −13.170 | 4.120 | 3.912 | 1.00 | 1.30 | ACSY |
| ATOM | 1252 | N | LEU | 73 | −12.363 | 2.429 | 2.621 | 1.00 | 1.12 | ACSY |
| ATOM | 1253 | HN | LEU | 73 | −12.573 | 1.653 | 2.026 | 1.00 | 1.17 | ACSY |
| ATOM | 1254 | CA | LEU | 73 | −10.994 | 2.851 | 2.828 | 1.00 | 1.07 | ACSY |
| ATOM | 1255 | HA | LEU | 73 | −10.894 | 3.156 | 3.878 | 1.00 | 1.09 | ACSY |
| ATOM | 1256 | CB | LEU | 73 | −10.049 | 1.701 | 2.490 | 1.00 | 1.07 | ACSY |
| ATOM | 1257 | HB1 | LEU | 73 | −10.307 | 1.293 | 1.513 | 1.00 | 1.3 | ACSY |
| ATOM | 1258 | HB2 | LEU | 72 | −9.034 | 2.080 | 2.411 | 1.00 | 1.08 | ACSY |
| ATOM | 1259 | CG | LEU | 73 | −10.098 | 0.587 | 3.536 | 1.00 | 1.12 | ACSY |
| ATOM | 1260 | HG | LEU | 73 | −11.121 | 0.215 | 3.600 | 1.00 | 1.31 | ACSY |
| ATOM | 1261 | CD1 | LEU | 73 | −9.187 | −0.567 | 3.120 | 1.00 | 1.13 | ACSY |
| ATOM | 1262 | HD11 | LEU | 73 | −9.263 | −1.397 | 3.822 | 1.00 | 1.55 | ACSY |
| ATOM | 1263 | HD12 | LEU | 73 | −9.455 | −0.937 | 2.130 | 1.00 | 1.77 | ACSY |
| ATOM | 1264 | HD13 | LEU | 73 | −8.145 | −0.248 | 3.087 | 1.00 | 1.22 | ACSY |
| ATOM | 1265 | CD2 | LEU | 73 | −9.680 | 1.120 | 4.909 | 1.00 | 1.21 | ACSY |
| ATOM | 1266 | HD21 | LEU | 73 | −8.705 | 1.606 | 4.858 | 1.00 | 1.53 | ACSY |
| ATOM | 1267 | HD22 | LEU | 73 | −10.400 | 1.848 | 5.281 | 1.00 | 1.71 | ACSY |

TABLE 24-continued

Coordinates for the 3D structure of SYK-C:peptide complex
created by user: dave

| ATOM | 1268 | HD23 | LEU | 73 | −9.615 | 0.311 | 5.637 | 1.00 | 1.59 | ACSY |
|---|---|---|---|---|---|---|---|---|---|---|
| ATOM | 1269 | C | LEU | 73 | −10.716 | 4.044 | 1.924 | 1.00 | 1.03 | ACSY |
| ATOM | 1270 | O | LEU | 73 | −11.383 | 4.262 | 0.923 | 1.00 | 1.10 | ACSY |
| ATOM | 1271 | N | SER | 74 | −9.696 | 4.802 | 2.346 | 1.00 | 0.98 | ACSY |
| ATOM | 1272 | HN | SER | 74 | −9.199 | 4.574 | 3.184 | 1.00 | 1.00 | ACSY |
| ATOM | 1273 | CA | SER | 74 | −9.350 | 5.969 | 1.562 | 1.00 | 0.95 | ACSY |
| ATOM | 1274 | HA | SER | 74 | −9.233 | 5.644 | 0.524 | 1.00 | 0.94 | ACSY |
| ATOM | 1275 | CB | SER | 74 | −10.470 | 6.999 | 1.685 | 1.00 | 1.02 | ACSY |
| ATOM | 1276 | HB1 | SER | 74 | −10.201 | 7.925 | 1.180 | 1.00 | 1.48 | ACSY |
| ATOM | 1277 | HB2 | SER | 74 | −11.392 | 6.626 | 1.240 | 1.00 | 1.56 | ACSY |
| ATOM | 1278 | OG | SER | 74 | −10.724 | 7.295 | 3.035 | 1.00 | 1.35 | ACSY |
| ATOM | 1279 | HG | SER | 74 | −11.419 | 7.940 | 3.046 | 1.00 | 1.36 | ACSY |
| ATOM | 1280 | C | SER | 74 | −8.034 | 6.564 | 2.052 | 1.00 | 0.91 | ACSY |
| ATOM | 1281 | O | SER | 74 | −7.308 | 5.984 | 2.851 | 1.00 | 1.21 | ACSY |
| ATOM | 1282 | N | ILE | 75 | −7.792 | 7.766 | 1.507 | 1.00 | 0.80 | ACSY |
| ATOM | 1283 | HN | ILE | 75 | −8.442 | 8.166 | 0.861 | 1.00 | 0.98 | ACSY |
| ATOM | 1284 | CA | ILE | 75 | −6.581 | 8.479 | 1.864 | 1.00 | 0.76 | ACSY |
| ATOM | 1285 | HA | ILE | 75 | −6.269 | 8.131 | 2.851 | 1.00 | 0.79 | ACSY |
| ATOM | 1286 | CB | ILE | 75 | −5.511 | 8.203 | 0.808 | 1.00 | 0.72 | ACSY |
| ATOM | 1287 | HB | ILE | 75 | −5.938 | 8.425 | −0.169 | 1.00 | 1.16 | ACSY |
| ATOM | 1288 | CG2 | ILE | 75 | −4.287 | 9.097 | 1.016 | 1.00 | 0.90 | ACSY |
| ATOM | 1289 | HG21 | ILE | 75 | −3.615 | 8.669 | 1.759 | 1.00 | 1.48 | ACSY |
| ATOM | 1290 | HG22 | ILE | 75 | −3.727 | 9.215 | 0.089 | 1.00 | 1.34 | ACSY |
| ATOM | 1291 | HG23 | ILE | 75 | −4.581 | 10.088 | 1.359 | 1.00 | 1.53 | ACSY |
| ATOM | 1292 | CG1 | ILE | 75 | −5.094 | 6.733 | 0.832 | 1.00 | 0.90 | ACSY |
| ATOM | 1293 | HG11 | ILE | 75 | −4.812 | 6.448 | 1.845 | 1.00 | 1.14 | ACSY |
| ATOM | 1294 | HG12 | ILE | 75 | −5.941 | 6.107 | 0.553 | 1.00 | 1.40 | ACSY |
| ATOM | 1295 | CD1 | ILE | 75 | −3.925 | 6.473 | −0.121 | 1.00 | 0.83 | ACSY |
| ATOM | 1296 | HD11 | ILE | 75 | −3.027 | 6.991 | 0.216 | 1.00 | 1.20 | ACSY |
| ATOM | 1297 | HD12 | ILE | 75 | −3.698 | 5.409 | −0.178 | 1.00 | 1.33 | ACSY |
| ATOM | 1298 | HD13 | ILE | 75 | −4.158 | 6.822 | −1.127 | 1.00 | 1.27 | ACSY |
| ATOM | 1299 | C | ILE | 75 | −6.906 | 9.973 | 1.961 | 1.00 | 0.81 | ACSY |
| ATOM | 1300 | O | ILE | 75 | −7.672 | 10.490 | 1.113 | 1.00 | 0.86 | ACSY |
| ATOM | 1301 | N | PRO | 76 | −6.283 | 10.643 | 2.910 | 1.00 | 0.84 | ACSY |
| ATOM | 1302 | CD | PRO | 76 | −5.351 | 10.026 | 3.835 | 1.00 | 0.85 | ACSY |
| ATOM | 1303 | HD1 | PRO | 76 | −4.570 | 9.501 | 3.288 | 1.00 | 0.92 | ACSY |
| ATOM | 1304 | HD2 | PRO | 76 | −5.872 | 9.307 | 4.466 | 1.00 | 0.94 | ACSY |
| ATOM | 1305 | CA | PRO | 76 | −6.467 | 12.066 | 3.108 | 1.00 | 0.92 | ACSY |
| ATOM | 1306 | HA | PRO | 76 | −7.478 | 12.256 | 3.461 | 1.00 | 1.01 | ACSY |
| ATOM | 1307 | CB | PRO | 76 | −5.437 | 12.470 | 4.167 | 1.00 | 0.95 | ACSY |
| ATOM | 1308 | HB1 | PRO | 76 | −4.694 | 13.143 | 3.740 | 1.00 | 0.94 | ACSY |
| ATOM | 1309 | HB2 | PRO | 76 | −5.921 | 12.993 | 4.991 | 1.00 | 1.05 | ACSY |
| ATOM | 1310 | CG | PRO | 76 | −4.770 | 11.176 | 4.664 | 1.00 | 0.93 | ACSY |
| ATOM | 1311 | HG1 | PRO | 76 | −3.689 | 11.230 | 4.540 | 1.00 | 0.92 | ACSY |
| ATOM | 1312 | HG2 | PRO | 76 | −4.974 | 11.023 | 5.724 | 1.00 | 1.02 | ACSY |
| ATOM | 1313 | C | PRO | 76 | −6.239 | 12.842 | 1.812 | 1.00 | 0.90 | ACSY |
| ATOM | 1314 | O | PRO | 76 | −7.151 | 13.420 | 1.232 | 1.00 | 1.03 | ACSY |
| ATOM | 1315 | N | GLU | 77 | −4.962 | 12.809 | 1.408 | 1.00 | 0.82 | ACSY |
| ATOM | 1316 | HN | GLU | 77 | −4.273 | 12.329 | 1.948 | 1.00 | 0.80 | ACSY |
| ATOM | 1317 | CA | GLU | 77 | −4.600 | 13.494 | 0.178 | 1.00 | 0.84 | ACSY |
| ATOM | 1318 | HA | GLU | 77 | −5.197 | 14.409 | 0.128 | 1.00 | 0.96 | ACSY |
| ATOM | 1319 | CB | GLU | 77 | −3.111 | 13.821 | 0.209 | 1.00 | 0.90 | ACSY |
| ATOM | 1320 | HB1 | GLU | 77 | −2.533 | 12.905 | 0.084 | 1.00 | 1.16 | ACSY |
| ATOM | 1321 | HB2 | GLU | 77 | −2.859 | 14.468 | −0.631 | 1.00 | 1.24 | ACSY |
| ATOM | 1322 | CG | GLU | 77 | −2.715 | 14.500 | 1.520 | 1.00 | 1.34 | ACSY |
| ATOM | 1323 | HG1 | GLU | 77 | −3.014 | 13.892 | 2.373 | 1.00 | 1.86 | ACSY |
| ATOM | 1324 | HG2 | HLU | 77 | −1.636 | 14.637 | 1.571 | 1.00 | 1.80 | ACSY |
| ATOM | 1325 | CD | GLU | 77 | −3.396 | 15.867 | 1.621 | 1.00 | 2.06 | ACSY |
| ATOM | 1326 | OE1 | GLU | 77 | −4.001 | 16.145 | 2.655 | 1.00 | 2.62 | ACSY |
| ATOM | 1327 | OE2 | GLU | 77 | −3.313 | 15.636 | 0.665 | 1.00 | 2.79 | ACSY |
| ATOM | 1328 | C | GLU | 77 | −4.931 | 12.612 | −1.035 | 1.00 | 0.73 | ACSY |
| ATOM | 1329 | O | GLU | 77 | −5.307 | 13.094 | −2.097 | 1.00 | 0.84 | ACSY |
| ATOM | 1330 | N | GLY | 78 | −4.766 | 11.293 | −0.802 | 1.00 | 0.65 | ACSY |
| ATOM | 1331 | HN | GLY | 78 | −4.457 | 10.971 | 0.091 | 1.00 | 0.74 | ACSY |
| ATOM | 1332 | CA | GLY | 78 | −5.037 | 10.353 | −1.876 | 1.00 | 0.58 | ACSY |
| ATOM | 1333 | HA1 | GLY | 78 | −4.888 | 9.351 | −1.483 | 1.00 | 0.95 | ACSY |
| ATOM | 1334 | HA2 | GLY | 78 | −4.305 | 10.533 | −2.663 | 1.00 | 0.69 | ACSY |
| ATOM | 1335 | C | GLY | 78 | −6.463 | 10.510 | −2.413 | 1.00 | 0.70 | ACSY |
| ATOM | 1336 | O | GLY | 78 | −6.861 | 11.564 | −2.893 | 1.00 | 0.97 | ACSY |
| ATOM | 1337 | N | LYS | 79 | −7.198 | 9.386 | −2.295 | 1.00 | 0.65 | ACSY |
| ATOM | 1338 | HN | LYS | 79 | −6.806 | 8.558 | −1.895 | 1.00 | 0.71 | ACSY |
| ATOM | 1339 | CA | LYS | 79 | −8.568 | 9.395 | −2.775 | 1.00 | 0.74 | ACSY |
| ATOM | 1340 | HA | LYS | 79 | −8.879 | 10.435 | −2.871 | 1.00 | 0.82 | ACSY |
| ATOM | 1341 | CB | LYS | 79 | −8.617 | 8.689 | −4.129 | 1.00 | 0.75 | ACSY |
| ATOM | 1342 | HB1 | LYS | 79 | −7.683 | 8.833 | −4.647 | 1.00 | 0.96 | ACSY |
| ATOM | 1343 | HB2 | LYS | 79 | −8.719 | 7.617 | −3.972 | 1.00 | 0.88 | ACSY |

TABLE 24-continued

Coordinates for the 3D structure of SYK-C:peptide complex
created by user: dave

| ATOM | 1344 | CG  | LYS | 79 | −9.764  | 9.200  | −4.998 | 1.00 | 1.02 | ACSY |
|------|------|-----|-----|----|---------|--------|--------|------|------|------|
| ATOM | 1345 | HG1 | LYS | 79 | −10.152 | 8.384  | −5.607 | 1.00 | 1.25 | ACSY |
| ATOM | 1346 | HG2 | LYS | 79 | −10.584 | 9.539  | −4.365 | 1.00 | 1.14 | ACSY |
| ATOM | 1347 | CD  | LYS | 79 | −9.303  | 10.342 | −5.904 | 1.00 | 1.32 | ACSY |
| ATOM | 1348 | HD1 | LYS | 79 | −9.106  | 11.229 | −5.303 | 1.00 | 1.40 | ACSY |
| ATOM | 1349 | HD2 | LYS | 79 | −8.360  | 10.069 | −6.381 | 1.00 | 1.43 | ACSY |
| ATOM | 1350 | CE  | LYS | 79 | −10.344 | 10.668 | −6.976 | 1.00 | 1.64 | ACSY |
| ATOM | 1351 | HE1 | LYS | 79 | −10.553 | 9.789  | −7.586 | 1.00 | 1.84 | ACSY |
| ATOM | 1352 | HE2 | LYS | 79 | −11.281 | 10.983 | −6.517 | 1.00 | 1.93 | ACSY |
| ATOM | 1353 | NZ  | LYS | 79 | −9.905  | 11.734 | −7.868 | 1.00 | 2.44 | ACSY |
| ATOM | 1354 | HZ1 | LYS | 79 | −9.728  | 12.597 | −7.316 | 1.00 | 2.79 | ACSY |
| ATOM | 1355 | HZ2 | LYS | 79 | −9.030  | 11.444 | −8.350 | 1.00 | 2.96 | ACSY |
| ATOM | 1356 | HZ3 | LYS | 79 | −10.644 | 11.920 | −8.575 | 1.00 | 2.83 | ACSY |
| ATOM | 1357 | C   | LYS | 79 | −9.481  | 8.689  | −1.770 | 1.00 | 0.85 | ACSY |
| ATOM | 1358 | O   | LYS | 79 | −9.352  | 8.823  | −0.561 | 1.00 | 1.10 | ACSY |
| ATOM | 1359 | N   | LYS | 80 | −10.405 | 7.932  | −2.379 | 1.00 | 0.88 | ACSY |
| ATOM | 1360 | HN  | LYS | 80 | −10.416 | 7.887  | −3.381 | 1.00 | 1.00 | ACSY |
| ATOM | 1361 | CA  | LYS | 80 | −11.366 | 7.178  | −1.581 | 1.00 | 0.95 | ACSY |
| ATOM | 1362 | HA  | LYS | 80 | −10.863 | 6.883  | −0.657 | 1.00 | 0.94 | ACSY |
| ATOM | 1363 | CB  | LYS | 80 | −12.586 | 8.049  | −1.285 | 1.00 | 1.07 | ACSY |
| ATOM | 1364 | HB1 | LYS | 80 | −12.873 | 8.595  | −2.183 | 1.00 | 1.37 | ACSY |
| ATOM | 1365 | HB2 | LYS | 80 | −13.431 | 7.413  | −1.020 | 1.00 | 1.48 | ACSY |
| ATOM | 1366 | CG  | LYS | 80 | −12.314 | 9.034  | −0.148 | 1.00 | 1.96 | ACSY |
| ATOM | 1367 | HG1 | LYS | 80 | −11.456 | 9.658  | −0.400 | 1.00 | 2.60 | ACSY |
| ATOM | 1368 | HG2 | LYS | 80 | −12.049 | 8.485  | 0.755  | 1.00 | 2.58 | ACSY |
| ATOM | 1369 | CD  | LYS | 80 | −13.528 | 9.919  | 0.133  | 1.00 | 2.13 | ACSY |
| ATOM | 1370 | HD1 | LYS | 80 | −13.769 | 10.504 | −0.755 | 1.00 | 2.69 | ACSY |
| ATOM | 1371 | HD2 | LYS | 80 | −14.396 | 9.294  | 0.342  | 1.00 | 2.42 | ACSY |
| ATOM | 1372 | CE  | LYS | 80 | −13.276 | 10.858 | 1.313  | 1.00 | 2.10 | ACSY |
| ATOM | 1373 | HE1 | LYS | 80 | −21.978 | 10.293 | 2.195  | 1.00 | 2.30 | ACSY |
| ATOM | 1374 | HE2 | LYS | 80 | −12.473 | 11.558 | 1.081  | 1.00 | 2.28 | ACSY |
| ATOM | 1375 | NZ  | LYS | 80 | −14.457 | 11.638 | 1.664  | 1.00 | 2.59 | ACSY |
| ATOM | 1376 | HZ1 | LYS | 80 | −14.752 | 12.210 | 0.847  | 1.00 | 2.95 | ACSY |
| ATOM | 1377 | HZ2 | LYS | 80 | −15.229 | 10.996 | 1.934  | 1.00 | 2.99 | ACSY |
| ATOM | 1378 | HZ3 | LYS | 80 | −14.233 | 12.266 | 2.463  | 1.00 | 2.80 | ACSY |
| ATOM | 1379 | C   | LYS | 80 | −11.777 | 5.923  | −2.354 | 1.00 | 0.98 | ACSY |
| ATOM | 1380 | O   | LYS | 80 | −12.191 | 5.986  | −3.505 | 1.00 | 1.01 | ACSY |
| ATOM | 1381 | N   | PHE | 81 | −11.632 | 4.782  | −1.649 | 1.00 | 1.00 | ACSY |
| ATOM | 1382 | HN  | PHE | 81 | −11.275 | 4.790  | −0.723 | 1.00 | 1.02 | ACSY |
| ATOM | 1383 | CA  | PHE | 81 | −11.970 | 3.532  | −2.289 | 1.00 | 1.05 | ACSY |
| ATOM | 1384 | HA  | PHE | 81 | −12.605 | 3.760  | −3.149 | 1.00 | 1.08 | ACSY |
| ATOM | 1385 | CB  | PHE | 81 | −10.678 | 2.874  | −2.724 | 1.00 | 1.00 | ACSY |
| ATOM | 1386 | HB1 | PHE | 81 | −9.970  | 2.868  | −1.899 | 1.00 | 0.95 | ACSY |
| ATOM | 1387 | HB2 | PHE | 81 | −10.863 | 1.847  | −2.995 | 1.00 | 1.07 | ACSY |
| ATOM | 1388 | CG  | PHE | 81 | −10.071 | 3.595  | −3.889 | 1.00 | 0.97 | ACSY |
| ATOM | 1389 | CD1 | OHE | 81 | −9.065  | 4.571  | −3.683 | 1.00 | 1.42 | ACSY |
| ATOM | 1390 | HD1 | PHE | 81 | −8.730  | 4.796  | −2.680 | 1.00 | 2.20 | ACSY |
| ATOM | 1391 | CD2 | PHE | 81 | −10.501 | 3.310  | −5.207 | 1.00 | 1.66 | ACSY |
| ATOM | 1392 | HD2 | PHE | 81 | −11.268 | 2.569  | −5.373 | 1.00 | 2.45 | ACSY |
| ATOM | 1393 | CE1 | PHE | 81 | −8.495  | 5.250  | −4.784 | 1.00 | 1.43 | ACSY |
| ATOM | 1394 | HE1 | PHE | 81 | −7.727  | 5.992  | −4.621 | 1.00 | 2.17 | ACSY |
| ATOM | 1395 | CE2 | PHE | 81 | −9.931  | 3.990  | −6.307 | 1.00 | 1.72 | ACSY |
| ATOM | 1396 | HE2 | PHE | 81 | −10.266 | 3.769  | −7.310 | 1.00 | 2.54 | ACSY |
| ATOM | 1397 | CZ  | PHE | 81 | −8.928  | 4.960  | −6.096 | 1.00 | 1.07 | ACSY |
| ATOM | 1398 | HZ  | PHE | 81 | −8.493  | 5.479  | −6.936 | 1.00 | 1.15 | ACSY |
| ATOM | 1399 | C   | PHE | 81 | −12.721 | 2.604  | −1.331 | 1.00 | 1.12 | ACSY |
| ATOM | 1400 | O   | PHE | 81 | −12.887 | 2.872  | −0.144 | 1.00 | 1.13 | ACSY |
| ATOM | 1401 | N   | ASP | 82 | −13.144 | 1.480  | −1.942 | 1.00 | 1.17 | ACSY |
| ATOM | 1402 | HN  | ASP | 82 | −12.957 | 1.330  | −2.913 | 1.00 | 1.17 | ACSY |
| ATOM | 1403 | CA  | ASP | 82 | −13.872 | 0.491  | −1.169 | 1.00 | 1.25 | ACSY |
| ATOM | 1404 | HA  | ASP | 82 | −14.572 | 1.031  | −0.524 | 1.00 | 1.29 | ACSY |
| ATOM | 1405 | CB  | ASP | 82 | −14.617 | −0.448 | −2.114 | 1.00 | 1.33 | ACSY |
| ATOM | 1406 | HB1 | ASP | 82 | −15.388 | 0.091  | −2.665 | 1.00 | 1.38 | ACSY |
| ATOM | 1407 | HB2 | ASP | 82 | −13.932 | −0.883 | −2.842 | 1.00 | 1.29 | ACSY |
| ATOM | 1408 | CG  | ASP | 82 | −15.273 | −1.576 | −1.315 | 1.00 | 1.43 | ACSY |
| ATOM | 1409 | OD1 | ASP | 82 | −15.202 | −2.724 | −1.753 | 1.00 | 1.70 | ACSY |
| ATOM | 1410 | OD2 | ASP | 82 | −15.845 | −1.295 | −0.263 | 1.00 | 1.95 | ACSY |
| ATOM | 1411 | C   | ASP | 82 | −12.895 | −0.295 | −0.299 | 1.00 | 1.22 | ACSY |
| ATOM | 1412 | O   | ASP | 82 | −13.065 | −0.421 | 0.908  | 1.00 | 1.25 | ACSY |
| ATOM | 1413 | N   | THR | 83 | −11.861 | −0.814 | −0.990 | 1.00 | 1.16 | ACSY |
| ATOM | 1414 | HN  | THR | 83 | −11.765 | −0.669 | −1.977 | 1.00 | 1.14 | ACSY |
| ATOM | 1415 | CA  | THR | 83 | −10.873 | −1.579 | −0.271 | 1.00 | 1.13 | ACSY |
| ATOM | 1416 | HA  | THR | 83 | −10.875 | −1.227 | 0.764  | 1.00 | 1.14 | ACSY |
| ATOM | 1417 | CB  | THR | 83 | −11.217 | −3.065 | −0.348 | 1.00 | 1.21 | ACSY |
| ATOM | 1418 | HB  | THR | 83 | −10.445 | −3.644 | 0.155  | 1.00 | 1.26 | ACSY |
| ATOM | 1419 | OG1 | THR | 83 | −11.227 | −3.472 | −1.694 | 1.00 | 1.23 | ACSY |

TABLE 24-continued

Coordinates for the 3D structure of SYK-C:peptide complex
created by user: dave

| ATOM | 1420 | HG1  | THR | 83 | -12.129 | -3.431  | -1.985 | 1.00 | 1.47 | ACSY |
|------|------|------|-----|----|---------|---------|--------|------|------|------|
| ATOM | 1421 | CG2  | THR | 83 | -12.573 | -3.368  | 0.289  | 1.00 | 1.25 | ACSY |
| ATOM | 1422 | HG21 | THR | 83 | -13.376 | -2.863  | -0.246 | 1.00 | 1.46 | ACSY |
| ATOM | 1423 | HG22 | THR | 83 | -12.779 | -4.439  | 0.274  | 1.00 | 1.73 | ACSY |
| ATOM | 1424 | HG23 | THR | 83 | -12.598 | -3.035  | 1.327  | 1.00 | 1.64 | ACSY |
| ATOM | 1425 | C    | THR | 83 | -9.515  | -1.308  | -0.894 | 1.00 | 1.03 | ACSY |
| ATOM | 1426 | O    | THR | 83 | -9.391  | -0.643  | -1.915 | 1.00 | 1.00 | ACSY |
| ATOM | 1427 | N    | LEU | 84 | -8.510  | -1.867  | -0.215 | 1.00 | 1.00 | ACSY |
| ATOM | 1428 | HN   | LEU | 84 | -8.666  | -2.396  | 0.613  | 1.00 | 1.05 | ACSY |
| ATOM | 1429 | CA   | LEU | 84 | -7.173  | -1.699  | -0.685 | 1.00 | 0.92 | ACSY |
| ATOM | 1430 | HA   | LEU | 84 | -6.979  | -0.632  | -0.760 | 1.00 | 0.87 | ACSY |
| ATOM | 1431 | CB   | LEU | 84 | -6.299  | -2.389  | 0.330  | 1.00 | 0.92 | ACSY |
| ATOM | 1432 | HB1  | LEU | 84 | -6.898  | -3.093  | 0.909  | 1.00 | 1.00 | ACSY |
| ATOM | 1433 | HB2  | LEU | 84 | -5.574  | -2.978  | -0.193 | 1.00 | 0.92 | ACSY |
| ATOM | 1434 | CG   | LEU | 84 | -5.622  | -1.416  | 1.282  | 1.00 | 0.90 | ACSY |
| ATOM | 1435 | HG   | LEU | 84 | -6.380  | -0.995  | 1.944  | 1.00 | 1.16 | ACSY |
| ATOM | 1436 | CD1  | LEU | 84 | -4.601  | -2.162  | 2.132  | 1.00 | 1.20 | ACSY |
| ATOM | 1437 | HD11 | LEU | 84 | -5.101  | -2.819  | 2.845  | 1.00 | 1.68 | ACSY |
| ATOM | 1438 | HD12 | LEU | 84 | -3.953  | -2.777  | 1.508  | 1.00 | 1.60 | ACSY |
| ATOM | 1439 | HD13 | LEU | 84 | -3.977  | -1.469  | 2.691  | 1.00 | 1.73 | ACSY |
| ATOM | 1440 | CD2  | LEU | 84 | -4.961  | -0.278  | 0.507  | 1.00 | 0.96 | ACSY |
| ATOM | 1441 | HD21 | LEU | 84 | -4.200  | 0.211   | 1.112  | 1.00 | 1.46 | ACSY |
| ATOM | 1442 | HD22 | LEU | 84 | -4.487  | -0.651  | -0.400 | 1.00 | 1.33 | ACSY |
| ATOM | 1443 | HD23 | LEU | 84 | -5.696  | 0.474   | 0.220  | 1.00 | 1.56 | ACSY |
| ATOM | 1444 | C    | LEU | 84 | -6.960  | -2.336  | -2.056 | 1.00 | 0.91 | ACSY |
| ATOM | 1445 | O    | LEU | 84 | -5.899  | -2.237  | -2.648 | 1.00 | 0.84 | ACSY |
| ATOM | 1446 | N    | TRP | 85 | -8.028  | -2.982  | -2.507 | 1.00 | 1.00 | ACSY |
| ATOM | 1447 | HN   | TRP | 85 | -8.873  | -2.979  | -1.975 | 1.00 | 1.06 | ACSY |
| ATOM | 1448 | CA   | TRP | 85 | -7.958  | -3.636  | -3.800 | 1.00 | 1.02 | ACSY |
| ATOM | 1449 | HA   | TRP | 85 | -6.931  | -3.986  | -3.945 | 1.00 | 0.97 | ACSY |
| ATOM | 1450 | CB   | TRP | 85 | -8.967  | -4.771  | -3.822 | 1.00 | 1.13 | ACSY |
| ATOM | 1451 | HB1  | TRP | 85 | -9.517  | -4.792  | -2.885 | 1.00 | 1.18 | ACSY |
| ATOM | 1452 | HB2  | TRP | 85 | -9.691  | -4.617  | -4.622 | 1.00 | 1.17 | ACSY |
| ATOM | 1453 | CG   | TRP | 85 | -8.258  | -6.083  | -4.046 | 1.00 | 1.14 | ACSY |
| ATOM | 1454 | CD2  | TRP | 85 | -8.087  | -7.145  | -3.107 | 1.00 | 1.33 | ACSY |
| ATOM | 1455 | CE2  | TRP | 85 | -7.350  | -8.172  | -3.774 | 1.00 | 1.26 | ACSY |
| ATOM | 1456 | CE3  | TRP | 85 | -8.487  | -7.308  | -1.787 | 1.00 | 1.64 | ACSY |
| ATOM | 1457 | HE3  | TRP | 85 | -9.044  | -6.530  | -1.287 | 1.00 | 1.71 | ACSY |
| ATOM | 1458 | CD1  | TRP | 85 | -7.640  | -6.471  | -5.232 | 1.00 | 1.08 | ACSY |
| ATOM | 1459 | HD1  | TRP | 85 | -7.597  | -5.877  | -6.135 | 1.00 | 1.13 | ACSY |
| ATOM | 1460 | NE1  | TRP | 85 | -7.098  | -7.716  | -5.073 | 1.00 | 1.10 | ACSY |
| ATOM | 1461 | HE1  | TRP | 85 | -6.609  | -8.2#2  | -5.762 | 1.00 | 1.10 | ACSY |
| ATOM | 1462 | CZ2  | TRP | 85 | -7.024  | -9.348  | -3.110 | 1.00 | 1.47 | ACSY |
| ATOM | 1463 | HZ2  | TRP | 85 | -6.467  | -10.122 | -3.618 | 1.00 | 1.42 | ACSY |
| ATOM | 1464 | CZ3  | TRP | 85 | -8.160  | -8.505  | -1.100 | 1.00 | 1.91 | ACSY |
| ATOM | 1465 | HZ3  | TRP | 85 | -8.467  | -8.640  | -0.074 | 1.00 | 2.21 | ACSY |
| ATOM | 1466 | CH2  | TRP | 85 | -7.428  | -9.526  | -1.763 | 1.00 | 1.81 | ACSY |
| ATOM | 1467 | HH2  | TRP | 85 | -7.178  | -10.437 | -1.240 | 1.00 | 2.03 | ACSY |
| ATOM | 1468 | C    | TRP | 85 | -8.303  | -2.649  | -4.891 | 1.00 | 1.01 | ACSY |
| ATOM | 1469 | O    | TRP | 85 | -7.844  | -2.737  | -6.023 | 1.00 | 1.00 | ACSY |
| ATOM | 1470 | N    | GLN | 86 | -9.143  | -1.707  | -4.468 | 1.00 | 1.04 | ACSY |
| ATOM | 1471 | HN   | GLN | 86 | -9.435  | -1.683  | -3.501 | 1.00 | 1.05 | ACSY |
| ATOM | 1472 | CA   | GLN | 86 | -9.564  | -0.712  | -5.420 | 1.00 | 1.05 | ACSY |
| ATOM | 1473 | HA   | GLN | 86 | -9.489  | -1.171  | -6.403 | 1.00 | 1.08 | ACSY |
| ATOM | 1474 | CB   | GLN | 86 | -10.992 | -0.263  | -5.119 | 1.00 | 1.15 | ACSY |
| ATOM | 1475 | HB1  | GLN | 86 | -11.019 | 0.247   | -4.157 | 1.00 | 1.16 | ACSY |
| ATOM | 1476 | HB2  | GLN | 86 | -11.314 | 0.460   | -5.868 | 1.00 | 1.18 | ACSY |
| ATOM | 1477 | CG   | GLN | 86 | -11.960 | -1.446  | -5.099 | 1.00 | 1.24 | ACSY |
| ATOM | 1478 | HG1  | GLN | 86 | -11.718 | -2.126  | -4.282 | 1.00 | 1.35 | ACSY |
| ATOM | 1479 | HG2  | GLN | 86 | -12.984 | -1.103  | -4.954 | 1.00 | 1.33 | ACSY |
| ATOM | 1480 | CD   | GLN | 86 | -11.875 | -2.210  | -6.421 | 1.00 | 1.40 | ACSY |
| ATOM | 1481 | OE1  | GLN | 86 | -11.463 | -1.684  | -7.448 | 1.00 | 1.73 | ACSY |
| ATOM | 1482 | NE2  | GLN | 86 | -12.291 | -3.485  | -6.319 | 1.00 | 1.91 | ACSY |
| ATOM | 1483 | HE21 | GLN | 86 | -12.614 | -3.848  | -5.445 | 1.00 | 2.33 | ACSY |
| ATOM | 1484 | HE22 | GLN | 86 | -12.285 | -4.090  | -7.115 | 1.00 | 2.19 | ACSY |
| ATOM | 1485 | C    | GLN | 86 | -8.604  | 0.450   | -5.387 | 1.00 | 0.94 | ACSY |
| ATOM | 1486 | O    | GLN | 86 | -8.206  | 0.978   | -6.406 | 1.00 | 0.92 | ACSY |
| ATOM | 1487 | N    | LEU | 87 | -8.239  | 0.813   | -4.163 | 1.00 | 0.89 | ACSY |
| ATOM | 1488 | HN   | LEU | 87 | -8.595  | 0.343   | -3.346 | 1.00 | 0.92 | ACSY |
| ATOM | 1489 | CA   | LEU | 87 | -7.304  | 1.910   | -4.075 | 1.00 | 0.79 | ACSY |
| ATOM | 1490 | HA   | LEU | 87 | -7.711  | 2.718   | -4.689 | 1.00 | 0.80 | ACSY |
| ATOM | 1491 | CB   | LEU | 87 | -7.136  | 2.341   | -2.623 | 1.00 | 0.76 | ACSY |
| ATOM | 1492 | HB1  | LEU | 87 | -8.075  | 2.740   | -2.250 | 1.00 | 0.82 | ACSY |
| ATOM | 1493 | HB2  | LEU | 87 | -6.896  | 1.473   | -2.008 | 1.00 | 0.77 | ACSY |
| ATOM | 1494 | CG   | LEU | 87 | -6.040  | 3.394   | -2.474 | 1.00 | 0.67 | ACSY |
| ATOM | 1495 | HG   | LEU | 87 | -6.152  | 4.126   | -3.274 | 1.00 | 0.67 | ACSY |

TABLE 24-continued

Coordinates for the 3D structure of SYK-C:peptide complex
created by user: dave

| ATOM | 1496 | CD1 | LEU | 87 | −6.175 | 4.116 | −1.135 | 1.00 | 0.69 | ACSY |
|---|---|---|---|---|---|---|---|---|---|---|
| ATOM | 1497 | HD11 | LEU | 87 | −6.047 | 3.422 | −0.304 | 1.00 | 1.19 | ACSY |
| ATOM | 1498 | HD12 | LEU | 87 | −5.423 | 4.899 | −1.038 | 1.00 | 1.21 | ACSY |
| ATOM | 1499 | HD13 | LEU | 87 | −7.157 | 4.578 | −1.040 | 1.00 | 1.26 | ACSY |
| ATOM | 1500 | CD2 | LEU | 87 | −4.661 | 2.743 | −2.592 | 1.00 | 0.59 | ACSY |
| ATOM | 1501 | HD21 | LEU | 87 | −4.747 | 1.657 | −2.644 | 1.00 | 1.19 | ACSY |
| ATOM | 1502 | HD22 | LEU | 87 | −4.145 | 3.084 | −3.489 | 1.00 | 1.08 | ACSY |
| ATOM | 1503 | HD23 | LEU | 87 | −4.041 | 2.990 | −1.733 | 1.00 | 1.22 | ACSY |
| ATOM | 1504 | C | LEU | 87 | −5.964 | 1.501 | −4.681 | 1.00 | 0.72 | ACSY |
| ATOM | 1505 | O | LEU | 87 | −5.212 | 2.332 | −5.165 | 1.00 | 0.66 | ACSY |
| ATOM | 1506 | N | VAL | 88 | −5.717 | 0.177 | −4.646 | 1.00 | 0.74 | ACSY |
| ATOM | 1507 | HN | VAL | 88 | −6.369 | −0.466 | −4.266 | 1.00 | 0.80 | ACSY |
| ATOM | 1508 | CA | VAL | 88 | −4.483 | −0.294 | −5.190 | 1.00 | 0.69 | ACSY |
| ATOM | 1509 | HA | VAL | 88 | −3.708 | 0.431 | −4.939 | 1.00 | 0.61 | ACSY |
| ATOM | 1510 | CB | VAL | 88 | −4.167 | −1.655 | −4.620 | 1.00 | 0.71 | ACSY |
| ATOM | 1511 | HB | VAL | 88 | −5.089 | −2.232 | −4.566 | 1.00 | 0.79 | ACSY |
| ATOM | 1512 | CG1 | VAL | 88 | −3.214 | −2.369 | −5.557 | 1.00 | 0.70 | ACSY |
| ATOM | 1513 | HG11 | VAL | 88 | −2.368 | −1.727 | −5.801 | 1.00 | 1.07 | ACSY |
| ATOM | 1514 | HG12 | VAL | 88 | −2.841 | −3.281 | −5.112 | 1.00 | 1.28 | ACSY |
| ATOM | 1515 | HG13 | VAL | 88 | −3.721 | −2.622 | −6.491 | 1.00 | 1.23 | ACSY |
| ATOM | 1516 | CG2 | VAL | 88 | −3.568 | −1.529 | −3.223 | 1.00 | 0.68 | ACSY |
| ATOM | 1517 | HG21 | VAL | 88 | −4.205 | −0.917 | −2.584 | 1.00 | 1.08 | ACSY |
| ATOM | 1579 | CB | SER | 92 | −2.853 | −0.680 | −10.324 | 1.00 | 0.84 | ACSY |
| ATOM | 1580 | HB1 | SER | 92 | −3.516 | −0.841 | −9.491 | 1.00 | 0.82 | ACSY |
| ATOM | 1581 | HB2 | SER | 92 | −3.431 | −0.811 | −11.233 | 1.00 | 0.91 | ACSY |
| ATOM | 1582 | OG | SER | 92 | −1.838 | −1.651 | −10.290 | 1.00 | 0.82 | ACSY |
| ATOM | 1583 | HG | SER | 92 | −2.269 | −2.496 | −10.305 | 1.00 | 1.21 | ACSY |
| ATOM | 1584 | C | SER | 92 | −2.325 | 1.363 | −11.641 | 1.00 | 0.87 | ACSY |
| ATOM | 1585 | O | SER | 92 | −1.539 | 1.064 | −12.533 | 1.00 | 0.91 | ACSY |
| ATOM | 1586 | N | TYR | 93 | −3.308 | 2.273 | −11.737 | 1.00 | 0.89 | ACSY |
| ATOM | 1587 | HN | TYR | 93 | −3.883 | 2.467 | −10.936 | 1.00 | 0.86 | ACSY |
| ATOM | 1588 | CA | TYR | 93 | −3.517 | 2.985 | −12.972 | 1.00 | 0.97 | ACSY |
| ATOM | 1589 | HA | TYR | 93 | −3.215 | 2.336 | −13.796 | 1.00 | 1.02 | ACSY |
| ATOM | 1590 | CB | TYR | 93 | −4.985 | 3.386 | −13.072 | 1.00 | 1.02 | ACSY |
| ATOM | 1591 | HB1 | TYR | 93 | −5.218 | 4.130 | −12.312 | 1.00 | 0.97 | ACSY |
| ATOM | 1592 | HB2 | TYR | 93 | −5.167 | 3.856 | −14.023 | 1.00 | 1.08 | ACSY |
| ATOM | 1593 | CG | TYR | 93 | −5.918 | 2.217 | −12.907 | 1.00 | 1.06 | ACSY |
| ATOM | 1594 | CD1 | TYR | 93 | −7.280 | 2.439 | −12.595 | 1.00 | 1.54 | ACSY |
| ATOM | 1595 | HD1 | TYR | 93 | −7.641 | 3.450 | −12.459 | 1.00 | 2.26 | ACSY |
| ATOM | 1596 | CE1 | TYR | 93 | −8.165 | 1.348 | −12.436 | 1.00 | 1.59 | ACSY |
| ATOM | 1597 | HE1 | TYR | 93 | −9.202 | 1.524 | −12.192 | 1.00 | 2.31 | ACSY |
| ATOM | 1598 | CD2 | TYR | 93 | −5.449 | 0.888 | −13.057 | 1.00 | 1.63 | ACSY |
| ATOM | 1599 | HD2 | TYR | 93 | −4.406 | 0.709 | −13.275 | 1.00 | 2.37 | ACSY |
| ATOM | 1600 | CE2 | TYR | 93 | −6.333 | −0.204 | −12.898 | 1.00 | 1.67 | ACSY |
| ATOM | 1601 | HE2 | TYR | 93 | −5.967 | −1.214 | −13.007 | 1.00 | 2.41 | ACSY |
| ATOM | 1602 | CZ | TYR | 93 | −7.691 | 0.026 | −12.588 | 1.00 | 1.16 | ACSY |
| ATOM | 1603 | OH | TYR | 93 | −8.554 | −1.039 | −12.434 | 1.00 | 1.23 | ACSY |
| ATOM | 1604 | HH | TYR | 93 | −8.085 | −1.849 | −12.582 | 1.00 | 1.48 | ACSY |
| ATOM | 1605 | C | TYR | 93 | −2.678 | 4.242 | −12.954 | 1.00 | 0.94 | ACSY |
| ATOM | 1606 | O | TYR | 93 | −1.841 | 4.488 | −13.809 | 1.00 | 0.98 | ACSY |
| ATOM | 1607 | N | LYS | 94 | −3.031 | 5.029 | −11.929 | 1.00 | 0.87 | ACSY |
| ATOM | 1608 | HN | LYS | 94 | −3.793 | 4.781 | −11.361 | 1.00 | 0.86 | ACSY |
| ATOM | 1609 | CA | LYS | 94 | −2.372 | 6.279 | −11.711 | 1.00 | 0.85 | ACSY |
| ATOM | 1610 | HA | LYS | 94 | −1.506 | 6.337 | −12.371 | 1.00 | 0.88 | ACSY |
| ATOM | 1611 | CB | LYS | 94 | −3.373 | 7.361 | −11.999 | 1.00 | 0.88 | ACSY |
| ATOM | 1612 | HB1 | LYS | 94 | −2.973 | 8.319 | −11.689 | 1.00 | 0.86 | ACSY |
| ATOM | 1613 | HB2 | LYS | 94 | −3.535 | 7.415 | −13.055 | 1.00 | 0.96 | ACSY |
| ATOM | 1614 | CG | LYS | 94 | −4.696 | 7.090 | −11.267 | 1.00 | 0.87 | ACSY |
| ATOM | 1615 | HG1 | LYS | 94 | −5.048 | 6.082 | −11.495 | 1.00 | 0.90 | ACSY |
| ATOM | 1616 | HG2 | LYS | 94 | −4.529 | 7.122 | −10.188 | 1.00 | 0.79 | ACSY |
| ATOM | 1617 | CD | LYS | 94 | −5.773 | 8.102 | −11.652 | 1.00 | 0.93 | ACSY |
| ATOM | 1618 | HD1 | LYS | 94 | −6.461 | 8.239 | −10.817 | 1.00 | 0.97 | ACSY |
| ATOM | 1619 | HD2 | LYS | 94 | −5.314 | 9.072 | −11.844 | 1.00 | 0.94 | ACSY |
| ATOM | 1620 | CE | LYS | 94 | −6.550 | 7.643 | −12.887 | 1.00 | 1.00 | ACSY |
| ATOM | 1621 | HE1 | LYS | 94 | −5.873 | 7.465 | −13.722 | 1.00 | 1.06 | ACSY |
| ATOM | 1622 | HE2 | LYS | 94 | −7.077 | 6.710 | −12.683 | 1.00 | 1.13 | ACSY |
| ATOM | 1623 | NZ | LYS | 94 | −7.538 | 8.625 | −13.318 | 1.00 | 1.05 | ACSY |
| ATOM | 1624 | HZ1 | LYS | 94 | −8.225 | 8.784 | −12.554 | 1.00 | 1.22 | ACSY |
| ATOM | 1625 | HZ2 | LYS | 94 | −7.060 | 9.520 | −13.546 | 1.00 | 1.48 | ACSY |
| ATOM | 1626 | HZ3 | LYS | 94 | −8.033 | 8.271 | −14.162 | 1.00 | 1.28 | ACSY |
| ATOM | 1627 | C | LYS | 94 | −1.950 | 6.436 | −10.267 | 1.00 | 0.74 | ACSY |
| ATOM | 1628 | O | LYS | 94 | −2.132 | 5.579 | −9.415 | 1.00 | 0.69 | ACSY |
| ATOM | 1629 | N | ALA | 95 | −1.379 | 7.619 | −10.084 | 1.00 | 0.73 | ACSY |
| ATOM | 1630 | HN | ALA | 95 | −1.244 | 8.223 | −10.867 | 1.00 | 0.79 | ACSY |
| ATOM | 1631 | CA | ALA | 95 | −0.943 | 8.000 | −8.756 | 1.00 | 0.65 | ACSY |
| ATOM | 1632 | HA | ALA | 95 | −0.569 | 7.101 | −8.261 | 1.00 | 0.61 | ACSY |

TABLE 24-continued

Coordinates for the 3D structure of SYK-C:peptide complex
created by user: dave

| ATOM | 1633 | CB | ALA | 95 | 0.147 | 9.064 | −8.862 | 1.00 | 0.68 | ACSY |
|---|---|---|---|---|---|---|---|---|---|---|
| ATOM | 1634 | HB1 | ALA | 95 | −0.193 | 9.911 | −9.458 | 1.00 | 1.18 | ACSY |
| ATOM | 1635 | HB2 | ALA | 95 | 0.424 | 9.437 | −7.876 | 1.00 | 1.19 | ACSY |
| ATOM | 1636 | HB3 | ALA | 9S | 1.043 | 8.659 | −9.333 | 1.00 | 1.17 | ACSY |
| ATOM | 1637 | C | ALA | 95 | −2.152 | 8.539 | −7.986 | 1.00 | 0.63 | ACSY |
| ATOM | 1638 | O | ALA | 95 | −2.392 | 8.199 | −6.836 | 1.00 | 0.57 | ACSY |
| ATOM | 1639 | N | ASP | 96 | −2.903 | 9.392 | −8.711 | 1.00 | 0.70 | ACSY |
| ATOM | 1640 | HN | ASP | 96 | −2.652 | 9.617 | −9.653 | 1.00 | 0.75 | ACSY |
| ATOM | 1641 | CA | ASP | 96 | −4.090 | 9.981 | −8.094 | 1.00 | 0.70 | ACSY |
| ATOM | 1642 | HA | ASP | 96 | −4.639 | 10.467 | −8.876 | 1.00 | 0.77 | ACSY |
| ATOM | 1643 | CB | ASP | 96 | −4.918 | 8.885 | −7.457 | 1.00 | 0.69 | ACSY |
| ATOM | 1644 | HB1 | ASP | 96 | −4.416 | 7.926 | −7.558 | 1.00 | 0.79 | ACSY |
| ATOM | 1645 | HB2 | ASP | 96 | −5.050 | 9.086 | −6.398 | 1.00 | 0.74 | ACSY |
| ATOM | 1646 | CG | ASP | 96 | −6.294 | 8.806 | −8.125 | 1.00 | 0.79 | ACSY |
| ATOM | 1647 | OD1 | ASP | 96 | −6.887 | 7.729 | −8.119 | 1.00 | 1.31 | ACSY |
| ATOM | 1648 | OD2 | ASP | 96 | −6.758 | 9.822 | −8.640 | 1.00 | 1.32 | ACSY |
| ATOM | 1649 | C | ASP | 96 | −3.708 | 11.031 | −7.049 | 1.00 | 0.66 | ACSY |
| ATOM | 1650 | O | ASP | 96 | −4.534 | 11.780 | −6.541 | 1.00 | 0.69 | ACSY |
| ATOM | 1651 | N | GLY | 97 | −2.410 | 11.019 | −6.779 | 1.00 | 0.63 | ACSY |
| ATOM | 1652 | HN | GLY | 97 | −1.826 | 10.370 | −7.253 | 1.00 | 0.62 | ACSY |
| ATOM | 1653 | CA | GLY | 97 | −1.873 | 11.951 | −5.807 | 1.00 | 0.61 | ACSY |
| ATOM | 1654 | HA1 | GLY | 97 | −2.565 | 11.987 | −4.966 | 1.00 | 0.73 | ACSY |
| ATOM | 1655 | HA2 | GLY | 97 | −1.836 | 12.931 | −6.279 | 1.00 | 0.75 | ACSY |
| ATOM | 1656 | C | GLY | 97 | −0.472 | 11.532 | −5.339 | 1.00 | 0.56 | ACSY |
| ATOM | 1657 | O | GLY | 97 | 0.337 | 12.354 | −4.926 | 1.00 | 0.58 | ACSY |
| ATOM | 1658 | N | LEU | 98 | −0.238 | 10.205 | −5.433 | 1.00 | 0.53 | ACSY |
| ATOM | 1659 | HN | LEU | 98 | −0.934 | 9.581 | −5.788 | 1.00 | 0.54 | ACSY |
| ATOM | 1660 | CA | LEU | 98 | 1.055 | 9.704 | −5.021 | 1.00 | 0.50 | ACSY |
| ATOM | 1661 | HA | LEU | 98 | 1.112 | 9.776 | −3.925 | 1.00 | 0.46 | ACSY |
| ATOM | 1662 | CB | LEU | 98 | 1.219 | 8.265 | −5.497 | 1.00 | 0.48 | ACSY |
| ATOM | 1663 | HB1 | LEU | 98 | 1.340 | 8.252 | −6.580 | 1.00 | 0.55 | ACSY |
| ATOM | 1664 | HB2 | LEU | 98 | 2.129 | 7.848 | −5.078 | 1.00 | 0.47 | ACSY. |
| ATOM | 1665 | CG | LEU | 98 | 0.038 | 7.395 | −5.110 | 1.00 | 0.43 | ACSY |
| ATOM | 1666 | HG | LEU | 98 | −0.873 | 7.896 | −5.408 | 1.00 | 0.47 | ACSY |
| ATOM | 1667 | CD1 | LEU | 98 | 0.100 | 6.066 | −5.843 | 1.00 | 0.47 | ACSY |
| ATOM | 1668 | HD11 | LEU | 98 | −0.738 | 5.965 | −6.534 | 1.00 | 1.15 | ACSY |
| ATOM | 1669 | HD12 | LEU | 98 | 1.022 | 5.980 | −6.417 | 1.00 | 1.15 | ACSY |
| ATOM | 1670 | HD13 | LEU | 98 | 0.058 | 5.239 | −5.139 | 1.00 | 1.03 | ACSY |
| ATOM | 1671 | CD2 | LEU | 98 | 0.026 | 7.185 | −3.598 | 1.00 | 0.35 | ACSY |
| ATOM | 1672 | HD21 | LEU | 98 | 0.770 | 6.455 | −3.298 | 1.00 | 1.06 | ACSY |
| ATOM | 1673 | HD22 | LEU | 98 | 0.246 | 8.116 | −3.082 | 1.00 | 0.99 | ACSY |
| ATOM | 1674 | HD23 | LEU | 98 | −0.948 | 6.840 | −3.260 | 1.00 | 0.89 | ACSY |
| ATOM | 1675 | C | LEU | 98 | 2.138 | 10.548 | −5.672 | 1.00 | 0.59 | ACSY |
| ATOM | 1676 | O | LEU | 98 | 1.872 | 11.478 | −6.424 | 1.00 | 0.68 | ACSY |
| ATOM | 1677 | N | LEU | 99 | 3.375 | 10.155 | −5.342 | 1.00 | 0.64 | ACSY |
| ATOM | 1678 | HN | LEU | 99 | 3.522 | 9.409 | −4.691 | 1.00 | 0.64 | ACSY |
| ATOM | 1679 | CA | LEU | 99 | 4.492 | 10.841 | −5.957 | 1.00 | 0.74 | ACSY |
| ATOM | 1680 | HA | LEU | 99 | 4.332 | 11.912 | −5.828 | 1.00 | 0.78 | ACSY |
| ATOM | 1681 | CB | LEU | 99 | 5.792 | 10.386 | −5.303 | 1.00 | 0.79 | ACSY |
| ATOM | 1682 | HB1 | LEU | 99 | 5.589 | 10.060 | −4.285 | 1.00 | 0.7S | ACSY |
| ATOM | 1683 | HB2 | LEU | 99 | 6.186 | 9.521 | −5.839 | 1.00 | 0.82 | ACSY |
| ATOM | 1684 | CG | LEU | 99 | 6.841 | 11.497 | −5.281 | 1.00 | 0.94 | ACSY |
| ATOM | 1685 | HG | LEU | 99 | 7.754 | 11.098 | −4.836 | 1.00 | 1.38 | ACSY |
| ATOM | 1686 | CD1 | LEU | 99 | 7.160 | 11.959 | −6.700 | 1.00 | 1.40 | ACSY |
| ATOM | 1687 | HD11 | LEU | 99 | 7.519 | 11.128 | −7.306 | 1.00 | 2.02 | ACSY |
| ATOM | 1688 | HD12 | LEU | 99 | 6.274 | 12.371 | −7.182 | 1.00 | 1.75 | ACSY |
| ATOM | 1689 | HD13 | LEU | 99 | 7.930 | 12.730 | −6.693 | 1.00 | 1.88 | ACSY |
| ATOM | 1690 | CD2 | LEU | 99 | 6.357 | 12.675 | −4.431 | 1.00 | 1.40 | ACSY |
| ATOM | 1691 | HD21 | LEU | 99 | 7.159 | 13.397 | −4.277 | 1.00 | 1.86 | ACSY |
| ATOM | 1692 | HD22 | LEU | 99 | 5.529 | 13.191 | −4.916 | 1.00 | 1.85 | ACSY |
| ATOM | 1693 | HD23 | LEU | 99 | 6.017 | 12.335 | −3.453 | 1.00 | 1.98 | ACSY |
| ATOM | 1694 | C | LEU | 99 | 4.478 | 10.492 | −7.450 | 1.00 | 0.78 | ACSY |
| ATOM | 1695 | O | LEU | 99 | 4.691 | 11.328 | −8.319 | 1.00 | 0.87 | ACSY |
| ATOM | 1696 | N | ARG | 100 | 4.202 | 9.187 | −7.665 | 1.00 | 0.73 | ACSY |
| ATOM | 1697 | HN | ARG | 100 | 4.074 | 8.568 | −6.894 | 1.00 | 0.68 | ACSY |
| ATOM | 1698 | CA | ARG | 100 | 4.120 | 8.684 | −9.017 | 1.00 | 0.78 | ACSY |
| ATOM | 1699 | HA | ARG | 100 | 3.668 | 9.464 | −9.635 | 1.00 | 0.82 | ACSY |
| ATOM | 1700 | CB | ARG | 100 | 5.516 | 8.332 | −9.501 | 1.00 | 0.85 | ACSY |
| ATOM | 1701 | HB1 | ARG | 100 | 6.226 | 9.084 | −9.154 | 1.00 | 0.88 | ACSY |
| ATOM | 1702 | HB2 | ARG | 100 | 5.815 | 7.387 | −9.055 | 1.00 | 0.83 | ACSY |
| ATOM | 1703 | CG | ARG | 100 | 5.575 | 8.227 | −11.026 | 1.00 | 0.95 | ACSY |
| ATOM | 1704 | HG1 | ARG | 100 | 6.477 | 7.692 | −11.320 | 1.00 | 1.53 | ACSY |
| ATOM | 1705 | HG2 | ARG | 100 | 4.731 | 7.639 | −11.386 | 1.00 | 1.34 | ACSY |
| ATOM | 1706 | CD | ARG | 100 | 5.560 | 9.606 | −11.684 | 1.00 | 1.59 | ACSY |
| ATOM | 1707 | HD1 | ARG | 100 | 6.372 | 10.236 | −11.317 | 1.00 | 2.22 | ACSY |
| ATOM | 1708 | HD2 | ARG | 100 | 4.617 | 10.123 | −11.517 | 1.00 | 2.14 | ACSY |

TABLE 24-continued

Coordinates for the 3D structure of SYK-C:peptide complex
created by user: dave

| ATOM | 1709 | NE | ARG | 100 | 5.724 | 9.481 | −13.121 | 1.00 | 2.14 | ACSY |
|---|---|---|---|---|---|---|---|---|---|---|
| ATOM | 1710 | HE | ARG | 100 | 5.797 | 8.581 | −13.550 | 1.00 | 2.41 | ACSY |
| ATOM | 1711 | CZ | ARG | 100 | 5.779 | 10.602 | −13.865 | 1.00 | 2.96 | ACSY |
| ATOM | 1712 | NH1 | ARG | 100 | 5.932 | 10.517 | −15.184 | 1.00 | 3.73 | ACSY |
| ATOM | 1713 | HH11 | ARG | 100 | 6.007 | 9.621 | −15.622 | 1.00 | 3.85 | ACSY |
| ATOM | 1714 | HH12 | ARG | 100 | 5.973 | 11.349 | −15.737 | 1.00 | 4.41 | ACSY |
| ATOM | 1715 | NH2 | ARG | 100 | 5.680 | 11.794 | −13.283 | 1.00 | 3.46 | ACSY |
| ATOM | 1716 | HH21 | ARG | 100 | 5.565 | 11.859 | −12.292 | 1.00 | 3.29 | ACSY |
| ATOM | 1717 | HH22 | ARG | 100 | 5.721 | 12.626 | −13.837 | 1.00 | 4.28 | ACSY |
| ATOM | 1718 | C | ARG | 100 | 3.227 | 7.440 | −9.018 | 1.00 | 0.73 | ACSY |
| ATOM | 1719 | O | ARG | 100 | 3.057 | 6.769 | −8.008 | 1.00 | 0.66 | ACSY |
| ATOM | 1720 | N | VAL | 101 | 2.672 | 7.184 | −10.213 | 1.00 | 0.78 | ACSY |
| ATOM | 1721 | HN | VAL | 101 | 2.847 | 7.767 | −10.997 | 1.00 | 0.84 | ACSY |
| ATOM | 1722 | CA | VAL | 101 | 1.813 | 6.038 | −10.359 | 1.00 | 0.76 | ACSY |
| ATOM | 1723 | HA | VAL | 101 | 0.882 | 6.226 | −9.800 | 1.00 | 0.71 | ACSY |
| ATOM | 1724 | CB | VAL | 101 | 1.532 | 5.858 | −11.835 | 1.00 | 0.85 | ACSY |
| ATOM | 1725 | HB | VAL | 101 | 2.404 | 5.399 | −12.291 | 1.00 | 0.90 | ACSY |
| ATOM | 1726 | CG1 | VAL | 101 | 0.361 | 4.930 | −12.035 | 1.00 | 0.85 | ACSY |
| ATOM | 1727 | HG11 | VAL | 101 | 0.680 | 3.892 | −12.001 | 1.00 | 1.38 | ACSY |
| ATOM | 1728 | HG12 | VAL | 101 | −0.384 | 5.078 | −11.262 | 1.00 | 1.24 | ACSY |
| ATOM | 1729 | HG13 | VAL | 101 | −0.100 | 5.115 | −12.995 | 1.00 | 1.32 | ACSY |
| ATOM | 1730 | CG2 | VAL | 101 | 1.267 | 7.205 | −12.512 | 1.00 | 0.90 | ACSY |
| ATOM | 1731 | HG21 | VAL | 101 | 0.415 | 7.709 | −12.054 | 1.00 | 1.41 | ACSY |
| ATOM | 1732 | HG22 | VAL | 101 | 2.133 | 7.861 | −12.424 | 1.00 | 1.26 | ACSY |
| ATOM | 1733 | HG23 | VAL | 101 | 1.050 | 7.073 | −13.572 | 1.00 | 1.35 | ACSY |
| ATOM | 1734 | C | VAL | 101 | 2.523 | 4.786 | −9.844 | 1.00 | 0.72 | ACSY |
| ATOM | 1735 | O | VAL | 101 | 3.678 | 4.806 | −9.439 | 1.00 | 0.72 | ACSY |
| ATOM | 1736 | N | LEU | 102 | 1.736 | 3.704 | −9.902 | 1.00 | 0.71 | ACSY |
| ATOM | 1737 | HN | LEU | 102 | 0.790 | 3.793 | −10.196 | 1.00 | 0.73 | ACSY |
| ATOM | 1738 | CA | LEU | 102 | 2.261 | 2.409 | −9.513 | 1.00 | 0.70 | ACSY |
| ATOM | 1739 | HA | LEU | 102 | 3.189 | 2.552 | −8.950 | 1.00 | 0.67 | ACSY |
| ATOM | 1740 | CB | LEU | 102 | 1.230 | 1.647 | −8.706 | 1.00 | 0.66 | ACSY |
| ATOM | 1741 | HB1 | LEU | 102 | 0.273 | 1.720 | −9.199 | 1.00 | 0.71 | ACSY |
| ATOM | 1742 | HB2 | LEU | 102 | 1.490 | 0.595 | −8.697 | 1.00 | 0.69 | ACSY |
| ATOM | 1743 | CG | LEU | 102 | 1.116 | 2.153 | −7.271 | 1.00 | 0.58 | ACSY |
| ATOM | 1744 | HG | LEU | 102 | 1.965 | 1.780 | −6.707 | 1.00 | 0.59 | ACSY |
| ATOM | 1745 | CD1 | LEU | 102 | 1.140 | 3.675 | −7.208 | 1.00 | 0.59 | ACSY |
| ATOM | 1746 | HD11 | LEU | 102 | 0.303 | 4.106 | −7.759 | 1.00 | 1.10 | ACSY |
| ATOM | 1747 | HD12 | LEU | 102 | 1.073 | 4.007 | −6.177 | 1.00 | 1.10 | ACSY |
| ATOM | 1748 | HD13 | LEU | 102 | 2.064 | 4.070 | −7.622 | 1.00 | 1.22 | ACSY |
| ATOM | 1749 | CD2 | LEU | 102 | −0.166 | 1.625 | −6.634 | 1.00 | 0.58 | ACSY |
| ATOM | 1750 | HD21 | LEU | 102 | −0.238 | 1.930 | −5.591 | 1.00 | 1.16 | ACSY |
| ATOM | 1751 | HD22 | LEU | 102 | −1.043 | 2.004 | −7.158 | 1.00 | 1.23 | ACSY |
| ATOM | 1752 | HD23 | LEU | 102 | −0.199 | 0.539 | −6.673 | 1.00 | 1.14 | ACSY |
| ATOM | 1753 | C | LEU | 102 | 2.569 | 1.641 | −10.778 | 1.00 | 0.81 | ACSY |
| ATOM | 1754 | O | LEU | 102 | 2.100 | 1.957 | −11.864 | 1.00 | 0.87 | ACSY |
| ATOM | 1755 | N | THR | 103 | 3.388 | 0.619 | −10.562 | 1.00 | 0.83 | ACSY |
| ATOM | 1756 | HN | THR | 103 | 3.745 | 0.435 | −9.651 | 1.00 | 0.79 | ACSY |
| ATOM | 1757 | CA | THR | 103 | 3.775 | −0.181 | −11.694 | 1.00 | 0.94 | ACSY |
| ATOM | 1758 | HA | THR | 103 | 2.939 | −0.178 | −12.397 | 1.00 | 0.98 | ACSY |
| ATOM | 1759 | CB | THR | 103 | 5.010 | 0.480 | −12.307 | 1.00 | 1.01 | ACSY |
| ATOM | 1760 | HB | THR | 103 | 5.287 | 1.338 | −11.699 | 1.00 | 0.96 | ACSY |
| ATOM | 1761 | OG1 | THR | 103 | 4.698 | 0.962 | −13.589 | 1.00 | 1.08 | ACSY |
| ATOM | 1762 | HG1 | THR | 103 | 5.148 | 1.791 | −13.686 | 1.00 | 1.35 | ACSY |
| ATOM | 1763 | CG2 | THR | 103 | 6.201 | −0.464 | −12.388 | 1.00 | 1.18 | ACSY |
| ATOM | 1764 | HG21 | THR | 103 | 5.989 | −1.298 | −13.052 | 1.00 | 1.35 | ACSY |
| ATOM | 1765 | HG22 | THR | 103 | 7.081 | 0.055 | −12.763 | 1.00 | 1.83 | ACSY |
| ATOM | 1766 | HG23 | THR | 103 | 6.438 | −0.862 | −11.402 | 1.00 | 1.58 | ACSY |
| ATOM | 1767 | C | THR | 103 | 4.071 | −1.619 | −11.267 | 1.00 | 0.96 | ACSY |
| ATOM | 1768 | O | THR | 103 | 3.769 | −2.575 | −11.971 | 1.00 | 1.04 | ACSY |
| ATOM | 1769 | N | VAL | 104 | 4.679 | −1.704 | −10.072 | 1.00 | 0.88 | ACSY |
| ATOM | 1770 | HN | VAL | 104 | 4.859 | −0.870 | −9.533 | 1.00 | 0.82 | ACSY |
| ATOM | 1771 | CA | VAL | 104 | 5.068 | −3.036 | −9.598 | 1.00 | 0.90 | ACSY |
| ATOM | 1772 | HA | VAL | 104 | 4.447 | −3.772 | −10.109 | 1.00 | 0.98 | ACSY |
| ATOM | 1773 | CB | VAL | 104 | 6.549 | −3.223 | −9.928 | 1.00 | 0.96 | ACSY |
| ATOM | 1774 | HB | VAL | 104 | 7.089 | −2.402 | −9.443 | 1.00 | 0.92 | ACSY |
| ATOM | 1775 | CG1 | VAL | 104 | 7.086 | −4.541 | −9.368 | 1.00 | 1.04 | ACSY |
| ATOM | 1776 | HG11 | VAL | 104 | 6.698 | −5.390 | −9.929 | 1.00 | 1.68 | ACSY |
| ATOM | 1777 | HG12 | VAL | 104 | 8.174 | −4.572 | −9.429 | 1.00 | 1.20 | ACSY |
| ATOM | 1778 | HG13 | VAL | 104 | 6.807 | −4.667 | −8.325 | 1.00 | 1.35 | ACSY |
| ATOM | 1779 | CG2 | VAL | 104 | 6.803 | −3.172 | −11.436 | 1.00 | 1.10 | ACSY |
| ATOM | 1780 | HG21 | VAL | 104 | 5.895 | −2.926 | −11.978 | 1.00 | 1.53 | ACSY |
| ATOM | 1781 | HG22 | VAL | 104 | 7.559 | −2.427 | −11.681 | 1.00 | 1.38 | ACSY |
| ATOM | 1782 | HG23 | VAL | 104 | 7.156 | −4.137 | −11.800 | 1.00 | 1.64 | ACSY |
| ATOM | 1783 | C | VAL | 104 | 4.929 | −3.187 | −8.087 | 1.00 | 0.76 | ACSY |
| ATOM | 1784 | O | VAL | 104 | 5.117 | −2.248 | −7.333 | 1.00 | 0.65 | ACSY |

TABLE 24-continued

Coordinates for the 3D structure of SYK-C:peptide complex
created by user: dave

| ATOM | 1785 | N    | PRO | 105 | 4.584  | -4.441  | -7.680 | 1.00 | 0.79 | ACSY |
|------|------|------|-----|-----|--------|---------|--------|------|------|------|
| ATOM | 1786 | CD   | PRO | 105 | 4.141  | -5.492  | -8.580 | 1.00 | 0.94 | ACSY |
| ATOM | 1787 | HD1  | PRO | 105 | 4.956  | -5.801  | -9.229 | 1.00 | 1.00 | ACSY |
| ATOM | 1788 | HD2  | PRO | 105 | 3.323  | -5.131  | -9.202 | 1.00 | 1.01 | ACSY |
| ATOM | 1789 | CA   | PRO | 105 | 4.526  | -4.805  | -6.277 | 1.00 | 0.70 | ACSY |
| ATOM | 1790 | HA   | PRO | 105 | 3.974  | -4.055  | -5.720 | 1.00 | 0.64 | ACSY |
| ATOM | 1791 | CB   | PRO | 105 | 3.848  | -6.170  | -6.222 | 1.00 | 0.82 | ACSY |
| ATOM | 1792 | HB1  | PRO | 105 | 4.435  | -6.878  | -5.639 | 1.00 | 0.81 | ACSY |
| ATOM | 1793 | HB2  | PRO | 105 | 2.887  | -6.081  | -5.741 | 1.00 | 0.86 | ACSY |
| ATOM | 1794 | CG   | PRO | 105 | 3.684  | -6.645  | -7.676 | 1.00 | 0.97 | ACSY |
| ATOM | 1795 | HG1  | PRO | 105 | 4.286  | -7.535  | -7.858 | 1.00 | 1.02 | ACSY |
| ATOM | 1796 | HG2  | PRO | 105 | 2.644  | -6.902  | -7.880 | 1.00 | 1.06 | ACSY |
| ATOM | 1797 | C    | PRO | 105 | 5.959  | -4.892  | -5.745 | 1.00 | 0.65 | ACSY |
| ATOM | 1798 | O    | PRO | 105 | 6.827  | -5.503  | -6.355 | 1.00 | 0.71 | ACSY |
| ATOM | 1799 | N    | CYS | 106 | 6.152  | -4.263  | -4.585 | 1.00 | 0.58 | ACSY |
| ATOM | 1800 | HN   | CYS | 106 | 5.383  | -3.882  | -4.072 | 1.00 | 0.57 | ACSY |
| ATOM | 1801 | CA   | CYS | 106 | 7.509  | -4.211  | -4.069 | 1.00 | 0.61 | ACSY |
| ATOM | 1802 | HA   | CYS | 106 | 8.176  | -4.252  | -4.931 | 1.00 | 0.64 | ACSY |
| ATOM | 1803 | CB   | CYS | 106 | 7.712  | -2.909  | -3.322 | 1.00 | 0.74 | ACSY |
| ATOM | 1804 | HB1  | CYS | 106 | 7.750  | -2.086  | -4.022 | 1.00 | 1.16 | ACSY |
| ATOM | 1805 | HB2  | CYS | 106 | 6.872  | -2.271  | -2.665 | 1.00 | 0.97 | ACSY |
| ATOM | 1806 | SG   | CYS | 106 | 9.228  | -2.923  | -2.337 | 1.00 | 1.05 | ACSY |
| ATOM | 1807 | HG   | CYS | 106 | 8.949  | -2.555  | -1.085 | 1.00 | 1.70 | ACSY |
| ATOM | 1808 | C    | CYS | 106 | 7.846  | -5.370  | -3.154 | 1.00 | 0.66 | ACSY |
| ATOM | 1809 | O    | CYS | 106 | 8.734  | -6.167  | -3.429 | 1.00 | 0.80 | ACSY |
| ATOM | 1810 | N    | GLN | 107 | 7.109  | -5.378  | -2.035 | 1.00 | 0.66 | ACSY |
| ATOM | 1811 | HN   | GLN | 107 | 6.392  | -4.706  | -1.893 | 1.00 | 0.68 | ACSY |
| ATOM | 1812 | CA   | GLN | 107 | 7.354  | -6.380  | -1.035 | 1.00 | 0.77 | ACSY |
| ATOM | 1813 | HA   | GLN | 107 | 8.163  | -6.001  | -0.405 | 1.00 | 0.87 | ACSY |
| ATOM | 1814 | CB   | GLN | 107 | 6.118  | -6.573  | -0.207 | 1.00 | 0.88 | ACSY |
| ATOM | 1815 | HB1  | GLN | 107 | 5.433  | -5.770  | -0.402 | 1.00 | 0.88 | ACSY |
| ATOM | 1816 | HB2  | GLN | 107 | 5.627  | -7.483  | -0.508 | 1.00 | 0.93 | ACSY |
| ATOM | 1817 | CG   | GLN | 107 | 6.448  | -6.608  | 1.278  | 1.00 | 1.08 | ACSY |
| ATOM | 1818 | HG1  | GLN | 107 | 7.149  | -5.810  | 1.520  | 1.00 | 1.10 | ACSY |
| ATOM | 1819 | HG2  | GLN | 107 | 5.555  | -6.456  | 1.869  | 1.00 | 1.31 | ACSY |
| ATOM | 1820 | CD   | GLN | 107 | 7.062  | -7.954  | 1.664  | 1.00 | 1.41 | ACSY |
| ATOM | 1821 | OE1  | GLN | 107 | 6.721  | -8.999  | 1.125  | 1.00 | 2.03 | ACSY |
| ATOM | 1822 | NE2  | GLN | 107 | 7.988  | -7.852  | 2.634  | 1.00 | 1.85 | ACSY |
| ATOM | 1823 | HE21 | GLN | 107 | 8.215  | -6.962  | 3.030  | 1.00 | 2.21 | ACSY |
| ATOM | 1824 | HE22 | GLN | 107 | 8.463  | -8.663  | 2.974  | 1.00 | 2.23 | ACSY |
| ATOM | 1825 | C    | GLN | 107 | 7.794  | -7.697  | -1.634 | 1.00 | 0.83 | ACSY |
| ATOM | 1826 | O    | GLN | 107 | 7.599  | -8.015  | -2.081 | 1.00 | 0.90 | ACSY |
| ATOM | 1827 | N    | LYS | 108 | 8.369  | -8.437  | -0.701 | 1.00 | 0.89 | ACSY |
| ATOM | 1828 | HN   | LYS | 108 | 8.418  | -8.089  | 0.238  | 1.00 | 0.91 | ACSY |
| ATOM | 1829 | CA   | LYS | 108 | 8.908  | -9.729  | -1.026 | 1.00 | 1.00 | ACSY |
| ATOM | 1830 | HA   | LYS | 108 | 9.706  | -9.569  | -1.756 | 1.00 | 1.10 | ACSY |
| ATOM | 1831 | CB   | LYS | 108 | 9.468  | -10.322 | 0.245  | 1.00 | 0.99 | ACSY |
| ATOM | 1832 | HB1  | LYS | 108 | 8.818  | -10.086 | 1.087  | 1.00 | 1.06 | ACSY |
| ATOM | 1833 | HB2  | LYS | 108 | 9.512  | -11.409 | 0.166  | 1.00 | 1.62 | ACSY |
| ATOM | 1834 | CG   | LYS | 108 | 10.850 | -9.764  | 0.480  | 1.00 | 1.43 | ACSY |
| ATOM | 1835 | HG1  | LYS | 108 | 11.522 | -10.228 | -0.226 | 1.00 | 2.09 | ACSY |
| ATOM | 1836 | HG2  | LYS | 108 | 10.853 | -8.697  | 0.259  | 1.00 | 1.80 | ACSY |
| ATOM | 1837 | CD   | LYS | 108 | 11.331 | -9.989  | 1.909  | 1.00 | 1.58 | ACSY |
| ATOM | 1838 | HD1  | LYS | 108 | 12.248 | -9.422  | 2.074  | 1.00 | 1.75 | ACSY |
| ATOM | 1839 | HD2  | LYS | 108 | 10.590 | -9.596  | 2.606  | 1.00 | 1.59 | ACSY |
| ATOM | 1840 | CE   | LYS | 108 | 11.581 | -11.470 | 2.199  | 1.00 | 1.99 | ACSY |
| ATOM | 1841 | HE1  | LYS | 108 | 11.877 | -11.611 | 3.238  | 1.00 | 2.24 | ACSY |
| ATOM | 1842 | HE2  | LYS | 108 | 10.675 | -12.052 | 2.030  | 1.00 | 2.32 | ACSY |
| ATOM | 1843 | NZ   | LYS | 108 | 12.633 | -12.031 | 1.359  | 1.00 | 2.54 | ACSY |
| ATOM | 1844 | HZ1  | LYS | 108 | 12.315 | -12.047 | 0.369  | 1.00 | 2.99 | ACSY |
| ATOM | 1845 | HZ2  | LYS | 108 | 13.489 | -11.466 | 1.439  | 1.00 | 2.75 | ACSY |
| ATOM | 1846 | HZ3  | LYS | 108 | 12.845 | -13.000 | 1.672  | 1.00 | 2.98 | ACSY |
| ATOM | 1847 | C    | LYS | 108 | 7.784  | -10.654 | -1.631 | 1.00 | 1.21 | ACSY |
| ATOM | 1848 | O    | LYS | 108 | 6.720  | -10.310 | -1.854 | 1.00 | 1.28 | ACSY |
| ATOM | 1849 | N    | ILE | 109 | 8.401  | -11.863 | -1.875 | 1.00 | 1.48 | ACSY |
| ATOM | 1850 | HN   | ILE | 109 | 9.363  | -12.046 | -1.647 | 1.00 | 1.55 | ACSY |
| ATOM | 1851 | CA   | ILE | 109 | 7.566  | -12.890 | -2.464 | 1.00 | 1.78 | ACSY |
| ATOM | 1852 | HA   | ILE | 109 | 6.748  | -12.385 | -2.982 | 1.00 | 1.89 | ACSY |
| ATOM | 1853 | CB   | ILE | 109 | 8.394  | -13.727 | -3.439 | 1.00 | 2.08 | ACSY |
| ATOM | 1854 | HB   | ILE | 109 | 9.120  | -14.307 | -2.865 | 1.00 | 2.22 | ACSY |
| ATOM | 1855 | CG2  | ILE | 109 | 7.495  | -14.698 | -4.206 | 1.00 | 2.57 | ACSY |
| ATOM | 1856 | HG21 | ILE | 109 | 6.458  | -14.363 | -4.189 | 1.00 | 2.80 | ACSY |
| ATOM | 1857 | HG22 | ILE | 109 | 7.535  | -15.697 | -3.774 | 1.00 | 2.00 | ACSY |
| ATOM | 1858 | HG23 | ILE | 109 | 7.807  | -14.772 | -5.248 | 1.00 | 3.08 | ACSY |
| ATOM | 1859 | CG1  | ILE | 109 | 9.151  | -12.856 | -4.423 | 1.00 | 2.79 | ACSY |
| ATOM | 1860 | HG11 | ILE | 109 | 9.511  | -13.493 | -5.221 | 1.00 | 3.11 | ACSY |

TABLE 24-continued

Coordinates for the 3D structure of SYK-C:peptide complex
created by user: dave

| ATOM | 1861 | HG12 | ILE | 109 | 8.476  | −12.128 | −4.874 | 1.00 | 3.35  | ACSY |
|------|------|------|-----|-----|--------|---------|--------|------|-------|------|
| ATOM | 1862 | CD1  | ILE | 109 | 10.333 | −12.138 | −3.768 | 1.00 | 3.27  | ACSY |
| ATOM | 1863 | HD11 | ILE | 109 | 10.720 | −12.713 | −2.927 | 1.00 | 3.76  | ACSY |
| ATOM | 1864 | HD12 | ILE | 109 | 11.144 | −11.997 | −4.482 | 1.00 | 3.43  | ACSY |
| ATOM | 1865 | HD13 | ILE | 109 | 10.038 | −11.156 | −3.399 | 1.00 | 3.61  | ACSY |
| ATOM | 1866 | C    | ILE | 109 | 6.992  | −13.779 | −1.358 | 1.00 | 1.95  | ACSY |
| ATOM | 1867 | O    | ILE | 109 | 6.314  | −13.325 | −0.445 | 1.00 | 2.27  | ACSY |
| ATOM | 1868 | N    | GLY | 110 | 7.318  | −15.075 | −1.515 | 1.00 | 2.16  | ACSY |
| ATOM | 1869 | HN   | GLY | 110 | 7.881  | −15.361 | −2.032 | 1.00 | 2.31  | ACSY |
| ATOM | 1870 | CA   | GLY | 110 | 6.846  | −16.042 | −0.543 | 1.00 | 2.55  | ACSY |
| ATOM | 1871 | HA1  | GLY | 110 | 6.075  | −16.645 | −1.024 | 1.00 | 2.98  | ACSY |
| ATOM | 1872 | HA2  | GLY | 110 | 6.405  | −15.489 | 0.286  | 1.00 | 2.78  | ACSY |
| ATOM | 1873 | C    | GLY | 110 | 7.992  | −16.927 | −0.050 | 1.00 | 2.95  | ACSY |
| ATOM | 1874 | O    | GLY | 110 | 8.812  | −16.529 | 0.768  | 1.00 | 3.24  | ACSY |
| ATOM | 1875 | N    | THR | 111 | 7.988  | −18.152 | −0.608 | 1.00 | 3.69  | ACSY |
| ATOM | 1876 | HN   | THR | 111 | 7.275  | −18.429 | −1.240 | 1.00 | 3.93  | ACSY |
| ATOM | 1877 | CA   | THR | 111 | 9.006  | −19.093 | −0.237 | 1.00 | 4.59  | ACSY |
| ATOM | 1878 | HA   | THR | 111 | 9.294  | −18.873 | 0.792  | 1.00 | 4.56  | ACSY |
| ATOM | 1879 | CB   | THR | 111 | 8.406  | −20.497 | −0.351 | 1.00 | 5.48  | ACSY |
| ATOM | 1880 | HB   | THR | 111 | 8.823  | −21.017 | −1.202 | 1.00 | 5.47  | ACSY |
| ATOM | 1881 | OG1  | THR | 111 | 7.016  | −20.413 | −0.568 | 1.00 | 6.29  | ACSY |
| ATOM | 1882 | HG1  | THR | 111 | 6.733  | −19.585 | −0.204 | 1.00 | 6.55  | ACSY |
| ATOM | 1883 | CG2  | THR | 111 | 8.659  | −21.301 | 0.902  | 1.00 | 6.06  | ACSY |
| ATOM | 1884 | HG21 | THR | 111 | 9.727  | −21.403 | 1.081  | 1.00 | 6.29  | ACSY |
| ATOM | 1885 | HG22 | THR | 111 | 8.229  | −22.295 | 0.812  | 1.00 | 6.36  | ACSY |
| ATOM | 1886 | HG23 | THR | 111 | 8.213  | −20.810 | 1.765  | 1.00 | 6.33  | ACSY |
| ATOM | 1887 | C    | THR | 111 | 10.223 | −18.920 | −1.152 | 1.00 | 5.25  | ACSY |
| ATOM | 1888 | O    | THR | 111 | 11.188 | −18.242 | −0.821 | 1.00 | 5.77  | ACSY |
| ATOM | 1889 | N    | GLN | 112 | 10.106 | −19.575 | −2.315 | 1.00 | 5.59  | ACSY |
| ATOM | 1890 | HN   | GLN | 112 | 9.300  | −20.129 | −2.502 | 1.00 | 5.45  | ACSY |
| ATOM | 1891 | HA   | GLN | 112 | 12.023 | −19.036 | −2.761 | 1.00 | 6.65  | ACSY |
| ATOM | 1892 | CB   | GLN | 112 | 11.526 | −20.900 | −3.757 | 1.00 | 7.76  | ACSY |
| ATOM | 1893 | HB1  | GLN | 112 | 10.613 | −21.428 | −4.033 | 1.00 | 7.73  | ACSY |
| ATOM | 1894 | HB2  | GLN | 112 | 12.131 | −20.835 | −4.654 | 1.00 | 8.48  | ACSY |
| ATOM | 1895 | CG   | GLN | 112 | 12.273 | −21.693 | −2.685 | 1.00 | 8.32  | ACSY |
| ATOM | 1896 | HG1  | GLN | 112 | 11.671 | −21.777 | −1.780 | 1.00 | 8.37  | ACSY |
| ATOM | 1897 | HG2  | GLN | 112 | 13.206 | −21.195 | −2.418 | 1.00 | 8.00  | ACSY |
| ATOM | 1898 | CD   | GLN | 112 | 12.590 | −23.098 | −3.202 | 1.00 | 9.59  | ACSY |
| ATOM | 1899 | OE1  | GLN | 112 | 12.590 | −23.363 | −4.398 | 1.00 | 10.22 | ACSY |
| ATOM | 1900 | NE2  | GLN | 112 | 12.859 | −23.973 | −2.216 | 1.00 | 10.08 | ACSY |
| ATOM | 1901 | HE21 | GLN | 112 | 12.840 | −23.684 | −1.259 | 1.00 | 9.69  | ACSY |
| ATOM | 1902 | HE22 | GLN | 112 | 13.081 | −24.925 | −2.425 | 1.00 | 10.94 | ACSY |
| ATOM | 1903 | C    | GLN | 112 | 10.750 | −18.616 | −4.449 | 1.00 | 6.55  | ACSY |
| ATOM | 1904 | OCT1 | GLN | 112 | 10.566 | −19.149 | −5.543 | 1.00 | 6.59  | ACSY |
| ATOM | 1905 | OCT2 | GLN | 112 | 10.606 | −17.410 | −4.259 | 1.00 | 6.79  | ACSY |
| ATOM | 1906 | CA   | GLN | 112 | 11.179 | −19.495 | −3.273 | 1.00 | 6.56  | ACSY |
| END  |      |      |     |     |        |         |        |      |       |      |

*Note:
See copyright notice on page 1.

What is claimed is:

1. A method for determining the three-dimensional structure of a co-complex of ZAP-NC (SEQ ID No. 36) with a ligand therefor, which comprises
   (a), obtaining x-ray diffraction data for crystals of the co-complex, and
   (b) utilizing a set of atomic coordinates selected from the group consisting of Table 21, 22, 23, and 24; a portion thereof; and coordinates having a root mean square deviation therefrom with respect to conserved protein backbone atoms of not more than 0.65 Å to define the three-dimensional structure of the co-complex.

2. A method of claim 1 wherein the structural coordinates are of a co-complex of ZAP-NC (SEQ ID No. 36), or a portion thereof, with a ligand other than the $\zeta^1$ peptide (SEQ ID No. 6).

3. The method of claim 1, wherein the atomic said set of coordinates of step (b) is selected from the group consisting of Table 21, 22, 23, and 24; a portion thereof; and coordinates having a root mean square deviation therefrom with respect to conserved protein backbone atoms of not more than 1.0 Å.

4. A method for determining a modeling structure of a protein containing an SH2 domain or co-complex of said protein with a ligand therefor, which method comprises:
   (a) providing a three-dimensional structure defined by a set of atomic coordinates of selected from the group consisting of Table 21, 22, 23, or 24, a portion thereof; and coordinates having a root mean square deviation therefrom with respect to conserved protein backbone atoms of not more than 0.65 Å, and
   (b) generating a three-dimensional model structure of the protein containing the SH2 domain using a homology modeling method and the structure of step (a) as a template; and
   (c) subjecting the resulting model to molecular mechanics energy minimizations.

5. The method of claim 4, wherein the said set of atomic coordinates of step (a) is selected from the group consisting of Table 21, 22, 23, or 24; a portion thereof; and coordinates having a root mean square deviation therefrom with respect to conserved protein backbone atoms of not more than 0.5 Å.

6. A method of claim 4 wherein the protein containing the SH2 domain is a ZAP-70 protein or a SYK protein.

7. A method of claim 4 wherein the protein containing the SH2 domain is a PLC$_\gamma$ protein, a rasGAP protein, a SH-PTP1 protein, or a SH-PTP2 protein.

* * * * *